US008440663B2

(12) United States Patent
Mann et al.

(10) Patent No.: US 8,440,663 B2
(45) Date of Patent: May 14, 2013

(54) 4-ARYL-2-AMINO-PYRIMIDINES OR 4-ARYL-2-AMINOALKYL-PYRIMIDINES AS JAK-2 MODULATORS AND METHODS OF USE

(75) Inventors: Grace Mann, San Mateo, CA (US); Naing Aay, San Mateo, CA (US); Arlyn Arcalas, South San Francisco, CA (US); S. David Brown, San Carlos, CA (US); Wai Ki Vicky Chan, San Francisco, CA (US); Jeff Chen, San Francisco, CA (US); Hongwang Du, Millbrae, CA (US); Sergey Epshteyn, Fremont, CA (US); Timothy Patrick Forsyth, Hayward, CA (US); Adam A. Galan, Alameda, CA (US); Tai Phat Huynh, New York City, NY (US); Mohamed Abdulkader Ibrahim, Mountain View, CA (US); Henry William Beecroft Johnson, San Bruno, CA (US); Brian Kane, Lynchburg, VA (US); Patrick Kearney, San Francisco, CA (US); Byung Gyu Kim, San Mateo, CA (US); Elena S. Koltun, Foster City, CA (US); James W. Leahy, San Leandro, CA (US); Matthew Sangyup Lee, San Bruno, CA (US); Gary L. Lewis, San Francisco, CA (US); Lisa E. Meyr, Seattle, WA (US); Robin Tammie Noguchi, San Bruno, CA (US); Michael Pack, San Francisco, CA (US); Brian Hugh Ridgway, Belmont, CA (US); Xian Shi, San Bruno, CA (US); John Woolfrey, Los Altos, CA (US); Peiwen Zhou, Palo Alto, CA (US)

(73) Assignee: Exelixis, Inc., South San Francisco, CA (US)

( * ) Notice: Subject to any disclaimer, the term of this patent is extended or adjusted under 35 U.S.C. 154(b) by 1372 days.

(21) Appl. No.: 11/992,224

(22) PCT Filed: Jan. 30, 2007

(86) PCT No.: PCT/US2007/002515
§ 371 (c)(1),
(2), (4) Date: Mar. 19, 2008

(87) PCT Pub. No.: WO2007/089768
PCT Pub. Date: Aug. 9, 2007

(65) Prior Publication Data
US 2009/0298830 A1 Dec. 3, 2009

Related U.S. Application Data

(60) Provisional application No. 60/840,420, filed on Aug. 25, 2006, provisional application No. 60/785,239, filed on Mar. 23, 2006, provisional application No. 60/763,426, filed on Jan. 30, 2006.

(51) Int. Cl.
*A61K 31/535* (2006.01)
*C07D 239/24* (2006.01)
*C07D 401/10* (2006.01)
*C07D 413/10* (2006.01)

(52) U.S. Cl.
USPC ......... 514/235.8; 544/323; 544/324; 544/333

(58) Field of Classification Search ............... 514/235.8; 544/323, 324, 333
See application file for complete search history.

(56) References Cited

FOREIGN PATENT DOCUMENTS

| WO | 97/19065 A | 5/1997 |
|---|---|---|
| WO | 2004/016597 A | 2/2004 |
| WO | 2004/041789 A | 5/2004 |
| WO | 2004/041810 A | 5/2004 |
| WO | 2006/021458 A | 3/2006 |

OTHER PUBLICATIONS

Kidemet et al., Novel synthesis of N-phenyl-2-aminopyrimidine derivatives under solvent-free conditions; Synlett, (2005), (16), 2531-2533.*

* cited by examiner

*Primary Examiner* — James O Wilson
*Assistant Examiner* — Ebenezer O Sackey
(74) *Attorney, Agent, or Firm* — McDonnell Boehnen Hulbert & Berghoff LLP

(57) ABSTRACT

This invention relates to certain pyrimidine derivative inhibitors of JAK-2, having Formula (I): wherein D, E, L, Z, $R^1$, $R^2$, $R^{25}$, and n1 are as defined in the specification, pharmaceutically acceptable salts thereof, pharmaceutical compositions thereof, and methods of use thereof.

33 Claims, No Drawings

4-ARYL-2-AMINO-PYRIMIDINES OR 4-ARYL-2-AMINOALKYL-PYRIMIDINES AS JAK-2 MODULATORS AND METHODS OF USE

CROSS REFERENCE TO RELATED APPLICATIONS

This application claims priority to U.S. Provisional Application Ser. No. 60/840,420, filed on Aug. 25, 2006, U.S. Provisional Application Ser. No. 60/785,239, filed on Mar. 23, 2006, and U.S. Provisional Application Ser. No. 60/763,426, filed on Jan. 30, 2006.

FIELD OF THE INVENTION

This invention relates to certain 4-aryl-2-amino-pyridines and 4-aryl-2-aminoalkyl-pyridines as inhibitors of protein tyrosine kinases. In particular, the invention relates to inhibitors of JAK-2 that involve the cytokine receptor signaling pathways.

BACKGROUND OF THE INVENTION

Janus kinases (JAKs) are protein tyrosine kinases ubiquitously expressed in cells. JAKs are involved in membrane signalling events which are triggered by a variety of extracellular factors that interact with cell surface receptors. JAKs initiate the cytoplasmic signal transduction cascades of cytokine receptors that lack a protein tyrosine kinase domain. The signal transduction cascades are initiated after oligomerisation of surface receptors due to ligand binding. Cytoplasmic receptor-associated JAKs are then activated which subsequently phosphorylate tyrosine residues along the receptor chains. These phosphotyrosine residues are targets for a variety of SH2 domain-containing transducer proteins, such as the signal transducers and activators of transcription (STAT) proteins. After STAT binds to receptor chains, they are phosphorylated by the JAK proteins, dimerise and translocate into the nucleus. In the nucleus, STAT alter the expression of cytokine-regulated genes.

Mammalian JAK-2 belongs to a kinase family that include JAK-1, JAK-3 and TYK-2. JAK-1, JAK-2, and TYK-2 are ubiquitously expressed, while JAK-3 is predominantly expressed in hematopoietic cells. These kinases consist of approximately 1150 amino acids, with molecular weights of about 120 kDa to 130 kDa. The amino acid sequences of the JAK kinase family are characterised by the presence of highly conserved domains. These domains include the JAK homology (JH) domains, C-terminal domain (JH1) responsible for the tyrosine kinase function, the tyrosine kinase-like domain (JH2) that shows high similarity to functional kinases but does not possess any catalytic activity, and the N-terminal domain that spans JH7 to JH3) that is important for receptor association and non-catalytic activity. Although the function of the N-terminal domain is not well established, there is some evidence for a regulatory role on the JH1 domain, thus modulating catalytic activity.

The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas.

Signal transducer and activator of transcription (STAT) proteins are activated by JAK family kinases. Recent studies suggested the possibility of modulating the JAK/STAT signaling pathway by targeting JAK family kinases with specific inhibitors for the treatment of leukemia (see Sudbeck, et al., Clin. Cancer Res. 5: 1569-1582 (1999)). In animal models, TEL/JAK-2 fusion proteins induced myeloproliferative disorders (Schwaller, et al., EMBO J. 17: 5321-5333 (1998)). In hematopoietic cell lines, introduction of TEL/JAK2 resulted in activation of STAT1, STAT3, STAT5, and cytokine-independent growth (Schwaller, et al., EMBO J. 17: 5321-5333 (1998)).

The JAK/STAT pathway is involved in abnormal cell growth (Yu, et al., J. Immunol. 159: 5206-5210 (1997)). STAT3, STAT5, JAK1 and JAK2 are constitutively activated in mouse T cell lymphoma characterized initially by LCK over-expression. In addition, IL-6-mediated STAT3 activation was blocked by inhibition of JAK, leading to sensitization of myeloma cells to apoptosis (Catlett-Falcone, et al., Immunity 10:105-115 (1999)).

One particularly attractive target for small-molecule modulation, with respect to antiproliferative and antiangiogenic activity, is JAK-2. Accumulating evidence shows that constitutive activation of JAK/STAT pathway promotes cell growth, survival, differentiation, neoplastic transformation, and angiogenesis in response to growth factors, cytokines, and hormones. JAK-2 is also activated in a wide variety of human cancers such as prostrate, colon, ovarian, breast cancers, melanoma, leukemia and other haematopoietic malignancies. In addition, somatic point mutation of the JAK-2 gene has been identified to be highly associated with classic myeloproliferative disorders (MPD) and infrequently in other myeloid disorders. Constitutive activation of JAK-2 activity is also caused by chromosomal translocation in hematopoeitic malignancies, such as in TEL-JAK-2 which is primarily associated with T-ALL, and in PCM1-JAK-2 which is associated with B-ALL and CML. It has been shown that inhibition of the JAK/STAT pathway, and in particular inhibition of JAK-2 activity, results in anti-proliferative and pro-apoptotic effects largely due to inhibition of phosphorylation of STAT. Furthermore, inhibition of JAK-2 activity by pharmacological agents or by expression of dominant negative JAK-2 effectively block tumor growth and induce apoptosis by reducing the STAT phosphorylation in cell culture and human tumor xenografts in vivo. Therefore, the JAK/STAT signal transduction pathway is a well-validated target pathway for therapeutic intervention.

Accordingly, the identification of small-molecule compounds that specifically inhibit, regulate and/or modulate the signal transduction of kinases, particularly JAK-2, is desirable as a means to treat or prevent diseases and conditions associated with cancers. Thus, an object of this invention is the identification of JAK-2 inhibitors as new therapeutic agents to treat human diseases.

SUMMARY OF THE INVENTION

The invention relates to compounds for inhibiting JAK-2 and pharmaceutical compositions of the compounds for inhibiting JAK-2. The invention is also related to methods of treating a disease mediated at least in part by JAK-2 using a compound of the invention, or a pharmaceutical composition thereof, as well as in combination with other therapies.

The foregoing only summarizes certain aspects of the invention and is not intended to be limiting in nature. These aspects and other aspects and embodiments are described more fully below. All references any sort referred to in this specification are hereby incorporated by reference in their entirety. In the event of a discrepancy between the express disclosure of this specification and the references incorporated by reference, the express disclosure of this specification shall control.

DETAILED DESCRIPTION OF THE INVENTION

A first aspect of the invention relates to a compound of Formula I:

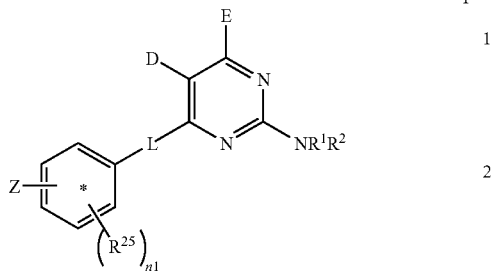

or a pharmaceutically acceptable salt thereof, wherein

D is hydrogen, halo, —$CF_3$, heterocycloalkyl or alkyl;

E is hydrogen, halo, —$CF_3$, heterocycloalkyl or alkyl; or

D and E, together with the carbon atoms to which they are attached, form a 5-7 membered heteroaryl or a 5-7 membered heterocycloalkyl, wherein the 5-7 membered heteroaryl or 5-7 membered heterocycloalkyl are each fused to the pyrimidinyl moiety to which D and E are attached;

L is a bond, —O— or —N(H)—;

Z is selected from alkoxy, cycloalkyl, heteroaryl optionally substituted with alkyl, halo, —C(O)O$R^{26}$, —C(=N—OH)alkyl, —C(O)$R^8$, —C(O)N$R^{30}R^{30a}$, —$CH_2R^2$, —$(CH_2)_{n5}NR^{26}R^{26a}$, —$CF_3$, —CN, —$SO_2R^{12}$, —S—$R^{12a}$, —O$R^{32a}$;

Z and $R^{25}$, together with the carbon atoms to which they are attached, join to form a 5 or 6 membered heterocycloalkyl, a 5 or 6 membered heteroaryl, or a 5 or 6 membered cycloalkyl ring, wherein the 5 or 6 membered heterocycloalkyl, 5 or 6 membered heteroaryl, and 5 or 6 membered cycloalkyl ring are fused to the phenyl moiety to which Z and $R^{25}$ are attached, and wherein the 5 or 6 membered heterocycloalkyl, 5 or 6 membered heteroaryl, or 5 or 6 membered cycloalkyl ring are each optionally substituted with 1, 2, or 3 groups independently selected from oxo, alkyl, alkoxy and halo;

n1 is 0, 1, 2, 3, or 4, and each n1 is independently selected when more than one n1 is present;

n2 is 0, 1, 2, 3, or 4, and each n2 is independently selected when more than one n2 is present;

n3 is 0, 1, 2, or 3, and each n3 is independently selected when more than one n3 is present;

n4 is 0, 1, 2, 3 or 4, and each n4 is independently selected when more than one n4 is present;

n5 is 0, 1, 2, 3 or 4, and each n5 is independently selected when more than one n5 is present;

p is 0-3;

r is 1-3;

$R^1$ is hydrogen;

$R^2$ is a group of formula:

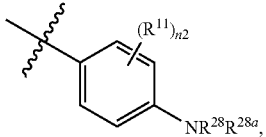
(a)

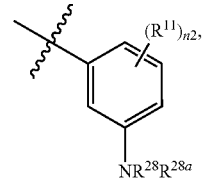
(b)

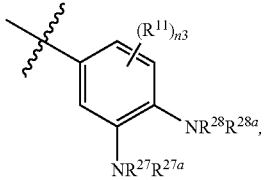
(c)

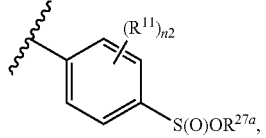
(c)

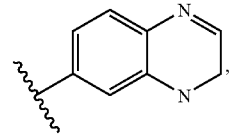
(d)

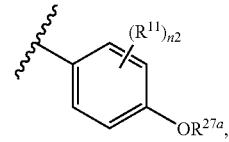
(e)

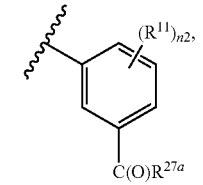
(f)

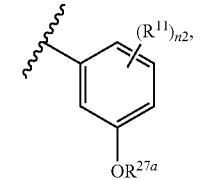
(g)

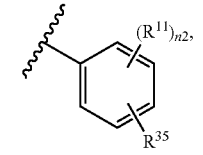
(h)

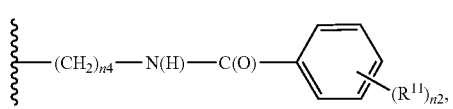
(i)

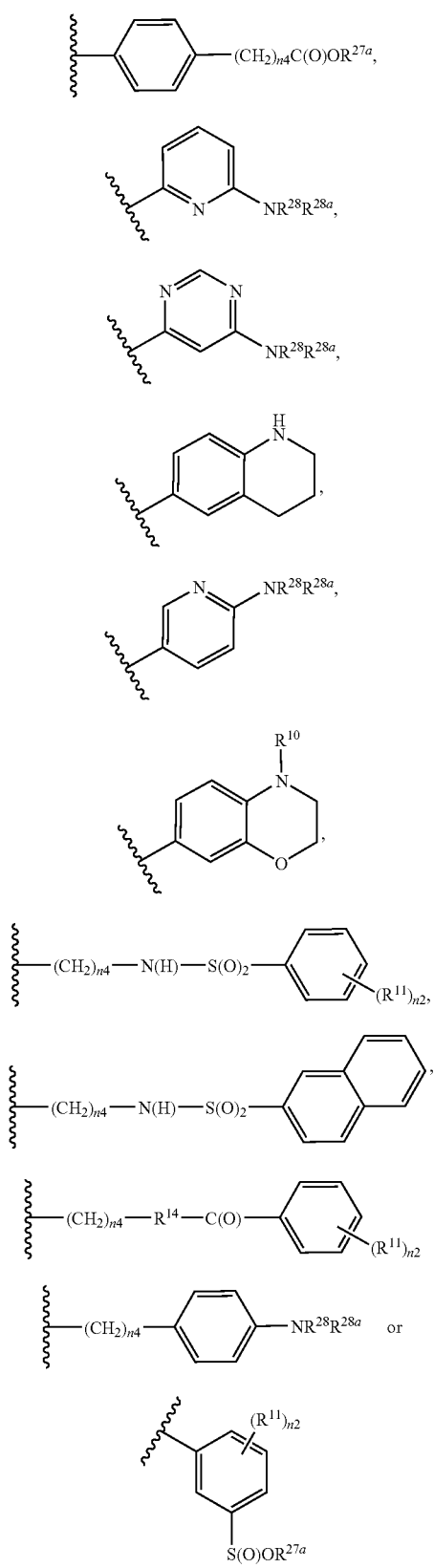

$R^7$, $R^{7'}$, $R^9$, $R^{10}$, $R^{12}$ and $R^{15}$ is are each independently hydrogen, alkyl, alkoxy, or alkoxyalkyl;

$R^8$ is selected from hydrogen, hydroxy, alkyl, alkenyl, lower alkynyl, hydroxylamino, hydroxyalkyl, alkoxyalkyl, dihydroxyalkyl, alkylamino, dialkylamino, aminoalkyl, aminocarbonylalkyl, alkylaminocarbonylalkyl, dialkylaminocarbonylalkyl, alkylaminoalkyl, dialkylaminoalkyl, —$(CH_2)_r$—C(O)OR$^7$, —$(CH_2)_r$—C(O)NR$^7$R$^{7'}$, aryl, heteroaryl, cycloalkyl, arylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, haloalkyl, haloalkoxy, lower alkoxy, amino, aryl, alkylamino, dialkylamino, heterocyclylalkoxy, oxo and haloalkyl;

each $R^{11}$, when $R^{11}$ is present, is independently selected from alkyl, alkenyl, lower alkynyl, —CF$_3$, alkoxy, halo, haloalkoxy, haloalkyl, aminoalkyl, aminoalkoxy, alkylaminoalkyl, alkylaminoalkoxy, dialkylaminoalkyl, dialkylaminoalkoxy, oxo, thioalkyl, alkylthioalkyl, —$(CH_2)_p$—OR$^{17}$, —CN, —O—CH$_2$—C(O)—R$^{17}$, —C(O)R$^{16}$, —$(CH_2)_p$—C(O)OR$^{17}$, —S(O)$_2$R$^{17}$, —S(O)$_2$NR$^{15}$R$^{17}$, aryl, heteroaryl, cycloalkyl, arylalkyl, arylalkoxy, heteroarylalkyl, cycloalkylalkyl, heterocycloalkyl, and heterocycloalkylalkyl; wherein the aryl, heteroaryl, cycloalkyl, arylalkyl, heteroarylalkyl, cycloalkylalkyl, heterocycloalkyl, and heterocycloalkylalkyl are each independently optionally substituted at any ring position with 1, 2, 3 or 4 $R^{21}$;

$R^{12}$ is hydrogen or alkyl;

$R^{12a}$ is hydrogen or alkyl;

$R^{13}$ is selected from hydrogen, hydroxy, alkyl, alkenyl, lower alkynyl, hydroxylamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, —$(CH_2)_r$—C(O)OR$^7$, —$(CH_2)_r$—C(O)NR$^7$R$^{7'}$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with 1, 2, 3, 4 or 5 groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl are independently optionally substituted with 1, 2, 3, 4, or 5 groups selected from halo and hydroxy;

$R^{14}$ is a bond, heterocycloalkyl or cycloalkyl;

$R^{16}$ is selected from hydrogen, hydroxy, alkyl, alkenyl, lower alkynyl, hydroxyamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, dialkylaminoalkyl, —$(CH_2)_r$—C(O)OR$^7$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl is optionally substituted with 1, 2, 3, 4, or 5 groups selected from halo and hydroxy;

$R^{17}$ is selected from hydrogen, hydroxy, alkyl, alkenyl, lower alkynyl, hydroxyamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, dialkylaminoalkyl,
—$(CH_2)_r$—$C(O)OR^7$, —$(CH_2)_r$—$C(O)NR^7R^{7'}$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl is optionally substituted with 1, 2, 3, 4, or 5 groups selected from halo and hydroxy;

each $R^{21}$, when $R^{21}$ is present, is independently selected from alkyl, alkenyl, lower alkynyl, cyano, halo, haloalkoxy, haloalkyl, hydroxyalkyl, amino, alkylamino, dialkylamino, dialkylaminoalkyl, dialkylaminoalkyloxy, haloalkyl, oxo, —$OR^{13}$, —$NHS(O)_2R^{17}$, —$S(O)_2R^{17}$, —$C(O)R^{17}$, —$C(O)OR^{17}$, —$C(O)NR^{15}R^{17}$, —$NR^{15}C(O)R^{17}$, aryl, arylalkyl, heteroarylalkyl, aryloxy, and heteroaryl; wherein each of the aryl, arylalkyl, heteroarylalkyl, aryloxy, and heteroaryl within $R^{21}$ are optionally substituted at any ring position with 1, 2, or 3 groups selected from alkyl, lower alkoxy halo, phenyl, heteroaryl and alkylheteroalkyl;

$R^{25}$ is selected from alkyl, alkenyl, lower alkyl, halo, haloalkyl, haloalkoxy, amino, alkylamino, dialkylamino, aminoalkyl, alkylaminoalkyl, —$OR^{12}$, cyano, —$C(O)R^8$, —$CH_2NHC(O)OR^7$, —$CH_2NHC(O)R^7$, —$SR^7$, —$S(O)_2R^7$, —$S(O)_2NR^7R^8$, —$C(O)OR^8$, —$C(O)NR^7R^8$, cycloalkyl, heterocycloalkyl, aryl and heteroaryl; wherein the cycloalkyl, heterocycloalkyl, aryl and heteroaryl are each optionally substituted with one, two or three groups independently selected from alkyl, alkenyl, halo, haloalkoxy, haloalkyl, amino, alkylamino, dialkylamino, aminoalkyl, alkylaminoalkyl, —$OR^8$, —$NHS(O)_2R^8$, cyano, —$C(O)R^8$, —$CH_2NHC(O)OR^7$, —$CH_2NHC(O)R^7$, —$SR^7$, —$S(O)_2R^7$, —$S(O)_2NR^7R^8$, —$C(O)OR^8$, —$C(O)NR^7R^8$, —$NR^7C(O)$—$CHR^3$—$OR^8$, —$NR^7C(O)$—$CHR^3$—$NR^7$—$R^8$, and —$NR^7C(O)R^8$;

$R^{26}$ is hydrogen, —C(O)-phenyl or alkyl, wherein the —C(O)-phenyl is optionally substituted at any ring position with 1, 2 or 3 halo;

$R^{26a}$ is hydrogen, alkyl, heteroaryl, —$C(O)R^{32}$, —$C(O)NHR^{32a}$, —$S(O)_2R^9$, —$SR^9$, —$C(O)OR^{32}$, or —$C(O)NR^{32a}R^{32}$;

$R^{27}$ and $R^{28}$ are each independently selected from alkyl, alkenyl, hydroxy, alkoxy, and alkoxyalkyl;

$R^{27a}$ and $R^{28a}$ are independently selected from hydrogen, alkyl, alkenyl, alkoxyalkyl, alkoxycarbonylalkyl, hydroxyalkyl, aryl, arylalkyl, cycloalkyl, cycloalkylalkyl, dialkylaminoalkyl, arylcarbonylalkyl, aryloxyalkyl, dialkylaminoalkyl, alkyl-O—C(O)heterocycloalkyl, —$(CH_2)_{n4}$heterocycloalkyl, heterocycloalkylalkyl, heteroaryl, heteroarylalkyl, —$(CH_2)_{n4}$—$C(O)R^{29}$, —$(CH_2)_{n4}NR^{28}R^{28a}$, —$(CH_2)_{n4}NHR^{28a}$, —$CH(phenyl)_2$, —$S(O)_2R^{29}$, —$C(O)R^{29}$, —$C(O)OR^{29}$, and —$C(O)NR^{29a}R^{29}$, wherein the aryl, arylalkyl, cycloalkyl, cycloalkylalkyl, heteroaryl, heteroarylalkyl, heterocycloalkyl, and heterocycloalkylalkyl groups within $R^{27a}$ and $R^{28a}$ are each independently optionally substituted at any ring position with 1, 2, 3, 4, or 5 groups selected from halo, alkyl, alkoxy, alkylcarbonyl, phenyl, phenoxy, arylcarbonyl, —$CF_3$, oxo, —$OCF_3$, alkoxyphenyl, and heteroaryl optionally substituted with alkyl or halo;

or $R^{27}$ and $R^{27a}$, together with the nitrogen to which they are attached, form heterocycloalkylamino, heterocycloalkyl or heteroaryl, wherein the heterocycloalkylamino and heteroaryl are each independently optionally substituted with 1, 2, 3, 4, or 5 $R^{31}$;

or $R^{28}$ and $R^{28a}$ together with the nitrogen to which they are attached form heterocycloalkyl or heteroaryl, wherein the heterocycloalkyl and heteroaryl are each optionally substituted with 1, 2, 3, 4, or 5 $R^{31}$;

$R^{29a}$ is hydrogen or alkyl;

$R^{29}$ is selected from alkyl, aryl, arylalkyl, cycloalkyl, cycloalkylalkyl, heteroaryl, heteroarylalkyl, heterocycloalkyl, and heterocycloalkylalkyl; wherein the aryl, arylalkyl, cycloalkyl, cycloalkylalkyl, heteroaryl, heteroarylalkyl, heterocycloalkyl, and heterocycloalkylalkyl groups within $R^{29}$ are each optionally substituted at any ring position with 1, 2, 3, 4, or 5 groups selected from halo, alkyl, alkoxy, alkylcarbonyl, phenyl, phenoxy, arylcarbonyl, —$CF_3$, oxo, —$OCF_3$, alkoxyphenyl, and heteroaryl optionally substituted with alkyl or halo;

$R^{30a}$ is hydrogen or alkyl;

$R^{30}$ is selected from hydrogen, alkyl, hydroxyalkyl, alkoxyalkyl, alkoxyalkoxyalkyl, alkoxycarbonylalkyl, amino, alkylamino, dialkylamino, aminoalkyl, alkylaminoalkyl, dialkylaminoalkyl, aryl, arylalkyl, phenoxyalkyl, cycloalkyl, cycloalkylalkyl, heteroaryl, heteroarylalkyl, arylheteroarylalkyl, heterocycloalkyl, and heterocycloalkylalkyl; wherein the aryl, arylalkyl, phenoxyalkyl, cycloalkyl, arylheteroarylalkyl, cycloalkylalkyl, heteroaryl, heteroarylalkyl, heterocycloalkyl, and heterocycloalkylalkyl groups within $R^{30}$ are each independently optionally substituted at any ring position with 1, 2, 3, 4, or 5 groups selected from halo, alkyl, alkoxy, alkoxyalkyl, —$C(O)OCH_3$, —$CF_3$, —$OCF_3$, alkylcarbonyl, phenyl, phenoxy, alkylphenoxy, dialkylaminoalkoxy and heteroaryl;

$R^{31}$ is selected from alkyl, hydroxyalkyl, alkoxy, alkoxyalkyl, alkylthioalkyl, —$C(O)R^{30}$, —$C(O)NR^{30}R^{30a}$, —$C(O)OR^{30}$, —$S(O)_2R^{30}$, amino, dihydroxyalkyl, arylcarbonyl, alkylcarbonylamino, alkoxyphenyl, phenylalkoxyalkyl, arylheteroarylalkyl, alkylamino, —O-dialkylamino, dialkylamino, aminoalkyl, alkylaminoalkyl, dialkylaminoalkyl, dialkylaminoalkoxy, oxo, aryl, arylalkyl, cycloalkyl, cycloalkylalkyl, heteroaryl, heteroarylalkyl, heterocycloalkyl, spirocyclic cycloalkyl, spirocyclic heterocycloalkyl, and heterocycloalkylalkyl, wherein the aryl, arylalkyl, cycloalkyl, arylheteroarylalkyl, arylalkoxyalkyl, cycloalkylalkyl, heteroaryl, heteroarylalkyl, heterocycloalkyl, and heterocycloalkylalkyl groups within $R^{31}$ are each independently optionally substituted at any ring position with 1, 2, 3, 4, or 5 groups selected from halo, alkyl, —CF$_3$, —OCF$_3$, cyano, alkoxy, alkoxyalkyl, —C(O)OCH$_3$, alkylcarbonyl, phenyl optionally substituted at any ring position with halo, phenoxy, alkylphenoxy, arylalkoxyalkyl, dialkylaminoalkoxy and heteroaryl;

R$^{32a}$ is hydrogen, —OCF$_3$, —CF$_3$, or alkyl;

R$^{32}$ is selected from aryl, arylalkyl, arylalkoxy, arylcycloalkyl, alkoxycarbonylalkoxy, cycloalkyl, cycloalkylalkyl, cycloalkylhydroxyalkyl, heteroaryl, heteroarylalkyl, heterocycloalkyl, and heterocycloalkylalkyl, wherein the aryl, arylalkyl, cycloalkyl, arylcycloalkyl, cycloalkylalkyl, heteroaryl, heteroarylalkyl, heterocycloalkyl, and heterocycloalkylalkyl are each independently optionally substituted at any ring position with 1, 2, 3, 4, or 5 groups selected from hydroxy, oxo, alkyl, alkoxy, amino, hydroxyalkyl, alkylcarbonyl, alkoxycarbonyl, halo; —CF$_3$, —OCF$_3$, aminoalkyl, alkylaminoalkyl, aryl and dialkylaminoalkyl, and wherein the alkyl portion of the heteroarylalkyl can be substituted with amino;

or R$^{32}$ is alkyl optionally substituted with 1, 2, 3, 4, or 5 groups independently selected from hydroxy, alkoxycarbonyl, alkoxy, —CF$_3$, halo, aminocarbonyl, alkylaminocarbonyl, alkoxycarbonylalkylamino, dialkylaminocarbonyl, —NR$^{34}$R$^{34a}$ and phenyl optionally substituted with 1, 2, or 3 halo;

or R$^{32}$ is alkylamino or arylalkylamino;

R$^{34}$ is hydrogen or alkyl;

R$^{34a}$ is selected from hydrogen, alkyl, heteroaryl, aryl, aminoalkyl, aminocarbonylalkyl, heteroarylalkyl, arylalkoxy and arylalkyloxycarbonylalkyl; wherein the heteroaryl, aryl, heteroarylalkyl, arylalkoxy or arylalkyloxycarbonylalkyl are each independently optionally substituted at any ring position with 1, 2, 3, 4, or 5 groups selected from hydroxy, oxo, alkyl, amino, hydroxyalkyl, alkylcarbonyl, alkoxycarbonyl, halo, aminoalkyl, alkylaminoalkyl, and dialkylaminoalkyl; and R$^{35}$ is selected from halo, —(CH$_2$)$_p$C(O)OR$_{17}$, cycloalkyl, heterocycloalkyl, and heterocycloalklylalkyl; wherein the heterocycloalkyl and heterocycloalklylalkyl are each optionally substituted with 1, 2, 3, 4, or 5 groups each independently selected from alkyl, alkoxy, and halo.

Another embodiment of the first aspect of the invention relates to a compound of Formula II:

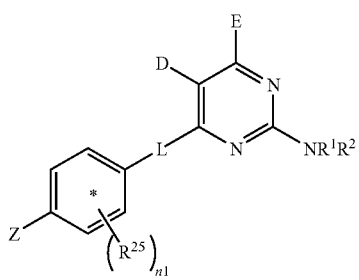

wherein E, D, L, Z, R$^1$, R$^2$ and R$^{25}$ are as defined above for the compound of Formula I.

Another embodiment of the first aspect of the invention relates to a compound of Formula III:

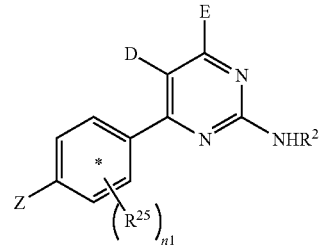

wherein E, D, L, Z, R$^1$, R$^2$ and R$^{25}$ are as defined above for the compound of Formula I.

Another embodiment of the first aspect of the invention relates to a compound of Formula IV:

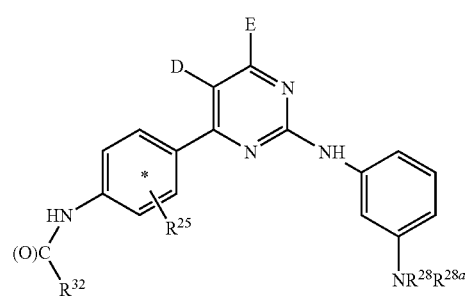

wherein D, E, R$^{25}$ and R$^{32}$ are as defined above for Formula I, and R$^{28}$ and R$^{28a}$, together with the nitrogen atom to which they are attached, form a heterocycloalkyl, wherein the heterocycloalkyl is optionally substituted with one or two R$^{31}$, and wherein R$^{31}$ is as defined above in Formula I.

Another embodiment of the first aspect of the invention relates to a compound of Formula V:

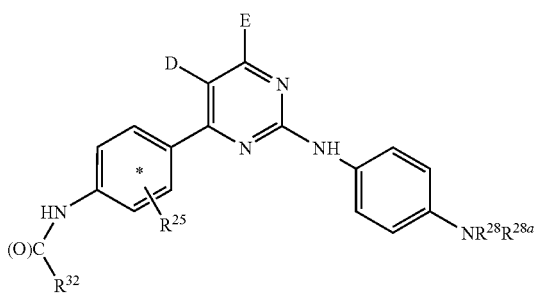

wherein D, E, R$^{25}$ and R$^{32}$ are as defined above for Formula I, and R$^{28}$ and R$^{28a}$, together with the nitrogen atom to which they are attached, form a heterocycloalkyl, wherein the heterocycloalkyl is optionally substituted with one or two R$^{31}$, and wherein R$^{31}$ is as defined above in Formula I.

Another embodiment of the first aspect of the invention relates to a compound of Formula VI:

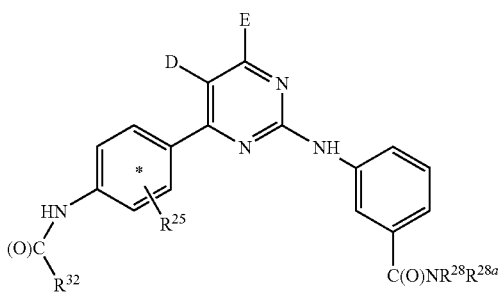

VI wherein D, E, $R^{25}$ and $R^{32}$ are as defined above for Formula I, and $R^{28}$ and $R^{28a}$, together with the nitrogen atom to which they are attached, form a heterocycloalkyl, wherein the heterocycloalkyl is optionally substituted with one or two $R^{31}$, and wherein $R^{31}$ is as defined above in Formula I.

In other embodiments of the first aspect of the invention, D, E and $R^{25}$ for Formula IV, Formula V or Formula VI are each hydrogen.

In other embodiments of the first aspect of the invention, $R^{32}$ for Formula IV, Formula V or Formula VI is heterocycloalkyl.

In other embodiments of the first aspect of the invention, $R^{32}$ for Formula IV, Formula V or Formula VI is alkyl optionally substituted with alkoxy, hydroxy, amino, alkylamino, or dialkylamino.

In other embodiments of the first aspect of the invention, $R^2$ in Formula I, II or III is

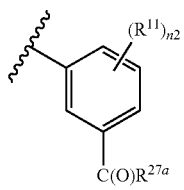

(f)

wherein $R^{27a}$, $R^{11}$ and n2 are as defined above for the compound of Formula I.

In other embodiments of the first aspect of the invention, $R^2$ in Formula I, II or III is

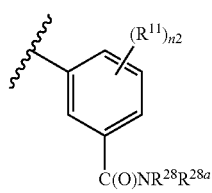

wherein $R^{28}$, $R^{11}$ and n2 are as defined above for the compound of Formula I, and $R^{28a}$ is arylalkyl or heteroarylalkyl, wherein the arylalkyl or heteroarylalkyl are each optionally substituted with 1, 2, 3, 4, or 5 substituents selected from halo or lower alkyl.

In other embodiments of the first aspect of the invention, $R^2$ in Formula I, II or III is

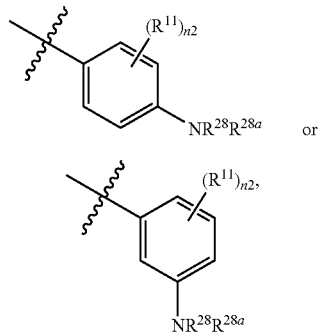

wherein $R^{28}$, $R^{28a}$, $R^{11}$ and n2 are as defined above for the compound of Formula I.

In other embodiments of the first aspect of the invention, $R^2$ in Formula I, II or III is

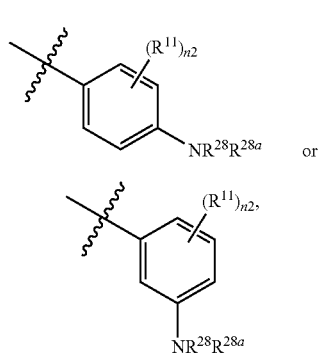

wherein $R^{28}$, $R^{11}$ and n2 are as defined above for the compound of Formula I, and $R^{28a}$ is selected from lower alkyl, dialkylaminoalkyl, alkoxyalkyl, arylalkyl, heteroarylalkyl, and heterocycloalkylalkyl.

In other embodiments of the first aspect of the invention, $R^2$ in Formula I, II or III is

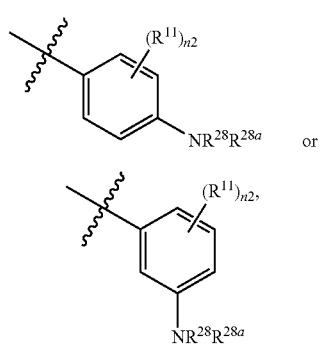

wherein $R^{11}$ and n2 are as defined above for the compound of Formula I, and $R^{28}$ and $R^{28a}$, together with the nitrogen atom to which they are attached, join together to form a ring structure selected from thiazolidinyl, piperazinyl, piperidinyl, morpholinyl, thiomorpholinyl, pyrimidinyl, and pyridinyl, wherein the ring structure is optionally substituted with 1, 2, 3, 4 or 5 substituents selected from halo, lower alkyl or alkoxy.

In other embodiments of the first aspect of the invention, $R^2$ in Formula I, II or III is

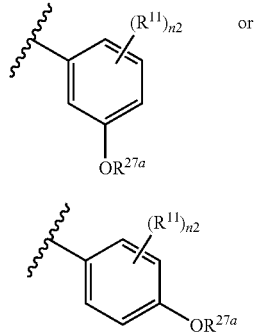

(g)

or (e)

wherein $R^{27a}$, $R^{11}$ and $_{n2}$ are as defined above for the compound of Formula I.

Other embodiments of the first aspect of the invention relate to a compound of Formula I, II or III, wherein L is a bond, and Z is

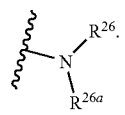

Other embodiments of the first aspect of the invention relate to a compound of Formula I, II or III, wherein Z is

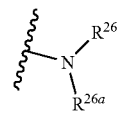

and $R^{25}$ is hydrogen.

Other embodiment of the first aspect of the invention relate to a compound of Formula I, II or III, wherein Z is

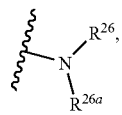

$R^{25}$ is hydrogen and E and D are hydrogen.

Other embodiments of the first aspect of the invention relate to a compound of in Formula I, II or II, wherein $R^{25}$ is on the 3 position.

Other embodiment of the first aspect of the invention relate to a compound of Formula I, II or III, wherein Z is

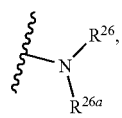

and $R^{26a}$ is —C(O)R$^{32}$.

Other embodiments of the first aspect of the invention relate to compound of Formula I, II or II, wherein Z is

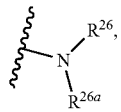

$R^{26a}$ is —C(O)R$^{32}$, and $R^{32}$ is selected from lower alkyl, cylcoalkyl, diaminoalkyl, aminoalkyl, arylalkyl, heterocycloalkyl, alkoxyalkyl, alkylamino, and hydroxyalkyl optionally substituted with amino.

Other embodiments of the first aspect of the invention relate to a compound of Formula I, II or III, wherein Z is

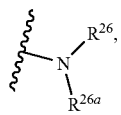

$R^{26a}$ is —C(O)R$^{32}$, and $R^{32}$ is cycloalkyl.

Other embodiments of the first aspect of the invention relate to a compound of Formula I, II or III, wherein Z is

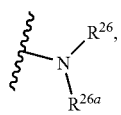

$R^{26a}$ is —C(O)R$^{32}$, and $R^{32}$ is lower alkyl.

Other embodiments of the first aspect of the invention relate to a compound of Formula I, II or III wherein Z is

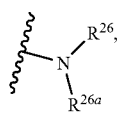

$R^{26a}$ is —C(O)R$^{32}$, $R^{26}$ is hydrogen, wherein $R^{32}$ selected from aryl, arylalkyl, cycloalkyl, alkoxycarbonylalkyl, heteroaryl, heteroarylalkyl, heterocycloalkyl, and heterocycloalkylalkyl, wherein $R^{32}$ optionally substituted with 1, 2, 3, 4 or 5 groups selected from hydroxyl, oxo, alkyl, alkoxy, amino, hydroxyalkyl or halo.

Other embodiments of the first as t of the invention relate to a compound of Formula I, II or III, wherein Z is

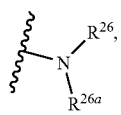

$R^{26a}$ is —C(O)R$^{32}$, $R^{26}$ is hydrogen, wherein $R^{32}$ selected from tetrahydrofuran, pyrrolidinyl or pryimidinyl, wherein $R^{32}$ optionally substituted with 1, 2, 3, 4 or 5 groups selected from hydroxyl, oxo, alkyl, alkoxy, amino, hydroxyalkyl or halo.

Other embodiments of the first aspect of the invention relate to a compound of Formula I, II or III, wherein Z is

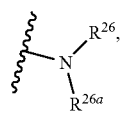

$R^{26a}$ is —C(O)$R^{32}$, $R^{26}$ is hydrogen, wherein $R^{32}$ is lower alkyl optionally substituted with 1, 2, 3, 4 or 5 groups selected from dialkylaminocarbonyl, hydroxy and —NR$^{34}$R$^{34a}$, wherein $R^{34}$ and $R^{34a}$ are as defined above for Formula I.

Other embodiments of the first aspect of the invention relate to a compound of Formula I, II or III, wherein $R^2$ is

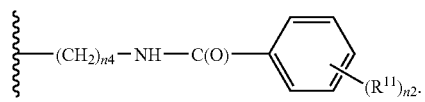

In another embodiment of the first aspect of the invention, $R^{32}$ is methyl.

In another embodiment of the first aspect of the invention, $R^{32}$ is alkyl substituted with —NR$^{34}$R$^{34a}$.

Other embodiments of the first aspect of the invention relate to a compound of Formula I, II or III, wherein $R^{32}$ is U or —CH$_2$—U, wherein U is selected from pyrrolidinyl, thiazolidinyl, morpholinyl, azetidinyl, cyclobutyl, cyclopropyl, tetrahydrofuranyl, pyrazinyl, imidazolyl, piperazinyl, thienyl, thienylmethyl, furanyl, phenyl, prolinamidyl, pyridinyl, tetrahydronaphthalene, tetrazolyl, isoindolinyl, pyranyl, cyclopentyl, and octahydro-1H-indolyl.

Other embodiments of the first aspect of the invention relate to a compound of Formula I, II or III, wherein $R^{11}$, when present, is halo or lower alkyl.

Other embodiments of the first aspect of the invention relate to a compound of Formula I, II or III, wherein $R^{11}$, when present, is lower alkyl.

Other embodiments of the first aspect of the invention relate to a compound of Formula I, II or III, wherein $R^{35}$ is heterocycloalkylalkyl, wherein the heterocycloalkyl is selected from piperazinyl, piperidinyl, morpholinyl and dioxanyl.

Other embodiments of the first aspect of the invention relate to a compound of Formula I, II or III, wherein n2 is 0.

Other embodiments of the first aspect of the invention relate to a compound of Formula I, II or III, wherein $R^2$ is

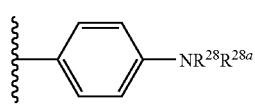

Other embodiments of the first aspect of the invention relate to a compound of Formula I, II or III, wherein $R^2$ is

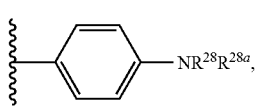

and wherein $R^{28}$ and $R^{28a}$, together with the nitrogen atom to which they are attached, form a heterocycloalkyl.

Other embodiments of the first aspect of the invention relate to a compound of Formula I, II or III, IV or V, wherein $R^{25}$ is hydrogen.

A second aspect of the invention relates to a pharmaceutical composition comprising a compound of Formula I, II, III, IV, V or VI, or a pharmaceutically acceptable salt thereof, and a pharmaceutically acceptable carrier, excipient, or diluent.

A third aspect of the invention relates to a method of inhibiting JAK-2 in a cell, comprising contacting the cell, in which inhibition of JAK-2 is desired, with a compound of Formula I, II, III, IV, V or VI, or a pharmaceutically salt thereof.

A fourth aspect of the invention relates to a method of inhibiting JAK-2 in a cell, comprising contacting the cell, in which inhibition of JAK-2 is desired, with a pharmaceutical composition comprising a compound of Formula I, II, III, IV, V or VI, or a pharmaceutically acceptable salt thereof.

A fifth aspect of the invention relates to a method for treating a disease, disorder, or syndrome mediated, at least in part, by inhibiting JAK-2, which method comprises administering to an animal in need of said treatment a therapeutically effective amount of a compound of Formula I, II, III, IV, V or VI, or a pharmaceutically acceptable salt thereof.

A sixth aspect of the invention relates to a method for treating a disease, disorder, or syndrome mediated, at least in part, by inhibiting JAK-2, which method comprises administering to an animal in need of said treatment a pharmaceutical composition comprising a therapeutically effective amount of a compound of Formula I, II, III, IV, V or VI, or a pharmaceutically acceptable salt thereof.

The disease being treated in these aspects of the invention can be a myeloproliferative disorder, cancer, cardiovascular disease, and/or hematopoietic abnormality where hyperactivation of JAK-STAT signaling is present. Nonlimiting examples of myeloproliferative disorders that are contemplated as being treatable by the compounds of the invention include myelofibrosis, thrombocythemia, polycythemia vera (PV), essential thrombocythemia (ET), agnogenic myeloid metaplasia (AMM), also referred to as idiopathic myelofibrosis (IMF), and chronic myelogenous leukemia (CML). Nonlimiting examples of cancers that are contemplated as being treatable by the compounds of the invention include leukemias, lymphomas, multiple myeloma, prostate cancers, lung cancers, breast cancers, and ovarian cancers. Nonlimiting examples of cardiovascular diseases that are contemplated as being treatable by the compounds of the invention include congestive heart failure and hypertension. Nonlimiting examples of hematopoietic abnormalities that are contemplated as being treatable by the compounds of the invention include thrombocytosis.

A seventh aspect of the invention relates to a method of treating a disease, disorder, or syndrome mediated, at least in part, by inhibiting JAK-2, which method comprises administering to an animal a compound of Formula I, II, III, IV, V or VI, or a pharmaceutically acceptable salt thereof, in combination with one or more treatment(s) selected from surgery, one or more therapeutic agent(s), plateletpheresis, and radiation.

An eighth aspect of the invention relates to a method of treating a disease, disorder, or syndrome mediated, at least in part, by inhibiting JAK-2, which method comprises administering to an animal a pharmaceutical composition comprising a therapeutically effective amount of a compound of Formula I, II, III, IV, V or VI, or a pharmaceutically acceptable salt thereof, in combination with one or more treatment(s) selected from surgery, one or more therapeutic agent(s), plateletpheresis, and radiation.

When treating myeloproliferative disorders, the compound of Formula I, II, III, IV, V or VI can also be administered with one or more additional treatment(s) selected from plateletpheresis and one or more therapeutic agent(s) selected from interferon-α; aspirin; a platelet-decreasing drug, such as anagrelide; and a myelosuppressive agent (such as a radiophosphorus and alkylating agents). Non-limiting examples of the myelosuppressive agent include hydroxyurea, melphalan, and busulfan.

When treating cancer, the compound of Formula I, II, III, IV, V or VI can be administered in combination with one or more chemotherapeutic agent(s) selected from fludaribine, vinblastine, adriamycin and cisplatin.

ABBREVIATIONS AND DEFINITIONS

The following abbreviations and terms have the indicated meanings throughout:

| Abbreviation | Meaning |
|---|---|
| Ac | Acetyl |
| Br | Broad |
| ° C. | degrees Celsius |
| c- | Cyclo |
| CBZ | CarboBenZoxy = benzyloxycarbonyl |
| D | doublet |
| Dd | doublet of doublet |
| Dt | doublet of triplet |
| DIPEA | N,N-diisopropylethylamine |
| DMF | N,N-dimethylformamide |
| DMSO | dimethyl sulfoxide |
| EI | Electron Impact ionization |
| Et | Ethyl |
| G | gram(s) |
| GC | gas chromatography |
| h or hr | hour(s) |
| HOAc | acetic acid |
| HOBt | Hydroxybenzotriazole |
| HPLC | high pressure liquid chromatography |
| L | liter(s) |
| M | molar or molarity |
| M | Multiplet |
| Me | Methyl |
| Mesyl | Methanesulfonyl |
| Mg | milligram(s) |
| MHz | megahertz (frequency) |
| Min | minute(s) |
| mL | milliliter(s) |
| mM | Millimolar |
| Mmol | millimole(s) |
| Mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | Phenyl |
| PhOH | Phenol |
| PfP | Pentafluorophenol |
| PfPy | Pentafluoropyridine |
| PPTS | Pyridinium p-toluenesulfonate |
| Py | Pyridine |
| PyBroP | bromo-tris-pyrrolidino-phosphonium hexafluorophosphate |
| Q | Quartet |
| RT | Room temperature |
| Sat'd | Saturated |
| S | Singlet |
| s- | Secondary |
| t- | Tertiary |
| t or tr | Triplet |
| TBDMS | t-butyldimethylsilyl |
| TES | Triethylsilyl |

-continued

| Abbreviation | Meaning |
|---|---|
| TFA | trifluoroacetic acid |
| THF | Tetrahydrofuran |
| TMOF | trimethyl orthoformate |
| TMS | Trimethylsilyl |
| Tosyl | p-toluenesulfonyl |
| Trt | triphenylmethyl |
| uL | microliter(s) |
| uM | Micromole(s) or micromolar |

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond, "⚌" means a single or double bond. When a group is depicted removed from its parent formula, the "⌇" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

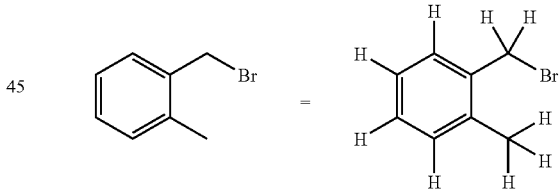

If a group "R" is depicted as "floating" on a ring system, as for example in the formula:

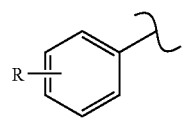

then, unless otherwise defined, a substituent "R" can reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

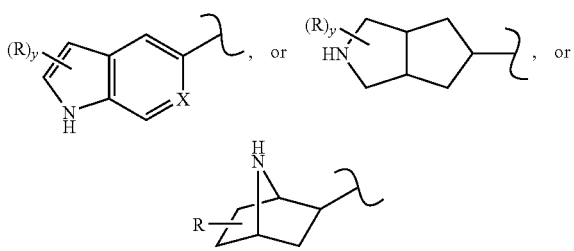

then, unless otherwise defined, a substituent "R" can reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group can reside on either the 5-membered or the 6-membered ring of the fused ring system. In the formula depicted above, when y is 2 for example, then the two "R's" can reside on any two atoms of the ring system, again assuming each replaces a depicted, implied, or expressly defined hydrogen on the ring.

When a group "R" is depicted as existing on a ring system containing saturated carbons, as for example in the formula:

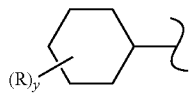

where, in this example, "y" can be more than one, assuming each replaces a currently depicted, implied, or expressly defined hydrogen on the ring; then, unless otherwise defined, where the resulting structure is stable, two "R's" can reside on the same carbon. A simple example is when R is a methyl group; there can exist a germinal dimethyl on a carbon of the depicted ring (an "annular" carbon). In another example, two R's on the same carbon, including that carbon, can form a ring, thus creating a spirocyclic ring (a "spirocyclyl" group) structure with the depicted ring as for example in the formula:

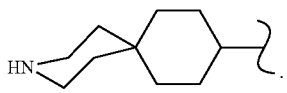

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkyl" is intended to include $C_1$-$C_{20}$, more typically, $C_1$-$C_{12}$ linear or branched structures and combinations thereof, inclusively. "Lower alkyl" is intended to include $C_1$-$C_6$ linear or branched structures and combinations thereof, inclusively. For example, "$C_6$ alkyl" can refer to an n-hexyl, iso-hexyl, cyclobutylethyl, and the like. Examples of lower alkyl groups include methyl, ethyl, propyl, isopropyl, butyl, s-butyl, t-butyl, isobutyl, pentyl, hexyl and the like. Higher alkyl refers to alkyl groups containing more that six carbon atoms. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl.

"Cycloalkyl" means a non-aromatic mono- or multicyclic ring system comprising about 3 to about 14 carbon atoms, 5 to 10 carbon atoms, or 5 to about 7 ring atoms. Non-limiting examples of monocyclic cycloalkyls include cyclopropyl, cyclopentyl, cyclohexyl, cycloheptyl and the like. Non-limiting examples of multicyclic cycloalkyls include 1-decalin, norbornyl, adamantyl and the like. Cycloalkyls can be fused or bridge ring systems or spirocyclic systems.

"Alkyl substituted with halo and hydroxy" means an alkyl group substituted with 1, 2, or 3 hydroxy and 1, 2, 3, 4, or 5 halo.

"Alkylene" refers to straight or branched chain divalent group consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent group consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent group consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above groups, "alkylene," "alkylidene" and "alkylidyne," when optionally substituted, can contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"Alkoxy" or "alkoxyl" refers to the group —O-alkyl, wherein the term "alkyl" is as defined hereinabove. Examples include methoxy, ethoxy, propoxy, isopropoxy, and the like. Lower alkoxy refers to groups containing one to six carbons.

"Substituted alkoxy" refers to the group —O-(substituted alkyl), the substitution on the alkyl group generally containing more than only carbon (as defined by alkoxy). Another exemplary substituted alkoxy group is hydroxyalkoxy or —O-alkyl-OH.

"Aryl" means a monovalent five- to fourteen-membered mono- or multicyclic ring, wherein the monocyclic ring is aromatic and at least one of the rings in the multicyclic ring is aromatic. An aryl can also be five- to ten membered, or six membered. Representative non-limiting examples of aryl include phenyl, naphthyl, and the like.

"Arylalkyl" means a residue in which an aryl moiety, as defined above, is attached to a parent structure via one of an alkylene, alkylidene, or alkylidyne group. Examples include benzyl, phenethyl, phenylvinyl, phenylallyl and the like. The "alkyl" portion of the group can be one to ten carbons, and in another embodiment, one to six carbons; the latter can also be referred to as $C_{1-6}$ arylalkyl. When a group is referred to as or "—$(C_1$-$C_6)$alkylaryl," an aryl moiety is attached to a parent structure via an alkylene group. Examples include benzyl, phenethyl, and the like.

In some examples, as appreciated by one of ordinary skill in the art, two adjacent groups on an aromatic system can be fused together to form a ring structure. The fused ring structure can contain heteroatoms and can be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems includes non-aromatic and aromatic systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention can themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Non-limiting examples of "haloalkyl" include —$CH_2F$, —$CHCl_2$ or —$CF_3$.

"Heteroatom" refers to O, S, N, or P.

"Heterocyclyl" refers to a stable three- to fifteen-membered ring substituent that consists of carbon atoms and from one to five heteroatoms selected from the group consisting of nitrogen, phosphorus, oxygen and sulfur. For purposes of this invention, the heterocyclyl substituent can be a monocyclic, bicyclic or tricyclic ring system, which can include fused or bridged ring systems as well as spirocyclic systems. The terms "heterocycloalkyl" and "heteroaryl" are groups that are encompassed by the broader term "heterocyclyl." The nitrogen, phosphorus, carbon or sulfur atoms in the heterocyclyl group can be optionally oxidized to various oxidation states. In a specific example, the group —$S(O)_{0-2}$—, refers to —S-(sulfide), —S(O)-(sulfoxide), and —$SO_2$-(sulfone) respectively. For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms can be optionally quaternized; and the ring substituent can be partially or fully saturated or aromatic. Examples of heterocyclyl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, tetrahydrofuranyl, tetrahydroisoquinolinyl, and tetrahydroquinolinyl.

"Heterocycloalkyl" refers to a stable 4-12 membered monocyclic, bicyclic or tricyclic ring containing one or more heteroatoms.

"Heterocycloalkylalkyl" refers to a heterocycloalkyl, as defined herein, attached to the parent moiety through an "alkyl," as defined herein. One non-limiting example of heterocycloalkyl includes piperadinyl. Another non-limiting example of heterocycloalkyl includes piperadinyl. Another non-limiting example of heterocycloalkyl includes piperazinyl. Another non-limiting example of heterocycloalkyl includes furanyl. Another non-limiting example of heterocycloalkyl includes pyrrolidinyl. Another non-limiting example of heterocycloalkyl includes morpholinyl.

"amino" refers to —$NH_2$.

"alkylamino" refers to —NH(alkyl), wherein "alkyl" is as defined above, and wherein the parent moiety is attached to the nitrogen atom.

"dialkylamino" refers to —$N(alkyl)_2$, wherein "alkyl" is as defined above, and wherein the parent moiety is attached to the nitrogen atom.

"dialkylaminoalkyl" refers to -$(alkyl)N(alkyl)_2$, wherein "alkyl" is as defined above. One such non-limiting example of "dialkylaminoalkyl" includes —$CH_2C(CH_3)_2CH_2N(CH_3)_2$.

"aminoalkyl" refers to -(alkyl)NH, wherein "alkyl" is as defined above, and wherein the parent moiety is attached to the alkyl group.

"aminoalkyl" refers to -$(alkyl)NH_2$, wherein "alkyl" is as defined above, and wherein the parent moiety is attached to the alkyl group. The amino group can be attached at any point along the alkyl group. Non-limiting examples of aminoalkyl include —$CH(NH_2)CH_3$, "Phenoxy" refers to a -alkyl-O-phenyl group, wherein "alkyl" is as defined above, and the parent moiety is attached to the alkyl group.

"Heteroaryl" means a 5- to 12-membered, monocyclic aromatic heterocyclyl (where heterocyclyl is defined herein) or bicyclic heterocyclyl ring system (where at least one of the rings in the bicyclic system is aromatic) where the monocyclic ring and at least one of the rings in the bicyclic ring system contains one, two, three, four, or five heteroatom(s) selected from nitrogen, oxygen, phosphorous, and sulfur. The ring containing the heteroatom can be aromatic or non-aromatic. Representative examples include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzodioxolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

"Carbonyl" refers to the group "—C(O)—", which is bivalent.

"Aminocarbonyl" refers to the group "—C(O)—NH$_2$," wherein the parent moiety is attached to the amino group.

"Alkoxycarbonyl" refers to the group "—C(O)alkoxy," wherein alkoxy is as defined above, and the parent moiety is attached to the carbonyl. A non-limiting example includes —C(O)—OC(CH$_3$)$_3$.

When a group is referred to as "—C$_1$-C$_6$ alkyl heterocyclyl" the heterocyclyl is attached to a parent structure via one of an alkylene, alkylidene, or alkylidyne group. Examples include (4-methylpiperazin-1-yl)methyl, (morpholin-4-yl)methyl, (pyridine-4-yl)methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group can be optionally substituted.

"Hydroxyalkyl" means -alkyl-OH, wherein alkyl is as defined hereinabove.

"Optional" or "optionally" means that the subsequently described event or circumstance can or can not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylalkyl," both the "alkyl" portion and the "aryl" portion of the molecule can or can not be substituted. A list of exemplary optional substitutions is presented below in the definition of "substituted."

"Saturated bridged ring system" refers to a bicyclic or polycyclic ring system that is not aromatic. Such a system can contain isolated or conjugated unsaturation, but not aromatic or heteroaromatic rings in its core structure (but can have aromatic substitution thereon). For example, hexahydro-furo[3,2-b]furan, 2,3,3a,4,7,7a-hexahydro-1H-indene, 7-aza-bicyclo[2.2.1]-heptane, and 1,2,3,4,4a,5,8,8a-octahydro-naphthalene are all included in the class "saturated bridged ring system.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

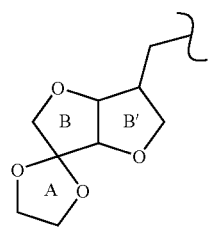

"Substituted" alkyl, aryl, and heterocyclyl, refer respectively to alkyl, aryl, and heterocyclyl, one or more (for example up to about five, in another example, up to about three) hydrogen atoms are replaced by a substituent independently selected from: alkyl (for example, fluoromethyl), aryl (for example, 4-hydroxyphenyl), arylalkyl (for example, 1-phenyl-ethyl), heterocyclylalkyl (for example, 1-pyridin-3-yl-ethyl), heterocyclyl (for example, 5-chloro-pyridin-3-yl or 1-methyl-piperidin-4-yl), alkoxy, alkylenedioxy (for example methylenedioxy), amino (for example, alkylamino and dialkylamino), amidino, aryloxy (for example, phenoxy), arylalkyloxy (for example, benzyloxy), carboxy (—CO$_2$H), carboalkoxy (that is, acyloxy or —OC(═O)R), carboxyalkyl (that is, esters or —CO$_2$R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido. And each substituent of a substituted group is optionally substituted, but these optional substituents themselves are not further substituted. Thus, an optionally substituted moiety is one that can or can not have one or more substituents, and each of the substituents can or can not have one or more substituents. But, the substituents of the substituents can not be substituted.

Some of the compounds of the invention can have imino, amino, oxo or hydroxy substituents off aromatic heterocyclyl systems. For purposes of this disclosure, it is understood that such imino, amino, oxo or hydroxy substituents can exist in their corresponding tautomeric form, i.e., amino, imino, hydroxy or oxo, respectively.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, can also modulate, either directly or indirectly, phosphatase activity. This additional modulation, if present, can be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostrate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences,* 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention can be prepared according to conventional methods. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt can be the biologically active form of the compound in the body. In one example, a prodrug can be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that can be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition can be necessary, and will be ascertainable with routine experimentation by one of ordinary skill in the art.

One of ordinary skill in the art would understand that certain crystallized, protein-ligand complexes, in particular JAK-2-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods can be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for kinase modulation, and determining whether said candidate agent modulates kinase activity in the assay. Such methods can also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method can be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

In addition to the preferred embodiments recited hereinabove, also preferred are embodiments comprising combinations of preferred embodiments.

Representative compounds of Formula I and/or II are depicted below. The examples are merely illustrative and do not limit the scope of the invention in any way. The compounds in Table 1 (Part A and Part B) below can be prepared using art recognized methods.

TABLE 1

| Cmpd No. | Name | Structure | Can Be Made According To Synthetic Example #: |
|---|---|---|---|
| (Part A) | | | |
| 1 | N-[3-({4-[4-(acetylamino)phenyl]pyrimidin-2-yl}amino)propyl]-2,6-dichlorobenzamide | 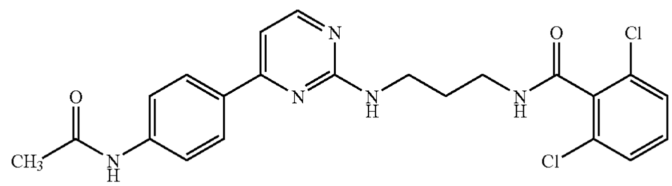 [SMILES: CC(=O)Nc1ccc(-c2ccnc(NCCCNC(=O)c3c(Cl)cccc3Cl)n2)cc1] | 27 |
| 2 | 2,6-dichloro-N-(3-{[4-(2,4-dichlorophenyl)pyrimidin-2-yl]amino}propyl)benzamide | 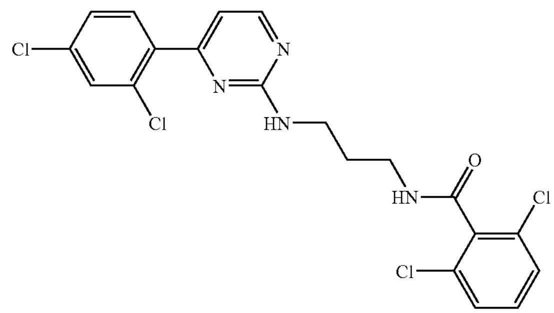 [SMILES: O=C(NCCCNc1nccc(-c2ccc(Cl)cc2Cl)n1)c1c(Cl)cccc1Cl] | 27 |
| 3 | 2,6-dichloro-N-[3-({4-[4-(dimethylamino)phenyl]pyrimidin-2-yl}amino)propyl]benzamide | 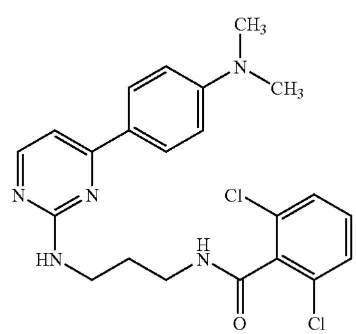 [SMILES: CN(C)c1ccc(-c2ccnc(NCCCNC(=O)c3c(Cl)cccc3Cl)n2)cc1] | 27 |
| 4 | 2,6-dichloro-N-(3-{[4-(2,3-dihydro-1-benzofuran-6-yl)pyrimidin-2-yl]amino}propyl)benzamide | 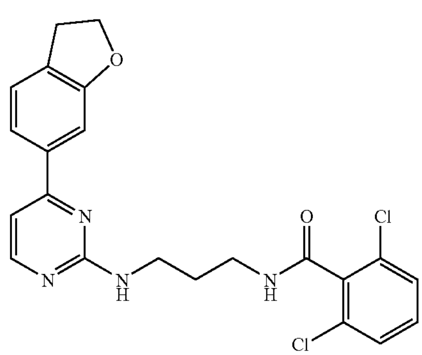 [SMILES: O=C(NCCCNc1nccc(-c2ccc3c(c2)OCC3)n1)c1c(Cl)cccc1Cl] | 27 |

TABLE 1-continued

| Cmpd No. | Name | Structure | Can Be Made According To Synthetic Example #: |
|---|---|---|---|
| 5 | N-[3-({4-[4-(acetylamino)phenyl]pyrimidin-2-yl}amino)propyl]-2-fluoro-6-iodobenzamide | 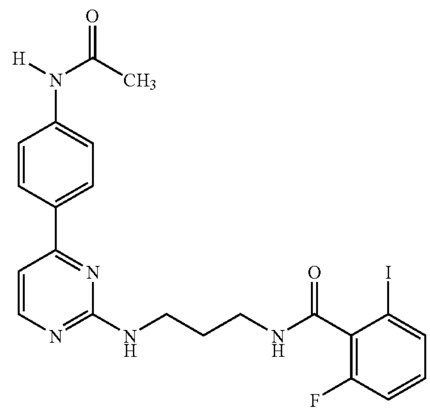 [SMILES: CC(=O)Nc1ccc(-c2ccnc(NCCCNC(=O)c3c(F)cccc3I)n2)cc1] | 27 |
| 6 | N-(3-{[4-(4-aminophenyl)pyrimidin-2-yl]amino}propyl)-2,6-dichlorobenzamide | 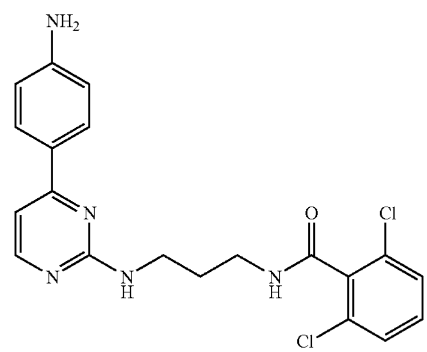 [SMILES: Nc1ccc(-c2ccnc(NCCCNC(=O)c3c(Cl)cccc3Cl)n2)cc1] | 27 |
| 7 | N-[4-({4-[4-(acetylamino)phenyl]pyrimidin-2-yl}amino)phenyl]-2,6-dichlorobenzamide | 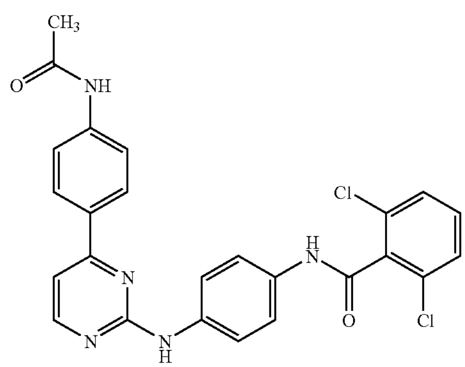 [SMILES: CC(=O)Nc1ccc(-c2ccnc(Nc3ccc(NC(=O)c4c(Cl)cccc4Cl)cc3)n2)cc1] | 2 |
| 8 | N-{4-[2-({3-[(4-ethylpiperazin-1-yl)carbonyl]phenyl}amino)pyrimidin-4-yl]phenyl}acetamide | 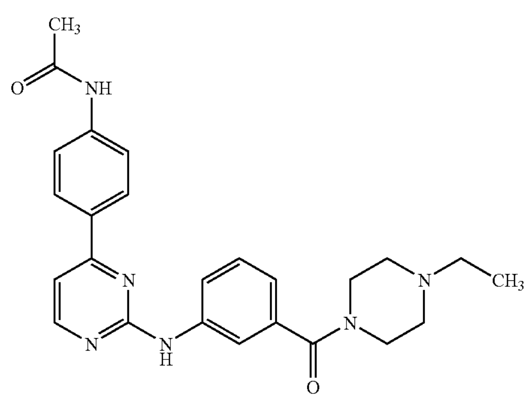 [SMILES: CCN1CCN(C(=O)c2cccc(Nc3nccc(-c4ccc(NC(C)=O)cc4)n3)c2)CC1] | 29 |

TABLE 1-continued

| Cmpd No. | Name | Structure | Can Be Made According To Synthetic Example #: |
|---|---|---|---|
| 9 | 3-({4-[4-(acetylamino)phenyl]pyrimidin-2-yl}amino)-N-[2-(dimethylamino)ethyl]benzamide | 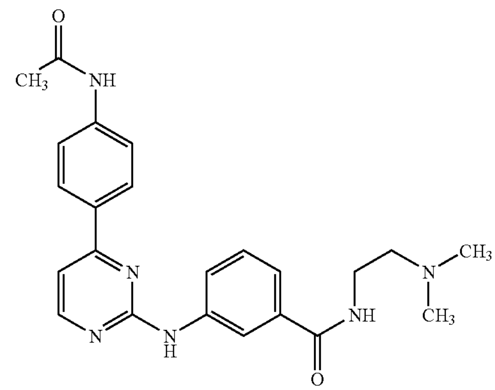 [SMILES: CC(=O)Nc1ccc(-c2ccnc(Nc3cccc(C(=O)NCCN(C)C)c3)n2)cc1] | 29 |
| 10 | N-[3-({4-[4-(acetylamino)phenyl]pyrimidin-2-yl}amino)phenyl]-2-fluorobenzamide | 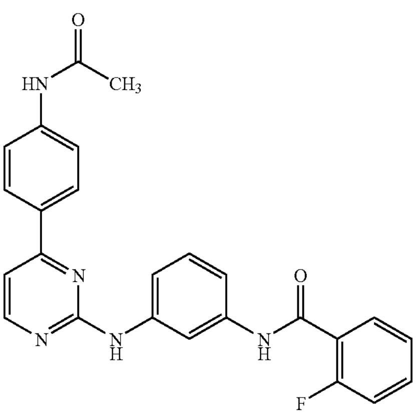 [SMILES: CC(=O)Nc1ccc(-c2ccnc(Nc3cccc(NC(=O)c4ccccc4F)c3)n2)cc1] | 39 |
| 11 | N-[3-({4-[4-(acetylamino)phenyl]pyrimidin-2-yl}amino)phenyl]-2-fluoro-6-iodobenzamide | 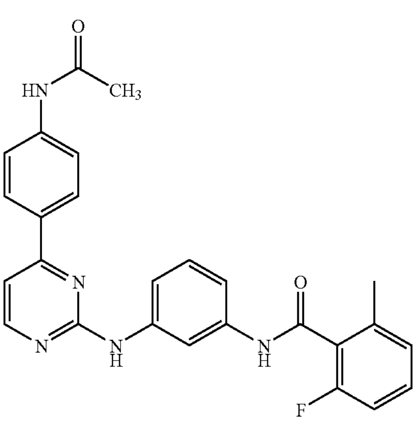 [SMILES: CC(=O)Nc1ccc(-c2ccnc(Nc3cccc(NC(=O)c4c(C)cccc4F)c3)n2)cc1] | 39 |

TABLE 1-continued

| Cmpd No. | Name | Structure | Can Be Made According To Synthetic Example #: |
|---|---|---|---|
| 12 | N-[3-({4-[4-(acetylamino)phenyl] pyrimidin-2-yl}amino) phenyl]-2,6-dimethylbenzamide | 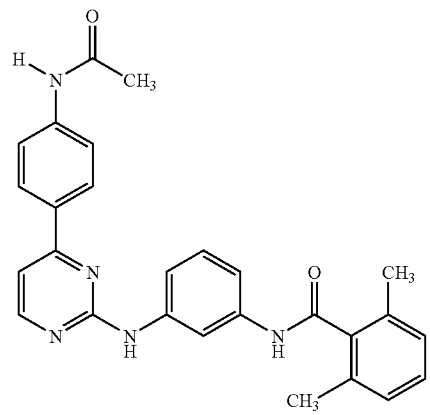 [SMILES: CC(=O)Nc1ccc(-c2ccnc(Nc3cccc(NC(=O)c4c(C)cccc4C)c3)n2)cc1] | 39 |
| 13 | N-(4-{2-{(3-aminophenyl)amino] pyrimidin-4-yl}phenyl)acetamade | 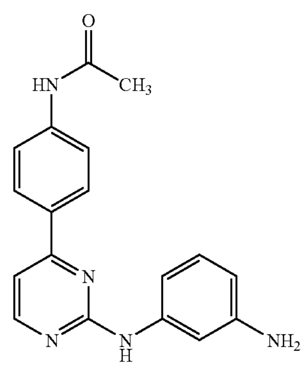 [SMILES: CC(=O)Nc1ccc(-c2ccnc(Nc3cccc(N)c3)n2)cc1] | 28 |
| 14 | N-[3-({4-[4-(acetylamino)phenyl] pyrimidin-2-yl}amino) phenyl]pyridine-4-carboxamide | 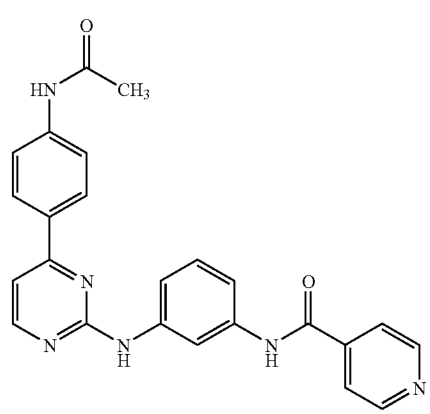 [SMILES: CC(=O)Nc1ccc(-c2ccnc(Nc3cccc(NC(=O)c4ccncc4)c3)n2)cc1] | 39 |

TABLE 1-continued
| Cmpd No. | Name | Structure | Can Be Made According To Synthetic Example #: |
|---|---|---|---|
| 15 | N-[3-({4-[4-(acetylamino)phenyl]pyrimidin-2-yl}amino)phenyl]-2,3,4,5,6-pentafluorobenzamide | 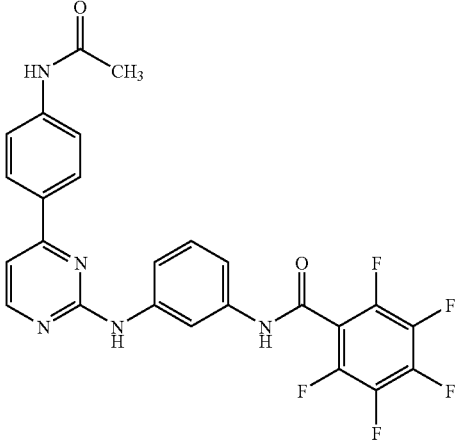 [SMILES: CC(=O)Nc1ccc(-c2ccnc(Nc3cccc(NC(=O)c4c(F)c(F)c(F)c(F)c4F)c3)n2)cc1] | 39 |
| 16 | 4-(4-chlorophenyl)-N-(4-morpholin-4-ylphenyl)pyrimidin-2-amine | 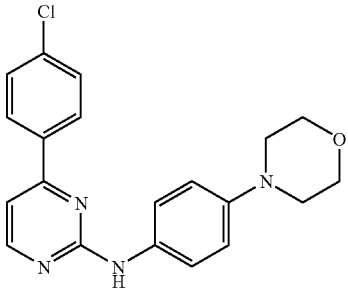 [SMILES: Clc1ccc(-c2ccnc(Nc3ccc(N4CCOCC4)cc3)n2)cc1] | 9 |
| 17 | N-[3-({4-[4-(acetylamino)phenyl]pyrimidin-2-yl}amino)phenyl]-2,6-dichlorobenzamide | 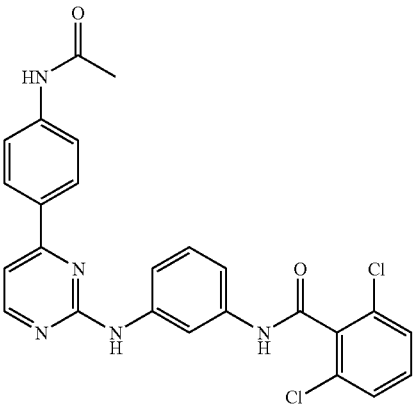 [SMILES: CC(=O)Nc1ccc(-c2ccnc(Nc3cccc(NC(=O)c4c(Cl)cccc4Cl)c3)n2)cc1] | 39 |
| 18 | N-(4-{2-[(4-morpholin-4-ylphenyl)amino]pyrimidin-4-yl}phenyl)acetamide | 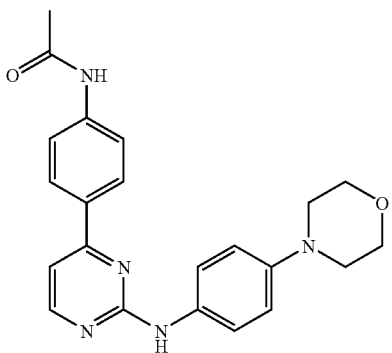 [SMILES: CC(=O)Nc1ccc(-c2ccnc(Nc3ccc(N4CCOCC4)cc3)n2)cc1] | 3 |

TABLE 1-continued

| Cmpd No. | Name | Structure | Can Be Made According To Synthetic Example #: |
|---|---|---|---|
| 19 | 4-(2,4-dichlorophenyl)-N-{3-[(2-piperidin-1-ylethyl)oxy]phenyl}pyrimidin-2-amine | 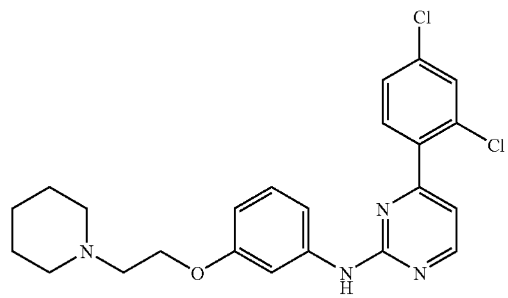 [SMILES: Clc1ccc(-c2ccnc(Nc3cccc(OCCN4CCCCC4)c3)n2)c(Cl)c1] | 33 |
| 20 | N-[3-({4-[4-(acetylamino)phenyl]pyrimidin-2-yl}amino)phenyl]-2-chlorobenzamide | 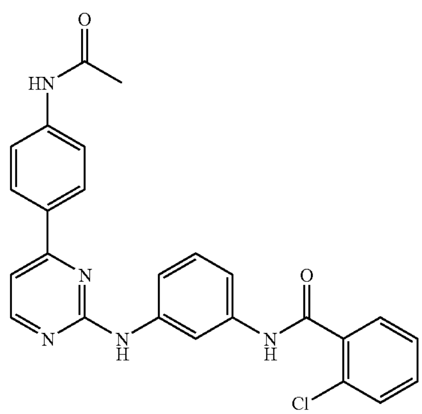 [SMILES: CC(=O)Nc1ccc(-c2ccnc(Nc3cccc(NC(=O)c4ccccc4Cl)c3)n2)cc1] | 39 |
| 21 | N-(4-{2-[(3-morpholin-4-ylphenyl)amino]pyrimidin-4-yl}phenyl)acetamide | 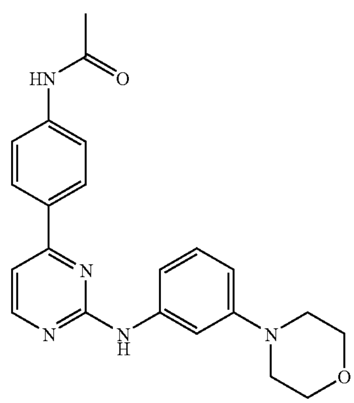 [SMILES: CC(=O)Nc1ccc(-c2ccnc(Nc3cccc(N4CCOCC4)c3)n2)cc1] | 3 |
| 22 | N-(4-{2-[(3-piperidin-1-ylphenyl)amino}pyrimidin-4-yl}phenyl)acetamide | 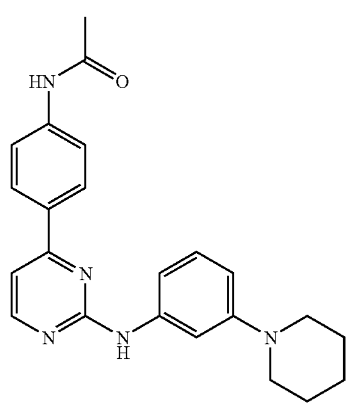 [SMILES: CC(=O)Nc1ccc(-c2ccnc(Nc3cccc(N4CCCCC4)c3)n2)cc1] | 3 |

TABLE 1-continued

| Cmpd No. | Name | Structure | Can Be Made According To Synthetic Example #: |
|---|---|---|---|
| 23 | N-[3-({4-[4-(acetylamino)phenyl]pyrimidin-2-yl}amino)phenyl]-2-bromobenzamide | 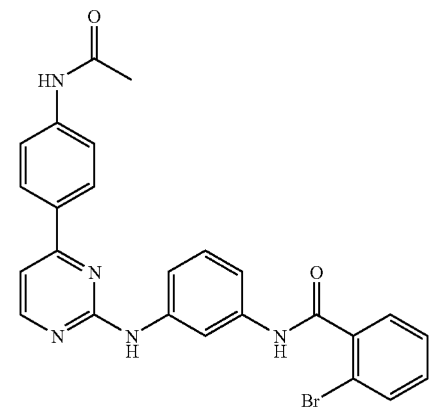 [SMILES: CC(=O)Nc1ccc(-c2ccnc(Nc3cccc(NC(=O)c4ccccc4Br)c3)n2)cc1] | 39 |
| 24 | N-[3-({4-[4-(acetylamino)phenyl]pyrimidin-2-yl}amino)phenyl]-3-fluorobenzamide | 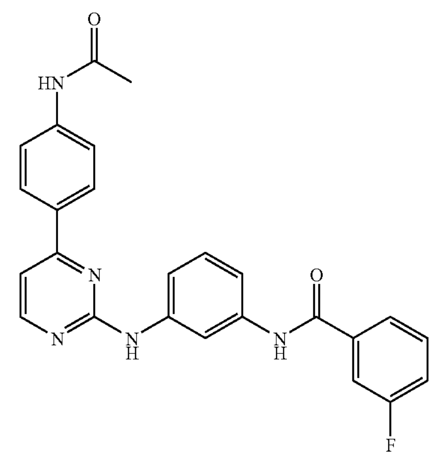 [SMILES: CC(=O)Nc1ccc(-c2ccnc(Nc3cccc(NC(=O)c4cccc(F)c4)c3)n2)cc1] | 39 |
| 25 | N-[3-({4-[4-(acetylamino)phenyl]-5-methylpyrimidin-2-yl}amino)phenyl]-2,6-dichlorobenzamide | 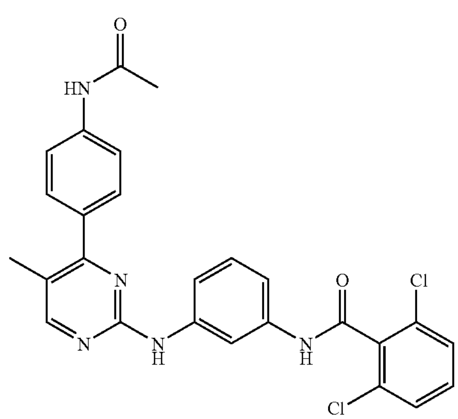 [SMILES: CC(=O)Nc1ccc(-c2nc(Nc3cccc(NC(=O)c4c(Cl)cccc4Cl)c3)ncc2C)cc1] | 39 |

TABLE 1-continued

| Cmpd No. | Name | Structure | Can Be Made According To Synthetic Example #: |
|---|---|---|---|
| 26 | N-(4-{2-[(3-{[(2,6-dichlorophenyl)sulfonyl]amino}phenyl)amino]-5-methylpyrimidin-4-yl}phenyl)acetamide | 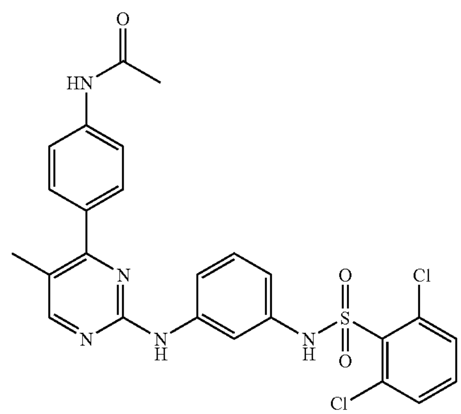 [SMILES: CC(=O)Nc1ccc(-c2nc(Nc3cccc(NS(=O)(=O)c4c(Cl)cccc4Cl)c3)ncc2C)cc1] | 36 |
| 27 | 2,6-dichloro-N-(3-{[4-(1H-indol-5-yl)pyrimidin-2-yl]amino}phenyl)benzamide | 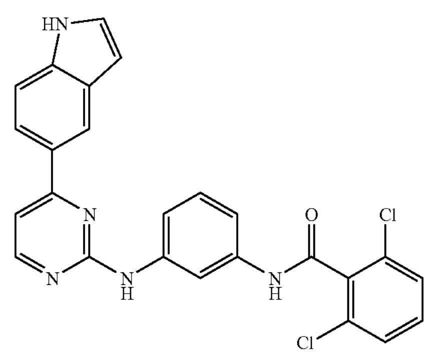 [SMILES: O=C(Nc1cccc(Nc2nccc(-c3ccc4[nH]ccc4c3)n2)c1)c1c(Cl)cccc1Cl] | 39 |
| 28 | N-[3-({4-[4-(acetylamino)phenyl]-5-fluoropyrimidin-2-yl}amino)phenyl]-2,6-dichlorobenzamide | 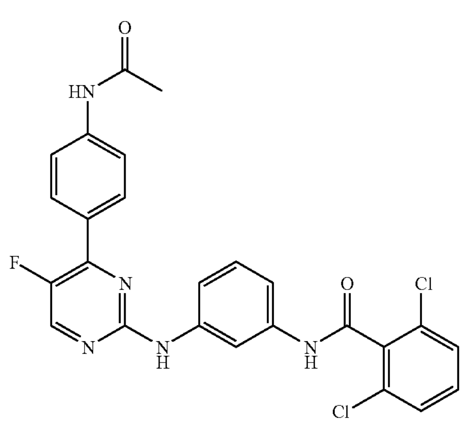 [SMILES: CC(=O)Nc1ccc(-c2nc(Nc3cccc(NC(=O)c4c(Cl)cccc4Cl)c3)ncc2F)cc1] | 36 |

TABLE 1-continued

| Cmpd No. | Name | Structure | Can Be Made According To Synthetic Example #: |
|---|---|---|---|
| 29 | N-[3-({4-[4-(acetylamino)phenyl]pyrimidin-2-yl}amino)phenyl]-2-methylbenzamide | 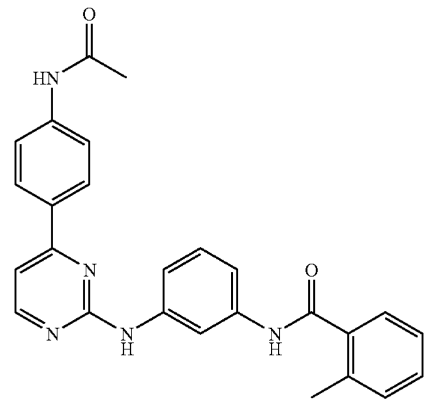 [SMILES: CC(=O)Nc1ccc(-c2ccnc(Nc3cccc(NC(=O)c4ccccc4C)c3)n2)cc1] | 39 |
| 30 | N-[3-({4-[4-(acetylamino)phenyl]pyrimidin-2-yl}amino)phenyl]-2,4-dichlorobenzamide | 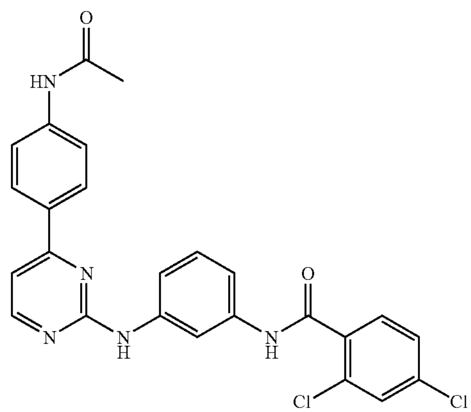 [SMILES: CC(=O)Nc1ccc(-c2ccnc(Nc3cccc(NC(=O)c4ccc(Cl)cc4Cl)c3)n2)cc1] | 39 |
| 31 | N-[3-({4-[4-(acetylamino)phenyl]pyrimidin-2-yl}amino)phenyl]-2,3-dichlorobenzamide | 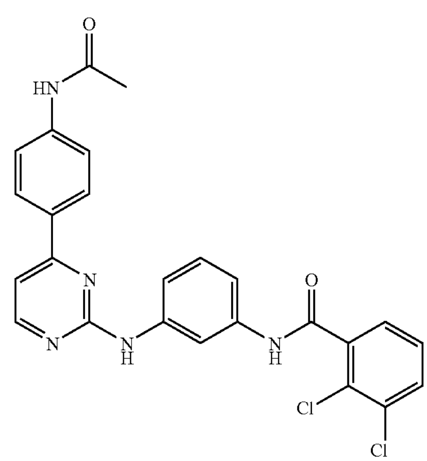 [SMILES: CC(=O)Nc1ccc(-c2ccnc(Nc3cccc(NC(=O)c4cccc(Cl)c4Cl)c3)n2)cc1] | 39 |

TABLE 1-continued
| Cmpd No. | Name | Structure | Can Be Made According To Synthetic Example #: |
|---|---|---|---|
| 32 | N-[3-({4-[4-(acetylamino)phenyl]pyrimidin-2-yl}amino)phenyl]-2,5-dichlorobenzamide | 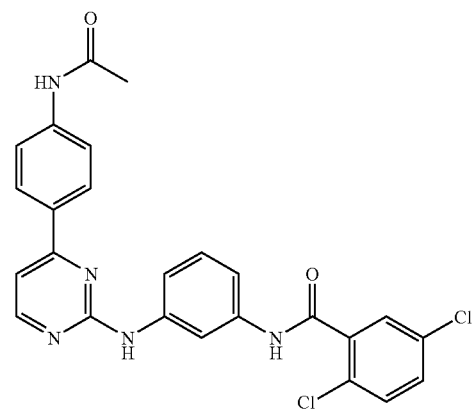 [SMILES: CC(=O)Nc1ccc(-c2ccnc(Nc3cccc(NC(=O)c4cc(Cl)ccc4Cl)c3)n2)cc1] | 39 |
| 33 | N-[4-(2-{[4-(4-ethylpiperazin-1-yl)phenyl]amino}pyrimidin-4-yl)phenyl]acetamide | 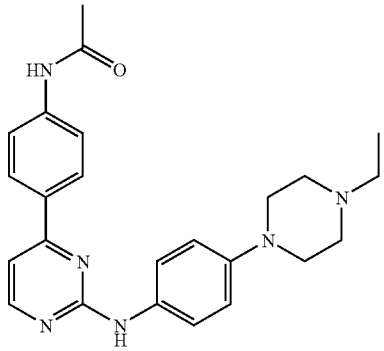 [SMILES: CCN1CCN(c2ccc(Nc3nccc(-c4ccc(NC(C)=O)cc4)n3)cc2)CC1] | 3 |
| 34 | N-(4-{2-[(4-piperidin-4-ylphenyl)amino]pyrimidin-4-yl}phenyl)acetamide | 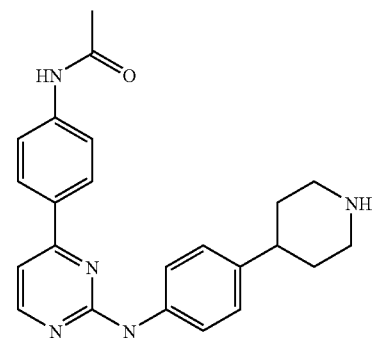 | 34 |
| 35 | N-(4-{2-[(2-methyl-4-piperazin-1-ylphenyl)amino]pyrimidin-4-yl}phenyl)acetamide | 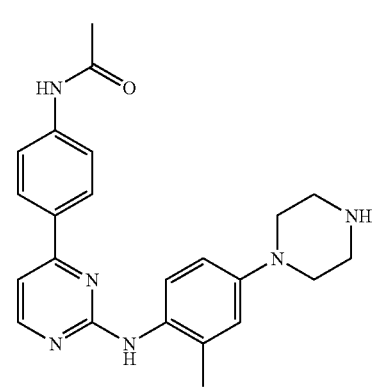 [SMILES: CC(=O)Nc1ccc(-c2ccnc(Nc3ccc(N4CCNCC4)cc3C)n2)cc1] | 34 |

TABLE 1-continued
| Cmpd No. | Name | Structure | Can Be Made According To Synthetic Example #: |
|---|---|---|---|
| 36 | N-(4-{2-[(3-aminophenyl)amino]pyrimidin-4-yl}phenyl)thiophene-2-carboxamide | 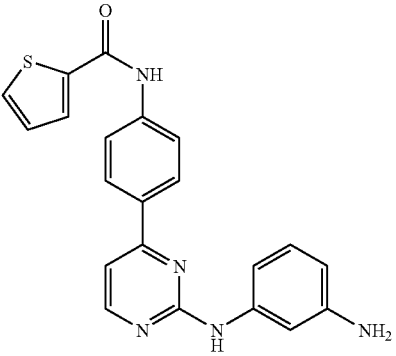 [SMILES: Nc1cccc(Nc2nccc(-c3ccc(NC(=O)c4cccs4)cc3)n2)c1] | 1 |
| 37 | N-(4-{5-methyl-2-[(3-morpholin-4-ylphenyl)amino]pyrimidin-4-yl}phenyl)acetamide | 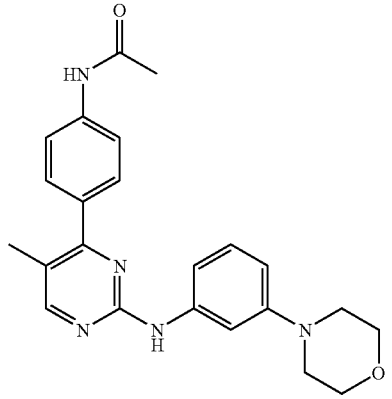 [SMILES: CC(=O)Nc1ccc(-c2nc(Nc3cccc(N4CCOCC4)c3)ncc2C)cc1] | 3 |
| 38 | N-(4-{2-[(3-aminophenyl)amino]pyrimidin-4-yl}phenyl)-2-(phenyloxy)acetamide | 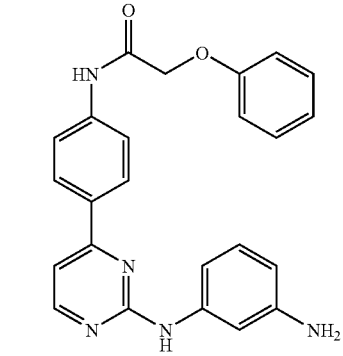 [SMILES: Nc1cccc(Nc2nccc(-c3ccc(NC(=O)COc4ccccc4)cc3)n2)c1] | 1 |
| 39 | N-(4-{6-methyl-2-[(4-morpholin-4-ylphenyl)amino]pyrimidin-4-yl}phenyl)acetamide | 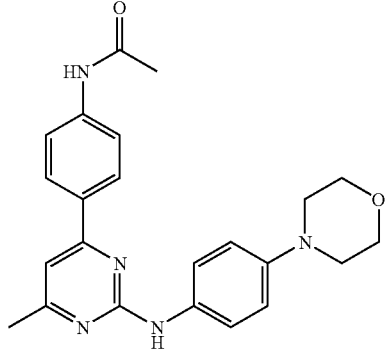 [SMILES: CC(=O)Nc1ccc(-c2cc(C)nc(Nc3ccc(N4CCOCC4)cc3)n2)cc1] | 5 |

TABLE 1-continued

| Cmpd No. | Name | Structure | Can Be Made According To Synthetic Example #: |
|---|---|---|---|
| 40 | N-(4-{2-[(3-aminophenyl)amino]pyrimidin-4-yl}phenyl)-2-morpholin-4-ylacetamide | 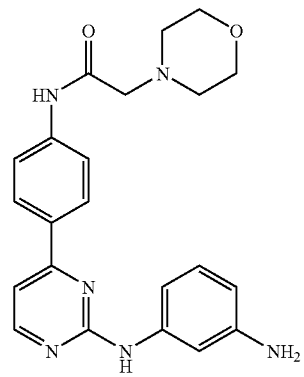 [SMILES: Nc1cccc(Nc2nccc(-c3ccc(NC(=O)CN4CCOCC4)cc3)n2)c1] | 1 |
| 41 | N-[4-(2-{[3-(methyloxy)phenyl]amino}pyrimidin-4-yl)phenyl]acetamide | 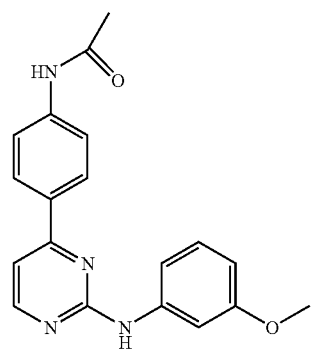 [SMILES: COc1cccc(Nc2nccc(-c3ccc(NC(C)=O)cc3)n2)c1] | |
| 42 | N-[3-({4-[4-(acetylamino)-2-chlorophenyl]pyrimidin-2-yl}amino)phenyl]-2,6-dichlorobenzamide | 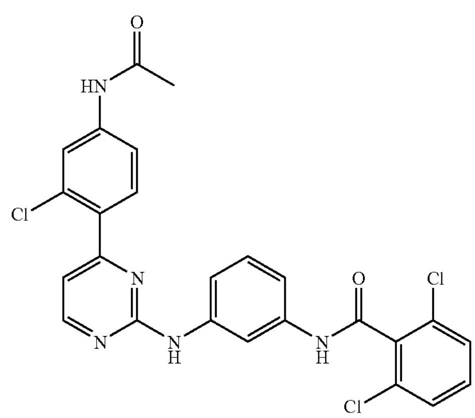 [SMILES: CC(=O)Nc1ccc(-c2ccnc(Nc3cccc(NC(=O)c4c(Cl)cccc4Cl)c3)n2)c(Cl)c1] | 39 |
| 43 | 2,6-dichloro-N-{3-[(4-phenylpyrimidin-2-yl)amino[phenyl}benzamide | 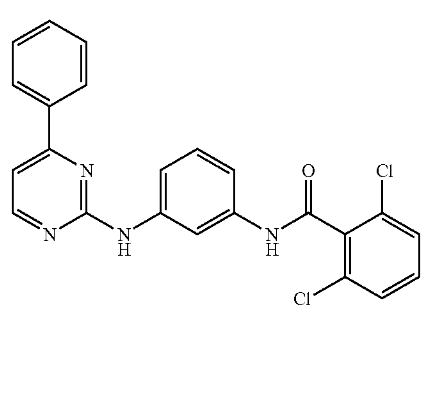 [SMILES: O=C(Nc1cccc(Nc2nccc(-c3ccccc3)n2)c1)c1c(Cl)cccc1Cl] | 39 |

TABLE 1-continued

| Cmpd No. | Name | Structure | Can Be Made According To Synthetic Example #: |
|---|---|---|---|
| 44 | N-[3-({4-[4-(acetylamino)phenyl]pyrimidin-2-yl}amino)phenyl]-2,6-difluorobenzamide | 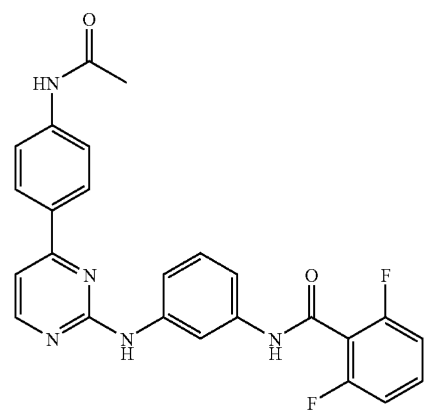 [SMILES: CC(=O)Nc1ccc(-c2ccnc(Nc3cccc(NC(=O)c4c(F)cccc4F)c3)n2)cc1] | 39 |
| 45 | N-[3-({4-[4-(acetylamino)phenyl]pyrimidin-2-yl}amino)phenyl]-2,4,5-trifluorobenzamide | 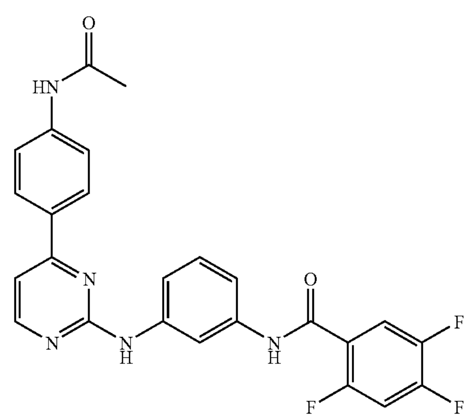 [SMILES: CC(=O)Nc1ccc(-c2ccnc(Nc3cccc(NC(=O)c4cc(F)c(F)cc4F)c3)n2)cc1] | 39 |
| 46 | N-[3-({4-[4-(acetylamino)phenyl]pyrimidin-2-yl}amino)phenyl]benzamide | 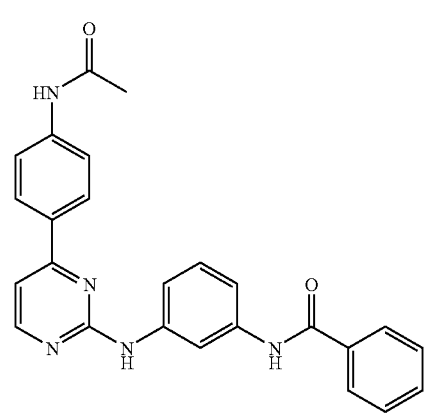 [SMILES: CC(=O)Nc1ccc(-c2ccnc(Nc3cccc(NC(=O)c4ccccc4)c3)n2)cc1] | 39 |

TABLE 1-continued

| Cmpd No. | Name | Structure | Can Be Made According To Synthetic Example #: |
|---|---|---|---|
| 47 | N-(4-{6-morpholin-4-yl-2-[(4-morpholin-4-ylphenyl)amino]pyrimidin-4-yl}phenyl)acetamide | 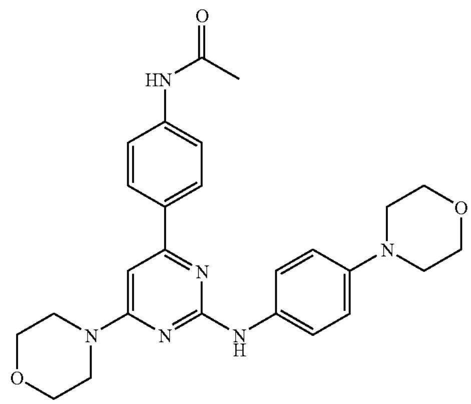 [SMILES: CC(=O)Nc1ccc(-c2cc(N3CCOCC3)nc(Nc3ccc(N4CCOCC4)cc3)n2)cc1] | 37 |
| 48 | N-[3-({4-[4-(acetylamino)phenyl]pyrimidin-2-yl}amino)phenyl]-3,5-difluorobenzamide | 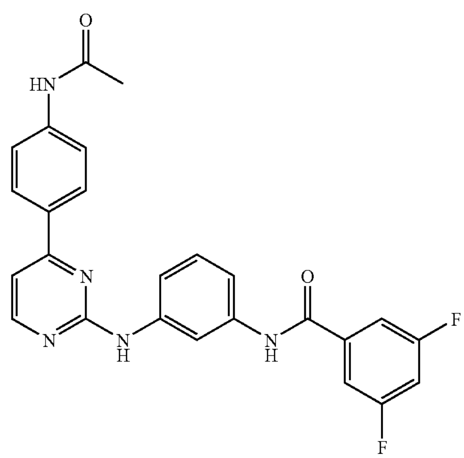 [SMILES: CC(=O)Nc1ccc(-c2ccnc(Nc3cccc(NC(=O)c4cc(F)cc(F)c4)c3)n2)cc1] | 39 |
| 49 | N-[3-({4-[4-(acetylamino)phenyl]pyrimidin-2-yl}amino)phenyl]-2-chloro-6-fluoro-3-(methyloxy)benzamide | 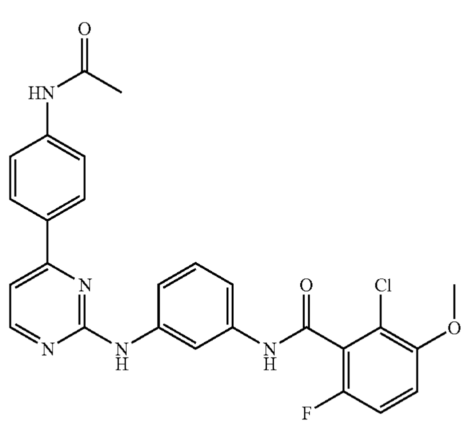 [SMILES: COc1ccc(F)c(C(=O)Nc2cccc(Nc3nccc(-c4ccc(NC(C)=O)cc4)n3)c2)c1Cl] | 39 |

TABLE 1-continued

| Cmpd No. | Name | Structure | Can Be Made According To Synthetic Example #: |
|---|---|---|---|
| 50 | N-[3-({4-[4-(acetylamino)phenyl]pyrimidin-2-yl}amino)phenyl]-2-chloro-6-fluoro-4-methylbenzamide | 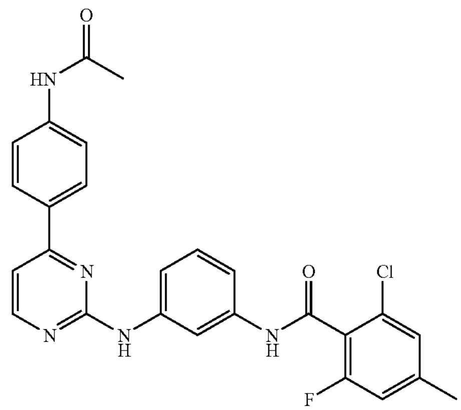 [SMILES: CC(=O)Nc1ccc(-c2ccnc(Nc3cccc(NC(=O)c4c(F)cc(C)cc4Cl)c3)n2)cc1] | 39 |
| 51 | N-(4-{2-[(3-{[(2,6-dimethylphenyl)methyl]amino}phenyl)amino]pyrimidin-4-yl}phenyl)acetamide | 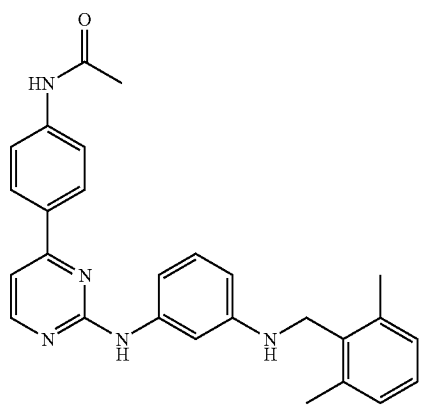 [SMILES: CC(=O)Nc1ccc(-c2ccnc(Nc3cccc(NCc4c(C)cccc4C)c3)n2)cc1] | 28 |
| 52 | 4-(2,4-dichlorophenyl)-N-(4-morpholin-4-ylphenyl)pyrimidin-2-amine | 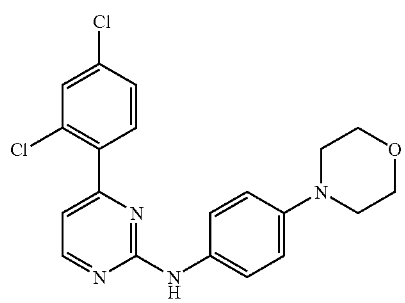 [SMILES: Clc1ccc(-c2ccnc(Nc3ccc(N4CCOCC4)cc3)n2)c(Cl)c1] | 9 |
| 53 | 4-(2,4-dichlorophenyl)-N-{3-[(4-ethylpiperazin-1-yl)carbonyl]phenyl}pyrimidin-2-amine | 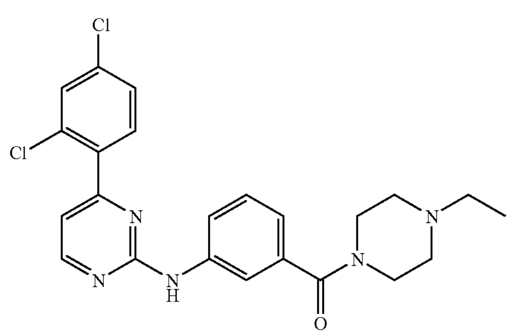 [SMILES: CCN1CCN(C(=O)c2cccc(Nc3nccc(-c4ccc(Cl)cc4Cl)n3)c2)CC1] | 29 |

TABLE 1-continued

| Cmpd No. | Name | Structure | Can Be Made According To Synthetic Example #: |
|---|---|---|---|
| 54 | N-(3-{[4-(4-aminophenyl)pyrimidin-2-yl]amino}phenyl)-2,6-dichlorobenzamide | 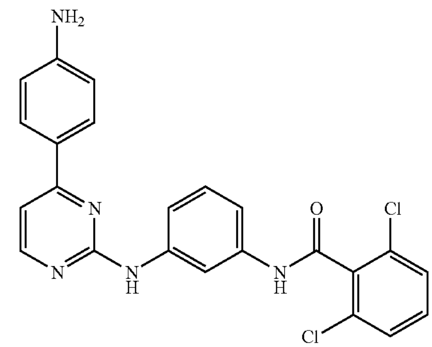 [SMILES: Nc1ccc(-c2ccnc(Nc3cccc(NC(=O)c4c(Cl)cccc4Cl)c3)n2)cc1] | 39 |
| 55 | 4-(4-aminophenyl)-N-(4-morpholin-4-ylphenyl)pyrimidin-2-amine | 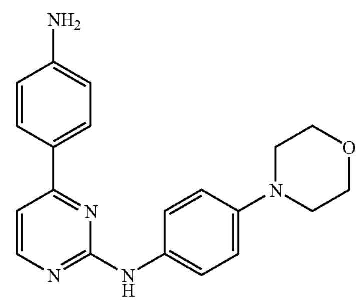 [SMILES: Nc1ccc(-c2ccnc(Nc3ccc(N4CCOCC4)cc3)n2)cc1] | 8 |
| 56 | 4-[4-(ethylamino)phenyl]-N-(4-morpholin-4-ylphenyl)pyrimidin-2-amine | 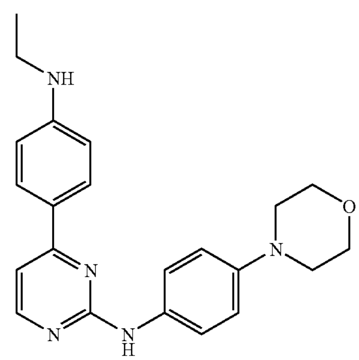 [SMILES: CCNc1ccc(-c2ccnc(Nc3ccc(N4CCOCC4)cc3)n2)cc1] | 49 |
| 57 | N-[4-(2-{[3-(methyloxy)phenyl]amino}pyrimidin-4-yl)phenyl]acetamide | 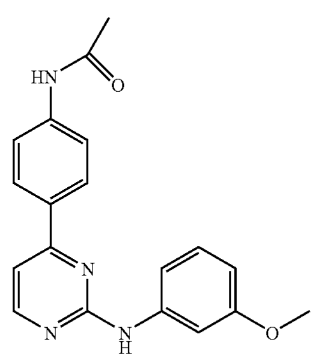 [SMILES: COc1cccc(Nc2nccc(-c3ccc(NC(C)=O)cc3)n2)c1] | 3 |

TABLE 1-continued

| Cmpd No. | Name | Structure | Can Be Made According To Synthetic Example #: |
|---|---|---|---|
| 58 | N-(4-{2-[(4-aminophenyl)amino]pyrimidin-4-yl}phenyl)acetamide | 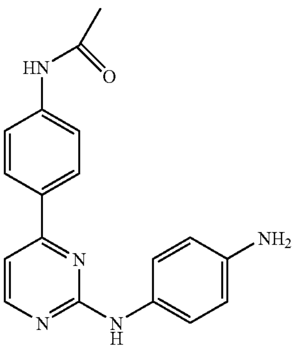 [SMILES: CC(=O)Nc1ccc(-c2ccnc(Nc3ccc(N)cc3)n2)cc1] | 1 |
| 59 | N-[4-(2-{[4-(methyloxy)phenyl]amino}pyrimidin-4-yl)phenyl]acetamide | 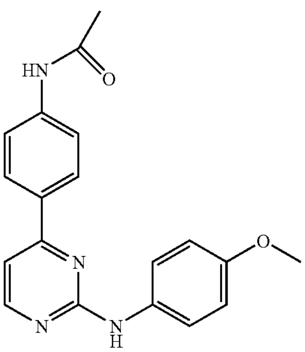 [SMILES: COc1ccc(Nc2nccc(-c3ccc(NC(C)=O)cc3)n2)cc1] | 3 |
| 60 | N-[4-(2-{[4-(methyloxy)phenyl]amino}pyrimidin-4-yl)phenyl]acetamide | 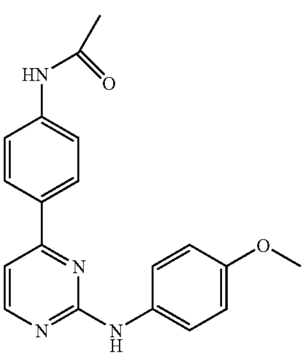 [SMILES: COc1ccc(Nc2nccc(-c3ccc(NC(C)=O)cc3)n2)cc1] | 3 |
| 61 | N-{4-[2-({3-[4-(pyridin-4-ylmethyl)piperazin-1-yl]phenyl}amino)pyrimidin-4-yl]phenyl}acetamide | 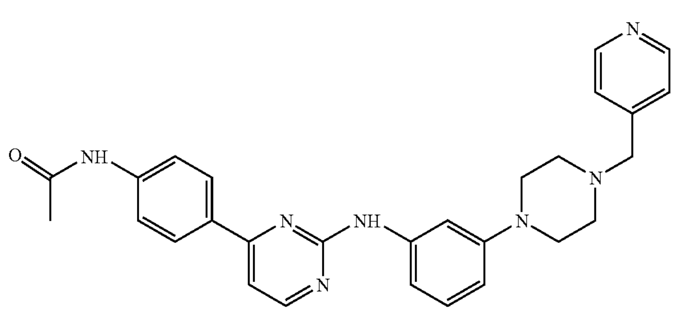 [SMILES: CC(=O)Nc1ccc(-c2ccnc(Nc3cccc(N4CCN(Cc5ccncc5)CC4)c3)n2)cc1] | 49 |

TABLE 1-continued

| Cmpd No. | Name | Structure | Can Be Made According To Synthetic Example #: |
|---|---|---|---|
| 62 | N-[5-({4-[4-(acetylamino)phenyl]pyrimidin-2-yl}amino)-2-morpholin-4-ylphenyl]-2,6-dichlorobenzamide | 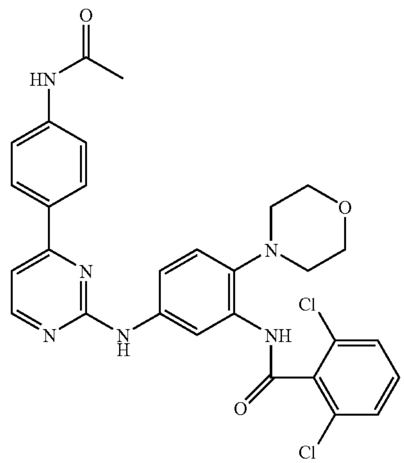 [SMILES: CC(=O)Nc1ccc(-c2ccnc(Nc3ccc(N4CCOCC4)c(NC(=O)c4c(Cl)cccc4Cl)c3)n2)cc1] | 30 |
| 63 | N-(4-{5-fluoro-2-[(4-morpholin-4-ylphenyl)amino]pyrimidin-4-yl}phenyl)acetamide | 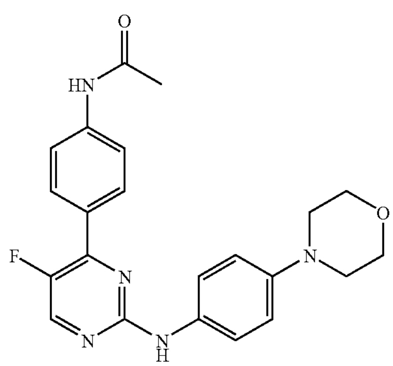 [SMILES: CC(=O)Nc1ccc(-c2nc(Nc3ccc(N4CCOCC4)cc3)ncc2F)cc1] | 5 |
| 64 | N-(4-{2-[(4-{[2-(4-ethylpiperazin-1-yl)-2-oxoethyl]oxy}phenyl)amino]pyrimidin-4-yl}phenyl)acetamide | 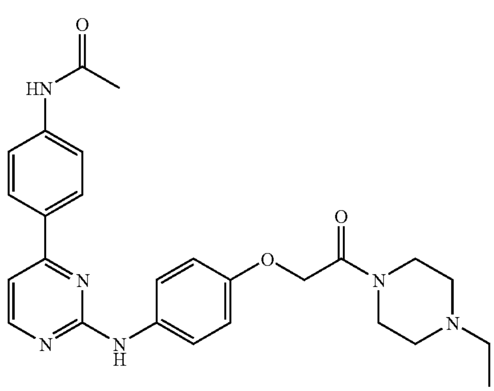 [SMILES: CCN1CCN(C(=O)COc2ccc(Nc3nccc(-c4ccc(NC(C)=O)cc4)n3)cc2)CC1] | 33 |

TABLE 1-continued

| Cmpd No. | Name | Structure | Can Be Made According To Synthetic Example #: |
|---|---|---|---|
| 65 | N-[4-(2-{[3-(morpholin-4-ylcarbonyl)phenyl]amino}pyrimidin-4-yl)phenyl]acetamide | 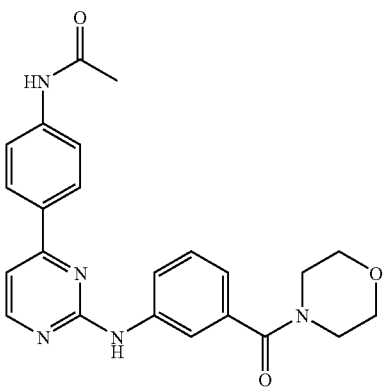 [SMILES: CC(=O)Nc1ccc(-c2ccnc(Nc3cccc(C(=O)N4CCOCC4)c3)n2)cc1] | 29 |
| 66 | N-{3-({4-[4-(acetylamino)phenyl]pyrimidin-2-yl}amino)-5-[(4-ethylpiperazin-1-yl)carbonyl]phenyl}-2,6-dichlorobenzamide | 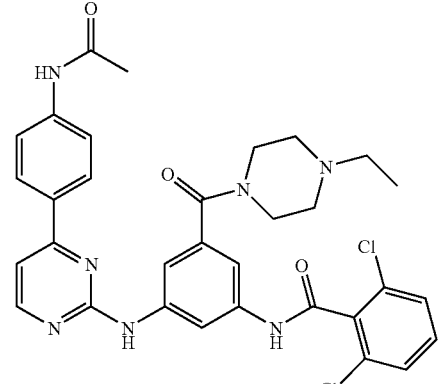 | 31 |
| 67 | 4-[4-(dimethylamino)phenyl]-N-(4-morpholin-4-ylphenyl)pyrimidin-2-amine | 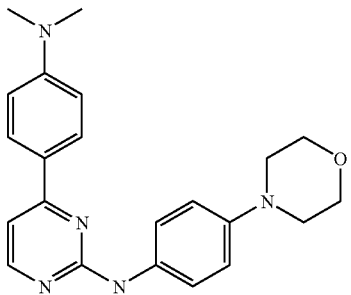 | 9 |
| 68 | 2,6-dichloro-N-(3-{[4-(2,4-dichlorophenyl)pyrimidin-2-yl]amino}phenyl)benzamide | 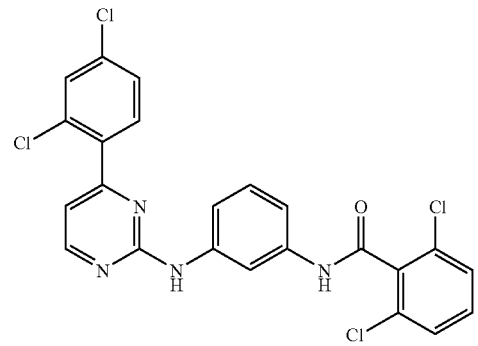 [SMILES: O=C(Nc1cccc(Nc2nccc(-c3ccc(Cl)cc3Cl)n2)c1)c1c(Cl)cccc1Cl] | 39 |

TABLE 1-continued

| Cmpd No. | Name | Structure | Can Be Made According To Synthetic Example #: |
|---|---|---|---|
| 69 | N-(4-{2-[(4-morpholin-4-ylphenyl)amino]-5-(trifluoromethyl)pyrimidin-4-yl}phenyl)acetamide | 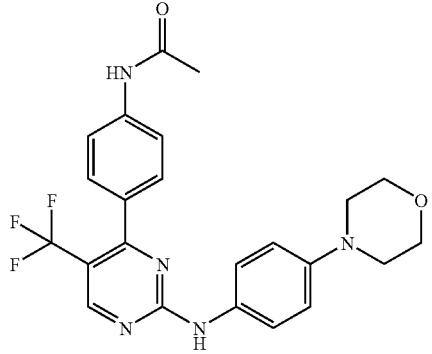 [SMILES: CC(=O)Nc1ccc(-c2nc(Nc3ccc(N4CCOCC4)cc3)ncc2C(F)(F)F)cc1] | 5 |
| 70 | N-(3-{2-[(3-aminophenyl)amino]pyrimidin-4-yl}phenyl)thiophene-2-carboxamide | 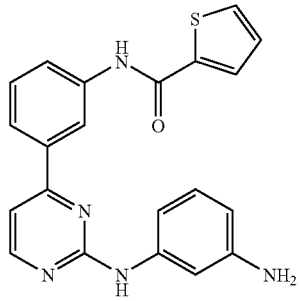 [SMILES: Nc1cccc(Nc2nccc(-c3cccc(NC(=O)c4cccs4)c3)n2)c1] | 1 |
| 71 | N-[3-({4-[4-(acetylamino)phenyl]pyrimidin-2-yl}amino)phenyl]-1-methylpiperidine-4-carboxamide | 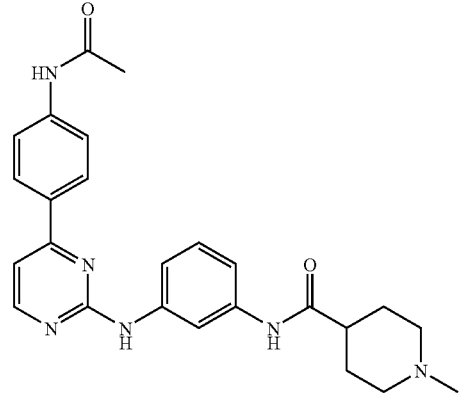 [SMILES: CC(=O)Nc1ccc(-c2ccnc(Nc3cccc(NC(=O)C4CCN(C)CC4)c3)n2)cc1] | 39 |
| 72 | N-{4-[2-({3-[(phenylmethyl)amino]phenyl}amino)pyrimidin-4-yl]phenyl}acetamide | 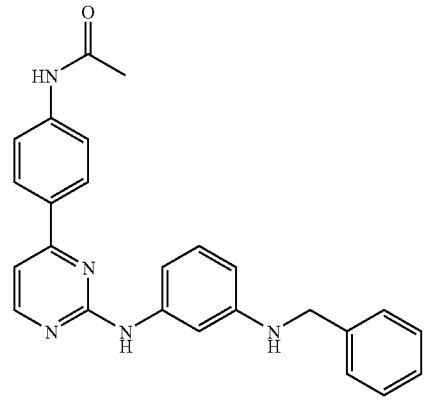 [SMILES: CC(=O)Nc1ccc(-c2ccnc(Nc3cccc(NCc4ccccc4)c3)n2)cc1] | 28 |

TABLE 1-continued

| Cmpd No. | Name | Structure | Can Be Made According To Synthetic Example #: |
|---|---|---|---|
| 73 | N-(4-{2-[(3-aminophenyl)amino]-5-methylpyrimidin-4-yl}phenyl)acetamide | 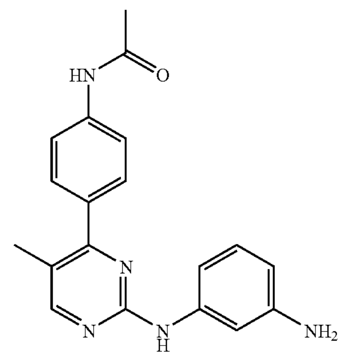 [SMILES: CC(=O)Nc1ccc(-c2nc(Nc3cccc(N)c3)ncc2C)cc1] | 1 |
| 74 | N-(4-{2-[(3-aminophenyl)amino]-5-fluoropyrimidin-4-yl}phenyl)acetamide | 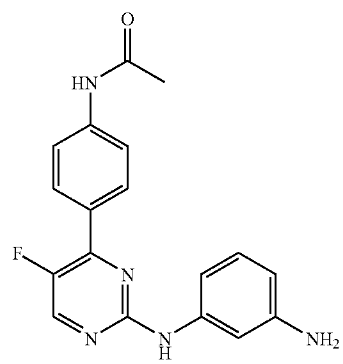 [SMILES: CC(=O)Nc1ccc(-c2nc(Nc3cccc(N)c3)ncc2F)cc1] | 5 |
| 75 | 3-({4-[4-(acetylamino)phenyl]pyrimidin-2-yl}amino)-N-(2-ethylphenyl)benzamide | 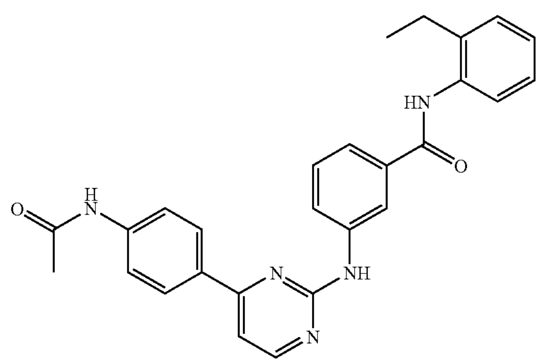 [SMILES: CCc1ccccc1NC(=O)c1cccc(Nc2nccc(-c3ccc(NC(C)=O)cc3)n2)c1] | 29 |
| 76 | 3-({4-[4-(acetylamino)phenyl]pyrimidin-2-yl}amino)-N-(phenylmethyl)benzamide | 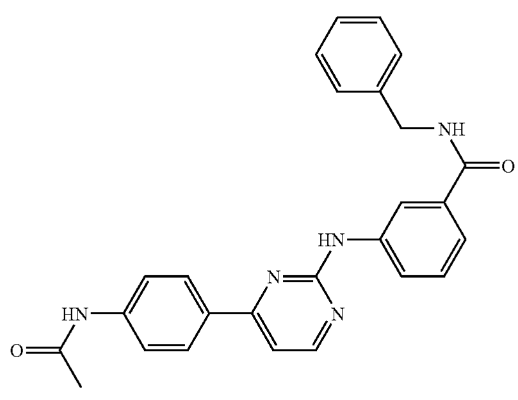 [SMILES: CC(=O)Nc1ccc(-c2ccnc(Nc3cccc(C(=O)NCc4ccccc4)c3)n2)cc1] | 29 |

TABLE 1-continued

| Cmpd No. | Name | Structure | Can Be Made According To Synthetic Example #: |
|---|---|---|---|
| 77 | N-{4-[2-({3-[(4-cyclo-pentylpiperazin-1-yl)carbonyl]phenyl}amino)pyrimidin-4-yl]phenyl}acetamide | 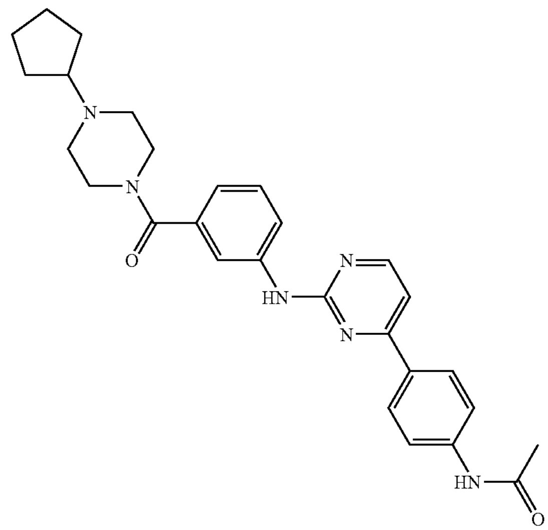 [SMILES: CC(=O)Nc1ccc(-c2ccnc(Nc3cccc(C(=O)N4CCN(C5CCCC5)CC4)c3)n2)cc1] | 29 |
| 78 | N-{4-[2-({3-[(4-phenyl-piperazin-1-yl)carbonyl]phenyl}amino)pyrimidin-4-yl]phenyl}acetamide | 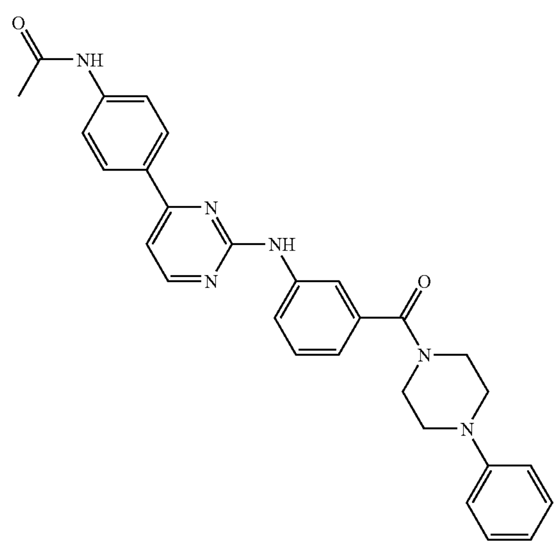 | 29 |
| 79 | N-(3-{2-[(4-morpholin-4-ylphenyl)amino]pyrimidin-4-yl}phenyl)acetamide | 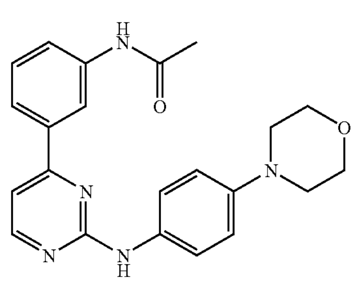 [SMILES: CC(=O)Nc1cccc(-c2ccnc(Nc3ccc(N4CCOCC4)cc3)n2)c1] | 9 |

TABLE 1-continued

| Cmpd No. | Name | Structure | Can Be Made According To Synthetic Example #: |
|---|---|---|---|
| 80 | N-(2-{2-[(4-morpholin-4-ylphenyl)amino]pyrimidin-4-yl}phenyl)acetamide | 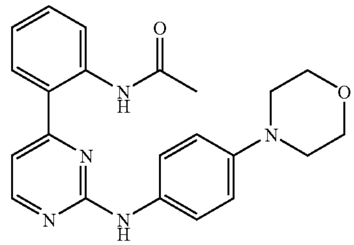 [SMILES: CC(=O)Nc1ccccc1-c1ccnc(Nc2ccc(N3CCOCC3)cc2)n1] | 9 |
| 81 | N-{4-[2-({3-[(4-pyrazin-2-ylpiperazin-1-yl)carbonyl]phenyl}amino)pyrimidin-4-yl]phenyl}acetamide | 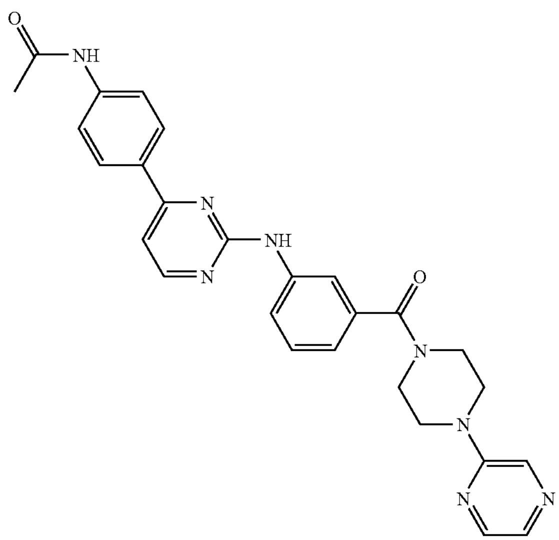 [SMILES: CC(=O)Nc1ccc(-c2ccnc(Nc3cccc(C(=O)N4CCN(c5cnccn5)CC4)c3)n2)cc1] | 29 |
| 82 | N-(4-{2-[(3-{[4-(3-chlorophenyl)piperazin-1-yl]carbonyl}phenyl)amino}pyrimidin-4-yl}phenyl)acetamide | 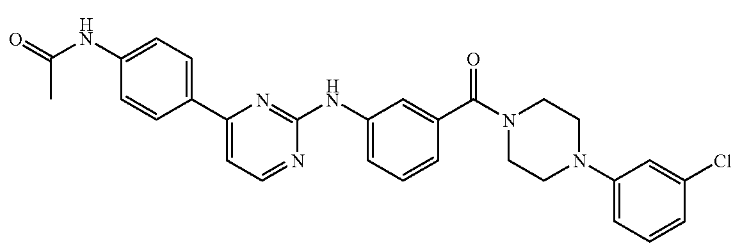 [SMILES: CC(=O)Nc1ccc(-c2ccnc(Nc3cccc(C(=O)N4CCN(c5cccc(Cl)c5)CC4)c3)n2)cc1] | 46 |
| 83 | 3-({4-[4-(acetylamino)phenyl]pyrimidin-2-yl}amino)-N-[(1-methyl-1H-benzimidazol-2-yl)methyl]benzamide | 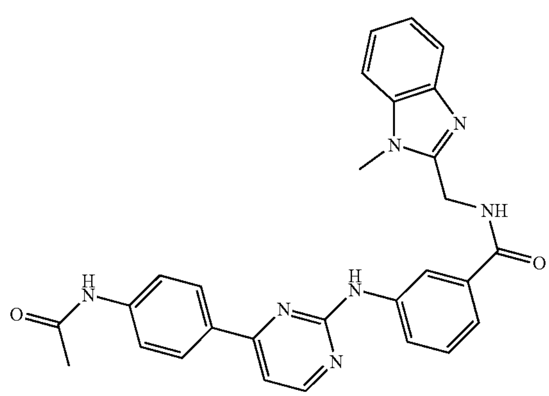 [SMILES: CC(=O)Nc1ccc(-c2ccnc(Nc3cccc(C(=O)NCc4nc5ccccc5n4C)c3)n2)cc1] | 46 |

TABLE 1-continued

| Cmpd No. | Name | Structure | Can Be Made According To Synthetic Example #: |
|---|---|---|---|
| 84 | 3-({4-[4-(acetylamino)phenyl] pyrimidin-2-yl}amino)-N-propylbenzamide | 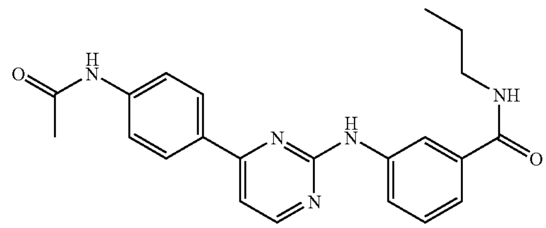 [SMILES: CCCNC(=O)c1cccc(Nc2nccc(-c3ccc(NC(C)=O)cc3)n2)c1] | 29 |
| 85 | 3-({4-[4-(acetylamino)phenyl] pyrimidin-2-yl}amino)-N-cyclopropylbenzamide | 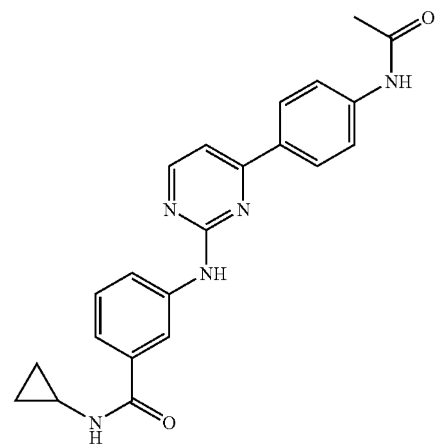 [SMILES: CC(=O)Nc1ccc(-c2ccnc(Nc3cccc(C(=O)NC4CC4)c3)n2)cc1] | 29 |
| 86 | 3-({4-[4-(acetylamino)phenyl] pyrimidin-2-yl)amino)-N-[(3-fluorophenyl)methyl]benzamide | 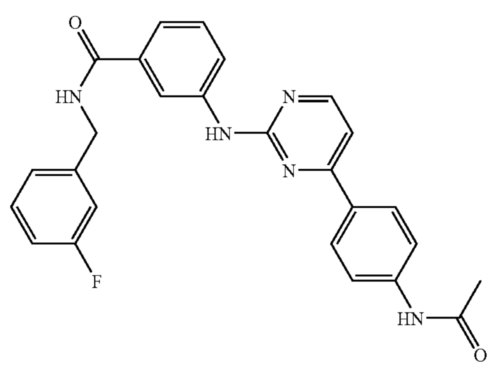 [SMILES: CC(=O)Nc1ccc(-c2ccnc(Nc3cccc(C(=O)NCc4cccc(F)c4)c3)n2)cc1] | 29 |
| 87 | 3-({4-[4-(acetylamino)phenyl] pyrimidin-2-yl}amino)-N-(naphthalen-1-ylmethyl)benzamide | 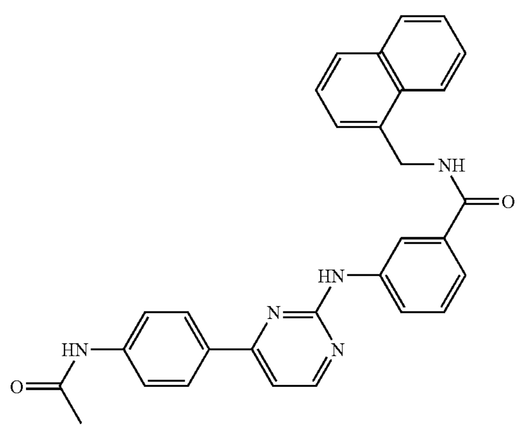 [SMILES: CC(=O)Nc1ccc(-c2ccnc(Nc3cccc(C(=O)NCc4cccc5ccccc45)c3)n2)cc1] | 29 |

TABLE 1-continued

| Cmpd No. | Name | Structure | Can Be Made According To Synthetic Example #: |
|---|---|---|---|
| 88 | 3-({4-[4-(acetylamino)phenyl]pyrimidin-2-yl}amino)-N-[2-(dimethylamino)ethyl]-N-methylbenzamide | 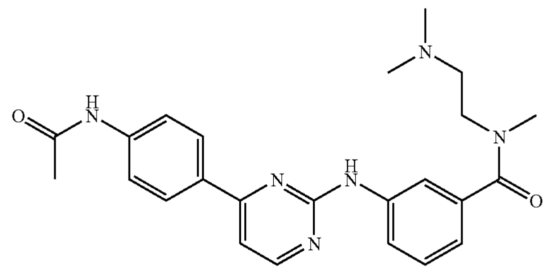 [SMILES: CC(=O)Nc1ccc(-c2ccnc(Nc3cccc(C(=O)N(C)CCN(C)C)c3)n2)cc1] | 29 |
| 89 | 3-({4-[4-(acetylamino)phenyl]pyrimidin-2-yl}amino)-N-[(2-methylphenyl)methyl]benzamide | 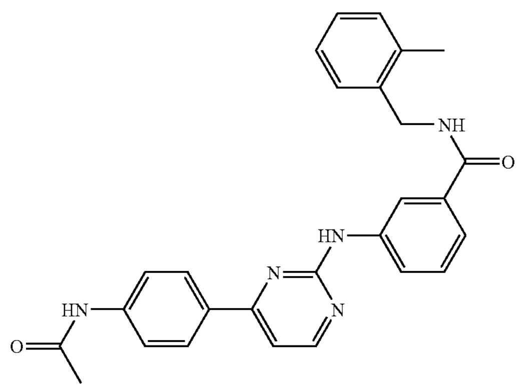 [SMILES: CC(=O)Nc1ccc(-c2ccnc(Nc3cccc(C(=O)NCc4ccccc4C)c3)n2)cc1] | 29 |
| 90 | 3-({4-[4-(acetylamino)phenyl]pyrimidin-2-yl}amino)-N-[(3-chlorophenyl)methyl]benzamide | 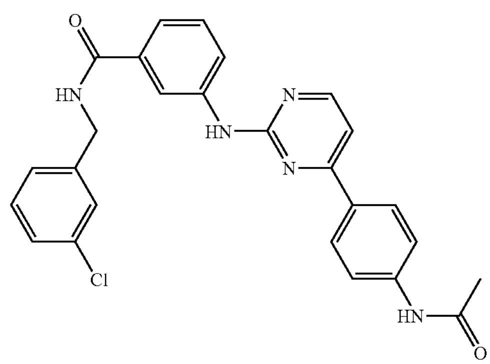 | 29 |
| 91 | 3-({4-[4-(acetylamino)phenyl]pyrimidin-2-yl}amino)-N-(2-phenylethyl)benzamide | 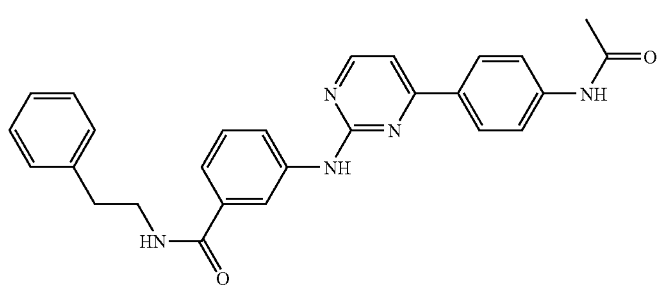 [SMILES: CC(=O)Nc1ccc(-c2ccnc(Nc3cccc(C(=O)NCCc4ccccc4)c3)n2)cc1] | 29 |

TABLE 1-continued

| Cmpd No. | Name | Structure | Can Be Made According To Synthetic Example #: |
|---|---|---|---|
| 92 | N-{4-[2-({3-[(4-methylpiperazin-1-yl)carbonyl]phenyl}amino)pyrimidin-4-yl]phenyl}acetamide | 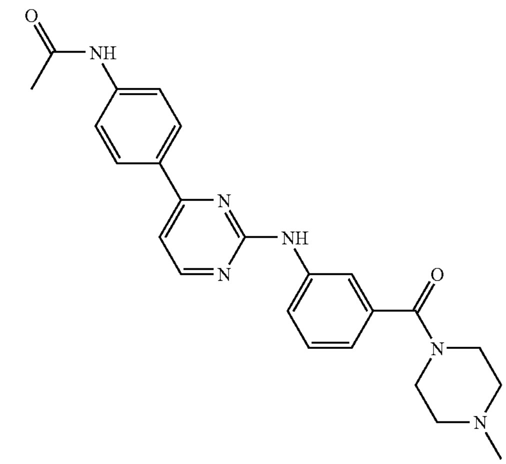 [SMILES: CC(=O)Nc1ccc(-c2ccnc(Nc3cccc(C(=O)N4CCN(C)CC4)c3)n2)cc1] | 29 |
| 93 | 3-({4-[4-(acetylamino)phenyl]pyrimidin-2-yl}amino)-N-(tetrahydrofuran-2-ylmethyl)benzamide | 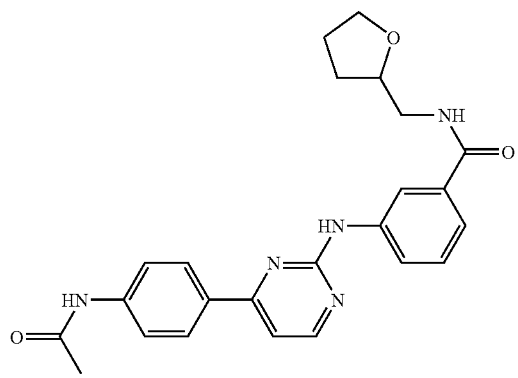 [SMILES: CC(=O)Nc1ccc(-c2ccnc(Nc3cccc(C(=O)NCC4CCCO4)c3)n2)cc1] | 29 |
| 94 | 3-({4-[4-(acetylamino)phenyl]pyrimidin-2-yl}amino)-N-{3-(2-oxopyrrolidin-1-yl)propyl]benzamide | 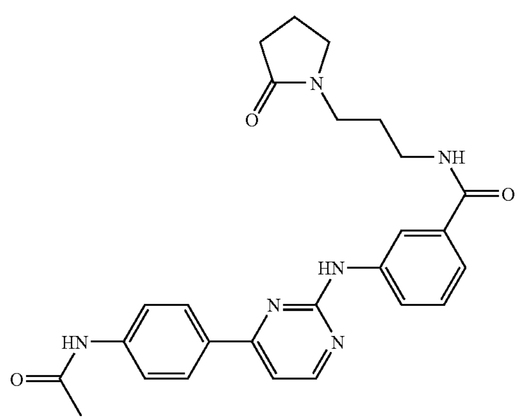 [SMILES: CC(=O)Nc1ccc(-c2ccnc(Nc3cccc(C(=O)NCCCN4CCCC4=O)c3)n2)cc1] | 29 |
| 95 | 3-({4-[4-(acetylamino)phenyl]pyrimidin-2-yl}amino)-N-[(3s,5s,7s)-tricyclo[3.3.1.1~3,7~]dec-1-yl]benzamide | 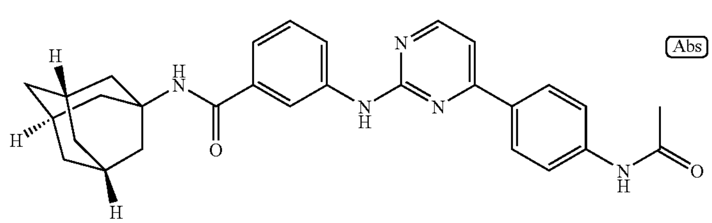 [SMILES: CC(=O)Nc1ccc(-c2ccnc(Nc3cccc(C(=O)NC45C[C@H]6C[C@@H](C4)C[C@@H](C5)C6)c3)n2)cc1] | 29 |

TABLE 1-continued

| Cmpd No. | Name | Structure | Can Be Made According To Synthetic Example #: |
|---|---|---|---|
| 96 | 3-({4-[4-(acetylamino)phenyl]pyrimidin-2-yl}amino)-N-[2-(methyloxy)ethyl]benzamide | 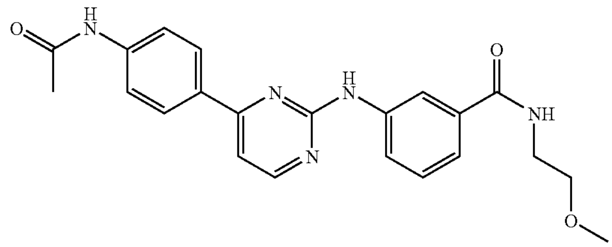 [SMILES: COCCNC(=O)c1cccc(Nc2nccc(-c3ccc(NC(C)=O)cc3)n2)c1] | 29 |
| 97 | N-[4-(2-{[3-(1,3-thiazolidin-3-ylcarbonyl)phenyl]amino}pyrimidin-4-yl}phenyl]acetamide | 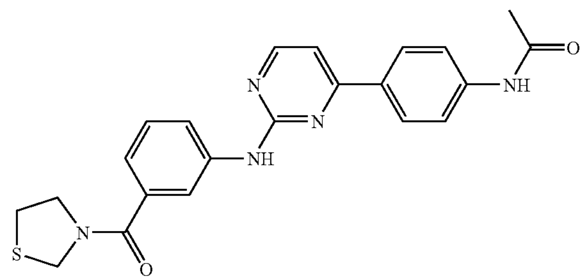 [SMILES: CC(=O)Nc1ccc(-c2ccnc(Nc3cccc(C(=O)N4CCSC4)c3)n2)cc1] | 29 |
| 98 | N-{4-[2-({3-[(4-pyridin-2-ylpiperazin-1-yl)carbonyl]phenyl}amino-pyrimidin-4-yl]phenyl}acetamide | 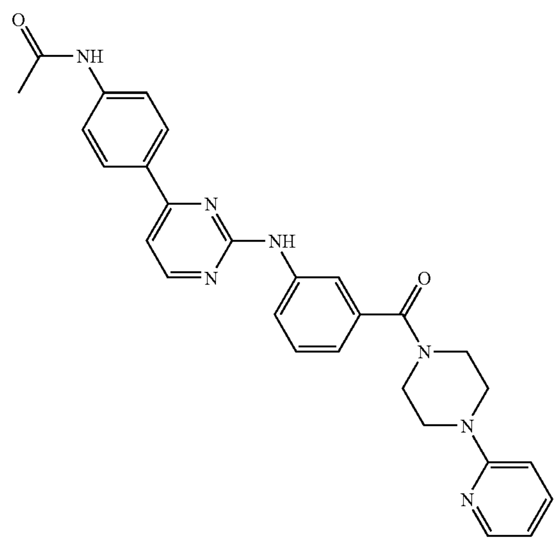 [SMILES: CC(=O)Nc1ccc(-c2ccnc(Nc3cccc(C(=O)N4CCN(c5ccccn5)CC4)c3)n2)cc1] | 29 |
| 99 | 3-(-{4-[4-(acetylamino)phenyl]pyrimidin-2-yl}amino)-N-{[2-(methyloxy)phenyl]methyl}benzamide | 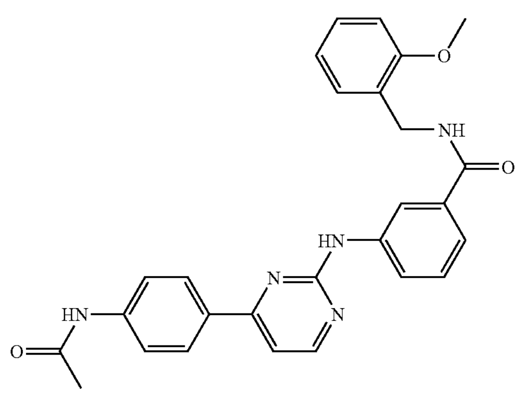 [SMILES: COc1ccccc1CNC(=O)c1cccc(Nc2nccc(-c3ccc(NC(C)=O)cc3)n2)c1] | 29 |

TABLE 1-continued

| Cmpd No. | Name | Structure | Can Be Made According To Synthetic Example #: |
|---|---|---|---|
| 100 | 3-({4-[4-(acetylamino) phenyl]pyrimidin-2-yl} amino)-N-{[3-(methyloxy) phenyl]methyl}benzamide | 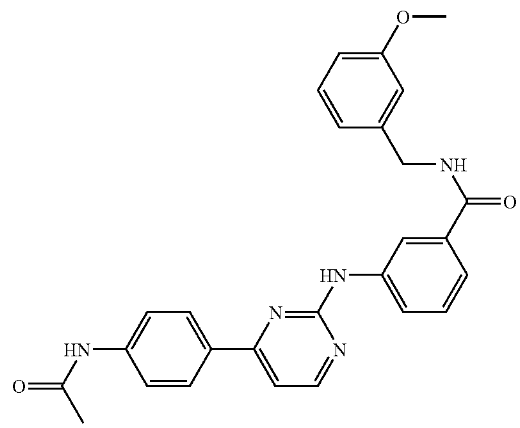 [SMILES: COc1cccc(CNC(=O)c2cccc(Nc3nccc(-c4ccc(NC(C)=O)cc4)n3)c2)c1] | 29 |
| 101 | 3-({4-[4-(acetylamino) phenyl]pyrimidin-2-yl} amino)-N-[(2-fluorophenyl) methyl]benzamide | 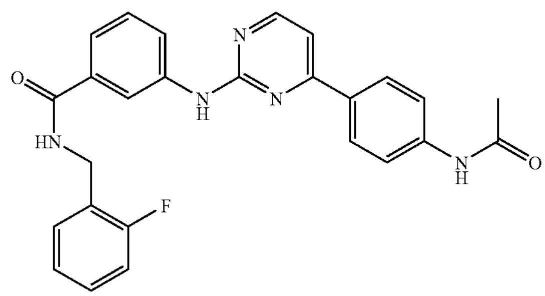 | 29 |
| 102 | 3-({4-[4-(acetylamino) phenyl]pyrimidin-2-yl} amino)-N-[(4-fluorophenyl) methyl]benzamide | 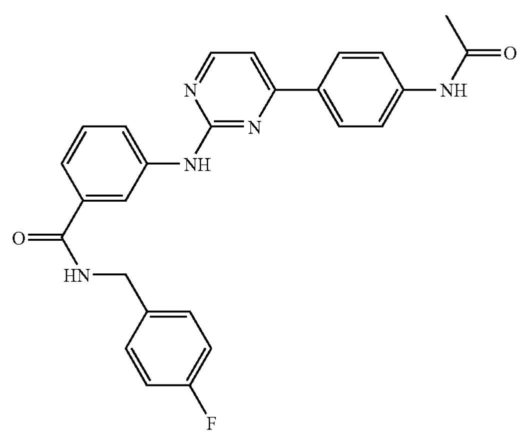 | 29 |
| 103 | 3-({4-[4-(acetylamino)phenyl] pyrimidin-2-yl}amino)-N- (3,3-dimethylbutyl)benzamide | 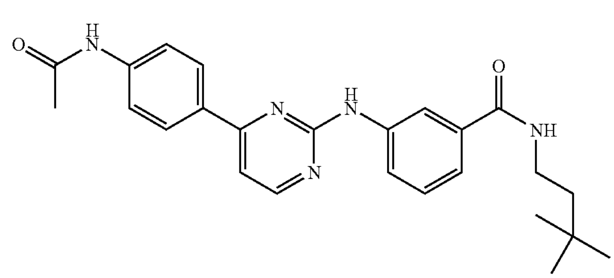 [SMILES: CC(=O)Nc1ccc(-c2ccnc(Nc3cccc(C(=O)NCCC(C)(C)C)c3)n2)cc1] | 29 |

TABLE 1-continued

| Cmpd No. | Name | Structure | Can Be Made According To Synthetic Example #: |
|---|---|---|---|
| 104 | N-[4-(2-{[3-(thiomorpholin-4-ylcarbonyl)phenyl]amino}pyrimidin-4-yl)phenyl]acetamide | 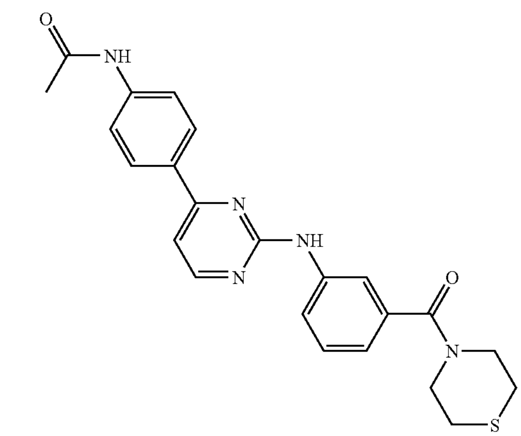 [SMILES: CC(=O)Nc1ccc(-c2ccnc(Nc3cccc(C(=O)N4CCSCC4)c3)n2)cc1] | 29 |
| 105 | 3-({4-(4-(acetylamino)phenyl]pyrimidin-2-yl}amino)-N-(2-thienylmethyl)benzamide | 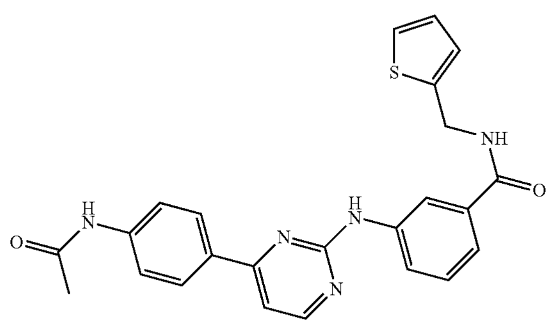 [SMILES: CC(=O)Nc1ccc(-c2ccnc(Nc3cccc(C(=O)NCc4cccs4)c3)n2)cc1] | 29 |
| 106 | 3-({4-[4-(acetylamino)phenyl]pyrimidin-2-yl}amino)-N-[3-(dimethylamino)propyl]benzamide | 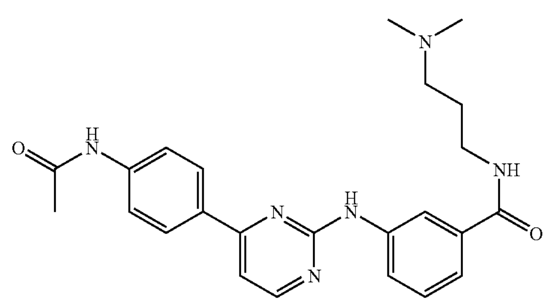 [SMILES: CC(=O)Nc1ccc(-c2ccnc(Nc3cccc(C(=O)NCCCN(C)C)c3)n2)cc1] | 29 |
| 107 | 3-({4-[4-(acetylamino)phenyl]pyrimidin-2-yl}amino)-N-{[2-(trifluoromethyl)phenyl]methyl}benzamide | 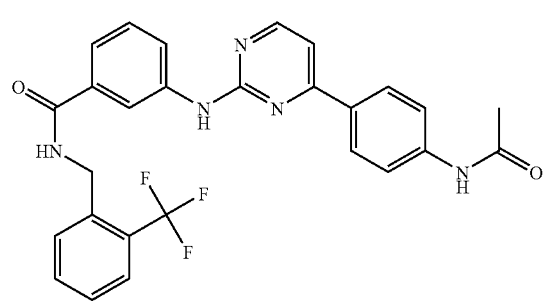 [SMILES: CC(=O)Nc1ccc(-c2ccnc(Nc3cccc(C(=O)NCc4ccccc4C(F)(F)F)c3)n2)cc1] | 29 |

TABLE 1-continued

| Cmpd No. | Name | Structure | Can Be Made According To Synthetic Example #: |
|---|---|---|---|
| 108 | 3-({4-[4-(acetylamino)phenyl]pyrimidin-2-yl}amino)-N-{[3-(trifluoromethyl)phenyl]methyl}benzamide | 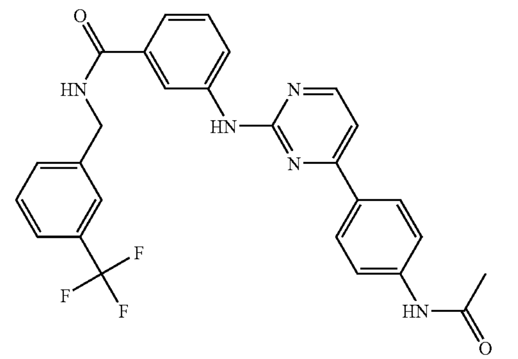 [SMILES: CC(=O)Nc1ccc(-c2ccnc(Nc3cccc(C(=O)NCc4cccc(C(F)(F)F)c4)c3)n2)cc1] | 29 |
| 109 | 3-({4-[4-(acetylamino)phenyl]pyrimidin-2-yl}amino)-N-{[4-(trifluoromethyl)phenyl]methyl}benzamide | 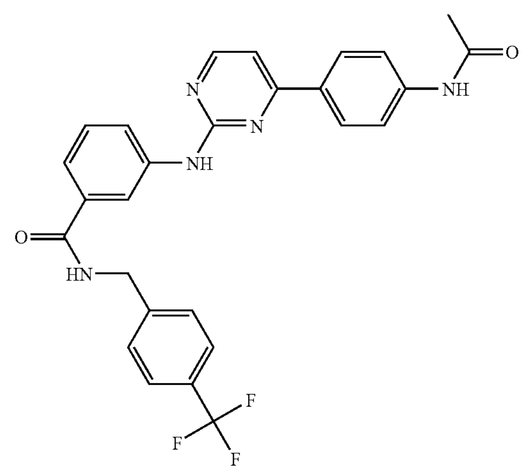 [SMILES: CC(=O)Nc1ccc(-c2ccnc(Nc3cccc(C(=O)NCc4ccc(C(F)(F)F)cc4)c3)n2)cc1] | 29 |
| 110 | 3-({4-[4-(acetylamino)phenyl]pyrimidin-2-yl}amino)-N-[(2,4-difluorophenyl)methyl]benzamide | 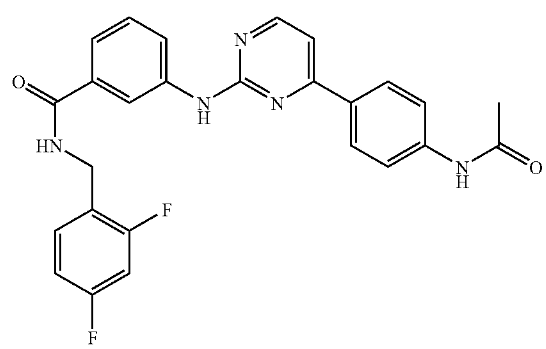 [SMILES: CC(=O)Nc1ccc(-c2ccnc(Nc3cccc(C(=O)NCc4ccc(F)cc4F)c3)n2)cc1] | 29 |
| 111 | 3-({4-[4-(aceylamino)phenyl]pyrimidin-2-yl]amino)-N-ethyl-N-methylbenzamide | 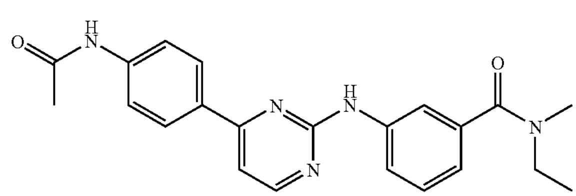 [SMILES: CCN(C)C(=O)c1cccc(Nc2nccc(-c3ccc(NC(C)=O)cc3)n2)c1] | 29 |

TABLE 1-continued

| Cmpd No. | Name | Structure | Can Be Made According To Synthetic Example #: |
|---|---|---|---|
| 112 | 3-({4-[4-(acetylamino)phenyl]pyrimidin-2-yl}amino)-N-({4-[(trifluoromethyl)oxy]phenyl}methyl)benzamide | 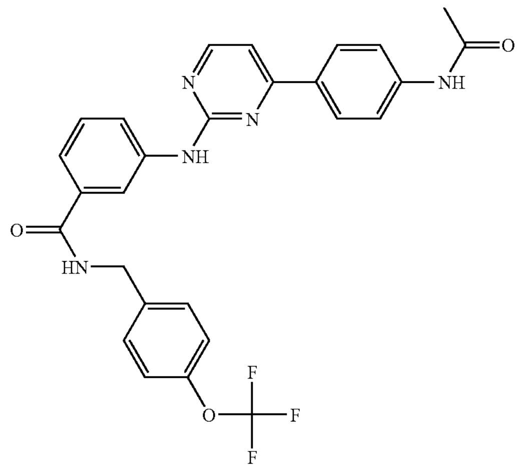 [SMILES: CC(=O)Nc1ccc(-c2ccnc(Nc3cccc(C(=O)NCc4ccc(OC(F)(F)F)cc4)c3)n2)cc1] | 29 |
| 113 | N-{4-[2-({3-[(4-acetylpiperazin-1-yl)carbonyl]phenyl}amino)pyrimidin-4-yl]phenyl}acetamide | 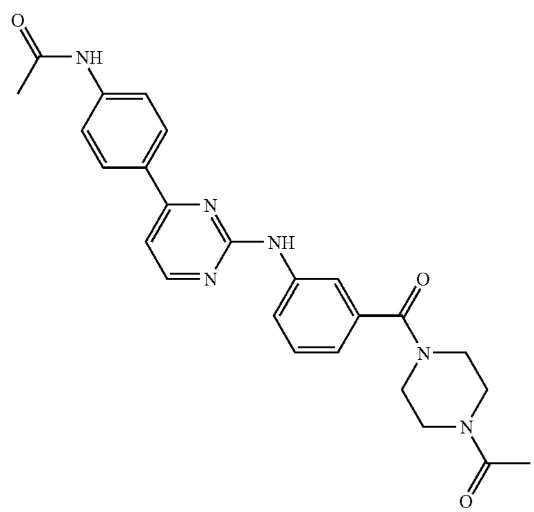 [SMILES: CC(=O)Nc1ccc(-c2ccnc(Nc3cccc(C(=O)N4CCN(C(C)=O)CC4)c3)n2)cc1] | 29 |
| 114 | 3-({4-[4-(acetylamino)phenyl]pyrimidin-2-yl}amino)-N-(cyclopropylmethyl)benzamide | 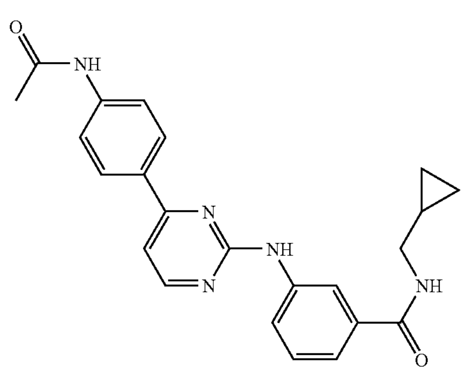 [SMILES: CC(=O)Nc1ccc(-c2ccnc(Nc3cccc(C(=O)NCC4CC4)c3)n2)cc1] | 29 |

TABLE 1-continued

| Cmpd No. | Name | Structure | Can Be Made According To Synthetic Example #: |
|---|---|---|---|
| 115 | 3-({4-[4-(acetylamino)phenyl]pyrimidin-2-yl}amino)-N-[2-(2-fluorophenyl)ethyl]benzamide | 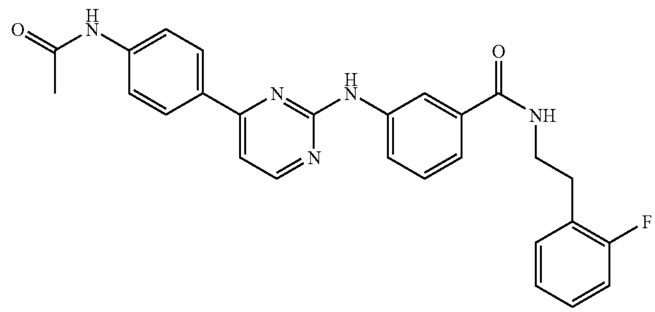 [SMILES: CC(=O)Nc1ccc(-c2ccnc(Nc3cccc(C(=O)NCCc4ccccc4F)c3)n2)cc1] | 29 |
| 116 | N-[4-(2-{[3-(pyrrolidin-1-ylcarbonyl)phenyl]amino}pyrimidin-4-yl)phenyl]acetamide | 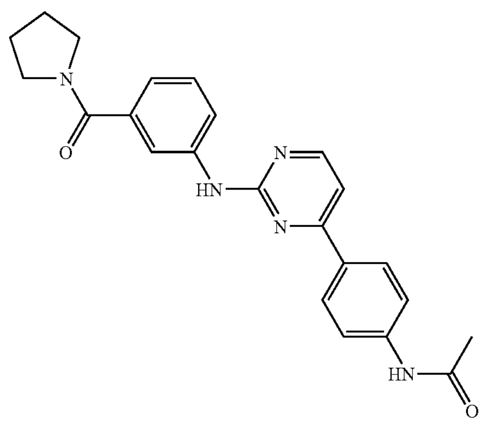 [SMILES: CC(=O)Nc1ccc(-c2ccnc(Nc3cccc(C(=O)N4CCCC4)c3)n2)cc1] | 29 |
| 117 | N-{4-[2-({3-[(4-pyrimidin-2-ylpiperazin-1-yl)carbonyl]phenyl}amino)pyrimidin-4-yl]phenyl}acetamide | 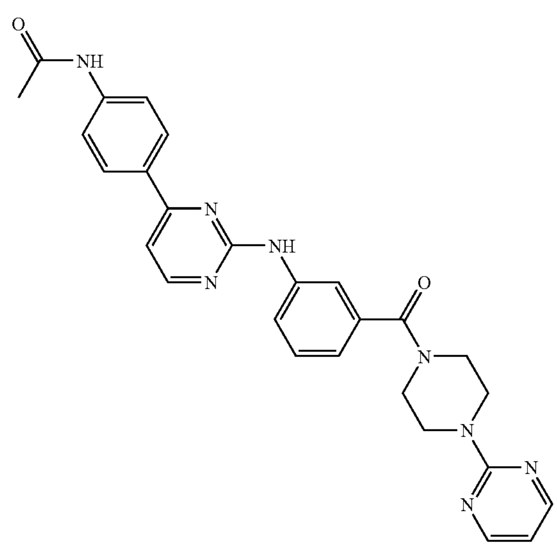 [SMILES: CC(=O)Nc1ccc(-c2ccnc(Nc3cccc(C(=O)N4CCN(c5ncccn5)CC4)c3)n2)cc1] | 29 |

TABLE 1-continued

| Cmpd No. | Name | Structure | Can Be Made According To Synthetic Example #: |
|---|---|---|---|
| 118 | N-methyl-N-(4-{2-[(4-morpholin-4-ylphenyl)amino]pyrimidin-4-yl}phenyl)acetamide | 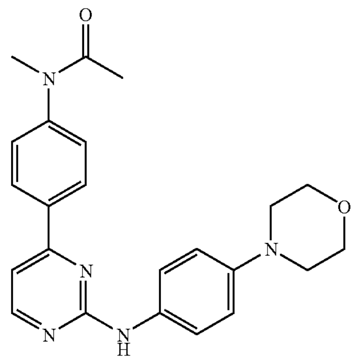 [SMILES: CC(=O)N(C)c1ccc(-c2ccnc(Nc3ccc(N4CCOCC4)cc3)n2)cc1] | 32 |
| 119 | N-(4-{2-[(4-morpholin-4-ylphenyl)amino]pyrimidin-4-yl}phenyl)benzamide | 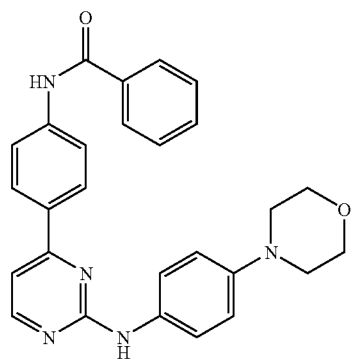 [SMILES: O=C(Nc1ccc(-c2ccnc(Nc3ccc(N4CCOCC4)cc3)n2)cc1)c1ccccc1] | 9 |
| 120 | N-[4-(2-{[3-(1,3-dioxan-2-yl)phenyl]amino}pyrimidin-4-yl)phenyl]acetamide | 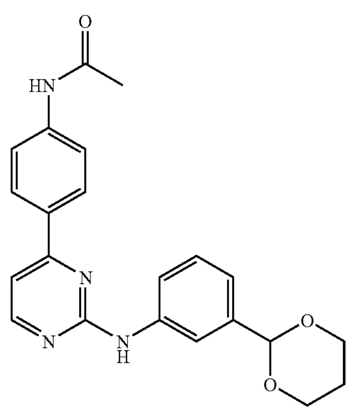 [SMILES: CC(=O)Nc1ccc(-c2ccnc(Nc3cccc(C4OCCCO4)c3)n2)cc1] | 3 |
| 121 | N-[4-(2-{[3-(morpholin-4-ylmethyl)phenyl]amino}pyrimidin-4-yl)phenyl]acetamide | 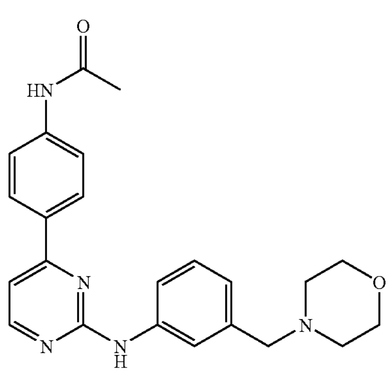 [SMILES: CC(=O)Nc1ccc(-c2ccnc(Nc3cccc(CN4CCOCC4)c3)n2)cc1] | 22 |

TABLE 1-continued

| Cmpd No. | Name | Structure | Can Be Made According To Synthetic Example #: |
|---|---|---|---|
| 122 | N-{4-[2-({3-[(4-ethylpiperazin-1-yl)methyl]phenyl}amino)pyrimidin-4-yl]phenyl}acetamide | 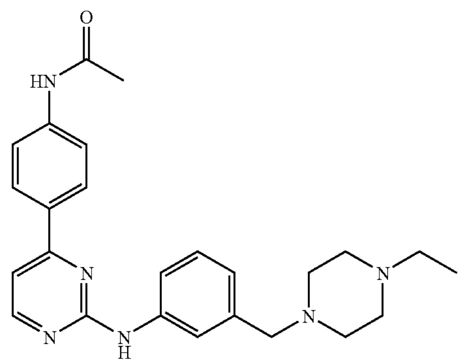 [SMILES: CCN1CCN(Cc2cccc(Nc3nccc(-c4ccc(NC(C)=O)cc4)n3)c2)CC1] | 29 |
| 123 | N-[3-({4-[4-(acetylamino)phenyl]pyrimidin-2-yl}amino)phenyl]-3-[(2-morpholin-4-ylethyl)oxy]benzamide | 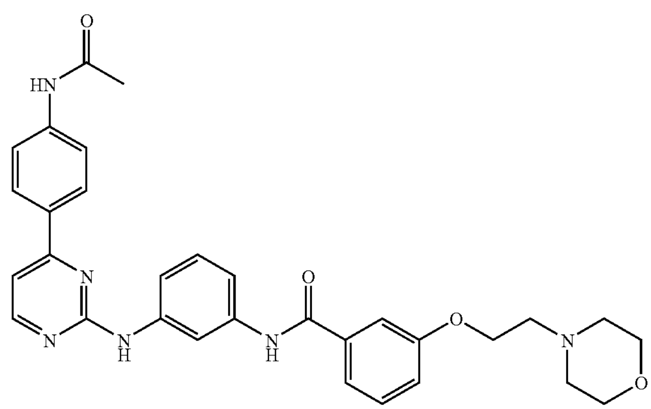 [SMILES: CC(=O)Nc1ccc(-c2ccnc(Nc3cccc(NC(=O)c4cccc(OCCN5CCOCC5)c4)c3)n2)cc1] | 39 |
| 124 | 4-[4-(methylamino)phenyl]-N-(4-morpholin-4-ylphenyl)pyrimidin-2-amine | 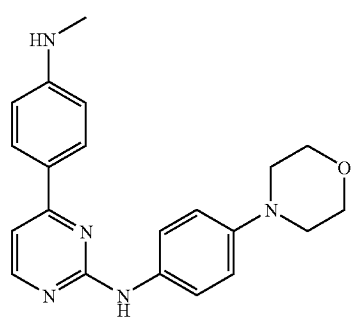 [SMILES: CNc1ccc(-c2ccnc(Nc3ccc(N4CCOCC4)cc3)n2)cc1] | 29 |
| 125 | N-[4-(2-{[4-(4-acetyl-piperazin-1-yl)phenyl]amino}pyrimidin-4-yl)phenyl]acetamide | 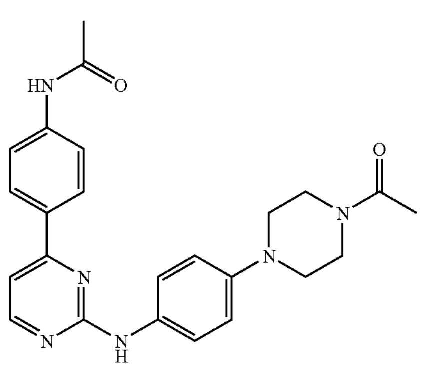 [SMILES: CC(=O)Nc1ccc(-c2ccnc(Nc3ccc(N4CCN(C(C)=O)CC4)cc3)n2)cc1] | 7 |

TABLE 1-continued

| Cmpd No. | Name | Structure | Can Be Made According To Synthetic Example #: |
|---|---|---|---|
| 126 | N-(4-{2-[(3-amino-2,4,5,6-tetrafluorophenyl)amino]pyrimidin-4-yl}phenyl)acetamide | 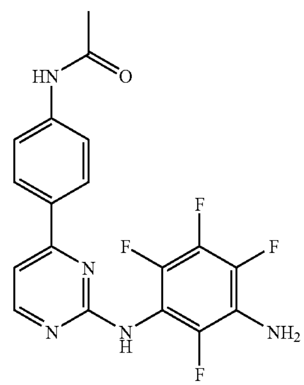 [SMILES: CC(=O)Nc1ccc(-c2ccnc(Nc3c(F)c(N)c(F)c(F)c3F)n2)cc1] | 1 |
| 127 | N-(4-{2-[(3-{[4-(2-fluorophenyl)piperazin-1-yl]carbonyl}phenyl)amino]pyrimidin-4-yl}phenyl)acetamide | 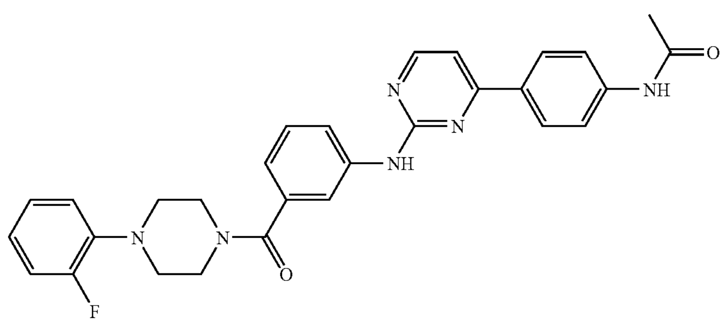 | |
| 128 | 3-({4-[4-(acetylamino)phenyl]pyrimidin-2-yl}amino)-N-[2-(phenyloxy)ethyl]benzamide | 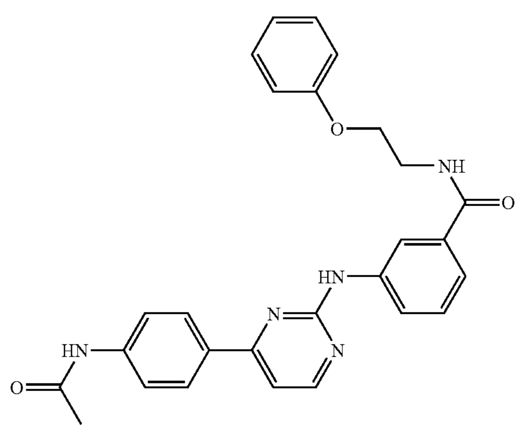 [SMILES: CC(=O)Nc1ccc(-c2ccnc(Nc3cccc(C(=O)NCCOc4ccccc4)c3)n2)cc1] | 29 |

TABLE 1-continued
| Cmpd No. | Name | Structure | Can Be Made According To Synthetic Example #: |
|---|---|---|---|
| 129 | methyl 1-{[3-({4-[4-(acetyl-amino)phenyl]pyrimidin-2-yl}amino)phenyl]carbonyl}piperidine-4-carboxylate | 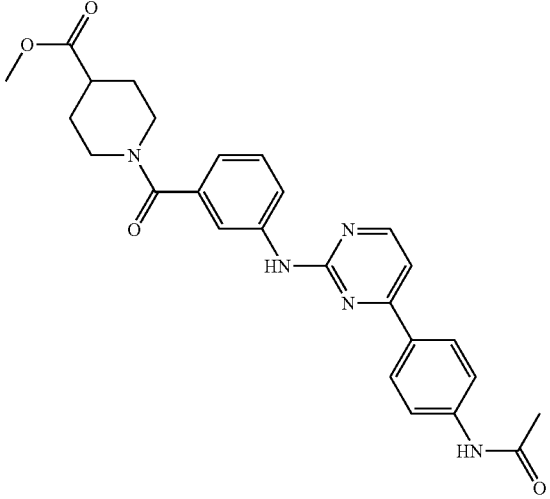 [SMILES: COC(=O)C1CCN(C(=O)c2cccc(Nc3nccc(-c4ccc(NC(C)=O)cc4)n3)c2)CC1] | 29 |
| 130 | N-[4-(2-{[3-({4-[3-(methyloxy)phenyl]piperazin-1-yl}carbonyl)phenyl]amino}pyrimidin-4-yl)phenyl]acetamide | 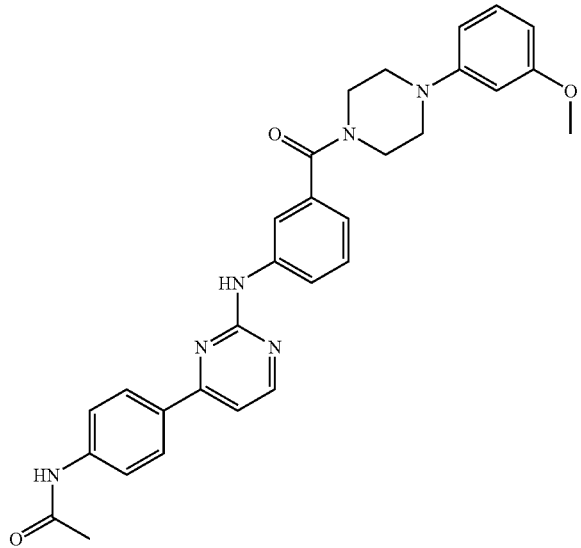 [SMILES: COc1cccc(N2CCN(C(=O)c3cccc(Nc4nccc(-c5ccc(NC(C)=O)cc5)n4)c3)CC2)c1] | 29 |
| 131 | 3-({4-[4-(acetylamino)phenyl]pyrimidin-2-yl}amino)-N-{2-[2-(methyloxy)phenyl]ethyl}benzamide | 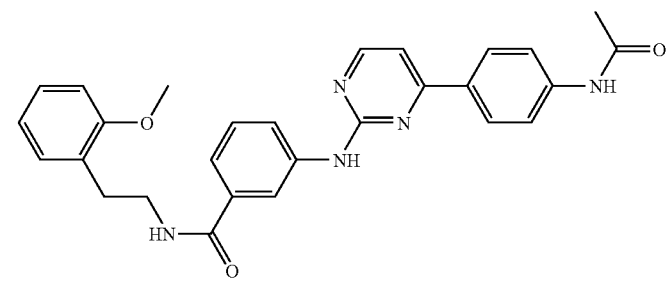 [SMILES: COc1ccccc1CCNC(=O)c1cccc(Nc2nccc(-c3ccc(NC(C)=O)cc3)n2)c1] | 29 |

TABLE 1-continued

| Cmpd No. | Name | Structure | Can Be Made According To Synthetic Example #: |
|---|---|---|---|
| 132 | N-[4-(2-{[3-(1,3-dihydro-2H-isoindol-2-ylcarbonyl)phenyl]amino}pyrimidin-4-yl)phenyl]acetamide | 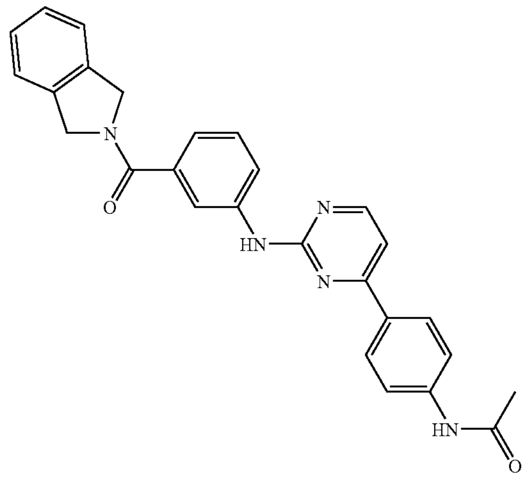 [SMILES: CC(=O)Nc1ccc(-c2ccnc(Nc3cccc(C(=O)N4Cc5ccccc5C4)c3)n2)cc1] | 29 |
| 133 | 3-({4-[4-(acetylamino)phenyl]pyrimidin-2-yl}amino)-N-(biphenyl-4-ylmethyl)benzamide | 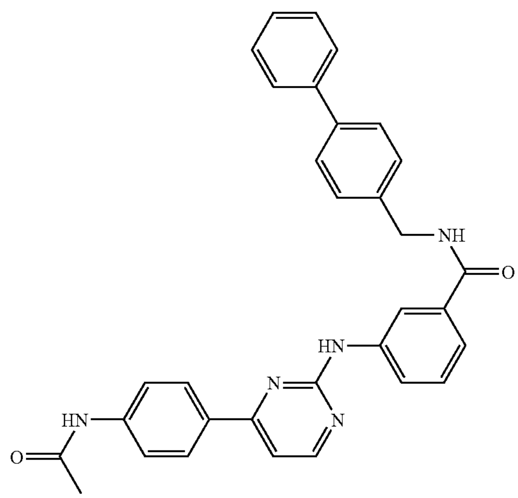 [SMILES: CC(=O)Nc1ccc(-c2ccnc(Nc3cccc(C(=O)NCc4ccc(-c5ccccc5)cc4)c3)n2)cc1] | 29 |
| 134 | N-(4-{2-[(3-{[4-(phenylcarbonyl)piperazin-1-yl]carbonyl}phenyl)amino}pyrimidin-4-yl}phenyl)acetamide | 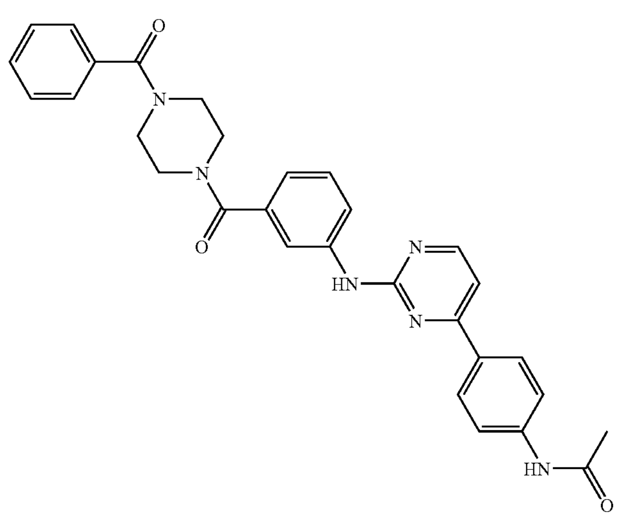 [SMILES: CC(=O)Nc1ccc(-c2ccnc(Nc3cccc(C(=O)N4CCN(C(=O)c5ccccc5)CC4)c3)n2)cc1] | 29 |

TABLE 1-continued

| Cmpd No. | Name | Structure | Can Be Made According To Synthetic Example #: |
|---|---|---|---|
| 135 | N-[4-(2-{[3-({4-[4-(methyloxy)phenyl]piperazin-1-yl}carbonyl)phenyl]amino}pyrimidin-4-yl)phenyl]acetamide | 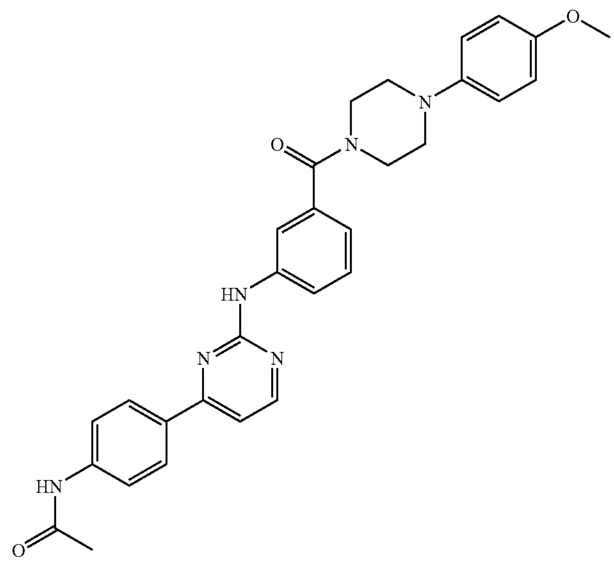 [SMILES: COc1ccc(N2CCN(C(=O)c3cccc(Nc4nccc(-c5ccc(NC(C)=O)cc5)n4)c3)CC2)cc1] | 29 |
| 136 | 3-({4-[4-(acetylamino)phenyl]pyrimidin-2-yl}amino)-N-methyl-N-{[2-(methyloxy)phenyl]methyl}benzamide | 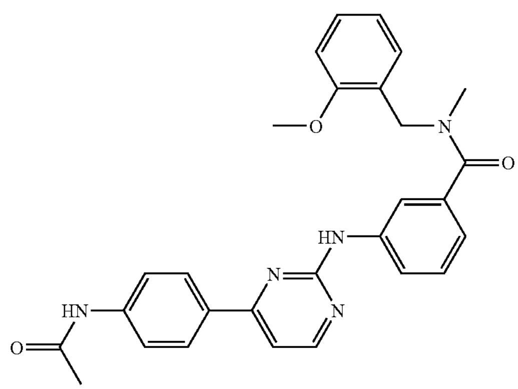 [SMILES: COc1ccccc1CN(C)C(=O)c1cccc(Nc2nccc(-c3ccc(NC(C)=O)cc3)n2)c1] | 29 |
| 137 | 3-({4-[4-(acetylamino)phenyl]pyrimidin-2-yl}amino)-N-[(2-fluorophenyl)methyl]-N-methylbenzamide | 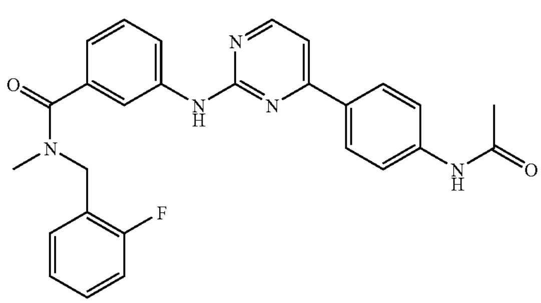 [SMILES: CC(=O)Nc1ccc(-c2ccnc(Nc3cccc(C(=O)N(C)Cc4ccccc4F)c3)n2)cc1] | 29 |

TABLE 1-continued

| Cmpd No. | Name | Structure | Can Be Made According To Synthetic Example #: |
|---|---|---|---|
| 138 | 3-({4-[4-(acetylamino)phenyl]pyrimidin-2-yl}amino)-N-(diphenylmethyl)benzamide | 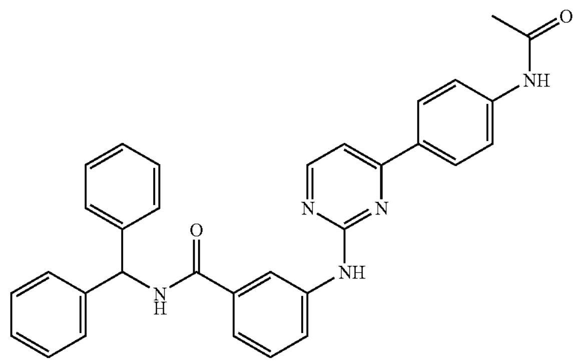 [SMILES: CC(=O)Nc1ccc(-c2ccnc(Nc3cccc(C(=O)NC(c4ccccc4)c4ccccc4)c3)n2)cc1] | 29 |
| 139 | 3-({4-[4-(acetylamino)phenyl]pyrimidin-2-yl}amino)-N-(2-pyridin-2-ylethyl)benzamide | 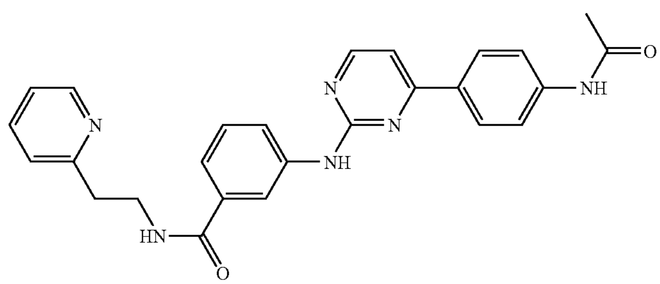 [SMILES: CC(=O)Nc1ccc(-c2ccnc(Nc3cccc(C(=O)NCCc4ccccn4)c3)n2)cc1] | 29 |
| 140 | 3-({4-[4-(acetylamino)phenyl]pyrimidin-2-yl}amino)-N-(pyridin-2-ylmethyl)benzamide | 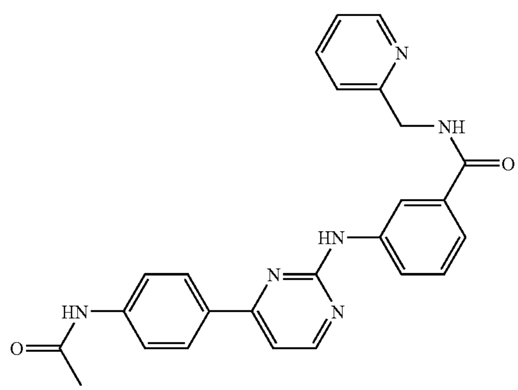 [SMILES: CC(=O)Nc1ccc(-c2ccnc(Nc3cccc(C(=O)NCc4ccccn4)c3)n2)cc1] | 29 |
| 141 | 3-({4-[4-(acetylamino)phenyl]pyrimidin-2-yl}amino)-N-[2-(2-chlorophenyl)ethyl]benzamide | 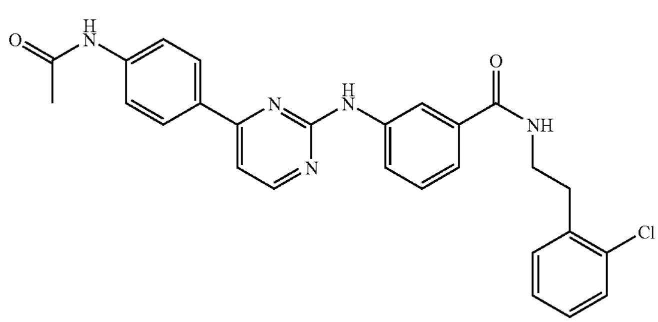 [SMILES: CC(=O)Nc1ccc(-c2ccnc(Nc3cccc(C(=O)NCCc4ccccc4Cl)c3)n2)cc1] | 29 |

TABLE 1-continued

| Cmpd No. | Name | Structure | Can Be Made According To Synthetic Example #: |
|---|---|---|---|
| 142 | N-[4-(2-{[4-(4-ethylpiperazin-1-yl)phenyl]amino}-5-fluoropyrimidin-4-yl)phenyl]acetamide | 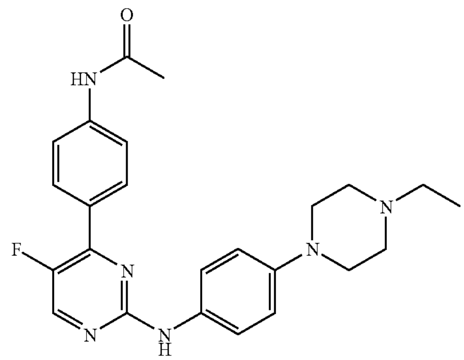 [SMILES: CCN1CCN(c2ccc(Nc3ncc(F)c(-c4ccc(NC(C)=O)cc4)n3)cc2)CC1] | 5 |
| 143 | N²-[3-(1H-imidazol-1-yl)propyl]-N-(4-{2-[(4-morpholin-4-ylphenyl)amino]pyrimidin-4-yl}phenyl)glycinamide | 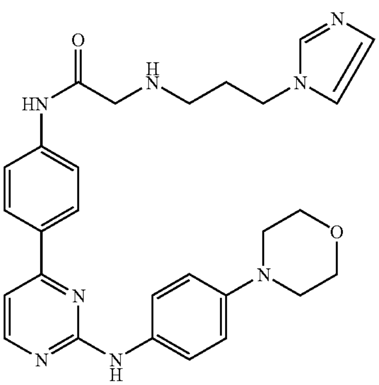 [SMILES: O=C(CNCCCn1ccnc1)Nc1ccc(-c2ccnc(Nc3ccc(N4CCOCC4)cc3)n2)cc1] | 23 |
| 144 | N-(4-{2-[(4-morpholin-4-ylphenyl)amino]pyrimidin-4-yl}phenyl)-N²-(2-pyridin-3-ylethyl)glycinamide | 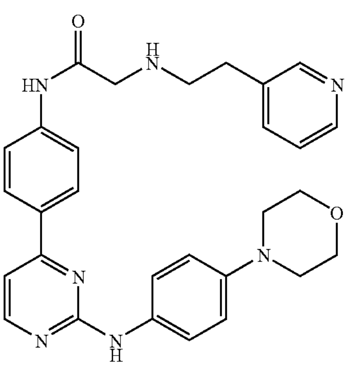 [SMILES: O=C(CNCCc1cccnc1)Nc1ccc(-c2ccnc(Nc3ccc(N4CCOCC4)cc3)n2)cc1] | 23 |
| 145 | 3-({4-[4-(acetylamino)phenyl]pyrimidin-2-yl}amino)-N-(pyridin-3-ylmethyl)benzamide | 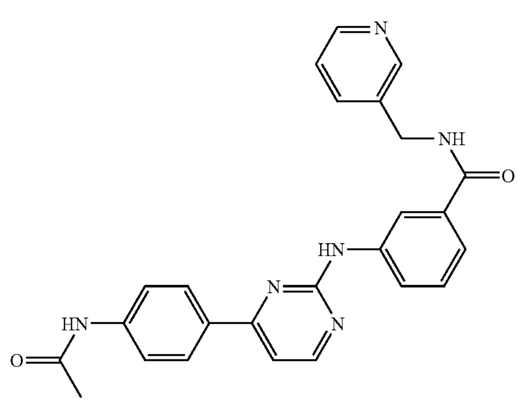 [SMILES: CC(=O)Nc1ccc(-c2ccnc(Nc3cccc(C(=O)NCc4cccnc4)c3)n2)cc1] | 29 |

TABLE 1-continued

| Cmpd No. | Name | Structure | Can Be Made According To Synthetic Example #: |
|---|---|---|---|
| 146 | 3-({4-[4-(acetylamino)phenyl]pyrimidin-2-yl}amino)-N-(pyridin-4-ylmethyl)benzamide | 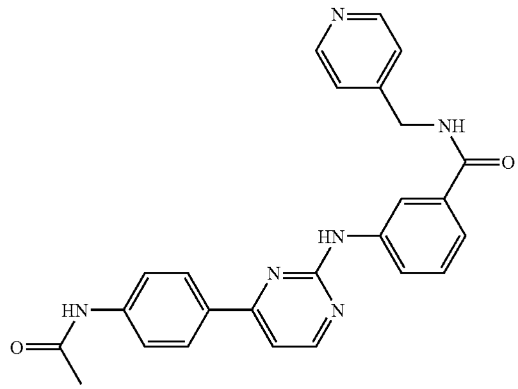 | 29 |
| 147 | 3-({4-[4-(acetylamino)phenyl]pyrimidin-2-yl}amino)-N-methyl-N-(phenylmethyl)benzamide | 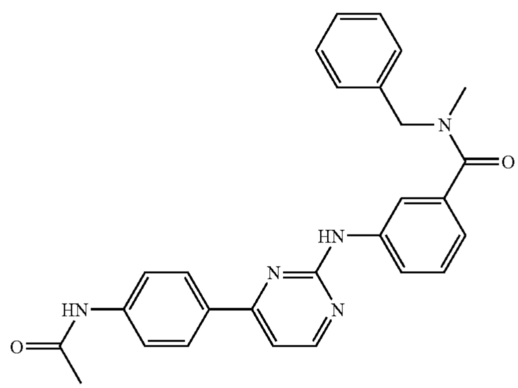 [SMILES: CC(=O)Nc1ccc(-c2ccnc(Nc3cccc(C(=O)N(C)Cc4ccccc4)c3)n2)cc1] | 29 |
| 148 | 3-({4-[4-(acetylamino)phenyl]pyrimidin-2-yl}amino)-N-cyclopentylbenzamide | 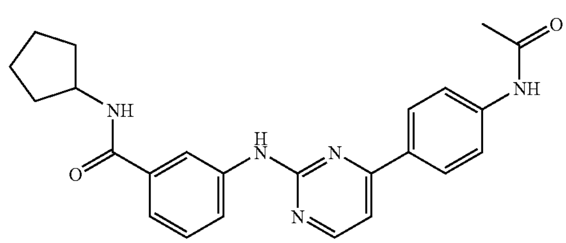 [SMILES: CC(=O)Nc1ccc(-c2ccnc(Nc3cccc(C(=O)NC4CCCC4)c3)n2)cc1] | 29 |
| 149 | 3-({4-[4-(acetylamino)phenyl]pyrimidin-2-yl}amino)-N-[(2-chlorophenyl)methyl]benzamide | 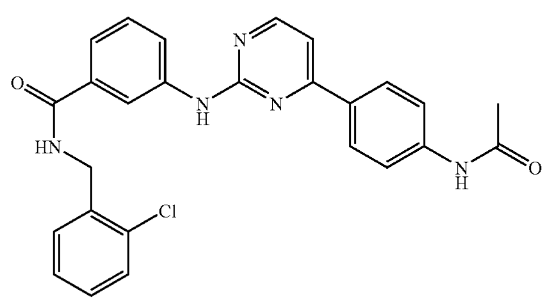 [SMILES: CC(=O)Nc1ccc(-c2ccnc(Nc3cccc(C(=O)NCc4ccccc4Cl)c3)n2)cc1] | 29 |

| Cmpd No. | Name | Structure | Can Be Made According To Synthetic Example #: |
|---|---|---|---|
| 150 | 3-({4-[4-(acetylamino)phenyl]pyrimidin-2-yl}amino)-N-[(4-chlorophenyl)methyl]benzamide | 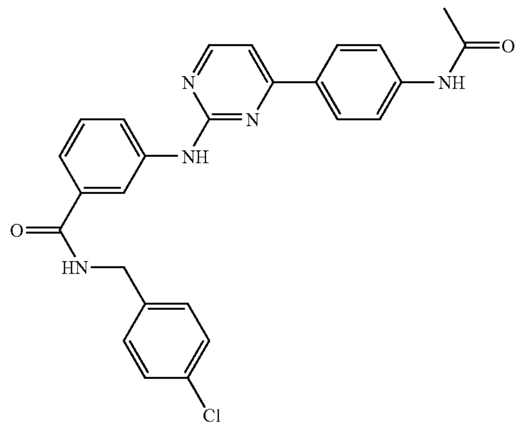 [SMILES: CC(=O)Nc1ccc(-c2ccnc(Nc3cccc(C(=O)NCc4ccc(Cl)cc4)c3)n2)cc1] | 29 |
| 151 | 3-({4-[4-(acetylamino)phenyl]pyrimidin-2-yl}amino)-N-(furan-2-ylmethyl)benzamide | 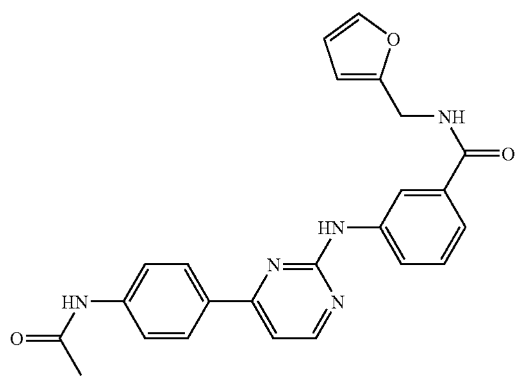 [SMILES: CC(=O)Nc1ccc(-c2ccnc(Nc3cccc(C(=O)NCc4ccco4)c3)n2)cc1] | 29 |
| 152 | 3-({4-[4-(acetylamino)phenyl]pyrimidin-2-yl}amino)-N-{[4-(methyloxy)phenyl]methyl}benzamide | 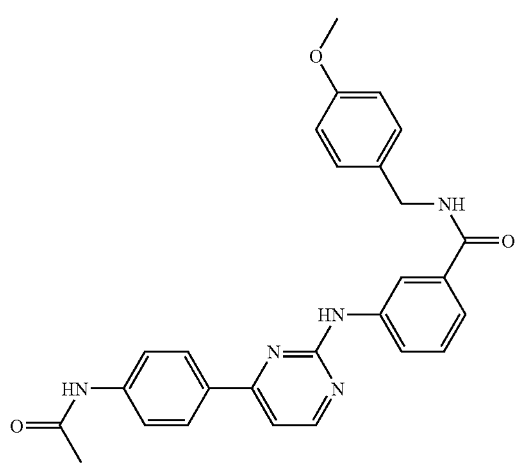 [SMILES: COc1ccc(CNC(=O)c2cccc(Nc3nccc(-c4ccc(NC(C)=O)cc4)n3)c2)cc1] | 29 |

TABLE 1-continued

| Cmpd No. | Name | Structure | Can Be Made According To Synthetic Example #: |
|---|---|---|---|
| 153 | N-[4-(2-{[3-({4-[2-(methyloxy)phenyl]piperazin-1-yl}carbonyl)phenyl]amino}pyrimidin-4-yl)phenyl]acetamide | 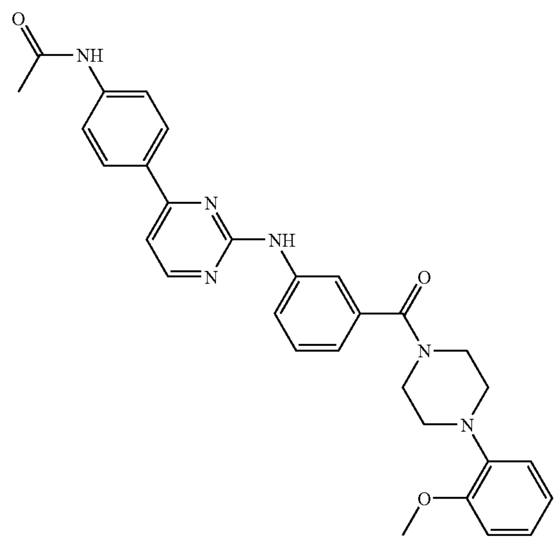 [SMILES: COc1ccccc1N1CCN(C(=O)c2cccc(Nc3nccc(-c4ccc(NC(C)=O)cc4)n3)c2)CC1] | 29 |
| 154 | 3-({4-[4-(acetylamino)phenyl]pyrimidin-2-yl}amino)-N-[3-(methyloxy)propyl]benzamide | 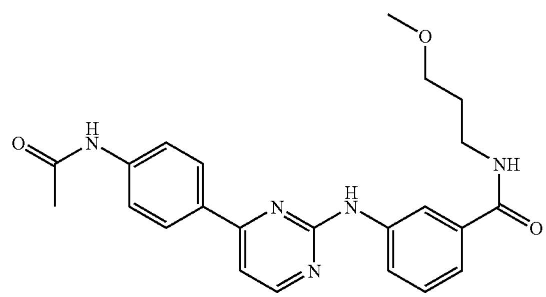 [SMILES: COCCCNC(=O)c1cccc(Nc2nccc(-c3ccc(NC(C)=O)cc3)n2)c1] | 29 |
| 155 | N-(4-{2-[(3-{[(2R,6S)-2,6-dimethylmorpholin-4-yl]carbonyl}phenyl)amino]pyrimidin-4-yl}phenyl)acetamide | 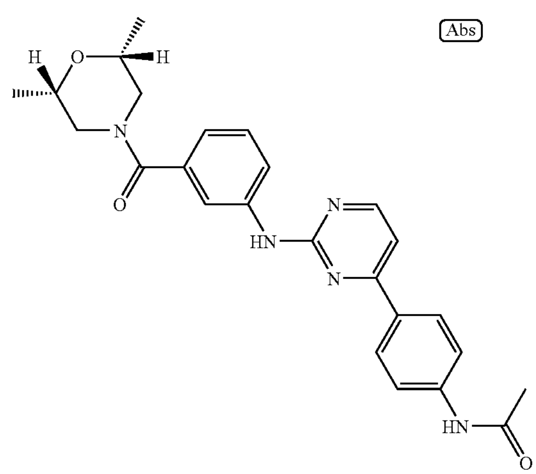 [SMILES: CC(=O)Nc1ccc(-c2ccnc(Nc3cccc(C(=O)N4C[C@@H](C)O[C@@H](C)C4)c3)n2)cc1] | 29 |

TABLE 1-continued

| Cmpd No. | Name | Structure | Can Be Made According To Synthetic Example #: |
|---|---|---|---|
| 156 | 3-({4-[4-(acetylamino)phenyl]pyrimidin-2-yl}amino)-N-[(6-chloropyridin-3-yl)methyl]benzamide | 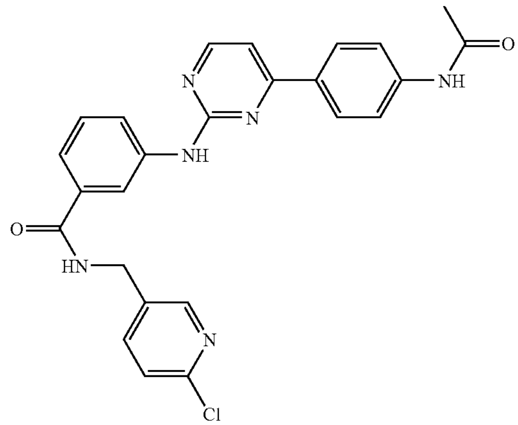 [SMILES: CC(=O)Nc1ccc(-c2ccnc(Nc3cccc(C(=O)NCc4ccc(Cl)nc4)c3)n2)cc1] | 29 |
| 157 | 3-({4-[4-(acetylamino)phenyl]pyrimidin-2-yl}amino)-N-butylbenzamide | 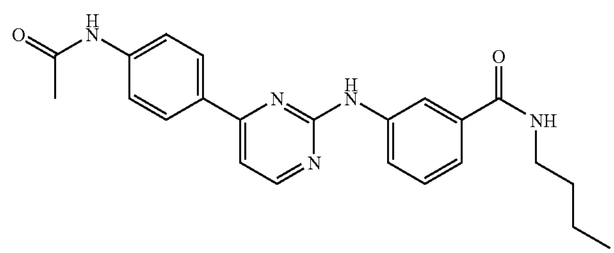 | 29 |
| 158 | N-(4-{2-[(3-{[4-(2-chloro-phenyl)piperazin-1-yl]carbonyl}phenyl)amino]pyrimidin-4-yl}phenyl)acetamide | 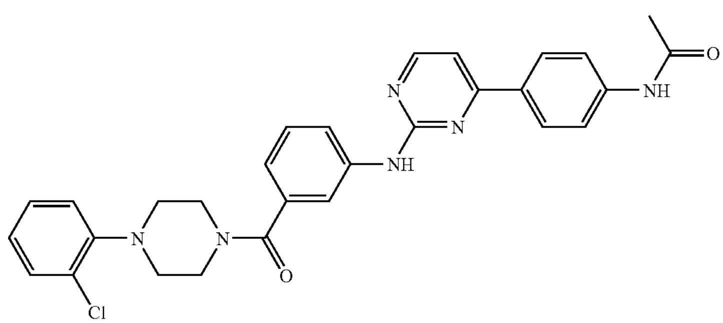 [SMILES: CC(=O)Nc1ccc(-c2ccnc(Nc3cccc(C(=O)N4CCN(c5ccccc5Cl)CC4)c3)n2)cc1] | 29 |
| 159 | 3-({4-[4-(acetylamino)phenyl]pyrimidin-2-yl}amino)-N-ethyl-N-[2-(methyloxy)ethyl]benzamide | 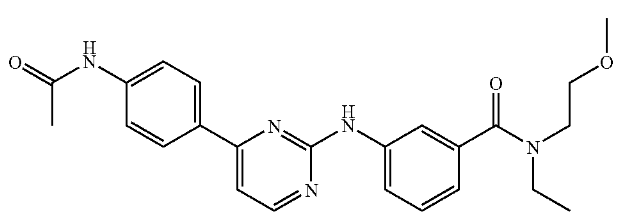 [SMILES: CCN(CCOC)C(=O)c1cccc(Nc2nccc(-c3ccc(NC(C)=O)cc3)n2)c1] | 29 |

TABLE 1-continued

| Cmpd No. | Name | Structure | Can Be Made According To Synthetic Example #: |
|---|---|---|---|
| 160 | N-(4-(2-(3-(3-morpholino-propoxy)phenylamino)pyrimidin-4-yl)phenyl)acetamide | 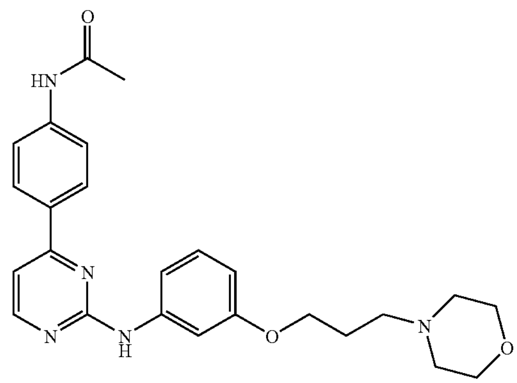 [SMILES: CC(=O)Nc1ccc(-c2ccnc(Nc3cccc(OCCCN4CCOCC4)c3)n2)cc1] | 35 |
| 161 | N-(4-(2-(3-(2-(dimethyl-amino)ethoxy)phenylamino)pyrimidin-4-yl)phenyl)acetamide | 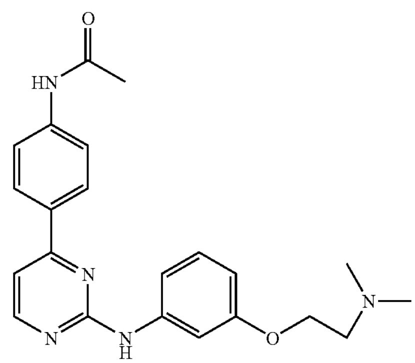 [SMILES: CC(=O)Nc1ccc(-c2ccnc(Nc3cccc(OCCN(C)C)c3)n2)cc1] | 33 |
| 162 | N-[3-({4-[4-(acetylamino)phenyl]-5-methylpyrimidin-2-yl}amino)phenyl]-2,6-dimethylbenzamide | 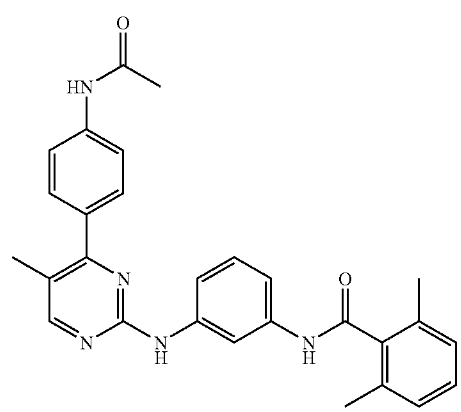 [SMILES: CC(=O)Nc1ccc(-c2nc(Nc3cccc(NC(=O)c4c(C)cccc4C)c3)ncc2C)cc1] | 39 |
| 163 | N-[4-(2-{[4-(phenyloxy)phenyl]amino}pyrimidin-4-yl)phenyl]acetamide | 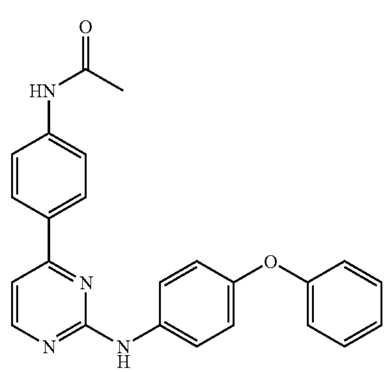 [SMILES: CC(=O)Nc1ccc(-c2ccnc(Nc3ccc(Oc4ccccc4)cc3)n2)cc1] | 3 |

TABLE 1-continued

| Cmpd No. | Name | Structure | Can Be Made According To Synthetic Example #: |
|---|---|---|---|
| 164 | 4-(4-aminophenyl)-N-[4-(phenyloxy)phenyl]pyrimidin-2-amine | 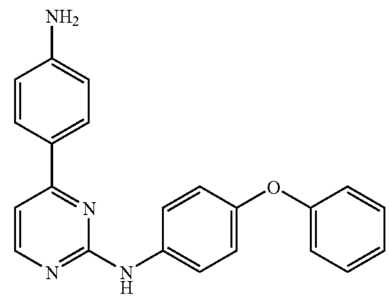 [SMILES: Nc1ccc(-c2ccnc(Nc3ccc(Oc4ccccc4)cc3)n2)cc1] | 8 |
| 165 | N-{4-[2-({4-[(phenyl-methyl)oxy]phenyl}amino)pyrimidin-4-yl]phenyl}acetamide | 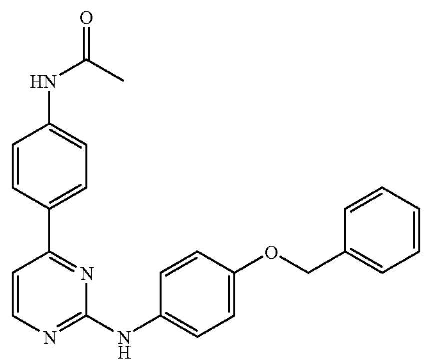 [SMILES: CC(=O)Nc1ccc(-c2ccnc(Nc3ccc(OCc4ccccc4)cc3)n2)cc1] | 3 |
| 166 | 4-(4-aminophenyl)-N-[3-(morpholin-4-ylsulfonyl)phenyl]pyrimidin-2-amine | 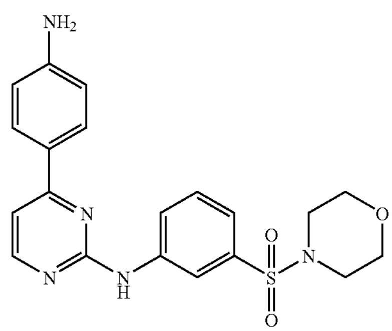 [SMILES: Nc1ccc(-c2ccnc(Nc3cccc(S(=O)(=O)N4CCOCC4)c3)n2)cc1] | 8 |
| 167 | N-(4-{2-[(3,5-dimorpholin-4-ylphenyl)amino]-5-fluoropyrimidin-4-yl}phenyl)acetamide | 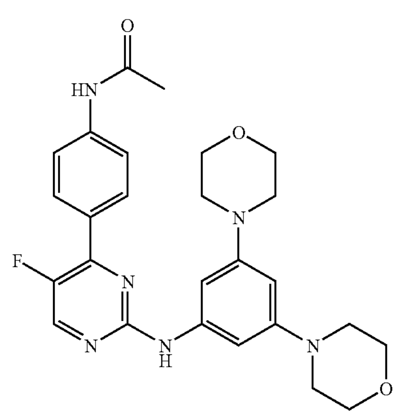 [SMILES: CC(=O)Nc1ccc(-c2nc(Nc3cc(N4CCOCC4)cc(N4CCOCC4)c3)ncc2F)cc1] | 6 |

TABLE 1-continued

| Cmpd No. | Name | Structure | Can Be Made According To Synthetic Example #: |
|---|---|---|---|
| 168 | N-{4-[2-({4-[4-(phenyl-methyl)piperazin-1-yl]phenyl}amino)pyrimidin-4-yl]phenyl}acetamide | 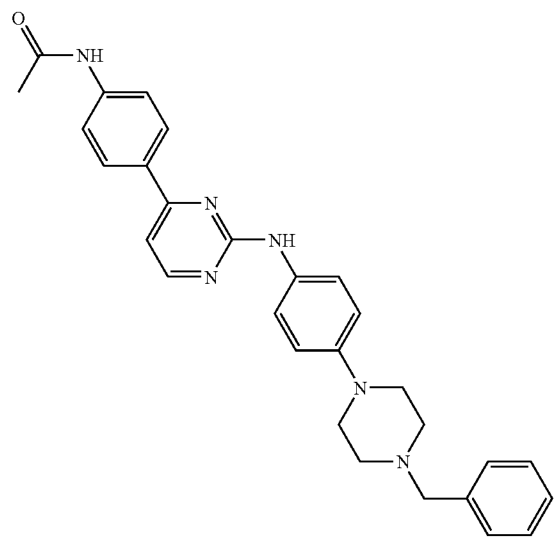 [SMILES: CC(=O)Nc1ccc(-c2ccnc(Nc3ccc(N4CCN(Cc5ccccc5)CC4)cc3)n2)cc1] | 49 |
| 169 | N-(4-{2-[(4-{4-[(5-methyl-3-phenylisoxazol-4-yl)methyl]piperazin-1-yl}phenyl)amino]pyrimidin-4-yl}phenyl)acetamide | 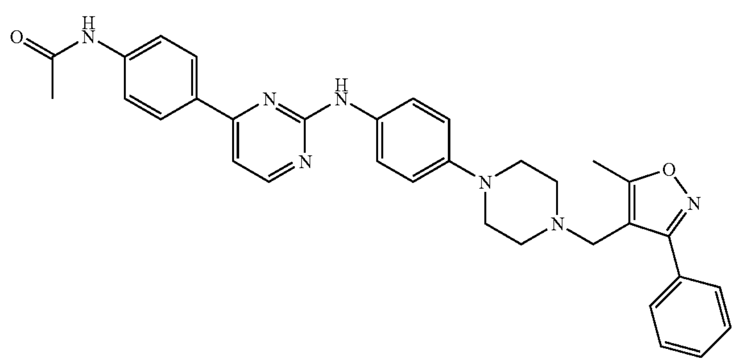 [SMILES: CC(=O)Nc1ccc(-c2ccnc(Nc3ccc(N4CCN(Cc5c(-c6ccccc6)noc5C)CC4)cc3)n2)cc1] | 49 |
| 170 | N-(4-{2-[(4-{4-[(5-methyl-1-phenyl-1H-pyrazol-4-yl)methyl]piperazin-1-yl}phenyl)amino]pyrimidin-4-yl}phenyl)acetamide | 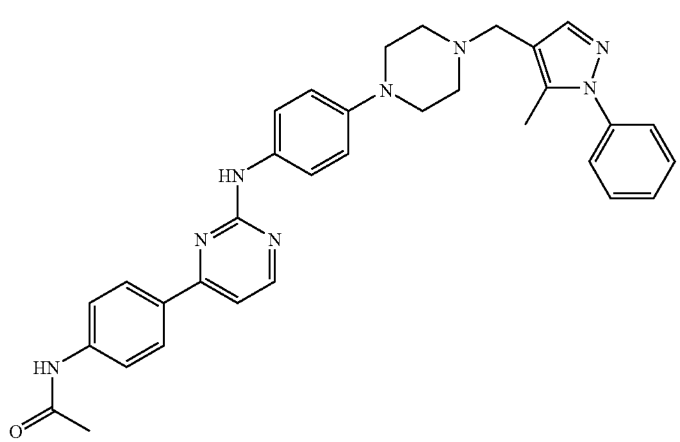 [SMILES: CC(=O)Nc1ccc(-c2ccnc(Nc3ccc(N4CCN(Cc5cnn(-c6ccccc6)c5C)CC4)cc3)n2)cc1] | 49 |

TABLE 1-continued

| Cmpd No. | Name | Structure | Can Be Made According To Synthetic Example #: |
|---|---|---|---|
| 171 | N-(4-{2-[(4-{4-[(2-phenyl-1,3-thiazol-4-yl)methyl]piperazin-1-yl}phenyl)amino]pyrimidin-4-yl}phenyl)acetamide | 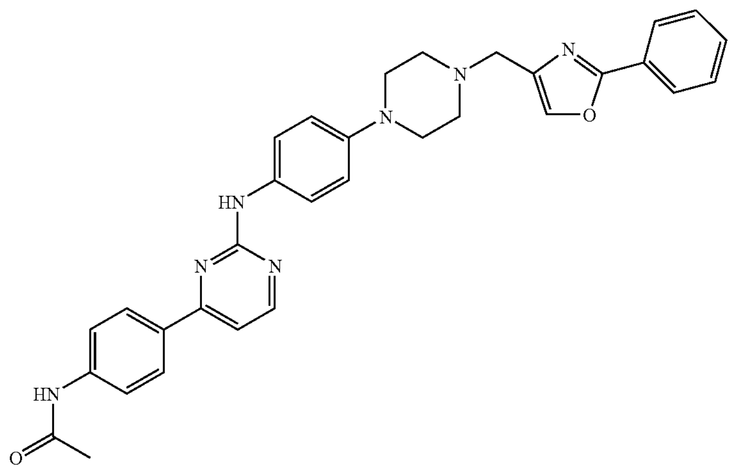 [SMILES: CC(=O)Nc1ccc(-c2ccnc(Nc3ccc(N4CCN(Cc5coc(-c6ccccc6)n5)CC4)cc3)n2)cc1] | 49 |
| 172 | N-[4-(2-{[4-(4-{[6-(phenyloxy)pyridin-3-yl]methyl}piperazin-1-yl)phenyl]amino}pyrimidin-4-yl)phenyl]acetamide | 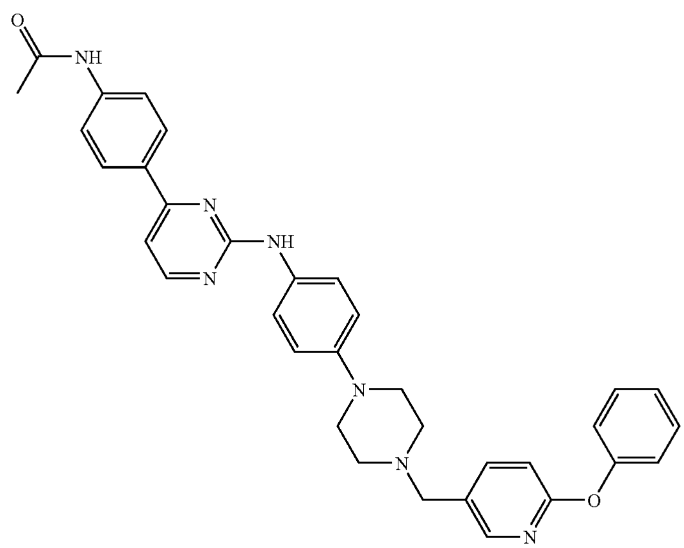 [SMILES: CC(=O)Nc1ccc(-c2ccnc(Nc3ccc(N4CCN(Cc5ccc(Oc6ccccc6)nc5)CC4)cc3)n2)cc1] | 49 |
| 173 | N-{4-[2-({4-[4-(cyclohexyl-methyl)piperazin-1-yl]phenyl}amino)pyrimidin-4-yl]phenyl}acetamide | 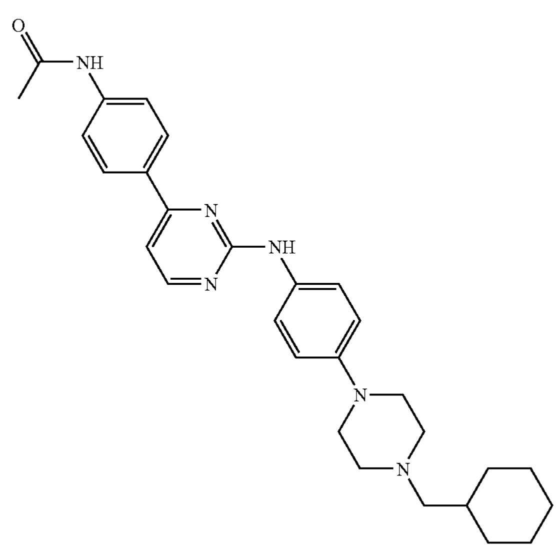 [SMILES: CC(=O)Nc1ccc(-c2ccnc(Nc3ccc(N4CCN(CC5CCCCC5)CC4)cc3)n2)cc1] | 49 |

| Cmpd No. | Name | Structure | Can Be Made According To Synthetic Example #: |
|---|---|---|---|
| 174 | N-(4-{2-[(4-{4-[(1S,4S)-bicyclo[2.2.1]hept-5-en-2-ylmethyl]piperazin-1-yl}phenyl)amino}pyrimidin-4-yl}phenyl)acetamide | 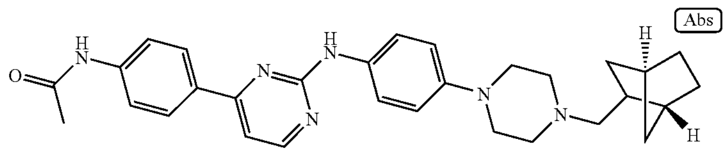 [SMILES: CC(=O)Nc1ccc(-c2ccnc(Nc3ccc(N4CCN(CC5C[C@H]6CC[C@@H]5C6)CC4)cc3)n2)cc1] | 49 |
| 175 | N-[4-(2-{[4-(4-pentyl-piperazin-1-yl)phenyl]amino}pyrimidin-4-yl)phenyl]acetamide | 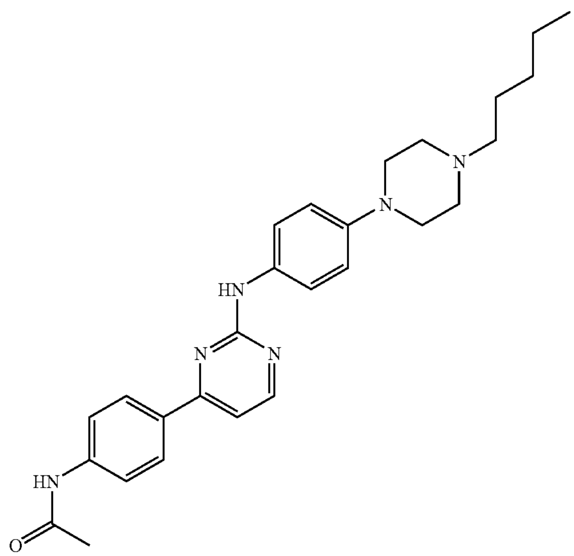 [SMILES: CCCCCN1CCN(c2ccc(Nc3nccc(-c4ccc(NC(C)=O)cc4)n3)cc2)CC1] | 49 |
| 176 | N-(4-{2-[(4-{4-[(2-chlorophenyl)methyl]piperazin-1-yl}phenyl)amino]pyrimidin-4-yl}phenyl)acetamide | 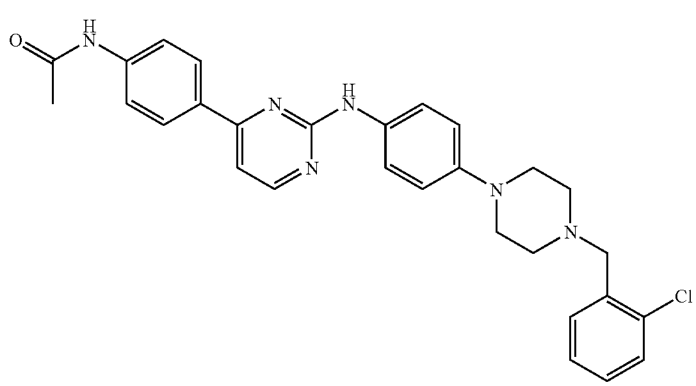 [SMILES: CC(=O)Nc1ccc(-c2ccnc(Nc3ccc(N4CCN(Cc5ccccc5Cl)CC4)cc3)n2)cc1] | 49 |

TABLE 1-continued

| Cmpd No. | Name | Structure | Can Be Made According To Synthetic Example #: |
|---|---|---|---|
| 177 | N-[4-(2-{[4-(4-{[3,5-bis(methyloxy)phenyl]methyl]piperazin-1-yl)phenyl]amino}pyrimidin-4-yl)phenyl]acetamide | 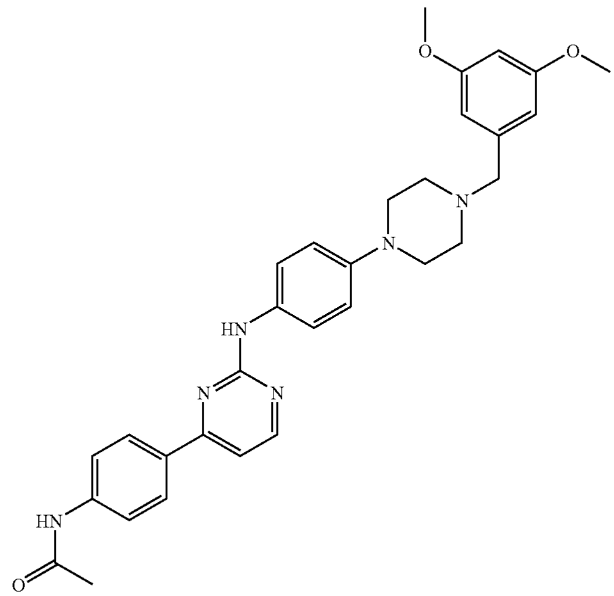 [SMILES: COc1cc(CN2CCN(c3ccc(Nc4nccc(-c5ccc(NC(C)=O)cc5)n4)cc3)CC2)cc(OC)c1] | 49 |
| 178 | N-(4-{2-[(4-{4-[(4-fluorophenyl)methyl]piperazin-1-yl]phenyl)amino]pyrimidin-4-yl}phenyl)acetamide | 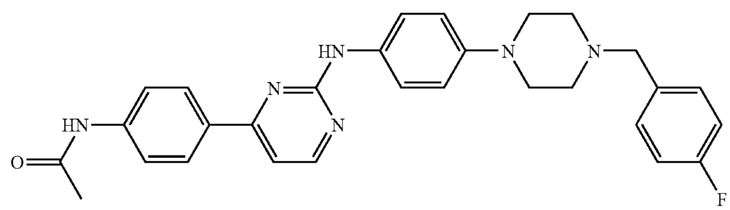 [SMILES: CC(=O)Nc1ccc(-c2ccnc(Nc3ccc(N4CCN(Cc5ccc(F)cc5)CC4)cc3)n2)cc1] | 49 |
| 179 | N-(4-{2-[(4-{4-[(1-methyl-1H-pyrrol-2-yl)methyl]piperazin-1-yl}phenyl)amino]pyrimidin-4-yl}phenyl)acetamide | 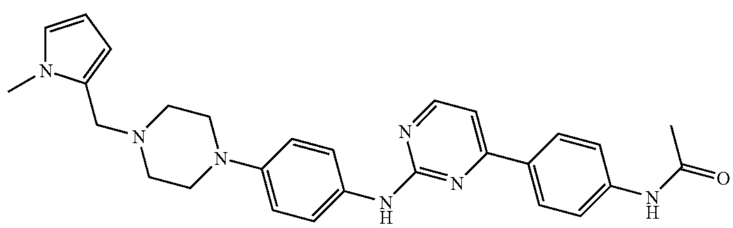 [SMILES: CC(=O)Nc1ccc(-c2ccnc(Nc3ccc(N4CCN(Cc5cccn5C)CC4)cc3)n2)cc1] | 49 |
| 180 | N-(4-{2-[(4-{4-[(2,4-dichlorophenyl)methyl]piperazin-1-yl}phenyl)amino]pyrimidin-4-yl}phenyl)acetamide | 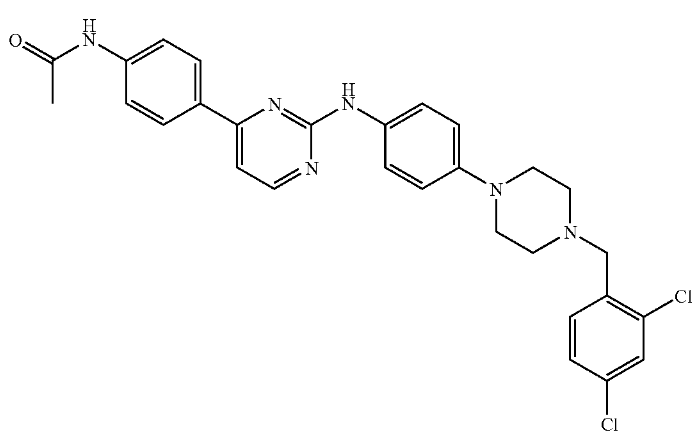 [SMILES: CC(=O)Nc1ccc(-c2ccnc(Nc3ccc(N4CCN(Cc5ccc(Cl)cc5Cl)CC4)cc3)n2)cc1] | 49 |

TABLE 1-continued

| Cmpd No. | Name | Structure | Can Be Made According To Synthetic Example #: |
|---|---|---|---|
| 181 | N-{4-[2-({4-[4-(9H-fluoren-2-ylmethyl)piperazin-1-yl]phenyl}amino)pyrimidin-4-yl]phenyl)acetamide | 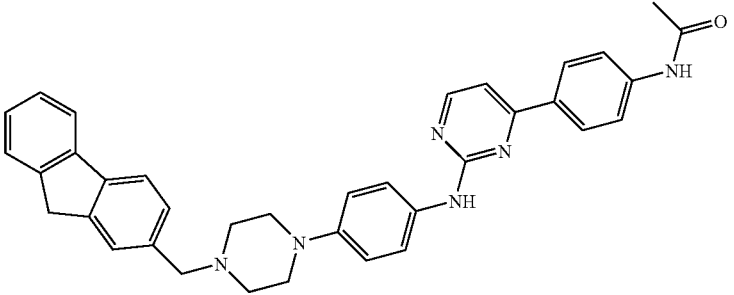 [SMILES: CC(=O)Nc1ccc(-c2ccnc(Nc3ccc(N4CCN(Cc5ccc6c(c5)Cc5ccccc5-6)CC4)cc3)n2)cc1] | 49 |
| 182 | N-(4-{2-[(4-{4-[(3-methyl-2-thienyl)methyl]piperazin-1-yl}phenyl)amino]pyrimidin-4-yl}phenyl)acetamide | 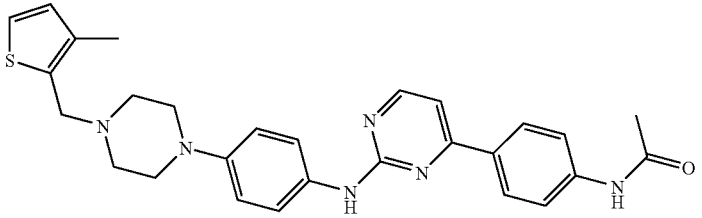 [SMILES: CC(=O)Nc1ccc(-c2ccnc(Nc3ccc(N4CCN(Cc5sccc5C)CC4)cc3)n2)cc1] | 49 |
| 183 | N-(4-{2-[(4-{4-[(5-ethylfuran-2-yl)methyl]piperazin-1-yl}phenyl)amino]pyrimidin-4-yl}phenyl)acetamide | 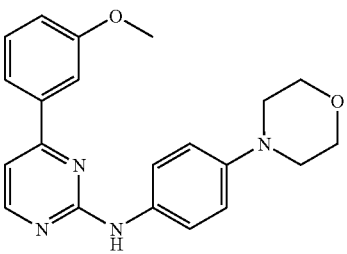 [SMILES: COc1cccc(-c2ccnc(Nc3ccc(N4CCOCC4)cc3)n2)c1] | 49 |
| 184 | N-(4-{2-[(4-{4-[(3-{[4-(1,1-dimethylethyl)phenyl]oxy}phenyl)methyl]piperazin-1-yl}phenyl)amino]pyrimidin-4-yl}phenyl)acetamide | 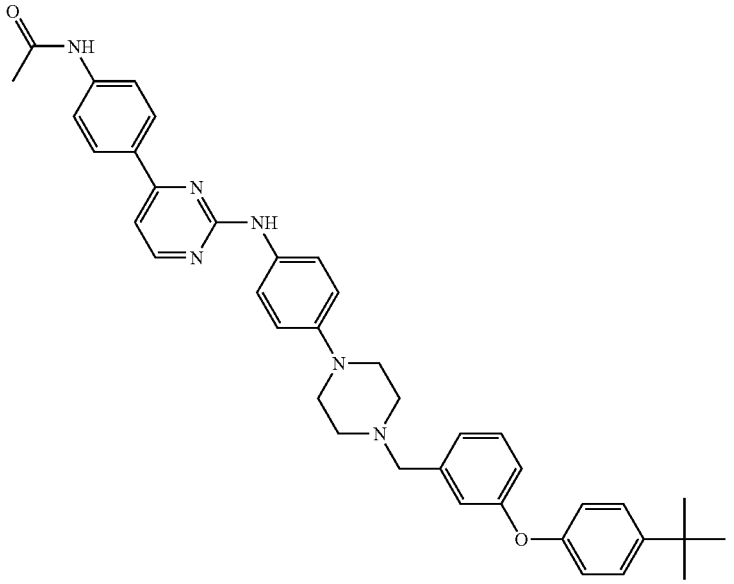 [SMILES: CC(=O)Nc1ccc(-c2ccnc(Nc3ccc(N4CCN(Cc5cccc(Oc6ccc(C(C)(C)C)cc6)c5)CC4)cc3)n2)cc1] | 49 |

TABLE 1-continued

| Cmpd No. | Name | Structure | Can Be Made According To Synthetic Example #: |
|---|---|---|---|
| 185 | N-{4-[2-({4-[4-(3-thienyl-methyl)piperazin-1-yl]phenyl}amino)pyrimidin-4-yl]phenyl}acetamide | 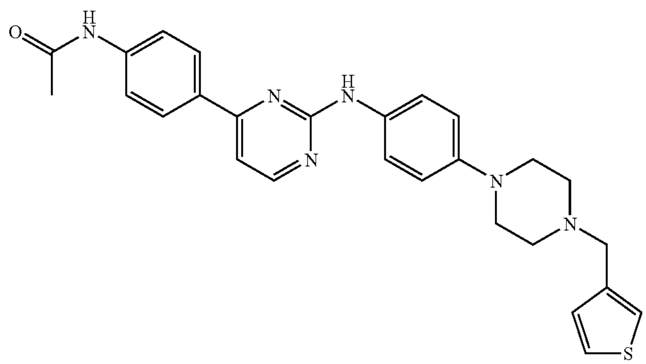 [SMILES: CC(=O)Nc1ccc(-c2ccnc(Nc3ccc(N4CCN(Cc5ccsc5)CC4)cc3)n2)cc1] | 49 |
| 186 | methyl 4-({4-[4-({4-[4-(acetylamino)phenyl]pyrimidin-2-yl}amino)phenyl]piperazin-1-yl}methyl)benzoate | 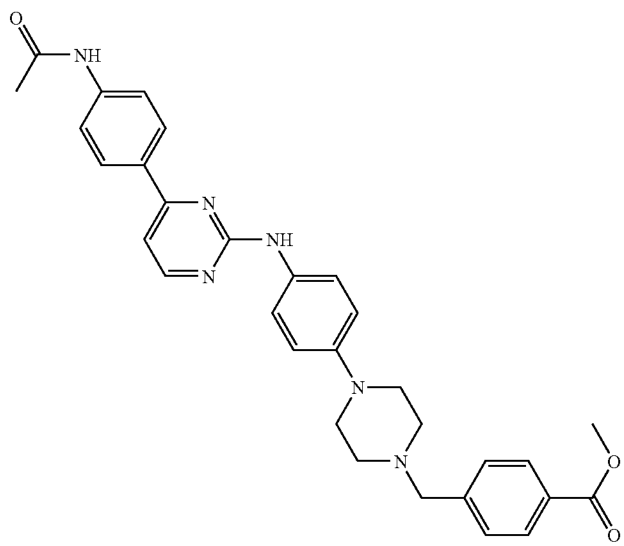 [SMILES: COC(=O)c1ccc(CN2CCN(c3ccc(Nc4nccc(-c5ccc(NC(C)=O)cc5)n4)cc3)CC2)cc1] | 49 |
| 187 | N-(4-{2-[(4-{4-[3-(methylthio)propyl]piperazin-1-yl}phenyl)amino]pyrimidin-4-yl}phenyl)acetamide | 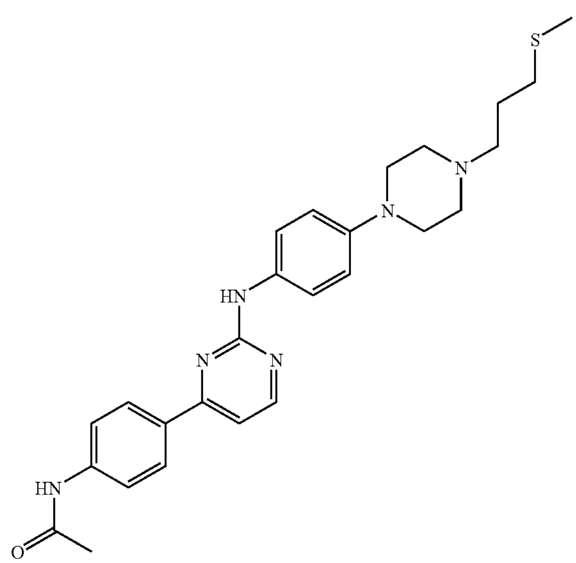 | 49 |

| Cmpd No. | Name | Structure | Can Be Made According To Synthetic Example #: |
|---|---|---|---|
| 188 | N-(4-{2-[(4-{4-[(4-{[3-(dimethylamino)propyl]oxy}phenyl)methyl]piperazin-1-yl}phenyl)amino]pyrimidin-4-yl}phenyl)acetamide | 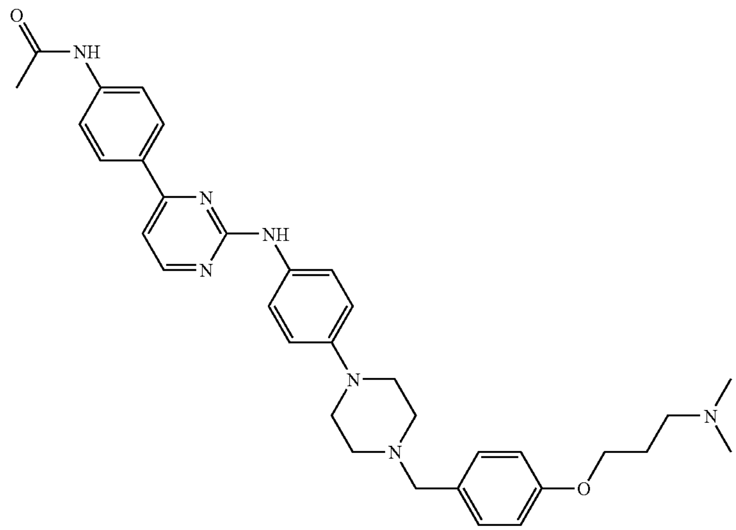 [SMILES: CC(=O)Nc1ccc(-c2ccnc(Nc3ccc(N4CCN(Cc5ccc(OCCCN(C)C)cc5)CC4)cc3)n2)cc1] | 49 |
| 189 | N-[4-(2-{[4-(4-{2-[(phenylmethyl)oxy]ethyl}piperazin-1-yl)phenyl]amino}pyrimidin-4-yl)phenyl]acetamide | 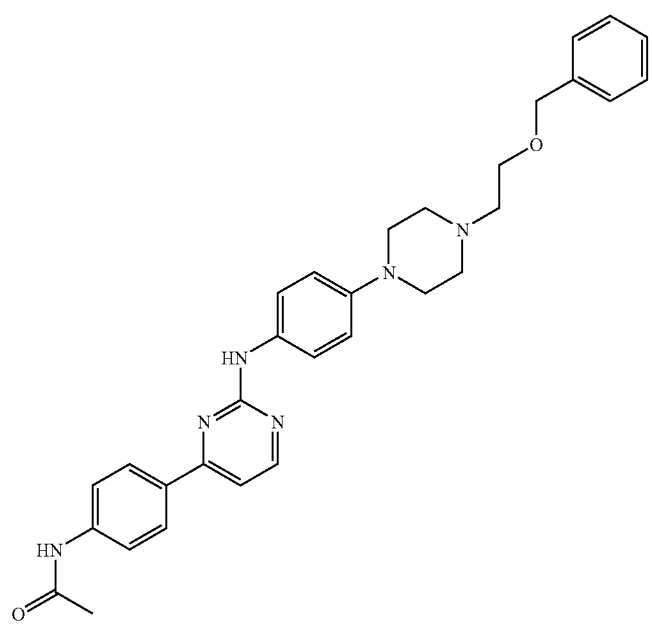 [SMILES: CC(=O)Nc1ccc(-c2ccnc(Nc3ccc(N4CCN(CCOCc5ccccc5)CC4)cc3)n2)cc1] | 49 |

TABLE 1-continued

| Cmpd No. | Name | Structure | Can Be Made According To Synthetic Example #: |
|---|---|---|---|
| 190 | N-(4-{2-[(4-{4-[(2-chloro-quinolin-3-yl)methyl]piperazin-1-yl}phenyl)amino]pyrimidin-4-yl}phenyl)acetamide | 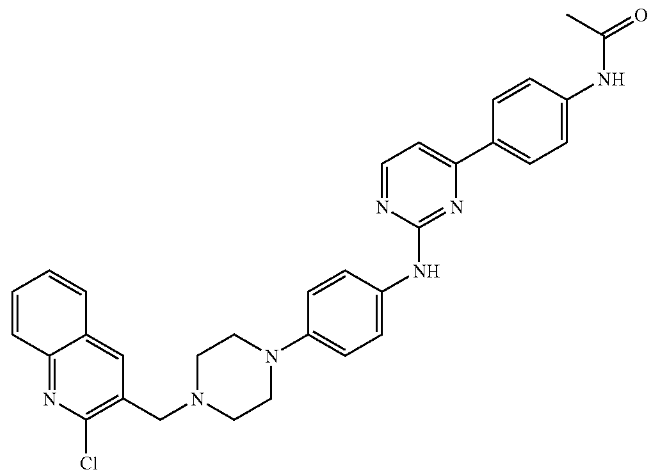 [SMILES: CC(=O)Nc1ccc(-c2ccnc(Nc3ccc(N4CCN(Cc5cc6ccccc6nc5Cl)CC4)cc3)n2)cc1] | 49 |
| 191 | N-(4-{2-[(4-{4-[(4-chloro-2,6-dimethylphenyl)sulfonyl]piperazin-1-yl}phenyl)amino]pyrimidin-4-yl}phenyl)acetamide | 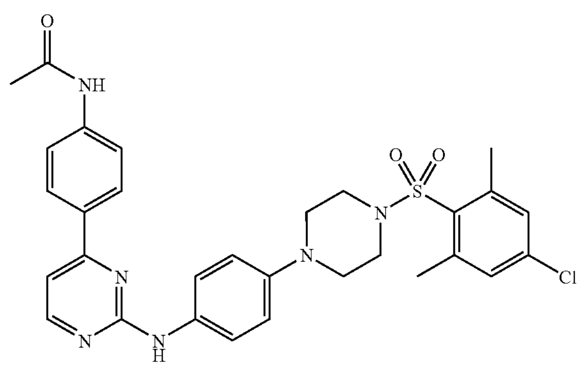 [SMILES: CC(=O)Nc1ccc(-c2ccnc(Nc3ccc(N4CCN(S(=O)(=O)c5c(C)cc(Cl)cc5C)CC4)cc3)n2)cc1] | 7 |
| 192 | N-{1-[4-({4-[4-(acetylamino)phenyl]pyrimidin-2-yl}amino)phenyl]pyrrolidin-3-yl}acetamide | 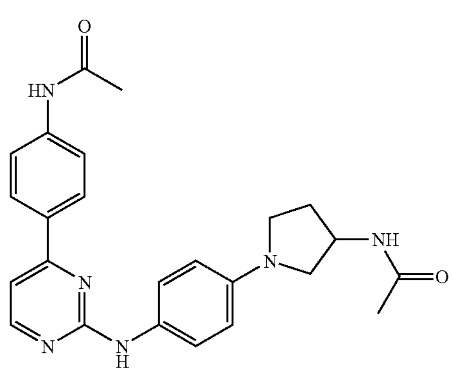 [SMILES: CC(=O)Nc1ccc(-c2ccnc(Nc3ccc(N4CCC(NC(C)=O)C4)cc3)n2)cc1] | 3 |

TABLE 1-continued

| Cmpd No. | Name | Structure | Can Be Made According To Synthetic Example #: |
|---|---|---|---|
| 193 | N²-[3-(4-methylpiperazin-1-yl)propyl]-N-(4-{2-[(4-morpholin-4-ylphenyl)amino}pyrimidin-4-yl}phenyl)glycinamide | 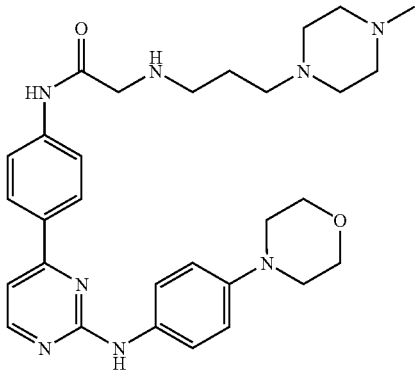 [SMILES: CN1CCN(CCCNCC(=O)Nc2ccc(-c3ccnc(Nc4ccc(N5CCOCC5)cc4)n3)cc2)CC1] | 23 |
| 194 | N²-(1-methylpiperidin-4-yl)-N-(4-{2-[(4-morpholin-4-ylphenyl)amino]pyrimidin-4-yl}phenyl)glycinamide | 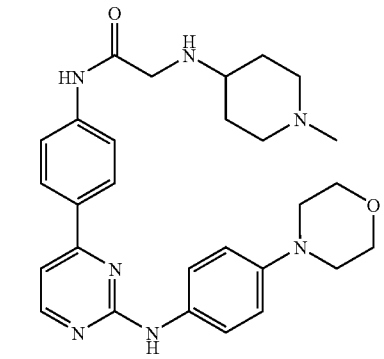 [SMILES: CN1CCC(NCC(=O)Nc2ccc(-c3ccnc(Nc4ccc(N5CCOCC5)cc4)n3)cc2)CC1] | 23 |
| 195 | N-{4-[2-({4-[(pyridin-4-ylmethyl)oxy]phenyl}amino)pyrimidin-4-yl]phenyl}acetamide | 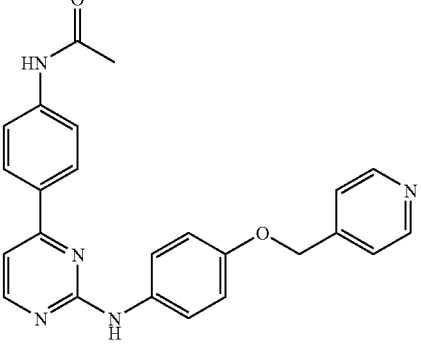 | 33 |
| 196 | N-(4-{2-[(4-{[2-(methyloxy)ethyl]amino}phenyl)amino]pyrimidin-4-yl}phenyl)aceamide | 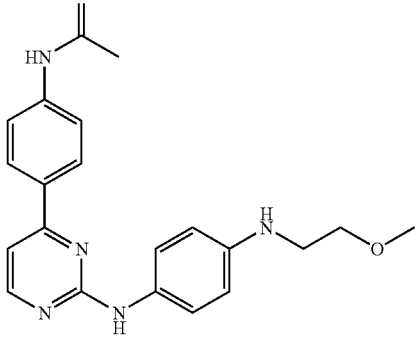 | 28 |

TABLE 1-continued

| Cmpd No. | Name | Structure | Can Be Made According To Synthetic Example #: |
|---|---|---|---|
| 197 | 2-(dimethylamino)-N-(4-(2-(4-morpholinophenylamino)pyrimidin-4-yl)phenyl)acetamide | 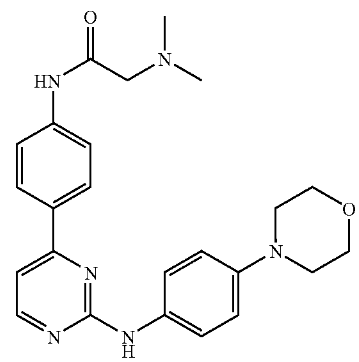 [SMILES: CN(C)CC(=O)Nc1ccc(-c2ccnc(Nc3ccc(N4CCOCC4)cc3)n2)cc1] | 12 |
| 198 | N-(4-{2-[(4-morpholin-4-ylphenyl)amino]pyrimidin-4-yl}phenyl)furan-2-carboxamide | 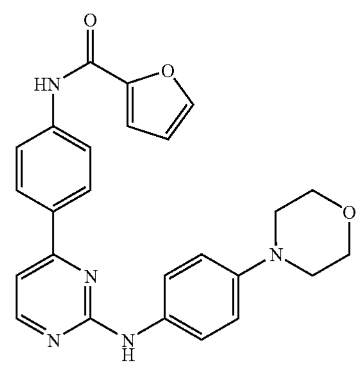 [SMILES: O=C(Nc1ccc(-c2ccnc(Nc3ccc(N4CCOCC4)cc3)n2)cc1)c1ccco1] | 12 |
| 199 | 2-(methyloxy)-N-(4-{2-[(4-morpholin-4-ylphenyl)amino]pyrimidin-4-yl}phenyl)acetamide | 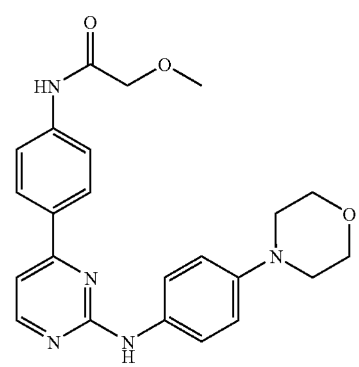 [SMILES: COCC(=O)Nc1ccc(-c2ccnc(Nc3ccc(N4CCOCC4)cc3)n2)cc1] | 12 |
| 200 | N-(4-{2-[(4-morpholin-4-ylphenyl)amino]pyrimidin-4-yl}phenyl)cyclobutanecarboxamide | 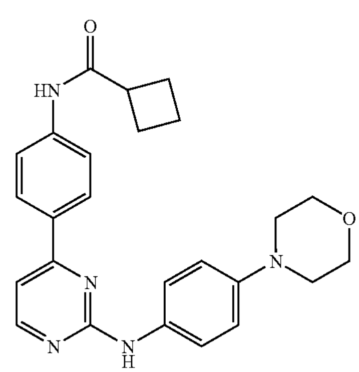 [SMILES: O=C(Nc1ccc(-c2ccnc(Nc3ccc(N4CCOCC4)cc3)n2)cc1)C1CCC1] | 12 |

TABLE 1-continued

| Cmpd No. | Name | Structure | Can Be Made According To Synthetic Example #: |
|---|---|---|---|
| 201 | N-(4-{2-[(4-morpholin-4-ylphenyl)amino]pyrimidin-4-yl}phenyl)azetidine-3-carboxamide | 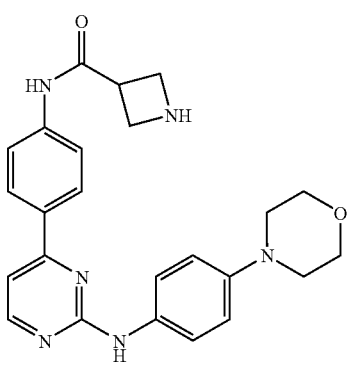 [SMILES: O=C(Nc1ccc(-c2ccnc(Nc3ccc(N4CCOCC4)cc3)n2)cc1)C1CNC1] | 13 |
| 202 | N-(4-{2-[(4-morpholin-4-ylphenyl)amino]pyrimidin-4-yl}phenyl)piperidine-2-carboxamide | 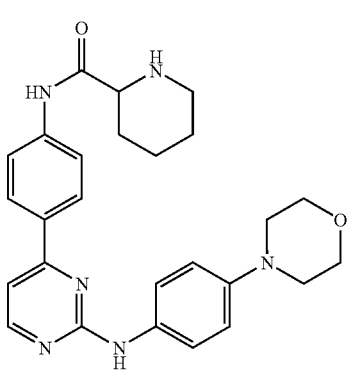 [SMILES: O=C(Nc1ccc(-c2ccnc(Nc3ccc(N4CCOCC4)cc3)n2)cc1)C1CCCCN1] | 13 |
| 203 | N-(4-{2-[(4-morpholin-4-ylphenyl)amino]pyrimidin-4-yl}phenyl)piperidine-3-carboxamide | 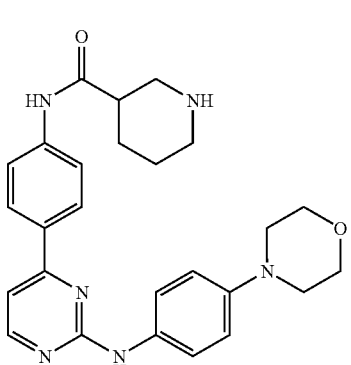 | 13 |
| 204 | N-[4-(2-{[4-(dimethylamino)phenyl]amino}pyrimidin-4-yl)phenyl]acetamide | 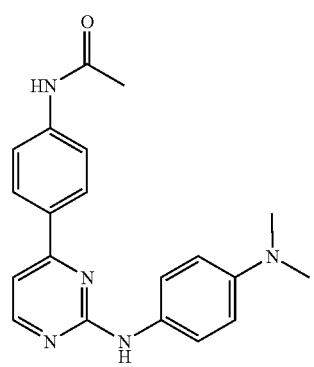 [SMILES: CC(=O)Nc1ccc(-c2ccnc(Nc3ccc(N(C)C)cc3)n2)cc1] | 3 |

TABLE 1-continued

| Cmpd No. | Name | Structure | Can Be Made According To Synthetic Example #: |
|---|---|---|---|
| 205 | N-(4-{2-[(4-chlorophenyl)amino]pyrimidin-4-yl}phenyl)acetamide | 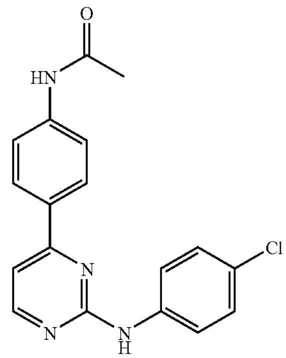 [SMILES: CC(=O)Nc1ccc(-c2ccnc(Nc3ccc(Cl)cc3)n2)cc1] | 3 |
| 206 | N-(4-{2-[(3-{[(2-fluorophenyl)methyl]amino}phenyl)amino]pyrimidin-4-yl}phenyl)acetamide | 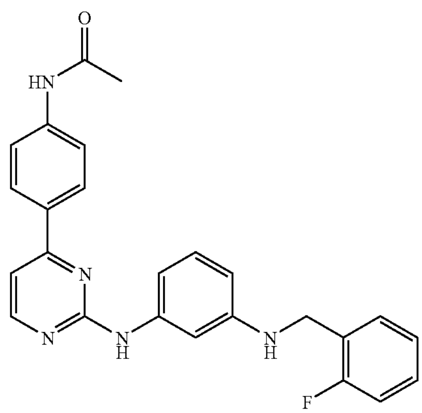 [SMILES: CC(=O)Nc1ccc(-c2ccnc(Nc3cccc(NCc4ccccc4F)c3)n2)cc1] | 28 |
| 207 | N-(4-{2-[(4-morpholin-4-ylphenyl)amino]pyrimidin-4-yl}phenyl)piperidine-4-carboxamide | 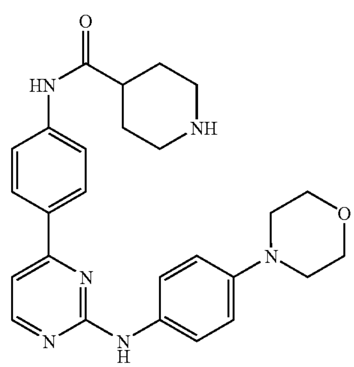 [SMILES: O=C(Nc1ccc(-c2ccnc(Nc3ccc(N4CCOCC4)cc3)n2)cc1)C1CCNCC1] | 13 |
| 208 | 2-amino-N-(4-(2-(4-morpholinophenylamino)pyrimidin-4-yl)phenyl)propanamide | 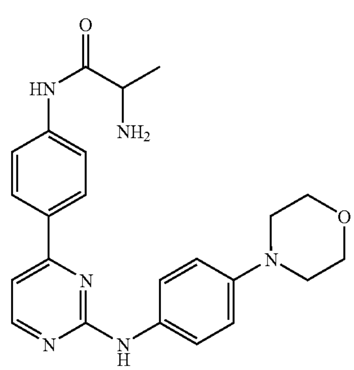 | 14 |

TABLE 1-continued
| Cmpd No. | Name | Structure | Can Be Made According To Synthetic Example #: |
|---|---|---|---|
| 209 | N-(4-{2-[(4-morpholin-4-ylphenyl)amino]pyrimidin-4-yl}phenyl)glycinamide | 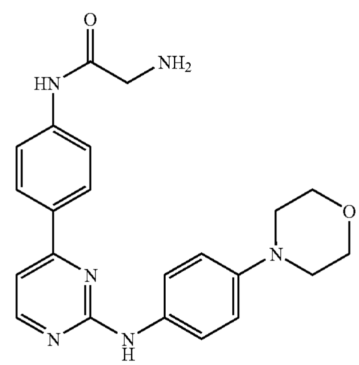 | 14 |
| 210 | N-(4-{2-[(4-morpholin-4-ylphenyl)amino]pyrimidin-4-yl}phenyl)morpholine-2-carboxamide | 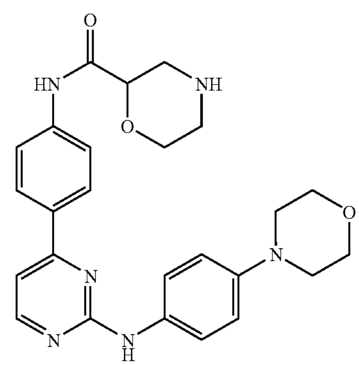 [SMILES: O=C(Nc1ccc(-c2ccnc(Nc3ccc(N4CCOCC4)cc3)n2)cc1)C1CNCCO1] | 13 |
| 211 | $N^2$-methyl-N-(4-{2-[(4-morpholin-4-ylphenyl)amino]pyrimidin-4-yl}phenyl)glycinamide | 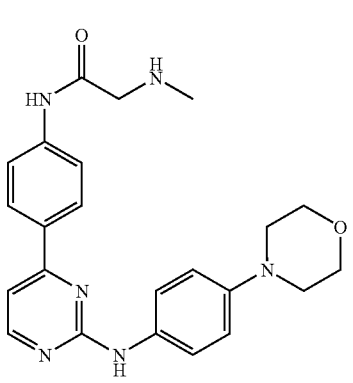 | 13 |
| 212 | N-(4-{2-[(4-morpholin-4-ylphenyl)amino]pyrimidin-4-yl}phenyl)-beta-alaninamide | 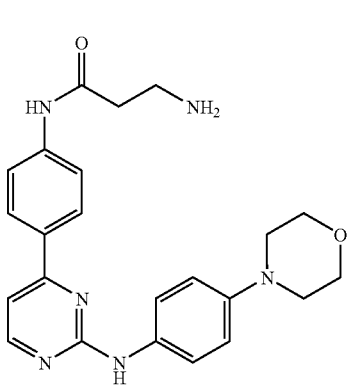 [SMILES: NCCC(=O)Nc1ccc(-c2ccnc(Nc3ccc(N4CCOCC4)cc3)n2)cc1] | 13 |

TABLE 1-continued

| Cmpd No. | Name | Structure | Can Be Made According To Synthetic Example #: |
|---|---|---|---|
| 213 | N-(4-{2-[(4-morpholin-4-ylphenyl)amino]pyrimidin-4-yl}phenyl)phenylalaninamide | 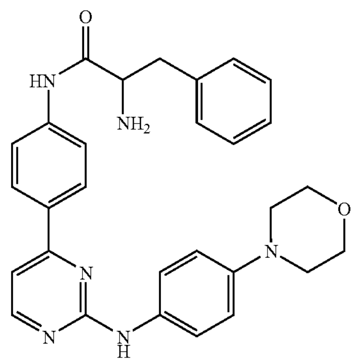 | 13 |
| 214 | N-[4-(2-{[4-(3-oxopiperazin-1-yl)phenyl]amino}pyrimidin-4-yl)phenyl]acetamide | 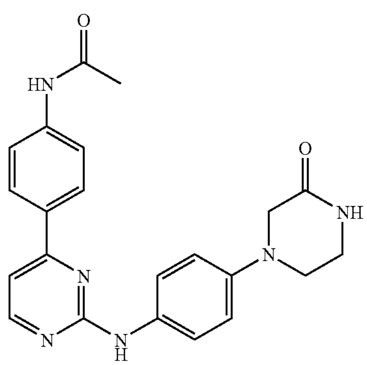 [SMILES: CC(=O)Nc1ccc(-c2ccnc(Nc3ccc(N4CCNC(=O)C4)cc3)n2)cc1] | 34 |
| 215 | N-[4-(2-{[4-(4-{[5-(3-chlorophenyl)furan-2-yl]methyl}piperazin-1-yl)phenyl]amino}pyrimidin-4-yl)phenyl]acetamide | 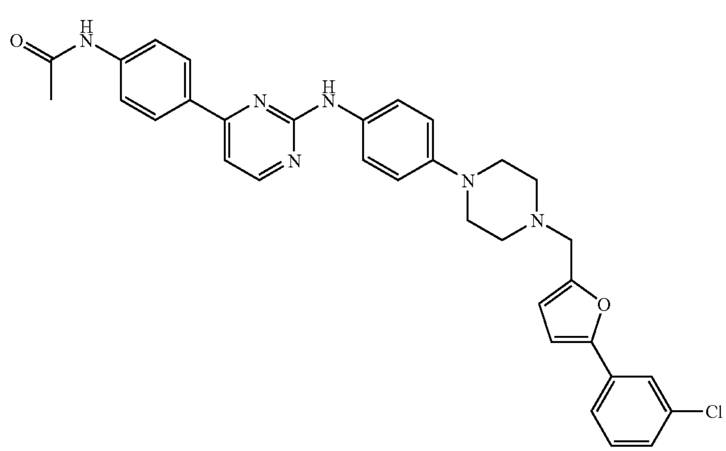 [SMILES: CC(=O)Nc1ccc(-c2ccnc(Nc3ccc(N4CCN(Cc5ccc(-c6cccc(Cl)c6)o5)CC4)cc3)n2)cc1] | 49 |

TABLE 1-continued

| Cmpd No. | Name | Structure | Can Be Made According To Synthetic Example #: |
|---|---|---|---|
| 216 | N-[4-(2-{[4-(4-{[4-fluoro-2-(trifluoromethyl)phenyl]methyl}piperzin-1-yl)phenyl]amino)pyrimidin-4-yl)phenyl]acetamide | 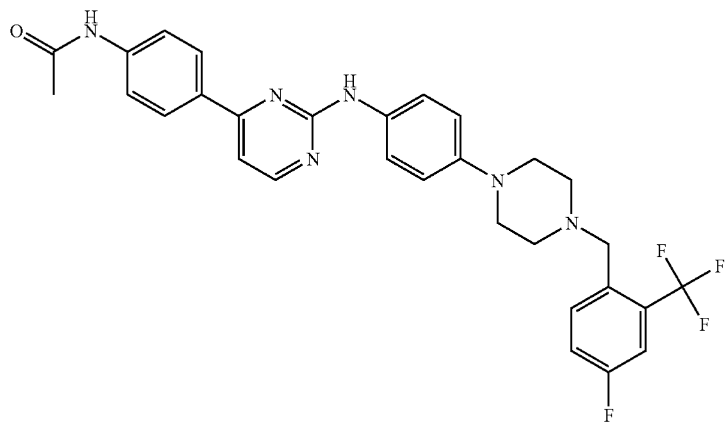 [SMILES: CC(=O)Nc1ccc(-c2ccnc(Nc3ccc(N4CCN(Cc5ccc(F)cc5C(F)(F)F)CC4)cc3)n2)cc1] | 49 |
| 217 | N-[4-(2-{[4-(4-{[4-(1H-imidazol-1-yl)phenyl]methyl}piperazin-1-yl)phenyl]amino}pyrimidin-4-yl)phenyl]acetamide | 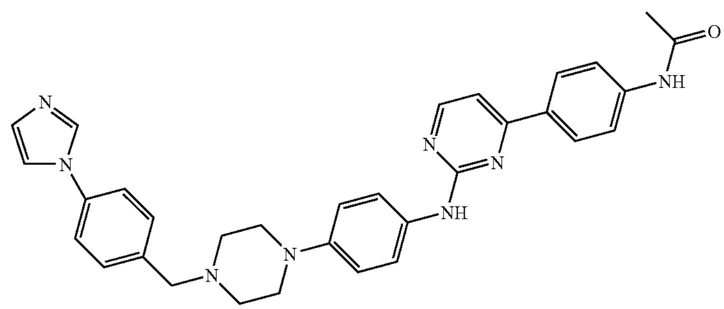 [SMILES: CC(=O)Nc1ccc(-c2ccnc(Nc3ccc(N4CCN(Cc5ccc(-n6ccnc6)cc5)CC4)cc3)n2)cc1] | 49 |
| 218 | N-[4-(2-{[4-(4-{[2,5-bis(trifluoromethyl)phenyl]methyl}piperazin-1-yl)phenyl]amino}pyrimidin-4-yl)phenyl]acetamide | 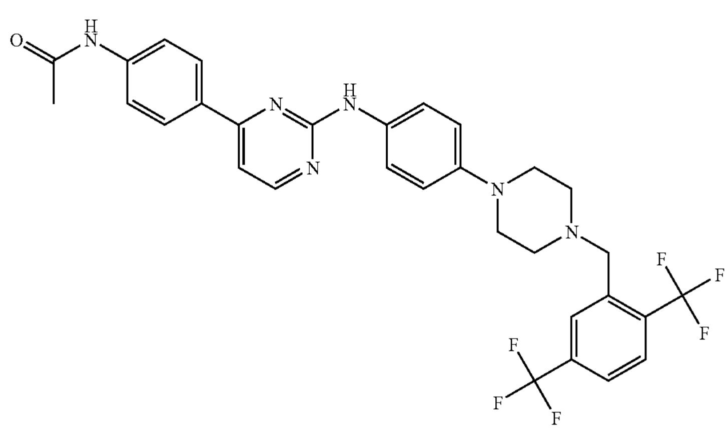 [SMILES: CC(=O)Nc1ccc(-c2ccnc(Nc3ccc(N4CCN(Cc5cc(C(F)(F)F)ccc5C(F)(F)F)CC4)cc3)n2)cc1] | 49 |

TABLE 1-continued
| Cmpd No. | Name | Structure | Can Be Made According To Synthetic Example #: |
|---|---|---|---|
| 219 | N-(4-{2-[(4-{4-[(2,6-dimethylphenyl)methyl]piperazin-1-yl}phenyl)amino]pyrimidin-4-yl}phenyl)acetamide | 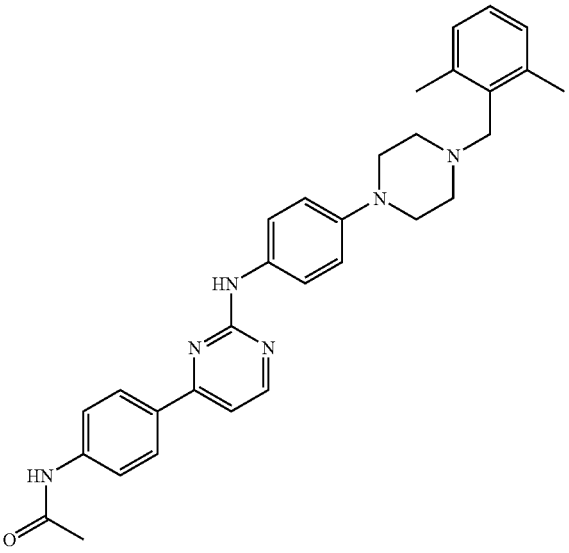 [SMILES: CC(=O)Nc1ccc(-c2ccnc(Nc3ccc(N4CCN(Cc5c(C)cccc5C)CC4)cc3)n2)cc1] | 49 |
| 220 | N-(4-{2-[(4-{4-[(2,3-dimethylphenyl)methyl]piperazin-1-yl}phenyl)amino}pyrimidin-4-yl}phenyl)acetamide | 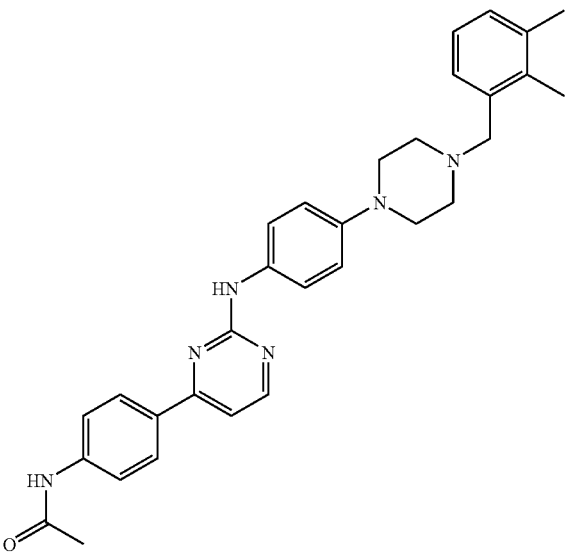 [SMILES: CC(=O)Nc1ccc(-c2ccnc(Nc3ccc(N4CCN(Cc5cccc(C)c5C)CC4)cc3)n2)cc1] | 49 |

TABLE 1-continued

| Cmpd No. | Name | Structure | Can Be Made According To Synthetic Example #: |
|---|---|---|---|
| 221 | N-[4-(2-{[4-(4-{[2,4-bis(ethyloxy)phenyl]methyl}piperazin-1-yl)phenyl]amino}pyrimidin-4-yl)phenyl]acetamide | 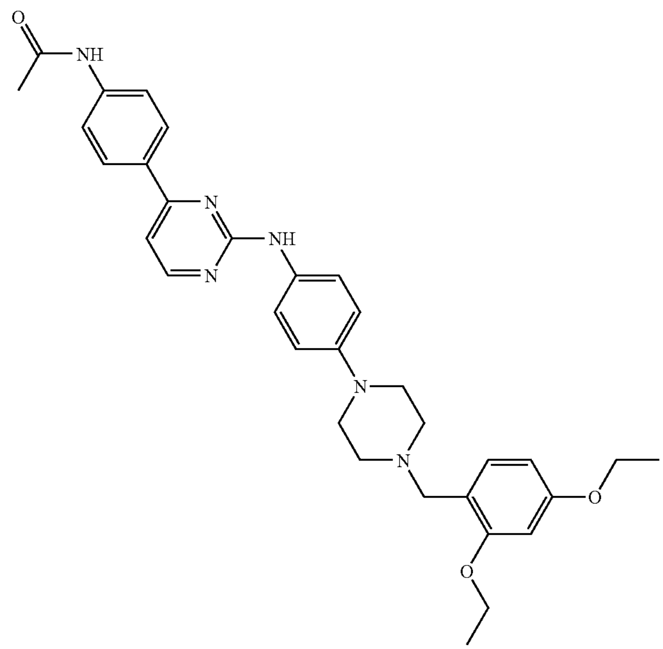 [SMILES: CCOc1ccc(CN2CCN(c3ccc(Nc4nccc(-c5ccc(NC(C)=O)cc5)n4)cc3)CC2)c(OCC)c1] | 49 |
| 222 | N-[4-(2-{[4-(4-{[3-(ethyloxy)phenyl]methyl}piperazin-1-yl)phenyl]amino}pyrimidin-4-yl)phenyl]acetamide | 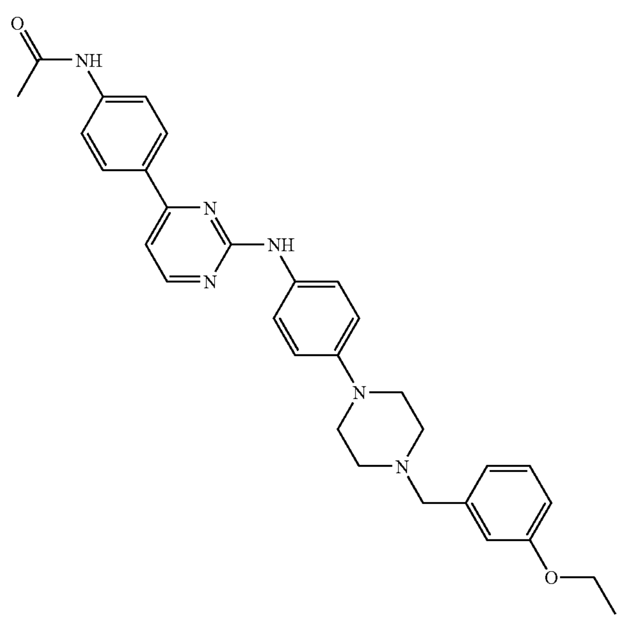 [SMILES: CCOc1cccc(CN2CCN(c3ccc(Nc4nccc(-c5ccc(NC(C)=O)cc5)n4)cc3)CC2)c1] | 49 |
| 223 | N-{4-[2-({4-[4-(2,2'-bithien-5-ylmethyl)piperazin-1-yl]phenyl}amino)pyrimidin-4-yl]phenyl}acetamide | 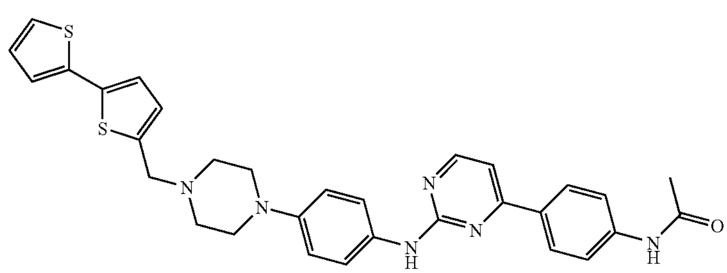 [SMILES: CC(=O)Nc1ccc(-c2ccnc(Nc3ccc(N4CCN(Cc5ccc(-c6cccs6)s5)CC4)cc3)n2)cc1] | 49 |

TABLE 1-continued

| Cmpd No. | Name | Structure | Can Be Made According To Synthetic Example #: |
|---|---|---|---|
| 224 | N-[4-(2-{[4-(4-{[4-(2-thienyl)phenyl]methyl}piperazin-1-yl)phenyl]amino}pyrimidin-4-yl)phenyl]acetamide | 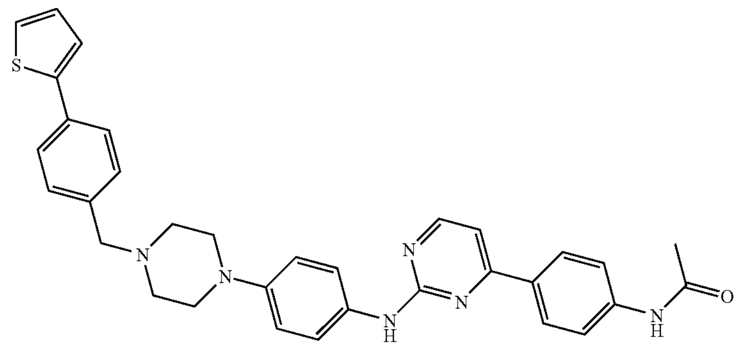 [SMILES: CC(=O)Nc1ccc(-c2ccnc(Nc3ccc(N4CCN(Cc5ccc(-c6cccs6)cc5)CC4)cc3)n2)cc1] | 49 |
| 225 | N-(4-{2-[(4-{4-[(4-cyanophenyl)methyl]piperazin-1-yl}phenyl)amino]pyrimidin-4-yl}phenyl)acetamide | 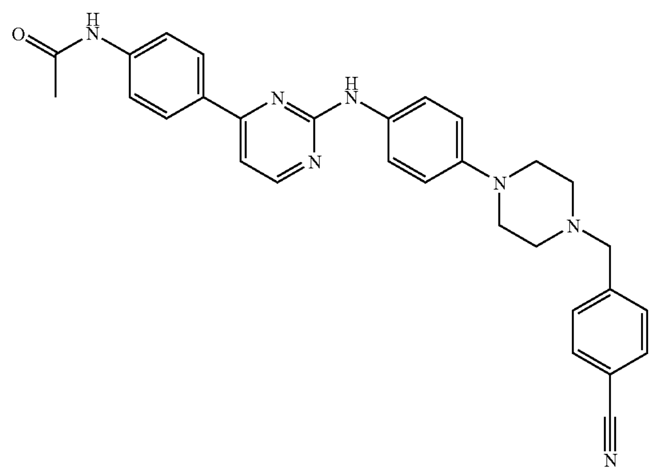 [SMILES: CC(=O)Nc1ccc(-c2ccnc(Nc3ccc(N4CCN(Cc5ccc(C#N)cc5)CC4)cc3)n2)cc1] | 49 |
| 226 | N-[4-(2-{[4-(4-{[2,5-bis(methyloxy)phenyl]methyl}piperazin-1-yl)phenyl]amino}pyrimidin-4-yl)phenyl]acetamide | 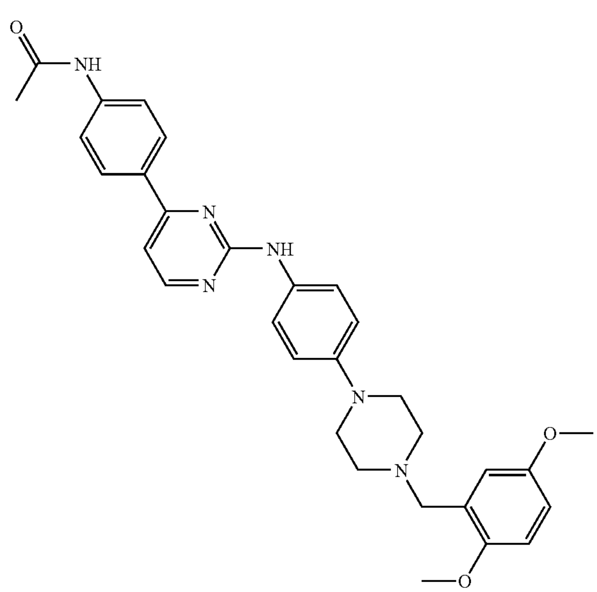 [SMILES: COc1ccc(OC)c(CN2CCN(c3ccc(Nc4nccc(-c5ccc(NC(C)=O)cc5)n4)cc3)CC2)c1] | 49 |

TABLE 1-continued

| Cmpd No. | Name | Structure | Can Be Made According To Synthetic Example #: |
|---|---|---|---|
| 227 | N-{4-[2-({4-[4-(2,2-diphenylethyl)piperazin-1-yl]phenyl}amino)pyrimidin-4-yl]phenyl}acetamide | 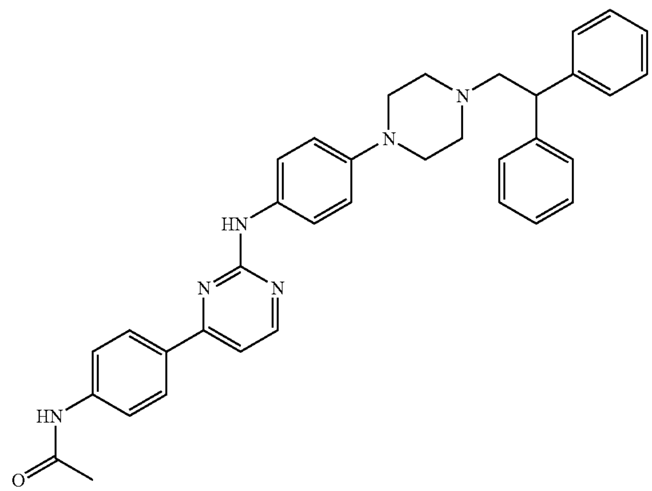 [SMILES: CC(=O)Nc1ccc(-c2ccnc(Nc3ccc(N4CCN(CC(c5ccccc5)c5ccccc5)CC4)cc3)n2)cc1] | 49 |
| 228 | N-{4-[2-({4-[4-(1H-pyrrol-2-ylmethyl)piperazin-1-yl]phenyl}amino)pyrimidin-4-yl]phenyl}acetamide | 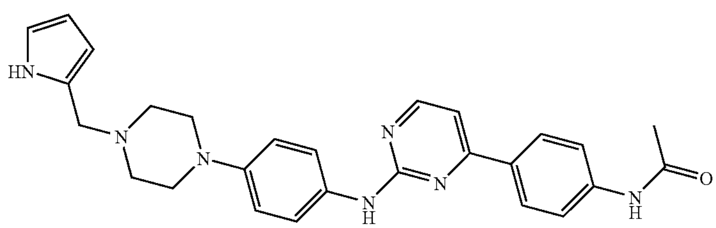 [SMILES: CC(=O)Nc1ccc(-c2ccnc(Nc3ccc(N4CCN(Cc5ccc[nH]5)CC4)cc3)n2)cc1] | 49 |
| 229 | N-{4-[2-(1H-indazol-6-ylamino)-5-methylpyrimidin-4-yl]phenyl}acetamide | 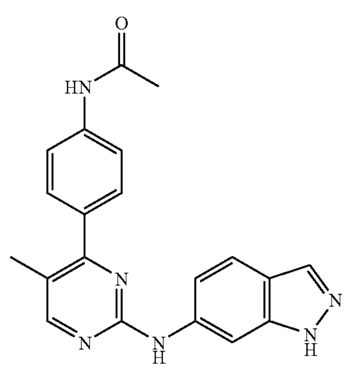 [SMILES: CC(=O)Nc1ccc(-c2nc(Nc3ccc4cn[nH]c4c3)ncc2C)cc1] | 3 |
| 230 | N-{4-[2-(1H-indol-5-ylamino)-5-methylpyrimidin-4-yl]phenyl}acetamide | 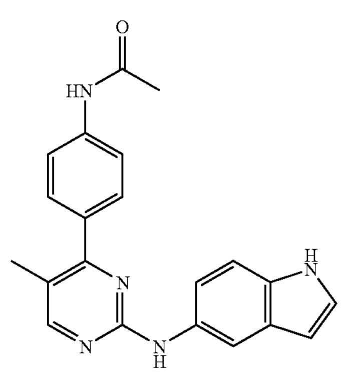 [SMILES: CC(=O)Nc1ccc(-c2nc(Nc3ccc4[nH]ccc4c3)ncc2C)cc1] | 3 |

TABLE 1-continued

| Cmpd No. | Name | Structure | Can Be Made According To Synthetic Example #: |
|---|---|---|---|
| 231 | N-[4-(2-{[4-(morpholin-4-ylmethyl)phenyl]amino}pyrimidin-4-yl)phenyl]acetamide | 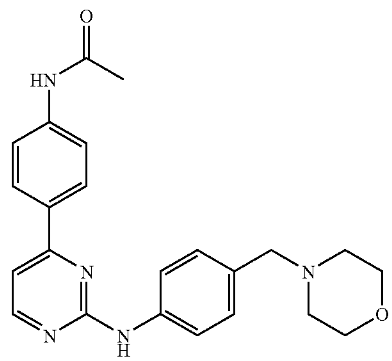 [SMILES: CC(=O)Nc1ccc(-c2ccnc(Nc3ccc(CN4CCOCC4)cc3)n2)cc1] | 22 |
| 232 | N-(4-{2-[(3-{[(3-fluorophenyl)methyl]amino}phenyl)amino]pyrimidin-4-yl}phenyl)acetamide | 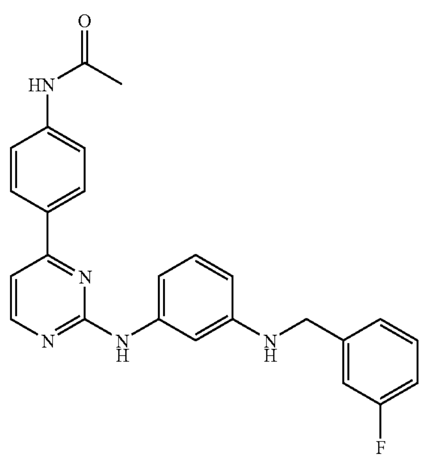 [SMILES: CC(=O)Nc1ccc(-c2ccnc(Nc3cccc(NCc4cccc(F)c4)c3)n2)cc1] | 28 |
| 233 | N-(4-{2-[(3-{[(4-fluorophenyl)methyl]amino}phenyl)amino]pyrimidin-4-yl}phenyl)acetamide | 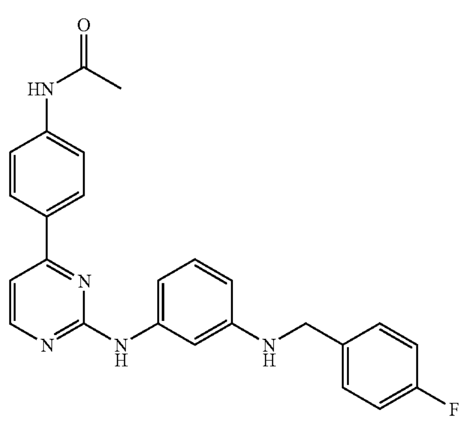 [SMILES: CC(=O)Nc1ccc(-c2ccnc(Nc3cccc(NCc4ccc(F)cc4)c3)n2)cc1] | 28 |

TABLE 1-continued

| Cmpd No. | Name | Structure | Can Be Made According To Synthetic Example #: |
|---|---|---|---|
| 234 | 4-[4-({4-[4-(acetylamino)phenyl]pyrimidin-2-yl}amino)phenyl]-N-ethylpiperazine-1-carboxamide | 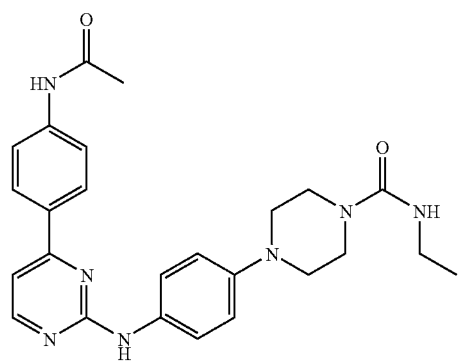 [SMILES: CCNC(=O)N1CCN(c2ccc(Nc3nccc(-c4ccc(NC(C)=O)cc4)n3)cc2)CC1] | 7 |
| 235 | N-{4-[2-({4-[4-(ethylsulfonyl)piperazin-1-yl]phenyl}amino)pyrimidin-4-yl]phenyl}acetamide | 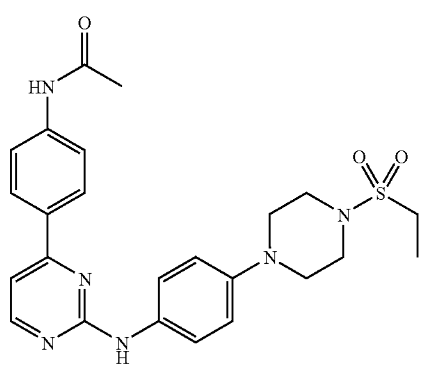 [SMILES: CCS(=O)(=O)N1CCN(c2ccc(Nc3nccc(-c4ccc(NC(C)=O)cc4)n3)cc2)CC1] | 36 |
| 236 | N-{4-[2-(1H-indazol-5-ylamino)-5-methylpyrimidin-4-yl]phenyl}acetamide | 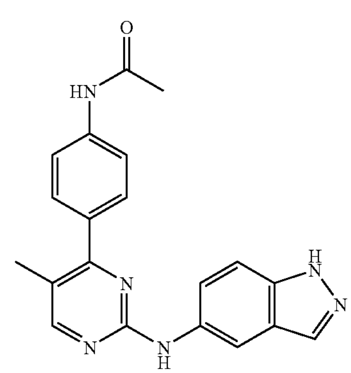 [SMILES: CC(=O)Nc1ccc(-c2nc(Nc3ccc4[nH]ncc4c3)ncc2C)cc1] | 3 |

TABLE 1-continued
| Cmpd No. | Name | Structure | Can Be Made According To Synthetic Example #: |
|---|---|---|---|
| 237 | N-[4-(2-{[4-(4-propyl-piperazin-1-yl)phenyl]amino}pyrimidin-4-yl)phenyl]acetamide | 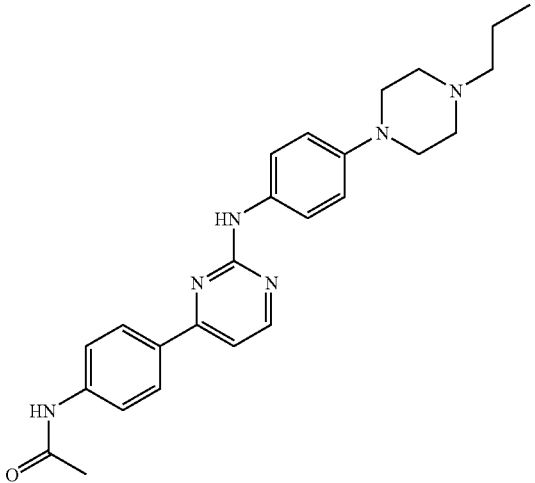 [SMILES: CCCN1CCN(c2ccc(Nc3nccc(-c4ccc(NC(C)=O)cc4)n3)cc2)CC1] | 49 |
| 238 | N-[4-(2-{[4-(4-butylpiperazin-1-yl)phenyl]amino}pyrimidin-4-yl)phenyl]acetamide | 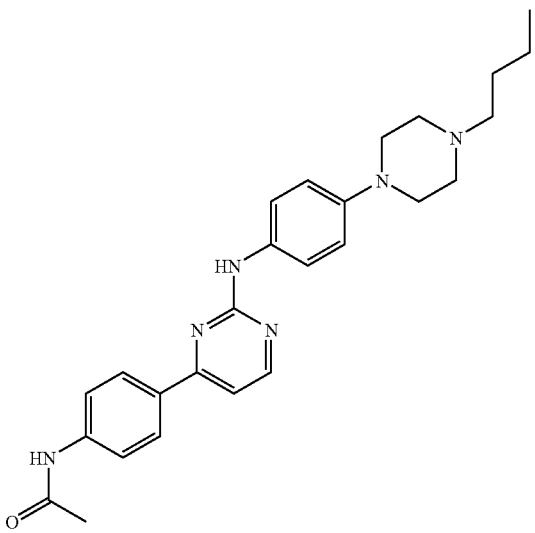 [SMILES: CCCCN1CCN(c2ccc(Nc3nccc(-c4ccc(NC(C)=O)cc4)n3)cc2)CC1] | 49 |
| 239 | N-{4-[2-({4-[4-(cyclopropylmethyl)piperazin-1-yl]phenyl}amino)pyrimidin-4-yl]phenyl}acetamide | 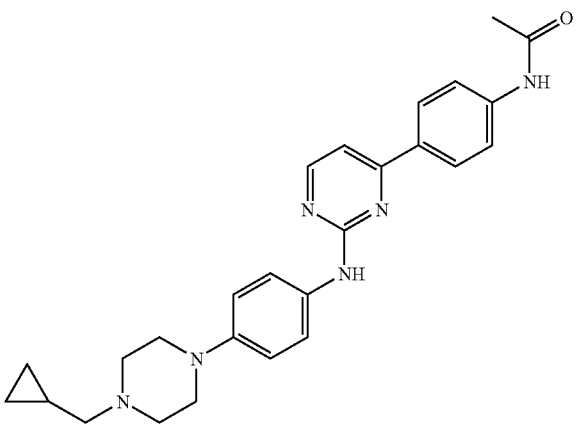 [SMILES: CC(=O)Nc1ccc(-c2ccnc(Nc3ccc(N4CCN(CC5CC5)CC4)cc3)n2)cc1] | 49 |

TABLE 1-continued

| Cmpd No. | Name | Structure | Can Be Made According To Synthetic Example #: |
|---|---|---|---|
| 240 | 4-[4-(methylsulfonyl)phenyl]-N-(4-morpholin-4-ylphenyl)pyrimidin-2-amine | 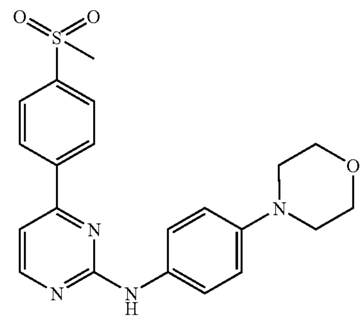 [SMILES: CS(=O)(=O)c1ccc(-c2ccnc(Nc3ccc(N4CCOCC4)cc3)n2)cc1] | 16 |
| 241 | ethyl N-[4-({4-[4-(acetylamino)phenyl]pyrimidin-2-yl}amino)phenyl]-N-methylglycinate | 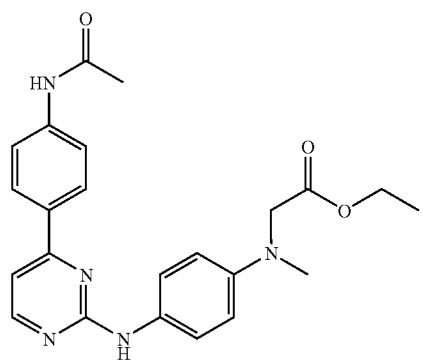 [SMILES: CCOC(=O)CN(C)c1ccc(Nc2nccc(-c3ccc(NC(C)=O)cc3)n2)cc1] | 3 |
| 242 | 4-[3-(methylsulfonyl)phenyl]-N-(4-morpholin-4-ylphenyl)pyrimidin-2-amine | 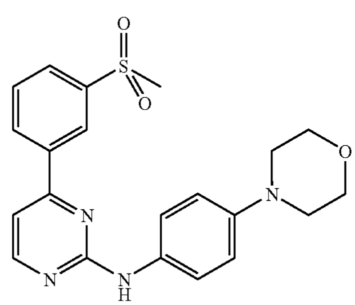 [SMILES: CS(=O)(=O)c1cccc(-c2ccnc(Nc3ccc(N4CCOCC4)cc3)n2)c1] | 9 |
| 243 | 4-[4-(methylthio)phenyl]-N-(4-morpholin-4-ylphenyl)pyrimidin-2-amine | 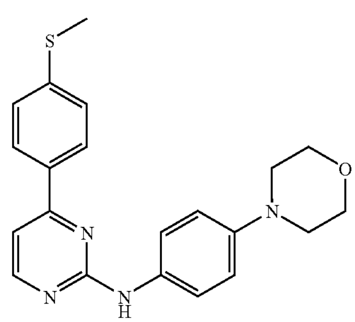 [SMILES: CSc1ccc(-c2ccnc(Nc3ccc(N4CCOCC4)cc3)n2)cc1] | 9 |

TABLE 1-continued

| Cmpd No. | Name | Structure | Can Be Made According To Synthetic Example #: |
|---|---|---|---|
| 244 | N-(4-{2-[(4-cyclohexyl-phenyl)amino]pyrimidin-4-yl}phenyl)acetamide | 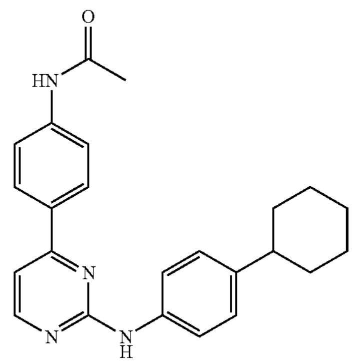 [SMILES: CC(=O)Nc1ccc(-c2ccnc(Nc3ccc(C4CCCCC4)cc3)n2)cc1] | 3 |
| 245 | N-{4-[2-({4-[(tetrahydro-furan-2-ylmethyl)amino]phenyl}amino)pyrimidin-4-yl]phenyl}acetamide | 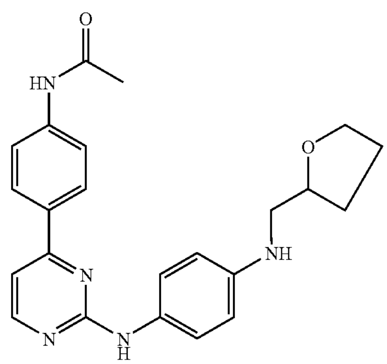 [SMILES: CC(=O)Nc1ccc(-c2ccnc(Nc3ccc(NCC4CCCO4)cc3)n2)cc1] | 28 |
| 246 | N-{4-[2-({4-[(phenylmethyl)amino]phenyl}amino)pyrimidin-4-yl]phenyl}acetamide | 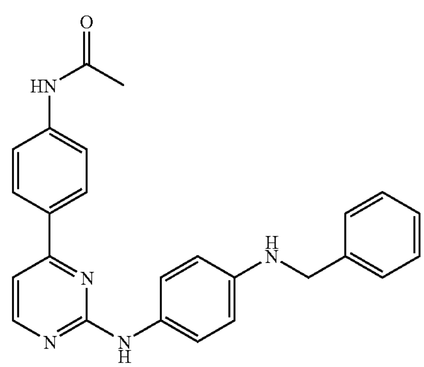 [SMILES: CC(=O)Nc1ccc(-c2ccnc(Nc3ccc(NCc4ccccc4)cc3)n2)cc1] | 28 |
| 247 | N-[4-(2-{[4-(acetylamino)phenyl]amino}pyrimidin-4-yl)phenyl]acetamide | 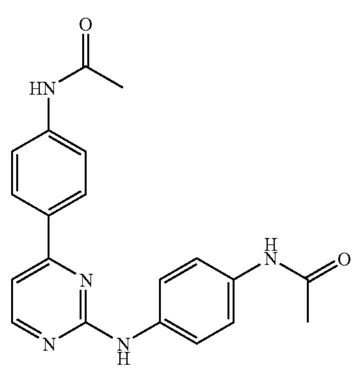 [SMILES: CC(=O)Nc1ccc(Nc2nccc(-c3ccc(NC(C)=O)cc3)n2)cc1] | 3 |

TABLE 1-continued

| Cmpd No. | Name | Structure | Can Be Made According To Synthetic Example #: |
|---|---|---|---|
| 248 | methyl (4-{2-[(4-morpholin-4-ylphenyl)amino]pyrimidin-4-yl}phenyl)carbamate | 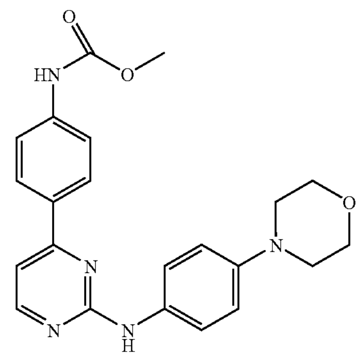 [SMILES: COC(=O)Nc1ccc(-c2ccnc(Nc3ccc(N4CCOCC4)cc3)n2)cc1] | 17 |
| 249 | 1-ethyl-3-(4-{2-[(4-morpholin-4-ylphenyl)amino]pyrimidin-4-yl}phenyl)urea | 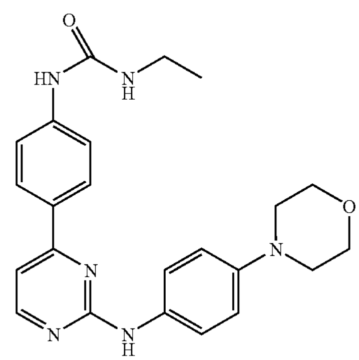 [SMILES: CCNC(=O)Nc1ccc(-c2ccnc(Nc3ccc(N4CCOCC4)cc3)n2)cc1] | 17 |
| 250 | ethyl 1-[4-({4-[4-(acetyl-amino)phenyl]pyrimidin-2-yl}amino)phenyl]piperidine-3-carboxylate | 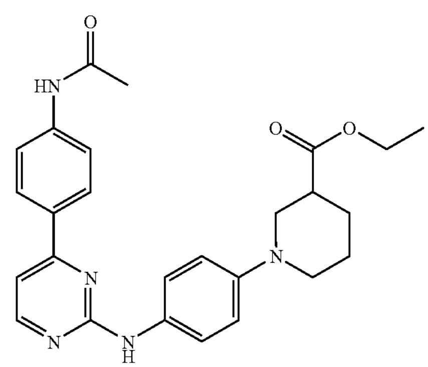 [SMILES: CCOC(=O)C1CCCN(c2ccc(Nc3nccc(-c4ccc(NC(C)=O)cc4)n3)cc2)C1] | 3 |
| 251 | ethyl [4-({4-[4-(acetyl-amino)phenyl]pyrimidin-2-yl}amino)phenyl]acetate | 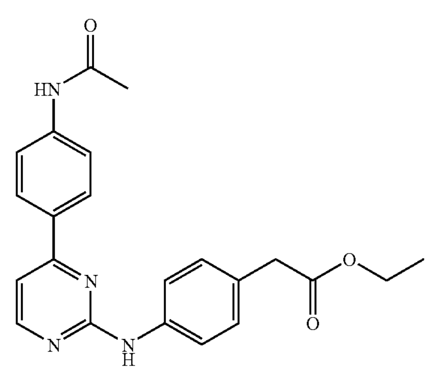 [SMILES: CCOC(=O)Cc1ccc(Nc2nccc(-c3ccc(NC(C)=O)cc3)n2)cc1] | 3 |

TABLE 1-continued
| Cmpd No. | Name | Structure | Can Be Made According To Synthetic Example #: |
|---|---|---|---|
| 252 | 4-[4-(methyloxy)phenyl]-N-(4-morpholin-4-ylphenyl)pyrimidin-2-amine | 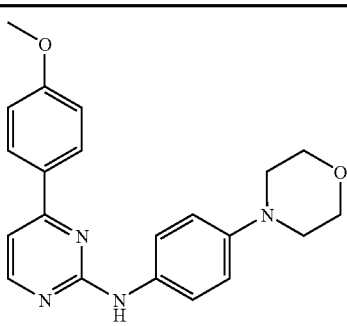 | 9 |
| 253 | 4-[3-(methyloxy)phenyl]-N-(4-morpholin-4-ylphenyl)pyrimidin-2-amine | 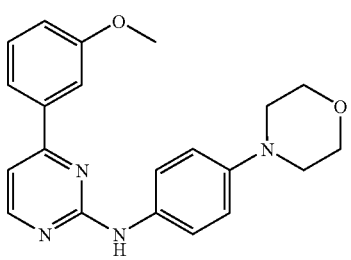 [SMILES: COc1cccc(-c2ccnc(Nc3ccc(N4CCOCC4)cc3)n2)c1] | 9 |
| 254 | 4-(1H-indol-5-yl)-N-(4-morpholin-4-ylphenyl)pyrimidin-2-amine | 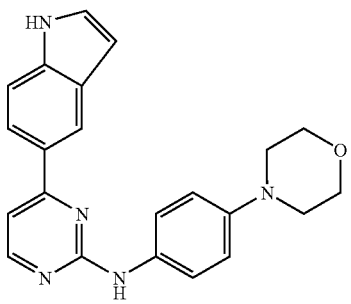 [SMILES: c1cc(-c2ccc3[nH]ccc3c2)nc(Nc2ccc(N3CCOCC3)cc2)n1] | 9 |
| 255 | 2-[(2-amino-2-oxoethyl)amino]-N-(4-{2-[(4-morpholin-4-ylphenyl)amino]pyrimidin-4-yl}phenyl)acetamide | 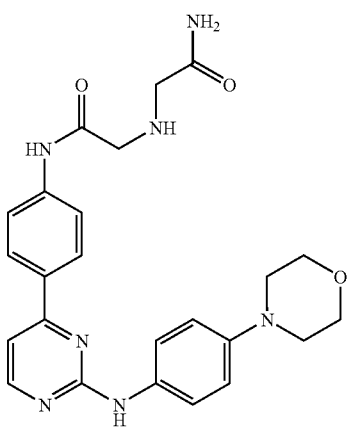 [SMILES: NC(=O)CNCC(=O)Nc1ccc(-c2ccnc(Nc3ccc(N4CCOCC4)cc3)n2)cc1] | 23 |

TABLE 1-continued

| Cmpd No. | Name | Structure | Can Be Made According To Synthetic Example #: |
|---|---|---|---|
| 256 | 2-morpholin-4-yl-N-(4-{2-[(4-morpholin-4-ylphenyl)amino]pyrimidin-4-yl}phenyl)acetamide | 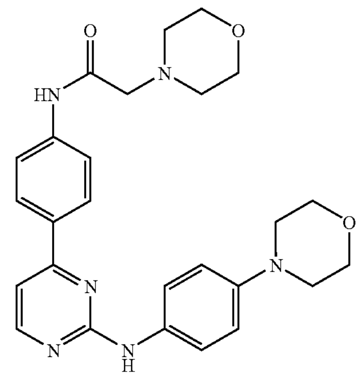 [SMILES: O=C(CN1CCOCC1)Nc1ccc(-c2ccnc(Nc3ccc(N4CCOCC4)cc3)n2)cc1] | 12 |
| 257 | 2,6-dichloro-N-{3-[(4-{4-[(cyclopropylcarbonyl)amino]phenyl}pyrimidin-2-yl)amino]phenyl}benzamide | 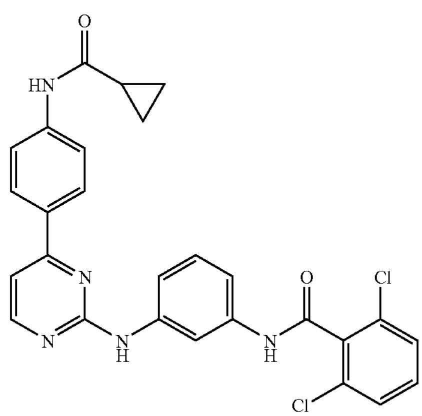 [SMILES: O=C(Nc1cccc(Nc2nccc(-c3ccc(NC(=O)C4CC4)cc3)n2)c1)c1c(Cl)cccc1Cl] | 2 |
| 258 | N²-(2-aminoethyl)-N~2~-methyl-N-(4-{2-[(4-morpholin-4-ylphenyl)amino]pyrimidin-4-yl}phenyl)glycinamide | 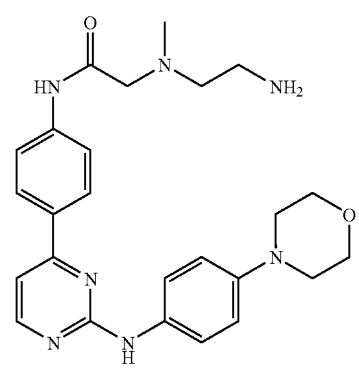 [SMILES: CN(CCN)CC(=O)Nc1ccc(-c2ccnc(Nc3ccc(N4CCOCC4)cc3)n2)cc1] | 1 |
| 259 | N-(4-{2-[(4-morpholin-4-ylphenyl)amino]pyrimidin-4-yl}phenyl)-N²-1H-pyrazol-5-ylglycinamide | 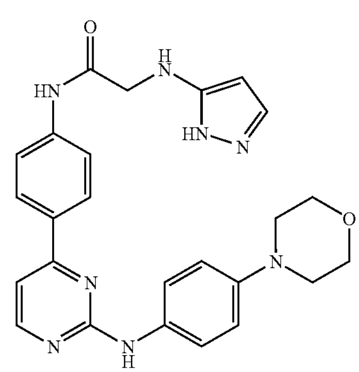 [SMILES: O=C(CNc1ccn[nH]1)Nc1ccc(-c2ccnc(Nc3ccc(N4CCOCC4)cc3)n2)cc1] | 23 |

TABLE 1-continued

| Cmpd No. | Name | Structure | Can Be Made According To Synthetic Example #: |
|---|---|---|---|
| 260 | phenylmethyl N-{2-[(4-{2-[(4-morpholin-4-ylphenyl)amino]pyrimidin-4-yl}phenyl)amino]-2-oxoethyl}-L-alaninate | 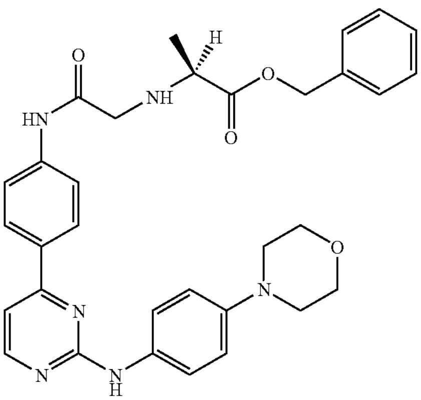 [SMILES: C[C@H](NCC(=O)Nc1ccc(-c2ccnc(Nc3ccc(N4CCOCC4)cc3)n2)cc1)C(=O)OCc1ccccc1] | 23 |
| 261 | 4-{2-[(4-morpholin-4-ylphenyl)amino]pyrimidin-4-yl}benzamide | 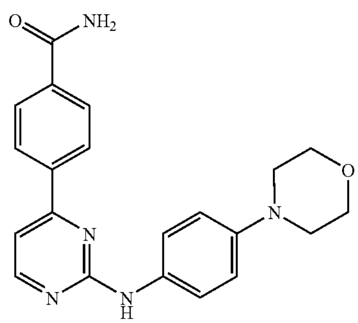 [SMILES: NC(=O)c1ccc(-c2ccnc(Nc3ccc(N4CCOCC4)cc3)n2)cc1] | 9 |
| 262 | 1,1-dimethylethyl [(4-{2-[(4-morpholin-4-ylphenyl)amino]pyrimidin-4-yl}phenyl)methyl]carbamate | 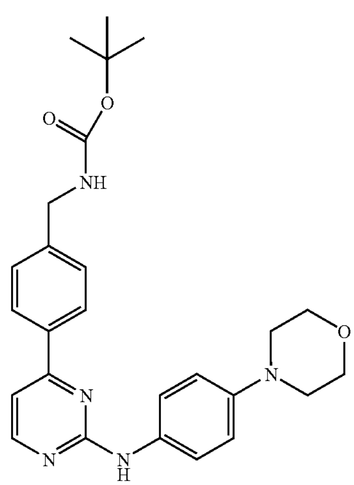 [SMILES: CC(C)(C)OC(=O)NCc1ccc(-c2ccnc(Nc3ccc(N4CCOCC4)cc3)n2)cc1] | 9 |

TABLE 1-continued
| Cmpd No. | Name | Structure | Can Be Made According To Synthetic Example #: |
|---|---|---|---|
| 263 | N-(4-{2-[(4-morpholin-4-ylphenyl)amino]pyrimidin-4-yl}phenyl)propanamide | 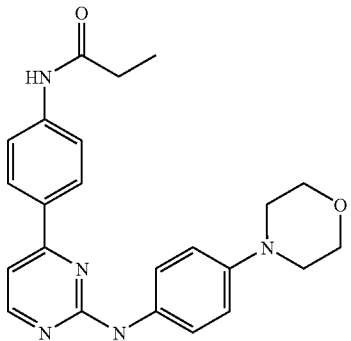 | 12 |
| 264 | N-(4-{2-[(4-morpholin-4-ylphenyl)amino]pyrimidin-4-yl}phenyl)-2-phenylacetamide | 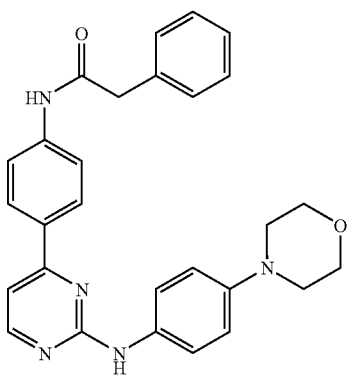 [SMILES: O=C(Cc1ccccc1)Nc1ccc(-c2ccnc(Nc3ccc(N4CCOCC4)cc3)n2)cc1] | 12 |
| 265 | N-(4-{2-[(4-morpholin-4-ylphenyl)amino]pyrimidin-4-yl}phenyl)-3-phenylpropanamide | 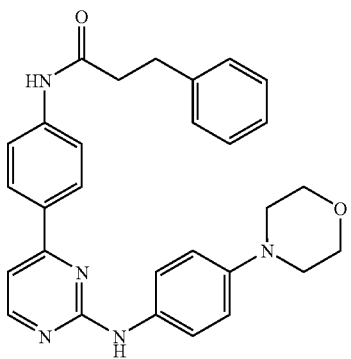 | 12 |
| 266 | N-(4-{2-[(4-morpholin-4-ylphenyl)amino]pyrimidin-4-yl}phenyl)tetrahydrofuran-2-carboxamide | 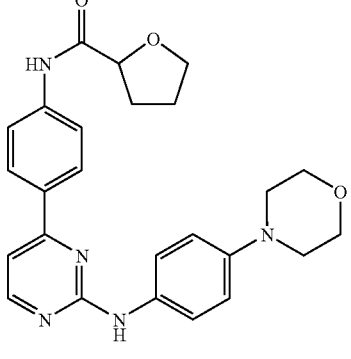 | 12 |

TABLE 1-continued

| Cmpd No. | Name | Structure | Can Be Made According To Synthetic Example #: |
|---|---|---|---|
| 267 | 5-methyl-N-(4-{2-[(4-morpholin-4-ylphenyl)amino]pyrimidin-4-yl}phenyl)pyrazine-2-carboxamide | 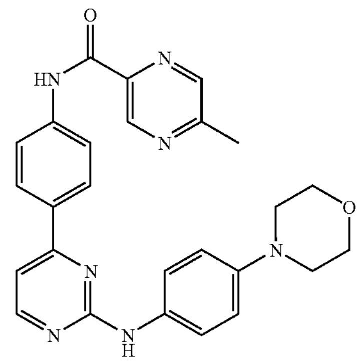 [SMILES: Cc1cnc(C(=O)Nc2ccc(-c3ccnc(Nc4ccc(N5CCOCC5)cc4)n3)cc2)cn1] | 12 |
| 268 | 2-(ethyloxy)-N-(4-{2-[(4-morpholin-4-ylphenyl)amino]pyrimidin-4-yl}phenyl)acetamide | 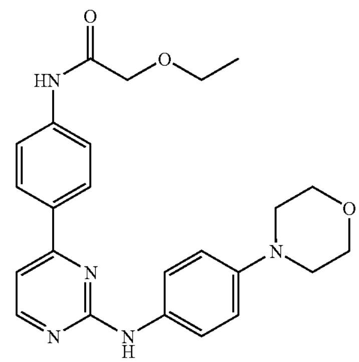 [SMILES: CCOCC(=O)Nc1ccc(-c2ccnc(Nc3ccc(N4CCOCC4)cc3)n2)cc1] | 23 |
| 269 | N-(4-{2-[(4-morpholin-4-ylphenyl)amino]pyrimidin-4-yl}phenyl)-2-(phenyloxy)acetamide | 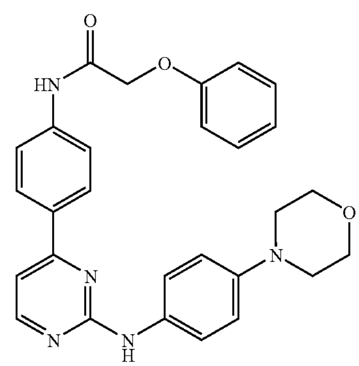 [SMILES: O=C(COc1ccccc1)Nc1ccc(-c2ccnc(Nc3ccc(N4CCOCC4)cc3)n2)cc1] | 23 |
| 270 | N-[4-(2-{[4-(1H-pyrrol-1-yl)phenyl]amino}pyrimidin-4-yl)phenyl]acetamide | 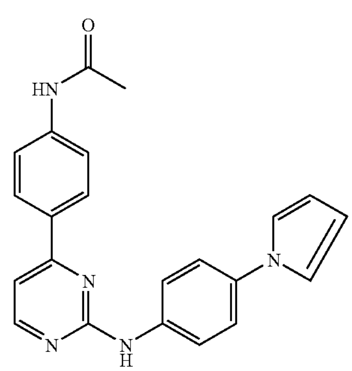 [SMILES: CC(=O)Nc1ccc(-c2ccnc(Nc3ccc(-n4cccc4)cc3)n2)cc1] | 3 |

TABLE 1-continued

| Cmpd No. | Name | Structure | Can Be Made According To Synthetic Example #: |
|---|---|---|---|
| 271 | N-[4-(2-{[4-(2,6-dimethyl-morpholin-4-yl)phenyl]amino}pyrimidin-4-yl)phenyl]acetamide | 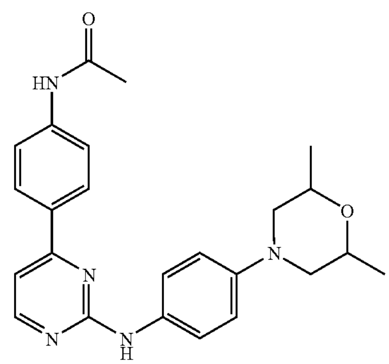 [SMILES: CC(=O)Nc1ccc(-c2ccnc(Nc3ccc(N4CC(C)OC(C)C4)cc3)n2)cc1] | 3 |
| 272 | ethyl 1-[4-({4-[4-(acetyl-amino)phenyl]pyrimidin-2-yl}amino)phenyl]piperidine-4-carboxylate | 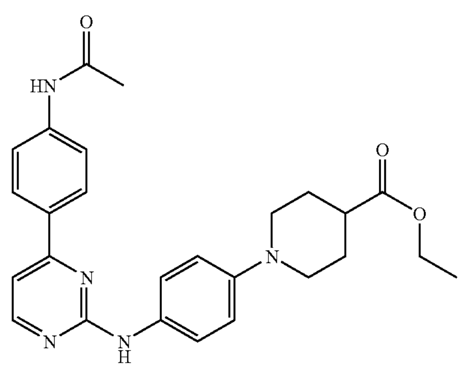 [SMILES: CCOC(=O)C1CCN(c2ccc(Nc3nccc(-c4ccc(NC(C)=O)cc4)n3)cc2)CC1] | 3 |
| 273 | 2-cyclopentyl-N-(4-{2-[(4-morpholin-4-ylphenyl)amino]pyrimidin-4-yl}phenyl)acetamide | 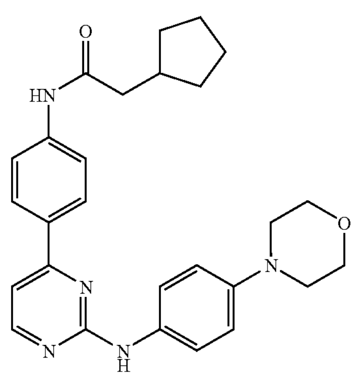 [SMILES: O=C(CC1CCCC1)Nc1ccc(-c2ccnc(Nc3ccc(N4CCOCC4)cc3)n2)cc1] | 12 |
| 274 | N-(4-{2-[(4-morpholin-4-ylphenyl)amino]pyrimidin-4-yl}phenyl)-3-pyridin-3-ylpropanamide | 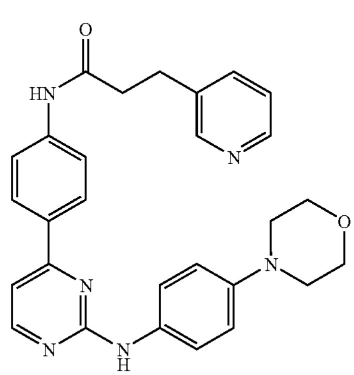 [SMILES: O=C(CCc1cccnc1)Nc1ccc(-c2ccnc(Nc3ccc(N4CCOCC4)cc3)n2)cc1] | 12 |

TABLE 1-continued

| Cmpd No. | Name | Structure | Can Be Made According To Synthetic Example #: |
|---|---|---|---|
| 275 | 6-(methyloxy)-N-(4-{2-[(4-morpholin-4-ylphenyl)amino]pyrimidin-4-yl}phenyl)pyridine-3-carboxamide | 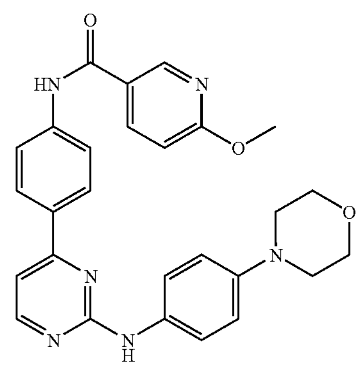 [SMILES: COc1ccc(C(=O)Nc2ccc(-c3ccnc(Nc4ccc(N5CCOCC5)cc4)n3)cc2)cn1] | 12 |
| 276 | methyl 4-[(4-{2-[(4-morpholin-4-ylphenyl)amino]pyrimidin-4-yl}phenyl)amino]-4-oxobutanoate | 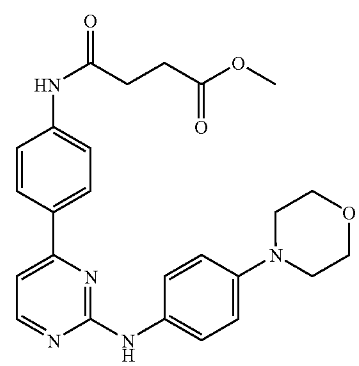 [SMILES: COC(=O)CCC(=O)Nc1ccc(-c2ccnc(Nc3ccc(N4CCOCC4)cc3)n2)cc1] | 12 |
| 277 | N-(4-{2-[(4-morpholin-4-ylphenyl)amino]pyrimidin-4-yl}phenyl)butanamide | 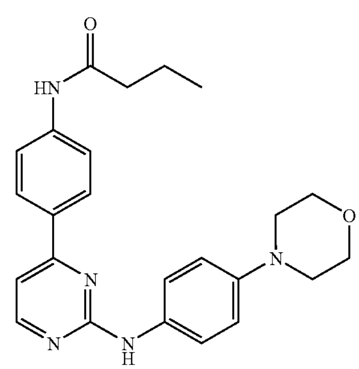 | 12 |
| 278 | N-(4-{2-[(4-{bis[2-(methyloxy)ethyl]amino}phenyl)amino]pyrimidin-4-yl}phenyl)acetamide | 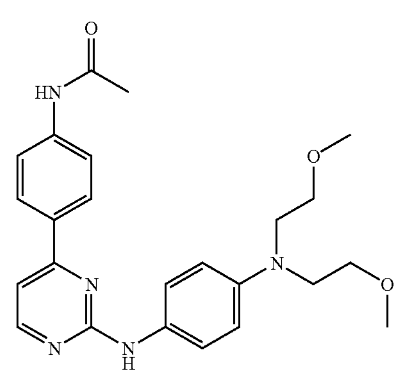 [SMILES: COCCN(CCOC)c1ccc(Nc2nccc(-c3ccc(NC(C)=O)cc3)n2)cc1] | 3 |

TABLE 1-continued

| Cmpd No. | Name | Structure | Can Be Made According To Synthetic Example #: |
|---|---|---|---|
| 279 | N-[4-(2-{[4-(morpholin-4-ylsulfonyl)phenyl]amino}pyrimidin-4-yl)phenyl]acetamide | 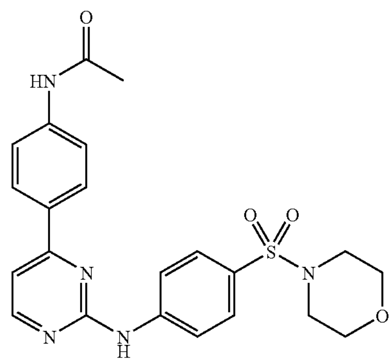 [SMILES: CC(=O)Nc1ccc(-c2ccnc(Nc3ccc(S(=O)(=O)N4CCOCC4)cc3)n2)cc1] | 3 |
| 280 | 4-(4-(aminomethyl)phenyl)-N-(4-morpholinophenyl)pyrimidin-2-amine | 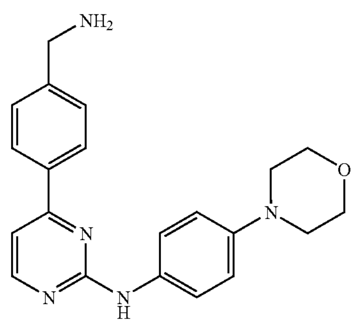 [SMILES: NCc1ccc(-c2ccnc(Nc3ccc(N4CCOCC4)cc3)n2)cc1] | 47 |
| 281 | N-[(4-{2-[(4-morpholin-4-ylphenyl)amino]pyrimidin-4-yl}phenyl)methyl]acetamide | 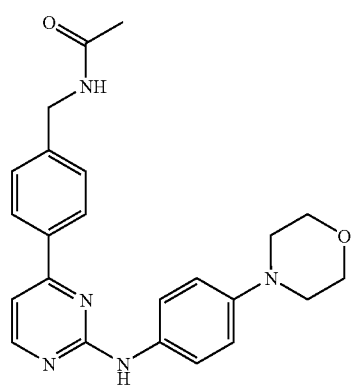 [SMILES: CC(=O)NCc1ccc(-c2ccnc(Nc3ccc(N4CCOCC4)cc3)n2)cc1] | 48 |
| 282 | N-(4-morpholin-4-ylphenyl)-4-{4-[(propylamino)methyl]phenyl}pyrimidin-2-amine | 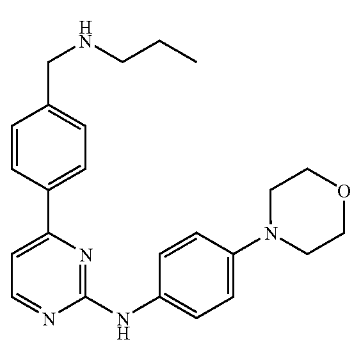 [SMILES: CCCNCc1ccc(-c2ccnc(Nc3ccc(N4CCOCC4)cc3)n2)cc1] | 47 |

TABLE 1-continued

| Cmpd No. | Name | Structure | Can Be Made According To Synthetic Example #: |
|---|---|---|---|
| 283 | N-(4-{2-[(4-piperidin-1-ylphenyl)amino]pyrimidin-4-yl}phenyl)acetamide | 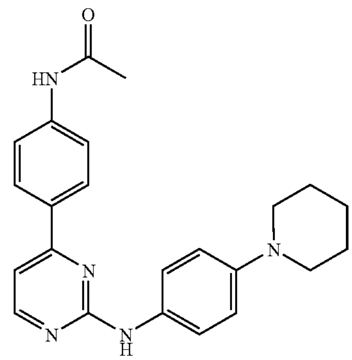 [SMILES: CC(=O)Nc1ccc(-c2ccnc(Nc3ccc(N4CCCCC4)cc3)n2)cc1] | 3 |
| 284 | N-(4-{2-[(3,5-dimorpholin-4-ylphenyl)amino]pyrimidin-4-yl}phenyl)acetamide | 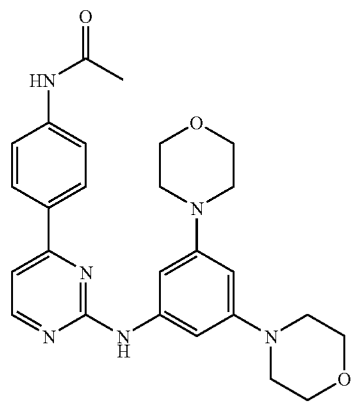 [SMILES: CC(=O)Nc1ccc(-c2ccnc(Nc3cc(N4CCOCC4)cc(N4CCOCC4)c3)n2)cc1] | 6 |
| 285 | 2-(2-methylphenyl)-N-(4-{2-[(4-morpholin-4-ylphenyl)amino]pyrimidin-4-yl}phenyl)acetamide | 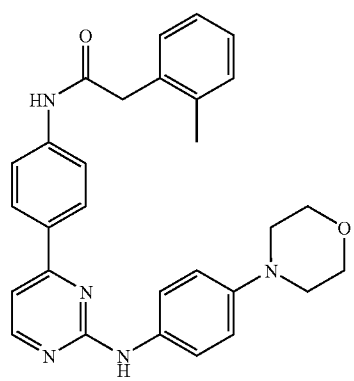 [SMILES: Cc1ccccc1CC(=O)Nc1ccc(-c2ccnc(Nc3ccc(N4CCOCC4)cc3)n2)cc1] | 12 |
| 286 | N-(4-{2-[(4-morpholin-4-ylphenyl)amino]pyrimidin-4-yl}phenyl)cyclopentanecarboxamide | 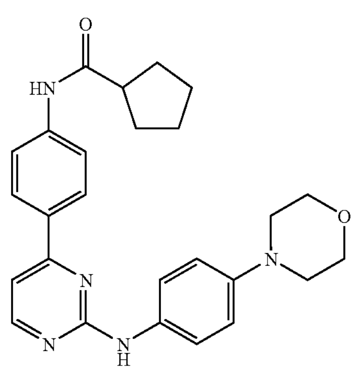 | 12 |

TABLE 1-continued

| Cmpd No. | Name | Structure | Can Be Made According To Synthetic Example #: |
|---|---|---|---|
| 287 | N,N-dimethyl-N'-(4-{2-[(4-morpholin-4-ylphenyl)amino]pyrimidin-4-yl}phenyl)butanediamide | 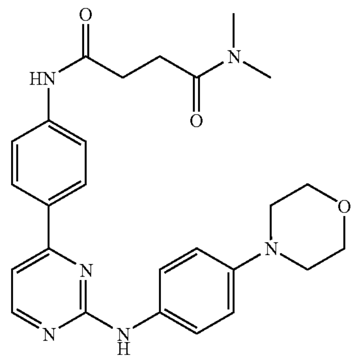 [SMILES: CN(C)C(=O)CCC(=O)Nc1ccc(-c2ccnc(Nc3ccc(N4CCOCC4)cc3)n2)cc1] | 12 |
| 288 | N-(4-{2-[(4-morpholin-4-ylphenyl)amino]pyrimidin-4-yl}phenyl)-N~2~-pyrimidin-4-ylglycinamide | 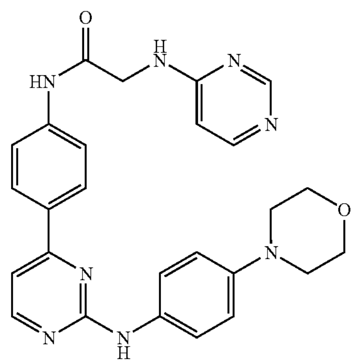 [SMILES: O=C(CNc1ccncn1)Nc1ccc(-c2ccnc(Nc3ccc(N4CCOCC4)cc3)n2)cc1] | 12 |
| 289 | 3-chloro-N-(4-{2-[(4-morpholin-4-ylphenyl)amino]pyrimidin-4-yl}phenyl)pyridine-4-carboxamide | 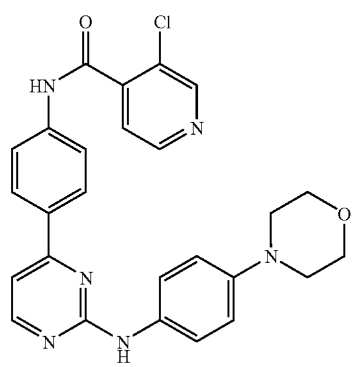 [SMILES: O=C(Nc1ccc(-c2ccnc(Nc3ccc(N4CCOCC4)cc3)n2)cc1)c1ccncc1Cl] | 12 |
| 290 | N-(4-{2-[(4-morpholin-4-ylphenyl)amino]pyrimidin-4-yl}phenyl)-2-piperadin-1-ylacetamide | 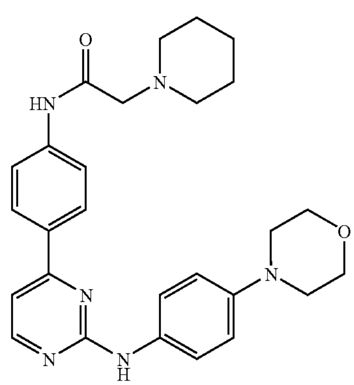 [SMILES: O=C(CN1CCCCC1)Nc1ccc(-c2ccnc(Nc3ccc(N4CCOCC4)cc3)n2)cc1] | 12 |

TABLE 1-continued

| Cmpd No. | Name | Structure | Can Be Made According To Synthetic Example #: |
|---|---|---|---|
| 291 | N²-ethyl-N-(4-{2-[(4-morpholin-4-ylphenyl)amino]pyrimidin-4-yl}phenyl)glycinamide | 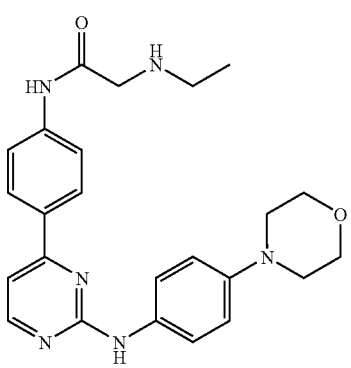 [SMILES: CCNCC(=O)Nc1ccc(-c2ccnc(Nc3ccc(N4CCOCC4)cc3)n2)cc1] | 12 |
| 292 | N-(4-{2-[(4-morpholin-4-ylphenyl)amino]pyrimidin-4-yl}phenyl)-2-pyrrolidin-1-ylacetamide | 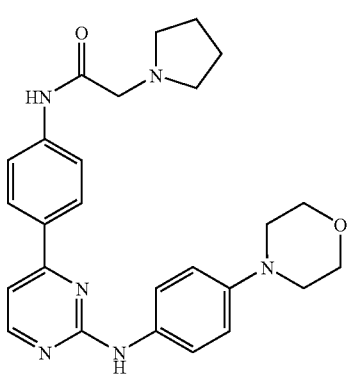 [SMILES: O=C(CN1CCCC1)Nc1ccc(-c2ccnc(Nc3ccc(N4CCOCC4)cc3)n2)cc1] | 11 |
| 293 | 2-(1H-imidazol-1-yl)-N-(4-{2-[(4-morpholin-4-ylphenyl)amino]pyrimidin-4-yl}phenyl)acetamide | 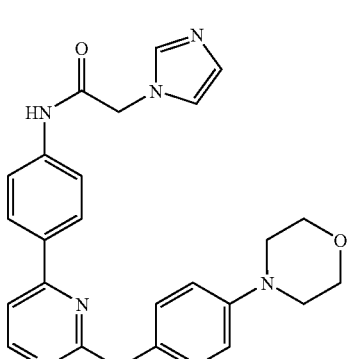 | 11 |
| 294 | N-(4-{2-[(4-morpholin-4-ylphenyl)amino]pyrimidin-4-yl}phenyl)-2-piperazin-1-ylacetamide | 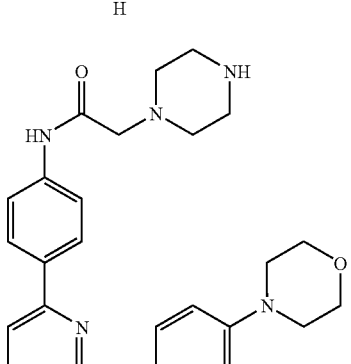 | 11 |

TABLE 1-continued

| Cmpd No. | Name | Structure | Can Be Made According To Synthetic Example #: |
|---|---|---|---|
| 295 | N-[4-(2-{[4-(4-phenyl-piperazin-1-yl)phenyl]amino}pyrimidin-4-yl)phenyl]acetamide | 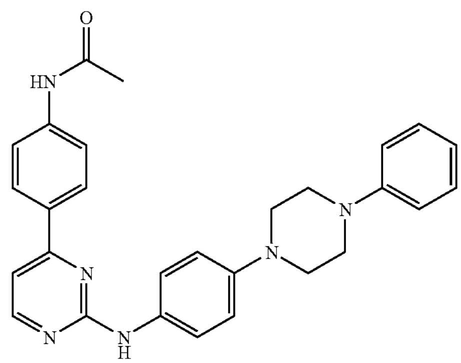 [SMILES: CC(=O)Nc1ccc(-c2ccnc(Nc3ccc(N4CCN(c5ccccc5)CC4)cc3)n2)cc1] | 3 |
| 296 | N-(4-{2-[(3-chloro-4-morpholin-4-ylphenyl)amino]pyrimidin-4-yl}phenyl)acetamide | 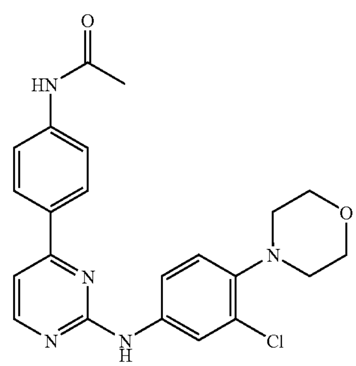 [SMILES: CC(=O)Nc1ccc(-c2ccnc(Nc3ccc(N4CCOCC4)c(Cl)c3)n2)cc1] | 15 |
| 297 | N-(4-{2-[(4-piperazin-1-ylphenyl)amino]pyrimidin-4-yl}phenyl)acetamide | 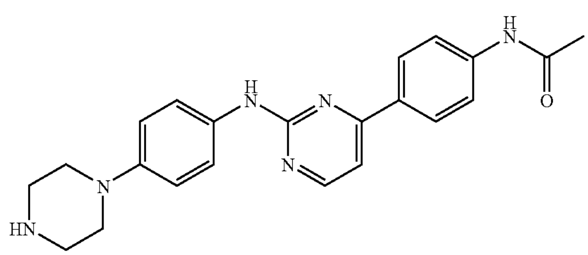 [SMILES: CC(=O)Nc1ccc(-c2ccnc(Nc3ccc(N4CCNCC4)cc3)n2)cc1] | 34 |
| 298 | 2,6-dichloro-N-(3-{[4-(4-fluorophenyl)pyrimidin-2-yl]amino}propyl)benzamide | 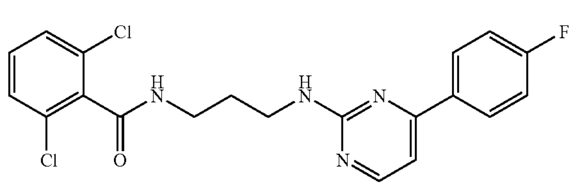 [SMILES: O=C(NCCCNc1nccc(-c2ccc(F)cc2)n1)c1c(Cl)cccc1Cl] | 27 |

TABLE 1-continued

| Cmpd No. | Name | Structure | Can Be Made According To Synthetic Example #: |
|---|---|---|---|
| 299 | 'N-[6-({4-[4-(acetylamino) phenyl]pyrimidin-2-yl} amino)pyridin-2-yl]-2,6-dichlorobenzamide | 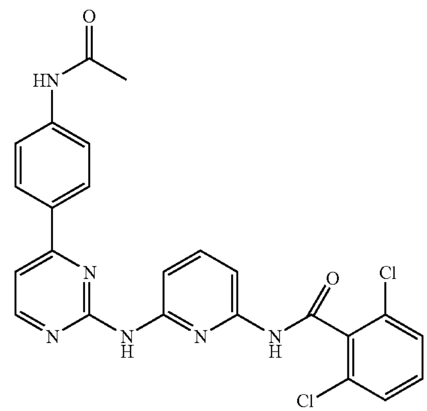 [SMILES: CC(=O)Nc1ccc(-c2ccnc(Nc3cccc(NC(=O)c4c(Cl)cccc4Cl)n3)n2)cc1] | 38 |
| 300 | 'N-[6-({4-[4-(acetylamino) phenyl]pyrimidin-2-yl} amino)pyrimidin-4-yl]-2,6-dichlorobenzamide | 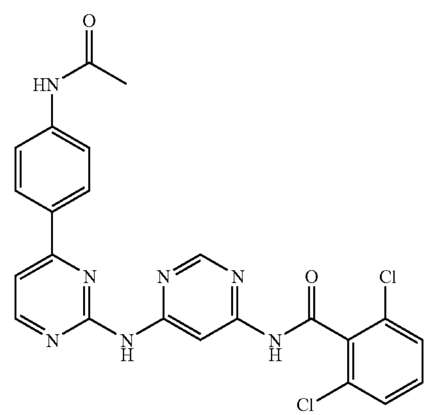 [SMILES: CC(=O)Nc1ccc(-c2ccnc(Nc3cc(NC(=O)c4c(Cl)cccc4Cl)ncn3)n2)cc1] | 38 |
| 301 | 'N-(4-{2-[(6-aminopyridin-2-yl)amino]pyrimidin-4-yl}phenyl)acetamide | 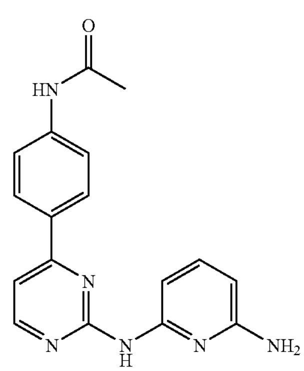 [SMILES: CC(=O)Nc1ccc(-c2ccnc(Nc3cccc(N)n3)n2)cc1] | 38 |

TABLE 1-continued

| Cmpd No. | Name | Structure | Can Be Made According To Synthetic Example #: |
|---|---|---|---|
| 302 | 'N-(4-{2-[(6-aminopyrimidin-4-yl)amino]pyrimidin-4-yl}phenyl)acetamide | 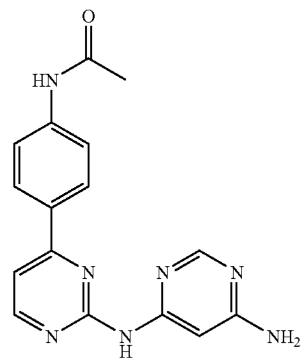 [SMILES: CC(=O)Nc1ccc(-c2ccnc(Nc3cc(N)ncn3)n2)cc1] | 38 |
| 303 | '5-fluoro-N⁴-[2-(methyloxy)phenyl]-N²-[3-(methyloxy)phenyl]pyrimidin-2,4-diamine | 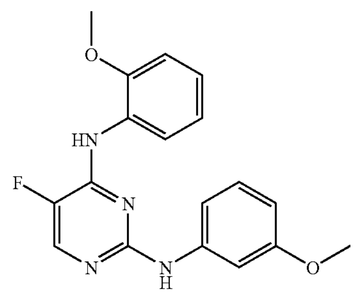 [SMILES: COc1cccc(Nc2ncc(F)c(Nc3ccccc3OC)n2)c1] | 50 |
| 304 | '2,6-dichloro-N-{3-[(4-{[3-chloro-4-(methyloxy)phenyl]oxy}pyrimidin-2-yl)amino]phenyl}benzamide | 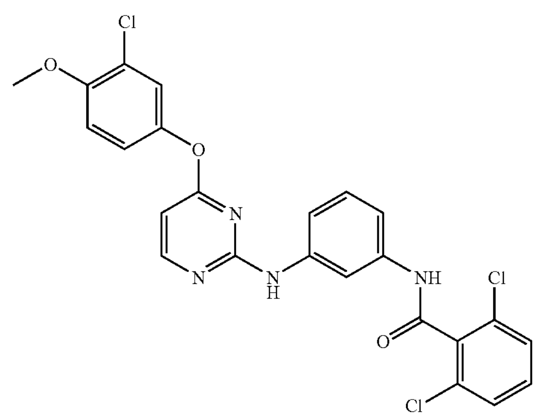 [SMILES: COc1ccc(Oc2ccnc(Nc3cccc(NC(=O)c4c(Cl)cccc4Cl)c3)n2)cc1Cl] | 41 |
| 305 | '4-{[2-chloro-4-(methyloxy)phenyl]oxy}-N-(4-morpholin-4-ylphenyl)pyrimidin-2-amine | 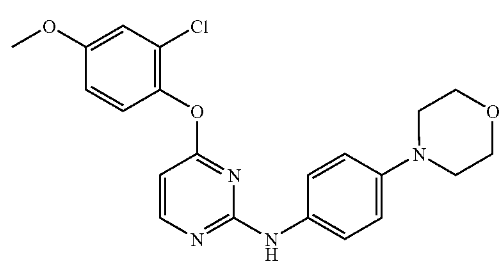 [SMILES: COc1ccc(Oc2ccnc(Nc3ccc(N4CCOCC4)cc3)n2)c(Cl)c1] | 41 |

TABLE 1-continued

| Cmpd No. | Name | Structure | Can Be Made According To Synthetic Example #: |
|---|---|---|---|
| 306 | 'N-[4-({2-[(4-morpholin-4-ylphenyl)amino]-7H-pyrrolo[2,3-d]pyrimidin-4-yl}amino)phenyl]acetamide | 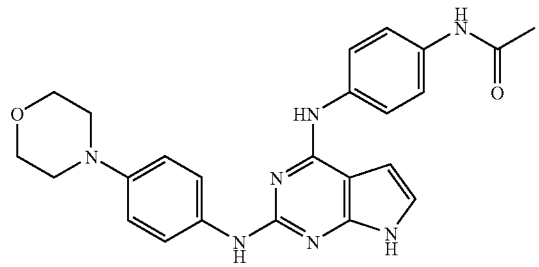 [SMILES: CC(=O)Nc1ccc(Nc2nc(Nc3ccc(N4CCOCC4)cc3)nc3[nH]ccc23)cc1] | 35 |
| 307 | 'N-[4-({2-[(4-morpholin-4-ylphenyl)amino]pyrimidin-4-yl}oxy)phenyl]acetamide | 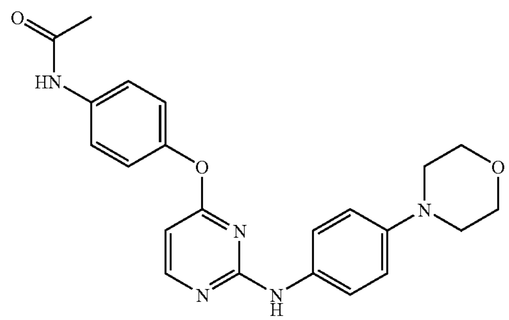 [SMILES: CC(=O)Nc1ccc(Oc2ccnc(Nc3ccc(N4CCOCC4)cc3)n2)cc1] | 41 |
| 308 | N-{4-[2-({4-[4-(pyridin-3'-ylcarbonyl)piperazin-1-yl]phenyl}amino)pyrimidin-4-yl]phenyl}acetamide | 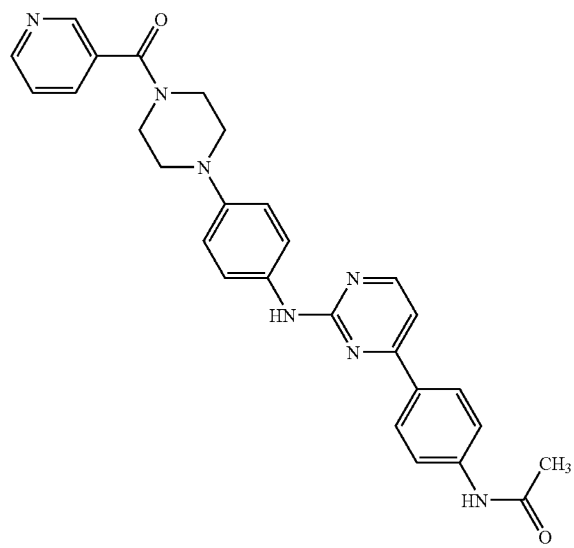 [SMILES: CC(=O)Nc1ccc(-c2ccnc(Nc3ccc(N4CCN(C(=O)c5cccnc5)CC4)cc3)n2)cc1] | 7 |
| 309 | N-{4-[2-({4-[(2R,6S)-2,6-dimethylmorpholin-4-yl]phenyl}amino)pyrimidin-4-yl]phenyl}acetamide | 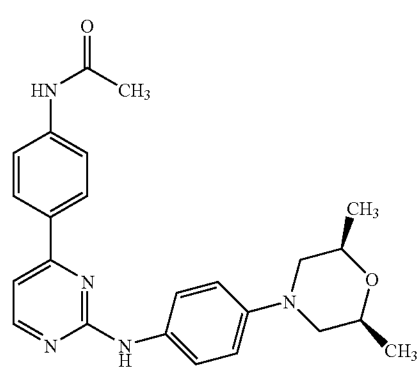 [SMILES: CC(=O)Nc1ccc(-c2ccnc(Nc3ccc(N4C[C@@H](C)O[C@@H](C)C4)cc3)n2)cc1] | 3 |

TABLE 1-continued

| Cmpd No. | Name | Structure | Can Be Made According To Synthetic Example #: |
|---|---|---|---|
| 310 | N-(4-{2-[(4-{4-[(2-methylphenyl)carbonyl]piperazin-1-yl}phenyl)amino]pyrimidin-4-yl}phenyl)acetamide | 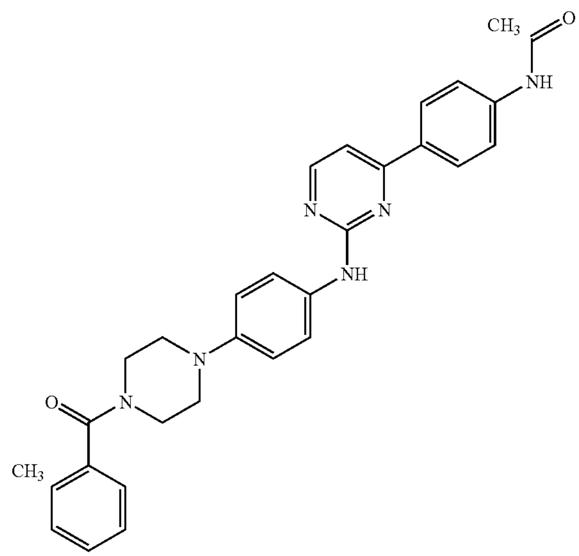 | 7 |
| 311 | N-{4-[2-({4-[4-(1H-pyrazol-4-ylcarbonyl)piperazin-1-yl]phenyl}amino)pyrimidin-4-yl]phenyl}acetamide | 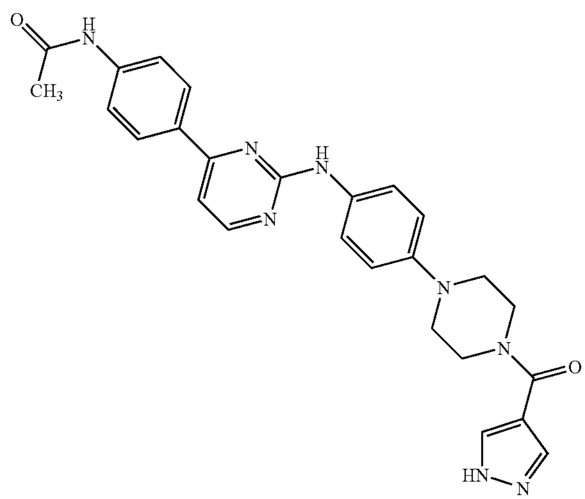 [SMILES: CC(=O)Nc1ccc(-c2ccnc(Nc3ccc(N4CCN(C(=O)c5cn[nH]c5)CC4)cc3)n2)cc1] | 7 |
| 312 | N-(4-{2-[(3-piperazin-1-ylphenyl)amino]pyrimidin-4-yl}phenyl)acetamide | 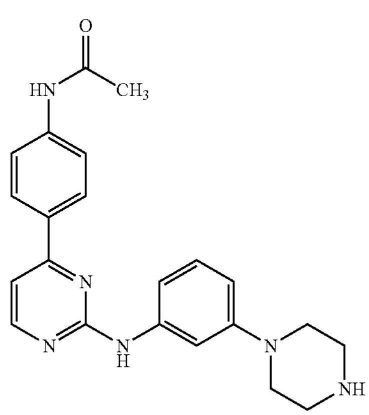 [SMILES: CC(=O)Nc1ccc(-c2ccnc(Nc3cccc(N4CCNCC4)c3)n2)cc1] | 34 |

TABLE 1-continued

| Cmpd No. | Name | Structure | Can Be Made According To Synthetic Example #: |
|---|---|---|---|
| 313 | N-[4-(2-{[3-(4-{[2-(methyloxy)phenyl]methyl}piperazin-1-yl)phenyl]amino}pyrimidin-4-yl)phenyl]acetamide | 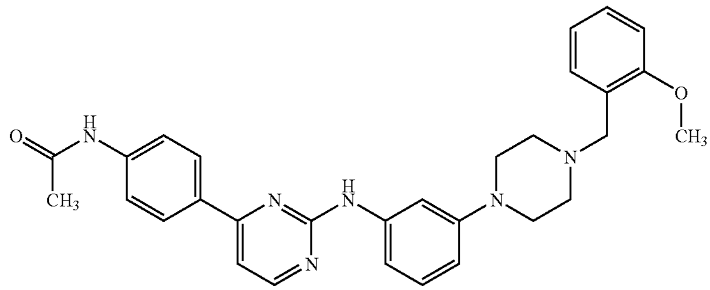 [SMILES: COc1ccccc1CN1CCN(c2cccc(Nc3nccc(-c4ccc(NC(C)=O)cc4)n3)c2)CC1] | 49 |
| 314 | N-{4-[2-({3-[4-(1,3-thiazol-2-ylmethyl)piperazin-1-yl]phenyl}amino)pyrimidin-4-yl]phenyl}acetamide | 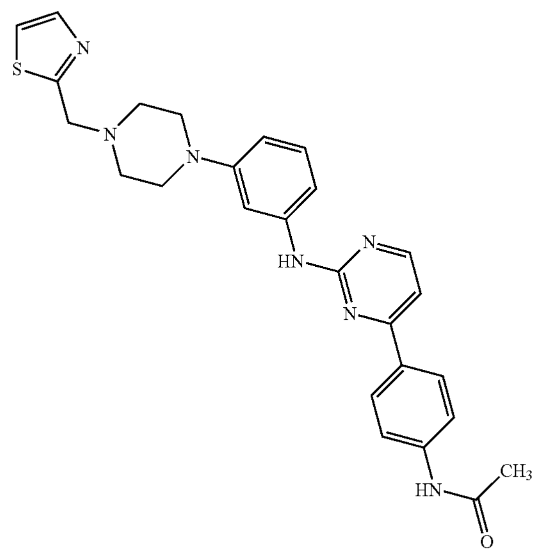 [SMILES: CC(=O)Nc1ccc(-c2ccnc(Nc3cccc(N4CCN(Cc5nccs5)CC4)c3)n2)cc1] | 49 |
| 315 | N-(4-{2-[(3-bromo-4-morpholin-4-ylphenyl)amino]pyrimidin-4-yl}phenyl)acetamide | 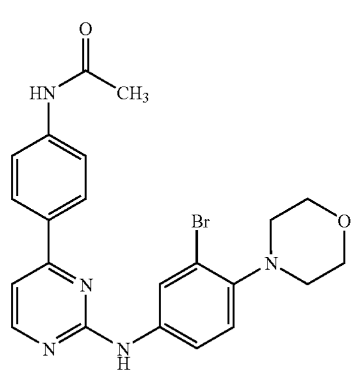 [SMILES: CC(=O)Nc1ccc(-c2ccnc(Nc3ccc(N4CCOCC4)c(Br)c3)n2)cc1] | 3 |

TABLE 1-continued

| Cmpd No. | Name | Structure | Can Be Made According To Synthetic Example #: |
|---|---|---|---|
| 316 | N-[4-(2-{[4-{[2-(diethylamino)ethyl]oxy}-3-(4-ethylpiperazin-1-yl)phenyl]amino}pyrimidin-4-yl)phenyl]acetamide | 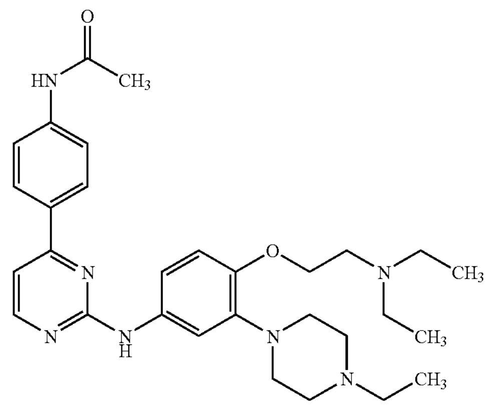 [SMILES: CCN(CC)CCOc1ccc(Nc2nccc(-c3ccc(NC(C)=O)cc3)n2)cc1N1CCN(CC)CC1] | 3 |
| 317 | 4-{2-[(4-morpholin-4-ylphenyl)amino]pyrimidin-4-yl}benzoic acid | 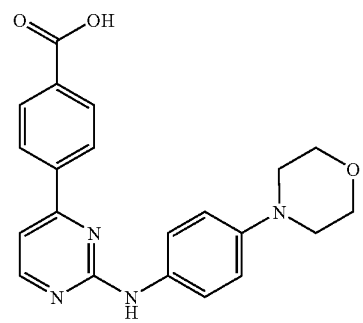 | 9 |
| 318 | 4-(4-furan-2-ylphenyl)-N-(4-morpholin-4-ylphenyl)pyrimidin-2-amine | 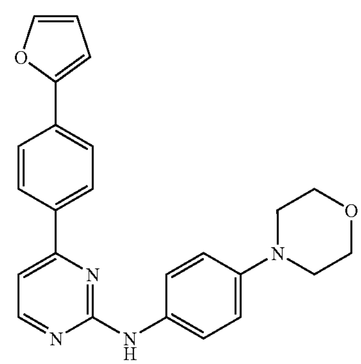 [SMILES: c1coc(-c2ccc(-c3ccnc(Nc4ccc(N5CCOCC5)cc4)n3)cc2)c1] | 9 |
| 319 | 4-[4-(3-methyl-1,2,4-oxadiazol-5-yl)phenyl]-N-(4-morpholin-4-ylphenyl)pyrimidin-2-amine | 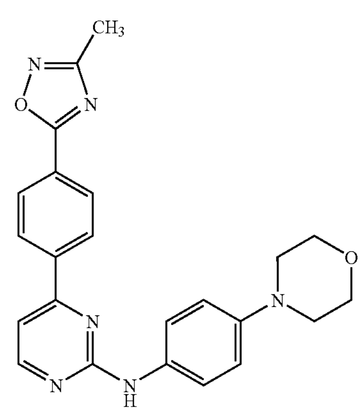 [SMILES: Cc1noc(-c2ccc(-c3ccnc(Nc4ccc(N5CCOCC5)cc4)n3)cc2)n1] | 10 |

| Cmpd No. | Name | Structure | Can Be Made According To Synthetic Example #: |
|---|---|---|---|
| 320 | 4-{2-[(4-morpholin-4-ylphenyl)amino]pyrimidin-4-yl}benzonitrile | 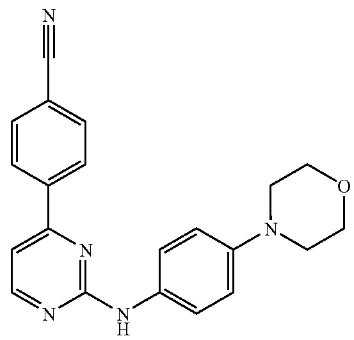 [SMILES: N#Cc1ccc(-c2ccnc(Nc3ccc(N4CCOCC4)cc3)n2)cc1] | 9 |
| 321 | methyl 4-{2-[(4-morpholin-4-ylphenyl)amino]pyrimidin-4-yl}benzoate | 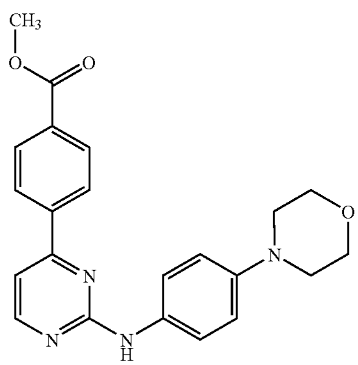 [SMILES: COC(=O)c1ccc(-c2ccnc(Nc3ccc(N4CCOCC4)cc3)n2)cc1] | 9 |
| 322 | 4-(4-fluorophenyl)-N-(4-morpholin-4-ylphenyl)pyrimidin-2-amine | 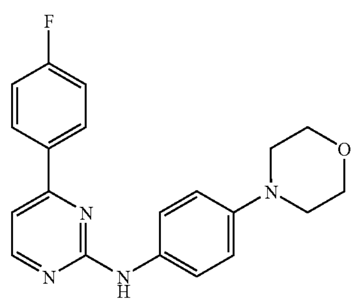 [SMILES: Fc1ccc(-c2ccnc(Nc3ccc(N4CCOCC4)cc3)n2)cc1] | 9 |
| 323 | N-[3-({2-[(4-morpholin-4-ylphenyl)amino]-7H-pyrrolo[2,3-d]pyrimidin-4-yl}amino)phenyl]acetamide | 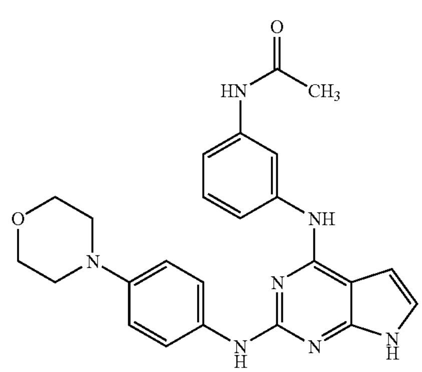 [SMILES: CC(=O)Nc1cccc(Nc2nc(Nc3ccc(N4CCOCC4)cc3)nc3[nH]ccc23)c1] | 35 |

TABLE 1-continued

| Cmpd No. | Name | Structure | Can Be Made According To Synthetic Example #: |
|---|---|---|---|
| 324 | N-(4-morpholin-4-ylphenyl)-4-[4-(pyridin-3-ylamino)phenyl]pyrimidin-2-amine | 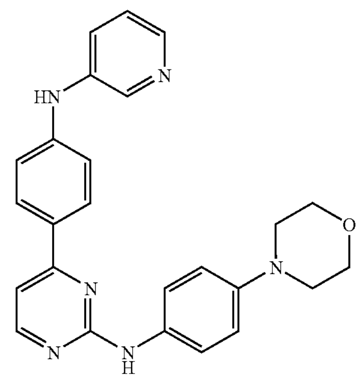 [SMILES: c1cncc(Nc2ccc(-c3ccnc(Nc4ccc(N5CCOCC5)cc4)n3)cc2)c1] | 9 |
| 325 | N-(4-morpholin-4-ylphenyl)-4-[4-(pyridin-2-ylamino)phenyl]pyrimidin-2-amine | 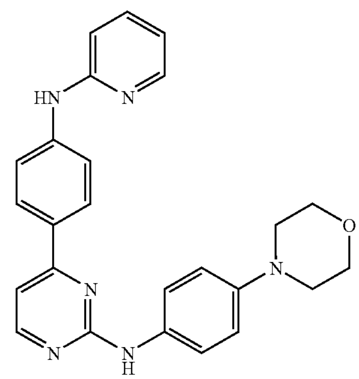 [SMILES: c1ccc(Nc2ccc(-c3ccnc(Nc4ccc(N5CCOCC5)cc4)n3)cc2)nc1] | 9 |
| 326 | N-(4-{2-[(4-morpholin-4-ylphenyl)amino]pyrimidin-4-yl}phenyl)methanesulfonamide | 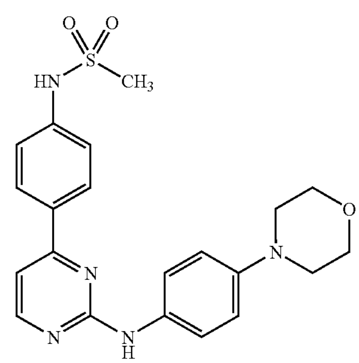 [SMILES: CS(=O)(=O)Nc1ccc(-c2ccnc(Nc3ccc(N4CCOCC4)cc3)n2)cc1] | 10 |
| 327 | 1-(4-{2-[(4-morpholin-4-ylphenyl)amino]pyrimidin-4-yl}phenyl)-3-(phenylmethyl)urea | 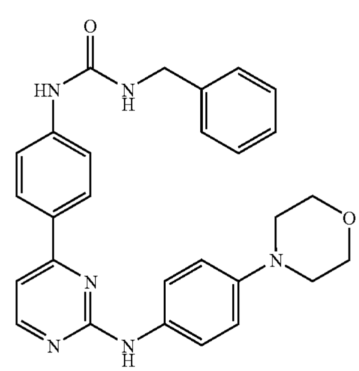 | 17 |

TABLE 1-continued

| Cmpd No. | Name | Structure | Can Be Made According To Synthetic Example #: |
|---|---|---|---|
| 328 | 4-(2,3-dihydro-1,4-benzodioxin-6-yl)-N-(4-morpholin-4-ylphenyl)pyrimidin-2-amine | 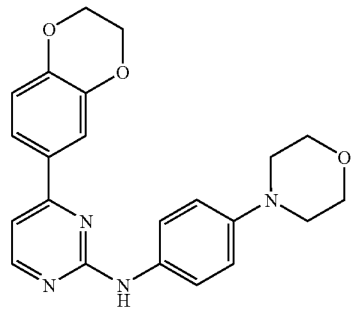 [SMILES: c1cc(-c2ccc3c(c2)OCCO3)nc(Nc2ccc(N3CCOCC3)cc2)n1] | 9 |
| 329 | N-(4-{2-[(4-morpholin-4-ylphenyl)amino]-7H-pyrrolo[2,3-d]pyrimidin-4-yl}phenyl)acetamide | 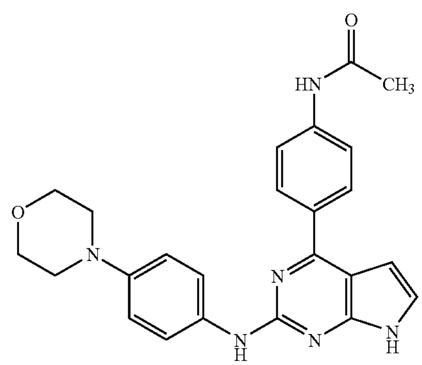 [SMILES: CC(=O)Nc1ccc(-c2nc(Nc3ccc(N4CCOCC4)cc3)nc3[nH]ccc23)cc1] | 43 |
| 330 | N-(4-morpholin-4-ylphenyl)-4-quinolin-6-ylpyrimidin-2-amine | 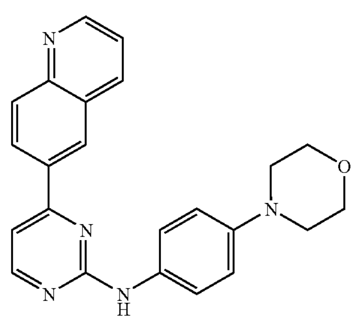 [SMILES: c1cnc2ccc(-c3ccnc(Nc4ccc(N5CCOCC5)cc4)n3)cc2c1] | 9 |
| 331 | 4-[4-(5-methyl-1,3,4-oxadiazol-2-yl)phenyl]-N-(4-morpholin-4-ylphenyl)pyrimidin-2-amine | 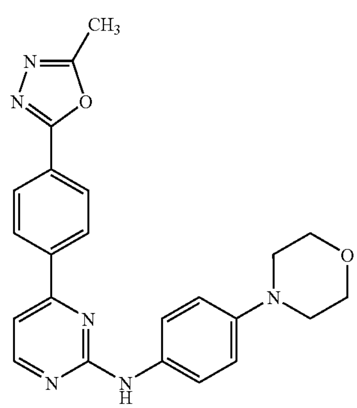 [SMILES: Cc1nnc(-c2ccc(-c3ccnc(Nc4ccc(N5CCOCC5)cc4)n3)cc2)o1] | 9 |

| Cmpd No. | Name | Structure | Can Be Made According To Synthetic Example #: |
|---|---|---|---|
| 332 | N-(4-morpholin-4-ylphenyl)-4-(4-pyrimidin-5-ylphenyl)pyrimidin-2-amine | 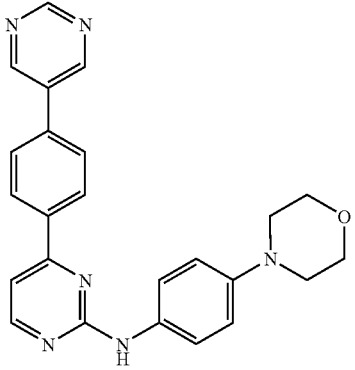 [SMILES: c1ncc(-c2ccc(-c3ccnc(Nc4ccc(N5CCOCC5)cc4)n3)cc2)cn1] | 9 |
| 333 | N-(4-morpholin-4-ylphenyl)-4-quinoxalin-6-ylpyrimidin-2-amine | 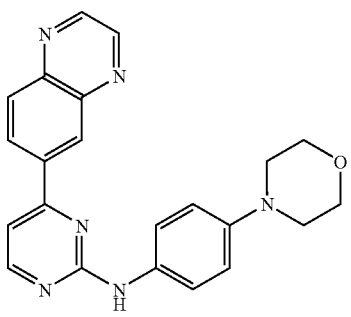 [SMILES: c1cc(-c2ccc3nccnc3c2)nc(Nc2ccc(N3CCOCC3)cc2)n1] | 9 |
| 334 | 2-chloro-N-(4-{2-[(4-morpholin-4-ylphenyl)amino}pyrimidin-4-yl}phenyl)benzamide | 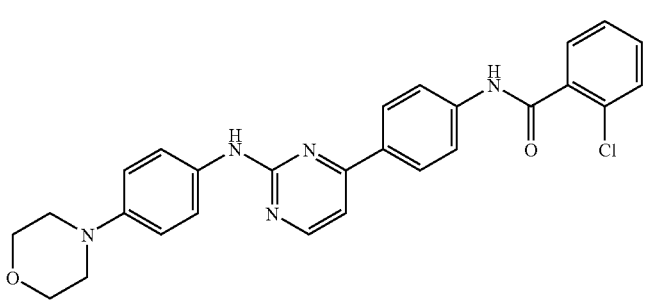 [SMILES: O=C(Nc1ccc(-c2ccnc(Nc3ccc(N4CCOCC4)cc3)n2)cc1)c1ccccc1Cl] | 12 |
| 335 | 2-(2-fluorophenyl)-N-(4-{2-[(4-morpholin-4-ylphenyl)amino]pyrimidin-4-yl}phenyl)acetamide | 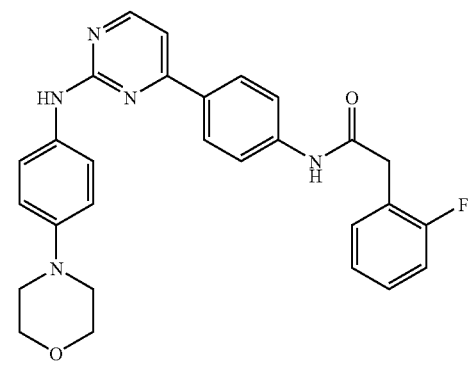 [SMILES: O=C(Cc1ccccc1F)Nc1ccc(-c2ccnc(Nc3ccc(N4CCOCC4)cc3)n2)cc1] | 12 |

| Cmpd No. | Name | Structure | Can Be Made According To Synthetic Example #: |
|---|---|---|---|
| 336 | N-(4-{2-[(4-morpholin-4-ylphenyl)amino]pyrimidin-4-yl}phenyl)pyrimidine-5-carboxamide | 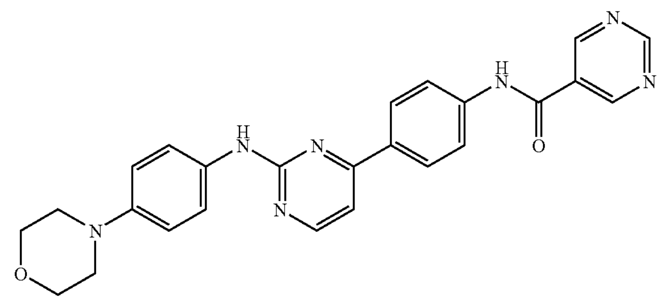 [SMILES: O=C(Nc1ccc(-c2ccnc(Nc3ccc(N4CCOCC4)cc3)n2)cc1)c1cncnc1] | 12 |
| 337 | (2S)-N-(4-{2-[(4-morpholin-4-ylphenyl)amino]pyrimidin-4-yl}phenyl)azetidine-2-carboxamide | 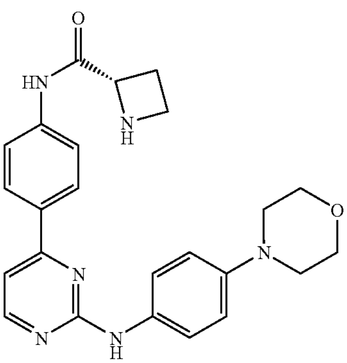 [SMILES: O=C(Nc1ccc(-c2ccnc(Nc3ccc(N4CCOCC4)cc3)n2)cc1)[C@@H]1CCN1] | 45 |
| 338 | N-(4-{2-[(4-morpholin-4-ylphenyl)amino]pyrimidin-4-yl}phenyl)-N~2~-phenylglycinamide | 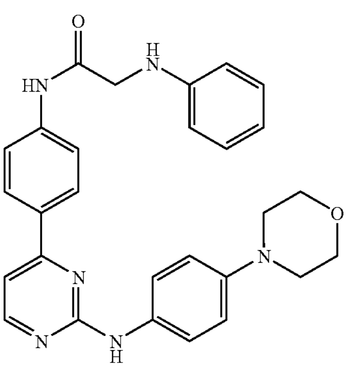 | 23 |
| 339 | 'N-{4-[2-({4-[(4-ethyl-piperazin-1-yl)carbonyl]phenyl}amino)pyrimidin-4-yl]phenyl}acetamide | 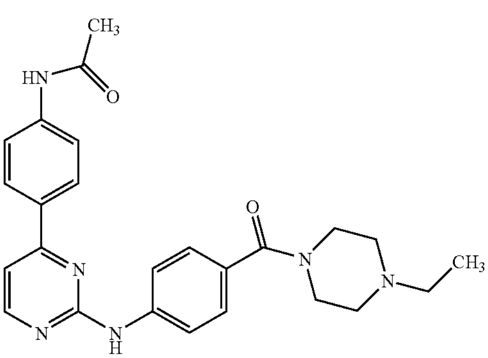 [SMILES: CCN1CCN(C(=O)c2ccc(Nc3nccc(-c4ccc(NC(C)=O)cc4)n3)cc2)CC1] | 29 |

TABLE 1-continued

| Cmpd No. | Name | Structure | Can Be Made According To Synthetic Example #: |
|---|---|---|---|
| 340 | N-(4-{2-[(4-morpholin-4-ylphenyl)amino]pyrimidin-4-yl}phenyl)-L-prolinamide | 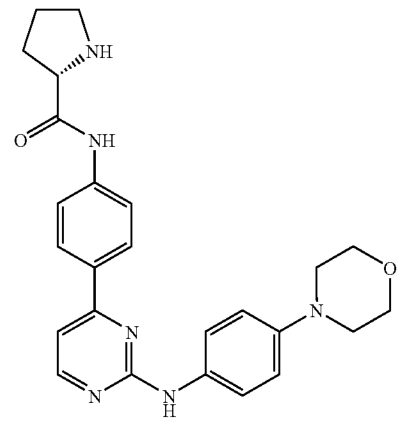 [SMILES: O=C(Nc1ccc(-c2ccnc(Nc3ccc(N4CCOCC4)cc3)n2)cc1)[C@@H]1CCCN1] | 14 |
| 341 | N-(4-(2-(3-methoxy-4-morpholino-phenylamino)pyrimidin-4-yl)phenyl)acetamide | 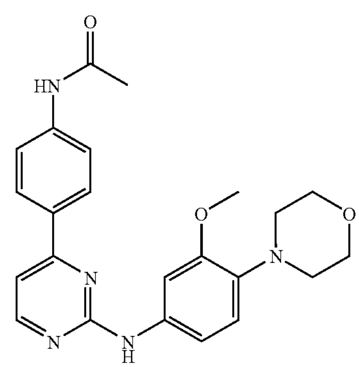 [SMILES: COc1cc(Nc2nccc(-c3ccc(NC(C)=O)cc3)n2)ccc1N1CCOCC1] | 15 |
| 342 | N-(4-(2-(4-(4-isobutyryl-piperazin-1-yl)phenylamino)-pyrimidin-4-yl)phenyl)acetamide | 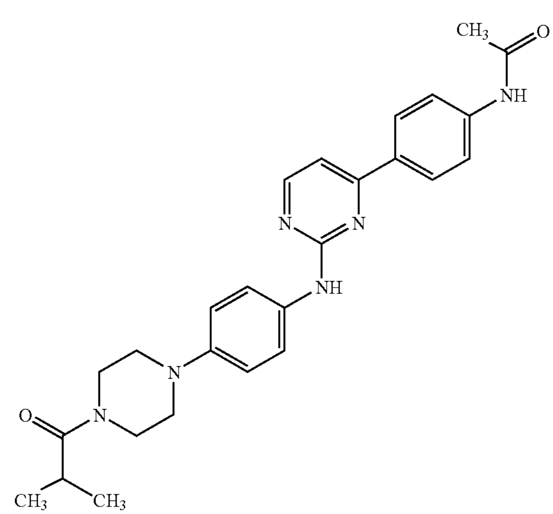 [SMILES: CC(=O)Nc1ccc(-c2ccnc(Nc3ccc(N4CCN(C(=O)C(C)C)CC4)cc3)n2)cc1] | 7 |

TABLE 1-continued

| Cmpd No. | Name | Structure | Can Be Made According To Synthetic Example #: |
|---|---|---|---|
| 343 | N-(4-(2-(4-(4-(3-methyl-butanoyl)piperazin-1-yl)phenylamino)pyrimidin-4-yl)phenyl)acetamide | 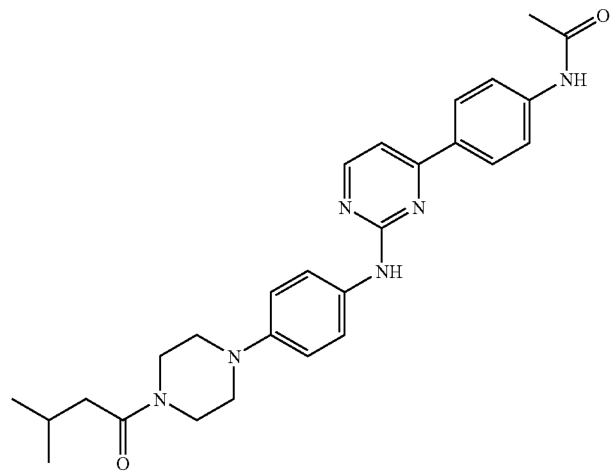 [SMILES: CC(=O)Nc1ccc(-c2ccnc(Nc3ccc(N4CCN(C(=O)CC(C)C)CC4)cc3)n2)cc1] | 7 |
| 344 | N-(4-(2-(4-(4-(cyclopropane-carbonyl)piperazin-1-yl)phenylamino)pyrimidin-4-yl)phenyl)acetamide | 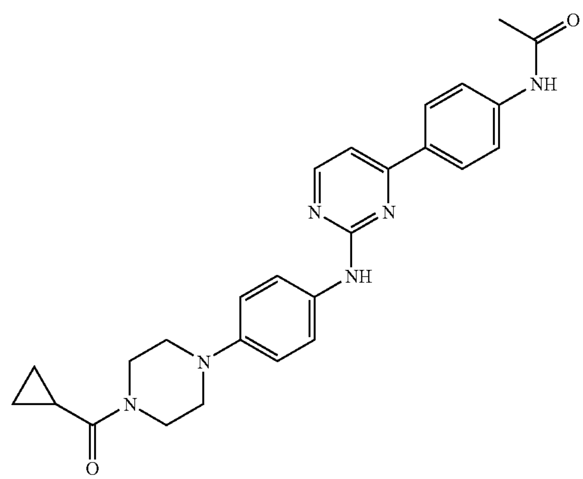 [SMILES: CC(=O)Nc1ccc(-c2ccnc(Nc3ccc(N4CCN(C(=O)C5CC5)CC4)cc3)n2)cc1] | 7 |
| 345 | N-(4-(2-(4-(4-(cyclobutane-carbonyl)piperazin-1-yl)phenylamino)pyrimidin-4-yl)phenyl)acetamide | 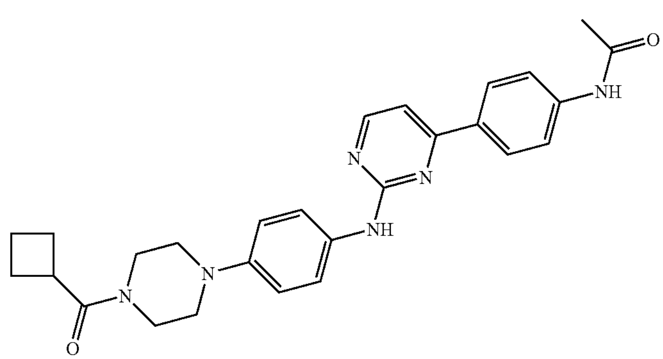 [SMILES: CC(=O)Nc1ccc(-c2ccnc(Nc3ccc(N4CCN(C(=O)C5CCC5)CC4)cc3)n2)cc1] | 7 |

TABLE 1-continued

| Cmpd No. | Name | Structure | Can Be Made According To Synthetic Example #: |
|---|---|---|---|
| 346 | N-(4-(2-(4-(4-(cyclopentane-carbonyl)piperazin-1-yl)phenylamino)pyrimidin-4-yl)phenyl)acetamide | 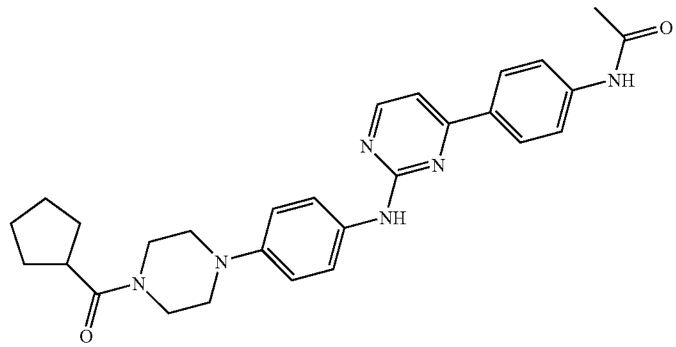 [SMILES: CC(=O)Nc1ccc(-c2ccnc(Nc3ccc(N4CCN(C(=O)C5CCCC5)CC4)cc3)n2)cc1] | 7 |
| 347 | N-(4-(2-(4-(4-(2-methoxy-benzoyl)piperazin-1-yl)phenylamino)pyrimidin-4-yl)phenyl)acetamide | 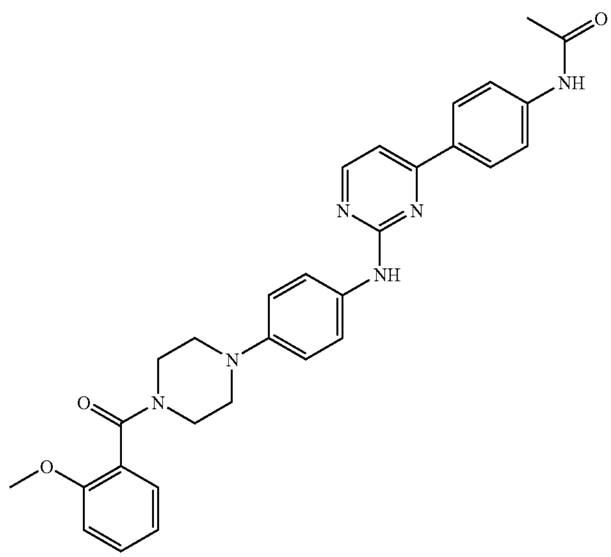 [SMILES: COc1ccccc1C(=O)N1CCN(c2ccc(Nc3nccc(-c4ccc(NC(C)=O)cc4)n3)cc2)CC1] | 7 |
| 348 | N-(4-(2-(4-(4-pentanoyl-piperazin-1-yl)phenylamino)pyrimidin-4-yl)phenyl)acetamide | 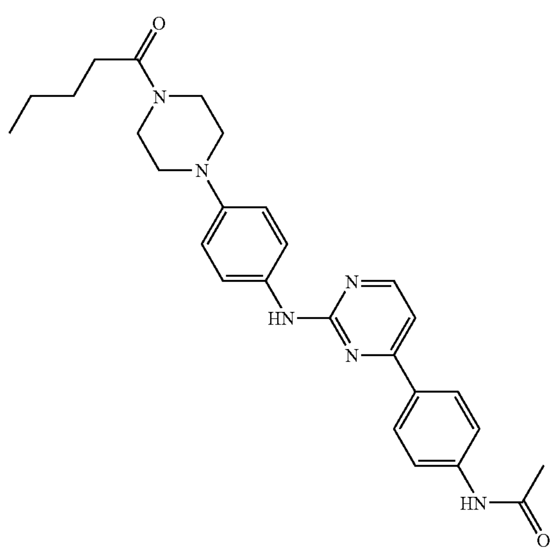 | 7 |

TABLE 1-continued

| Cmpd No. | Name | Structure | Can Be Made According To Synthetic Example #: |
|---|---|---|---|
| 349 | N-(4-(2-(4-(4-picolinoyl-piperazin-1-yl)phenylamino)pyrimidin-4-yl)phenyl)acetamide | 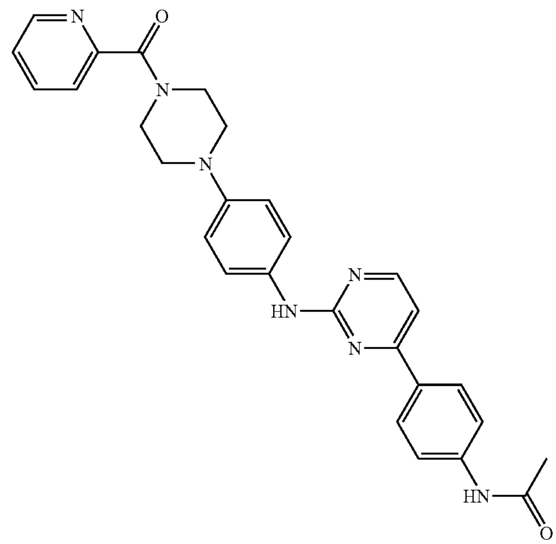 [SMILES: CC(=O)Nc1ccc(-c2ccnc(Nc3ccc(N4CCN(C(=O)c5ccccn5)CC4)cc3)n2)cc1] | 7 |
| 350 | N-(4-(2-(4-(4-isonicotinoyl-piperazin-1-yl)phenylamino)pyrimidin-4-yl)phenyl)acetamide | 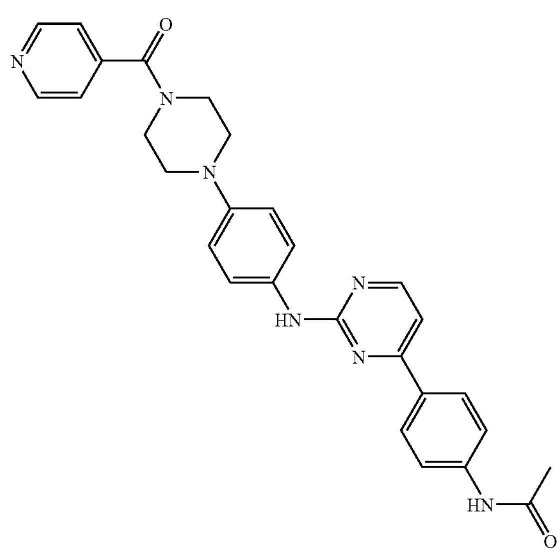 [SMILES: CC(=O)Nc1ccc(-c2ccnc(Nc3ccc(N4CCN(C(=O)c5ccncc5)CC4)cc3)n2)cc1] | 7 |

TABLE 1-continued

| Cmpd No. | Name | Structure | Can Be Made According To Synthetic Example #: |
|---|---|---|---|
| 351 | N-(4-(2-(4-(4-(1-acetyl-piperidine-4-carbonyl)piperazin-1-yl)phenylamino)pyrimidin-4-yl)phenyl)acetamide | 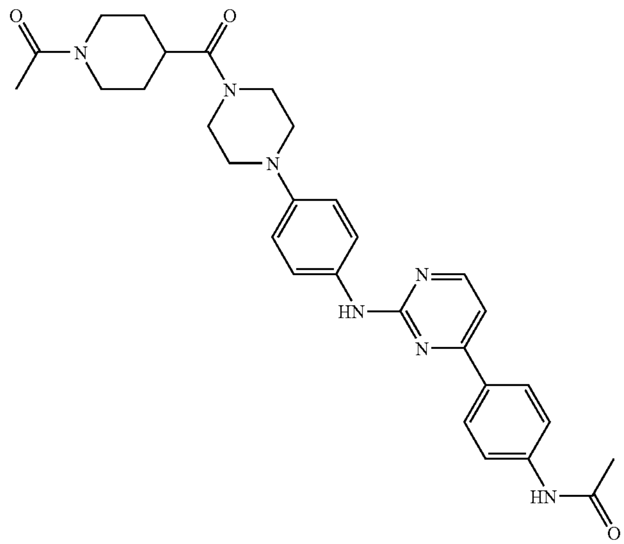 [SMILES: CC(=O)Nc1ccc(-c2ccnc(Nc3ccc(N4CCN(C(=O)C5CCN(C(C)=O)CC5)CC4)cc3)n2)cc1] | 7 |
| 352 | N-(4-(2-(4-(4-(2-cyclopropyl-acetyl)piperazin-1-yl)phenylamino)pyrimidin-4-yl)phenyl)acetamide | 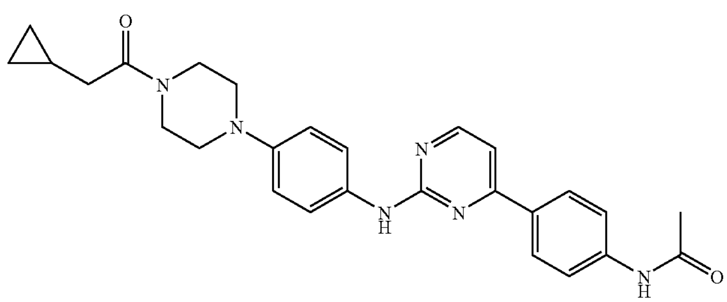 [SMILES: CC(=O)Nc1ccc(-c2ccnc(Nc3ccc(N4CCN(C(=O)CC5CC5)CC4)cc3)n2)cc1] | 7 |
| 353 | N-(4-(2-(4-(4-(3-methoxy-propanoyl)piperazin-1-yl)phenylamino)pyrimidin-4-yl)phenyl)acetamide | 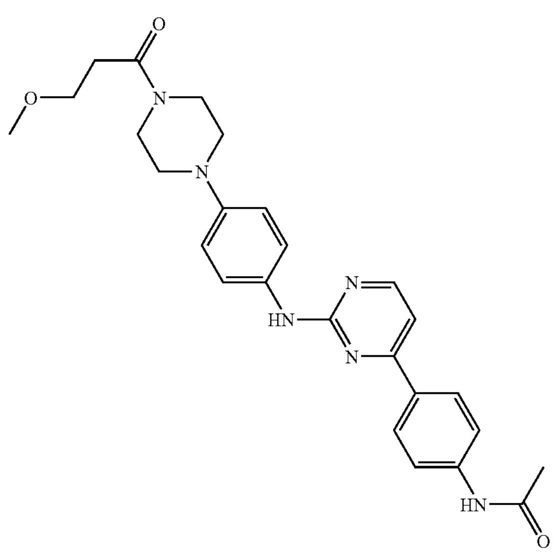 [SMILES: COCCC(=O)N1CCN(c2ccc(Nc3nccc(-c4ccc(NC(C)=O)cc4)n3)cc2)CC1] | 7 |

TABLE 1-continued
| Cmpd No. | Name | Structure | Can Be Made According To Synthetic Example #: |
|---|---|---|---|
| 354 | N-(4-(2-(4-(4-(2-(2-methoxy-ethoxy)acetyl)piperazin-1-yl)phenylamino)pyrimidin-4-yl)phenyl)acetamide | 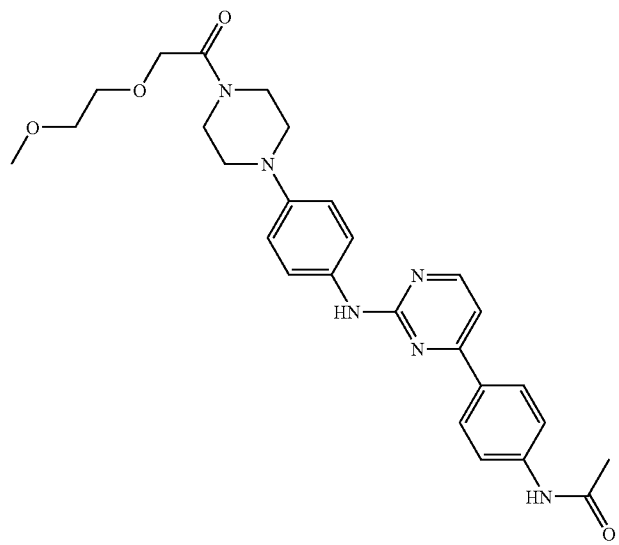 [SMILES: COCCOCC(=O)N1CCN(c2ccc(Nc3nccc(-c4ccc(NC(C)=O)cc4)n3)cc2)CC1] | 7 |
| 355 | N-(4-(2-(4-(4-(2-(pyridin-3-yl)acetyl)piperazin-1-yl)phenylamino)pyrimidin-4-yl)phenyl)acetamide | 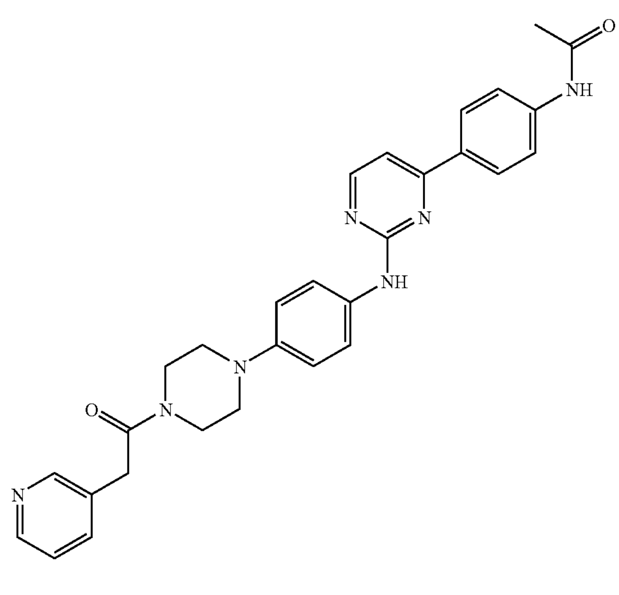 [SMILES: CC(=O)Nc1ccc(-c2ccnc(Nc3ccc(N4CCN(C(=O)Cc5cccnc5)CC4)cc3)n2)cc1] | 7 |

TABLE 1-continued

| Cmpd No. | Name | Structure | Can Be Made According To Synthetic Example #: |
|---|---|---|---|
| 356 | N-(4-(2-(4-(4-(3-(pyridin-3-yl)propanoyl)piperazin-1-yl)phenylamino)pyrimidin-4-yl)phenyl)acetamide | 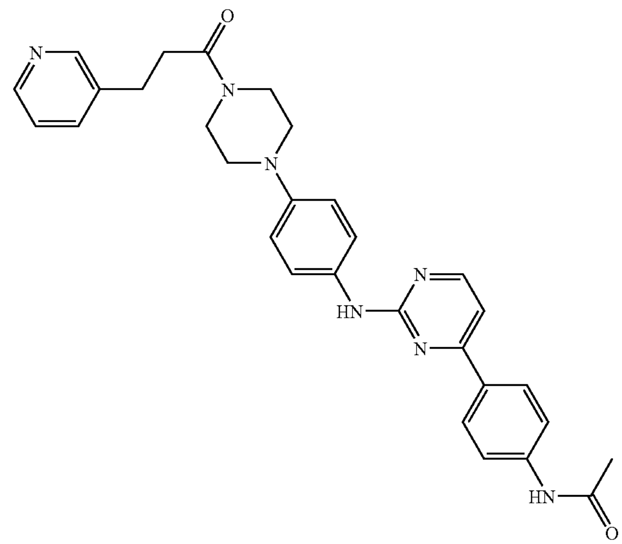 [SMILES: CC(=O)Nc1ccc(-c2ccnc(Nc3ccc(N4CCN(C(=O)CCc5cccnc5)CC4)cc3)n2)cc1] | 7 |
| 357 | N-(4-(2-(4-morpholinophenyl-amino)pyimidin-4-yl)phenyl)tetrahydrofuran-3-carboxamide | 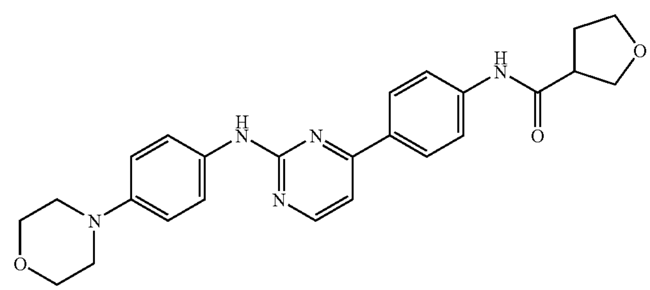 [SMILES: O=C(Nc1ccc(-c2ccnc(Nc3ccc(N4CCOCC4)cc3)n2)cc1)C1CCOC1] | 12 |
| 358 | N-(4-(2-(4-morpholino-phenylamino)pyrimidin-4-yl)phenyl)-2-(pyridin-3-yl)acetamide | 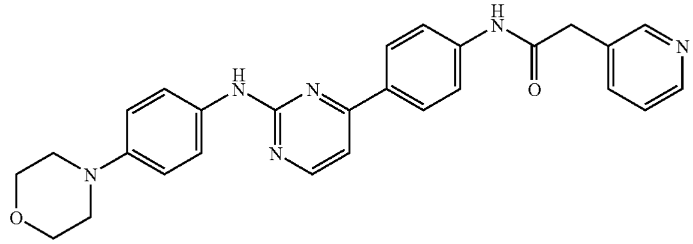 [SMILES: O=C(Cc1cccnc1)Nc1ccc(-c2ccnc(Nc3ccc(N4CCOCC4)cc3)n2)cc1] | 12 |

TABLE 1-continued

| Cmpd No. | Name | Structure | Can Be Made According To Synthetic Example #: |
|---|---|---|---|
| 359 | N-(4-(2-(4-morpholinophenyl-amino)pyrimidin-4-yl)phenyl)isonicotinamide | 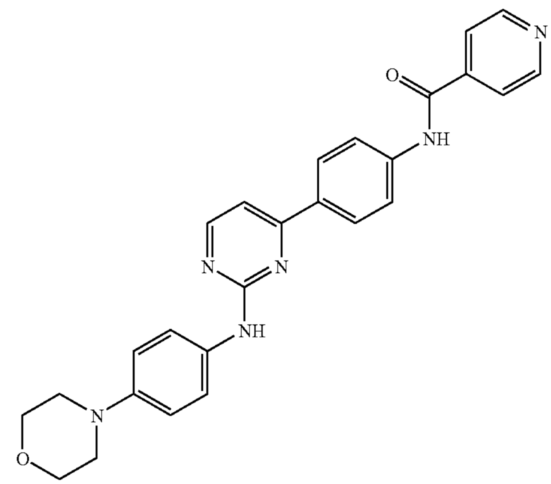 [SMILES: O=C(Nc1ccc(-c2ccnc(Nc3ccc(N4CCOCC4)cc3)n2)cc1)c1ccncc1] | 12 |
| 360 | N-(4-{2-[(4-morpholin-4-ylphenyl)amino]pyrimidin-4-yl}phenyl)-D-prolinamide | 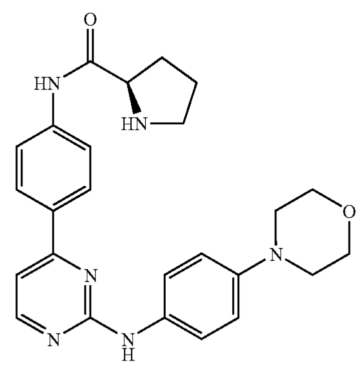 [SMILES: O=C(Nc1ccc(-c2ccnc(Nc3ccc(N4CCOCC4)cc3)n2)cc1)[C@H]1CCCN1] | 45 |
| 361 | N-[4-(2-{[3-(methyloxy)-4-morpholin-4-ylphenyl]amino}pyrimidin-4-yl)phenyl]-D-prolinamide | 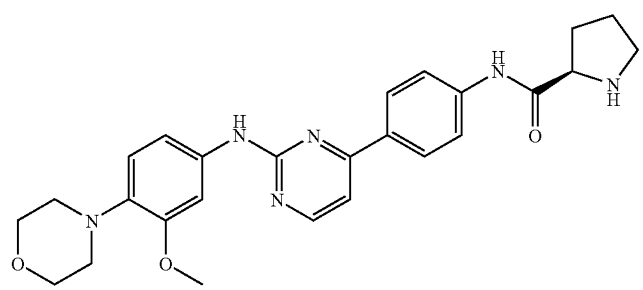 [SMILES: COc1cc(Nc2nccc(-c3ccc(NC(=O)[C@H]4CCCN4)cc3)n2)ccc1N1CCOCC1] | 45 |
| 362 | O-methyl-N-(4-{2-[(4-morpholin-4-ylphenyl)amino]pyrimidin-4-yl}phenyl)-L-serinamide | 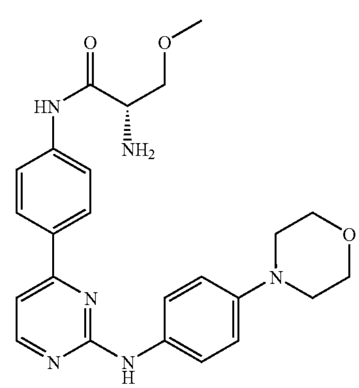 [SMILES: COC[C@H](N)C(=O)Nc1ccc(-c2ccnc(Nc3ccc(N4CCOCC4)cc3)n2)cc1] | 14 |

TABLE 1-continued

| Cmpd No. | Name | Structure | Can Be Made According To Synthetic Example #: |
|---|---|---|---|
| 363 | (S)-3-hydroxy-N-(4-(2-(4-morpholino-phenylamino)-pyrimdin-4-yl)-phenyl)-butanamide | 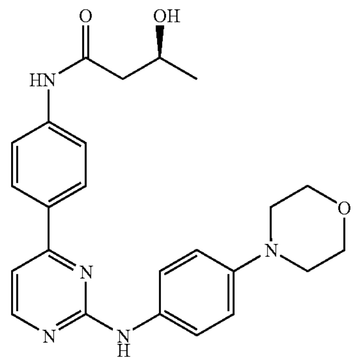 [SMILES: C[C@H](O)CC(=O)Nc1ccc(-c2ccnc(Nc3ccc(N4CCOCC4)cc3)n2)cc1] | 18 |
| 364 | (R)-3-hydroxy-N-(4-(2-(4-morpholinophenylamino)pyrimidin-4-yl)phenyl)butanamide | 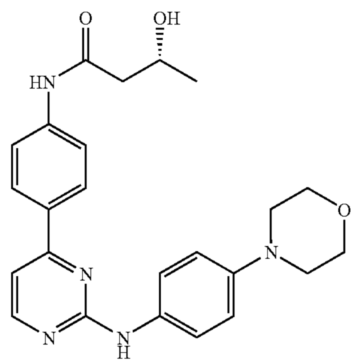 [SMILES: C[C@@H](O)CC(=O)Nc1ccc(-c2ccnc(Nc3ccc(N4CCOCC4)cc3)n2)cc1] | 20 |
| 365 | (R)-2-amino-3-hydroxy-N-(4-(2-(4-morpholinophenyl-amino)pyrimidin-4-yl)phenyl)propanamide | 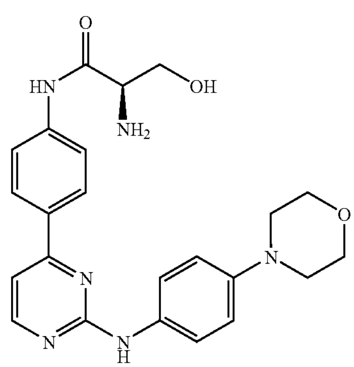 [SMILES: N[C@H](CO)C(=O)Nc1ccc(-c2ccnc(Nc3ccc(N4CCOCC4)cc3)n2)cc1] | 21 |
| 366 | 2-Hydroxy-2-methyl-N-(4-(2-(4-morpholinophenyl-amino)pyrimidin-4-yl)phenyl)propanamide | 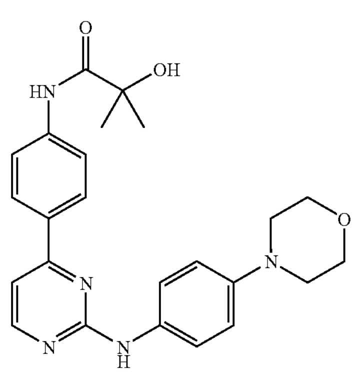 [SMILES: CC(C)(O)C(=O)Nc1ccc(-c2ccnc(Nc3ccc(N4CCOCC4)cc3)n2)cc1] | 11 |

TABLE 1-continued

| Cmpd No. | Name | Structure | Can Be Made According To Synthetic Example #: |
|---|---|---|---|
| 367 | 2-methyl-N-(4-(2-(4-morpholinophenylamino)pyrimidin-4-yl)phenyl)pyrrolidine-2-carboxamide | 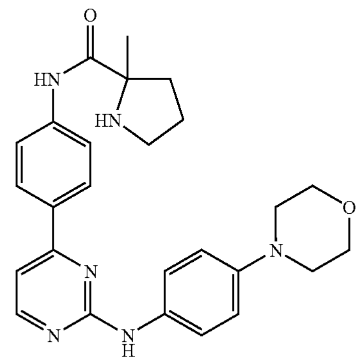 [SMILES: CC1(C(=O)Nc2ccc(-c3ccnc(Nc4ccc(N5CCOCC5)cc4)n3)cc2)CCCN1] | 44 |
| 368 | (R)-N-(4-(2-(4-((R)-3-(dimethylamino)pyrrolidin-1-yl)phenylamino)pyrimidin-4-yl)phenyl)pyrrolidine-2-carboxamide | 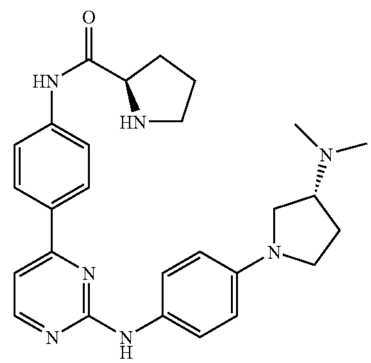 [SMILES: CN(C)[C@@H]1CCN(c2ccc(Nc3nccc(-c4ccc(NC(=O)[C@H]5CCCN5)cc4)n3)cc2)C1] | 45 |
| 369 | 4-amino-1,1-dioxo-N-(4-(2-(4-morpholinophenylamino)pyrimidin-4-yl)phenyl)tetrahydro-2H-thiopyran-4-carboxamide | 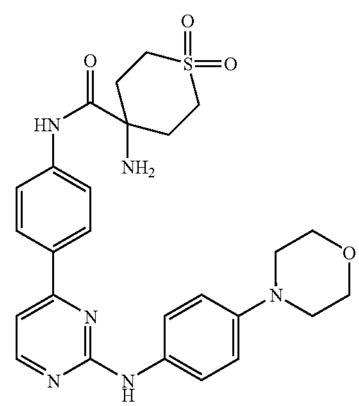 [SMILES: NC1(C(=O)Nc2ccc(-c3ccnc(Nc4ccc(N5CCOCC5)cc4)n3)cc2)CCS(=O)(=O)CC1] | 44 |
| 370 | (R)-4-(4-aminophenyl)-N-(4-(3-(dimethylamino)-pyrrolidin-1-yl)phenyl)-pyrimidin-2-amine | 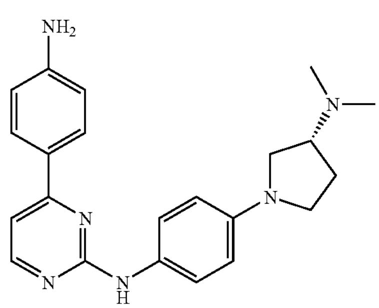 [SMILES: CN(C)[C@@H]1CCN(c2ccc(Nc3nccc(-c4ccc(N)cc4)n3)cc2)C1] | 8 |

TABLE 1-continued

| Cmpd No. | Name | Structure | Can Be Made According To Synthetic Example #: |
|---|---|---|---|
| 371 | (R)-N-(4-(2-(4-(3-(dimethyl-amino)pyrrolidin-1-yl)phenylamino)-pyrimidin-4-yl)phenyl)-3-methoxy-propanamide | 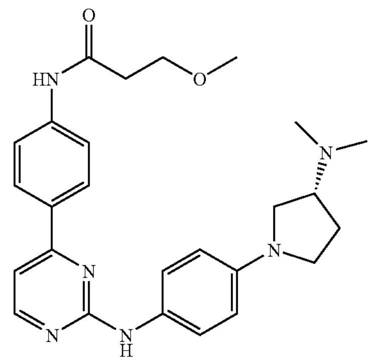 [SMILES: COCCC(=O)Nc1ccc(-c2ccnc(Nc3ccc(N4CC[C@@H](N(C)C)C4)cc3)n2)cc1] | 12 |
| 372 | N-(4-(2-(4-morpholinophenyl-amino)pyrimidin-4-yl)phenyl)piperazine-2-carboxamide | 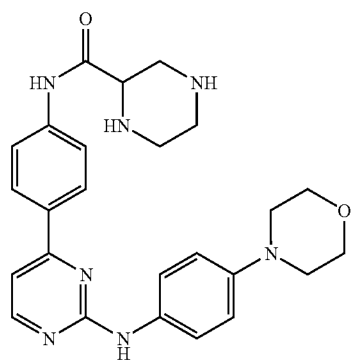 [SMILES: O=C(Nc1ccc(-c2ccnc(Nc3ccc(N4CCOCC4)cc3)n2)cc1)C1CNCCN1] | 12 |
| 373 | 2-amino-N-(4-(2-(4-morpholinophenylamino)pyrimidin-4-yl)phenyl)-1,2,3,4-tetrahydro-naphthalene-2-carboxamide | 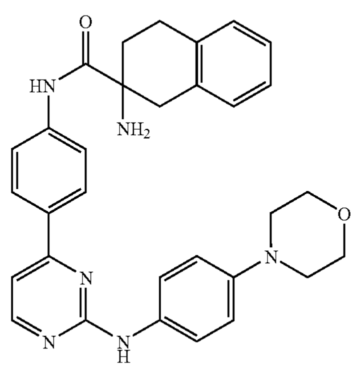 [SMILES: NC1(C(=O)Nc2ccc(-c3ccnc(Nc4ccc(N5CCOCC5)cc4)n3)cc2)CCc2ccccc2C1] | 44 |
| 374 | 4-(4-(1,1-dioxo-isothiazolidin-2-yl)phenyl)-N-(4-morpholinophenyl)-pyrimidin-2-amine | 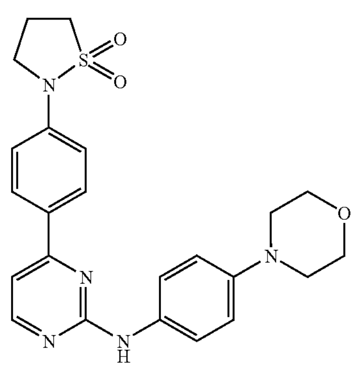 [SMILES: O=S1(=O)CCCN1c1ccc(-c2ccnc(Nc3ccc(N4CCOCC4)cc3)n2)cc1] | 25 |

TABLE 1-continued

| Cmpd No. | Name | Structure | Can Be Made According To Synthetic Example #: |
|---|---|---|---|
| 375 | 4-(4-(1H-tetrazol-1-yl) phenyl)-N-(4-morpholino-phenyl)-pyrimidin-2-amine | 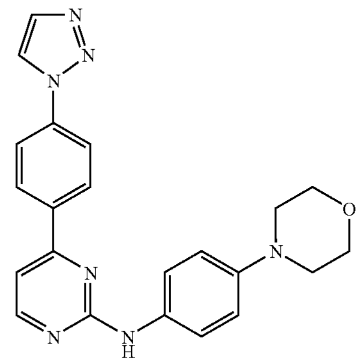 [SMILES: c1cn(-c2ccc(-c3ccnc(Nc4ccc(N5CCOCC5)cc4)n3)cc2)nn1] | 25 |
| 376 | (R)-N-(4-(2-(3-(benzyloxy)-4-morpholino-phenylamino)-pyrimidin-4-yl)phenyl)-pyrrolidine-2-carboxamide | 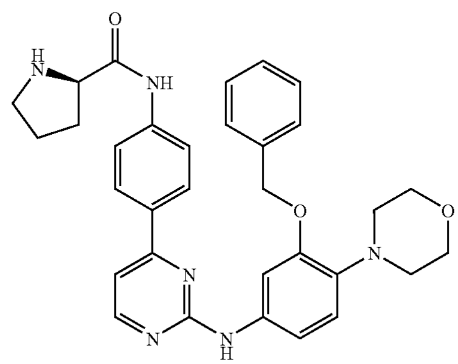 [SMILES: O=C(Nc1ccc(-c2ccnc(Nc3ccc(N4CCOCC4)c(OCc4ccccc4)c3)n2)cc1)[C@H]1CCCN1] | 45 |
| 377 | (S)-2-amino-3-hydroxy-N-(4-(2-(3-methoxy-4-morpholinophenylamino) pyrimidin-4-yl)phenyl)propanamide | 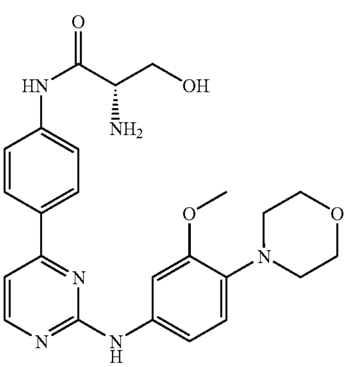 [SMILES: COc1cc(Nc2nccc(-c3ccc(NC(=O)[C@@H](N)CO)cc3)n2)ccc1N1CCOCC1] | 21 |
| 378 | N-(4-(2-(4-morpholinophenyl-amino)pyrimidin-4-yl) phenyl)-2-(1H-tetrazol-1-yl)acetamide | 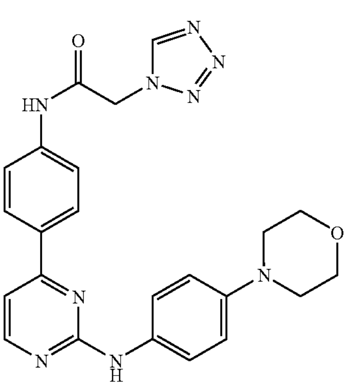 [SMILES: O=C(Cn1cnnn1)Nc1ccc(-c2ccnc(Nc3ccc(N4CCOCC4)cc3)n2)cc1] | 24 |

TABLE 1-continued

| Cmpd No. | Name | Structure | Can Be Made According To Synthetic Example #: |
|---|---|---|---|
| 379 | (R)-N-(4-(2-(3-ethoxy-4-morpholinophenylamino)pyrimidin-4-yl)phenyl)-pyrrolidine-2-carboxamide | 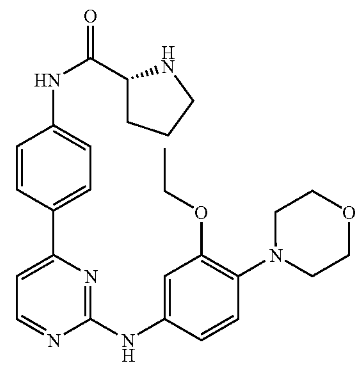 [SMILES: CCOc1cc(Nc2nccc(-c3ccc(NC(=O)[C@H]4CCCN4)cc3)n2)ccc1N1CCOCC1] | 45 |
| 380 | (R)-N-(4-(2-(1,2,3-4-tetrahydroquinolin-6-ylamino)-pyrimidin-4-yl)phenyl)-pyrrolidine-2-carboxamide | 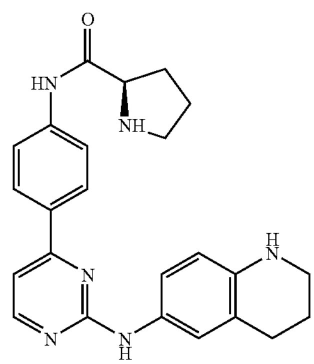 [SMILES: O=C(Nc1ccc(-c2ccnc(Nc3ccc4c(c3)CCCN4)n2)cc1)[C@H]1CCCN1] | 45 |
| 381 | 3-hydroxy-N-(4-(2-(3-methoxy-4-morpholino-phenylamino)pyrimidin-4-yl)phenyl)-3-methylbutanamide | 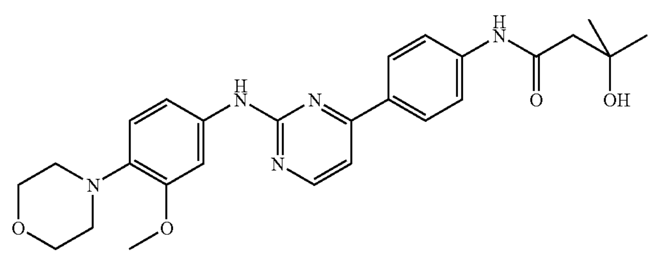 [SMILES: COc1cc(Nc2nccc(-c3ccc(NC(=O)CC(C)(C)O)cc3)n2)ccc1N1CCOCC1] | 18 |
| 382 | (3S,7S)-7-(hydroxymethyl)-N-(4-(2-(4-morpholinophenyl-amino)pyrimidin-4-yl)phenyl)quinuclidine-3-carboxamide | 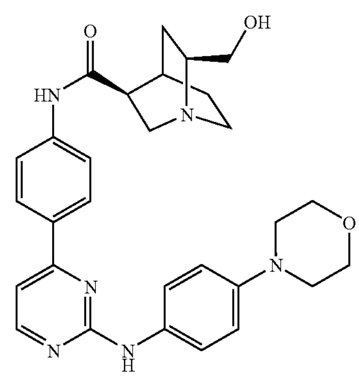 [SMILES: O=C(Nc1ccc(-c2ccnc(Nc3ccc(N4CCOCC4)cc3)n2)cc1)[C@@H]1CN2CCC1C[C@H]2CO] | 18 |

TABLE 1-continued

| Cmpd No. | Name | Structure | Can Be Made According To Synthetic Example #: |
|---|---|---|---|
| 383 | 1-hydroxy-N-(4-(2-(4-morpholino-phenylamino)-pyrimidin-4-yl)phenyl)cyclopropanecarboxamide | 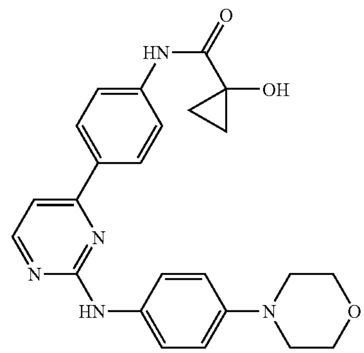 [SMILES: O=C(Nc1ccc(-c2ccnc(Nc3ccc(N4CCOCC4)cc3)n2)cc1)C1(O)CC1] | 18 |
| 384 | (S)-2-amino-N-(4-(2-(3-methyl-4-morpholinophenyl-amino)pyrimidin-4-yl)phenyl)propanamide | 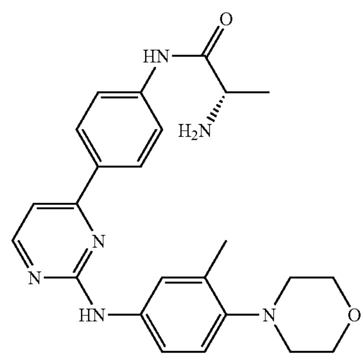 [SMILES: Cc1cc(Nc2nccc(-c3ccc(NC(=O)[C@H](C)N)cc3)n2)ccc1N1CCOCC1] | 14 |
| 385 | (R)-N-(4-(2-(3-methyl-4-morpholinophenylamino)pyrimidin-4-yl)phenyl)pyrrolidine-2-carboxamide | 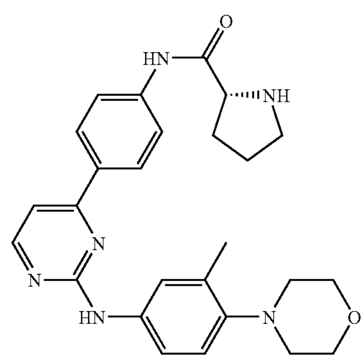 [SMILES: Cc1cc(Nc2nccc(-c3ccc(NC(=O)[C@H]4CCCN4)cc3)n2)ccc1N1CCOCC1] | 45 |
| 386 | (R)-N-(4-(2-(4-morpholino-3-(trifluoromethyl)-phenylamino)pyrimidin-4-yl)-phenyl)-pyrrolidine-2-carboxamide | 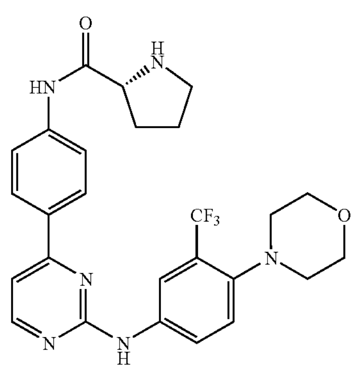 [SMILES: O=C(Nc1ccc(-c2ccnc(Nc3ccc(N4CCOCC4)c(C(F)(F)F)c3)n2)cc1)[C@H]1CCCN1] | 45 |

TABLE 1-continued

| Cmpd No. | Name | Structure | Can Be Made According To Synthetic Example #: |
|---|---|---|---|
| 387 | (R)-N-(4-(2-(4-(4-((S)-tetrahydrofuran-2-carbonyl)-piperazin-1-yl)-phenylamino)-pyrimidin-4-yl)phenyl)-pyrrolidine-2-carboxamide | 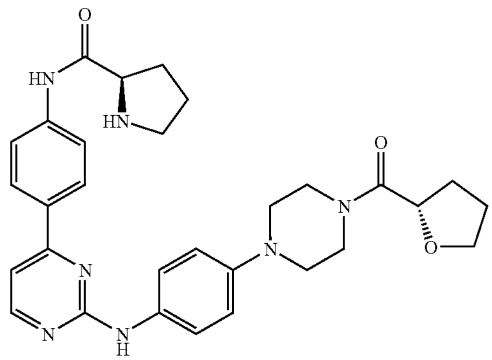 [SMILES: O=C(Nc1ccc(-c2ccnc(Nc3ccc(N4CCN(C(=O)[C@@H]5CCCO5)CC4)cc3)n2)cc1)[C@H]1CCCN1] | 45 |
| 388 | (R)-N-(4-(2-(4-(4-((R)-tetrahydrofuran-2-carbonyl)-piperazin-1-yl)-phenylamino)-pyrimidin-4-yl)phenyl)-pyrrolidine-2-carboxamide | 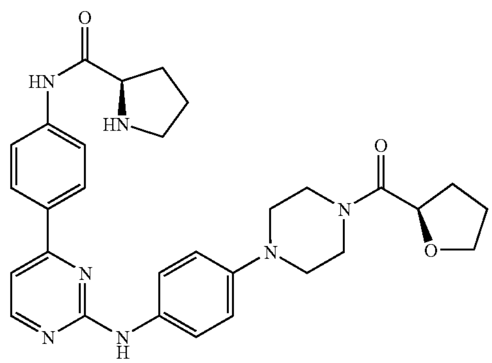 [SMILES: O=C(Nc1ccc(-c2ccnc(Nc3ccc(N4CCN(C(=O)[C@H]5CCCO5)CC4)cc3)n2)cc1)[C@H]1CCCN1] | 45 |
| 389 | 4-methyl-N-(4-(2-(4-morpholinophenylamino)pyrimidin-4-yl)phenyl)piperazine-1-carboxamide | 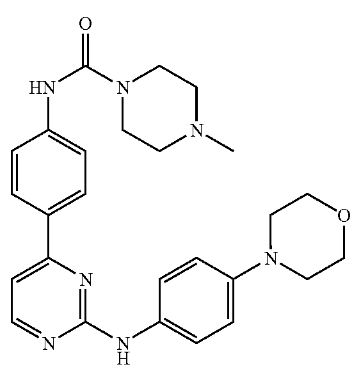 [SMILES: CN1CCN(C(=O)Nc2ccc(-c3ccnc(Nc4ccc(N5CCOCC5)cc4)n3)cc2)CC1] | 12 |
| 390 | 3-methoxy-N-(4-(2-(4-morpholino-3-(trifluoromethyl)phenylamino)pyrimidin-4-yl)phenyl)propanamide | 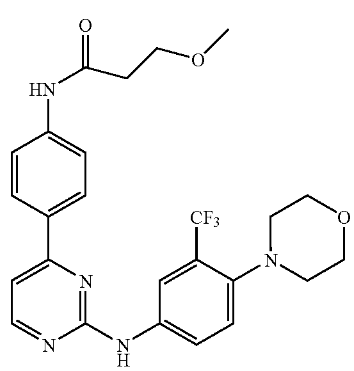 [SMILES: COCCC(=O)Nc1ccc(-c2ccnc(Nc3ccc(N4CCOCC4)c(C(F)(F)F)c3)n2)cc1] | 12 |

TABLE 1-continued

| Cmpd No. | Name | Structure | Can Be Made According To Synthetic Example #: |
|---|---|---|---|
| 391 | 3-methoxy-N-(4-(2-(4-morpholino-phenylamino)pyrimidin-4-yl)phenyl)-propane-1-sulfonamide | 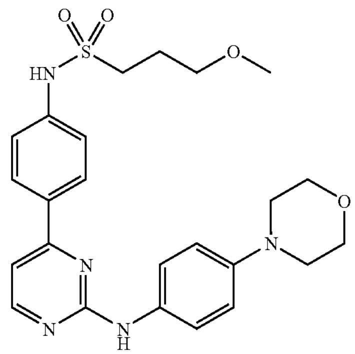 [SMILES: COCCCS(=O)(=O)Nc1ccc(-c2ccnc(Nc3ccc(N4CCOCC4)cc3)n2)cc1] | 16 |
| 392 | 2-methoxy-N-(4-(2-(4-morpholino-phenylamino)pyrimidin-4-yl)phenyl)-ethanesulfonamide | 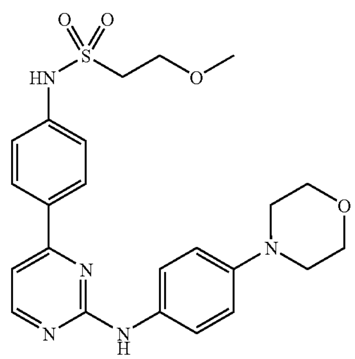 [SMILES: COCCS(=O)(=O)Nc1ccc(-c2ccnc(Nc3ccc(N4CCOCC4)cc3)n2)cc1] | 16 |
| 393 | (S)-3-hydroxy-N-(4-(2-(3-methoxy-4-morpholino-phenylamino)pyrimidin-4-yl)phenyl)butanamide | 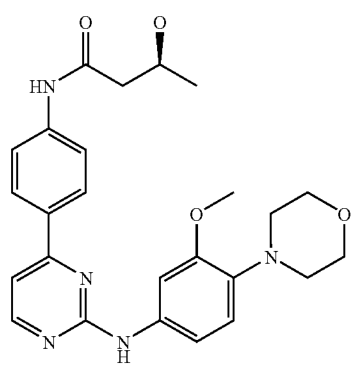 [SMILES: COc1cc(Nc2nccc(-c3ccc(NC(=O)C[C@H](C)O)cc3)n2)ccc1N1CCOCC1] | 18 |
| 394 | (R)-3-hydroxy-N-(4-(2-(3-methoxy-4-morpholino-phenylamino)pyrimidin-4-yl)phenyl)butanamide | 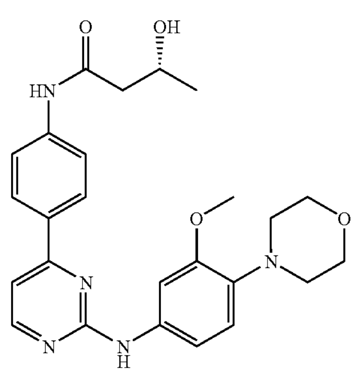 [SMILES: COc1cc(Nc2nccc(-c3ccc(NC(=O)C[C@@H](C)O)cc3)n2)ccc1N1CCOCC1] | 20 |

TABLE 1-continued

| Cmpd No. | Name | Structure | Can Be Made According To Synthetic Example #: |
|---|---|---|---|
| 395 | N-(4-(2-(4-morpholino-phenylamino)pyrimidin-4-yl)phenyl)-2,5-dihydro-1H-pyrrole-2-carboxamide | 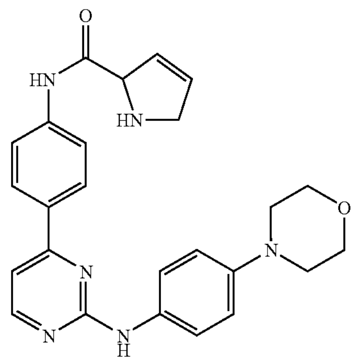 [SMILES: O=C(Nc1ccc(-c2ccnc(Nc3ccc(N4CCOCC4)cc3)n2)cc1)C1C=CCN1] | 13 |
| 396 | 1-(3-(dimethylamino)propyl)-3-(4-(2-(4-morpholinophenyl-amino)pyrimidin-4-yl)phenyl)urea | 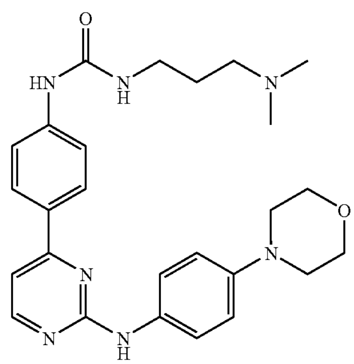 [SMILES: CN(C)CCCNC(=O)Nc1ccc(-c2ccnc(Nc3ccc(N4CCOCC4)cc3)n2)cc1] | 17 |
| 397 | (R)-N-(4-(2-(4-(4-((S)-pyrrolidin-2-ylmethyl)piperazin-1-yl)phenylamino)pyrimidin-4-yl)phenyl)pyrrolidine-2-carboxamide | 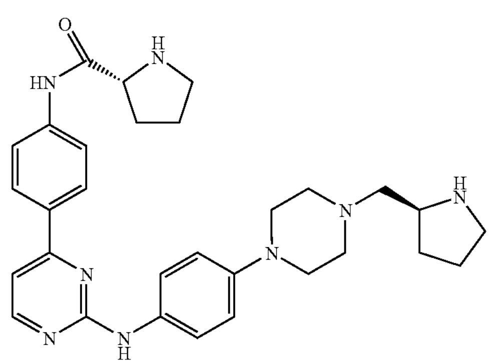 [SMILES: O=C(Nc1ccc(-c2ccnc(Nc3ccc(N4CCN(C[C@@H]5CCCN5)CC4)cc3)n2)cc1)[C@H]1CCCN1] | 45 |
| 398 | (R)-2-amino-N-(4-(2-(4-(4-ethylpiperazin-1-yl)phenyl-amino)-5-methylpyrimidin-4-yl)phenyl)propanamide | 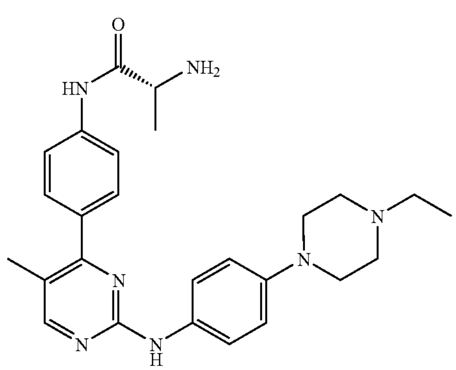 [SMILES: CCN1CCN(c2ccc(Nc3ncc(C)c(-c4ccc(NC(=O)[C@@H](C)N)cc4)n3)cc2)CC1] | 14 |

TABLE 1-continued

| Cmpd No. | Name | Structure | Can Be Made According To Synthetic Example #: |
|---|---|---|---|
| 399 | 1-(3-methoxypropyl)-3-(4-(2-(4-morpholinophenyl-amino)pyrimidin-4-yl)phenyl) urea | 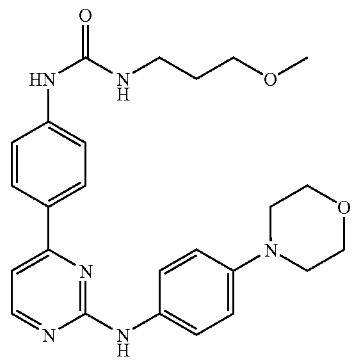 [SMILES: COCCCNC(=O)Nc1ccc(-c2ccnc(Nc3ccc(N4CCOCC4)cc3)n2)cc1] | 17 |
| 400 | (R)-N-(4-(2-(4-(4-ethyl-piperazin-1-yl)phenylamino)-5-methylpyrimidin-4-yl)phenyl)pyrrolidine-2-carboxamide | 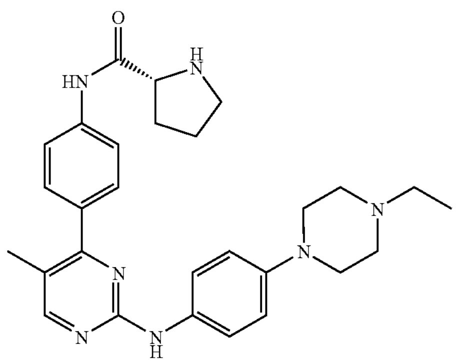 [SMILES: CCN1CCN(c2ccc(Nc3ncc(C)c(-c4ccc(NC(=O)[C@H]5CCCN5)cc4)n3)cc2)CC1] | 45 |
| 401 | (S)-N-(4-(2-(4-(4-(3-(dimethylamino)-2,2-dimethylpropyl)piperazin-1-yl)-3-fluorophenylamino)pyrimidin-4-yl)phenyl)-5-oxopyrrolidine-2-carboxamide | 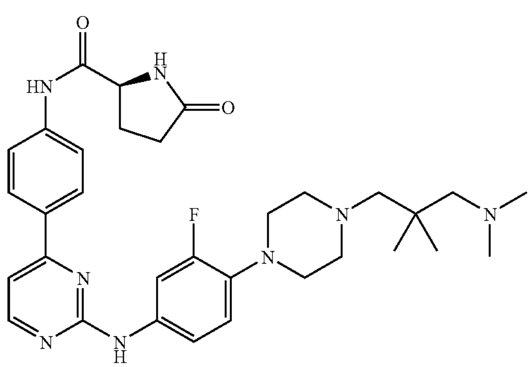 [SMILES: CN(C)CC(C)(C)CN1CCN(c2ccc(Nc3nccc(-c4ccc(NC(=O)[C@@H]5CCC(=O)N5)cc4)n3)cc2F)CC1] | 45 |
| 402 | (R)-N-(4-(2-(3-chloro-4-morpholinophenylamino)pyrimidin-4-yl)phenyl)pyrrolidine-2-carboxamide | 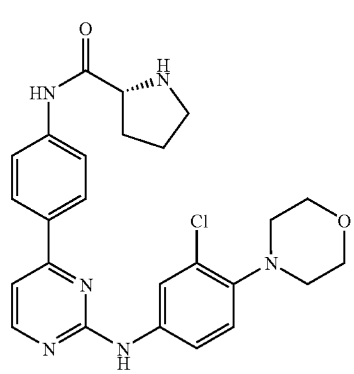 [SMILES: O=C(Nc1ccc(-c2ccnc(Nc3ccc(N4CCOCC4)c(Cl)c3)n2)cc1)[C@H]1CCCN1] | 45 |

TABLE 1-continued

| Cmpd No. | Name | Structure | Can Be Made According To Synthetic Example #: |
|---|---|---|---|
| 403 | 1-(2-morpholinoethyl)-3-(4-(2-(4-morpholinophenylamino)pyrimidin-4-yl)phenyl)urea | 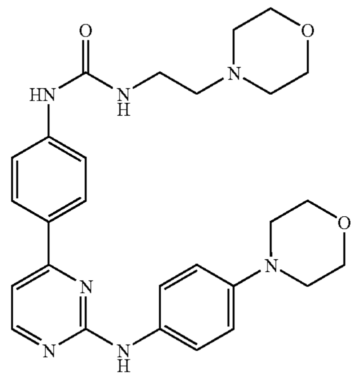 [SMILES: O=C(NCCN1CCOCC1)Nc1ccc(-c2ccnc(Nc3ccc(N4CCOCC4)cc3)n2)cc1] | 17 |
| 404 | 1-(2-(dimethylamino)ethyl)-3-(4-(2-(4-morpholinophenyl-amino)pyrimidin-4-yl)phenyl)urea | 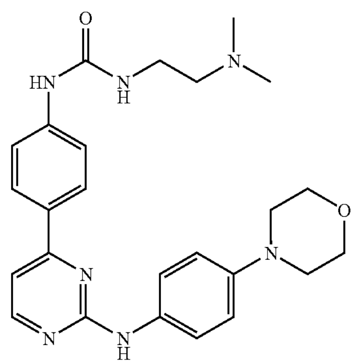 [SMILES: CN(C)CCNC(=O)Nc1ccc(-c2ccnc(Nc3ccc(N4CCOCC4)cc3)n2)cc1] | 17 |
| 405 | (S)-N-(4-(2-(4-morpholino-phenylamino)pyrimidin-4-yl)phenyl)-2-(pyrrolidin-2-yl)acetamide | 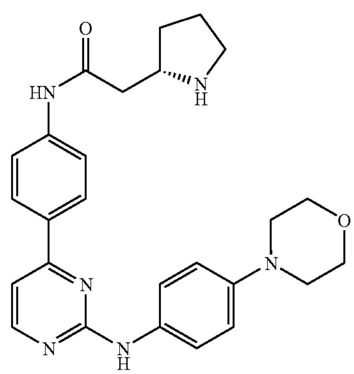 [SMILES: O=C(C[C@@H]1CCCN1)Nc1ccc(-c2ccnc(Nc3ccc(N4CCOCC4)cc3)n2)cc1] | 12 |
| 406 | 2,3-dihydroxy-N-(4-(2-(4-morpholino-phenylamino)pyrimidin-4-yl)phenyl)-propanamide | 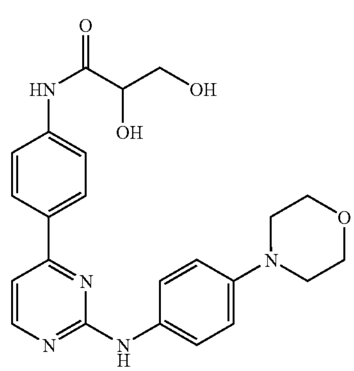 [SMILES: O=C(Nc1ccc(-c2ccnc(Nc3ccc(N4CCOCC4)cc3)n2)cc1)C(O)CO] | 18 |

TABLE 1-continued

| Cmpd No. | Name | Structure | Can Be Made According To Synthetic Example #: |
|---|---|---|---|
| 407 | (S)-2-amino-4-methyl-N-(4-(2-(4-morpholinophenyl-amino)pyrimidin-4-yl)phenyl)pentanamide | 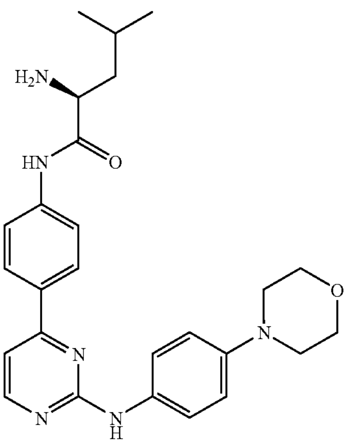 [SMILES: CC(C)C[C@H](N)C(=O)Nc1ccc(-c2ccnc(Nc3ccc(N4CCOCC4)cc3)n2)cc1] | 14 |
| 408 | (R)-2-amino-4-methyl-N-(4-(2-(4-morpholinophenyl-amino)pyrimidin-4-yl)phenyl)pentanamide | 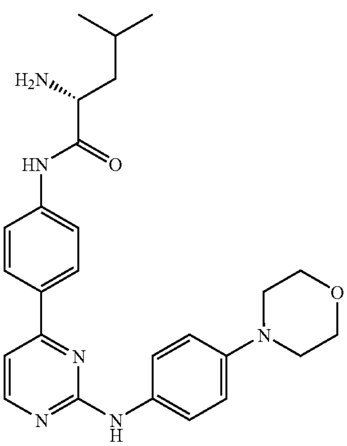 [SMILES: CC(C)C[C@@H](N)C(=O)Nc1ccc(-c2ccnc(Nc3ccc(N4CCOCC4)cc3)n2)cc1] | 14 |
| 409 | N-(4-(2-(4-morpholino-phenylamino)pyrimidin-4-yl)phenyl)isoindoline-1-carboxamide | 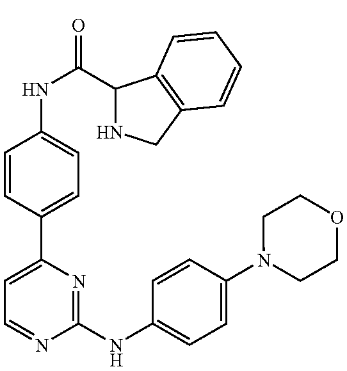 [SMILES: O=C(Nc1ccc(-c2ccnc(Nc3ccc(N4CCOCC4)cc3)n2)cc1)C1NCc2ccccc21] | 13 |

TABLE 1-continued

| Cmpd No. | Name | Structure | Can Be Made According To Synthetic Example #: |
|---|---|---|---|
| 410 | N-ethyl-4-(4-(4-(4-(tetra-hydrofuran-2-carboxamido)phenyl)pyrimidin-2-ylamino)phenyl)piperazine-1-carboxamide | 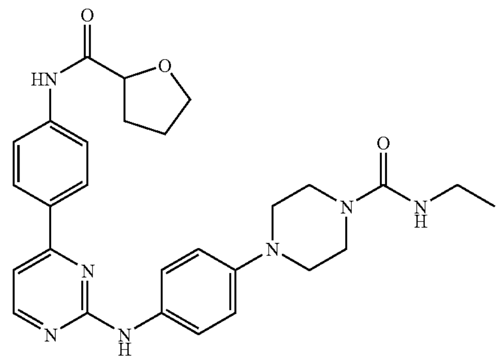 [SMILES: CCNC(=O)N1CCN(c2ccc(Nc3nccc(-c4ccc(NC(=O)C5CCCO5)cc4)n3)cc2)CC1] | 12 |
| 411 | N-(4-(2-(4-(4-(2-(piperazin-1-yl)acetyl)piperazin-1-yl)phenylamino)pyrimidin-4-yl)phenyl)tetrahydrofuran-2-carboxamide | 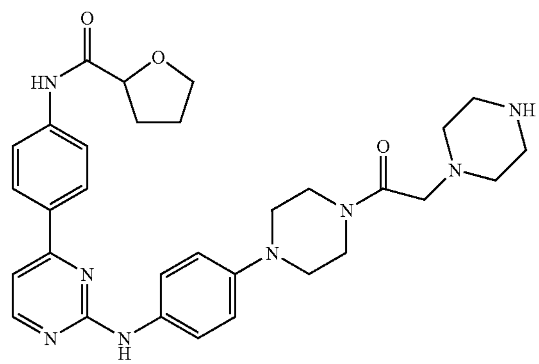 [SMILES: O=C(Nc1ccc(-c2ccnc(Nc3ccc(N4CCN(C(=O)CN5CCNCC5)CC4)cc3)n2)cc1)C1CCCO1] | 12 |
| 412 | (R)-N-(4-(2-(4-(4-((R)-2-aminopropanoyl)piperazin-1-yl)phenylamino)pyrimidin-4-yl)phenyl)pyrrolidine-2-carboxamide | 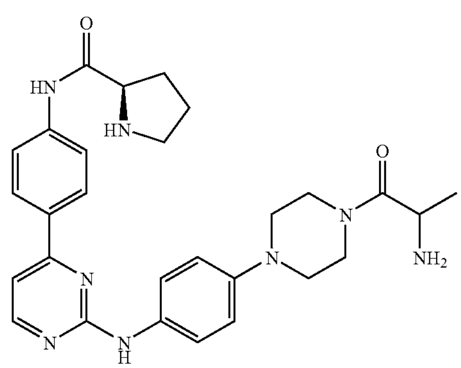 | 45 |
| 413 | (R)-N-(4-(2-(4-(4-((S)-2-aminopropanoyl)piperazin-1-yl)phenylamino)pyrimidin-4-yl)phenyl)pyrrolidine-2-carboxamide | 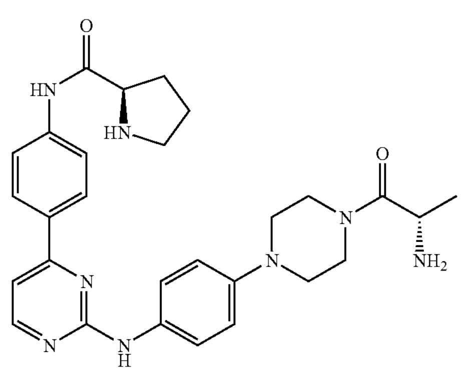 [SMILES: C[C@H](N)C(=O)N1CCN(c2ccc(Nc3nccc(-c4ccc(NC(=O)[C@H]5CCCN5)cc4)n3)cc2)CC1] | 45 |

TABLE 1-continued

| Cmpd No. | Name | Structure | Can Be Made According To Synthetic Example #: |
|---|---|---|---|
| 414 | N-(4-(2-(4-(4-(2-(piperazin-1-yl)acetyl)piperazin-1-yl)phenylamino)pyrimidin-4-yl)phenyl)tetrahydrofuran-3-carboxamide | 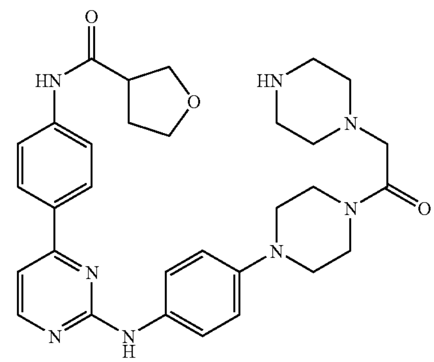 [SMILES: O=C(Nc1ccc(-c2ccnc(Nc3ccc(N4CCN(C(=O)CN5CCNCC5)CC4)cc3)n2)cc1)C1CCOC1] | 12 |
| 415 | 3-methoxy-N-(4-(2-(4-(4-(2-(piperazin-1-yl)acetyl)piperazin-1-yl)phenylamino)pyrimidin-4-yl)phenyl)propanamide | 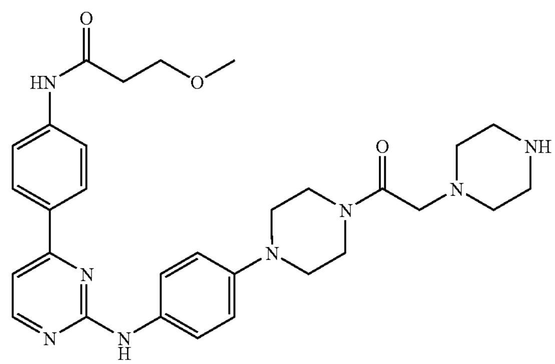 [SMILES: COCCC(=O)Nc1ccc(-c2ccnc(Nc3ccc(N4CCN(C(=O)CN5CCNCC5)CC4)cc3)n2)cc1] | 12 |
| 416 | N-(4-(2-(4-(4-pivaloyl-piperazin-1-yl)phenylamino)pyrimidin-4-yl)phenyl)tetrahydrofuran-3-carboxamide | 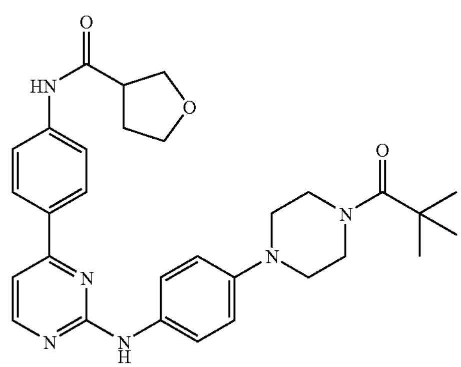 [SMILES: CC(C)(C)C(=O)N1CCN(c2ccc(Nc3nccc(-c4ccc(NC(=O)C5CCOC5)cc4)n3)cc2)CC1] | 12 |
| 417 | (R)-N-(4-(2-(3-methoxy-4-morpholinophenylamino)pyrimidin-4-yl)phenyl)-1-methylpyrrolidine-2-carboxamide | 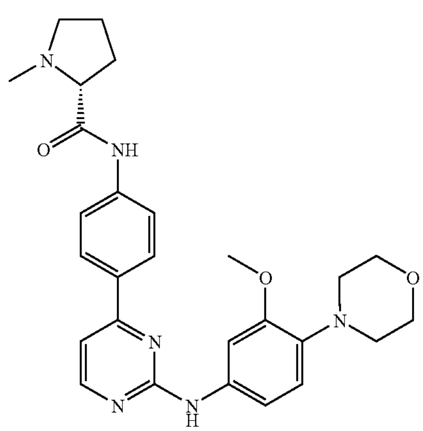 [SMILES: COc1cc(Nc2nccc(-c3ccc(NC(=O)[C@H]4CCCN4C)cc3)n2)ccc1N1CCOCC1] | 12 |

TABLE 1-continued

| Cmpd No. | Name | Structure | Can Be Made According To Synthetic Example #: |
|---|---|---|---|
| 418 | (R)-N-(4-(2-(4-(4-(2-(piperazin-1-yl)acetyl)piperazin-1-yl)phenylamino)pyrimidin-4-yl)phenyl)pyrrolidine-2-carboxamide | 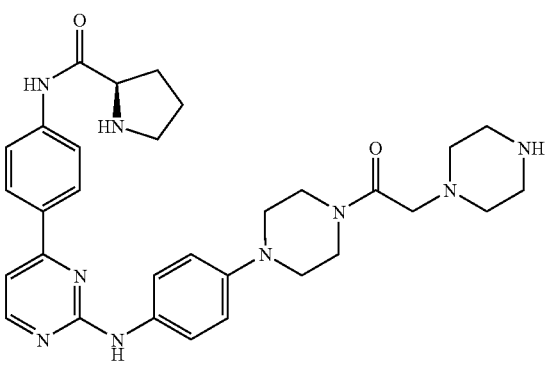 [SMILES: O=C(Nc1ccc(-c2ccnc(Nc3ccc(N4CCN(C(=O)CN5CCNCC5)CC4)cc3)n2)cc1)[C@H]1CCCN1] | 45 |
| 419 | (R)-4-(4-(4-(2-amino-propanamido)phenyl)-pyrimidin-2-ylamino)phenyl)-N-ethylpiperazine-1-carboxamide | 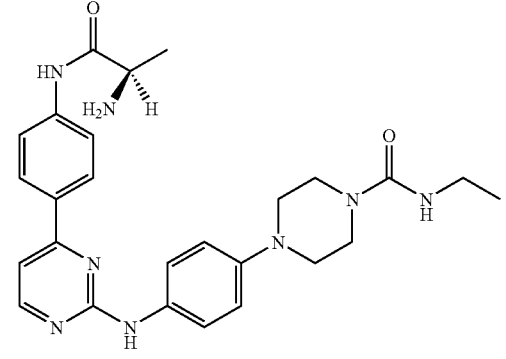 [SMILES: CCNC(=O)N1CCN(c2ccc(Nc3nccc(-c4ccc(NC(=O)[C@@H](C)N)cc4)n3)cc2)CC1] | 14 |
| 420 | (R)-2-amino-N-(4-(2-(4-(4-((R)-pyrrolidine-2-carbonyl)piperazin-1-yl)phenylamino)pyrimidin-4-yl)phenyl)propanamide | 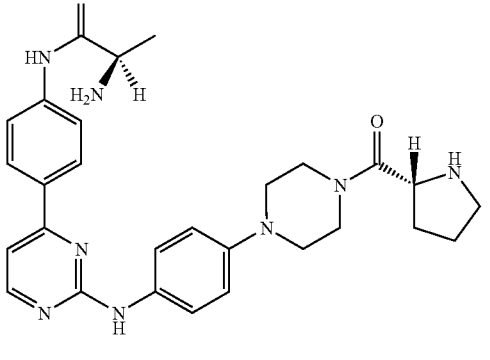 | 14 |
| 421 | (R)-2-amino-N-(4-(2-(4-(4-((S)-pyrrolidine-2-carbonyl)piperazin-1-yl)phenylamino)pyrimidin-4-yl)phenyl)propanamide | 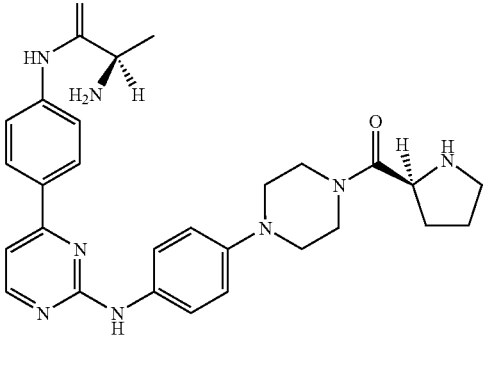 | 14 |

TABLE 1-continued

| Cmpd No. | Name | Structure | Can Be Made According To Synthetic Example #: |
|---|---|---|---|
| 422 | (R)-2-amino-N-(4-(2-(4-(4-((S)-2-aminopropanoyl)piperazin-1-yl)phenylamino)pyrimidin-4-yl)phenyl)propanamide | 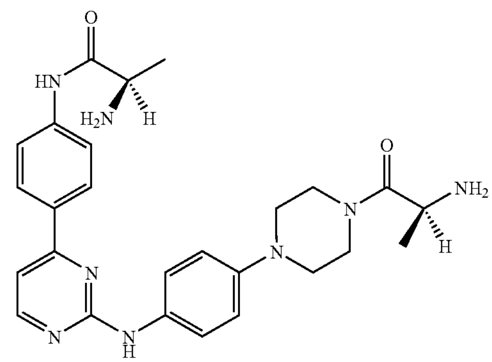 [SMILES: C[C@H](N)C(=O)N1CCN(c2ccc(Nc3nccc(-c4ccc(NC(=O)[C@@H](C)N)cc4)n3)cc2)CC1] | 14 |
| 423 | (R)-N-(4-(2-(4-(4-(3-methoxypropanoyl)piperazin-1-yl)phenylamino)pyrimidin-4-yl)phenyl)pyrrolidine-2-carboxamide | 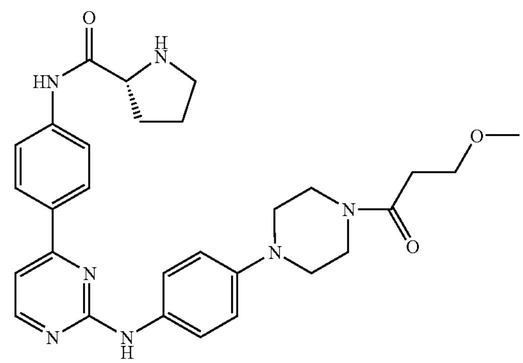 [SMILES: COCCC(=O)N1CCN(c2ccc(Nc3nccc(-c4ccc(NC(=O)[C@H]5CCCN5)cc4)n3)cc2)CC1] | 45 |
| 424 | (S)-N-(4-(2-(4-(4-(pyrrolidine-2-carbonyl)piperazin-1-yl)phenylamino)pyrimidin-4-yl)phenyl)cyclopropanecarboxamide | 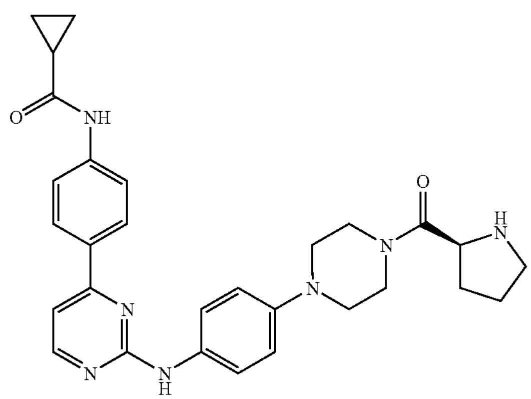 [SMILES: O=C(Nc1ccc(-c2ccnc(Nc3ccc(N4CCN(C(=O)[C@@H]5CCCN5)CC4)cc3)n2)cc1)C1CC1] | 11 |
| 425 | N-(4-(2-(4-(4-(2-(piperazin-1-yl)acetyl)piperazin-1-yl)phenylamino)pyrimidin-4-yl)phenyl)cyclopropanecarboxamide | 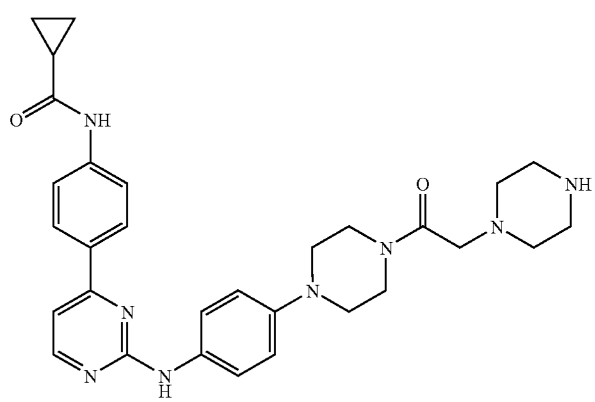 [SMILES: O=C(Nc1ccc(-c2ccnc(Nc3ccc(N4CCN(C(=O)CN5CCNCC5)CC4)cc3)n2)cc1)C1CC1] | 11 |

TABLE 1-continued

| Cmpd No. | Name | Structure | Can Be Made According To Synthetic Example #: |
|---|---|---|---|
| 426 | (R)-N-(4-(2-(4-(4-(pyrrolidine-2-carbonyl)piperazin-1-yl)phenylamino)pyrimidin-4-yl)phenyl)cyclopropanecarboxamide | 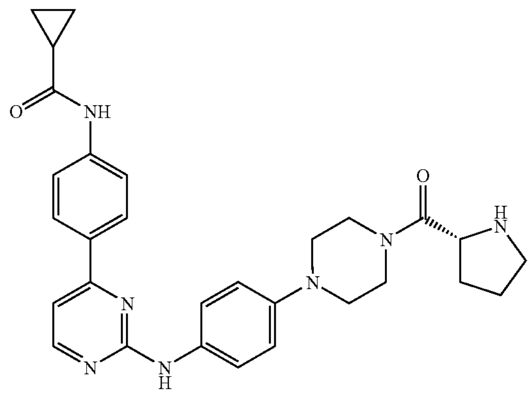 [SMILES: O=C(Nc1ccc(-c2ccnc(Nc3ccc(N4CCN(C(=O)[C@H]5CCCN5)CC4)cc3)n2)cc1)C1CC1] | 11 |
| 427 | 1-ethyl-3-(4-(5-methyl-2-(4-morpholinophenylamino)pyrimidin-4-yl)phenyl)urea | 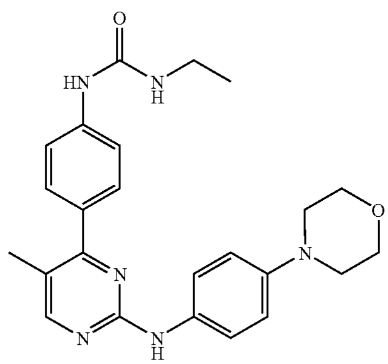 [SMILES: CCNC(=O)Nc1ccc(-c2nc(Nc3ccc(N4CCOCC4)cc3)ncc2C)cc1] | 17 |
| 428 | (S)-N-(4-(2-(4-(4-(2-aminopropanoyl)piperazin-1-yl)phenylamino)pyrimidin-4-yl)phenyl)cyclopropanecarboxamide | 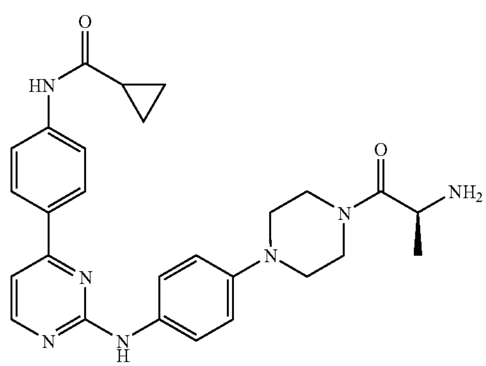 [SMILES: C[C@H](N)C(=O)N1CCN(c2ccc(Nc3nccc(-c4ccc(NC(=O)C5CC5)cc4)n3)cc2)CC1] | 11 |
| 429 | (R)-N-(4-(2-(4-(4-(2-aminopropanoyl)piperazin-1-yl)phenylamino)pyrimidin-4-yl)phenyl)-3-methoxypropanamide | 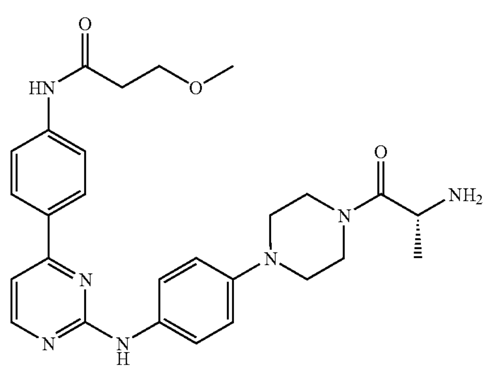 [SMILES: COCCC(=O)Nc1ccc(-c2ccnc(Nc3ccc(N4CCN(C(=O)[C@@H](C)N)CC4)cc3)n2)cc1] | 12 |

TABLE 1-continued

| Cmpd No. | Name | Structure | Can Be Made According To Synthetic Example #: |
|---|---|---|---|
| 430 | (S)-3-methoxy-N-(4-(2-(4-(4-(pyrrolidine-2-carbonyl)piperazin-1-yl)phenylamino)pyrimidin-4-yl)phenyl)propanamide | 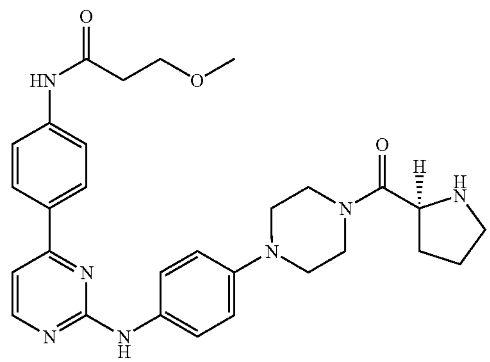 [SMILES: COCCC(=O)Nc1ccc(-c2ccnc(Nc3ccc(N4CCN(C(=O)[C@@H]5CCCN5)CC4)cc3)n2)cc1] | 12 |
| 431 | (R)-N-(4-(2-(4-(4-(2-aminopropanoyl)piperazin-1-yl)phenylamino)pyrimidin-4-yl)phenyl)cyclopropanecarboxamide | 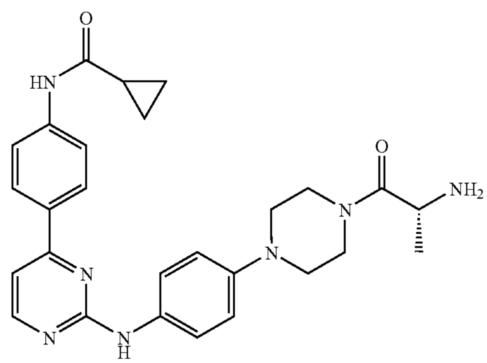 [SMILES: C[C@@H](N)C(=O)N1CCN(c2ccc(Nc3nccc(-c4ccc(NC(=O)C5CC5)cc4)n3)cc2)CC1] | 1 |
| 432 | N-(4-(2-(4-(4-(cyclobutanecarbonyl)piperazin-1-yl)phenylamino)pyrimidin-4-yl)phenyl)cyclopropanecarboxamide | 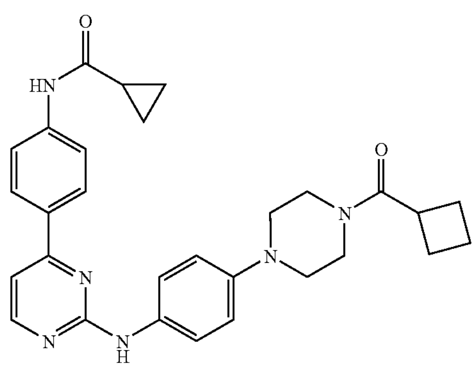 [SMILES: O=C(Nc1ccc(-c2ccnc(Nc3ccc(N4CCN(C(=O)C5CCC5)CC4)cc3)n2)cc1)C1CC1] | 11 |
| 433 | N-(4-(2-(4-(4-isobutyryl-piperazin-1-yl)phenylamino)pyrimidin-4-yl)phenyl)cyclopropanecarboxamide | 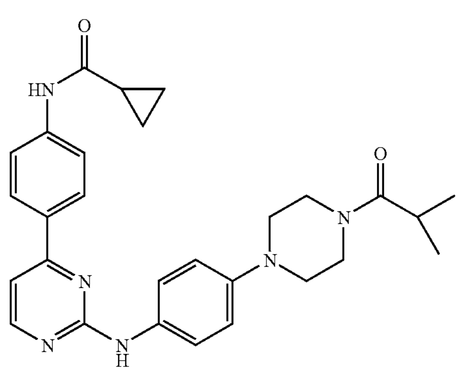 [SMILES: CC(C)C(=O)N1CCN(c2ccc(Nc3nccc(-c4ccc(NC(=O)C5CC5)cc4)n3)cc2)CC1] | 11 |

TABLE 1-continued

| Cmpd No. | Name | Structure | Can Be Made According To Synthetic Example #: |
|---|---|---|---|
| 434 | N-(4-(2-(4-(1-butyryl-1,2,4-triazinan-4-yl)phenylamino)pyrimidin-4-yl)phenyl)butyramide | 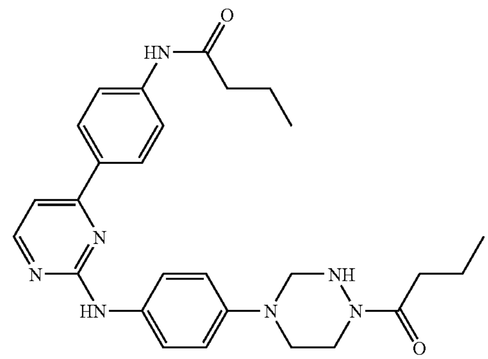 [SMILES: CCCC(=O)Nc1ccc(-c2ccnc(Nc3ccc(N4CCN(C(=O)CCC)NC4)cc3)n2)cc1] | 11 |
| 435 | 1-(4-(2-(4-(4-(2-(dimethylamino)acetyl)piperazin-1-yl)phenylamino)pyrimidin-4-yl)phenyl)-3-ethylurea | 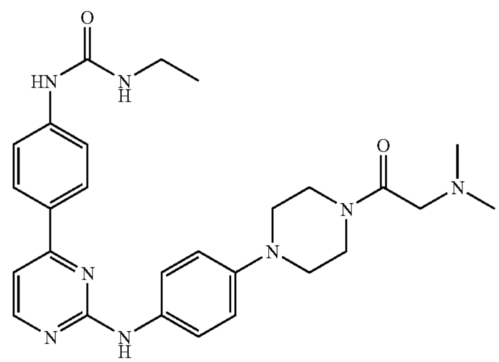 [SMILES: CCNC(=O)Nc1ccc(-c2ccnc(Nc3ccc(N4CCN(C(=O)CN(C)C)CC4)cc3)n2)cc1] | 17 |
| 436 | N-(4-(2-(4-(4-(2-(dimethylamino)acetyl)piperazin-1-yl)phenylamino)pyrimidin-4-yl)phenyl)-3-methoxypropanamide | 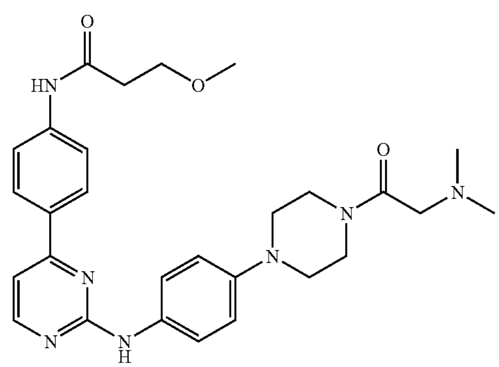 [SMILES: COCCC(=O)Nc1ccc(-c2ccnc(Nc3ccc(N4CCN(C(=O)CN(C)C)CC4)cc3)n2)cc1] | 11 |
| 437 | N-(4-(2-(4-(4-(2-(dimethylamino)acetyl)piperazin-1-yl)phenylamino)pyrimidin-4-yl)phenyl)cyclopropanecarboxamide | 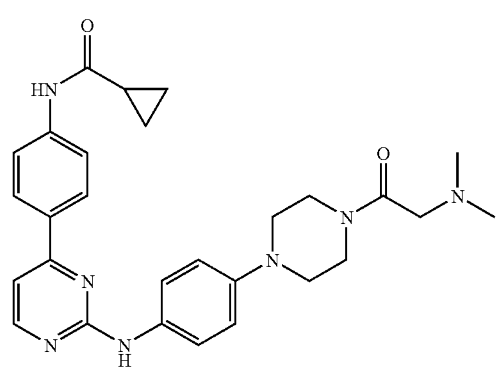 [SMILES: CN(C)CC(=O)N1CCN(c2ccc(Nc3nccc(-c4ccc(NC(=O)C5CC5)cc4)n3)cc2)CC1] | 11 |

TABLE 1-continued

| Cmpd No. | Name | Structure | Can Be Made According To Synthetic Example #: |
|---|---|---|---|
| 438 | N-(4-(2-(4-(4-(2-(dimethyl-amino)acetyl)piperazin-1-yl)phenylamino)pyrimidin-4-yl)phenyl)butyramide | 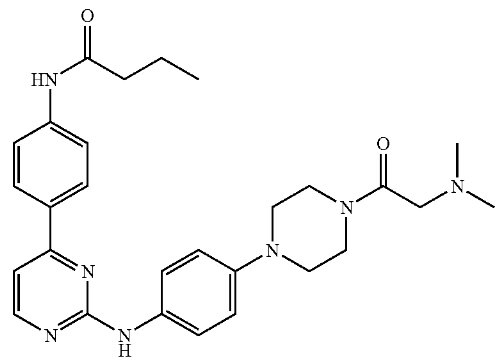 [SMILES: CCCC(=O)Nc1ccc(-c2ccnc(Nc3ccc(N4CCN(C(=O)CN(C)C)CC4)cc3)n2)cc1] | 11 |
| 439 | 1-ethyl-3-(4-(2-(4-(4-pivaloylpiperazin-1-yl)phenylamino)pyrimidin-4-yl)phenyl)urea | 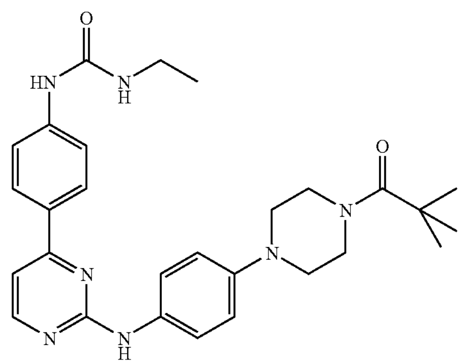 [SMILES: CCNC(=O)Nc1ccc(-c2ccnc(Nc3ccc(N4CCN(C(=O)C(C)(C)C)CC4)cc3)n2)cc1] | 17 |
| 440 | 1-(4-(2-(4-(4-(cyclobutane-carbonyl)piperazin-1-yl)phenylamino)pyrimidin-4-yl)phenyl)-3-ethylurea | 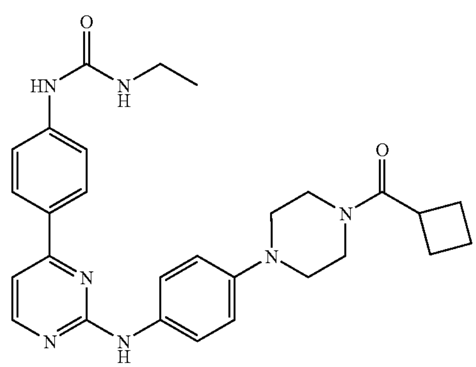 [SMILES: CCNC(=O)Nc1ccc(-c2ccnc(Nc3ccc(N4CCN(C(=O)C5CCC5)CC4)cc3)n2)cc1] | 17 |
| 441 | 1-ethyl-3-(4-(2-(4-(4-isobutyrylpiperazin-1-yl)phenylamino)pyrimidin-4-yl)phenyl)urea | 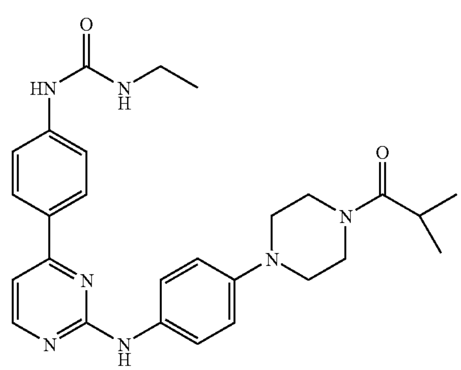 [SMILES: CCNC(=O)Nc1ccc(-c2ccnc(Nc3ccc(N4CCN(C(=O)C(C)C)CC4)cc3)n2)cc1] | 17 |

TABLE 1-continued

| Cmpd No. | Name | Structure | Can Be Made According To Synthetic Example #: |
|---|---|---|---|
| 442 | N-ethyl-4-(4-(4-(4-(3-ethylureido)phenyl)pyrimidin-2-ylamino)phenyl)piperazine-1-carboxamide | 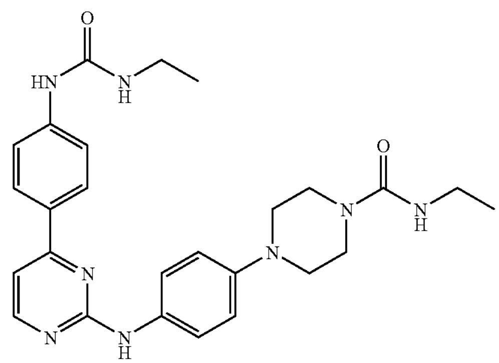 [SMILES: CCNC(=O)Nc1ccc(-c2ccnc(Nc3ccc(N4CCN(C(=O)NCC)CC4)cc3)n2)cc1] | 17 |
| 443 | (S)-1-ethyl-N-(4-(2-(4-morpholinophenylamino)pyrimidin-4-yl)phenyl)pyrrolidine-2-carboxamide | 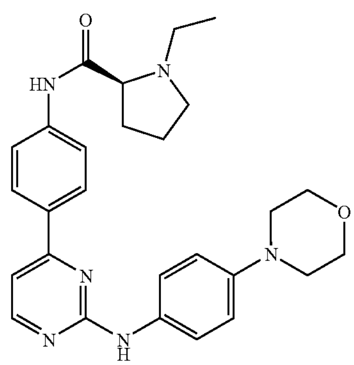 [SMILES: CCN1CCC[C@H]1C(=O)Nc1ccc(-c2ccnc(Nc3ccc(N4CCOCC4)cc3)n2)cc1] | 45 |
| 444 | (R)-1-(2-hydroxyethyl)-N-(4-(2-(4-morpholinobenzyl)pyrimidin-4-yl)phenyl)pyrrolidine-2-carboxamide | 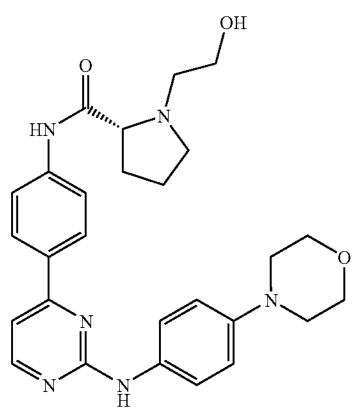 [SMILES: O=C(Nc1ccc(-c2ccnc(Nc3ccc(N4CCOCC4)cc3)n2)cc1)[C@H]1CCCN1CCO] | 47 |
| 445 | (R)-1-isopropyl-N-(4-(2-(4-morpholinophenylamino)pyrimidin-4-yl)phenyl)pyrrolidine-2-carboxamide | 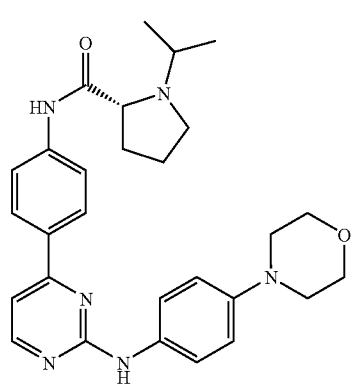 [SMILES: CC(C)N1CCC[C@@H]1C(=O)Nc1ccc(-c2ccnc(Nc3ccc(N4CCOCC4)cc3)n2)cc1] | 42 |

TABLE 1-continued

| Cmpd No. | Name | Structure | Can Be Made According To Synthetic Example #: |
|---|---|---|---|
| 446 | (S)-2-(dimethylamino)-N-(4-(2-(4-(4-(pyrrolidine-2-carbonyl)piperazin-1-yl)phenylamino)pyrimidin-4-yl)phenyl)acetamide | 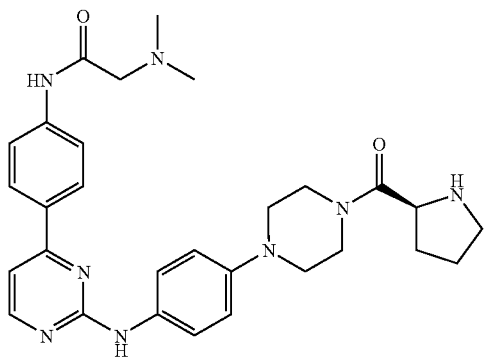 [SMILES: CN(C)CC(=O)Nc1ccc(-c2ccnc(Nc3ccc(N4CCN(C(=O)[C@@H]5CCCN5)CC4)cc3)n2)cc1] | 12 |
| 447 | 1-(4-(2-(4-(4-(3-(dimethyl-amino)-2,2-dimethylpropyl)piperazin-1-yl)phenylamino)pyrimidin-4-yl)phenyl)-3-ethylurea | 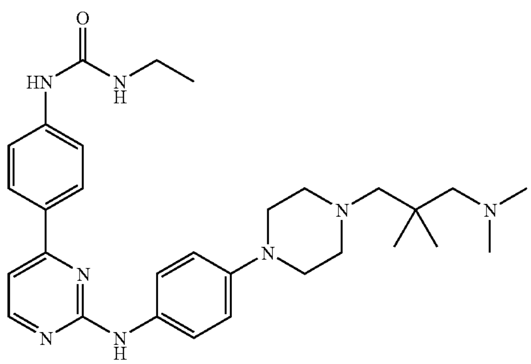 [SMILES: CCNC(=O)Nc1ccc(-c2ccnc(Nc3ccc(N4CCN(CC(C)(C)CN(C)C)CC4)cc3)n2)cc1] | 17 |
| 448 | (R)-1-ethyl-N-(4-(2-(4-morpholinophenylamino)pyrimidin-4-yl)phenyl)pyrrolidine-2-carboxamide | 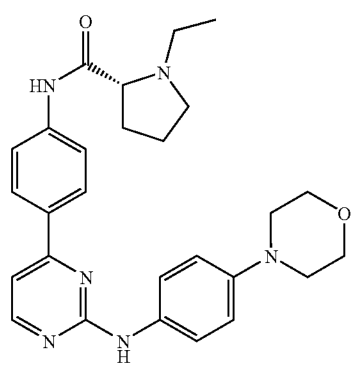 [SMILES: CCN1CCC[C@@H]1C(=O)Nc1ccc(-c2ccnc(Nc3ccc(N4CCOCC4)cc3)n2)cc1] | 45 |
| 449 | 4-amino-N-(4-(2-(4-morpholinophenylamino)pyrimidin-4-yl)phenyl)tetrahydro-2H-pyran-4-carboxamide | 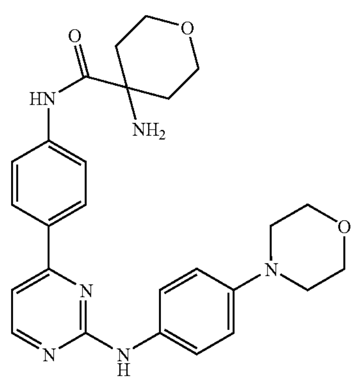 [SMILES: NC1(C(=O)Nc2ccc(-c3ccnc(Nc4ccc(N5CCOCC5)cc4)n3)cc2)CCOCC1] | 44 |

TABLE 1-continued

| Cmpd No. | Name | Structure | Can Be Made According To Synthetic Example #: |
|---|---|---|---|
| 450 | (R)-2-amino-N-(4-(2-(4-(4-isobutyrylpiperazin-1-yl)phenylamino)pyrimidin-4-yl)phenyl)propanamide | 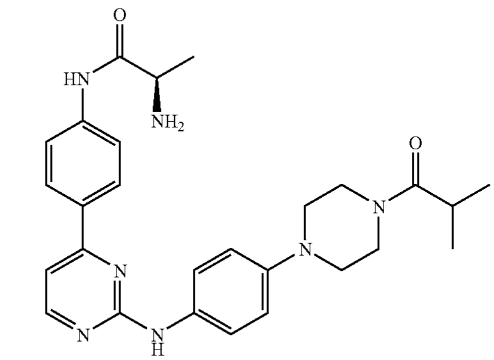 [SMILES: CC(C)C(=O)N1CCN(c2ccc(Nc3nccc(-c4ccc(NC(=O)[C@@H](C)N)cc4)n3)cc2)CC1] | 14 |
| 451 | (R)-2-amino-N-(4-(2-(4-(4-((R)-2-aminopropanoyl)piperazin-1-yl)phenylamino)pyrimidin-4-yl)phenyl)propanamide | 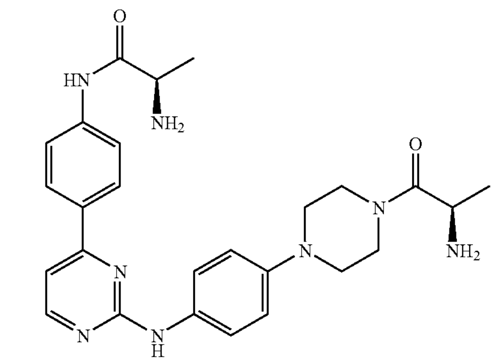 [SMILES: C[C@@H](N)C(=O)Nc1ccc(-c2ccnc(Nc3ccc(N4CCN(C(=O)[C@@H](C)N)CC4)cc3)n2)cc1] | 14 |
| 452 | (R)-N-(4-(5-methyl-2-(4-(4-((1-methyl-1H-imidazol-2-yl)methyl)piperazin-1-yl)phenylamino)pyrimidin-4-yl)phenyl)pyrrolidine-2-carboxamide | 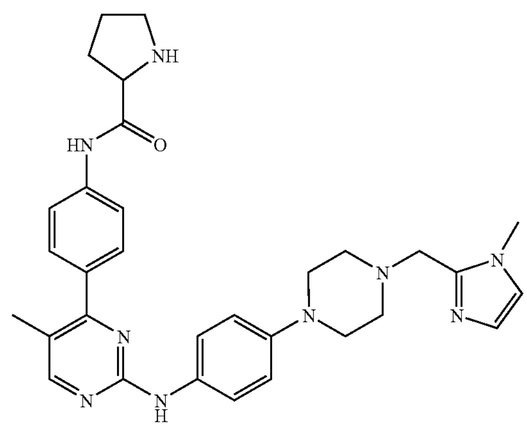 [SMILES: Cc1cnc(Nc2ccc(N3CCN(Cc4nccn4C)CC3)cc2)nc1-c1ccc(NC(=O)C2CCCN2)cc1] | 45 |
| 453 | (R)-2-amino-N-(4-(5-methyl-2-(4-(4-((1-methyl-1H-imidazol-2-yl)methyl)piperazin-1-yl)phenylamino)pyrimidin-4-yl)phenyl)propanamide | 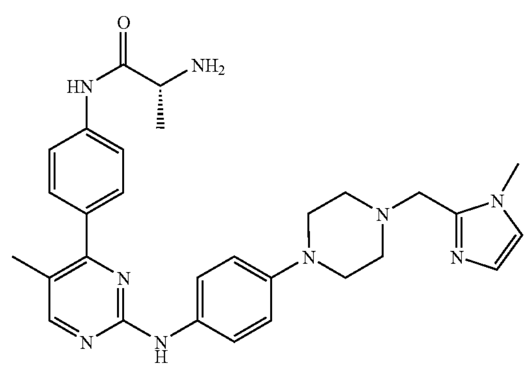 [SMILES: Cc1cnc(Nc2ccc(N3CCN(Cc4nccn4C)CC3)cc2)nc1-c1ccc(NC(=O)[C@@H](C)N)cc1] | 14 |

TABLE 1-continued

| Cmpd No. | Name | Structure | Can Be Made According To Synthetic Example #: |
|---|---|---|---|
| 454 | (R)-2-(dimethylamino)-N-(4-(2-(4-(4-(pyrrolidine-2-carbonyl)piperazin-1-yl)phenylamino)pyrimidin-4-yl)phenyl)acetamide | 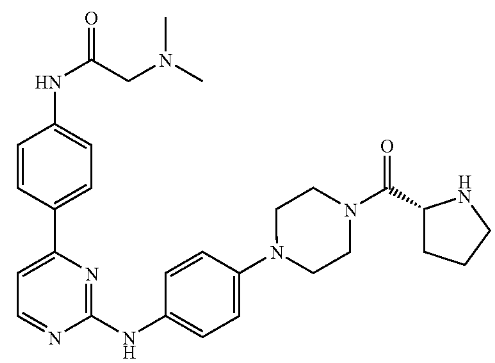 [SMILES: CN(C)CC(=O)Nc1ccc(-c2ccnc(Nc3ccc(N4CCN(C(=O)[C@H]5CCCN5)CC4)cc3)n2)cc1] | 12 |
| 455 | (R)-N-(4-(2-(4-(4-(2-(dimethylamino)acetyl)piperazin-1-yl)phenylamino)pyrimidin-4-yl)phenyl)pyrrolidine-2-carboxamide | 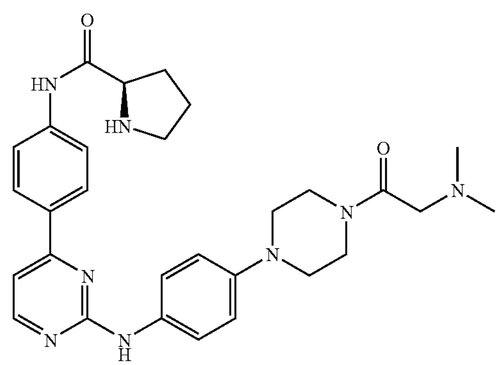 [SMILES: CN(C)CC(=O)N1CCN(c2ccc(Nc3nccc(-c4ccc(NC(=O)[C@H]5CCCN5)cc4)n3)cc2)CC1] | 45 |
| 456 | (S)-N-(4-(5-methyl-2-(4-(4-((1-methyl-1H-imidazol-2-yl)methyl)piperazin-1-yl)phenylamino)pyrimidin-4-yl)phenyl)pyrrolidine-2-carboxamide | 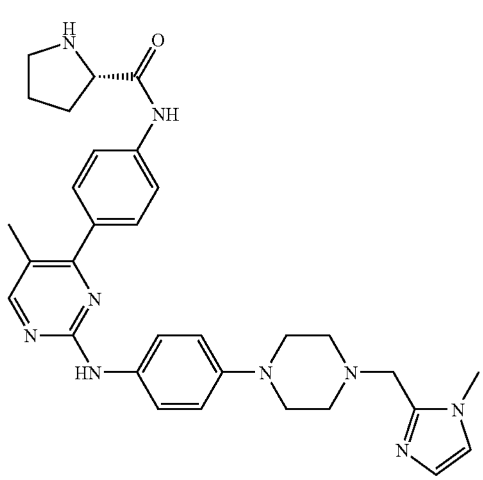 [SMILES: Cc1cnc(Nc2ccc(N3CCN(Cc4nccn4C)CC3)cc2)nc1-c1ccc(NC(=O)[C@@H]2CCCN2)cc1] | 45 |

TABLE 1-continued

| Cmpd No. | Name | Structure | Can Be Made According To Synthetic Example #: |
|---|---|---|---|
| 457 | (R)-2-amino-N-(4-(2-(4-(4-(2-(piperazin-1-yl)acetyl)piperazin-1-yl)phenylamino)pyrimidin-4-yl)phenyl)propanamide | 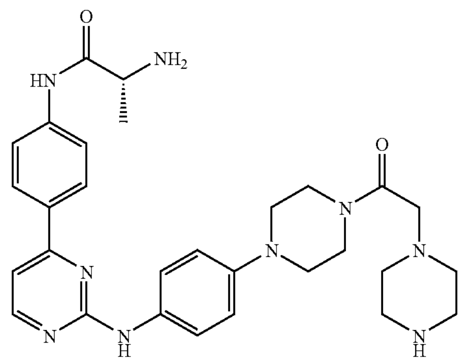 [SMILES: C[C@@H](N)C(=O)Nc1ccc(-c2ccnc(Nc3ccc(N4CCN(C(=O)CN5CCNCC5)CC4)cc3)n2)cc1] | 14 |
| 458 | (2R)-N-(4-(2-(4-(4-(tetrahydrofuran-3-carbonyl)piperazin-1-yl)phenylamino)pyrimidin-4-yl)phenyl)pyrrolidine-2-carboxamide | 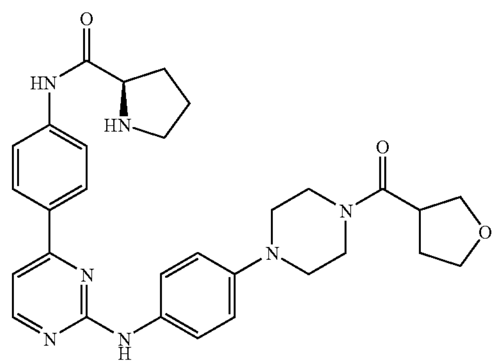 [SMILES: O=C(Nc1ccc(-c2ccnc(Nc3ccc(N4CCN(C(=O)C5CCOC5)CC4)cc3)n2)cc1)[C@H]1CCCN1] | 45 |
| 459 | (S)-1-ethyl-3-(4-(2-(4-(4-(pyrrolidine-2-carbonyl)piperazin-1-yl)phenylamino)pyrimidin-4-yl)phenyl)urea | 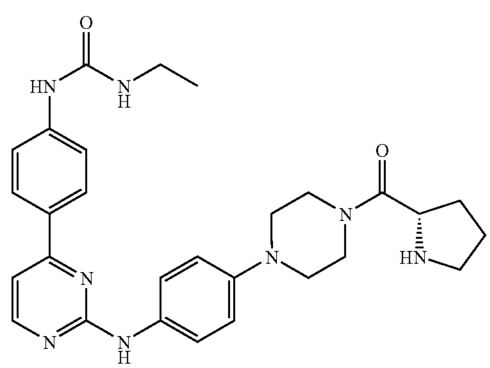 [SMILES: CCNC(=O)Nc1ccc(-c2ccnc(Nc3ccc(N4CCN(C(=O)[C@@H]5CCCN5)CC4)cc3)n2)cc1] | 17 |
| 460 | (S)-1-(4-(2-(4-(4-(2-amino-propanoyl)piperazin-1-yl)phenylamino)pyrimidin-4-yl)phenyl)-3-ethylurea | 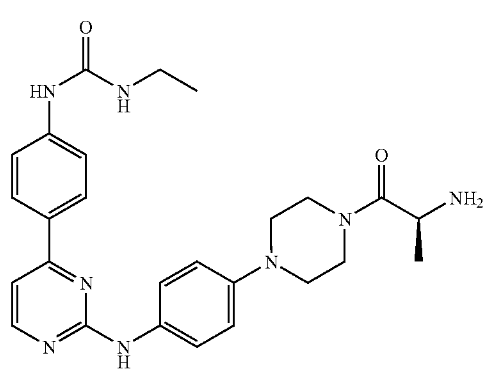 [SMILES: CCNC(=O)Nc1ccc(-c2ccnc(Nc3ccc(N4CCN(C(=O)[C@H](C)N)CC4)cc3)n2)cc1] | 17 |

TABLE 1-continued

| Cmpd No. | Name | Structure | Can Be Made According To Synthetic Example #: |
|---|---|---|---|
| 461 | N-(4-(2-(4-(4-(2-(piperazin-1-yl)acetyl)piperazin-1-yl)phenylamino)pyrimidin-4-yl)phenyl)butyramide | 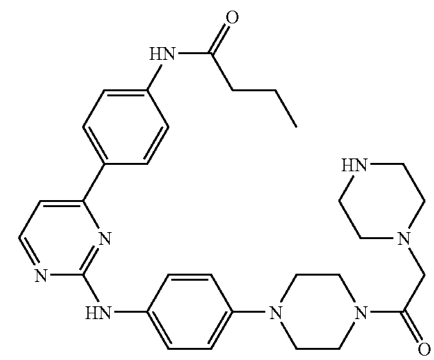 [SMILES: CCCC(=O)Nc1ccc(-c2ccnc(Nc3ccc(N4CCN(C(=O)CN5CCNCC5)CC4)cc3)n2)cc1] | 11 |
| 462 | (S)-N-(4-(2-(4-(4-(2-amino-propanoyl)piperazin-1-yl)phenylamino)pyrimidin-4-yl)phenyl)butyramide | 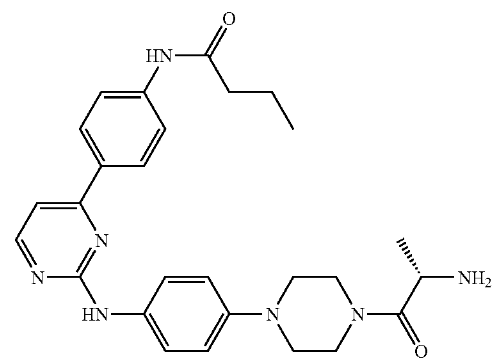 [SMILES: CCCC(=O)Nc1ccc(-c2ccnc(Nc3ccc(N4CCN(C(=O)[C@H](C)N)CC4)cc3)n2)cc1] | 11 |
| 463 | 3-methoxy-N-(4-(5-methyl-2-(4-morpholinophenylamino)pyrimidin-4-yl)phenyl)propanamide | 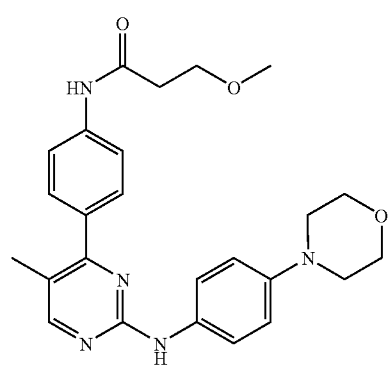 [SMILES: COCCC(=O)Nc1ccc(-c2nc(Nc3ccc(N4CCOCC4)cc3)ncc2C)cc1] | 12 |
| 464 | (R)-2-amino-N-(4-(5-methyl-2-(4-morpholinophenylamino)pyrimidin-4-yl)phenyl)propanamide | 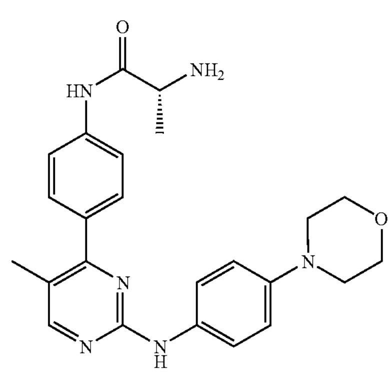 [SMILES: Cc1cnc(Nc2ccc(N3CCOCC3)cc2)nc1-c1ccc(NC(=O)[C@@H](C)N)cc1] | 14 |

TABLE 1-continued

| Cmpd No. | Name | Structure | Can Be Made According To Synthetic Example #: |
|---|---|---|---|
| 465 | 2-(dimethylamino)-N-(4-(2-(4-(4-(3-methoxypropanoyl)piperazin-1-yl)phenylamino)pyrimidin-4-yl)phenyl)acetamide | 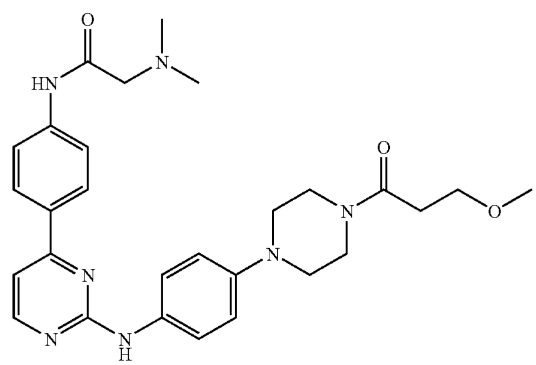 [SMILES: COCCC(=O)N1CCN(c2ccc(Nc3nccc(-c4ccc(NC(=O)CN(C)C)cc4)n3)cc2)CC1] | 12 |
| 466 | 1-ethyl-3-(4-(2-(4-(4-(3-methoxypropanoyl)piperazin-1-yl)phenylamino)pyrimidin-4-yl)phenyl)urea | 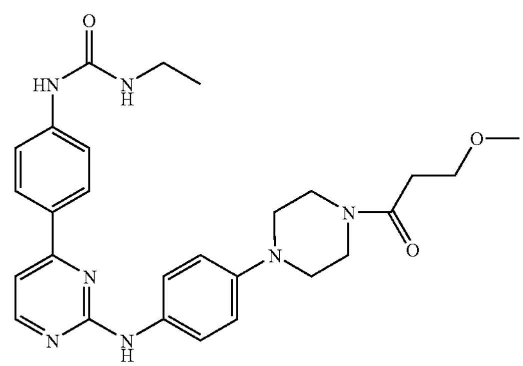 [SMILES: CCNC(=O)Nc1ccc(-c2ccnc(Nc3ccc(N4CCN(C(=O)CCOC)CC4)cc3)n2)cc1] | 17 |
| 467 | 3-methoxy-N-(4-(2-(4-(4-(3-methoxypropanoyl)piperazin-1-yl)phenylamino)pyrimidin-4-yl)phenyl)propanamide | 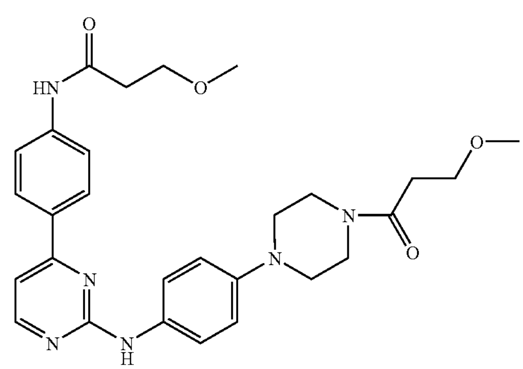 [SMILES: COCCC(=O)Nc1ccc(-c2ccnc(Nc3ccc(N4CCN(C(=O)CCOC)CC4)cc3)n2)cc1] | 12 |
| 468 | (R)-N-(4-(2-(4-morpholinophenylamino)pyrimidin-4-yl)phenyl)-5-oxopyrrolidine-2-carboxamide | 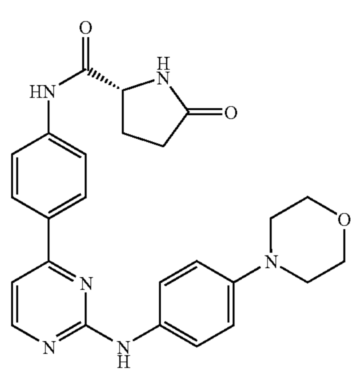 [SMILES: O=C1CC[C@H](C(=O)Nc2ccc(-c3ccnc(Nc4ccc(N5CCOCC5)cc4)n3)cc2)N1] | 45 |

| Cmpd No. | Name | Structure | Can Be Made According To Synthetic Example #: |
|---|---|---|---|
| 469 | (S)-N-(4-(2-(4-morpholino-phenylamino)pyrimidin-4-yl)phenyl)-5-oxopyrrolidine-2-carboxamide | 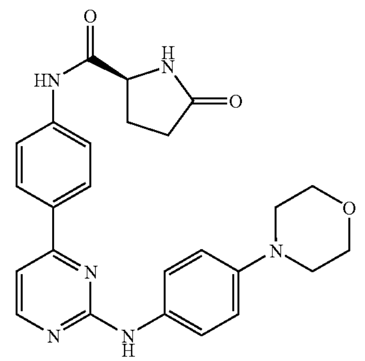 [SMILES: O=C1CC[C@@H](C(=O)Nc2ccc(-c3ccnc(Nc4ccc(N5CCOCC5)cc4)n3)cc2)N1] | 45 |
| 470 | (S)-N-(4-(2-(4-morpholino-phenylamino)pyrimidin-4-yl)phenyl)pyrrolidine-3-carboxamide | 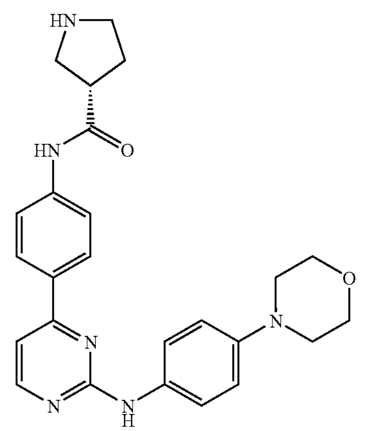 [SMILES: O=C(Nc1ccc(-c2ccnc(Nc3ccc(N4CCOCC4)cc3)n2)cc1)[C@H]1CCNC1] | 42 |
| 471 | (2R,3S)-2-amino-3-hydroxy-N-(4-(2-(4-morpholinophenyl-amino)pyrimidin-4-yl)phenyl)butanamide | 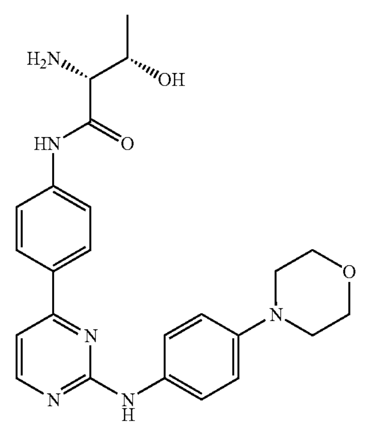 [SMILES: C[C@H](O)[C@@H](N)C(=O)Nc1ccc(-c2ccnc(Nc3ccc(N4CCOCC4)cc3)n2)cc1] | 18 |
| 472 | (R)-2-amino-N-(4-(2-(3-methoxy-4-morpholino-phenylamino)pyrimidin-4-yl)phenyl)propanamide | 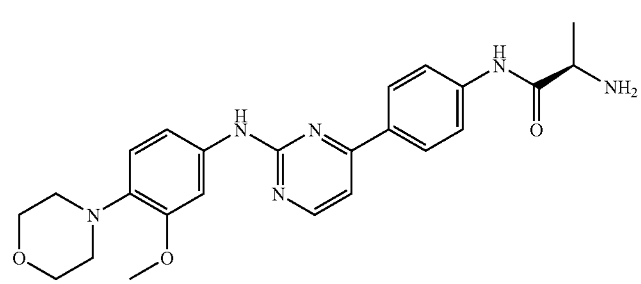 [SMILES: COc1cc(Nc2nccc(-c3ccc(NC(=O)[C@@H](C)N)cc3)n2)ccc1N1CCOCC1] | 14 |

TABLE 1-continued

| Cmpd No. | Name | Structure | Can Be Made According To Synthetic Example #: |
|---|---|---|---|
| 473 | N-(4-(2-(3-methoxy-4-morpholinophenylamino)pyrimidin-4-yl)phenyl)cyclopropanecarboxamide | 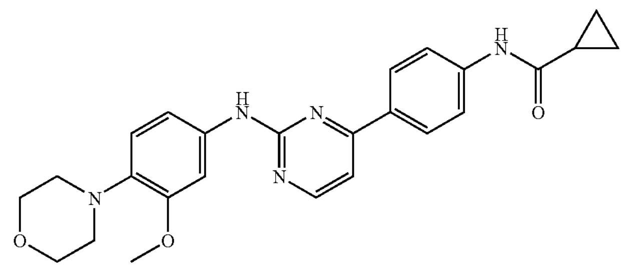 [SMILES: COc1cc(Nc2nccc(-c3ccc(NC(=O)C4CC4)cc3)n2)ccc1N1CCOCC1] | 11 |
| 474 | N-(4-(2-(3-methoxy-4-morpholinophenylamino)pyrimidin-4-yl)phenyl)buyramide | 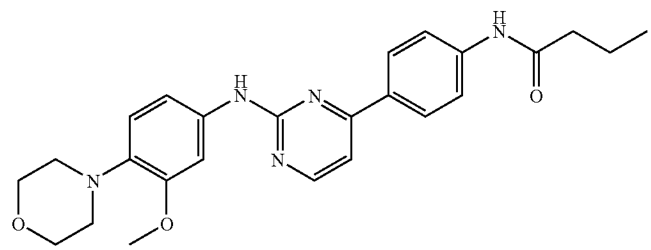 [SMILES: CCCC(=O)Nc1ccc(-c2ccnc(Nc3ccc(N4CCOCC4)c(OC)c3)n2)cc1] | 12 |
| 475 | N-(4-(2-(4-(4-(3-methoxy-propanoyl)piperazin-1-yl)phenylamino)pyrimidin-4-yl)phenyl)butyramide | 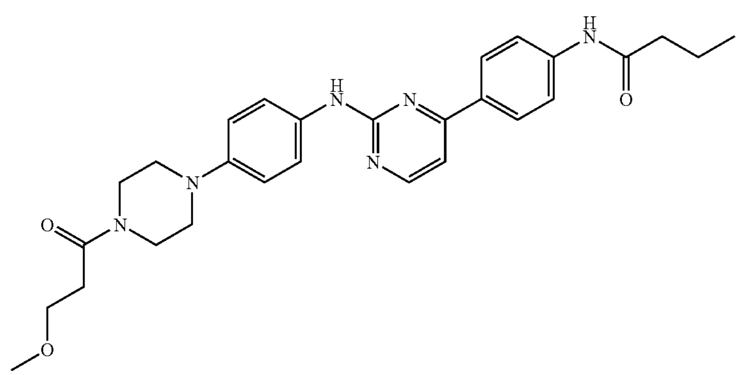 [SMILES: CCCC(=O)Nc1ccc(-c2ccnc(Nc3ccc(N4CCN(C(=O)CCOC)CC4)cc3)n2)cc1] | 12 |
| 476 | N-(4-(2-(4-(4-(3-methoxy-propanoyl)piperazin-1-yl)phenylamino)pyrimidin-4-yl)phenyl)cyclopropane-carboxamide | 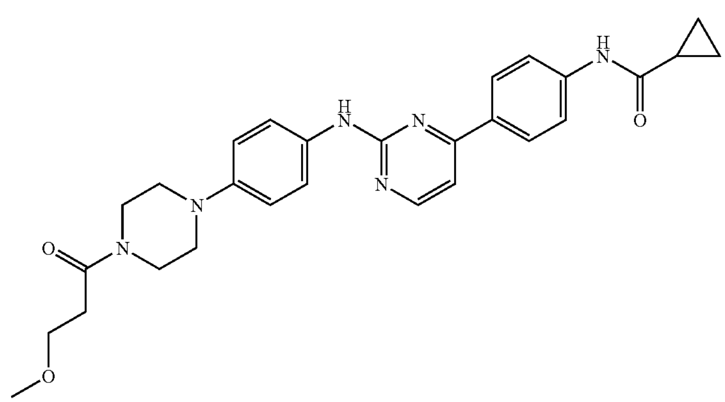 [SMILES: COCCC(=O)N1CCN(c2ccc(Nc3nccc(-c4ccc(NC(=O)C5CC5)cc4)n3)cc2)CC1] | 12 |

TABLE 1-continued

| Cmpd No. | Name | Structure | Can Be Made According To Synthetic Example #: |
|---|---|---|---|
| 477 | (R)-2-amino-N-(4-(2-(4-(4-(3-methoxypropanoyl)piperazin-1-yl)phenylamino)pyrimidin-4-yl)phenyl)propanamide | 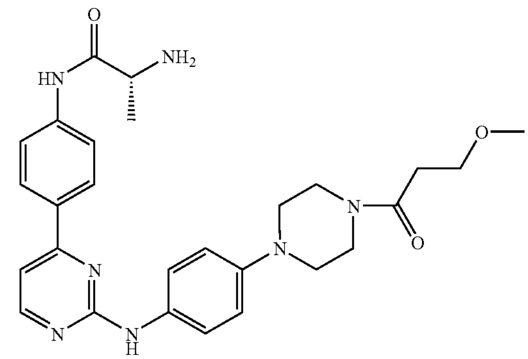 [SMILES: COCCC(=O)N1CCN(c2ccc(Nc3nccc(-c4ccc(NC(=O)[C@@H](C)N)cc4)n3)cc2)CC1] | 14 |
| 478 | (2S,3R)-2-amino-3-hydroxy-N-(4-(2-(4-morpholino-phenylamino)pyrimidin-4-yl)phenyl)butanamide | 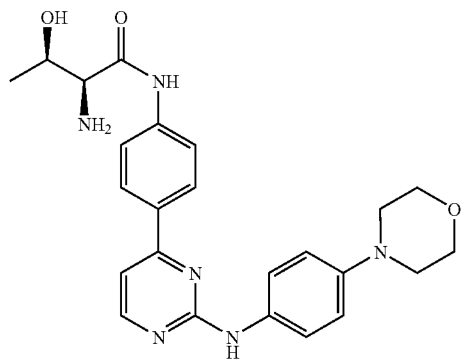 [SMILES: C[C@@H](O)[C@H](N)C(=O)Nc1ccc(-c2ccnc(Nc3ccc(N4CCOCC4)cc3)n2)cc1] | 14 |
| 479 | (R)-N-(4-(2-(4-((2S,6R)-2,6-dimethylmorpholino)phenyl amino)pyrimidin-4-yl)phenyl)pyrrolidine-2-carboxamide | 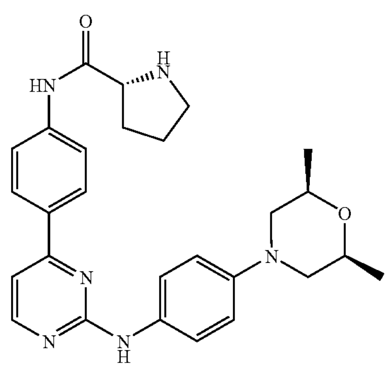 [SMILES: C[C@@H]1CN(c2ccc(Nc3nccc(-c4ccc(NC(=O)[C@H]5CCCN5)cc4)n3)cc2)C[C@H](C)O1] | 45 |
| 480 | (R)-N-(4-(2-(4-(4-(3-hydroxypropanoyl)piperazin-1-yl)phenylamino)pyrimidin-4-yl)phenyl)pyrrolidine-2-carboxamide | 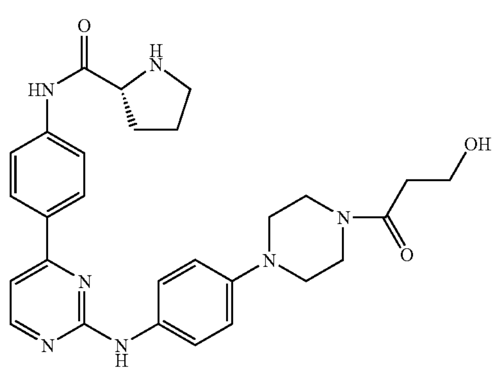 [SMILES: O=C(Nc1ccc(-c2ccnc(Nc3ccc(N4CCN(C(=O)CCO)CC4)cc3)n2)cc1)[C@H]1CCCN1] | 45 |

TABLE 1-continued

| Cmpd No. | Name | Structure | Can Be Made According To Synthetic Example #: |
|---|---|---|---|
| 481 | 1-ethyl-3-(4-(2-(4-(4-(2-(piperazin-1-yl)acetyl)piperazin-1-yl)phenylamino)pyrimidin-4-yl)phenyl)urea | 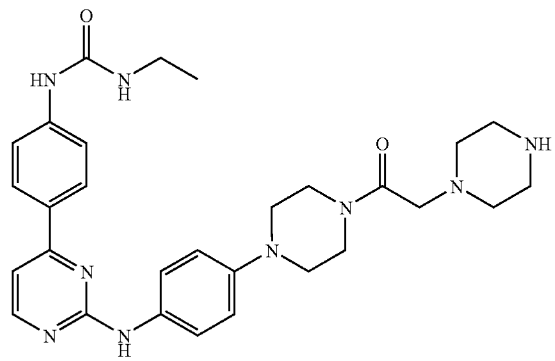 [SMILES: CCNC(=O)Nc1ccc(-c2ccnc(Nc3ccc(N4CCN(C(=O)CN5CCNCC5)CC4)cc3)n2)cc1] | 12 |
| 482 | (R)-1-ethyl-3-(4-(2-(4-(4-(pyrrolidine-2-carbonyl)piperazin-1-yl)phenylamino)pyrimidin-4-yl)phenyl)urea | 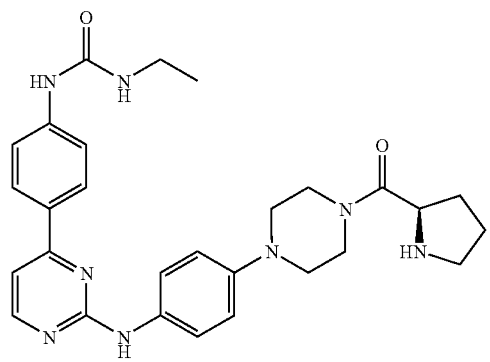 [SMILES: CCNC(=O)Nc1ccc(-c2ccnc(Nc3ccc(N4CCN(C(=O)[C@H]5CCCN5)CC4)cc3)n2)cc1] | 12 |
| 483 | 3,3,3-trifluoro-2-hydroxy-N-(4-(2-(4-morpholinophenylamino)pyrimidin-4-yl)phenyl)propanamide | 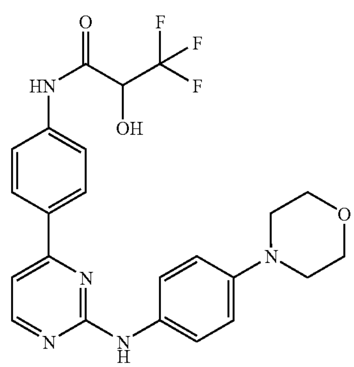 | 18 |
| 484 | (R)-1-(4-(2-(4-(4-(2-aminopropanoyl)piperazin-1-yl)phenylamino)pyrimidin-4-yl)phenyl)-3-ethylurea | 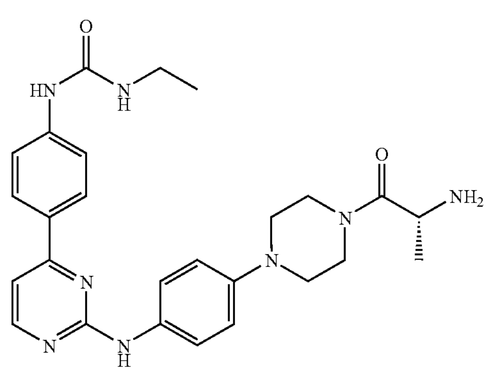 [SMILES: CCNC(=O)Nc1ccc(-c2ccnc(Nc3ccc(N4CCN(C(=O)[C@@H](C)N)CC4)cc3)n2)cc1] | 17 |

TABLE 1-continued

| Cmpd No. | Name | Structure | Can Be Made According To Synthetic Example #: |
|---|---|---|---|
| 485 | 2-(dimethylamino)-N-(4-(2-(4-(4-(2-(dimethylamino)acetyl)piperazin-1-yl)phenylamino)pyrimidin-4-yl)phenyl)acetamide | 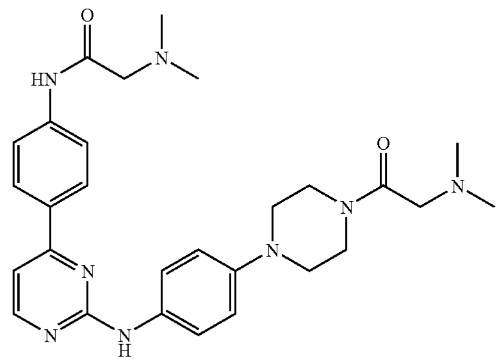 | 12 |
| 486 | (R)-2-amino-N-(4-(2-(4-(4-(2-(dimethylamino)acetyl)piperazin-1-yl)phenylamino)pyrimidin-4-yl)phenyl)propanamide | 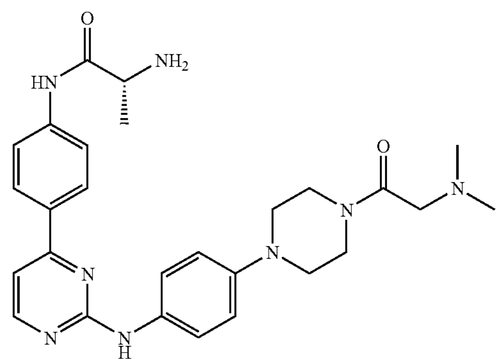 [SMILES: C[C@@H](N)C(=O)Nc1ccc(-c2ccnc(Nc3ccc(N4CCN(C(=O)CN(C)C)CC4)cc3)n2)cc1] | 20 |
| 487 | (R)-N-(4-(2-(4-(4-(3-(dimethylamino)-2,2-dimethylpropyl)piperazin-1-yl)phenylamino)pyrimidin-4-yl)phenyl)pyrrolidine-2-carboxamide | 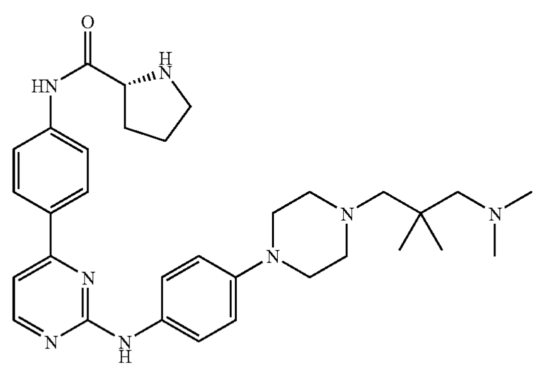 [SMILES: CN(C)CC(C)(C)CN1CCN(c2ccc(Nc3nccc(-c4ccc(NC(=O)[C@H]5CCCN5)cc4)n3)cc2)CC1] | 45 |
| 488 | (R)-2-amino-N-(4-(2-(4-(4-(3-(dimethylamino)-2,2-dimethylpropyl)piperazin-1-yl)phenylamino)pyrimidin-4-yl)phenyl)propanamide | 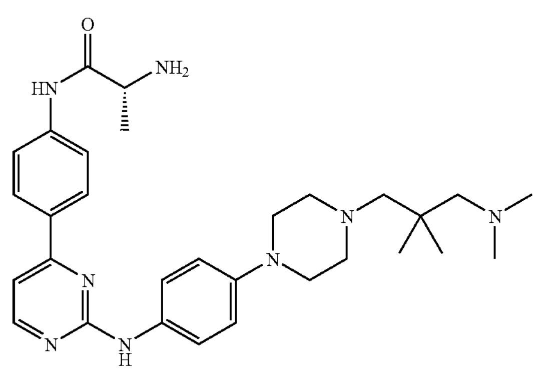 [SMILES: C[C@@H](N)C(=O)Nc1ccc(-c2ccnc(Nc3ccc(N4CCN(CC(C)(C)CN(C)C)CC4)cc3)n2)cc1] | 14 |

| Cmpd No. | Name | Structure | Can Be Made According To Synthetic Example #: |
|---|---|---|---|
| 489 | N-(4-(2-(4-(4-(3-(dimethyl-amino)-2,2-dimethylpropyl)piperazin-1-yl)phenylamino)pyrimidin-4-yl)phenyl)-3-methoxypropanamide | 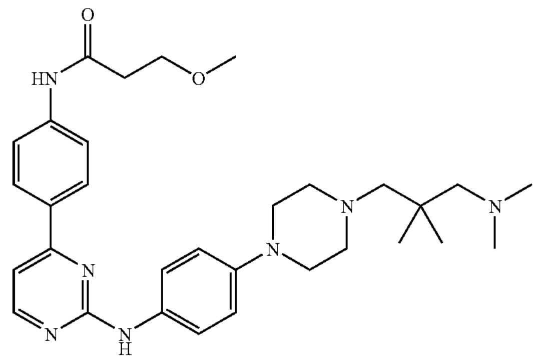 [SMILES: COCCC(=O)Nc1ccc(-c2ccnc(Nc3ccc(N4CCN(CC(C)(C)CN(C)C)CC4)cc3)n2)cc1] | 12 |
| 490 | N-(4-(2-(4-(4-(3-(dimethyl-amino)-2,2-dimethylpropyl)piperazin-1-yl)phenylamino)pyrimidin-4-yl)phenyl)butyramide | 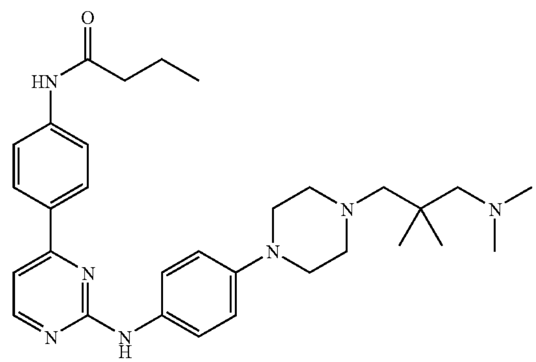 [SMILES: CCCC(=O)Nc1ccc(-c2ccnc(Nc3ccc(N4CCN(CC(C)(C)CN(C)C)CC4)cc3)n2)cc1] | 12 |
| 491 | N-(4-(2-(4-(4-(2-(dimethyl-amino)acetyl)piperazin-1-yl)phenylamino)pyrimidin-4-yl)phenyl)tetrahydrofuran-3-carboxamide | 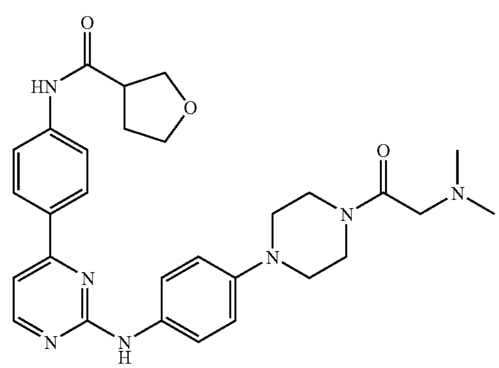 [SMILES: CN(C)CC(=O)N1CCN(c2ccc(Nc3nccc(-c4ccc(NC(=O)C5CCOC5)cc4)n3)cc2)CC1] | 11 |
| 492 | N-(4-(2-(4-(4-(3-(dimethyl-amino)-2,2-dimethylpropyl)piperazin-1-yl)phenylamino)pyrimidin-4-yl)phenyl)tetra-hydrofuran-3-carboxamide | 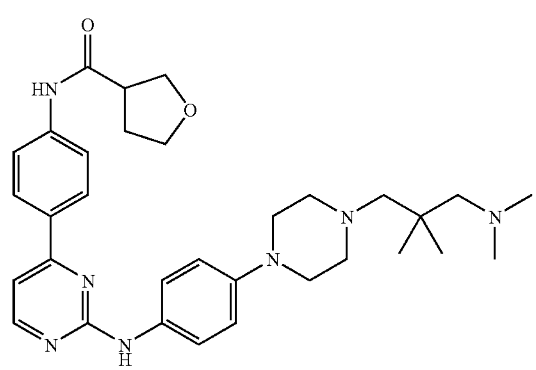 | 11 |

| Cmpd No. | Name | Structure | Can Be Made According To Synthetic Example #: |
|---|---|---|---|
| 493 | (R)-N-(4-(2-(4-(4-(2-(dimethylamino)acetyl)piperazin-1-yl)phenylamino)pyrimidin-4-yl)phenyl)tetrahydrofuran-2-carboxamide | 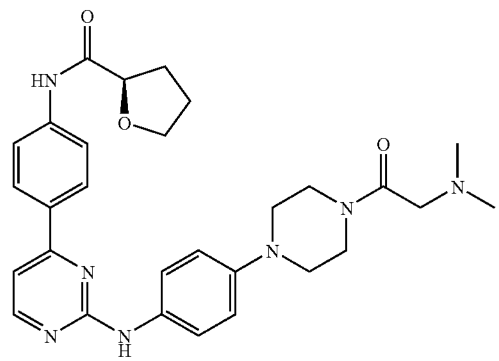 | 11 |
| 494 | 2-(dimethylamino)-N-(4-(2-(4-(4-(3-(dimethylamino)-2,2-dimethylpropyl)piperazin-1-yl)phenylamino)pyrimidin-4-yl)phenyl)acetamide | 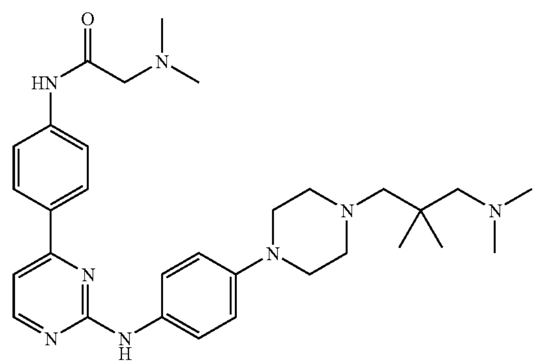 [SMILES: CN(C)CC(=O)Nc1ccc(-c2ccnc(Nc3ccc(N4CCN(CC(C)(C)CN(C)C)CC4)cc3)n2)cc1] | 12 |
| 495 | (R)-N-(4-(2-(4-(4-(piperidine-4-carbonyl)piperazin-1-yl)phenylamino)pyrimidin-4-yl)phenyl)pyrrolidine-2-carboxamide | 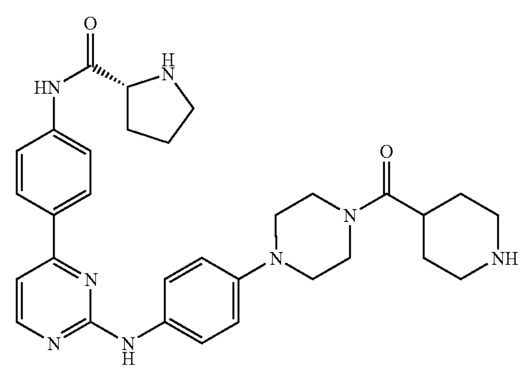 [SMILES: O=C(Nc1ccc(-c2ccnc(Nc3ccc(N4CCN(C(=O)C5CCNCC5)CC4)cc3)n2)cc1)[C@H]1CCCN1] | 45 |
| 496 | 3-methoxy-N-(4-(2-(4-(4-(piperidine-4-carbonyl)piperazin-1-yl)phenylamino)pyrimidin-4-yl)phenyl)propanamide | 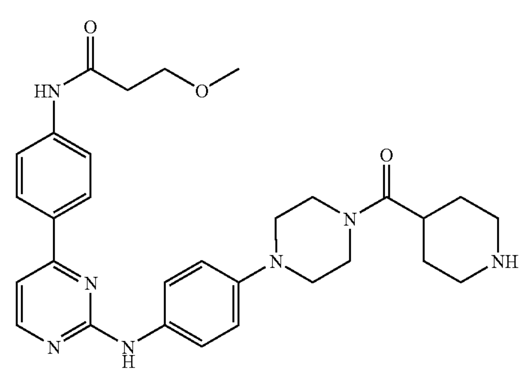 [SMILES: COCCC(=O)Nc1ccc(-c2ccnc(Nc3ccc(N4CCN(C(=O)C5CCNCC5)CC4)cc3)n2)cc1] | 12 |

| Cmpd No. | Name | Structure | Can Be Made According To Synthetic Example #: |
|---|---|---|---|
| 497 | 1-ethyl-3-(4-(2-(4-(4-(piperidine-4-carbonyl)piperazin-1-yl)phenylamino)pyrimidin-4-yl)phenyl)urea | 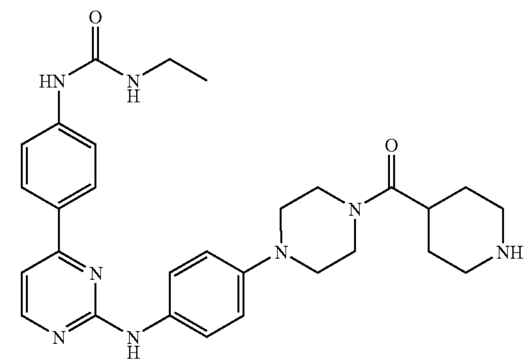 [SMILES: CCNC(=O)Nc1ccc(-c2ccnc(Nc3ccc(N4CCN(C(=O)C5CCNCC5)CC4)cc3)n2)cc1] | 17 |
| 498 | N-(4-(2-(4-(4-(3-(dimethyl-amino)-2,2-dimethyl-propanoyl)piperazin-1-yl)benzyl)pyrimidin-4-yl)phenyl)acetamide | 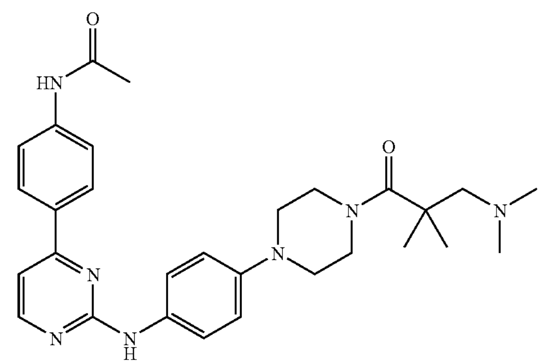 [SMILES: CC(=O)Nc1ccc(-c2ccnc(Nc3ccc(N4CCN(C(=O)C(C)(C)CN(C)C)CC4)cc3)n2)cc1] | 49 |
| 499 | (S)-N-(4-(2-(4-(4-(2-(dimethylamino)acetyl)piperazin-1-yl)phenylamino)pyrimidin-4-yl)phenyl)tetra-hydrofuran-2-carboxamide | 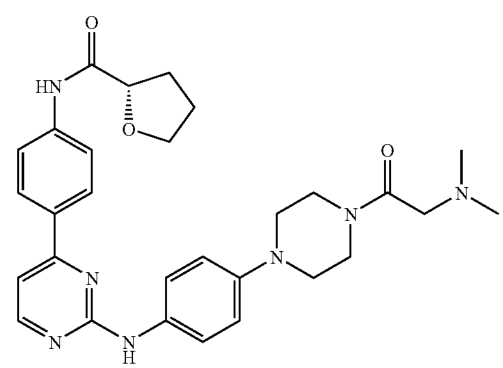 [SMILES: CN(C)CC(=O)N1CCN(c2ccc(Nc3nccc(-c4ccc(NC(=O)[C@@H]5CCCO5)cc4)n3)cc2)CC1] | 12 |
| 500 | (R)-N-(4-(2-(4-(4-(3-methoxypropanoyl)piperazin-1-yl)phenylamino)pyrimidin-4-yl)phenyl)tetrahydrofuran-2-carboxamide | 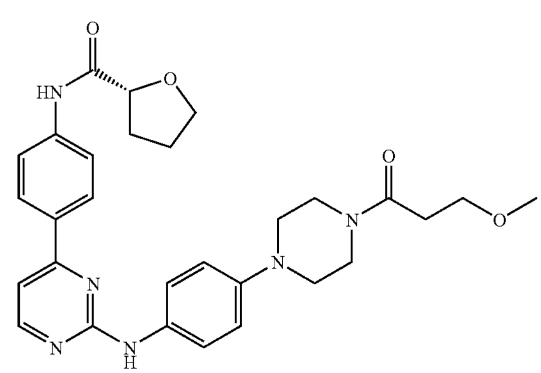 | 12 |

TABLE 1-continued

| Cmpd No. | Name | Structure | Can Be Made According To Synthetic Example #: |
|---|---|---|---|
| 501 | (4S)-4-hydroxy-N-(4-(2-(4-morpholinophenylamino)pyrimidin-4-yl)phenyl)pyrrolidine-2-carboxamide | 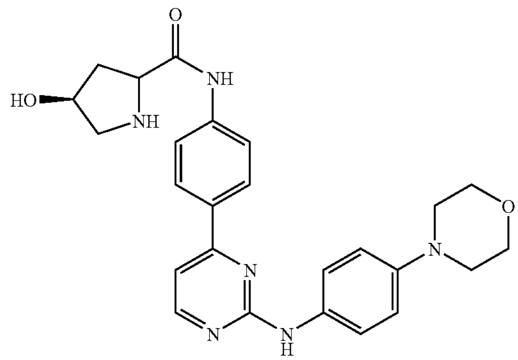 [SMILES: O=C(Nc1ccc(-c2ccnc(Nc3ccc(N4CCOCC4)cc3)n2)cc1)C1C[C@H](O)CN1] | 21 |
| 502 | (R)-N-(4-(2-(4-(4-(3-(dimethylamino)-2,2-dimethylpropyl)piperazin-1-yl)phenylamino)pyrimidin-4-yl)phenyl)tetrahydrofuran-2-carboxamide | 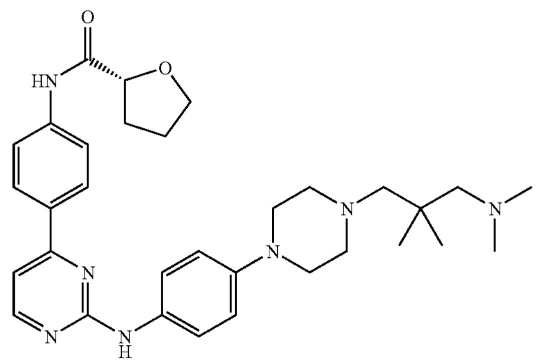 [SMILES: CN(C)CC(C)(C)CN1CCN(c2ccc(Nc3nccc(-c4ccc(NC(=O)[C@H]5CCCO5)cc4)n3)cc2)CC1] | 12 |
| 503 | (S)-N-(4-(2-(4-(4-(3-methoxypropanoyl)piperazin-1-yl)phenylamino)pyrimidin-4-yl)phenyl)tetrahydrofuran-2-carboxamide | 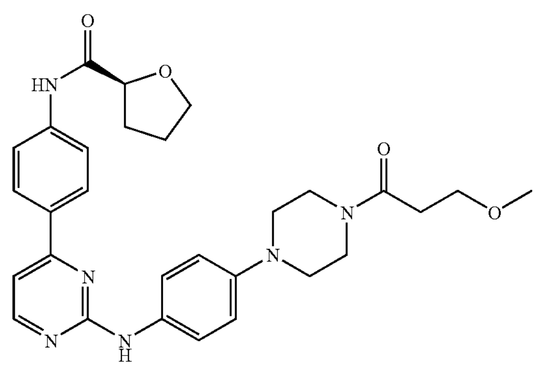 [SMILES: COCCC(=O)N1CCN(c2ccc(Nc3nccc(-c4ccc(NC(=O)[C@@H]5CCCO5)cc4)n3)cc2)CC1] | 12 |
| 504 | N-(4-(2-(4-(4-(3-(dimethylamino)-2,2-dimethylpropyl)piperazin-1-yl)phenylamino)pyrimidin-4-yl)phenyl)cyclopropanecarboxamide | 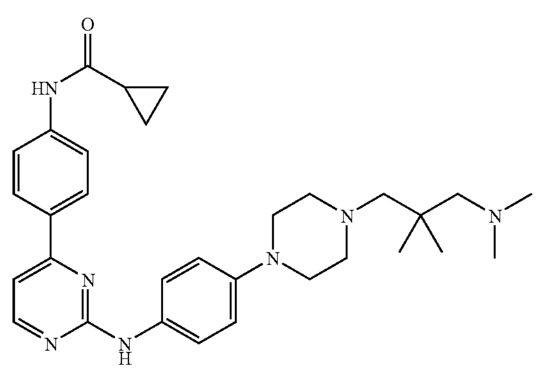 [SMILES: CN(C)CC(C)(C)CN1CCN(c2ccc(Nc3nccc(-c4ccc(NC(=O)C5CC5)cc4)n3)cc2)CC1] | 11 |

TABLE 1-continued

| Cmpd No. | Name | Structure | Can Be Made According To Synthetic Example #: |
|---|---|---|---|
| 505 | N-(4-(2-(4-(4-(3-methoxy-propanoyl)piperazin-1-yl)phenylamino)pyrimidin-4-yl)phenyl)tetrahydrofuran-3-carboxamide | 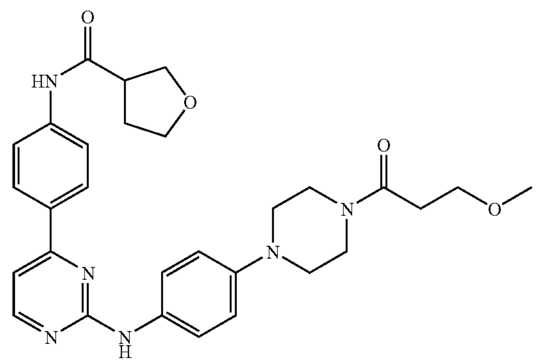 [SMILES: COCCC(=O)N1CCN(c2ccc(Nc3nccc(-c4ccc(NC(=O)C5CCOC5)cc4)n3)cc2)CC1] | 11 |
| 506 | (S)-N-(4-(2-(4-(4-(pyrrolidine-2-carbonyl)piperazin-1-yl)phenylamino)pyrimidin-4-yl)phenyl)butyramide | 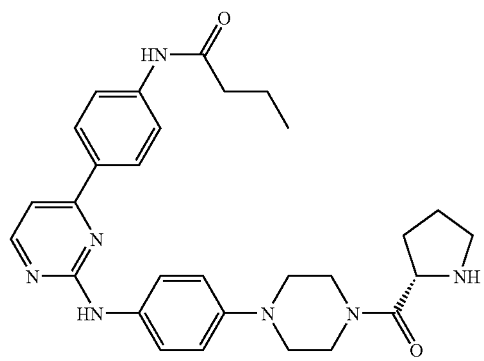 [SMILES: CCCC(=O)Nc1ccc(-c2ccnc(Nc3ccc(N4CCN(C(=O)[C@@H]5CCCN5)CC4)cc3)n2)cc1] | 11 |
| 507 | (2R)-N-(4-(2-(4-(4-(tetrahydrofuran-2-carbonyl)piperazin-1-yl)phenylamino)pyrimidin-4-yl)phenyl)pyrrolidine-2-carboxamide | 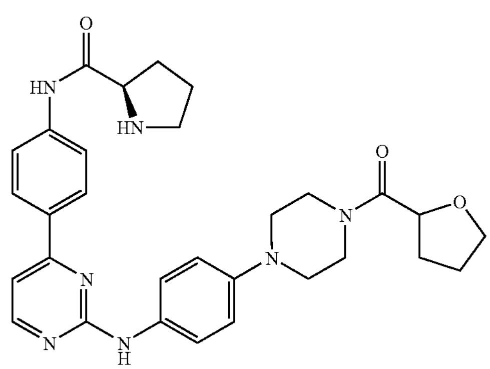 [SMILES: O=C(Nc1ccc(-c2ccnc(Nc3ccc(N4CCN(C(=O)C5CCCO5)CC4)cc3)n2)cc1)[C@H]1CCCN1] | 45 |
| 508 | (R)-N-(4-(5-chloro-2-(4-morpholinophenylamino)pyrimidin-4-yl)phenyl)pyrrolidine-2-carboxamide | 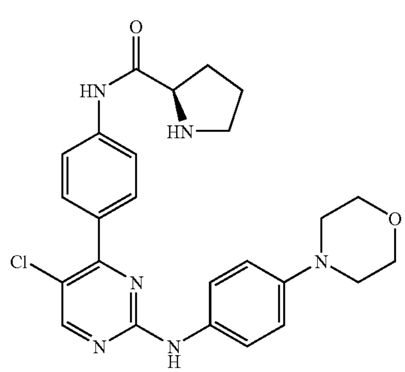 [SMILES: O=C(Nc1ccc(-c2nc(Nc3ccc(N4CCOCC4)cc3)ncc2Cl)cc1)[C@H]1CCCN1] | 45 |

TABLE 1-continued

| Cmpd No. | Name | Structure | Can Be Made According To Synthetic Example #: |
|---|---|---|---|
| 509 | N-(4-(2-(4-(4-(3-(diethyl-amino)propanoyl)piperazin-1-yl)benzyl)pyrimidin-4-yl)phenyl)acetamide | 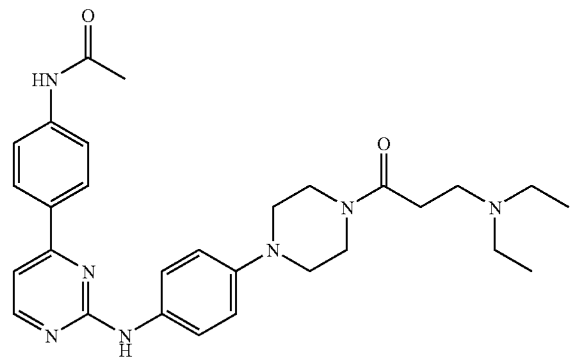 [SMILES: CCN(CC)CCC(=O)N1CCN(c2ccc(Nc3nccc(-c4ccc(NC(C)=O)cc4)n3)cc2)CC1] | 7 |
| 510 | (S)-1-(2-hydroxyethyl)-N-(4-(2-(4-morpholinophenyl-amino)pyrimidin-4-yl)phenyl)pyrrolidine-3-carboxamide | 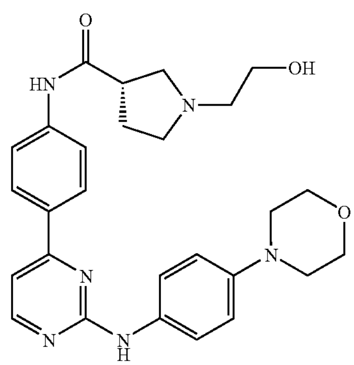 [SMILES: O=C(Nc1ccc(-c2ccnc(Nc3ccc(N4CCOCC4)cc3)n2)cc1)[C@H]1CCN(CCO)C1] | 42 |
| 511 | (S)-2-amino-N1-(4-(2-(4-morpholinophenylamino)pyrimidin-4-yl)phenyl)pentanediamide | 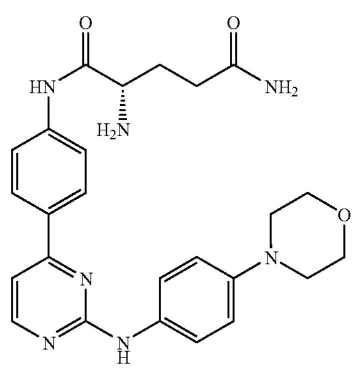 [SMILES: NC(=O)CC[C@H](N)C(=O)Nc1ccc(-c2ccnc(Nc3ccc(N4CCOCC4)cc3)n2)cc1] | 14 |
| 512 | (R)-2-amino-N1-(4-(2-(4-morpholinophenylamino)pyrimidin-4-yl)phenyl)pentanediamide | 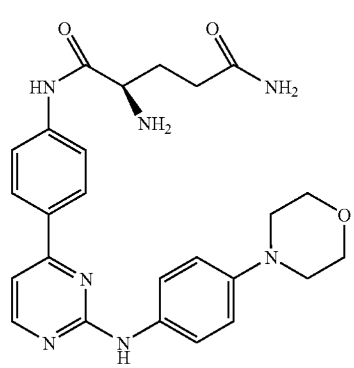 [SMILES: NC(=O)CC[C@@H](N)C(=O)Nc1ccc(-c2ccnc(Nc3ccc(N4CCOCC4)cc3)n2)cc1] | 18 |

| Cmpd No. | Name | Structure | Can Be Made According To Synthetic Example #: |
|---|---|---|---|
| 513 | (R)-2-amino-N1-(4-(2-(4-morpholinophenylamino)pyrimidin-4-yl)phenyl)succinamide | 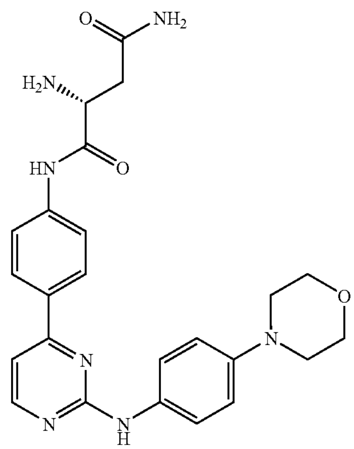 [SMILES: NC(=O)C[C@@H](N)C(=O)Nc1ccc(-c2ccnc(Nc3ccc(N4CCOCC4)cc3)n2)cc1] | 20 |
| 514 | (R)-N-(4-(2-(4-(4-((4-chloro-1-methyl-1H-pyrazol-3-yl)methyl)piperazin-1-yl)phenylamino)pyrimidin-4-yl)phenyl)pyrrolidine-2-carboxamide | 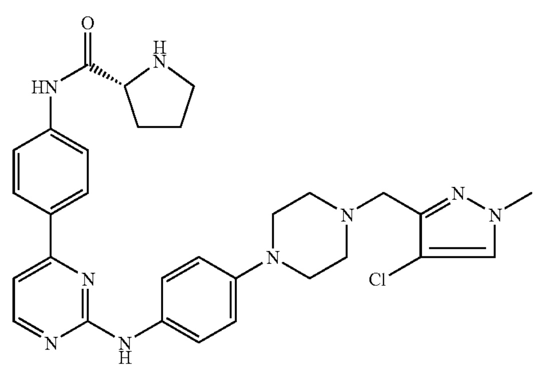 [SMILES: Cn1cc(Cl)c(CN2CCN(c3ccc(Nc4nccc(-c5ccc(NC(=O)[C@H]6CCCN6)cc5)n4)cc3)CC2)n1] | 45 |
| 515 | (S)-1-ethyl-N-(4-(2-(4-morpholinophenylamino)pyrimidin-4-yl)phenyl)pyrrolidine-3-carboxamide | 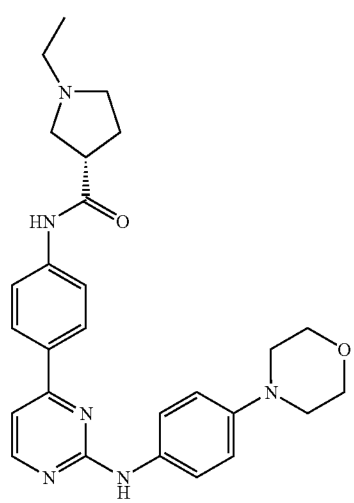 [SMILES: CCN1CC[C@H](C(=O)Nc2ccc(-c3ccnc(Nc4ccc(N5CCOCC5)cc4)n3)cc2)C1] | 42 |

TABLE 1-continued

| Cmpd No. | Name | Structure | Can Be Made According To Synthetic Example #: |
|---|---|---|---|
| 516 | (R)-N-(4-(2-(4-(4-(2-ethoxyacetyl)piperazin-1-yl)phenylamino)pyrimidin-4-yl)phenyl)pyrrolidine-2-carboxamide | 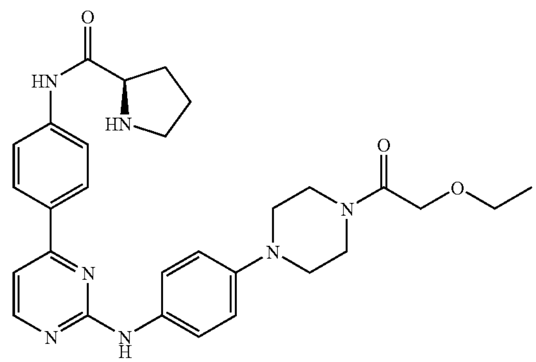 [SMILES: CCOCC(=O)N1CCN(c2ccc(Nc3nccc(-c4ccc(NC(=O)[C@H]5CCCN5)cc4)n3)cc2)CC1] | 45 |
| 517 | (R)-N-(4-(2-(4-(4-(2-(pyrrolidin-1-yl)acetyl)piperazin-1-yl)phenylamino)pyrimidin-4-yl)phenyl)pyrrolidine-2-carboxamide | 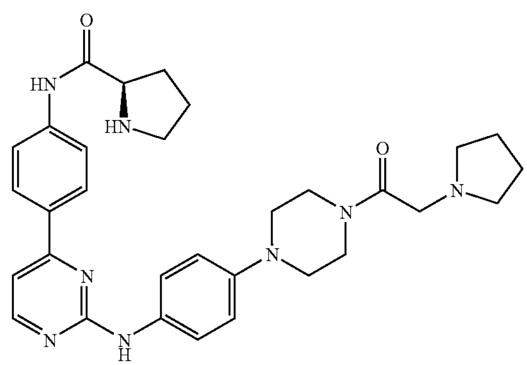 [SMILES: O=C(Nc1ccc(-c2ccnc(Nc3ccc(N4CCN(C(=O)CN5CCCC5)CC4)cc3)n2)cc1)[C@H]1CCCN1] | 45 |
| 518 | (R)-N-(4-(2-(4-(4-(2-morpholinoacetyl)piperazin-1-yl)phenylamino)pyrimidin-4-yl)phenyl)pyrrolidine-2-carboxamide | 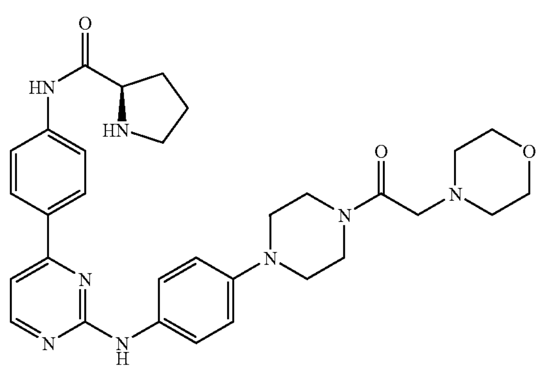 [SMILES: O=C(Nc1ccc(-c2ccnc(Nc3ccc(N4CCN(C(=O)CN5CCOCC5)CC4)cc3)n2)cc1)[C@H]1CCCN1] | 45 |
| 519 | N-(4-(2-(4-morpholinophenylamino)pyrimidin-4-yl)phenyl)-1H-imidazole-4-carboxamide | 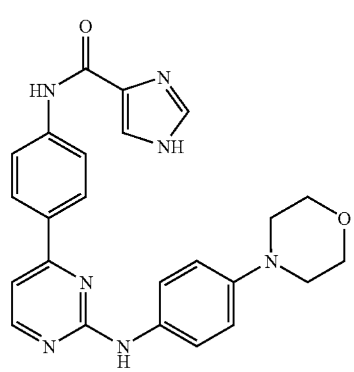 [SMILES: O=C(Nc1ccc(-c2ccnc(Nc3ccc(N4CCOCC4)cc3)n2)cc1)c1c[nH]cn1] | 12 |

TABLE 1-continued

| Cmpd No. | Name | Structure | Can Be Made According To Synthetic Example #: |
|---|---|---|---|
| 520 | 2-(dimethylamino)-N-(4-(2-(4-(4-(2-(piperazin-1-yl)acetyl)piperazin-1-yl)phenylamino)pyrimidin-4-yl)phenyl)acetamide | 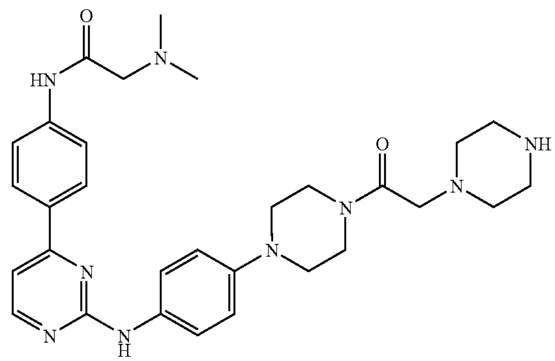 [SMILES: CN(C)CC(=O)Nc1ccc(-c2ccnc(Nc3ccc(N4CCN(C(=O)CN5CCNCC5)CC4)cc3)n2)cc1] | 12 |
| 521 | (S)-N-(4-(2-(4-(4-(3-(dimethylamino)-2,2-dimethylpropyl)piperazin-1-yl)phenylamino)pyrimidin-4-yl)phenyl)tetrahydrofuran-2-carboxamide | 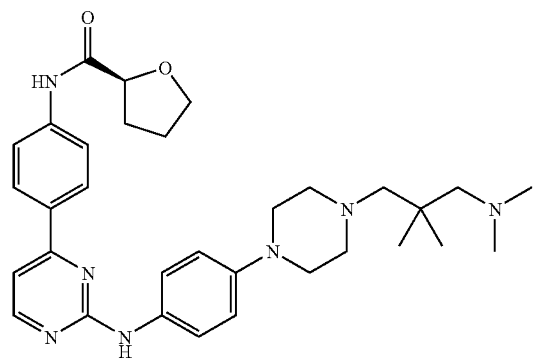 [SMILES: CN(C)CC(C)(C)CN1CCN(c2ccc(Nc3nccc(-c4ccc(NC(=O)[C@@H]5CCCO5)cc4)n3)cc2)CC1] | 12 |
| 522 | (R)-2-hydroxy-2-methyl-N-(4-(2-(4-morpholinophenyl-amino)pyrimidin-4-yl)phenyl)butanamide | 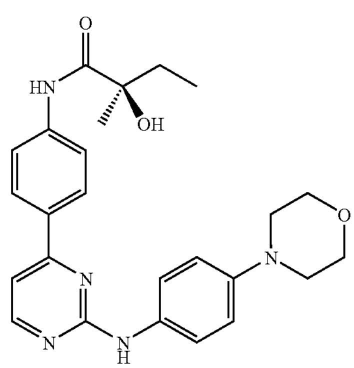 [SMILES: CC[C@@](C)(O)C(=O)Nc1ccc(-c2ccnc(Nc3ccc(N4CCOCC4)cc3)n2)cc1] | 18 |
| 523 | (S)-2-hydroxy-2-methyl-N-(4-(2-(4-morpholinobenzyl)pyrimidin-4-yl)phenyl)butanamide | 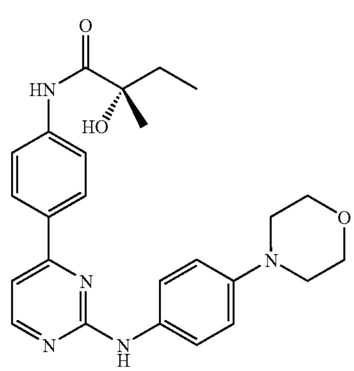 [SMILES: CC[C@](C)(O)C(=O)Nc1ccc(-c2ccnc(Nc3ccc(N4CCOCC4)cc3)n2)cc1] | 18 |

TABLE 1-continued

| Cmpd No. | Name | Structure | Can Be Made According To Synthetic Example #: |
|---|---|---|---|
| 524 | (R)-2-methoxy-N-(4-(2-(4-morpholinophenylamino)pyrimidin-4-yl)phenyl)propanamide | 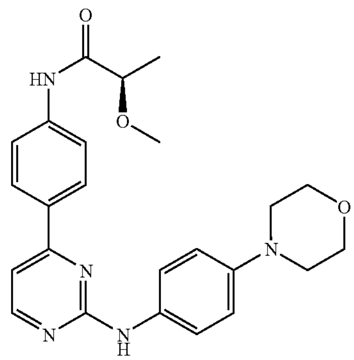 [SMILES: CO[C@H](C)C(=O)Nc1ccc(-c2ccnc(Nc3ccc(N4CCOCC4)cc3)n2)cc1] | 11 |
| 525 | (S)-2-methoxy-N-(4-(2-(4-morpholinophenylamino)pyrimidin-4-yl)phenyl)propanamide | 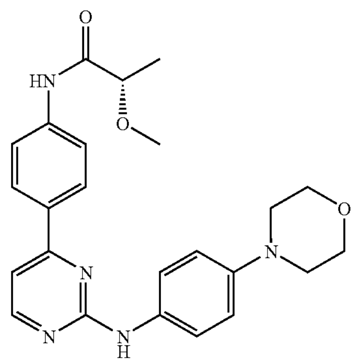 [SMILES: CO[C@@H](C)C(=O)Nc1ccc(-c2ccnc(Nc3ccc(N4CCOCC4)cc3)n2)cc1] | 11 |
| 526 | (R)-N-(4-(2-(4-(4-(2-methoxyacetyl)piperazin-1-yl)phenylamino)pyrimidin-4-yl)phenyl)pyrrolidine-2-carboxamide | 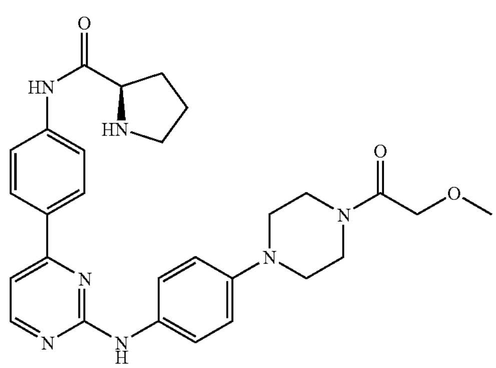 | 49 |
| 527 | (R)-N-(4-(2-(4-(4-acetyl-piperazin-1-yl)phenylamino)pyrimidin-4-yl)phenyl)pyrrolidine-2-carboxamide | 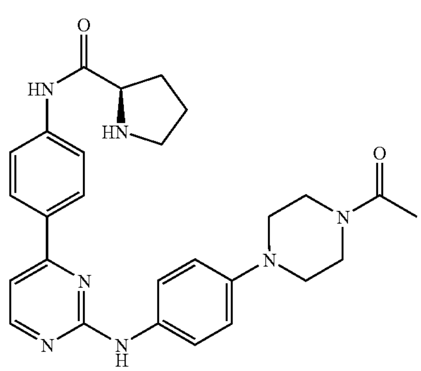 [SMILES: CC(=O)N1CCN(c2ccc(Nc3nccc(-c4ccc(NC(=O)[C@H]5CCCN5)cc4)n3)cc2)CC1] | 49 |

TABLE 1-continued

| Cmpd No. | Name | Structure | Can Be Made According To Synthetic Example #: |
|---|---|---|---|
| 528 | (S)-2-amino-N-(4-(5-methyl-2-(4-(4-((1-methyl-1H-imidazol-2-yl)methyl)piperazin-1-yl)phenylamino)pyrimidin-4-yl)phenyl)propanamide | 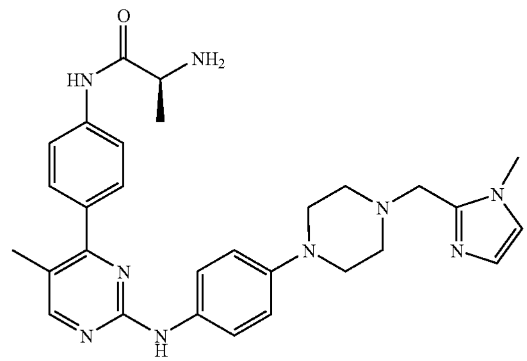 [SMILES: Cc1cnc(Nc2ccc(N3CCN(Cc4nccn4C)CC3)cc2)nc1-c1ccc(NC(=O)[C@H](C)N)cc1] | 14 |
| 529 | N-(4-(2-(4-(4-(pipendine-4-carbonyl)piperazin-1-yl)phenylamino)pyrimidin-4-yl)phenyl)tetrahydrofuran-3-carboxamide | 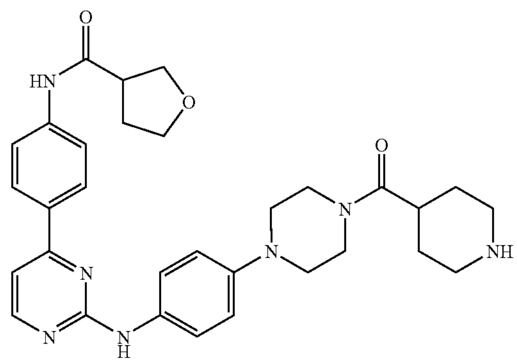 [SMILES: O=C(Nc1ccc(-c2ccnc(Nc3ccc(N4CCN(C(=O)C5CCNCC5)CC4)cc3)n2)cc1)C1CCOC1] | 12 |
| 530 | (2R,4S)-4-hydroxy-N-(4-(2-(4-4-3-methoxypropanoyl)piperazin-1-yl)phenylamino)pyrimidin-4-yl)phenyl)pyrrolidine-2-carboxamide | 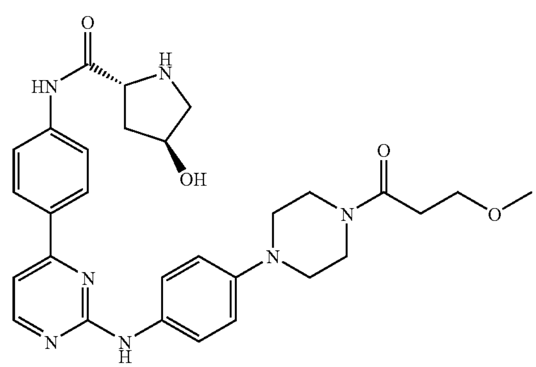 [SMILES: COCCC(=O)N1CCN(c2ccc(Nc3nccc(-c4ccc(NC(=O)[C@H]5C[C@H](O)CN5)cc4)n3)cc2)CC1] | 21 |
| 531 | 1-amino-N-(4-(2-(4-morpholinophenylamino)pyrimidin-4-yl)phenyl)cyclopentanecarboxamide | 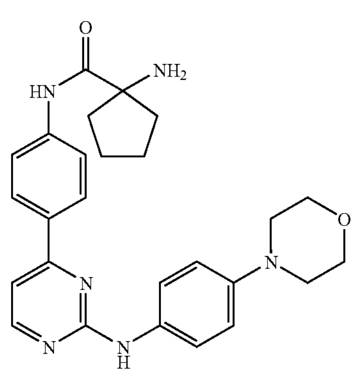 [SMILES: NC1(C(=O)Nc2ccc(-c3ccnc(Nc4ccc(N5CCOCC5)cc4)n3)cc2)CCCC1] | 44 |

TABLE 1-continued

| Cmpd No. | Name | Structure | Can Be Made According To Synthetic Example #: |
|---|---|---|---|
| 532 | (R)-N-(4-(2-(4-(4-formyl-piperazin-1-yl)phenylamino) pyrimidin-4-yl)phenyl) pyrrolidine-2-carboxamide | 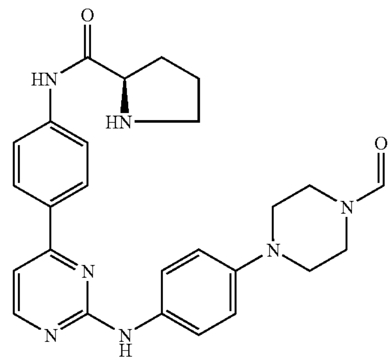 [SMILES: O=CN1CCN(c2ccc(Nc3nccc(-c4ccc(NC(=O)[C@H]5CCCN5)cc4)n3)cc2)CC1] | 45 |
| 533 | (R)-1-(2-hydroxyethyl)-N-(4-(2-(4-morpholinophenyl-amino)pyrimidin-4-yl)phenyl) pyrrolidine-3-carboxamide | 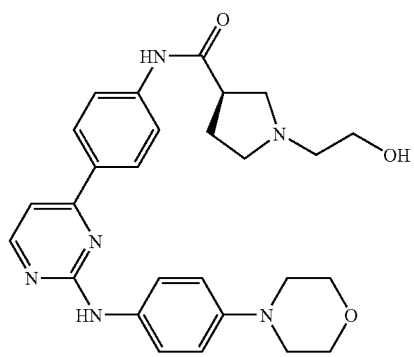 [SMILES: O=C(Nc1ccc(-c2ccnc(Nc3ccc(N4CCOCC4)cc3)n2)cc1)[C@@H]1CCN(CCO)C1] | 42 |
| 534 | 1-amino-N-(4-(2-(4-morpholinophenylamino) pyrimidin-4-yl)phenyl) cyclopropanecarboxamide | 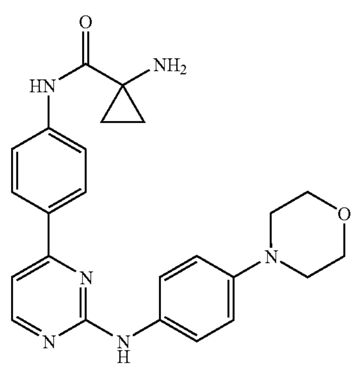 [SMILES: NC1(C(=O)Nc2ccc(-c3ccnc(Nc4ccc(N5CCOCC5)cc4)n3)cc2)CC1] | 12 |
| 535 | N-(4-(2-(4-morpholinophenyl-amino)pyrimidin-4-yl) phenyl)-1H-pyrrole-2-carboxamide | 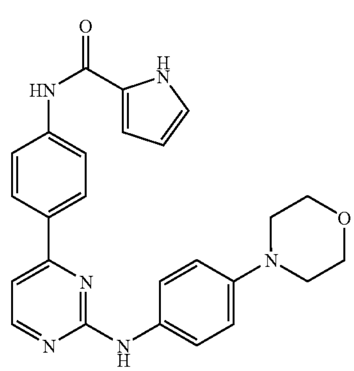 | 12 |

TABLE 1-continued

| Cmpd No. | Name | Structure | Can Be Made According To Synthetic Example #: |
|---|---|---|---|
| 536 | N-(4-(2-(4-morpholinophenyl-amino)pyrimidin-4-yl)phenyl)-1H-imidazole-2-carboxamide | 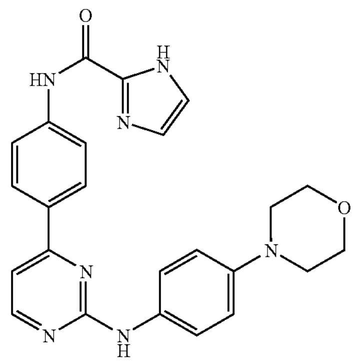 [SMILES: O=C(Nc1ccc(-c2ccnc(Nc3ccc(N4CCOCC4)cc3)n2)cc1)c1ncc[nH]1] | 12 |
| 537 | (S)-2-hydroxy-3-3-dimethyl-N-(4-(2-(4-morpholinophenyl-amino)pyrimidin-4-yl)phenyl)butanamide | 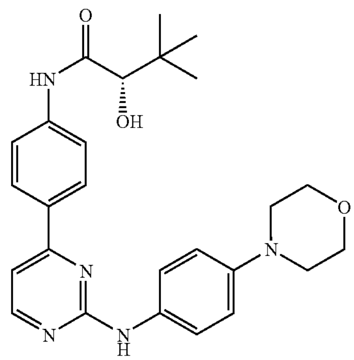 [SMILES: CC(C)(C)[C@H](O)C(=O)Nc1ccc(-c2ccnc(Nc3ccc(N4CCOCC4)cc3)n2)cc1] | 20 |
| 538 | (R)-2-cyclohexyl-2-hydroxy-N-(4-(2-(4-morpholinophenyl-amino)pyrimidin-4-yl)phenyl)acetamide | 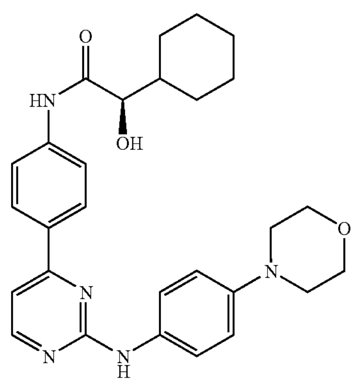 [SMILES: O=C(Nc1ccc(-c2ccnc(Nc3ccc(N4CCOCC4)cc3)n2)cc1)[C@H](O)C1CCCCC1] | 18 |
| 539 | (S)-2-cyclohexyl-2-hydroxy-N-(4-(2-(4-morpholinophenylamino)pyrimidin-4-yl)phenyl)acetamide | 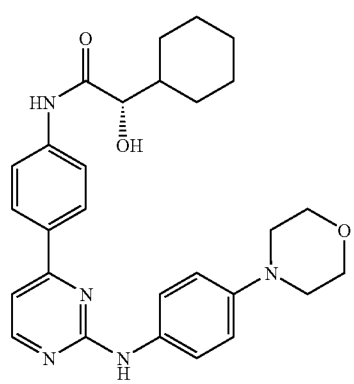 [SMILES: O=C(Nc1ccc(-c2ccnc(Nc3ccc(N4CCOCC4)cc3)n2)cc1)[C@@H](O)C1CCCCC1] | 20 |

TABLE 1-continued

| Cmpd No. | Name | Structure | Can Be Made According To Synthetic Example #: |
|---|---|---|---|
| 540 | (S)-2-hydroxy-N-(4-(2-(4-morpholinophenylamino)pyrimidin-4-yl)phenyl)propanamide | 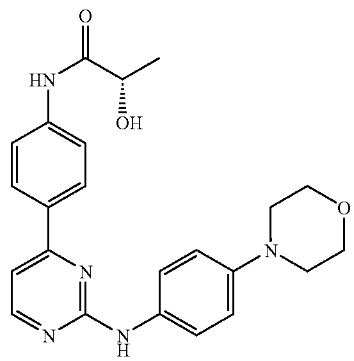 [SMILES: C[C@H](O)C(=O)Nc1ccc(-c2ccnc(Nc3ccc(N4CCOCC4)cc3)n2)cc1] | 20 |
| 541 | 1-amino-N-(4-(2-(4-morpholinophenylamino)pyrimidin-4-yl)phenyl)cyclobutanecarboxamide | 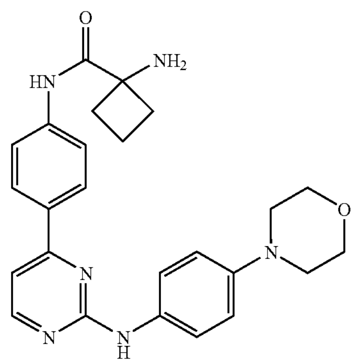 [SMILES: NC1(C(=O)Nc2ccc(-c3ccnc(Nc4ccc(N5CCOCC5)cc4)n3)cc2)CCC1] | 14 |
| 542 | (R)-N-(4-(2-(6-morpholinopyridin-3-ylamino)pyrimidin-4-yl)phenyl)pyrrolidine-2-carboxamide | 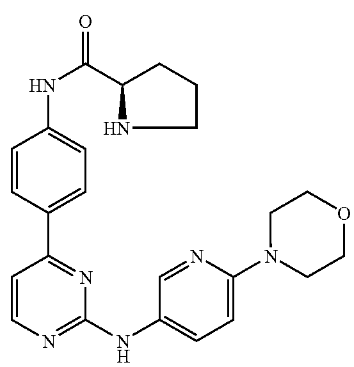 [SMILES: O=C(Nc1ccc(-c2ccnc(Nc3ccc(N4CCOCC4)nc3)n2)cc1)[C@H]1CCCN1] | 45 |
| 543 | (S)-N-(4-(2-(3-chloro-4-morpholinophenylamino)pyrimidin-4-yl)phenyl)pyrrolidine-2-carboxamide | 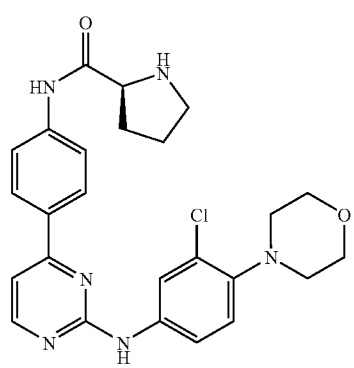 [SMILES: O=C(Nc1ccc(-c2ccnc(Nc3ccc(N4CCOCC4)c(Cl)c3)n2)cc1)[C@@H]1CCCN1] | 45 |

TABLE 1-continued

| Cmpd No. | Name | Structure | Can Be Made According To Synthetic Example #: |
|---|---|---|---|
| 544 | (2R,3R)-2-amino-3-methyl-N-(4-(2-(4-morpholinophenyl-amino)pyrimidin-4-yl)phenyl)pentanamide | 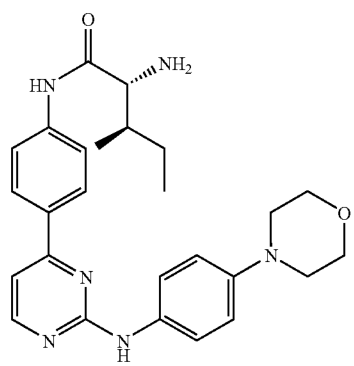 [SMILES: CC[C@@H](C)[C@@H](N)C(=O)Nc1ccc(-c2ccnc(Nc3ccc(N4CCOCC4)cc3)n2)cc1] | 14 |
| 545 | 1-hydroxy-N-(4-(2-(4-morpholinophenylamino)pyrimidin-4-yl)phenyl)cyclopentanecarboxamide | 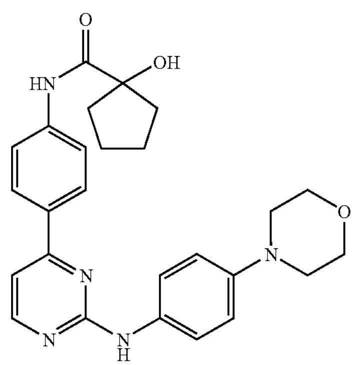 [SMILES: O=C(Nc1ccc(-c2ccnc(Nc3ccc(N4CCOCC4)cc3)n2)cc1)C1(O)CCCC1] | 18 |
| 546 | (R)-N-(4-(2-(4-(4-(4-(dimethylamino)butanoyl)perazin-1-yl)phenylamino)pyrimidin-4-yl)phenyl)pyrrolidine-2-carboxamide | 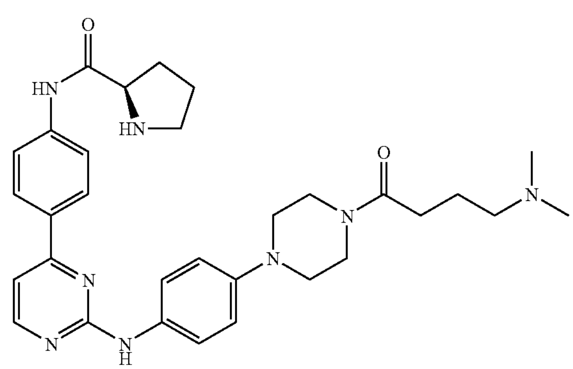 [SMILES: CN(C)CCCC(=O)N1CCN(c2ccc(Nc3nccc(-c4ccc(NC(=O)[C@H]5CCCN5)cc4)n3)cc2)CC1] | 45 |
| 547 | (R)-N-(4-(2-(4-(2-methoxy-ethyl)-3,4-dihydro-2H-benzo[b][1,4]oxazin-7-ylamino)pyrimidin-4-yl)phenyl)pyrrolidine-2-carboxamide | 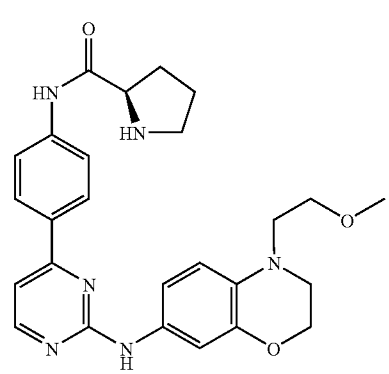 [SMILES: COCCN1CCOc2cc(Nc3nccc(-c4ccc(NC(=O)[C@H]5CCCN5)cc4)n3)ccc21] | 45 |

TABLE 1-continued

| Cmpd No. | Name | Structure | Can Be Made According To Synthetic Example #: |
|---|---|---|---|
| 548 | (R)-2-amino-N-(4-(2-(4-morpholinophenylamino)pyrimidin-4-yl)phenyl)butanamide | 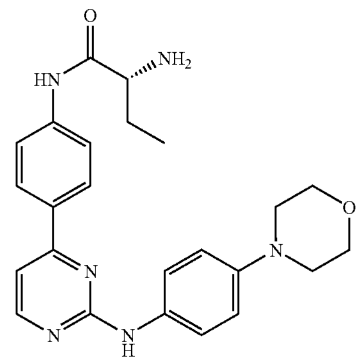 | 14 |
| 549 | (R)-2-amino-N-(4-(2-(4-morpholinophenylamino)pyrimidin-4-yl)phenyl)pentanamide | 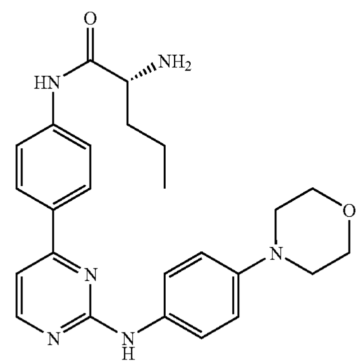 [SMILES: CCC[C@@H](N)C(=O)Nc1ccc(-c2ccnc(Nc3ccc(N4CCOCC4)cc3)n2)cc1] | 14 |
| 550 | (R)-2-amino-N-(4-(2-(4-morpholinophenylamino)pyrimidin-4-yl)phenyl)hexanamide | 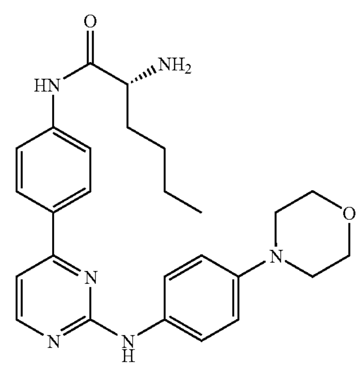 [SMILES: CCCC[C@@H](N)C(=O)Nc1ccc(-c2ccnc(Nc3ccc(N4CCOCC4)cc3)n2)cc1] | 14 |
| 551 | (R)-2-amino-3-methoxy-N-(4-(2-(3-methoxy-4-morpholinophenylamino)pyrimidin-4-yl)phenyl)propanamide | 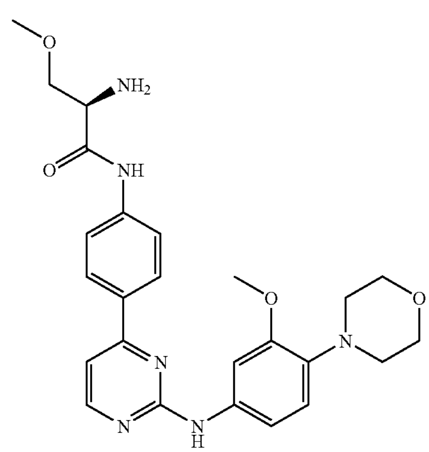 [SMILES: COC[C@@H](N)C(=O)Nc1ccc(-c2ccnc(Nc3ccc(N4CCOCC4)c(OC)c3)n2)cc1] | 14 |

TABLE 1-continued
| Cmpd No. | Name | Structure | Can Be Made According To Synthetic Example #: |
|---|---|---|---|
| 552 | (2S,3R)-2-amino-3-methyl-morpholinophenylamino) N-(4-(2-(4-pyrimidin-4-yl)phenyl) pentanamide | 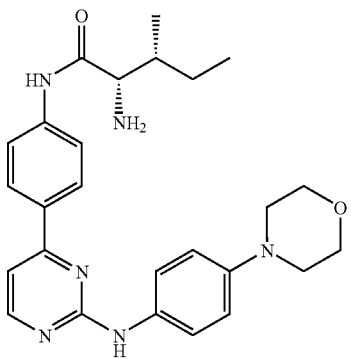 [SMILES: CC[C@@H](C)[C@H](N)C(=O)Nc1ccc(-c2ccnc(Nc3ccc(N4CCOCC4)cc3)n2)cc1] | 14 |
| 553 | (R)-N-(4-(2-(3-fluoro-4-morpholinophenylamino) pyrimidin-4-yl)phenyl) pyrrolidine-2-carboxamide | 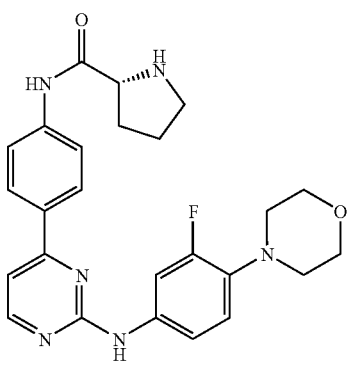 [SMILES: O=C(Nc1ccc(-c2ccnc(Nc3ccc(N4CCOCC4)c(F)c3)n2)cc1)[C@H]1CCCN1] | 45 |
| 554 | N-(4-(2-(3-methoxy-4-morpholinophenylamino) pyrimidin-4-yl)phenyl)-2-(1H-tetrazol-1-yl)acetamide | 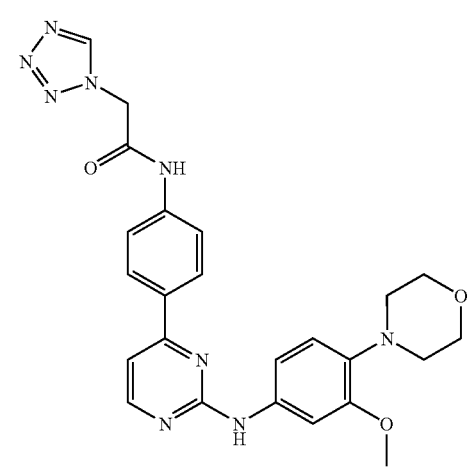 [SMILES: COc1cc(Nc2nccc(-c3ccc(NC(=O)Cn4cnnn4)cc3)n2)ccc1N1CCOCC1] | 24 |

TABLE 1-continued

| Cmpd No. | Name | Structure | Can Be Made According To Synthetic Example #: |
|---|---|---|---|
| 555 | (S)-N-(4-(2-(4-morpholinophenylamino)pyrimidin-4-yl)phenyl)indoline-2-carboxamide | 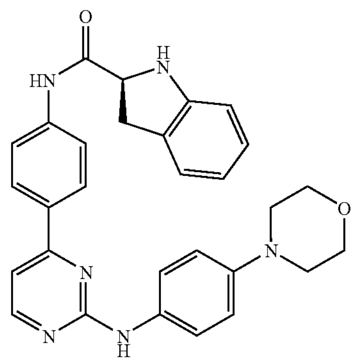 [SMILES: O=C(Nc1ccc(-c2ccnc(Nc3ccc(N4CCOCC4)cc3)n2)cc1)[C@@H]1Cc2ccccc2N1] | 45 |
| 556 | (R)-tert-butyl 2-(4-(2-(4-morpholinophenylamino)pyrimidin-4-yl)phenyl-carbamoyl)pyrrolidine-1-carboxylate | 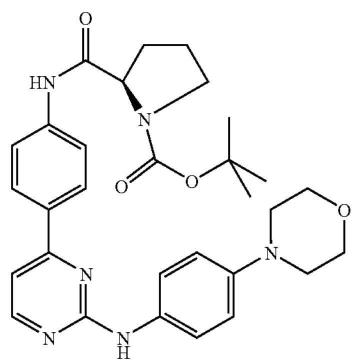 [SMILES: CC(C)(C)OC(=O)N1CCC[C@@H]1C(=O)Nc1ccc(-c2ccnc(Nc3ccc(N4CCOCC4)cc3)n2)cc1] | 45 |
| 557 | 1-acetyl-4-amino-N-(4-(2-(4-morpholinophenylamino)pyrimidin-4-yl)phenyl)piperidine-4-carboxamide | 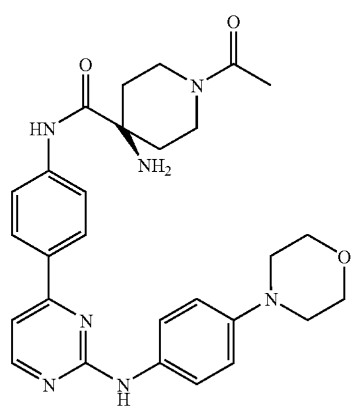 | 44 |
| 558 | (R)-2-amino-3-methoxy-N-(4-(2-(4-morpholinophenyl-amino)pyrimidin-4-yl)phenyl)propanamide | 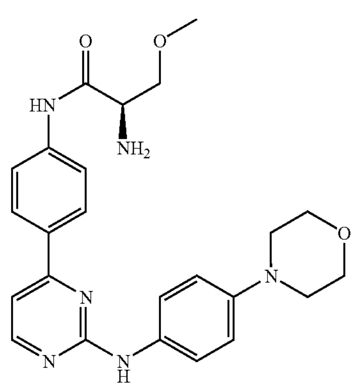 [SMILES: COC[C@@H](N)C(=O)Nc1ccc(-c2ccnc(Nc3ccc(N4CCOCC4)cc3)n2)cc1] | 14 |

TABLE 1-continued

| Cmpd No. | Name | Structure | Can Be Made According To Synthetic Example #: |
|---|---|---|---|
| 559 | (S)-N-(4-(2-(3-fluoro-4-morpholinophenylamino)pyrimidin-4-yl)phenyl)pyrrolidine-2-carboxamide | 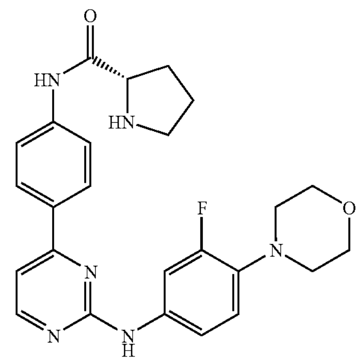 [SMILES: O=C(Nc1ccc(-c2ccnc(Nc3ccc(N4CCOCC4)c(F)c3)n2)cc1)[C@@H]1CCCN1] | 45 |
| 560 | (R)-2-amino-N-(4-(2-(3-fluoro-4-morpholinophenyl-amino)pyrimidin-4-yl)phenyl)propanamide | 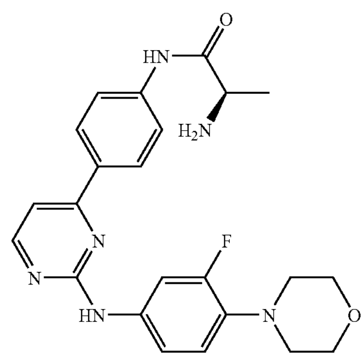 [SMILES: C[C@@H](N)C(=O)Nc1ccc(-c2ccnc(Nc3ccc(N4CCOCC4)c(F)c3)n2)cc1] | 14 |
| 561 | 2-hydroxy-N-(4-(2-(4-morpholinophenylamino)pyrimidin-4-yl)phenyl)acetamide | 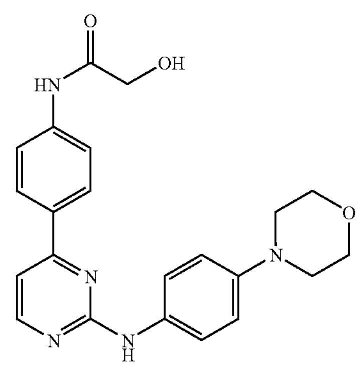 [SMILES: O=C(CO)Nc1ccc(-c2ccnc(Nc3ccc(N4CCOCC4)cc3)n2)cc1] | 18 |
| 562 | (R)-N-(4-(2-(4-(4-(2-hydroxyethyl)piperazin-1-yl)phenylamino)pyrrolidin-4-yl)phenyl)pyrrolidine-2-carboxamide | 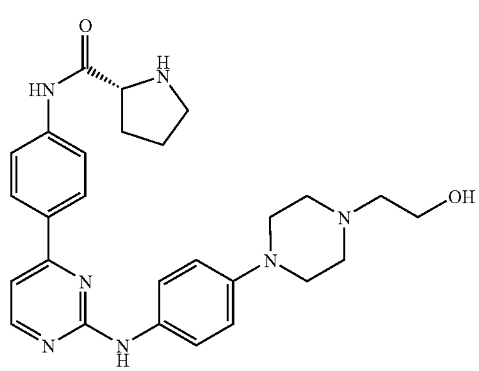 [SMILES: O=C(Nc1ccc(-c2ccnc(Nc3ccc(N4CCN(CCO)CC4)cc3)n2)cc1)[C@H]1CCCN1] | 45 |

TABLE 1-continued

| Cmpd No. | Name | Structure | Can Be Made According To Synthetic Example #: |
|---|---|---|---|
| 563 | (R)-N-(4-(2-(4-(4-((1-methyl-1H-pyrrol-2-yl)methyl)piperazin-1-yl)phenylamino)pyrimidin-4-yl)phenyl)pyrrolidine-2-carboxamide | 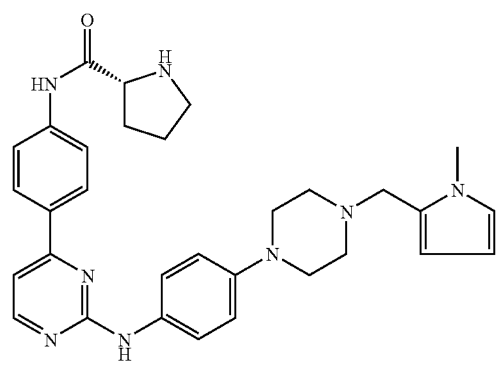 [SMILES: Cn1cccc1CN1CCN(c2ccc(Nc3nccc(-c4ccc(NC(=O)[C@H]5CCCN5)cc4)n3)cc2)CC1] | 45 |
| 564 | (R)-N-(4-(2-(4-(4-((R)-pyrrolidin-2-ylmethyl)piperazin-1-yl)phenylamino)pyrimidin-4-yl)phenyl)pyrrolidine-2-carboxamide | 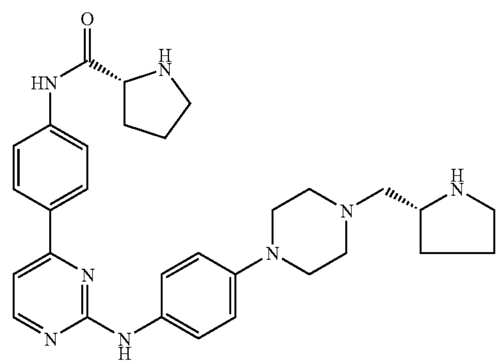 [SMILES: O=C(Nc1ccc(-c2ccnc(Nc3ccc(N4CCN(C[C@H]5CCCN5)CC4)cc3)n2)cc1)[C@H]1CCCN1] | 45 |
| 565 | (2S,3aS,7aS)-N-(4-(2-(4-morpholinophenylamino)pyrimidin-4-yl)phenyl)octahydro-1H-indole-2-carboxamide | 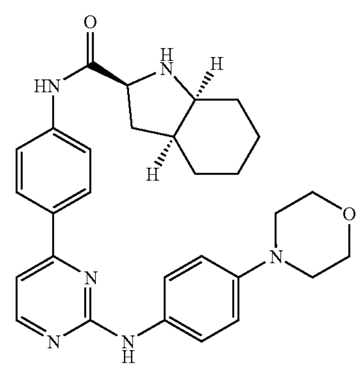 [SMILES: O=C(Nc1ccc(-c2ccnc(Nc3ccc(N4CCOCC4)cc3)n2)cc1)[C@@H]1C[C@@H]2CCCC[C@@H]2N1] | 45 |
| 566 | N-(4-{2-[(4-morpholin-4-ylphenyl)amino]pyrimidin-4-yl}phenyl)cyclopropane-carboxamide | 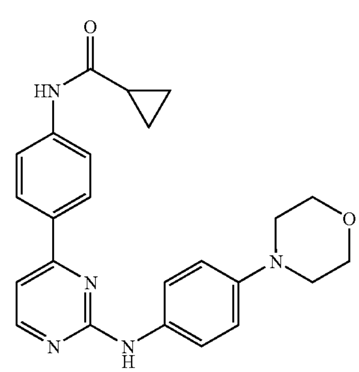 [SMILES: O=C(Nc1ccc(-c2ccnc(Nc3ccc(N4CCOCC4)cc3)n2)cc1)C1CC1] | 12 |

TABLE 1-continued

| Cmpd No. | Name | Structure | Can Be Made According To Synthetic Example #: |
|---|---|---|---|
| 567 | N-(4-{5-methyl-2-[(4-morpholin-4-ylphenyl)amino]pyrimidin-4-yl}phenyl)cyclopropanecarboxamide | 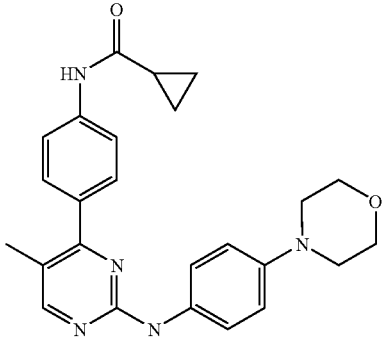 | 12 |
| 568 | N-(4-{2-[(4-morpholin-4-ylphenyl)amino]pyrimidin-4-yl}phenyl)valinamide | 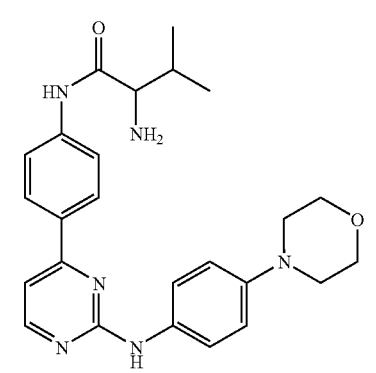 [SMILES: CC(C)C(N)C(=O)Nc1ccc(-c2ccnc(Nc3ccc(N4CCOCC4)cc3)n2)cc1] | 14 |
| 569 | N-(4-{2-[(4-{4-[(1-methyl-1H-imidazol-2-yl)methyl]piperazin-1-yl}phenyl)amino]pyrimidin-4-yl}phenyl)acetamide | 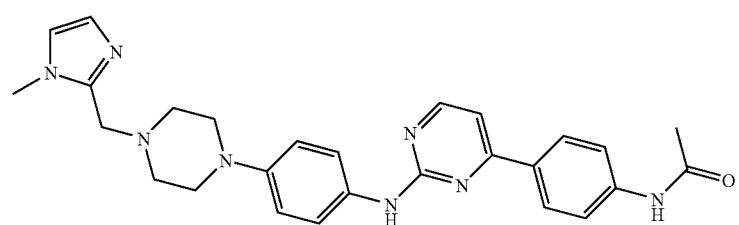 | 49 |
| 570 | N-(4-{2-[(3,5-dimorpholin-4-ylphenyl)amino]-5-methylpyrimidin-4-yl}phenyl)acetamide | 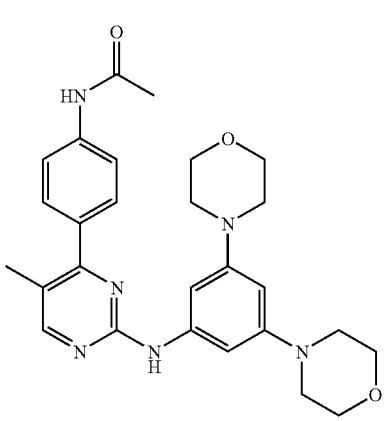 [SMILES: CC(=O)Nc1ccc(-c2nc(Nc3cc(N4CCOCC4)cc(N4CCOCC4)c3)ncc2C)cc1] | 6 |

| Cmpd No. | Name | Structure | Can Be Made According To Synthetic Example #: |
|---|---|---|---|
| 571 | N-(4-{2-[(4-morpholin-4-ylphenyl)amino]pyrimidin-4-yl}phenyl)-D-alaninamide | 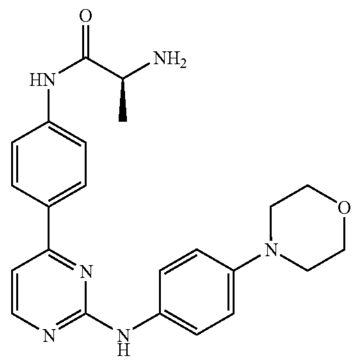 [SMILES: C[C@H](N)C(=O)Nc1ccc(-c2ccnc(Nc3ccc(N4CCOCC4)cc3)n2)cc1] | 14 |
| 572 | N-{4-[2-({4-[4-(2-methylpropanoyl)piperazin-1-yl]phenyl}amino)pyrimidin-4-yl]phenyl}acetamide | 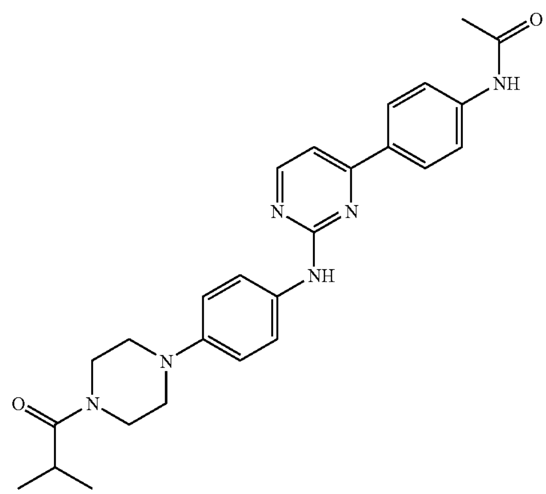 [SMILES: CC(=O)Nc1ccc(-c2ccnc(Nc3ccc(N4CCN(C(=O)C(C)C)CC4)cc3)n2)cc1] | 7 |
| 573 | 2-amino-N-(4-{2-[(4-morpholin-4-ylphenyl)amino}pyrimidin-4-yl}phenyl)-2-phenylacetamide | 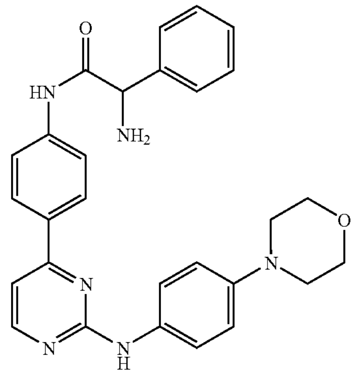 [SMILES: NC(C(=O)Nc1ccc(-c2ccnc(Nc3ccc(N4CCOCC4)cc3)n2)cc1)c1ccccc1] | 4 |

TABLE 1-continued

| Cmpd No. | Name | Structure | Can Be Made According To Synthetic Example #: |
|---|---|---|---|
| 574 | N-(4-{5-methyl-2-[(4-morpholin-4-ylphenyl)amino]pyrimidin-4-yl}phenyl)acetamide | 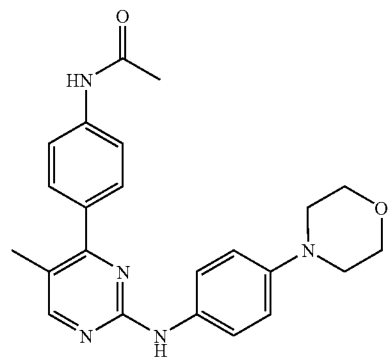 [SMILES: CC(=O)Nc1ccc(-c2nc(Nc3ccc(N4CCOCC4)cc3)ncc2C)cc1] | 5 |
| 575 | 3-(methyloxy)-N-(4-{2-[(4-morpholin-4-ylphenyl)amino]pyrimidin-4-yl}phenyl)propanamide | 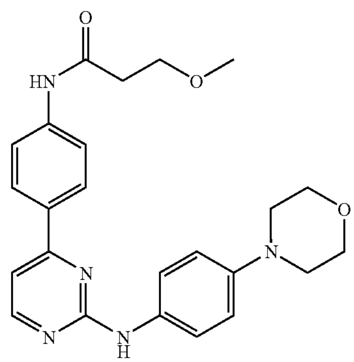 [SMILES: COCCC(=O)Nc1ccc(-c2ccnc(Nc3ccc(N4CCOCC4)cc3)n2)cc1] | 12 |
| 576 | N-(4-{2-[(4-morpholin-4-ylphenyl)amino]pyrimidin-4-yl}phenyl)prolinamide | 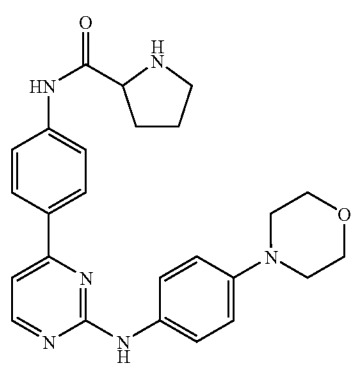 [SMILES: O=C(Nc1ccc(-c2ccnc(Nc3ccc(N4CCOCC4)cc3)n2)cc1)C1CCCN1] | 13 |
| 577 | N-(4-{2-[(4-morpholin-4-ylphenyl)amino]pyrimidin-4-yl}phenyl)-L-alaninamide | 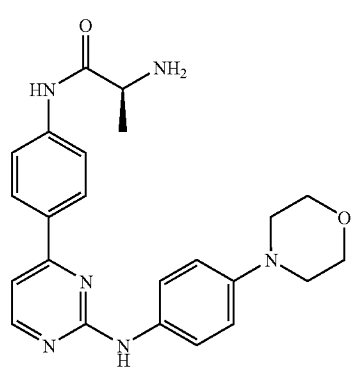 [SMILES: C[C@H](N)C(=O)Nc1ccc(-c2ccnc(Nc3ccc(N4CCOCC4)cc3)n2)cc1] | 14 |

TABLE 1-continued

| Cmpd No. | Name | Structure | Can Be Made According To Synthetic Example #: |
|---|---|---|---|
| 578 | N-(4-{2-[(4-{4-[3-(dimethylamino)-2,2-dimethylpropyl]piperazin-1-yl}phenyl)amino]pyrimidin-4-yl}phenyl)acetamide | 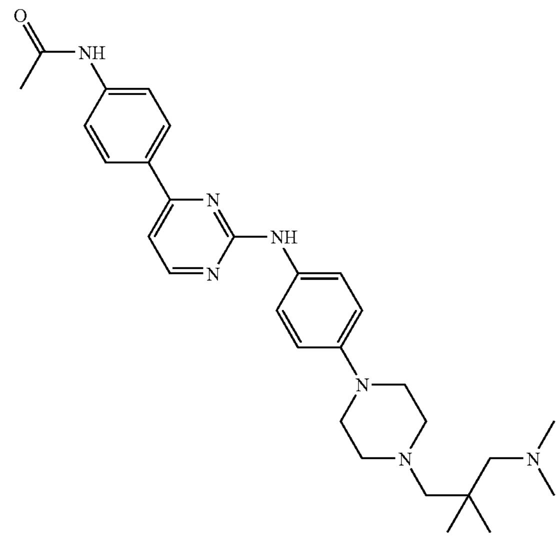 [SMILES: CC(=O)Nc1ccc(-c2ccnc(Nc3ccc(N4CCN(CC(C)(C)CN(C)C)CC4)cc3)n2)cc1] | 49 |
| 579 | N-(4-{2-[(4-{4-[3-(methyloxy)propanoyl]piperazin-1-yl}phenyl)amino]pyrimidin-4-yl}phenyl)acetamide | 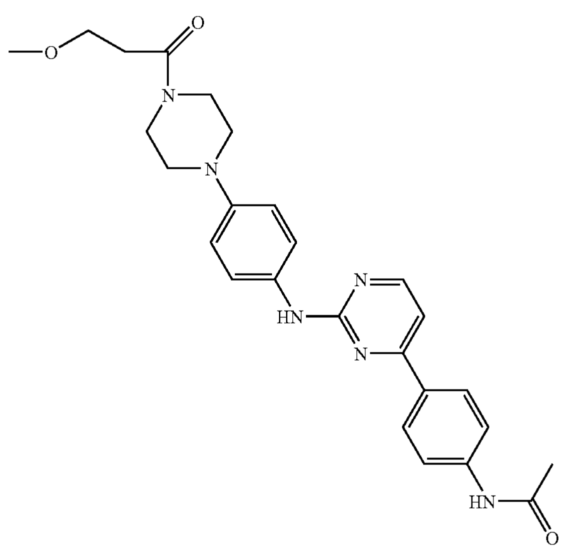 [SMILES: COCCC(=O)N1CCN(c2ccc(Nc3nccc(-c4ccc(NC(C)=O)cc4)n3)cc2)CC1] | 7 |
| 580 | N-(4-{2-[(4-morpholin-4-ylphenyl)amino]pyrimidin-4-yl}phenyl)-1,3-thiazole-4-carboxamide | 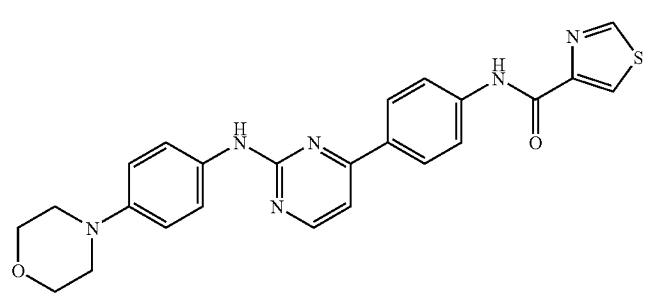 [SMILES: O=C(Nc1ccc(-c2ccnc(Nc3ccc(N4CCOCC4)cc3)n2)cc1)c1cscn1] | 12 |

TABLE 1-continued
| Cmpd No. | Name | Structure | Can Be Made According To Synthetic Example #: |
|---|---|---|---|
| 581 | 2,6-dichloro-N-(3-{[4-(2,3-dihydro-1,4-benzodioxin-6-yl}pyrimidin-2-yl]amino}propyl)benzamide | 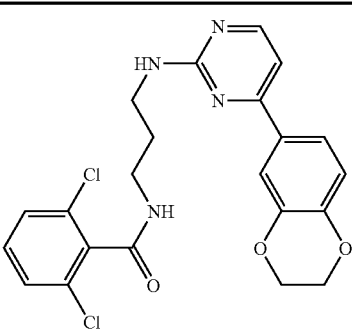 | 27 |
(Part B)
| 582 | N-(4-{2-[(2-methyl-4-morpholin-4-ylphenyl)amino]pyrimidin-4-yl}phenyl)acetamide | 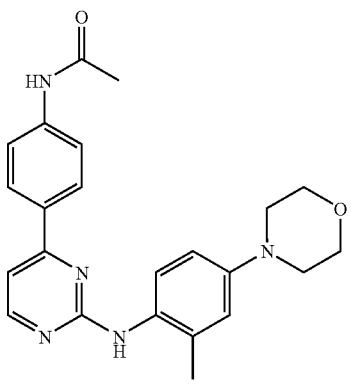 [SMILES: CC(=O)Nc1ccc(-c2ccnc(Nc3ccc(N4CCOCC4)cc3C)n2)cc1] | 3 |
| 583 | N-(4-{2-[(4-pyrrolidin-1-ylphenyl)amino]pyrimidin-4-yl}phenyl)acetamide | 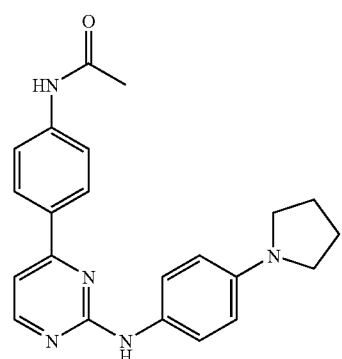 | 3 |
| 584 | N-[4-(2-{(4-(diethylamino)phenyl]amino}pyrimidin-4-yl)phenyl]acetamide | 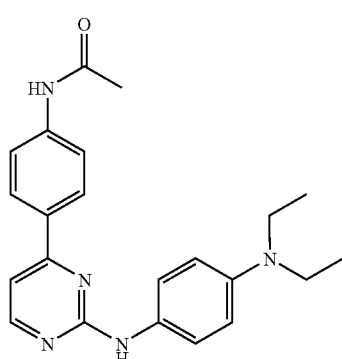 | 3 |

TABLE 1-continued

| Cmpd No. | Name | Structure | Can Be Made According To Synthetic Example #: |
|---|---|---|---|
| 585 | N-(4-{2-[(4-azepan-1-ylphenyl)amino]pyrimidin-4-yl}phenyl)acetamide | 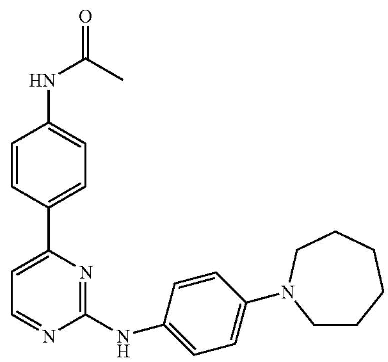 [SMILES: CC(=O)Nc1ccc(-c2ccnc(Nc3ccc(N4CCCCCC4)cc3)n2)cc1] | 3 |
| 586 | N-{4-[2-({4-[methyl(2-phenylethyl)amino]phenyl}amino)pyrimidin-4-yl]phenyl]acetamide | 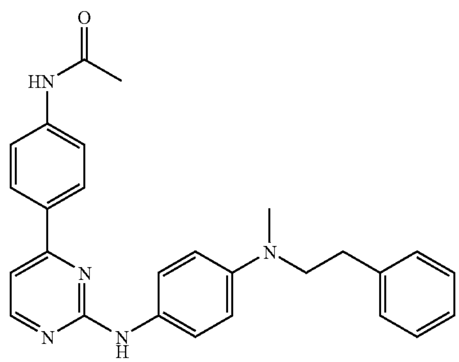 [SMILES: CC(=O)Nc1ccc(-c2ccnc(Nc3ccc(N(C)CCc4ccccc4)cc3)n2)cc1] | 3 |
| 587 | N-[4-(2-{[4-(1,4-dioxa-8-azaspiro[4.5]dec-8-yl)phenyl]amino}pyrimidin-4-yl)phenyl]acetamide | 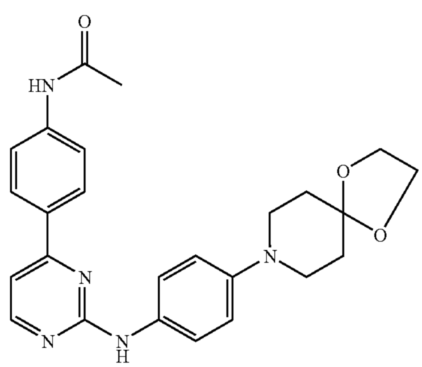 [SMILES: CC(=O)Nc1ccc(-c2ccnc(Nc3ccc(N4CCC5(CC4)OCCO5)cc3)n2)cc1] | 3 |
| 588 | N-[4-(2-{[4-(2-oxo-piperidin-1-yl)phenyl]amino}pyrimidin-4-yl)phenyl]acetamide | 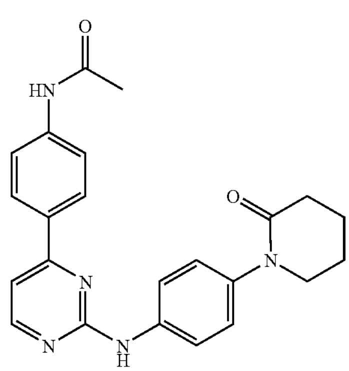 [SMILES: CC(=O)Nc1ccc(-c2ccnc(Nc3ccc(N4CCCCC4=O)cc3)n2)cc1] | 3 |

TABLE 1-continued

| Cmpd No. | Name | Structure | Can Be Made According To Synthetic Example #: |
|---|---|---|---|
| 589 | N-[4-(2-{[4-(2-methyl-piperidin-1-yl)phenyl]amino}pyrimidin-4-yl)phenyl]acetamide | 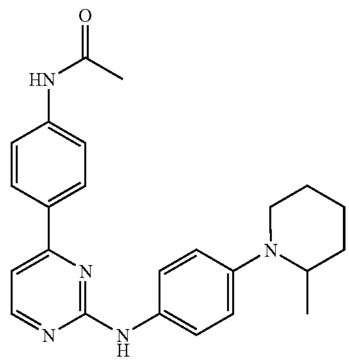 [SMILES: CC(=O)Nc1ccc(-c2ccnc(Nc3ccc(N4CCCCC4C)cc3)n2)cc1] | 3 |
| 590 | N-(4-{2-[(4-morpholin-4-ylphenyl)amino]pyrimidin-4-yl}phenyl)-L-valinamide | Chiral | 45 |
| 591 | N-(4-{2-[(4-morpholin-4-ylphenyl)amino]pyrimidin-4-yl}phenyl)-D-valinamide | Chiral | 45 |
| 592 | 2-methyl-N-(4-{2-[(4-morpholin-4-ylphenyl)amino]pyrimidin-4-yl}phenyl)alaninamide | 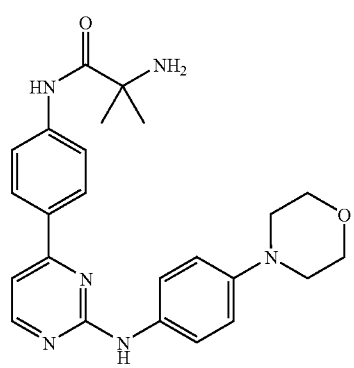 [SMILES: CC(C)(N)C(=O)Nc1ccc(-c2ccnc(Nc3ccc(N4CCOCC4)cc3)n2)cc1] | 14 |

TABLE 1-continued

| Cmpd No. | Name | Structure | Can Be Made According To Synthetic Example #: |
|---|---|---|---|
| 593 | N-(4-{2-[(4-morpholin-4-ylphenyl)amino]pyrimidin-4-yl}phenyl)tryptophanamide | 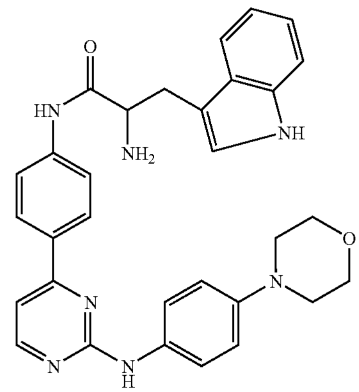 [SMILES: NC(Cc1c[nH]c2ccccc12)C(=O)Nc1ccc(-c2ccnc(Nc3ccc(N4CCOCC4)cc3)n2)cc1] | 14 |
| 594 | N-(4-{2-[(4-morpholin-4-ylphenyl)amino]pyrimidin-4-yl}phenyl)-1,2,3,4-tetrahydroisoquinoline-1-carboxamide | 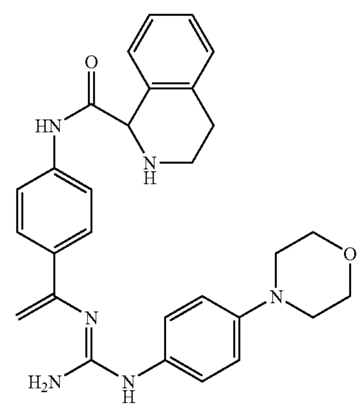 [SMILES: C=C(/N=C(\N)Nc1ccc(N2CCOCC2)cc1)c1ccc(NC(=O)C2NCCc3ccccc32)cc1] | 14 |
| 595 | O-(1,1-dimethylethyl)-N-(4-{2-[(4-morpholin-4-ylphenyl)amino]pyrimidin-4-yl}phenyl)-L-serinamide | Chiral | 45 |

TABLE 1-continued

| Cmpd No. | Name | Structure | Can Be Made According To Synthetic Example #: |
|---|---|---|---|
| 596 | 3-amino-N-(4-{2-[(4-morpholin-4-ylphenyl)amino]pyrimidin-4-yl}phenyl)tetrahydrofuran-3-carboxamide | 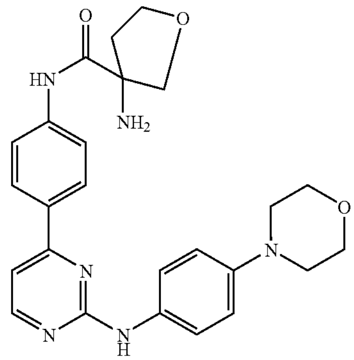 [SMILES: NC1(C(=O)Nc2ccc(-c3ccnc(Nc4ccc(N5CCOCC5)cc4)n3)cc2)CCOC1] | 14 |
| 597 | bis(1,1-dimethylethyl)(2R)-2-{[(4-{2-[(4-morpholin-4-ylphenyl)amino]pyrimidin-4-yl}phenyl)amino]carbonyl}piperazine-1,4-dicarboxylate | 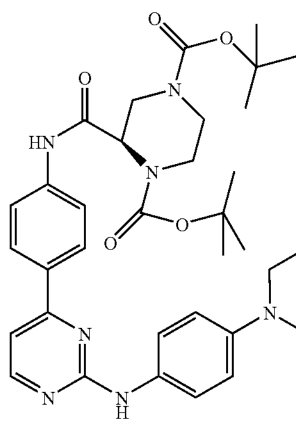 | 14 |
| 598 | N-(4-{2-[(4-{4-[2-(2-fluorophenyl)acetyl]piperazin-1-yl}phenyl)amino]pyrimidin-4-yl}phenyl)acetamide | 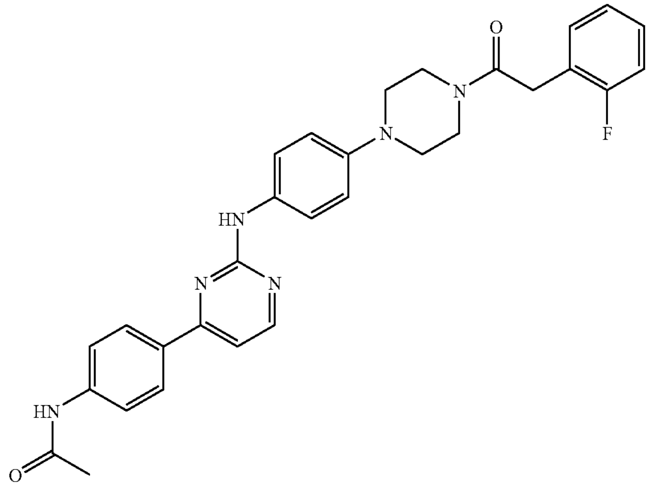 [SMILES: CC(=O)Nc1ccc(-c2ccnc(Nc3ccc(N4CCN(C(=O)Cc5ccccc5F)CC4)cc3)n2)cc1] | 7 |

TABLE 1-continued

| Cmpd No. | Name | Structure | Can Be Made According To Synthetic Example #: |
|---|---|---|---|
| 599 | N-(4-{2-[(4-{4-[2-(2-methyl-phenyl)acetyl]piperazin-1-yl}phenyl)amino]pyrimidin-4-yl}phenyl)acetamide | 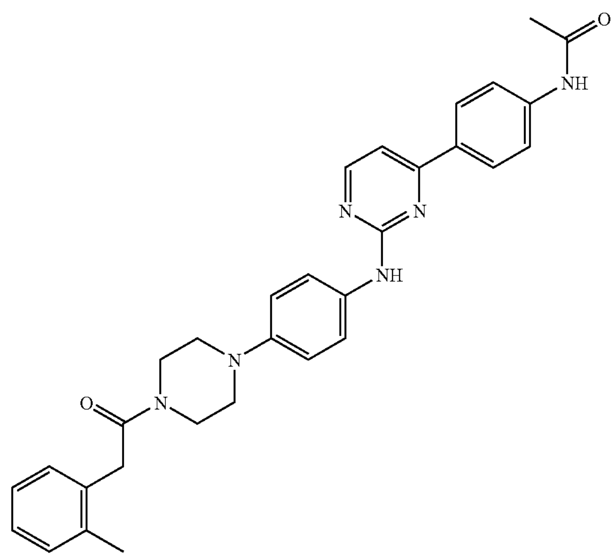 [SMILES: CC(=O)Nc1ccc(-c2ccnc(Nc3ccc(N4CCN(C(=O)Cc5ccccc5C)CC4)cc3)n2)cc1] | 7 |
| 600 | N-(4-{2-[(4-{4-[2-(3-fluoro-phenyl)acetyl]piperazin-1-yl}phenyl)amino]pyrimidin-4-yl}phenyl)acetamide | 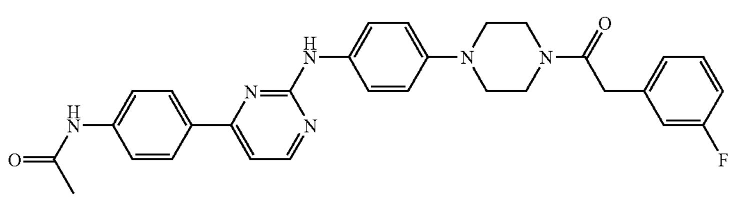 [SMILES: CC(=O)Nc1ccc(-c2ccnc(Nc3ccc(N4CCN(C(=O)Cc5cccc(F)c5)CC4)cc3)n2)cc1] | 7 |
| 601 | N-{4-[2-({4-[4-(3-thienyl-carbonyl)piperazin-1-yl]phenyl}amino)pyrimidin-4-yl]phenyl}acetamide | 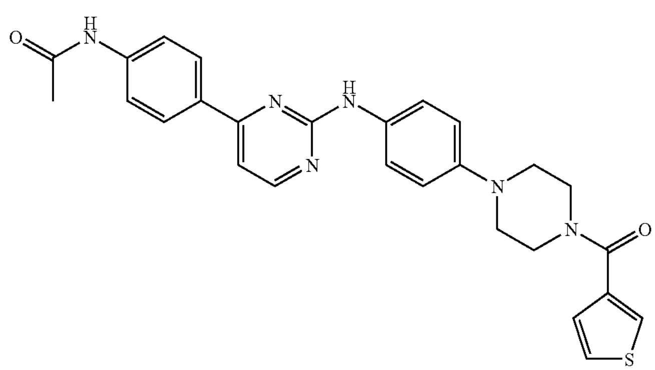 [SMILES: CC(=O)Nc1ccc(-c2ccnc(Nc3ccc(N4CCN(C(=O)c5ccsc5)CC4)cc3)n2)cc1] | 7 |
| 602 | N-(4-{2-[(4-{4-[(6-chloro-pyridin-3-yl)carbonyl]piperazin-1-yl}phenyl)amino]pyrimidin-4-yl}phenyl)acetamide | 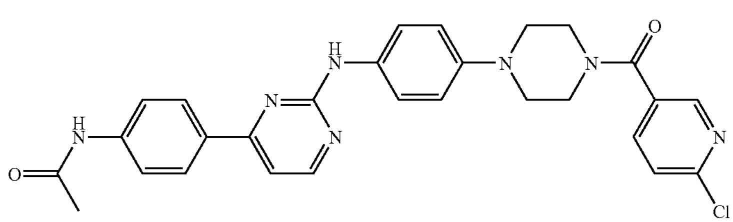 [SMILES: CC(=O)Nc1ccc(-c2ccnc(Nc3ccc(N4CCN(C(=O)c5ccc(Cl)nc5)CC4)cc3)n2)cc1] | 7 |

TABLE 1-continued

| Cmpd No. | Name | Structure | Can Be Made According To Synthetic Example #: |
|---|---|---|---|
| 603 | N-(4-{2-[(4-{4-[(3-methyl-furan-2-yl)carbonyl]piperazin-1-yl}phenyl)amino]pyrimidin-4-yl}phenyl)acetamide | 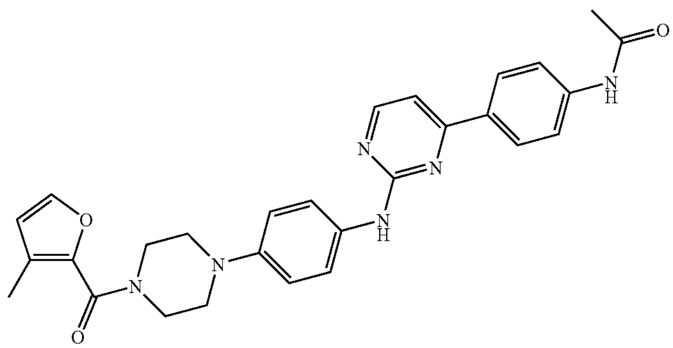 [SMILES: CC(=O)Nc1ccc(-c2ccnc(Nc3ccc(N4CCN(C(=O)c5occc5C)CC4)cc3)n2)cc1] | 7 |
| 604 | N-(4-(2-(4-(4-(3-fluoro-2-methylbenzoyl)piperazin-1-yl)phenylamino)pyrimidin-4-yl)phenyl)acetamide | 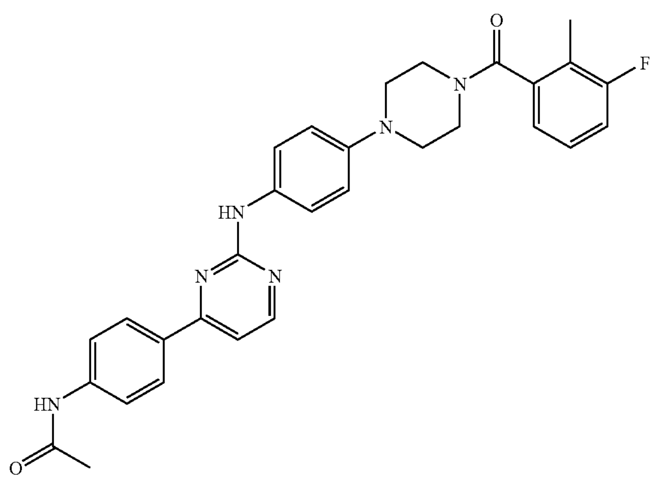 [SMILES: CC(=O)Nc1ccc(-c2ccnc(Nc3ccc(N4CCN(C(=O)c5cccc(F)c5C)CC4)cc3)n2)cc1] | 7 |
| 605 | N-(4-(2-(4-(4-(1H-imidazole-4-carbonyl)piperazin-1-yl)phenylamino)pyrimidin-4-yl)phenyl)acetamide | 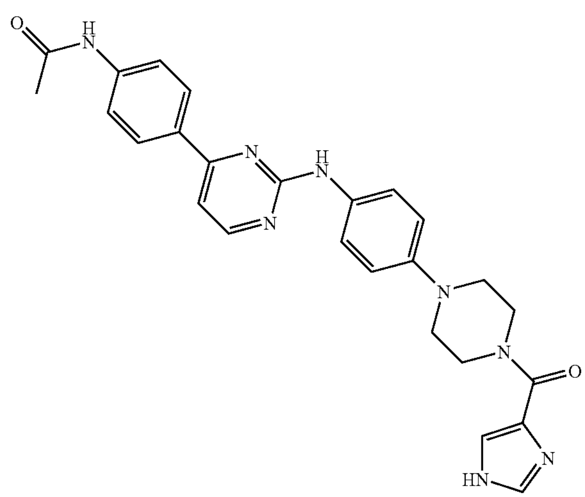 [SMILES: CC(=O)Nc1ccc(-c2ccnc(Nc3ccc(N4CCN(C(=O)c5c[nH]cn5)CC4)cc3)n2)cc1] | 7 |

TABLE 1-continued

| Cmpd No. | Name | Structure | Can Be Made According To Synthetic Example #: |
|---|---|---|---|
| 606 | N-(4-(2-(4-(4-(2-methoxy-nicotinoyl)piperazin-1-yl)phenylamino)pyrimidin-4-yl)phenyl)acetamide | 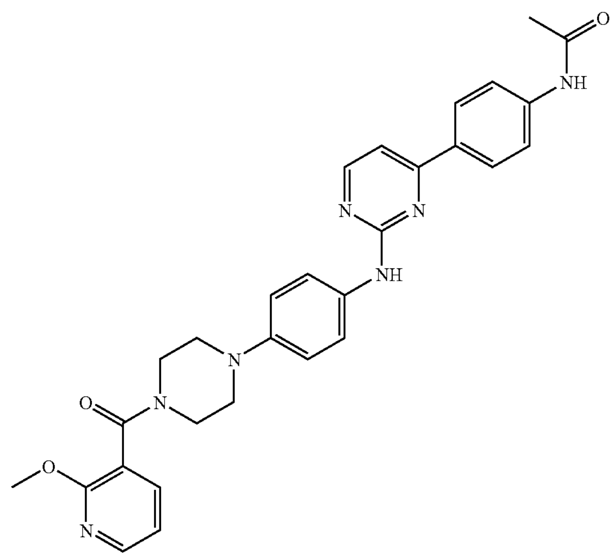 [SMILES: COc1ncccc1C(=O)N1CCN(c2ccc(Nc3nccc(-c4ccc(NC(C)=O)cc4)n3)cc2)CC1] | 7 |
| 607 | N-(4-(2-(4-(4-(4-fluoro-3-methylbenzoyl)piperazin-1-yl)phenylamino)pyrimidin-4-yl)phenyl)acetamide | 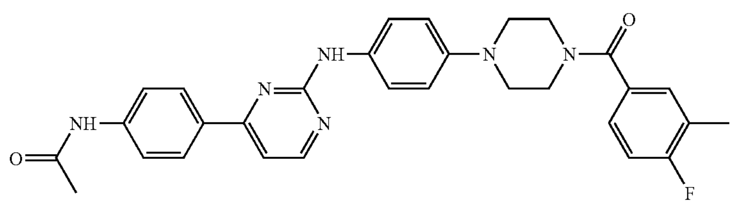 [SMILES: CC(=O)Nc1ccc(-c2ccnc(Nc3ccc(N4CCN(C(=O)c5ccc(F)c(C)c5)CC4)cc3)n2)cc1] | 7 |
| 608 | N-{4-[2-({4-[4-(naphthalen-2-ylsulfonyl)piperazin-1-yl]phenyl}amino)pyrimidin-4-yl]phenyl}acetamide | 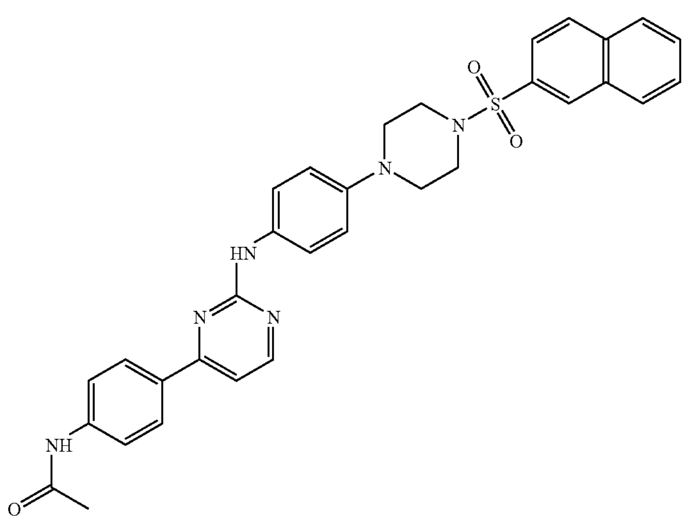 [SMILES: CC(=O)Nc1ccc(-c2ccnc(Nc3ccc(N4CCN(S(=O)(=O)c5ccc6ccccc6c5)CC4)cc3)n2)cc1] | 36 |

TABLE 1-continued
| Cmpd No. | Name | Structure | Can Be Made According To Synthetic Example #: |
|---|---|---|---|
| 609 | N-{4-[2-({4-[4-(quinolin-8-ylsulfonyl)piperazin-1-yl]phenyl}amino)pyrimidin-4-yl]phenyl}acetamide | 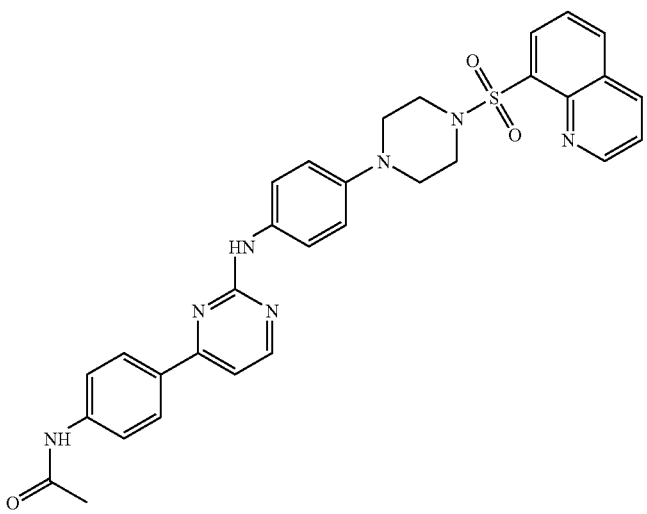 [SMILES: CC(=O)Nc1ccc(-c2ccnc(Nc3ccc(N4CCN(S(=O)(=O)c5cccc6cccnc56)CC4)cc3)n2)cc1] | 36 |
| 610 | N-[4-(2-{[4-(4-{[4-(1,1-dimethylethyl)phenyl]sulfonyl}piperazin-1-yl)phenyl]amino}pyrimidin-4-yl)phenyl]acetamide | 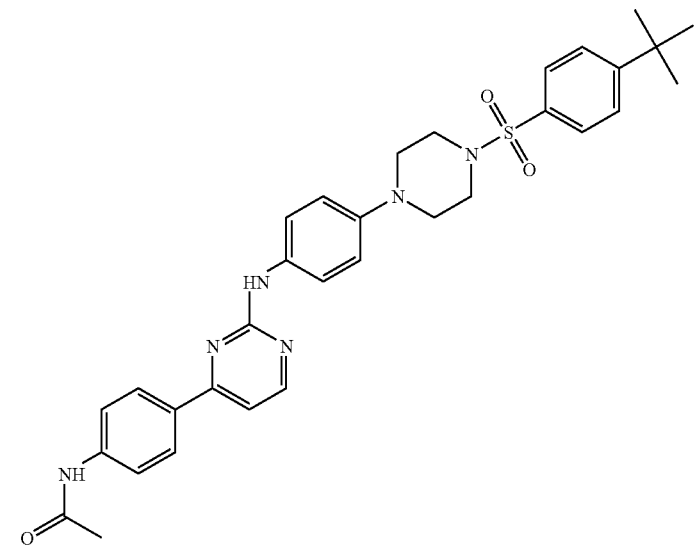 [SMILES: CC(=O)Nc1ccc(-c2ccnc(Nc3ccc(N4CCN(S(=O)(=O)c5ccc(C(C)(C)C)cc5)CC4)cc3)n2)cc1] | 36 |
| 611 | N-[4-(2-{[4-(4-{[5-bromo-2-(methyloxy)phenyl]sulfonyl}piperazin-1-yl)phenyl]amino}pyrimidin-4-yl)phenyl]acetamide | 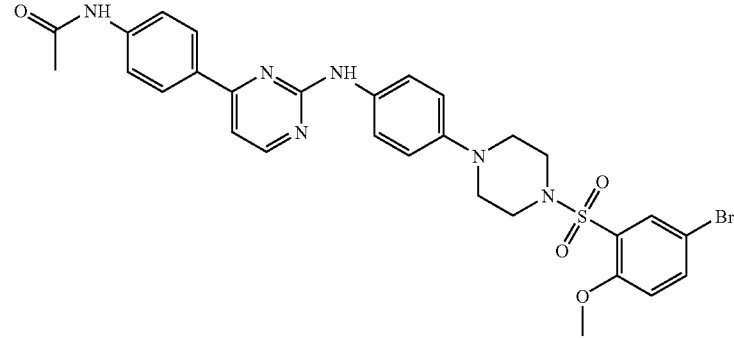 [SMILES: COc1ccc(Br)cc1S(=O)(=O)N1CCN(c2ccc(Nc3nccc(-c4ccc(NC(C)=O)cc4)n3)cc2)CC1] | 36 |

TABLE 1-continued

| Cmpd No. | Name | Structure | Can Be Made According To Synthetic Example #: |
|---|---|---|---|
| 612 | N-(4-{2-[(4-{4-[(phenyl-methyl)sulfonyl]piperazin-1-yl}phenyl)amino]pyrimidin-4-yl}phenyl)acetamide | 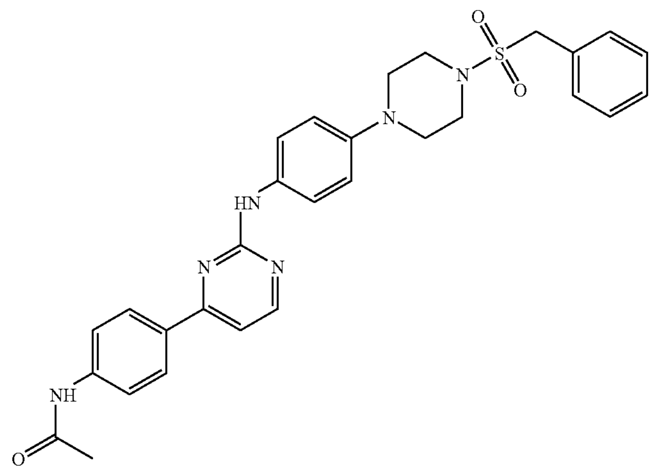 [SMILES: CC(=O)Nc1ccc(-c2ccnc(Nc3ccc(N4CCN(S(=O)(=O)Cc5ccccc5)CC4)cc3)n2)cc1] | 36 |
| 613 | N-[4-(2-{[4-(4-{[3-(tri-fluoromethyl)phenyl]sulfonyl}piperazin-1-yl)phenyl]amino}pyrimidin-4-yl)phenyl]acetamide | 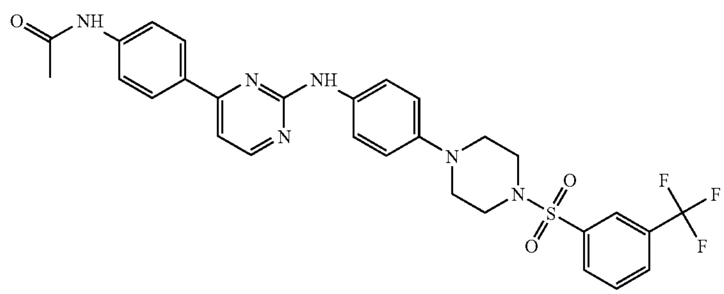 [SMILES: CC(=O)Nc1ccc(-c2ccnc(Nc3ccc(N4CCN(S(=O)(=O)c5cccc(C(F)(F)F)c5)CC4)cc3)n2)cc1] | 36 |
| 614 | N-(4-{2-[(4-{4-[(2-methyl-phenyl)sulfonyl]piperazin-1-yl}phenyl)amino}pyrimidin-4-yl)phenyl)acetamide | 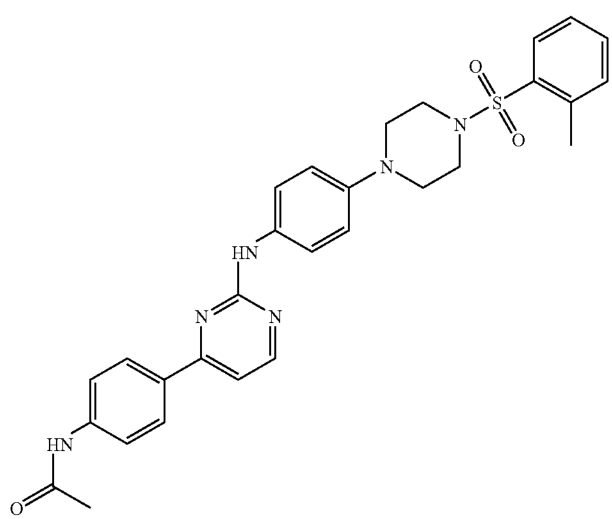 [SMILES: CC(=O)Nc1ccc(-c2ccnc(Nc3ccc(N4CCN(S(=O)(=O)c5ccccc5C)CC4)cc3)n2)cc1] | 36 |

TABLE 1-continued

| Cmpd No. | Name | Structure | Can Be Made According To Synthetic Example #: |
|---|---|---|---|
| 615 | N-(4-{2-[(4-{4-[(3-fluoro-phenyl)sulfonyl]piperazin-1-yl}phenyl)amino]pyrimidin-4-yl}phenyl)acetamide | 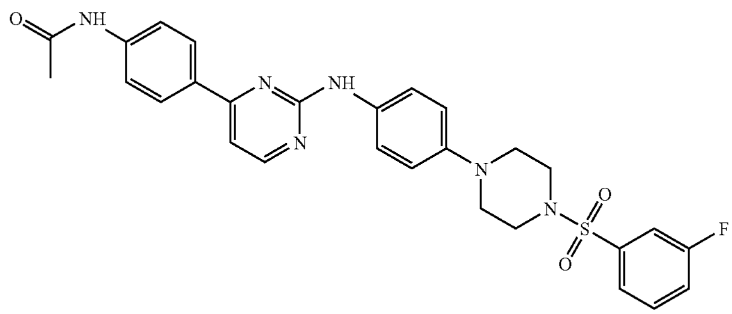 [SMILES: CC(=O)Nc1ccc(-c2ccnc(Nc3ccc(N4CCN(S(=O)(=O)c5cccc(F)c5)CC4)cc3)n2)cc1] | 36 |
| 616 | N-(4-{2-[(4-(4-[(2,4-difluorophenyl)sulfonyl]piperazin-1-yl}phenyl)amino]pyrimidin-4-yl}phenyl)acetamide | 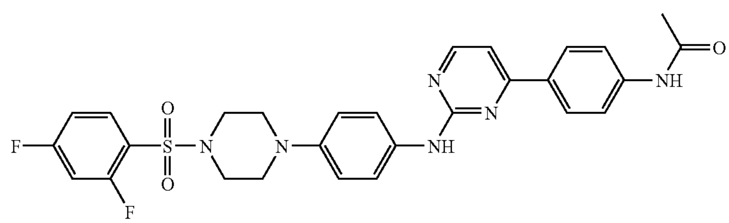 [SMILES: CC(=O)Nc1ccc(-c2ccnc(Nc3ccc(N4CCN(S(=O)(=O)c5ccc(F)cc5F)CC4)cc3)n2)cc1] | 36 |
| 617 | N-{4-[2-({3-[4-({4-[(tri-fluoromethyl)oxy]phenyl}methyl)piperazin-1-yl]phenyl}amino)pyrimidin-4-yl]phenyl}acetamide | 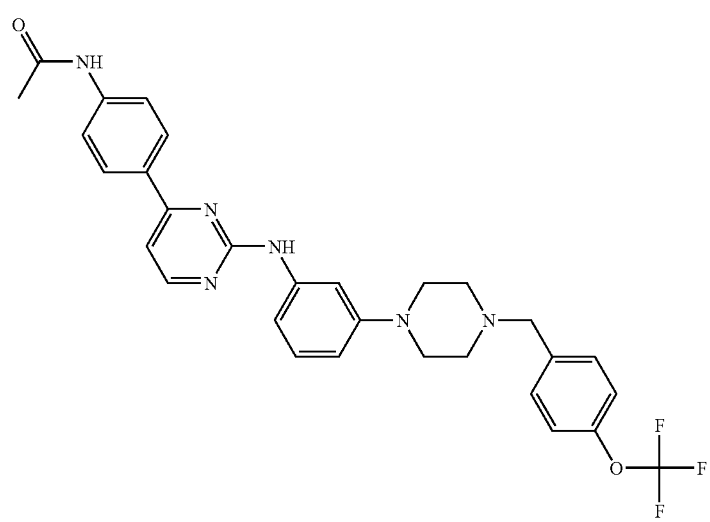 [SMILES: CC(=O)Nc1ccc(-c2ccnc(Nc3cccc(N4CCN(Cc5ccc(OC(F)(F)F)cc5)CC4)c3)n2)cc1] | 49 |

TABLE 1-continued

| Cmpd No. | Name | Structure | Can Be Made According To Synthetic Example #: |
|---|---|---|---|
| 618 | N-(4-{2-[(3-{4-[(1-methyl-1H-imidazol-2-yl)methyl]piperazin-1-yl}phenyl)amino]pyrimidin-4-yl}phenyl)acetamide | 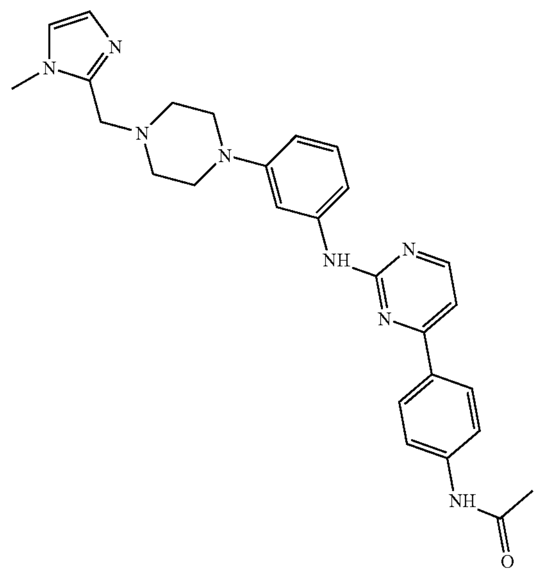 [SMILES: CC(=O)Nc1ccc(-c2ccnc(Nc3cccc(N4CCN(Cc5nccn5C)CC4)c3)n2)cc1] | 49 |
| 619 | N-{4-[2-({3-[4-({2-[(trifluoromethyl)oxy]phenyl}methyl)piperazin-1-yl]phenyl}amino)pyrimidin-4-yl]phenyl}acetamide | 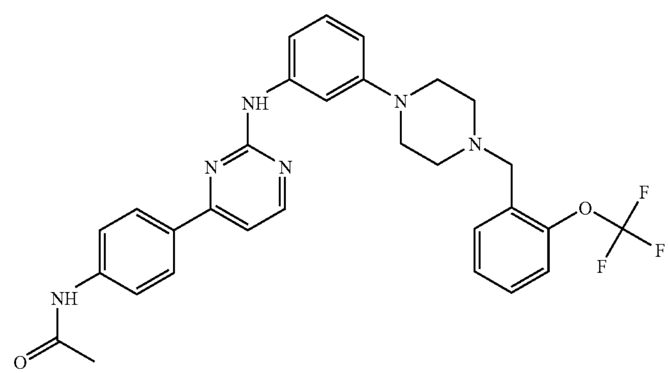 [SMILES: CC(=O)Nc1ccc(-c2ccnc(Nc3cccc(N4CCN(Cc5ccccc5OC(F)(F)F)CC4)c3)n2)cc1] | 49 |
| 620 | N-(4-{2-[(3-{4-[(3-chlorophenyl)methyl]piperazin-1-yl}phenyl)amino]pyrimidin-4-yl}phenyl)acetamide | 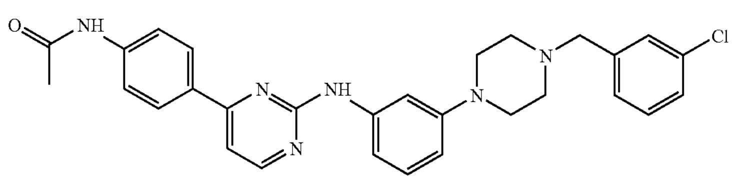 [SMILES: CC(=O)Nc1ccc(-c2ccnc(Nc3cccc(N4CCN(Cc5cccc(Cl)c5)CC4)c3)n2)cc1] | 49 |
| 621 | N-{4-[2-({3-[4-(2,3-dihydroxypropyl)piperazin-1-yl]phenyl}amino)pyrimidin-4-yl]phenyl}acetamide | 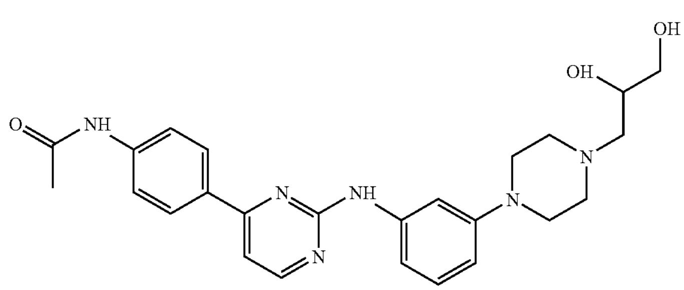 [SMILES: CC(=O)Nc1ccc(-c2ccnc(Nc3cccc(N4CCN(CC(O)CO)CC4)c3)n2)cc1] | 49 |

TABLE 1-continued

| Cmpd No. | Name | Structure | Can Be Made According To Synthetic Example #: |
|---|---|---|---|
| 622 | N-{4-[2-({3-[4-(1,3-benzodioxol-5-ylmethyl)piperazin-1-yl]phenyl}amino)pyrimidin-4-yl]phenyl}acetamide | 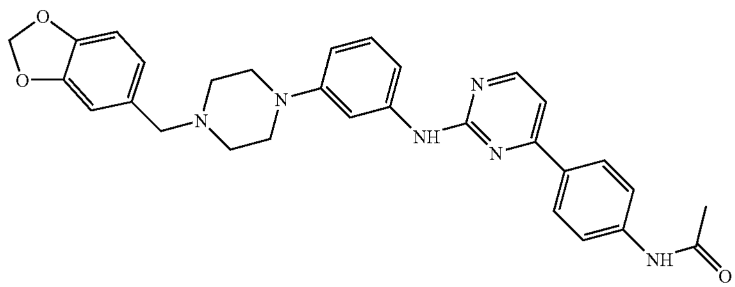 [SMILES: CC(=O)Nc1ccc(-c2ccnc(Nc3cccc(N4CCN(Cc5ccc6c(c5)OCO6)CC4)c3)n2)cc1] | 49 |
| 623 | N-{4-[2-({3-[4-(pyridin-2-ylmethyl)piperazin-1-yl]phenyl}amino)pyrimidin-4-yl]phenyl}acetamide | 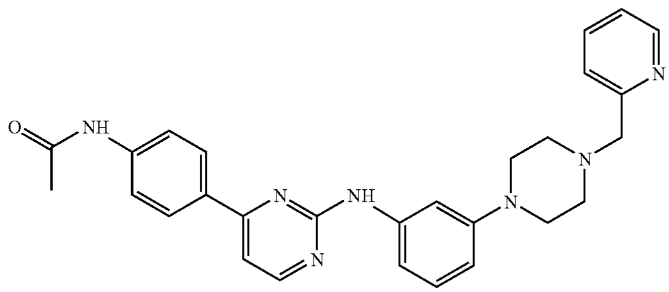 [SMILES: CC(=O)Nc1ccc(-c2ccnc(Nc3cccc(N4CCN(Cc5ccccn5)CC4)c3)n2)cc1] | 49 |
| 624 | N-{4-[2-({3-[4-(pyridin-3-ylmethyl)piperazin-1-yl]phenyl}amino)pyrimidin-4-yl]phenyl}acetamide | 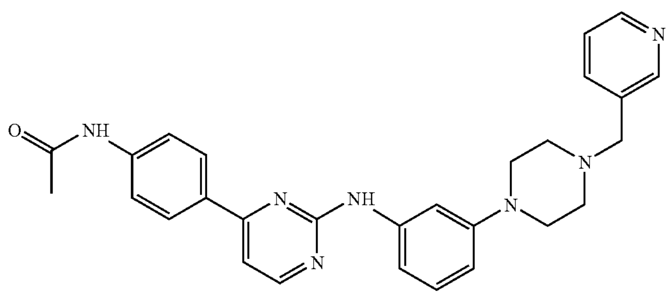 [SMILES: CC(=O)Nc1ccc(-c2ccnc(Nc3cccc(N4CCN(Cc5cccnc5)CC4)c3)n2)cc1] | 49 |
| 625 | N-{4-[2-({3-[4-(1H-pyrrol-2-ylmethyl)piperazin-1-yl]phenyl}amino)pyrimidin-4-yl]phenyl}acetamide | 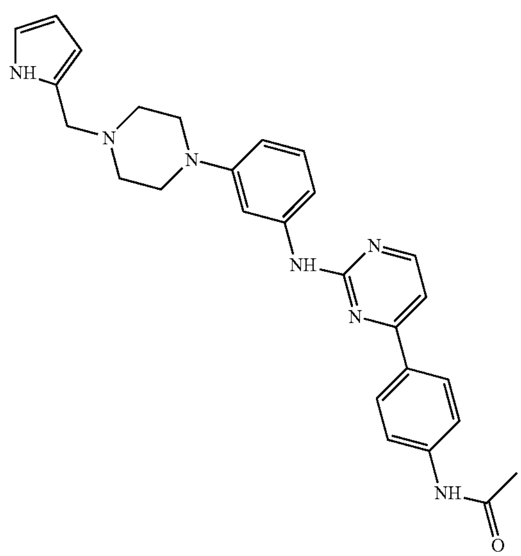 [SMILES: CC(=O)Nc1ccc(-c2ccnc(Nc3cccc(N4CCN(Cc5ccc[nH]5)CC4)c3)n2)cc1] | 49 |

| Cmpd No. | Name | Structure | Can Be Made According To Synthetic Example #: |
|---|---|---|---|
| 626 | 4-[4-({4-[4-(acetylamino) phenyl]pyrimidin-2-yl}amino) phenyl]-N-(phenylmethyl) piperazine-1-carboxamide | 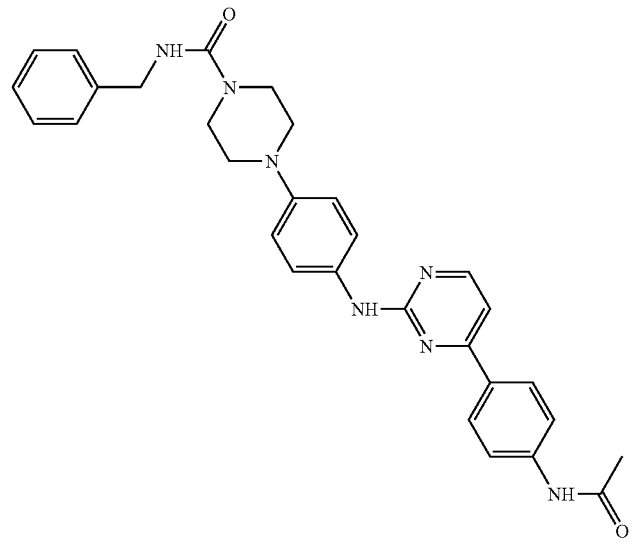 [SMILES: CC(=O)Nc1ccc(-c2ccnc(Nc3ccc(N4CCN(C(=O)NCc5ccccc5)CC4)cc3)n2)cc1] | 53 |
| 627 | N-[4-(2-{[3-(4-{[2-(methyloxy)phenyl]carbonyl} piperazin-1-yl)phenyl]amino} pyrimidin-4-yl)phenyl] acetamide | 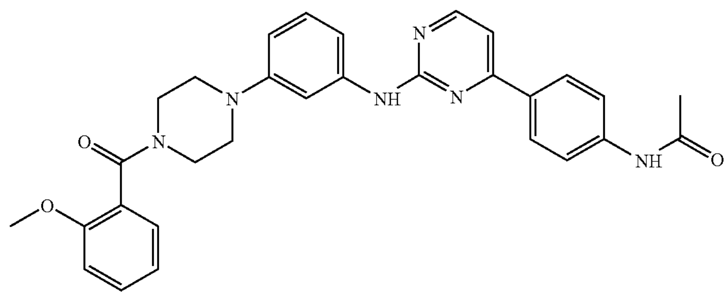 [SMILES: COc1ccccc1C(=O)N1CCN(c2cccc(Nc3nccc(-c4ccc(NC(C)=O)cc4)n3)c2)CC1] | 7 |
| 628 | N-{4-[2-({3-[4-(1H-pyrazol-4-ylcarbonyl)piperazin-1-yl] phenyl}amino)pyrimidin-4-yl]phenyl}acetamide | 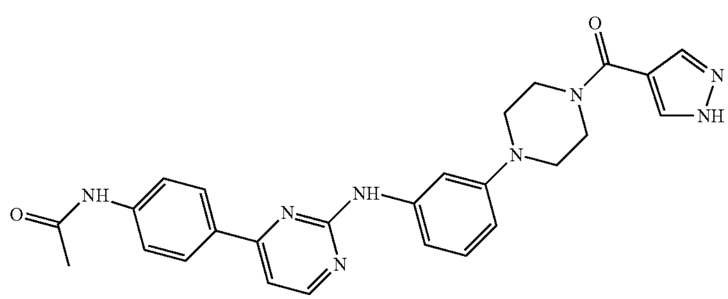 [SMILES: CC(=O)Nc1ccc(-c2ccnc(Nc3cccc(N4CCN(C(=O)c5cn[nH]c5)CC4)c3)n2)cc1] | 7 |
| 629 | N-{4-[2-({3-[4-(3-pyridin-3-ylpropanoyl)piperazin-1-yl] phenyl}amino)pyrimidin-4-yl]phenyl}acetamide | 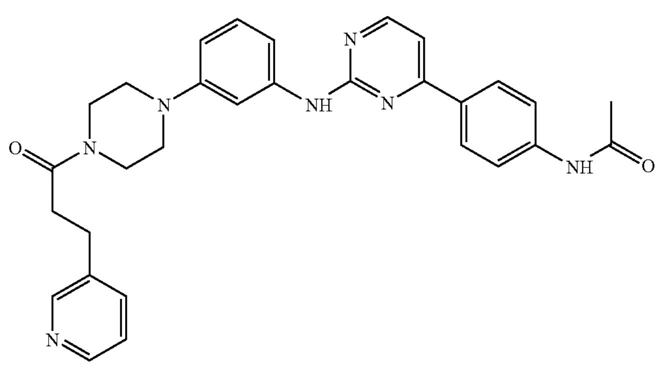 [SMILES: CC(=O)Nc1ccc(-c2ccnc(Nc3cccc(N4CCN(C(=O)CCc5cccnc5)CC4)c3)n2)cc1] | 7 |

TABLE 1-continued

| Cmpd No. | Name | Structure | Can Be Made According To Synthetic Example #: |
|---|---|---|---|
| 630 | N-(4-{2-[(3-{4-[3-(methyloxy)propanoyl]piperazin-1-yl}phenyl)amino]pyrimidin-4-yl}phenyl)acetamide | 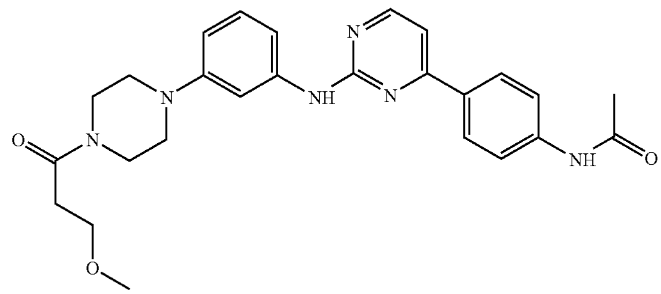 [SMILES: COCCC(=O)N1CCN(c2cccc(Nc3nccc(-c4ccc(NC(C)=O)cc4)n3)c2)CC1] | 7 |
| 631 | N-[4-(2-{[3-(4-{2-[(4-fluorophenyl)oxy]acetyl}piperazin-1-yl)phenyl]amino}pyrimidin-4-yl)phenyl]acetamide | 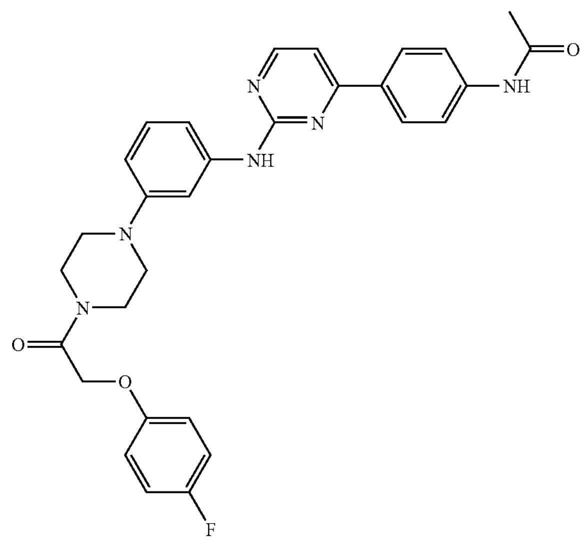 [SMILES: CC(=O)Nc1ccc(-c2ccnc(Nc3cccc(N4CCN(C(=O)COc5ccc(F)cc5)CC4)c3)n2)cc1] | 7 |
| 632 | N-{4-[2-({3-[4-(cyclobutylcarbonyl)piperazin-1-yl]phenyl}amino)pyrimidin-4-yl]phenyl}acetamide | 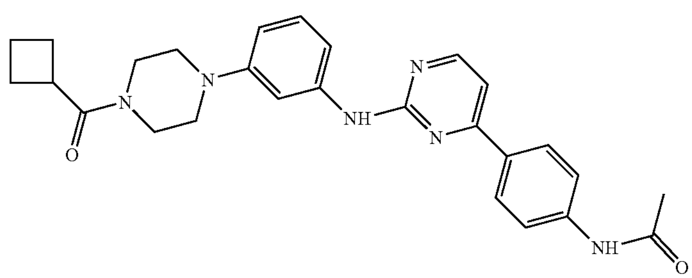 [SMILES: CC(=O)Nc1ccc(-c2ccnc(Nc3cccc(N4CCN(C(=O)C5CCC5)CC4)c3)n2)cc1] | 7 |
| 633 | N-{4-[2-({3-[4-(pyridin-4-ylcarbonyl)piperazin-1-yl]phenyl}amino)pyrimidin-4-yl]phenyl}acetamide | 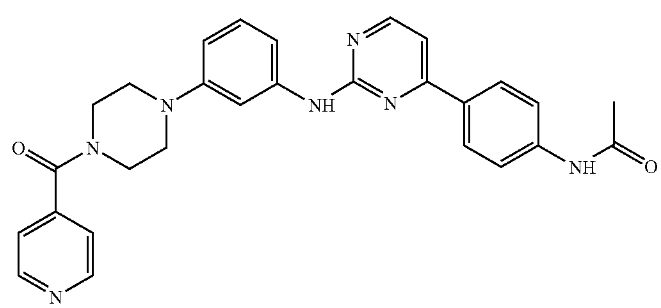 [SMILES: CC(=O)Nc1ccc(-c2ccnc(Nc3cccc(N4CCN(C(=O)c5ccncc5)CC4)c3)n2)cc1] | 7 |

TABLE 1-continued

| Cmpd No. | Name | Structure | Can Be Made According To Synthetic Example #: |
|---|---|---|---|
| 634 | N-{4-[2-({3-[4-(pyridin-2-ylcarbonyl)piperazin-1-yl]phenyl}amino)pyrimidin-4-yl]phenyl}acetamide | 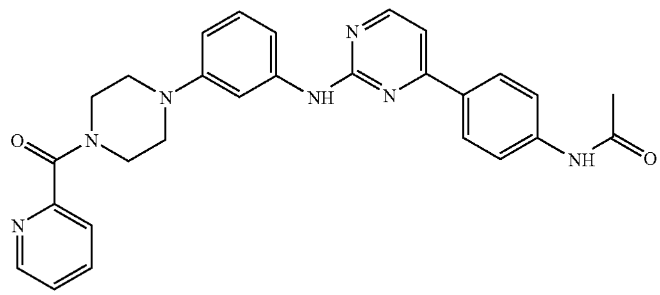 [SMILES: CC(=O)Nc1ccc(-c2ccnc(Nc3cccc(N4CCN(C(=O)c5ccccn5)CC4)c3)n2)cc1] | 7 |
| 635 | N-(4-{2-[(3-{4-[(2-methylphenyl)carbonyl]piperazin-1-yl}phenyl)amino]pyrimidin-4-yl}phenyl)acetamide | 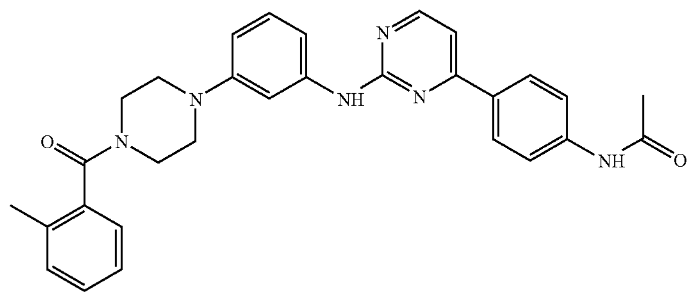 [SMILES: CC(=O)Nc1ccc(-c2ccnc(Nc3cccc(N4CCN(C(=O)c5ccccc5C)CC4)c3)n2)cc1] | 7 |
| 636 | N-{4-[2-({3-[4-(2,2-dimethylpropanoyl)piperazin-1-yl]phenyl}amino)pyrimidin-4-yl]phenyl}acetamide | 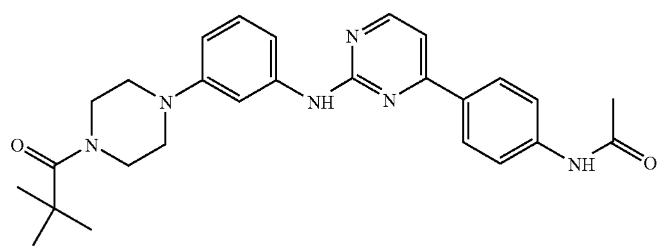 [SMILES: CC(=O)Nc1ccc(-c2ccnc(Nc3cccc(N4CCN(C(=O)C(C)(C)C)CC4)c3)n2)cc1] | 7 |
| 637 | N-{4-[2-({3-[4-(pyridin-3-ylcarbonyl)piperazin-1-yl]phenyl}amino)pyrimidin-4-yl]phenyl}acetamide | 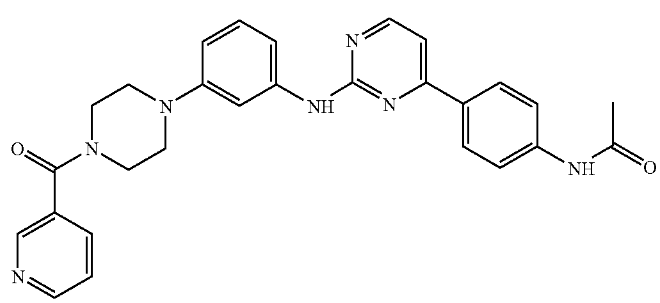 [SMILES: CC(=O)Nc1ccc(-c2ccnc(Nc3cccc(N4CCN(C(=O)c5cccnc5)CC4)c3)n2)cc1] | 7 |
| 638 | N-{4-[2-({3-[4-(2-methylpropanoyl)piperazin-1-yl]phenyl}amino)pyrimidin-4-yl]phenyl}acetamide | 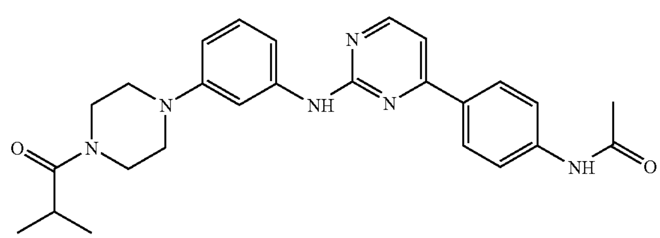 [SMILES: CC(=O)Nc1ccc(-c2ccnc(Nc3cccc(N4CCN(C(=O)C(C)C)CC4)c3)n2)cc1] | 7 |

| Cmpd No. | Name | Structure | Can Be Made According To Synthetic Example #: |
|---|---|---|---|
| 639 | N-[4-(2-{[3-(methyloxy)-4-morpholin-4-ylphenyl]amino}pyrimidin-4-yl)phenyl]tetrahydrofuran-3-carboxamide | 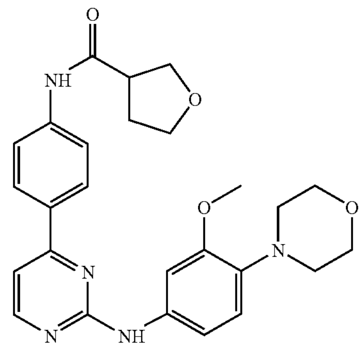 [SMILES: COc1cc(Nc2nccc(-c3ccc(NC(=O)C4CCOC4)cc3)n2)ccc1N1CCOCC1] | 12 |
| 640 | (2R)-N-[4-(2-{[3-(methyloxy)-4-morpholin-4-ylphenyl]amino}pyrimidin-4-yl)phenyl]tetrahydrofuran-2-carboxamide | 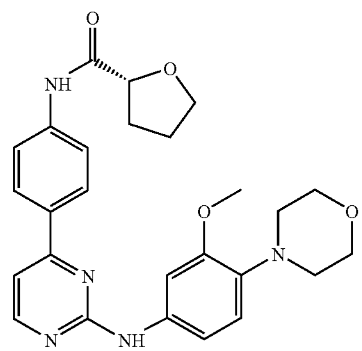 | 12 |
| 641 | (2S)-N-[4-(2-{[3-(methyloxy)-4-morpholin-4-ylphenyl]amino}pyrimidin-4-yl)phenyl]tetrahydrofuran-2-carboxamide | 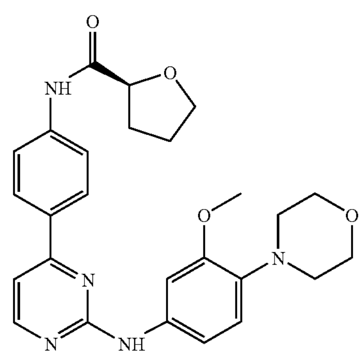 [SMILES: COc1cc(Nc2nccc(-c3ccc(NC(=O)[C@@H]4CCCO4)cc3)n2)ccc1N1CCOCC1] | 12 |
| 642 | N-(4-{2-[(4-{4-[(2-fluorophenyl)sulfonyl]piperazin-1-yl}phenyl)amino]pyrimidin-4-yl}phenyl)acetamide | 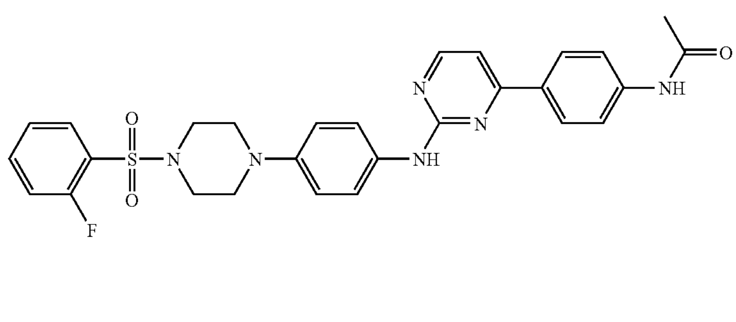 | 36 |

TABLE 1-continued

| Cmpd No. | Name | Structure | Can Be Made According To Synthetic Example #: |
|---|---|---|---|
| 643 | N-(4-{2-[(3-{4-[(3,5-dichlorophenyl)carbonyl]piperazin-1-yl}phenyl)amino]pyrimidin-4-yl}phenyl)acetamide | 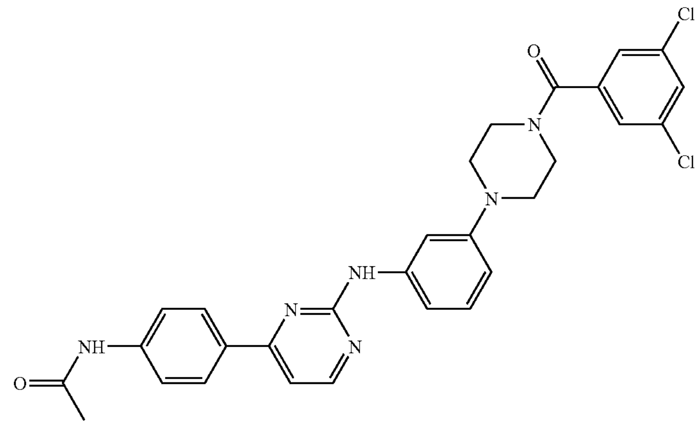 [SMILES: CC(=O)Nc1ccc(-c2ccnc(Nc3cccc(N4CCN(C(=O)c5cc(Cl)cc(Cl)c5)CC4)c3)n2)cc1] | 7 |
| 644 | ethyl 3-[(4-{2-[(4-morpholin-4-ylphenyl)amino]pyrimidin-4-yl}phenyl)amino]-3-oxopropanoate | 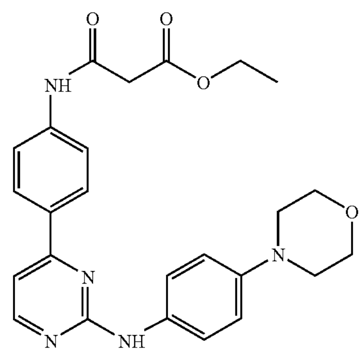 [SMILES: CCOC(=O)CC(=O)Nc1ccc(-c2ccnc(Nc3ccc(N4CCOCC4)cc3)n2)cc1] | 12 |
| 645 | N-{4-[2-({4-[4-(2-methylpropanoyl)piperazin-1-yl]phenyl}amino)pyrimidin-4-yl]phenyl}tetrahydrofuran-3-carboxamide | 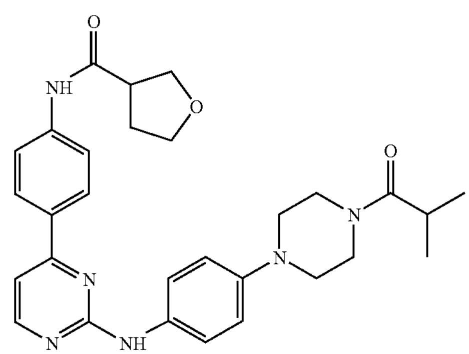 [SMILES: CC(C)C(=O)N1CCN(c2ccc(Nc3nccc(-c4ccc(NC(=O)C5CCOC5)cc4)n3)cc2)CC1] | 7 |
| 646 | N-{4-[2-{4-[4-(cyclobutylcarbonyl)piperazin-1-yl]phenyl}amino)pyrimidin-4-yl]phenyl}tetrahydrofuran-3-carboxamide | 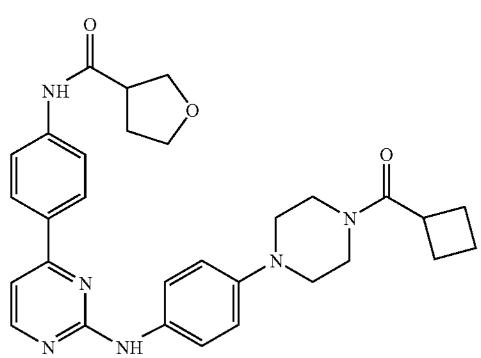 [SMILES: O=C(Nc1ccc(-c2ccnc(Nc3ccc(N4CCN(C(=O)C5CCC5)CC4)cc3)n2)cc1)C1CCOC1] | 7 |

TABLE 1-continued

| Cmpd No. | Name | Structure | Can Be Made According To Synthetic Example #: |
|---|---|---|---|
| 647 | N-ethyl-4-{4-[(4-{(4-[(tetrahydrofuran-3-ylcarbonyl)amino]phenyl}pyrimidin-2-yl)amino]phenyl}piperazine-1-carboxamide | 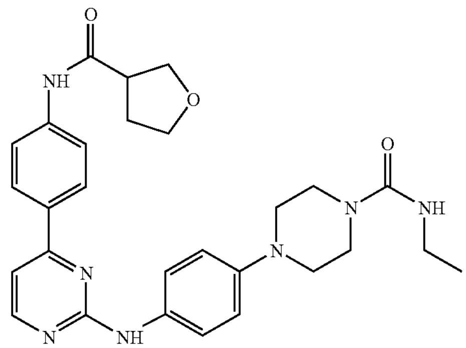 [SMILES: CCNC(=O)N1CCN(c2ccc(Nc3nccc(-c4ccc(NC(=O)C5CCOC5)cc4)n3)cc2)CC1] | 53 |
| 648 | N-[4-(2-{[4-(4-D-alanyl-piperazin-1-yl)phenyl]amino}pyrimidin-4-yl)phenyl]tetrahydrofuran-3-carboxamide | 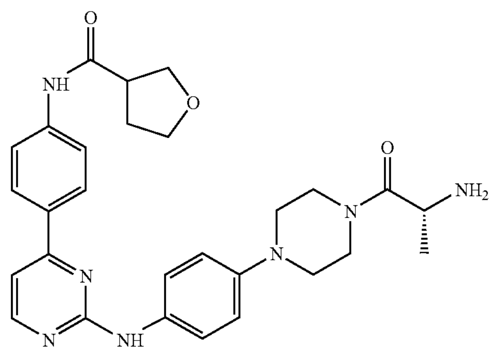 [SMILES: C[C@@H](N)C(=O)N1CCN(c2ccc(Nc3nccc(-c4ccc(NC(=O)C5CCOC5)cc4)n3)cc2)CC1] | 7 |
| 649 | N-[4-(2-{[4-(4-L-alanyl-piperazin-1-yl)phenyl]amino}pyrimidin-4-yl)phenyl]tetrahydrofuran-3-carboxamide | 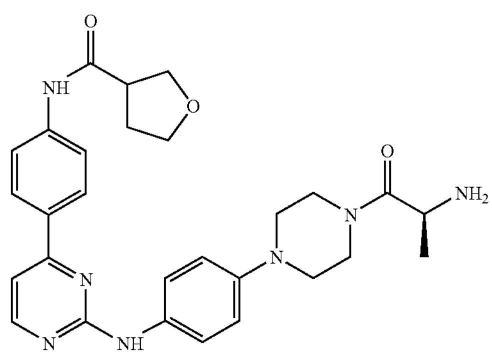 [SMILES: C[C@H](N)C(=O)N1CCN(c2ccc(Nc3nccc(-c4ccc(NC(=O)C5CCOC5)cc4)n3)cc2)CC1] | 7 |
| 650 | N-[4-(2-{[4-(4-D-prolyl-piperazin-1-yl)phenyl]amino}pyrimidin-4-yl)phenyl]tetrahydrofuran-3-carboxamide | 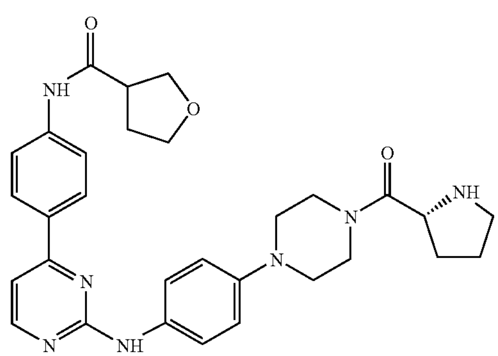 [SMILES: O=C(Nc1ccc(-c2ccnc(Nc3ccc(N4CCN(C(=O)[C@H]5CCCN5)CC4)cc3)n2)cc1)C1CCOC1] | 7 |

TABLE 1-continued

| Cmpd No. | Name | Structure | Can Be Made According To Synthetic Example #: |
|---|---|---|---|
| 651 | N-[4-(2-{[4-(4-L-prolyl-piperazin-1-yl)phenyl]amino}pyrimidin-4-yl)phenyl]tetra-hydrofuran-3-carboxamide | 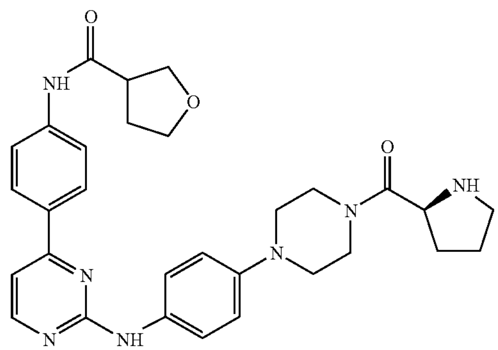 [SMILES: O=C(Nc1ccc(-c2ccnc(Nc3ccc(N4CCN(C(=O)[C@@H]5CCCN5)CC4)cc3)n2)cc1)C1CCOC1] | 7 |
| 652 | N-{4-[2-(1H-benzamidazol-6-ylamino)-5-methylpyrimidin-4-yl]phenyl}acetamide | 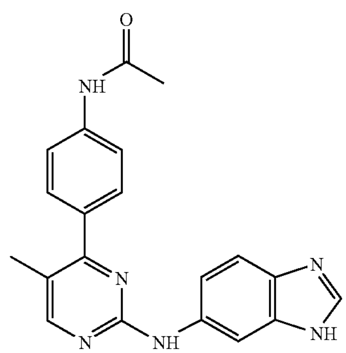 [SMILES: CC(=O)Nc1ccc(-c2nc(Nc3ccc4nc[nH]c4c3)ncc2C)cc1] | 5 |
| 653 | 4-(4-furan-2-ylphenyl)-N-(4-morpholin-4-ylphenyl)pyrimidin-2-amine | 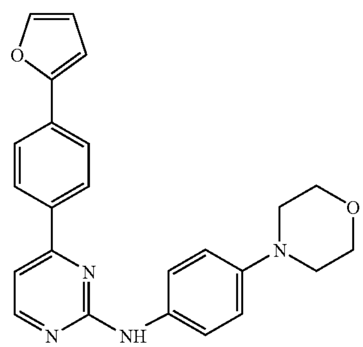 [SMILES: c1coc(-c2ccc(-c3ccnc(Nc4ccc(N5CCOCC5)cc4)n3)cc2)c1] | 9 |
| 654 | N-(4-morpholin-4-ylphenyl)-4-[4-(pyrimidin-2-ylamino)phenyl]pyrimidin-2-amine | 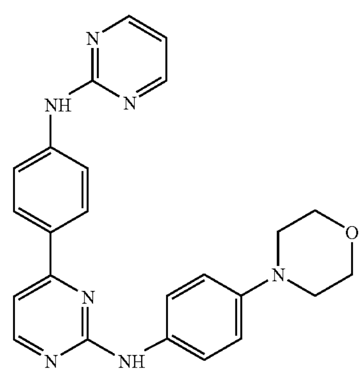 [SMILES: c1cnc(Nc2ccc(-c3ccnc(Nc4ccc(N5CCOCC5)cc4)n3)cc2)nc1] | 9 |

TABLE 1-continued

| Cmpd No. | Name | Structure | Can Be Made According To Synthetic Example #: |
|---|---|---|---|
| 655 | N-[4-(2-{[4-(4-ethyl-piperazin-1-yl)phenyl]amino}-5-methylpyrimidin-4-yl)phenyl]cyclopropane-carboxamide | 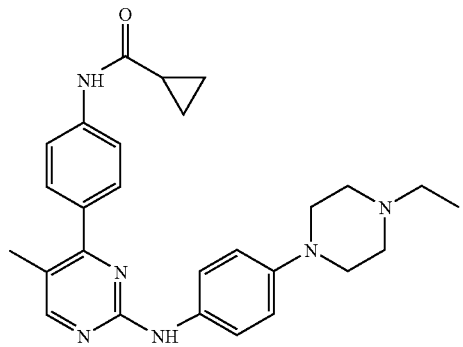 [SMILES: CCN1CCN(c2ccc(Nc3ncc(C)c(-c4ccc(NC(=O)C5CC5)cc4)n3)cc2)CC1] | 51 |
| 656 | N-[4-(2-{[4-(4-ethylpiperazin-1-yl)phenyl]amino}pyrimidin-4-yl)phenyl]cyclopropane-carboxamide | 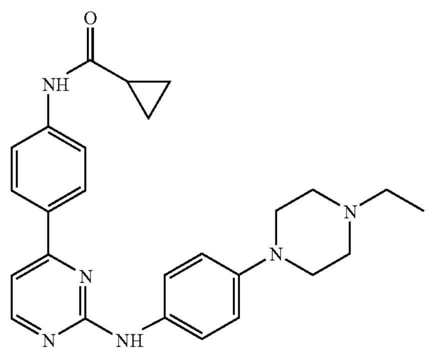 [SMILES: CCN1CCN(c2ccc(Nc3nccc(-c4ccc(NC(=O)C5CC5)cc4)n3)cc2)CC1] | 51 |
| 657 | N-(4-{2-[(3,5-dimorpholin-4-ylphenyl)amino]-5-methyl-pyrimidin-4-yl}phenyl)-N~2~,N~2~-dimethyl-glycinamide | 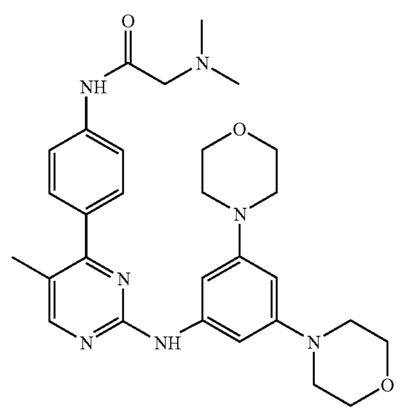 [SMILES: Cc1cnc(Nc2cc(N3CCOCC3)cc(N3CCOCC3)c2)nc1-c1ccc(NC(=O)CN(C)C)cc1] | 6 |
| 658 | N$^2$,N~2~-dimethyl-N-(4-{5-methyl-2-[(4-morpholin-4-ylphenyl)amino]pyrimidin-4-yl}phenyl)glycinamide | 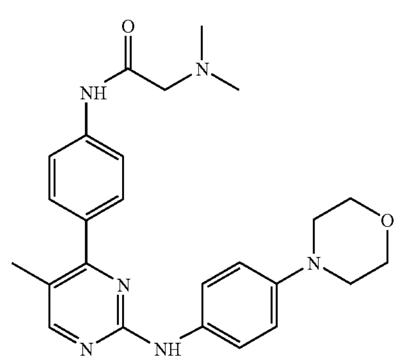 [SMILES: Cc1cnc(Nc2ccc(N3CCOCC3)cc2)nc1-c1ccc(NC(=O)CN(C)C)cc1] | 12 |

TABLE 1-continued

| Cmpd No. | Name | Structure | Can Be Made According To Synthetic Example #: |
|---|---|---|---|
| 659 | N-(4-{5-methyl-2-[(4-morpholin-4-ylphenyl)amino]pyrimidin-4-yl}phenyl)-D-prolinamide | 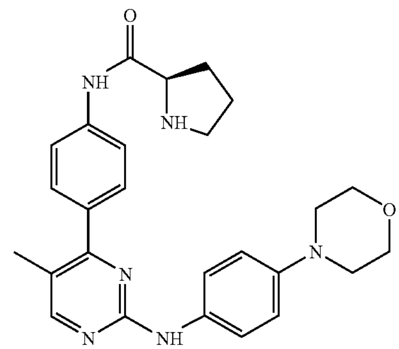 [SMILES: Cc1cnc(Nc2ccc(N3CCOCC3)cc2)nc1-c1ccc(NC(=O)[C@H]2CCCN2)cc1] | 45 |
| 660 | N-{4-[2-({4-[4-(2-methyl-propanoyl)piperazin-1-yl]phenyl}amino)pyrimidin-4-yl]phenyl}-D-prolinamide | 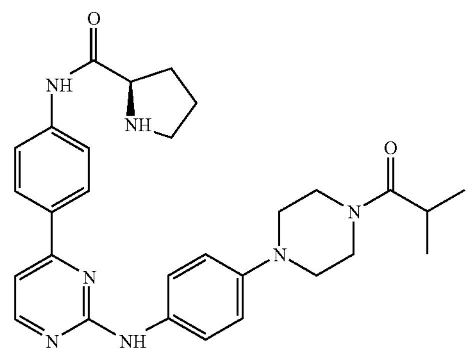 [SMILES: CC(C)C(=O)N1CCN(c2ccc(Nc3nccc(-c4ccc(NC(=O)[C@H]5CCCN5)cc4)n3)cc2)CC1] | 52 |
| 661 | N-{4-[2-({4-[4-(2,2-dimethylpropanoyl)piperazin-1-yl]phenyl}amino)pyrimidin-4-yl]phenyl}-D-prolinamide | 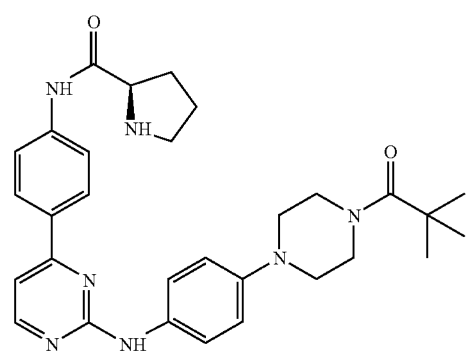 [SMILES: CC(C)(C)C(=O)N1CCN(c2ccc(Nc3nccc(-c4ccc(NC(=O)[C@H]5CCCN5)cc4)n3)cc2)CC1] | 52 |
| 662 | N-{4-[2-({4-[4-(cyclobuyl-carbonyl)piperazin-1-yl]phenyl}amino)pyrimidin-4-yl]phenyl}-D-prolinamide | 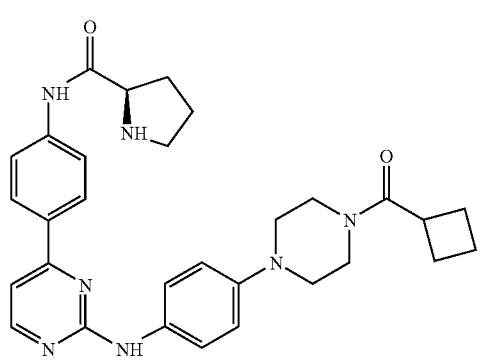 [SMILES: O=C(Nc1ccc(-c2ccnc(Nc3ccc(N4CCN(C(=O)C5CCC5)CC4)cc3)n2)cc1)[C@H]1CCCN1] | 52 |

TABLE 1-continued

| Cmpd No. | Name | Structure | Can Be Made According To Synthetic Example #: |
|---|---|---|---|
| 663 | N-ethyl-4-[4-({4-[4-(D-prolylamino)phenyl]pyrimidin-2-yl}amino)phenyl]piperazine-1-carboxamide | 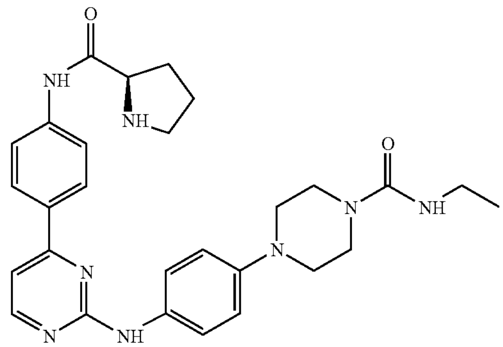 [SMILES: CCNC(=O)N1CCN(c2ccc(Nc3nccc(-c4ccc(NC(=O)[C@H]5CCCN5)cc4)n3)cc2)CC1] | 53 |
| 664 | N-[4-(2-{[4-(4-D-prolylpiperazin-1-yl)phenyl]amino}pyrimidin-4-yl)phenyl]-D-prolinamide | 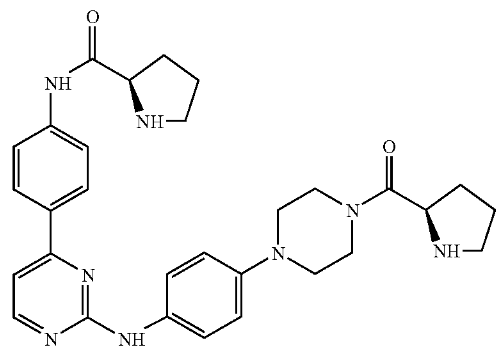 [SMILES: O=C(Nc1ccc(-c2ccnc(Nc3ccc(N4CCN(C(=O)[C@H]5CCCN5)CC4)cc3)n2)cc1)[C@H]1CCCN1] | 52 |
| 665 | N-[4-(2-{[4-(4-L-prolyl-piperazin-1-yl)phenyl]amino}pyrimidin-4-yl)phenyl]-D-prolinamide | 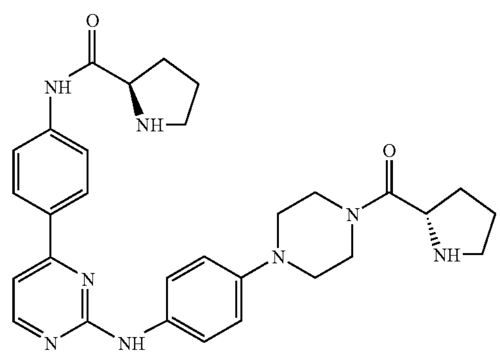 [SMILES: O=C(Nc1ccc(-c2ccnc(Nc3ccc(N4CCN(C(=O)[C@@H]5CCCN5)CC4)cc3)n2)cc1)[C@H]1CCCN1] | 52 |
| 666 | 1-methyl-N-(4-{2-[(4-morpholin-4-ylphenyl)amino]pyrimidin-4-yl}phenyl)piperidine-2-carboxamide | 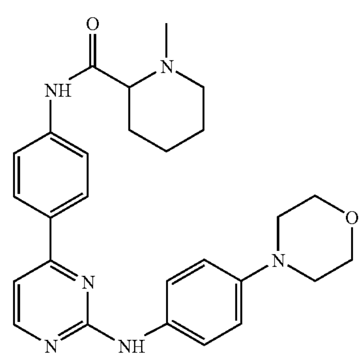 [SMILES: CN1CCCCC1C(=O)Nc1ccc(-c2ccnc(Nc3ccc(N4CCOCC4)cc3)n2)cc1] | 12 |

TABLE 1-continued

| Cmpd No. | Name | Structure | Can Be Made According To Synthetic Example #: |
|---|---|---|---|
| 667 | N-{4-[2-({4-[4-(piperidin-4-ylcarbonyl)piperazin-1-yl]phenyl}amino)pyrimidin-4-yl]phenyl}acetamide | 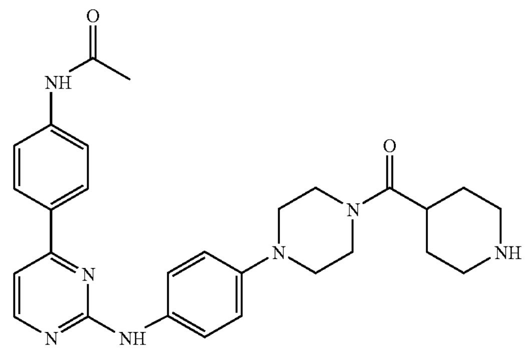 [SMILES: CC(=O)Nc1ccc(-c2ccnc(Nc3ccc(N4CCN(C(=O)C5CCNCC5)CC4)cc3)n2)cc1] | 7 |
| 668 | 1-methyl-N-(4-{2-[(4-morpholin-4-ylphenyl)amino]pyrimidin-4-yl}phenyl)-L-prolinamide | 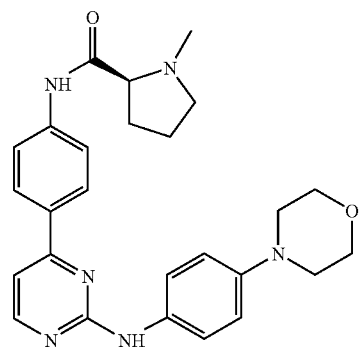 [SMILES: CN1CCC[C@H]1C(=O)Nc1ccc(-c2ccnc(Nc3ccc(N4CCOCC4)cc3)n2)cc1] | 12 |
| 669 | N-(4-{2-[(4-morpholin-4-ylphenyl)amino]pyrimidin-4-yl}phenyl)-2-pyridin-4-ylacetamide | 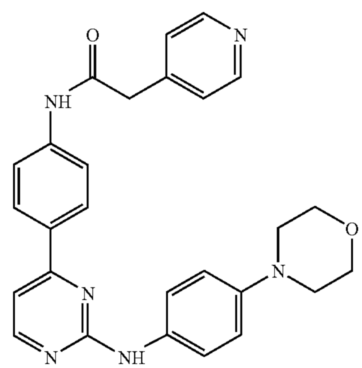 [SMILES: O=C(Cc1ccncc1)Nc1ccc(-c2ccnc(Nc3ccc(N4CCOCC4)cc3)n2)cc1] | 12 |
| 670 | 2-(3-fluorophenyl)-N-(4-{2-[(4-morpholin-4-ylphenyl)amino]pyrimidin-4-yl}phenyl)acetamide | 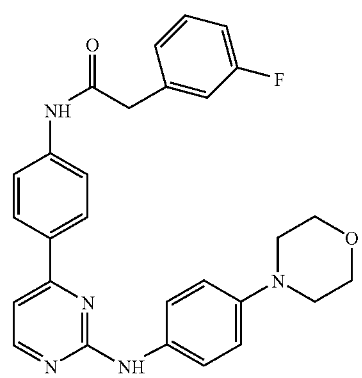 [SMILES: O=C(Cc1cccc(F)c1)Nc1ccc(-c2ccnc(Nc3ccc(N4CCOCC4)cc3)n2)cc1] | 12 |

TABLE 1-continued

| Cmpd No. | Name | Structure | Can Be Made According To Synthetic Example #: |
|---|---|---|---|
| 671 | 3-(4-chlorophenyl)-N-(4-{2-[(4-morpholin-4-ylphenyl)amino]pyrimidin-4-yl}phenyl)propanamide | 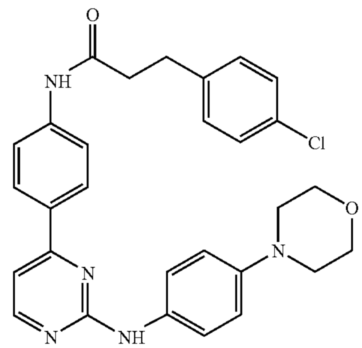 [SMILES: O=C(CCc1ccc(Cl)cc1)Nc1ccc(-c2ccnc(Nc3ccc(N4CCOCC4)cc3)n2)cc1] | 12 |
| 672 | 2-(3-chlorophenyl)-N-(4-{2-[(4-morpholin-4-ylphenyl)amino]pyrimidin-4-yl}phenyl)acetamide | 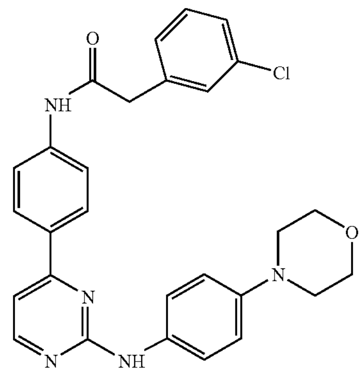 [SMILES: O=C(Cc1cccc(Cl)c1)Nc1ccc(-c2ccnc(Nc3ccc(N4CCOCC4)cc3)n2)cc1] | 12 |
| 673 | 2-methyl-N-(4-{2-[(4-morpholin-4-ylphenyl)amino]pyrimidin-4-yl}phenyl)-3-phenylpropanamide | 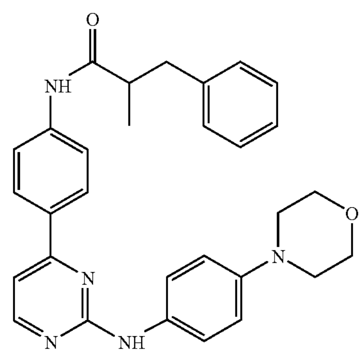 [SMILES: CC(Cc1ccccc1)C(=O)Nc1ccc(-c2ccnc(Nc3ccc(N4CCOCC4)cc3)n2)cc1] | 12 |
| 674 | (1R,2R)-N-(4-{2-[(4-morpholin-4-ylphenyl)amino]pyrimidin-4-yl}phenyl)-2-phenylcyclopropane-carboxamide | 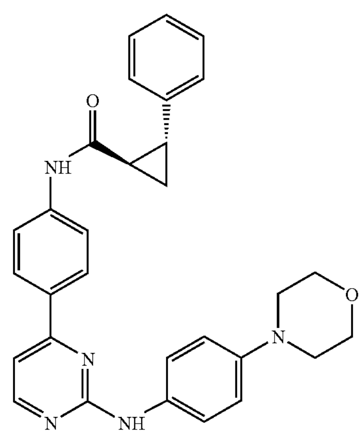 [SMILES: O=C(Nc1ccc(-c2ccnc(Nc3ccc(N4CCOCC4)cc3)n2)cc1)[C@@H]1C[C@H]1c1ccccc1] | 12 |

TABLE 1-continued

| Cmpd No. | Name | Structure | Can Be Made According To Synthetic Example #: |
|---|---|---|---|
| 675 | 2-(4-fluorophenyl)-N-(4-{2-[(4-morpholin-4-ylphenyl)amino]pyrimidin-4-yl}phenyl)acetamide | 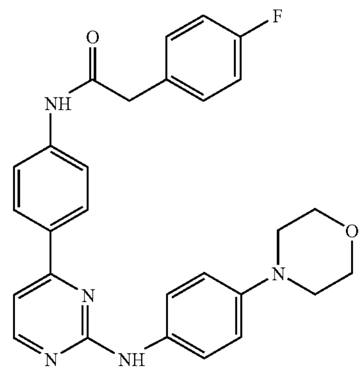 [SMILES: O=C(Cc1ccc(F)cc1)Nc1ccc(-c2ccnc(Nc3ccc(N4CCOCC4)cc3)n2)cc1] | 12 |
| 676 | 3-(2-chlorophenyl)-N-(4-{2-[(4-morpholin-4-ylphenyl)amino]pyrimidin-4-yl}phenyl)propanamide | 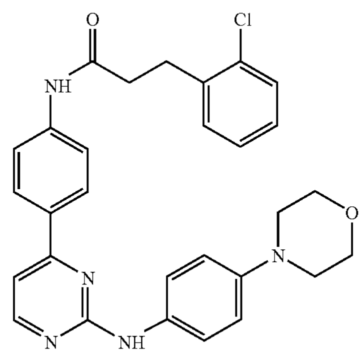 | 12 |
| 677 | 3-(3-chlorophenyl)-N-(4-{2-[(4-morpholin-4-ylphenyl)amino]pyrimidi-4-yl}phenyl)propanamide | 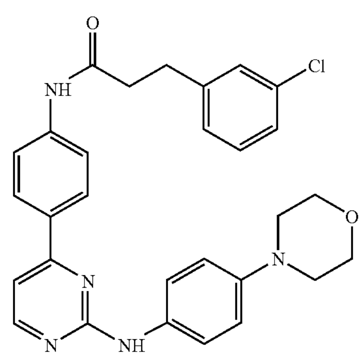 [SMILES: O=C(CCc1cccc(Cl)c1)Nc1ccc(-c2ccnc(Nc3ccc(N4CCOCC4)cc3)n2)cc1] | 12 |
| 678 | 3-(2-fluorophenyl)-N-(4-{2-[(4-morpholin-4-ylphenyl)amino]pyrimidin-4-yl}phenyl)propanamide | 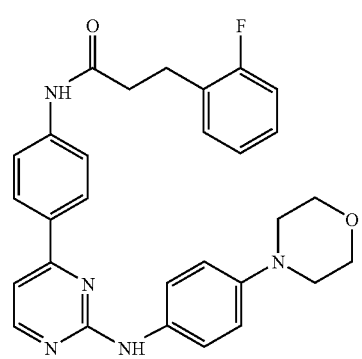 [SMILES: O=C(CCc1ccccc1F)Nc1ccc(-c2ccnc(Nc3ccc(N4CCOCC4)cc3)n2)cc1] | 678 |

TABLE 1-continued

| Cmpd No. | Name | Structure | Can Be Made According To Synthetic Example #: |
|---|---|---|---|
| 679 | Nalpha,Nalpha-dimethyl-N-(4-{2-[(4-morpholin-4-ylphenyl)amino]pyrimidin-4-yl}phenyl)-L-phenylalaninamide | 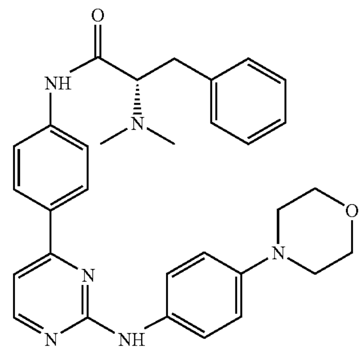 [SMILES: CN(C)[C@@H](Cc1ccccc1)C(=O)Nc1ccc(-c2ccnc(Nc3ccc(N4CCOCC4)cc3)n2)cc1] | 12 |
| 680 | 2-(2-chlorophenyl)-N-(4-{2-[(4-morpholin-4-ylphenyl)amino]pyrimidin-4-yl}phenyl)acetamide | 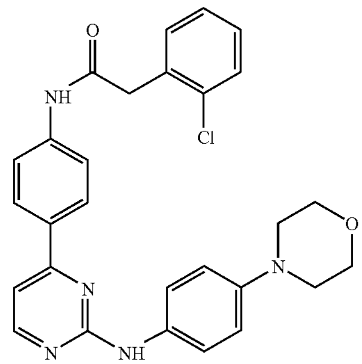 [SMILES: O=C(Cc1ccccc1Cl)Nc1ccc(-c2ccnc(Nc3ccc(N4CCOCC4)cc3)n2)cc1] | 12 |
| 681 | N-(4-{2-[(4-morpholin-4-ylphenyl)amino]pyrimidin-4-yl}phenyl)-2-pyridin-2-ylacetamide | 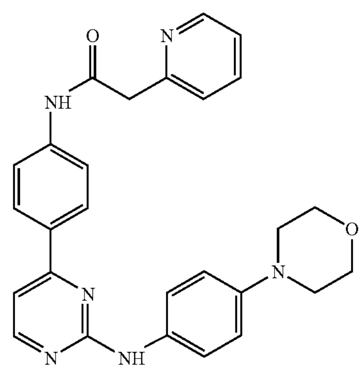 [SMILES: O=C(Cc1ccccn1)Nc1ccc(-c2ccnc(Nc3ccc(N4CCOCC4)cc3)n2)cc1] | 12 |
| 682 | 2-(4-chlorophenyl)-N-(4-{2-[(4-morpholin-4-ylphenyl)amino]pyrimidin-4-yl}phenyl)acetamide | 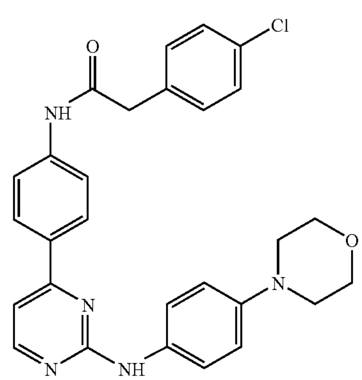 | 12 |

TABLE 1-continued

| Cmpd No. | Name | Structure | Can Be Made According To Synthetic Example #: |
|---|---|---|---|
| 683 | N-(4-{2-[(4-morpholin-4-ylphenyl)amino]pyrimidin-4-yl}phenyl)-2-{4-[(trifluoromethyl)oxy]phenyl}acetamide | 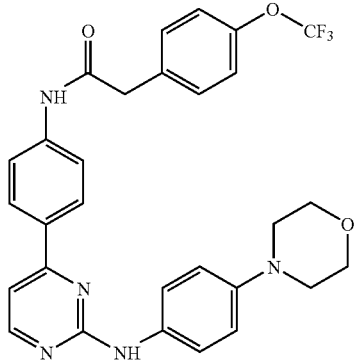 [SMILES: O=C(Cc1ccc(OC(F)(F)F)cc1)Nc1ccc(-c2ccnc(Nc3ccc(N4CCOCC4)cc3)n2)cc1] | 12 |
| 684 | 2-[2-(methyloxy)phenyl]-N-(4-{2-[(4-morpholin-4-ylphenyl)amino]pyrimidin-4-yl}phenyl)acetamide | 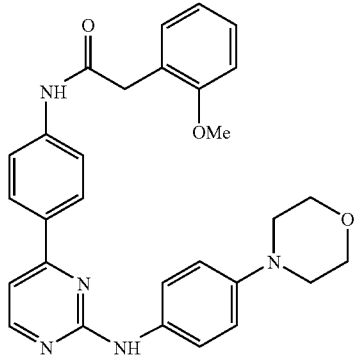 [SMILES: COc1ccccc1CC(=O)Nc1ccc(-c2ccnc(Nc3ccc(N4CCOCC4)cc3)n2)cc1] | 12 |
| 685 | 2-[3-(methyloxy)phenyl]-N-(4-{2-[(4-morpholin-4-ylphenyl)amino]pyrimidin-4-yl}phenyl)acetamide | 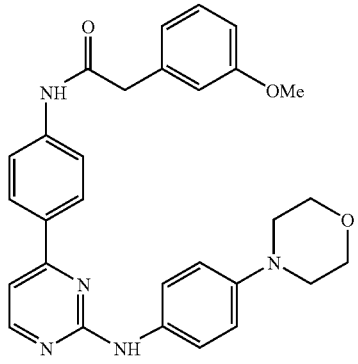 [SMILES: COc1cccc(CC(=O)Nc2ccc(-c3ccnc(Nc4ccc(N5CCOCC5)cc4)n3)cc2)c1] | 12 |
| 686 | 2-[4-(methyloxy)phenyl]-N-(4-{2-[(4-morpholin-4-ylphenyl)amino]pyrimidin-4-yl}phenyl)acetamide | 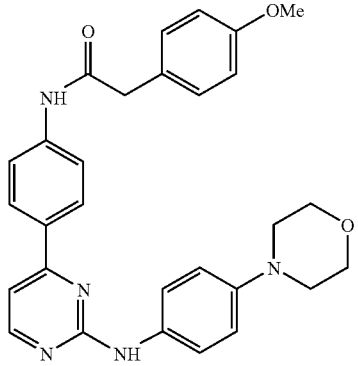 [SMILES: COc1ccc(CC(=O)Nc2ccc(-c3ccnc(Nc4ccc(N5CCOCC5)cc4)n3)cc2)cc1] | 12 |

TABLE 1-continued

| Cmpd No. | Name | Structure | Can Be Made According To Synthetic Example #: |
|---|---|---|---|
| 687 | N-[4-(2-{[4-(4-ethyl-piperazin-1-yl)phenyl]amino}pyrimidin-4-yl)phenyl]-D-alaninamide | 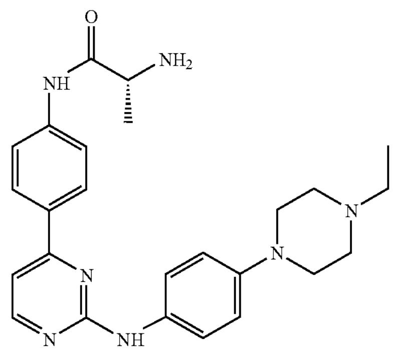 [SMILES: CCN1CCN(c2ccc(Nc3nccc(-c4ccc(NC(=O)[C@@H](C)N)cc4)n3)cc2)CC1] | 51 |
| 688 | N-{4-[2-({4-[4-(N,N-dimethylglycyl)piperazin-1-yl]phenyl}amino)pyrimidin-4-yl]phenyl}acetamide | 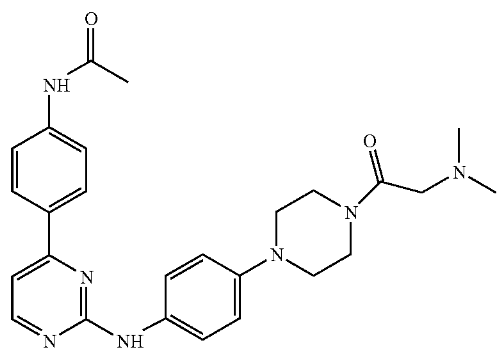 [SMILES: CC(=O)Nc1ccc(-c2ccnc(Nc3ccc(N4CCN(C(=O)CN(C)C)CC4)cc3)n2)cc1] | 7 |
| 689 | N-[4-(2-{(4-(4-ethyl-piperazin-1-yl)phenyl]amino}pyrimidin-4-yl)phenyl]-3-(methyloxy)propanamide | 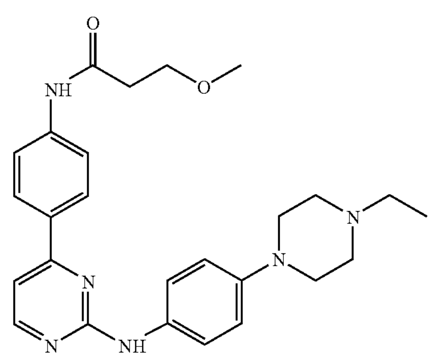 [SMILES: CCN1CCN(c2ccc(Nc3nccc(-c4ccc(NC(=O)CCOC)cc4)n3)cc2)CC1] | 51 |
| 690 | (2R)-2-amino-N-(4-{2-[(4-morpholin-4-ylphenyl)amino}pyrimidin-4-yl}phenyl)-2-phenylethanamide | 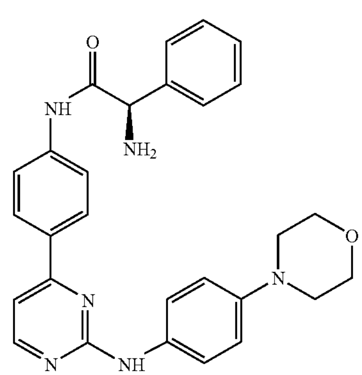 [SMILES: N[C@@H](C(=O)Nc1ccc(-c2ccnc(Nc3ccc(N4CCOCC4)cc3)n2)cc1)c1ccccc1] | 45 |

TABLE 1-continued

| Cmpd No. | Name | Structure | Can Be Made According To Synthetic Example #: |
|---|---|---|---|
| 691 | $N^2,N^2$-dimethyl-N-(4-{2-[(4-morpholin-4-ylphenyl)amino]pyrimidin-4-yl}phenyl)-D-alaninamide | 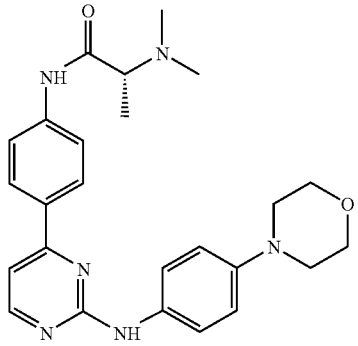 [SMILES: C[C@H](C(=O)Nc1ccc(-c2ccnc(Nc3ccc(N4CCOCC4)cc3)n2)cc1)N(C)C] | 12 |
| 692 | 1-methyl-N-(4-{2-[(4-morpholin-4-ylphenyl)amino]pyrimidin-4-yl}phenyl)-D-prolinamide | 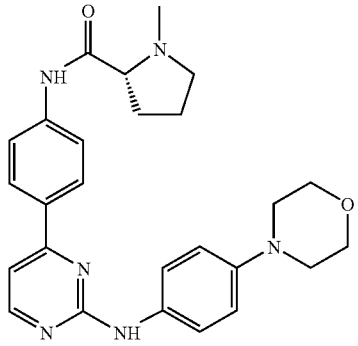 [SMILES: CN1CCC[C@@H]1C(=O)Nc1ccc(-c2ccnc(Nc3ccc(N4CCOCC4)cc3)n2)cc1] | 12 |
| 693 | $N^2,N^2$-dimethyl-N-(4-{2-[(4-morpholin-4-ylphenyl)amino]pyrimidin-4-yl}phenyl)-L-alaninamide | 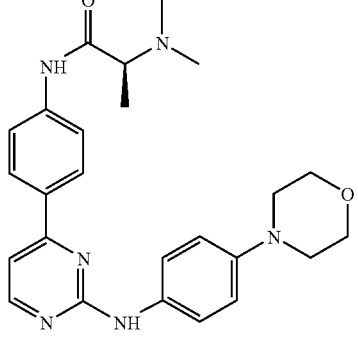 | 12 |
| 694 | N-(4-{2-[(4-morpholin-4-ylphenyl)amino]pyrimidin-4-yl}phenyl)-1-phenyl-cyclopropanecarboxamide | 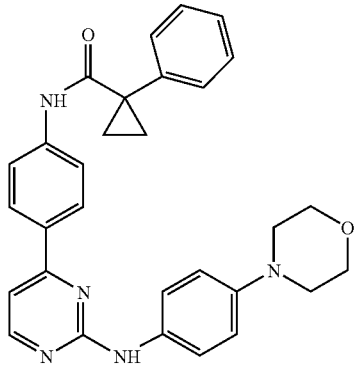 [SMILES: O=C(Nc1ccc(-c2ccnc(Nc3ccc(N4CCOCC4)cc3)n2)cc1)C1(c2ccccc2)CC1] | 12 |

TABLE 1-continued

| Cmpd No. | Name | Structure | Can Be Made According To Synthetic Example #: |
|---|---|---|---|
| 695 | 2-methyl-N-(4-{2-[(4-morpholin-4-ylphenyl)amino]pyrimidin-4-yl}phenyl)butanamide | 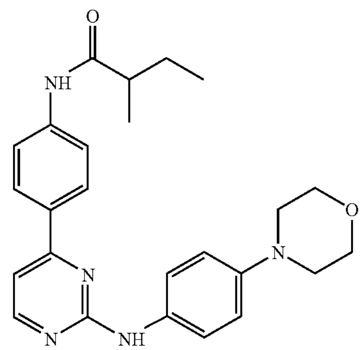 [SMILES: CCC(C)C(=O)Nc1ccc(-c2ccnc(Nc3ccc(N4CCOCC4)cc3)n2)cc1] | 12 |
| 696 | (2S)-1-methyl-N-(4-{2-[(4-morpholin-4-ylphenyl)amino]pyrimidin-4-yl}phenyl)azetidine-2-carboxamide | 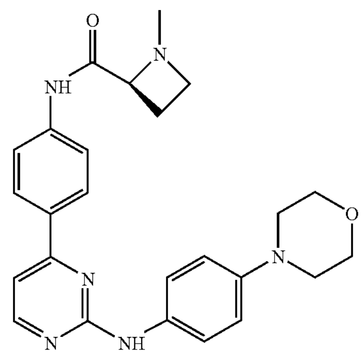 [SMILES: CN1CC[C@H]1C(=O)Nc1ccc(-c2ccnc(Nc3ccc(N4CCOCC4)cc3)n2)cc1] | 12 |
| 697 | 2,4,6-trichloro-N-(3-{[4-(4-methyl-2-thienyl)pyrimidin-2-yl]amino}propyl)benzamide | 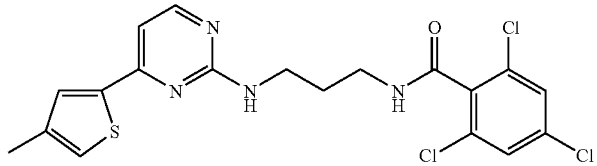 [SMILES: Cc1csc(-c2ccnc(NCCCNC(=O)c3c(Cl)cc(Cl)cc3Cl)n2)c1] | 27 |
| 698 | N-[3-({4-[3,4-bis(methyloxy)phenyl]pyrimidin-2-yl}amino)propyl]-2,6-dichlorobenzamide | 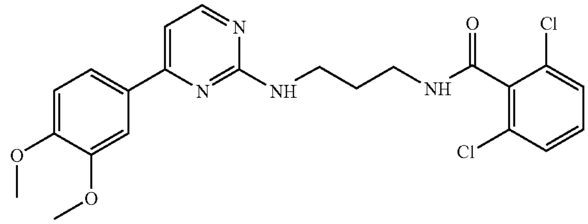 [SMILES: COc1ccc(-c2ccnc(NCCCNC(=O)c3c(Cl)cccc3Cl)n2)cc1OC] | 27 |
| 699 | 2,6-dichloro-N-[3-({4-[(4-morpholin-4-ylphenyl)amino]pyrimidin-2-yl}amino)propyl]benzamide | 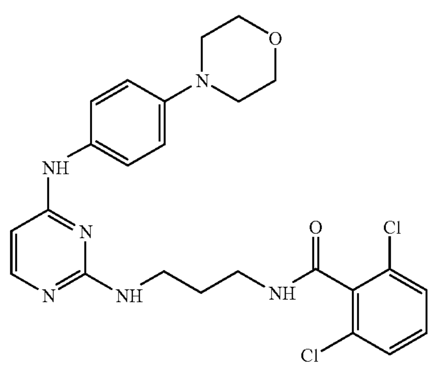 [SMILES: O=C(NCCCNc1nccc(Nc2ccc(N3CCOCC3)cc2)n1)c1c(Cl)cccc1Cl] | 27 |

TABLE 1-continued

| Cmpd No. | Name | Structure | Can Be Made According To Synthetic Example #: |
|---|---|---|---|
| 700 | 2,6-dichloro-N-(3-{[4-(2,3-dihydro-1,4-benzodioxin-6-yl)-5-fluoropyrimidin-2-yl]amino}propyl)benzamide | 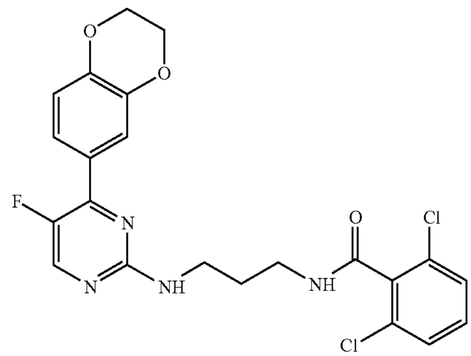 [SMILES: O=C(NCCCNc1ncc(F)c(-c2ccc3c(c2)OCCO3)n1)c1c(Cl)cccc1Cl] | 27 |
| 701 | 2,6-dichloro-N-{3-[(4-{(3-[(dimethylamino)methyl]phenyl}pyrimidin-2-yl)amino]propyl}benzamide | 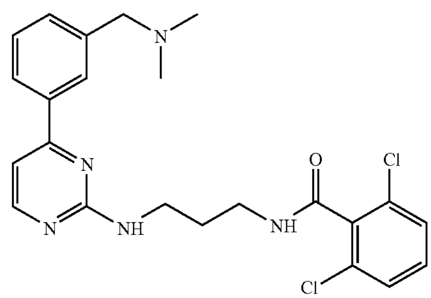 [SMILES: CN(C)Cc1cccc(-c2ccnc(NCCCNC(=O)c3c(Cl)cccc3Cl)n2)c1] | 27 |
| 702 | 2,6-dichloro-N-[3-({4-[3-(1-methylethyl)phenyl]pyrimidin-2-yl}amino)propyl]benzamide | 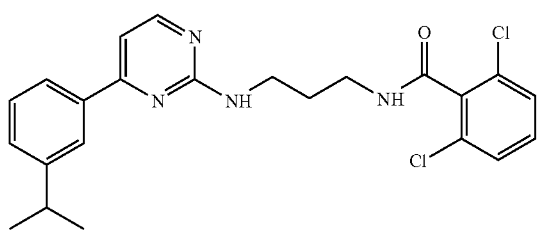 [SMILES: CC(C)c1cccc(-c2ccnc(NCCCNC(=O)c3c(Cl)cccc3Cl)n2)c1] | 27 |
| 703 | 2,6-dichloro-N-{3-[(4-{4-[(1-methylethyl)oxy]phenyl}pyrimidin-2-yl)amino]propyl}benzamide | 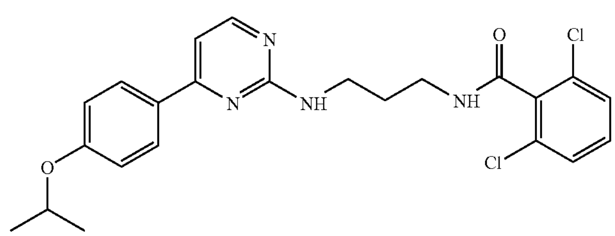 [SMILES: CC(C)Oc1ccc(-c2ccnc(NCCCNC(=O)c3c(Cl)cccc3Cl)n2)cc1] | 27 |
| 704 | N-[3-({4-[3-(acetylamino)phenyl]pyrimidin-2-yl}amino)propyl]-2,6-dichlorobenzamide | 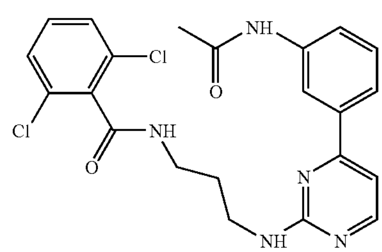 [SMILES: CC(=O)Nc1cccc(-c2ccnc(NCCCNC(=O)c3c(Cl)cccc3Cl)n2)c1] | 27 |

TABLE 1-continued

| Cmpd No. | Name | Structure | Can Be Made According To Synthetic Example #: |
|---|---|---|---|
| 705 | 2,6-dichloro-N-[3-({4-[(E)-2-phenylethenyl]pyrimidin-2-yl}amino)propyl]benzamide | 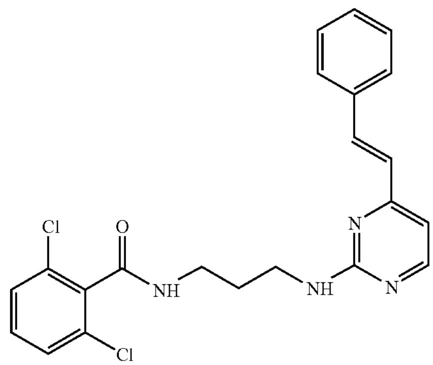 [SMILES: O=C(NCCCNc1nccc(/C=C/c2ccccc2)n1)c1c(Cl)cccc1Cl] | 27 |
| 706 | phenyl (4-{2-[(4-morpholin-4-ylphenyl)amino]pyrimidin-4-yl}phenyl)carbamate | 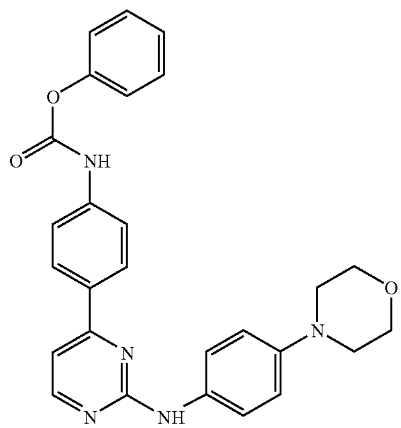 [SMILES: O=C(Nc1ccc(-c2ccnc(Nc3ccc(N4CCOCC4)cc3)n2)cc1)Oc1ccccc1] | 27 |
| 707 | phenylmethyl (4-{2-[(4-morpholin-4-ylphenyl)amino]pyrimidin-4-yl}phenyl)carbamate | 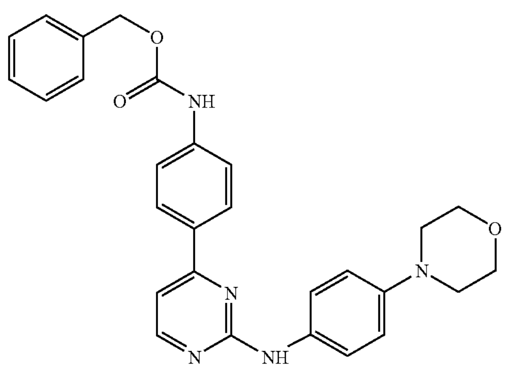 [SMILES: O=C(Nc1ccc(-c2ccnc(Nc3ccc(N4CCOCC4)cc3)n2)cc1)OCc1ccccc1] | 17 |
| 708 | N-{4-[2-({4-[4-(2,2-dimethylpropanoyl)piperazin-1-yl]phenyl}amino)pyrimidin-4-yl]phenyl}-3-(methyloxy)propanamide | 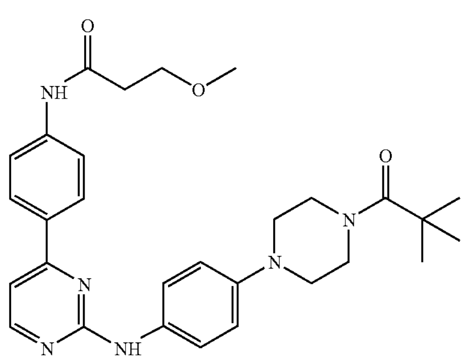 [SMILES: COCCC(=O)Nc1ccc(-c2ccnc(Nc3ccc(N4CCN(C(=O)C(C)(C)C)CC4)cc3)n2)cc1] | 7 |

TABLE 1-continued

| Cmpd No. | Name | Structure | Can Be Made According To Synthetic Example #: |
|---|---|---|---|
| 709 | N-{4-[2-({4-[4-(2,2-dimethylpropanoyl)piperazin-1-yl]phenyl}amino)pyrimidin-4-yl]phenyl}cyclopropanecarboxamide | 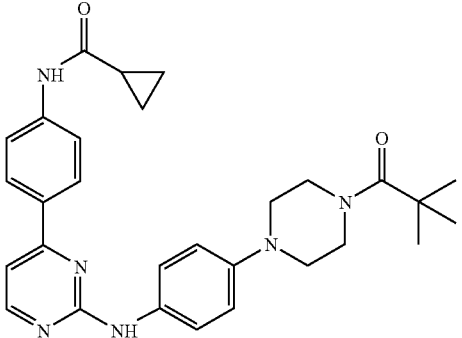 [SMILES: CC(C)(C)C(=O)N1CCN(c2ccc(Nc3nccc(-c4ccc(NC(=O)C5CC5)cc4)n3)cc2)CC1] | 7 |
| 710 | 4-{4-[(4-{4-[(cyclo-propylcarbonyl)amino]phenyl}pyrimidin-2-yl)amino]phenyl}-N-ethyl-piperazine-1-carboxamide | 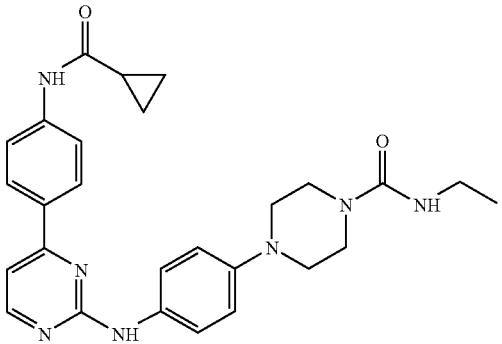 [SMILES: CCNC(=O)N1CCN(c2ccc(Nc3nccc(-c4ccc(NC(=O)C5CC5)cc4)n3)cc2)CC1] | 7 |
| 711 | N-{4-[2-({4-[4-(cyclo-butylcarbonyl)piperazin-1-yl]phenyl}amino)pyrimidin-4-yl]phenyl}-3-(methyloxy)propanamide | 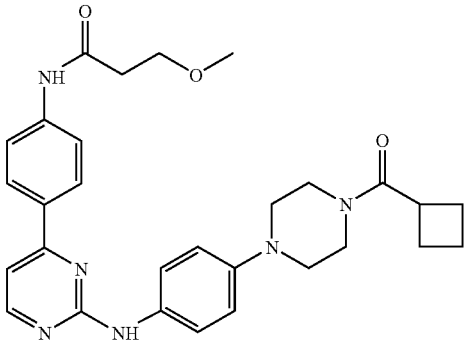 [SMILES: COCCC(=O)Nc1ccc(-c2ccnc(Nc3ccc(N4CCN(C(=O)C5CCC5)CC4)cc3)n2)cc1] | 7 |
| 712 | 3-(methyloxy)-N-{4-[2-({4-[4-(2-methylpropanoyl)piperazin-1-yl]phenyl}amino)pyrimidin-4-yl]phenyl}propanamide | 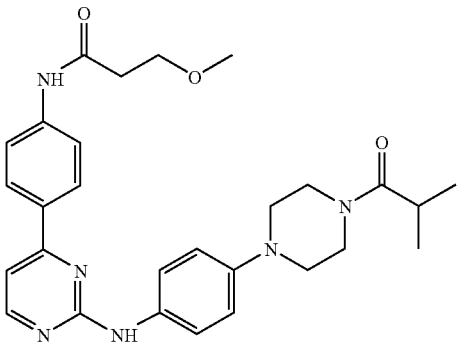 [SMILES: COCCC(=O)Nc1ccc(-c2ccnc(Nc3ccc(N4CCN(C(=O)C(C)C)CC4)cc3)n2)cc1] | 7 |

TABLE 1-continued

| Cmpd No. | Name | Structure | Can Be Made According To Synthetic Example #: |
|---|---|---|---|
| 713 | N-ethyl-4-(4-{[4-(4-{[3-(methyloxy)propanoyl]amino}phenyl)pyrimidin-2-yl]amino}phenyl)piperazine-1-carboxamide | 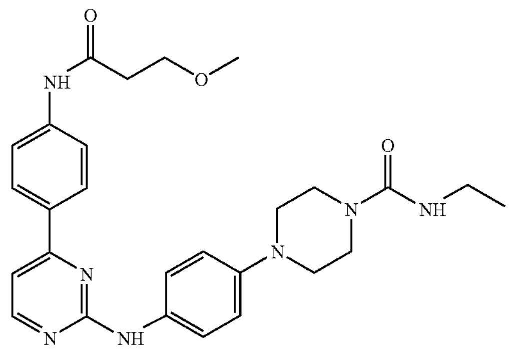 [SMILES: CCNC(=O)N1CCN(c2ccc(Nc3nccc(-c4ccc(NC(=O)CCOC)cc4)n3)cc2)CC1] | 53 |
| 714 | N-[4-(2-{[4-(4-ethyl-piperazin-1-yl)phenyl]amino}pyrimidin-4-yl)phenyl]-2-phenylacetamide | 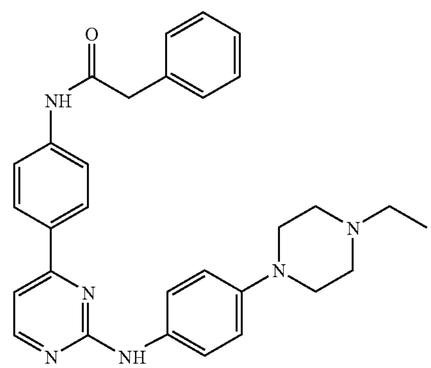 [SMILES: CCN1CCN(c2ccc(Nc3nccc(-c4ccc(NC(=O)Cc5ccccc5)cc4)n3)cc2)CC1] | 51 |
| 715 | 1-(4-{2-[(4-morpholin-4-ylphenyl)amino]pyrimidin-4-yl}phenyl)pyrrolidin-2-one | 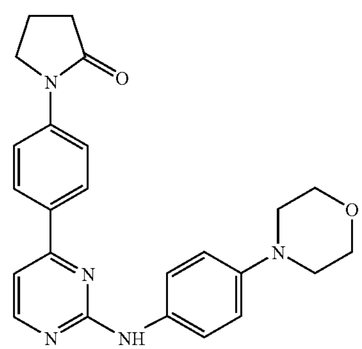 [SMILES: O=C1CCCN1c1ccc(-c2ccnc(Nc3ccc(N4CCOCC4)cc3)n2)cc1] | 25 |
| 716 | N-{4-[2-({4-[4-(cyclo-butylcarbonyl)piperazin-1-yl]phenyl}amino)pyrimidin-4-yl]phenyl}-D-alaninamide | 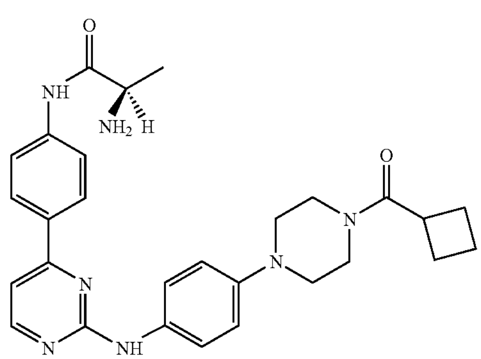 [SMILES: C[C@@H](N)C(=O)Nc1ccc(-c2ccnc(Nc3ccc(N4CCN(C(=O)C5CCC5)CC4)cc3)n2)cc1] | 52 |

TABLE 1-continued

| Cmpd No. | Name | Structure | Can Be Made According To Synthetic Example #: |
|---|---|---|---|
| 717 | N-{4-[2-({4-[4-(2,2-dimethylpropanoyl)piperazin-1-yl]phenyl}amino)pyrimidin-4-yl]phenyl}-D-alaninamide | 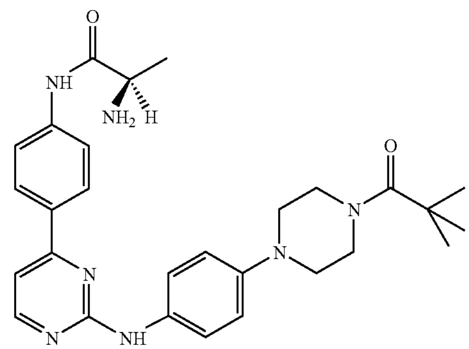 [SMILES: C[C@@H](N)C(=O)Nc1ccc(-c2ccnc(Nc3ccc(N4CCN(C(=O)C(C)(C)C)CC4)cc3)n2)cc1] | 52 |
| 718 | (2S)-2-hydroxy-3-methyl-N-(4-{2-[(4-morpholin-4-ylphenyl)amino]pyrimidin-4-yl}phenyl)butanamide | 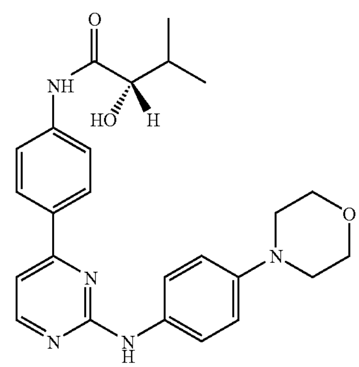 [SMILES: CC(C)[C@H](O)C(=O)Nc1ccc(-c2ccnc(Nc3ccc(N4CCOCC4)cc3)n2)cc1] | 18 |
| 719 | (2R)-2-hydroxy-3-methyl-N-(4-{2-[(4-morpholin-4-ylphenyl)amino]pyrimidin-4-yl}phenyl)butanamide | 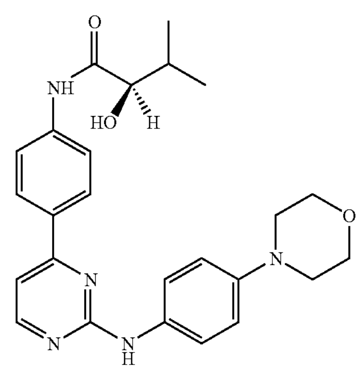 [SMILES: CC(C)[C@@H](O)C(=O)Nc1ccc(-c2ccnc(Nc3ccc(N4CCOCC4)cc3)n2)cc1] | 18 |
| 720 | N-{4-[2-({4-[4-(cyclopropylcarbonyl)piperazin-1-yl]phenyl}amino)pyrimidin-4-yl]phenyl}-D-alaninamide | 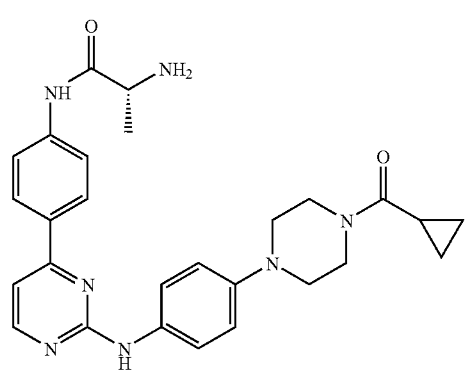 [SMILES: C[C@@H](N)C(=O)Nc1ccc(-c2ccnc(Nc3ccc(N4CCN(C(=O)C5CC5)CC4)cc3)n2)cc1] | 52 |

TABLE 1-continued

| Cmpd No. | Name | Structure | Can Be Made According To Synthetic Example #: |
|---|---|---|---|
| 721 | (2S)-2-amino-N-(4-{2-[(4-morpholin-4-ylphenyl)amino]pyrimidin-4-yl}phenyl)-2-phenylethanamide | 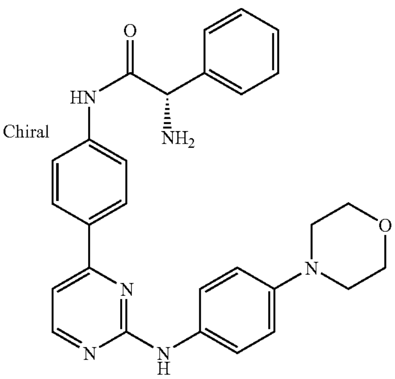 [SMILES: N[C@H](C(=O)Nc1ccc(-c2ccnc(Nc3ccc(N4CCOCC4)cc3)n2)cc1)c1ccccc1] | 45 |
| 722 | 2-amino-2-(4-chlorophenyl)-N-(4-{2-[(4-morpholin-4-ylphenyl)amino]pyrimidin-4-yl}phenyl)acetamide | 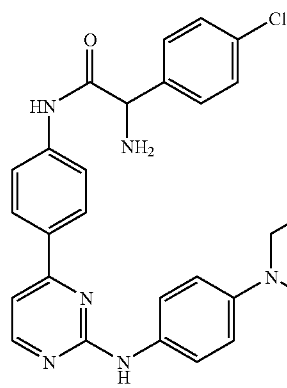 | 14 |
| 723 | N-(4-{2-[(4-morpholin-4-ylphenyl)amino]pyrimidin-4-yl}phenyl)morpholine-3-carboxamide | 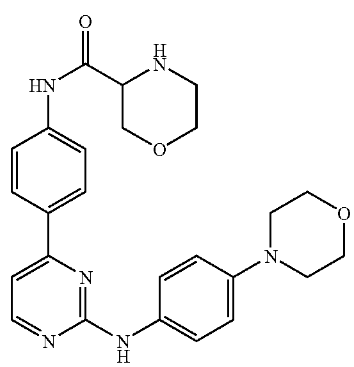 [SMILES: O=C(Nc1ccc(-c2ccnc(Nc3ccc(N4CCOCC4)cc3)n2)cc1)C1COCCN1] | 14 |
| 724 | 1-ethyl-3-[4-(2-{[4-(4-ethyl-piperazin-1-yl)-3-(methyloxy)phenyl]amino}pyrimidin-4-yl)phenyl]urea | 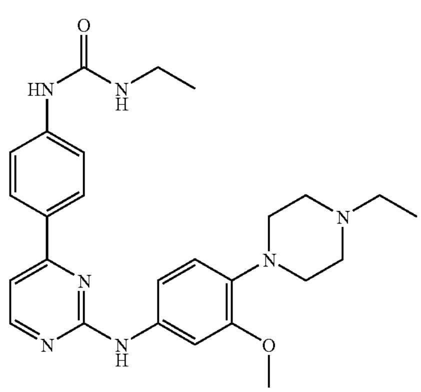 [SMILES: CCNC(=O)Nc1ccc(-c2ccnc(Nc3ccc(N4CCN(CC)CC4)c(OC)c3)n2)cc1] | 53 |

TABLE 1-continued

| Cmpd No. | Name | Structure | Can Be Made According To Synthetic Example #: |
|---|---|---|---|
| 725 | N-[4-(2-{[4-(4-ethyl-piperazin-1-yl)-3-(methyloxy)phenyl]amino}pyrimidin-4-yl)phenyl]-D-prolinamide | 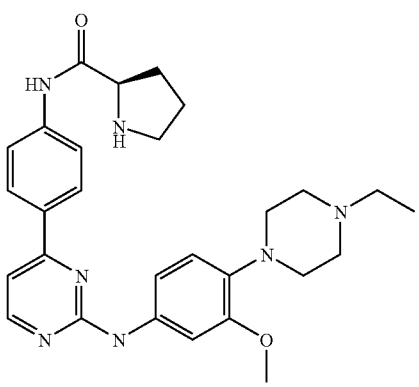 [SMILES: CCN1CCN(c2ccc(Nc3nccc(-c4ccc(NC(=O)[C@H]5CCCN5)cc4)n3)cc2OC)CC1] | 24 |
| 726 | N-[4-(2-{[4-(4-ethyl-piperazin-1-yl)-3-(methyloxy)phenyl]amino}pyrimidin-4-yl)phenyl]acetamide | 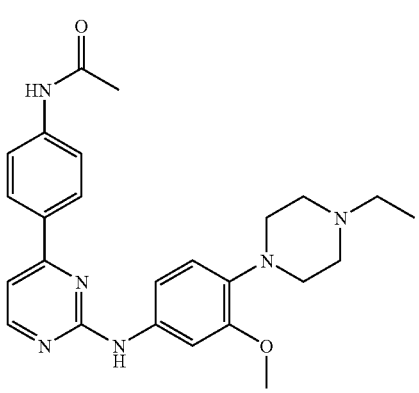 [SMILES: CCN1CCN(c2ccc(Nc3nccc(-c4ccc(NC(C)=O)cc4)n3)cc2OC)CC1] | 3 |
| 727 | 1-(2,6-dichlorophenyl)-3-(3-{[4-(4-methyl-2-thienyl)pyrimidin-2-yl]amino}propyl)urea | 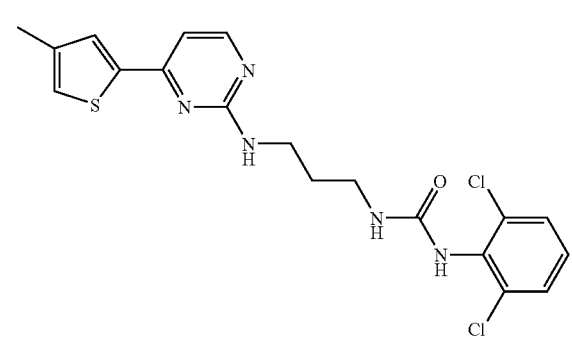 [SMILES: Cc1csc(-c2ccnc(NCCCNC(=O)Nc3c(Cl)cccc3Cl)n2)c1] | 27 |
| 728 | 1-[2-fluoro-5-(trifluoromethyl)phenyl]-3-(3-{[4-(4-methyl-2-thienyl)pyrimidin-2-yl]amino}propyl)urea | 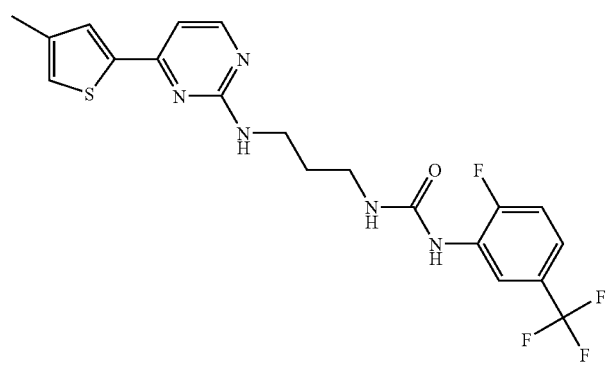 [SMILES: Cc1csc(-c2ccnc(NCCCNC(=O)Nc3cc(C(F)(F)F)ccc3F)n2)c1] | 27 |

TABLE 1-continued

| Cmpd No. | Name | Structure | Can Be Made According To Synthetic Example #: |
|---|---|---|---|
| 729 | 2,6-dichloro-N-[3-({4-[4-(dimethylamino)phenyl]pyrimidin-2-yl}amino)propyl]benzenesulfonamide | 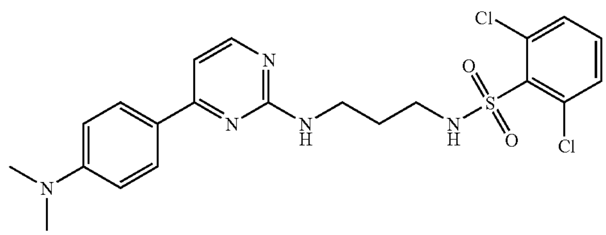 | 36 |
| 730 | N-[3-({4-[4-(dimethylamino)phenyl]pyrimidin-2-yl}amino)propyl]-2,6-difluoro-benzenesulfonamide | 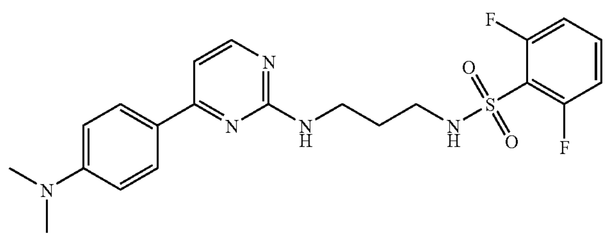 [SMILES: CN(C)c1ccc(-c2ccnc(NCCCNS(=O)(=O)c3c(F)cccc3F)n2)cc1] | 36 |
| 731 | N-[3-({4-[4-(dimethylamino)phenyl]pyrimidin-2-yl}amino)propyl]naphthalene-2-sulfonamide | 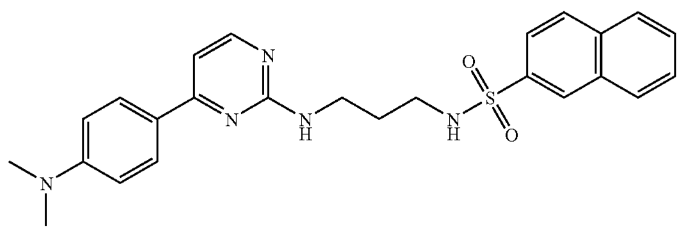 [SMILES: CN(C)c1ccc(-c2ccnc(NCCCNS(=O)(=O)c3ccc4ccccc4c3)n2)cc1] | 36 |
| 732 | N-[3-({4-[4-(dimethylamino)phenyl]pyrimidin-2-yl}amino)propyl]-3,4-bis(methyloxy)benzenesulfonamide | 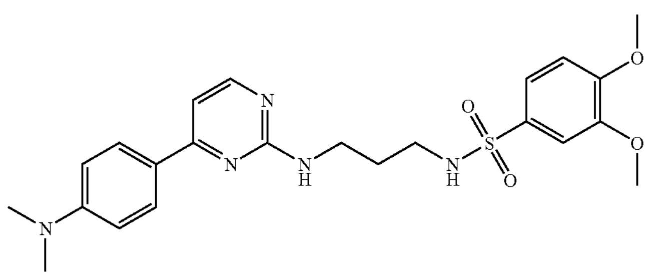 | 36 |
| 733 | 3-chloro-N-[3-({4-[4-(dimethylamino)phenyl]pyrimidin-2-yl}amino)propyl]propane-1-sulfonamide | 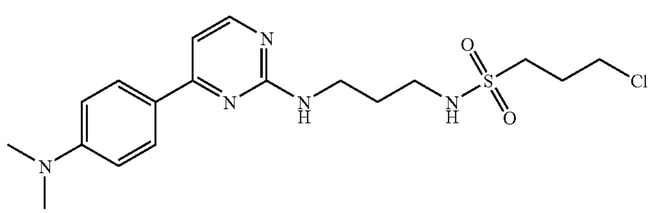 [SMILES: CN(C)c1ccc(-c2ccnc(NCCCNS(=O)(=O)CCCCl)n2)cc1] | 36 |
| 734 | N-[3-({4-[4-(dimethylamino)phenyl]pyrimidin-2-yl}amino)propyl]propane-1-sulfonamide | 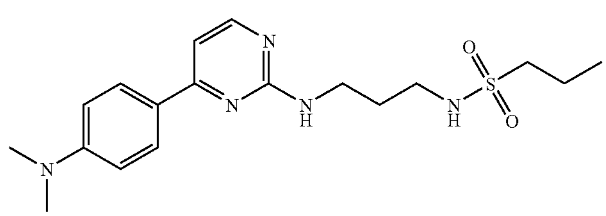 [SMILES: CCCS(=O)(=O)NCCCNc1nccc(-c2ccc(N(C)C)cc2)n1] | 17 |

TABLE 1-continued

| Cmpd No. | Name | Structure | Can Be Made According To Synthetic Example #: |
|---|---|---|---|
| 735 | methyl (3-{[4-(2,4-dichlorophenyl)pyrimidin-2-yl]amino}propyl)carbamate | 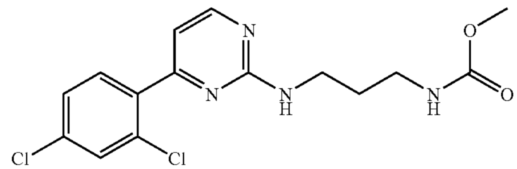 [SMILES: COC(=O)NCCCNc1nccc(-c2ccc(Cl)cc2Cl)n1] | 17 |
| 736 | 1-methylethyl (3-{[4-(2,4-dichlorophenyl)pyrimidin-2-yl]amino}propyl)carbamate | 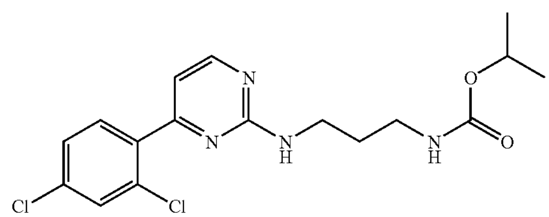 [SMILES: CC(C)OC(=O)NCCCNc1nccc(-c2ccc(Cl)cc2Cl)n1] | 17 |
| 737 | phenylmethyl (3-{[4-(2,4-dichlorophenyl)pyrimidin-2-yl]amino}propyl)carbamate | 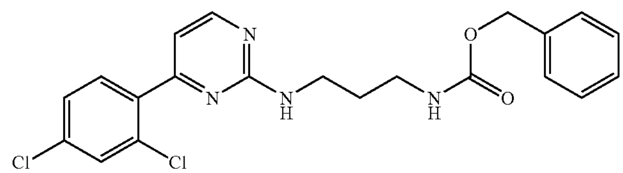 [SMILES: O=C(NCCCNc1nccc(-c2ccc(Cl)cc2Cl)n1)OCc1ccccc1] | 17 |
| 738 | N-{4-[2-({[3-(3-chlorophenyl)isoxazol-5-yl]methyl}amino)pyrimidin-4-yl]phenyl}acetamide | 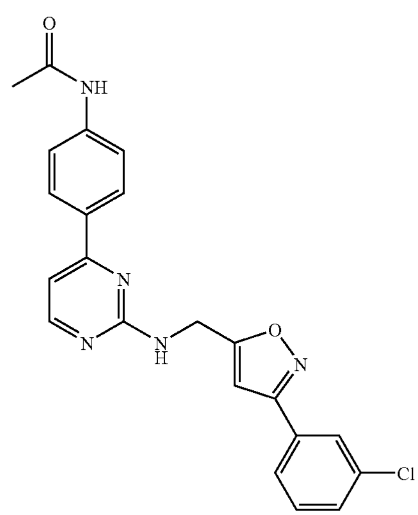 [SMILES: CC(=O)Nc1ccc(-c2ccnc(NCc3cc(-c4cccc(Cl)c4)no3)n2)cc1] | 3 |
| 739 | ethyl 4-({4-[4-(acetylamino)phenyl]pyrimidin-2-yl}amino)piperidine-1-carboxylate | 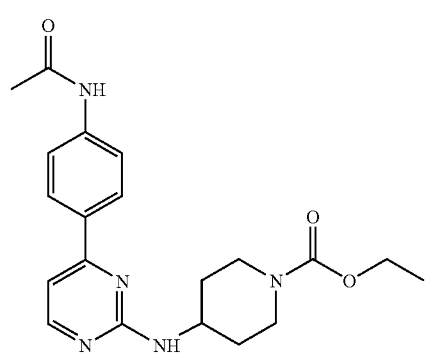 [SMILES: CCOC(=O)N1CCC(Nc2nccc(-c3ccc(NC(C)=O)cc3)n2)CC1] | 17 |

TABLE 1-continued

| Cmpd No. | Name | Structure | Can Be Made According To Synthetic Example #: |
|---|---|---|---|
| 740 | 1,1-dimethylethyl 4-({4-[4-(acetylamino)phenyl]pyrimidin-2-yl}amino)piperidine-1-carboxylate | 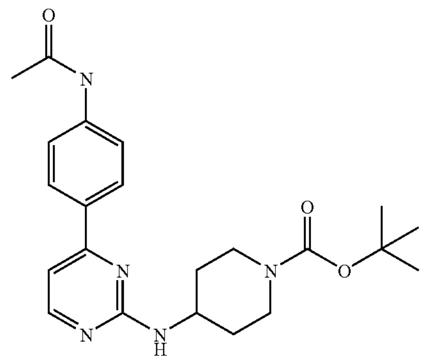 [SMILES: CC(=O)Nc1ccc(-c2ccnc(NC3CCN(C(=O)OC(C)(C)C)CC3)n2)cc1] | 1 |
| 741 | N-(4-{2-[(4-cyanophenyl)amino]pyrimidin-4-yl}phenyl)acetamide | 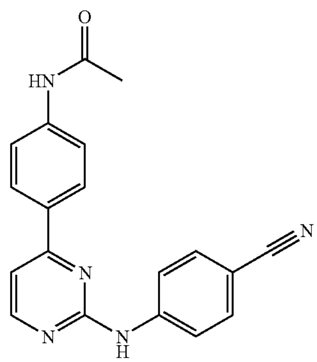 [SMILES: CC(=O)Nc1ccc(-c2ccnc(Nc3ccc(C#N)cc3)n2)cc1] | 3 |
| 742 | N-(4-{2-[(4-morpholin-4-ylphenyl)amino]pyridin-4-yl}phenyl)acetamide | 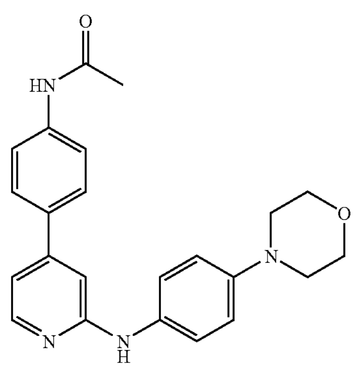 [SMILES: CC(=O)Nc1ccc(-c2ccnc(Nc3ccc(N4CCOCC4)cc3)c2)cc1] | 51 |
| 743 | 1,1-dimethylethyl {1-[4-({4-[4-(acetylamino)phenyl]pyrimidin-2-yl}amino)phenyl]piperidin-4-yl}carbamate | 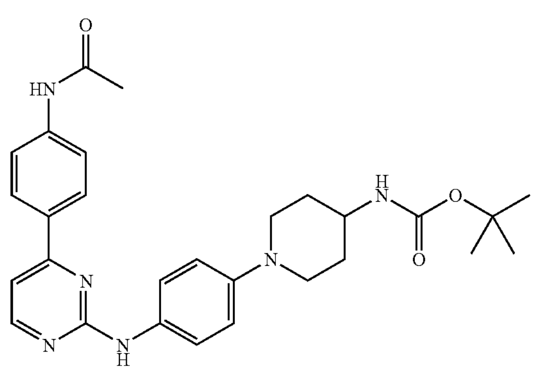 [SMILES: CC(=O)Nc1ccc(-c2ccnc(Nc3ccc(N4CCC(NC(=O)OC(C)(C)C)CC4)cc3)n2)cc1] | 1 |

TABLE 1-continued

| Cmpd No. | Name | Structure | Can Be Made According To Synthetic Example #: |
|---|---|---|---|
| 744 | N-{4-[2-({4-[4-(cyclo-propylcarbonyl)piperazin-1-yl]phenyl}amino)pyrimidin-4-yl]phenyl}cyclopropane-carboxamide | 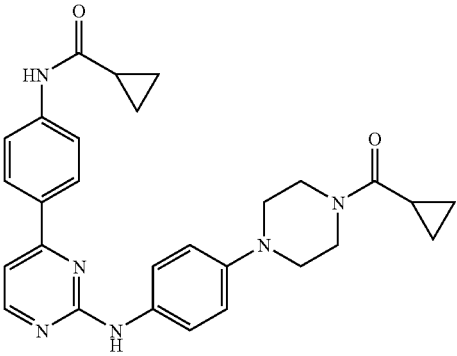 [SMILES: O=C(Nc1ccc(-c2ccnc(Nc3ccc(N4CCN(C(=O)C5CC5)CC4)cc3)n2)cc1)C1CC1] | 52 |
| 745 | N-{1-[4-({4-[4-(acetylamino)phenyl]pyrimidin-2-yl}amino)phenyl]piperidin-4-yl}acetamide | 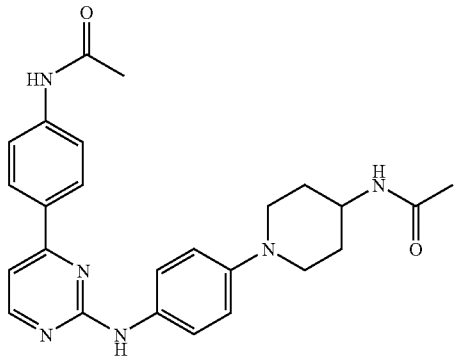 [SMILES: CC(=O)Nc1ccc(-c2ccnc(Nc3ccc(N4CCC(NC(C)=O)CC4)cc3)n2)cc1] | 1 |
| 746 | 4-(4-aminophenyl)-N-[4-(4-aminopiperidin-1-yl)phenyl]pyrimidin-2-amine | 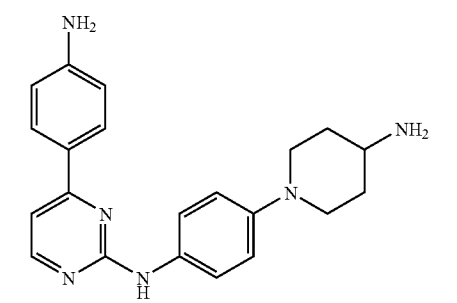 [SMILES: Nc1ccc(-c2ccnc(Nc3ccc(N4CCC(N)CC4)cc3)n2)cc1] | 1 |
| 747 | N-[4-(2-{[4-(4-ethyl-piperazin-1-yl)phenyl]amino}-5-methylpyrimidin-4-yl)phenyl]-3-(methyloxy)propanamide | 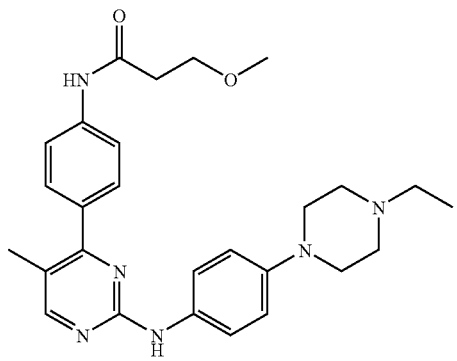 [SMILES: CCN1CCN(c2ccc(Nc3ncc(C)c(-c4ccc(NC(=O)CCOC)cc4)n3)cc2)CC1] | 51 |

TABLE 1-continued

| Cmpd No. | Name | Structure | Can Be Made According To Synthetic Example #: |
|---|---|---|---|
| 748 | N-{4-[2-({4-[4-(2-methyl-propanoyl)piperazin-1-yl]phenyl}amino)pyrimidin-4-yl]phenyl}tetrahydrofuran-2-carboxamide | 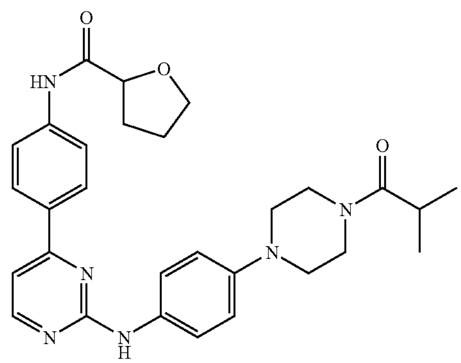 [SMILES: CC(C)C(=O)N1CCN(c2ccc(Nc3nccc(-c4ccc(NC(=O)C5CCCO5)cc4)n3)cc2)CC1] | 52 |
| 749 | N-{4-[2-({4-[4-(cyclobutyl-carbonyl)piperazin-1-yl]phenyl}amino)pyrimidin-4-yl]phenyl}tetrahydrofuran-2-carboxamide | 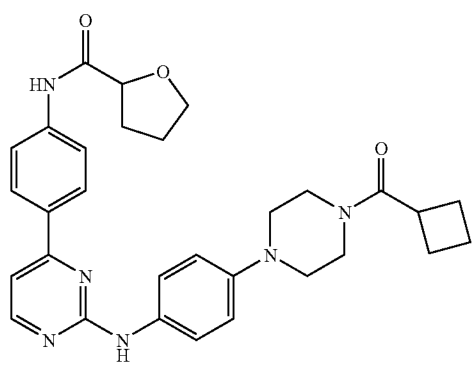 [SMILES: O=C(Nc1ccc(-c2ccnc(Nc3ccc(N4CCN(C(=O)C5CCC5)CC4)cc3)n2)cc1)C1CCCO1] | 52 |
| 750 | N-{4-[2-({4-[4-(2,2-dimethylpropanoyl)piperazin-1-yl]phenyl}amino)pyrimidin-4-yl]phenyl}tetrahydrofuran-2-carboxamide | 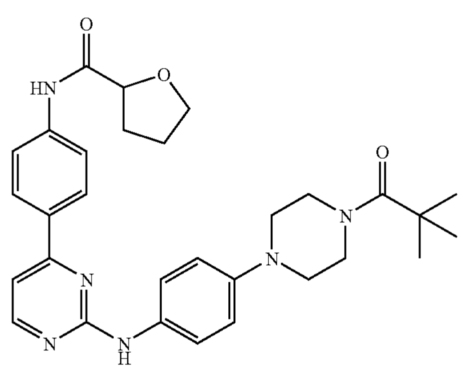 [SMILES: CC(C)(C)C(=O)N1CCN(c2ccc(Nc3nccc(-c4ccc(NC(=O)C5CCCO5)cc4)n3)cc2)CC1] | 52 |
| 751 | N-cyclopropyl-4-{2-[(4-morpholin-4-ylphenyl)amino]pyrimidin-4-yl}benzamide | 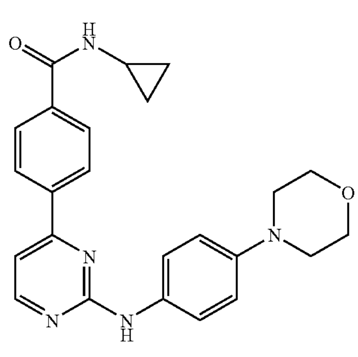 [SMILES: O=C(NC1CC1)c1ccc(-c2ccnc(Nc3ccc(N4CCOCC4)cc3)n2)cc1] | 9 |

TABLE 1-continued

| Cmpd No. | Name | Structure | Can Be Made According To Synthetic Example #: |
|---|---|---|---|
| 752 | N-[2-(methyloxy)ethyl]-4-{2-[(4-morpholin-4-ylphenyl)amino]pyrimidin-4-yl}benzamide | 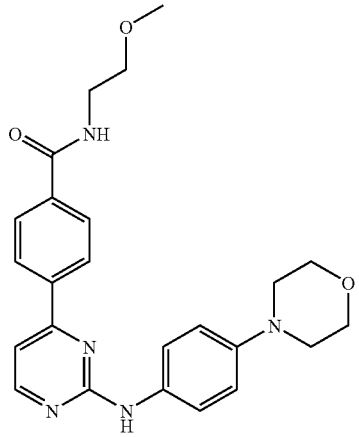 [SMILES: COCCNC(=O)c1ccc(-c2ccnc(Nc3ccc(N4CCOCC4)cc3)n2)cc1] | 9 |
| 753 | 2,6-dichloro-N-{3-[(4-pyridin-3-ylpyrimidin-2-yl)amino]propyl}benzamide | 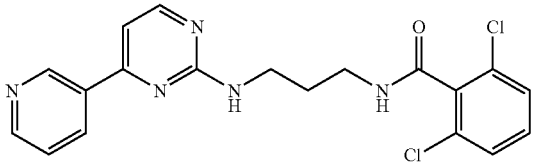 [SMILES: O=C(NCCCNc1nccc(-c2cccnc2)n1)c1c(Cl)cccc1Cl] | 27 |
| 754 | 2,6-dichloro-N-(3-{[4-(4-methyl-3,4-dihydro-2H-1,4-benzoxazin-7-yl)pyrimidin-2-yl]amino}propyl)benzamide | 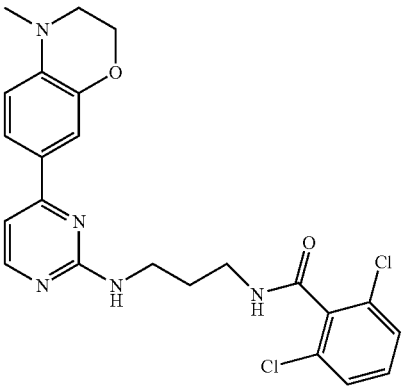 [SMILES: CN1CCOc2cc(-c3ccnc(NCCCNC(=O)c4c(Cl)cccc4Cl)n3)ccc21] | 27 |
| 755 | 2,6-dichloro-N-(3-{[4-(2,3-dihydro-1,4-benzodioxin-6-yl)-6-methylpyrimidin-2-yl]amino}propyl)benzamide | 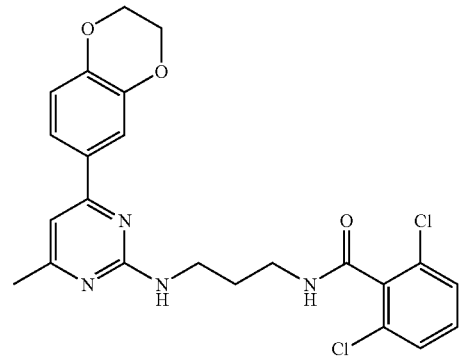 [SMILES: Cc1cc(-c2ccc3c(c2)OCCO3)nc(NCCCNC(=O)c2c(Cl)cccc2Cl)n1] | 27 |

TABLE 1-continued

| Cmpd No. | Name | Structure | Can Be Made According To Synthetic Example #: |
|---|---|---|---|
| 756 | N-(4-{2-[(3-{[(2,6-dichlorophenyl)carbonyl]amino}propyl)amino]pyrimidin-4-yl}phenyl)morpholine-4-carboxamide | 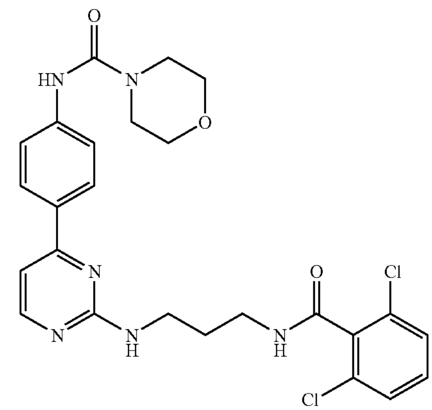 [SMILES: O=C(NCCCNc1nccc(-c2ccc(NC(=O)N3CCOCC3)cc2)n1)c1c(Cl)cccc1Cl] | 27 |
| 757 | 2,6-dichloro-N-{3-[(4-{4-[(cyclopropyrcarbonyl)amino]phenyl}pyrimidin-2-yl)amino]propyl}benzamide | 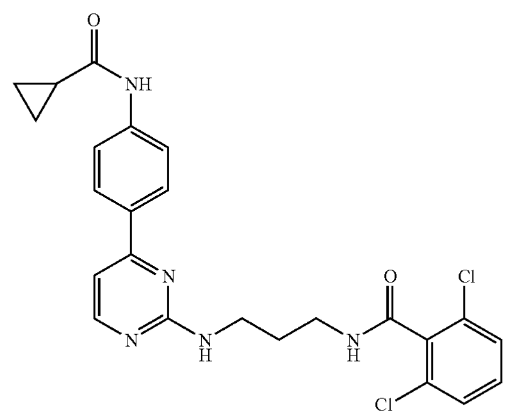 [SMILES: O=C(NCCCNc1nccc(-c2ccc(NC(=O)C3CC3)cc2)n1)c1c(Cl)cccc1Cl] | 27 |
| 758 | N-(4-{2-[(3-{[(2,6-dichlorophenyl)carbonyl]amino}propyl)amino]pyrimidin-4-yl}phenyl)thiophene-2-carboxamide | 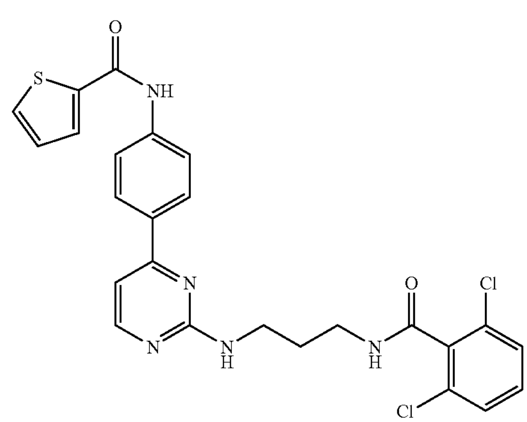 [SMILES: O=C(Nc1ccc(-c2ccnc(NCCCNC(=O)c3c(Cl)cccc3Cl)n2)cc1)c1cccs1] | 27 |

TABLE 1-continued

| Cmpd No. | Name | Structure | Can Be Made According To Synthetic Example #: |
|---|---|---|---|
| 759 | 2,6-dichloro-N-(3-{[4-(4-{[N-(2-morpholin-4-ylethyl)glycyl]amino}phenyl)pyrimidin-2-yl]amino}propyl)benzamide | 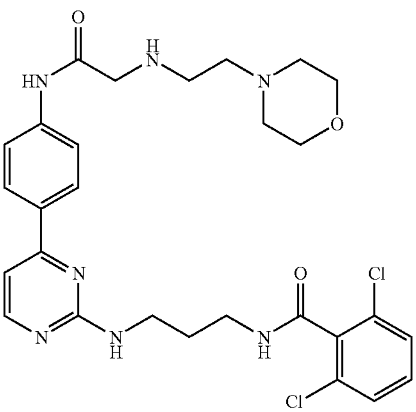 [SMILES: O=C(CNCCN1CCOCC1)Nc1ccc(-c2ccnc(NCCCNC(=O)c3c(Cl)cccc3Cl)n2)cc1] | 27 |
| 760 | 1-(4-{2-[(4-morpholin-4-ylphenyl)amino]pyrimidin-4-yl}phenyl)ethanone | 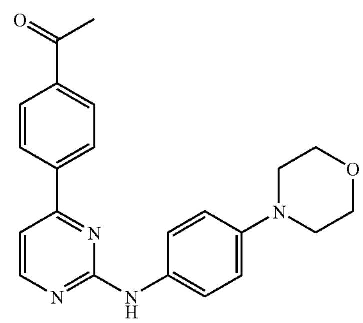 [SMILES: CC(=O)c1ccc(-c2ccnc(Nc3ccc(N4CCOCC4)cc3)n2)cc1] | 9 |
| 761 | (1E)-1-(4-{2-[(4-morpholin-4-ylphenyl)amino]pyrimidin-4-yl}phenyl)ethanoneoxime | 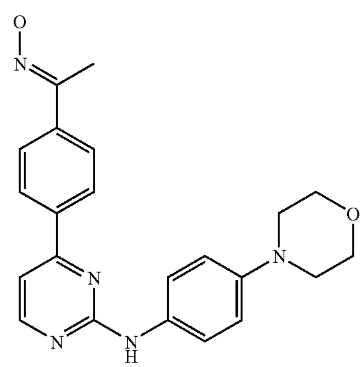 [SMILES: C/C(=N\O)c1ccc(-c2ccnc(Nc3ccc(N4CCOCC4)cc3)n2)cc1] | 9 |
| 762 | N-{4-[2-({4-[4-(cyclopropylcarbonyl)piperazin-1-yl]phenyl}amino)pyrimidin-4-yl]phenyl}-2-phenylacetamide | 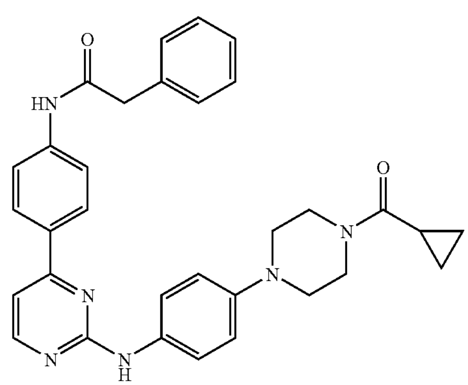 [SMILES: O=C(Cc1ccccc1)Nc1ccc(-c2ccnc(Nc3ccc(N4CCN(C(=O)C5CC5)CC4)cc3)n2)cc1] | 7 |

TABLE 1-continued

| Cmpd No. | Name | Structure | Can Be Made According To Synthetic Example #: |
|---|---|---|---|
| 763 | N-[3-({4-[4-(acetylamino) phenyl]pyrimidin-2-yl} amino)propyl]-2-bromobenzamide | 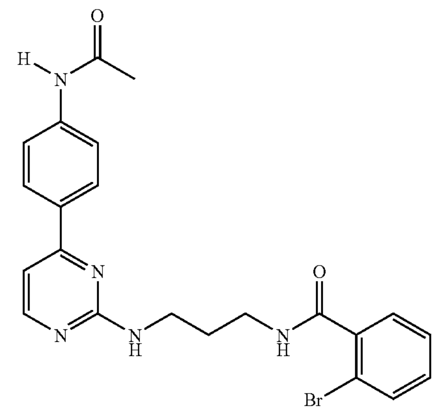 | 27 |
| 764 | N-[3-({4-[4-(acetylamino) phenyl]pyrimidin-2-yl} amino)propyl]-2-fluorobenzamide | 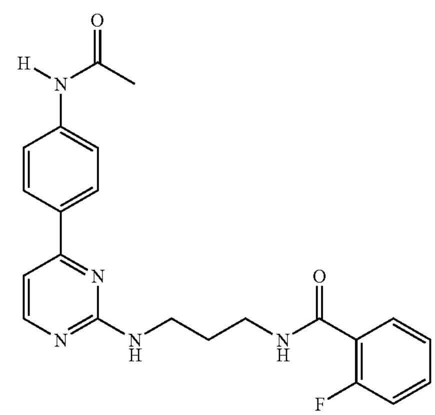 [SMILES: CC(=O)Nc1ccc(-c2ccnc(NCCCNC(=O)c3ccccc3F)n2)cc1] | 27 |
| 765 | N-[3-({4-[4-(acetylamino) phenyl]pyrimidin-2-yl} amino)propyl]-2-chlorobenzamide | 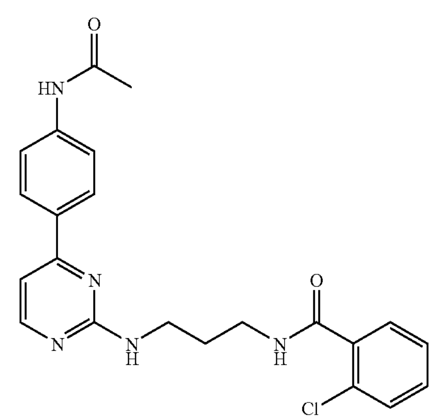 [SMILES: CC(=O)Nc1ccc(-c2ccnc(NCCCNC(=O)c3ccccc3Cl)n2)cc1] | 27 |

TABLE 1-continued

| Cmpd No. | Name | Structure | Can Be Made According To Synthetic Example #: |
|---|---|---|---|
| 766 | N-[4-(2-{[3-(morpholin-4-ylsulfonyl)phenyl]amino}pyrimidin-4-yl)phenyl]acetamide | 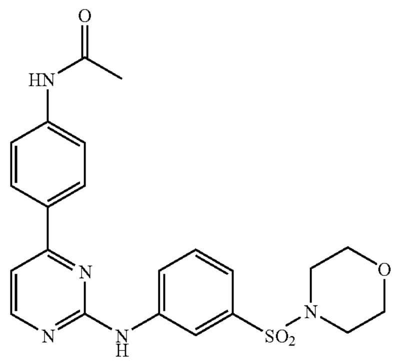 | 36 |
| 767 | N-{4-[2-({3-[(cyclohexylmethyl)amino]phenyl}amino)pyrimidin-4-yl]phenyl}acetamide | 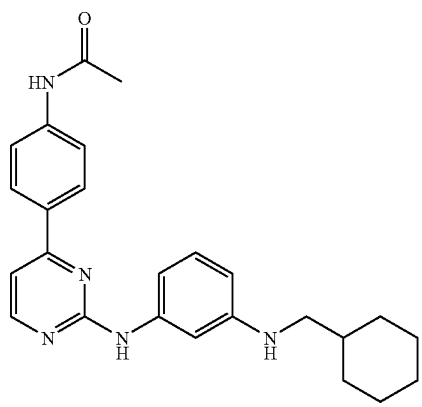 [SMILES: CC(=O)Nc1ccc(-c2ccnc(Nc3cccc(NCC4CCCCC4)c3)n2)cc1] | 28 |
| 768 | N-(4-{2-[(3-{[(5-bromo-2-fluorophenyl)methyl]amino}phenyl)amino]pyrimidin-4-yl}phenyl)acetamide | 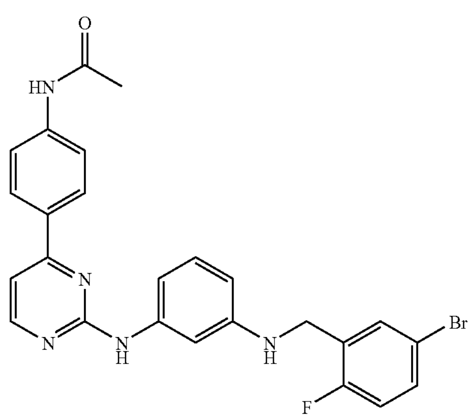 [SMILES: CC(=O)Nc1ccc(-c2ccnc(Nc3cccc(NCc4cc(Br)ccc4F)c3)n2)cc1] | 28 |

TABLE 1-continued

| Cmpd No. | Name | Structure | Can Be Made According To Synthetic Example #: |
|---|---|---|---|
| 769 | N-(4-{2-[(3-{[(2,5-dimethyl-phenyl)methyl]amino}phenyl)amino]pyrimidin-4-yl}phenyl)acetamide | 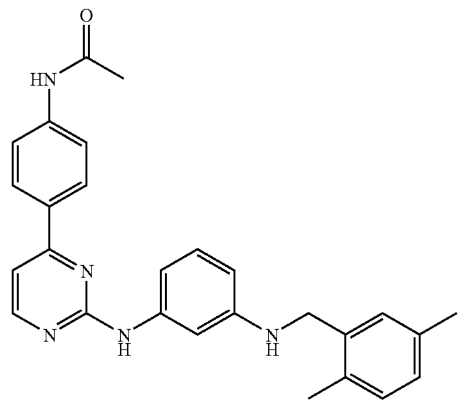 [SMILES: CC(=O)Nc1ccc(-c2ccnc(Nc3cccc(NCc4cc(C)ccc4C)c3)n2)cc1] | 28 |
| 770 | N-(4-{2-[(3,4-dimorpholin-4-ylphenyl)amino]pyrimidin-4-yl}phenyl)acetamide | 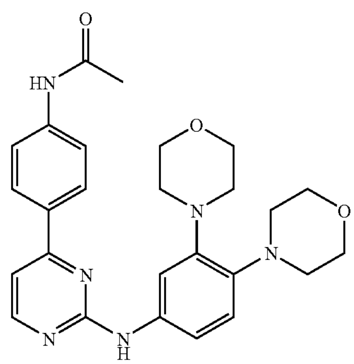 [SMILES: CC(=O)Nc1ccc(-c2ccnc(Nc3ccc(N4CCOCC4)c(N4CCOCC4)c3)n2)cc1] | 6 |
| 771 | N-{4-[2-({4-[4-(pyridin-3-ylcarbonyl)piperazin-1-yl]phenyl}amino)pyrimidin-4-yl]phenyl}cyclopropane-carboxamide | 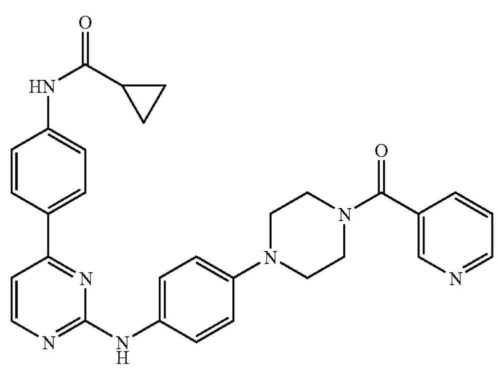 [SMILES: O=C(Nc1ccc(-c2ccnc(Nc3ccc(N4CCN(C(=O)c5cccnc5)CC4)cc3)n2)cc1)C1CC1] | 52 |
| 772 | N-{4-[2-({4-[4-(2-methyl-propanoyl)piperazin-1-yl]phenyl}amino)pyrimidin-4-yl]phenyl}butanamide | 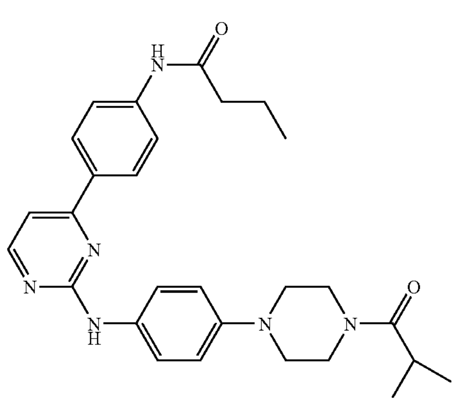 [SMILES: CCCC(=O)Nc1ccc(-c2ccnc(Nc3ccc(N4CCN(C(=O)C(C)C)CC4)cc3)n2)cc1] | 52 |

TABLE 1-continued

| Cmpd No. | Name | Structure | Can Be Made According To Synthetic Example #: |
|---|---|---|---|
| 773 | N-{4-[2-({4-[4-(2,2-dimethylpropanoyl)piperazin-1-yl]phenyl}amino)pyrimidin-4-yl]phenyl}butanamide | 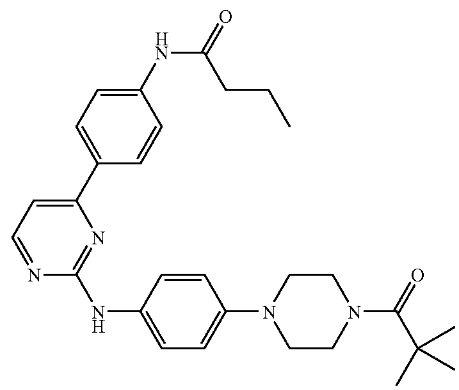 [SMILES: CCCC(=O)Nc1ccc(-c2ccnc(Nc3ccc(N4CCN(C(=O)C(C)(C)C)CC4)cc3)n2)cc1] | 52 |
| 774 | N-{4-[2-((4-[4-(cyclobutylcarbonyl)piperazin-1-yl]phenyl}amino)pyrimidin-4-yl]phenyl}butanamide | 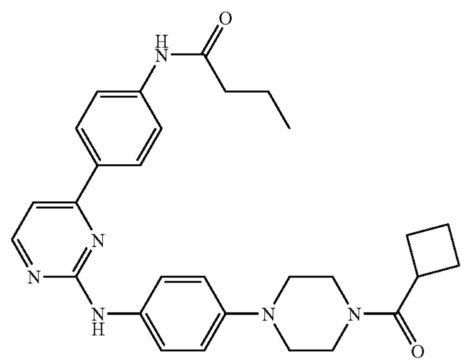 [SMILES: CCCC(=O)Nc1ccc(-c2ccnc(Nc3ccc(N4CCN(C(=O)C5CCC5)CC4)cc3)n2)cc1] | 52 |
| 775 | N-(4-{2-[(4-morpholin-4-ylphenyl)amino]pyrimidin-4-yl}phenyl)pyridine-2-carboxamide | 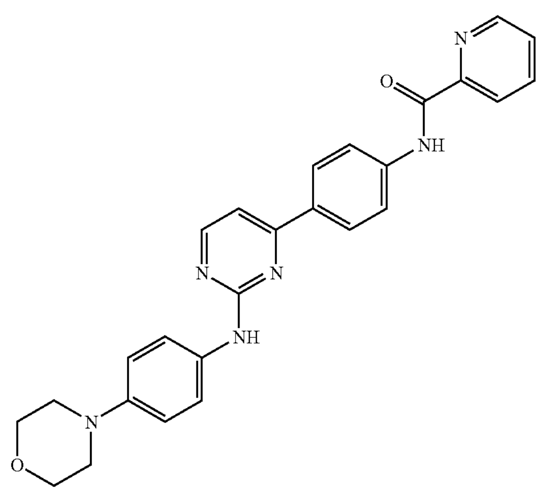 [SMILES: O=C(Nc1ccc(-c2ccnc(Nc3ccc(N4CCOCC4)cc3)n2)cc1)c1ccccn1] | 12 |

TABLE 1-continued

| Cmpd No. | Name | Structure | Can Be Made According To Synthetic Example #: |
|---|---|---|---|
| 776 | 2-hydroxy-N-(4-{2-[(4-morpholin-4-ylphenyl)amino]pyrimidin-4-yl}phenyl)benzamide | 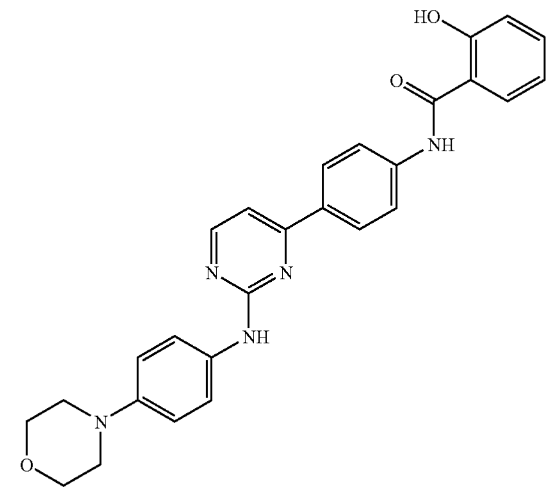 [SMILES: O=C(Nc1ccc(-c2ccnc(Nc3ccc(N4CCOCC4)cc3)n2)cc1)c1ccccc1O] | 12 |
| 777 | 3-(methyloxy)-N-(4-{2-[(4-morpholin-4-ylphenyl)amino]pyrimidin-4-yl}phenyl)benzamide | 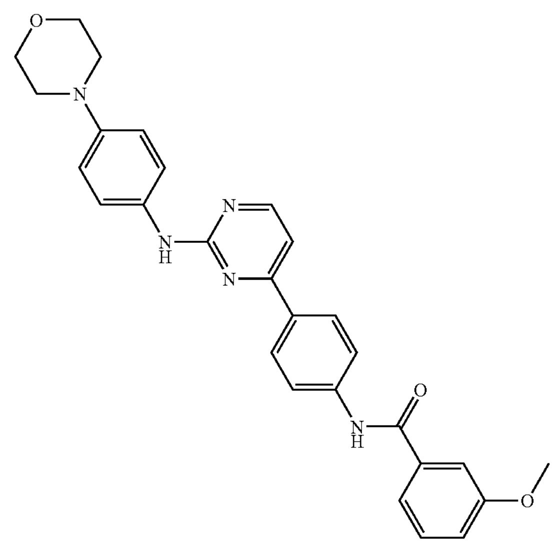 [SMILES: COc1cccc(C(=O)Nc2ccc(-c3ccnc(Nc4ccc(N5CCOCC5)cc4)n3)cc2)c1] | 12 |
| 778 | 4-(methyloxy)-N-(4-{2-[(4-morpholin-4-ylphenyl)amino]pyrimidin-4-yl}phenyl)benzamide | 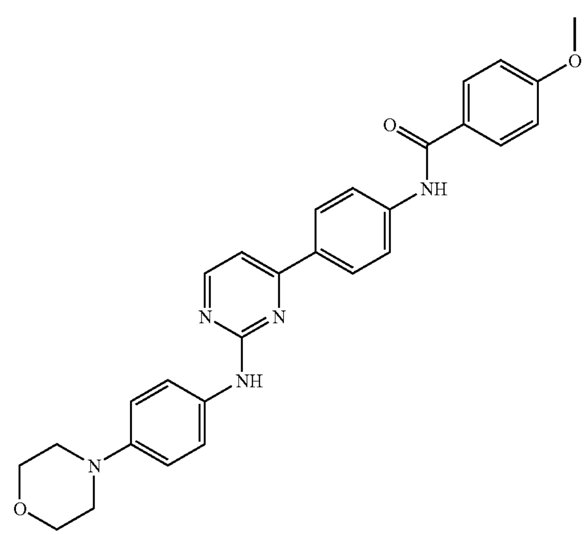 [SMILES: COc1ccc(C(=O)Nc2ccc(-c3ccnc(Nc4ccc(N5CCOCC5)cc4)n3)cc2)cc1] | 12 |

TABLE 1-continued

| Cmpd No. | Name | Structure | Can Be Made According To Synthetic Example #: |
|---|---|---|---|
| 779 | 4-chloro-N-(4-{2-[(4-morpholin-4-ylphenyl)amino]pyrimidin-4-yl}phenyl)benzamide | 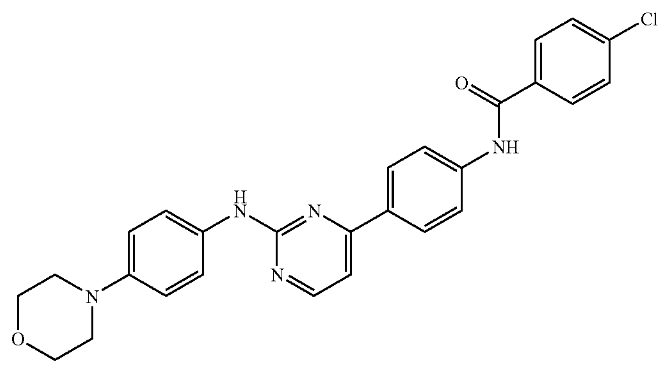 [SMILES: O=C(Nc1ccc(-c2ccnc(Nc3ccc(N4CCOCC4)cc3)n2)cc1)c1ccc(Cl)cc1] | 12 |
| 780 | (2R)-N-[4-(2-{[4-(4-ethyl-piperazin-1-yl)phenyl]amino}pyrimidin-4-yl)phenyl]tetra-hydrofuran-2-carboxamide | 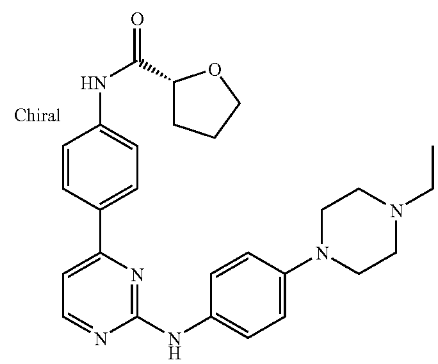 [SMILES: CCN1CCN(c2ccc(Nc3nccc(-c4ccc(NC(=O)[C@H]5CCCO5)cc4)n3)cc2)CC1] | 51 |
| 781 | (2S)-N-[4-(2-{[4-(4-ethyl-piperazin-1-yl)phenyl]amino}pyrimidin-4-yl)phenyl]tetra-hydrofuran-2-carboxamide | 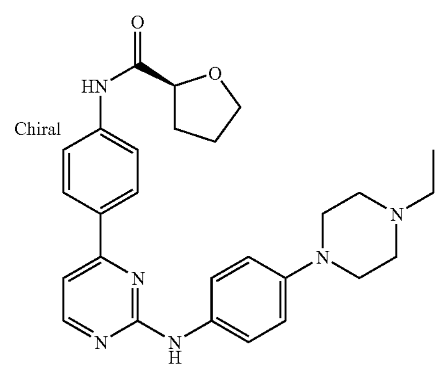 [SMILES: CCN1CCN(c2ccc(Nc3nccc(-c4ccc(NC(=O)[C@@H]5CCCO5)cc4)n3)cc2)CC1] | 51 |
| 782 | 1-(2-hydroxyethyl)-N-(4-{2-[(4-morpholin-4-ylphenyl)amino]pyrimidin-4-yl}phenyl)-L-prolinamide | 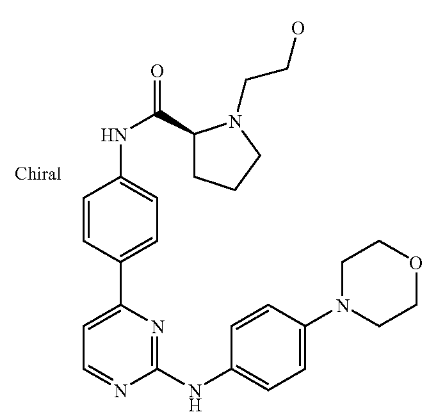 [SMILES: O=C(Nc1ccc(-c2ccnc(Nc3ccc(N4CCOCC4)cc3)n2)cc1)[C@@H]1CCCN1CCO] | 42 |

TABLE 1-continued

| Cmpd No. | Name | Structure | Can Be Made According To Synthetic Example #: |
|---|---|---|---|
| 783 | N-(4-{2-[(4-morpholin-4-ylphenyl)amino]pyrimidin-4-yl}phenyl)thiophene-2-carboxamide | 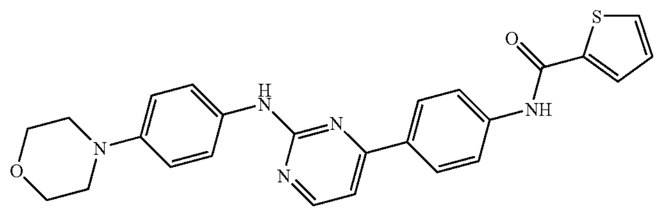 [SMILES: O=C(Nc1ccc(-c2ccnc(Nc3ccc(N4CCOCC4)cc3)n2)cc1)c1cccs1] | 12 |
| 784 | N-[4-(2-{[4-(4-ethylpiperazin-1-yl)phenyl]amino}pyrimidin-4-yl)phenyl]tetrahydrofuran-3-carboxamide | 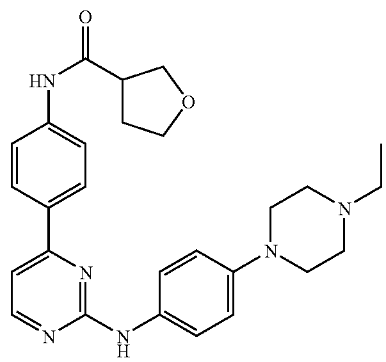 [SMILES: CCN1CCN(c2ccc(Nc3nccc(-c4ccc(NC(=O)C5CCOC5)cc4)n3)cc2)CC1] | 51 |
| 785 | 2-phenyl-N-{4-[2-({4-[4-(pyridin-3-ylcarbonyl)piperazin-1-yl]phenyl}amino)pyrimidin-4-yl]phenyl}acetamide | 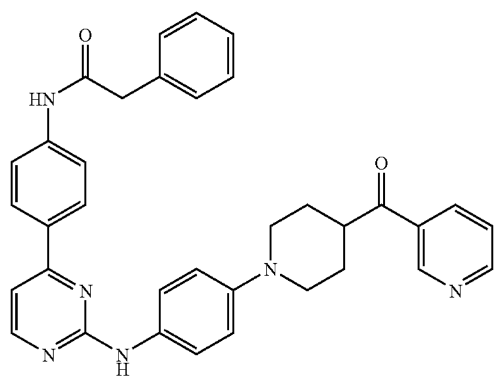 [SMILES: O=C(Cc1ccccc1)Nc1ccc(-c2ccnc(Nc3ccc(N4CCC(C(=O)c5cccnc5)CC4)cc3)n2)cc1] | 52 |
| 786 | 3-({4-[4-(acetylamino)phenyl]pyrimidin-2-yl}amino)-N-(diphenylmethyl)benzamide | 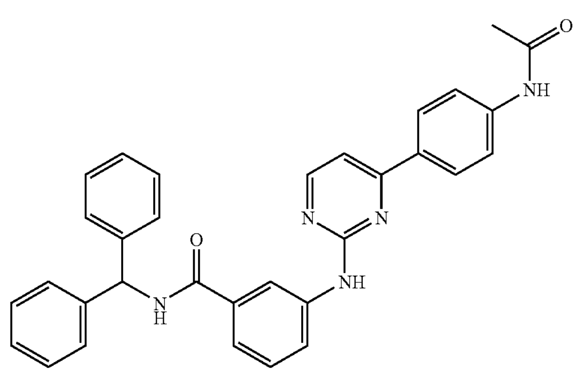 [SMILES: CC(=O)Nc1ccc(-c2ccnc(Nc3cccc(C(=O)NC(c4ccccc4)c4ccccc4)c3)n2)cc1] | 3 |

| Cmpd No. | Name | Structure | Can Be Made According To Synthetic Example #: |
|---|---|---|---|
| 787 | N-[4-(2-{[4-(4-methyl-piperazin-1-yl)phenyl]amino}pyrimidin-4-yl)phenyl]acetamide | 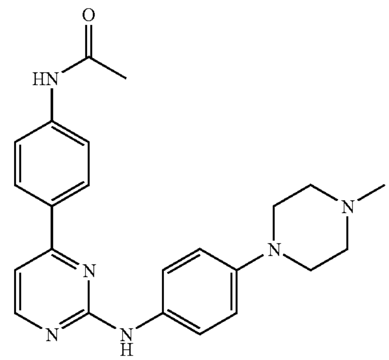 [SMILES: CC(=O)Nc1ccc(-c2ccnc(Nc3ccc(N4CCN(C)CC4)cc3)n2)cc1] | 51 |
| 788 | N-{4-[2-({4-[4-(phenyl-carbonyl)piperazin-1-yl]phenyl}amino)pyrimidin-4-yl]phenyl}acetamide | 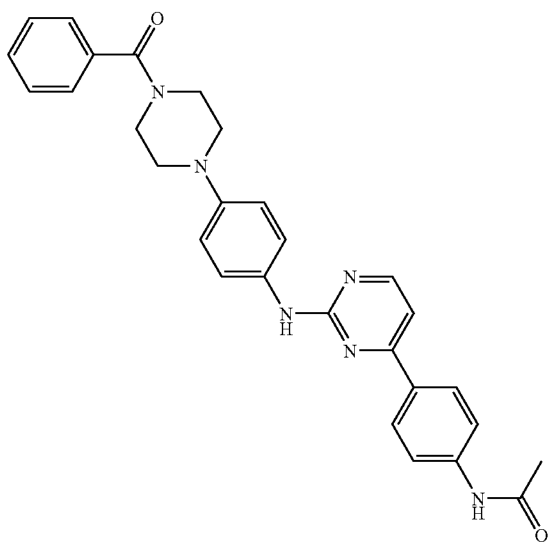 [SMILES: CC(=O)Nc1ccc(-c2ccnc(Nc3ccc(N4CCN(C(=O)c5ccccc5)CC4)cc3)n2)cc1] | 7 |
| 789 | N-{4-[2-({4-[4-(2-cyclo-pentylacetyl)piperazin-1-yl]phenyl}amino)pyrimidin-4-yl]phenyl}acetamide | 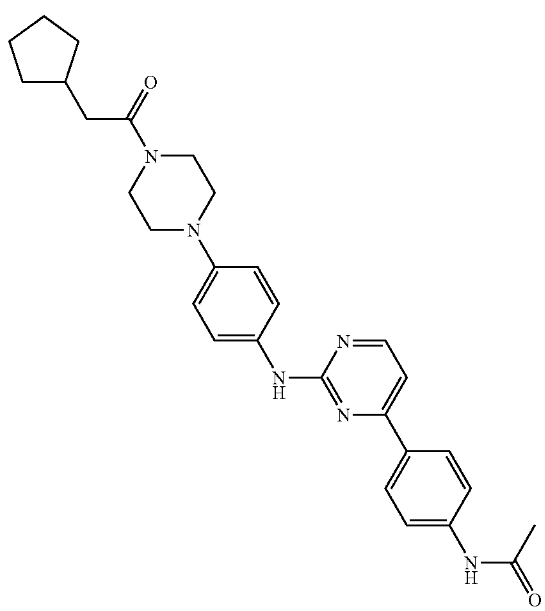 [SMILES: CC(=O)Nc1ccc(-c2ccnc(Nc3ccc(N4CCN(C(=O)CC5CCCC5)CC4)cc3)n2)cc1] | 7 |

TABLE 1-continued

| Cmpd No. | Name | Structure | Can Be Made According To Synthetic Example #: |
|---|---|---|---|
| 790 | N-{4-[2-({4-[4-(cyclo-hexylcarbonyl)piperazin-1-yl]phenyl}amino)pyrimidin-4-yl]phenyl}acetamide | 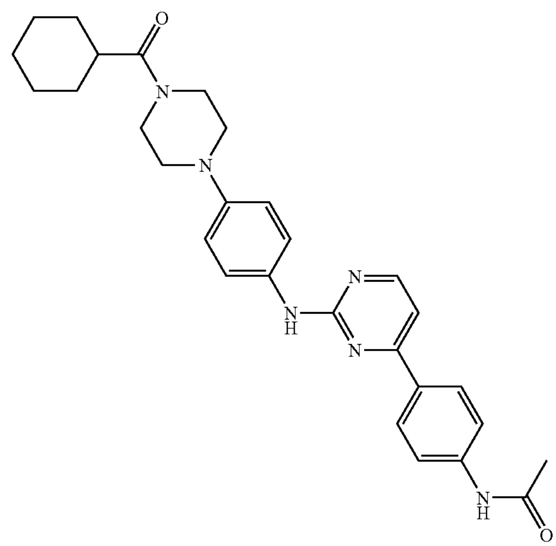 [SMILES: CC(=O)Nc1ccc(-c2ccnc(Nc3ccc(N4CCN(C(=O)C5CCCCC5)CC4)cc3)n2)cc1] | 7 |
| 791 | N-(4-{2-[(4-{4-[(2-chloro-phenyl)carbonyl]piperazin-1-yl}phenyl)amino]pyrimidin-4-yl}phenyl)acetamide | 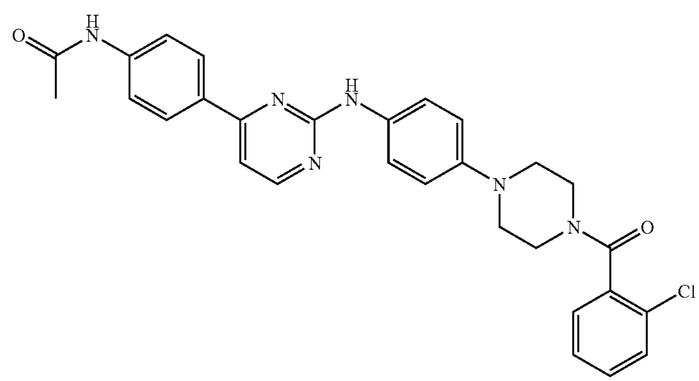 [SMILES: CC(=O)Nc1ccc(-c2ccnc(Nc3ccc(N4CCN(C(=O)c5ccccc5Cl)CC4)cc3)n2)cc1] | 7 |
| 792 | N-(4-{2-[(4-{4-[(3-fluoro-phenyl)carbonyl]piperazin-1-yl}phenyl)amino]pyrimidin-4-yl}phenyl)acetamide | 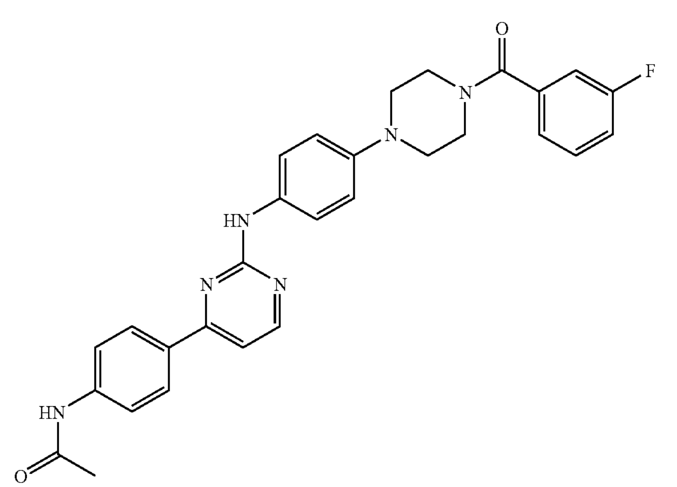 [SMILES: CC(=O)Nc1ccc(-c2ccnc(Nc3ccc(N4CCN(C(=O)c5cccc(F)c5)CC4)cc3)n2)cc1] | 7 |

TABLE 1-continued

| Cmpd No. | Name | Structure | Can Be Made According To Synthetic Example #: |
|---|---|---|---|
| 793 | N-(4-{2-[(4-{4-[(3-fluoro-4-methylphenyl)carbonyl]piperazin-1-yl}phenyl)amino]pyrimidin-4-yl}phenyl)acetamide | 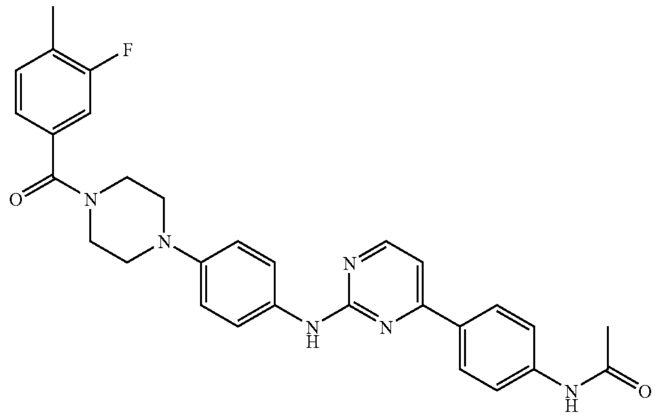 [SMILES: CC(=O)Nc1ccc(-c2ccnc(Nc3ccc(N4CCN(C(=O)c5ccc(C)c(F)c5)CC4)cc3)n2)cc1] | 7 |
| 794 | N-(4-{2-[(4-{4-[(3,4-dichlorophenyl)carbonyl]piperazin-1-yl}phenyl)amino]pyrimidin-4-yl}phenyl)acetamide | 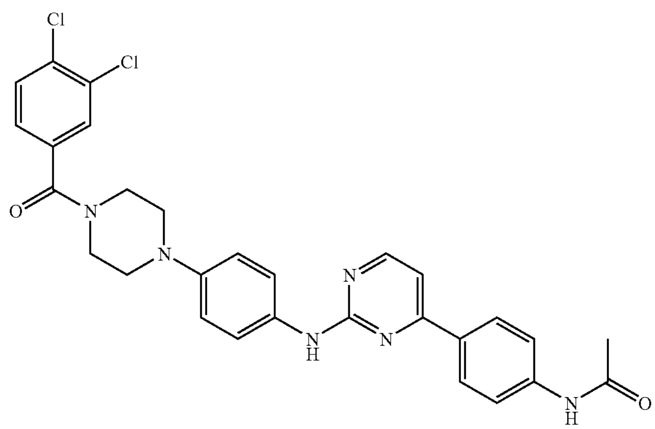 [SMILES: CC(=O)Nc1ccc(-c2ccnc(Nc3ccc(N4CCN(C(=O)c5ccc(Cl)c(Cl)c5)CC4)cc3)n2)cc1] | 7 |
| 795 | N-(4-{2-[(4-{4-[(3,5-dichlorophenyl)carbonyl]piperazin-1-yl}phenyl)amino]pyrimidin-4-yl}phenyl)acetamide | 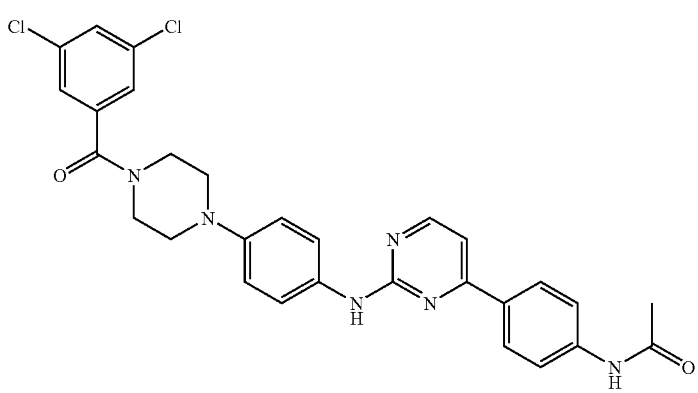 [SMILES: CC(=O)Nc1ccc(-c2ccnc(Nc3ccc(N4CCN(C(=O)c5cc(Cl)cc(Cl)c5)CC4)cc3)n2)cc1] | 7 |

TABLE 1-continued

| Cmpd No. | Name | Structure | Can Be Made According To Synthetic Example #: |
|---|---|---|---|
| 796 | N-[4-(2-{[4-(4-{[3-(methyloxy)phenyl]carbonyl}piperazin-1-yl)phenyl]amino}pyrimidin-4-yl)phenyl]acetamide | 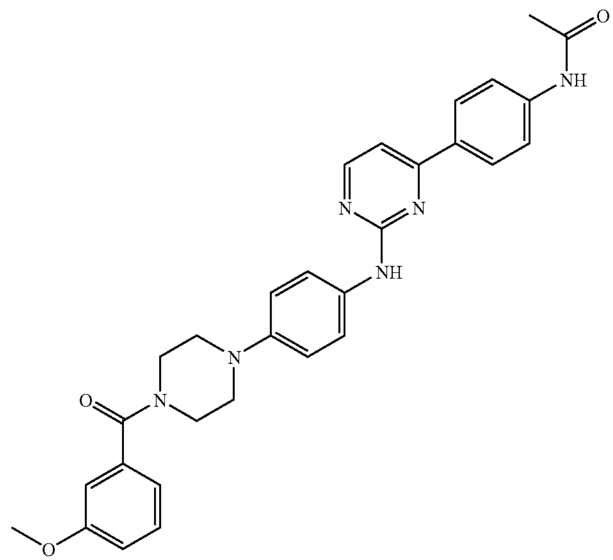 [SMILES: COc1cccc(C(=O)N2CCN(c3ccc(Nc4nccc(-c5ccc(NC(C)=O)cc5)n4)cc3)CC2)c1] | 7 |
| 797 | N-(4-{2-[(4-{4-[(4-chlorophenyl)carbonyl]piperazin-1-yl}phenyl)amino]pyrimidin-4-yl}phenyl)acetamide | 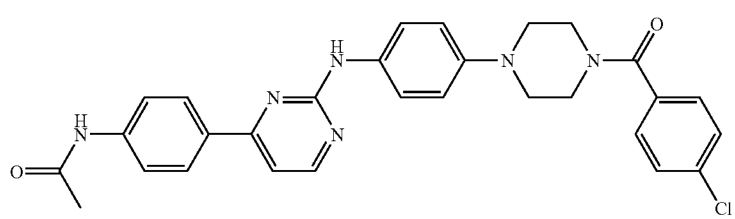 [SMILES: CC(=O)Nc1ccc(-c2ccnc(Nc3ccc(N4CCN(C(=O)c5ccc(Cl)cc5)CC4)cc3)n2)cc1] | 7 |
| 798 | N-(4-{2-[(4-{4-[(4-methylphenyl)carbonyl]piperazin-1-yl}phenyl)amino]pyrimidin-4-yl}phenyl)acetamide | 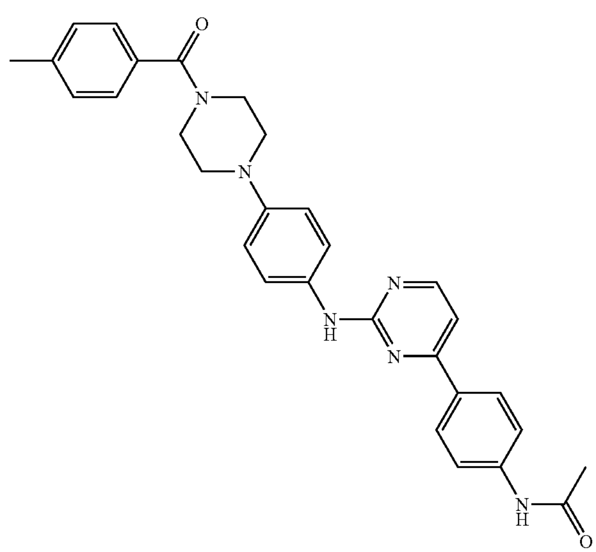 [SMILES: CC(=O)Nc1ccc(-c2ccnc(Nc3ccc(N4CCN(C(=O)c5ccc(C)cc5)CC4)cc3)n2)cc1] | 7 |

| Cmpd No. | Name | Structure | Can Be Made According To Synthetic Example #: |
|---|---|---|---|
| 799 | N-(4-{2-[(4-{4-[(1-methyl-1H-pyrrol-2-yl)carbonyl]piperazin-1-yl}phenyl)amino]pyrimidin-4-yl}phenyl)acetamide | 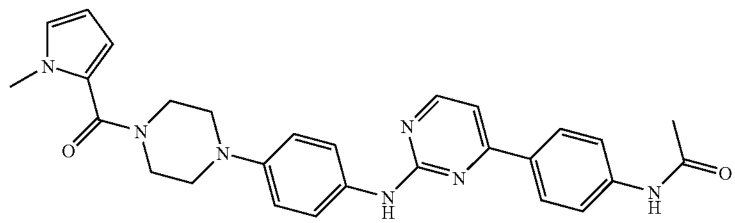 [SMILES: CC(=O)Nc1ccc(-c2ccnc(Nc3ccc(N4CCN(C(=O)c5cccn5C)CC4)cc3)n2)cc1] | 7 |
| 800 | N-{4-[2-({4-[4-(furan-2-ylcarbonyl)piperazin-1-yl]phenyl}amino)pyrimidin-4-yl]phenyl}acetamide | 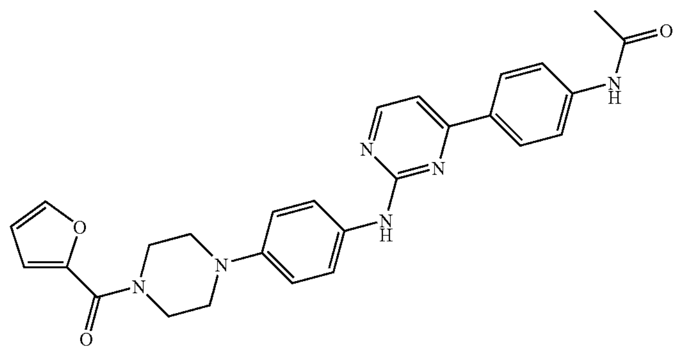 [SMILES: CC(=O)Nc1ccc(-c2ccnc(Nc3ccc(N4CCN(C(=O)c5ccco5)CC4)cc3)n2)cc1] | 7 |
| 801 | N-[4-(2-{[4-(4-{2-[(4-fluorophenyl)oxy]acetyl}piperazin-1-yl)phenyl]amino}pyrimidin-4-yl)phenyl]acetamide | 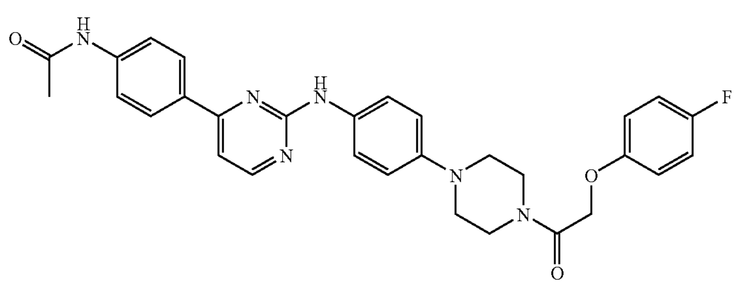 [SMILES: CC(=O)Nc1ccc(-c2ccnc(Nc3ccc(N4CCN(C(=O)COc5ccc(F)cc5)CC4)cc3)n2)cc1] | 7 |
| 802 | N-(4-{2-[(4-morpholin-4-ylphenyl)amino]pyrimidin-4-yl}phenyl)furan-3-carboxamide | 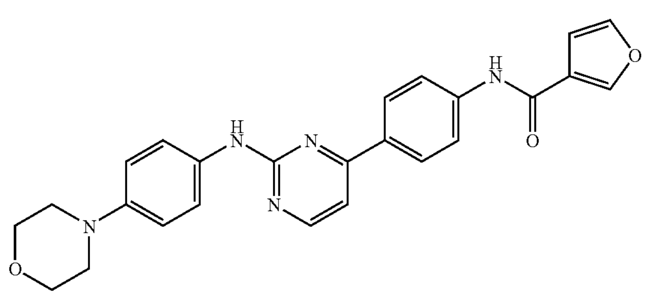 [SMILES: O=C(Nc1ccc(-c2ccnc(Nc3ccc(N4CCOCC4)cc3)n2)cc1)c1ccoc1] | 12 |

TABLE 1-continued

| Cmpd No. | Name | Structure | Can Be Made According To Synthetic Example #: |
|---|---|---|---|
| 803 | N-{4-[2-({4-[4-(phenyl-sulfonyl)piperazin-1-yl]phenyl}amino)pyrimidin-4-yl]phenyl}acetamide | 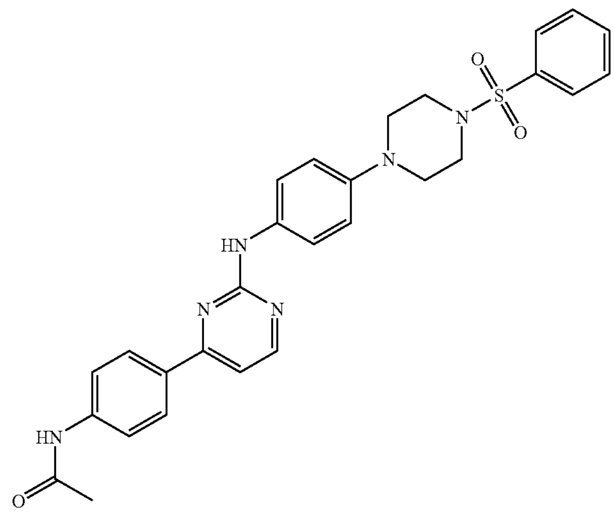 [SMILES: CC(=O)Nc1ccc(-c2ccnc(Nc3ccc(N4CCN(S(=O)(=O)c5ccccc5)CC4)cc3)n2)cc1] | 36 |
| 804 | N-{4-[2-({4-[4-(2-thienyl-sulfonyl)piperazin-1-yl]phenyl}amino)pyrimidin-4-yl]phenyl}acetamide | 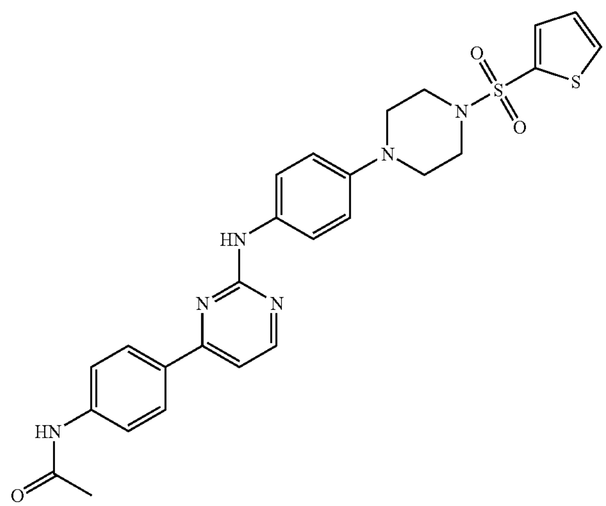 [SMILES: CC(=O)Nc1ccc(-c2ccnc(Nc3ccc(N4CCN(S(=O)(=O)c5cccs5)CC4)cc3)n2)cc1] | 36 |
| 805 | N-(4-{2-[(4-{4-[(4-fluoro-phenyl)sulfonyl]piperazin-1-yl}phenyl)amino]pyrimidin-4-yl}phenyl)acetamide | 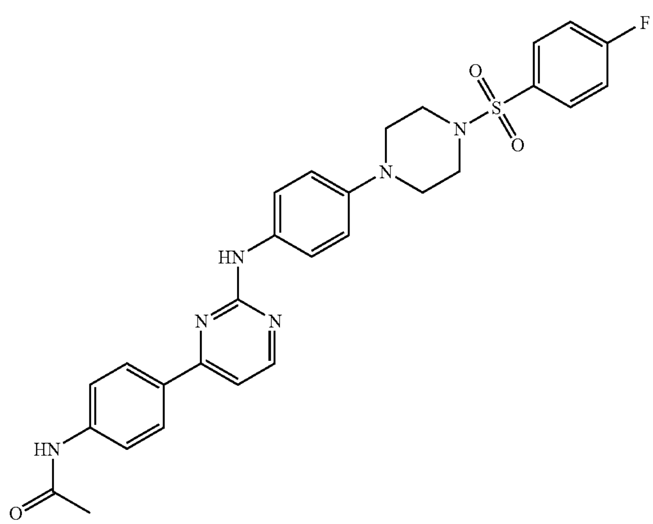 [SMILES: CC(=O)Nc1ccc(-c2ccnc(Nc3ccc(N4CCN(S(=O)(=O)c5ccc(F)cc5)CC4)cc3)n2)cc1] | 36 |

| Cmpd No. | Name | Structure | Can Be Made According To Synthetic Example #: |
|---|---|---|---|
| 806 | N-[4-(2-{[4-(4-{[4-(methyloxy)phenyl]sulfonyl}piperazin-1-yl)phenyl]amino}pyrimidin-4-yl)phenyl]acetamide | 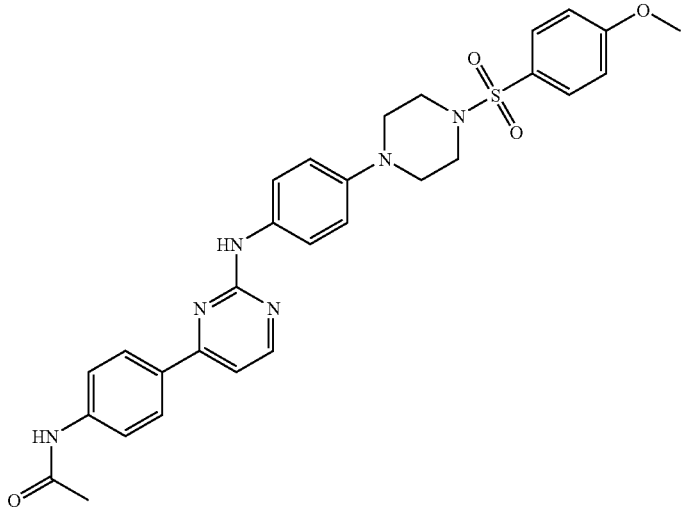 [SMILES: COc1ccc(S(=O)(=O)N2CCN(c3ccc(Nc4nccc(-c5ccc(NC(C)=O)cc5)n4)cc3)CC2)cc1] | 36 |
| 807 | N-(4-{2-[(4-{4-[(4-chlorophenyl)sulfonyl]piperazin-1-yl}phenyl)amino]pyrimidin-4-yl}phenyl)acetamide | 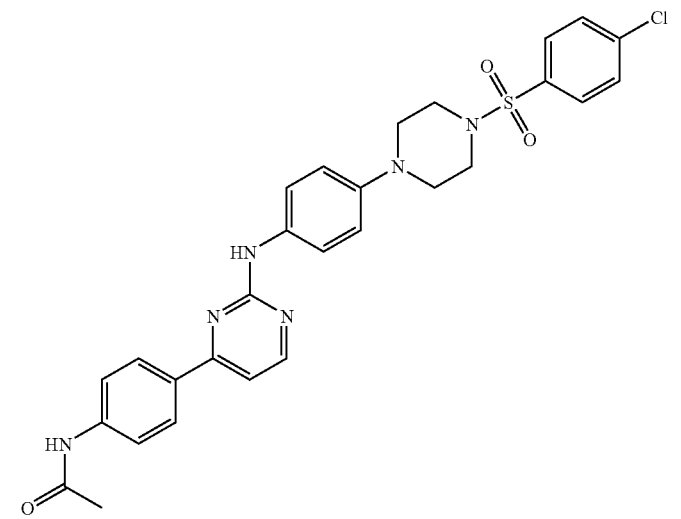 [SMILES: CC(=O)Nc1ccc(-c2ccnc(Nc3ccc(N4CCN(S(=O)(=O)c5ccc(Cl)cc5)CC4)cc3)n2)cc1] | 36 |
| 808 | N-(4-{2-[(4-{4-[(3-chlorophenyl)sulfonyl]piperazin-1-yl}phenyl)amino]pyrimidin-4-yl}phenyl)acetamide | 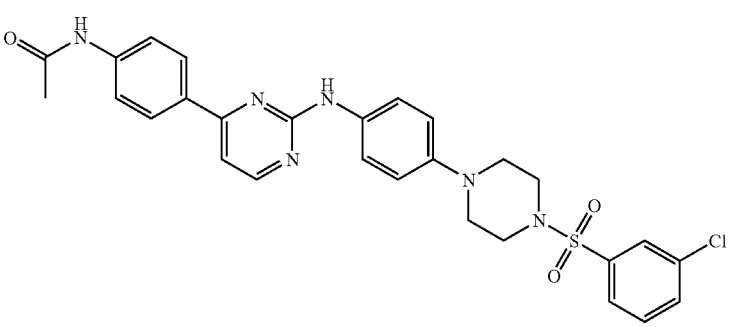 [SMILES: CC(=O)Nc1ccc(-c2ccnc(Nc3ccc(N4CCN(S(=O)(=O)c5cccc(Cl)c5)CC4)cc3)n2)cc1] | 36 |

TABLE 1-continued
| Cmpd No. | Name | Structure | Can Be Made According To Synthetic Example #: |
|---|---|---|---|
| 809 | N-{4-[2-({4-[4-(biphenyl-4-ylsulfonyl)piperazin-1-yl]phenyl}amino)pyrimidin-4-yl]phenyl}acetamide | 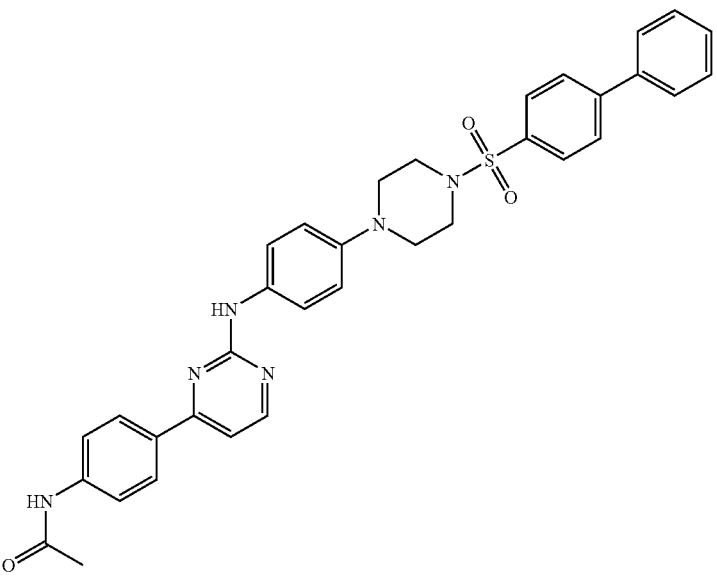 [SMILES: CC(=O)Nc1ccc(-c2ccnc(Nc3ccc(N4CCN(S(=O)(=O)c5ccc(-c6ccccc6)cc5)CC4)cc3)n2)cc1] | 36 |
| 810 | N-{4-[2-({4-[4-(naphthalen-1-ylsulfonyl)piperazin-1-yl]phenyl}amino)pyrimidin-4-yl]phenyl)acetamide | 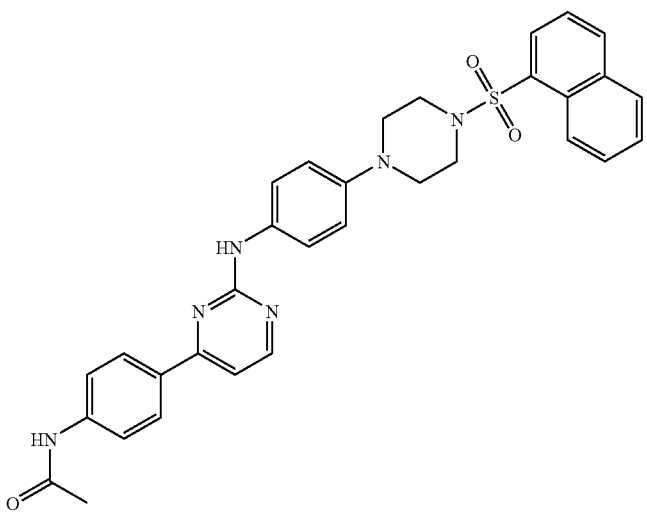 [SMILES: CC(=O)Nc1ccc(-c2ccnc(Nc3ccc(N4CCN(S(=O)(=O)c5cccc6ccccc56)CC4)cc3)n2)cc1] | 36 |
| 811 | N-(4-{2-[(3-{4-[(2-chlorophenyl)methyl]piperazin-1-yl}phenyl)amino]pyrimidin-4-yl}phenyl)acetamide | 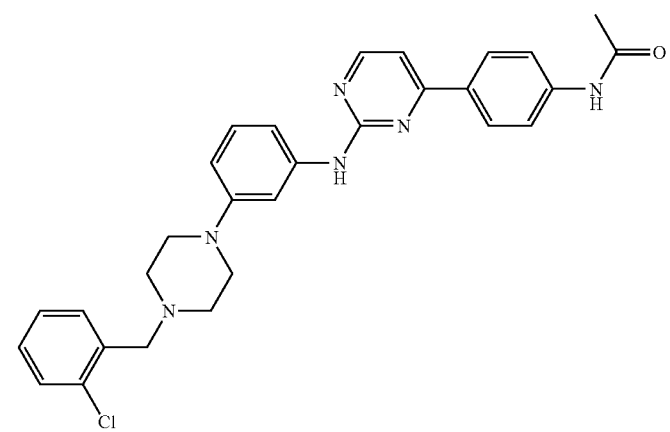 [SMILES: CC(=O)Nc1ccc(-c2ccnc(Nc3cccc(N4CCN(Cc5ccccc5Cl)CC4)c3)n2)cc1] | 49 |

TABLE 1-continued

| Cmpd No. | Name | Structure | Can Be Made According To Synthetic Example #: |
|---|---|---|---|
| 812 | N-[4-(2-{[3-(4-{[3-(methyloxy)phenyl]methyl}pyrimidin-1-yl)phenyl]amino}pyrimidin-4-yl)phenyl]acetamide | 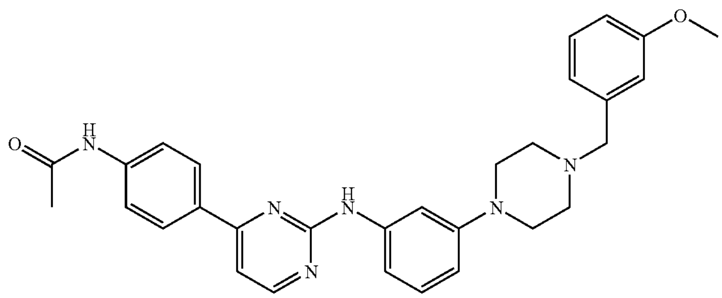 [SMILES: COc1cccc(CN2CCN(c3cccc(Nc4nccc(-c5ccc(NC(C)=O)cc5)n4)c3)CC2)c1] | 49 |
| 813 | N-{4-[2-({3-[4-(3-methyl-butyl)piperazin-1-yl]phenyl}amino)pyrimidin-4-yl]phenyl}acetamide | 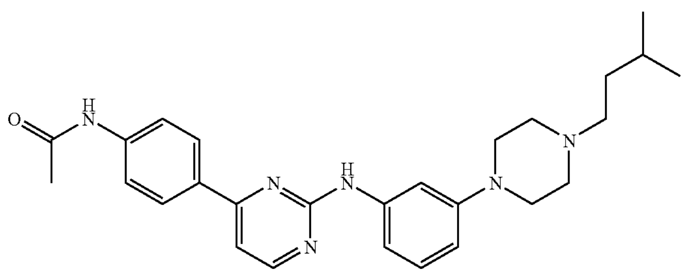 [SMILES: CC(=O)Nc1ccc(-c2ccnc(Nc3cccc(N4CCN(CCC(C)C)CC4)c3)n2)cc1] | 49 |
| 814 | N-{4-[2-({3-[4-(2,3-dihydro-1,4-benzodioxin-6-ylmethyl)piperazin-1-yl]phenyl}amino)pyrimidin-4-yl]phenyl}acetamide | 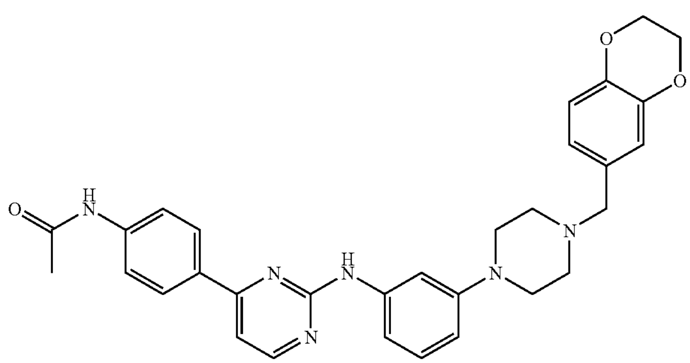 [SMILES: CC(=O)Nc1ccc(-c2ccnc(Nc3cccc(N4CCN(Cc5ccc6c(c5)OCCO6)CC4)c3)n2)cc1] | 49 |
| 815 | N-{4-[2-({3-[4-(cyclopropylmethyl)piperazin-1-yl]phenyl}amino)pyrimidin-4-yl]phenyl}acetamide | 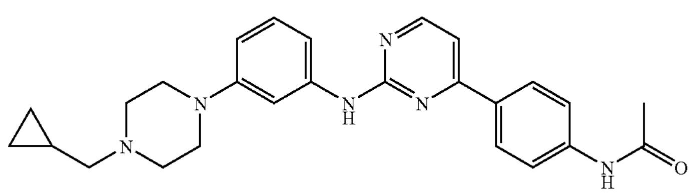 [SMILES: CC(=O)Nc1ccc(-c2ccnc(Nc3cccc(N4CCN(CC5CC5)CC4)c3)n2)cc1] | 49 |
| 816 | N-(4-{2-[(3-{4-[3-(methylthio)propyl]piperazin-1-yl}phenyl)amino]pyrimidin-4-yl}phenyl)acetamide | 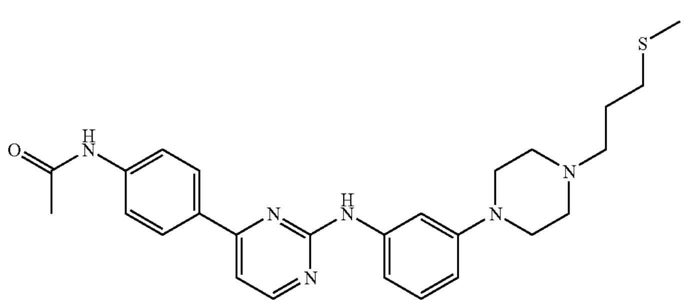 [SMILES: CSCCCN1CCN(c2cccc(Nc3nccc(-c4ccc(NC(C)=O)cc4)n3)c2)CC1] | 49 |

TABLE 1-continued

| Cmpd No. | Name | Structure | Can Be Made According To Synthetic Example #: |
|---|---|---|---|
| 817 | N-(4-{2-[(3-{4-[(4-{[3-(dimethylamino)propyl]oxy}phenyl)methyl]piperazin-1-yl}phenyl)amino]pyrimidin-4-yl}phenyl)acetamide | 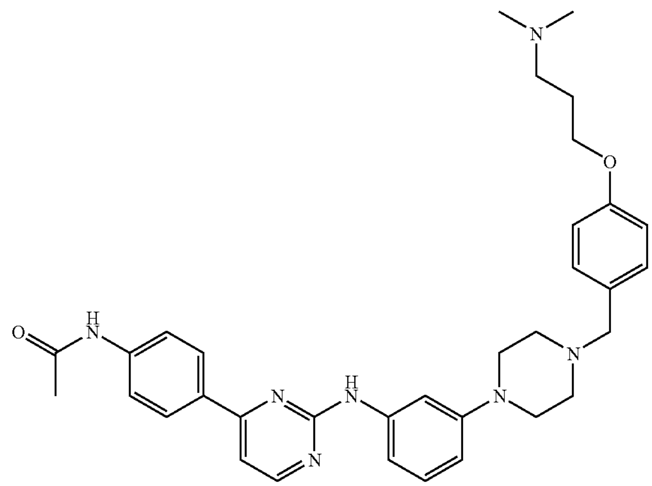 [SMILES: CC(=O)Nc1ccc(-c2ccnc(Nc3cccc(N4CCN(Cc5ccc(OCCCN(C)C)cc5)CC4)c3)n2)cc1] | 49 |
| 818 | N-{4-[2-({3-[4-({3-[(trifluoromethyl)oxy]phenyl}methyl)piperazin-1-yl]phenyl}amino)pyrimidin-4-yl]phenyl}acetamide | 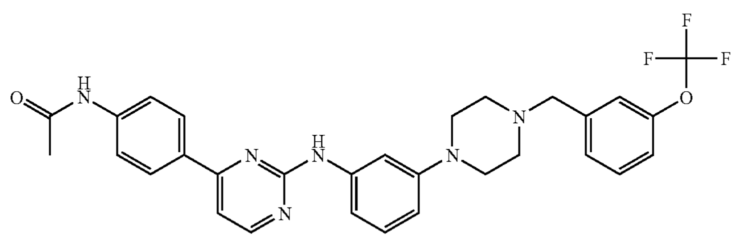 [SMILES: CC(=O)Nc1ccc(-c2ccnc(Nc3cccc(N4CCN(Cc5cccc(OC(F)(F)F)c5)CC4)c3)n2)cc1] | 49 |
| 819 | 4-[4-({4-[4-(acetylamino)phenyl]pyrimidin-2-yl}amino)phenyl]-N-phenyl-piperazine-1-carboxamide | 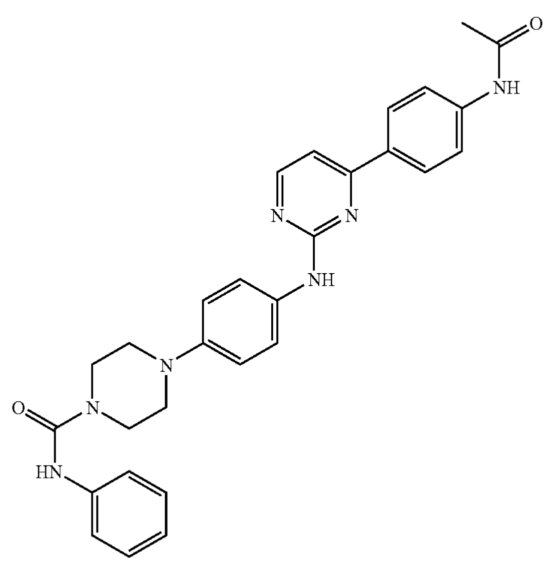 [SMILES: CC(=O)Nc1ccc(-c2ccnc(Nc3ccc(N4CCN(C(=O)Nc5ccccc5)CC4)cc3)n2)cc1] | 53 |
| 820 | N-[4-(2-{[3-(4-propanoyl-piperazin-1-yl)phenyl]amino}pyrimidin-4-yl)phenyl]acetamide | 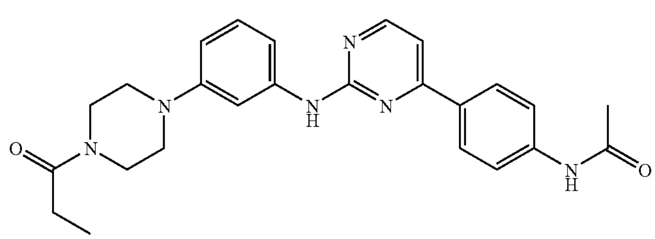 [SMILES: CCC(=O)N1CCN(c2cccc(Nc3nccc(-c4ccc(NC(C)=O)cc4)n3)c2)CC1] | 7 |

TABLE 1-continued

| Cmpd No. | Name | Structure | Can Be Made According To Synthetic Example #: |
|---|---|---|---|
| 821 | N-{4-[2-{(3-[4-(phenyl-carbonyl)piperazin-1-yl]phenyl}amino)pyrimidin-4-yl]phenyl}acetamide | 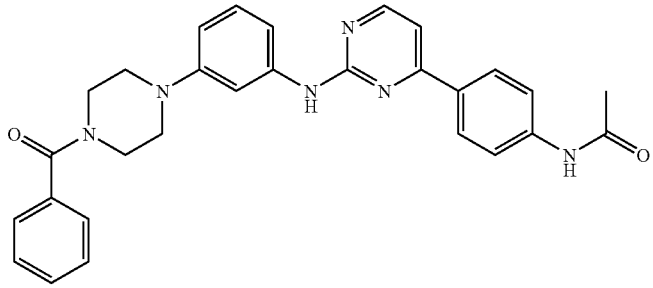 [SMILES: CC(=O)Nc1ccc(-c2ccnc(Nc3cccc(N4CCN(C(=O)c5ccccc5)CC4)c3)n2)cc1] | 7 |
| 822 | N-(4-[2-{(3-[4-(2-phenyl-acetyl)piperazin-1-yl]phenyl}amino)pyrimidin-4-yl]phenyl)acetamide | 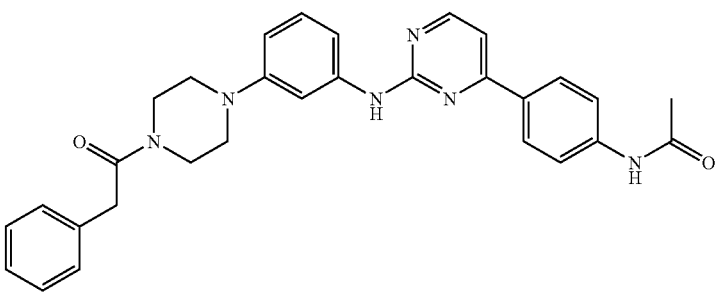 [SMILES: CC(=O)Nc1ccc(-c2ccnc(Nc3cccc(N4CCN(C(=O)Cc5ccccc5)CC4)c3)n2)cc1] | 7 |
| 823 | N-(4-[2-({3-[4-(cyclopentyl-carbonyl)piperazin-1-yl]phenyl}amino)pyrimidin-4-yl]phenyl}acetamide | 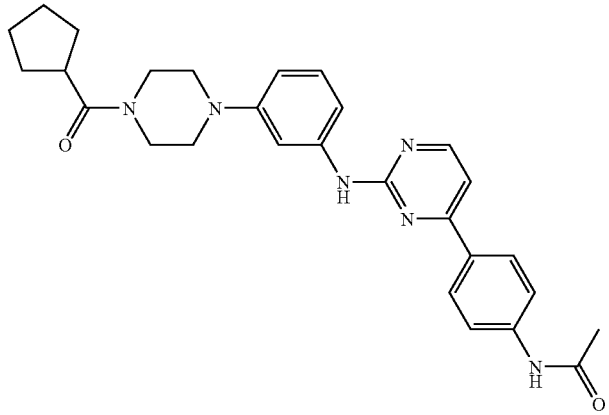 [SMILES: CC(=O)Nc1ccc(-c2ccnc(Nc3cccc(N4CCN(C(=O)C5CCCC5)CC4)c3)n2)cc1] | 7 |
| 824 | N-{4-[2-({3-[4-(2-pyridin-3-ylacetyl)piperazin-1-yl]phenyl}amino)pyrimidin-4-yl]phenyl}acetamide | 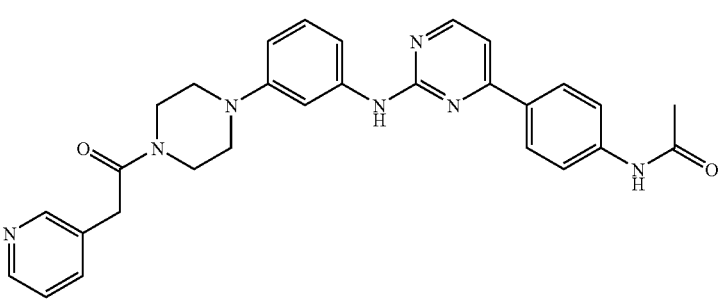 [SMILES: CC(=O)Nc1ccc(-c2ccnc(Nc3cccc(N4CCN(C(=O)Cc5cccnc5)CC4)c3)n2)cc1] | 7 |

TABLE 1-continued

| Cmpd No. | Name | Structure | Can Be Made According To Synthetic Example #: |
|---|---|---|---|
| 825 | N-{4-[2-({3-[4-(2-cyclopentylacetyl)piperazin-1-yl]phenyl}amino)pyrimidin-4-yl]phenyl}acetamide | 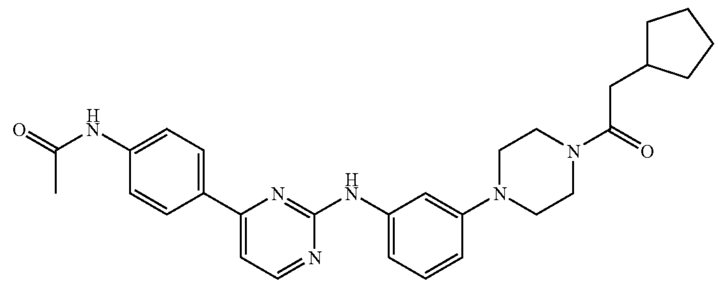 [SMILES: CC(=O)Nc1ccc(-c2ccnc(Nc3cccc(N4CCN(C(=O)CC5CCCC5)CC4)c3)n2)cc1] | 7 |
| 826 | N-(4-{2-[(3-{4-[(2-chlorophenyl)carbonyl]piperazin-1-yl}phenyl)amino]pyrimidin-4-yl}phenyl)acetamide | 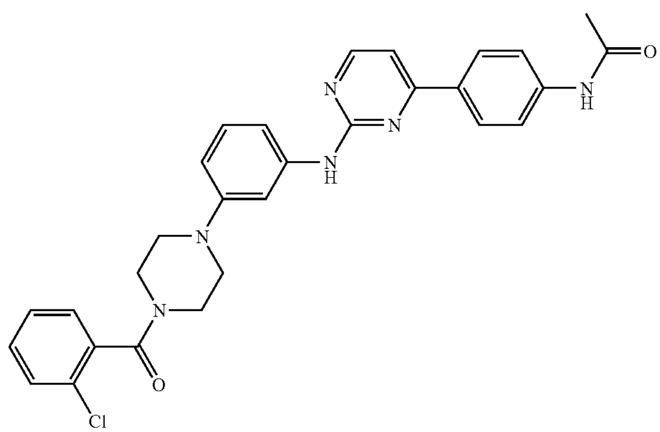 [SMILES: CC(=O)Nc1ccc(-c2ccnc(Nc3cccc(N4CCN(C(=O)c5ccccc5Cl)CC4)c3)n2)cc1] | 7 |
| 827 | N-(4-{2-[(3-{4-[(4-chlorophenyl)carbonyl]piperazin-1-yl}phenyl)amino]pyrimidin-4-yl}phenyl)acetamide | 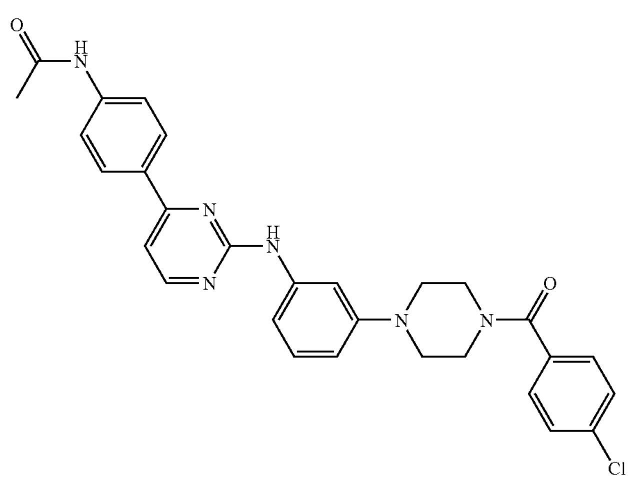 [SMILES: CC(=O)Nc1ccc(-c2ccnc(Nc3cccc(N4CCN(C(=O)c5ccc(Cl)cc5)CC4)c3)n2)cc1] | 7 |

TABLE 1-continued
| Cmpd No. | Name | Structure | Can Be Made According To Synthetic Example #: |
|---|---|---|---|
| 828 | N-(4-{2-[(3-{4-[(3,4-dichlorophenyl)carbonyl]piperazin-1-yl}phenyl)amino]pyrimidin-4-yl}phenyl)acetamide | 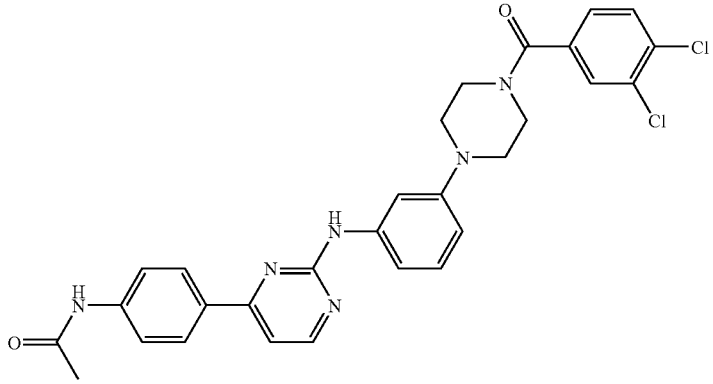 [SMILES: CC(=O)Nc1ccc(-c2ccnc(Nc3cccc(N4CCN(C(=O)c5ccc(Cl)c(Cl)c5)CC4)c3)n2)cc1] | 7 |
| 829 | N-(4-{2-[(3-{4-[(1-methyl-1H-pyrrol-2-yl)carbonyl]piperazin-1-yl}phenyl)amino]pyrimidin-4-yl}phenyl)acetamide | 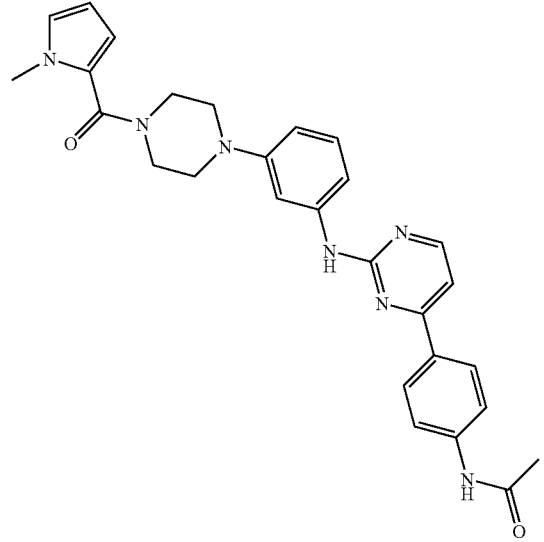 [SMILES: CC(=O)Nc1ccc(-c2ccnc(Nc3cccc(N4CCN(C(=O)c5cccn5C)CC4)c3)n2)cc1] | 7 |
| 830 | $N^2,N^2$-dimethyl-N-[4-(2-{[3-(methyloxy)-4-morpholin-4-ylphenyl]amino}pyrimidin-4-yl)phenyl]glycinamide | 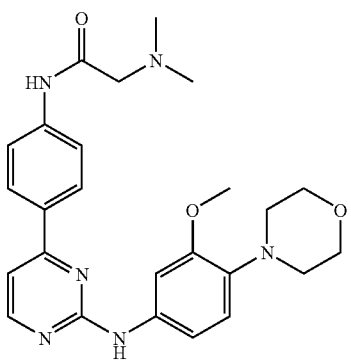 [SMILES: COc1cc(Nc2nccc(-c3ccc(NC(=O)CN(C)C)cc3)n2)ccc1N1CCOCC1] | 24 |

TABLE 1-continued

| Cmpd No. | Name | Structure | Can Be Made According To Synthetic Example #: |
|---|---|---|---|
| 831 | 3-(methyloxy)-N-[4-(2-{[3-(methyloxy)-4-morpholin-4-ylphenyl]amino}pyrimidin-4-yl)phenyl]propanamide | 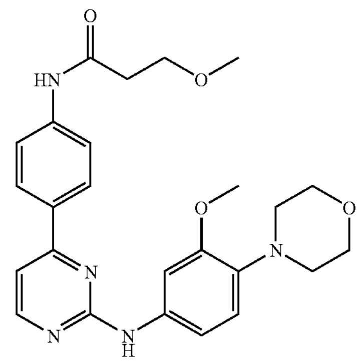 [SMILES: COCCC(=O)Nc1ccc(-c2ccnc(Nc3ccc(N4CCOCC4)c(OC)c3)n2)cc1] | 24 |
| 832 | N-(4-{2-[(4-{[(2-chlorophenyl)sulfonyl]piperazin-1-yl}phenyl)amino]pyrimidin-4-yl}phenyl)acetamide | 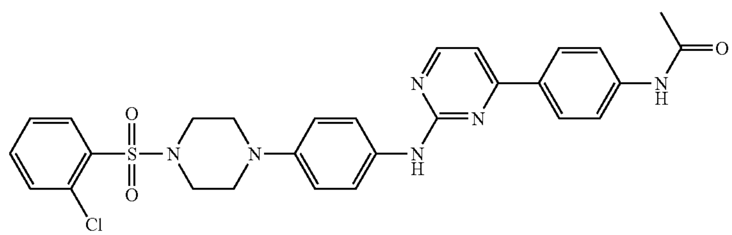 [SMILES: CC(=O)Nc1ccc(-c2ccnc(Nc3ccc(N4CCN(S(=O)(=O)c5ccccc5Cl)CC4)cc3)n2)cc1] | 36 |
| 833 | N-{4-[2-({3-[4-(cyclopropylcarbonyl)piperazin-1-yl]phenyl}amino)pyrimidin-4-yl]phenyl}acetamide | 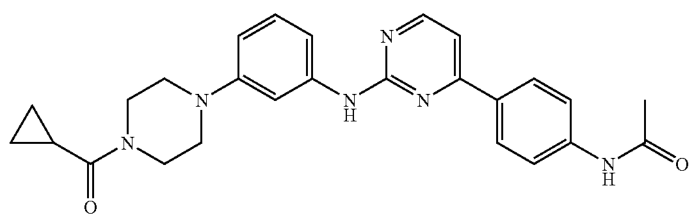 [SMILES: CC(=O)Nc1ccc(-c2ccnc(Nc3cccc(N4CCN(C(=O)C5CC5)CC4)c3)n2)cc1] | 7 |
| 834 | N-{4-[2-({3-[4-(2-cyclopropylacetyl)piperazin-1-yl]phenyl}amino)pyrimidin-4-yl]phenyl}acetamide | 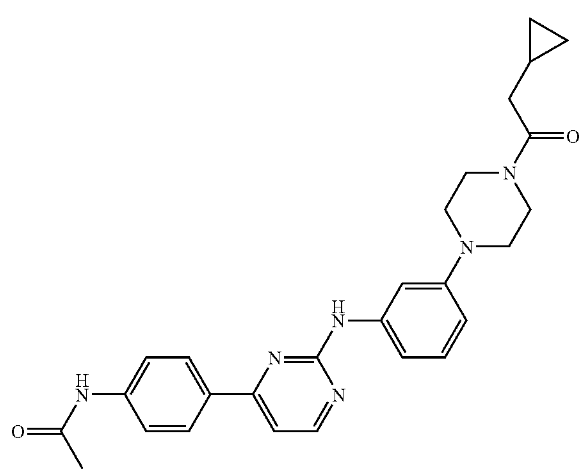 [SMILES: CC(=O)Nc1ccc(-c2ccnc(Nc3cccc(N4CCN(C(=O)CC5CC5)CC4)c3)n2)cc1] | 7 |

TABLE 1-continued

| Cmpd No. | Name | Structure | Can Be Made According To Synthetic Example #: |
|---|---|---|---|
| 835 | N-[4-(2-{[3-(4-{[3-(methyloxy)phenyl]carbonyl}piperazin-1-yl)phenyl]amino}pyrimidin-4-yl)phenyl]acetamide | 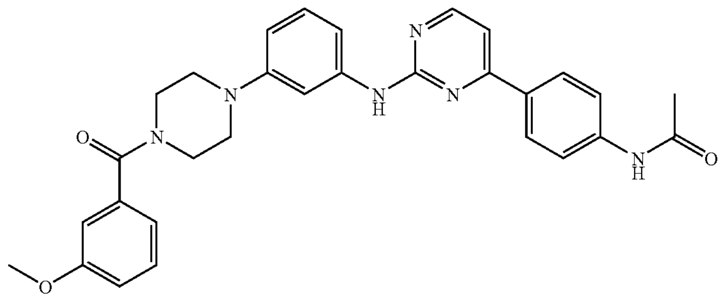 [SMILES: COc1cccc(C(=O)N2CCN(c3cccc(Nc4nccc(-c5ccc(NC(C)=O)cc5)n4)c3)CC2)c1] | 7 |
| 836 | N-{4-[2-({4-[4-(2,2-dimethylpropanoyl)piperazin-1-yl]phenyl}amino)pyrimidin-4-yl]phenyl}acetamide | 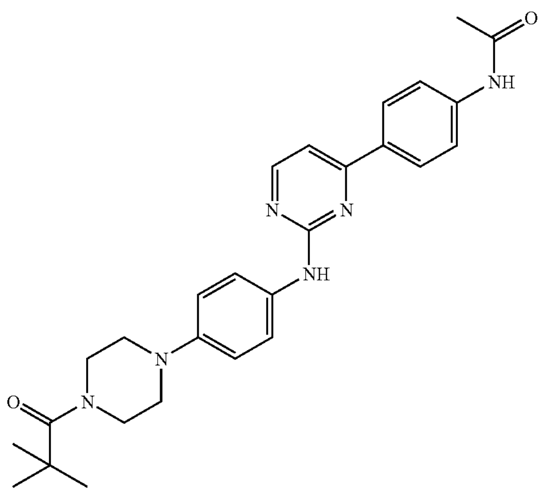 | 7 |
| 837 | 1-[4-({4-[4-(acetylamino)phenyl]pyrimidin-2-yl}amino)phenyl]piperidine-3-carboxylic acid | 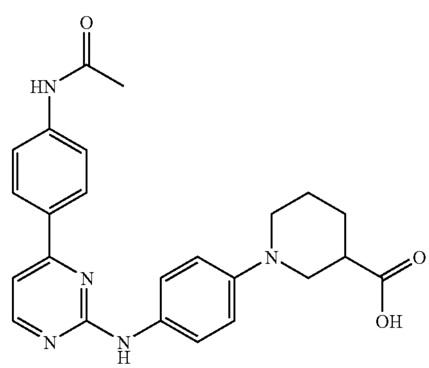 [SMILES: CC(=O)Nc1ccc(-c2ccnc(Nc3ccc(N4CCCC(C(=O)O)C4)cc3)n2)cc1] | 3 |
| 838 | 1,1-dimethylethyl methyl{2-[(4-{2-[(4-morpholin-4-ylphenyl)amino]pyrimidin-4-yl}phenyl)amino]-2-oxoethyl}carbamate | 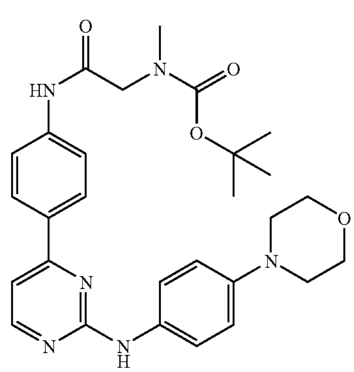 [SMILES: CN(CC(=O)Nc1ccc(-c2ccnc(Nc3ccc(N4CCOCC4)cc3)n2)cc1)C(=O)OC(C)(C)C] | 14 |

TABLE 1-continued

| Cmpd No. | Name | Structure | Can Be Made According To Synthetic Example #: |
|---|---|---|---|
| 839 | 1,1-dimethylethyl [4-(2-{[4-(4-ethylpiperazin-1-yl)phenyl]amino}pyrimidin-4-yl)phenyl]carbamate | 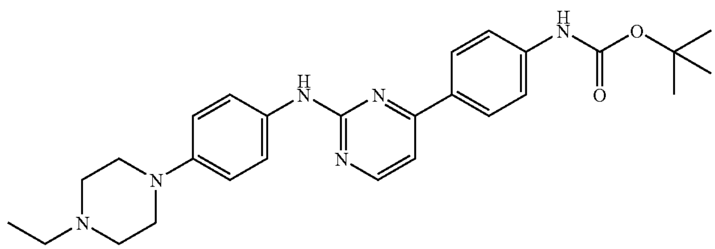 [SMILES: CCN1CCN(c2ccc(Nc3nccc(-c4ccc(NC(=O)OC(C)(C)C)cc4)n3)cc2)CC1] | 51 |
| 840 | N-[4-(2-{[4-(4-ethylpiperazin-1-yl)phenyl]amino}pyrimidin-4-yl)phenyl]-N²,N²-dimethylglycinamide | 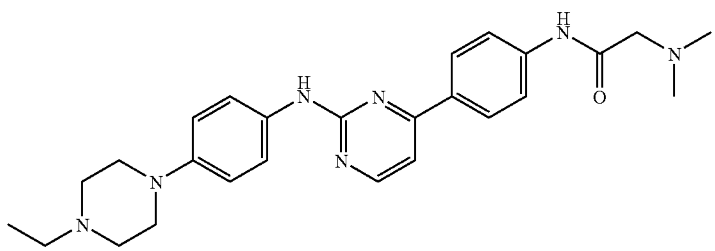 [SMILES: CCN1CCN(c2ccc(Nc3nccc(-c4ccc(NC(=O)CN(C)C)cc4)n3)cc2)CC1] | 51 |
| 841 | 4-(4-aminophenyl)-N-[4-(4-ethylpiperazin-1-yl)phenyl]pyrimidin-2-amine | 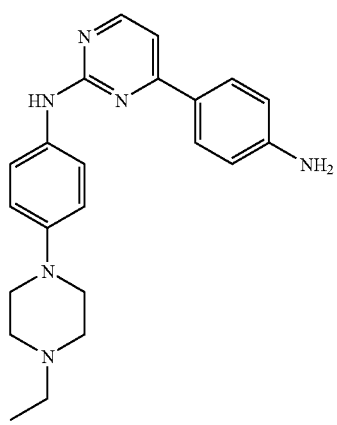 [SMILES: CCN1CCN(c2ccc(Nc3nccc(-c4ccc(N)cc4)n3)cc2)CC1] | 51 |
| 842 | Nalpha-{[(1,1-dimethylethyl)oxy]carbonyl}-N-(4-{2-[(4-morpholin-4-ylphenyl)amino]pyrimidin-4-yl}phenyl)-L-phenylalaninamide | Chiral | 45 |

TABLE 1-continued

| Cmpd No. | Name | Structure | Can Be Made According To Synthetic Example #: |
|---|---|---|---|
| 843 | Nalpha-{[(1,1-dimethyl-ethyl)oxy]carbonyl}-N-(4-{2-[(4-morpholin-4-ylphenyl)amino]pyrimidin-4-yl}phenyl)-D-phenylalaninamide | Chiral | 45 |
| 844 | N-(4-{2-[(4-morpholin-4-ylphenyl)amino]pyrimidin-4-yl}phenyl)-D-phenylalaninamide | Chiral | 45 |
| 845 | N-(4-{2-[(4-morpholin-4-ylphenyl)amino]pyrimidin-4-yl}phenyl)-L-phenylalaninamide | Chiral | 45 |
| 846 | N-[4-(2-{[4-(4-ethyl-piperazin-1-yl)phenyl]amino}pyrimidin-4-yl)phenyl]-L-valinamide | Chiral | 45 |

TABLE 1-continued

| Cmpd No. | Name | Structure | Can Be Made According To Synthetic Example #: |
|---|---|---|---|
| 847 | N-[4-(2-{[4-(4-ethyl-piperazin-1-yl)phenyl]amino}pyrimidin-4-yl)phenyl]-D-valinamide | Chiral | 45 |
| 848 | 1-ethyl-3-[4-(2-{[3-(methyloxy)-4-morpholin-4-ylphenyl]amino}pyrimidin-4-yl)phenyl]urea | 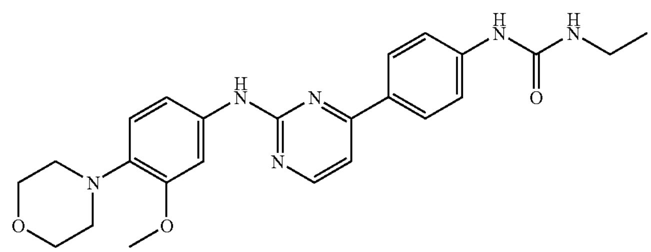 [SMILES: CCNC(=O)Nc1ccc(-c2ccnc(Nc3ccc(N4CCOCC4)c(OC)c3)n2)cc1] | 53 |
| 849 | (2R)-N-(4-{2-[(4-morpholin-4-ylphenyl)amino]pyrimidin-4-yl}phenyl)piperidine-2-carboxamide | Chiral | 45 |
| 850 | N-[4-(2-{[4-(4-ethyl-piperazin-1-yl)phenyl]amino}-5-methylpyrimidin-4-yl)phenyl]acetamide | 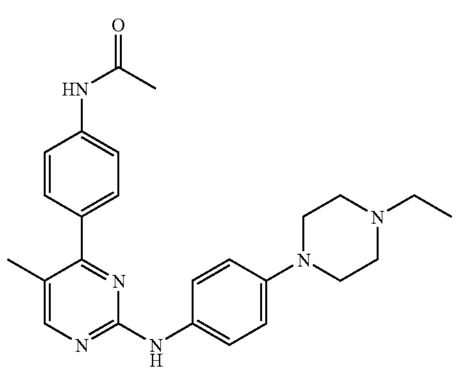 [SMILES: CCN1CCN(c2ccc(Nc3ncc(C)c(-c4ccc(NC(C)=O)cc4)n3)cc2)CC1] | 51 |

TABLE 1-continued

| Cmpd No. | Name | Structure | Can Be Made According To Synthetic Example #: |
|---|---|---|---|
| 851 | 4-{4-[(4-{4-[(N,N-dimethyl-glycyl)amino]phenyl}pyrimidin-2-yl)amino]phenyl}-N-ethylpiperazine-1-carboxamide | 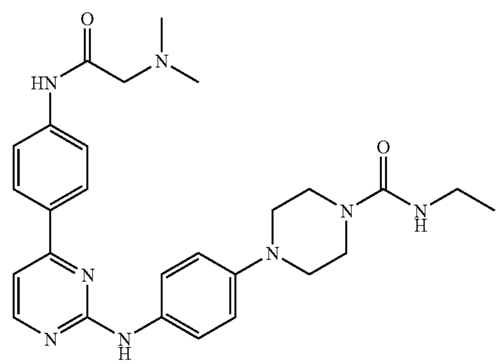 [SMILES: CCNC(=O)N1CCN(c2ccc(Nc3nccc(-c4ccc(NC(=O)CN(C)C)cc4)n3)cc2)CC1] | 53 |
| 852 | N-{4-[2-({4-[4-(2,2-dimethylpropanoyl)piperazin-1-yl]phenyl}amino)pyrimidin-4-yl]phenyl}-$N^2,N^2$-dimethylglycinamide | 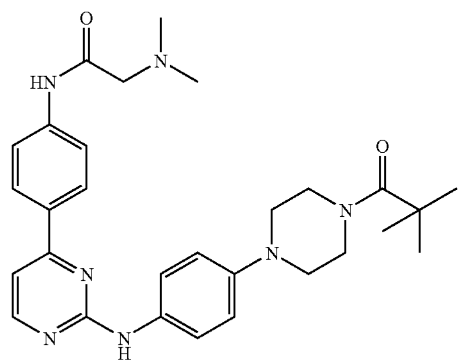 [SMILES: CN(C)CC(=O)Nc1ccc(-c2ccnc(Nc3ccc(N4CCN(C(=O)C(C)(C)C)CC4)cc3)n2)cc1] | 52 |
| 853 | N-{4-[2-({4-[4-(cyclobutyl-carbonyl)piperazin-1-yl]phenyl}amino)pyrimidin-4-yl]phenyl}-$N^2,N^2$-dimethylglycinamide | 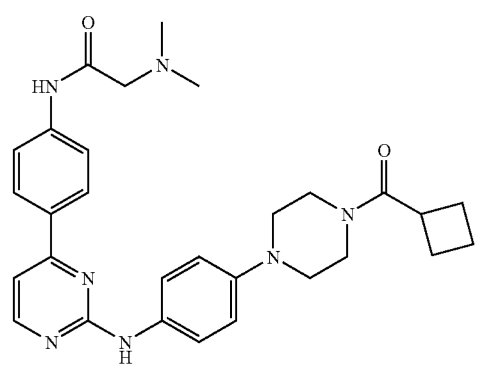 [SMILES: CN(C)CC(=O)Nc1ccc(-c2ccnc(Nc3ccc(N4CCN(C(=O)C5CCC5)CC4)cc3)n2)cc1] | 52 |
| 854 | $N^2,N^2$-dimethyl-N-{4-[2-({4-[4-(2-methylpropanoyl)piperazin-1-yl]phenyl}amino)pyrimidin-4-yl]phenyl}glycinamide | 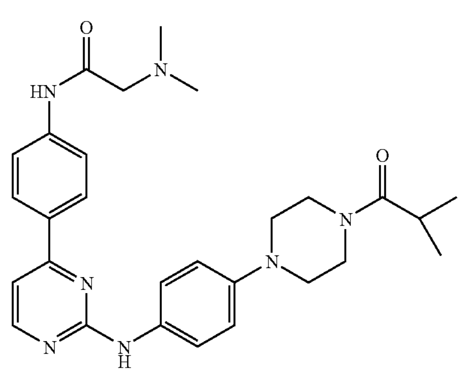 [SMILES: CC(C)C(=O)N1CCN(c2ccc(Nc3nccc(-c4ccc(NC(=O)CN(C)C)cc4)n3)cc2)CC1] | 52 |

TABLE 1-continued

| Cmpd No. | Name | Structure | Can Be Made According To Synthetic Example #: |
|---|---|---|---|
| 855 | N-(4-{2-({4-[4-(cyclopropyl-carbonyl)piperazin-1-yl]phenyl}amino)pyrimidin-4-yl]phenyl}-N²,N²-dimethylglycinamide | 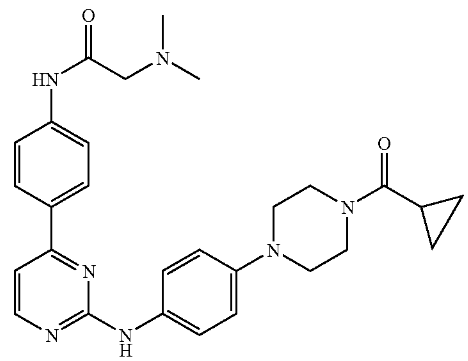 [SMILES: CN(C)CC(=O)Nc1ccc(-c2ccnc(Nc3ccc(N4CCN(C(=O)C5CC5)CC4)cc3)n2)cc1] | 52 |
| 856 | N-[4-(2-{[4-(4-D-alanyl-piperazin-1-yl)phenyl]amino}pyrimidin-4-yl)phenyl]-N²,N²-dimethylglycinamide | 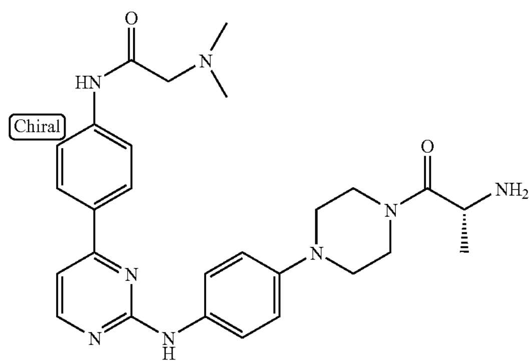 [SMILES: C[C@@H](N)C(=O)N1CCN(c2ccc(Nc3nccc(-c4ccc(NC(=O)CN(C)C)cc4)n3)cc2)CC1] | 52 |
| 857 | N-[4-(2-{[4-(4-L-alanyl-piperazin-1-yl)phenyl]amino}pyrimidin-4-yl)phenyl]-N²,N²-dimethylglycinamide | 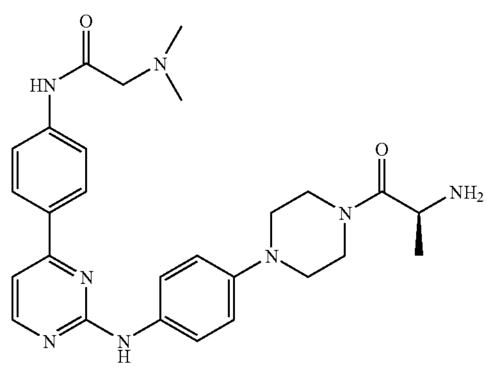 [SMILES: C[C@H](N)C(=O)N1CCN(c2ccc(Nc3nccc(-c4ccc(NC(=O)CN(C)C)cc4)n3)cc2)CC1] | 52 |
| 858 | N-(4-{2-[({1-[(2,6-dichloro-phenyl)carbonyl]azetidin-3-yl}methyl)amino]pyrimidin-4-yl}phenyl)acetamide | 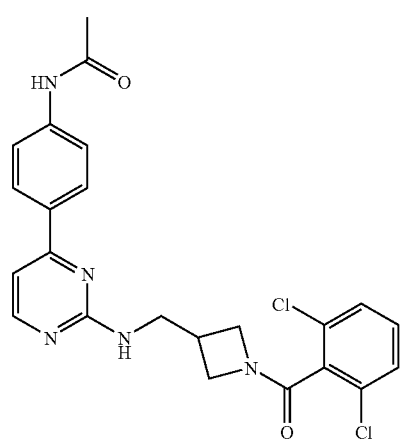 [SMILES: CC(=O)Nc1ccc(-c2ccnc(NCC3CN(C(=O)c4c(Cl)cccc4Cl)C3)n2)cc1] | 41 |

| Cmpd No. | Name | Structure | Can Be Made According To Synthetic Example #: |
|---|---|---|---|
| 859 | N-(4-{2-[(3-morpholin-4-ylphenyl)amino]pyrimidin-4-yl}phenyl)acetamide | 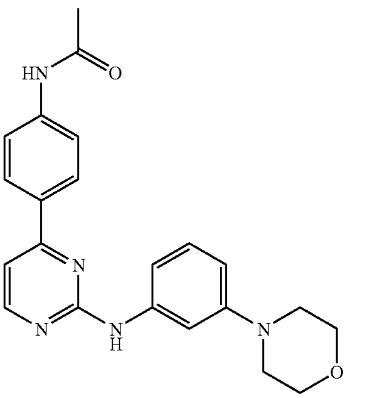 [SMILES: CC(=O)Nc1ccc(-c2ccnc(Nc3cccc(N4CCOCC4)c3)n2)cc1] | 3 |
| 860 | N-[3-({4-[4-(acetylamino)phenyl]pyrimidin-2-yl}amino)cyclohexyl]-2,6-dichlorobenzamide | 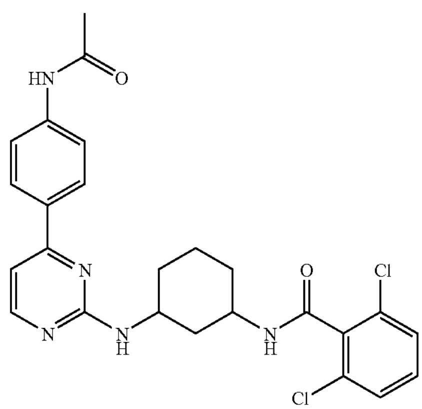 [SMILES: CC(=O)Nc1ccc(-c2ccnc(NC3CCCC(NC(=O)c4c(Cl)cccc4Cl)C3)n2)cc1] | 2 |
| 861 | N-{4-[2-({[4-(4-methyl-piperazin-1-yl)phenyl]methyl}amino)pyrimidin-4-yl]phenyl}acetamide | 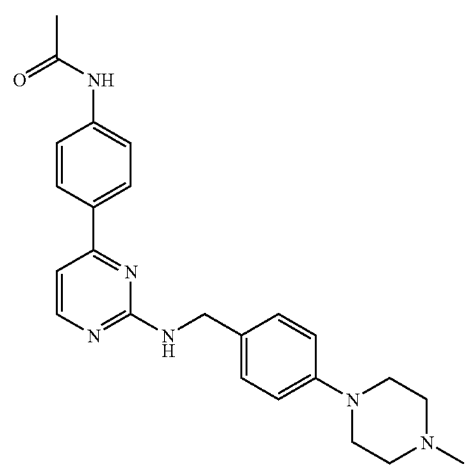 [SMILES: CC(=O)Nc1ccc(-c2ccnc(NCc3ccc(N4CCN(C)CC4)cc3)n2)cc1] | 3 |

TABLE 1-continued

| Cmpd No. | Name | Structure | Can Be Made According To Synthetic Example #: |
|---|---|---|---|
| 862 | N-[4-({4-[4-(acetylamino)phenyl]pyrimidin-2-yl}amino)phenyl]-2,6-dichlorobenzamide | 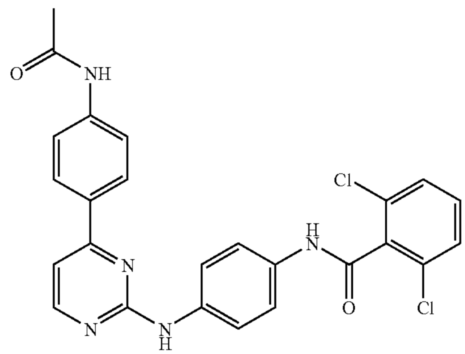 [SMILES: CC(=O)Nc1ccc(-c2ccnc(Nc3ccc(NC(=O)c4c(Cl)cccc4Cl)cc3)n2)cc1] | 2 |
| 863 | N-{4-[2-(piperidin-4-ylamino)pyrimidin-4-yl]phenyl}acetamide | 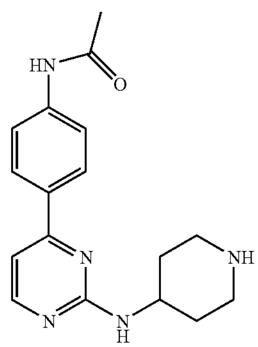 [SMILES: CC(=O)Nc1ccc(-c2ccnc(NC3CCNCC3)n2)cc1] | 1 |
| 864 | N-{4-[2-({1-[(2,6-dichlorophenyl)carbonyl]piperidin-4-yl}amino)pyrimidin-4-yl]phenyl}acetamide | 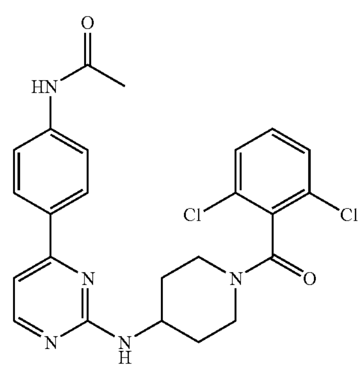 [SMILES: CC(=O)Nc1ccc(-c2ccnc(NC3CCN(C(=O)c4c(Cl)cccc4Cl)CC3)n2)cc1] | 2 |
| 865 | N-{4-[2-({4-[(2-hydroxyethyl)oxy]phenyl}amino)pyrimidin-4-yl]phenyl}acetamide | 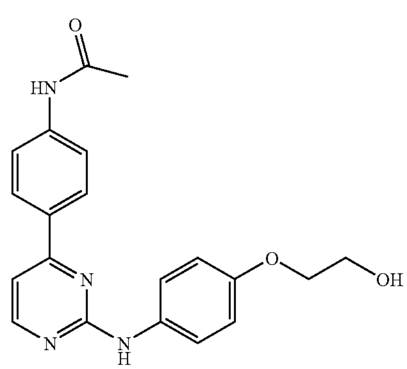 [SMILES: CC(=O)Nc1ccc(-c2ccnc(Nc3ccc(OCCO)cc3)n2)cc1] | 33 |

TABLE 1-continued

| Cmpd No. | Name | Structure | Can Be Made According To Synthetic Example #: |
|---|---|---|---|
| 866 | 1-(4-{2-[(4-morpholin-4-ylphenyl)amino]pyrimidin-4-yl}phenyl)-3-phenylurea | 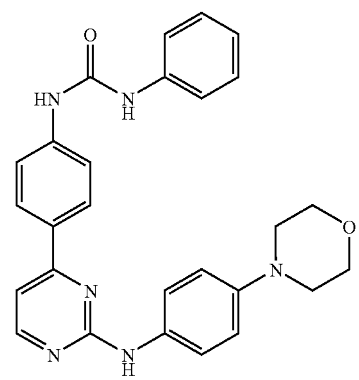 | 53 |
| 867 | N-[5-({4-[4-(acetylamino)phenyl]pyrimidin-2-yl}amino)-2-(4-ethylpiperazin-1-yl)phenyl]-2,6-dichlorobenzamide | 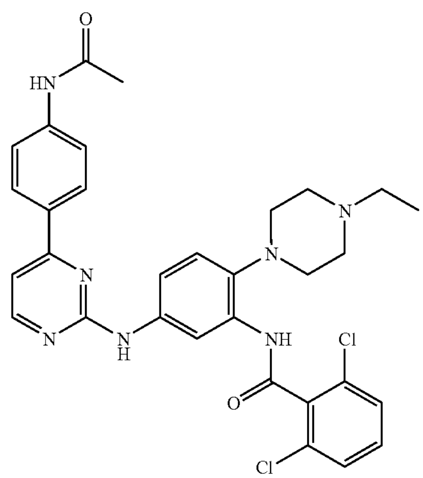 [SMILES: CCN1CCN(c2ccc(Nc3nccc(-c4ccc(NC(C)=O)cc4)n3)cc2NC(=O)c2c(Cl)cccc2Cl)CC1] | 30 |
| 868 | 1-[4-(2-{[4-(4-ethylpiperazin-1-yl)phenyl]amino}pyrimidin-4-yl)phenyl]-3-(phenylmethyl)urea | 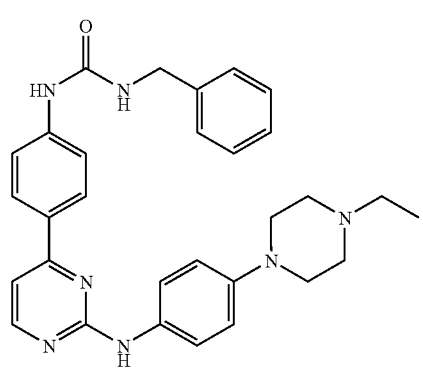 [SMILES: CCN1CCN(c2ccc(Nc3nccc(-c4ccc(NC(=O)NCc5ccccc5)cc4)n3)cc2)CC1] | 53 |

TABLE 1-continued

| Cmpd No. | Name | Structure | Can Be Made According To Synthetic Example #: |
|---|---|---|---|
| 869 | N²,N²-dimethyl-N-{4-[2-({4-[4-pyridin-3-ylcarbonyl)piperazin-1-yl]phenyl}amino)pyrimidin-4-yl]phenyl}glycinamide | 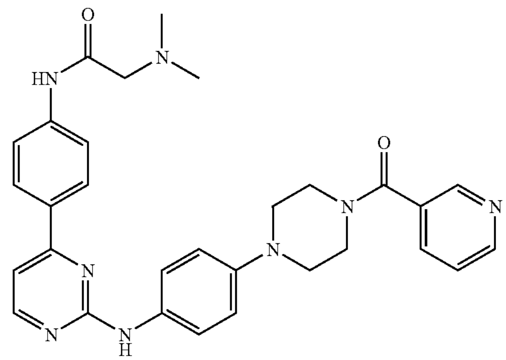 [SMILES: CN(C)CC(=O)Nc1ccc(-c2ccnc(Nc3ccc(N4CCN(C(=O)c5cccnc5)CC4)cc3)n2)cc1] | 52 |
| 870 | N-(3-fluoro-4-{2-[(4-morpholin-4-ylphenyl)amino]pyrimidin-4-yl}phenyl)cyclopropanecarboxamide | 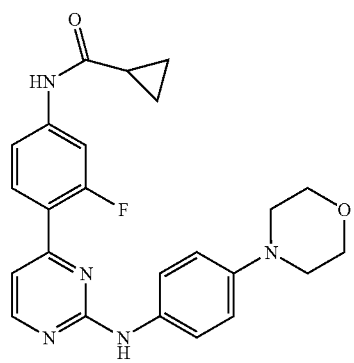 [SMILES: O=C(Nc1ccc(-c2ccnc(Nc3ccc(N4CCOCC4)cc3)n2)c(F)c1)C1CC1] | 9 |
| 871 | N-(4-{2-[(4-{4-[(1-methyl-1H-imidazol-2-yl)methyl]piperazin-1-yl}phenyl)amino]pyrimidin-4-yl}phenyl)cyclopropanecarboxamide | 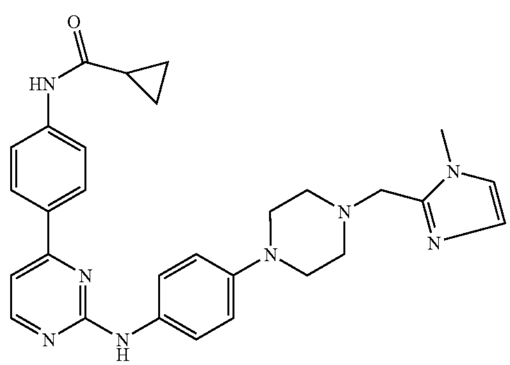 [SMILES: Cn1ccnc1CN1CCN(c2ccc(Nc3nccc(-c4ccc(NC(=O)C5CC5)cc4)n3)cc2)CC1] | 52 |
| 872 | N-[4-(2-{[4-(4-L-alanyl-piperazin-1-yl)phenyl]amino}pyrimidin-4-yl)phenyl]acetamide | 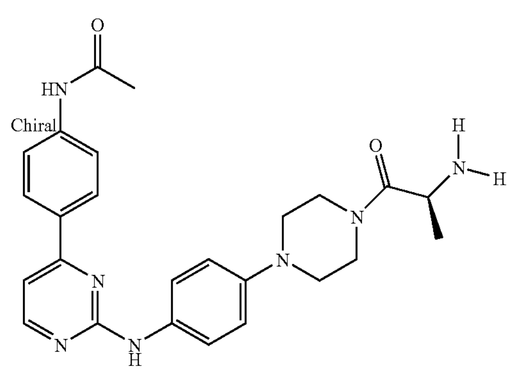 [SMILES: CC(=O)Nc1ccc(-c2ccnc(Nc3ccc(N4CCN(C(=O)[C@H](C)N)CC4)cc3)n2)cc1] | 52 |

TABLE 1-continued

| Cmpd No. | Name | Structure | Can Be Made According To Synthetic Example #: |
|---|---|---|---|
| 873 | N-[4-(2-{[4-(4-L-prolyl-piperazin-1-yl)phenyl]amino}pyrimidin-4-yl)phenyl]acetamide | 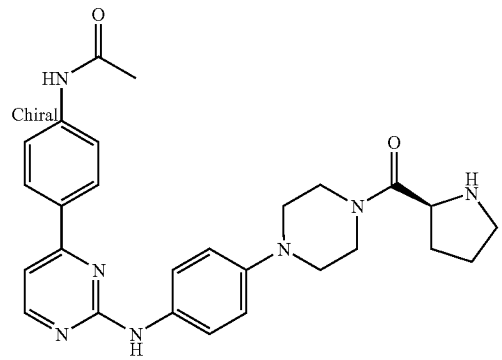 [SMILES: CC(=O)Nc1ccc(-c2ccnc(Nc3ccc(N4CCN(C(=O)[C@@H]5CCCN5)CC4)cc3)n2)cc1] | 7 |
| 874 | N-[4-(2-{[4-(4-D-alanyl-piperazin-1-yl)phenyl]amino}pyrimidin-4-yl)phenyl]acetamide | 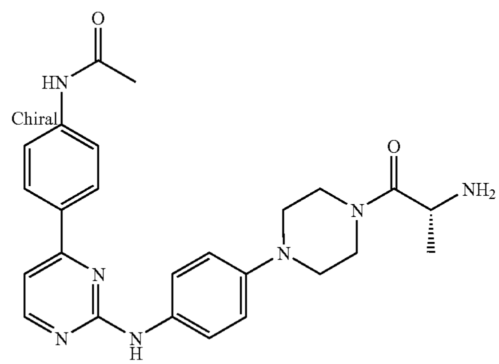 [SMILES: CC(=O)Nc1ccc(-c2ccnc(Nc3ccc(N4CCN(C(=O)[C@@H](C)N)CC4)cc3)n2)cc1] | 7 |
| 875 | N-[4-(2-{[4-(4-D-prolyl-piperazin-1-yl)phenyl]amino}pyrimidin-4-yl)phenyl]acetamide | 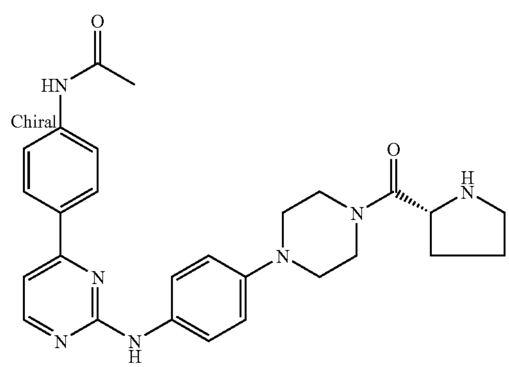 [SMILES: CC(=O)Nc1ccc(-c2ccnc(Nc3ccc(N4CCN(C(=O)[C@H]5CCCN5)CC4)cc3)n2)cc1] | 7 |
| 876 | N-{4-[2-({4-[4-(2-piperazin-1-ylacetyl)piperazin-1-yl]phenyl}amino)pyrimidin-4-yl]phenyl}acetamide | 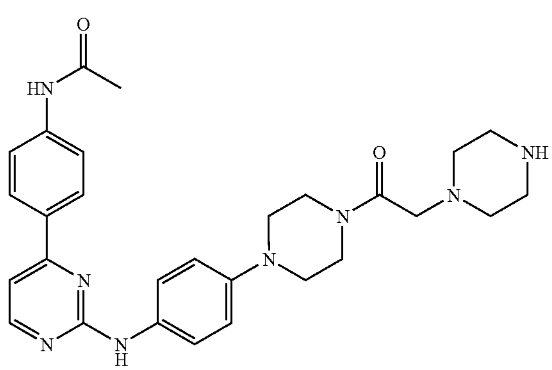 [SMILES: CC(=O)Nc1ccc(-c2ccnc(Nc3ccc(N4CCN(C(=O)CN5CCNCC5)CC4)cc3)n2)cc1] | 7 |

TABLE 1-continued

| Cmpd No. | Name | Structure | Can Be Made According To Synthetic Example #: |
|---|---|---|---|
| 877 | N-[4-(2-{[4-(4-L-alanyl-piperazin-1-yl)phenyl]amino}pyrimidin-4-yl)phenyl]tetrahydrofuran-2-carboxamide | 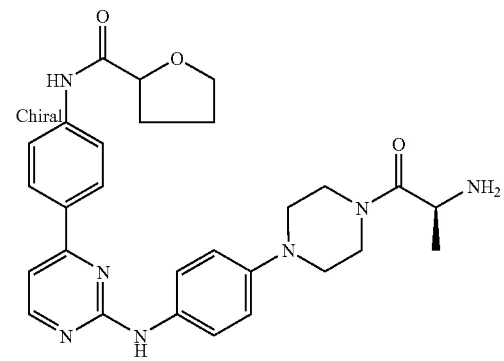 [SMILES: C[C@H](N)C(=O)N1CCN(c2ccc(Nc3nccc(-c4ccc(NC(=O)C5CCCO5)cc4)n3)cc2)CC1] | 52 |
| 878 | N-[4-(2-{[4-(4-L-prolyl-piperazin-1-yl)phenyl]amino}pyrimidin-4-yl)phenyl]tetrahydrofuran-2-carboxamide | 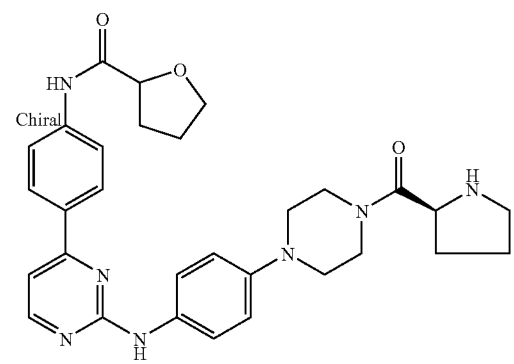 [SMILES: O=C(Nc1ccc(-c2ccnc(Nc3ccc(N4CCN(C(=O)[C@@H]5CCCN5)CC4)cc3)n2)cc1)C1CCCO1] | 52 |
| 879 | N-[4-(2-{[4-(4-D-alanyl-piperazin-1-yl)phenyl]amino}pyrimidin-4-yl)phenyl]tetrahydrofuran-2-carboxamide | 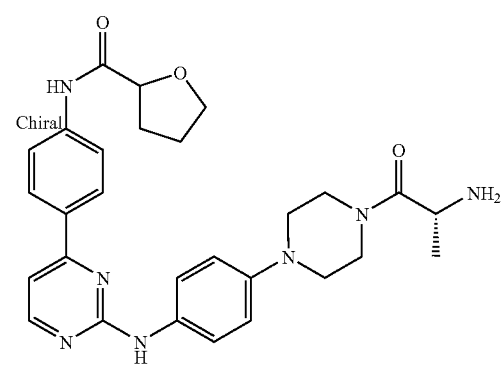 [SMILES: C[C@@H](N)C(=O)N1CCN(c2ccc(Nc3nccc(-c4ccc(NC(=O)C5CCCO5)cc4)n3)cc2)CC1] | 52 |
| 880 | N-[4-(2-{[4-(4-D-prolyl-piperazin-1-yl)phenyl]amino}pyrimidin-4-yl}phenyl]tetrahydrofuran-2-carboxamide | 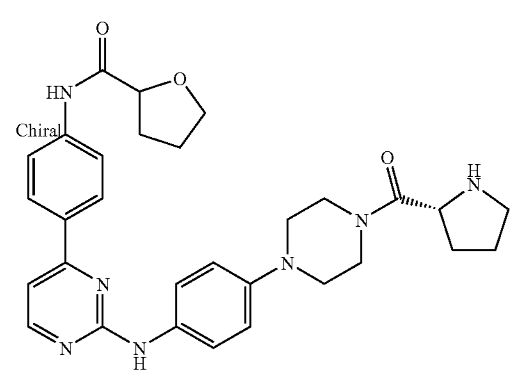 [SMILES: O=C(Nc1ccc(-c2ccnc(Nc3ccc(N4CCN(C(=O)[C@H]5CCCN5)CC4)cc3)n2)cc1)C1CCCO1] | 52 |

TABLE 1-continued

| Cmpd No. | Name | Structure | Can Be Made According To Synthetic Example #: |
|---|---|---|---|
| 881 | 1-methyl-N-(4-{2-[(4-morpholin-4-ylphenyl)amino]pyrimidin-4-yl}phenyl)-1H-pyrrole-2-carboxamide | 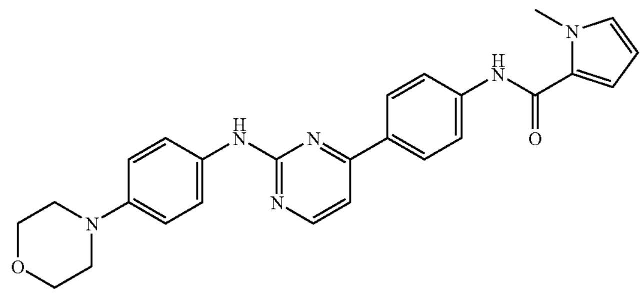 [SMILES: Cn1cccc1C(=O)Nc1ccc(-c2ccnc(Nc3ccc(N4CCOCC4)cc3)n2)cc1] | 12 |
| 882 | 3-fluoro-N-(4-{2-[(4-morpholin-4-ylphenyl)amino]pyrimidin-4-yl}phenyl)pyridine-4-carboxamide | 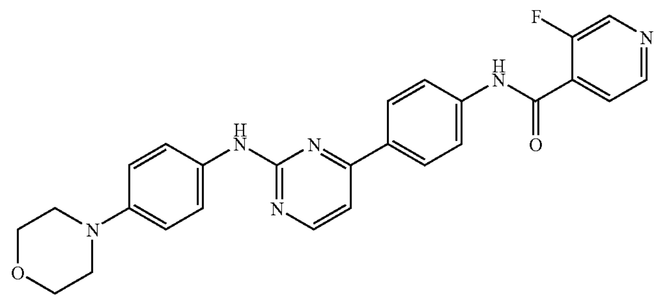 [SMILES: O=C(Nc1ccc(-c2ccnc(Nc3ccc(N4CCOCC4)cc3)n2)cc1)c1ccncc1F] | 12 |
| 883 | 6-methyl-N-(4-{2-[(4-morpholin-4-ylphenyl)amino]pyrimidin-4-yl}phenyl)pyridine-3-carboxamide | 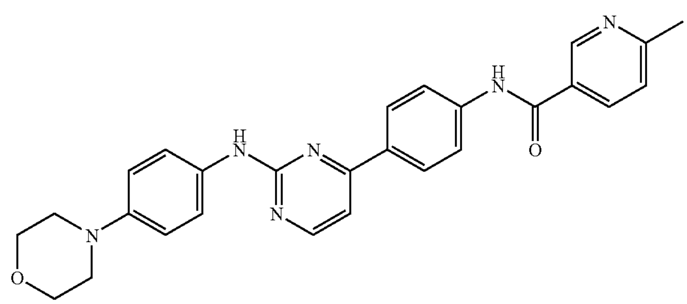 [SMILES: Cc1ccc(C(=O)Nc2ccc(-c3ccnc(Nc4ccc(N5CCOCC5)cc4)n3)cc2)cn1] | 12 |
| 884 | N-(4-{2-[(4-morpholin-4-ylphenyl)amino]pyrimidin-4-yl}phenyl)pyridazine-4-carboxamide | 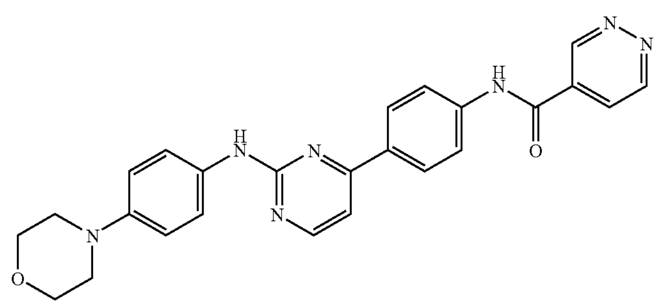 | 12 |
| 885 | 2-cyclopropyl-N-(4-{2-[(4-morpholin-4-ylphenyl)amino]pyrimidin-4-yl}phenyl)acetamide | 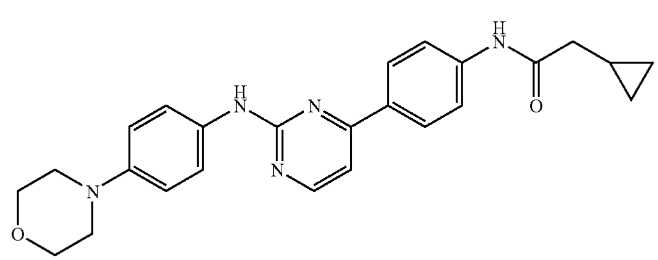 [SMILES: O=C(CC1CC1)Nc1ccc(-c2ccnc(Nc3ccc(N4CCOCC4)cc3)n2)cc1] | 12 |

TABLE 1-continued

| Cmpd No. | Name | Structure | Can Be Made According To Synthetic Example #: |
|---|---|---|---|
| 886 | N-(4-{2-[(4-morpholin-4-ylphenyl)amino]pyrimidin-4-yl}phenyl)isoxazole-5-carboxamide | 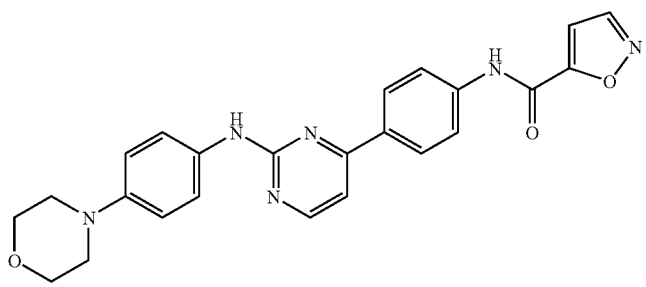 [SMILES: O=C(Nc1ccc(-c2ccnc(Nc3ccc(N4CCOCC4)cc3)n2)cc1)c1ccno1] | 12 |
| 887 | N-(4-{2-[(4-morpholin-4-ylphenyl)amino]pyrimidin-4-yl}phenyl)pyridine-3-carboxamide | 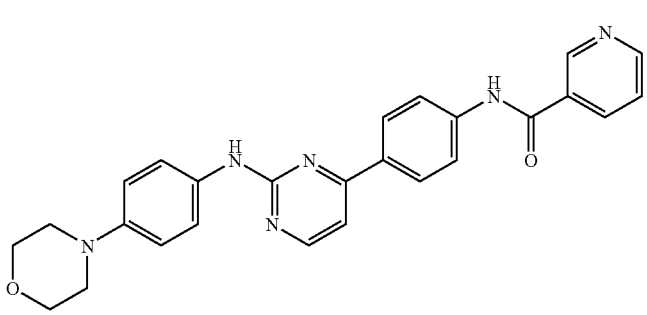 [SMILES: O=C(Nc1ccc(-c2ccnc(Nc3ccc(N4CCOCC4)cc3)n2)cc1)c1cccnc1] | 12 |
| 888 | 4-methyl-N-(4-{2-[(4-morpholin-4-ylphenyl)amino]pyrimidin-4-yl}phenyl)benzamide | 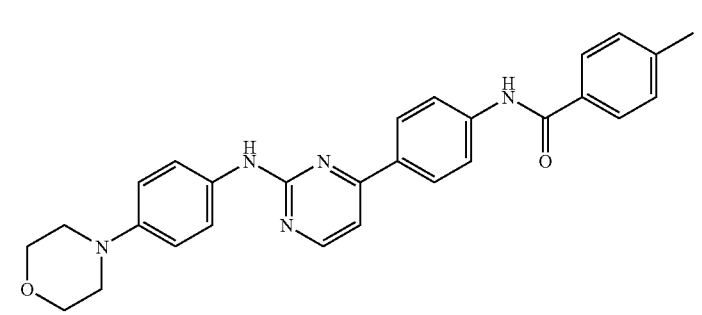 [SMILES: Cc1ccc(C(=O)Nc2ccc(-c3ccnc(Nc4ccc(N5CCOCC5)cc4)n3)cc2)cc1] | 12 |
| 889 | N-[4-(2-{[4-(4-ethyl-piperazin-1-yl)phenyl]amino}pyrimidin-4-yl)phenyl]-D-prolinamide | 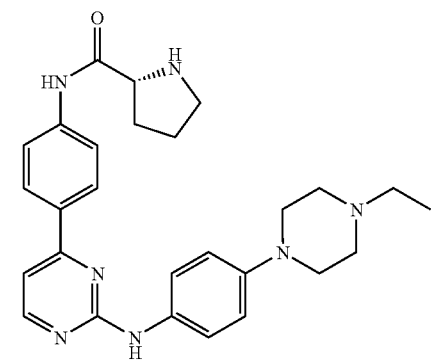 [SMILES: CCN1CCN(c2ccc(Nc3nccc(-c4ccc(NC(=O)[C@H]5CCCN5)cc4)n3)cc2)CC1] | 52 |

TABLE 1-continued

| Cmpd No. | Name | Structure | Can Be Made According To Synthetic Example #: |
|---|---|---|---|
| 890 | N-[4-(2-{[4-(4-ethyl-piperazin-1-yl)phenyl]amino}pyrimidin-4-yl)phenyl]butanamide | 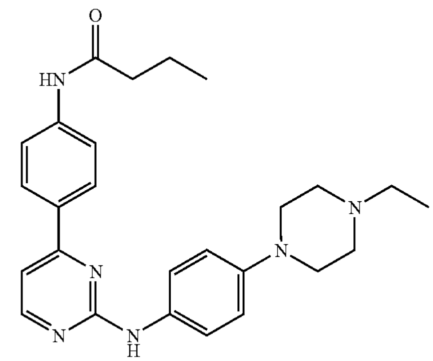 [SMILES: CCCC(=O)Nc1ccc(-c2ccnc(Nc3ccc(N4CCN(CC)CC4)cc3)n2)cc1] | 51 |
| 891 | 1-ethyl-3-[4-(2-{[4-(4-ethylpiperazin-1-yl)phenyl]amino}pyrimidin-4-yl)phenyl]urea | 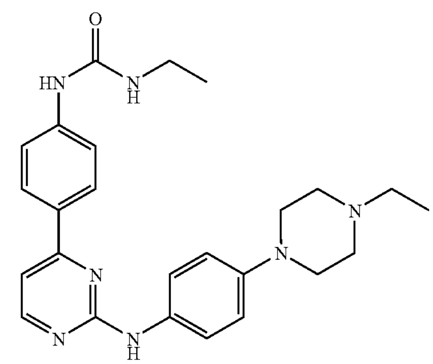 | 53 |

In another embodiment, the compound of the invention is selected from a compound from Table 2:

TABLE 2

N-[4-(2-{[4-(4-ethylpiperazin-1-yl)phenyl]amino}pyrimidin-4-yl)phenyl]acetamide;
N-(4-{2-[(4-morpholin-4-ylphenyl)amino]pyrimidin-4-yl}phenyl)cyclopropanecarboxamide;
N-(4-{5-methyl-2-[(4-morpholin-4-ylphenyl)amino]pyrimidin-4-yl}phenyl)cyclopropane-carboxamide;
N-(4-{2-[(4-morpholin-4-ylphenyl)amino]pyrimidin-4-yl}phenyl)valinamide;
N-(4-{2-[(4-{4-[(1-methyl-1H-imidazol-2-yl)methyl]piperazin-1-yl}phenyl)amino]pyrimidin-4-yl}phenyl)acetamide;
N-(4-{2-[(3,5-dimorpholin-4-ylphenyl)amino]-5-methylpyrimidin-4-yl}phenyl)acetamide;
N-(4-{2-[(4-morpholin-4-ylphenyl)amino]pyrimidin-4-yl}phenyl)-D-alaninamide;
N-{4-[2-({4-[4-(2-methylpropanoyl)piperazin-1-yl]phenyl}amino)pyrimidin-4-yl]phenyl}-acetamide;
2-amino-N-(4-{2-[(4-morpholin-4-ylphenyl)amino]pyrimidin-4-yl}phenyl)-2-phenylacetamide;
N-(4-{5-methyl-2-[(4-morpholin-4-ylphenyl)amino]pyrimidin-4-yl}phenyl)acetamide;
3-(methyloxy)-N-(4-{2-[(4-morpholin-4-ylphenyl)amino]pyrimidin-4-yl}phenyl)propanamide;
N-(4-{2-[(4-morpholin-4-ylphenyl)amino]pyrimidin-4-yl}phenyl)prolinamide;
N-(4-{2-[(4-morpholin-4-ylphenyl)amino]pyrimidin-4-yl}phenyl)-L-alaninamide;
N-(4-{2-[(4-{4-[3-(dimethylamino)-2,2-dimethylpropyl]piperazin-1-yl}phenyl)amino]pyrimidin-4-yl}phenyl)acetamide;
N-(4-{2-[(4-{4-[3-(methyloxy)propanoyl]piperazin-1-yl}phenyl)amino]pyrimidin-4-yl}phenyl)-acetamide;
N-(4-{2-[(4-morpholin-4-ylphenyl)amino]pyrimidin-4-yl}phenyl)-D-prolinamide;
N-[4-(2-{[3-(methyloxy)-4-morpholin-4-ylphenyl]amino}pyrimidin-4-yl)phenyl]-D-prolinamide;
N-(4-{2-[(4-morpholin-4-ylphenyl)amino]pyrimidin-4-yl}phenyl)tetrahydrofuran-3-carboxamide;
O-methyl-N-(4-{2-[(4-morpholin-4-ylphenyl)amino]pyrimidin-4-yl}phenyl)-L-serinamide;
1-ethyl-3-{4-[2-({4-[4-(2-methylpropanoyl)piperazin-1-yl]phenyl}amino)pyrimidin-4-yl]phenyl}urea;

TABLE 2-continued

N-ethyl-4-(4-{[4-(4-{[(ethylamino)carbonyl]amino}phenyl)pyrimidin-2-yl]amino}phenyl)-piperazine-1-carboxamide;
N~2~,N~2~-dimethyl-N-(4-{2-[(4-{4-[3-(methyloxy)propanoyl]piperazin-1-yl}phenyl)amino]-pyrimidin-4-yl}phenyl)glycinamide;
N-(4-{2-[(4-morpholin-4-ylphenyl)amino]pyrimidin-4-yl}phenyl)-D-serinamide;
(3R)-3-hydroxy-N-(4-{2-[(4-morpholin-4-ylphenyl)amino]pyrimidin-4-yl}phenyl)butanamide;
(3S)-3-hydroxy-N-(4-{2-[(4-morpholin-4-ylphenyl)amino]pyrimidin-4-yl}phenyl)butanamide;
N-{4-[2-({4-[4-(tetrahydrofuran-2-ylcarbonyl)piperazin-1-yl]phenyl}amino)pyrimidin-4-yl]phenyl}-D-prolinamide;
2-hydroxy-2-methyl-N-(4-{2-[(4-morpholin-4-ylphenyl)amino]pyrimidin-4-yl}phenyl)propanamide;
N-(4-{2-[(4-morpholin-4-ylphenyl)amino]pyrimidin-4-yl}phenyl)prolinamide;
N-(4-{2-[(4-morpholin-4-ylphenyl)amino]pyrimidin-4-yl}phenyl)-L-prolinamide;
N-(4-{2-[(4-morpholin-4-ylphenyl)amino]pyrimidin-4-yl}phenyl)-D-prolinamide;
O-methyl-N-(4-{2-[(4-morpholin-4-ylphenyl)amino]pyrimidin-4-yl}phenyl)-L-serinamide;
O-methyl-N-(4-{2-[(4-morpholin-4-ylphenyl)amino]pyrimidin-4-yl}phenyl)-D-serinamide;
O-methyl-N-(4-{2-[(4-morpholin-4-ylphenyl)amino]pyrimidin-4-yl}phenyl)-D-serinamide; and
N-(4-{2-[(3-fluoro-4-morpholin-4-ylphenyl)amino]pyrimidin-4-yl}phenyl)-D-prolinamide.

In another embodiment, the invention relates to a pharmaceutical composition comprising a compound according to Table 1 or Table 2, or a pharmaceutically acceptable salt thereof, and a pharmaceutically acceptable carrier, excipient, or diluent.

In another embodiment, the invention relates to a method of inhibiting JAK-2 in a cell, comprising contacting the cell, in which inhibition of JAK-2 is desired, with a compound according to Table 1 or Table 2, or a pharmaceutically salt thereof.

In another embodiment, the invention relates to a method of inhibiting JAK-2 in a cell, comprising contacting the cell, in which inhibition of JAK-2 is desired, with a pharmaceutical composition comprising a compound according to Table 1 or Table 2, or a pharmaceutically acceptable salt thereof.

In another embodiment, the invention relates to a method for treating a disease, disorder, or syndrome mediated, at least in part, by inhibiting JAK-2, which method comprises administering to an animal in need of said treatment a therapeutically effective amount of a compound according to Table 1 or Table 2, or a pharmaceutically acceptable salt thereof.

In another embodiment, the invention relates to a method for treating a disease, disorder, or syndrome mediated, at least in part, by inhibiting JAK-2, which method comprises administering to an animal in need of said treatment a pharmaceutical composition comprising a therapeutically effective amount of a compound according to Table 1 or Table 2, or a pharmaceutically acceptable salt thereof.

General Administration

In certain other preferred embodiments, administration can preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, can include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention can also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid dosage forms, as described above, can be prepared with coatings and shells, such as enteric coatings and others well known in the art. They can contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as can be required. Ophthalmic formulations, eye ointments, powders, and solutions are also contemplated as being within the scope of this invention.

Compressed gases can be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

The compositions will include a conventional pharmaceutical carrier or excipient and a compound of the invention as the/an active agent, and, in addition, can include other medicinal agents and pharmaceutical agents. Compositions of the invention can be used in combination with anticancer and/or other agents that are generally administered to a patient being treated for cancer, e.g. surgery, radiation and/or chemotherapeutic agent(s). Chemotherapeutic agents that can be useful for administration in combination with compounds of Formula I in treating cancer include alkylating agents, platinum containing agents.

If formulated as a fixed dose, such combination products employ the compounds of this invention within the dosage range described above and the other pharmaceutically active agent(s) within its approved dosage range. Compounds of the instant invention can alternatively be used sequentially with known pharmaceutically acceptable agent(s) when a combination formulation is inappropriate.

Representative pharmaceutical formulations containing a compound of Formula I are described below.

Utility

The compounds of this invention are JAK-2 inhibitors. As such the compounds of Formula I are useful for treating diseases, particularly myeloproliferative disorders, for example, myelofibrosis, thrombocythemia, polycythemia vera (PV), essential thrombocythemia (ET), agnogenic myeloid metaplasia (AMM), also referred to as idiopathic myelofibrosis (IMF), and chronic myelogenous leukemia (CML); and cancer, for example, ovarian cancer, cervical cancer, breast cancer, colorectal cancer, glioblastomas, prostrate, colon, melanoma, leukemia and haematopoietic malignancies, as described above, in which JAK-2 activity contributes to the pathology and/or symptomatology of the disease.

Suitable in vitro assays for measuring JAK-2 activity and the inhibition thereof by compounds are known. For further details of an in vitro assay for measuring JAK-2 activity see Biological Examples, Example 1 infra.

Assays for measurement of efficacy in treatment of various cancers are described in Biological Examples, Example 3, 5, and 6, infra.

Suitable in vivo models of various cancers are known to those of ordinary skill in the art. For further details of in vivo assays see Biological Examples 2 and 4, infra.

Utility of Compounds of the Invention as Screening Agents

To employ the compounds of the invention in a method of screening for candidate agents that bind to, for example JAK-2, the protein is bound to a support, and a compound of the invention is added to the assay. Alternatively, the compound of the invention is bound to the support and the protein is added. Classes of candidate agents among which novel binding agents can be sought include specific antibodies, non-natural binding agents identified in screens of chemical libraries, peptide analogs, etc. Of particular interest are screening assays for candidate agents that have a low toxicity for human cells. A wide variety of assays can be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, JAK-2 can be done in a number of ways. In one example, the candidate agent (the compound of the invention) is labeled, for example, with a fluorescent or radioactive moiety and binding determined directly. For example, this can be done by attaching all or a portion of the JAK-2 protein to a solid support, adding a labeled agent (for example a compound of the invention in which at least one atom has been replaced by a detectable isotope), washing off excess reagent, and determining whether the amount of the label is that present on the solid support. Various blocking and washing steps can be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, JAK-2 protein can be labeled at tyrosine positions using $^{125}I$, or with fluorophores. Alternatively, more than one component can be labeled with different labels; using $^{125}I$ for the proteins, for example, and a fluorophor for the candidate agents.

The compounds of the invention can also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They can be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to JAK-2.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to IGF1R, such as an antibody, peptide, binding partner, ligand, etc. Under certain circumstances, there can be competitive binding as between the candidate agent and the binding moiety, with the binding moiety displacing the candidate agent.

In some embodiments, the candidate agent is labeled. Either the candidate agent, or the competitor, or both, is added first to JAK-2 protein for a time sufficient to allow binding, if present. Incubations can be performed at any temperature that facilitates optimal activity, typically between 4° C. and 40° C.

Incubation periods are selected for optimum activity, but can also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to JAK-2 and thus is capable of binding to, and potentially modulating the activity of the JAK-2. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor can indicate the candidate agent is bound to JAK-2 with a higher affinity. Thus, if the candidate agent is labeled, the presence of the label on the support, coupled with a lack of competitor binding, can indicate the candidate agent is capable of binding to JAK-2.

It can be of value to identify the binding site of JAK-2. This can be done in a variety of ways. In one embodiment, once JAK-2 is identified as binding to the candidate agent, the JAK-2 is fragmented or modified and the assays repeated to identify the necessary components for binding.

Modulation is tested by screening for candidate agents capable of modulating the activity of JAK-2 comprising the steps of combining a candidate agent with JAK-2, as above, and determining an alteration in the biological activity of the JAK-2. Thus, in this embodiment, the candidate agent should both bind to (although this can not be necessary), and alter its biological or biochemical activity as defined herein. The methods include both in vitro screening methods and in vivo screening of cells for alterations in cell viability, morphology, and the like.

Alternatively, differential screening can be used to identify drug candidates that bind to native JAK-2, but cannot bind to modified JAK-2.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which can be used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components can be added in any order that provides for the requisite binding.

One of ordinary skill in the art would understand that certain crystallized, protein-ligand complexes, in particular JAK-2-ligand complexes, and their corresponding x-ray structure coordinates can be used to reveal new structural information useful for understanding the biological activity of JAK-2 kinase's as described herein. As well, the key structural features of the aforementioned proteins, particularly, the shape of the ligand binding site, are useful in methods for designing or identifying selective modulators of JAK-2 kinase's and in solving the structures of other proteins with similar features. Ligands of such complexes can include compounds of the invention as described herein.

As well, one of ordinary skill in the art would appreciate that such suitable x-ray quality crystals can be used as part of a method of identifying a candidate agent capable of binding to and modulating the activity of JAK-2 kinases. Such methods can be characterized by the following aspects: a) introducing into a suitable computer program, information defining a ligand binding domain of a JAK-2 kinase in a conformation (e.g. as defined by x-ray structure coordinates obtained from suitable x-ray quality crystals as described above) the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for JAK-2 kinase modulation, and determining whether said candidate agent modulates JAK-2 kinase activity in the assay. Such methods can also include administering the candidate agent, determined to modulate JAK-2 kinase activity, to a mammal suffering from a condition treatable by JAK-2 kinase modulation, such as those described above.

Also, one skilled in the art would appreciate that compounds of the invention can be used in a method of evaluating the ability of a test agent to associate with a molecule or molecular complex comprising a ligand binding domain of a JAK-2 kinase. Such a method can be characterized by the following aspects: a) creating a computer model of a JAK-2 kinase binding pocket using structure coordinates obtained from suitable x-ray quality crystals of the JAK-2 kinase, b) employing computational algorithms to perform a fitting operation between the test agent and the computer model of the binding pocket, and c) analyzing the results of the fitting operation to quantify the association between the test agent and the computer model of the binding pocket.

The disclosures in this application of all articles and references, including patents, are incorporated herein by reference.

Synthetic Procedures

The compounds of the invention, or their pharmaceutically acceptable salts, can have asymmetric carbon atoms, oxidized sulfur atoms or quaternized nitrogen atoms in their structure.

The compounds of the invention and their pharmaceutically acceptable salts can exist as single stereoisomers, racemates, and as mixtures of enantiomers and diastereomers. The compounds can also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

Methods for the preparation and/or separation and isolation of single stereoisomers from racemic mixtures or non-racemic mixtures of stereoisomers are well known in the art. For example, optically active (R)- and (S)-isomers can be prepared using chiral synthons or chiral reagents, or resolved using conventional techniques. Enantiomers (R- and S-isomers) can be resolved by methods known to one of ordinary skill in the art, for example by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step can be required to liberate the desired enantiomeric form. Alternatively, specific enantiomer can be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer can be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

Scheme 1 depicts the general synthetic procedure for the compounds of the invention. Synthesis of the compounds of the invention is not limited by the procedure of Scheme 1. One skilled in the art will know that other procedures can be used to synthesize the compounds of the invention, and that the procedure described in Scheme 1 is only one such procedure. In the descriptions below, one of ordinary skill in the art would recognize that specific reaction conditions, added reagents, solvents, and reaction temperatures can be modified for the synthesis of specific compounds of the invention. Thus, the general synthetic procedure depicted in Scheme I in conjunction with the specific examples that follow provide sufficient information and guidance to allow one of ordinary skill in the art to synthesize compounds of the invention.

Compounds of formula I can be prepared according to Scheme 1:

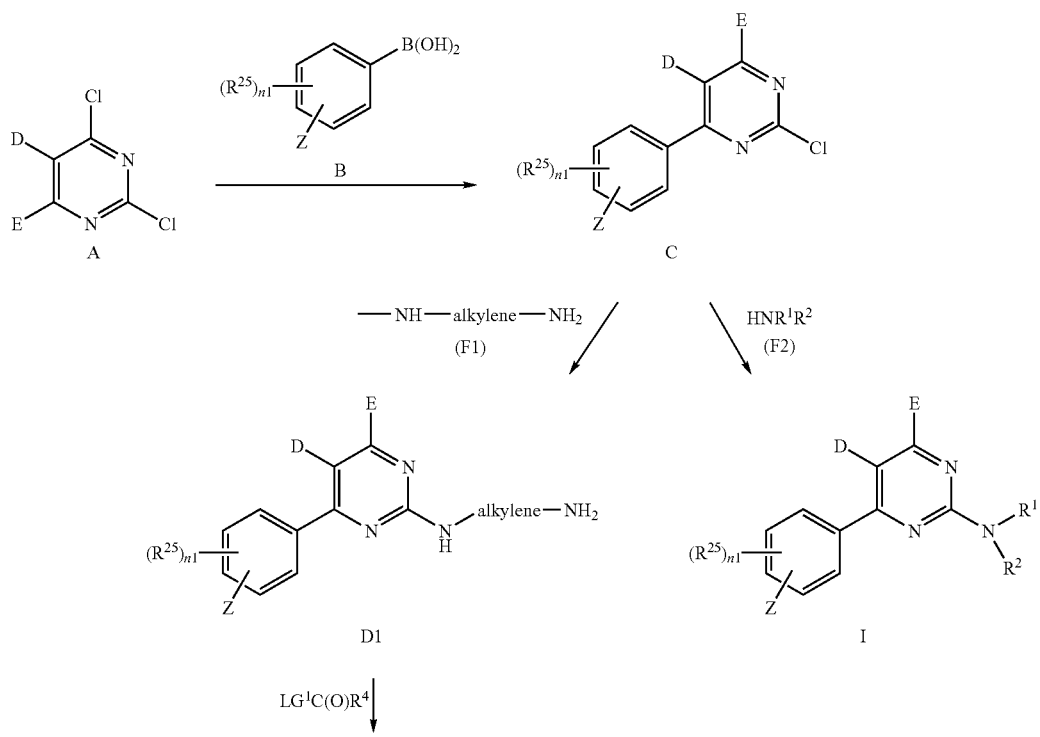

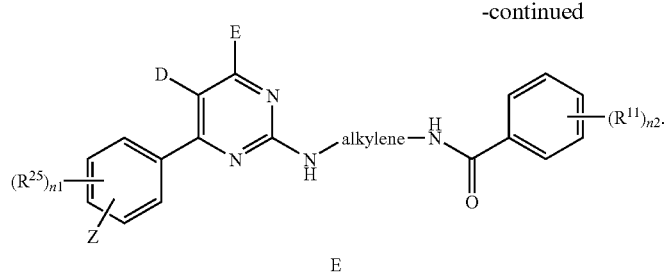

The synthesis of compounds of Formula I proceeds from commercially available reagents and employs standard techniques. Standard Suzuki coupling reactions conditions can be used to convert dichloropyrimindines of formula A (commercially available from Sigma Aldrich) and boronic acids of formula B (commercially available from Sigma Aldrich, Fisher Scientific, or Combi-Blocks Inc.), where $R^{25}$, Z and n1 are as defined in the Detailed Description of the Invention, to 4-substituted-2-chloropyrimidines of formula C. Compounds of Formula D1 and I can be generated by reaction of C with the corresponding amines (F1, available from Fluka) or anilines (F2, available from Sigma Aldrich). Compounds of formula D1 can be further transformed to amides of formula E using standard peptide coupling conditions with carboxylic acids or reaction with acid chlorides. For instance, D1 can be reacted with an intermediate of formula $LG^1C(O)R^4$ where $LG^1$ is a leaving group under acylation conditions and $R^4$ is phenyl optionally substituted with 1, 2, 3, 4, or 5 $R^{11}$ groups, wherein $R^{11}$ is as defined in the Detailed Description of the Invention to yield a compound of formula E.

EXAMPLES

The following examples serve to more fully describe the manner of making the compounds of the invention, as well as to set forth the best modes contemplated for carrying out the invention. These examples in no way serve to limit the scope of the invention, but rather are presented for illustrative purposes. All references cited herein are incorporated by reference in their entirety. Generally, each example is set out below with a corresponding multi-step synthesis procedure. Following the specific examples is a list of compounds that were made in a similar way.

Example 1

N-(4-{2-[(3-aminophenyl)amino]pyrimidin-4-yl}phenyl)acetamide (Compound 58)

a) N-(4-(2-chloropyrimidin-4-yl)phenyl)acetamide ($C_1$)

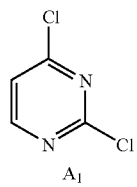

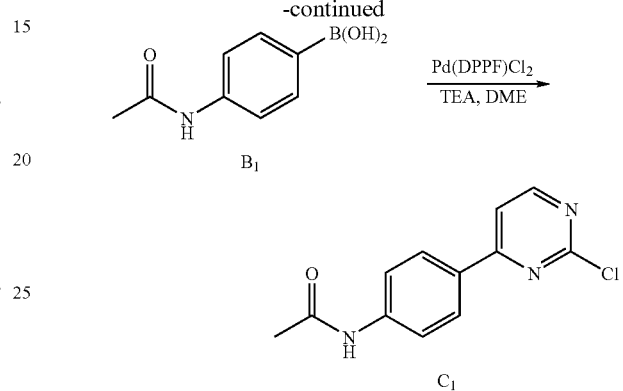

A flask was charged with 2,4-dichloropyrimindine $A_1$ (650 mg, 4.4 mmol), 4-acetoamidophenylboronic acid $B_1$ (820 mg, 4.6 mmol), dichloro[1,1'-bis(diphenyl-phosphino)ferrocene-palladium (480 mg, 0.56 mmol, 15 mol %), and triethylamine (1.5 mL, 11 mmol). Ethyleneglycoldimethylether (30 mL) was added to the flask and the mixture was purged with $N_2$ for 5 minutes. The reaction mixture was stirred under an $N_2$ atmosphere at 80° C. for 12 hours, after which time, ether was added and the reaction mixture was filtered. The product, $C_1$, was isolated by removal of the solvent with a rotary evaporator and used without further purification. LCMS: m/z 248 $(M+H)^+$.

b) N-(4-{2-[(3-aminophenyl)amino]pyrimidin-4-yl}phenyl)acetamide (58)

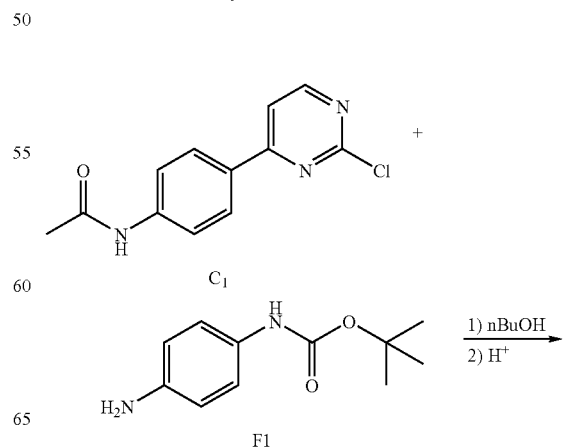

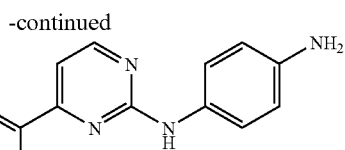

A flask containing a solution of C₁ (500 mg, 2.0 mmol) and 3-boc-amino-aniline F (687 mg, 3.3 mmol) in nBuOH (5 mL) was immersed in an oil bath at 180° C. for 30 mins. The mixture was cooled to ambient temperature and to the black residue was added aqueous HCl and MeOH. The aqueous layer was twice washed with ethylacetate. The aqueous layer was then basified with NaOH and extracted twice with ethylacetate. The organic layer was washed with brine and dried with sodium sulfate. The solvent was removed on a rotary evaporator and the product was purified by HPLC with TFA/ACN as eluent. The TFA salt was removed by extraction with sodium hydroxide and ethylacetate to afford the title compound 58.

Example 2

N-[3-({4-[4-(acetylamino)phenyl]pyrimidin-2-yl}amino)phenyl]-2,6-dichlorobenzamide (Compound 7)

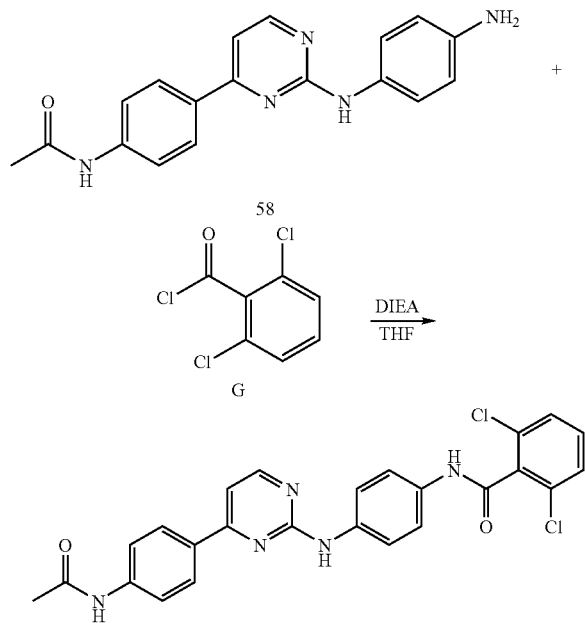

A flask was charged with 58 (638 mg, 2.0 mmol), 2,6-dichlorobenzoylchloride G (350 µL, 2.4 mmol), diisopropylethylamine (1.1 mL, 6 mmol) and THF (50 mL). The reaction mixture was stirred at 70° C. for 6 hours. The crude mixture was concentrated on a rotary evaporator and the crude product was purified by HPLC with TFA/ACN as eluent. The title compound 7 was isolated by precipitation from ACN and washed with ether.

¹H-NMR (400 MHz, d₆-DMSO): 10.718 ppm (s, 1H), 10.269 ppm (s, 1H), 9.678 ppm (s, 1H), 8.507 ppm (d, 1H), 8.419 ppm (s, 1H), 8.215 ppm (d, 2H), 7.758 ppm (d, 2H), 7.608 ppm (d, 2H), 7.532 ppm (t, 1H), 7.472 ppm (d, 1H), 7.380 ppm (d, 1H), 7.301 ppm (t, 1H), 7.216 ppm (d, 1H), 2.085 ppm (s, 3H); MS (EI) $C_{25}H_{19}Cl_2N_5O_2$: 492.2 (MH⁺).

Example 3

N-(4-{2-[(4-morpholin-4-ylphenyl)amino]pyrimidin-4-yl}phenyl)acetamide (18)

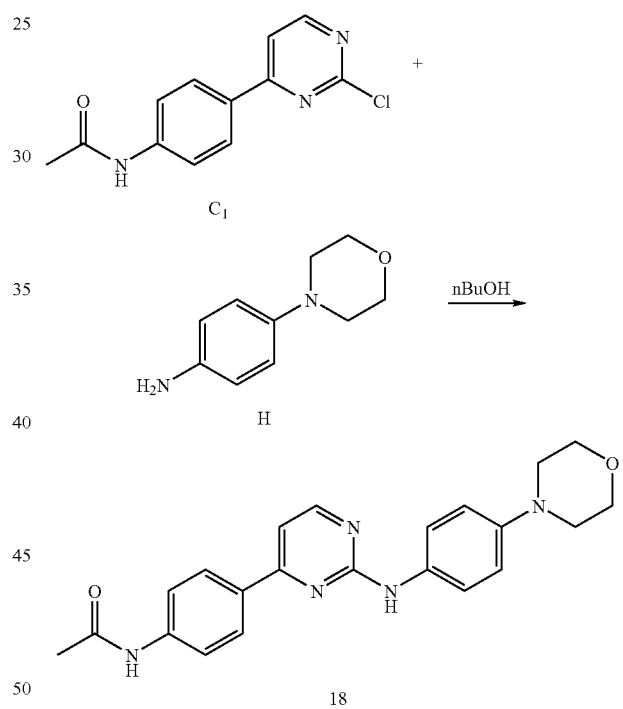

A flask was charged with C₁ (500 mg, 2.0 mmol), 4-morpholinoaniline H (540 mg, 3.0 mmol) and nBuOH (10 mL). The flask was immersed in a 180° C. oil bath for 30 minutes. The reaction mixture was cooled to ambient temperature and the black residue dissolved in DMF and MeOH. The product was purified by HPLC with TFA/ACN as eluent. The TFA salt was removed by extracting with sodium hydroxide and ethylacetate to afford the title compound (18).

¹H-NMR (400 MHz, d₆-DMSO): 10.533 ppm (s, 1H), 9.408 ppm (s, 1H), 8.447 ppm (d, 1H), 8.114 ppm (d, 2H), 7.813 ppm (d, 2H), 7.705 ppm (d, 2H), 7.288 ppm (d, 1H), 6.982 ppm (br s, 2H), 4.65 ppm (br s, 4H), 3.072 ppm (br s, 2H), 2.108 ppm (s, 3H); MS (EI) $C_2H_{23}N_5O_2$: 390.3 (MH⁺).

Example 4

N-{1-[(2,6-dichlorophenyl)carbonyl]piperidin-4-yl}-4-(4-methyl-2-thienyl)pyrimidin-2-amine

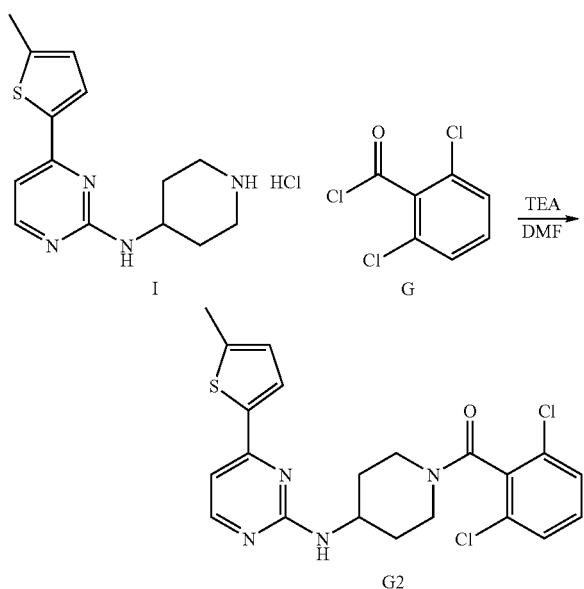

To a solution of {4-[4-(5-Methyl-thiophen-2-yl)-phenyl]-pyrimidin-2-yl}-piperidin-4-yl-amine hydrochloride I (274 mg, 1 mmoL) and TEA (0.69 mL, 5 mmol) in DMF (5 mL) was added 2,6-dichlorobenzoyl chloride G (0.2 mL, 1.5 mmol) and the solution was stirred for 4 h. To the resulting solution was added ethyl acetate (100 mL) and the organic layer was washed with 5% LiCl (3×50 mL), dried over anhydrous sodium sulfate, filtered, and concentrated to yield a residue. This residue was purified by reverse phase HPLC to yield the product G2 (195 mg, 38.9% yield, acetate salt) as a tan solid.

$^1$H NMR (400 MHz, d$_6$-DMSO): 8.28 (m, 1H), 7.73 (m, 1H), 7.58-7.54 (m, 2H), 7.48-7.46 (m, 1H), 7.32 (s, 1H), 7.27 (m, 1H), 7.01 (m, 1H), 4.47 (m, 1H), 4.03 (m, 1H), 3.30-3.05 (m, 2H), 2.25 (s, 3H), 2.03 (m, 1H), 1.88 (m, 1H), 1.58-1.48 (m, 3H); MS (EI) for C$_{21}$H$_{20}$Cl$_2$N$_4$OS: 447 (MH$^+$).

Example 5

N-(4-{5-methyl-2-[(4-morpholin-4-ylphenyl)amino]pyrimidin-4-yl}phenyl)acetamide (Compound 574)

a) N-(4-(2-chloro-5-methylpyrimidin-4-yl)phenyl)acetamide (C$_2$)

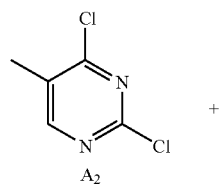

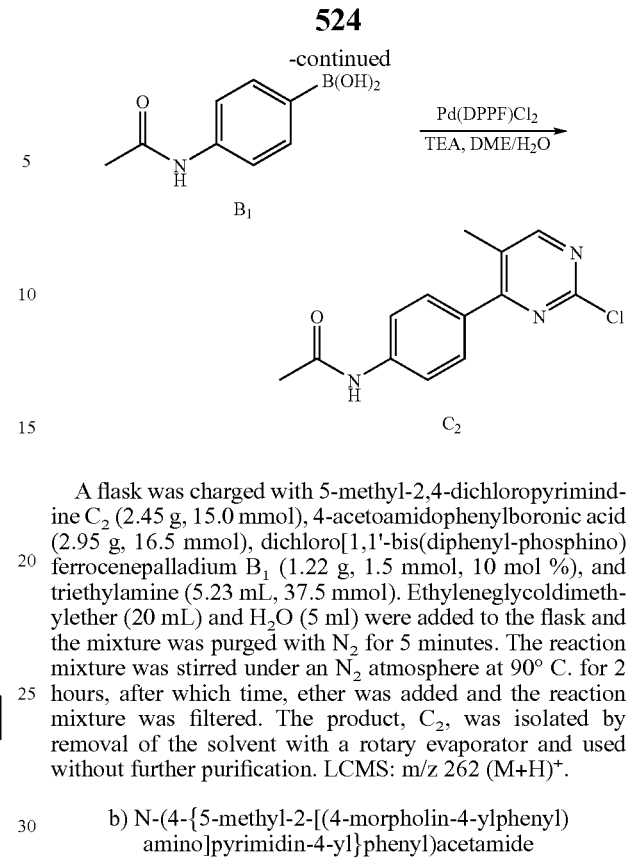

A flask was charged with 5-methyl-2,4-dichloropyrimindine C$_2$ (2.45 g, 15.0 mmol), 4-acetoamidophenylboronic acid (2.95 g, 16.5 mmol), dichloro[1,1'-bis(diphenyl-phosphino)ferrocenepalladium B$_1$ (1.22 g, 1.5 mmol, 10 mol %), and triethylamine (5.23 mL, 37.5 mmol). Ethyleneglycoldimethylether (20 mL) and H$_2$O (5 ml) were added to the flask and the mixture was purged with N$_2$ for 5 minutes. The reaction mixture was stirred under an N$_2$ atmosphere at 90° C. for 2 hours, after which time, ether was added and the reaction mixture was filtered. The product, C$_2$, was isolated by removal of the solvent with a rotary evaporator and used without further purification. LCMS: m/z 262 (M+H)$^+$.

b) N-(4-{5-methyl-2-[(4-morpholin-4-ylphenyl)amino]pyrimidin-4-yl}phenyl)acetamide

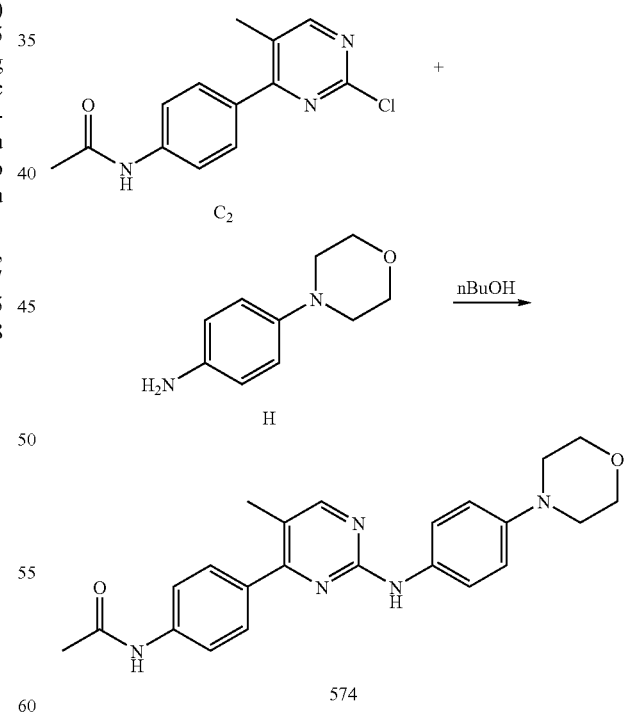

A flask containing a solution of C$_2$ (523 mg, 2.0 mmol) and H (392 mg, 2.2 mmol) in n-BuOH (6 mL) was immersed in an oil bath at 180° C. for 3 hr. The mixture was cooled to ambient temperature and concentrated in vacuo. The residue was purified by HPLC with Ammonium acetate/ACN as eluent to afford the title compound 574 (531 mg, 66%).

¹H-NMR (400 MHz, d₆-DMSO): 10.15 ppm (s, 1H), 9.27 ppm (s, 1H), 8.31 ppm (s, 1H), 7.72 ppm (d, J=8.8 Hz, 2H), 7.66-7.62 ppm (m, 4H), 6.88 ppm (d, J=8.8 Hz, 2H), 3.73 (t, J=4.8 Hz, 4H), 3.01 (t, J=4.8 Hz, 4H), 2.21 ppm (s, 3H), 2.09 (s, 3H); MS (EI) $C_{23}H_{25}N_5O_2$: 404 (M+H)⁺.

Example 6

N-(4-(2-(3,5-dimorpholinophenylamino)-5-methylpyrimidin-4-yl)phenyl)acetamide (Compound 570)

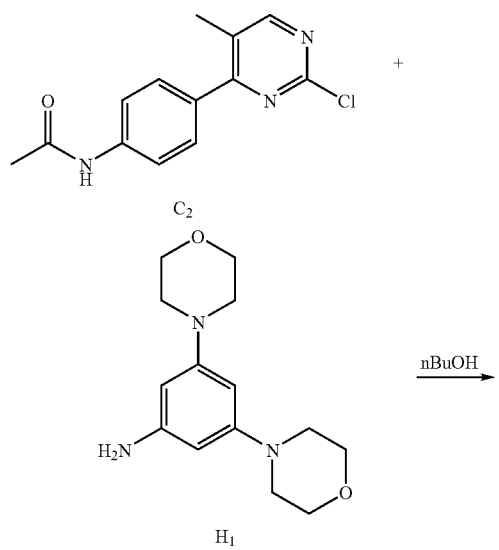

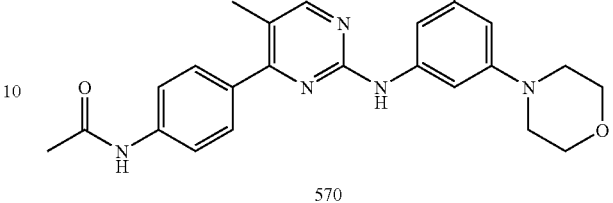

A flask containing a solution of C₂ (288 mg, 1.1 mmol) and H₁ (263 mg, 1.0 mmol) in n-BuOH (3 mL) was immersed in an oil bath at 180° C. for 4 hr. The mixture was cooled to ambient temperature and concentrated in vacuo. The residue was purified by HPLC with ammonium acetate/acetonitrile (ACN) as eluent to afford the title compound 570 (205 mg, 42%).

¹H-NMR (400 MHz, d₆-DMSO): 10.15 ppm (s, 1H), 9.22 ppm (s, 1H), 8.34 ppm (s, 1H), 7.72 ppm (d, J=9.2 Hz, 2H), 7.69 ppm (d, J=8.8 Hz, 2H), 7.10 ppm (d, J=2.0 Hz, 2H), 6.09 ppm (s, 1H), 3.71 (t, J=4.8 Hz, 8H), 3.03 (t, J=4.8 Hz, 8H), 2.26 ppm (s, 3H), 2.07 (s, 3H); MS (EI) $C_{27}H_{32}N_6O_3$: 489 (M+H)⁺.

Example 7

'N-{4-[2-({4-[4-(2-methylpropanoyl)piperazin-1-yl]phenyl}amino)pyrimidin-4-yl]phenyl}acetamide

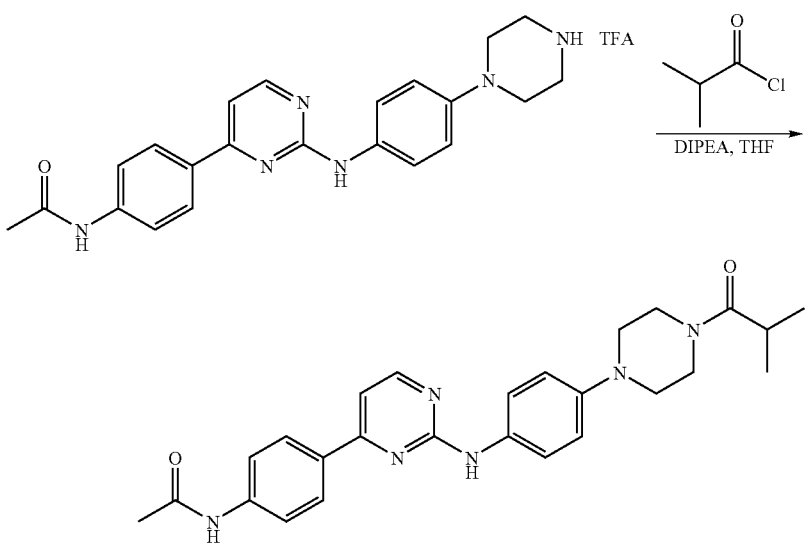

A solution of N-(4-(2-(4-(piperazin-1-yl)phenylamino)pyrimidin-4-yl)phenyl)acetamide (300 mg, 0.6 mmol) and DIPEA (261 ul, 1.50 mmol) was treated with isobutyryl chloride at room temperature. After stirring for 10 minutes, the reaction mixture was directly concentrated in vacuo and the residue was purified by HPLC TFA/ACN as eluent. TFA salt was removed by using basic resin to afford 111 mg (40%) of the title compound 572.

$^1$H-NMR (400 MHz, $d_6$-DMSO): 10.21 ppm (s, 1H), 9.40 ppm (s, 1H), 8.44 ppm (d, J=4.8 Hz, 1H), 8.11 ppm (d, J=9.2 Hz, 2H), 8.10 ppm (s, 1H), 7.74 ppm (d, J=8.8 Hz, 2H), 7.68 ppm (d, J=8.8 Hz, 1H), 7.28 ppm (d, J=5.6 Hz, 1H), 6.97 (d, J=9.6 Hz, 2H), 3.65-3.61 (m, 4H), 3.08-3.02 (m, 4H), 2.92 ppm (penth, J=6.8 Hz, 1H), 2.09 ppm (s, 3H), 1.03 ppm (s, 3H), 1.01 ppm (s, 3H); MS (EI) $C_{26}H_{30}N_6O_2$: 459 (M+H)$^+$.

Example 8

Methyl(4-{2-[(4-morpholin-4-ylphenyl)amino]pyrimidin-4-yl}phenyl)carbamate (Compound 248)

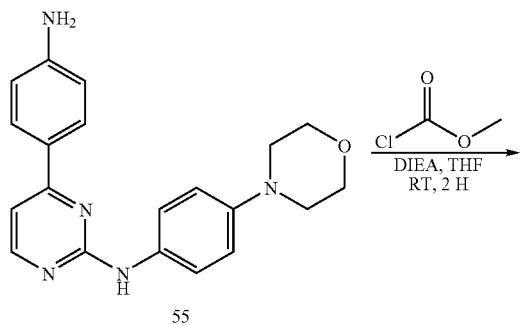

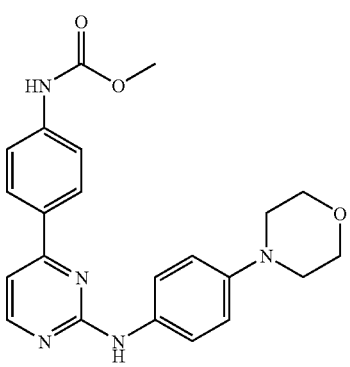

To a solution of 4-(4-aminophenyl)-N-(4-morpholinophenyl)pyrimidin-2-amine 55 (100 mg, 0.29 mmol) and DIEA (0.435 mmol, 75 μl) in THF (50 mL) was added methyl chloroformate (0.348 mmol, 27 μl) and the solution was stirred at room temperature for 2 hours. The solution mixture was concentrated, redissolved with MeOH and purified using reverse phase HPLC. The product obtained from the reverse phase HPLC was free base 248, converted to HCl salt using 3 N HCl and lyophilized to yield the product 248 (60 mg, 47% yield) as a yellow solid.

$^1$H-NMR (400 MHz, $d_6$-DMSO): 10.063 ppm (s, 1H), 9.976 ppm (s, 1H), 8.521 ppm (d, 1H), 8.153 ppm (d, 2H), 7.878 ppm (d, 2H), 7.661 ppm (d, 2H), 7.554 ppm (bs, 2H), 7.432 ppm (d, 1H), 3.983 ppm (bs, 4H), 3.707 ppm (s, 3H), 4.435 ppm (bs, 4H); MS (EI) $C_{22}H_{23}N_5O_3$HCl: 475.4 (MH$^+$).

Example 9

4-[4-(dimethylamino)phenyl]-N-(4-morpholin-4-ylphenyl)pyrimidin-2-amine (67)

a) 4-(2-chloropyrimidin-4-yl)-N,N-dimethylaniline ($C_3$)

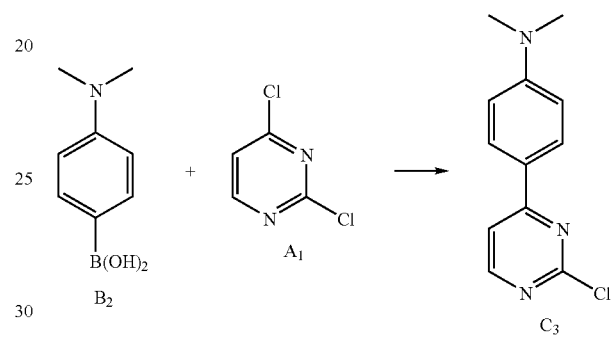

A flask was charged with $A_1$ (650 mg, 4.4 mmol), 4-(dimethylamino)phenylboronic acid $B_2$ (797 mg, 4.8 mmol), dichloro[1,1'-bis(diphenylphosphino)ferrocenepalladium (480 mg, 0.56 mmol, 15 mol %), and triethylamine (1.5 mL, 11 mmol). Ethyleneglycoldimethylether (30 mL) was added to the flask and the mixture was purged with $N_2$ for 5 minutes. The reaction mixture was stirred under an $N_2$ atmosphere at 80° C. for 12 hours, after which time, ether was added and the reaction mixture was filtered. The product, $C_3$, was isolated by removal of the solvent with a rotary evaporator and used without further purification. LCMS: m/z 234 (M+H)$^+$.

b) 4-[4-(dimethylamino)phenyl]-N-(4-morpholin-4-ylphenyl)pyrimidin-2-amine (67)

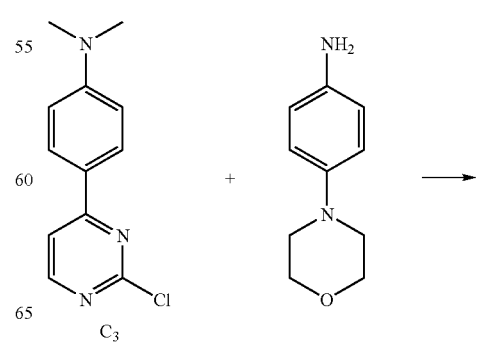

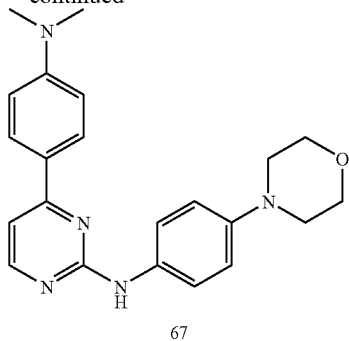

A flask was charged with C$_3$ (500 mg, 2.1 mmol), 4-morpholinoaniline (573 mg, 3.2 mmol) and nBuOH (10 mL). The flask was immersed in a 180° C. oil bath for 30 minutes. The reaction mixture was cooled to ambient temperature and the black residue dissolved in DMF and MeOH. The product 67 was purified by HPLC with TFA/ACN as eluent. The TFA salt was removed by extracting with sodium hydroxide and ethylacetate to afford the free base of 67.

$^1$H-NMR (400 MHz, d$_6$-DMSO): 9.24 ppm (s, 1H), 8.33 (d, 1H), 8.03 (d, 2H), 7.68 (d, 2H), 7.18 (d, 1H), 6.92 (d, 2H), 6.81 (d, 2H), 3.72-3.77 (m, 4H), 3.04-3.08 (m, 4H), 3.00 (s, 6H). MS (EI) C$_{22}$H$_{25}$N$_5$O: 376.1 (MH$^+$).

Example 10

4-[4-(3-methyl-1,2,4-oxadiazol-5-yl)phenyl]-N-(4-morpholin-4-ylphenyl)pyrimidin-2-amine (Compound 319)

a) 4-(2-chloropyrimidin-4-yl)benzonitrile

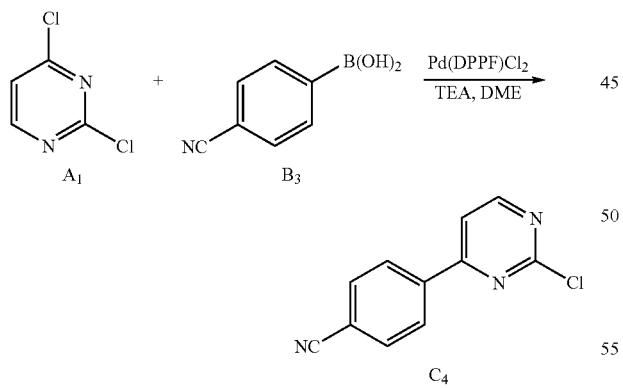

A flask was charged with A$_1$ (763 mg, 5.16 mmol), 4-cyanophenylboronic acid B$_3$ (848 mg, 5.77 mmol), dichloro[1,1'-bis(diphenylphosphino)ferrocenepalladium (375 mg, 0.437 mmol, 10 mol %), and triethylamine (1.76 mL, 12.9 mmol). Ethylene glycol dimethyl ether (5.0 mL) was added to the flask and the mixture was purged with N$_2$. The reaction mixture was stirred under an N$_2$ atmosphere at 90° C. for 1 hour, after which time, it was cooled to ambient temperature and filtered. The product, C$_4$, was isolated by removal of the solvent with a rotary evaporator and used without further purification. LCMS: m/z 216 (M+H)$^+$.

b) 4-(2-(4-morpholinophenylamino)pyrimidin-4-yl)benzonitrile (S)

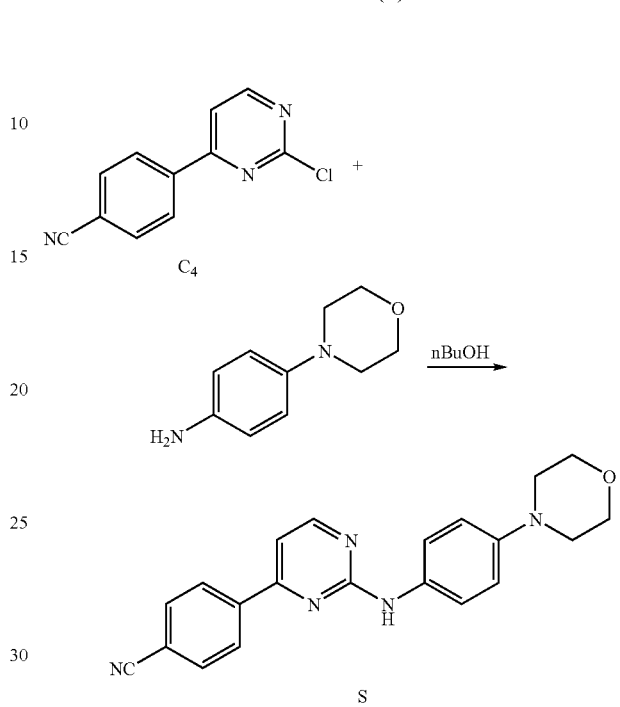

A flask containing a solution of C$_4$ (400 mg, 1.85 mmol) and 4-morphilinoaniline (362 mg, 2.04 mmol) in 1-butanol (10 mL) was immersed in an oil bath at 180° C. for 2 h. The mixture was cooled to ambient temperature, concentrated, and the crude product S was used without further purification. LCMS: m/z 358 (M+H)$^+$.

c) 4-(2-(4-morpholinophenylamino)pyrimidin-4-yl)benzoic acid

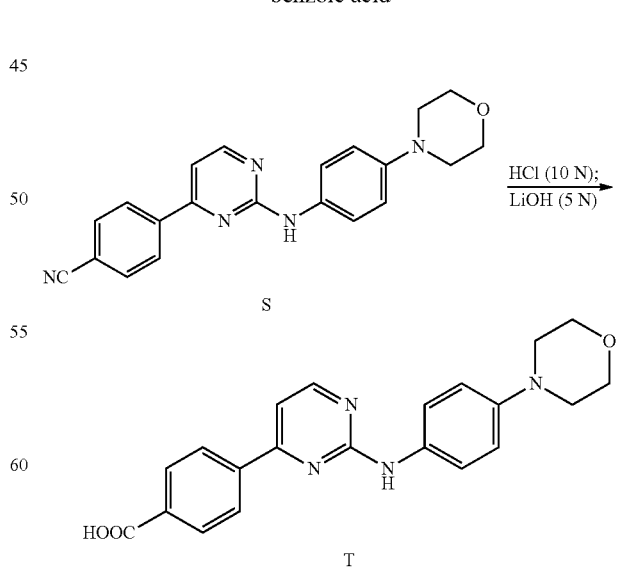

A flask containing a solution of S (600 mg, 1.68 mmol) and 10 N HCl (aq., 20 mL) was immersed in an oil bath at 100° C.

for 5 hours. The mixture was cooled to ambient temperature, after which time, 5 N LiOH was added until the reaction mixture was pH 6. The white precipitate was filtered and dried to give the product T, which was used without further purification. LCMS: m/z 377 (M+H)+.

d) 4-[4-(3-methyl-1,2,4-oxadiazol-5-yl)phenyl]-N-(4-morpholin-4-ylphenyl)pyrimidin-2-amine (323)

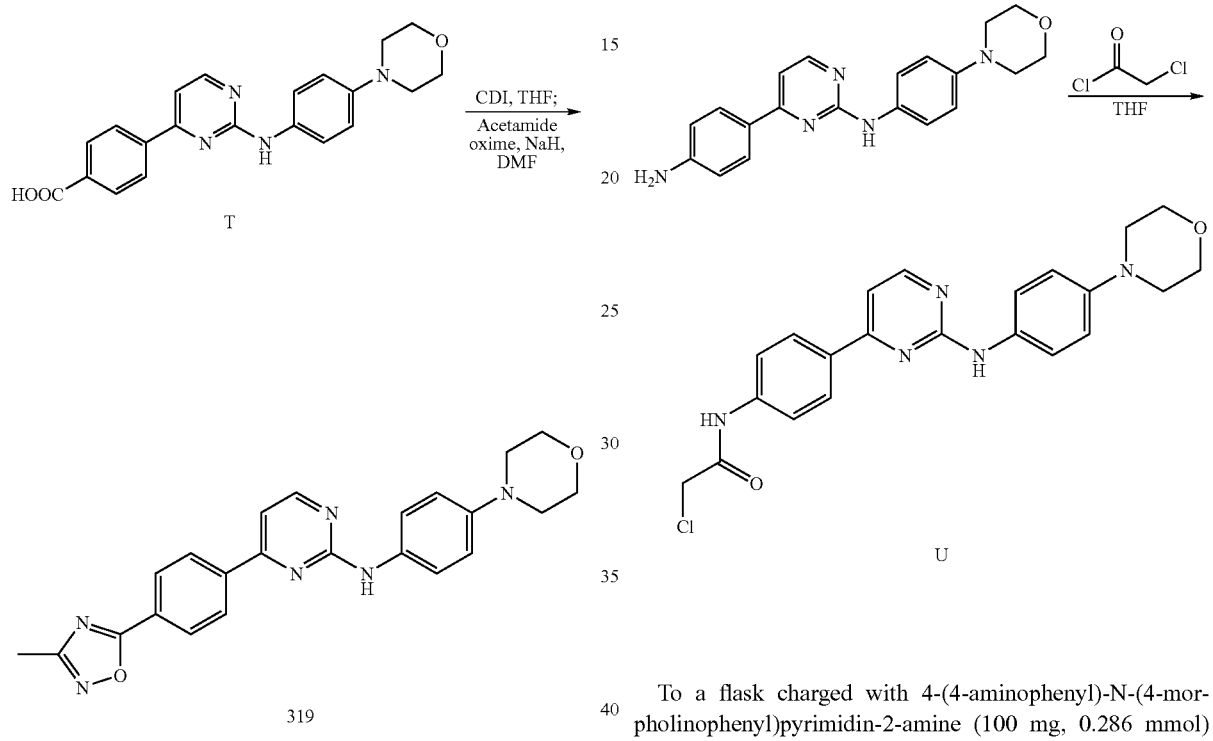

To a flask containing a solution of T (570 mg, 1.47 mmol) and THF (10 mL) was added 1,1'-carbonyldiimidazole (475 mg, 2.93 mmol). The reaction mixture was immersed in an oil bath at 60° C. for 2 h, after which time, it was cooled to ambient temperature. A mixture of acetamide oxime (120 mg, 1.62 mmol) and NaH (39 mg, 1.6 mmol) in DMF (5 mL) was added to the reaction mixture, after which time, the reaction mixture was immersed in an oil bath at 80° C. for 2 hours. The reaction mixture was then cooled to ambient temperature, quenched with saturated NH$_4$Cl (aq., 10 mL), extracted with ethyl acetate (50 mL), dried over anhydrous sodium sulfate, filtered, and concentrated to yield a residue. The residue was purified by reverse phase HPLC to yield the product 319 (49.6 mg, 8.10% yield) as a light brown solid.
$^1$H-NMR (400 MHz, d$_6$-DMSO): 9.57 ppm (s, 1H), 8.57 ppm (d, 1H), 8.38 ppm (d, 2H), 8.25 ppm (d, 2H), 7.67 ppm (d, 2H), 7.44 ppm (d, 1H), 6.95 ppm (d, 2H), 3.75 ppm (t, 4H), 3.06 ppm (t, 4H), 2.46 ppm (s, 3H); MS (EI) C$_{23}$H$_{22}$N$_6$O$_2$: 415.0 (MH+).

Example 11

N-(4-{2-[(4-morpholin-4-ylphenyl)amino]pyrimidin-4-yl}phenyl)-2-pyrrolidin-1-ylacetamide (Compound 292)

a) 2-chloro-N-(4-(2-(4-morpholinophenylamino)pyrimidin-4-yl)phenyl)acetamide

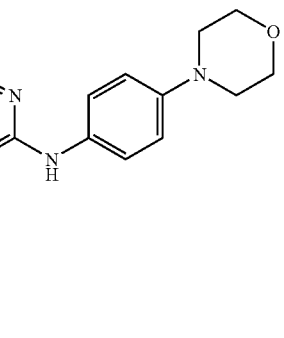

To a flask charged with 4-(4-aminophenyl)-N-(4-morpholinophenyl)pyrimidin-2-amine (100 mg, 0.286 mmol) and THF (1 mL) was added chloroacetyl chloride (0.0230 mL, 0.286 mmol). The solution was stirred at ambient temperature for 1 hour. The crude mixture was then concentrated and used without further purification. LCMS: m/z 424 (M+H)+.

b) N-(4-{2-[(4-morpholin-4-ylphenyl)amino]pyrimidin-4-yl}phenyl)-2-pyrrolidin-1-ylacetamide (292)

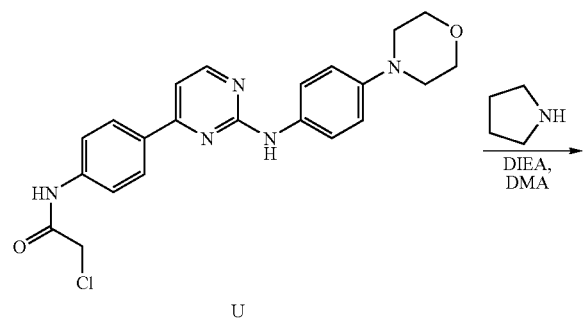

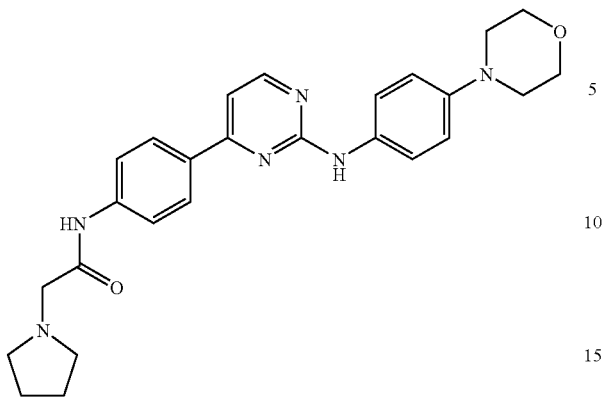

292

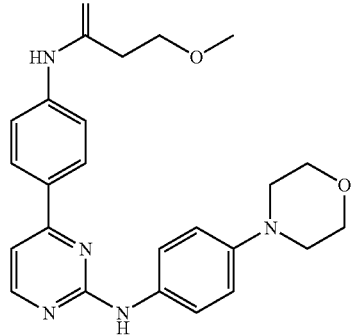

575

To a flask charged with U (100 mg, 0.236 mmol), diisopropylethylamine (0.2 mL, 1 mmol), and dimethylacetamide (1 mL) was added pyrrolidine (0.021 mL, 1.3 mmol). The reaction mixture was stirred at 80° C. for 1 hour. The crude mixture was concentrated on a rotary evaporator and the product 292 was purified by reverse phase HPLC.

$^1$H-NMR (400 MHz, d$_6$-DMSO): 10.90 ppm (s, 1H), 10.20 ppm (br. s, 1H), 9.64 ppm (s, 1H), 8.50 ppm (d, 1H), 8.19 ppm (d, 2H), 7.78 ppm (d, 2H), 7.74 ppm (d, 2H), 7.36 ppm (d, 1H), 7.11 ppm (d, 2H), 4.32 ppm (s, 2H), 3.80 ppm (t, 4H), 3.70-3.65 ppm (m, 2H), 3.19-3.06 ppm (m, 6H), 2.10-1.86 (m, 4H); MS (EI) $C_{26}H_{30}N_6O_2$: 459.4 (MH$^+$).

To a solution of 249(a) (0.18 g, 0.05 mmol), HATU (0.4 g, 1.1 mmol), and DIEA (0.5 mL, 4.0 mmol) in DMA (5 mL) was added 3-methoxypropanoic acid (0.1 mL, 1.05 mmol) and the solution was stirred at 60° C. for 2 hours. The solution mixture was diluted with ethyl acetate and the mixture was extracted with 10% LiCL (3×) and brine (1×). The resulting organic layer was dried with sodium sulfate and concentrated in vacuo. The product was purified by silica column chromatography (5% MeOH/DCM as eluent) to afford 0.1 g of the title compound 575 (49% yield) as a white solid.

$^1$H-NMR (400 MHz, d$_6$-DMSO): 10.20 ppm (s, 1H), 9.37 ppm (s, 1H), 8.42 ppm (d, 1H), 8.10 ppm (d, 2H), 7.74 ppm (d, 2H), 7.65 ppm (d, 2H), 7.25 pm (d, 1H), 6.91 ppm (d, 2H), 3.72 ppm (m, 4H), 3.61 ppm (t, 2H), 3.23 ppm (s, 3H), 3.03 ppm (m, 4H), 2.57 ppm (t, 2H); MS (EI) $C_{22}H_{23}N_5O_3$HCl: 434.3 (MH$^+$).

Example 12

3-methoxy-N-(4-(2-(4-morpholinophenylamino)pyrimidin-4-yl)phenyl)propanamide (Compound 575)

Example 13

N-(4-{2-[(4-morpholin-4-ylphenyl)amino]pyrimidin-4-yl}phenyl)prolinamide (576)

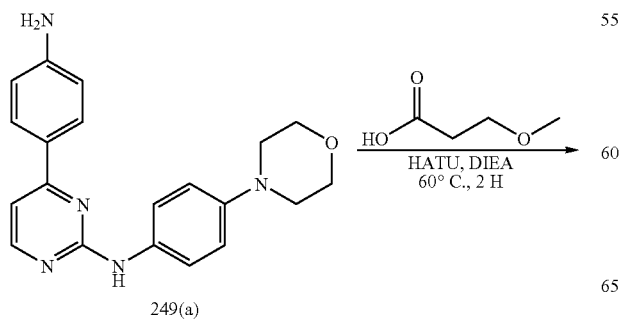

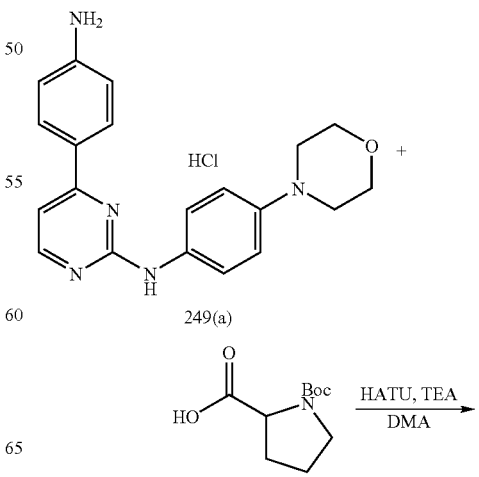

249(a)

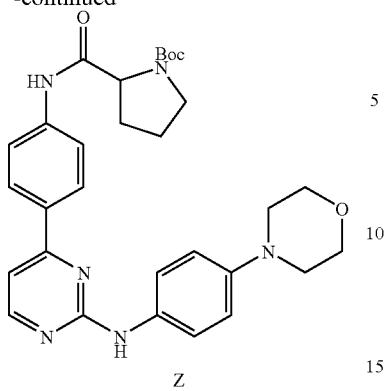

To a solution of 249(a) (5HCl) (0.2 g, 0.37 mmol) in DMA (5 mL) was added a solution of 1-(tert-butoxycarbonyl)pyrrolidine-2-carboxylic acid, (d,l-boc-proline) (0.1 g, 0.46 mmol), Hunigs base (0.5 mL, 2.5 mmol), HATU (0.2 g, 0.52 mmol) and the solution was stirred at RT for 14 hours. The resulting solution was loaded on the silica gel and was purified by silica gel column chromatography (10-100% gradient of ethyl acetate/hexanes) to yield Z (160 mg) in 79% yield as yellow solid. LCMS: m/z 545 (M+H)$^+$.

d) N-(4-(2-(4-morpholinophenylamino)pyrimidin-4-yl)phenyl)pyrrolidine-2-carboxamide (Compound 585)

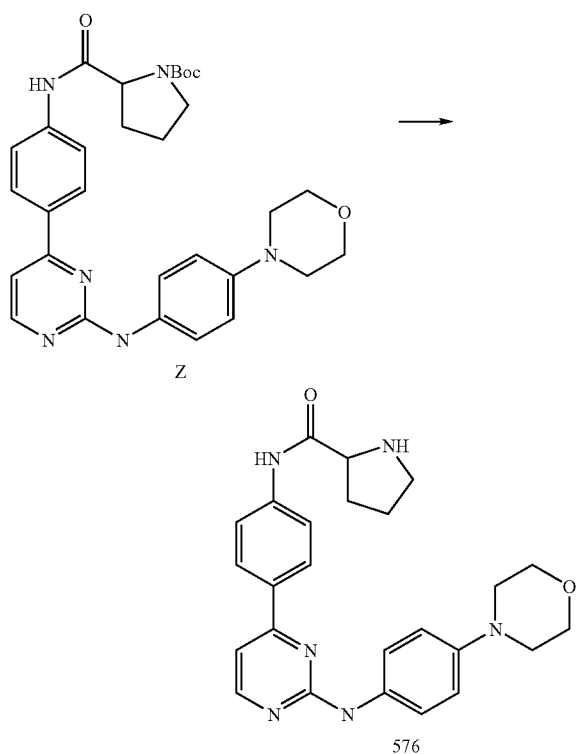

A flask containing a solution of Z (160 mg, 0.29 mmol) in 4M HCl in 1,4-dioxane (5 mL) and MeOH (5 mL) was stirred at 50 C for 1 hour. Concentration of the solvent gave a yellow solid that was purified by reverse phase HPLC using an ammonium acetate buffer to yield 105 mg (68%) of 576 as a yellow solid.

$^1$H NMR (400 MHz, d$_4$-MeOD): 8.36 (m, 1H), 8.14 (m, 2H), 7.78 (m, 2H), 7.62 (m, 2H), 7.22 (m, 1H), 6.98 (m, 2H), 4.15 (m, 1H), 3.83 (m, 4H), 3.21 (m, 2H), 3.13 (m, 4H), 2.41 (m, 1H), 2.06-1.91 (m, 3H); LCMS: for C$_{25}$H$_{28}$N$_6$O$_2$: 445 (M+H)$^+$.

Example 14

2-amino-N-(4-(2-(4-morpholinophenylamino)pyrimidin-4-yl)phenyl)propanamide (Compound 208)

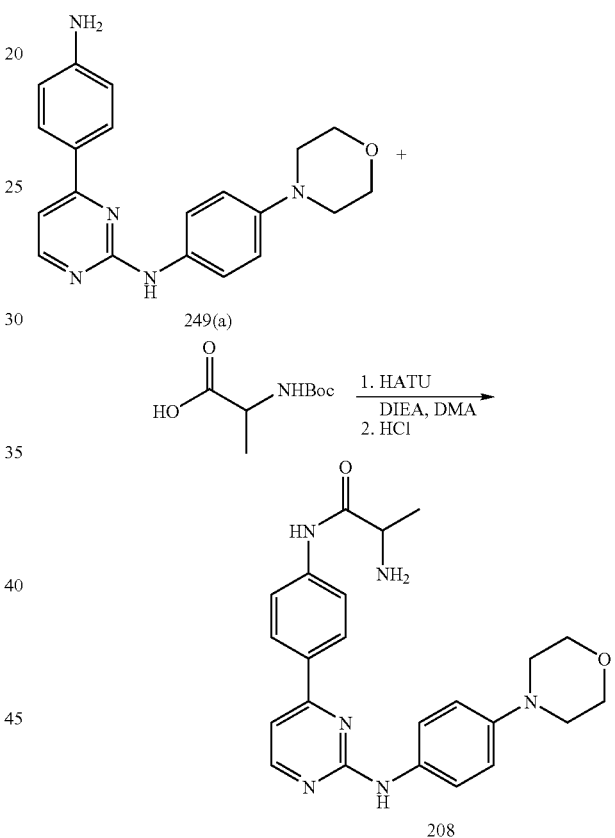

A flask was charged with 249(a) (140 mg, 0.3 mmol), N-(tert-butoxycarbonyl)-alanine (57 mg, 0.3 mmol, purchased from Chem-Impex International), HATU (140 mg, 0.37 mmol), diisopropylethylamine (0.6 mL, 3.0 mmol) and DMA (5 mL). The reaction mixture was stirred at RT for 12 hours. The crude mixture was concentrated on a rotary evaporator and the residue was dissolved in 10 mL of MeOH and 5 mL of 4N HCl in dioxane. The reaction mixture was stirred at 70° C. for 1 hour. The crude mixture was concentrated on a rotary evaporator and the product was purified by HPLC with NH$_4$OAc/ACN as eluent. The resulting solution was concentrated on a rotary evaporator and the final product, 208, was dried by lyophilization.

$^1$H-NMR (400 MHz, d$_6$-DMSO): 9.387 ppm (s, 1H), 8.443 ppm (d, 1H), 8.127 ppm (d, 2H), 7.825 ppm (d, 2H), 7.676 ppm (d, 2H), 7.287 ppm (d, 1H), 6.939 ppm (d, 2H), 3.747 ppm (m, 4H), 3.457 ppm (q, 1H), 3.050 ppm (m, 4H), 1.896 ppm (s, 3H (AcOH)) 1.243 ppm (d, 3H); MS (EI) $C_{23}H_{26}N_6O_2$: 419.1 (MH$^+$).

Example 15

N-(4-(2-(3-methoxy-4-morpholinophenylamino)pyrimidin-4-yl)phenyl)acetamide (Compound 341)

a) 4-(2-methoxy-4-nitrophenyl)morpholine (AA)

A pressure bottle was charged with 1-chloro-2-methoxy-4-nitrobenzene (10.0 g mg, 53.3 mmol, purchased from TCI America) and morpholine (15 mL, 172.0 mmol). The reaction mixture was stirred at 120° C. for 15 hours and it was allowed to cool to room temperature by itself. The resulting solid was suspended in 20 mL of ethyl acetate, filtered, and washed with 20 mL of tert-butyl methyl ether. 8.8 g of yellow solid as the desired product AA was collected (69% yield). $^1$H-NMR (400 MHz, $d_6$-DMSO): 7.83 (dd, 1H), 7.67 (d, 1H), 6.98 (d, 1H), 3.88 (s, 3H), 3.71 (m, 4H), 3.16 (m, 4H). MS (EI) $CH_{11}H_{14}N_2O_4$: 239 (M+H)$^+$.

b) 3-methoxy-4-morpholinoaniline

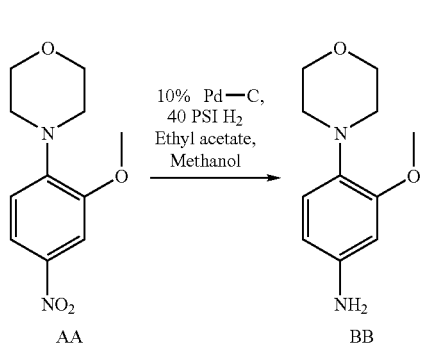

To a solution of AA (8.8 g, 37.0 mmol) in ethyl acetate (30 mL) and methanol (10 mL) in a Parr bottle was added 1 g 10% palladium on carbon. The reaction mixture was hydrogenated at 40 PSI H$_2$ for 1 hour, filtered and concentrated. 8.0 g of a pink solid as the product BB was obtained as a crude product and used without further purification. MS (EI) $C_{11}H_{16}N_2O_2$: 209 (M+H)$^+$.

c) N-(4-(2-(3-methoxy-4-morpholinophenylamino)pyrimidin-4-yl)phenyl)acetamide

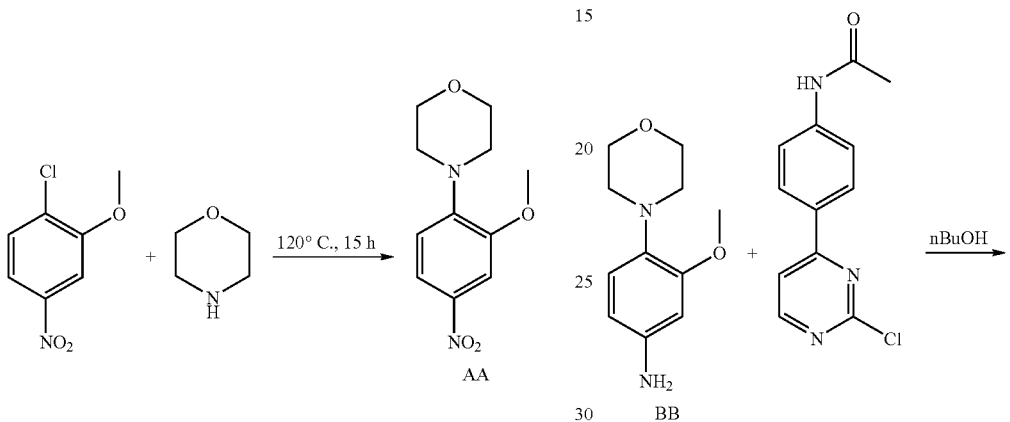

A flask was charged with BB (51 mg, 0.24 mmol), N-(4-(2-chloropyrimidin-4-yl)phenyl)acetamide (50 mg, 0.2 mmol) and nBuOH (2 mL). The flask was immersed in a 180° C. oil bath for 30 minutes, and then cooled to ambient temperature. The residue was suspended in 5 mL of ethyl acetate, stirred for 1 hour, filtered, and washed with 10 mL of ethyl acetate. 50 mg of an off-white powder was obtained as the title compound (341) (60% yield).

$^1$H-NMR (400 MHz, $d_6$-DMSO): 10.33 (s, 1H), 9.50 (br, 1H), 8.54 (d, 1H), 8.15 (d, 2H), 7.95 (br, 1H), 7.77 (d, 2H), 7.42 (m, 2H), 3.94 (s, 3H), 3.77 (br, 4H), 3.40 (br, 2H), 2.15 (s, 2H). MS (EI) $C_{23}H_{25}N_5O_3$: 420 (M+H)$^+$.

Example 16

N-(4-(2-(4-morpholinophenylamino)pyrimidin-4-yl)phenyl)methanesulfonamide (Compound 326)

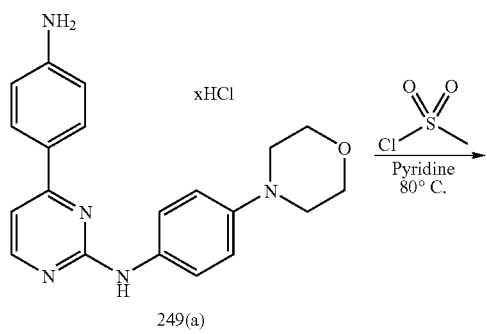

Example 17

Methyl(4-{2-[(4-morpholin-4-ylphenyl)amino]pyrimidin-4-yl}phenyl)carbamate (Compound 248)

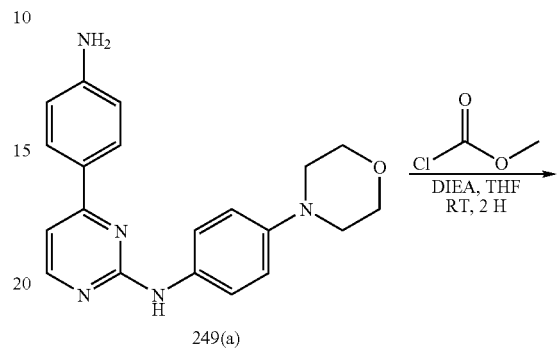

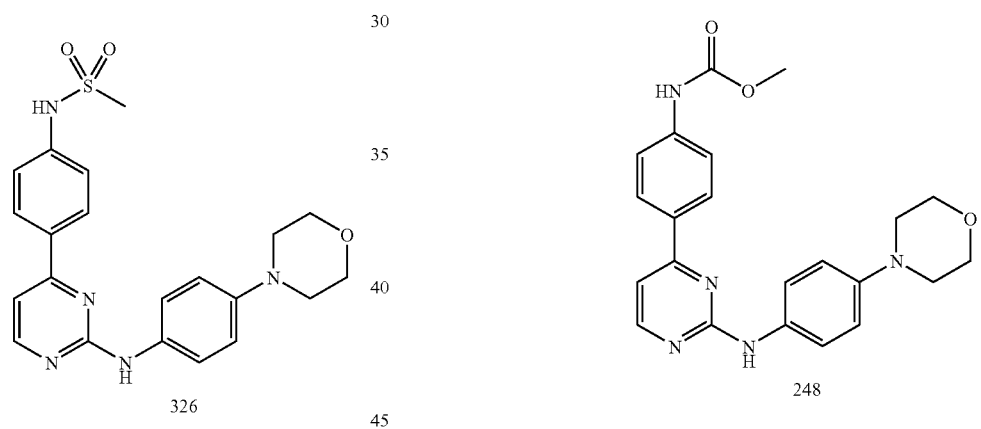

82 (500 mg, 0.94 mmol) was dissolved in 4 mL of pyridine. Methanesulfonyl chloride (730 L, 9.4 mmol) was added dropwise to the vigorously stirred pyridine solution. The addition of the sulfonyl chloride was exothermic and caused a significant increase in the temperature of the reaction. The reaction was maintained at 80° C. for several hours. After cooling, the solvent was removed under vacuum and the residue was purified by reverse phase HPLC to afford 200 mg (52% yield) of the title compound (326).

$^1$H-NMR (400 MHz, $d_6$-DMSO): 10.16 ppm (s, 1H), 9.41 ppm (s, 1H), 8.45 ppm (d, 1H), 8.13 ppm (d, 2H), 7.67 ppm (d, 2H), 7.33 ppm (d, 2H), 7.28 ppm (d, 1H), 6.94 ppm (d, 2H), 3.74 ppm (br s, 4H), 3.09 ppm (s, 3H), 3.05 ppm (br s, 4H); MS (EI) $C_{21}H_{23}N_5O_3S$: 426 (MH$^+$).

To a solution of 4-(4-aminophenyl)-N-(4-morpholinophenyl)pyrimidin-2-amine 249(a) (100 mg, 0.29 mmol) and DIEA (0.435 mmol; 75 µl) in THF (50 mL) was added methyl chloroformate (0.348 mmol, 27 µl) and the solution was stirred at room temperature for 2 hours. The solution mixture was concentrated, redissolved with MeOH and purified using reverse phase HPLC. The product obtained from the reverse phase HPLC was free base 248, converted to HCl salt using 3 N HCl and lyophilized to yield the product 248 (60 mg, 47% yield) as a yellow solid.

$^1$H-NMR (400 MHz, $d_6$-DMSO): 10.063 ppm (s, 1H), 9.976 ppm (s, 1H), 8.521 ppm (d, 1H), 8.153 ppm (d, 2H), 7.878 ppm (d, 2H), 7.661 ppm (d, 2H), 7.554 ppm (bs, 2H), 7.432 ppm (d, 1H), 3.983 ppm (bs, 4H), 3.707 ppm (s, 3H), 4.435 ppm (bs, 4H); MS (EI) $C_{22}H_{23}NO_3$·HCl: 475.4 (MH$^+$).

Example 18

(S)-3-hydroxy-N-(4-(2-(4-morpholinophenylamino)pyrimidin-4-yl)phenyl)butanamide (Compound 363)

Example 19

2-Hydroxy-2-methyl-N-(4-(2-(4-morpholinophenylamino)pyrimidin-4-yl)phenyl)propanamide (Compound 366)

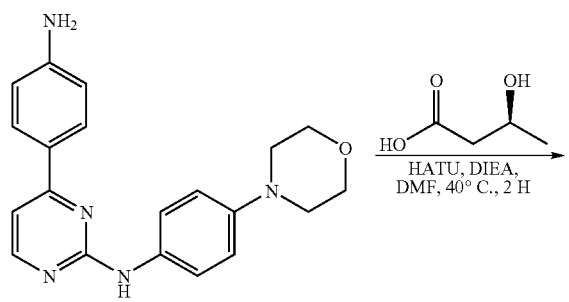

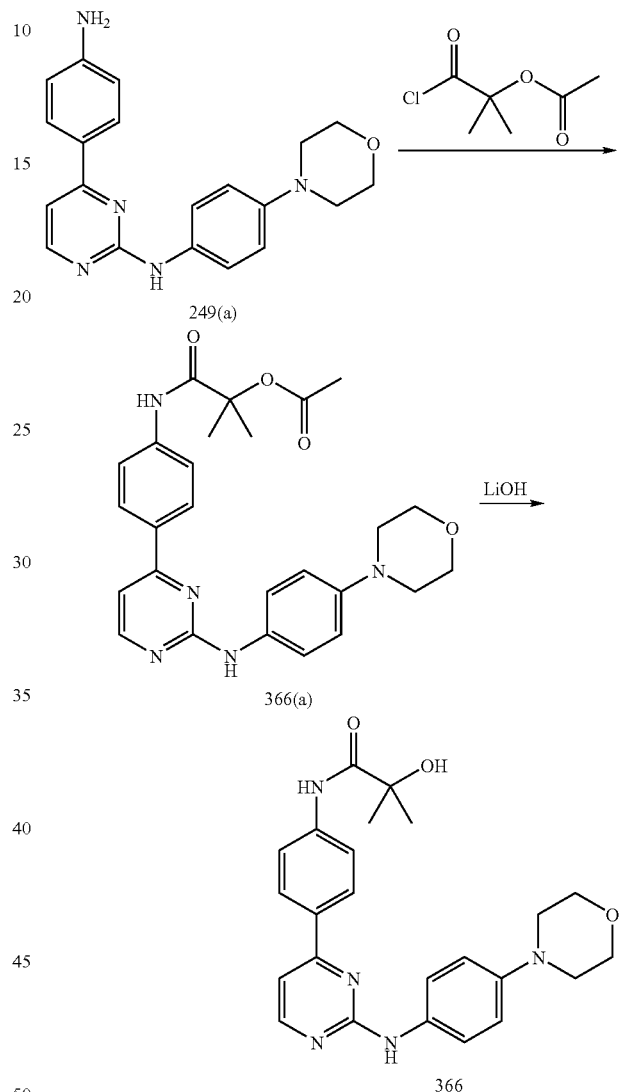

To a solution of (S)-3-hydroxybutyrate (0.180 g, 1.73 mmol), HATU (0.602 g, 1.58 mmol), DIEA (1.0 mL, 5.4 mmol) in DMF (3.0 mL) was added a solution of 4-(4-aminophenyl)-N-(4-morpholinophenyl)pyrimidin-2-amine (0.500 g, 1.44 mmol) in DMF (1.0 mL). The reaction mixture was stirred at rt for 2 hours, at which time it was quenched with saturated $NaHCO_3$ (10 mL, aq.), extracted into DCM (3×), and washed with brine (1×). The organic layers were dried with sodium sulfate and concentrated. The product was purified by reverse phase HPLC to afford (S)-3-hydroxy-N-(4-(2-(4-morpholinophenylamino)pyrimidin-4-yl)phenyl)butanamide (0.136 g, 22% yield) as a light brown solid. (363) $^1$H-NMR (400 MHz, DMSO-$d_6$): 10.14 (s, 1H), 9.38 (s, 1H), 8.44 (d, 1H), 8.12 (d, 2H), 7.77 (d, 2H), 7.68 (d, 2H), 7.27 (d, 1H), 6.94 (d, 2H), 4.79 (d, 1H), 4.11 (m, 1H), 3.74 (m, 4H), 3.05 (m, 4H), 2.47 (dd, 1H), 2.35 (dd, 1H)), 1.15 (d, 3H); MS (EI) m/z for $C_{24}H_{28}N_5O_3$: 434.3 ($MH^+$).

To a solution of 4-(4-aminophenyl)-N-(4-morpholinophenyl)pyrimidin-2-amine (1.0 g, 2.8 mol) 249(a) and DIPEA (0.5 mL, 1 eq.) in anhydrous DMA (5 mL) was added dropwise 2-acetoxy-2-methylpropionyl chloride (3 mol, 1.05 eq., 0.44 mL) at 0° C. The mixture was stirred for 20 min at room temperature. The solution was diluted with water and EtOAc. The organic layer was concentrated in vacuo. The residue 366(a) was suspended in MeOH (10 mL) and a solution of LiOH—$H_2O$ (8.3 mmol, 3 eq. 0.35 g) in water (3 mL) was added. The reaction was complete within 20 min and then was neutralized. The organic solvent was removed in vacuo. The residue was purified to afford 2-hydroxy-2-methyl-N-(4-(2-(4-morpholino-phenylamino)pyrimidin-4-yl)phenyl)propanamide (366) (1.0 g, 85% yield) as a pale yellow solid. ¹H-NMR (400 MHz, DMSO-d₆): 9.86 (s, 1H), 9.41 (s, 1H), 8.47 (d, 1H), 8.12 (d, 2H), 7.94 (d, 2H), 7.68 (d, 2H), 7.30 pm (d, 1H), 6.94 (d, 2H), 5.82 (s, 1H), 3.75 (m, 4H), 3.08 (m, 4H), 1.38 (s, 6H); MS (EI) m/z for $C_{22}H_{23}N_5O_3HCl$: 434.2 (MH⁺).

Example 20

(R)-3-hydroxy-N-(4-(2-(4-morpholinophenylamino)pyrimidin-4-yl)phenyl)butanamide (Compound 364)

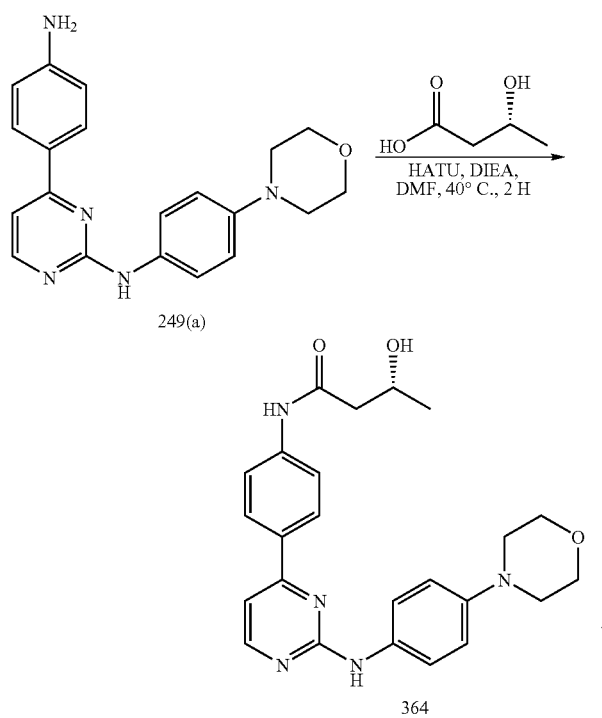

Example 21

(R)-2-amino-3-hydroxy-N-(4-(2-(4-morpholinophenylamino)pyrimidin-4-yl)phenyl)-propanamide (Compound 365)

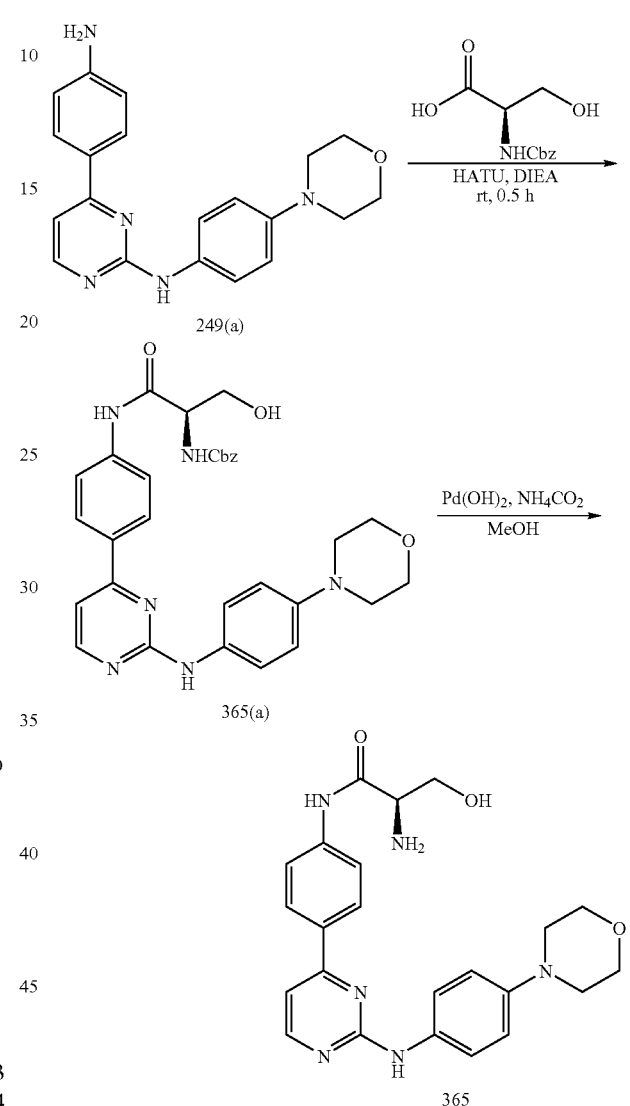

To a solution of (R)-3-hydroxybutyrate (0.180 g, 1.73 mmol), HATU (0.602 g, 1.58 mmol), DIEA (1.0 mL, 5.4 mmol) in DMF (3.0 mL) was added and a solution of 4-(4-aminophenyl)-N-(4-morpholinophenyl)pyrimidin-2-amine (249(a)) (0.500 g, 1.44 mmol) in DMF (1.0 mL). The reaction mixture was stirred at room temperature for 2 hours, at which time it was quenched with saturated NaHCO₃ (10 mL, aq.), extracted into DCM (3×), washed with brine (1×), and the organic layers were dried with sodium sulfate. The solution was concentrated and the product was purified by reverse phase HPLC to afford (R)-3-hydroxy-N-(4-(2-(4-morpholinophenylamino)pyrimidin-4-yl)phenyl)butanamide (364) (0.129 g, 21% yield) as a light brown solid. ¹H-NMR (400 MHz, DMSO)-d₆: 10.14 (s, 1H), 9.38 (s, 1H), 8.44 (d, 1H), 8.12 (d, 2H), 7.77 (d, 2H), 7.68 (d, 2H), 7.27 (d, 1H), 6.94 (d, 2H), 4.79 (d, 1H), 4.11 (m, 1H), 3.74 (m, 4H), 3.05 (m, 4H), 2.47 (dd, 1H), 2.35 (dd, 1H), 1.15 (d, 3H); MS (EI) m/z for $C_{24}H_{28}N_5O_3$: 434.3 (MH⁺).

To a solution of 4-(4-aminophenyl)-N-(4-morpholinophenyl)pyrimidin-2-amine 249(a) (521 mg, 1.5 mmol), N-CBZ-D-Serine (359 mg, 1.5 mmol), and DIEA (0.653 mL, 3.75 mol) in DMA (4 mL) was added HATU (855 mg, 2.25 mmol) and the solution was stirred at room temperature for 0.5 hour. Excess H₂O was added to the reaction mixture. The precipitate was collected and were redissolved in CH₂Cl₂, washed with NaHCO₃ (aq) (2×), brine, dried over Na₂SO₄, and concentrated in vacuo. The residue was purified by silica column chromatography. (1% MeOH/DCM as eluent) to afford (R)-benzyl 3-hydroxy-1-(4-(2-(4-morpholino-phenylamino)pyrimidin-4-yl)phenylamino)-1-oxopropan-2-ylcarbamate 365 (a) (668 mg, 78% yield).

To a stirred solution of (R)-benzyl 3-hydroxy-1-(4-(2-(4-morpholinophenylamino)-pyrimidin-4-yl)phenylamino)-1-oxopropan-2-ylcarbamate from the step above in MeOH (10 mL) was added Pd(OH)$_2$ (134 mg) and ammonium formate (369 mg, 5.85). The mixture was heated at 60° C. for 2 hours, cooled down to room temperature, and filtered on Celite by eluting with MeOH. The filtrate was concentrated in vacuo and the residue was purified by preparatory HPLC (TFA). The TFA salt was removed by using basic resin to afford (R)-2-amino-3-hydroxy-N-(4-(2-(4-morpholinophenylamino)pyrimidin-4-yl)phenyl)propanamide 365 (346 mg, 68%). $^1$H-NMR (400 MHz, DMSO-d$_6$): 9.39 (s, 1H), 8.44 (d, 1H), 8.13 (d, 2H), 7.83 (d, 2H), 7.67 (d, 2H), 7.29 (d, 1H), 6.94 pm (d, 2H), 4.94 (m, 1H), 3.75 (m, 4H), 3.60 (m, 2H), 3.46 (m, 1H), 3.05 (m, 4H); MS (EI) m/z for C$_{23}$H$_{26}$N$_6$O$_3$: 435.4 (MH$^+$).

Example 22

N-{4-[2-({3-[(4-ethylpiperazin-1-yl)methyl]phenyl}amino)pyrimidin-4-yl]phenyl}-acetamide (Compound 122)

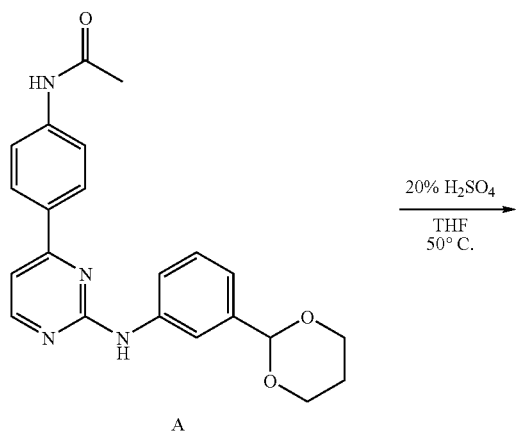

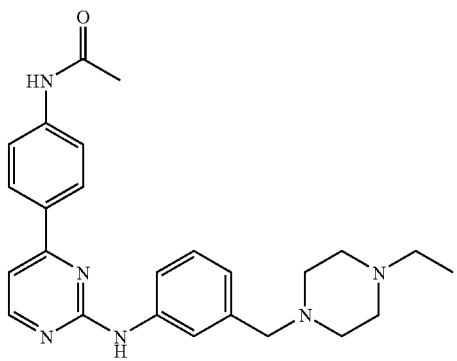

122

Intermediate A (0.5 g) was dissolved in THF (5 ml), 20% aqueous H$_2$SO$_4$ solution (5 ml) was then added to the solution. The mixture was stirred at 50° C. for 2 hours and monitored by LC/MS (MH$^+$, 333). The solution was then neutralized with 2N NaOH solution and extracted with ethyl acetate. The organic layer was washed with brine, dried over Na$_2$SO$_4$, and concentrated to afford 0.38 g of the aldehyde B. (90% yield).

A flask was charged with aldehyde B (0.1 g, 0.3 mmol), dichloromethane (10 ml), sodiumtriacetoxyborohydride (0.32 g, 1.5 mmol), and 1-ethylpiperazine (0.19 ml, 1.5 mmol). The reaction mixture was stirred at room temperature overnight and checked with LC/MS. The product 122 was isolated by removal of the solvent with a rotary evaporator and then purified with a preparative HPLC.

$^1$H NMR (400 MHz, d$_6$-DMSO): 10.23 (s, 1H), 9.6 (s, 1H), 8.5 (d, 1H), 8.14 (d, 2H), 7.9 (s, 1H), 7.76 (d, 2H), 7.65 (d, 1H), 7.36 (d, 1H), 7.24 (t, 1H), 6.89 (d, 1H), 3.43 (s, 2H), 2.4 (br, 6H), 2.3 (q, 2H), 2.1 (s, 3H), 0.96 (t, 3H). MS (EI) for C$_{25}$H$_{30}$N$_6$O: 431 (MH$^+$).

Example 23

2-(3-(1H-imidazol-1-yl)propylamino)-N-(4-(2-(4-morpholinophenylamino)pyrimidin-4-yl)phenyl)acetamide (Compound 143)

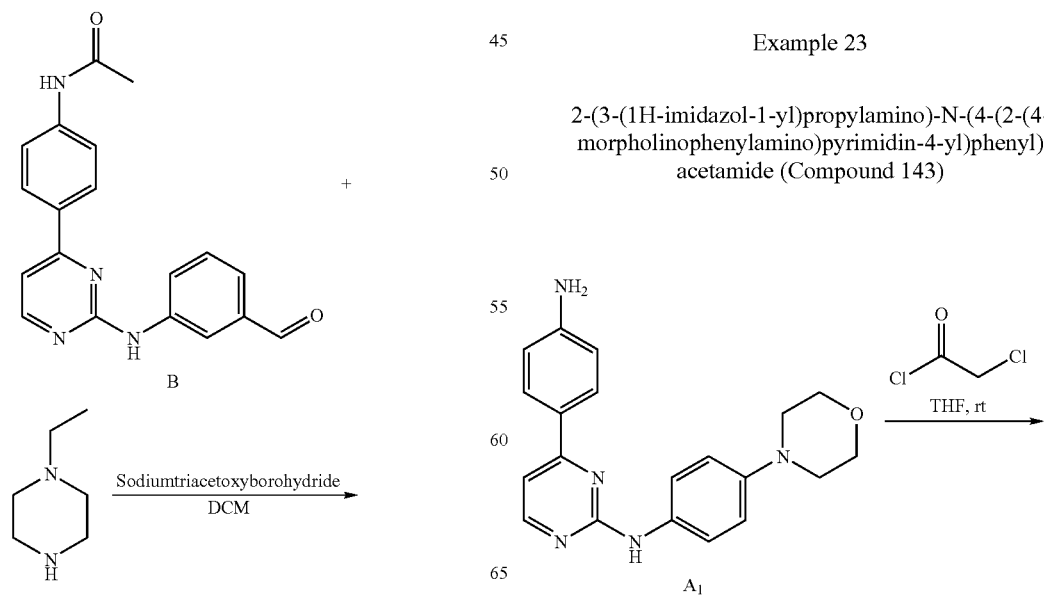

547
-continued

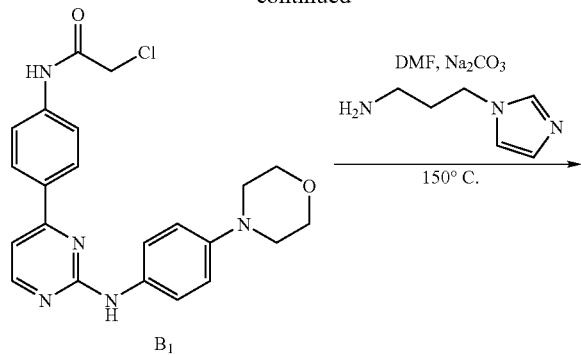

A flask was charged with aniline $A_1$ (100 mg, 0.29 mmol), and THF (1.0 mL). Chloroacetylchloride (23 µL, 0.29 mmol) was added and the mixture was stirred at ambient temperature for 1 hr, after which time it was concentrated. The product, $B_1$, was isolated by removal of the solvent with a rotary evaporator and used without further purification.

A flask was charged with alkyl chloride $B_1$ (20 mg, 0.047 mmol), $Na_2CO_3$ (30 mg, 0.28 mmol), 1-(3-Aminopropyl)imidazole (5.6 µL, 0.047 mmol), and DMF (1.0 mL). The mixture was stirred at 150° C. for 1 hr, after which time it was concentrated. The product 143 was purified by reverse phase HPLC to afford 9.7 mg (40% yield from $B_1$) as a white solid.

$^1$H-NMR (400 MHz, d6-DMSO): 8.35 (d, 1H), 8.13 (d, 2H), 7.78-7.63 (m, 3H), 7.61 (d, 2H), 7.22 (d, 1H), 7.17 (s, 1H), 7.05-6.95 (m, 2H), 4.62 (s, br, 1H), 4.16 (t, 2H), 3.87-3.77 (m; 4H), 3.49 (s, 1H), 3.34 (s, 1H), 3.15-3.07 (m, 4H), 2.67 (t, 2H), 2.11-2.01 (m, 2H), 1.95 (s, 2H). MS (EI) $C_{28}H_{32}N_8O_2$: 513.1 (MH+).

548

Example 24

N-chloro-N-(4-(2-(3-methoxy-4-morpholinophenylamino)pyrimidin-4-yl)phenyl)-2-(1H-tetrazol-1-yl)acetamide (Compound 554)

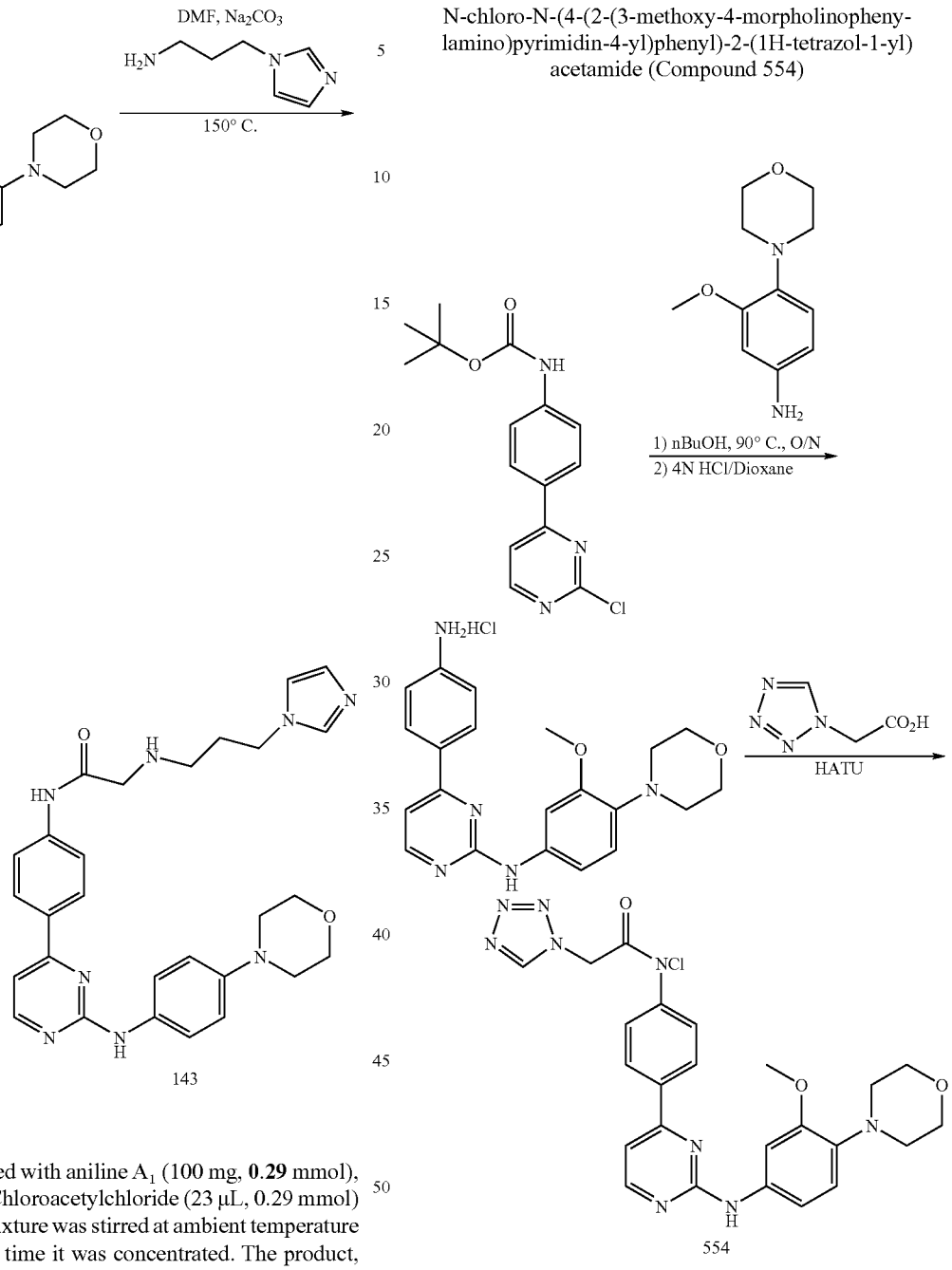

4-(4-aminophenyl)-N-(3-methoxy-4-morpholinophenyl)pyrimidin-2-amine hydrochloride: A flask was charged with tert-butyl 4-(2-chloropyrimidin-4-yl)phenylcarbamate A (12.2 g, 40.0 mmol), 3-Methoxy-4-morpholinoaniline (9.7 g, 40.76 mmol) and 50 mL n-butanol. The reaction mixture was stirred under an $N_2$ atmosphere at 100° C. for 12 hours, after which time, then, cooled to room temperature. 25 mL of 4N HCl in dioxane was added, the reaction mixture was stirred at 50° C. for 5 hours. After cooled to room temperature, it was filtered, washed with ethyl acetate, dried in the air to collect 16 g of yellow-green solid as the desired product. NMR (400 MHz, d6-DMSO): 10.40 (s, 1H), 8.60 (d, 1H), 8.20 (s, 2H), 7.94 (s, 1H), 7.84 (d, 1H), 7.54 (d, 1H), 7.41 (d, 1H), 7.30 (m, 2H), 4.10 (m, 2H), 3.99 (s, 3H), 3.60 (br, 2H), 3.39 (m, 2H), 1.25-1.42 (m, 4H). MS (EI) for $C_{21}H_{23}N_5O_2$: 378 (MH+).

A flask was charged with 4-(4-aminophenyl)-N-(3-methoxy-4-morpholinophenyl)pyrimidin-2-amine hydrochloride B (471.0 mg, 0.84 mmol), 2-(1H-tetrazol-1-yl)acetic acid (216.0 mg, 1.69 mmol), HATU (1276.0 mg, 3.38 mmol) and 2 mL of DMA. The reaction mixture was stirred at room temperature for 24 hours, and then quenched with 50 mL of water, extracted with ethyl acetate (3×50 mL). The combined organics were washed with water and then brine (50 mL each), dried over anhydrous sodium sulfate, and then concentrated. The crude product was purified with a silica gel column (ethyl acetate to 10% methanol in ethyl acetate), 345.0 mg of the desired product 554 was obtained as yellowish powder. NMR (400 MHz, d6-DMSO): 10.85 (s, 1H), 9.50 (s, 1H), 9.43 (s, 1H), 8.47 (s, 1H), 8.19 (d, 2H), 7.75 (d, 2H), 7.63 (s, 1H), 7.20 (m, 3H), 6.84 (d, 1H), 5.56 (s, 2H), 3.80 (s, 3H), 3.74 (m, 4H), 2.94 (m, 4H). MS (EI) for $C_{24}H_{25}N_9O_3$: 488 (MH+).

Example 25

4-[4-(1,1-Dioxidoisothiazolidin-2-yl)phenyl]-N-(4-morpholin-4-ylphenyl)pyrimidin-2-amine (Compound 374)

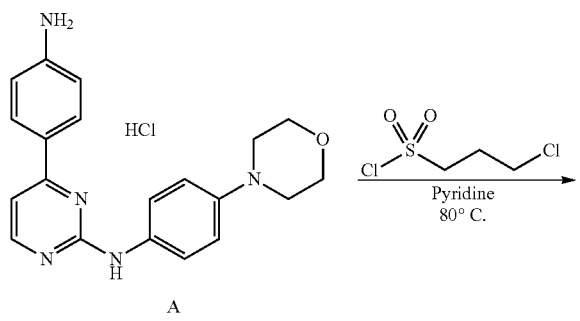

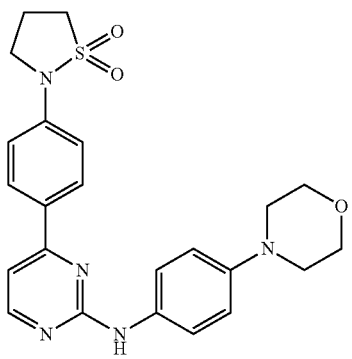

374

Aniline A (300 mg, 0.78 mmol) was dissolved in 4 mL of dry pyridine. 3-Chloropropanesulfonyl chloride (950 uL, 7.8 mmol) was added dropwise. The reaction mixture was heated to 80° C. and stirred overnight under a nitrogen atmosphere. The solvent was removed under vacuum and the residue was re-dissolved in 25 mL of ethyl acetate. The reaction mixture was washed one time each with 10 mL portions of water, 0.1 M HCl, and saturated aqueous NaCl. The organic layer was dried with MgSO₄ and concentrated under vacuum. The residue was taken up in DMF (4 mL) and triethylamine (1100 uL, 7.9 mmol). The reaction mixture was heated to 80° C. and stirred overnight. The product was purified by preparative HPLC to give 85 mg of 374. ¹H NMR (400 MHz, d₆-DMSO): 9.78 (s, 1H), 8.49 (d, 1H), 8.20 (d, 2H), 7.78 (d, 2H), 7.39 (d, 1H), 7.33 (d, 2H), 7.25 (br s, 2H), 3.84 (br s, 4H), 3.73 (t, 2H), 3.60 (t, 2H), 2.54 (m, 2H), 2.45 (m, 2H) 2.01 (m, 2H); MS (EI) for $C_{23}H_{25}N_5O_3S$: 452 (MH⁺).

Example 26

N-(4-Morpholin-4-ylphenyl)-4-[4-(1H-tetrazol-1-yl)phenyl]pyrimidin-2-amine

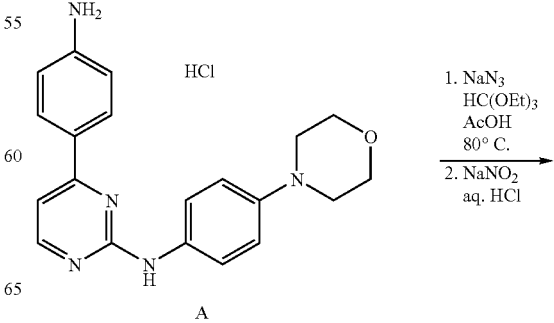

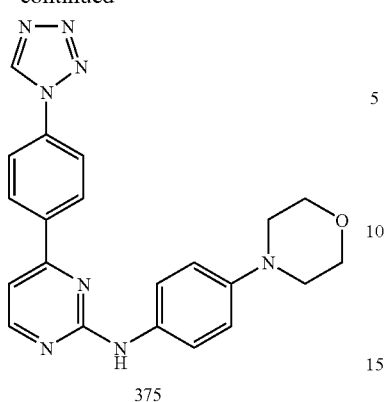

375

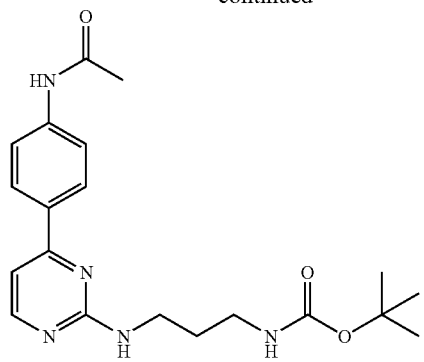

Aniline A (200 mg, 0.52 mmol), sodium azide (45 mg, 0.69 mmol), triethylorthoformate (280 uL, 1.7 mmol) and acetic acid (480 uL, 8.4 mmol) were combined in a 25 mL round bottom flask. The reaction mixture was stirred for 2 hours at 80° C. The reaction mixture was allowed to cool to room temperature and then it was cooled further in an ice bath. A solution of 670 uL of 6.0 M HCl in 1.25 mL of water was added to the reaction mixture. After stirring in the ice bath for 5 minutes, another solution of sodium nitrite (50 mg, 0.72 mmol) in water (200 uL) was added slowly. The precipitate was filtered off and purified by reverse phase HPLC to give 24 mg of 375. $^1$H NMR (400 MHz, d$_6$-DMSO): 10.19 (s, 1H), 9.51 (s, 1H), 8.53 (d, 1H), 8.40 (dd, 2H), 8.10 (d, 2H), 7.65 (d, 2H), 7.43 (d, 1H), 6.92 (d, 2H), 3.73 (m, 4H), 3.03 (m, 4H); MS (EI) for C$_{21}$H$_{20}$N$_8$O: 401 (MH$^+$).

Example 27

N-[3-({4-[4-(acetylamino)phenyl]pyrimidin-2-yl}amino)propyl]-2-fluoro-6-iodobenzamide (Compound 289)

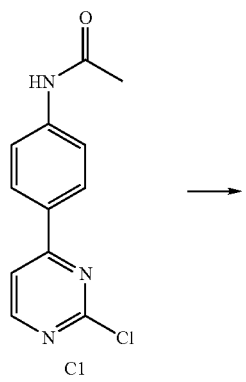

C1

289

A flask was charged with C1 (5.0 g, 20.2388 mmol) and (3-aminopropyl)-carbamicacid-t-butyl ester (6 mL, 30.3582 mmol). N-butanol (40 mL) were added to the flask and heated to 175° C. for an hour. Solvent was evaporated and reaction mixture was checked with LC/MS. The reaction mixture was cooled to room temperature and ethyl acetate was added. The precipitate, B, was filtered and used without further purification. LC/MS: m/z 386 (M+H)$^+$.

A flask was charged with B. 4 N HCl in dioxane was added and stirred at room temperature for 3 hours. The reaction mixture was checked with LC/MS. The product, E, was isolated by removal of the solvent with a rotary evaporation and used without further purification. LC/MS; m/z 286 (M+H)$^+$.

A flask was charged with E (254 mg, 0.8902 mmol), 2-fluoro-6-iodobenzoyl chloride (90 µL, 0.6231 mmol), tetrahydrofuran (25 mL), and n-ethyldiisopropylamine (108 µL, 0.6231 mmol). The reaction mixture was stirred at room temperature for 12 hours. The reaction mixture was monitored with LC/MS. The product, 289, was isolated by removal of the solvent with a rotary evaporator and purified with a TFA preparative HPLC (10:90, 11 min run).

$^1$H-NMR (400 MHz, $d_6$-DMSO): 10.16 ppm (s, 1H), 8.64 ppm (t, 1H), 8.30 ppm (d, 1H), 8.06 ppm (d, 2H), 7.70 ppm (m, 3H), 7.30 ppm (m, 1H), 7.20 ppm (m, 1H), 7.13 ppm (m, 1H), 7.07 ppm (m, 1H), 3.34 ppm (m, 4H), 2.08 ppm (s, 3H), 1.83 ppm (m, 2H); MS (EI) $C_{22}H_{21}FIN_5O_2$: 533.9 (MH$^+$).

Example 28

N-(4-{2-[(3-{[(2,6-dimethylphenyl)methyl]amino}phenyl)amino]pyrimidin-4-yl}phenyl)acetamide (Compound 51)

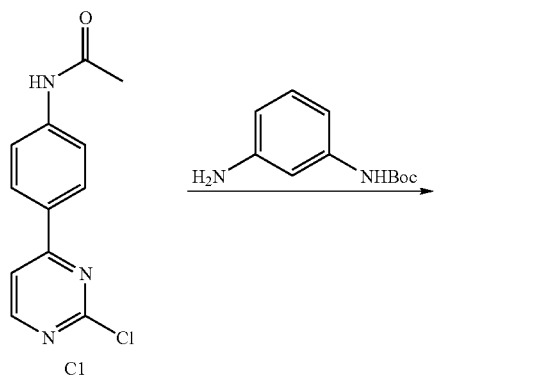

A flask was charged with C1 (5.0 g, 20.2388 mmol) and tert-butyl 3-aminophenylcarbamate (4.6 g, 22.2627 mmol). N-butanol (40 mL) were added to the flask and heated to 175° C. for 4 hours. Solvent was evaporated and reaction mixture was checked with LC/MS. The reaction mixture was cooled to room temperature and ethyl acetate was added. The precipitate, D, was filtered and used without further purification. LC/MS: m/z 320 (M+H)$^+$.

A flask was charged with D (463 mg, 1.4514 mmol), dichloromethane/tetrahydrofuran (2; 1, 15 mL), sodium triacetoxyborohydride (615 mg, 2.9028 mmol), and 2,6-dimethylbenzaldehyde (196 µL, 1.4514 mmol) The reaction mixture was stirred at room temperature for 12 hours and monitored with LC/MS. The product, 51, was isolated by removal of the solvent with a rotary evaporator and purified with a TFA preparative HPLC (10:90, 11 min run). $^1$H-NMR (400 MHz, $d_6$-DMSO): 10.20 ppm (s, 1H), 9.36 ppm (s, 1H), 8.47 ppm (d, 1H), 8.16 ppm (d, 2H), 7.72 ppm (d, 2H), 7.35 ppm (s, 1H), 7.31 ppm (d, 1H), 7.12 ppm (m, 1H), 7.07 ppm (m, 2H), 6.99 ppm (m, 3H), 6.38 ppm (d, 1H), 5.46 ppm (t, 1H), 4.14 ppm (d, 2H), 2.36 ppm (s, 6H), 2.08 ppm (s, 3H); MS (EI) $C_{27}H_{27}N_5O$: 438.1 (MH$^+$).

Example 29

3-({4-[4-(acetylamino)phenyl]pyrimidin-2-yl}amino)-N-[2-(dimethylamino)ethyl]benzamide (Compound 9)

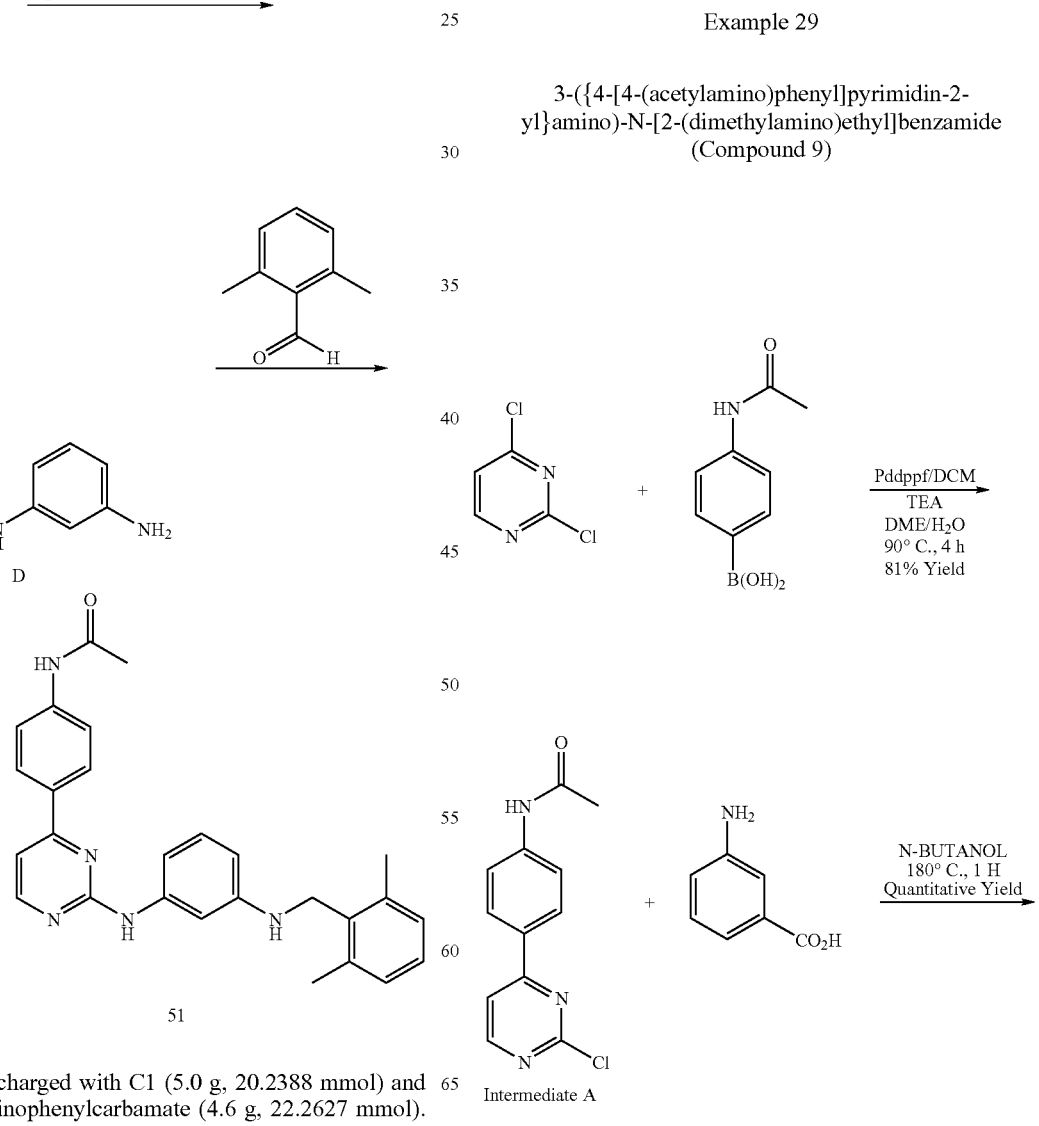

555
-continued

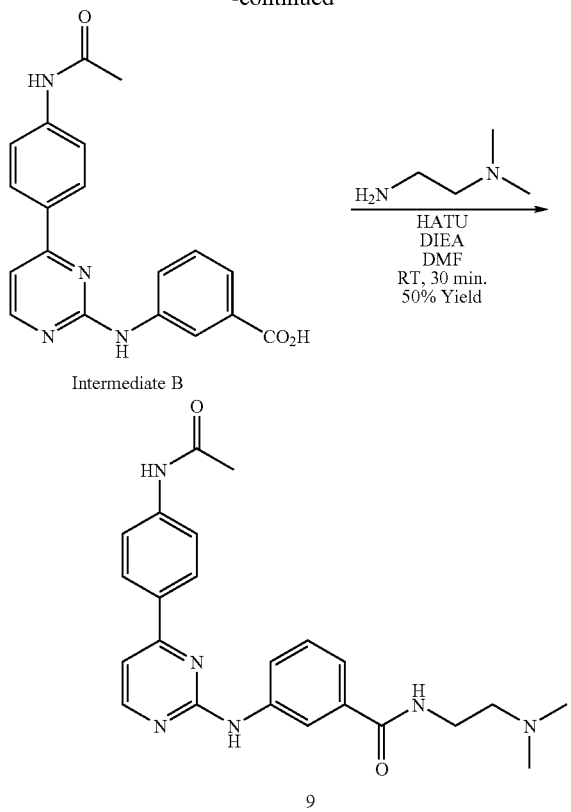

Intermediate B

9

A flask was charged with 2,4-dichloropyrimindine (22.7 g, 152.38 mmol), 4-acetoamidophenylboronic acid (30.0 g, 167.62 mmol), dichloro[1,1'-bis(diphenylphosphino)ferrocenepalladium (16.726 g, 22.86 mmol, 15 mol %), and triethylamine (53 mL, 380.95 mmol). Ethyleneglycoldimethylether (500 mL) and $H_2O$ (20 mL) was added to the flask. The reaction mixture was stirred at 80° C. for 4 hours. The product, Intermediate A, was isolated 0.5 by removal of the solvent with a rotary evaporator and purified using glass column chromatography and eluted with ethyl acetate to afford 30.5 g (123.14 mmol, 81% yield) of intermediate A as a yellow solid.

A seal tube was charged with intermediate A (400 mg, 1.62 mmol) and 3-aminobenzoic acid (222 mg, 1.62 mmol). N-butanol (15 mL) was added to the seal tube and stirred at 180° C. The reaction was done in 1 according to LCMS to afford intermediate B as a yellow solid. Intermediate B was placed on a rotary evaporator to remove excess n-butanol. Intermediate B was carried on to the next step without further purification.

A flask was charged with intermediate B (282 mg, 0.81 mmol), HATU (464 mg, 1.22 mmol), DMF (15 mL) and DIEA (212 µL, 1.22 mmol). The reaction mixture was stirred at rt and completed in 30 min. to afford the final product (9). The final product was purified using Preparative HPLC and ammonium acetate buffer and lyophilized to afford the product as ACE salt (170 mg, 0.41 mmol). $^1$H-NMR (400 MHz, $d_6$-$CD_3OD$): 8.523 ppm (t, 1H), 8.45 ppm (d, 1H), 8.176 ppm (m, 2H), 7.828 ppm (m, 1H), 7.2 ppm (d, 2H), 7.475-7.404 ppm (m, 2H), 7.326 ppm (d, 1H), 3.738 ppm (t, 2H), 3.244 ppm (t, 2H), 2.877 ppm (s, 6H), 2.162 ppm (s, 3H), 1.955 (s, 3H, ACE). MS (EI) $C_{23}H_{26}N_6O_2$: 419.1 (MH$^+$).

556
Example 30

N-[5-({4-[4-(acetylamino)phenyl]pyrimidin-2-yl}amino)-2-morpholin-4-ylphenyl]-2,6-dichlorobenzamide (Compound 62)

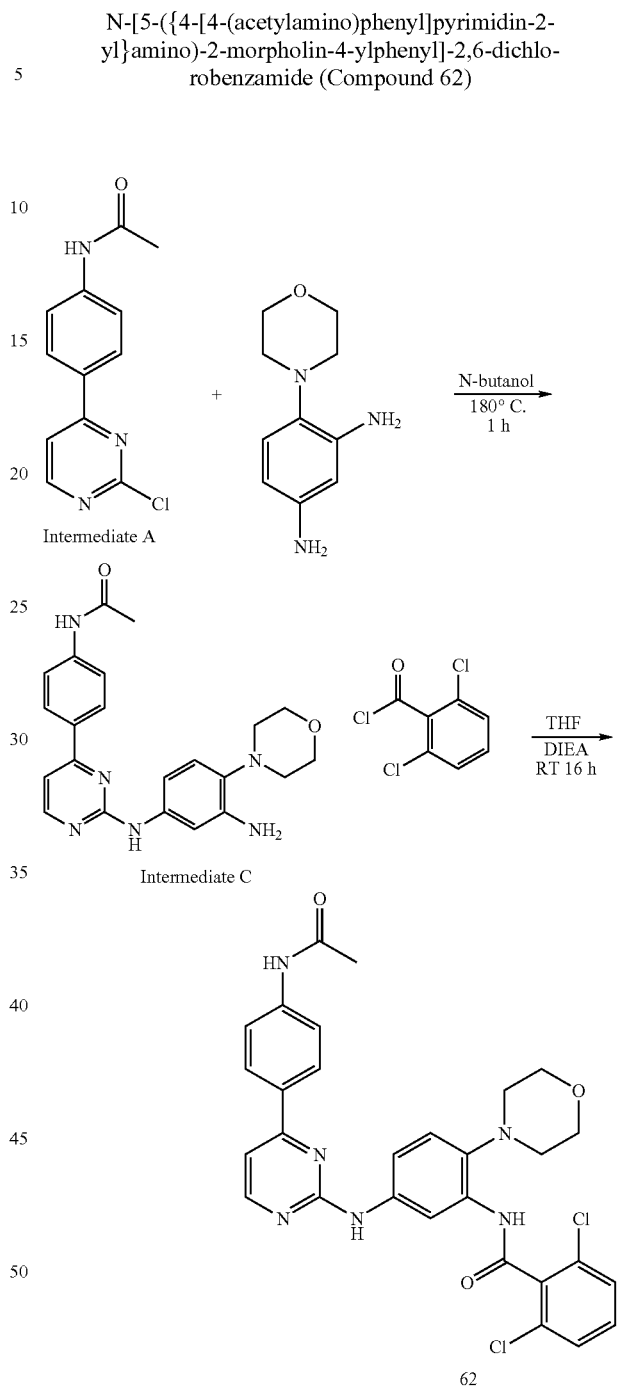

A seal tube was charged with intermediate A (500 mg, 2.02 mmol) and 4-morpholinobenzene-1,3-diamine (400 mg, 2.02 mmol, Zerenex Limited). N-butanol (15 mL) was added to the seal tube and stirred at 180° C. The reaction was done in 1 h according to LCMS to afford intermediate C as a yellow solid. Intermediate C was placed on a rotary evaporator to remove excess n-butanol. Intermediate C was carried on to the next step without further purification.

A flask was charged with intermediate C (816 mg, 2.02 mmol), THF (100 mL), DIEA (705 µL, 4.04 mmol), and 2,6-dichlorobenzoyl chloride (290 µL, 2.02 mmol). The reaction mixture was stirred at rt over night to afford the final product 62. The final product was purified using Preparative HPLC and TFA buffer, then was free-based and lyophilized (165 mg, 0.28 mmol, 14% Yield).

$^1$H NMR (400 MHz, DMSO): 10.194 (s, 1H), 9.8 (s, 1H), 9.607 (s, 1H), 8.585 (s, 1H), 8.484 (d, 1H), 8.235 (d, 2H), 7.711 (d, 2H), 7.592 (d, 2H), 7.496 (m, 2H), 7.356 (d, 1H), 7.183 (d, 1H), 3.74 (t, 4H)), 2.89 (t, 4H), 2.07 (s, 3H). MS (EI) for $C_{29}H_{26}Cl_2N_6O_3$: 579.1 (MH$^+$).

Example 31

N-{3-({4-[4-(acetylamino)phenyl]pyrimidin-2-yl}amino)-5-[(4-ethylpiperazin-1-yl)carbonyl]phenyl}-2,6-dichlorobenzamide (Compound 66)

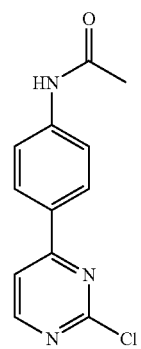
Intermediate A

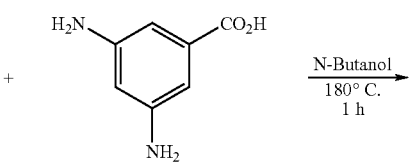

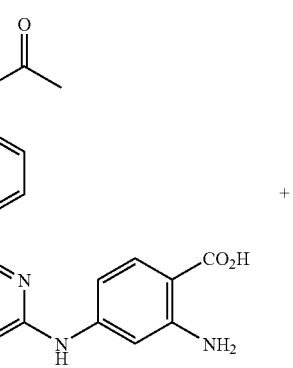
Intermediate D

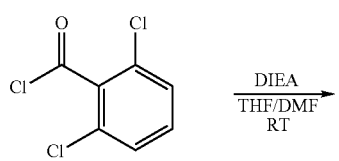

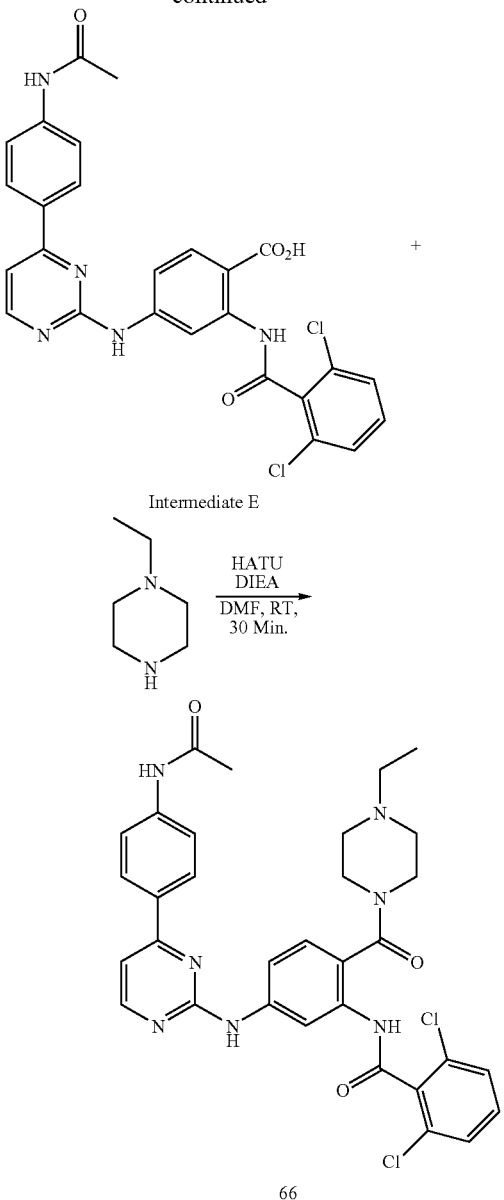

A seal tube was charged with intermediate A (300 mg, 1.21 mmol) and 3,5-diaminobenzoic acid (204 mg, 1.34 mmol). N-butanol (15 mL) was added to the seal tube and stirred at 180° C. The reaction was done in 1 h according to LCMS to afford intermediate D as a yellow solid. Intermediate D was placed on a rotary evaporator to remove excess n-butanol. Intermediate D was carried on to the next step without further purification.

A flask was charged with intermediate D (439 mg, 1.21 mmol), THF (30 mL), DMF (5 mL), DIEA (632 µL, 3.63 mmol), and 2,6-dichlorobenzoyl chloride (174 µL, 1.21 mmol). The reaction mixture was stirred at rt over night. The reaction mixture was quenched with 2 M NaOH (100 mL) and extracted with ethyl acetate (3×) and the organic layer was discarded. The aqueous NaOH layer was neutralized with conc. HCl. The solid formed was collected via filtration and washed with excess water to afford intermediate E (274 mg, 0.51 mmol, 62% yield) as a yellow solid. Intermediate E was carried on to the next step without further purification.

A flask was charged with intermediate E (274 mg, 0.51 mmol), HATU (291 mg, 0.765 mmol), DMF (25 mL), ethylpiperazine (78 µL, 0.61 mmol) and DIEA (133 µL, 0.765 mmol). The reaction was stirred at rt and completed in 15 min. The final product 66 was purified using Preperative HPLC and TFA buffer, free-based and lyophilized to afford the product (166 mg, 52% yield).

$^1$H NMR (400 MHz, DMSO): 10.896 (s, 1H), 10.33 (s, 1H), 9.881 (s, 1H), 8.533 (d, 1H), 8.374 (s, 1H), 8.202 (d, 2H), 7.776 (d, 2H), 7.636-7.6 (m, 3H), 7.529 (m, 1H), 7.419 (d, 1H), 7.296 (s, 1H), 3.628 (br s, 2H), 3.415 (br s, 2H), 2.427-2.314 (m, 6H), 2.091 (s, 3H), 0.996 (t, 3H). MS (EI) for $C_{32}H_{31}Cl_2N_7O_3$: 634.1 (MH$^+$).

Example 32

N-methyl-N-(4-{2-[(4-morpholin-4-ylphenyl)amino]pyrimidin-4-yl}phenyl)acetamide (Compound 118)

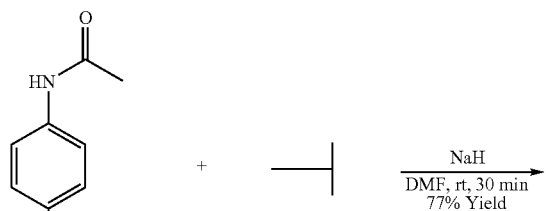

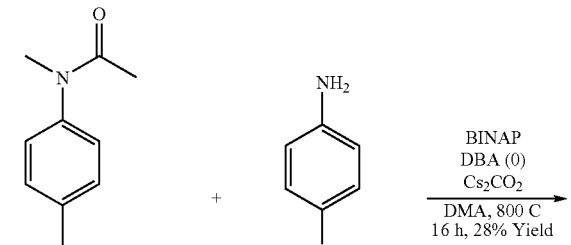

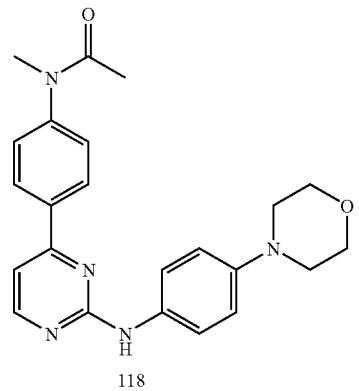

118

A flask was charged with intermediate A (250 mg, 1.01 mmol), DMF (10 mL), NaH (30.0 g, 167.62 mmol), dichloro[1,1'-bis(diphenylphosphino)ferrocenepalladium (60 mg, 1.5 mmol), and methyl iodide (94 µL, 1.5 mmol). The reaction mixture was stirred at rt and completed in 30 min. The reaction mixture was quenched with $H_2O$ and extracted with ethyl acetate (3×) and washed with 10% LiCl solution (IX), brine (IX), dried over sodium sulfate, and filtered. The organic layer was removed with a rotary evaporator to afford intermediate F (200 mg, 0.766 mmol) as a yellow gelatin. Intermediate F was carried on to the next step without further purification.

A seal tube was charged with intermediate F (200 mg, 0.766 mmol), anhydrous DMA (15 mL), cesium carbonate (374 mg, 1.15 mmol), racemic-2,2'-Bis(diphenylphosphino)-1,1'-binaphthyl (70 mg, 0.115 mmol), and tris(dibenzylideneacetone)dipalladium(0). The reaction was flushed with $N_2$ gas for five minutes and the seal tube was sealed and stirred at 80° C. over night. The reaction was filtered and washed with ethyl acetate and the solid was discarded. The organic solvent was removed using the rotary evaporator. The final product 66 was purified using Preperative HPLC and TFA buffer, free-based and lyophilized to afford the product (95 mg, 0.235 mmol, 28% Yield).

$^1$H-NMR (400 MHz, $d_6$-DMSO): 9.464 ppm (s, 1H), 8.511 ppm (d, 1H), 8.209 ppm (d, 2H), 7.67 ppm (m, 2H), 7.516 ppm (d, 2H), 7.366 ppm (d, 1H), 6.926 ppm (m, 2H), 3.743 ppm (t, 4H), 3.22 ppm (s, 3H), 3.048 ppm (t, 4H). MS (EI) $C_{23}H_{25}N_5O_2$: 404.3 (MH$^+$).

Example 33

N-(4-(2-(3-(3-morpholinopropoxy)phenylamino)pyrimidin-4-yl)phenyl)acetamide (Compound 160)

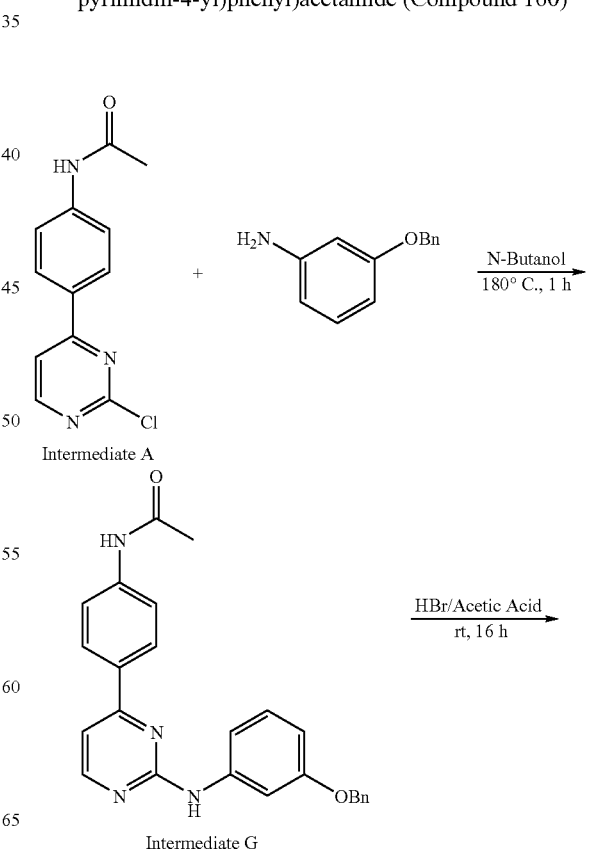

561
-continued

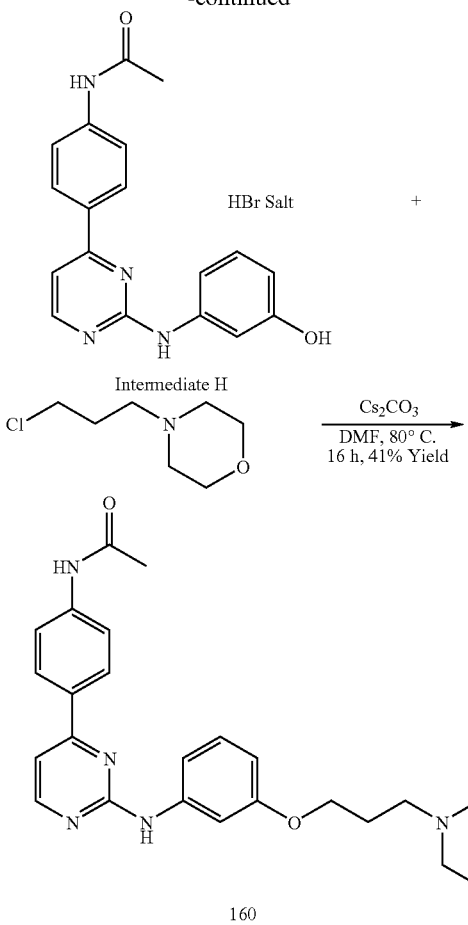

A seal tube was charged with intermediate A (500 mg, 2.02 mmol) and 3-benzyloxyaniline (404 mg, 2.02 mmol). N-butanol (15 mL) was added to the seal tube and stirred at 180° C. The reaction was done in 1 h according to LCMS to afford intermediate G as a yellow solid. Intermediate G was placed on a rotary evaporator to remove excess n-butanol. Intermediate G was carried on to the next step without further purification. A flask was charged with intermediate G and HBr/Acetic acid (33%, 10 mL) and stirred at rt over night. The reaction was done and the solid was collected via filtration and washed with ether to afford intermediate H as a yellow and HBr salt solid (800 mg, 1.66 mmol, 82% yield).

A flask was charged with intermediate H (250 mg, 0.52 mmol), DMF (15 mL), $Cs_2CO_3$ (847 mg, 2.6 mmol) and 4-(3-chloropropyl)morpholine HCl salt (135 mg, 0.676 mmol, purchased from Apin Chemicals, Ltd.) and stirred at 80° C. over night. The reaction mixture had approximately 85% desired product and 15% bis-alkylated by-product. The solid was filtered and washed with ethyl acetate and discarded. The filtrate was concentrated using the rotary evaporator. The final product was purified using Preperative HPLC and TFA buffer, free-based, converted to HCl salt and lyophilized to afford the product (115 mg, 0.237 mmol, 46% Yield).

$^1$H NMR (400 MHz, DMSO): 11.058 (s, 1H), 10.403 (s, 1H), 9.761 (s, 1H), 8.532 (d, 1H), 8.158 (d, 2H), 7.81 (d, 2H), 7.677 (s, 1H), 7.4-7.345 (m, 2H), 7.231 (t, 1H), 6.569 (m, 1H), 4.081 (t, 2H), 3.962 (m, 2H), 3.82 (t, 2H), 3.46 (m, 2H), 3.267 (m, 2H), 3.123 (m, 2H), 2.254 (m, 2H), 2.104 (s, 3H). MS (EI) for $C_{25}H_{29}N_5O_3$: 448.3 (MH$^+$).

562
Example 34

N-(4-{2-[(2-methyl-4-piperazin-1-ylphenyl)amino]pyrimidin-4-yl}phenyl)acetamide (Compound 35)

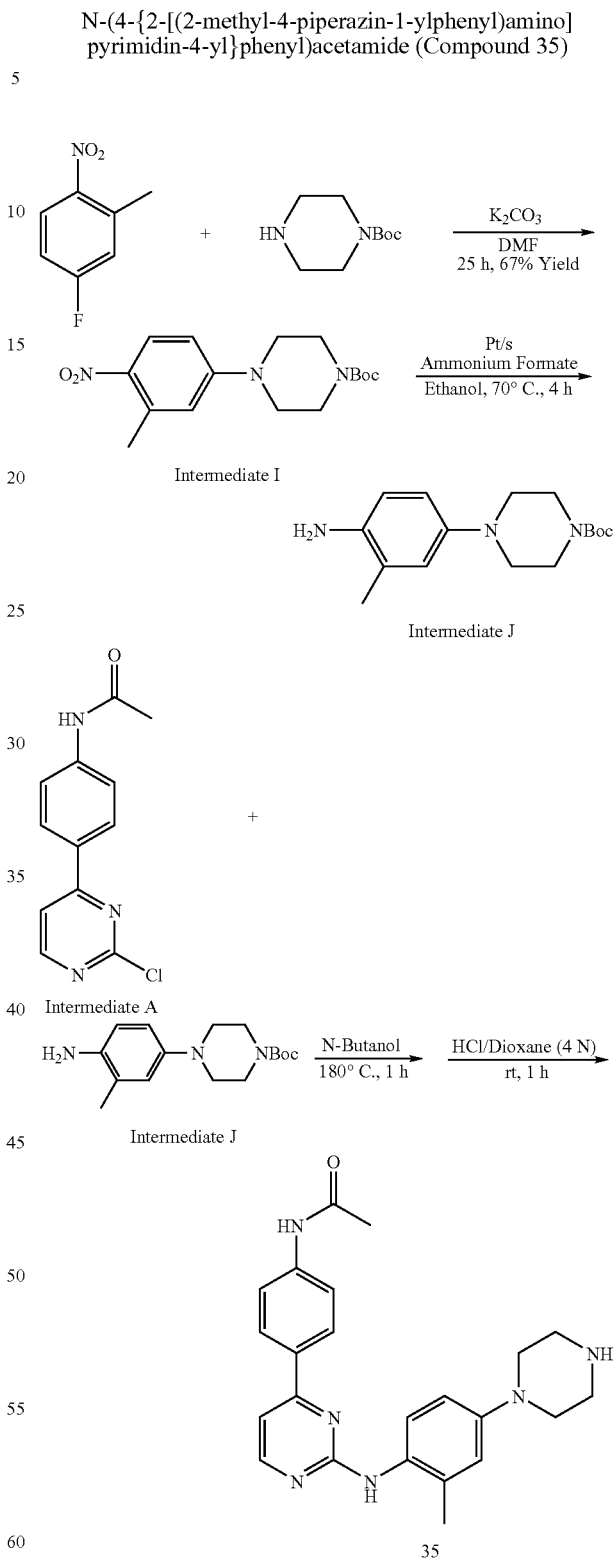

A flask was charged with 5-fluoro-2-nitrotoluene (1 mL, 8.2 mmol), DMF (15 mL), Bocpiperazine (1.68 g, 9.02 mmol), and $K_2CO_3$ (2.27 g, 16.4 mmol). The reaction mixture was stirred at 50° C. for about 25 h. The reaction was quenched with $H_2O$ and the solid precipitated out of the solution and collected via filtration and washed with excess H₂O to obtain intermediate I (1.765 g, 5.4 mmol). Intermediate I was carried on to the next step without further purification. A flask was charged with intermediate I (290 mg, 0.9 mmol), ethanol (18 mL), ammonium formate (340 mg, 5.4 mmol) and Pt/S (10.2 mg, 0.04 mmol). The reaction mixture was stirred at 70° C. (for 3 h and 78° C. for 4 h. The reaction mixture was filtered through celite and washed with ethanol. The filtrate was removed using the rotary evaporator and then treated with ethyl acetate and washed with H₂O, dried over sodium sulfate, and filtered. The ethyl acetate layer was concentrated using rotary evaporator to afford intermediate J.

A seal tube was charged with intermediate A (200 mg, 0.81 mmol), and intermediate J (235 mg, 0.81 mmol). N-butanol (15 mL) was added to the seal tube and stirred at 180° C. The reaction was done in 1 h and concentrated to remove excess n-butanol and then treated with 4N HCl/dioxane. The reaction mixture was stirred at rt for 1 h to afford the final product 35. The final product was purified using Preperative HPLC and ammonium acetate buffer, then free-based and lyophilized (90 mg, 0.22 mmol, 27% Yield).

¹H-NMR (400 MHz, d₆-DMSO): 10.31 ppm (s, 1H), 8.569 ppm (s, 1H), 8.323 ppm (d, 1H), 8.022 ppm (d, 2H), 7.715 ppm (d, 2H), 7.271 ppm (d, 1H), 7.186 ppm (d, 1H), 6.8 ppm (m, 2H), 3.023 ppm (t, 4H), 2.844 ppm (t, 4H), 2.175 ppm (s, 3H), 2.077 ppm (s, 3H), 1.605 ppm (s, 2H); MS (EI) $C_{23}H_{26}N_6O$: 403.1 (MH⁺).

Example 35

N-[4-({2-[(4-morpholin-4-ylphenyl)amino]-7H-pyrrolo[2,3-d]pyrimidin-4-yl}amino)-phenyl]acetamide (Compound 306)

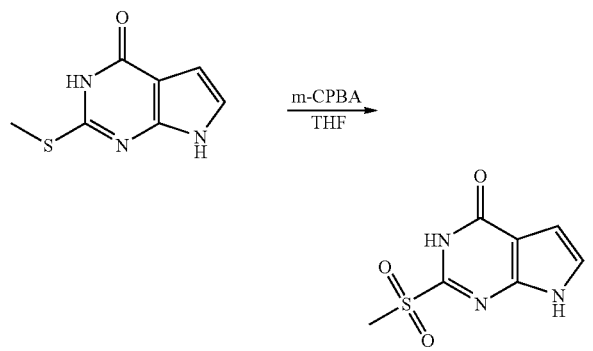

A flask was charged with methylsulfide (2.1 g, 11.6 mmol) and THF (50 mL). To this, m-CPBA (7.9 g, 46 mmol) was added and the mixture was stirred at ambient temperature for 20 hours. Volatiles were removed under vacuo. The crude mixture was partitioned between EtOAc and DI H₂O. The aqueous layer was extracted with EtOAc (3×15 mL). The combined organics were washed with 1N NaHCO₃ (×2), DI H₂O (×2), brine, (×1), dried over sodium sulfate, filtered and concentrated under vacuo. The product (1.8 g, 75%) was used without further purification. LCMS: m/z 214 (M+H)⁺.

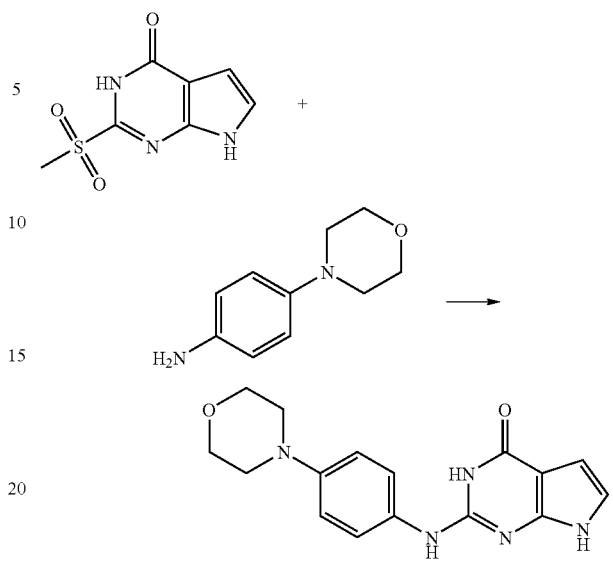

A pressure tube was charged with methylsulfone (1.15 g, 5.4 mmol) and aniline (2.8 g, 16.2 mmol). The tube was sealed and the mixture heated at 140° C. for 30 minutes. The mixture was cooled. Methanol was added and the resulting solid collected via filtration then washed with methanol. The product (270 mg, 8.7%) was used without further purification. LCMS: 312 (M+H)⁺.

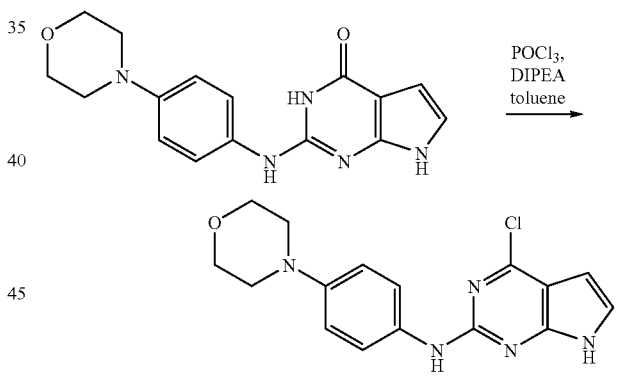

A flask was charged with pyrrolopyrimidinone (250 mg, 0.8 mmol) and toluene (5 mL). Phosphorous oxychloride (218 µL, 2.41 mmol) and DIPEA (165 µL, 0.96 mmol) were added and the mixture stirred at 110° C. for 6 hours. The volatiles were removed under vacuo and the product used without further purification. LCMS: 330 (M+H)⁺.

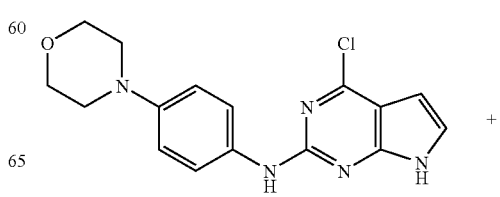

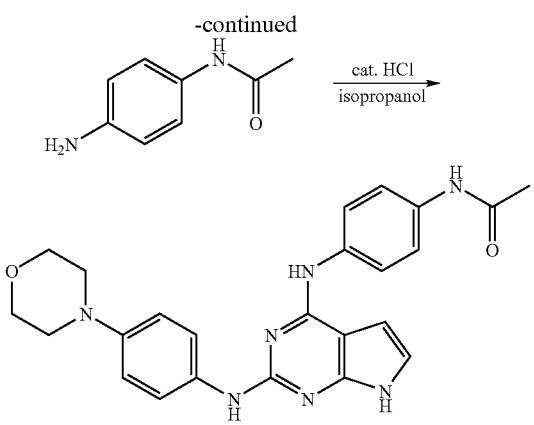

A flask was charged with pyrrolopyrimidine (100 mg, 0.3 mmol) and isopropanol (1 mL). Aniline (55 mg, 0.036 mmol) and two drops of conc. HCl were added and the mixture heated to reflux for 6 hours. Volatiles were removed under vacuo. The product was purified by preparative HPLC to afford the title compound (306) (12.8 mg, 9.6%).

$^1$H NMR (400 MHz, d6-DMSO): 11.13 (s, 1H), 9.95 (s, 1H), 9.04 (s, 1H), 8.56 (s, 1H), 7.86 (d, 2H), 7.66 (d, 2H), 7.54 (d, 2H), 6.88-6.82 (m, 3H), 6.65-6.61 (m, 1H), 3.78-3.71 (m, 4H), 3.05-2.99 (m, 4H), 2.04 (s, 3H). MS (EI) for $C_{24}H_{25}N_7O_2$: 444 (MH$^+$).

Example 36

(N-(4-{2-[(3-{[(2,6-dichlorophenyl)sulfonyl]amino}phenyl)amino]-5-methylpyrimidin-4-yl}phenyl)acetamide) (Compound 26)

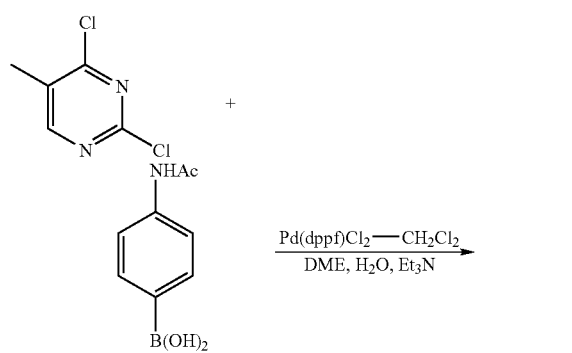

To a mixture of 2,4-dichloro-5-methylpyrimidine (4.17 g, 25.6 mmol) and 4-acetamidophenylboronic acid (5.0 g, 27.9 mmol) in DME (40 ml) was added Et$_3$N (8.92 ml, 64.0 mmol), H$_2$O (4 ml), and dichloro[1,1'-bis(diphenylphosphino)ferrocenepalladium (2.81 g, 3.44 mmol, 13%). The mixture was allowed to stir at reflux for 5 hrs. After the mixture was cooled down to rt, the crude mixture was directly filtered on silica gel and eluted with EtOAc. The filtrate was concentrated in vacuo. Further purification was conducted by flash chromatography to afford Intermediate 1 (5.94 g, 89%) as a white solid. LCMS: m/z 262 (M+H)$^+$.

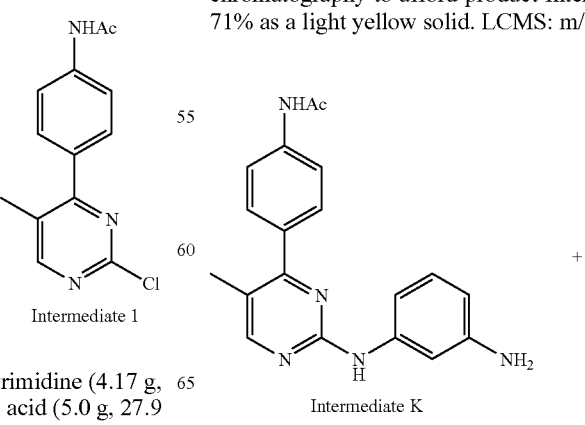

To a stirred solution of chloropyrimidine (1.05 g, 4.0 mmol) in 1-butanol (10 ml) was added N-Boc-amino-3-aniline (920 mg, 4.4 mmol) and the mixture was heated in the sealed tube at 180° C. for 1.5 hr. The mixture was cooled down to rt and acidified with 1N HCl (20 ml). The aqueous layer was washed with EtOAc (50 ml). The separated aqueous layer was basified with 2N NaOH to pH 8-9 and extracted with EtOAc (50 ml*3). The combined organic layer was dried over Na$_2$SO$_4$, concentrated in vacuo, and purified by flash chromatography to afford product Intermediate K (943 mg, 71% as a light yellow solid. LCMS: m/z 334 (M+H)$^+$.

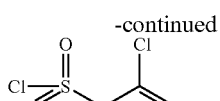
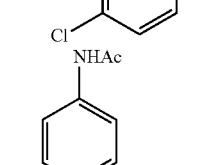

26

To a stirred suspension of aniline (250 mg, 0.75 mmol) in THF (5 ml) was added DIPEA (157 ml, 0.90 mmol) and 2,6-dichlorobenzenesulfonyl chloride (203 mg, 0.83 mmol) and the mixture containing intermediate K was stirred at reflux for 2 hrs. After cooling down to rt, the mixture was diluted with EtOAc, washed with H$_2$O, brine, and dried over Na$_2$SO$_4$. After concentrated in vacuo, the residue was purified by flash chromatography to give product 26 (299 mg, 73%) as a light pink solid.

$^1$H-NMR (400 MHz, d$_6$-DMSO): 10.71 (s, 1H), 10.16 (s, 1H), 9.54 (s, 1H), 8.34 (s, 1H), 7.75-7.69 (m, 5H), 7.60 (dd, 2H), 7.51 (dd, 1H), 7.31 (dd, 1H), 7.09 (t, 1H), 6.66 (dd, 1H), 2.25 (s, 3H), 2.08 (s, 3H); MS (EI) C$_{25}$H$_{21}$Cl$_2$N$_5$O$_3$S: 542.2 (M+H)$^+$.

Example 37

N-(4-{6-morpholin-4-yl-2-[(4-morpholin-4-ylphenyl)amino]pyrimidin-4-yl}phenyl)acetamide (Compound 47)

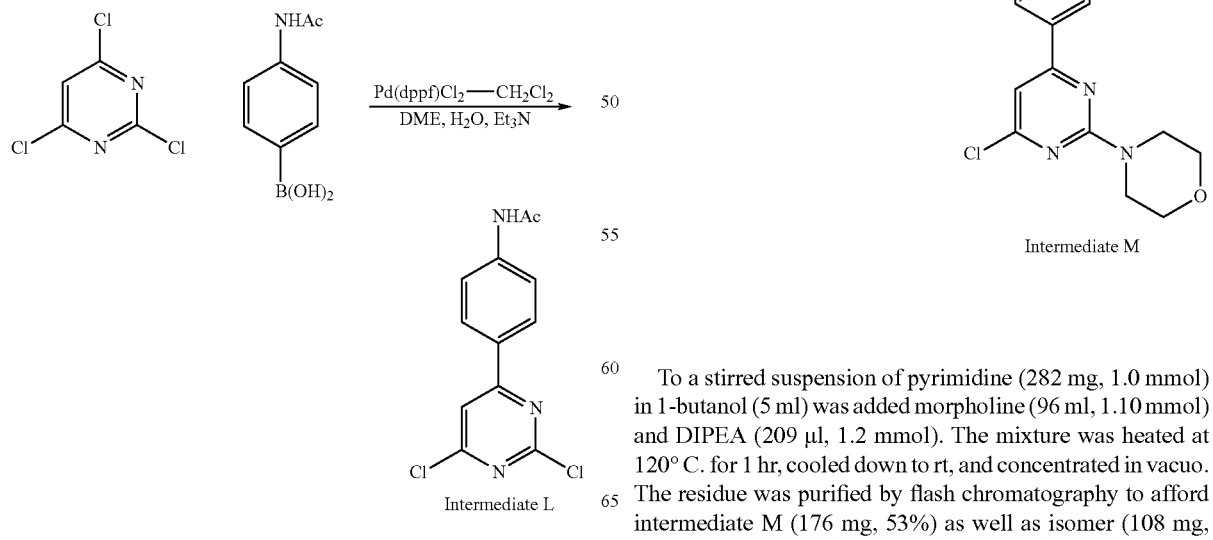

The mixture of 2,4,6-trichloropyrimidine (1.72 ml, 15 mmol) 4-acetamidophenyl-boronic acid (1.79 g, 10 mmol) in DME (20 ml) was added Et$_3$N (3.5 ml, 25.0 mmol), H$_2$O (2 ml), and dichloro[1,1'-bis(diphenylphosphino)ferrocenepalladium (1.22 g, 1.5 mmol, 15%). The mixture was allowed to stir at reflux for 2 hrs. After the mixture was cooled down to rt, the crude mixture was directly filtered on silica gel and eluted with EtOAc. The filtrate was concentrated in vacuo. Further purification was conducted by flash chromatography to afford intermediate L (1.91 g, 68%) as a white solid. LCMS: m/z 282 (M+H)$^+$.

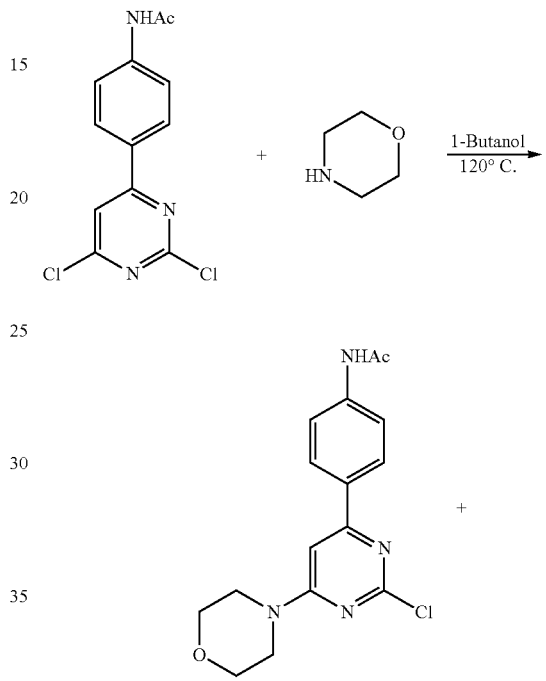

To a stirred suspension of pyrimidine (282 mg, 1.0 mmol) in 1-butanol (5 ml) was added morpholine (96 ml, 1.10 mmol) and DIPEA (209 μl, 1.2 mmol). The mixture was heated at 120° C. for 1 hr, cooled down to rt, and concentrated in vacuo. The residue was purified by flash chromatography to afford intermediate M (176 mg, 53%) as well as isomer (108 mg, 32%). LCMS: m/z 333 (M+H)$^+$.

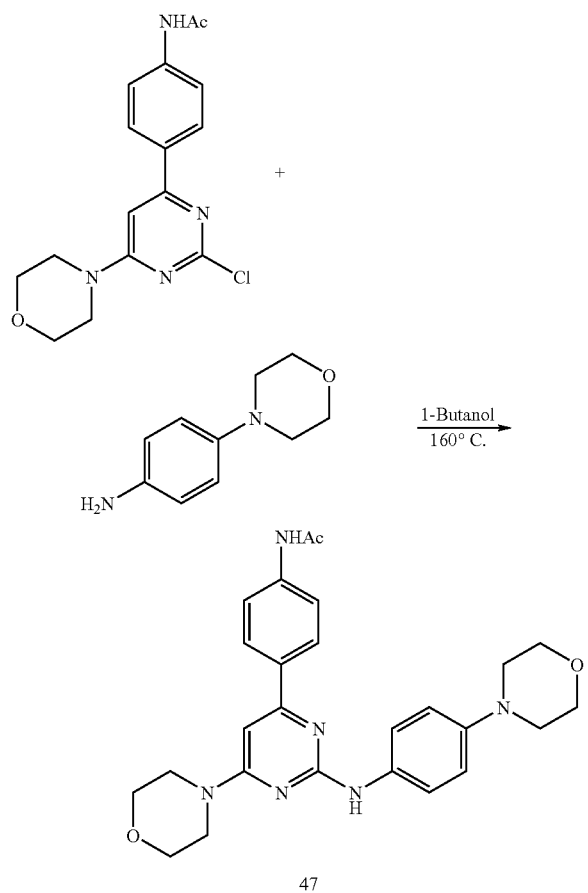

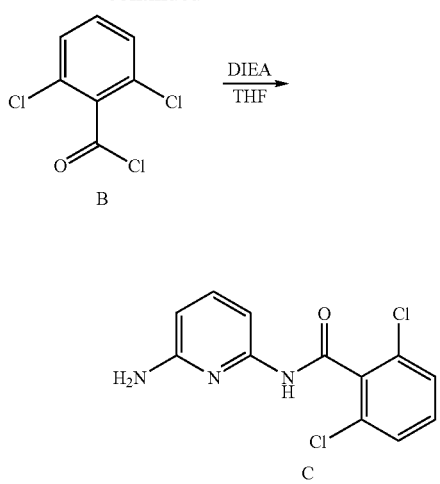

To a mixture of 2,6-diaminopyridine A (9.2 mmol, 1.0 g), and diisopropylethylamine (6.9 mmol, 1.2 ml) in 20 ml of THF, was added 2,6-dichlorobenzoylchloride B (4.6 mmol, 0.67 ml) dropwise. The mixture was stirred at room temperature for 1 hour and LCMS indicated it was done (M+H: 283). THF was removed and replaced with ethyl acetate. The reaction mixture was then extracted with water, brine, and dried over sodium sulfate. The product, C, was isolated by removal of the solvent with a rotary evaporator and used without further purification. LCMS: 283 (M+H).

The mixture of chloropyrimidine (176 mg, 0.53 mmol) and 4-morpholinoaniline (104 mg, 0.58 mmol) in 1-butanol (5 ml) was heated in the sealed tube at 160° C. for 3 hrs. The reaction mixture was cooled down to rt and the crude mixture was directly subjected on silica gel to afford product 47 (122 mg, 49%) as a pale pink solid. LCMS: m/z 475 (M+H)$^+$.

$^1$H-NMR (400 MHz, d$_6$-DMSO): 10.13 (s, 1H), 8.87 (s, 1H), 8.07 (d, 2H), 7.70-7.64 (m, 4H), 6.90 (d, 2H), 6.71 (d, 1H), 3.74-3.68 (m, 12H), 3.03 (t, 4H), 2.08 (s, 3H); MS (EI) C$_{26}$H$_{30}$N$_6$O$_3$: 475 (MH+).

Example 38

N-[6-({4-[4-(acetylamino)phenyl]pyrimidin-2-yl}amino)pyridin-2-yl]-2,6-dichlorobenzamide (Compound 299)

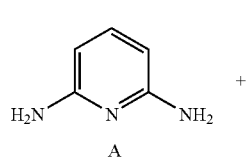

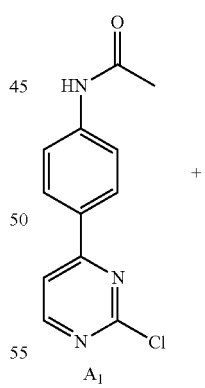

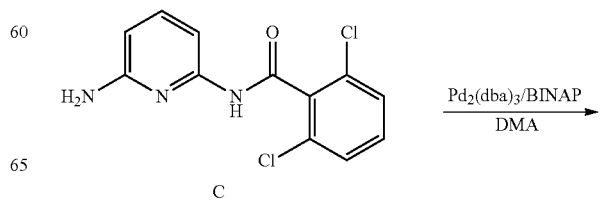

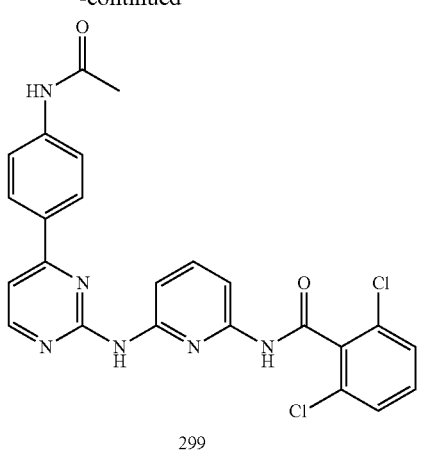

299

A seal tube was charged with intermediate A, (0.2 g, 0.81 mmol), compound C from the previous step (0.56 g, 2.0 mmol), tris(dibenzylideneacetone)dipalladium(0) (0.15 g, 0.16 mmol), racemic-2,2'-bis(diphenylphosphino)-1,1'binaphthyl (0.12 g, 0.2 mmol), cesium carbonate (0.4 g, 1.22 mmol). Dimethylacetamide (10 ml) was added and the mixture was purged with $N_2$ for 5 minutes. The tube was sealed and the reaction mixture was stirred at 80° C. overnight. LCMS showed the reaction was done (M+H: 493). The reaction mixture was partitioned between ethyl acetate and water, the organic layer extracted with 10% LiCl solution, followed by brine, dried over $Na_2SO_4$, and then evaporated. The crude product 299 was then purified via prep HPLC.

$^1$H NMR (400 MHz, $d_6$-DMSO): 11.12 (s, 1H), 10.25 (s, 1H), 9.43 (s, 1H), 8.58 (d, 1H), 8.2-8.13 (m, 3H), 7.9 (t, 1H), 7.83 (d, 1H), 7.78 (d, 2H), 7.55 (d, 2H), 7.52-7.45 (m, 2H), 2.1 (s, 3H). MS (EI) for $C_{24}H_{18}Cl_2N_6O_2$: 493 (MH$^+$).

Example 39

N-(3-(4-(4-acetamidophenyl)pyrimidin-2-ylamino) phenyl)-3-(2-morpholinoethoxy)-benzamide (Compound 123)

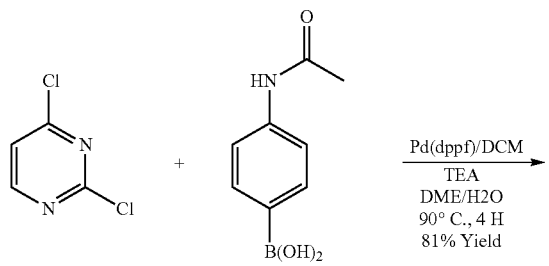

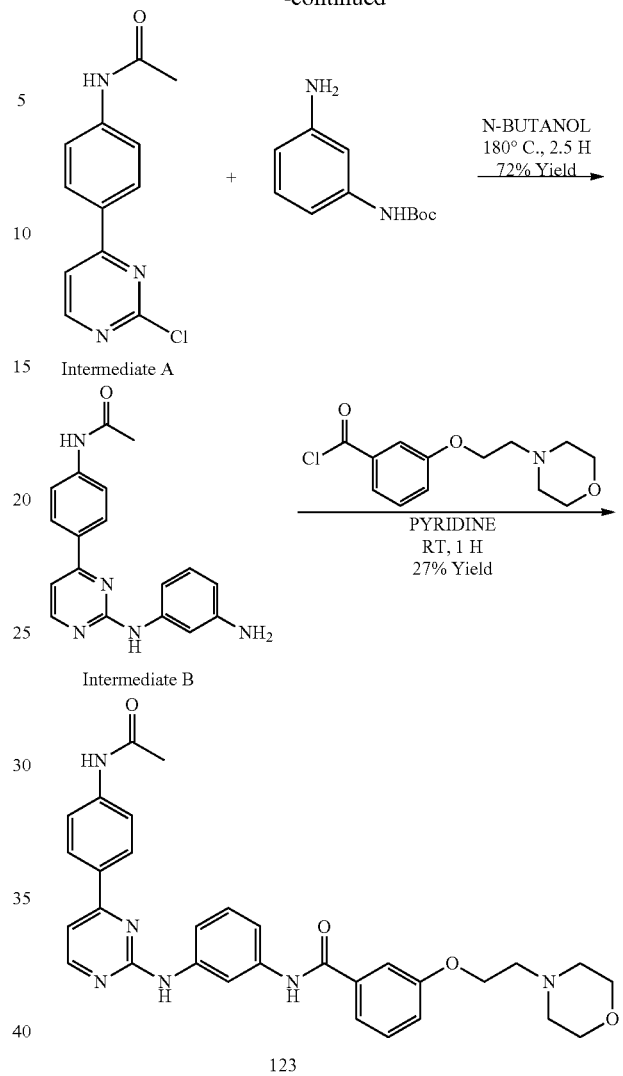

123

A flask was charged with 2,4-dichloropyrimindine (22.7 g, 152.38 mmol), 4-acetoamido-phenylboronic acid (30.0 g, 167.62 mmol), dichloro[1,1'-bis(diphenylphosphino)-ferrocene-palladium (16.726 g, 22.86 mmol, 15 mol %), and triethylamine (53 mL, 380.95 mmol). Ethyleneglycoldimethylether (500 mL) and $H_z$ O (20 mL) were added to the flask. The reaction mixture was stirred at 80° C. for 4 hours. The product, Intermediate A, was isolated by removal of the solvent with a rotary evaporator and purified using glass column chromatography and eluted with ethyl acetate to afford 30.5 g (123.14 mmol, 81% yield) of intermediate A as a yellow solid.

A seal tube was charged with intermediate A (400 mg, 1.62 mmol) and 3-(tert-butoxycarbonylamino)aniline (1.99 g, 9.57 mmol). N-butanol (50 mL) was added to the seal tube and stirred at 180° C. The reaction was stopped after 2.5 h, monitored by LCMS. The reaction mixture was diluted with methanol and the solid precipitate was filtered to afford intermediate B as a yellow solid. The filter pad was washed with ethyl-acetate, 72% yield. Intermediate B was carried on to the next step without further purification.

A flask was charged with intermediate B (159 mg, 0.5 mmol), 3-(2-morpholinoethoxy)benzoyl chloride (169 mg, 0.63 mmol), and Pyridine (8 mL). The reaction mixture was stirred at RT under nitrogen. Reaction was complete after 1 h.

The final product 123 was purified using Preperative HPLC and trifluoroacetic acid buffer then free based with hydroxide resin in methanol. The filtrate was then concentrated, the yellow oil was then freezed and lyophilized.

1H-NMR (400 MHz, d6-DMSO): 10.206 (s, br, 2H), 9.665 (s, br, 1H), 8.512 (d, 1H), 8.502 (s, 1H), 8.440 (d, 2H), 7.755 (d, 2H), 7.582 (m, 2H), 7.483 (m, 2H), 7.375 (d, 1H), 7.287 (m, 2H), 7.163 (d, 1H), 4.188 (m, 2H), 3.595 (m, 4H), 3.174 (m, 4H), 2.732 (m, 2H), 2.083 (s, 3H). MS (EI) for $C_{31}H_{32}N_6O_4$: 553 (MH+).

Example 40

4-[4-(methylamino)phenyl]-N-(4-morpholin-4-ylphenyl)pyrimidin-2-amine (Compound 124)

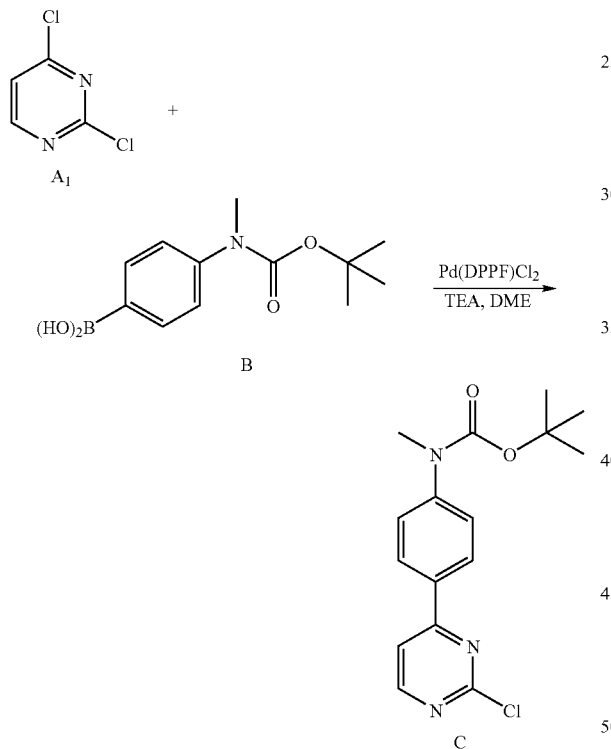

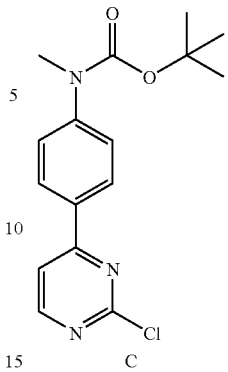

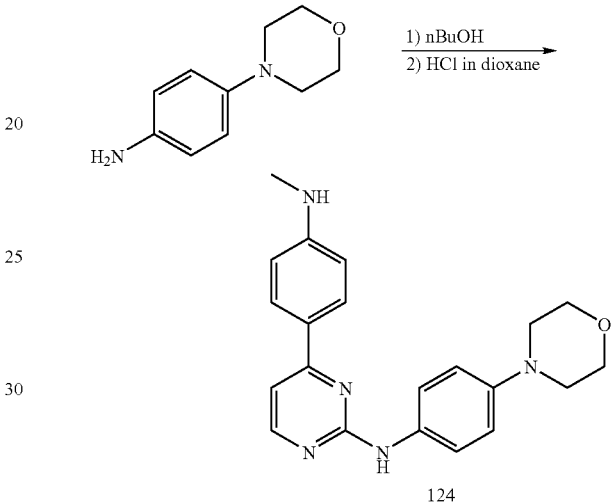

A flask was charged with 2,4-dichloropyrimidine (810 mg, 5.5 mmol), 4-(tert-butoxycarbonyl(methyl)amino)phenylboronic acid B (4.93 g, 15 mmol), dichloro[1,1'-bis(diphenylphosphino)ferrocenepalladium (590 mg, 0.81 mmol, 15 mol %), triethylamine (1.8 mL, 13 mmol), and water (2 mL). Ethylene glycol dimethyl ether (5.0 mL) was added to the flask and the mixture was purged with $N_2$. The reaction mixture was stirred under an $N_2$ atmosphere at 90° C. for 1 hour, after which time, it was cooled to ambient temperature and filtered. The product, C, was isolated by removal of the solvent with a rotary evaporator and used without further purification. LCMS: m/z 319 (M+H)+.

A flask containing a solution of C (1.9 g, 5.8 mmol) and 4-morpholinoaniline (1.5 g, 8.2 mmol) in 1-butanol (10 mL) was immersed in an oil bath at 180° C. for 4 h. The mixture was cooled to ambient temperature, concentrated, and the residue was dissolved in dichloromethane (10 mL) and 4N HCl in dioxane (10 mL). A portion of this crude product (200 mg) was purified by reverse phase HPLC to yield the product 124 (20 mg) in >99% purity.

$^1$H-NMR (400 MHz, $d_6$-DMSO): 9.92-9.99 ppm (bs, 1H), 8.20-8.29 (bs, 1H), 8.02 (d, 2H), 7.52-7.68 (bs, 2H), 7.33 (d, 1H), 7.04-7.17 (bs, 1H), 6.67 (d, 2H), 3.71-3.82 (bs, 4H), 3.14-3.24 (bs, 4H), 2.78 (s, 3H). MS (EI) $C_{21}H_{23}N_5O$: 362.1 (MH+).

Example 41

2,6-dichloro-N-{3-[(4-{[3-chloro-4-(methyloxy)phenyl]oxy}pyrimidin-2-yl)amino]phenyl}-benzamide (Compound 304)

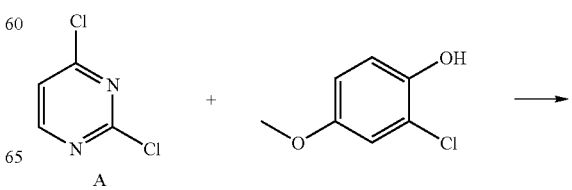

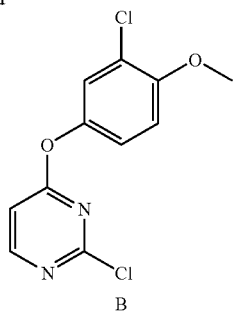

B

A flask was charged with 2,4-dichloropyrimidine (500 mg, 3.4 mmol), 2-chloro-4-methoxyphenol (580 mg, 3.7 mmol), and diisopropylethylamine (1.2 mL, 6.9 mmol). Dimethylformamide (20 mL) was added to the flask and the mixture was stirred at 70° C. for 15 hours. The reaction mixture was diluted with water and the mixture was extracted with dichloromethane 2× and 5% LiCL 3×. The crude product, B, was isolated by removal of the solvent with a rotary evaporator and the resultant brown oil was used without further purification. LCMS: m/z 272 (M+H)$^+$.

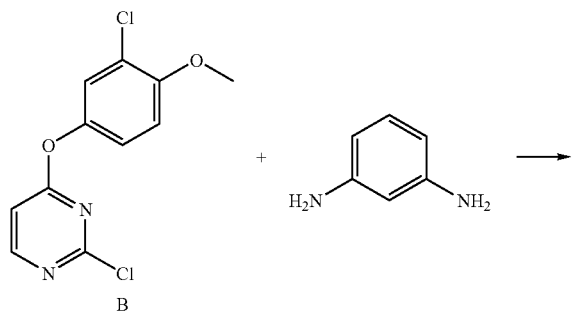

B

C

A flask containing a solution of intermediate B (910 mg, 3.4 mmol) and benzene-1,3-diamine (540 mg, 5.0 mmol) in nBuOH (5 mL) was immersed in an oil bath at 180° C. for mins. The intermediate, C, was isolated by removal of the solvent with a rotary evaporator and used without further purification. LCMS: m/z 343 (M+H)$^+$.

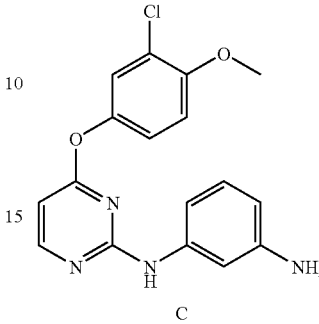

C

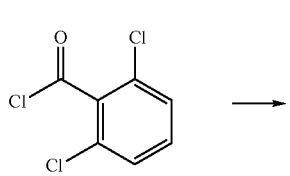

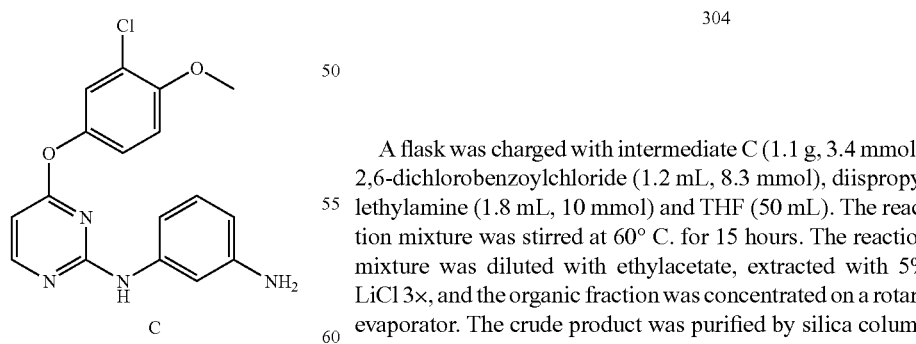

304

A flask was charged with intermediate C (1.1 g, 3.4 mmol), 2,6-dichlorobenzoylchloride (1.2 mL, 8.3 mmol), diisopropylethylamine (1.8 mL, 10 mmol) and THF (50 mL). The reaction mixture was stirred at 60° C. for 15 hours. The reaction mixture was diluted with ethylacetate, extracted with 5% LiCl 3×, and the organic fraction was concentrated on a rotary evaporator. The crude product was purified by silica column chromatography (1:1 ethylacetate:hexanes as eluent) followed by reverse phase HPLC (TFA/ACN as eluent) to yield the product, 304 (24 mg, 1% yield).

$^1$H-NMR (400 MHz, d6-DMSO): 10.7 (s, 1H), 9.65 (s, 1H), 8.36 (d, 1H), 7.77 (s, 1H), 7.58-7.47 (m, 3H), 7.36-7.28 (m, 3H), 7.23 (d, 1H), 7.04-6.98 (m, 2H), 6.47 (d, 1H), 3.83 (s, 3H). MS (EI) $C_{24}H_{17}Cl_3N_4O_3$: 514.8 (MH−).

Example 42

(3S)-1-(2-hydroxyethyl)-N-(4-{2-[(4-morpholin-4-ylphenyl)amino]pyrimidin-4-yl}phenyl)pyrrolidine-3-carboxamide (Compound 510)

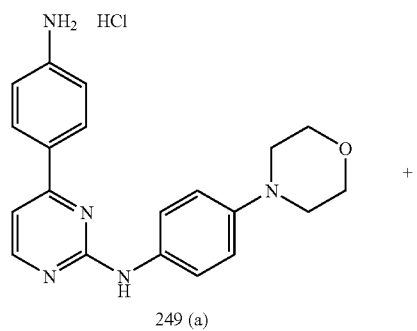

249 (a)

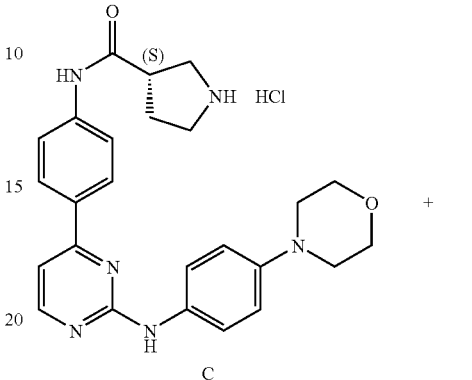

C

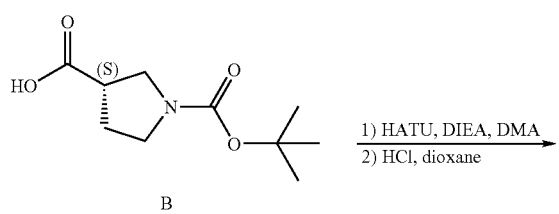

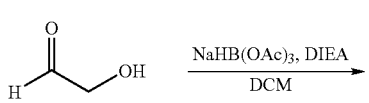

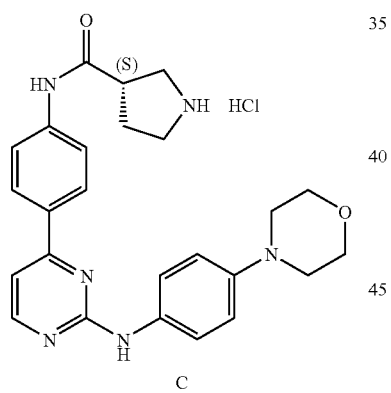

C

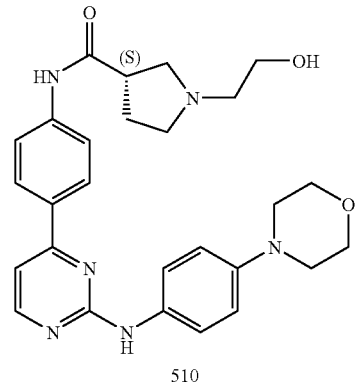

510

To a solution of 249(a) (300 mg, 0.78 mmol) in DMA (10 mL) was added a solution of (S)-1-(tert-butoxycarbonyl)pyrrolidine-3-carboxylic acid (350 g, 1.6 mmol) diisopropylethylamine (0.5 mL, 2.7 mmol), and HATU (600 mg, 1.6 mmol) in DMA (10 mL) and the solution was stirred at room temperature 15 hours. The solution was diluted with ethyl acetate (100 mL), washed with 10% LiCl (2×) and brine. The resultant solution was dried over $Na_2SO_4$, filtered and concentrated to yield a residue that was purified by silica gel column chromatography (3:1 ethyl acetate/hexanes). The Boc intermediate was isolated as a solid (340 mg, 78% yield). LC/MS: m/z 545 (M+H)⁺. A flask containing the Boc-intermediate was dissolved in 4N HCl in dioxane (10 mL) and dichloromethane (10 mL) and the mixture was stirred at room temperature for 15 hours. Intermediate C was isolated as a yellow solid after filtration and used without purification.

A flask was charged with intermediate C (450 mg, 0.78 mmol), 2-hydroxy-acetaldehyde (45 mg, 0.75 mmol), sodium triacetoxyborohydride (150 mg, 0.71 mmol), diisopropylethylamine (0.7 mL, 3.8 mmol) and dichloromethane (20 mL) and the mixture was stirred at room temperature for 4 hours. The reaction mixture was diluted with water and the solution was extracted with saturated $NaHCO_3$ (2×) and brine. The residue was purified by reverse phase HPLC (ammonium acetate/ACN as eluent) to afford the product 510 (120 mg, 31% yield).

$^1$H-NMR (400 MHz, d6-DMSO): 10.2 (s, 1H), 9.38 (s, 1H), 8.44 (d, 1H), 8.11 (d, 2H), 7:75 (d, 2H), 7.67 (d, 2H), 7.28-7.27 (m, 1H), 6.93 (d, 2H), 4.47 (br 1H), 3.76-3.73 (m, 4H), 3.49 (t, 2H), 3.06-3.03 (m, 4H), 2.91 (t, 1H), 2.70-2.65 (m, 1H), 2.58-2.56 (m, 1H), 2.54-2.49 (m, 4H), 1.99 (t, 2H). MS (EI) $C_{27}H_{32}N_6O_3$: 489.2 (MH+).

Example 43

N-(4-{2-[(4-morpholin-4-ylphenyl)amino]-7H-pyrrolo[2,3-d]pyrimidin-4-yl}phenyl)acetamide (Compound 329)

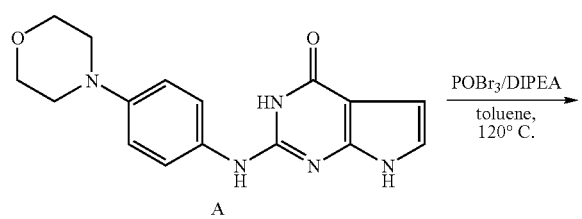

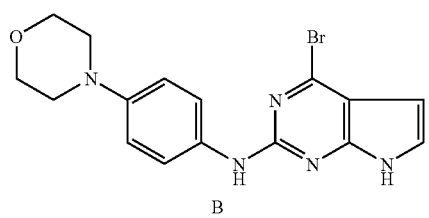

A mixture of 2-[(4-morpholin-4-ylphenyl)amino]-3,7-dihydro-4H-pyrrolo[2,3-d]pyrimidin-4-one A (312 mg, 1 mmol), phosphorous oxybromide (717 mg, 2.5 mmol), and diisopropylethylamine (130 mg, 1 mmol) in anhydrous toluene (15 ml) was heated at reflux under $N_2$ overnight. The mixture was cooled down to room temperature, and the solid was filtered, washed with sat. $NaHCO_3$, water, and dried over $MgSO_4$. The solvent was removed in vacuo to give the product 4-bromo-N-(4-morpholin-4-ylphenyl)-7H-pyrrolo[2,3-d]pyrimidin-2-amine B (284 mg, 76%) as a black solid. This was clean and used as such without further purification.

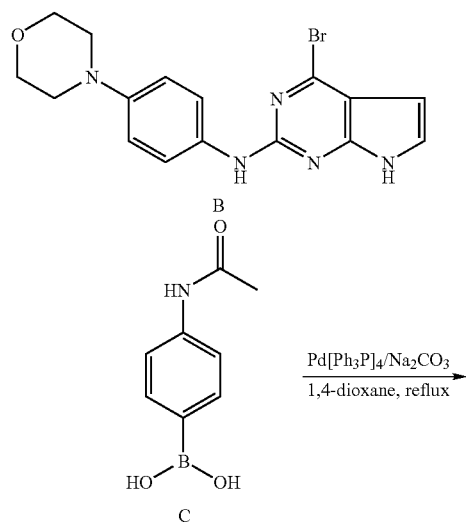

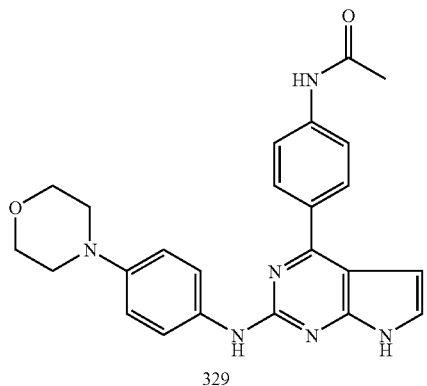

A mixture of 4-bromo-N-(4-morpholin-4-ylphenyl)-7H-pyrrolo[2,3-d]pyrimidin-2-amine B (284 mg, 0.76 mmol), 4-acetoamidophenylboronic acid C (340 mg, 2.5 eq), tetrakis(triphenyl-phosphine)palladium(0) (120 mg, 0.1 mmol), and 1M $Na_2CO_3$ (1 ml, 1 mmol) in 1,4-dioxane (15 ml) was heated at reflux overnight. The mixture was cooled, extracted with 3N HCl. The aqueous layer was washed with ethylacetate, and then basified with 6N NaOH. The solid was filtered, and the crude product was purified by preparative HPLC to give the product N-(4-{2-[(4-morpholin-4-ylphenyl)amino]-7H-pyrrolo[2,3-d]pyrimidin-4-yl}phenyl)acetamide D (0.8 mg, 0.25%) as a yellow solid.

$^1$H NMR (400 MHz, $CD_3OD$): 8.10 (d, 2H), 7.75 (d, 2H), 7.68 (d, 2H), 7.12 (d, 1H), 6.98 (d, 2H), 6.70 (d, 1H), 3.85 (t, 4H), 3.09 (t, 4H), 2.17 (s, 3H). MS (EI) for $C_{24}H_{24}N_6O_2$: 429 (MH$^+$).

Example 44

2-Methyl-N-(4-{2-[(4-morpholin-4-ylphenyl)amino]pyrimidin-4-yl}phenyl)prolinamide (Compound 367)

Preparation of tert-butyl 2-methyl-2-(4-(2-(4-morpholinophenylamino)pyrimidin-4-yl)phenylcarbamoyl)pyrrolidine-1-carboxylate

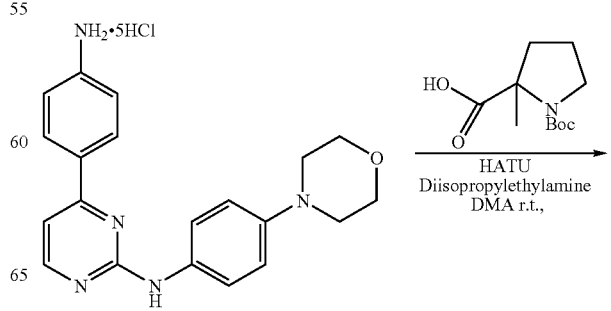

Preparation of 2-methyl-N-(4-{2-[(4-morpholin-4-ylphenyl)amino]pyrimidin-4-yl}phenyl)prolinamide

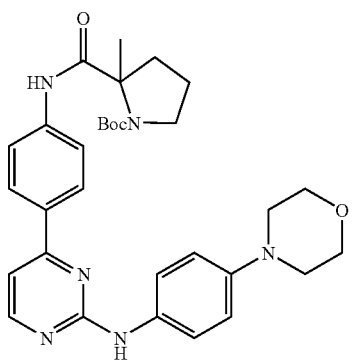

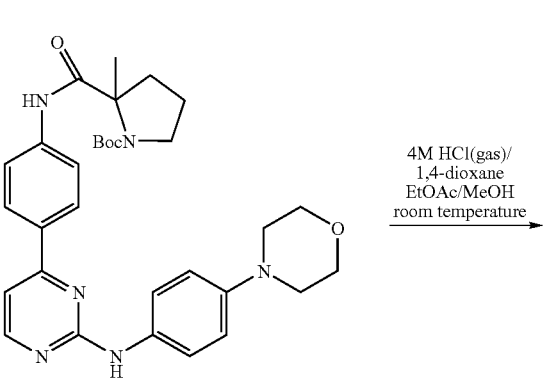

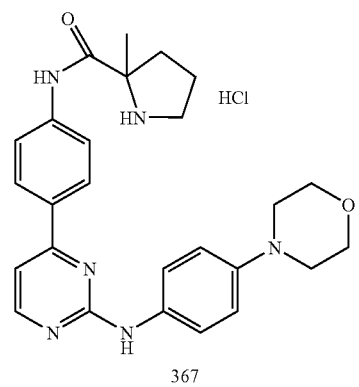

367

An oven dried 50 ml round bottomed flask fitted with a Teflon stirrer and gas inlet was flushed with dry nitrogen and allowed to cool to room temperature. The flask was charged with 4-(4-aminophenyl)-N-(4-morpholinophenyl)pyrimidin-2-amine pentahydrochloride (1 equiv., 0.52 g, 0.9631 mmoles) and anhydrous dimethylacetamide (15 ml). The mixture was stirred for 10 minutes to allow for the complete dissolution of the amine. Diisoproplyethylamine (10 equiv., 1.24 g, 1.67 ml, 9.631 mmoles) was added in one lot and the reaction mixture was stirred for 5 minutes. 1-(tert-Butoxycarbonyl)-2-methylpyrrolidine-2-carboxylic acid (4 equiv., 3.852 mmoles, 0.883 g, purchased from Fluka-Sigma Aldrich) was added to the reaction mixture in one lot, followed by 2-(7-aza-1H-benzotriazole-1-yl)-1,1,3,3-tetramethyluronium hexafluorophosphate (HATU, 4 equiv., 3.852 mmoles, 1.464 g, purchased from Oakland Products). The reaction mixture was stirred at room temperature and the progress of the reaction was monitored by LC/MS. After 72 hours, the reaction mixture was quenched with ethyl acetate (20 ml), and transferred to separatory funnel. The reaction flask was further rinsed with ethyl acetate (20 ml), transferred to the separatory funnel, shaken and the layer separated off. The aqueous layer was further washed with ethyl acetate (3×50 ml). The combined ethyl acetate solutions were washed with cold water (2×50 ml) and saturated sodium chloride solution (2×50 ml). The ethyl acetate solution was dried over anhydrous sodium sulfate, filtered and evaporated under reduced pressure to give orange oil. The resulting crude-material was purified by silica phase flash chromatography (45 mm×250 mm) using 3:1 ethyl acetate-hexane to give 0.147 g of tert-butyl 2-methyl-2-(4-(2-(4-morpholinophenylamino)pyrimidin-4-yl)phenylcarbamoyl)-pyrrolidine-1-carboxylate as a white solid (27% yield). 1H NMR (400 MHz, d6-DMSO) 10.01 (br s, 1H), 9.45 (br s 1H), 8.19 (d, 1H), 7.70 (d, 2H), 7.46 (d, 2H), 6.74 (d, 1H), 6.66 (d, 2H), 6.28 (d, 2H), 3.67 (m, 4H), 3.40 (m, 1H), 3.30 (m, 1H), 2.29 (m, 4H), 1.76 (m, 1H), 1.64 (m, 1H), 1.58 (s, 3H), 1.54 (m, 1H), 1.40 (s, 9H). MS (EI) for $C_{31}H_{38}N_6O_4$: 559 (M+).

tert-Butyl 2-methyl-2-(4-(2-(4-morpholinophenylamino)pyrimidin-4-yl)phenyl-carbamoyl)pyrrolidine-1-carboxylate (0.140 g, 0.250 mmoles), was dissolved in an ethyl acetate (5 ml) and methanol (1 ml) mixture. 4 M hydrogen chloride in 1,4-dioxane (0.625 ml, 2.5 mmoles, 10 equivalents, purchased from Sigma-Aldrich) was then added in a drop wise fashion over 5-10 minutes. Upon completion of addition, the reaction mixture was stirred at room temperature, and the progress of the reaction monitored by LC/MS. After 16 hours, additional 4M hydrogen chloride in 1,4-dioxane (0.312 ml, 1.25 mmoles, 5 equivalents) was added. After a total of 48 hours the reaction was complete and the resulting slurry was filtered off. The reaction flask was rinsed with ethyl acetate to ensure complete transfer of product. The resulting solid was washed with ethyl acetate (3×10 ml) and diethyl ether (2×25 ml) and dried under reduced pressure to give of 0.061 mg 2-methyl-N-(4-{2-[(4-morpholin-4-ylphenyl)amino]pyrimidin-4-yl}phenyl)prolinamide 367 as its hydrochloride salt (53% yield).

1H NMR (400 MHz, d6-DMSO): 10.88 (s, 1H), 9.79 (br s, 1H), 8.47 (d, 1H), 8.12 (d, 1H), 8.10 (d, 1H), 7.80 (br d, 2H), 7.75 (d, 2H), 7.37 (d, 2H), 5.26 (br s, 3H), 3.72 (br s, 4H), 3.27 (br s, 4H), 2.80 (m, 1H), 2.70 (m, 1H), 2.01 (m, 1H), 1.76 (m, 1H), 1.64 (m, 1H), 1.54 (m, 1H), 1.38 (s, 3H). MS (EI) for $C_{26}H_{30}N_6O_2$: 459 (MH+).

Example 45

2-Methyl-N-(4-{2-[(4-morpholin-4-ylphenyl)amino]-pyrimidin-4-yl}phenyl)prolinamide (Compound 360)

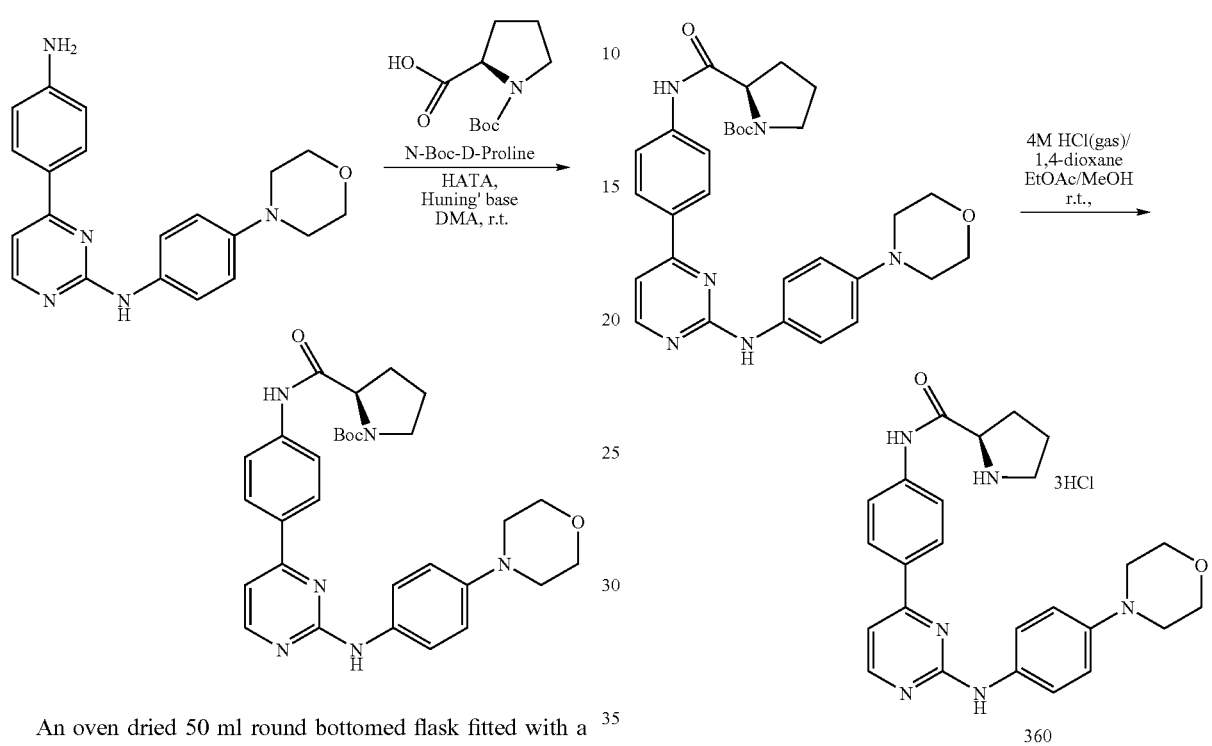

An oven dried 50 ml round bottomed flask fitted with a Teflon stirrer and gas inlet was flushed with dry nitrogen and allowed to cool to room temperature. The flask was charged with 4-(4-aminophenyl)-N-(4-morpholinophenyl)pyrimidin-2-amine pentahydrochloride (1 equiv., 0.4 g, 0.756 mmoles) and anhydrous dimethylacetamide (15 ml). The mixture was stirred for 10 minutes to allow for the complete dissolution of the amine. Diisoproplyethylamine (10 equiv., 0.977 g, 1.31 ml, 7.561 mmoles) was added in one lot and the reaction mixture was stirred for 5 minutes. N-Boc-D-proline (4 equiv., 3.204 mmoles, 0.65 g, purchased from Fluka-Sigma Aldrich) was added to the reaction mixture in one lot, followed by 2-(7-aza-1H-benzotriazole-1-yl)-1,1,3,3-tetramethyluronium hexafluorophosphate (HATU, 4 equiv., 3.024 mmoles, 1.149 g, purchased from Oakland Products). The reaction mixture was stirred at room temperature and the progress of the reaction was monitored by LC/MS. After 72 hours, the reaction mixture was quenched with ethyl acetate (20 ml), and transferred to separatory funnel. The reaction flask was further rinsed with ethyl acetate (20 ml), transferred to the separatory funnel, shaken and the layer separated off. The aqueous layer was further washed with ethyl acetate (3×50 ml). The combined ethyl acetate solutions were washed with chloride solution (2×50 ml). The ethyl acetate solution was dried over anhydrous sodium sulfate, filtered and evaporated under reduced pressure to give an orange oil. The resulting crude material was purified by silica phase flash chromatography (45 mm×250 mm) using 3:1 ethyl acetate-hexane to give 0.39 g of 1,1-dimethylethyl (2R)-2-{([(4-{2-[(4-morpholin-4-ylphenyl)amino]pyrimidin-4-yl}phenyl)amino]carbonyl}pyrrolidine-1-carboxylate as a white solid (94% yield).

1H NMR (400 MHz, d6-DMSO): 10.26 (br s, 1H), 9.38 (br s, 1H), 8.45 (d, 1H), 8.13 (d, 2H), 7.78 (d, 2H)<7.68 (d, 2H), 7.28 (d, 1H), 6.94 (d, 2H), 4.22 (m, 1H), 3.74 (m, 4H), 3.43 (m, 1H), 3.34 (m, 1H), 3.04 (m, 4H), 2.20 (m, 1H), 1.90 (m, 1H), 1.81 (m, 1H)<1.40 (s, 3H), 1.27 (s, 6H). MS (EI) for $C_{30}H_{36}N_6O_4$: 545 (MH$^+$).

1,1-Dimethylethyl (2R)-2-{([(4-{2-[(4-morpholin-4-ylphenyl)amino]pyrimidin-4-yl}-phenyl)amino]carbonyl}pyrrolidine-1-carboxylate (0.38 g, 0.698 mmoles), was dissolved in an ethyl acetate (10 ml) and methanol (2 ml) mixture. 4 M hydrogen chloride in 1,4-dioxane (1.75 ml, 6.98 mmoles, 10 equivalents, purchased from Sigma-Aldrich) was then added in a drop wise fashion over 5-10 minutes. Upon completion of addition, the reaction mixture was stirred at room temperature, and the progress of the reaction monitored by LC/MS. After 16 hours, additional 4M hydrogen chloride in 1,4-dioxane (0.87, 1.25 mmoles, 5 equivalents) was added. After a total of 48 hours the reaction was complete and the resulting slurry was filtered off. The reaction flask was rinsed with ethyl acetate to ensure complete transfer of product. The resulting solid was washed with ethyl acetate (3×10 ml), followed by diethyl ether (3×25 ml) and dried under reduced pressure to give of 0.264 mg 2-methyl-N-(4-{2-[(4-morpholin-4-ylphenyl)amino]-pyrimidin-4-yl}phenyl)prolinamide (68% yield).

1H NMR (400 MHz, d6-DMSO): 11.43 (br s, 1H), 10.07 (br s, 2H), 8.73 (d, 1H), 8.57 (d, 1H), 8.21 (d, 2H), 7.91 (d, 2H), 7.98 (d, 2H), 7.71 (br s, 2H), 7.48 (d, 1H), 4.48 (m, 1H), 4.08 (s, 4H), 3.74 (m, 4H), 3.42 (m, 1H), 3.36 (m, 1H), 3.04 (m, 4H), 2.22 (m, 1H), 1.90 (m, 2H), 1.82 (m, 2H). MS (EI) for $C_{25}H_{28}N_6O_2$: 445 (MH$^+$).

Example 46

3-({4-[4-(acetylamino)phenyl]pyrimidin-2-yl}amino)-N-[(1-methyl-1H-benzimidazol-2-yl)methyl]benzamide (Compound 83)

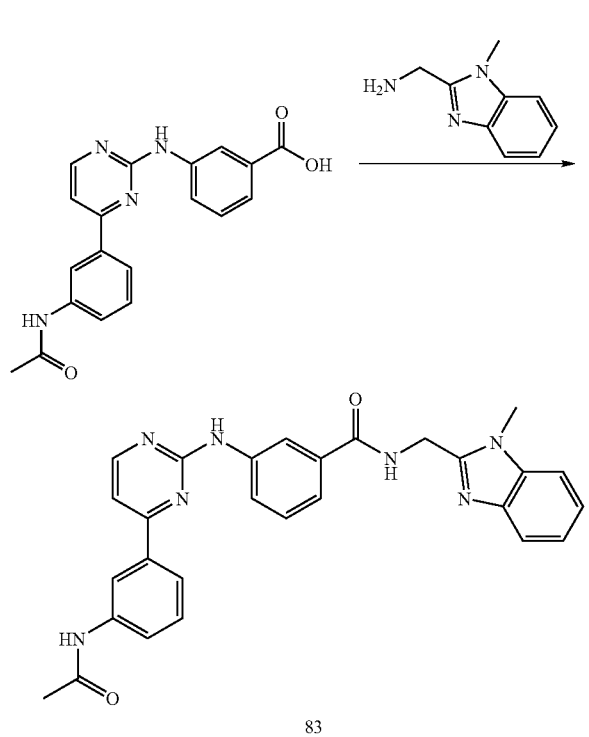

7.9 grams (11.04 mmol, 1.9 eq) of PL-TFP Resin (source: Polymer Laboratories) was weighed into a pressure tube. 60 ml of DCM was added. 2 g (5.74 mmol) of 3-(4-(3-acetamidophenyl)pyrimidin-2-ylamino)benzoic acid was dissolved in 15 ml of DMF and After 10 min, this solution was added to the pressure tube. Dimethylaminopyridine (4.41 mmol, 0.6 eq, source: Acros) was added to the pressure tube as a solid, followed by 1,3-diisopropylcarbodiimide (33.08 mmol, 4.5 eq, source: Acros). The pressure tube was sealed and the reaction was placed on a vertical shaker overnight. The resin was filtered, and then washed 3 times with DMF, followed by three times with THF, followed by three times with DCM. The resin was then dried overnight by vacuum.

300 mg of resin prepared above (loading=0.6 mmol/g, 0.18 mmol) was added to a 1 dram vial. 2 ml of DMA were added. 1 ml of (1-methyl-1H-benzo[d]imidazol-2-yl)methanamine (0.12 mmol, 0.67 eq) dissolved in DMA was added to the vial. The reaction was stirred overnight at room temperature. The reaction was filtered and rinsed twice with 4 ml of MeOH. The solution was further purified by HPLC to yield (3-(4-(4-acetamidophenyl)pyrimidin-2-ylamino)-N-((1-methyl-1H-benzo[d]imidazol-2-yl)methyl)benzamide 83 (10.2 mg, 17%).

$^1$H-NMR (400 MHz, $d_6$-DMSO): 10.23 (s, 1H), 9.80 (s, 1H), 9.01 (t, 1H), 8.52 (t, 2H), 8.17-8.19 (m, 2H), 7.91-7.93 (m, 1H), 7.75 (d, 2H), 7.50-7.59 (m, 3H), 7.39-7.43 (m, 2H), 7.16-7.26 (m, 2H), 4.80 (d, 2H), 3.86 (s, 3H), 2.10 (s, 3H). MS (EI) for $C_{28}H_2N_7O_2$: 492.4 (MH$^+$).

Example 47

N-(4-morpholin-4-ylphenyl)-4-{4-[(propylamino)methyl]phenyl}pyrimidin-2-amine (Compound 283)

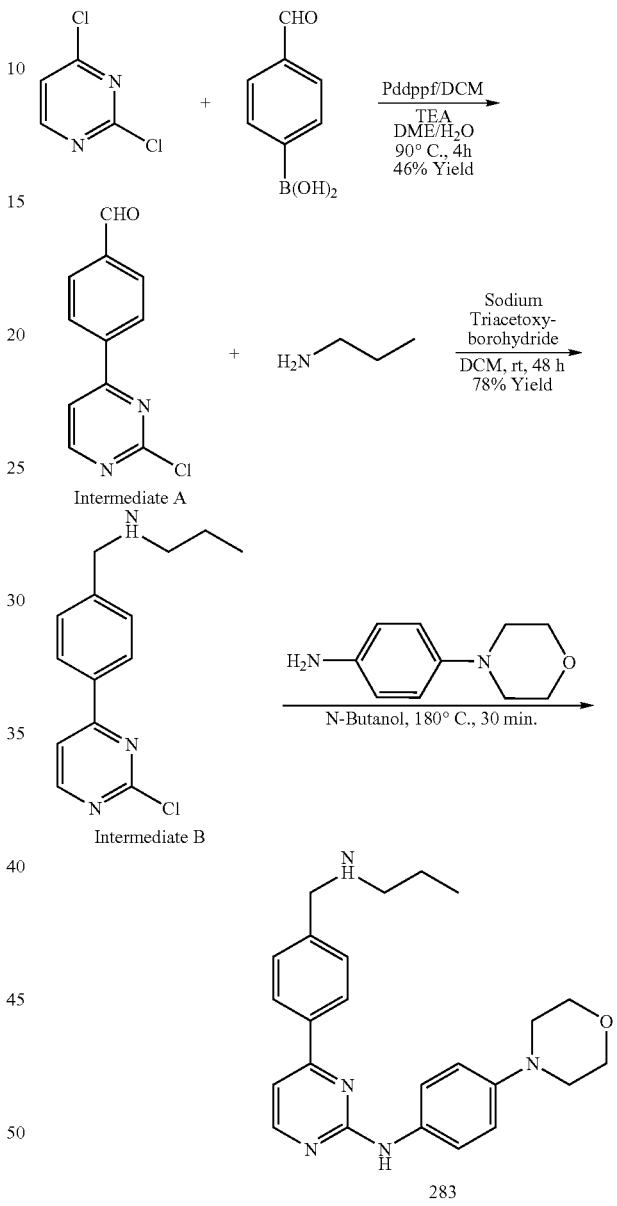

A flask was charged with 2,4-dichloropyrimindine (1.5 g, 10 mmol), 4-formylphenyl boronic acid (1.65 g, 11 mmol), dichloro[1,1'-bis(diphenylphosphino)ferrocenepalladium (731 mg, 1 mmol, 10 mol %), and triethylamine (2.6 mL, 15 mmol). Ethyleneglycoldimethylether (50 mL) and H$_2$O (2 mL) was added to the flask. The reaction mixture was stirred at 80° C. for 4 hours. The product, Intermediate A, was isolated by removal of the solvent with a rotary evaporator and purified using glass column chromatography and eluted with ethyl acetate to afford 1.0 g (4.58 mmol, 46% yield) of intermediate A as a yellow solid.

A flask was charged with intermediate A (150 mg, 0.668 mmol), sodium triacetoxy-borohydride (220 mg, 1.032 mmol), propylamine (63 μl, 0.756 mmol). Dichloromethane (50 mL) was added to the flask and the reaction mixture was stirred at room temperature for 48 h. The reaction was quenched with 2 N NaOH and extracted with ethyl acetate, washed with brine, dried over sodium sulfate, and filtered. The solvent was removed using the rotary evaporator to afford intermediate B as a yellow solid (140 mg, 0.536 mmol, 80% Yield). Intermediate B was carried on without further purification.

A seal tube was charged with intermediate B (140 mg, 0.536 mmol) and 4-morpholinoaniline (95 mg, 0.536 mmol). N-butanol (15 mL) was added to the seal tube and stirred at 180° C. The reaction was done in 1 h according to LCMS to afford 283 as a yellow solid. Compound 283 was purified using preparative HPLC and TFA buffer. Compound 283 was free-based, converted to HCl salt, and lyophilized (20 mg, 0.455 mmol).

$^1$H NMR (400 MHz, DMSO): 9.93 (br s, 1H), 9.396 (br s, 2H), 8.607 (d, 1H), 8.233 (d, 2H), 7.905 (d, 2H), 7.767 (d, 2H), 7.571-7.494 (m, 3H), 4.226 (br s, 2H), 3.998 (br s, 4H), 3.436 (br s, 4H), 2.865 (m, 2H), 1.708 (m, 2H), 0.914 (t, 3H). MS (EI) for $C_{24}H_{29}N_5O$: 404.4 (MH$^+$).

Example 48

N-[(4-{2-[(4-morpholin-4-ylphenyl)amino]pyrimidin-4-yl}phenyl)methyl]acetamide (Compound 282)

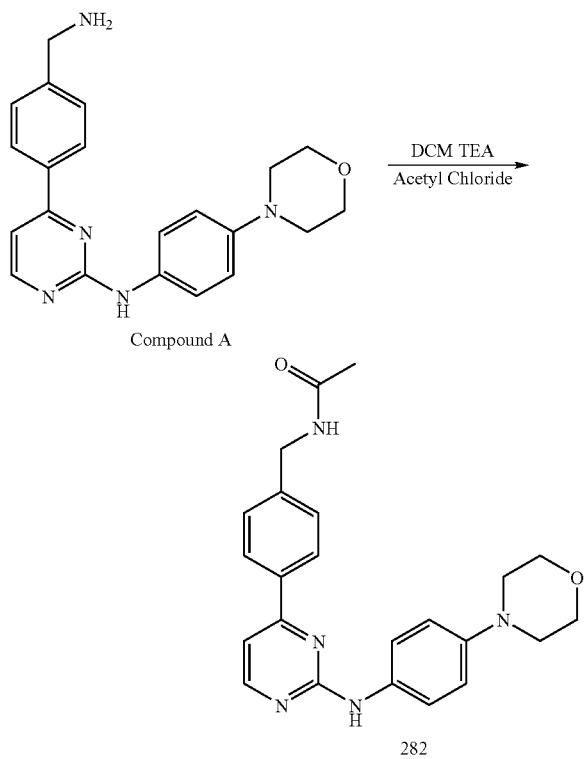

In a 20 ml round bottomed flask, 36 mg (1 mmol) of compound A was dissolved in 5 ml of dichloromethane and 0.5 ml of triethylamine was added. It was cooled in ice bath and 10 mg (1.2 mmol) of acetyl chloride was added and stirred for 30 min. Compound 282 precipitated out and purified in a Waters prep column. Yield 40 mg (90%).

$^1$H NMR (400 MHz, CD$_3$CN): 11.20-11.22 (b, 1H), 8.40 (d, 2H), 8.05 (d, 2H), 7.80 (d, 2H), 7.50 (d, 2H), 7.45 (s, 1H), 7.20 (d, 1H), 7.05-7.10 (b, 1H), 4.40-4.44 (b, 2H), 3.90 (t, 4H), 3.40 (t, 4H), 2.01 (s, 3H); MS (EI) for $C_{23}H_{25}N_5O_2$: 404 (MH$^+$).

Example 49

N-(4-{2-[(4-{4-[(2,4-dichlorophenyl)methyl]piperazin-1-yl}phenyl)amino]pyrimidin-4-yl}phenyl) acetamide (Compound 180)

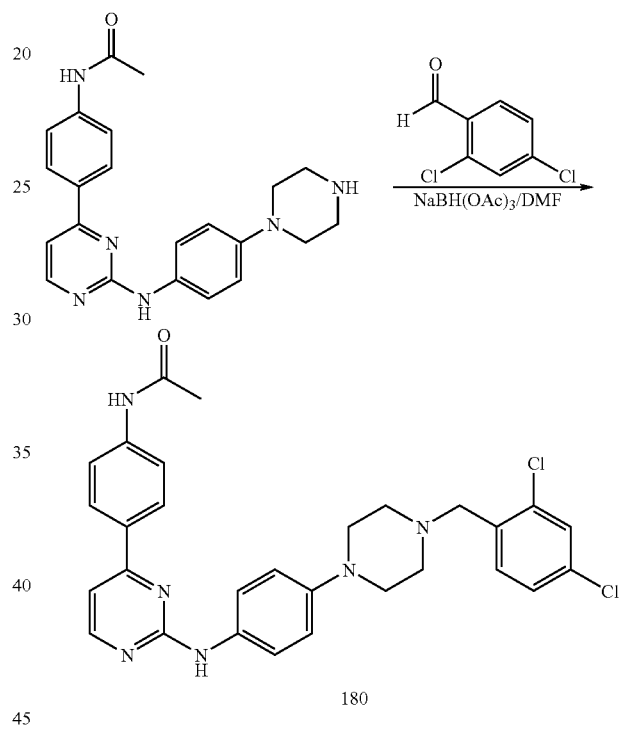

To a 1 ml vial was added N-(4-{2-[(4-piperazin-1-ylphenyl)amino]pyrimidin-4-yl}-phenyl)acetamide (38.85 mg, 0.1 mmol), 2,4-dichlorobenzaldehyde (350 mg, 2.0 mmol, 20 eq, source: Aldrich) and 1 ml of DMF. To this mixture was added sodium triacetoxyborohydride (106 mg, 0.5 mmol, 5 eq). The mixture was stirred over night at room temperature. Upon completion of the reaction as determined by LC/MS, 0.1 ml of 2M HCl was added. The residue was purified via reverse phase HPLC (ammonium acetate/ACN) to yield N-(4-{2-[(4-{4-[(2,4-dichlorophenyl)methyl]piperazin-1-yl}phenyl)amino]pyrimidin-4-yl}phenyl)acetamide 180 (20.2 mg, 37%).

$^1$H NMR (400 MHz, d6-DMSO): 10.21 (s, 1H), 9.80 (s, 1H), 9.10 (t, 1H), 8.53 (d, 2H), 8.18 (d, 2H), 7.94-7.91 (m, 1H), 7.75 (d, 1H), 7.69-7.57 (m, 4H), 7.48-7.39 (m, 2H), 4.58 (d, 6H), 2.50 (m, 4H), 2.09 (s, 3H). MS (EI) for $C_{29}H_{28}Cl_2N_6O$: 548.5 (MH+).

Example 50

5-fluoro-N~4~-[2-(methyloxy)phenyl]-N~2~-[3-(methyloxy)phenyl]pyrimidine-2,4-diamine (Compound 306)

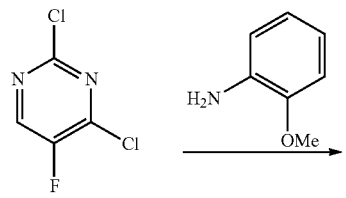

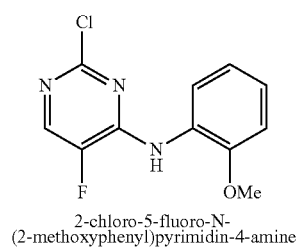 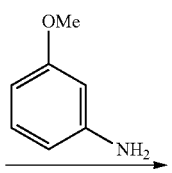

2-chloro-5-fluoro-N-
(2-methoxyphenyl)pyrimidin-4-amine

306

A round-bottomed flask was charged with 2,4-dichloro-5-fluoropyrimidine (0.84 g, 5 mmol), 2-methoxyaniline (0.61 g, 5 mmol) and dioxane (5 mL). The reaction mixture was heated at 85° C. overnight. The reaction was cooled down and diluted with acetonitrile/water, stirred for 30 min. and filtered. The collected solid was re-suspended in acetonitrile/water, stirred and filtered to give a 2-chloro-5-fluoro-N-(2-methoxyphenyl)pyrimidin-4-amine (0.9 g, 70% yield). To a seal tube was added 2-chloro-5-fluoro-N-(2-methoxyphenyl)pyrimidin-4-amine (254 mg), 3-methoxyaniline (500 mg, 4 eq.) and dioxane (5 mL). The mixture was heated to 130° C. overnight. The reaction mixture was cooled and partitioned between EtOAc and water. The organic layer was concentrated; the residue was triturated with a 1:1 mixture of dichloromethane and acetonitrile, then filtered to give the title product as a white solid (150 mg).

$^{1}$H NMR (400 MHz, d6-DMSO): 9.16 (s, 1H), 8.37 (s, 1H), 8.09 (s, 1H), 7.88 (d, 1H), 7.26 (t, 2H), 7.22-7.16 (m, 2H), 7.12-7.08 (m, 1H), 7.08-6.93 (m, 2H), 3.81 (s, 3H), 3.62 (s, 3H). MS (EI) for $C_{18}H_{17}FN_4O_2$: 341 (MH+).

Example 51

N-(4-{2-[(4-morpholin-4-ylphenyl)amino]-7H-pyrrolo[2,3-d]pyrimidin-4-yl}phenyl)-acetamide (Compound 329)

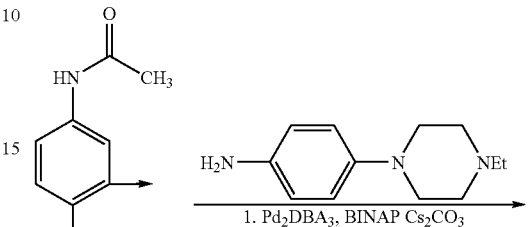

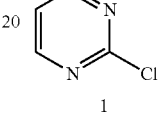

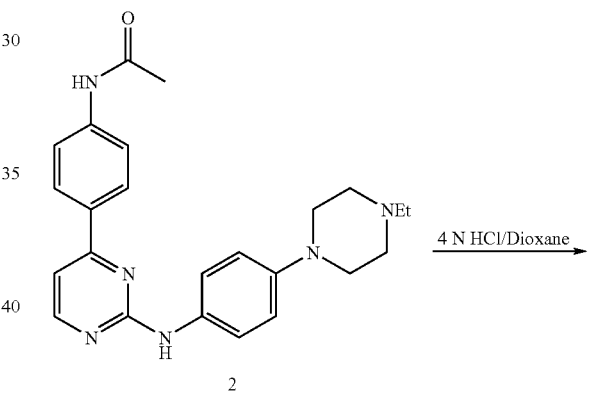

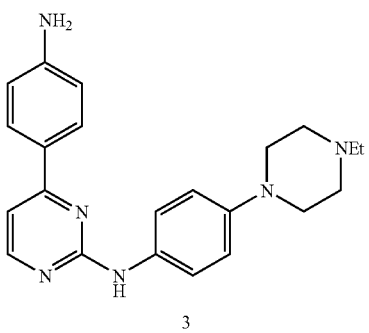

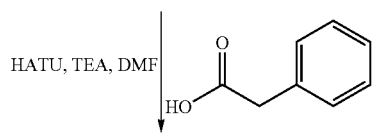

-continued

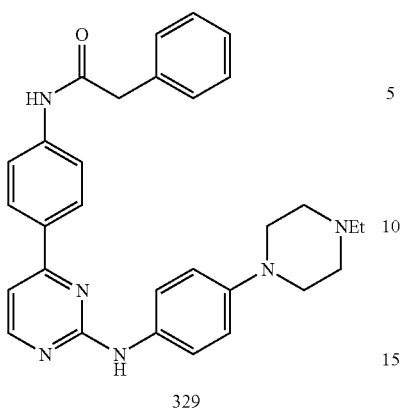

329

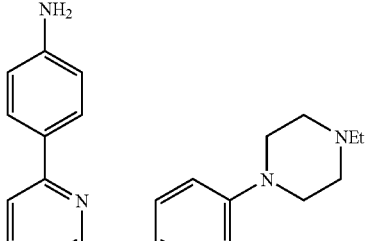

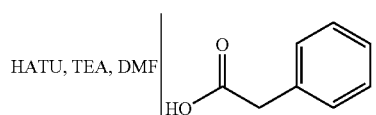

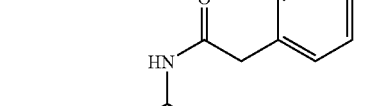

3

HATU, TEA, DMF

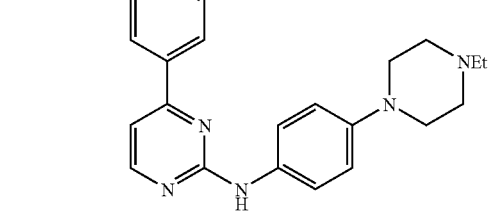

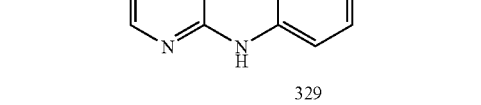

329

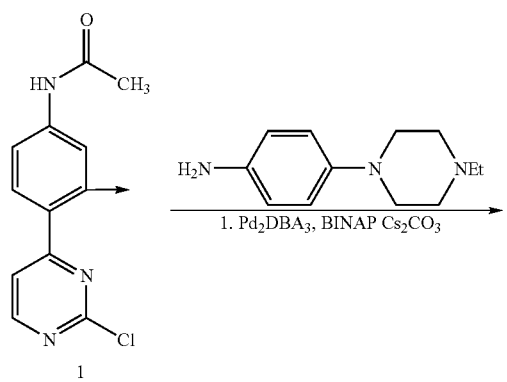

1

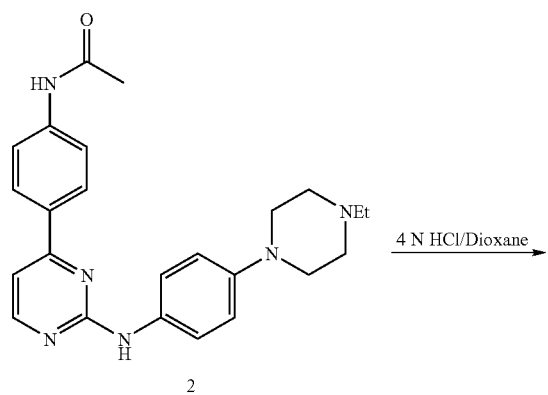

2

4 N HCl/Dioxane

To a flask containing a solution of 1 (0.25 g, 1 mmol), 4-(4-ethylpiperazin-1-yl)aniline (0.23 g, 1.1 mmol), cesium carbonate (0.5 g, 1.5 mmol), racemic-2,2'-bis(diphenylphosphino)-1,1'-binaphthyl (95 mg, 0.15 mmol) in N,N-dimethylacetamide (5 mL) purged with $N_2$ was added tris(dibenzylideneacetone)dipalladium(0) (0.14 g, 0.15 mmol). This reaction was heated to 90° C. for 16 h under $N_2$. At this time the reaction was concentrated and the residue was purified via silica gel column chromatography. The column was eluted with ethyl acetate to remove the impurities and then with 85:10:5 (ethyl acetate/methanol/7M ammonia in methanol) to elute the desired product. The solid obtained was sonicated first in acetone (5 mL) and then in ether (10 mL) to yield intermediate 2 (0.23 g, 48% yield) as a yellow solid. LCMS: m/z 417 (MH+). To a flask containing 2 (0.23 g, 0.45 mmol) was added 4N HCl in dioxane (5 mL) and the solution was heated at 50° C. for 4 h. To the cooled solution was added a 2N aqueous solution of sodium hydroxide (10 mL) and the resulting precipitate was filtered and dried to yield 3 (0.2 g, 99% yield) as a yellow solid. LCMS: m/z 375 $(M+H)^+$. To a flask with 3 (0.3 g, 0.8 mmol), phenylacetic acid (0.125 mL, 1 mmol), triethylamine (0.97 mL, 7 mmol), and DMF (5 mL) was added O-(7-azabenzotriazole-1-yl)-N,N,N',N'-tetramethyluronium hexafluorophosphate (HATU) (0.46 g, 1.2 mmol). The reaction mixture was stirred at ambient temperature for 1 h then diluted with 5% aqueous solution of lithium chloride (100 mL) and extracted with ethyl acetate (3×50 mL). The combined organic layers were washed with an aqueous 5% sodium bicarbonate solution, a saturated aqueous solution of sodium chloride, dried over anhydrous sodium sulfate, filtered and concentrated. The residue obtained was purified by silica gel column chromatography (98:2 ethylacetate/methanol) to provide Compound 329 (0.25 g, 63% yield) as an off-white solid.

Example 52

N-{4-[2-({4-[4-(cyclobutylcarbonyl)piperazin-1-yl]phenyl}amino)pyrimidin-4-yl]phenyl}-D-prolinamide (Compound 662)

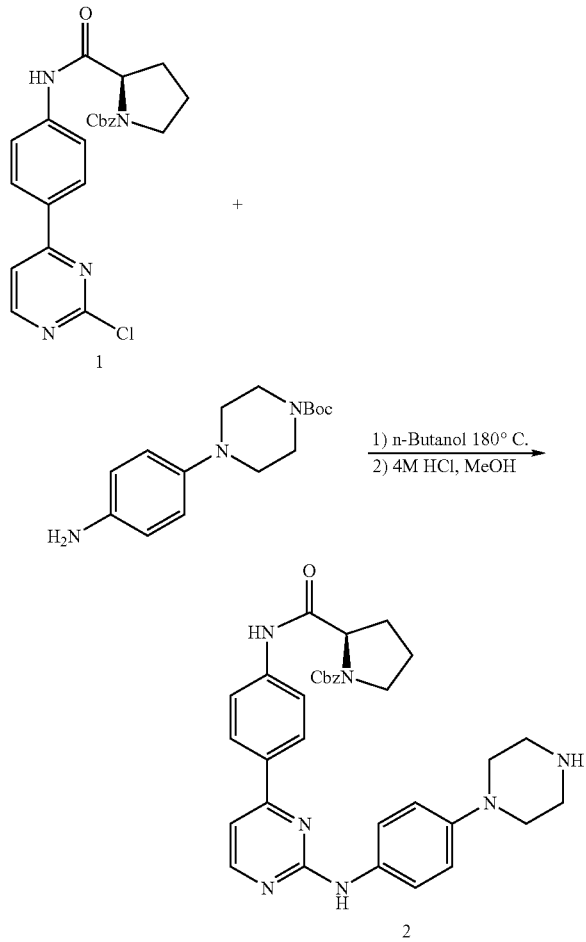

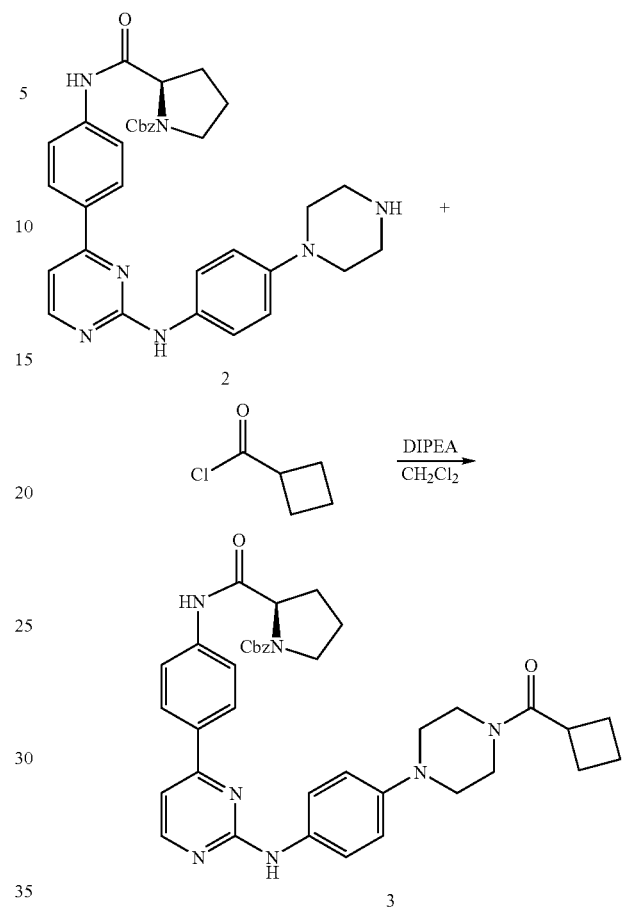

A solution of chloropyrimidine (1) (0.28 g, 0.64 mmol) and tert-butyl 4-(4-aminophenyl)piperazine-1-carboxylate (0.18 g, 0.6 mmol) in n-butanol (5 ml) was heated at 180° C. in a sealed tube for 7 h. The reaction mixture was concentrated, the residue dissolved in methanol (5 ml) and treated with HCl (3 ml, 4M in dioxane) for 1 h at room temperature. After concentration, the residue was dissolved in $H_2O$ (200 mL) and the pH adjusted to ca. 8-9 with 1N NaOH. The aqueous layer was extracted with $CH_2Cl_2$ (2×10 ml) and the combined organic layers were dried over anhydrous sodium sulfate, filtered and concentrated. The residue was purified by silica gel column chromatography (85:15 ethyl acetate/methanol) to afford 2 (0.26 g, 69%). $C_{33}H_{35}N_7O_3$: 578 (MH$^+$).

To a solution of 2 (0.41 g, 0.7 mmol) and DIPEA (0.31 ml, 1.75 mmol) in $CH_2Cl_2$ (7 ml) was added cyclobutylcarbonyl chloride (0.80 ml, 0.7 mmol) at room temperature. After 10 min, the reaction mixture was diluted with $H_2O$ (10 mL) and $CH_2Cl_2$ (10 mL). The aqueous layer was extracted with $CH_2Cl_2$ (3×5 mL). The combined organic layers were dried over anhydrous sodium sulfate, filtered, and concentrated. The residue obtained was purified by silica gel column chromatography (98:2 ethyl acetate/methanol) to afford 3 (0.31 g, 68%) as a white powder. $C_{38}H_{41}N_7O_4$: 660 (MH$^+$).

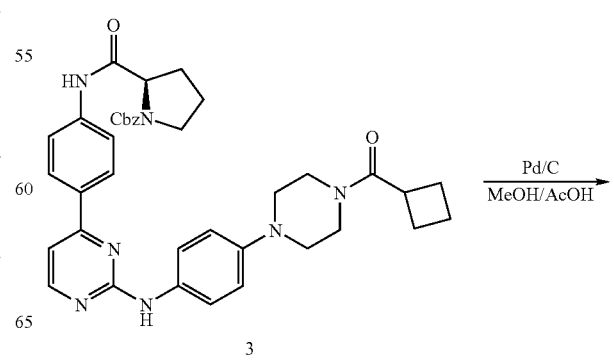

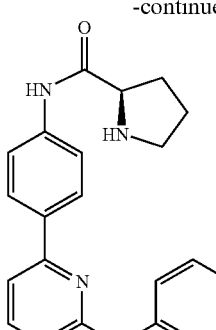

662

The mixture of 3 (0.31 g, 0.47 mmol) and Pd/C (0.94 g) AcOH (1 mL) and MeOH (5 mL) was stirred at room temperature for 24 h under a H₂ balloon. The palladium was filtered through celite and the filtrate was concentrated. The residue was purified by silica gel column chromatography (90:10 ethyl acetate/methanol) to afford product which was then washed with acetonitrile several times to afford Compound 662 (0.14 g, 59% yield).

Example 53

N-ethyl-4-[4-({4-[4-(D-propylamino)phenyl]pyrimidin-2-yl}amino)phenyl]piperazine-1-carboxamide (Compound 663)

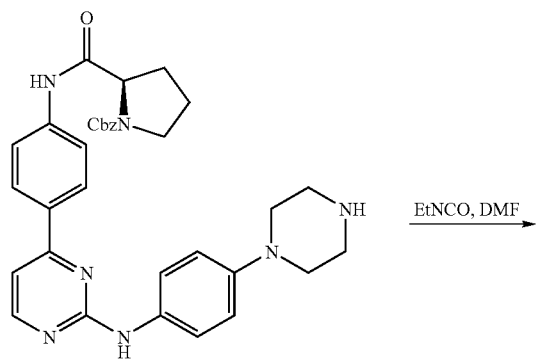

To a stirred solution of 2 (0.58 g, 1 mmol) in DMF (4 ml) was added ethyl isocyanate (3 mL) at room temperature. After stirring for 30 min, the mixture was diluted with H₂O (5 mL) and CH₂Cl₂ (5 mL). The separated aqueous layer was extracted with CH₂CH₂Cl₂ (3×5 mL). The combined extracts were dried over anhydrous sodium sulfate, filtered, and concentrated. The residue was purified by silica gel column chromatography (98:2 ethyl acetate/methanol) to afford 4 (0.46 g, 71%). $C_{36}H_{40}N_8O_4$: 649 (M+H)⁺.

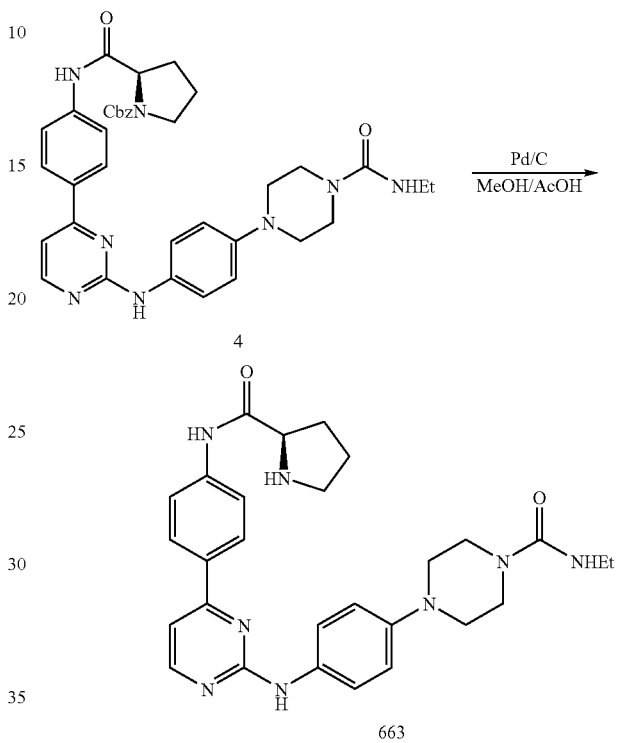

663

A solution of 4 (0.46 g, 0.71 mmol) and Pd/C (0.14 g) in AcOH (1 mL) and MeOH (5 mL) was stirred for 24 h under a H₂ balloon. The palladium was filtered through celite and the filtrate was concentrated. The residue obtained was purified by silica gel column chromatography (90:10 ethyl acetate/methanol) to afford product which was then washed with acetonitrile several times to afford N-ethyl-4-[4-({4-[4-(D-propylamino)phenyl]pyrimidin-2-yl}amino)phenyl]piperazine-1-carboxamide (663) (0.19 g, 51%) as a white powder.

2-{[2-(dimethylamino)ethyl]oxy}-3-(4-ethylpiperazin-1-yl)aniline

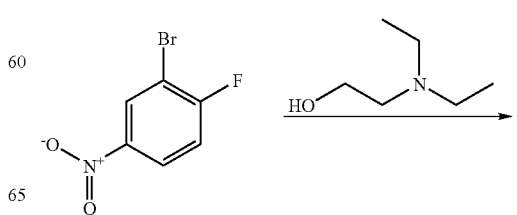

-continued

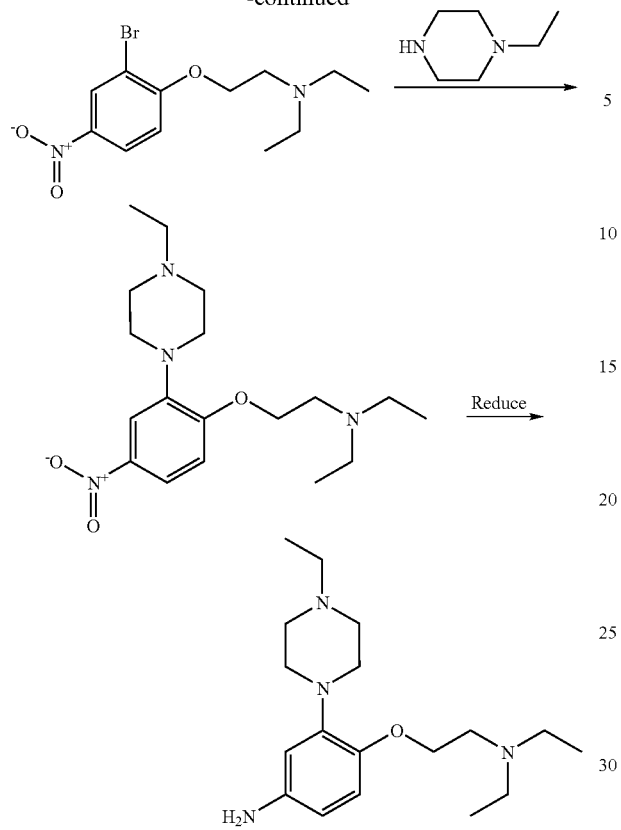

To a solution of 2-(diethylamino)ethanol (0.59 g, 5 mmol) in DMA (5 ml), sodium hydride (0.24 g, 10 mmol) was added in one portion. Fifteen minute later 2-bromo-4-nitroaniline (1.1 g, 5 mmol) was added and the content was stirred for 4 hr. Water (50 ml) was added to the reaction mixture followed by chloroform. The organic layer was separated, washed with saturated sodium bicarbonate follow by brine. The organic layer was dried over sodium sulfate and concentrated to oil. The oil was dissolved in methanol and saturated with HCl gas. The resulting solution was concentrated and diethyl ester was added. The resulting precipitate was washed with ether and dried to yield 0.8 g of 2-[(2-bromo-4-nitrophenyl)Oxy]-N,N-diethylethanamine hydrochloride as a solid. LCMS: m/z 318 (M+H)+.

A mixture of 2-[(2-bromo-4-nitrophenyl)Oxy]-N,N-diethanamine hydrochloride (0.5 g, 1.4 mmol), Pd(dba)$_2$ (0.192 g, 021 mmol), BINAP (0.139 g, 0.21 mmol), 1-ethylpiperazine (0.182 g, 1.68 mmol), and cesium carbonate (0.91 g, 2.8 mmol) in DMA was heated at 80° C. with stirring for 72 hr. Saturated aqueous sodium bicarbonate and ethyl acetate was added, the phases separated, the solvent was removed under vacuum and the residue chromatographed on silica with ethyl acetate/methanol to give 0.32 g of N,N-diethyl-2-{[2-(4-ethylpiperazin-1-yl)-4-nitrophenyl]oxy}ethanamine. LCMS: m/z 351 (M+H)+.

A solution of N,N-diethyl-2-{[2-(4-ethylpiperazin-1-yl)-4-nitrophenyl]oxy}ethanamine (0.280 mg, 0.8 mmol) in methanol (10 ml) was added 10% Pd/C and stirred in hydrogen atmosphere at ambient temperature for 2 hr. The reaction mixture was filtered through a pad of Celite and concentrated in vacuum. The residue was taken up in methanol, ether/HCl was added and the hydrochloride (0.270 mg) was precipitated. LCMS: m/z 321 (M+H)+.

Example 54

(R)—N-(4-(2-(3-(benzyloxy)-4-morpholino-phenylamino)-pyrimidin-4-yl)phenyl)-pyrrolidine-2-carboxamide (Compound 376)

R)—N-(4-(2-(3-(benzyloxy)-4-morpholino-phenylamino)-pyrimidin-4-yl)phenyl)-pyrrolidine-2-carboxamide was synthesized in an analogous fashion to Example 3, wherein 4-morpholinoaniline was substituted with 3-(benzyloxy)-4-morpholinoaniline to afford the title compound.

3-(benzyloxy)-4-morpholinoaniline

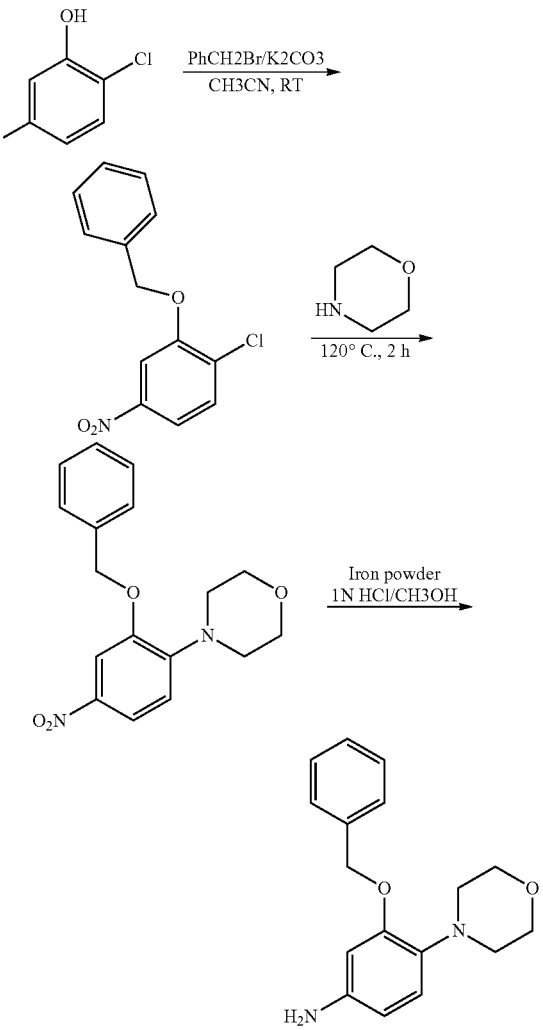

4-(2-(Benzyloxy)-4-nitrophenyl)morpholine: A flask was charged with 2-chloro-5-nitrophenol (3.5 g, 20.2 mmol), potassium carbonate (4.0 g, 30.3 mmol), benzyl bromide (2.9 mL, 24.24 mmol,) and acetonitrile (25 mL). The reaction mixture was stirred under an N$_2$ atmosphere at room temperature for 12 hours, after which time, the reaction mixture was filtered through Celite pat and washed with ethyl acetate (50 mL). The product was isolated by removal of the solvent with a rotary evaporator and used without further purification. NMR (400 MHz, CDCl$_3$): 7.80 (m, 2H), 7.27-7.58 (m, 6H), 5.24 (s, 2H). MS (EI) for C$_{13}$H$_{10}$ClNO$_3$: 264 (MH+).

Example 55

(S)-2-amino-N-(4-(2-(3-methyl-4-morpholinophenylamino)pyrimidin-4-yl)phenyl)propanamide (Compound 384) was synthesized in an analogous fashion to Example 3, wherein 4-morpholinoaniline was substituted with 3-Methyl-4-morpholinoaniline to afford the title compound.

3-Methyl-4-morpholinoaniline

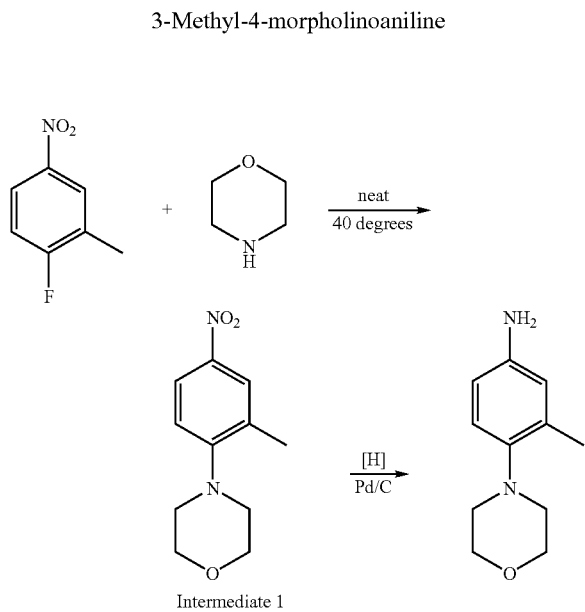

A flask was charged with 2-fluoro-5-nitrotuloene (3.0 mL, 20.2388 mmol). Excess amount of morpholine (10 mL) were added to the flask and heated to 40° C. for 6 hours. The reaction mixture was checked with LC/MS. Water was added to the reaction mixture and the precipitate, intermediate 1, was filtered and used without further purification. LC/MS: m/z 223 (M+H)$^+$.

A hydrogenation flask was charged with intermediate 1 (1.0 g, 4.4209 mmol) and palladium/carbon (200 mg). Ethyl alcohol (50 mL) was added to the flask and hydrogenation technique was used. The reaction mixture was checked with LC/MS. The reaction mixture was filtered through a celite plug and washed with methanol. The product, 3-methyl-4-morpholinoaniline, was isolated by removal of the solvent with a rotary evaporator and used without further purification. LC/MS: m/z 197 (M+H)$^+$.

Example 56

N-[3-({4-[4-(acetylamino)phenyl]pyrimidin-2-yl}amino)phenyl]-2-chloro-6-fluoro-3-(methyloxy)benzamide (Compound 49) was synthesized in an analogous fashion to Example 2, wherein benzoylchloride was substituted with 2-chloro-3-methoxy-6-fluorobenzoylchloride (JRD Fluorochemicals) to afford the title compound.

Example 57

N-(4-{2-[(3-chloro-4-morpholin-4-ylphenyl)amino]pyrimidin-4-yl}phenyl)acetamide (Compound 296) was synthesized in an analogous fashion to Example 3, wherein aniline was substituted with 3-chloro-4-morpholinoaniline (Pfaltz and Bauer, Inc.) to afford the title compound.

Example 58

N-(4-{2-[(3-bromo-4-morpholin-4-ylphenyl)amino]pyrimidin-4-yl}phenyl)acetamide (Compound 315) was synthesized in an analogous fashion to Example 3, wherein aniline was substituted with 3-bromo-4-morpholinoaniline (Ryan Scientific, Inc.) to afford the title compound.

Example 59

(R)—N-(4-(2-(4-morpholino-3-(trifluoromethyl)-phenylamino)pyrimidin-4-yl)-phenyl)-pyrrolidine-2-carboxamide was synthesized in an analogous fashion to Example 3, wherein aniline was substituted with 3-trifluoromethyl-4-morpholinoaniline (Zerenex Limited) to afford the title compound.

Example 60

(R)—N-(4-(2-(3-fluoro-4-morpholinophenylamino)pyrimidin-4-yl)phenyl)pyrrolidine-2-carboxamide was synthesized in an analogous fashion to Example 3, wherein aniline was substituted with 3-fluoro-4-morpholinoaniline (Astatech, Inc.) to afford the title compound.

Example 61

N-[4-(2-{[3-(1,3-dioxan-2-yl)phenyl]amino}pyrimidin-4-yl)phenyl]acetamide was synthesized in an analogous fashion to Example 3, wherein aniline was substituted 3-(1,3-dioxan-2-yl)aniline (Oakwood Products, Inc.) to afford the title compound.

Example 62

N-(4-{2-[(4-morpholin-4-ylphenyl)amino]-5-(trifluoromethyl)pyrimidin-4-yl}phenyl)acetamide was synthesized in an analogous fashion to Example 5, wherein pyrimidine was substituted with 5-trifluoromethyl-2,4-dichloropyrimidine (Astatech, Inc.) to afford the title compound.

Using the same or analogous techniques as illustrated in the preceding examples the following compounds herein below were made. The skilled artisan would be able to make the necessary modifications and/or substitutions in the above synthetic procedures to arrive at the following compounds:

N-(4-{2-[(3-morpholin-4-ylphenyl)amino]pyrimidin-4-yl}phenyl)acetamide (Cmpd 21): $^1$H-NMR (400 MHz, d$_6$-DMSO): 10.22 ppm (s, 1H), 9.511 ppm (s, 1H), 8.504 ppm (d, 1H), 8.154 ppm (d, 2H), 7.76 ppm (d, 3H), 7.343 ppm (d, 1H), 7.215-7.153 ppm (m, 2H), 6.584 ppm (d, 1H), 3.775 ppm (t, 4H), 3.14 ppm (t, 4H), 2.094 ppm (s, 3H); MS (EI) $C_{22}H_{23}N_5O_2$: 390.1 (MH$^+$).

N-(4-{2-[(3-piperidin-1-ylphenyl)amino]pyrimidin-4-yl}phenyl)acetamide (Cmpd 22): $^1$H-NMR (400 MHz, d$_6$-DMSO): 10.231 ppm (s, 1H), 9.466 ppm (s, 1H), 8.497 ppm (d, 1H), 8.16 ppm (d, 2H), 7.765 ppm (d, 3H), 7.337 ppm (d, 1H), 7.119 ppm (d, 2H), 6.553 ppm (m, 1H), 3.176 ppm (t, 4H), 2.092 ppm (s, 31-1), 1.658 ppm (m, 4H), 1.571 ppm (m, 2H); MS (EI) $C_{23}H_{25}N_5O$: 388.1 (MH$^+$).

N-[4-(2-{[4-(4-ethylpiperazin-1-yl)phenyl]amino}pyrimidin-4-yl)phenyl]acetamide (Cmpd 33): $^1$H-NMR (400 MHz, d$_6$-DMSO): 10.269 ppm (s, 1H), 9.317 ppm (s, 1H), 8.411 ppm (d, 1H), 8.089 ppm (d, 2H), 7.743 ppm (d, 2H), 7.638 ppm (d, 2H), 7.243 ppm (d, 1H), 6.908 ppm (d, 2H), 3.048 ppm (br s, 4H), 2.350 ppm (q, 2H), 2.07 ppm (s, 3H), 1.027 ppm (t, 3H); MS (EI) $C_{24}H_{28}N_6O$: 417.4 (MH$^+$).

N-(4-{2-[(4-piperidin-4-ylphenyl)amino]pyrimidin-4-yl}phenyl)acetamide (Cmpd 34): $^1$H-NMR (400 MHz, d$_6$-DMSO): 10.229 ppm (s, 1H), 9.53 ppm (s, 1H), 8.481 ppm (d, 1H), 8.135 ppm (d, 2H), 7.76 ppm (t, 4H), 7.325 ppm (d, 1H), 7.178 ppm (d, 1H), 3.025 ppm (br d, 2H), 2.59 ppm (m, 2H), 2.094 ppm (s, 3H), 2.08 ppm (br d, 2H), 1.54-1.439 ppm (m, 2H); MS (EI) C$_{23}$H$_{25}$N$_5$O: 388.3 (MH$^+$).

N-[3-({4-[4-(acetylamino)phenyl]pyrimidin-2-yl}amino)phenyl]-2,6-dichloro-benzamide (Cmpd 17): $^1$H-NMR (400 MHz, d$_6$-DMSO): 10.718 ppm (s, 1H), 10.269 ppm (s, 1H), 9.678 ppm (s, 1H), 8.507 ppm (d, 1H), 8.419 ppm (s, 1N), 8.215 ppm (d, 2H), 7.758 ppm (d, 2H), 7.608 ppm (d, 2H), 7.532 ppm (t, 1H), 7.472 ppm (d, 1H), 7.380 ppm (d, 1H), 7.301 ppm (t, 1H), 7.216 ppm (d, 1H), 2.085 ppm (s, 3H); MS (EI) C$_{25}$H$_{19}$Cl$_2$N$_5$O$_2$: 492.2 (MH$^+$).

N-{4-[2-({3-[(4-ethylpiperazin-1-yl)carbonyl]phenyl}amino)pyrimidin-4-yl]phenyl}acetamide (Cmpd 8): $^1$H-NMR (400 MHz, d$_6$-MEOD): 8.455 ppm (d, 1H), 8.15 ppm (m, 3H), 7.76-7.7 ppm (m, 3H), 7.435 ppm (t, 1H), 7.311 ppm (d, 1H), 7.1 ppm (d, 1H), 3.832 ppm (br s, 4H), 3.13 ppm (br s, 4H), 3.016 ppm (q, 2H), 2.162 ppm (s, 3H), 1.975 ppm (s, 3H, ACE), 1.299 ppm (t, 3H); MS (EI) C$_{25}$H$_{28}$N$_6$O$_2$: 445.4 (MH$^+$).

N-[3-({4-[4-(acetylamino)phenyl]pyrimidin-2-yl}amino)phenyl]-2-fluorobenzamide (Cmpd 10): $^1$H NMR (DMSO-D$_6$) 10.40 (S, 1H), 10.21 (S, 1H), 9.66 (S, 1H), 8.49 (D, 1H), 8.41 (S, 1H), 8.20 (D, 2H), 7.74 (D, 2H), 7.69 (M, 1H), 7.58 (M, 1H), 7.48 (M, 1H), 7.37 (M, 3H), 7.28 (M, 2H), 2.09 (S, 3H). LCMS: M/Z 442 (M+H).

N-[3-({4-[4-(acetylamino)phenyl]pyrimidin-2-yl}amino)phenyl]-2-fluoro-6-iodobenzamide (Cmpd 11): $^1$H NMR (DMSO-D$_6$) 10.65 (S, 1H), 10.19 (S, 1H), 9.67 (S, 1H), 8.50 (D, 1H), 8.41 (S, 1H), 8.21 (D, 2H), 7.76 (M, 3H), 7.41 (M, 3H), 7.28 (M, 3H), 2.08 (S, 3H). LCMS: M/Z 567 (M+H)$^+$.

N-[3-({4-[4-(acetylamino)phenyl]pyrimidin-2-yl}amino)phenyl]-2-bromobenzamide (Cmpd 23): $^1$H NMR (DMSO-D$_6$) 10.48 (S, 1H), 10.20 (S, 1H), 9.66 (S, 1H), 8.49 (D, 1H), 8.42 (S, 1H), 8.20 (D, 2H), 7.73 (D, 3H), 7.55 (M, 2H), 7.45 (M, 2H), 7.36 (M, 1H), 7.37 (D, 1H), 7.25 (M, 2H), 2.08 (S, 3H). LCMS: M/Z 502, 503, 504, 505 (M+H)$^+$.

N-[3-({4-[4-(acetylamino)phenyl]pyrimidin-2-yl}amino)phenyl]-3-fluorobenzamide (Cmpd 24): $^1$H NMR (DMSO-D$_6$) 10.33 (S, 1H), 10.23 (S, 1H), 9.69 (S, 1H), 8.50 (D, 1H), 8.44 (S, 1H), 8.21 (D, 2H), 7.85 (M, 1H), 7.79 (M, 1H), 7.73 (D, 2H), 7.61 (M, 1H), 7.50 (M, 1H), 7.36 (M, 1H), 7.29 (M, 2H), 2.09 (S, 3H). LCMS: M/Z 442 (M+H)$^+$.

N-[3-({4-[4-(acetylamino)phenyl]pyrimidin-2-yl}amino)phenyl]-2,6-dimethyl-benzamide (Cmpd 12): $^1$H NMR (DMSO-D$_6$) 10.37 (S, 1H), 10.20 (S, 1H), 8.55 (S, 1H), 8.49 (D, 1H), 8.22 (D, 2H), 7.72 (D, 2H), 7.36 (D, 2H), 7.22 (M, 3H), 7.12 (D, 2H), 2.33 (S, 6H), 2.08 (S, 3H). LCMS: M/Z 452 (M+H)$^+$.

N-[3-({4-[4-(acetylamino)phenyl]pyrimidin-2-yl}amino)phenyl]pyridine-4-carboxamide (Cmpd 14): $^1$H NMR (DMSO-D$_6$) 10.59 (S, 1H), 10.34 (S, 1H), 9.71 (S, 1H), 8.80 (DD, 2H), 8.50 (M, 2H), 8.21 (D, 2H), 7.90 (DD, 2H), 7.75 (D, 2H), 7.51 (M, 1H), 7.37 (M, 1H), 7.31 (M, 2H), 2.09 (S, 3H). LCMS: M/Z 425 (M+H)$^+$.

N-[3-({4-[4-(acetylamino)phenyl]pyrimidin-2-yl}amino)phenyl]-2,3,4,5,6-pentafluorobenzamide (Cmpd 15): $^1$H NMR (DMSO-D$_6$) 10.97 (S, 1H), 10.20 (S, 1H), 9.75 (S, 1H), 8.50 (D, 1H), 8.33 (S, 1H), 8.17 (D, 2H), 7.72 (D, 2H), 7.55 (M, 1H), 7.38 (D, 1H), 7.32 (T, 1H), 7.24 (D, 2H), 2.08 (S, 3H). LCMS: M/Z 514 (M+H)$^+$.

N-3-({4-[4-(acetylamino)phenyl]pyrimidin-2-yl}amino)propyl)-2,6-dichloro-benzamide (Cmpd 1): $^1$H NMR (DMSO-d$_6$) 10.15 (s, 1H), 8.68 (t, 1H), 8.27 (d, 1H), 8.04 (d, 2H), 7.67 (d, 2H), 7.49 (d, 2H), 7.41 (m, 1H), 7.13 (t, 1H), 7.06 (d, 1H), 3.41 (m, 2H), 3.30 (m, 2H), 2.06 (s, 3H), 1.80 (m, 2H). LCMS: m/z 458 (M+H)$^+$.

2,6-dichloro-N-(3-{[4-(2,4-dichlorophenyl)pyrimidin-2-yl]amino}propyl)benzamide (Cmpd 2): $^1$H NMR (DMSO-d$_6$) 8.63 (s, 1H), 8.36 (d, 1H), 7.73 (s, 1H), 7.58 (d, 1H), 7.52 (d, 1H), 7.47 (m, 2H), 7.40 (m, 2H), 6.79 (d, 2H), 3.37 (m, 2H), 3.27 (m, 2H), 1.75 (t, 2H). LCMS: m/z 471 (M+H)$^+$.

4-(2,4-dichlorophenyl)-N-{3-[(2-piperidin-1-ylethyl)oxy]phenyl}pyrimidin-2-amine (Cmpd 19): $^1$H NMR (DMSO-d$_6$) 9.79 (s, 1H), 8.58 (d, 1H), 7.77 (d, 1H), 7.68 (d, 1H), 7.58 (m, 2H), 7.24 (d, 1H), 7.10 (m, 2H), 6.50 (dd, 1H), 3.98 (t, 2H), 2.60 (t, 2H), 2.47 (m, 4H), 1.46 (m, 4H), 1.36 (m, 2H). LCMS: m/z 443 (M+H)$^+$.

N-(3-{[4-(4-aminophenyl)pyrimidin-2-yl]amino}propyl)-2,6-dichlorobenzamide (Cmpd 6): $^1$H NMR (400 MHz, DMSO): δ 8.76-8.79 (m, 1H), 8.45 (d, 6.0 Hz, 1H), 7.94-8.06 (m, 3H), 7.56 (m. 1H), 7.52-7.51 (m, 1H), 7.50 (s, 2H), 7.43-7.52 (m, 2H), 7.36-7.42 (m, 1H), 7.22-7.34 (bs, 1H), 3.44-3.64 (bs, 2H), 3.32-3.40 (m, 2H), 1.02-1.52 (bs, 2H). LC/MS MH=416.

2,6-dichloro-N-(3-{[4-(2,3-dihydro-1-benzofuran-6-yl)pyrimidin-2-yl]amino}-propyl)benzamide (Cmpd 4): $^1$H NMR (400 MHz, DMSO): δ 8.724 (t, 5.6 Hz, 1H), 8.29 (d, 5.6 Hz, 1H), 8.41-8.18 (bs, 1H), 7.92-8.15 (bs, 1H), 7.49-7.52 (m, 2H), 7.41-7.45 (m, 2H), 7.14-7.23 (bs, 1H), 6.88 (d, 8.4 Hz, 1H), 4.61-4.65 (m, 2H), 3.62-3.93 (bs, 1H), 3.39-3.51 (bs, 1H), 3.33-3.36 (m, 2H), 3.23-3.27 (m, 2H), 1.80-1.87 (bs, 2H). LC/MS MH=443.

2,6-dichloro-N-[3-({4-[4-(dimethylamino)phenyl]pyrimidin-2-yl}amino)propyl]-benzamide (Cmpd 3): $^1$H NMR (400 MHz, DMSO): δ 8.66 (t, 5.6 Hz, 1H), 8.17 (d, 5.2 Hz, 1H), 7.95 (d, 8.8 Hz, 2H), 7.47-7.49 (m, 2H), 7.38-7.42 (m, 1H), 6.95-6.97 (m, 2H), 6.72-6.75 (m, 2H), 3.37-3.43 (m, 2H), 3.26-3.32 (m, 2H), 2.96 (s, 6H), 1.79 (t, 6.8 Hz, 2H). LC/MS M−H=442.

N-[3-({4-[4-(acetylamino)phenyl]-5-methylpyrimidin-2-yl}amino)phenyl]-2,6-dichlorobenzamide (Cmpd 25): $^1$H NMR (400 MHz, DMSO-d$_6$) δ 10.67 (s, 1H), 10.15 (s, 1H), 9.57 (s, 1H), 8.38 (s, 1H), 8.16 (s, 1H), 7.72 (s, 4H), 7.60-7.50 (m, 4H), 7.26-7.23 (m, 2H), 2.26 (s, 3H), 2.09 (s, 3H). LCMS (EI) C$_{26}$H$_{22}$Cl$_2$N$_5$O$_2$: 506 (M+H).

N-[3-({4-[4-(acetylamino)phenyl]-5-fluoropyrimidin-2-yl}amino)phenyl]-2,6-dichlorobenzamide (Cmpd 28): $^1$H NMR (400 MHz, DMSO-d$_6$) δ 10.72 (s, 1H), 10.25 (s, 1H), 9.78 (s, 1H), 8.59 (d, J=4.0 Hz, 1H), 8.32 (s, 1H), 8.12 (d, J=8.4 Hz, 2H), 7.77 (d, J=8.8 Hz, 2H), 7.61-7.58 (m, 2H), 7.51 (dd, J=8.8, 6.8 Hz, 1H), 7.44 (d, J=8.4 Hz, 1H), 7.28 (t, J=8.0 Hz, 1H), 7.23 (t, J=8.0 Hz, 1H), 2.09 (s, 3H). LCMS (EI) C$_{25}$H$_{18}$Cl$_2$FN$_5$O$_2$: 510 (M+H).

N-(4-{2-[(4-{[2-(4-ethylpiperazin-1-yl)-2-oxoethyl]oxy}phenyl)amino]pyrimidin-4-yl}phenyl)acetamide (Cmpd 64): $^1$H-NMR (400 MHz, d$_6$-DMSO): 10.222 ppm (s, 1H), 9.445 ppm (s, 1H), 8.457 ppm (d, 1H), 8.119 ppm (d, 2H), 7.75 ppm (d, 2H), 7.686 ppm (d, 2H), 7.299 ppm (d, 1H), 6.922 ppm (d, 2H), 4.76 ppm (s, 2H), 3.465 ppm (bs, 4H), 2.4 ppm (m, 4H), 2.31 ppm (m, 2H), 2.091 ppm (s, 3H), 1.02 ppm (t, 3H); MS (EI) C$_{26}$H$_{30}$N$_6$O$_3$: 475.4 (MH$^+$).

1-ethyl-3-(4-{2-[(4-morpholin-4-ylphenyl)amino]pyrimidin-4-yl}phenyl)urea (cmpd 250.HCl) (Cmpd 250): $^1$H-NMR (400 MHz, d$_6$-DMSO): 10.064 ppm (s, 1H), 9.305- ppm (s, 1H), 8.483 ppm (d, 1H), 8.105 ppm (d, 2H), 7.832 ppm (bd, 1H), 7.603 ppm (d, 2H), 7.54 ppm (bs, 2H), 7.431 ppm (d, 1H), 6.55 ppm (bs, 1H), 3.89 ppm (bs, 4H), 3.426 ppm (bs, 4H), 3.15 ppm (m, 2H), 1.08 ppm (t, 3H)); MS (EI) C$_{23}$H$_{26}$N$_6$O$_2$HCl: 419.3 (MH$^+$).

N-[6-({4-[4-(acetylamino)phenyl]pyrimidin-2-yl}amino)pyrimidin-4-yl]-2,6-dichlorobenzamide (Cmpd 301): $^1$H NMR (400 MHz, d$_6$-DMSO): 11.55 (s, 1H), 10.5 (s, 1H), 10.2 (s, 1H), 9.32 (s, 1H), 8.68 (d, 1H), 8.6 (s, 1H), 8.4 (d, 2H), 7.74 (d, 2H), 7.64 (d, 1H), 7.62-7.5 (m, 3H), 2.03 (s, 3H); MS (EI) for $C_{23}H_{17}Cl_2N_7O_2$: 494 (MH$^+$).

N-[4-(2-{[4-(morpholin-4-ylmethyl)phenyl]amino}pyrimidin-4-yl)phenyl]acetamide (Cmpd 232): $^1$H NMR (400 MHz, d$_6$-DMSO): 10.3 (s, 1H), 9.6 (s, 1H), 8.46 (d, 1H), 8.13 (d, 2H), 7.78 (t, 4H), 7.35 (d, 1H), 7.47 (d, 1H), 7.23 (d, 2H), 3.58 (t, 4H), 3.4 (s, 2H), 2.33 (t, 4H), 2.1 (s, 3H); MS (EI) for $C_{23}H_{25}N_5O_2$: 404 (MH$^+$).

4-(1H-indol-5-yl)-N-(4-morpholin-4-ylphenyl)pyrimidin-2-amine (Cmpd 254): $^1$H-NMR (400 MHz, d$_6$-DMSO): 11.35 ppm (s, 1H), 9.33 ppm (s, 1H), 8.41 ppm (m, 2H), 7.94 ppm (dd, 1H), 7.71 ppm (d, 2H), 7.50 ppm (d, 1H), 7.44 ppm (t, 1H), 7.33 ppm (d, 1H), 6.94 ppm (d, 2H), 6.57 ppm (s, 1H), 3.75 ppm (m, 4H), 3.05 ppm (m, 4H), 2.09 ppm (s, 3H); MS (EI) $C_{24}H_{25}N_5O_2$: 372.3 (MH$^+$).

N-(3-{2-[(4-morpholin-4-ylphenyl)amino]pyrimidin-4-yl}phenyl)acetamide (Cmpd 79): $^1$H-NMR (400 MHz, d$_6$-DMSO): 10.14 ppm (s, 1H), 9.45 ppm (s, 1H), 8.49 ppm (d, 1H), 8.40 ppm (s, 1H), 7.77 ppm (d, 1H), 7.70 ppm (d, 3H), 7.45 ppm (t, 1H), 7.20 ppm (d, 1H), 6.93 ppm (d, 2H), 3.74 ppm (m, 4H), 3.04 ppm (m, 4H), 2.09 ppm (s, 3H); MS (EI) $C_{24}H_{25}N_5O_2$: 390.1 (MH$^+$).

4-[4-(methyloxy)phenyl]-N-(4-morpholin-4-ylphenyl)pyrimidin-2-amine (Cmpd 252): $^1$H-NMR (400 MHz, d$_6$-DMSO): 9.37 ppm (s, 1H), 8.42 ppm (d, 1H), 8.13 ppm (d, 2H), 7.67 ppm (d, 2H), 7.27 ppm (d, 1H), 7.08 ppm (d, 2H), 6.92 ppm (d, 2H), 3.84 ppm (s, 3H), 3.74 ppm (m, 4H), 3.04 ppm (m, 4H); MS (EI) $C_{24}H_{25}N_5O_2$: 363.1 (MH$^+$).

N-(4-{2-[(3-piperazin-1-ylphenyl)amino]pyrimidin-4-yl}phenyl)acetamide (Cmpd 312): $^1$H-NMR (400 MHz, d$_6$-DMSO): 10.32 ppm (s, 1H), 9.55 ppm (s, 1H), 8.50 ppm (d, 1H), 8.13 ppm (d, 2H), 7.78 ppm (d, 2H), 7.68 ppm (s, 1H), 7.35 ppm (dd, 2H), 7.20 ppm (t, 1H), 6.63 (dd, 1H), 3.38 (m, 4H), 3.25 (m, 4H), 2.13 ppm (s, 3H); MS (EI) $C_{22}H_{24}N_6O$: 389.1 (MH$^+$).

2-amino-N-(4-(2-(4-morpholinophenylamino)pyrimidin-4-yl)phenyl)-2-phenyl-acetamide (Cmpd 573): $^1$H-NMR (400 MHz, d$_6$-DMSO): 11.93 ppm (s, 1H), 10.18 (s, 1H), 9.08 ppm (s, 2H), 8.58 ppm (d, 1H), 8.18 ppm (d, 2H), 7.98-7.88 ppm (m, 2H), 7.82-7.75 ppm (m, 2H), 7.60-7.40 ppm (m, 6H), 7.30 ppm (s, 2H), 5.52-5.46 (m, 1H), 4.10 (t, 4H), 3.57 (t, 4H); MS (EI) $C_{28}H_{28}N_6O_2$: 481.3 (MH$^+$).

N-(4-{2-[(4-morpholin-4-ylphenyl)amino]pyrimidin-4-yl}phenyl)-L-alaninamide (Cmpd 577): $^1$H-NMR (400 MHz, d$_6$-DMSO): 9.387 ppm (s, 1H), 8.443 ppm (d, 1H), 8.127 ppm (d, 2H), 7.825 ppm (d, 2H), 7.676 ppm (d, 2H), 7.287 ppm (d, 1H), 6.939 ppm (d, 2H), 3.747 ppm (m, 4H), 3.457 ppm (q, 1H), 3.050 ppm (m, 4H), 1.896 ppm (s, 3H (AcOH)), 1.243 ppm (d, 3H); MS (EI) $C_{23}H_{26}N_6O_2$: 419.1 (MH$^+$).

N-(4-{2-[(4-morpholin-4-ylphenyl)amino]pyrimidin-4-yl}phenyl)valinamide (Cmpd 575): $^1$H-NMR (400 MHz, d$_6$-DMSO): 9.390 ppm (s, 1H), 8.449 ppm (d, 1H), 8.124 ppm (d, 2H), 7.815 ppm (d, 2H), 7.686 ppm (d, 2H), 7.284 ppm (d, 1H), 6.939 ppm (d, 2H), 3.747 ppm (m, 4H), 3.147 ppm (d, 1H), 3.051 ppm (m, 4H), 1.953 ppm (m, 1H), 1.864 ppm (s, 3H (AcOH)), 0.943 ppm (d, 3H), 0.871 ppm (d, 3H); MS (EI) $C_{25}H_{30}N_6O_2$: 446.2 (MH$^+$).

2-(dimethylamino)-N-(4-(2-(4-morpholinophenylamino)pyrimidin-4-yl)phenyl)-acetamide (Cmpd 197): $^1$H-NMR (400 MHz, d$_6$-DMSO): 10.001 ppm (s, 1H), 9.384 ppm (s, 1H), 8.440 ppm (d, 1H), 8.118 ppm (d, 2H), 7.836 ppm (d, 2H), 7.673 ppm (d, 2H), 7.287 ppm (d, 1H), 6.939 ppm (d, 2H), 3.745 ppm (m, 4H), 3.114 ppm (s, 2H), 3.049 ppm (m, 4H), 2.290 ppm (s, 6H); MS (EI) $C_{24}H_{28}N_6O_2$: 432.5 (MH$^+$).

N-(4-{2-[(4-{4-[3-(dimethylamino)-2,2-dimethylpropyl]piperazin-1-yl}phenyl)-amino]pyrimidin-4-yl}phenyl)acetamide (Cmpd 578): $^1$H-NMR (400 MHz, d$_6$-DMSO): 10.208 ppm (s, 1H), 9.358 ppm (s, 1H), 8.433 ppm (d, 1), 8.106 ppm (d, 2H), 7.741 ppm (d, 2H), 7.648 ppm (d, 2H), 7.262 ppm (d, 1H), 6.909 ppm (d, 2H), 3.050 ppm (m, 4H), 2.595 ppm (m, 4H), 2.212 ppm (s, 6H), 2.172 ppm (s, 2H), 2.091 ppm (m, 5H), 0.843 ppm (s, 6H); MS (EI) $C_{29}H_{39}N_7O$: 502.2 (MH$^+$).

N-(4-{2-[(4-{4-[(1-methyl-1H-imidazol-2-yl)methyl]piperazin-1-yl}phenyl)amino]-pyrimidin-4-yl}phenyl)acetamide (Cmpd 576): $^1$H-NMR (400 MHz, d$_6$-DMSO): 10.23 ppm (s, 1H), 9.37 ppm (s, 1H), 8.43 ppm (d, 1H), 8.106 ppm (d, 2H), 7.74 ppm (d, 2H), 7.65 ppm (d, 2H), 7.26 ppm (d, 1H), 7.10 ppm (s, 1H), 6.92 ppm (d, 2H), 6.78 ppm (s, 1H), 3.67 ppm (s, 3H), 3.58 ppm (s, 2H), 3.39-3.34 ppm (m, 4H), 3.02-3.08 ppm (M, 4H), 2.10 ppm (s, 3H); MS (EI) $C_{27}H_{30}N_8O$ 482.6 (MH$^+$).

N-(4-(2-(4-(4-(cyclopropanecarbonyl)piperazin-1-yl)phenylamino)pyrimidin-4-yl)phenyl)acetamide (Cmpd 349): $^1$H-NMR (400 MHz, d$_6$-DMSO): 10.22 ppm (s, 1H), 9.41 ppm, (s, 1H), 8.44 ppm (d, 1H), 8.11 ppm (d, 2H), 7.74 ppm (d, 2H), 7.69 ppm (d, 2H), 7.28 ppm (d, 1H), 6.97 ppm (d, 2H), 3.83 ppm (s, 2H), 3.62 ppm (s, 2H), 3.15 ppm (s, 2H), 3.03 ppm (s, 2H), 2.09 ppm (s, 3H), 2.02-2.05 ppm (m, 1H), 0.74-0.76 ppm (m, 4H); MS (EI) $C_{26}H_{28}N_6O_2$: 456.5 (MH$^+$).

N-{4-[2-({3-[(4-phenylpiperazin-1-yl)carbonyl]phenyl}amino)pyrimidin-4-yl]-phenyl}acetamide (Cmpd 78): $^1$H-NMR (400 MHz, d$_6$-DMSO): 10.21 ppm (s, 1H), 9.83 ppm (s, 1H), 8.53 ppm (d, 1H), 8.13 ppm (d, 2H), 8.05 ppm (s, 1H), 7.95 ppm (s, 1H), 7.87 ppm (d, 1H), 7.75 ppm (d, 2H), 7.38-7.43 ppm (m, 2H), 7.20-7.242 ppm (m, 2H), 7.02 ppm (d, 2H), 6.95 ppm (d, 2H), 6.81 ppm (t, 1H), 3.68-3.88 ppm (m, 2H), 3.44-3.65 ppm (m, 2H), 3.02-3.11 ppm (m, 4H), 2.09 ppm (s, 3H); MS (EI) $C_{29}H_{28}N_6O_2$: 492.6 (MH$^+$).

N-(4-{2-[(4-morpholin-4-ylphenyl)amino]pyrimidin-4-yl})phenyl)-D-alaninamide (Cmpd 578): $^1$H-NMR (400 MHz, d$_6$-DMSO): 11.13 ppm (s, 1H), 9.89 ppm (s, 1H), 8.53 ppm (d, 1H), 8.35 ppm (d, 3H), 8.20 ppm (d, 2H), 7.85 ppm (d, 4H), 7.49 ppm (br s, 2H), 7.43 ppm (d, 1H), 4.14 ppm (m, 1H), 3.96 ppm (br s, 4H), 3.40 ppm (br s, 4H), 1.50 ppm (s, 3H); MS (EI) $C_{23}H_{26}N_6O_2$: 419 (MH$^+$).

(N-(4-{5-methyl-2-[(3-morpholin-4-ylphenyl)amino]pyrimidin-4-yl}phenyl-acetamide): $^1$H-NMR (400 MHz, d$_6$-DMSO): 10.17 (s, 1H), 9.41 (s, 1H), 8.38 (s, 1H), 7.84 (s, 1H), 7.72 (s, 4H), 7.09 (d, 2H), 6.51 (dd, 1H), 3.74 (t, 4H), 3.07 (t, 4H), 2.26 (s, 3H), 2.09 (s, 3H); MS (EI) $C_{23}H_{25}N_5O_2$: 404.3 (M+H)$^+$.

(N-(4-{6-methyl-2-[(4-morpholin-4-ylphenyl)amino]pyrimidin-4-yl}phenyl)-acetamide): $^1$H-NMR (400 MHz, d$_6$-DMSO): 10.18 (s, 1H), 9.31 (s, 1H), 8.09 (d, 2H), 7.74-7.70 (m, 4H), 7.19 (s, 1H), 6.93 (d, 2H), 3.74 (t, 4H), 3.04 (t, 4H), 2.38 (s, 3H), 2.09 (s, 3H); MS (EI) $C_{23}H_{25}N_5O_2$: 404.3 (M+H)$^+$.

(N-(4-{2-[(4-morpholin-4-ylphenyl)amino]-5-(trifluoromethyl)pyrimidin-4-yl}-phenyl)acetamide): $^1$H-NMR (400 MHz, CDCl$_3$): 8.66 (s, 1H), 7.65-7.59 (m, 4H), 7.51 (d, 2H), 7.33 (d, 2H), 6.93 (d, 2H), 3.87 (t, 4H), 3.14 (t, 4H); MS (EI) $C_{26}H_{30}N_6O_3$: 458.1 (M+H)$^+$.

(N-(4-{2-[(3-aminophenyl)amino]-5-methylpyrimidin-4-yl}phenyl)acetamide): $^1$H-NMR (400 MHz, d$_6$-DMSO): 10.14 (s, 1H), 9.19 (s, 1H), 8.33 (d, 1H), 7.72 (d, 2H), 7.67 (dd, 2H), 7.03 (t, 1H), 6.94 (dd, 1H), 6.87 (t, 1H), 6.17-6.14 (m, 1H), 4.92 (s, 2H), 2.23 (s, 3H), 2.08 (s, 3H); MS (EI) $C_{19}H_{19}N_5O$: 334.0 (M+H)$^+$.

(N-(4-{2-[(3-aminophenyl)amino]-5-fluoropyrimidin-4-yl}phenyl)acetamide): $^1$H-NMR (400 MHz, $d_6$-DMSO): 10.26 (s, 1H), 9.41 (s, 1H), 8.54 (d, 1H), 8.04 (d, 2H), 7.78 (d, 2H), 7.03 (s, 1H), 6.95-6.91 (m, 2H), 6.20 (d, 1H), 5.00 (s, 2H), 2.10 (s, 3H); MS (EI) $C_{18}H_{16}FN_5O$: 338.3 $(M+H)^+$.

(N-[4-(2-{[4-(4-ethylpiperazin-1-yl]phenyl]amino)-5-fluoropyrimidin-4-yl)phenyl]acetamide): $^1$H-NMR (400 MHz, $d_6$-DMSO): 10.26 (s, 1H), 9.45 (s, 1H), 8.52 (d, 1H), 8.02 (d, 2H), 7.78 (d, 2H), 7.59 (d, 2H), 6.91 (d, 2H), 3.35 (bs, 4H), 3.07 (bs, 4H), 2.50 (q, 2H), 2.10 (s, 3H), 1.04 (t, 3H); MS (EI) $C_{24}H_{27}FN_6O$: 435.3 $(M+H)^+$.

(N-[3-({4-[4-(acetylamino)phenyl]-5-methylpyrimidin-2-yl}amino)phenyl]-2,6-dimethylbenzamide): $^1$H-NMR (400 MHz, $d_6$-DMSO): 10.32 (s, 1H), 10.15 (s, 1H), 9.51 (s, 1H), 8.37 (s, 1H), 8.29 (s, 1H), 7.76-7.70 (m, 4H), 7.42-7.41 (m, 1H), 7.25-7.17 (m, 3H), 7.11 (d, 2H), 2.29 (s, 6H), 2.26 (s, 3H), 2.09 (s, 3H); MS (EI) $C_{28}H_{27}N_5O_2$: 466.3 $(M+H)^+$.

(N-(4-{2-[(3,5-dimorpholin-4-ylphenyl)amino]-5-fluoropyrimidin-4-yl}phenyl)-acetamide): $^1$H-NMR (400 MHz, $d_6$-DMSO): 10.27 (s, 1H), 9.45 (s, 1H), 8.58 (d, 1H), 8.07 (d, 2H), 7.77 (d, 2H), 7.06 (s, 2H), 6.17 (s, 1H), 3.75 (t, 8H), 3.10 (t, 8H), 2.10 (s, 3H); MS (EI) $C_{26}H_{29}FN_6O_3$: 493.4 $(M+H)^+$.

(N-{4-[2-(1H-indazol-6-ylamino)-5-methylpyrimidin-4-yl]phenyl}acetamide): $^1$H-NMR (400 MHz, $d_6$-DMSO): 12.80 (s, 1H), 10.18 (s, 1H), 9.72 (s, 1H), 8.44 (d, 1H), 8.37 (d, 1H), 7.90 (s, 1H), 7.77-7.70 (m, 4H), 7.59 (d, 1H), 7.28 (dd, 1H), 2.27 (s, 3H), 2.10 (s, 3H); MS (EI) $C_{20}H_{15}N_6O$: 359.3 $(M+H)^+$.

(N-{4-[2-(1H-indol-5-ylamino)-5-methylpyrimidin-4-yl]phenyl}acetamide): $^1$H-NMR (400 MHz, $d_6$-DMSO): 10.90 (s, 1H), 10.15 (s, 1H), 9.21 (s, 1H), 8.32 (s, 1H), 8.00 (d, 1H), 7.72 (dd, 2H), 7.66 (dd, 2H), 7.36 (dd, 1H), 7.28-7.25 (m, 2H), 6.33 (t, 1H), 2.22 (s, 3H), 2.09 (s, 3H); MS (EI) $C_{21}H_{19}N_5O$: 358.3 $(M+H)^+$.

(N-(4-(5-fluoro-2-[(4-morpholin-4-ylphenyl)amino]pyrimidin-4-yl)phenyl)-acetamide): $^1$H-NMR (400 MHz, $d_6$-DMSO): 10.26 (s, 1H), 9.48 (s, 1H), 8.52 (d, 1H), 8.02 (d, 2H), 7.77 (d, 2H), 7.61 (d, 2H), 6.93 (d, 2H), 3.74 (t, 4H), 3.03 (t, 4H), 2.10 (s, 3H); MS (EI) $C_{22}H_{22}FN_5O_2$: 408.3 $(M+H)^+$.

N-(4-{5-methyl-2-[(4-morpholin-4-ylphenyl)amino]pyrimidin-4-yl}phenyl)-cyclopropanecarboxamide: $^1$H-NMR (400 MHz, $d_6$-DMSO): 10.41 (s, 1H), 9.28 (s, 1H), 8.31 (d, 1H), 7.73 (d, 2H), 7.66-7.62 (m, 4H), 6.89 (d, 2H), 3.73 (bs, 4H), 3.02 (bs, 4H), 2.22 (s, 3H), 1.85-1.79 (m, 1H), 0.84-0.81 (m, 4H); MS (EI) $C_{25}H_{27}N_5O_2$: 430 (MH+).

N-{4-[2-(1H-indazol-5-ylamino)-5-methylpyrimidin-4-yl]phenyl}acetamide: $^1$H-NMR (400 MHz, $d_6$-DMSO): 12.88 (s, 1H), 10.16 (s, 1H), 9.49 (s, 1H), 8.37 (s, 1H), 8.29 (d, 1H), 7.97 (s, 1H), 7.73 (d, 2H), 7.67 (d, 2H), 7.59 (dd, 1H), 7.44 (d, 1H), 2.24 (s, 3H), 2.10 (s, 3H); MS (EI) $C_{20}H_{18}N_6O$: 359 (MH+).

N-(4-{2-[(3,5-dimorpholin-4-ylphenyl)amino]pyrimidin-4-yl}phenyl)acetamide: $^1$H-NMR (400 MHz, $d_6$-DMSO): 10.21 (s, 1H), 9.36 (s, 1H), 8.48 (d, 1H), 8.15 (d, 2H), 7.74 (d, 2H), 7.32 (d, 1H), 7.12 (d, 2H), 6.17 (s, 1H), 3.75 (t, 4H), 3.11 (t, 4H), 2.09 (s, 3H); MS (EI) $C_{26}H_{30}N_6O_3$: 475 (MH+).

4-{2-[(4-morpholin-4-ylphenyl)amino]pyrimidin-4-yl}benzonitrile: $^1$H-NMR (400 MHz, $d_6$-DMSO): 9.60 (s, 1H), 8.57 (d, 1H), 8.32 (d, 2H), 8.03 (d, 2H), 7.65 (d, 2H), 7.44 (d, 1H), 6.94 (d, 2H), 3.75 (t, 4H), 3.05 (t, 4H); MS (EI) $C_{21}H_{19}N_5O$: 358 (MH+).

4-(4-fluorophenyl)-N-(4-morpholin-4-ylphenyl)pyrimidin-2-amine: $^1$H-NMR (400 MHz, $d_6$-DMSO): 9.46 (s, 1H), 8.49 (d, 1H), 8.22 (dd, 2H), 7.66 (d, 2H), 7.38 (d, 1H), 7.33 (d, 1H), 6.93 (dd, 2H), 3.74 (t, 4H), 3.05 (t, 4H); MS (EI) $C_{20}H_{19}FN_4O$: 358.3 $(M+H)^+$.

N-(4-morpholin-4-ylphenyl)-4-(4-pyrimidin-5-ylphenyl)pyrimidin-2-amine: $^1$H-NMR (400 MHz, $d_6$-DMSO): 9.50 (s, 1H), 9.26 (s, 2H), 9.24 (s, 1H), 8.53 (d, 1H), 8.32 (d, 2H), 8.02 (d, 2H), 7.69 (d, 2H), 7.44 (s, 1H), 6.94 (d, 2H), 3.75 (t, 4H), 3.06 (t, 4H); MS (EI) $C_{24}H_{22}N_6O$: 411 (MH+).

N-(4-morpholin-4-ylphenyl)-4-[4-(pyridin-2-ylamino)phenyl]pyrimidin-2-amine: $^1$H-NMR (400 MHz, $d_6$-DMSO): 9.42 (s, 1H), 9.33 (s, 1H), 8.40 (d, 1H), 8.23 (dd, 1H), 8.09 (dd, 2H), 7.86 (d, 2H), 7.70 (d, 2H), 7.65-7.61 (m, 1H), 7.25 (d, 1H), 6.96-6.90 (m, 3H), 6.84-6.81 (m, 1H). 3.75 (t, 4H), 3.05 (t, 4H); MS (EI) $C_{25}H_{24}N_6O$: 425 (MH+).

N-(4-morpholin-4-ylphenyl)-4-[4-(pyridin-3-ylamino)phenyl]pyrimidin-2-amine: $^1$H-NMR (400 MHz, $d_6$-DMSO): 9.33 (s, 1H), 8.81 (s, 1H), 8.45 (d, 1H), 8.40 (d, 1H), 8.14 (dd, 1H), 8.08 (d, 2H), 7.68 (d, 2H), 7.63-7.60 (m, 1H), 7.32 (dd, 1H), 7.23 (d, 1H), 7.19 (dd, 2H), 6.93 (d, 2H), 3.74 (t, 4H), 3.05 (t, 4H); MS (EI) $C_{25}H_{24}N_6O$: 425 (MH+).

N-[4-(2-{[4-(4-D-alanylpiperazin-1-yl)phenyl]amino}pyrimidin-4-yl)phenyl]-D-prolinamide: $^1$H-NMR (400 MHz, $d_6$-DMSO): 10.23 (s, 1H), 9.42 (s, 1H), 8.45 (d, 1H), 8.31 (s, 1H), 8.13 (d, 2H), 7.84 (d, 2H), 7.69 (d, 2H), 7.30 (d, 1H), 6.97 (d, 2H), 4.09-4.04 (m, 1H), 3.77-3.73 (m, 1H), 3.67-3.61 (m, 4H), 3.09-3.03 (m, 4H), 2.92 (t, 2H), 2.10-2.03 (m, 1H), 1.85-1.77 (m, 1H), 1.71-1.64 (m, 2H), 1.19 (d, 3H); MS (EI) $C_{28}H_{34}N_8O_2$: 515 (MH+).

N-[4-(2-{[4-(4-L-alanylpiperazin-1-yl)phenyl]amino}pyrimidin-4-yl)phenyl]-D-prolinamide: $^1$H-NMR (400 MHz, $d_6$-DMSO): 10.23 (s, 1H), 9.42 (s, 1H), 8.45 (d, 1H), 8.34 (s, 1H), 8.13 (d, 2H), 7.84 (d, 2H), 7.69 (d, 2H), 7.30 (d, 1H), 6.97 (d, 2H), 4.06-4.01 (m, 1H), 3.77-3.73 (m, 1H), 3.67-3.61 (m, 4H), 3.09-3.02 (m, 4H), 2.92 (t, 2H), 2.10-2.03 (m, 1H), 1.85-1.77 (m, 1H), 1.71-1.64 (m, 2H), 1.18 (d, 3H); MS (EI) $C_{28}H_{34}N_8O_2$: 515 (MH+).

N-{4-[2-({4-[4-(piperazin-1-ylacetyl)piperazin-1-yl]phenyl}amino)pyrimidin-4-yl]phenyl}-D-prolinamide: $^1$H-NMR (400 MHz, $d_6$-DMSO): 10.22 (s, 1H), 9.41 (s, 1H), 8.45 (d, 1H), 8.28 (s, 1H), 8.13 (d, 2H), 7.84 (d, 2H), 7.68 (d, 2H), 7.30 (d, 1H), 6.96 (d, 2H), 3.76-3.73 (m, 1H), 3.69-3.59 (m, 4H), 3.19 (s, 2H), 3.10-3.02 (m, 4H), 2.91 (t, 2H), 2.81 (bs, 4H), 2.44 (bs, 4H), 2.10-2.04 (m, 1H), 1.85-1.77 (m, 1H), 1.71-1.64 (m, 2H); MS (EI) $C_{31}H_{39}N_9O_2$: 570 (MH+).

N-{4-[2-({4-[4-(2-methylpropanoyl)piperazin-1-yl]phenyl}amino)pyrimidin-4-yl]phenyl}-D-alaninamide: $^1$H-NMR (400 MHz, $d_6$-DMSO): 9.43 (s, 1H), 8.47 (d, 1H), 8.17 (d, 2H), 7.80 (d, 2H), 7.69 (d, 2H), 7.31 (d, 1H), 6.98 (d, 2H), 3.82-3.78 (m, 4H), 3.66-3.62 (m, 4H), 3.09-3.03 (m, 4H), 2.97-2.90 (m, 1H), 1.39 (d, 3H), 1.03 (d, 6H); MS (EI) $C_{27}H_{33}N_7O_2$: 488 (MH+).

N-[4-(2-{[4-(4-D-alanylpiperazin-1-yl)phenyl]amino}pyrimidin-4-yl)phenyl]-D-alaninamide: $^1$H-NMR (400 MHz, $d_6$-DMSO): 9.42 (s, 1H), 8.45 (d, 1H), 8.33 (s, 1H), 8.13 (d, 2H), 7.82 (d, 2H), 7.69 (d, 2H), 7.30 (d, 1H), 6.98 (d, 2H), 4.13-4.07 (m, 1H), 3.70-3.59 (m, 5H), 3.11-3.01 (m, 4H), 1.27 (d, 3H), 1.21 (d, 3H); MS (EI) $C_{26}H_{32}N_8O_2$: 489 (MH+).

N-{4-[2-({4-[4-(tetrahydrofuran-3-ylcarbonyl)piperazin-1-yl]phenyl}amino)-pyrimidin-4-yl]phenyl}-D-prolinamide: $^1$H-NMR (400 MHz, $d_6$-DMSO): 10.19 (s, 1H), 9.42 (s, 1H), 8.44 (d, 1H), 8.13 (d, 2H), 7.84 (d, 2H), 7.68 (d, 2H), 7.30 (d, 1H), 6.96 (d, 2H), 3.89 (t, 1H), 3.74-3.69 (m, 4H), 3.67-3.63 (m, 4H), 3.45-3.37 (m, 1H), 3.09-3.02 (m, 4H), 2.90 (t, 2H), 2.08-1.99 (m, 3H), 1.84-1.76 (m, 1H), 1.70-1.64 (m, 2H); MS (EI) $C_{30}H_{35}N_7O_3$: 542 (MH+).

N-{4-[2-({4-[4-(tetrahydrofuran-2-ylcarbonyl)piperazin-1-yl]phenyl}amino)-pyrimidin-4-yl]phenyl}-D-prolinamide: $^1$H-NMR (400 MHz, $d_6$-DMSO): 10.22 (s, 1H), 9.41 (s, 1H), 8.45 (d, 1H), 8.13 (d, 2H), 7.83 (d, 2H), 7.68 (d, 2H), 7.30 (d, 1H), 6.96 (d, 2H), 4.72 (dd, 1H), 3.82-3.72 (m, 3H), 3.69-3.58 (m, 4H), 3.08-3.02 (m, 4H), 2.91 (t, 2H), 2.11-1.99 (m, 3H), 1.88-1.79 (m, 3H), 1.71-1.66 (m, 2H); MS (EI) $C_{30}H_{35}N_7O_3$: 542 (MH+).

N-(4-{5-chloro-2-[(4-morpholin-4-ylphenyl)amino]pyrimidin-4-yl}phenyl)-D-prolinamide: $^1$H-NMR (400 MHz, $d_6$-DMSO): 10.30 (s, 1H), 9.67 (s, 1H), 8.52 (s, 1H), 7.82 (s, 4H), 7.59 (d, 2H), 6.90 (dd, 2H), 3.84 (dd, 1H), 3.74-3.72 (m, 4H), 3.04-3.02 (m, 4H), 2.97 (t, 2H), 2.15-2.09 (m, 1H), 1.86-1.79 (m, 1H), 1.75-1.69 (m, 2H); MS (EI) $C_{25}H_{27}ClN_6O_2$: 479 (MH+).

(R)—N-(4-(2-(4-(4-(2-(pyrrolidin-1-yl)acetyl)piperazin-1-yl)phenylamino)pyrimidin-4-yl)phenyl)pyrrolidine-2-carboxamide: $^1$H-NMR (400 MHz, $d_6$-DMSO): 10.21 (s, 1H), 9.41 (s, 1H), 8.44 (d, 1H), 8.12 (d, 2H), 7.84 (d, 2H), 7.68 (d, 2H), 7.30 (d, 1H), 6.95 (d, 2H), 3.75-3.71 (m, 1H), 3.69-3.59 (m, 4H), 3.07-3.01 (m, 4H), 2.91 (t, 2H), 2.50 (t, 4H), 2.48 (s, 2H), 2.11-2.02 (m, 1H), 1.86-1.78 (m, 1H), 1.72-1.63 (m, 6H); MS (EI) $C_{31}H_{38}N_8O_2$: 555 (MH+).

(R)—N-(4-(2-(4-(4-(2-morpholinoacetyl)piperazin-1-yl)phenylamino)pyrimidin-4-yl)phenyl)pyrrolidine-2-carboxamide: $^1$H-NMR (400 MHz, $d_6$-DMSO): 10.19 (s, 1H), 9.41 (s, 1H), 8.45 (d, 1H), 8.13 (d, 2H), 7.84 (dd, 2H), 7.68 (d, 2H), 7.30 (d, 1H), 6.96 (d, 2H), 3.74-3.69 (m, 3H), 3.61-3.57 (m, 6H), 3.19 (s, 2H), 3.11-3.09 (m, 2H), 33.04-3.01 (m, 2H), 2.90 (t, 2H), 2.41 (bs, 4H), 2.11-2.02 (m, 1H), 1.84-1.76 (m, 1H), 1.70-1.63 (m, 2H); MS (EI) $C_{31}H_{38}N_8O_3$: 571 (MH+).

N-{4-[2-({4-[2-(methyloxy)ethyl]-3,4-dihydro-2H-1,4-benzoxazin-7-yl}amino)-pyrimidin-4-yl]phenyl}-D-prolinamide: $^1$H-NMR (400 MHz, $d_6$-DMSO): 10.19 (s, 1H), 9.25 (s, 1H), 8.42 (d, 1H), 8.11 (d, 2H), 7.83 (d, 2H), 7.28-7.25 (m, 2H), 7.17 (dd, 1H), 6.68 (d, 1H), 4.15 (t, 2H), 3.72 (dd, 1H), 3.52 (t, 2H)), 3.41-3.36 (m, 4H), 3.27 (s, 3H), 2.90 (t, 2H), 2.10-2.01 (m, 1H), 1.84-1.75 (m, 1H), 1.70-1.63 (m, 2H); MS (EI) $C_{26}H_{30}N_6O_3$: 475 (MH+).

N-(4-{2-[(4-{4-[(2R)-tetrahydrofuran-2-ylcarbonyl]piperazin-1-yl}phenyl)amino]pyrimidin-4-yl}phenyl)-D-prolinamide: $^1$H-NMR (400 MHz, $d_6$-DMSO): 10.20 (s, 1H), 9.41 (s, 1H), 8.45 (d, 1H), 8.13 (d, 2H), 7.84 (d, 2H), 7.68 (d, 2H), 7.30 (d, 1H), 6.96 (d, 2H), 4.72 (dd, 1H), 3.82-3.72 (m, 3H), 3.69-3.58 (m, 4H), 3.08-3.03 (m, 4H), 2.90 (t, 2H), 2.11-1.98 (m, 3H), 1.88-1.75 (m, 3H), 1.70-1.65 (m, 2H); MS (EI) $C_{30}H_{35}N_7O_3$: 542 (MH+).

N-(4-{2-[(4-{4-[(2S)-tetrahydrofuran-2-ylcarbonyl]piperazin-1-yl}phenyl)-amino]pyrimidin-4-yl}phenyl)-D-prolinamide: $^1$H-NMR (400 MHz, $d_6$-DMSO): 10.20 (s, 1H), 9.41 (s, 1H), 8.45 (d, 1H), 8.13 (d, 2H), 7.84 (d, 2H), 7.68 (d, 2H), 7.30 (d, 1H), 6.96 (d, 2H), 4.72 (dd, 1H), 3.82-3.72 (m, 3H), 3.69-3.58 (m, 4H), 3.08-3.03 (m, 4H), 2.91 (t, 2H), 2.09-1.98 (m, 3H), 1.88-1.75 (m, 3H), 1.70-1.63 (m, 2H); MS (EI) $C_{30}H_{35}N_7O_3$: 542 (MH+).

N-{4-[2-(1,2,3,4-tetrahydroquinolin-6-ylamino)pyrimidin-4-yl]phenyl}-D-prolinamide: $^1$H-NMR (400 MHz, $d_6$-DMSO): 10.17 (s, 1H), 9.05 (s, 1H), 8.38 (d, 1H), 8.10 (dd, 2H), 7.84-7.81 (m, 2H), 7.29 (s, 1H), 7.21-7.18 (m, 2H), 6.40 (d, 1H), 5.36 (s, 1H), 3.72 (dd, 1H), 3.15 (t, 2H), 2.90 (t, 2H), 2.67 (t, 2H), 2.10-2.01 (m, 1H), 1.84-1.76 (m, 3H), 1.69-1.63 (m, 2H); MS (EI) $C_{24}H_{26}N_6O$: 415 (MH+).

N-{4-[2-({4-[(phenylmethyl)oxy]phenyl})amino)pyrimidin-4-yl]phenyl}acetamide: $^1$H-NMR (400 MHz, d6-DMSO): 10.20 (s, 1H), 9.42 (s, 1H), 8.42 (d, 1H), 8.06 (d, 2H), 7.75-7.65 (m, 4H), 7.42-7.24 (m, 6H), 6.95 (d, 2H), 5.08 (s, 2H), 2.04 (s, 3H). MS (EI) for $C_{23}H_{22}N_4O_2$: 411 (MH+).

4-(4-aminophenyl)-N-[4-(phenyloxy)phenyl]pyrimidin-2-amine: $^1$H-NMR (400 MHz, d6-DMSO): 10.42 (s, 1H), 8.43 (d, 1H), 8.08 (d, 2H), 7.72 (d, 2H), 7.43-7.37 (m, 3H), 7.26-7.15 (m, 3H), 7.07-6.95 (m, 3H). MS (EI) for $C_{22}H_{18}N_4O$: 355 (MH+).

N-[4-(2-{[4-(phenyloxy)phenyl]amino}pyrimidin-4-yl)phenyl]acetamide: $^1$H-NMR (400 MHz, d6-DMSO): 10.20 (s, 1H), 9.64 (s, 1H), 8.49 (d, 1H), 8.11 (d, 2H), 7.85 (d, 2H), 7.75 (d, 2H), 7.38-7.32 (m, 3H), 7.10-7.03 (m, 3H), 6.97 (d, 1H). MS (EI) for $C_{24}H_{20}N_4O_2$: 397 (MH+).

N-(4-{2-[(4-{[2-(methyloxy)ethyl]amino}phenyl)amino]pyrimidin-4-yl}-phenyl)acetamide: $^1$H-NMR (400 MHz, d6-DMSO): 10.18 (s, 1H), 9.08 (s, 1H), 8.38 (d, 1H), 8.05 (d, 2H), 7.73 (d, 2H), 7.43 (d, 2H), 7.19 (d, 1H), 6.58 (d, 2H), 5.20 (t, 1H), 3.43 (t, 2H), 3.25 (s, 3H), 3.16 (t, 2H), 2.04 (s, 3H). MS (EI) for $C_{21}H_{23}N_5O_2$: 378 (MH+).

N-{4-[2-({4-[(pyridin-4-ylmethyl)oxy]phenyl}amino)pyrimidin-4-yl]phenyl}acetamide: $^1$H-NMR (400 MHz, d6-DMSO): 10.20 (s, 1H), 9.43 (s, 1H), 8.60 (s, 2H), 8.43 (d, 1H), 8.10 (d, 2H), 7.79-7.72 (m, 4H), 7.43 (d, 1H), 7.30 (d, 1H), 7.01 (d, 2H), 5.08 (s, 2H), 2.03 (s, 3H). MS (EI) for $C_{24}H_{21}N_5O_2$: 412 (MH+).

N-(4-{2-[(4-cyclohexylphenyl)amino]pyrimidin-4-yl}phenyl)acetamide: $^1$H-NMR (400 MHz, d6-DMSO): 10.21 (s, 1H), 9.53 (s, 1H), 8.45 (d, 1H), 8.15 (d, 2H), 7.78-7.70 (m, 4H), 7.35 (d, 1H), 7.18 (d, 1H), 2.43-2.40 (m, 1H), 2.08 (s, 3H), 1.82-1.68 (m, 4H), 1.42-1.20 (m, 6H). MS (EI) for $C_{24}H_{26}N_4O$: 387 (MH+).

N-{4-[2-({4-[(tetrahydrofuran-2-ylmethyl)amino]phenyl}amino)pyrimidin-4-yl]phenyl}acetamide: $^1$H-NMR (400 MHz, d6-DMSO): 10.20 (s, 1H), 9.18 (s, 1H), 8.39 (d, 1H), 8.08 (d, 2H), 7.76 (d, 2H), 7.45 (d, 2H), 7.20 (d, 1H), 6.60 (d, 2H), 5.23 (t, 1H), 4.02-3.97 (m, 1H), 3.80-3.77 (m, 1H), 3.65-3.60 (m, 1H), 3.08-3.00 (m, 2H), 2.07 (s, 3H), 2.00-1.80 (m, 3H), 1.62-1.57 (m, 1H). MS (EI) for $C_{23}H_{25}N_5O_2$: 404 (MH+).

N-{4-[2-({4-[(phenylmethyl)amino]phenyl}amino)pyrimidin-4-yl]phenyl}acetamide: $^1$H-NMR (400 MHz, d6-DMSO): 10.20 (s, 1H), 9.17 (s, 1H), 8.05 (d, 2H), 7.72 (d, 2H), 7.44-7.27 (m, 5H), 7.22-7.17 (m, 2H), 6.57 (d, 2H), 6.00 (t, 1H), 4.25 (d, 2H), 2.08 (s, 3H). MS (EI) for $C_{25}H_{23}N_5O$: 410 (MH+).

ethyl[4-({4-[4-(acetylamino)phenyl]pyrimidin-2-yl}amino)phenyl]acetate: $^1$H-NMR (400 MHz, d6-DMSO): 10.21 (s, 1H), 9.53 (s, 1H), 8.45 (d, 1H), 8.15 (d, 2H), 7.78-7.70 (m, 4H), 7.32 (d, 2H), 7.17 (d, 2H), 4.05 (q, 2H), 3.45 (s, 2H), 1.35 (t, 3H). MS (EI) for $C_{22}H_{22}N_4O_3$: 391 (MH+).

N-(4-{2-[(3-chloro-4-morpholin-4-ylphenyl)amino]pyrimidin-4-yl}phenyl)-acetamide: $^1$H-NMR (400 MHz, d6-DMSO): 10.25 (s, 1H), 9.73 (s, 1H), 8.55 (d, 1H), 8.12 (d, 2H), 8.05 (s, 1H), 7.80-7.70 (m, 3H), 7.37 (d, 2H), 7.20 (d, 2H), 3.75 (t, 4H), 2.95 (t, 4H), 2.05 (s, 3H). MS (EI) for $C_{22}H_{22}ClN_5O_2$: 425 (MH+).

N-[4-(2-{[3-(methyloxy)-4-morpholin-4-ylphenyl]amino}pyrimidin-4-yl)phenyl]-L-serinamide: $^1$H NMR (400 MHz, d6-DMSO): 9.50 (s, 1H), 8.45 (d, 1H), 8.18 (d, 2H), 7.83 (d, 2H), 7.70 (s, 1H), 7.37-7.30 (m, 2H), 6.90 (d, 1H), 3.82 (s, 3H), 3.72 (t, 4H), 3.60-3.57 (m, 2H), 3.43 (t, 1H), 2.92 (t, 4H). MS (EI): 465 (MH+).

N-(4-{2-[(4-morpholin-4-ylphenyl)amino]pyrimidin-4-yl}phenyl)-2-(1H-tetrazol-1-yl)acetamide: $^1$H NMR (400 MHz, d6-DMSO): 10.90 (s, 1H), 9.47 (s, 1H), 9.41 (s, 1H), 8.44 (d, 1H), 8.18 (d, 2H), 7.77 (d, 2H), 7.67 (d, 2H), 7.30 (d, 1H), 6.95 (d, 2H), 5.58 (s, 2H), 3.77 (t, 4H), 3.03 (t, 4H). MS (EI): 458 (MH+).

(3S)-3-hydroxy-N-[4-(2-{[3-(methyloxy)-4-morpholin-4-yl]amino}pyrimidin-4-yl)phenyl]butanamide: $^1$H NMR (400 MHz, d6-DMSO): 10.19 (s, 1H), 9.48 (s, 1H), 8.48 (s, 1H), 8.17 (d, 2H), 7.78 (d, 2H), 7.65 (s, 1H), 7.31 (d, 2H), 6.88 (d, 1H), 4.80 (s, 1H), 4.15-4.07 (m, 1H), 3.81 (s, 3H), 3.75 (t, 4H), 2.96 (t, 4H), 2.44-2.37 (m, 2H), 1.14 (d, 3H). MS (EI): 464 (MH+).

(3R)-3-hydroxy-N-[4-(2-{[3-(methyloxy)-4-morpholin-4-ylphenyl]amino}pyrimidin-4-yl)phenyl]butanamide: $^1$H-NMR (400 MHz, d6-DMSO): 10.19 (s, 1H), 9.48 (s, 1H), 8.48 (s, 1H), 8.17 (d, 2H), 7.78 (d, 2H), 7.65 (s, 1H), 7.31 (d, 2H), 6.88 (d, 1H), 4.80 (s, 1H), 4.15-4.07 (m, 1H), 3.83 (s, 3H), 3.75 (t, 4H), 2.96 (t, 4H), 2.44-2.37 (m, 2H), 1.14 (d, 3H). MS (EI): 464 (MH+).

N-(4-{2-[(4-morpholin-4-ylphenyl)amino]pyrimidin-4-yl}phenyl)-2,5-dihydro-1H-pyrrole-2-carboxamide: $^1$H-NMR (400 MHz, d6-DMSO): 10.19 (s, 1H), 9.40 (s, 1H), 8.43 (s, 1H), 8.17 (d, 2H), 7.83 (d, 2H), 7.68 (d, 2H), 7.30 (s, 1H), 6.96 (d, 2H), 6.02-5.98 (m, 1H), 5.93-5.89 (m, 1H), 4.60 (s, 1H), 3.82 (s, 2H), 3.75 (t, 4H), 3.05 (t, 4H). MS (EI): 443 (MH+).

N-(4-{2-[(4-morpholin-4-ylphenyl)amino]pyrimidin-4-yl}phenyl)-2-[(2S)-pyrrolidin-2-yl]acetamide: $^1$H-NMR (400 MHz, d6-DMSO): 10.86 (s, 1H), 10.10 (s, 1H), 9.37 (s, br, 1H), 9.28 (s, br, 1H), 8.55 (d, 1H), 8.20 (d, 2H), 7.95-7.85 (m, 4H), 7.70 (s, 2H), 7.45 (d, 1H), 4.10 (t, 4H), 3.83-3.78 (m, 2H), 3.73 (t, 4H), 3.25-3.18 (m, 1H), 3.03-2.95 (m, 2H), 2.20-2.10 (m, 1H), 2.00-1.80 (m, 2H), 1.68-1.56 (m, 1H). MS (EI): 459 (MH+).

2,3-dihydroxy-N-(4-{2-[(4-morpholin-4-ylphenyl)amino]pyrimidin-4-yl}phenyl)propanamide: $^1$H-NMR (400 MHz, d6-DMSO): 9.95 (s, 1H), 9.40 (s, 1H), 8.43 (d, 1H), 8.12 (d, 2H), 7.90 (d, 2H), 7.68 (d, 2H), 7.25 (s, 1H), 6.96 (d, 2H), 5.95 (s, br, 1H), 4.95 (s, br, 1H), 4.08 (t, 1H), 3.78-3.60 (m, 6H), 3.03 (t, 4H). MS (EI): 436 (MH+).

1-{4-[2-({4-[4-(N,N-dimethylglycyl)piperazin-1-yl]phenyl}amino)pyrimidin-4-yl]phenyl}-3-ethylurea: $^1$H-NMR (400 MHz, d6-DMSO): 9.37 (s, 1H), 9.19 (s, 1H), 9.40 (d, 1H), 8.03 (d, 2H), 7.70 (d, 2H), 7.58 (d, 2H), 7.23 (d, 2H), 6.95 (d, 2H), 6.75 (t, 1H), 3.58 (t, 4H), 3.60 (t, 3H), 3.15-3.00 (m, 8H), 2.18 (s, 6H), 1.05 (t, 3H). MS (EI): 503 (MH+).

N-{4-[2-({4-[4-(N,N-dimethylglycyl)piperazin-1-yl]phenyl}amino) pyrimidin-4-yl]phenyl]-3-(methyloxy)propanamide: $^1$H-NMR (400 MHz, d6-DMSO): 10.22 (s, 1H), 9.40 (s, 1H), 8.43 (d, 1H), 8.10 (d, 2H), 7.78 (d, 2H), 7.67 (d, 2H), 7.27 (d, 1H), 6.95 (d, 2H), 3.73-3.58 (m, 6H), 3.24 (s, 3H), 3.14-3.00 (m, 6H), 2.60 (t, 3H), 2.20 (s, 6H). MS (EI): 518 (MH+).

N-{4-[2-({4-[4-(N,N-dimethylglycyl)piperazin-1-yl]phenyl}amino) pyrimidin-4-yl]phenyl}cyclopropanecarboxamide: $^1$H-NMR (400 MHz, d6-DMSO): 10.26 (s, 1H), 9.40 (s, 1H), 8.43 (d, 1H), 8.14 (d, 2H), 7.78 (d, 2H), 7.67 (d, 2H), 7.27 (d, 1H), 6.95 (d, 2H), 3.70-3.58 (m, 4H), 3.10-3.00 (m, 6H), 2.20 (s, 6H), 1.84-1.80 (m, 1H), 0.83-0.80 (m, 4H). MS (EI): 500 (MH+).

N-{4-[2-({4-[4-(N,N-dimethylglycyl)piperazin-1-yl]phenylamino)pyrimidin-4-yl]-phenyl}butanamide: $^1$H-NMR (400 MHz, d6-DMSO): 10.18 (s, 1H), 9.40 (s, 1H), 8.12-8.05 (m, 3H), 7.80-7.68 (m, 3H), 7.28 (d, 1H), 6.99 (d, 2H), 2H), 3.70-3.60 (m, 4H), 3.28 (s, 2H), 3.14-3.00 (m, 4H), 2.35-2.20 (m, 8H), 1.64-1.58 (m, 2H), 0.95-0.88 (m, 3H). MS (EI): 502 (MH+).

N-{4-[2-({4-[4-(N,N-dimethylglycyl)piperazin-1-yl]phenyl}amino)pyrimidin-4-yl]phenyl}-$N^2$,$N^2$-dimethylglycinamide: $^1$H-NMR (400 MHz, d6-DMSO): 10.00 (s, 1H), 9.40 (s, 1H), 8.43 (d, 1H), 8.10 (d, 2H), 7.82 (d, 2H), 7.65 (d, 2H), 7.25 (d, 1H), 6.95 (d, 2H), 3.65-3.57 (m, 4H), 3.23 (s, 2H), 3.12-3.00 (m, 6H), 2.28 (s, 6H), 2.20 (s, 6H). MS (EI): 517 (MH+).

N-{4-[2-({4-[4-(N,N-dimethylglycyl)piperazin-1-yl]phenyl}amino)pyrimidin-4-yl]phenyl}-D-alaninamide: $^1$H-NMR (400 MHz, d6-DMSO): 9.40 (s, 1H), 8.43 (d, 1H), 8.15 (d, 2H), 7.85 (d, 2H), 7.70 (d, 2H), 7.30 (d, 1H), 6.95 (d, 2H), 3.70-3.57 (m, 4H), 3.50 (q, 1H), 3.18-3.00 (m, 6H), 1.83 (s, 6H), 1.21 (d, 3H). MS (EI): 503 (MH+).

N-{4-[2-({4-[4-(N,N-dimethylglycyl)piperazin-1-yl]phenyl}amino) pyrimidin-4-yl]phenyl}tetrahydrofuran-3-carboxamide: $^1$H-NMR (400 MHz, d6-DMSO): 10.30 (s, 1H), 9.40 (s, 1H), 8.43 (d, 1H), 8.15 (d, 2H), 7.78 (d, 2H), 7.68 (d, 2H), 7.25 (d, 1H), 6.95 (d, 2H), 3.97 (t, 1H), 3.82-3.70 (m, 3H), 3.67-3.60 (m, 4H), 3.22-3.17 (m, 1H), 3.12-3.00 (m, 4H), 2.35 (s, 6H), 2.12-2.05 (m, 2H). MS (EI): 530 (MH+).

(2R)—N-{4-[2-({4-[4-(N,N-dimethylglycyl)piperazin-1-yl]phenyl}amino)pyrimidin-4-yl]phenyl}tetrahydrofuran-2-carboxamide: $^1$H-NMR (400 MHz, d6-DMSO): 9.95 (s, 1H), 9.40 (s, 1H), 8.43 (d, 1H), 8.16 (d, 2H), 7.88 (d, 2H), 7.70 (d, 2H), 7.30 (d, 1H), 6.97 (d, 2H), 4.44-4.41 (m, 1H), 4.02-3.98 (m, 1H), 3.85-3.80 (m, 1H), 3.68-3.57 (m, 4H), 3.18-3.00 (m, 6H), 2.20 (s, 6H), 2.05-1.85 (m, 4H). MS (EI): 530 (MH+).

(2S)—N-{4-[2-({4-[4-(N,N-dimethylglycyl)piperazin-1-yl]phenyl}amino)pyrimidin-4-yl]phenyl}tetrahydrofuran-2-carboxamide: $^1$H-NMR (400 MHz, d6-DMSO): 9.95 (s, 1H), 9.40 (s, 1H), 8.43 (d, 1H), 8.16 (d, 2H), 7.88 (d, 2H), 7.70 (d, 2H), 7.30 (d, 1H), 6.98 (d, 2H), 4.45-4.42 (m, 1H), 4.02-3.98 (m, 1H), 3.85-3.80 (m, 1H), 3.70-3.57 (m, 4H), 3.20 (s, 2H), 3.10-3.00 (m, 6H), 2.22 (s, 6H), 2.05-1.85 (m, 4H). MS (EI): 530 (MH+).

N-(4-{2-[(6-morpholin-4-ylpyridin-3-yl)amino]pyrimidin-4-yl}phenyl)-D-prolinamide: $^1$H NMR (400 MHz, d6-DMSO): 11.38 (s, 1H), 10.10 (s, 2H), 9.03 (s, br, 1H), 8.75 (s, br, 1H), 8.60 (d, 2H), 8.30-8.20 (m, 3H), 7.85 (d, 2H), 7.55 (d, 2H), 4.48-4.42 (m, 1H), 3.82-3.70 (m, 8H), 3.37-3.20 (m, 2H), 2.43-2.40 (m, 1H), 2.10-1.95 (m, 3H). MS (EI): 446 (MH+).

1-hydroxy-N-(4-{2-[(4-morpholin-4-ylphenyl)amino]pyrimidin-4-yl}phenyl)-cyclopentanecarboxamide: $^1$H-NMR (400 MHz, d6-DMSO): 9.95 (s, 1H), 9.45 (s, 1H), 8.42 (d, 1H), 8.10 (d, 2H), 7.95 (d, 2H), 7.70 (d, 2H), 7.30 (d, 1H), 7.05-6.95 (m, 2H), 5.68 (s, br, 1H), 3.80-3.70 (m, 4H), 3.15-3.05 (m, 4H), 2.10-1.97 (m, 3H), 1.87-1.68 (m, 5H). MS (EI): 460 (MH+).

2-hydroxy-N-(4-{2-[(4-morpholin-4-ylphenyl)amino]pyrimidin-4-yl}phenyl)-acetamide: $^1$H NMR (400 MHz, d6-DMSO): 9.95 (s, 1H), 9.39 (s, 1H), 8.43 (d, 1H), 8.12 (d, 2H), 7.90 (d, 2H), 7.70 (d, 2H), 7.28 (d, 1H), 6.95 (d, 2H), 5.75 (t, 1H), 4.03 (d, 2H), 3.78-3.70 (m, 4H), 3.10-3.00 (m, 4H). MS (EI): 406 (MH+).

3-chloro-N-(4-{2-[(4-morpholin-4-ylphenyl)amino]pyrimidin-4-yl}phenyl)pyridine-4-carboxamide: $^1$H NMR (400 MHz, d6-DMSO): 11.68 (s, 1H), 11.00 (s, 1H), 9.43 (s, 2H), 8.83 (s, 1H), 8.70 (d, 1H), 8.50 (d, 1H), 8.20 (d, 2H), 7.87 (d, 2H), 7.75-7.65 (m, 3H), 7.32 (d, 1H), 6.95 (d, 2H), 3.75 (t, 4H), 3.05 (t, 4H). MS (EI): 487 (MH+).

N-{4-[2-({4-[4-(N,N-dimethylglycyl)piperazin-1-yl]phenyl}amino)pyrimidin-4-yl]phenyl}-D-prolinamide: $^1$H NMR (400 MHz, d6-DMSO): 10.24 (s, br, 1H), 9.41 (s, 1H), 8.44 (d, 2H), 8.13 (d, 2H), 7.82 (d, 2H), 7.68 (d, 2H), 7.27 (d, 1H), 6.95 (d, 2H), 3.78-3.57 (m, 5H), 3.15-3.00 (m, 6H), 2.93 (t, 2H), 2.18 (s, 6H), 2.08-2.00 (m, 1H), 1.93-1.88 (m, 1H), 1.90-1.80 (m, 2H). MS (EI): 529 (MH+).

N-(4-{2-[(4-morpholin-4-ylphenyl)amino]pyrimidin-4-yl}phenyl)propanamide: $^1$H-NMR (400 MHz, d6-DMSO): 10.18 (s, br, 1H), 9.18 (s, 1H), 8.40 (d, 1H), 8.13 (d, 2H), 7.78 (d, 2H), 7.63 (d, 2H), 7.25 (d, 1H), 6.93 (d, 2H), 3.77 (t, 4H), 3.07 (t, 4H), 2.16 (q, 2H), 1.10 (t, 3H). MS (EI): 404 (MH+).

N-(4-{2-[(4-morpholin-4-ylphenyl)amino]pyrimidin-4-yl}phenyl)-2-pyridin-3-ylacetamide: $^1$H NMR (400 MHz, d6-DMSO): 10.90 (s, 1H), 9.40 (s, 1H), 8.43 (s, 1H), 8.18 (d, 2H), 7.88 (d, 2H), 7.73-7.45 (m, 5H), 7.32 (d, 1H), 6.95 (d, 2H), 3.77 (t, 4H), 3.03 (t, 4H). MS (EI): 467 (MH+).

N-(4-{2-[(4-morpholin-4-ylphenyl)amino]pyrimidin-4-yl}phenyl)pyrimidine-5-carboxamide: $^1$H NMR (400 MHz, d6-DMSO): 10.82 (s, 1H), 9.42 (s, 1H), 9.38 (s, 1H), 9.31 (s, 2H), 8.45 (d, 1H), 8.20 (d, 2H), 7.97 (d, 2H), 7.70 (d, 2H), 7.33 (d, 1H), 6.95 (d, 2H), 3.77 (t, 4H), 3.03 (t, 4H). MS (EI): 454 (MH+).

N-[4-(2-{[3-(morpholin-4-ylmethyl)phenyl]amino}pyrimidin-4-yl)phenyl]acetamide: $^1$H NMR (400 MHz, d$_6$-DMSO): 10.25 (s, 1H), 9.62 (s, 1H), 8.5 (d, 1H), 8.16 (d, 2H), 7.94 (s, 1H), 7.76 (d, 2H), 7.62 (d, 1H), 7.36 (d, 1H), 7.26 (t, 1H), 6.9 (d, 1H), 3.6 (t, 4H), 3.45 (s, 2H), 2.39 (t, 4H), 2.1 (s, 3H), 1.86 (s, 3H). MS (EI) for $C_{23}H_{25}N_5O_2$: 404 (MH$^+$).

N-[4-(2-{[3-(1,3-dioxan-2-yl)phenyl]amino}pyrimidin-4-yl)phenyl]acetamide: $^1$H-NMR (400 MHz, d$_6$-DMSO): 10.22 (s, 1H), 9.68 (s, 1H), 8.5 (d, 1H), 8.32 (s, 1H), 8.21 (d, 2H), 7.77 (d, 2H), 7.58 (d, 1H), 7.39 (d, 1H), 7.28 (t, 1H), 6.98 (d, 1H), 5.52 (s, 1H), 4.2 (dd, 2H), 4.0 (t, 2H), 2.1 (s, 3H), 2.05 (m, 1H), 1.5 (dd, 1H). MS (EI) for $C_{22}H_{22}N_4O_3$: 391 (MH$^+$).

N-(4-{2-[(6-aminopyridin-2-yl)amino]pyrimidin-4-yl}phenyl)acetamide: $^1$H-NMR (400 MHz, d$_6$-DMSO): 10.22 (s, 1H), 8.93 (s, 1H), 8.55 (d, 1H), 8.14 (d, 2H), 7.75 (d, 2H), 7.57 (d, 1H), 7.45-7.4 (m, 2H), 6.12 (d, 1H), 5.78 (s, 2H), 2.08 (s, 3H). MS (EI) for $C_{17}H_{15}N_6O$: 321 (MH$^+$).

N-(4-{2-[(6-aminopyrimidin-4-yl)amino]pyrimidin-4-yl}phenyl)acetamide: $^1$H-NMR (400 MHz, d$_6$-DMSO): 10.25 (s, 1H), 9.72 (s, 1H), 8.6 (d, 1H), 8.2-8.15 (m, 3H), 7.8 (d, 2H), 7.52 (d, 1H), 7.42 (s, 1H), 6.8 (br, 2H), 2.08 (s, 3H). MS (EI) for $C_{16}H_{15}N_7O$: 322 (MH$^+$).

N-(4-morpholin-4-ylphenyl)-4-quinolin-6-ylpyrimidin-2-amine: $^1$H NMR (400 MHz, d$_6$-DMSO): 9.57 (s, 1H), 9.0 (d, 1H), 8.8 (s, 1H), 8.58 (d, 1H), 8.52 (d, 2H), 8.18 (d, 1H), 7.72 (d, 2H), 7.63 (q, 1H), 7.51 (d, 1H), 6.96 (d, 2H), 3.75 (t, 4H), 3.07 (4H). MS (EI) for $C_{23}H_{21}N_5O$: 384 (MH$^+$).

N-(4-morpholin-4-ylphenyl)-4-quinoxalin-6-ylpyrimidin-2-amine: $^1$H NMR (400 MHz, d$_6$-DMSO): 9.6 (s, 1H), 9.04 (d, 2H), 8.88 (s, 1H), 8.63 (d, 1H), 8.6 (d, 1H), 8.27 (d, 1H), 7.7 (d, 2H), 7.63 (d, 1H), 6.95 (d, 2H), 3.75 (t, 4H), 3.06 (t, 4H). MS (EI) for $C_{22}H_{20}N_6O$: 385 (MH$^+$).

N-[4-(2-{[4-(4-ethylpiperazin-1-yl)phenyl]amino}-5-methylpyrimidin-4-yl)phenyl]-D-alaninamide: $^1$H NMR (400 MHz, d$_6$-DMSO): 9.25 (s, 1H), 8.3 (s, 1H), 7.7 (d, 2H), 7.66 (d, 2H), 7.6 (d, 2H), 6.85 (d, 2H), 3.5 (q, 1H), 3.03 (t, 4H), 2.5 (t, 4H), 2.35 (q, 2H), 2.21 (s, 3H), 1.23 (d, 3H), 1.02 (t, 3H). MS (EI) for $C_{26}H_{33}N_7O$: 460.5 (MH$^+$).

N-[4-(2-{[4-(4-ethylpiperazin-1-yl)phenyl]amino}-5-methylpyrimidin-4-yl)phenyl]-D-prolinamide: $^1$H NMR (400 MHz, d$_6$-DMSO): 10.27 (s, 1H), 9.25 (s, 1H), 8.3 (s, 1H), 7.8 (d, 2H), 7.65 (d, 2H), 7.61 (d, 2H), 6.86 (d, 2H), 3.73 (m, 1H), 3.03 (t, 4H), 2.9 (t, 2H), 2.5 (t, 4H), 2.36 (q, 2H), 2.2 (s, 3H), 2.1-2.0 (m, 1H), 1.85-1.75 (m, 1H), 1.67 (p, 2H), 1.02 (t, 3H). MS (EI) for $C_{28}H_{35}N_7O$: 486 (MH$^+$).

N-ethyl-4-{(4-[(tetrahydrofuran-2-ylcarbonyl)amino]phenyl}pyrimidin-2-yl)amino]phenyl)piperazine-1-carboxamide: $^1$H NMR (400 MHz, d$_6$-DMSO): 9.93 (s, 1H), 9.4 (s, 1H), 8.44 (d, 1H), 8.13 (d, 2H), 7.88 (d, 2H), 7.67 (d, 2H), 7.3 (d, 1H), 6.96 (d, 2H), 6.6 (t, 1H), 4.43 (t, 1H), 4.0 (q, 1H), 3.86 (q, 1H), 3.42 (t, 4H), 3.05 (p, 2H), 3.01 (t, 4H), 2.27-2.17 (m, 1H), 2.06-1.97 (m, 1H), 1.88 (p, 2H), 1.02 (t, 3H). MS (EI) for $C_{28}H_{33}N_7O_3$: 516 (MH$^+$).

N-(4-(2-(4-morpholinophenylamino)pyrimidin-4-yl)phenyl)-1H-imidazole-4-carboxamide: $^1$H NMR (400 MHz, d$_6$-DMSO): 12.76 (br, 1H), 10.12 (s, 1H), 9.39 (s, 1H), 8.43 (d, 1H), 8.13 (d, 2H), 8.01 (d, 2H), 7.87 (s, 2H), 7.7 (d, 2H), 7.3 (d, 1H), 6.93 (d, 2H), 3.74 (t, 4H), 3.05 (t, 4H). MS (EI) for $C_{24}H_{23}N_7O_2$: 442 (MH$^+$).

N-(4-{2-[(4-morpholin-4-ylphenyl)amino]pyrimidin-4-yl}phenyl)-1H-pyrrole-2-carboxamide: $^1$H NMR (400 MHz, d$_6$-DMSO): $^1$H NMR (400 MHz, d$_6$-DMSO): 11.75 (s, 1H), 10.0 (s, 1H), 9.39 (s, 1H), 8.44 (d, 1H), 8.15 (d, 2H), 7.92 (d, 2H), 7.7 (d, 2H), 7.3 (d, 1H), 7.12 (s, 1H), 7.0 (s, 1H), 6.93 (d, 2H), 6.2 (d, 1H), 3.74 (t, 4H), 3.05 (t, 4H). MS (EI) for $C_{25}H_{24}N_6O_2$: 441 (MH$^+$).

N-(4-{2-[(4-morpholin-4-ylphenyl)amino]pyrimidin-4-yl}phenyl)-1H-imidazole-2-carboxamide: $^1$H NMR (400 MHz, d$_6$-DMSO): 13.2 (br, 1H), 10.65 (s, 1H), 9.4 (s, 1H), 8.44 (d, 1H), 8.15 (d, 2H), 8.04 (d, 2H), 7.68 (d, 2H), 7.4-7.2 (m, 3H), 6.95 (d, 2H), 3.74 (t, 4H), 3.05 (t, 4H). MS (EI) for $C_{24}H_{23}N_7O_2$: 442 (MH$^+$).

N-(4-(2-(4-morpholinophenylamino)pyrimidin-4-yl)phenyl)-2-(2-(pyridin-3-yl)-ethylamino)acetamide: $^1$H-NMR (400 MHz, d6-DMSO): 9.00 (s, 1H), 8.92 (d, 1H), 8.64 (d, 1H), 8.35 (d, 1H), 8.17-8.14 (m, 3H), 7.75 (d, 2H), 7.61 (d, 2H), 7.22 (d, 1H), 7.00 (d, 2H), 3.89-3.79 (m, 4H), 3.33-3.21 (m, 2H), 3.15-3.07 (m, 4H), 1.92 (s, 2H); MS (EI): 510.4 (MH+).

2-(3-(4-methylpiperazin-1-yl)propylamino)-N-(4-(2-(4-morpholinophenyl-amino)pyrimidin-4-yl)phenyl)acetamide: $^1$H-NMR (400 MHz, d6-DMSO): 8.36 (d, 1H), 8.14 (d, 2H), 7.75 (d, 2H), 7.61 (d, 2H), 7.22 (d, 1H), 6.99 (d, 2H), 3.87-3.81 (m, 4H), 3.68 (s, 2H), 3.13-3.07 (m, 4H), 2.98-2.88 (m, 2H), 2.82-2.62 (m, 8H), 2.39 (s, 3H), 1.93 (s, 3H), 1.89-1.79 (m, 2H); MS (EI): 512.6 (MH+).

2-(1-methylpiperidin-4-ylamino)-N-(4-(2-(4-morpholinophenylamino)-pyrimidin-4-yl)phenyl)acetamide: $^1$H-NMR (400 MHz, d6-DMSO): 8.35 (d, 1H), 8.14 (d, 2H), 7.75 (d, 2H), 7.61 (d, 2H), 7.22 (d, 1H), 6.99 (d, 2H), 3.87-3.81 (m, 4H), 3.47 (s, 2H), 3.15-3.09 (m, 4H), 3.06-2.95 (m, 2H), 2.69-2.55 (m, 1H), 2.39 (s, 3H), 2.38-2.22 (m, 2H), 2.03-1.93 (m, 2H), 1.90 (s, 2H), 1.63-1.43 (m, 2H); MS (EI): 545.2 (MH+).

2-(2-amino-2-oxoethylamino)-N-(4-(2-(4-morpholinophenylamino)pyrimidin-4-yl)phenyl)acetamide: $^1$H-NMR (400 MHz, d6-DMSO): 8.27 (d, 1H), 8.04 (d, 2H), 7.68 (d, 2H), 7.53 (d, 2H), 7.13 (d, 1H), 6.91 (d, 2H), 4.54 (s, 2H), 3.79-3.73 (m, 4H), 3.39 (s, 2H), 3.06-3.00 (m, 4H), 1.86 (s, 2H); MS (EI): 462.1 (MH+).

2-morpholino-N-(4-(2-(4-morpholinophenylamino)pyrimidin-4-yl)phenyl)-acetamide: $^1$H-NMR (400 MHz, d6-DMSO): 10.0 (s, 1H), 9.40 (s, 1H), 8.45 (d, 1H), 8.13 (d, 2H), 7.82 (d, 2H), 7.68 (d, 2H), 7.29 (d, 1H), 6.94 (d, 2H), 3.78-3.70 (m, 4H), 3.69-3.61 (m, 4H), 3.08-3.02 (m, 4H), 2.56-2.46 (m, 4H); MS (EI): 475.3 (MH+).

2-((2-aminoethyl)(methyl)amino)-N-(4-(2-(4-morpholinophenylamino)-pyrimidin-4-yl)phenyl)acetamide: $^1$H-NMR (400 MHz, d6-DMSO): 8.36 (d, 1H), 8.13 (d, 2H), 7.76 (d, 2H), 7.62 (d, 2H), 7.22 (d, 1H), 7.00 (d, 2H), 3.89-3.81 (m, 4H), 3.51 (s, 2H), 3.14-3.07 (m, 4H), 3.03-3.96 (m, 2H), 2.94-2.88 (m, 2H), 2.67 (s, 3H); MS (EI) $C_{25}H_{31}N_7O_2$: 462.4 (MH+).

2-(1H-pyrazol-5-ylamino)-N-(4-(2-(4-morpholinophenylamino)pyrimidin-4-yl)-phenyl)acetamide: $^1$H-NMR (400 MHz, d6-DMSO): 8.35 (d, 2H), 8.12 (d, 2H), 7.74 (d, 2H), 7.61 (d, 2H), 7.40 (s, 1H), 7.21 (d, 1H), 6.99 (d, 2H), 5.69 (s, 1H), 3.95 (s, 2H), 3.86-3.80 (m, 4H), 3.14-3.07 (m, 4H), 1.96 (s, 2H); MS (EI): 471.1 (MH+).

N-(4-(2-(4-morpholinophenylamino)pyrimidin-4-yl)phenyl)-2-(piperazin-1-yl)-acetamide: $^1$H-NMR (400 MHz, d6-DMSO): 10.39 (s, 1H), 9.53 (s, 1H), 8.87 (s, 2H), 8.48 (d, 1H), 8.17 (d, 1H), 7.80 (d, 2H), 7.10 (d, 2H), 7.33 (d, 1H), 7.04 (d, 2H), 3.82-3.74 (m, 4H), 3.32-3.24 (m, 2H), 3.19-3.09 (m, 4H), 3.08-3.02 (m, 2H), 2.95 (s, 2H), 2.79 (s, 2H), 1.96 (s, 2H); MS (EI): 474.2 (MH+).

(S)-benzyl 2-(2-(4-(2-(4-morpholinophenylamino)pyrimidin-4-yl)phenylamino)-2-oxoethylamino)propanoate: $^1$H-NMR (400 MHz, CD3OD): 8.25 (d, 2H), 8.01 (d, 2H), 7.61 (d, 2H), 7.51 (d, 2H), 7.30-7.08 (m, 5H), 7.12 (d, 1H), 6.90 (d, 2H), 5.15-5.05 (m, 2H), 3.78-3.73 (m, 4H), 3.43 (q, 1H), 3.33 (d, 2H), 3.05-2.97 (m, 4H), 1.28 (d, 3H); MS (EI): 567.2 (MH+).

N-(4-(2-(4-morpholinophenylamino)pyrimidin-4-yl)phenyl)-2-(pyrimidin-4-yl-amino)acetamide: $^1$H-NMR (400 MHz, CD3OD): 10.90 (s, 1H), 9.63 (s, 1H), 9.18 (d, 2H), 8.78 (s, 1H), 8.50 (s, 1H), 8.26 (d, 1H), 8.18 (d, 2H), 7.82-7.68 (m, 4H), 7.36 (d, 1H), 7.11 (d, 2H), 6.84 (s, 1H), 5.16 (s, 2H), 3.83-3.77 (m, 4H), 2.54-2.47 (m, 4H); MS (EI): 483.2 (MH+).

N-(4-(2-(4-morpholinophenylamino)pyrimidin-4-yl)phenyl)-2-(piperidin-1-yl)-acetamide: $^1$H-NMR (400 MHz, d6-DMSO): 10.98 (s, 1H), 9.84 (s, 1H), 9.65 (s, 1H), 8.50 (d, 1H), 8.20 (d, 2H), 7.90-7.70 (m, 4H), 7.36 (d, 1H), 7.11 (d, 2H), 4.12-4.07 (m, 2H), 3.87-3.77 (m, 4H), 3.62-3.42 (m, 2H), 3.23-3.13 (m, 4H), 2.51 (s, 2H), 1.94-1.64 (m, 6H), 1.45-1.38 (m, 2H); MS (EI): 473.4 (MH+).

2-(ethylamino)-N-(4-(2-(4-morpholinophenylamino)pyrimidin-4-yl)phenyl)-acetamide: $^1$H-NMR (400 MHz, d6-DMSO): 10.78 (s, 1H), 9.45 (s, 1H), 8.87 (s, 2H), 8.48 (d, 1H), 8.17 (d, 2H), 7.77 (d, 2H), 7.71 (d, 2H), 7.33 (d, 1H), 7.04 (d, 2H), 4.04-3.97 (m, 2H), 3.82-3.74 (m, 4H), 3.19-3.02 (m, 6H), 1.12 (t, 3H); MS (EI): 433.3 (MH+).

2-(1H-imidazol-1-yl)-N-(4-(2-(4-morpholinophenylamino)pyrimidin-4-yl)phenyl)-acetamide: $^1$H-NMR (400 MHz, d6-DMSO): 10.87 (s, 1H), 9.56 (s, 1H), 9.11 (s, 1H), 8.45 (d, 1H), 8.15 (d, 2H), 7.76 (d, 2H), 7.70 (d, 2H), 7.32 (d, 1H), 7.05 (d, 2H); 5.26 (s, 2H), 3.82-3.72 (m, 4H), 3.18-3.08 (m, 4H); MS (EI): 456.3 (MH+).

4-(2-(4-morpholinophenylamino)pyrimidin-4-yl)benzoic acid: $^1$H-NMR (400 MHz, d6-DMSO): 9.56 (s, 1H), 8.55 (d, 1H), 8.27 (d, 2H), 8.09 (d, 2H), 7.68 (d, 2H), 7.41 (d, 1H), 6.97 (d, 2H), 3.80-3.72 (m, 4H), 3.11-3.03 (m, 4H); MS (EI): 377.3 (MH+).

N-(4-(2-(4-morpholinophenylamino)pyrimidin-4-yl)phenyl)-2-(phenylamino)-acetamide: $^1$H-NMR (400 MHz, d6-DMSO): 10.29 (s, 1H), 9.59 (s, 1H), 8.46 (d, 1H), 8.14 (d, 2H), 7.79 (d, 2H), 7.73 (d, 2H), 7.33 (d, 1H), 7.19-7.00 (m, 4H), 6.70-6.50 (m, 3H), 3.96-3.88 (m, 4H), 3.22-3.12 (m, 4H); MS (EI): 481.1 (MH+).

4-(4-(5-methyl-1,3,4-oxadiazol-2-yl)phenyl)-N-(4-morpholinophenyl)-pyrimidin-2-amine: $^1$H-NMR (400 MHz, d6-DMSO): 9.53 (s, 1H), 8.54 (d, 1H), 8.35 (d, 2H), 8.12 (d, 2H), 7.65 (d, 2H), 7.40 (d, 1H), 6.92 (d, 1H), 3.76-3.70 (m, 4H), 3.06-3.00 (m, 4H), 2.59 (s, 3H); MS (EI): 415.3 (MH+).

(R)-4-(4-(4-(2-aminopropanamido)phenyl)pyrimidin-2-ylamino)phenyl)-N-ethylpiperazine-1-carboxamide: $^1$H-NMR (400 MHz, d6-DMSO): 9.41 (s, 1H), 8.44 (d, 1H), 8.13 (d, 2H), 7.82 (d, 2H), 7.68 (d, 2H), 7.29 (d, 1H), 6.96 (d, 2H), 6.59 (t, 1H), 3.54-3.46 (m, 1H), 3.44-3.36 (m, 4H), 3.12-2.97 (m, 6H), 1.24 (d, 3H), 1.02 (t, 2H), 0.95 (t, 2H); MS (EI): 487.1 (MH−).

(R)-2-amino-N-(4-(2-(4-(4-((R)-pyrrolidine-2-carbonyl)piperazin-1-yl)phenyl-amino)pyrimidin-4-yl)phenyl)propanamide: $^1$H-NMR (400 MHz, d6-DMSO): 9.41 (s, 1H), 8.45 (d, 1H), 8.13 (d, 2H), 7.82 (d, 2H), 7.69 (d, 2H), 7.29 (d, 1H), 6.97 (d, 2H), 3.97-3.92 (m, 1H), 3.72-3.58 (m, 3H), 3.51-3.42 (m, 2H), 3.14-2.99 (m, 4H), 2.68-2.62 (m, 1H), 2.12-2.00 (m, 1H), 1.74-1.70 (m, 1H), 1.70-1.56 (m, 2H), 1.24 (d, 3H); MS (EI): 513.2 (MH−).

(R)-2-amino-N-(4-(2-(4-(4-((S)-pyrrolidine-2-carbonyl)piperazin-1-yl)phenyl-amino)pyrimidin-4-yl)phenyl)propanamide: $^1$H-NMR (400 MHz, d6-DMSO): 9.41 (s, 1H), 8.45 (d, 1H), 8.13 (d, 2H), 7.83 (d, 2H), 7.69 (d, 2H), 7.29 (d, 1H), 6.97 (d, 2H), 4.65 (t, 1H), 3.89-3.81 (m, 1H), 3.75-3.58 (m, 3H), 3.54-3.28 (m, 2H), 3.15-2.98 (m, 4H), 2.72-2.58 (m, 1H), 2.06-1.97 (m, 2H), 1.74-1.54 (m, 2H), 1.24 (d, 3H); MS (EI): 515.4 (MH+).

N-[4-(2-{[4-(4-L-alanylpiperazin-1-yl)phenyl]amino}pyrimidin-4-yl)phenyl]-D-alaninamide: $^1$H-NMR (400 MHz, d6-DMSO): 9.40 (s, 1H), 8.44 (d, 1H), 8.13 (d, 2H), 7.83 (d, 2H), 7.68 (d, 2H), 7.29 (d, 1H), 6.97 (d, 2H), 3.57 (dd, 1H), 3.68-3.58 (m, 4H), 3.46 (dd, 1H), 3.12-2.98 (m, 4H), 1.23 (d, 3H), 1.12 (d, 3H); MS (EI): 489.4 (MH+).

(R)-2-amino-N-(4-(2-(4-(4-((S)-2-aminopropanoyl)piperazin-1-yl)phenylamino)-pyrimidin-4-yl)phenyl)propanamide: $^1$H-NMR (400 MHz, d6-DMSO): 9.40 (s, 1H), 8.44 (d, 1H), 8.13 (d, 2H), 7.83 (d, 2H), 7.68 (d, 2H), 7.29 (d, 1H), 6.97 (d, 2H), 3.17 (s, 2H), 3.12-3.07 (m, 1H), 3.05-2.98 (m, 1H), 2.70-2.64 (m, 4H), 2.36-2.28 (m, 4H), 1.23 (d, 3H); MS (EI): 544.4 (MH+).

3,3,3-trifluoro-2-hydroxy-N-(4-(2-(4-morpholinophenylamino)pyrimidin-4-yl)phenyl)propanamide: $^1$H-NMR (400 MHz, d6-DMSO): 10.42 (br s, 1H), 9.41 (s, 1H), 8.46 (d, 1H), 8.15 (d, 2H), 7.89 (d, 2H), 7.68 (d, 2H), 7.57 (br s, 1H), 7.31 (d, 1H), 6.94 (d, 2H), 4.83-4.74 (m, 1H), 3.78-3.70 (m, 4H), 3.09-3.01 (m, 4H); MS (EI): 474.3 (MH+).

(R)-2-hydroxy-2-methyl-N-(4-(2-(4-morpholinophenylamino)pyrimidin-4-yl)phenyl)butanamide: $^1$H-NMR (400 MHz, d6-DMSO): 9.72 (s, 1H), 9.34 (s, 1H), 8.41 (d, 1H), 8.08 (d, 2H), 7.89 (d, 2H), 7.64 (d, 2H), 7.27 (d, 1H), 6.91 (d, 2H), 5.66 (s, 1H), 4.21-4.13 (m, 1H), 3.72 (q, 1H), 3.15 (d, 3H), 3.12-3.02 (m, 4H), 1.80-1.72 (m, 1H), 1.59-1.51 (m, 1H), 1.32 (s, 3H), 0.82 (t, 3H); MS (EI): 448.4 (MH+).

(S)-2-hydroxy-2-methyl-N-(4-(2-(4-morpholinophenylamino)pyrimidin-4-yl)-phenyl)butanamide: $^1$H-NMR (400 MHz, d6-DMSO): 9.72 (s, 1H), 9.34 (s, 1H), 8.41 (d, 1H), 8.08 (d, 2H), 7.89 (d, 2H), 7.64 (d, 2H), 7.27 (d, 1H), 6.91 (d, 2H), 5.66 (s, 1H), 4.21-4.13 (m, 1H), 3.72 (q, 1H), 3.19-3.11 (d, 3H), 3.07-3.02 (m, 4H), 1.81-1.71 (m, 1H), 1.60-1.50 (m, 1H), 1.32 (s, 3H), 0.82 (t, 3H); MS (EI): 448.1 (MH+).

(R)-2-methoxy-N-(4-(2-(4-morpholinophenylamino)pyrimidin-4-yl)phenyl)-propanamide: $^1$H-NMR (400 MHz, d6-DMSO): 10.07 (s, 1H), 9.35 (s, 1H), 8.41 (d, 1H), 8.11 (d, 2H), 7.84 (d, 2H), 7.64 (d, 2H), 7.26 (d, 1H), 6.90 (d, 2H), 3.89 (q, 1H), 3.75-3.67 (m, 4H), 3.30 (s, 3H), 3.04-2.96 (m, 4H), 1.31 (d, 3H); MS (EI): 434.3 (MH+).

(S)-2-methoxy-N-(4-(2-(4-morpholinophenylamino)pyrimidin-4-yl)phenyl)-propanamide: $^1$H-NMR (400 MHz, d6-DMSO): 10.07 (s, 1H), 9.35 (s, 1H), 8.41 (d, 1H), 8.11 (d, 2H), 7.84 (d, 2H), 7.64 (d, 2H), 7.26 (d, 1H), 6.90 (d, 2H), 3.89 (q, 1H), 3.75-3.67 (m, 4H), 3.30 (s, 3H), 3.04-2.96 (m, 4H), 1.31 (d, 3H); MS (EI): 434.3 (MH+).

1-amino-N-(4-(2-(4-morpholinophenylamino)pyrimidin-4-yl)phenyl)-cyclopentanecarboxamide: $^1$H-NMR (400 MHz, d6-DMSO): 9.39 (s, 1H), 8.44 (d, 1H), 8.14 (d, 2H), 7.87 (d, 2H), 7.68 (d, 2H), 7.30 (d, 1H), 6.94 (d, 2H), 3.78-3.70 (m, 4H), 3.08-3.00 (m, 4H), 2.10-2.00 (m, 2H), 1.86-1.75 (m, 2H), 1.74-1.62 (m, 2H), 1.60-1.50 (m, 2H); MS (EI): 459.4 (MH+).

(S)-2-hydroxy-3,3-dimethyl-N-(4-(2-(4-morpholinophenylamino)pyrimidin-4-yl)phenyl)butanamide: $^1$H-NMR (400 MHz, d6-DMSO): 9.83 (s, 1H), 9.39 (s, 1H), 8.45 (d, 1H), 8.11 (d, 2H), 7.89 (d, 2H), 7.68 (d, 2H), 7.29 (d, 1H), 6.95 (d, 2H), 5.85 (d, 1H), 3.78-3.70 (m, 4H), 3.47 (q, 1H), 3.09-3.01 (m, 4H), 0.97 (d, 9H); MS (EI): 462.4 (MH+).

(R)-2-cyclohexyl-2-hydroxy-N-(4-(2-(4-morpholinophenylamino)pyrimidin-4-yl)phenyl)acetamide: ¹H-NMR (400 MHz, d6-DMSO): 9.91 (s, 1H), 9.39 (s, 1H), 8.45 (d, 1H), 8.12 (d, 2H), 7.89 (d, 2H), 7.68 (d, 2H), 7.29 (d, 1H), 6.94 (d, 2H), 5.76 (br s, 1H), 3.85 (d, 1H), 3.77-3.69 (m, 4H), 3.10-3.02 (m, 4H), 1.80-1.51 (m, 6H), 1.30-1.02 (m, 5H); MS (EI): 488.1 (MH+).

(S)-2-cyclohexyl-2-hydroxy-N-(4-(2-(4-morpholinophenylamino)pyrimidin-4-yl)phenyl)acetamide: ¹H-NMR (400 MHz, d6-DMSO): 9.91 (s, 1H), 9.39 (s, 1H), 8.45 (d, 1H), 8.12 (d, 2H), 7.89 (d, 2H), 7.68 (d, 2H), 7.29 (d, 1H), 6.94 (d, 2H), 5.76 (br s, 1H), 3.85 (d, 1H), 3.77-3.69 (m, 4H), 3.07-2.98 (m, 4H), 1.78-1.50 (m, 6H), 1.25-1.00 (m, 5H); MS (EI): 488.1 (MH+).

(S)-2-hydroxy-N-(4-(2-(4-morpholinophenylamino)pyrimidin-4-yl)phenyl)-propanamide: ¹H-NMR (400 MHz, d6-DMSO): 9.95 (s, 1H), 9.39 (s, 1H), 8.45 (d, 1H), 8.12 (d, 2H), 7.90 (d, 2H), 7.68 (d, 2H), 7.29 (d, 1H), 6.94 (d, 2H), 5.87 (br s, 1H), 4.23-4.15 (m, 1H), 3.79-3.71 (m, 4H), 3.08-3.00 (m, 4H), 2.51 (d, 3H); MS (EI): 420.4 (MH+).

1-amino-N-(4-(2-(4-morpholinophenylamino)pyrimidin-4-yl)phenyl)-cyclobutanecarboxamide: ¹H-NMR (400 MHz, d6-DMSO): 9.39 (s, 1H), 8.44 (d, 1H), 8.13 (d, 2H), 7.87 (d, 2H), 7.68 (d, 2H), 7.29 (d, 1H), 6.94 (d, 2H), 3.79-3.71 (m, 4H), 3.09-3.00 (m, 4H), 2.00-1.85 (m, 4H), 1.84-1.76 (m, 2H); MS (EI): 445.4 (MH+).

4-(4-(3-methyl-1,2,4-oxadiazol-5-yl)phenyl)-N-(4-morpholinophenyl)pyrimidin-2-amine: ¹H-NMR (400 MHz, d6-DMSO): 9.57 (s, 1H), 8.57 (d, 1H), 8.39 (d, 2H), 8.26 (d, 2H), 7.67 (d, 2H), 7.44 (d, 1H), 6.95 (d, 2H), 3.78-3.72 (m, 4H), 3.09-3.03 (m, 4H), 2.46 (s, 3H); MS (EI): 415.0 (MH+).

N-(4-(2-(4-(4-ethylpiperazin-1-yl)phenylamino)pyrimidin-4-yl)phenyl)-2-phenylacetamide: ¹H-NMR (400 MHz, d6-DMSO): 10.45 (s, 1H), 9.36 (s, 1H), 8.43 (d, 1H), 8.12 (d, 2H), 7.76 (d, 2H), 7.64 (d, 2H), 7.38-7.33 (m, 3H), 7.27 (d, 1H), 6.92 (d, 2H), 3.69 (s, 2H), 3.10-3.04 (m, 4H), 2.35 (q, 3H), 1.89 (s, 2H), 1.03 (t, 2H); MS (EI): 493.1 (MH+).

1-(4-(2-(4-morpholinophenylamino)pyrimidin-4-yl)phenyl)pyrrolidin-2-one: ¹H-NMR (400 MHz, d6-DMSO): 8.26 (d, 1H), 8.14 (d, 2H), 7.77 (d, 2H), 7.65 (d, 2H), 7.36 (d, 1H), 7.25 (d, 2H), 3.92-3.84 (m, 5H), 3.82-3.74 (m, 1H), 3.74-3.60 (m, 1H), 3.42-3.30 (m, 4H), 3.06-3.02 (m, 1H), 2.16-2.06 (m, 2H); MS (EI): 416.1 (MH+).

(S)-2-hydroxy-3-methyl-N-(4-(2-(4-morpholinophenylamino)pyrimidin-4-yl)phenyl)butanamide: ¹H-NMR (400 MHz, d6-DMSO): 9.90 (s, 1H), 9.39 (s, 1H), 8.45 (d, 1H), 8.12 (d, 2H), 7.90 (d, 2H), 7.68 (d, 2H), 7.29 (d, 1H), 6.94 (d, 2H), 5.76 (d, 1H), 3.86 (dd, 1H), 3.78-3.73 (m, 4H), 3.08-3.02 (m, 4H), 0.96 (d, 3H), 0.87 (d, 3H); MS (EI): 448.3 (MH+).

(R)-2-hydroxy-3-methyl-N-(4-(2-(4-morpholinophenylamino)pyrimidin-4-yl)phenyl)butanamide: ¹H-NMR (400 MHz, d6-DMSO): 9.90 (s, 1H), 9.39 (s, 1H), 8.45 (d, 1H), 8.12 (d, 2H), 7.90 (d, 2H), 7.68 (d, 2H), 7.29 (d, 1H), 6.94 (d, 2H), 5.76 (d, 1H), 3.86 (dd, 1H), 3.78-3.73 (m, 4H), 3.08-3.02 (m, 4H), 0.96 (d, 3H), 0.87 (d, 3H); MS (EI): 448.3 (MH+).

(R)-2-amino-N-(4-(2-(4-(4-(cyclobutanecarbonyl)piperazin-1-yl)phenylamino)pyrimidin-4-yl)phenyl)propanamide: ¹H-NMR (400 MHz, d6-DMSO): 9.41 (s, 1H), 8.44 (d, 1H), 8.13 (d, 2H), 7.82 (d, 2H), 7.68 (d, 2H), 7.29 (d, 1H), 6.95 (d, 2H), 3.63-3.56 (m, 2H), 3.43-3.37 (m, 3H), 3.18 (d, 1H), 3.07-2.98 (m, 4H), 2.25-2.02 (m, 4H), 1.98-1.83 (m, 1H), 1.82-1.70 (m, 1H), 1.23 (d, 3H); MS (EI): 500.2 (MH+).

(R)-2-amino-N-(4-(2-(4-(4-pivaloylpiperazin-1-yl)phenylamino)pyrimidin-4-yl)phenyl)propanamide: ¹H-NMR (400 MHz, d6-DMSO): 9.41 (s, 1H), 8.45 (d, 1H), 8.13 (d, 2H), 7.82 (d, 2H), 7.68 (d, 2H), 7.29 (d, 1H), 6.95 (d, 2H), 3.73-3.67 (m, 4H), 3.52-4.42 (m, 1H), 3.08-3.02 (m, 4H), 1.25 (s, 3H), 1.23 (d, 3H); MS (EI): 502.4 (MH+).

4-[4-(ethylamino)phenyl]-N-(4-morpholin-4-ylphenyl)pyrimidin-2-amine: ¹H-NMR (400 MHz, DMSO): 9.202 (s, 1H), 8.3 (d, 2H), 7.948 (d, 2H), 7.689 (q, 2H), 7.134 (d, 1H), 6.93 (d, 2H), 6.657 (d, 2H), 6.285 (t, 1H), 3.754 (t, 4H), 3.132-3.113 (m, 2H), 3.04 (t, 4H), 1.187 (t, 3H). MS (EI) for $C_{22}H_{25}N_5O$: 376.3 (MH⁺).

N-{4-[2-(phenylamino)pyrimidin-4-yl]phenyl}acetamide: ¹H NMR (400 MHz, DMSO): 10.233 (s, 1H), 9.63 (s, 1H), 8.513 (d, 1H), 8.147 (d, 2H), 7.854 (d, 2H), 7.774 (d, 2H), 7.362-7.305 (m, 3H), 6.961 (t, 1H), 2.098 (s, 3H). MS (EI) for $C_{18}H_{16}N_4O$: 305.3 (MH⁺).

N-{4-[2-({4-[(4-ethylpiperazin-1-yl)carbonyl]phenyl}amino)pyrimidin-4-yl]-phenyl}acetamide: ¹H NMR (400 MHz, DMSO): 10.236 (s, 1H), 9.889 (s, 1H), 8.549 (d, 1H), 8.167-8.134 (m, 2H), 7.93-7.903 (m, 2H), 7.782 (d, 2H), 7.418-7.369 (m, 3H), 3.509 (br s, 4H), 2.378-2.324 (m, 6H), 2.097 (s, 3H), 1.025 (t, 3H). MS (EI) for $C_{25}H_{28}N_6O_2$: 445.4 (MH⁺).

N-[4-(2-{[3-(morpholin-4-ylcarbonyl)phenyl]amino}pyrimidin-4-yl)phenyl]-acetamide: ¹H NMR (400 MHz, DMSO): 10.237 (s, 1H), 9.823 (s, 1H), 8.541 (d, 1H), 8.152 (d, 2H), 8.026 (t, 1H), 7.847 (d, 1H), 7.772 (d, 2H), 7.392 (m, 2H), 6.996 (d, 1H), 3.76-3.36 (br s, 8H), 2.094 (s, 3H). MS (EI) for $C_{23}H_{23}NO_3$: 418.3 (MH⁺).

N-(4-(2-(3-(2-(dimethylamino)ethoxy)phenylamino)pyrimidin-4-yl)phenyl)-acetamide: ¹H NMR (400 MHz, DMSO): 10.471 (br s, 1H), 10142 (s, 1H), 9.816 (s, 1H), 8.534 (d, 1H), 8.158 (d, 2H), 7.804 (d, 2H), 7.7 (t, 1H), 7.413-7.383 (m, 2H), 7.29 (t, 1H), 6.636 (m, 1H), 4.381 (t, 2H), 3.531 (q, 2H), 2.883 (d, 6H), 2.106 (s, 3H). MS (EI) for $C_{22}H_{25}N_5O_2$: 392.3 (MH⁺).

N-(4-{2-[(4-morpholin-4-ylphenyl)amino]pyrimidin-4-yl}phenyl)benzamide: ¹H-NMR (400 MHz, DMSO): 10.532 (s, 1H), 9.407 (s, 1H), 8.47 (d, 1H) 8.189 (d, 2H), 7.982 (m, 4H), 7.7-7.54 (m, 5H), 7.325 (d, 1H), 6.959 (d, 2H), 3.747 (t, 4H), 3.054 (t, 4H). MS (EI) for $C_{27}H_{25}N_5O_2$: 452.1 (MH⁺).

N-[4-(2-{[4-(methyloxy)phenyl]amino}pyrimidin-4-yl)phenyl]acetamide: ¹H-NMR (400 MHz, DMSO): 10.222 (s, 1H), 9.433 (s, 1H), 8.455 (s, 1H), 8.121 (d, 2H), 7.725 (q, 4H), 7.293 (d, 1H), 6.91 (d, 2H), 3.739 (s, 3H), 2.093 (s, 3H). MS (EI) for $C_{19}H_{18}N_4O_2$: 335 (MH⁺).

4-(4-chlorophenyl)-N-(4-morpholin-4-ylphenyl)pyrimidin-2-amine: ¹H-NMR (400 MHz, DMSO): 9.488 (s, 1H), 8.514 (d, 1H), 8.185 (d, 2H), 7.665-7.606 (q, 4H), 7.354 (d, 1H), 6.918 (d, 2H), 3.757 (t, 4H), 3.048 (t, 4H). MS (EI) for $C_{20}H_{19}ClN_4O$: 367 (MH⁺).

N-[4-(2-{[3-(methyloxy)phenyl]amino}pyrimidin-4-yl)phenyl]acetamide: ¹H-NMR (400 MHz, DMSO): 10.235 (s, 1H), 1H), 9.633 (s, 1H), 8:52 (d, 1H), 8.15 (d, 2H), 7.65 (t, 1H), 7.369 (d, 2H), 7.209 (t, 1H), 6.535 (q, 1H), 3.77 (s, 3H), 2.092 (s, 3H). MS (EI) for $C_{19}H_{18}N_4O_2$: 335 (MH⁺).

1-(4-{2-[(4-morpholin-4-ylphenyl)amino]pyrimidin-4-yl}phenyl)-3-phenyl-methyl)urea: ¹H NMR (400 MHz, DMSO): 9.347 (s, 1H), 9 (s, 1H), 8.414 (d, 1H), 8.067 (d, 2H), 7.688 (d, 2H), 7.583 (d, 2H), 7.351-7.31 (m, 4H), 7.237 (d, 2H), 6.943 (d, 2H), 6.831 (t, 1H), 4.33 (d, 2H), 3.742 (t, 4H), 3.044 (t, 4H). MS (EI) for $C_{28}H_{28}N_6O_2$: 481.4 (MH⁺).

N-(4-{2-[(4-{4-[(2S)-pyrrolidin-2-ylmethyl]piperazin-1-yl}phenyl)amino]-pyrimidin-4-yl}phenyl)-D-prolinamide: ¹H NMR (400 MHz, DMSO): 10.231 (br s, 1H), 9.376 (s, 1H), 8.443 (d, 1H), 8.134 (d, 2H), 7.848 (d, 2H), 7.663 (d, 2H), 7.29 (d, 1H), 6.936 (d, 2H), 3.74 (m, 1H), 3.505 (m, 1H), 3.08-2.89 (m, 6H), 2.64 (m, 2H), 2.374 (m, 1H), 2.069 (m, 1H), 1.938-1.648 (m, 9H), 1.452 (m, 1H). MS (EI) for $C_{30}H_{38}N_8O$: 527.3 (MH$^+$).

N-(4-{2-[(4-morpholin-4-ylphenyl)amino]pyrimidin-4-yl}phenyl)-2,3-dihydro-1H-isoindole-1-carboxamide: $^1$H NMR (400 MHz, DMSO): 11.345 (s, 1H), 10.326 (br s, 1H), 9.525 (s, 1H), 9.479 (br s, 1H), 8.474 (d, 1H), 8.19 (d, 2H), 7.799 (d, 2H), 7.7-7.627 (m, 3H), 7.469-7.415 (m, 3H), 7.323 (d, 1H), 7.025 (d, 2H), 5.688 (br s, 1H), 4.578 (m, 2H), 3.757 (s, 4H), 3.105 (s, 4H). MS (EI) for $C_{29}H_{28}N_6O_2$: 492.58 (MH$^+$).

N-{4-[2-({4-[4-(2-piperazin-1-ylacetyl)piperazin-1-yl]phenyl}amino)pyrimidin-4-yl]phenyl}tetrahydrofuran-2-carboxamide: $^1$H NMR (400 MHz, DMSO): 9.938 (s, 1H), 9.412 (s, 1H), 8.456 (d, 1H), 7.135 (d, 2H), 7.886 (d, 2H), 7.691 (d, 2H), 7.304 (d, 1H), 6.975 (d, 2H), 4.45 (m, 1H), 4.01 (q, 1H), 3.878 (q, 1H), 3.705 (br s, 4H), 3.592 (br s, 4H), 3.148 (s, 2H), 3.1 (br s, 2H), 3.02 (br s, 2H), 2.719 (br s, 4H), 2.354 (br s, 4H), 2.21 (m, 1H), 2.021 (m, 1H), 1.862 (m, 2H). MS (EI) for $C_{31}H_{38}N_8O_3$: 571 (MH$^+$).

N-(4-{2-[(4-{4-[(4-chloro-1-methyl-1H-pyrazol-3-yl)methyl]piperazin-1-yl}-phenyl)amino]pyrimidin-4-yl}phenyl)-D-prolinamide: $^1$H NMR (400 MHz, DMSO): 10.215 (s, 1H), 9.363 (s, 1H), 8.439 (d, 1H), 8.131 (d, 2H), 7.901 (s, 1H), 7.841 (d, 2H), 7.651 (d, 2H), 7.286 (d, 1H), 6.916 (d, 2H), 3.802 (s, 3H), 3.7 (m, 1H), 3.47 (s, 2H), 3.048 (br s, 4H), 2.92 (t, 2H), 2.568 (t, 4H), 2.08 (m, 1H), 1.816 (m, 1H), 1.691 (m, 2H). MS (EI) for $C_{30}H_{34}ClN_9O$: 572.4 (MH$^+$).

N-{4-[2-({4-[4-(2-hydroxyethyl)piperazin-1-yl]phenyl}amino)pyrimidin-4-yl]-phenyl}-D-prolinamide: $^1$H NMR (400 MHz, DMSO): 10.176 (s, 1H), 9.927 (s, 1H), 8.374 (d, 1H), 8.065 (d, 2H), 7.773 (d, 2H), 7.587 (d, 2H), 7.219 (d, 1H), 6.857 (d, 2H), 4.396 (br s, 1H), 3.715 (t, 1H), 3.468 (br s, 4H), 2.996-2.954 (m, 6H), 2.873 (t, 2H), 2.74 (s, 1H), 2.368 (t, 2H) 2.369 (t, 2H) 2.368 (t, 2H), 2.038 (m, 1H), 1.749 (m, 1H), 1.61 (m, 2H). MS (EI) for $C_{27}H_{33}N_7O_2$: 488.3 (MH$^+$).

N-(4-{2-[(4-{4-[(1-methyl-1H-pyrrol-2-yl)methyl]piperazin-1-yl}phenyl)amino]-pyrimidin-4-yl})phenyl)-D-prolinamide: $^1$H NMR (400 MHz, DMSO): 10.194 (s, 1H), 9.349 (s, 1H), 8.42 (d, 1H), 8.11 (d, 2H), 7.822 (d, 2H), 7.636 (d, 2H), 7.267 (d, 1H), 7.076 (s, 1H), 6.902 (d, 2H), 6.75 (s, 1H), 3.738 (m, 1H), 3.701 (s, 3H), 3.553 (s, 2H), 3.306 (m, 4H), 3.031 (br s, 4H), 2.892 (t, 2H), 2.728 (s, 1H), 2.054 (m, 1H), 1.803 (m, 1H), 1.647 (m, 2H). MS (EI) for $C_{31}H_{36}N_8O$: 538.3 (MH$^+$).

N-(4-{2-[(4-{4-[(2R)-pyrrolidin-2-ylmethyl]piperazin-1-yl}phenyl)amino]-pyrimidin-4-yl}phenyl)-D-prolinamide: $^1$H NMR (400 MHz, DMSO): 8.319-8.251 (m, 3H), 7.86 (d, 2H), 7.636 (d, 2H), 7.56 (d, 1H), 7.282 (d, 2H), 4.479 (t, 1H), 4.106 (m, 1H), 3.514 (br s, 4H), 3.496-3.303 (m, 1H), 2.252 (m, 1H), 2.342 (m, 1H), 2.19-2.094 (m, 6H), 1.835 (m, 1H). MS (EI) for $C_{30}H_{36}N_8O$: 528.5 (MH$^+$).

(2S,3aS,7aS)—N-(4-{2-[(4-morpholin-4-ylphenyl)amino]pyrimidin-4-yl}phenyl)-octahydro-1H-indole-2-carboxamide: $^1$H NMR (400 MHz, DMSO): 10.857 (s, 1H), 9.84 (s, 1H), 9.714 (br s, 1H), 8.531 (d, 1H), 8.207 (m, 3H), 7.816 (d, 4H), 7.42 (d, 1H), 4.448 (m, 1H), 3.874 (t, 4H), 3.681 (br s, 1H), 3.322 (t, 4H), 2.504 (m, 2H), 2.09 (m, 1H), 1.913 (m, 1H), 1.615 (m, 4H), 1.371-1.259 (m, 3H). MS (EI) for $C_{29}H_{34}N_6O_2$: 499.5 (MH$^+$).

N-(4-{2-[(4-morpholin-4-ylphenyl)amino]pyrimidin-4-yl}phenyl)-cyclopropane-carboxamide: $^1$H NMR (400 MHz, DMSO): 10.476 (s, 1H), 9.383 (s, 1H), 8.443 (d, 1H), 8.123 (d, 2H), 7.768 (d, 2H), 7.686 (d, 2H), 7.279 (d, 1H), 6.946 (d, 2H), 3.74 (t, 4H), 3.046 (t, 4H), 1.824 (m, 1H), 0.829 (m, 4H). MS (EI) for $C_{24}H_{25}N_5O_2$: 416 (MH+).

N-[4-(2-{[4-(dimethylamino)phenyl]amino}pyrimidin-4-yl)phenyl]acetamide: $^1$H-NMR (400 MHz, d6-DMSO): 10.38 (s, br, 1H), 9.92 (s, br, 1H), 8.85 (d, 2H), 8.11 (d, 2H), 7.92 (d, 2H), 7.79 (d, 2H), 7.67 (s, 2H), 7.42 (d, 1H), 3.10 (s, 6H), 2.10 (s, 3H). MS (EI): 348 (MH+).

N-(4-{2-[(4-chlorophenyl)amino]pyrimidin-4-yl}phenyl)acetamide: $^1$H NMR (400 MHz, d6-DMSO): 10.30 (s, 1H), 9.88 (s, 1H), 8.53 (d, 1H), 8.14 (d, 2H), 7.87 (d, 2H), 7.75 (d, 2H), 7.41 (d, 2H), 7.37 (1H), 2.10 (s, 3). MS (EI): 339 (MH+).

N-[4-(2-{[4-(1H-pyrrol-1-yl)phenyl]amino}pyrimidin-4-yl)phenyl]acetamide: $^1$H-NMR (400 MHz, d6-DMSO): 10.26 (br s, 1H), 9.78 (br s, 1H), 8.52 (d, 1H), 8.15 (d, 2H), 7.92 (d, 2H), 7.77 (d, 2H), 7.54 (d, 2H), 7.38 (d, 1H), 7.31 (m, 2H), 6.24 (m, 2H). 2.09 (s, 3H). MS (EI): 370 (MH+).

ethyl 1-[4-({4-[4-(acetylamino)phenyl]pyrimidin-2-yl}amino)phenyl]-piperidine-4-carboxylate: $^1$H NMR (400 MHz, d6-DMSO): 10.25 (s, 1H), 9.49 (br s, 1H), 8.45 (d, 1H), 8.11 (d, 2H), 7.75 (d, 4H), 7.30 (d, 1H), 4.10 (q, 2H), 3.56 (d, 2H), 2.86 (br s, 2H), 2.09 (s, 3H), 1.97 (br d, 2H), 1.35 (m, 2H), 1.30 (m, 2H), 0.88 (t, 3H). MS (EI): 460 (MH+).

N-[4-(2-{[4-(4-phenylpiperazin-1-yl)phenyl]amino}pyrimidin-4-yl)phenyl]-acetamide: $^1$H NMR (400 MHz, d6-DMSO): 10.28 (s, 1H), 9.68 (br s 1H), 9.49 (d, 1H), 8.14 (d, 2H), 7.82 (br s 1H), 7.70 (d, 2H), 7.35 (d, 1H), 7.28 (t, 2H), 7.08 (d, 2H), 6.88 (t, 1H), 3.45 (br s, 8H), 2.09 (s, 3H). MS (EI): 465 (MH+).

N-{4-[2-({4-[(2R,6S)-2,6-dimethylmorpholin-4-yl]phenyl}amino)pyrimidin-4-yl]phenyl}acetamide: $^1$H NMR (400 MHz, d6-DMSO): 10.28 (s, 1H), 9.79 (br s, 1H), 8.47 (d, 1H), 8.12 (d, 1H), 8.10 (d, 1H), 7.80 (br d, 2H), 7.75 (d, 2H), 7.37 (d, 2H), 3.69 (br s, 4H), 3.54 (d, 2H), 2.07 (s, 3H), 1.16 (s, 3H), 1.14 (s, 3H) MS (EI): 418 (MH+).

4-amino-N-(4-{2-[(4-morpholin-4-ylphenyl)amino]pyrimidin-4-yl}phenyl)-tetrahydro-2H-thiopyran-4-carboxamide 1,1-dioxide: $^1$H NMR (400 MHz, d6-DMSO): 11.06 (br s, 1H), 9.97 (br s, 1H), 9.29 (s, 2H), 8.56 (d, 1H), 8.21 (d, 2H), 7.94 (d, 2H), 7.89 (d, 1H), 7.58 (s, 1H), 7.47 (d, 1H), 5.32 (br s, 3H), 3.99 (s, 4H), 3.48 (m, 4H), 3.38 (m, 4H), 2.84 (m, 2H), 2.46 (m, 2H). MS (EI): 523 (MH+).

(2R)—N-(4-{2-[(4-morpholin-4-ylphenyl)amino]pyrimidin-4-yl})phenyl)-piperazine-2-carboxamide: $^1$H NMR (400 MHz, d6-DMSO): 10.33 (br s, 1H), 10.31 (br s, 1H), 8.58 (d, 1H), 8.22 (d, 2H), 7.94 (d, 2H), 7.89 (d, 2H), 7.77 (d, 2H), 7.53 (d, 1H), 4.55 (d, 1H), 4.08 (s, 5H), 3.54 (s, 5H), 3.43 (m, 2H), 3.28 (m, 2H). MS (EI): 460 (MH+).

2-amino-N-(4-{2-[(4-morpholin-4-ylphenyl)amino]pyrimidin-4-yl}phenyl)-1,2,3,4-tetrahydronaphthalene-2-carboxamide: $^1$H NMR (400 MHz, d6-DMSO): 11.10 (br s, 1H), 10.07 (br s, 1H), 8.89 (d, 2H), 8.56 (d, 1H), 8.20 (d, 2H), 7.98 (d, 2H), 7.92 (d, 2H), 7.70 (d, 2H), 7.48 (d, 1H), 7.10 (m, 4H), 6.10 (br s, 3H), 4.40 (s, 4H), 3.70 (d, 4H), 3.50 (s, 4H), 3.39 (d, 4H), 2.89 (m, 1H), 2.71 (m, 1H), 2.1 (m, 1H), 1.26 (m, 1H), 1.17 (m, 1H). MS (EI): 521 (MH+).

4-amino-N-(4-{2-[(4-morpholin-4-ylphenyl)amino]pyrimidin-4-yl}phenyl)-tetrahydro-2H-pyran-4-carboxamide: $^1$H NMR (400 MHz, d6-DMSO): 10.85 (br s, 1H), 9.85 (br s, 1H), 8.97 (s, 2H), 8.53 (d, 1H), 8.20 (d, 2H), 7.94 (d, 2H), 7.83 (d, 2H), 7.43 (d, 2H), 4.39 (br s, 3H), 3.94 (s, 4H), 3.87 (d, 4H), 3.72 (m, 4H), 2.45 (m, 2H), 1.97 (d, 2H). MS (EI): 475 (MH+).

(4S)-4-hydroxy-N-(4-{2-[(4-morpholin-4-ylphenyl)amino]pyrimidin-4-yl}phenyl)prolinamide: $^1$H NMR (400 MHz, d6-DMSO): 11.38 (s, 1H), 10.25 (m, 1H), 10.31 (s, 1H), 8.84 (m, 1H), 8.57 (d, 1H), 8.21 (d, 2H), 7.93 (d, 2H), 7.87 (d, 2H), 7.75 (d, 4H), 7.49 (d, 1H), 6.62 (m, 1H), 4.50 (s, 1H), 4.06 (s, 4H), 3.53 (s, 4H), 3.42 (m, 1H)<3.17 (m, 1H), 2.45 (t, 1H), MS (EI): 461 (MH+).

1-acetyl-4-amino-N-(4-{2-[(4-morpholin-4-ylphenyl)amino]pyrimidin-4-yl}-phenyl)piperidine-4-carboxamide: $^1$H NMR (400 MHz, d6-DMSO): 9.72 (s, 1H), 8.51 (d, 1H), 8.14 (dd, 2H), 8.12 (d, 1H), 8.08 (d, 1H), 7.00 (dd, 1H), 7.39 (d, 1H), 7.17 (d, 1H), 4.15 (d, 1H), 3.70 (m, 4H), 3.68 (d, 1H), 4.41 (m, 4H), 3.41 (m, 4H), 3.01 (m, 1H), 2.93 (m, 4H), 2.02 (s, 3H), 1.98 (m, 1H), 1.84 (m, 1H). MS (EI): 516 (MH+).

O-methyl-N-(4-{2-[(4-morpholin-4-ylphenyl)amino]pyrimidin-4-yl}phenyl)-D-serinamide: $^1$H NMR (400 MHz, d6-DMSO): 11.51 (br s, 1H), 9.99 (br s, 1H), 8.55 (d, 1H), 8.50 (br s, 2H), 8.19 (d, 2H), 7.88 (m, 4H), 7.46 (d, 1H), 5.19 (br s, 3H), 4.36 M, 1H), 4.02 (br s, 4H), 3.88 (m, 1H), 3.46 br s, 4H), 3.33 (s, 3H). MS (EI): 449 (MH+).

N-[4-(2-{[4-(2,6-dimethylmorpholin-4-yl)phenyl]amino}pyrimidin-4-yl)phenyl]acetamide: $^1$H NMR (400 MHz, d$_6$-DMSO); 10.30 (br s, 1H), 9.83 (br s, 1H), 8.50 (d, 1H), 8.14 (d, 2H), 7.81 (br s, 1H), 7.77 (d, 2H), 7.39 (d, 1H), 4.10 (br s, 4H), 3.56 (d, 2H), 2.10 (s, 3H), 1.18 (s, 3H), 1.71 (s, 3H). MS (EI): 418 (MH+).

N-(4-{2-[(4-piperidin-1-ylphenyl)amino]pyrimidin-4-yl}phenyl)acetamide: $^1$H-NMR (400 MHz, d6-DMSO): 10.32 (br s, 1H), 9.89 (br s, 1H), 8.52 (d, 1H), 8.11 (d, 2H), 7.94 (d, 2H), 7.76 (d, 4H), 7.40 (d, 1H), 3.45 (Br s, 4H), 3.36 (6H), 2.07 (s, 3H). MS (EI): 388 (MH+).

O-methyl-N-(4-{2-[(4-morpholin-4-ylphenyl)amino]pyrimidin-4-yl}phenyl)-L-serinamide: $^1$H NMR (400 MHz, d6-DMSO): 11.51 (br s, 1H), 9.99 (br s, 1H), 8.55 (d, 1H), 8.50 (br s, 2H), 8.19 (d, 2H), 7.88 (m, 4H), 7.46 (d, 1H), 5.19 (br s, 3H), 4.36 M, 1H), 4.02 (br s, 4H), 3.88 (m, 1H), 3.46 br s, 4H), 3.33 (s, 3H). MS (EI): 449 (MH+).

1,1-dimethylethyl (2R)-2-{[(4-{2-[(4-morpholin-4-ylphenyl)amino]pyrimidin-4-yl}phenyl)amino]carbonyl}pyrrolidine-1-carboxylate: $^1$H NMR (400 MHz, d6-DMSO): 10.26 (br s, 1H), 9.38 (br s, 1H), 8.45 (d, 1H), 8.13 (d, 2H), 7.78 (d, 2H), 7.68 (d, 2H), 7.28 (d, 1H), 6.94 (d, 2H), 4.22 (m, 1H), 3.74 (m, 4H), 3.43 (m, 1H), 3.34 (m, 1H), 3.04 (m, 4H), 2.20 (m, 1H), 1.90 (m, 1H), 1.81 (m, 1H), 1.40 (s, 3H), 1.27 (s, 6H). (MS (EI) 4: 545 (MH+).

4-[4-(methylsulfonyl)phenyl]-N-(4-morpholin-4-ylphenyl)pyrimidin-2-amine: $^1$H-NMR (400 MHz, d6-DMSO): 9.62 (s, 1H), 8.59 (d, 1H), 8.39 (d, 2H), 8.09 (d, 2H), 7.68 (d, 2H), 7.45 (d, 1H), 7.0 (s, br, 1H), 3.81-3.71 (m, 4H), 3.29 (s, 3H), 3.04-3.14 (m, 4H). MS (EI): 411 (MH+).

4-[3-(methylsulfonyl)phenyl]-N-(4-morpholin-4-ylphenyl)pyrimidin-2-amine: $^1$H-NMR (400 MHz, d6-DMSO): 9.60 (s, 1H), 8.72 (s, 1H), 8.57 (d, 1H), 8.47 (d, 1H), 8.10 (d, 1H), 7.85 (d, 1H), 7.66 (d, 1H), 7.46 (d, 1H), 6.92 (d, 1H), 3.81-3.71 (m, 4H), 3.31 (s, 3H), 3.0-3.11 (m, 4H). MS (EI): 411 (MH+).

4-[4-(methylthio)phenyl]-N-(4-morpholin-4-ylphenyl)pyrimidin-2-amine: $^1$H-NMR (400 MHz, d6-DMSO): 9.42 (s, 1H), 8.46 (d, 1H), 8.09 (d, 2H), 7.66 (d, 2H), 7.40 (d, 2H), 7.31 (d, 1H), 6.92 (d, 2H), 3.79-3.69 (m, 4H), 3.1-3.0 (m, 4H), 2.55 (s, 3H). MS (EI): 379 (MH+).

N-(4-{2-[(3-bromo-4-morpholin-4-ylphenyl)amino]pyrimidin-4-yl}phenyl)-acetamide: $^1$H NMR (400 MHz, d6-DMSO): 10.23 (s, 1H), 9.72 (s, 1H), 8.52 (d, 1H), 8.27 (d, 1H), 8.13 (d, 2H), 7.81-7.71 (m, 3H), 7.42-7.32 (m, 1H), 7.18 (d, 1H), 3.78-3.69 (m, 4H), 2.97-2.87 (m, 4H), 2.09 (s, 3H). MS (EI): 469 (MH+).

N-[4-(2-{[4-{[2-(diethylamino)ethyl]oxy}-3-(4-ethylpiperazin-1-yl)phenyl]-amino}pyrimidin-4-yl)phenyl]acetamide: $^1$H NMR (400 MHz, d6-DMSO): 10.21 (s, 1H), 9.36 (s, 1H), 8.44 (d, 1H), 8.13 (d, 2H), 7.73 (d, 2H), 7.54 (s, 1H), 7.36-7.26 (m, 2H), 6.88 (d, 1H), 4.02-3.92 (m, 2H), 2.81-2.71 (m, 2H), 2.59-2.49 (m, 4H), 2.45-2.35 (m, 4H), 1.04 (t, 3H), 0.98 (t, 6H). MS (EI): 533 (MH+).

N$^2$,N$^2$-dimethyl-N-(4-{2-[(4-{4-[3-(methyloxy)propanoyl]piperazin-1-yl}phenyl)amino]pyrimidin-4-yl}phenyl)glycinamide: $^1$H NMR (400 MHz, d6-DMSO): 9.99 (s, 1H), 9.41 (s, 1H), 8.45 (d, 1H), 8.11 (d, 2H), 7.84 (d, 2H), 7.68 (d, 2H), 7.28 (d, 1H), 6.95 (d, 2H), 3.63-3.59 (m, 4H), 3.25 (s, 3H), 3.11 (s, 2H), 3.10-3.05 (m, 2H, 3.04-2.99 (m, 2H), 2.65 (t, 2h), 2.29 (s, 6H). MS (EI): 519 (MH+).

N-(4-{2-[(4-morpholin-4-ylphenyl)amino]pyrimidin-4-yl}phenyl)-cyclobutane-carboxamide: $^1$H NMR (400 MHz, d6-DMSO): 9.99 (s, 1H), 9.37 (s, 1H), 8.43 (d, 1H), 8.10 (d, 2H), 7.77 (d, 2H), 7.67 (d, 2H), 7.27 (d, 1H), 6.93 (d, 2H), 3.75 (m, 4H), 3.32 (m, 1H), 3.05 (m, 4H), 2.24 (m, 2H), 2.12 (m, 2H), 1.93 (m, 1H), 1.82 (m, 1H). MS (EI): 430 (MH+).

N-(4-{2-[(4-morpholin-4-ylphenyl)amino]pyrimidin-4-yl}phenyl)azetidine-3-carboxamide: $^1$H NMR (400 MHz, d6-DMSO): 10.10 (s, 1H), 9.36 (s, 1H), 8.42 (d, 1H), 8.09 (d, 2H), 7.74 (d, 2H), 7.64 (d, 2H), 7.24 (d, 1H), 6.91 (d, 2H), 3.71 (m, 4H), 3.61 (m, 1H), 3.52 (m, 4H), 3.02 (m, 4H). MS (EI): 431 (MH+).

N-(4-{2-[(4-morpholin-4-ylphenyl)amino]pyrimidin-4-yl}phenyl)piperidine-3-carboxamide: $^1$H NMR (400 MHz, d6-DMSO): 10.22 (s, 1H), 9.35 (s, 1H), 8.40 (d, 1H), 8.08 (d, 2H), 7.73 (d, 2H), 7.64 (d, 2H), 7.24 (d, 1H), 6.90 (d, 2H), 3.72 (m, 4H), 3.41 (m, 4H), 3.02 (m, 4H), 2.83 (m, 1H), 2.62 (m, 1H), 1.58 (m, 2H), 1.37 (m, 1H), MS (EI): 459 (MH+).

N-(4-{2-[(4-morpholin-4-ylphenyl)amino]pyrimidin-4-yl}phenyl)piperidine-4-carboxamide: $^1$H NMR (400 MHz, d6-DMSO): 10.12 (s, 1H), 9.38 (s, 1H), 8.43 (d, 1H), 8.10 (d, 2H), 7.76 (d, 2H), 7.67 (d, 2H), 7.27 (d, 1H), 6.93 (d, 2H), 3.74 (m, 4H), 3.37 (m, 1H), 3.03 (m, 4H), 3.00 (m, 1H), 2.50 (m, 2H), 2.47 (m, 1H), 1.73 (m, 2H), 1.54 (m, 2H). MS (EI): 459 (MH+).

2-(methyloxy)-N-(4-{2-[(4-morpholin-4-ylphenyl)amino]pyrimidin-4-yl}-phenyl)acetamide: $^1$H NMR (400 MHz, d6-DMSO): 10.05 (s, 1H), 9.36 (s, 1H), 8.42 (d, 1H), 8.09 (d, 2H), 7.82 (d, 2H), 7.65 (d, 2H), 7.26 (d, 1H), 6.91 (d, 2H), 4.02 (s, 2H), 3.72 (m, 4H), 3.38 (s, 3H), 3.02 (m, 4H). MS (EI): 420 (MH+).

N-(4-{2-[(4-morpholin-4-ylphenyl)amino]pyrimidin-4-yl}phenyl)piperidine-2-carboxamide: $^1$H NMR (400 MHz, d6-DMSO): 9.85 (s, br, 1H), 9.31 (s, 1H), 8.36 (d, 1H), 8.04 (d, 2H), 7.75 (d, 2H), 7.60 (d, 2H), 7.21 (d, 1H), 6.87 (d, 2H), 3.67 (m, 4H), 3.21 (m, 1H), 2.98 (m, 4H), 2.93 (m, 1H), 2.47 (m, 1H), 1.70 (m, 2H), 1.37 (m, 4H). MS (EI) 2: 459 (MH+).

N-(4-{2-[(4-morpholin-4-ylphenyl)amino]pyrimidin-4-yl}phenyl)glycinamide: $^1$H NMR (400 MHz, d6-DMSO): 9.37 (s, 1H), 8.44 (d, 1H), 8.11 (d, 2H), 7.82 (d, 2H), 7.66 (d, 2H), 7.27 (d, 1H), 6.93 (d, 2H), 3.75 (m, 4H), 3.62 (br s, 2H), 3.32 (m, 2H), 3.05 (m, 4H). MS (EI): 405 (MH+).

N-(4-{2-[(4-morpholin-4-ylphenyl)amino]pyrimidin-4-yl}phenyl)furan-2-carboxamide: $^1$H NMR (400 MHz, d6-DMSO): 10.44 (s, 1H), 9.40 (s, 1H), 8.46 (d, 1H), 8.16 (d, 2H), 7.98 (m, 1H), 7.93 (m, 2H), 7.68 (d, 2H), 7.39 (d, 1H), 7.30 (d, 1H), 6.93 (d, 2H), 6.74 (d, 1H), 3.75 (m, 4H), 3.05 (m, 4H). MS (EI): 3: 442 (MH+).

N-(4-{2-[(4-morpholin-4-ylphenyl)amino]pyrimidin-4-yl}phenyl)tetra-hydrofuran-2-carboxamide: $^1$H NMR (400 MHz, d6-DMSO): 9.91 (s, 1H), 9.36 (s, 1H), 8.41 (d, 1H), 8.09 (d, 2H), 7.84 (d, 2H), 7.67 (d, 2H), 7.22 (d, 1H), 6.91 (d, 2H), 4.41 (dd, 1H), 3.96 (q, 1H), 3.83 (q, 1H), 3.72 (m, 4H), 3.02 (m, 4H), 2.19 (m, 1H), 1.99 (m, 1H), 1.88 (m, 2H). MS (EI): 446 (MH+).

5-methyl-N-(4-{2-[(4-morpholin-4-ylphenyl)amino]pyrimidin-4-yl}phenyl)-pyrazine-2-carboxamide: $^1$H NMR (400 MHz, d6-DMSO): 10.90 (s, 1H), 9.38 (s, 1H), 9.17 (s, 1H), 8.71 (s, 1H), 8.43 (d, 1H), 8.16 (d, 2H), 8.08 (d, 2H), 7.66 (d, 2H), 7.31 (d, 1H), 6.92 (d, 2H), 3.71 (m, 4H), 3.03 (m, 4H), 2.62 (s, 3H), MS (EI): 468 (MH+).

2-(ethyloxy)-N-(4-{2-[(4-morpholin-4-ylphenyl)amino]pyrimidin-4-yl}phenyl)-acetamide: $^1$H NMR (400 MHz, d6-DMSO): 9.94 (s, 1H), 9.36 (s, 1H), 8.43 (d, 1H), 8.10 (d, 2H), 7.80 (d, 2H), 7.65 (d, 2H), 7.26 (d, 1H), 6.91 (d, 2H), 4.05 (s, 2H), 3.72 (m, 4H), 3.55 (q, 2H), 3.02 (m, 4H), 1.17 (t, 3H). MS (EI): 434 (MH+).

N-(4-{2-[(4-morpholin-4-ylphenyl)amino]pyrimidin-4-yl}phenyl)-2-(phenyloxy)acetamide: $^1$H NMR (400 MHz, d6-DMSO): 10.37 (s, 1H), 9.39 (s, 1H), 8.44 (d, 1H), 8.14 (d, 2H), 7.82 (d, 2H), 7.67 (d, 2H), 7.31 (m, 3H), 6.98 (m, 4H), 4.75 (s, 2H), 3.73 (m, 4H), 3.04 (m, 4H). MS (EI): 482 (MH+).

methyl 4-[(4-{(2-[(4-morpholin-4-ylphenyl)amino]pyrimidin-4-yl}phenyl)amino]-4-oxobutanoate: $^1$H NMR (400 MHz, d6-DMSO): 10.28 (s, 1H), 9.37 (s, 1H), 8.43 (d, 1H), 8.11 (d, 2H), 7.74 (d, 2H), 7.67 (d, 2H), 7.27 (d, 1H), 6.93 (d, 2H), 3.74 (m, 4H), 3.60 (s, 3H), 3.06 (m, 4H), 2.65 (m, 4H). MS (EI): 462 (MH+).

N-(4-{2-[(4-morpholin-4-ylphenyl)amino]pyrimidin-4-yl}phenyl)butanamide: $^1$H NMR (400 MHz, d6-DMSO): 10.15 (s, 1H), 9.37 (s, 1H), 8.43 (d, 1H), 8.11 (d, 2H), 7.75 (d, 2H), 7.67 (d, 2H), 7.26 (d, 1H), 6.93 (d, 2H), 3.73 (m, 4H), 3.04 (m, 4H), 2.33 (t, 2H), 1.63 (q, 2H), 0.93 (t, 3H). MS (EI): 418 (MH+).

2-(2-methylphenyl)-N-(4-{2-[(4-morpholin-4-ylphenyl)amino]pyrimidin-4-yl}-phenyl)acetamide: $^1$H NMR (400 MHz, d6-DMSO): 10.44 (s, 1H), 9.38 (s, 1H), 8.43 (d, 1H), 8.11 (d, 2H), 7.76 (d, 2H), 7.67 (d, 2H), 7.27 (m, 2H), 7.16 (m, 3H), 6.93 (d, 2H), 3.75 (m, 6H), 3.03 (m, 4H), 2.31 (m, 3H). MS (EI): 480 (MH+).

N-(4-{2-[(4-morpholin-4-ylphenyl)amino]pyrimidin-4-yl}phenyl)-cyclopentane-carboxamide: $^1$H NMR (400 MHz, d6-DMSO): 10.14 (s, 1H), 9.38 (s, 1H), 8.43 (d, 1H), 8.10 (d, 2H), 7.77 (d, 2H), 7.67 (d, 2H), 7.27 (d, 1H), 6.93 (d, 2H), 3.75 (m, 4H), 3.04 (m, 4H), 2.80 (m, 1H), 1.87 (m, 2H), 1.72 (m, 4H), 1.55 (m, 2H). MS (EI): 444 (MH+).

(2S)—N-(4-{2-[(4-morpholin-4-ylphenyl)amino]pyrimidin-4-yl}phenyl-azetidine-2-carboxamide: $^1$H NMR (400 MHz, d6-DMSO): 10.09 (br s, 1H), 9.38 (s, 1H), 8.44 (d, 1H), 8.13 (d, 2H), 7.86 (d, 2H), 7.67 (d, 2H), 7.29 (d, 1H), 6.94 (d, 2H), 4.32 (t, 1H), 3.73 (m, 4H), 3.62 (m, 1H), 3.06 (m, 4H), 2.58 (m, 1H), 2.29 (m, 1H), 0.99 (m, 1H). MS (EI): 431 (MH+).

N-{4-[2-({4-[(3R)-3-(dimethylamino)pyrrolidin-1-yl]phenyl}amino)pyrimidin-4-yl]phenyl}-D-prolinamide: $^1$H NMR (400 MHz, d6-DMSO): 10.19 (s, 1H), 9.19 (s, 1H), 8.40 (d, 1H), 8.11 (d, 2H), 7.83 (d, 2H), 7.56 (d, 2H), 7.22 (d, 1H), 6.53 (d, 2H), 3.72 (m, 1H), 3.41 (m, 1H), 3.33 (m, 1H), 3.22 (m, 1H), 3.02 (m, 1H), 2.90 (m, 2H), 2.78 (m, 1H), 2.20 (s, 6H), 2.05 (m, 2H), 1.75 (m, 2H), 1.66 (m, 2H). MS (EI): 472 (MH+).

4-(4-aminophenyl)-N-{4-[(3R)-3-(dimethylamino)pyrrolidin-1-yl]phenyl}-pyrimidine-2-amine: $^1$H NMR (400 MHz, d6-DMSO): 8.99 (s, 1H), 8.25 (s, 1H), 7.87 (d, 2H), 7.57 (d, 2H), 7.05 (d, 1H), 6.63 (d, 2H), 6.52 (d, 2H), 5.70 (s, 2H), 3.41 (m, 1H), 3.31 (m, 1H), 3.21 (m, 1H), 3.01 (m, 1H), 2.77 (m, 1H), 2.20 (s, 6H), 2.15 (m, 1H), 1.77 (m, 1H). MS (EI): 375 (MH+).

N-{4-[2-({4-[(3R)-3-(dimethylamino)pyrrolidin-1-yl]phenyl}amino)pyrimidin-4-yl]phenyl}-3-(methyloxy)propanamide: $^1$H NMR (400 MHz, d6-DMSO): 10.21 (s, 1H), 9.19 (s, 1H), 8.40 (d, 1H), 8.10 (d, 2H), 7.75 (d, 2H), 7.58 (d, 2H), 7.23 (d, 1H), 6.54 (d, 2H), 3.63 (t, 2H), 3.41 (m, 1H), 3.25 (m, 3H), 3.21 (m, 1H), 3.01 (m, 1H), 2.77 (m, 1H), 2.59 (t, 2H), 2.52 (m, 1H) 2.20 (s, 6H), 2.13 (m, 1H), 1.79 (m, 1H). MS (EI): 461 (MH+).

1-ethyl-3-(4-{2-[(4-{4-[3-(methyloxy)propanoyl]piperazin-1-yl}phenyl)-amino]pyrimidin-4-yl}phenyl)urea: $^1$H NMR (400 MHz, d6-DMSO): 9.35 (s, 1H), 8.76 (s, 1H), 8.41 (d, 1H), 8.04 (d, 2H), 7.68 (d, 2H), 7.54 (d, 2H), 7.23 (d, 1H), 6.95 (d, 2H), 6.26 (t, 1H), 3.59 (m, 4H), 3.56 (q, 2H), 3.23 (s, 3H), 3.14 (m, 2H), 3.07 (m, 2H), 3.01 (m, 2H), 2.61 (t, 2H), 1.06 (t, 3H). MS (EI): 504 (MH+).

3-(methyloxy)-N-(4-{2-[(4-{4-[3-(methyloxy)propanoyl]piperazin-1-yl}phenyl)-amino]pyrimidin-4-yl}phenyl)propanamide: $^1$H NMR (400 MHz, d6-DMSO): 10.22 (s, 1H), 9.40 (s, 1H), 8.44 (d, 1H), 8.11 (d, 2H), 7.76 (d, 2H), 7.68 (d, 2H), 7.27 (d, 1H), 6.95 (d, 2H), 3.60 (m, 8H), 3.25 (s, 3H), 3.23 (s, 3H), 3.08 (m, 2H), 3.01 (m, 2H), 2.61 (m, 4H). MS (EI): 519 (MH+).

N-{4-[2-({4-[4-(3-hydroxypropanoyl)piperazin-1-yl]phenyl}amino)pyrimidin-4-yl]phenyl}-D-prolinamide: $^1$H NMR (400 MHz, d6-DMSO): 10.19 (s, 1H), 9.40 (s, 1H), 8.42 (d, 1H), 8.10 (d, 2H), 7.84 (d, 2H), 7.67 (d, 2H), 7.28 (d, 1H), 6.95 (d, 2H), 3.74 (dd, 1H), 3.66 (t, 2H), 3.62 (m, 4H), 3.09 (m, 2H), 3.03 (m, 2H), 2.91 (t, 2H), 2.52 (m, 2H), 2.05 (m, 1H), 1.79 (m, 1H), 1.66 (m, 2H). MS (EI): 516 (MH+).

N-(4-{2-[(4-{4-[3-(methyloxy)propanoyl]piperazin-1-yl}phenyl)amino]-pyrimidin-4-yl}phenyl)-D-alaninamide: $^1$H NMR (400 MHz, d6-DMSO): 9.40 (s, 1H), 8.45 (d, 1H), 8.12 (d, 2H), 7.82 (d, 2H), 7.68 (d, 2H), 7.28 (d, 1H), 6.95 (d, 2H), 3.59 (m, 4H), 3.57 (t, 2H), 3.46 (m, 1H), 3.23 (s, 3H), 3.07 (m, 2H), 3.02 (m, 2H), 2.61 (m, 2H), 1.24 (d, 3H). MS (EI): 504 (MH+).

N-(4-{2-[(4-{4-[3-(methyloxy)propanoyl]piperazin-1-yl}phenyl)amino]-pyrimidin-4-yl}phenyl)-D-prolinamide: $^1$H NMR (400 MHz, d6-DMSO): 10.21 (s, 1H), 9.41 (s, 1H), 8.45 (d, 1H), 8.11 (d, 2H), 7.83 (d, 2H), 7.66 (d, 2H), 7.28 (d, 1H), 6.95 (d, 2H), 3.75 (dd, 1H), 3.60 (m, 4H), 3.56 (t, 2H), 3.23 (s, 3H), 3.08 (m, 2H), 3.03 (m, 2H), 2.91 (t, 2H), 2.61 (t, 2H), 2.17 (m, 1H), 1.80 (m, 1H), 1.67 (m, 2H). MS (EI): 530 (MH+).

N-2-,N-2-dimethyl-N-(4-{2-[(4-morpholin-4-ylphenyl)amino]pyrimidin-4-yl}phenyl)glycinamide: $^1$H NMR (400 MHz, d6-DMSO): 9.98 (s, 1H), 9.39 (s, 1H), 8.44 (d, 1H), 8.11 (d, 2H), 7.83 (d, 2H), 7.68 (d, 2H), 7.28 (d, 1H), 6.93 (d, 2H), 3.74 (m, 4H), 3.11 (s, 2H), 3.05 (m, 4H), 2.29 (s, 6H). MS (EI): 433 (MH+).

N-(4-{2-[(4-morpholin-4-ylphenyl)amino]pyrimidin-4-yl}phenyl)prolinamide: $^1$H NMR (400 MHz, d6-DMSO): 10.18 (s, 1H), 9.38 (s, 1H), 8.43 (d, 1H), 8.13 (d, 2H), 7.83 (d, 2H), 7.67 (d, 2H), 7.27 (d, 1H), 6.93 (d, 2H), 3.74 (m, 4H), 3.71 (m, 1H), 3.04 (m, 4H), 2.90 (t, 2H), 2.05 (m, 1H), 1.80 (m, 1H), 1.66 (m, 2H). MS (EI): 445 (MH+).

N-(4-{2-[(4-morpholin-4-ylphenyl)amino]pyrimidin-4-yl}phenyl)-3-phenyl-propanamide: $^1$H NMR (400 MHz, d6-DMSO): 10.12 (s, 1H), 9.31 (s, 1H), 8.37 (d, 1H), 8.05 (d, 2H), 7.67 (d, 2H), 7.60 (d, 2H), 7.21 (m, 5H), 7.12 (m, 1H), 6.83 (d, 2H), 3.67 (m, 4H), 2.98 (m, 4H), 2.86 (t, 2H), 2.61 (t, 2H). MS (EI): 480 (MH+).

N-(4-{2-[(4-morpholin-4-ylphenyl)amino]pyrimidin-4-yl}phenyl)-2-phenyl-acetamide: $^1$H NMR (400 MHz, d6-DMSO): 10.44 (s, 1H), 9.38 (s, 1H), 8.43 (d, 1H), 8.11 (d, 2H), 7.77 (d, 2H), 7.67 (d, 2H), 7.34 (m, 4H), 7.26 (m, 2H), 6.93 (d, 2H), 3.75 (m, 4H), 3.69 (m, 2H), 3.04 (m, 4H). MS (EI): 466 (MH+).

N-[3-({4-[4-(acetylamino)phenyl]pyrimidin-2-yl}amino)propyl]-2-fluoro-6-iodobenzamide: $^1$H-NMR (400 MHz, d$_6$-DMSO): 10.16 ppm (s, 1H), 8.64 ppm (t, 1H), 8.3.0 ppm (d, 1H), 8.06 ppm (d, 2H), 7.70 ppm (m, 3H), 7.30 ppm (m, 1H), 7.20 ppm (m, 1H), 7.13 ppm (m, 1H), 7.07 ppm (m, 1H), 3.34 ppm (m, 4H), 2.08 ppm (s, 3H), 1.83 ppm (m, 2H); MS (EI) $C_{22}H_{21}FIN_5O_2$: 533.9 (MH$^+$).

N-[3-({4-[4-(acetylamino)phenyl]pyrimidin-2-yl}amino)phenyl]-2,6-difluoro-benzamide: $^1$H-NMR (400 MHz, d$_6$-DMSO): 10.78 ppm (s, 1H), 10.12 ppm (s, 1H), 9.70 ppm (s, 1H), 8.50 ppm (d, 1H), 8.39 ppm (s, 1H), 8.12 ppm (d, 2H), 7.73 ppm (d, 2H), 7.61 ppm (m, 1H), 7.47 ppm (m, 1H), 7.40 ppm (m, 1H), 7.27 ppm (m, 4H), 2.09 ppm (s, 3H); MS (EI) $C_{25}H_{19}F_2N_5O_2$: 460 (MH$^+$).

N-[3-({4-[4-(acetylamino)phenyl]pyrimidin-2-yl}amino)phenyl]-2,4,5-trifluoro-benzamide: $^1$H-NMR (400 MHz, d$_6$-DMSO): 10.52 ppm (s, 1H), 10.29 ppm (s, 1H), 9.71 ppm (s, 1H), 8.50 ppm (d, 1H), 8.36 ppm (s, 1H), 8.20 ppm (d, 2H), 7.87 ppm (m, 1H), 7.75 ppm (d, 3H), 7.51 ppm (m, 1H), 7.37 ppm (d, 1H), 7.28 ppm (m, 2H), 2.09 ppm (s, 3H); MS (EI) $C_{25}H_{18}F_3N_5O_2$: 478 (MH$^+$).

N-[3-({4-[4-(acetylamino)phenyl]pyrimidin-2-yl}amino)phenyl]benzamide: $^1$H-NMR (400 MHz, d$_6$-DMSO): 10.27 ppm (s, 1H), 10.21 ppm (s, 1H), 9.67 ppm (s, 1H), 8.51 ppm (d, 1H), 8.47 ppm (s, 1H), 8.13 ppm (d, 2H), 8.00 ppm (m, 2H), 7.75 ppm (m, 2H), 7.58 ppm (m, 3H), 7.48 ppm (m, 1H), 7.37 ppm (d, 1H), 7.29 ppm (m, 2H), 2.09 ppm (s, 3H); MS (EI) $C_{25}H_{21}N_5O_2$: 424 (MH$^+$).

N-[3-({4-[4-(acetylamino)phenyl]pyrimidin-2-yl}amino)phenyl]-3,5-difluoro-benzamide: $^1$H-NMR (400 MHz, d$_6$-DMSO): 10.37 ppm (s, 1H), 10.20 ppm (s, 1H), 9.70 ppm (s, 1H), 8.51 ppm (s, 1H), 8.41 ppm (s, 1H), 8.21 ppm (d, 2H), 7.73 ppm (m, 4H), 7.55 ppm (m, 2H), 7.37 ppm (d, 1H), 7.29 ppm (m, 2H), 2.08 ppm (s, 3H); MS (EI) $C_{25}H_{19}F_2N_5O_2$: 468.0 (MH$^+$).

N-[3-({4-[4-(acetylamino)phenyl]pyrimidin-2-yl}amino)phenyl]-2-chloro-6-fluoro-4-methylbenzamide: $^1$H-NMR (400 MHz, d$_6$-DMSO): 10.72 ppm (s, 1H), 10.20 ppm (s, 1H), 9.69 ppm (s, 1H), 8.50 ppm (d, 1H), 8.41 ppm (s, 1H), 8.21 ppm (d, 2H), 7.74 ppm (d, 2H), 7.50 ppm (m, 2H), 7.37 ppm (d, 1H), 7.28 ppm (m, 8H), 2.38 ppm (s, 3H), 2.08 ppm (s, 3H); MS (EI) $C_{26}H_{21}ClFN_5O_2$: 490.0 (MH$^+$).

N-(4-{2-[(3-{[(2,6-dimethylphenyl)methyl]amino}phenyl)amino]pyrimidin-4-yl}-phenyl)acetamide: $^1$H-NMR (400 MHz, d$_6$-DMSO): 10.20 ppm (s, 1H), 9.36 ppm (s, 1H), 8.47 ppm (d, 1H), 8.16 ppm (d, 2H), 7.72 ppm (d, 2H), 7.35 ppm (s, 1H), 7.31 ppm (d, 1H), 7.12 ppm (m, 1H), 7.07 ppm (m, 2H), 6.99 ppm (m, 3H), 6.38 ppm (d, 1H), 5.46 ppm (t, 1H), 4.14 ppm (d, 2H), 2.36 ppm (s, 6H), 2.08 ppm (s, 3H); MS (EI) $C_{27}H_{27}N_5O$: 438.1 (MH$^+$).

N-(3-{2-[(3-aminophenyl)amino]pyrimidin-4-yl}phenyl)thiophene-2-carboxamide: $^1$H-NMR (400 MHz, d$_6$-DMSO): 10.66 ppm (s, 1H), 10.28 ppm (s, br, 2H), 10.10 ppm (s, 1H), 8.74 ppm (s, 1H), 8.63 ppm (d, 1H), 8.25 ppm (m, 2H), 7.94 ppm (m, 3H), 7.75 ppm (t, 1H), 7.55 ppm (t, 1H), 7.45 ppm (m, 2H), 7.26 ppm (m, 1H), 6.97 ppm (m, 1H); MS (EI) $C_{21}H_{17}N_5O_2S$: 388.0 (MH$^+$).

N-[3-({4-[4-(acetylamino)phenyl]pyrimidin-2-yl}amino)phenyl]-1-methylpiperidine-4-carboxamide: $^1$H-NMR (400 MHz, d$_6$-DMSO): 10.21 ppm (s, 1H), 9.84 ppm (s, 1H), 9.60 ppm (s, 1H), 8.49 ppm (d, 1H), 8.29 ppm (s, 1H), 8.20 ppm (d, 2H), 7.74 ppm (d, 2H), 7.36 ppm (m, 2H), 7.18 ppm (m, 2H), 2.84 ppm (m, 2H), 2.31 ppm (m, 1H), 2.17 ppm (s, 3H), 2.09 ppm (s, 3H), 1.87 ppm (m, 2H), 1.72 ppm (m, 4H); MS (EI) $C_{25}H_{28}N_5O_2$: 445 (MH$^+$).

4-(4-aminophenyl)-N-[3-(morpholin-4-ylsulfonyl)phenyl]pyrimidin-2-amine: $^1$H-NMR (400 MHz, d$_6$-DMSO): 9.94 ppm (s, 1H), 8.76 ppm (s, 1H), 8.42 ppm (d, 1H), 7.98 ppm (m, dH), 7.90 ppm (m, 1H), 7.57 ppm (t, 1H), 7.28 ppm (m, 2H), 6.65 ppm (s, 2H), 5.81 ppm (s, 2H), 3.64 ppm (m, 4H), 2.90 ppm (m, 4H); MS (EI) $C_{20}H_{21}N_5O_3S$: 412 (MH$^+$).

N-(4-{2-[(3-{[(2-fluorophenyl)methyl]amino}phenyl)amino]pyrimidin-4-yl}phenyl)acetamide: $^1$H-NMR (400 MHz, d$_6$-DMSO): 10.22 ppm (s, 1H), 9.35 ppm (s, 1H), 8.45 ppm (d, 1H), 8.12 ppm (d, 2H), 7.74 ppm (d, 2H), 7.43 ppm (m, 2H), 7.29 ppm (m, 2H), 7.16 ppm (m, 3H), 6.99 ppm (m, 2H), 6.21 ppm (m, 2H), 4.33 ppm (d, 2H), 2.09 ppm (s, 3H); MS (EI) $C_{25}H_{22}FN_5O$; 428 (MH$^+$).

N-(4-{2-[(3-aminophenyl)amino]pyrimidin-4-yl}phenyl)acetamide: $^1$H-NMR (400 MHz, d$_6$-DMSO): 10.21 ppm (s, 1H), 9.31 ppm (s, 1H), 8.46 ppm (d, 1H), 8.13 ppm (d, 2H), 7.75 ppm (d, 2H), 7.30 ppm (d, 1H), 7.13 ppm (s, 1H), 6.94 ppm (m, 2H), 6.20 ppm (d, 1H), 5.01 ppm (s, 2H), 2.10 ppm (s, 3H); MS (EI) $C_{18}H_{17}N_5O$: 320 (MH$^+$).

N-(4-{2-[(3-{[(4-fluorophenyl)methyl]amino}phenyl)amino]pyrimidin-4-yl}-phenyl)acetamide: $^1$H-NMR (400 MHz, d$_6$-DMSO): 10.26 ppm (s, 1H), 9.33 ppm (s, 1H), 8.45 ppm (d, 1H), 8.13 ppm (d, 2H), 7.75 ppm (d, 2H), 7.37 ppm (m, 2H), 7.31 ppm (m, 3H), 7.21 ppm (m, 2H), 6.97 ppm (m, 2H), 6.23 ppm (m, 2H), 4.48 ppm (d, 2H), 2.09 ppm (s, 3H); MS (EI) $C_{25}H_{23}N_5O$: 410 (MH$^+$).

N-(4-{2-[(3-({[(3-fluorophenyl)methyl]amino}phenyl)amino]pyrimidin-4-yl}-phenyl)acetamide: $^1$H-NMR (400 MHz, d$_6$-DMSO): 10.36 ppm (s, 1H), 9.35 ppm (s, 1H), 8.45 ppm (d, 1H), 8.12 ppm (d, 2H), 7.76 ppm (d, 2H), 7.33 ppm (m, 2H), 7.19 ppm (m, 3H), 6.99 ppm (m, 3H), 6.32 ppm (t, 1H), 6.20 ppm (m, 2H), 4.30 ppm (d, 2H), 2.09 ppm (s, 3H); MS (EI) $C_{25}H_{22}FN_5O$: 428 (MH$^+$).

N-(4-{2-[(3-{[(4-fluorophenyl)methyl]amino}phenyl)amino]pyrimidin-4-yl}-phenyl)acetamide: $^1$H-NMR (400 MHz, d$_6$-DMSO): 10.20 ppm (s, 1H), 9.33 ppm (s, 1H), 8.45 ppm (d, 1H), 8.12 ppm (d, 2H), 7.74 ppm (d, 2H), 7.39 ppm (m, 2H), 7.30 ppm (d, 1H), 7.21 ppm (s, 1H), 7.13 ppm (t, 2H), 6.96 ppm (m, 2H), 6.22 ppm (m, 2H), 2.09 ppm (s, 3H); MS (EI) $C_{25}H_{22}FN_5O$: 428 (MH$^+$).

4-[4-({4-[4-(butanoylamino)phenyl]pyrimidin-2-yl}amino)phenyl]-N-ethyl-piperazine-1-carboxamide: $^1$H-NMR (400 MHz, d$_6$-DMSO): 10.21 ppm (s, 1H), 9.39 ppm (s, 1H), 8.44 ppm (d, 1H), 8.11 ppm (d, 2H), 7.77 ppm (d, 2H), 7.68 ppm (d, 2H), 7.28 ppm (d, 1H), 6.96 ppm (d, 2H), 6.59 ppm (t, 1H), 3.43 ppm (t, 4H), 3.07 ppm (m, 2H), 3.02 ppm (t, 4H), 2.34 ppm (t, 2H), 1.63 ppm (m, 2H), 1.02 ppm (t, 3H), 0.98 ppm (t, 3H); MS (EI) $C_{27}H_{33}N_7O_2$: 488 (MH$^+$).

N-{4-[2-({4-[4-(2-piperazin-1-ylacetyl)piperazin-1-yl]phenyl}amino)pyrimidin-4-yl]phenyl}butanamide: $^1$H-NMR (400 MHz, d$_6$-DMSO): 10.18 ppm (s, 1H), 9.40 ppm (s, 1H), 8.44 ppm (d, 1H), 8.11 ppm (d, 2H), 7.77 ppm (d, 2H), 7.68 ppm (d, 2H), 7.28 ppm (d, 1H), 6.97 ppm (d, 2H), 3.72 ppm (m, 2H), 3.59 ppm (m, 2H), 3.13 ppm (m, 4H), 3.01 ppm (m, 2H), 2.67 ppm (m, 4H), 2.33 ppm (m, 4H), 1.63 ppm (m, 2H), 0.93 ppm (t, 3H); MS (EI) $C_{30}H_{38}N_8O_2$: 543 (MH$^+$).

N-[4-(2-{[4-(4-L-alanylpiperazin-1-yl)phenyl]amino}pyrimidin-4-yl)phenyl]-butanamide: $^1$H-NMR (400 MHz, d$_6$-DMSO): 10.15 ppm (s, 1H), 9.40 ppm (s, 1H), 8.44 ppm (d, 1H), 8.11 ppm (d, 2H), 7.76 ppm (d, 2H), 7.69 ppm (d, 2H), 7.28 ppm (d, 1H), 6.97 ppm (d, 2H), 3.79 ppm (m, 1H), 3.62 ppm (m, 4H), 3.06 ppm (m, 4H), 2.33 ppm (t, 2H), 1.91 ppm (br. s, 2H), 1.63 ppm (m, 2H), 1.09 ppm (d, 3H), 0.93 ppm (t, 3H); MS (EI) $C_{27}H_{33}N_7O_2$: 488 (MH$^+$).

N-[4-(2-{[4-(4-L-prolylpiperazin-1-yl)phenyl]amino}pyrimidin-4-yl)phenyl]-butanamide: $^1$H-NMR (400 MHz, d$_6$-DMSO): 10.21 ppm (s, 1H), 9.41 ppm (s, 1H), 8.44 ppm (d, 1H), 8.11 ppm (d, 2H), 7.77 ppm (d, 2H), 7.69 ppm (d, 2H), 7.28 ppm (d, 1H), 6.97 ppm (d, 2H), 3.85 ppm (m, 1H), 3.62 ppm (m, 4H), 3.04 ppm (m, 5H), 2.62 ppm (m, 1H), 2.34 ppm (t, 2H), 2.00 ppm (m, 1H), 1.62 ppm (m, 6H), 0.93 ppm (t, 3H); MS (EI) $C_{29}H_{35}N_7O_2$: 514 (MH$^+$).

(3R)-1-(2-hydroxyethyl)-N-(4-{2-[(4-morpholin-4-ylphenyl)amino]pyrimidin-4-yl}phenyl)pyrrolidine-3-carboxamide: $^1$H-NMR (400 MHz, d$_6$-DMSO): 10.22 ppm (s, 1H), 9.38 ppm (s, 1H), 8.44 ppm (d, 1H), 8.11 ppm (d, 2H), 7.76 ppm (d, 2H), 7.67 ppm (d, 2H), 7.28 ppm (d, 1H), 6.94 ppm (d, 2H), 4.50 ppm (m, 1H), 3.75 ppm (m, 4H), 3.49 ppm (m, 2H), 3.05 ppm (m, 6H), 2.91 ppm (t, 1H), 2.67 ppm (m, 1H), 2.56 ppm (m, 3H), 1.98 ppm (m, 2H); MS (EI) C$_{27}$H$_{32}$N$_6$O$_3$: 489 (MH$^+$).

N-(4-{2-[(3-fluoro-4-morpholin-4-ylphenyl)amino]pyrimidin-4-yl}phenyl)-L-prolinamide: $^1$H-NMR (400 MHz, d$_6$-DMSO): 10.21 ppm (s, 1H), 9.69 ppm (s, 1H), 8.51 ppm (d, 1H), 8.13 ppm (d, 2H), 7.85 ppm (d, 2H), 7.79 ppm m, 1H), 7.52 ppm (m, 1H), 7.37 ppm (d, 1H), 7.03 ppm (t, 1H), 3.74 ppm (m, 5H), 3.14 ppm (br.s, 1H), 2.95 ppm (m, 4H), 2.91 ppm (m, 2H), 2.06 ppm (m, 1H), 1.80 ppm (m, 1H), 1.66 ppm (m, 2H); MS (EI) C$_{25}$H$_{27}$FN$_6$O$_2$: 463 (MH$^+$).

N-(4-{2-[(3-fluoro-4-morpholin-4-ylphenyl)amino]pyrimidin-4-yl}phenyl)-D-alaninamide: $^1$H-NMR (400 MHz, d$_6$-DMSO): 9.69 ppm (s, 1H), 8.51 ppm (d, 1H), 8.13 ppm (d, 2H), 7.84 ppm (d, 2H), 7.79 ppm (m, 1H), 7.54 ppm (m, 1H), 7.37 ppm (m, 1H), 7.37 ppm (m, 1H), 7.03 ppm (t, 1H), 3.74 ppm (m, 4H), 3.47 ppm (m, 1H), 2.95 ppm (m, 4H), 1.23 ppm (d, 3H); MS (EI) C$_{23}$H$_{25}$FN$_6$O$_2$: 437 (MH$^+$).

N-(4-{2-[(3-methyl-4-morpholin-4-ylphenyl)amino]pyrimidin-4-yl}phenyl)-D-prolinamide: $^1$H-NMR (400 MHz, d$_6$-DMSO): 10.22 ppm (s, 1H), 9.45 ppm (s, 1H), 8.46 ppm (d, 1H), 8.14 ppm (d, 2H), 7.85 ppm (d, 2H), 7.63 ppm (d, 2H), 7.32 ppm (d, 1H), 7.32 ppm (d, 1H), 3.73 ppm (m, 5H), 3.08 ppm (br.s., 1H), 2.90 ppm (t, 2H), 2.80 ppm (m, 4H), 2.27 ppm (s, 3H), 2.06 ppm (m, 1H), 1.80 ppm (m, 1H), 1.66 ppm (m, 2H); MS (EI) C$_{26}$H$_{30}$N$_6$O$_2$: 459 (MH$^+$).

N-(4-{2-[(3-methyl-4-morpholin-4-ylphenyl)amino]pyrimidin-4-yl}phenyl)-L-alaninamide: $^1$H-NMR (400 MHz, d$_6$-DMSO): 9.44 ppm (s, 1H), 8.47 ppm (d, 1H), 8.14 ppm (d, 2H), 7.83 ppm (d, 2H), 7.64 ppm (m, 2H), 7.32 ppm (d, 1H), 7.02 ppm (m, 1H), 3.73 ppm (m, 4H), 3.46 ppm (m, 1H), 2.80 ppm (m, 4H), 2.28 ppm (m, 4H), 1.23 ppm (d, 3H); MS (EI) C$_{24}$H$_{28}$N$_6$O$_2$: 433 (MH$^+$).

1-hydroxy-N-(4-{2-[(4-morpholin-4-ylphenyl)amino]pyrimidin-4-yl}phenyl)-cyclopropanecarboxamide: $^1$H-NMR (400 MHz, d$_6$-DMSO): 10.14 ppm (s, 1H), 9.39 ppm (s, 1H), 8.44 ppm (d, 1H), 8.11 ppm (d, 2H), 7.94 ppm (d, 2H), 7.68 ppm (d, 2H), 7.29 ppm (d, 1H), 6.94 ppm (d, 2H), 6.81 ppm (s, 1H), 3.74 ppm (m, 4H), 3.05 ppm (m., 4H), 1.18 ppm (m, 2H), 1.00 ppm (m, 2H); MS (EI) C$_{24}$H$_{25}$N$_5$O$_3$: 432 (MH$^+$).

N-(4-(2-(4-(4-(4-chloro-2,6-dimethylphenylsulfonyl)piperazin-1-yl)phenyl-amino)pyrimidin-4-yl)phenyl)acetamide: $^1$H NMR (400 MHz, d6-DMSO): 10.20 (s, 1H), 9.42 (s, 1H), 8.41 (m, 1H), 8.08 (d, 2H), 7.77 (s, 1H), 7.71 (d, 2H), 7.64 (m, 2H), 7.57 (s, 1H), 7.27 (m, 1H), 6.93 (m, 2H), 3.41 (m, 4H), 3.15 (m, 4H), 2.53 (s, 3H), 2.37 (s, 3H), 2.06 (s, 3H). MS (EI): 591 (MH+).

N-(4-(2-(4-(4-(2-(piperazin-1-yl)acetyl)piperazin-1-yl)phenylamino)pyrimidin-4-yl)phenyl)tetrahydrofuran-3-carboxamide: $^1$H NMR (400 MHz, d6-DMSO): 10.31 (s, 1H), 9.41 (s, 1H), 8.45 (d, 1H), 8.13 (d, 2H), 7.77 (d, 2H), 7.68 (d, 2H), 7.28 (d, 1H), 6.96 (d, 2H), 3.96 (t, 2H), 3.75 (m, 5H), 3.60 (m, 2H), 3.32 (m, 1H), 3.19 (m, 1H), 3.12 (s, 2H), 3.10 (m, 2H), 3.01 (m, 2H), 2.68 (m, 4H), 2.32 (m, 4H), 2.10 (m, 2H). MS (EI): 571 (MH+).

N-(4-(2-(4-(4-pivaloylpiperazin-1-yl)phenylamino)pyrimidin-4-yl)phenyl)-tetrahydrofuran-3-carboxamide: $^1$H NMR (400 MHz, d6-DMSO): 10.30 (s, 1H), 9.41 (s, 1H), 8.45 (d, 1H), 8.13 (d, 2H), 7.77 (d, 2H), 7.68 (d, 2H), 7.29 (d, 1H), 6.95 (d, 2H), 3.96 (t, 2H), 3.74 (d, 2H), 3.19 (m, 2H), 3.05 (m, 4H), 2.10 (q, 2H), 1.23 (s, 9H). MS (EI): 529 (MH+).

1-ethyl-3-(4-(5-methyl-2-(4-morpholinophenylamino)pyrimidin-4-yl)phenyl)urea: $^1$H NMR (400 MHz, d6-DMSO): 9.24 (s, 1H), 8.87 (s, 1H), 8.29 (s, 1H), 7.64 (d, 2H), 7.59 (m, 2H), 7.53 (m, 2H), 6.88 (d, 2H), 6.41 (m, 1H), 3.73 (m, 4H), 3.12 (m, 2H), 3.02 (m, 4H), 2.23 (s, 3H), 1.06 (t, 3H). MS (EI): 433 (MH+).

3-methoxy-N-(4-(5-methyl-2-(4-morpholinophenylamino)pyrimidin-4-yl)phenyl)propanamide: $^1$H NMR (400 MHz, d6-DMSO): 10.17 (s, 1H), 9.30 (s, 1H), 8.31 (s, 1H), 7.74 (m, 2H), 7.66 (m, 4H), 6.90 (m, 2H), 3.74 (m, 4H), 3.64 (t, 2H), 3.26 (s, 3H), 3.03 (m, 4H), 2.59 (m, 2H), 2.22 (s, 3H). MS (EI): 448 (MH+).

N-(4-(2-(4-(4-(ethylsulfonyl)piperazine-1-yl)phenylamino)pyrimidin-4-yl)phenyl)acetamide: $^1$H NMR (400 MHz, d6-DMSO): 10.21 (s, 1H), 9.38 (s, 1H), 8.42 (d, 1H), 8.08 (d, 2H), 7.72 (d, 2H), 7.66 (d, 2H), 7.26 (d, 1H), 6.95 (d, 2H), 3.36 (m, 4H), 3.12 (m, 4H), 2.48 (m, 2H), 2.07 (s, 3H), 1.22 (t, 3H). MS (EI): 481 (MH+).

4-(4-(4-(4-acetamidophenyl)pyrimidin-2-ylamino)phenyl)-N-ethylpiperazine-1-carboxamide: $^1$H NMR (400 MHz, d6-DMSO): 10.20 (s, 1H), 9.35 (s, 1H), 8.41 (d, 1H), 8.08 (d, 2H), 7.72 (d, 2H), 7.64 (d, 2H), 7.25 (d, 1H), 6.94 (d, 2H), 6.57 (d, 1H), 3.50 (m, 2H), 3.39 (m, 4H), 2.99 (m, 4H), 2.07 (s, 3H), 1.00 (t, 3H). MS (EI): 460 (MH+).

N-(4-{2-[(4-morpholin-4-ylphenyl)amino]pyrimidin-4-yl}phenyl)morpholine-2-carboxamide: $^1$H NMR (400 MHz, d6-DMSO): 9.87 (s, 1H), 9.37 (s, 1H), 8.43 (s, 1H), 8.04-8.16 (d, 2H), 7.81-7.93 (d, 2H), 7.60-7.72 (d, 2H), 7.27 (s, 1H), 6.85-6.99 (d, 2H), 4.08-4.69 (s, br, 1H), 4.00-4.07 (d, 1H), 3.85-3.94 (d, ii), 3.72 (s, 3H), 3.51-3.63 (d, 1H), 2.58-2.80 (m, 3H), 1.86 (s, 6H). MS (EI): 461 (MH+).

N-(4-{2-[(4-morpholin-4-ylphenyl)amino]pyrimidin-4-yl}phenyl)-beta-alaninamide: $^1$H NMR (400 MHz, d6-DMSO): 9.38 (s, 1H), 10.65 (d, 1H), 8.07-8.16 (d, 2H), 7.72-7.81 (d, 2H), 7.62-7.72 (d, 2H), 7.28 (s, 1H), 6.89-6.98 (d, 2H). MS (EI): 419 (MH+).

N-(4-{2-[(4-morpholin-4-ylphenyl)amino]pyrimidin-4-yl}phenyl)phenylalaninamide: $^1$H NMR (400 MHz, d6-DMSO): 9.39 (s, 1H), 8.42-8.46 (d, 1H), 8.09-8.14 (d, 2H), 7.75-7.81 (d, 2H), 7.64-7.70 (d, 2H), 7.23-7.32 (m, 6H), 7.16-7.22 (m, 2H), 6.90-6.97 (d, 2H), 3.71-3.78 (m, 4H), 3.57-3.63 (m, 1H), 3.02-3.08 (m, 4H), 2.98-3.02 (m, 1H), 2.71-2.79 (m, 1H). MS (EI): 495 (MH+).

N$^2$-methyl-N-(4-{2-[(4-morpholin-4-ylphenyl)amino]pyrimidin-4-yl}phenyl)-glycinamide: $^1$H NMR (400 MHz, d6-DMSO): 9.39 (s, 1H), 8.45 (s, 1H), 8.09-8.17 (d, 2H), 7.78-7.86 (d, 2H), 7.65-7.73 (d, 2H), 7.29 (s, 1H), 6.90-7.00 (d, 2H), 3.74 (s, 4H), 3.05 (s, 4H), 2.33 (s, 3H), 1.92 (s, 1H). MS (EI): 419 (MH+).

2-cyclopentyl-N-(4-{2-[(4-morpholin-4-ylphenyl)amino]pyrimidin-4-yl}phenyl)acetamide: $^1$H NMR (400 MHz, d6-DMSO): 10.13 (s, 1H), 9.37 (s, 1H), 8.42-8.45 (d, 1H), 8.07-8.14 (d, 2H), 7.73-7.79 (d, 2H), 7.65-7.71 (d, 2H), 7.25-7.28 (d, 1H), 6.90-6.97 (d, 2H), 3.71-3.77 (m, 4H), 3.02-3.07 (m, 4H), 2.33-2.37 (d, 2H), 2.20-2.30 (m, 1H), 1.71-1.82 (m, 2H), 1.48-1.66 (m, 4H), 1.14-1.25 (m, 2H). MS (EI): 458 (MH+).

6-(methyloxy)-N-(4-{2-[(4-morpholin-4-ylphenyl)amino]pyrimidin-4-yl}-phenyl)pyridine-3-carboxamide: $^1$H NMR (400 MHz, d6-DMSO): 10.50 (s, 1H), 9.44 (s, 1H), 8.80-8.83 (d, 1H), 8.44-8.49 (d, 1H), 8.24-8.28 (m, 1H), 8.15-8.21 (d, 2H), 7.92-7.97 (d, 2H), 7.67-7.72 (d, 2H), 7.30-7.34 (d, 1H), 6.93-7.02 (m, 3H), 3.94-3.96 (s, 3H), 3.72-3.79 (m, 4H), 3.04-3.11 (m, 4H). MS (EI): 483 (MH+).

N,N-dimethyl-N'-(4-{2-[(4-morpholin-4-ylphenyl)amino]pyrimidin-4-yl}phenyl)butanediamide: $^1$H NMR (400 MHz, d6-DMSO): 10.22 (s, 1H), 9.36 (s, 1H), 8.43 (s, 1H), 8.05-8.17 (d, 2H), 7.71-7.79 (d, 2H), 7.61-7.71 (d, 2H), 7.26-7.31 (d, 1H), 6.89-7.00 (d, 2H), 3.68-3.79 (m, 4H), 3.02-3.08 (m, 4H), 3.00 (s, 3H), 2.82 (s, 3H), 2.56-2.66 (m, 4H). MS (EI): 475 (MH+).

N-[4-(2-{[4-morpholin-4-yl-3-(trifluoromethyl)phenyl]amino}pyrimidin-4-yl)-phenyl]-D-prolinamide: $^1$H NMR (400 MHz, d6-DMSO): 10.31 (s, 1H), 9.94 (s, 1H), 8.53-8.57 (d, 1H), 8.48 (s, 1H), 8.14-8.21 (d, 2H), 7.93-7.98 (m, 1H), 7.82-7.88 (d, 2H), 7.56-7.61 (d, 1H), 7.42-7.46 (d, 1H), 3.79-3.86 (m, 1H), 3.67-3.75 (m, 4H), 2.93-3.00 (m, 2H), 2.79-2.86 (m, 4H), 2.05-2.17 (m, 1H), 1.79-1.89 (m, 1H), 1.65-1.75 (m, 2H). MS (EI): 513 (MH+).

3-(methyloxy)-N-[4-(2-{[4-morpholin-4-yl-3-(trifluoromethyl)phenyl]amino}-pyrimidin-4-yl)phenyl]propanamide: $^1$H NMR (400 MHz, d6-DMSO): 10.24 (s, 1H), 9.94 (s, 1H), 8.53-8.56 (d, 1H), 8.47 (s, 1H), 8.13-8.19 (d, 2H), 7.94-8.00 (d, 1H), 7.76-7.81 (d, 1H), 7.56-7.62 (d, 1H), 7.41-7.45 (d, 1H), 3.67-3.74 (m, 4H), 3.60-3.67 (m, 2H), 3.35 (s, 3H), 2.80-2.86 (d, 4H), 2.57-2.63 (m, 2H). MS (EI): 502 (MH+).

N-(4-{2-[(4-{4-[3-(dimethylamino)-2,2-dimethylpropyl]piperazin-1-yl}phenyl)-amino]pyrimidin-4-yl}phenyl)-5-oxo-L-prolinamide: $^1$H NMR (400 MHz, d6-DMSO): 10.34 (s, 1H), 9.37 (s, 1H), 8.43-8.46 (d, 1H), 8.12-8.16 (d, 2H), 7.94 (s, 1H), 7.77-7.81 (d, 2H), 7.62-7.67 (d, 2H), 7.26-7.30 (d, 1H), 6.88-6.94 (d, 2H), 4.20-4.26 (m, 1H), 3.02-3.08 (m, 4H), 2.57-2.64 (m, 4H), 2.21 (s, 6H), 2.17 (s, 2H), 2.10 (s, 2H), 1.89 (s, 4H), 0.84 (s, 6H). MS (EI): 571 (MH+).

(2R)—N-(4-{2-[(4-{4-[3-(methyloxy)propanoyl]piperazin-1-yl}phenyl)amino]-pyrimidin-4-yl}phenyl)tetrahydrofuran-2-carboxamide: $^1$H NMR (400 MHz, d6-DMSO): 9.94 (s, 1H), 9.41 (s, 1H), 8.43-8.46 (d, 1H), 8.09-8.15 (d, 2H), 7.85-7.90 (d, 2H), 7.65-7.71 (d, 1H), 6.92-6.98 (d, 2H), 4.39-4.48 (m, 1H), 3.95-4.05 (m, 1H), 3.79-3.89 (m, 1H), 3.52-3.64 (m, 6H), 3.32 (s, 1H), 3.23 (s, 2H), 2.98-3.11 (m, 4H), 2.58-2.65 (m, 2H), 2.15-2.25 (m, 1H), 1.96-2.07 (m, 1H), 1.83-1.93 (m, 2H). MS (EI): 531 (MH+).

(2S)—N-(4-{2-[(4-{4-[3-(methyloxy)propanoyl]piperazin-1-yl}phenyl)amino]-pyrimidin-4-yl}phenyl)tetrahydrofuran-2-carboxamide: $^1$H NMR (400 MHz, d6-DMSO): 9.94 (s, 1H), 9.41 (s, 1H), 8.42-8.47 (d, 2H), 8.09-8.16 (d, 2H), 7.84-7.91 (d, 2H), 7.64-7.72 (d, 2H), 7.27-7.37 (d, 1H), 6.93-6.99 (d, 2H), 4.40-4.47 (m, 1H), 3.95-4.05 (m, 1H), 3.80-3.89 (m, 1H), 3.53-3.65 (m, 6H), 3.32 (s, 1H), 3.23 (s, 2H), 2.98-3.10 (m, 4H), 2.59-2.65 (m, 2H), 2.15-2.27 (m, 1H), 1.95-2.07 (m, 1H), 1.83-1.93 (m, 2H). MS (EI): 531 (MH+).

(2R,4S)-4-hydroxy-N-(4-(2-(4-(4-(3-methoxypropanoyl)piperazin-1-yl)phenyl-amino)pyrimidin-4-yl)phenyl)pyrrolidine-2-carboxamide: $^1$H NMR (400 MHz, d6-DMSO): 10.21 (s, 1H), 9.40 (s, 1H), 8.42-8.46 (d, 1H), 8.09-8.15 (d, 2H), 7.80-7.86 (d, 2H), 7.65-7.71 (d, 2H), 7.27-7.31 (d, 1H), 6.93-6.98 (d, 1H), 4.20-4.26 (m, 1H), 3.88-3.94 (m, 1H), 3.53-3.64 (m, 6H), 3.17 (s, 1H), 2.99-3.10 (m, 4H), 2.89-2.93 (m, 1H), 2.77-2.84 (m, 1H), 2.58-2.64 (m, 3H), 1.99-2.07 (m, 2H), 1.73-1.83 (m, 2H). MS (EI): 546 (MH+).

N-(4-{2-[(3-fluoro-4-morpholin-4-ylphenyl)amino]pyrimidin-4-yl}phenyl)-D-prolinamide: $^1$H NMR (400 MHz, d6-DMSO): 11.07 (s, 1H), 9.89 (s, 1H), 8.46-8.56 (d, 1H), 8.08-8.21 (d, 2H), 7.74-7.91 (m, 3H), 7.47-7.57 (d, 1H), 7.35-7.41 (d, 1H), 6.98-7.08 (m, 1H), 3.70-3.82 (m, 5H), 2.87-3.03 (m, 5H), 2.01-2.16 (m, 1H), 1.92 (s, 2H), 1.75-1.87 (m, 1H), 1.61-1.74 (m, 2H). MS (EI): 463 (MH+).

N-(4-{2-[(4-{4-[3-(methyloxy)propanoyl]piperazin-1-yl}phenyl)amino]pyrimidin-4-yl}phenyl)tetrahydrofuran-3-carboxamide: $^1$H NMR (400 MHz, d6-DMSO): 10.30 (s, 1H), 9.40 (s, 1H), 8.42-8.47 (d, 1H), 8.09-8.15 (d, 2H), 7.74-7.80 (d, 2H), 7.64-7.71 (d, 2H), 7.27-7.30 (d, 1H), 6.92-7.00 (d, 2H), 3.92-3.99 (m, 1H), 3.68-3.84 (m, 4H), 3.53-3.64 (m, 5H), 3.32 (s, 1H), 3.23 (s, 2H), 3.16-3.22 (m, 1H), 2.98-3.10 (m, 4H), 2.59-2.65 (m, 1H), 2.06-2.15 (m, 2H). MS (EI): 531 (MH+).

N-(4-{2-[(4-morpholin-4-ylphenyl)amino]pyrimidin-4-yl}phenyl)-3-pyridin-3-ylpropanamide: $^1$H NMR (400 MHz, d6-DMSO): 10.21 (s, 1H), 9.37 (s, 1H), 8.39-8.51 (m, 3H), 8.08-8.13 (d, 2H), 7.64-7.76 (m, 5H), 7.25-7.35 (m, 2H), 6.91-6.98 (d, 2H), 3.72-3.77 (m, 4H), 3.01-3.08 (m, 4H), 2.91-2.98 (m, 2H), 2.65-2.75 (m, 2H). MS (EI): 481 (MH+).

N-(3-(4-(4-acetamidophenyl)pyrimidin-2-ylamino)phenyl)-2-chlorobenzamide: $^1$H-NMR (400 MHz, d6-DMSO): 10.497 (s, 1H), 10.201 (s, 1H), 9.668 (s, 1H), 8.505 (d, 1H), 8.505 (d, 1H), 8.427 (s, 1H), 8.223 (d, 2H), 7.748 (d, 2H), 7.59 (m, 2H), 7.477 (m, 3H), 7.374 (d, 1H), 7.253 (m, 2H), 2.083 (s, 3H). MS (EI): 458 (MH+).

N-(3-(4-(4-acetamidophenyl)pyrimidin-2-ylamino)phenyl)-2-methylbenzamide: $^1$H-NMR (400 MHz, d6-DMSO): 10.284 (d, 2H), 9.622 (s, 1H), 8.487 (m, 2H), 8.235 (d, 2H), 7.749 (d, 2H), 7.352 (m, 8H), 2.084 (s, 3H). MS (EI): 438 (MH+).

N-(3-(4-(4-acetamoidophenyl)pyrimidin-2-ylamino)phenyl)-2,4-dichlorobenzamide: $^1$H-NMR (400 MHz, d6-DMSO): 10.533 (s, 1H), 10.198 (s, 1H), 9.687 (s, 1H), 8.506 (d, 1H), 8.406 (s, br, 1H), 8.220 (d, 2H), 7.787 (d, 1H), 7.747 (d, 2H), 7.659 (d, 1H), 7.591 (d, 1H), 7.464 (d, 1H), 7.377 (d, 1H), 7.247 (m, 2H), 2.085 (s, 3H). MS (EI): 492 (MH+).

N-(3-(4-(4-acetamidophenyl)pyrimidin-2-ylamino)phenyl)-2,5-dichlorobenzamide: $^1$H-NMR (400 MHz, d6-DMSO): 10.510 (s, 1H), 10.198 (s, 1H), 9.696 (s, 1H), 8.507 (s, 1H), 8.389 (s, 1H), 8.220 (d, 2H), 7.744 (m, 3H), 7.617 (m, 2H), 7.487 (m, 1H), 7.379 (d, 1H), 7.282 (m, 2H), 2.081 (s, 3H). MS (EI): 492 (MH+).

N-(3-(4-(4-acetamidophenyl)pyrimidin-2-ylamino)phenyl)-2-chloro-6-fluoro-3-methoxybenzamide: $^1$H-NMR (400 MHz, d6-DMSO): 10.726 (s, 1H), 10.204 (s, 1H), 9.709 (s, 1H), 8.509 (d, 1H), 8.402 (s, 1H), 8.217 (d, 2H), 7.743 (d, 2H), 7.488 (d, 1H), 7.386 (m, 2H), 7.282 (m, 2H), 7.221 (d, 1H), 3.904 (s, 3H), 2.082 (s, 3H). MS (EI): 506 (MH+).

N-(3-(4-(4-acetamidophenyl)pyrimidin-2-ylamino)phenyl)-2,3-dichlorobenzamide: $^1$H-NMR (400 MHz, d6-DMSO): 10.6 (s, 1H), 10.2 (s, 1H), 9.7 (s, 1H), 8.5 (d, 1H), 8.4 (s, 1H), 8.2 (d, 2H), 7.8 (m, 3H), 7.6 (d, 1H), 7.5 (m, 2H), 7.4 (d, 1H), 7.2 (m, 2H), 2.081 (s, 3H). MS (EI): 492 (MH+).

(R)—N-(4-(2-(4-(4-(pyrrolidine-2-carbonyl)piperazin-1-yl)phenylamino)-pyrimidin-4-yl)phenyl)cyclopropanecarboxamide: $^1$H-NMR (400 MHz, d6-DMSO): 10.476 (s, 1H), 9.406 (s, 1H), 8.448 (d, 1H), 8.124 (d, 2H), 7.767 (m, 4H), 7.287 (d, 1H), 6.977 (d, 2H), 3.85 (m, 1H), 3.65 (m, 4H), 3.0 (m, 4H), 2.95 (m, 1H), 2.6 (m, 1H), 2.0 (m, 1H), 1.8 (m, 1H), 1.613 (m, 3H), 0.84 (m, 4H). MS (EI): 512 (MH+).

N-(4-(2-(4-(4-(2-(piperazin-1-yl)acetyl)piperazin-1-yl)phenylamino)pyrimidin-4-yl)phenyl)cyclopropanecarboxamide: $^1$H-NMR (400 MHz, d6-DMSO): 10.480 (s, 1H), 9.399 (s, 1H), 8.447 (d, 1H), 8.124 (d, 2H), 7.769 (d, 2H), 7.692 (d, 2H), 7.285 (d, 1H), 6.975 (d, 2H), 3.170 (m, 2H), 3.592 (m, 2H), 3.134 (s, 2H), 3.099 (m, 2H), 3.028 (m, 2H), 2.694 (m, 4H), 2.331 (m, 4H), 0.842 (m, 4H). MS (EI): 541 (MH+).

4-(2-(4-morpholinophenylamino)pyrimidin-4-yl)benzamide: $^1$H-NMR (400 MHz, d6-DMSO): 9.5 (s, 1H), 8.5 (d, 1H), 8.2 (d, 2H), 8.15 (s, 1H), 8 (d, 2H), 7.7 (s, 1H), 7.5 (s, 1H), 7.4 (d, 1H), 6.9 (d, 1H), 4.8 (m, 4h), 3.0 (m, 4H). MS (EI): 376 (MH+).

(R)—N-(4-(2-(4-(4-(pyrrolidine-2-carbonyl)piperazin-1-yl)phenylamino)pyrimidin-4-yl)phenyl)cyclopropanecarboxamide: $^1$H-NMR (400 MHz, d6-MeOD): 8.355 (d, 1H), 8.114 (d, 2H), 7.177 (d, 2H), 7.639 (d, 2H), 7.217 (d, 1H), 7.028 (d, 2H), 4.394 (m, 1H), 3.797 (m, 2H), 3.692 (m, 2H), 3.137 (m, 4H), 3.1 (m, 1H), 2.410 (m, 1H), 1.992 (m, 2H), 1.827 (m, 2H), 0.981 (m, 2H), 0.85 (m, 2H). MS (EI): 512 (MH+).

(S)—N-(4-(2-(4-(4-(2-aminopropanoyl)piperazin-1-yl) phenylamino)pyrimidin-4-yl)phenyl)cyclopropanecarboxamide: $^1$H-NMR (400 MHz, MeOD): 8.357 (d, 1H), 8.116 (d, 2H), 7.718 (d, 2H), 7.642 (d, 2H), 7.221 (d, 1H), 7.033 (d, 2H), 4.1 (m, 1H), 3.85 (m, 1H), 3.7 (m, 4H), 3.2 (m, 4H), 1.8 (m, 1H), 1.4 (d, 3H), 0.9 (m, 2H), 0.85 (m, 2H). MS (EI): 486 (MH+).

(R)—N-(4-(2-(4-(4-(2-aminopropanoyl)piperazin-1-yl) phenylamino)pyrimidin-4-yl)phenyl)cyclopropanecarboxamide: $^1$H-NMR (400 MHz, MeOD): 8.4 (d, 1H), 8.15 (d, 2H), 7.8 (d, 2H), 7.6 (d, 2H), 7.2 (d, 1H), 7.0 (d, 2H), 4.0 (m, 1H), 3.7 (m, 4H), 3.2 (m, 4H), 1.8 (m, 1H), 1.3 (d, 3H), 0.9 (m, 2H), 0.85 (m, 2H). MS (EI): 486 (MH+).

(R)—N-(4-(2-(4-(4-acetylpiperazin-1-yl)phenylamino) pyrimidin-4-yl)phenyl)-pyrrolidine-2-carboxamide: $^1$H-NMR (400 MHz, d6-DMSO): 10.193 (s, 1H), 9.411 (s, 1H), 8.452-8.439 (d, 1H), 8.136-8.144 (d, 2H), 7.849-7.828 ((d, 2H), 7.690-7.688 (d, 2H), 7.302-7.289 (d, 1H), 6.971-6.948 (d, 2H), 3.743 (m, 1H), 3.588 (m, 4H), 3.085-3.016 (m, 4H), 2.905 (t, 2H), 2.046 (s, 3H), 1.808 (m, 1H), 1.663 (m, 2H). MS (EI): 486 (MH+).

(R)—N-(4-(2-(4-(4-(2-methoxyacetyl)piperazin-1-yl) phenylamino)pyrimidin-4-yl)phenyl)pyrrolidine-2-carboxamide: $^1$H-NMR (400 MHz, d6-DMSO): 10.198 (s, 1H), 9.414 (s, 1H), 8.452 (d, 1H), 8.136 (d, 2H), 7.850 (d, 2H), 7.691 (d, 2H), 7.302 (d, 1H), 6.970 (d, 2H), 4.136 (s, 2H), 3.744 (m, 1H), 3.599-3.535 (m, 4H), 3.302 (s, 3H), 3.078 (m, 4H), 2.905 (t, 2H), 2.079 (m, 1H), 1.791 (m, 1H), 1.646 ((m, 2H). MS (EI): 516 (MH+).

N-{1-[4-({4-[4-(acetylamino)phenyl]pyrimidin-2-yl}amino)phenyl]pyrrolidin-3-yl}acetamide: NMR (400 MHz, d6-DMSO): 10.20 (s, 1H), 9.20 (s, 1H), 8.60 (s, 1H), 8.15-8.20 (m, 3H), 7.79-7.86 (m, 4H), 7.20 (s, 1H), 6.58 (d, 2H), 4.39 (m, 1H), 3.43 (m, 1H), 3.23 (m, 1H), 3.10 (m, 1H), 2.18 (m, 1H), 2.07 (s, 3H), 1.85 (m, 1H), 1.80 (s, 3H). MS (EI): 431 (MH+).

N-[4-(2-({[4-(3-oxopiperazin-1-yl)phenyl]amino}pyrimidin-4-yl)phenyl]acetamide: NMR (400 MHz, d6-DMSO): 10.22 (s, 1H), 9.40 (s, 1H), 8.41 (s, 1H), 8.06 (d, 2H), 8.02 (s, 1H), 7.65-7.80 (m, 4H), 7.25 (m, 1H), 6.97 (d, 2H), 3.64 (s, 2H), 3.35-3.40 (m, 4H), 2.05 (s, 3H). MS (EI): 403 (MH+).

ethyl N-[4-({4-[4-(acetylamino)phenyl]pyrimidin-2-yl}amino)phenyl]-N-methylglycinate: MS (EI): 420 (MH+).

ethyl 1-[4-({4-[4-(acetylamino)phenyl]pyrimidin-2-yl}amino)phenyl]piperidine-3-carboxylate: NMR (400 MHz, d6-DMSO): 10.40 (s, 1H), 10.00 (s, 2H), 8.65 (d, 1H), 8.14 (d, 2H), 7.78 (d, 2H), 7.50-7.62 (m, 4H), 7.40 (d, 1H), 2.09 (s, 3H), 2.00 (s, 3H). MS (EI): 362 (MH+).

ethyl 1-[4-({4-[4-(acetylamino)phenyl]pyrimidin-2-yl}amino)phenyl]piperidine-3-carboxylate: MS (EI): 460 (MH+).

N-(4-{2-[(4-{bis[2-(methyloxy)ethyl]amino}phenyl) amino]pyrimidin-4-yl}phenyl)acetamide: MS (EI) for $C_{24}H_{29}N_5O_3$: 436 (MH+).

N-[4-(2-{[4-(morpholin-4-ylsulfonyl)phenyl]amino}pyrimidin-4-yl)phenyl]-acetamide: MS (EI) for $C_{22}H_{23}N_5O_4S$: 454 (MH+).

3-hydroxy-3-methyl-N-[4-(2-{[3-(methyloxy)-4-morpholin-4-ylphenyl]amino}pyrimidin-4-yl)phenyl]butanamide: NMR (400 MHz, d6-DMSO): 10.04 (s, 1H), 9.46 (s, 1H), 8.45 (d, 1H), 8.11 (d, 2H), 7.75 (d, 2H), 7.65 (s, 1H), 7.29 (d, 1H), 6.91 (d, 1H), 3.79 (s, 3H), 3.68 (m, 4H), 2.89 (m, 4H), 2.44 (s, 2H), 1.23 (s, 6H). MS (EI) for $C_{26}H_{31}N_5O_4$: 478 (MH+).

1-methyl-N-[4-(2-{[3-(methyloxy)-4-morpholin-4-ylphenyl]amino}pyrimidin-4-yl)phenyl]-D-prolinamide: NMR (400 MHz, d6-DMSO): 10.0 (s, 1H), 9.44 (s, 1H), 8.42 (d, 1H), 8.18 (d, 2H), 7.82 (d, 2H), 7.62 (s, 1H), 7.30 (m, 2H), 6.81 (d, 1H), 3.80 (s, 3H), 3.68 (m, 4H), 2.85-3.10 (m, 6H), 2.37-2.48 (m, 5H), 2.20 (m, 1H), 1.80 (m, 2H). MS (EI) for $C_{27}H_{32}N_6O_3$: 489 (MH+).

N-[4-(2-{[3-(methyloxy)-4-morpholin-4-ylphenyl]amino}pyrimidin-4-yl)phenyl]-D-alaninamide: NMR (400 MHz, d6-DMSO): 11.40 (s, 1H), 10.10 (s, 1H), 8.57 (d, 1H), 8.45 (d, 2H), 8.02 (d, 2H), 7.87 (m, 3H), 7.47 (m, 2H), 4.15 (m, 1H), 3.95-4.10 (m, 7H), 3.58 (m, 4H), 1.48 (d, 3H). MS (EI) for $C_{24}H_{28}N_6O_3$: 449 (MH+).

N-[4-(2-{[3-(methyloxy)-4-morpholin-4-ylphenyl]amino}pyrimidin-4-yl)phenyl]-cyclopropanecarboxamide: NMR (400 MHz, d6-DMSO): 10.45 (s, 1H), 9.43 (s, 1H), 8.42 (d, 1H), 8.17 (d, 2H), 7.75 (d, 2H), 7.64 (s, 1H), 7.15 (m, 2H), 6.84 (d, 1H), 3.80 (s, 3H), 3.75 (m, 4H), 2.96 (m, 4H), 2.52 (m, 2H), 0.80 (m, 2H). MS (EI) for $C_{25}H27N_5O_3$: 446 (MH+).

N-[4-(2-{[3-(methyloxy)-4-morpholin-4-ylphenyl]amino}pyrimidin-4-yl)phenyl]-butanamide: NMR (400 MHz, d6-DMSO): 10.18 (s, 1H), 9.43 (s, 1H), 8.44 (d, 1H), 8.17 (m, 2H), 7.75 (d, 2H), 7.64 (s, 1H), 7.25 (m, 2H), 6.84 (d, 1H), 3.80 (s, 3H), 3.75 (m, 4H), 2.96 (m, 4H), 2.35 (q, 2H), 1.62 (m, 2H), 0.92 (q, 3H). MS (EI) for $C_{25}H_{29}N_5O_3$: 448 (MH+).

N-(4-{2-[(4-{4-[3-(methyloxy)propanoyl]piperazin-1-yl}phenyl)amino]-pyrimidin-4-yl}phenyl)butanamide: NMR (400 MHz, d6-DMSO): 10.18 (s, 1H), 9.40 (s, 1H), 8.41 (d, 1H), 8.17 (d, 2H), 7.78 (d, 2H), 7.68 (d, 2H), 7.24 (s, 1H), 6.94 (d, 2H), 3.60 (m, 6H), 3.21 (s, 3H), 3.0-3.09 (m, 4H), 2.60 (q, 2H), 2.35 (m, 2H), 1.60 (m, 2H), 0.95 (q, 3H). MS (EI) for $C_{28}H_{34}N_6O_3$: 503 (MH+).

O-methyl-N-[4-(2-{[3-(methyloxy)-4-morpholin-4-ylphenyl]amino}pyrimidin-4-yl)phenyl]-L-serinamide: NMR (400 MHz, d6-DMSO): 11.60 (s, 1H), 10.1 (s, 1H), 8.60 (s, 1H), 8.55 (m, 2H), 8.20 (m, 2H), 7.98 (s, 1H), 7.90 (d, 2H), 7.80 (s, 1H), 7.48 (m, 2H), 4.35 (m, 1H), 4.04 (m, 5H), 3.98 (s, 3H), 3.85 (m, 4H), 3.60 (m, 4H). MS (EI) for $C_{25}H_{30}N_6O_4$: 479 (MH+).

N-[4-(2-{[3-(methyloxy)-4-morpholin-4-ylphenyl]amino}pyrimidin-4-yl)phenyl]-D-prolinamide: NMR (400 MHz, d6-DMSO): 11.57 (s, 1H), 10.25 (br, 1H), 10.06 (s, 1H), 8.76 (br, 1H), 8.60 (d, 1H), 8.22 (d, 2H), 8.05 (s, 1H), 7.87 (m, 3H), 7.50 (m, 2H), 4.18-4.52 (m, 5H), 4.08 (m, 2H), 3.99 (s, 3H), 3.62 (m, 4H), 3.30 (m, 2H), 1.95 (m, 2H). MS (EI) for $C_{26}H_{30}N_6O_3$: 475 (MH+).

N-(4-{2-[(4-{4-[3-(methyloxy)propanoyl]piperazin-1-yl}phenyl)amino]-pyrimidin-4-yl}phenyl)cyclopropanecarboxamide: NMR (400 MHz, d6-DMSO): 10.45 (s, 1H), 9.40 (s, 1H), 8.41 (s, 1H), 8.12 (d, 2H), 7.75 (d, 2H), 7.68 (d, 2H), 7.28 (d, 1H), 6.98 (d, 2H), 3.60 (m, 6H), 3.22 (s, 3H), 3.0-3.11 (m, 4H), 6.62 (q, 2H), 0.82 (m, (4H). MS (EI) for $C_{28}H_{32}N_6O_3$: 501 (MH+).

N-{4-[2-({4-[4-(Piperidin-4-ylcarbonyl)piperazin-1-yl] phenyl}amino)-pyrimidin-4-yl]phenyl}-D-prolinamide: $^1$H NMR (400 MHz, d6-DMSO): 11.40 (s, 1H), 10.0 (m, 1H), 9.96 (s, 1H), 9.11 (br d, 1H), 8.7-8.8 (m, 2H), 8.55 (d, 1H), 8.20 (d, 2H), 7.87 (m, 4H), 7.59 (br s, 2H), 7.45 (d, 1H), 4.48 (m, 1H), 3.4-3.5 (m, 4H), 3.25-3.30 (m, 4H) 3.0-3.1 (m, 1H), 2.9-3.0 (m, 2H), 2.4-2.5 (m, 1H), 1.9-2.0 (m, 3H), 1.7-1.9 (m, 4H); MS (EI) for $C_{31}H_{38}N_8O_2$: 555 (MH+).

3-(Methyloxy)-N-{4-[2-({4-[4-(piperidin-4-ylcarbonyl)piperazin-1-yl]phenyl}amino)pyrimidin-4-yl]phenyl}propanamide: $^1$H NMR (400 MHz, d6-DMSO): 10.49 (s, 1H), 9.93 (s, 1H), 9.07 (m, 1H), 8.72 (m, 1H), 8.50 (d, 1H), 8.13 (d, 2H), 7.85 (d, 2H), 7.79 (d, 2H), 7.56 (br s, 2H), 7.42 (d, 1H), 3.61 (t, 2H), 3.3-3.5 (m, 4H), 3.2-3.30 (m, 5H) 3.0-3.1 (m, 1H), 2.85-3.0 (m, 2H), 2.59 (t, 2H), 1.7-1.9 (m, 4H); MS (EI) for $C_{30}H_{37}N_7O_3$: 544 (MH$^+$).

1-Ethyl-3-{4-[2-({4-[4-(piperidin-4-ylcarbonyl)piperazin-1-yl]phenyl}amino)-pyrimidin-4-yl]phenyl}urea: $^1$H NMR (400 MHz, d6-DMSO): 9.96 (s, 1H), 9.20 (s, 1H), 8.93 (m, 1H), 8.65 (m, 1H), 8.46 (d, 1H), 8.09 (d, 2H), 7.79 (m, 2H), 7.58 (d, 2H), 7.41 (m, 3H), 6.51 (br s, 1H), 3.2-3.4 (m, 6H), 3.13 (q, 2H) 3.0-3.1 (m, 1H), 2.9-3.0 (m, 2H), 1.7-1.9 (m, 4H), 1.06 (t, 3H); MS (EI) for $C_{29}H_{36}N_8O_2$: 529 (MH+).

N-(4-{2-[(4-{(4-[3-(Dimethylamino)-2,2-dimethylpropanoyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.44 (d, 1H), 8.11 (d, 2H), 7.74 (d, 2H), 7.69 (d, 2H), 7.28 (d, 1H), 6.96 (d, 2H), 6.57 (br s, 1H), 3.70 (m, 4H), 3.07 (m, 4H) 2.60 (br s, 2H), 2.28 (br s, 6H), 2.09 (s, 3H), 1.23 (s, 6H); MS (EI) for $C_{29}H_{37}N_7O_2$: 516 (MH+).

2-(Methyloxy)-N-(4-{2-[(4-morpholin-4-ylphenyl)amino]pyrimidin-4-yl})phenyl)-ethanesulfonamide: $^1$H NMR (400 MHz, d6-DMSO): 9.39 (s, 1H), 9.40 (s, 1H), 8.44 (d, 1H), 8.11 (d, 2H), 7.67 (d, 2H), 7.31 (d, 2H), 7.26 (d, 1H), 6.94 (d, 2H), 3.74 (m, 4H), 3.67 (t, 2H) 3.43 (t, 2H), 3.18 (s, 3H), 3.05 (m, 4H); MS (EI) for $C_{23}H_{27}N_5O_4S$: 470 (MH+).

3-(Methyloxy)-N-(4-{2-[(4-morpholin-4-ylphenyl)amino]pyrimidin-4-yl}phenyl)propane-1-sulfonamide: MS (EI) for $C_{24}H_{29}N_5O_4S$: 484 (MH+).

3-({4-[4-(acetylamino)phenyl]pyrimidin-2-yl}amino)-N-(tetrahydrofuran-2-ylmethyl)benzamide: $^1$H NMR (400 MHz, d6-DMSO): 10.23 (s, 1H), 9.77 (s, 1H), 8.52 (d, 1H), 8.45 (d, 1H), 8.43 (d, 1H), 8.19 (d, 1H), 8.17 (d, 1H), 7.88-7.86 (m, 1H), 7.76 (s, 1H), 7.74 (s, 1H), 7.43-7.38 (m, 3H), 4.01-3.98 (m, 1H), 3.81-3.76 (m, 2H), 3.65-3.62 (m, 2H), 2.09 (s, 3H), 1.85-1.80 (m, 3H), 1.64-1.61 (m, 1H). MS (EI): 432.5 (MH+).

3-({4-[4-(acetylamino)phenyl]pyrimidin-2-yl}amino)-N-[3-(2-oxopyrrolidin-1-yl)propyl]benzamide: $^1$H NMR (400 MHz, d6-DMSO): 10.23 (s, 1H), 9.78 (s, 1H), 8.52 (d, 1H), 8.49 (s, 1H), 8.41 (t, 1H), 8.19 (dd, 2H), 7.87-7.84 (m, 1H), 7.76 (s, 1H), 7.74 (s, 1H), 7.40-7.38 (m, 3H), 3.27-3.23 (m, 6H), 2.22 (t, 2H), 2.09 (s, 3H), 1.96-1.88 (m, 2H), 1.73-1.70 (m, 2H). MS (EI): 473.5 (MH+).

3-({4-[4-(acetylamino)phenyl]pyrimidin-2-yl}amino)-N-[(3s,5s,7s)-tricyclo-[3.3.1.1~3,7~]dec-1-yl]benzamide: $^1$H NMR (400 MHz, d6-DMSO): 10.21 (s, 1H), 9.73 (s, 1H), 8.52 (d, 1H), 8.35 (s, 1H), 8.16 (d, 2H), 7.84-7.81 (m, 1H), 7.76 (d, 2H), 7.55 (s, 1H), 7.39-7.31 (m, 3H), 2.09 (s, 3H), 1.67 (m, 15H). MS (EI): 482.6 (MH+).

3-({4-[4-(acetylamino)phenyl]pyrimidin-2-yl}amino)-N-[2-(methyloxy)ethyl]-benzamide: $^1$H NMR (400 MHz, d6-DMSO): 10.23 (s, 1H), 9.77 (s, 1H), 8.52 (d, 1H), 8.46 (d, 2H), 8.19 (d, 1H), 8.18 (d, 1H), 7.88-7.85 (m, 1H), 7.77 (s, 1H), 7.75 (s, 1H), 7.43-7.39 (m, 3H), 3.48-3.41 (m, 4H), 3.29-3.27 (m, 3H), 2.09 (s, 3H). MS (EI): 406.3 (MH+).

N-[4-(2-{[3-(1,3-thiazolidin-3-ylcarbonyl)phenyl]amino}pyrimidin-4-yl)phenyl]-acetamide: $^1$H NMR (400 MHz, d6-DMSO): 10.23 (s, 1H), 9.84 (s, 1H), 8.52 (d, 1H), 8.19-8.12 (m, 3H), 7.90-7.87 (m, 1H), 7.77-7.75 (m, 2H), 7.43-7.38 (m, 2H), 7.11 (d, 1H), 4.64 (m, 2H), 3.77 (m, 2H), 3.06 (m, 2H), 2.09 (s, 3H). MS (EI): 420.6 (MH+).

N-{4-[2-({3-[(4-pyridin-2-ylpiperazin-1-yl)carbonyl]phenyl}amino)pyrimidin-4-yl]phenyl}acetamide: $^1$H NMR (400 MHz, d6-DMSO): 10.20 (s, 1H), 9.83 (s, 1H), 8.53 (d, 1H), 8.14-8.11 (m, 3H), 8.04 (t, 1H), 7.89-7.86 (m, 1H), 7.73 (d, 2H), 7.57-7.53 (m, 1H), 7.43-7.39 (m, 2H), 7.03-7.01 (m, 1H), 6.83 (d, 1H), 6.69-6.66 (m, 1H), 3.74 (m, 4H), 3.49 (m, 4H), 2.08 (s, 3H). MS (EI): 494.5 (MH+).

3-({4-[4-(acetylamino)phenyl]pyrimidin-2-yl}amino)-N-{[2-(methyloxy)phenyl]-methyl}benzamide: $^1$H NMR (400 MHz, d6-DMSO): 10.22 (s, 1H), 9.79 (s, 1H), 8.80 (d, 1H), 8.53-8.49 (m, 2H), 8.19 (dd, 2H), 7.94-7.91 (m, 1H), 7.74 (d, 2H), 7.52-7.49 (m, 1H), 7.44-7.39 (m, 1H), 7.26-7.19 (m, 2H), 6.99 (dd, 1H), 6.93-6.89 (m, 1H), 4.46 (d, 2H), 3.84 (s, 3H), 2.09 (s, 3H). MS (EI): 468.5 (MH+).

3-({4-[4-(acetylamino)phenyl]pyrimidin-2-yl}amino)-N-{[3-(methyloxy)phenyl]-methyl}benzamide: $^1$H NMR (400 MHz, d6-DMSO): 10.22 (s, 1H), 9.79 (s, 1H), 8.97 (t, 1H), 8.53-8.49 (m, 2H), 8.20-8.18 (m, 2H), 7.93-7.90 (m, 1H), 7.75 (d, 2H), 7.48-7.46 (m, 1H), 7.43-7.39 (m, 1H), 7.27-7.23 (m, 1H), 6.92-6.90 (m, 2H), 6.83-6.80 (m, 1H), 4.47 (d, 2H), 3.71 (s, 3H), 2.09 (s, 3H). MS (EI): 468.4 (MH+).

3-({4-[4-(acetylamino)phenyl]pyrimidin-2-yl}amino)-N-[(2-fluorophenyl)methyl]-benzamide: $^1$H NMR (400 MHz, d6-DMSO): 10.22 (s, 1H), 9.79 (s, 1H), 8.97 (t, 1H), 8.53-8.49 (m, 2H), 8.19-8.17 (m, 2H), 7.93-7.90 (m, 1H), 7.75 (d, 2H), 7.50-7.47 (m, 1H), 7.43-7.37 (m, 2H), 7.32-7.29 (m, 1H), 7.22-7.16 (m, 2H), 4.40 (d, 2H), 2.09 (s, 3H). MS (EI): 456.4 (MH+).

3-({4-[4-(acetylamino)phenyl]pyrimidin-2-yl}amino)-N-[(4-fluorophenyl)methyl]-benzamide: $^1$H NMR (400 MHz, d6-DMSO): 10.22 (s, 1H), 9.79 (s, 1H), 9.00 (t, 1H), 8.53-8.50 (m, 2H), 8.19-8.17 (m, 2H), 7.90-7.88 (m, 1H), 7.75 (d, 2H), 7.47-7.36 (m, 4H), 7.19-7.13 (m, 2H), 4.47 (d, 2H), 2.09 (s, 3H). MS (EI): 456.5 (MH+).

3-({4-[4-(acetylamino)phenyl]pyrimidin-2-yl}amino)-N-(3,3-dimethylbutyl)-benzamide: $^1$H NMR (400 MHz, d6-DMSO): 10.21 (s, 1H), 9.76 (s, 1H), 8.53-8.51 (d, 1H), 8.41 (s, 1H), 8.33 (t, 1H), 8.18-8.17 (m, 2H), 7.88-7.85 (m, 1H), 7.75 (d, 2H), 7.39-7.37 (m, 2H), 3.30-3.26 (m, 2H), 2.08 (s, 3H), 1.48-1.44 (m, 2H), 0.94 (s, 9H). MS (EI): 432.4 (MH+).

N-[4-(2-{[3-(thiomorpholin-4-ylcarbonyl)phenyl]amino}pyrimidin-4-yl)phenyl]-acetamide: $^1$H NMR (400 MHz, d6-DMSO): 10.23 (s, 1H), 9.82 (s, 1H), 8.53 (d, 1H), 8.15-8.20 (m, 2H), 7.99 (t, 1H), 7.85-7.82 (m, 1H), 7.76 (d, 2H), 7.41-7.37 (m, 2H), 6.98-6.96 (m, 1H), 3.88 (m, 4H), 3.60 (m, 4H), 2.09 (s, 3H). MS (EI): 434.5 (MH+).

3-({4-[4-(acetylamino)phenyl]pyrimidin-2-yl}amino)-N-(2-thienylmethyl)benzamide: $^1$H NMR (400 MHz, d6-DMSO): 10.22 (s, 1H), 9.79 (s, 1H), 9.09 (t, 1H), 8.53-8.50 (m, 2H), 8.18 (d, 2H), 7.89-7.86 (m, 1H), 7.75 (d, 2H), 7.44-7.38 (m, 3H), 7.03 (m, 1H), 6.98-6.96 (m, 1H), 4.64 (d, 2H), 2.09 (s, 3H). MS (EI): 444.4 (MH+).

3-({4-[4-(acetylamino)phenyl]pyrimidin-2-yl}amino)-N-[3-(dimethylamino)-propyl]benzamide: $^1$H NMR (400 MHz, d6-DMSO): 10.22 (s, 1H), 9.79 (s, 1H), 8.74 (m, 1H), 8.55-8.50 (m, 2H), 8.21-8.18 (m, 2H), 7.95-7.87 (m, 1N), 7.75 (d, 2H), 7.45-7.40 (m, 2H), 3.05 (s, 2H), 2.75 (s, 6H), 2.55-2.54 (m, 2H), 2.09 (s, 3H), 1.25-1.21 (m, 2H). MS (EI): 433.4 (MH+).

3-({4-[4-(acetylamino)phenyl]pyrimidin-2-yl}amino)-N-[2-(2-chlorophenyl)-ethyl]benzamide: $^1$H NMR (400 MHz, d6-DMSO): 10.21 (s, 1H), 9.77 (s, 1H), 8.54-8.51 (m, 2H), 8.44 (m, 1H), 8.18 (d, 2H), 7.88-7.86 (m, 1H), 7.75 (d, 2H), 7.45-7.36 (m, 4H), 7.28-7.25 (m, 2H), 3.55-3.50 (m, 2H), 3.01-2.98 (m, 2H), 2.08 (s, 3H). MS (EI): 486.8 (MH+).

3-({4-[4-(acetylamino)phenyl]pyrimidin-2-yl}amino)-N-{[2-(trifluoromethyl)-phenyl]methyl}benzamide: $^1$H NMR (400 MHz, d6-DMSO): 10.21 (s, 1H), 9.81 (s, 1H), 9.07 (t, 1H), 8.53-8.49 (m, 2H), 8.19-8.17 (m, 2H), 7.96-7.94 (m, 1H), 7.75-7.72 (m, 2H), 7.55-7.39 (m, 6H), 4.68 (d, 2H), 2.08 (s, 3H). MS (EI): 506.5 (MH+).

3-({4-[4-(acetylamino)phenyl]pyrimidin-2-yl)}amino)-N-{[3-(trifluoromethyl)-phenyl]methyl}benzamide: ¹H NMR (400 MHz, d6-DMSO): 10.21 (s, 1H), 9.80 (s, 1H), 9.10 (t, 1H), 8.53-8.49 (m, 2H), 8.19-8.17 (m, 2H), 7.94-7.91 (m, 1H), 7.74 (d, 2H), 7.68-7.58 (m, 3H), 7.48-7.39 (m, 3H), 4.58 (d, 2H), 2.09 (s, 3H). MS (EI): 506.4 (MH+).

3-({4-[4-(acetylamino)phenyl]pyrimidin-2-yl}amino)-N-{[4-(trifluoromethyl)-phenyl]methyl}benzamide: ¹H NMR (400 MHz, d6-DMSO): 10.21 (s, 1H), 9.80 (s, 1H), 9.10 (t, 1H), 8.52 (m, 2H), 8.18 (d, 2H), 7.91-7.89 (m, 1H), 7.75-7.69 (m, 4H), 7.55 (d, 2H), 7.49-7.38 (m, 3H), 4.58 (d, 2H), 2.08 (s, 3H). MS (EI): 506.5 (MH+).

3-({4-[4-(acetylamino)phenyl]pyrimidin-2-yl}amino)-N-[(2,4-difluorophenyl)-methyl]benzamide: ¹H NMR (400 MHz, d6-DMSO): 10.21 (s, 1H), 9.79 (s, 1H), 8.98 (t, 1H), 8.52 (m, 2H), 8.18 (d, 2H), 7.91-7.89 (m, 1H), 7.54 (d, 2H), 7.47-7.38 (m, 4H), 7.27-7.22 (m, 1H), 7.09-7.04 (m, 1H), 4.48 (d, 2H), 2.09 (s, 3H). MS (EI): 474.4 (MH+).

3-({4-[4-(acetylamino)phenyl]pyrimidin-2-yl}amino)-N-ethyl-N-methylbenzamide: ¹H NMR (400 MHz, d6-DMSO): 10.23 (s, 1H), 9.80 (s, 1H), 8.53 (d, 1H), 8.13 (d, 2H), 7.76-7.74 (m, 2H), 7.40-7.32 (m, 3H), 6.94 (m, 2H), 3.28-3.24 (m, 2H), 2.94 (m, 3H), 2.09 (s, 3H), 1.15-1.08 (m, 3H). MS (EI): 390.4 (MH+).

3-({4-[4-(acetylamino)phenyl]pyrimidin-2-yl}amino)-N-({4-[(trifluoromethyl)-oxy]phenyl)}methyl)benzamide: ¹H NMR (400 MHz, d6-DMSO): 10.21 (s, 1H), 9.79 (s, 1H), 9.04 (t, 1H), 8.52 (m, 2H), 8.18 (d, 2H), 7.91-7.88 (m, 1H), 7.75 (d, 2H), 7.48-7.39 (m, 4H), 7.34-7.32 (m, 2H), 4.51 (d, 2H), 2.09 (s, 3H). MS (EI): 522.5 (MH+).

N-{4-[2-({3-[(4-acetylpiperazin-1-yl)carbonyl]phenyl}amino)pyrimidin-4-yl]-phenyl}acetamide: ¹H NMR (400 MHz, d6-DMSO): 10.22 (s, 1N), 9.82 (s, 1H), 8.53 (t, 1H), 8.19 (d, 2H), 8.14-8.12 (m, 2H), 7.84-7.84 (m, 1H), 7.75 (d, 2H), 7.40-7.38 (m, 2H), 3.53-3.44 (m, 8H), 2.09 (s, 6H). MS (EI): 459.5 (MH+).

3-({4-[4-(acetylamino)phenyl]pyrimidin-2-yl}amino)-N-(cyclopropylmethyl)-benzamide: ¹H NMR (400 MHz, d6-DMSO): 10.22 (s, 1H), 9.77 (s, 1H), 8.53-8.50 (m, 2H), 8.48 (d, 1H), 8.19 (dd, 2H), 7.86-7.84 (m, 1H), 7.75 (d, 2H), 7.41-7.38 (m, 2H), 3.17-3.14 (m, 2H), 2.09 (s, 3H), 1.06 (m, 1H), 0.45-0.42 (m, 2H), 0.25-0.23 (m, 2H). MS (EI): 402.5 (MH+).

3-({4-[4-(acetylamino)phenyl]pyrimidin-2-yl}amino)-N-[2-(2-fluorophenyl)-ethyl]benzamide: ¹H NMR (400 MHz, d6-DMSO): 10.21 (s, 1H), 9.77 (s, 1H), 8.54-8.51 (m, 2H), 8.44 (m, 1H), 8.20-8.17 (m, 2H), 7.88-7.86 (m, 1H), 7.75 (d, 2H), 7.40-7.26 (m, 4H), 7.18-7.13 (m, 2H), 3.52-3.49 (m, 2H), 2.92-3.88 (m, 2H), 2.09 (s, 3H). MS (EI): 470.4 (MH+).

N-[4-(2-{[3-(pyrrolidin-1-ylcarbonyl)phenyl]amino}pyrimidin-4-yl)phenyl]-acetamide: ¹H NMR (400 MHz, d6-DMSO): 10.22 (s, 1H), 9.78 (s, 1H), 8.53 (d, 1H), 8.20-8.12 (m, 4H), 7.83 (d, 1H), 7.76-7.73 (m, 2H), 7.39-7.35 (m, 2H), 3.50-3.40 (m, 4H), 2.09 (s, 3H), 1.95-1.80 (m, 4H). MS (EI): 402.5 (MH+).

N-{4-[2-({3-[(4-pyrimidin-2-ylpiperazin-1-yl)carbonyl]phenyl}amino)pyrimidin-4-yl]phenyl}acetamide: ¹H NMR (400 MHz, d6-DMSO): 10.20 (s, 1H), 9.83 (s, 1H), 8.53 (d, 2H), 8.39 (d, 1H), 8.14-8.12 (m, 2H), 8.04 (t, 1H), 7.89-7.87 (m, 1H), 7.74 (d, 1H), 7.43-7.38 (m, 2H), 7.03-7.01 (m, 1H), 6.67 (t, 2H), 3.81 (m, 4H), 3.73 (m, 4H), 2.08 (s, 3H). MS (EI): 495.6 (MH+).

N-{4-[2-({4-[4-(9H-fluoren-2-ylmethyl)piperazin-1-yl]phenyl}amino)pyrimidin-4-yl]phenyl}acetamide: ¹H NMR (400 MHz, d6-DMSO): 10.20 (s, 1H), 9.35 (s, 1H), 8.43 (d, 1H), 8.11 (d, 2H), 7.87 (t, 2H), 7.73 (d, 2H), 7.65 (d, 2H), 7.59-7.56 (m, 2H), 7.37-7.25 (m, 4H), 6.92 (d, 2H), 3.92 (s, 2H), 3.60 (s, 2H), 3.10 (m, 4H), 2.56 (m, 4H), 2.08 (s, 3H). MS (EI): 567.7 (MH+).

N-(4-{2-[(4-{4-[(3-methyl-2-thienyl)methyl]piperazin-1-yl}phenyl)amino]pyrimidin-4-yl}phenyl)acetamide: ¹H NMR (400 MHz, d6-DMSO): 10.20 (s, 1H), 9.35 (s, 1H), 8.43 (d, 1H), 8.11 (d, 2H), 7.73 (d, 2H), 7.65 (d, 2H), 7.33 (d, 1H), 7.26 (d, 1H), 6.92 (d, 2H), 6.85 (d, 1H), 3.63 (s, 2H), 3.07 (m, 4H), 2.56 (m, 4H), 2.17 (s, 3H), 2.08 (s, 3H). MS (EI): 499.5 (MH+).

N-(4-{2-[(4-{4-[(5-ethylfuran-2-yl)methyl]piperazin-1-yl}phenyl)amino]-pyrimidin-4-yl}phenyl)acetamide: ¹H NMR (400 MHz, d6-DMSO): 10.20 (s, 1H), 9.35 (s, 1H), 8.43 (d, 1H), 8.11 (d, 2H), 7.73° (d, 2H), 7.64 (d, 2H), 7.26 (d, 1H), 6.92 (d, 2H), 6.18 (d, 1H), 6.01 (d, 1H), 3.48 (s, 2H), 3.07 (m, 4H), 2.62-2.56 (m, 6H), 2.09 (s, 3H), 1.16 (t, 3H). MS (EI): 497.6 (MH+).

N-(4-{2-[(4-{4-[(3-{[4-(1,1-dimethylethyl)phenyl]oxy}phenyl)methyl]piperazin-1-yl}phenyl)amino]pyrimidin-4-yl}phenyl)acetamide: ¹H NMR (400 MHz, d6-DMSO): 10.20 (s, 1H), 9.35 (s, 1H), 8.43 (d, 1H), 8.11 (d, 2H), 7.74 (d, 2H), 7.64 (d, 2H), 7.42-7.38 (m, 2H), 7.33 (t, 1H), 7.26 (d, 1H), 7.08 (d, 1H), 6.97-6.86 (m, 6H), 3.52 (s, 2H), 3.06 (m, 4H), 2.52 (m, 4H), 2.09 (s, 3H), 1.27 (s, 9H). MS (EI): 627.7 (MH+).

N-{4-[2-({4-[4-(3-thienylmethyl)piperazin-1-yl]phenyl}amino)pyrimidin-4-yl]-phenyl}acetamide: ¹H NMR (400 MHz, d6-DMSO): 10.20 (s, 1H), 9.35 (s, 1H), 8.43 (d, 1H), 8.11 (d, 2H), 7.73 (d, 2H), 7.64 (d, 2H), 7.51-7.45 (m, 1H), 7.35 (d, 1H), 7.29-7.25 (m, 1H), 7.08-7.04 (m, 1H), 6.91 (d, 2H), 3.53 (s, 2H), 3.07 (m, 4H), 2.52 (m, 4H), 2.09 (s, 3H). MS (EI): 485.6 (MH+).

methyl 4-({4-[4-({4-[4-(acetylamino)phenyl]pyrimidin-2-yl}amino)-phenyl]piperazin-1-yl}methyl)benzoate: ¹H NMR (400 MHz, d6-DMSO): 10.20 (s, 1H), 9.35 (s, 1H), 8.43 (d, 1H), 8.11 (d, 2H), 7.94 (d, 2H), 7.73 (d, 2H), 7.65 (d, 2H), 7.50 (d, 2H), 7.26 (d, 1H), 6.92 (d, 2H), 3.85 (s, 3H), 3.61 (s, 2H), 3.09 (m, 4H), 2.54 (m, 4H), 2.09 (s, 3H). MS (EI): 537.7 (MH+).

N-(4-{2-[(4-{4-[3-(methylthio)propyl]piperazin-1-yl}phenyl)amino]pyrimidin-4-yl}phenyl)acetamide: ¹H NMR (400 MHz, d6-DMSO): 10.21 (s, 1H), 9.36 (s, 1H), 8.43 (d, 1H), 8.11 (d, 2H), 7.74 (d, 2H), 7.65 (d, 2H), 7.26 (d, 1H), 6.92 (d, 2H), 3.34 (m, 4H), 3.07 (m, 4H), 2.39 (m, 4H), 2.09 (s, 3H), 2.03 (m, 3H), 1.75-1.68 (m, 2H). MS (EI): 477.5 (MH+).

N-(4-{2-[(4-{4-[(4-{[3-(dimethylamino)propyl]oxy}phenyl)methyl]piperazin-1-yl}phenyl)amino]pyrimidin-4-yl}phenyl)acetamide: ¹H NMR (400 MHz, d6-DMSO): 10.20 (s, 1H), 9.35 (s, 1H), 8.43 (d, 1H), 8.11 (d, 2H), 7.73 (d, 2H), 7.64 (d, 2H), 7.26-7.21 (m, 3H), 6.92-6.87 (m, 4H), 3.97 (t, 2H), 3.44 (m, 6H), 3.06 (m, 4H), 2.37 (t, 2H), 2.16 (s, 6H), 2.09 (s, 3H), 1.87-1.82 (m, 2H). MS (EI): 580.7 (MH+).

N-[4-(2-{[4-(4-{2-[(phenylmethyl)oxy]ethyl}piperazin-1-yl)phenyl]amino}pyrimidin-4-yl)phenyl]acetamide: ¹H NMR (400 MHz, d6-DMSO): 10.20 (s, 1H), 9.35 (s, 1H), 8.43 (d, 1H), 8.11 (d, 2H), 7.74 (d, 2H), 7.65 (d, 2H), 7.38-7.26 (m, 6H), 6.92 (d, 2H), 4.50 (s, 2H), 3.59 (m, 3H), 3.07 (m, 3H), 2.58 (m, 6H), 2.09 (s, 3H). MS (EI): 523.5 (MH+).

N-(4-{2-[(4-{4-[(2-chloroquinolin-3-yl)methyl]piperazin-1-yl}phenyl)amino]-pyrimidin-4-yl}phenyl)acetamide: ¹H NMR (400 MHz, d6-DMSO): 10.20 (s, 1H), 9.37 (s, 1H), 8.49 (s, 1H), 8.44 (d, 1H), 8.13-8.09 (m, 3H), 7.96 (d, 1H), 7.83-7.79 (m, 1H), 7.74 (d, 1H), 7.69-7.65 (m, 3H), 7.26

(d, 2H), 6.95 (d, 2H), 3.78 (s, 2H), 3.15 (m, 4H), 2.69 (m, 4H), 2.09 (s, 3H). MS (EI): 565.1 (MH+).

N-{4-[2-({4-[4-(2,2'-bithien-5-ylmethyl)piperazin-1-yl]phenyl}amino)-pyrimidin-4-yl]phenyl}acetamide: $^1$H NMR (400 MHz, d6-DMSO): 10.20 (s, 1H), 9.36 (s, 1H), 8.43 (d, 1H), 8.11 (d, 2H), 7.74 (d, 2H), 7.65 (d, 2H), 7.49 (dd, 1H), 7.27-7.25 (m, 2H), 7.15 (d, 1H), 7.09-7.07 (m, 1H), 6.96-6.92 (m, 3H), 3.73 (s, 2H), 3.10 (m, 4H), 2.59 (m, 4H), 2.09 (s, 3H). MS (EI): 567.6 (MH+).

N-[4-(2-{[4-(4-{[4-(2-thienyl)phenyl]methyl}piperazin-1-yl)phenyl]amino}-pyrimidin-4-yl)phenyl]acetamide: $^1$H NMR (400 MHz, d6-DMSO): 10.20 (s, 1H), 9.36 (s, 1H), 8.43 (d, 1H), 8.11 (d, 2H), 7.73 (d, 2H), 7.66-7.62 (m, 4H), 7.54-7.50 (m, 2H), 7.38 (d, 2H), 7.26 (d, 1H), 7.15-7.13 (m, 1H), 6.92 (d, 2H), 3.54 (s, 2H), 3.09 (m, 4H), 2.55-2.52 (m, 4H), 2.09 (s, 3H). MS (EI): 561.6 (MH+).

N-(4-{2-[(4-{4-[(4-cyanophenyl)methyl]piperazin-1-yl}phenyl)amino]-pyrimidin-4-yl}phenyl)acetamide: $^1$H NMR (400 MHz, d6-DMSO): 10.20 (s, 1H), 9.36 (s, 1H), 8.43 (d, 1H), 8.11 (d, 2H), 7.82 (d, 2H), 7.73 (d, 2H), 7.65 (d, 2H), 7.56 (d, 2H), 7.26 (d, 1H), 6.92 (d, 2H), 3.63 (s, 2H), 3.10-3.08 (m, 4H), 2.54-2.52 (m, 4H), 2.09 (s, 3H). MS (EI): 504.5 (MH+).

N-[4-(2-{[4-(4-{[2,5-bis(methyloxy)phenyl]methyl}piperazin-1-yl)phenyl]-amino}pyrimidin-4-yl)phenyl]acetamide: $^1$H NMR (400 MHz, d6-DMSO): 10.20 (s, 1H), 9.35 (s, 1H), 8.43 (d, 1H), 8.11 (d, 2H), 7.74 (d, 2H), 7.65 (d, 2H), 7.26 (d, 1H), 6.95-6.90 (m, 4H), 6.81-6.78 (m, 1H), 3.74 (s, 3H), 3.70 (s, 3H), 3.50 (s, 2H), 3.09 (m, 4H), 2.55 (m, 4H), 2.09 (s, 3H). MS (EI): 539.7 (MH+).

N-{4-[2-({4-[4-(2,2-diphenylethyl)piperazin-1-yl]phenyl}amino)pyrimidin-4-yl]phenyl}acetamide: $^1$H NMR (400 MHz, d6-DMSO): 10.20 (s, 1H), 9.35 (s, 1H), 8.43 (d, 1H), 8.11 (d, 2H), 7.82 (d, 2H), 7.65-7.59 (m, 6H), 7.50-7.46 (m, 4H), 7.26 (d, 1H), 7.21 (d, 2H), 6.92 (d, 2H), 4.45 (t, 1H), 3.61 (t, 2H), 3.09 (m, 4H), 2.54 (m, 4H), 2.09 (s, 3H). MS (EI): 569.6 (MH+).

N-{4-[2-({4-[4-(1H-pyrrol-2-ylmethyl)piperazin-1-yl]phenyl}amino)pyrimidin-4-yl]phenyl}acetamide: $^1$H NMR (400 MHz, d6-DMSO): 10.71 (s, 1H), 10.20 (s, 1H), 9.35 (s, 1H), 8.43 (d, 1H), 8.11 (d, 2H), 7.73 (d, 2H), 7.64 (d, 2H), 7.26 (d, 1H), 6.91 (d, 2H), 6.65-6.63 (m, 1H), 5.94-5.90 (m, 2H), 3.44 (s, 2H), 3.06 (m, 4H), 2.48 (m, 4H), 2.09 (s, 3H). MS (EI): 468.6 (MH+).

N-[4-(2-{[4-(4-propylpiperazin-1-yl)phenyl]amino}pyrimidin-4-yl)phenyl]-acetamide: $^1$H NMR (400 MHz, d6-DMSO): 10.22 (s, 1H), 9.36 (s, 1H), 8.43 (d, 1H), 8.11 (d, 2H), 7.73 (d, 2H), 7.65 (d, 2H), 7.26 (d, 1H), 6.92 (d, 2H), 3.06 (m, 4H), 2.27 (m, 4H), 2.08 (s, 3H), 1.80 (s, 2H), 1.48 (m, 2H), 0.88 (t, 3H). MS (EI): 431.6 (MH+).

N-[4-(2-{[4-(4-butylpiperazin-1-yl)phenyl]amino}pyrimidin-4-yl)phenyl]acetamide: $^1$H NMR (400 MHz, d6-DMSO): 10.22 (s, 1H), 9.36 (s, 1H), 8.43 (d, 1H), 8.12 (d, 2H), 7.74 (d, 2H), 7.64 (d, 2H), 7.25 (d, 1H), 6.92 (d, 2H), 3.07 (m, 4H), 2.31 (m, 4H), 2.09 (s, 3H), 1.87 (m, 2H), 1.44 (m, 2H), 1.30 (m, 2H), 0.90 (t, 3H). MS (EI): 445.6 (MH+).

N-{4-[2-({4-[4-(cyclopropylmethyl)piperazin-1-yl]phenyl}amino)pyrimidin-4-yl]phenyl}acetamide: $^1$H NMR (400 MHz, d6-DMSO): 10.22 (s, 1H), 9.36 (s, 1H), 8.43 (d, 1H), 8.10 (d, 2H), 7.73 (d, 2H), 7.65 (d, 2H), 7.25 (d, 1H), 6.92 (d, 2H), 3.08 (m, 4H), 2.58 (m, 4H), 2.22 (d, 2H), 2.09 (s, 3H), 1.86 (s, 1H), 0.49 (m, 2H), 0.09 (m, 2H). MS (EI): 443.6 (MH+).

N-[4-(2-{[4-(4-pentanoylpiperazin-1-yl)phenyl]amino}pyrimidin-4-yl)phenyl]-acetamide: $^1$H NMR (400 MHz, d6-DMSO): 10.22 (s, 1H), 9.40 (s, 1H), 8.44 (d, 1H), 8.11 (d, 2H), 7.74 (d, 2H), 7.68 (d, 2H), 7.28 (d, 1H), 6.96 (d, 2H), 3.60 (m, 4H), 3.07 (m, 2H), 3.02 (m, 2H), 2.35 (t, 2H), 2.09 (s, 3H), 1.49 (m, 2H), 1.31 (m, 2H), 0.89 (t, 3H). MS (EI): 473.6 (MH+).

N-{4-[2-({4-[4-(pyridin-2-ylcarbonyl)piperazin-1-yl]phenyl}amino)pyrimidin-4-yl]phenyl}acetamide: $^1$H NMR (400 MHz, d6-DMSO): 10.22 (s, 1H), 9.41 (s, 1H), 8.62 (d, 1H), 8.44 (d, 1H), 8.10 (d, 2H), 7.95 (t, 1H), 7.74 (d, 2H), 7.69 (d, 2H), 7.61 (d, 1H), 7.27 (d, 1H), 6.97 (d, 2H), 3.82 (t, 2H), 3.57 (t, 2H), 3.18 (t, 2H), 3.06 (t, 2H), 2.09 (s, 3H). MS (EI): 494.6 (MH+).

N-{4-[2-({4-[4-(pyridin-3-ylcarbonyl)piperazin-1-yl]phenyl}amino)pyrimidin-4-yl]phenyl}acetamide: $^1$H NMR (400 MHz, d6-DMSO): 10.22 (s, 1H), 9.41 (s, 1H), 8.68 (m, 2H), 8.44 (d, 1H), 8.10 (d, 2H), 7.89 (d, 1H), 7.74 (d, 2H), 7.69 (d, 2H), 7.51 (m, 1H), 7.28 (d, 2H), 3.80 (m, 2H), 3.49 (m, 2H), 3.18 (m, 2H), 3.09 (m, 2H), 2.09 (s, 3H). MS (EI): 494.6 (MH+).

N-{4-[2-({4-[4-(pyridin-4-ylcarbonyl)piperazin-1-yl]phenyl}amino)pyrimidin-4-yl]phenyl}acetamide: $^1$H NMR (400 MHz, d6-DMSO): 10.22 (s, 1H), 9.41 (s, 1H), 8.69 (d, 2H), 8.44 (d, 1H), 8.10 (d, 2H), 7.74 (d, 2H), 7.69 (d, 2H), 7.44 (d, 2H), 7.28 (d, 1H), 6.96 (d, 2H), 3.79 (m, 2H), 3.41 (m, 2H), 3.18 (m, 2H), 3.07 (m, 2H), 2.09 (s, 3H). MS (EI): 494.6 (MH+).

N-{4-[2-({4-[4-(1H-pyrazol-4-ylcarbonyl)piperazin-1-yl]phenyl}amino)pyrimidin-4-yl]phenyl}acetamide: $^1$H NMR (400 MHz, d6-DMSO): 10.22 (s, 1H), 9.41 (s, 1H), 8.44 (d, 1H), 8.10 (d, 2H), 7.75-7.68 (m, 4H), 7.28 (d, 2H), 6.97 (d, 3H), 3.75 (m, 4H), 3.11 (m, 4H), 2.09 (s, 3H). MS (EI): 483.5 (MH+).

N-(4-{2-[(4-{4-[(1-acetylpiperidin-4-yl)carbonyl]piperazin-1-yl}phenyl)amino]-pyrimidin-4-yl}phenyl)acetamide: $^1$H NMR (400 MHz, d6-DMSO): 10.21 (s, 1H), 9.41 (s, 1H), 8.44 (d, 1H), 8.10 (d, 2H), 7.74 (d, 2H), 7.69 (d, 2H), 7.26 (d, 1H), 6.97 (d, 2H), 3.65 (m, 4H), 3.02 (m, 8H), 2.62 (m, 1H), 2.09 (s, 3H), 1.99 (s, 3H), 1.66 (m, 2H), 1.56 (m, 2H). MS (EI): 542.7 (MH+).

N-(4-(2-(4-(4-(2-cyclopropylacetyl)piperazin-1-yl)phenylamino)pyrimidin-4-yl)phenyl)acetamide: $^1$H NMR (400 MHz, d6-DMSO): 10.22 (s, 1H), 9.40 (s, 1H), 8.44 (d, 1H), 8.10 (d, 2H), 7.54 (d, 2H), 7.68 (d, 2H), 7.28 (d, 1H), 6.96 (d, 2H), 3.59 (m, 4H), 3.04 (m, 4H), 2.30 (d, 2H), 2.09 (s, 3H), 0.97 (m, 1H), 0.45 (m, 2H), 0.14 (m, 2H). MS (EI): 471.6 (MH+).

N-(4-{2-[(4-{4-[3-(methyloxy)propanoyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.44 (d, 1H), 8.10 (d, 2H), 7.74 (d, 2H), 7.68 (d, 2H), 7.27 (d, 1H), 6.95 (d, 2H), 3.58 (m, 6H), 3.23 (s, 3H), 3.08 (m, 2H), 3.02 (m, 2H), 2.62 (t, 2H), 2.09 (s, 3H). MS (EI): 475.6 (MH+).

N-{4-[2-({4-[4-(2-{[2-(methyloxy)ethyl]oxy}acetyl)piperazin-1-yl]phenyl}amino)-pyrimidin-4-yl]phenyl}acetamide: $^1$H NMR (400 MHz, d6-DMSO): 10.23 (s, 1H), 9.40 (s, 1H), 8.44 (d, 1H), 8.10 (d, 2H), 7.74 (d, 2H), 7.68 (d, 1H), 7.27 (d, 1H), 6.96 (d, 2H), 4.20 (s, 2H), 3.58 (m, 6H), 3.47 (m, 2H), 3.25 (s, 3H), 3.06 (m, 4H), 2.09 (s, 3H). MS (EI): 505.6 (MH+).

N-(4-(2-(4-(4-(2-(pyridin-3-yl)acetyl)piperazin-1-yl)phenylamino)pyrimidin-4-yl)phenyl)acetamide: $^1$H NMR (400 MHz, d6-DMSO): 10.22 (s, 1H), 9.41 (s, 1H), 8.44 (m, 3H), 8.10 (d, 2H), 7.75 (d, 2H), 7.68 (d, 2H), 7.64 (m, 1H), 7.34 (m, 1H), 7.28 (d, 1H), 6.96 (d, 1H), 3.83 (s, 2H), 3.70 (m, 2H), 3.63 (m, 2H), 3.05 (m, 4H), 2.09 (s, 3H). MS (EI): 508.6 (MH+).

(2R,4S)-4-hydroxy-N-(4-(2-(4-(4-(3-methoxypropanoyl)piperazin-1-yl)phenyl-amino)pyrimidin-4-yl)phenyl)pyrrolidine-2-carboxamide: $^1$H NMR (400 MHz, d6-DMSO): 10.22 (s, 1H), 9.40 (s, 1H), 8.48 (d, 1H), 8.44 (d, 1H), 8.39 (dd, 1H), 8.11 (d, 1H), 7.74 (d, 2H), 7.69 (m, 3H), 7.28 (m, 3H), 6.94 (d, 2H), 3.59 (m, 4H), 3.01 (m, 4H), 2.86 (t, 2H), 2.73 (t, 2H), 2.09 (s, 3H). MS (EI): 522.6 (MH+).

N-{4-[2-({3-[4-(1,3-thiazol-2-ylmethyl)piperazin-1-yl]phenyl}amino)-pyrimidin-4-yl]phenyl}acetamide: $^1$H NMR (400 MHz, d6-DMSO): 10.19 (s, 1H), 9.45 (s, 1H), 8.47 (d, 1H), 8.11 (d, 2H), 7.73 (d, 2H), 7.66 (d, 1H), 7.60 (s, 1H), 7.31 (d, 1H), 7.21 (d, 1H), 7.12 (t, 1H), 6.55 (dd, 1H), 3.90 (s, 2H), 3.17 (m, 4H), 2.66 (m, 4H), 2.07 (s, 3H). MS (EI): 486.6 (MH+).

N-(4-{2-[(4-morpholin-4-ylphenyl)amino]pyrimidin-4-yl}phenyl)-5-oxo-L-prolinamide: $^1$H NMR (400 MHz, d6-DMSO): 10.33 (s, 1H), 9.40 (s, 1H), 8.45 (d, 1H), 8.14 (d, 2H), 7.93 (s, 1H), 7.79 (d, 2H), 7.67 (d, 2H), 7.29 (d, 1H), 6.93 (d, 2H), 4.23 (dd, 1H), 3.75 (m, 4H), 3.06 (m, 4H), 2.35 (m, 1H), 2.21 (m, 2H), 2.02 (m, 1H). MS (EI): 459.5 (MH+).

(3S)—N-(4-{2-[(4-morpholin-4-ylphenyl)amino]pyrimidin-4-yl}phenyl)pyrrolidine-3-carboxamide: $^1$H NMR (400 MHz, d6-DMSO): 10.75 (s, 1H), 9.84 (s, 1H), 9.34 (m, 1H), 9.14 (m, 1H), 8.51 (d, 1H), 8.16 (d, 2H), 7.82 (d, 3H), 7.41 (d, 2H), 3.93 (m, 4H), 3.82 (m, 6H), 3.36 (m, 2H), 3.24 (m, 2H), 2.33-2.24 (m, 1H), 2.11-2.04 (m, 2H). MS (EI): 445.5 (MH+).

N-(4-{2-[(4-morpholin-4-ylphenyl)amino]pyrimidin-4-yl}phenyl)-L-threoninamide: $^1$H NMR (400 MHz, d6-DMSO): 11.53 (s, 1H), 10.11 (s, 1H), 8.51 (d, 1H), 8.31 (d, 2H), 8.15 (d, 2H), 7.86 (t, 3H), 7.73 (d, 2H), 7.44 (d, 2H), 4.01 (m, 6H), 3.48 (m, 4H), 1.18 (s, 3H). MS (EI): 449.5 (MH+).

N-{4-[2-({4-[4-(N,N-diethyl-beta-alanyl)piperazin-1-yl]phenyl}amino)-pyrimidin-4-yl]phenyl}acetamide: $^1$H NMR (400 MHz, d6-DMSO): 10.20 (s, 1H), 9.38 (s, 1H), 8.42 (d, 1H), 8.09 (d, 2H), 7.73 (d, 2H), 7.67 (d, 2H), 7.25 (d, 1H), 6.95 (d, 2H), 3.58 (m, 4H), 3.05 (m, 4H), 2.81 (t, 2H), 2.66-2.55 (m, 6H), 1.93 (s, 3H), 0.99 (t, 6H). MS (EI): 516.7 (MH+).

N$^1$-(4-{2-[(4-morpholin-4-ylphenyl)amino]pyrimidin-4-yl}phenyl)-D-glutamamide: $^1$H NMR (400 MHz, d6-DMSO): 9.36 (s, 1H), 8.42 (d, 2H), 8.11 (d, 3H), 7.80 (d, 2H), 7.66 (d, 2H), 7.26 (d, 2H), 6.92 (d, 3H), 3.72 (m, 4H), 3.32 (m, 1H), 3.02 (m, 4H), 1.93 (s, 2H), 1.82 (s, 2H). MS (EI): 476.6 (MH+).

(S)-1-ethyl-N-(4-(2-(4-morpholinophenylamino)pyrimidin-4-yl)phenyl)pyrrolidine-3-carboxamide: $^1$H NMR (400 MHz, d6-DMSO): 10.19 (s, 1H), 9.38 (s, 1H), 8.44 (d, 1H), 8.12 (d, 2H), 7.77 (d, 2H), 7.68 (d, 2H), 7.28 (d, 1H), 6.94 (d, 2H), 3.04 (m, 4H), 2.90 (m, 2H), 2.65 (m, 2H), 2.43 (m, 3H), 1.98 (m, 6H), 1.03 (t, 3H). MS (EI): 473.6 (MH+).

N-(4-{2-[(4-morpholin-4-ylphenyl)amino]pyrimidin-4-yl}phenyl)-D-norvalinamide: $^1$H NMR (400 MHz, d6-DMSO): 11.50 (s, 1H), 10.15 (s, 1H), 8.56 (m, 3H), 8.24 (d, 2H), 7.94 (d, 2H), 7.76 (m, 3H), 7.51 (d, 2H), 4.08 (m, 4H), 3.67 (d, 1H), 1.97 (m, 4H), 1.43 (m, 2H), 1.19 (m, 2H), 0.94 (m, 3H). MS (EI): 447.6 (MH+).

N-(4-{2-[(4-morpholin-4-ylphenyl)amino]pyrimidin-4-yl}phenyl)-D-norleucinamide: $^1$H NMR (400 MHz, d6-DMSO): 11.55 (s, 1H), 10.19 (s, 1H), 8.57 (d, 2H), 8.26 (d, 1H), 8.01 (m, 4H), 7.80 (m, 3H), 7.53 (d, 2H), 4.05 (m, 4H), 3.68 (d, 1H), 1.92 (m, 4H), 1.36 (m, 4H), 1.19 (m, 2H), 0.99 (d, 3H). MS (EI): 461.6 (MH+).

N-(4-{2-[(4-morpholin-4-ylphenyl)amino]pyrimidin-4-yl}phenyl)-L-alloisoleucinamide: $^1$H NMR (400 MHz, d6-DMSO): 11.32 (s, 1H), 10.01 (s, 1H), 8.56 (d, 2H), 8.44 (d, 3H), 8.21 (d, 2H), 7.89 (m, 3H), 7.46 (d, 2H), 4.02 (m, 4H), 3.56 (d, 1H), 1.99 (m, 4H), 1.63 (m, 1H), 1.17 (m, 2H), 1.00 (d, 3H), 0.91 (d, 3H). MS (EI): 461.6 (MH+).

N-(4-{2-[(4-morpholin-4-ylphenyl)amino]pyrimidin-4-yl}phenyl)-L-leucinamide: $^1$H NMR (400 MHz, d6-DMSO): 11.32 (s, 1H), 9.97 (s, 1H), 8.56 (d, 2H), 8.45 (d, 3H), 8.21 (d, 2H), 7.89 (m, 3H), 7.46 (d, 2H), 4.02 (m, 4H), 3.57 (d, 1H), 1.99 (m, 4H), 1.91 (m, 1H), 1.71 (t, 2H), 1.17 (t, 3H), 0.95 (t, 3H). MS (EI): 461.6 (MH+).

3-({4-[4-(acetylamino)phenyl]pyrimidin-2-yl}amino)-N-(2-ethylphenyl)benzamide: $^1$H-NMR (400 MHz, d$_6$-DMSO): 10.21 (s, 1H), 9.85 (d, 2H), 8.59 (s, 1H), 8.53 (d, 1H), 8.18 (d, 2H), 7.93 (m, 1H), 7.73 (d, 2H), 7.57 (d, 1H), 7.46 (t, 1H), 7.40 (d, 1H), 7.30-7.34 (m, 2H), 7.24-7.27 (m, 2H), 2.62-2.67 (m, 2H), 2.08 (s, 3H), 1.13-1.7 (t, 3H). MS (EI) for $C_{27}H_{25}N_5O_2$: 452.58 (MH$^+$).

3-({4-[4-(acetylamino)phenyl]pyrimidin-2-yl}amino)-N-(phenylmethyl)-benzamide: $^1$H-NMR (400 MHz, d$_6$-DMSO): 10.22 (s, 1H), 9.80 (s, 1H), 8.98-9.01 (t, 1H), 8.52 (d, 1H), 8.50 (s, 1H), 8.18 (d, 2H), 7.9 (dd, 1H), 7.76 (s, 1H), 7.74 (s, 1N), 7.47 (d, 1H), 7.39-7.43 (m, 2H), 7.43 (s, 2H), 7.34 (d, 2H), 7.23-7.25 (m, 1H), 4.50 (d, 2H), 2.09 (s, 3H). MS (EI) for $C_{26}H_{23}N_5O_2$: 438.48 (MH$^+$).

N-{4-[2-({3-[(4-cyclopentylpiperazin-1-yl) carbonyl]phenyl}amino) pyrimidin-4-yl]phenyl}acetamide: $^1$H-NMR (400 MHz, d$_6$-DMSO): 10.23 (s, 1H), 9.82 (s, 1H), 8.53 (d, 1H), 8.12 (s, 2H), 8.05 (s, 1H), 7.81 (dd, 1H), 7.76 (d, 2H), 7.38 (t, 2H), 6.95 (d, 1H), 2.89 (s, 2H), 2.73 (s, 2H), 2.34-2.45 (m, 5H), 2.09 (s, 3H), 2.73-2.75 (m, 2H), 1.52-1.59 (m, 2H), 1.46-1.50 (m, 2H), 1.27-1.33 (m, 2H): MS (EI) for $C_{28}H_{32}N_6O_2$: 485.8 (MH$^+$).

N-{4-[2-({3-[(4-pyrazin-2-ylpiperazin-1-yl)carbonyl]phenyl}amino)pyrimidin-4-yl]phenyl}acetamide: $^1$H-NMR (400 MHz, d$_6$-DMSO): 10.17 (s, 1H), 9.84 (s, 1H), 8.54 (d, 1H), 8.43 (d, 1H), 8.11 (d, 2H), 8.06-8.10 (m, 2H), 7.86-7.88 (m, 2H), 7.73 (d, 2H), 7.42 (d, 1H), 7.39 (d, 1H), 7.02-7.04 (m, 1H), 3.69 (m, 4H), 3.57 (m, 4H), 2.08 (s, 3H). MS (EI) for $C_{27}H_{26}N_8O_2$: 495.7 (MH$^+$).

N-(4-{2-[(3-{[4-(3-chlorophenyl)piperazin-1-yl]carbonyl}phenyl)amino]pyrimidin-4-yl}phenyl)acetamide: $^1$H-NMR (400 MHz, d$_6$-DMSO): 10.20 (s, 1H), 9.84 (s, 1H), 8.53 (d, 1H), 8.13 (dd, 2H), 8.064 (t, 1H), 7.85-7.87 (m, 1H), 7.74 (d, 1H), 7.39-7.43 (m, 2H), 7.22 (t, 1H), 7.01-7.03 (m, 1H), 6.96 (t, 1H), 6.90 (dd, 1H), 6.81 (dd, 1H), 3.76 (m, 4H), 3.52 (m, 4H), 2.08 (s, 3H). MS (EI) for $C_{29}H_{27}ClN_6O_2$: 528.1 (MH$^+$).

3-({4-[4-(acetylamino)phenyl]pyrimidin-2-yl}amino)-N-[(1-methyl-1H-benzimidazol-2-yl)methyl]benzamide: $^1$H-NMR (400 MHz, d$_6$-DMSO): 10.23 (s, 1H), 9.80 (s, 1H), 9.01 (t, 1H), 8.52 (t, 2H), 8.17-8.19 (m, 2H), 7.91-7.93 (m, 1H), 7.75 (d, 2H), 7.50-7.59 (m, 3H), 7.39-7.43 (m, 2H), 7.16-7.26 (m, 2H), 4.80 (d, 2H), 3.86 (s, 3H), 2.10 (s, 3H). MS (EI) for $C_{25}H_{25}N_7O_2$: 492.4 (MH$^+$).

3-({4-[4-(acetylamino)phenyl]pyrimidin-2-yl}amino)-N-propylbenzamide: $^1$H-NMR (400 MHz, d$_6$-DMSO): 10.22 (s. 1H), 9.77 (s, 1H), 8.52 (d, 1H), 8.46 (s, 1H), 8.40 (t, 1H), 8.18 (d, 2H), 7.83-7.86 (m, 1H), 7.75 (d, 2H), 7.38-7.40 (m, 3H), 3.21-3.26 (m, 2H), 2.09 (s, 3H), 1.52-1.58 (m, 2H), 089-0.93 (t, 3H). MS (EI) for $C_{22}H_{23}N_5O_2$: 390.7 (MH$^+$).

3-({4-[4-(acetylamino)phenyl]pyrimidin-2-yl}amino)-N-cyclopropylbenzamide: $^1$H-NMR (400 MHz, d$_6$-DMSO): 10.24 (s 1H), 9.77 (s, 1H), 8.52 (d, 1H), 8.47 (s, 1H), 8.40 (d, 1H), 8.18 (d, 2H), 7.82-7.85 (m, 1H), 7.76 (d, 2H), 7.39 (d, 1H), 7.36-7.37 (m, 2H), 2.84-2.89 (m, 1H), 2.09 (s, 3H), 0.69-0.73 (m, 2H), 0.56-0.60 (m, 2H). MS (EI) for $C_{22}H_{21}N_5O_2$: 388.7 (MH$^+$).

3-({4-[4-(acetylamino)phenyl]pyrimidin-2-yl}amino)-N-[(3-fluorophenyl)-methyl]benzamide: $^1$H-NMR (400 MHz, d$_6$-DMSO): 10.22 (s, 1H), 9.80 (s, 1H), 9.04 (t, 1H), 8.53 (d, 1H), 8.50 (s, 1H), 8.17-8.20 (m, 2H), 7.90-7.93 (m, 1H), 7.74 (d, 2H), 7.46-7.50 (m, 1H), 7.36-7.43 (m, 3H), 7.08-7.19 (m, 3H), 4.51 (d, 2H), 2.09 (s, 3H). MS (EI) for C$_{26}$H$_{22}$FN$_5$O$_2$: 456.5 (MH$^+$).

3-({4-[4-(acetylamino)phenyl]pyrimidin-2-yl}amino)-N-(naphthalen-1-ylmethyl)-benzamide: $^1$H-NMR (400 MHz, d$_6$-DMSO): 10.21 (s, 1H), 9.79 (s, 1H), 9.03 (t, 1H), 8.52 (d, 2H), 8.15-8.23 (m, 3H), 7.95-7.97 (m, 1H), 7.90-7.93 (m, 1H), 7.85-7.87 (dd, 1H), 7.75 (d, 2H), 7.55-760 (m, 2H), 7.48-7.50 (m, 3H), 7.38-7.42 (m, 2H), 4.97 (d, 2H), 2.08 (s, 3H). MS (EI) for C$_{30}$H$_{25}$N$_6$O$_2$: 488.6 (MH$^+$).

3-({4-[4-(acetylamino)phenyl]pyrimidin-2-yl}amino)-N-[2-(dimethylamino)ethyl]-N-methylbenzamide: $^1$H-NMR (400 MHz, d$_6$-DMSO): 10.23 (s, 1H), 9.80 (s, 1H), 8.53 (d, 1H), 8.13 (d, 2H), 8.00 (d, 1H), 7.82 (s, 1H), 7.75 (d, 2H), 7.35-7.39 (m, 2H) 6.93 (d, 1H), 3.39-3.419 (m, 2H), 2.94 (s, 3H), 2.21 (m, 2H), 2.09 (s, 6H), 1.95 (s, 3H). MS (EI) for C$_{24}$H$_{28}$N$_6$O$_2$: 433.7 (MH$^+$).

3-({4-[4-(acetylamino)phenyl]pyrimidin-2-yl}amino)-N-[(2-methylphenyl)-methyl]benzamide: $^1$H-NMR (400 MHz, d$_6$-DMSO): 10.22 (s, 1H), 9.79 (s, 1H), 8.56 (t, 1H), 8.52 (d, 1H), 8.50 (s, 1H), 8.17-8.19 (m, 2H), 7.90-7.90 (m, 1H), 7.75 (d, 2H), 7.45-7.50 (m, 1H), 7.39-7.43 (m, 2H), 7.25-7.27 (1H), 7.14-7.18 (m, 3H), 4.47 (d, 2H), 2.34 (s, 3H), 2.09 (s, 3H). MS (EI) for C$_{27}$H$_{25}$NO$_2$: 452.6 (MH$^+$).

3-({4-[4-(acetylamino)phenyl]pyrimidin-2-yl}amino)-N-[(3-chlorophenyl)methyl]-benzamide: $^1$H-NMR (400 MHz, d$_6$-DMSO): 10.25 (s, 1H), 9.80 (s, 1H), 9.05 (t, 1H), 8.53 (d, 1H), 8.50 (s, 1H), 8.17-8.20 (m, 2H), 7.91-7.94 (m, 1H), 7.60 (s, 1H), 7.40 (s, 1H), 7.46-7.48 (m, 1H), 7.43 (d, 1H), 7.36-7.40 (m, 3H), 7.30-7.32 (m, 2H), 4.95 (d, 2H), 2.09 (s, 3H). MS (EI) for C$_{26}$H$_{22}$ClN$_5$O$_2$: 472.8 (MH$^+$).

3-({4-[4-(acetylamino)phenyl]pyrimidin-2-yl}amino)-N-(2-phenylethyl)-benzamide: $^1$H-NMR (400 MHz, d$_6$-DMSO): 10.22 (s, 1H), 9.78 (s, 1H), 8.51-8.53 (m, 2H), 8.46 (s, 1H), 8.19 (d, 2H), 7.85-7.88 (m, 1H), 7.76 (d, 2H), 7.37-7.38 (m, 3H), 7.27-7.32 (m, 4H), 7.19-7.23 (m, 1H), 3.47-3.52 (m, 2H), 2.84-2.88 (m, 2H), 2.08 (s, 3H). MS (EI) for C$_{27}$H$_{25}$N$_5$O$_2$: 452.6 (MH$^+$).

N-{4-[2-({3-[(4-methylpiperazin-1-yl)carbonyl]phenyl}amino)pyrimidin-4-yl]-phenyl}acetamide: $^1$H-NMR (400 MHz, d$_6$-DMSO): 10.24 (s, 1H), 9.82 (s, 1H), 8.53 (d, 1H), 8.12-8.15 (m, 2H), 8.04 (s, 1H), 7.80-7.82 (m, 1H), 7.76 (d, 2H), 7.36-7.40 (m, 2H), 6.94-6.96 (m, 1H), 2.94 (m, 2H), 2.78 (s, 2H), 2.37 (s, 2H), 2.27 (s, 2H), 2.18 (s, 3H), 2.09 (s, 3H). MS (EI) for C$_{24}$H$_{26}$N$_6$O$_2$: 431.6 (MH$^+$).

N-(4-{2-[(3-{[4-(2-fluorophenyl)piperazin-1-yl]carbonyl}phenyl)amino]-pyrimidin-4-yl}phenyl)acetamide: $^1$H-NMR (400 MHz, d$_6$-DMSO): 10.22 (s, 1H), 9.84 (s, 1H), 8.53 (d, 1H), 8.14 (d, 2H), 8.08 (d, 1H), 7.85 (d, 1H), 7.77 (d, 2H), 7.39-7.43 (m, 2H), 7.05-7.17 (m, 2H), 6.99-7.05 (m, 4H), 3.81 (s, 2H), 3.55 (s, 2H), 3.09 (s, 2H), 2.98 (s, 2H), 2.09 (s, 3H). MS (EI) for C$_{29}$H$_{27}$FN$_6$O$_2$: 511.7 (MH$^+$).

3-({4-[4-(acetylamino)phenyl]pyrimidin-2-yl}amino)-N-[2-(phenyloxy)ethyl]-benzamide: $^1$H-NMR (400 MHz, d$_6$-DMSO): 10.22 (s, 1H), 9.79 (s, 1H), 8.65 (t, 1H), 8.2 (d, 2H), 8.50 (s br, 1H), 8.9 (d, 2H), 7.88-7.90 (m, 1H), 7.76 (d, 2H), 7.38-7.45 (m, 3H), 7.27-7.30 (m, 2H), 6.91-6.98 (m, 3H), 4.11-4.14 (m, 2H), 3.63-3.78 (m, 2H), 2.09 (s, 3H). MS (EI) for C$_{27}$H$_{25}$N$_5$O$_3$: 468.4 (MH$^+$).

methyl 1-{[3-({4-[4-(acetylamino)phenyl]pyrimidin-2-yl}amino)phenyl]carbonyl}-piperidine-4-carboxylate: $^1$H-NMR (400 MHz, d$_6$-DMSO): 10.23 (s, 1H), 9.82 (s, 1H), 8.53 (d, 1H), 8.14 (d, 2H), 7.97 (t, 1H), 7.86-7.88 (m, 1H), 7.75 (d, 2H), 7.36-7.70 (m, 2H), 6.94-6.96 (m, 1H), 3.61 (s, 3H), 3.30-3.36 (m, 2H), 2.77-3.29 (m, 2H), 2.65-2.70 (m, 1H), 2.09 (s, 3H), 1.99-2.19 (m, 2H), 1.79-1.88 (m, 2H). MS (EI) for C$_{26}$H$_{27}$N$_5$O$_4$: 474.6 (MH$^+$).

N-[4-(2-{[3-({4-[3-(methyloxy)phenyl]piperazin-1-yl}carbonyl)phenyl]amino}-pyrimidin-4-yl)phenyl]acetamide: $^1$H-NMR (400 MHz, d$_6$-DMSO): 10.21 (s, 1H), 9.83 (s, 1H), 8.53 (d, 1H), 8.14 (d, 2H), 8.04 (m, 1H), 7.86-7.89 (m, 1H), 7.75 (d, 2H), 7.39-7.43 (m, 2H), 7.12 (t, 1H), 7.00-7.03 (m, 1H), 6.53 (dd, 1H), 6.47 (t, 1H), 6.40 (dd, 1H), 3.78-3.80 (m, 2H), 3.71 (s, 3H), 3.20-3.24 (m, 2H), 3.12-3.19 (m, 2H), 2.09 (s, 3H). MS (EI) for C$_{30}$H$_{30}$N$_6$O$_3$: 523.5 (MH$^+$).

3-({4-[4-(acetylamino)phenyl]pyrimidin-2-yl}amino)-N-{2-[2-(methyloxy)phenyl]-ethyl}benzamide: $^1$H-NMR (400 MHz, d$_6$-DMSO): 10.22 (s, 1H), 9.78 (s, 1H), 8.52-8.53 (m, 1H), 8.45 (s, 2H), 8.19 (d, 2H), 7.88 (s, 1H), 7.75 (d, 2H), 7.38-7.39 (m, 3H), 7.17-7.23 (m, 2H), 6.97 (d, 1H), 6.87 (t, 1H), 3.78 (s, 3H), 3.45-3.47 (m, 2H), 2.84-2.87 (m, 2H), 2.09 (s, 3H). MS (EI) for C$_{28}$H$_{27}$N$_5$O$_3$: 482.7 (MH$^+$).

N-[4-(2-{[3-(1,3-dihydro-2H-isoindol-2-ylcarbonyl)phenyl]amino}pyrimidin-4-yl)-phenyl]acetamide: $^1$H-NMR (400 MHz, d$_6$-DMSO): 10.21 (s, 1H), 9.82 (s, 1H), 8.53 (d, 1H), 8.16 (s, 1H), 8.12-8.14 (m, 2H), 7.94-7.97 (m, 1H), 7.74 (s, 1H), 7.72 (s, 1H), 7.39-7.45 (m, 3H), 7.27-7.32 (m, 1H), 7.26 (d, 2H), 7.19-7.21 (m, 1H), 7.89 (s, 2H), 4.82 (s, 2H), 2.09 (s, 3H). MS (EI) for C$_{27}$H$_{23}$N$_5$O$_2$: 450.7 (MH$^+$).

3-({4-[4-(acetylamino)phenyl]pyrimidin-2-yl}amino)-N-(biphenyl-4-ylmethyl)-benzamide: $^1$H-NMR (400 MHz, d$_6$-DMSO): 10.23 (s, 1H), 9.80 (s, 1H), 9.04 (s br, 1H), 8.53 (d, 2H), 8.19 (d, 2H), 7.89 (d, 1H), 7.76 (d, 2H), 7.64 (m, 4H), 7.35-7.50 (m, 8H), 4.55 (s, 2H), 2.08 (s, 3H). MS (EI) for C$_{32}$H$_{27}$N$_5$O$_2$: 514.8 (MH$^+$).

N-(4-{2-[(3-{[4-(phenylcarbonyl)piperazin-1-yl]carbonyl}phenyl)amino]pyrimidin-4-yl}phenyl)acetamide: $^1$H-NMR (400 MHz, d$_6$-DMSO): 10.25 (s, 1H), 9.83 (s, 1H), 8.53 (d, 1H), 8.14 (d, 2H), 8.04 (s, 1H), 7.86 (d, 1H), 7.76 (d, 2H), 7.44 (m, 5H), 7.39 (d, 2H), 7.00 (d, 1H), 3.56 (m, 8H) 2.09 (s, 3H). MS (EI) for C$_{30}$H$_{28}$N$_6$O$_3$: 521.6 (MH$^+$).

N-[4-(2-{[3-({4-[4-(methyloxy)phenyl]piperazin-1-yl}carbonyl)phenyl]amino}-pyrimidin-4-yl)phenyl]acetamide: $^1$H-NMR (400 MHz, d$_6$-DMSO): 10.21 (s, 1H), 9.83 (s, 1H), 8.53 (d, 1H), 8.13 (m, 2H), 8.05 (m, 1H), 7.86 (m, 1H), 7.75 (d, 2H), 7.37-7.43 (m, 2H), 7.01 (m, 1H), 6.90 (m, 2H), 6.82 (m, 2H), 3.77 (m, 2H), 3.68 (s, 3H), 3.53 (m, 2H), 3.08 (m, 2H), 2.97 (m, 2H), 2.09 (s, 3H). MS (EI) for C$_{30}$H$_{30}$N$_6$O$_3$: 523.7 (MH$^+$).

3-({4-[4-(acetylamino)phenyl]pyrimidin-2-yl}amino)-N-methyl-N-{[2-(methyloxy)-phenyl]methyl}benzamide: $^1$H-NMR (400 MHz, d$_6$-DMSO): 10.23 (s, 1H), 9.80 (s, 1H), 8.37 (m, 1H), 8.14 (d, 2H), 7.76 (m, 3H), 7.39 (d, 2H), 7.25-7.32 (m, 2H), 7.14-7.18 (m, 1H), 7.04 (m, 1H), 6.95 (d, 2H), 4.57 (d, 2H), 3.76 (d, 3H), 2.88 (s, 3H), 2.09 (s, 3H). MS (EI) for C$_{25}$H$_{27}$N$_5$O$_3$: 482.7 (MH$^+$).

3-({4-[4-(acetylamino)phenyl]pyrimidin-2-yl}amino)-N-[(2-fluorophenyl)methyl]-N-methylbenzamide: $^1$H-NMR (400 MHz, d$_6$-DMSO): 10.23 (s, 1H), 9.08 (s, 1H), 8.52 (m, 1H), 8.14 (d, 2H), 8.01 (m, 1H), 7.89 (m, 1H), 7.75 (d, 2H), 7.38 (m, 4H), 7.21 (m, 2H), 7.01 (m, 1H), 4.67 (d, 2H), 2.91 (s, 3H), 2.09 (s, 3H). MS (EI) for C$_{27}$H$_{24}$FN$_5$O$_2$: 470.6 (MH$^+$).

3-({4-[4-(acetylamino)phenyl]pyrimidin-2-yl}amino)-N-(2-pyridin-2-ylethyl)-benzamide: $^1$H-NMR (400 MHz, d$_6$-DMSO): 10.22 (s, 1H), 9.78 (s, 1H), 8.51-8.54 (m, 3H), 8.46 (s, 1H), 8.18 (d, 2H), 7.86-7.88 (m, 1H), 7.76 (d, 2H), 7.69-7.73 (m, 1H), 7.37-7.40 (m, 3H), 7.31 (m, 1H), 7.21-7.24 (m, 1H), 3.61-3.66 (m, 2H), 3.02 (m, 2H), 2.09 (s, 3H). MS (EI) for C$_{26}$H$_{24}$N$_6$O$_2$: 453.6 (MH$^+$).

3-({4-[4-(acetylamino)phenyl]pyrimidin-2-yl}amino)-N-(pyridin-2-ylmethyl)-benzamide: $^1$H-NMR (400 MHz, d$_6$-DMSO): 10.22 (s, 1H), 9.81 (s, 1H), 9.06 (m, 1H), 8.52 (m, 2H), 8.19 (d, 2H), 7.91 (m, 1H), 7.73-7.79 (m, 3H), 7.51 (d, 1H), 7.40 (m, 2H), 7.30 (d, 1H), 7.25-7.27 (m, 1H), 4.59 (d, 2H), 2.09 (s, 3H). MS (EI) for C$_{25}$H$_{22}$N$_6$O$_2$: 439.8 (MH$^+$).

3-({4-[4-(acetylamino)phenyl]pyrimidin-2-yl}amino)-N-(pyridin-3-ylmethyl)-benzamide: $^1$H-NMR (400 MHz, d$_6$-DMSO): 10.22 (s, 1H), 9.78 (s, 1H), 8.52 (d, 1H), 8.45 (s br, 1H), 8.25 (d, 1H), 7.18 (d, 3H), 7.82-7.85 (m, 1H), 7.76 (d, 3H), 7.35-7.41 (m, 4H), 4.25 (m, 2H), 2.09 (s, 3H). MS (EI) for C$_{25}$H$_{22}$N$_6$O$_2$: 438.6 (MH$^+$).

3-({4-[4-(acetylamino)phenyl]pyrimidin-2-yl}amino)-N-(pyridin-4-ylmethyl)-benzamide: $^1$H-NMR (400 MHz, d$_6$-DMSO): 10.22 (s, 1H), 9.80 (s, 1H), 9.08 (t, 1H), 8.50-8.54 (m, 4H), 8.18 (d, 2H), 7.92 (d, 1H), 7.74 (d, 2H), 7.49 (d, 1H), 7.42 (t, 1H), 7.40 (d, 1H), 7.31 (d, 2H), 4.51 (d, 2H), 2.09 (s, 3H). MS (EI) for C$_{25}$H$_{22}$N$_6$O$_2$: 438.5 (MH$^+$).

3-({4-[4-(acetylamino)phenyl]pyrimidin-2-yl}amino)-N-methyl-N-(phenylmethyl)-benzamide: $^1$H-NMR (400 MHz, d$_6$-DMSO): 10.23 (s, 1H), 9.81 (s, 1H), 8.53 (s br, 1H), 8.14 (d, 2H), 7.46 (d, 2H), 7.23-7.46 (m, 8H), 7.21 (s br, 1H), 7.02 (s br, 1H), 4.56 (d, 2H), 2.95 (s, 3H), 2.09 (s, 3H). MS (EI) for C$_{27}$H$_{25}$N$_5$O$_2$: 452.7 (MH$^+$).

3-({4-[4-(acetylamino)phenyl]pyrimidin-2-yl}amino)-N-cyclopentylbenzamide: $^1$H-NMR (400 MHz, d$_6$-DMSO): 10.22 (s, 1H), 9.75 (s, 1H), 8.52 (d, 1H), 8.45 (s br, 1H), 8.25 (d, 1H), 8.17 (d, 2H), 7.84 (d, 1H) 7.75 (d, 2H), 7.35-7.42 (m, 3H), 4.22-4.27 (m, 1H), 2.09 (s, 3H), 1.88-1.93 (m, 2H), 1.70 (m, 2H), 1.49-1.59 (m, 4H). MS (EI) for C$_{24}$H$_{25}$N$_5$O$_2$: 416.8 (MH$^+$).

3-({4-[4-(acetylamino)phenyl]pyrimidin-2-yl}amino)-N-[(2-chlorophenyl)methyl]-benzamide: $^1$H-NMR (400 MHz, d$_6$-DMSO): 10.21 (s, 1H), 9.80 (s, 1H), 9.00 (t, 1H), 8.53 (d, 1H), 8.50 (s br, 1H), 8.18 (d, 2H), 7.93 (d, 1H), 7.63 (d, 2H), 7.52 (d, 1H), 7.28-7.48 (m, 6H), 4.56 (d, 2H), 2.09 (s, 3H). MS (EI) for C$_{26}$H$_{22}$ClN$_5$O$_2$: 473.0 (MH$^+$).

3-({4-[4-(acetylamino)phenyl]pyrimidin-2-yl}amino)-N-[(4-chlorophenyl)methyl]-benzamide: $^1$H-NMR (400 MHz, d$_6$-DMSO): 10.22 (s, 1H), 9.79 (s, 1H), 9.02 (t, 1H), 8.52 (d, 1H), 8.50 (s br, 1H), 8.18 (d, 2H), 7.90 (d, 1H), 7.74 (d, 2H), 7.46 (d, 1H), 7.41 (m, 2H), 7.38 (s, 2H), 7.36 (m, 2H), 4.48 (d, 2H), 2.09 (s, 3H). MS (EI) for C$_{26}$H$_{22}$ClN$_5$O$_2$: 473.1 (MH$^+$).

3-({4-[4-(acetylamino)phenyl]pyrimidin-2-yl}amino)-N-(furan-2-ylmethyl)-benzamide: $^1$H-NMR (400 MHz, d$_6$-DMSO): 10.22 (s, 1H), 9.78 (s, 1H), 8.91 (t, 1H), 8.52 (d, 1H), 8.48 (s br, 1H), 8.17 (d, 1H), 7.88 (d, 1H), 7.76 (d, 2H), 7.58 (m, 1H), 7.44 (d; 1H), 7.37-7.41 (m, 2H), 6.41 (m, 1H), 6.28 (dd, 1H), 4.48 (d, 2H), 2.09 (s, 3H). MS (EI) for C$_{24}$H$_{21}$N$_5$O$_3$: 428.6 (MH$^+$).

3-({4-[4-(acetylamino)phenyl]pyrimidin-2-yl}amino)-N-{[4-(methyloxy)phenyl]-methyl}benzamide: $^1$H-NMR (400 MHz, d$_6$-DMSO): 10.22 (s, 1H), 9.77 (s, 1H), 8.92 (t, 1H), 8.52 (d, 1H), 8.49 (s br, 1H), 8.19 (d, 2H), 7.88 (d, 1H), 7.76 (d, 2H), 7.45 (d, 1H), 7.37-7.41 (m, 2H), 7.27 (d, 2H), 6.89 (d, 2H), 4.42 (d, 2H), 3.72 (s, 3H), 2.08 (s, 3H). MS (EI) for C$_{27}$H$_{25}$N$_5$O$_3$: 468.4 (MH$^+$).

N-[4-(2-{[3-({4-[2-(methyloxy)phenyl]piperazin-1-yl}carbonyl)phenyl]amino}-pyrimidin-4-yl)phenyl]acetamide: $^1$H-NMR (400 MHz, d$_6$-DMSO): 10.22 (s, 1H), 9.82 (s, 1H), 8.53 (d, 1H), 8.14 (d, 2H), 8.06 (s, 1H) 7.86 (m, 1H), 7.76 (d, 2H), 7.40 (m, 2H), 7.01 (d, 1H), 6.59 (m, 2H), 6.88 (s, 2H), 3.78 (s, 3H), 3.55 (m, 2H), 3.03 (m, 2H), 2.94 (s, 2H), 2.79 (s, 2H), 2.09 (s, 3H). MS (EI) for C$_{30}$H$_{30}$N$_6$O$_3$: 523.5 (MH$^+$).

3-({4-[4-(acetylamino)phenyl]pyrimidin-2-yl}amino)-N-[3-(methyloxy)propyl]-benzamide: $^1$H-NMR (400 MHz, d$_6$-DMSO): 10.22 (s, 1H), 9.76 (s, 1H), 8.52 (d, 1H), 8.46 (s br, 1H), 8.40 (t, 1H), 8.18 (d, 2H), 7.85-7.88 (m, 1H), 7.75 (d, 2H), 7.38-7.40 (m, 3H), 3.40 (m, 2H), 3.30 (m, 2H), 3.24 (s, 3H), 2.09 (s, 3H), 1.74-1.80 (m, 2H). MS (EI) for C$_{23}$H$_{25}$N$_5$O$_3$: 420.5 (MH$^+$).

N-(4-{2-[(3-{[(2R,6S)-2,6-dimethylmorpholin-4-yl]carbonyl}phenyl)amino]-pyrimidin-4-yl}phenyl)acetamide: $^1$H-NMR (400 MHz, d$_6$-DMSO): 10.23 (s, 1H), 9.81 (s, 1H), 8.53 (d, 1H), 8.13 (d, 2H), 7.99 (m, 1H), 7.86 (d, 1H), 7.76 (d, 2H), 7.37-7.41 (m, 2H), 6.98 (d, 1H), 2.94 (s, 2H), 2.79 (s, 2H), 2.09 (s, 3H), 1.96 (s, 1H), 1.16 (m, 3H), 0.99 (m, 3H). MS (EI) for C$_{25}$H$_{27}$N$_5$O$_3$: 445.5 (MH$^+$).

3-({4-[4-(acetylamino)phenyl]pyrimidin-2-yl}amino)-N-[6-chloropyridin-3-yl)methyl]benzamide: $^1$H-NMR (400 MHz, d$_6$-DMSO): 10.22 (s, 1H), 9.79 (s, 1H), 9.06 (t, 1H), 8.52 (d, 1H), 8.49 (s, 1H), 8.40 (d, 1H), 8.18 (d, 2H), 7.91 (m, 2H), 7.81 (dd, 1H), 7.74 (d, 2H), 7.49 (d, 1H), 7.41-7.46 (m, 2H), 7.39 (d, 1H), 4.50 (d, 2H), 2.09 (s, 3H). MS (EI) for C$_{25}$H$_{21}$ClN$_6$O$_2$: 474.1 (MH$^+$).

3-({4-[4-(acetylamino)phenyl]pyrimidin-2-yl}amino)-N-butylbenzamide: $^1$H-NMR (400 MHz, d$_6$-DMSO): 10.24 (s, 1H), 9.80 (s, 1H), 8.53 (d, 1H), 8.13 (d, 2H), 8.02 (s br, 1H), 7.78 (m, 1H), 7.75 (d, 2H), 7.39 (d, 1H), 7.35 (d, 1H), 6.91 (d, 2H), 3.26 (m, 2H), 2.09 (s, 3H), 1.62 (m, 2H), 1.32 (m, 2H), 1.08 (m, 3H). MS (EI) for C$_{23}$H$_{25}$N$_5$O$_2$: 404.5 (MH$^+$).

N-(4-{2-[(3-{[4-(2-chlorophenyl)piperazin-1-yl]carbonyl}phenyl)amino]-pyrimidin-4-yl}phenyl)acetamide: $^1$H-NMR (400 MHz, d$_6$-DMSO): 10.22 (s, 1H), 9.83 (s, 1H), 8.53 (d, 1H), 8.14 (d, 2H), 7.90 (s br, 1H), 7.85 (d, 1H), 7.76 (d 2H), 7.38-7.43 (m, 3H), 7.28 (m, 1H), 7.13 (dd, 1H), 7.07 (dd, 1H), 7.03 (m, 1H), 3.81 (m, 4H), 3.58 (m, 4H), 2.09 (s, 3H). MS (EI) for C$_{29}$H$_{27}$ClN$_6$O$_2$: 528.1 (MH$^+$).

3-({4-[4-(acetylamino)phenyl]pyrimidin-2-yl}amino)-N-ethyl-N-[2-(methyloxy)-ethyl]benzamide: $^1$H-NMR (400 MHz, d$_6$-DMSO): 10.22 (s, 1H), 9.80 (s, 1H), 8.53 (d, 1H), 8.13 (d, 2H), 7.99 (m, 2H), 7.82 (m, 1H), 7.76 (d, 2H), 7.39 (d, 2H), 7.36 (d, 2H), 6.92 (d, 1H), 3.57 (m, 2H), 3.12 (m, 2H), 2.94 (s, 3H), 2.09 (s, 3H), 1.10 (m, 3H). MS (EI) for C$_{24}$H$_{27}$N$_5$O$_3$: 434.4 (MH$^+$).

N-{4-[2-({4-[4-(phenylmethyl)piperazin-1-yl]phenyl}amino)pyrimidin-4-yl]-phenyl}acetamide: $^1$H-NMR (400 MHz, d$_6$-DMSO): 10.20 (s, 1H), 9.35 (s, 1H), 8.43 (d, 1H), 8.10 (d, 2H), 7.74 (d, 2H), 7.65 (d, 2H), 7.35 (d, 4H), 7.27 (m, 2H), 6.92 (d, 2H), 3.54 (s, 2H), 3.9 (m, 4H), 2.53 (m, 4H), 2.09 (s, 3H). MS (EI) for C$_{29}$H$_{30}$N$_6$O: 479.7 (MH$^+$).

N-(4-{2-[(4-{4-[(5-methyl-3-phenylisoxazol-4-yl)methyl]piperazin-1-yl}phenyl)-amino]pyrimidin-4-yl}phenyl)acetamide: $^1$H-NMR (400 MHz, d$_6$-DMSO): 10.20 (s, 1H), 9.36 (s, 1H), 8.43 (d, 1H), 8.10 (d, 2H), 7.93-7.96 (m, 2H), 7.74 (d, 2H), 7.66 (d, 2H), 7.50-7.53 (m, 3H), 7.26 (d, 1H), 6.93 (d, 2H), 3.43 (s, 2H), 3.09 (m, 4H), 2.56 (m, 4H), 2.48 (s, 3H), 2.09 (s, 3H). MS (EI) for C$_{33}$H$_{33}$N$_7$O$_2$: 560.4 (MH$^+$).

N-(4-{2-[(4-{4-[(5-methyl-1-phenyl-1H-pyrazol-4-yl)methyl]piperazin-1-yl}-phenyl)amino]pyrimidin-4-yl}phenyl)acetamide: $^1$H-NMR (400 MHz, d$_6$-DMSO): 10.20 (s, 1H), 9.35 (s, 1H), 8.43 (d, 1H), 8.10 (d, 2H), 7.74 (d, 2H), 7.65 (d, 2H), 7.56 (s, 1H), 7.53 (d, 4H), 7.40-7.45 (m, 1H), 7.26 (d, 1H), 6.92 (d, 2H), 3.43 (s, 2H), 3.09 (m, 4H), 2.56 (m, 4H), 2.31 (s, 3H), 2.09 (s, 3H). MS (EI) for C$_{33}$H$_{34}$N$_8$O: 559.7 (MH$^+$).

N-(4-{2-[(4-{4-[(2-phenyl-1,3-thiazol-4-yl)methyl]piperazin-1-yl}phenyl)amino]-pyrimidin-4-yl}phenyl)acetamide: $^1$H-NMR (400 MHz, d$_6$-DMSO): 10.20 (s, 1H), 9.35 (s, 1H), 8.43 (d, 1H), 8.10 (d, 2H), 7.94 (d, 2H), 7.74 (d, 2H), 7.65 (d, 2H), 7.57 (s, 1H), 7.48-7.53 (m, 3H), 7.26 (d, 1H), 6.93 (d, 2H), 3.73 (s, 2H), 3.11 (m, 4H), 2.65 (m, 4H), 2.09 (s, 3H). MS (EI) for C$_{32}$H$_{31}$N$_7$OS: 562.5 (MH$^+$).

N-[4-(2-{[4-(4-{[6-(phenyloxy)pyridin-3-yl]methyl}piperazin-1-yl)phenyl]amino}-pyrimidin-4-yl)phenyl]acetamide: $^1$H-NMR (400 MHz, d$_6$-DMSO): 10.23 (s, 1H), 9.36 (s, 1H), 8.43 (d, 1H), 8.10 (d, 2H), 8.07 (d, 1H), 7.81 (dd, 1H), 7.74 (d, 2H), 7.65 (d, 2H), 7.43 (t, 2H), 7.26 (d, 1H), 7.19-7.23 (m, 1H), 7.14 (d, 2H), 7.01 (d, 1H), 6.92 (d, 2H), 3.21 (s, 2H), 3.08 (m, 4H), 2.48 (m, 4H), 2.09 (s, 3H). MS (EI) for $C_{34}H_{33}N_7O_2$: 572.4 (MH$^+$).

N-{4-[2-({4-[4-(cyclohexylmethyl)piperazin-1-yl]phenyl}amino)pyrimidin-4-yl]-phenyl}acetamide: $^1$H-NMR (400 MHz, d$_6$-DMSO): 10.20 (s, 1H), 9.35 (s, 1H), 8.43 (d, 1H), 8.10 (d, 2H), 7.74 (d, 2H), 7.65 (d, 2H), 7.26 (d, 1H), 6.92 (d, 2H), 3.06 (m, 4H), 2.47 (m, 4H), 2.13 (d, 2H), 2.09 (s, 3H), 1.76 (d, 2H), 1.65 (m, 3H), 1.49-1.54 (m, 1H), 1.12-1.17 (m, 3H), 080-0.89 (m, 2H). MS (EI) for $C_{29}H_{36}N_6O$: 485.8 (MH$^+$).

N-(4-{2-[(4-{4-[(1S,4S)-bicyclo[2.2.1]hept-5-en-2-ylmethyl]piperazin-1-yl}phenyl)-amino]pyrimidin-4-yl}phenyl)acetamide: $^1$H-NMR (400 MHz, d$_6$-DMSO): 10.21 (s, 1H), 9.35 (s, 1H), 8.43 (d, 1H), 8.11 (d, 2H), 7.74 (d, 2H), 7.65 (d, 2H), 7.26 (d, 1H), 6.92 (d, 2H), 6.14-6.16 (m, 1H), 5.95-5.97 (m, 1H), 3.07 (m, 4H), 2.79 (d, 2H), 2.45 (m, 4H), 2.32-2.39 (m, 2H), 2.09 (s, 3H), 1.95-1.99 (m, 1H), 1.81-1.87 (m, 1H), 1.31 (m, 1H), 1.23 (m, 1H), 0.51 (m, 1H). MS (EI) for $C_{30}H_{34}N_6O$: 495.7 (MH$^+$).

N-[4-(2-{[4-(4-pentylpiperazin-1-yl)phenyl]amino}pyrimidin-4-yl)phenyl]acetamide: $^1$H-NMR (400 MHz, d$_6$-DMSO): 10.21 (s, 1H), 9.35 (s, 1H), 8.43 (d, 1H), 8.11 (d, 2H), 7.74 (d, 2H), 7.65 (d, 2H), 7.26 (d, 1H), 6.92 (d, 2H), 3.07 (m, 4H), 2.55 (m, 4H), 2.307 (t, 2H), 2.09 (s, 3H), 1.43-1.49 (m, 2H), 1.22-1.34 (m, 4H), 0.88 (t, 3H). MS (EI) for $C_{27}H_{34}N_6O$: 459.7 (MH$^+$).

N-(4-{2-[(4-{4-[(2-chlorophenyl)methyl]piperazin-1-yl}phenyl)amino]pyrimidin-4-yl}phenyl)acetamide: $^1$H-NMR (400 MHz, d$_6$-DMSO): 10.21 (s, 1H), 9.36 (s, 1H), 8.43 (d, 1H), 8.10 (d, 2H), 7.74 (d, 2H), 7.66 (d, 2H), 7.54 (dd, 1H), 7.45 (dd, 1H), 7.29-7.39 (m, 2H), 7.26 (d, 1H), 6.93 (d, 2H), 3.64 (s, 2H), 3.10 (m, 4H), 2.60 (m, 4H), 2.09 (s, 3H). MS (EI) for $C_{29}H_{29}ClN_6$: 514.1 (MH$^+$).

N-[4-(2-{[4-(4-{[3,5-bis(methyloxy)phenyl]methyl}piperazin-1-yl)phenyl]amino}-pyrimidin-4-yl)phenyl]acetamide: $^1$H-NMR (400 MHz, d$_6$-DMSO): 10.21 (s, 1H), 9.35 (s, 1H), 8.43 (d, 1H), 8.10 (d, 2H), 7.74 (d, 2H), 7.65 (d, 2H), 7.26 (d, 1H), 6.93 (d, 2H), 6.51 (d, 2H), 6.39 (t, 1H), 3.75 (s, 6H), 3.46 (s, 2H), 3.09 (m, 4H), 2.61 (m, 4H), 2.09 (s, 3H). MS (EI) for $C_{31}H_{34}N_6O_3$: 539.8 (MH$^+$).

N-(4-{2-[(4-{4-[(4-fluorophenyl)methyl]piperazin-1-yl}phenyl)amino]pyrimidin-4-yl}phenyl)acetamide: $^1$H-NMR (400 MHz, d$_6$-DMSO): 10.21 (s, 1H), 9.35 (s, 1H), 8.43 (d, 1H), 8.10 (d, 2H), 7.74 (d, 2H), 7.65 (d, 2H), 7.36-7.39 (m, 2H), 7.26 (d, 1H), 7.16 (t, 2H), 6.92 (d, 2H), 3.51 (S, 2H), 3.08 (m, 4H), 2.28 (m, 4H), 2.09 (s, 3H). MS (EI) for $C_{29}H_{29}FN_6O$: 497.8 (MH$^+$).

N-(4-{2-[(4-{4-[(1-methyl-1H-pyrrol-2-yl)methyl]piperazin-1-yl}phenyl)amino]-pyrimidin-4-yl}phenyl)acetamide: $^1$H-NMR (400 MHz, d$_6$-DMSO): 10.21 (s, 1H), 9.35 (s, 1H), 8.43 (d, 1H), 8.10 (d, 2H), 7.74 (d, 2H), 7.65 (d, 2H), 7.26 (d, 1H), 6.92 (d, 2H), 6.68 (t, 1H), 5.88-5.91 (m, 2H), 3.61 (s, 2H), 3.4 (s, 3H), 3.06 (m, 4H), 2.58 (m, 4H), 2.09 (s, 3H). MS (EI) for $C_{28}H_{31}N_7O$: 482.8 (MH$^+$).

N-[4-(2-{[4-{[5-(3-chlorophenyl)furan-2-yl]methyl}piperazin-1-yl)phenyl]-amino}pyrimidin-4-yl)phenyl]acetamide: $^1$H-NMR (400 MHz, d$_6$-DMSO): 10.20 (s, 1H), 9.36 (s, 1H), 8.43 (d, 1H), 8.10 (d, 2H), 7.72-7.76 (m, 3H), 7.63-7.66 (m, 3H), 7.45 (t, 1H), 7.33 (d, 1H), 7.26 (d, 1H), 7.06 (d, 1H), 6.92 (d, 2H), 6.48 (d, 1H), 3.64 (s, 2H), 3.10 (m, 4H), 2.60 (m, 4H), 20.9 (s, 3H). MS (EI) for $C_{33}H_{31}ClN_6O$: 580.3 (MH$^+$).

N-[4-(2-{[4-(4-([4-fluoro-2-(trifluoromethyl)phenyl]methyl)piperazin-1-yl)phenyl]-amino}pyrimidin-4-yl)phenyl]acetamide: $^1$H-NMR (400 MHz, d$_6$-DMSO): 10.21 (s, 1H), 9.37 (s, 1H), 8.43 (d, 1H), 8.10 (d, 2H), 7.84-7.88 (m, 1H), 7.74 (d, 2H), 7.66 (d, 2H), 7.54-7.72 (m, 2H), 7.26 (d, 1H), 6.93 (d, 2H), 3.66 (s, 2H), 3.10 (m, 4H), 2.56 (m, 4H), 2.09 (s, 3H). MS (EI) for $C_{30}H_{25}F_4N_6O$: 565.3 (MH$^+$).

N-[4-(2-{[4-(4-{[4-(1H-imidazol-1-yl)phenyl]methyl}piperazin-1-yl)phenyl]amino}-pyrimidin-4-yl)phenyl]acetamide: $^1$H-NMR (400 MHz, d$_6$-DMSO): 10.21 (s, 1H), 9.36 (s, 1H), 8.43 (d, 1H), 8.25 (t, 1H), 7.11 (d, 2H), 7.74 (d, 3H), 7.61-7.67 (m, 4H), 7.48 (d, 2H), 7.26 (d, 1H), 7.11 (t, 1H), 6.93 (d, 2H), 3.58 (s, 2H), 3.10 (m, 4H), 2.55 (m, 4H), 20.9 (s, 3H). MS (EI) for $C_{32}H_{32}N8O$: 545.8 (MH$^+$).

N-[4-(2-{[4-(4-{[2,5-bis(trifluoromethyl)phenyl]methyl}piperazin-1-yl)phenyl]-amino}pyrimidin-4-yl)phenyl]acetamide: $^1$H-NMR (400 MHz, d$_6$-DMSO): 10.20 (s, 1H), 9.37 (s, 1H), 8.43 (d, 1H), 8.17 (s, 1H), 8.10 (d, 2H), 8.00 (d, 1H), 7.89 (d, 1H), 7.74 (d, 2H), 7.67 (d, 2H), 7.26 (d, 1H), 6.94 (d, 2H), 3.79 (s, 2H), 3.12 (m, 4H), 2.60 (m, 4H), 2.09 (s, 3H). MS (EI) for $C_{31}H_{28}F_6N_6O$: 615.7 (MH$^+$).

N-(4-{2-[(4-4-[(2,6-dimethylphenyl)methyl]piperazin-1-yl)phenyl)amino]-pyrimidin-4-yl}phenyl)acetamide: $^1$H-NMR (400 MHz, d$_6$-DMSO): 10.20 (s, 1H), 9.35 (s, 1H), 8.43 (d, 1H), 8.10 (d, 2H), 7.24 (d, 2H), 7.64 (d, 2H), 7.26 (d, 1H), 7.00-7.08 (m, 3H), 6.90 (d, 2H), 3.50 (s, 2H), 3.02 (m, 4H), 2.54 (m, 4H), 2.37 (s, 6H), 2.09 (s, 3H). MS (EI) for $C_{31}H_{34}N_6O$: 507.7 (MH$^+$).

N-(4-{2-[(4-4-[(2,3-dimethylphenyl)methyl]piperazin-1-yl)phenyl)amino]-pyrimidin-4-yl}phenyl)acetamide: $^1$H-NMR (400 MHz, d$_6$-DMSO): 10.21 (s, 1H), 9.35 (s, 1H), 8.43 (d, 1H), 8.10 (d, 2H), 7.74 (d 2H), 7.65 (d, 2H), 7.26 (d, 1H), 7.01-7.09 (m, 3H), 6.91 (d, 2H), 3.45 (s, 2H), 3.05 (m, 4H), 2.53 (m, 4H), 2.24 (d, 6H), 2.09 (s, 3H). MS (EI) for $C_{31}H_{34}N_6O$: 507.8 (MH$^+$).

N-[4-(2-{[4-(4-{[2,4-bis(ethyloxy)phenyl]methyl}piperazin-1-yl)phenyl]amino}-pyrimidin-4-yl)phenyl]acetamide: $^1$H-NMR (400 MHz, d$_6$-DMSO): 10.21 (s, 1H), 9.35 (s, 1H), 8.43 (d, 1H), 8.10 (d, 2H), 7.74 (d, 2H), 7.64 (d, 2H), 7.26 (d, 1H), 7.19 (d, 1H), 6.91 (d, 2H), 6.47-6.51 (m, 2H), 3.97-4.04 (m, 4H), 3.46 (s, 2H), 3.06 (m, 4H), 2.52 (m, 4H), 2.09 (s, 3H), 1.30-1.35 (m, 6H). MS (EI) for $C_{33}H_{38}N_6O_3$: 567.8 (MH$^+$).

N-[4-(2-{[4-(4-{[3-(ethyloxy)phenyl]methyl}piperazin-1-yl)phenyl]amino}-pyrimidin-4-yl)phenyl]acetamide: $^1$H-NMR (400 MHz, d$_6$-DMSO): 10.21 (s, 1H), 9.36 (s, 1H), 8.45 (d, 1H), 8.10 (d, 2H), 7.74 (d, 2H), 7.24 (t, 1H), 7.11-7.19 (m, 3H), 7.02-7.09 (m, 3H), 6.91 (d, 2H), 3.96-4.00 (m, 2H), 3.40 (s, 2H), 3.07 (m, 4H), 2.59 (m, 4H), 2.09 (s, 3H), 1.32-1.38 (m, 3H). MS (EI) for $C_{31}H_{34}N_6O_2$: 523.8 (MH$^+$).

N-{4-[2-({4-[4-(3-methylbutanoyl)piperazin-1-yl]phenyl}amino)pyrimidin-4-yl]phenyl}acetamide: $^1$H-NMR (400 MHz, d$_6$-DMSO): 10.23 (s, 1H), 9.04 (s, 1H), 8.44 (d, 1H), 8.11 (d, 2H), 7.74 (d, 2H), 7.69 (d, 2H), 7.27 (d, 1H), 6.96 (d, 2H) 3.67 (m, 4H), 3.06 (m, 2H), 3.02 (m, 2H), 2.24 (d, 2H), 2.09 (s, 3H), 1.97-2.09 (m, 1H), 0.92 (d, 6H). MS (EI) for $C_{27}H_{32}N_6O_2$: 473.8 (MH$^+$).

N-{4-[2-({4-[4-(cyclobutylcarbonyl)piperazin-1-yl]phenyl}amino)pyrimidin-4-yl]-phenyl}acetamide: $^1$H-NMR (400 MHz, d$_6$-DMSO): 10.22 (s, 1H), 9.40 (s, 1H), 8.44 (d, 1H), 8.11 (d, 2H), 7.74 (d, 2H), 7.69 (d, 2H), 7.27 (d, 1H), 6.95 (d, 2H), 3.59 (m, 2H), 3.46 (m, 2H), 3.39 (t, 1H), 3.02 (m, 4H), 2.11-2.23 (m, 4H), 2.09 (s, 3H), 1.89-1.92 (m, 1H), 1.72-1.78 (m, 1H). MS (EI) for $C_{27}H_{30}N_6O_2$: 470.7 (MH$^+$).

N-{4-[2-({4-[4-(cyclopentylcarbonyl)piperazin-1-yl]phenyl}amino)pyrimidin-4-yl]-phenyl}acetamide: $^1$H-NMR (400 MHz, d$_6$-DMSO): 10.21 (s, 1H), 9.40 (s, 1H), 8.44 (d, 1H), 8.11 (d, 2H), 7.74 (d, 2H), 7.69 (d, 2H), 7.27 (d, 1H), 6.96 (d, 2H), 3.63 (m, 4H), 3.04 (m, 4H), 2.98 (m, 1H), 2.09 (s, 3H), 1.74-2.09 (m, 2H), 1.51-1.72 (m, 6H). MS (EI) for C$_{28}$H$_{32}$N$_6$O$_2$: 485.5 (MH$^+$).

N-[4-(2-{[4-4-{[2-(methyloxy)phenyl]carbonyl}piperazin-1-yl]phenyl]amino}-pyrimidin-4-yl)phenyl]acetamide: $^1$H-NMR (400 MHz, d$_6$-DMSO): 10.22 (s, 1H), 9.40 (s, 1H), 8.44 (d, 1H), 8.10 (d, 2H), 7.74 (d, 2H), 7.68 (d, 2H), 7.42 (m, 1H), 7.27 (d, 1H), 7.22 (dd, 1H), 7.10 (d, 1H), 7.02 (m, 1H), 6.96 (d, 2H), 3.81 (s, 3H), 3.77 (m, 2H), 3.27 (m, 2H), 3.12 (m, 2H), 3.01 (m, 2H), 2.09 (s, 3H). MS (EI) for C$_{30}$H$_{30}$N$_6$O$_3$: 523.7 (MH$^+$).

N-(4-{2-[(4-{4-[(2-methylphenyl)carbonyl]piperazin-1-yl}phenyl)amino]pyrimidin-4-yl}phenyl)acetamide: $^1$H-NMR (400 MHz, d$_6$-DMSO): 10.22 (s, 1H), 9.41 (s, 1H), 8.44 (d, 1H), 8.11 (d, 2H), 7.74 (d, 2H), 7.69 (d, 2H), 7.30-7.36 (m, 2H), 7.28 (d, 2H), 7.19-7.24 (m, 1H), 6.96 (d, 2H), 3.82 (m, 2H), 3.28 (m, 2H), 3.16 (m, 2H), 3.00 (m, 2H), 2.25 (s, 3H), 2.09 (s, 3H). MS (EI) for C$_{30}$H$_{30}$N$_6$O$_2$: 507.8 (MH$^+$).

N-[4-(2-{[3-(4-{[2-(methyloxy)phenyl]methyl}piperazin-1-yl)phenyl]amino}-pyrimidin-4-yl)phenyl]acetamide: $^1$H NMR (400 MHz, d6-DMSO): 11.21 (s, 1H), 9.46 (s, 1H), 8.49 (d, 1H), 8.12 (d, 2H), 7.73 (d, 2H), 7.63 (s, 1H), 7.36 (d, 1H), 7.32 (d, 1H), 7.21 (m, 2H), 7.10 (t, 1H), 6.98 (m, 2H), 6.55 (d, 1H), 3.80 (s, 3H), 3.54 (s, 2H), 3.16 (m, 4H), 2.57 (m, 4H), 2.09 (s, 3H). MS (EI) for C$_{30}$H$_{32}$N$_6$O$_2$: 509.6 (MH+).

N-{4-[2-({4-[(2R,6S)-2,6-dimethylmorpholin-4-yl]phenyl}amino)pyrimidin-4-yl]phenyl}-D-prolinamide: $^1$H NMR (400 MHz, d6-DMSO): 11.44 (s, 1H), 10.07 (s, 1H), 8.74 (s, 1H), 8.57 (d, 1H), 8.21 (s, 2H), 7.90 (m, 4H), 7.73 (s, 2H), 7.48 (d, 1H), 4.49 (m, 1H), 4.24 (m, 2H), 4.02 (m, 1H), 3.57 (m, 3H), 3.29 (m, 2H), 1.99 (m, 4H), 1.18 (m, 7H). MS (EI) for C$_{27}$H$_{32}$N$_6$O$_2$: 473.5 (MH+).

N-(4-{2-[(4-morpholin-4-ylphenyl)amino]pyrimidin-4-yl}phenyl)-5-oxo-D-prolinamide: $^1$H NMR (400 MHz, d6-DMSO): 10.33 (s, 1H), 9.39 (s, 1H), 8.45 (d, 1H), 8.14 (d, 2H), 7.93 (m, 1H), 7.79 (d, 2H), 7.67 (d, 2H), 7.28 (d, 1H), 6.93 (d, 2H), 4.23 (m, 1H), 3.75 (m, 4H), 3.05 (m, 4H), 2.35 (m, 1H), 2.21 (m, 2H), 2.03 (m, 1H). MS (EI) for C$_{25}$H$_{26}$N$_6$O$_3$: 459.5 (MH+).

N$^1$-(4-{2-[(4-morpholin-4-ylphenyl)amino]pyrimidin-4-yl}phenyl)-D-aspartamide: $^1$H NMR (400 MHz, d6-DMSO): 11.71 (s, 1H), 10.09 (s, 1H), 8.94 (s, 3H), 8.58 (d, 1H), 8.23 (d, 2H), 7.91 (m, 4H), 7.73 (s br, 2H), 7.49 (d, 1H), 4.52 (m, 4H), 4.05 (m, 5H), 3.33 (d, 1H), 3.29 (d, 1H). MS (EI) for C$_{24}$H$_{27}$N$_7$O$_3$: 462.5 (MH+).

N$^1$-(4-{2-[(4-morpholin-4-ylphenyl)amino]pyrimidin-4-yl}phenyl)-L-glutamamide: $^1$H NMR (400 MHz, d6-DMSO): 9.39 (s, 1H), 8.44 (d, 1H), 8.12 (d, 2H), 7.83 (d, 2H), 7.67 (d; 2H), 7.35 (s, 1H), 7.29 (d, 1H), 6.93 (d, 2H), 6.77 (s, 1H), 3.75 (m, 4H), 3.37 (t, 1H), 3.05 (m, 4H), 1.88 (m, 2H), 1.70 (m, 1H). MS (EI) for C$_{25}$H$_{29}$N$_7$O$_3$: 476.5 (MH+).

N-(4-{2-[(4-morpholin-4-ylphenyl)amino]pyrimidin-4-yl}phenyl)-D-threoninamide: $^1$H NMR (400 MHz, d6-DMSO): 11.26 (s, 1H), 9.89 (s, 1H), 8.54 (d, 1H), 8.31 (s, 2H), 8.19 (d, 2H), 7.86 (d, 3H), 7.44 (m, 3H), 4.11 (m, 2H), 3.96 (m, 4H), 3.39 (m, 4H), 1.23 (d, 3H). MS (EI) for C$_{24}$H$_{28}$N$_6$O$_3$: 449.5 (MH+).

N-(4-{2-[(3-chloro-4-morpholin-4-ylphenyl)amino]pyrimidin-4-yl}phenyl)-L-prolinamide: $^1$H NMR (400 MHz, d6-DMSO): 11.43 (s, 1H), 9.99 (s, 1H), 8.55 (d, 1H), 8.20 (d, 2H), 8.03 (s, 1H), 7.89 (d, 2H), 7.71 (dd, 1H), 7.46 (d, 2H), 7.20 (d, 1H), 4.49 (m, 1H), 3.76 (m, 4H), 3.28 (m, 2H), 2.96 (m, 4H), 1.97 (m, 4H). MS (EI) for C$_{25}$H$_{27}$ClN$_6$O$_2$: 479.9 (MH+).

N-(4-{2-[(3-chloro-4-morpholin-4-ylphenyl)amino]pyrimidin-4-yl}phenyl)-D-prolinamide: $^1$H NMR (400 MHz, d6-DMSO): 11.55 (s, 1H), 10.15 (s, 1H), 8.56 (d, 1H), 8.21 (d, 2H), 8.01 (s, 1H), 7.89 (d, 2H), 7.71 (dd, 1H), 7.49 (d, 2H), 7.23 (d, 1H), 4.51 (m, 1H), 3.76 (m, 4H), 3.29 (m, 2H), 2.97 (m, 4H), 1.97 (m, 4H). MS (EI) for C$_{25}$H$_{27}$ClN$_6$O$_2$: 479.9 (MH+).

N-(4-{2-[(4-morpholin-4-ylphenyl)amino]pyrimidin-4-yl}phenyl)-D-leucinamide: $^1$H NMR (400 MHz, d6-DMSO): 11.41 (s, 1H), 10.05 (s, 1H), 8.56 (d, 1H), 8.60 (m, 3H), 8.25 (d, 2H), 7.96 (m, 3H), 7.69 (m, 2H), 7.47 (d, 1H), 4.14 (m, 1H), 4.04 (m, 4H), 3.57 (m, 4H), 1.71 (m, 2H), 1.19 (m, 1H), 1.00 (s, 6H). MS (EI) for C$_{26}$H$_{32}$N$_6$O$_2$: 461.5 (MH+).

N-(4-{2-[(4-morpholin-4-ylphenyl)amino]pyrimidin-4-yl}phenyl)-D-isoleucinamide: $^1$H NMR (400 MHz, d6-DMSO): 11.41 (s, 1H), 10.10 (s, 1H), 8.56 (d, 1H), 8.47 (m, 2H), 8.20 (d, 2H), 7.92 (m, 3H), 7.73 (m, 2H), 7.47 (d, 1H), 4.12 (m, 4H), 3.57 (m, 4H), 1.65 (m, 2H), 1.18 (m, 2H), 1.00 (d, 3H), 0.89 (t, 3H). MS (EI) for C$_{26}$H$_{32}$N$_6$O$_2$: 461.5 (MH+).

(2R)-2-amino-N-(4-{2-[(4-morpholin-4-ylphenyl)amino]pyrimidin-4-yl}phenyl)-butanamide: $^1$H NMR (400 MHz, d6-DMSO): 11.57 (s, 1H), 10.20 (s, 1H), 8.56 (m, 3H), 8.24 (m, 2H), 7.97 (m, 4H), 7.82 (s, 1H), 7.54 (s, 1H), 4.05 (m, 5H), 1.96 (m, 4H), 1.10 (m, 5H). MS (EI) for C$_{24}$H$_{28}$N$_6$O$_2$: 433.5 (MH+).

N-(4-{2-[(3-aminophenyl)amino]pyrimidin-4-yl}phenyl)thiophene-2-carboxamide: $^1$H-NMR (400 MHz, d6-DMSO): 10.5 (s, 1H), 9.40 (br s, 1H), 8.55 (d, 1H), 8.23 (d, 2H), 8.09 (dd, 1H), 7.96-7.91 (m, 5H), 7.53 (m, 1H), 7.45 (d, 1H), 7.32-7.25 (m, 3H), 6.74 (br s, 1H). MS (EI): 388.0 (MH+).

N-(3-{[4-(4-aminophenyl)pyrimidin-2-yl]amino}phenyl)-2,6-dichlorobenzamide: $^1$H-NMR (400 MHz, d6-DMSO): 10.7 (s, 1H), 9.67 (s, 1H), 8.37-8.35 (m, 2H), 8.01 (d, 2H), 7.61-7.58 (m, 2H), 7.51-7.49 (m, 1H), 7.44 (dt, 1H), 7.31-7.22 (m, 3H), 6.69 (d, 2H), 5.95 (br, 2H)); MS (EI): 450.0 (MH+).

4-{[2-chloro-4-(methyloxy)phenyl]oxy}-N-(4-morpholin-4-ylphenyl)pyrimidin-2-amine: $^1$H-NMR (400 MHz, d6-DMSO): 9.37 (s, 1H), 8.31 (d, 1H), 7.33-7.23 (m, 4H), 7.02 (dd, 1H), 7.00 (br d, 2H), 6.41 (d, 1H), 3.83 (s, 3H), 3.73-3.71 (m, 4H), 2.98-2.96 (m, 4H). MS (EI): 412.8 (MH+).

N-[4-({2-[(4-morpholin-4-ylphenyl)amino]pyrimidin-4-yl}oxy)phenyl]acetamide: $^1$H-NMR (400 MHz, d6-DMSO): 10.2 (s, 1H), 9.92 (br s, 1H), 8.33 (d, 1H), 7.66 (d, 2H), 7.42 (br s, 2H), 7.17 (d, 2H), 7.10 (br s, 2H), 6.50 (d, 1H), 3.86 (br s, 4H), 3.24 (br s, 4H), 2.08 (s, 3H); MS (EI): 406.1 (MH+).

N-[4-(2-{[4-(4-D-alanylpiperazin-1-yl)phenyl]amino}pyrimidin-4-yl)phenyl]-3-(methyloxy)propanamide: $^1$H-NMR (400 MHz, d6-DMSO): 10.3 (s, 1H), 9.61 (br s, 1H), 8.46 (d, 1H), 8.16-8.12 (m, 4H), 7.78 (d, 2H), 7.72 (d, 2H), 7.34 (d, 1H), 7.12 (br s, 2H), 4.47-4.44 (m, 1H), 3.80 (br s, 4H), 3.64 (t, 2H), 3.64 (s, 3H), 3.07 (br s, 4H), 2.60 (t, 2H), 1.34 (d, 3H); MS (EI): 504.2 (MH+).

3-(methyloxy)-N-[4-(2-{[4-(4-L-prolylpiperazin-1-yl)phenyl]amino}pyrimidin-4-yl)phenyl]propanamide: $^1$H-NMR (400 MHz, d6-DMSO): 10.3 (s, 1H), 9.51 (s, 1H), 8.54 (m, 1H), 8.45 (d, 1H), 8.12 (d, 2H), 7.77 (d, 2H), 7.71 (d, 2H), 7.31 (d, 1H), 7.04 (br d, 2H), 4.68 (m, 1H), 4.07 (br s, 4H), 3.64 (t, 2H), 3.25 (s, 3H), 3.17 (br s, 4H), 2.60 (t, 2H), 2.43-2.39 (m, 2H), 1.94-1.81 (m, 4H); MS (EI): 530.2 (MH+).

N-{4-[2-({4-[4-(cyclobutylcarbonyl)piperazin-1-yl]phenyl}amino)pyrimidin-4-yl]phenyl}cyclopropanecarboxamide: $^1$H-NMR (400 MHz, d6-DMSO): 10.5 (s, 1H), 9.60 (br s, 1H), 8.46 (d, 1H), 8.12 (d, 2H), 7.78-7.76 (m, 4H), 7.34 (m, 1H), 7.13 (br s, 2H), 3.70 (m, 1H), 3.54 (br s, 4H), 3.41 (m, 1H), 3.16 (br s, 4H), 2.23-2.08 (m, 3H), 1.95-1.74 (m, 3H), 0.84-0.83 (m, 4H); MS (EI): 497.2 (MH+).

N-{4-[2-({4-[4-(2-methylpropanoyl)piperazin-1-yl]phenyl}amino)pyrimidin-4-yl]-phenyl}cyclopropanecarboxamide: $^1$H-NMR (400 MHz, d6-DMSO): 10.5 (s, 1H), 9.69 (br s, 1H), 8.47 (d, 1H), 8.13 (d, 2H), 7.77 (d, 4H), 7.36 (d, 2H), 7.23 (br s, 1H), 3.76 (br s, 4H), 3.25 (br s, 4H), 2.94 (septet, 1H), 1.84 (p, 1H), 1.03 (d, 6H), 0.84-0.83 (m, 4H). MS (EI): 485.1 (MH+).

2,6-dichloro-N-{3-[(4-(4-[(cyclopropylcarbonyl)amino]phenyl)pyrimidin-2-yl)-amino]phenyl}benzamide: $^1$H-NMR (400 MHz, d6-DMSO): 10.7 (s, 1H), 10.5 (s, 1H), 9.74 (s, 1H), 8.50 (d, 1H), 8.40 (s, 1H), 8.21 (d, 2H), 7.76 (d, 2H), 7.61-7.59 (m, 2H), 7.53-7.49 (m, 1H), 7.47-7.45 (m, 1H), 7.39 (d, 1H), 7.31-7.22 (m, 2H), 1.83 (p, 1H), 0.83-0.81 (m, 4H); MS (EI): 518.1 (MH+).

2,6-dichloro-N-(3-{[4-(1H-indol-5-yl)pyrimidin-2-yl]amino}phenyl)benzamide: $^1$H-NMR (400 MHz, d6-DMSO): 11.3 (s, 1H), 10.7 (s, 1H), 9.56 (s, 1H), 8.45 (s, 1H), 8.39 (d, 1H), 8.31 (s, 1H), 7.96 (dd, 1H), 7.54-7.52 (m, 2H), 7.46-7.41 (m, 3H), 7.37-7.34 (m, 2H), 7.21 (d, 2H), 6.48-6.48 (m, 1H). MS (EI): 474.0 (MH+).

N-(4-{2-[(3-aminophenyl)amino]pyrimidin-4-yl}phenyl)-2-morpholin-4-ylacetamide: $^1$H-NMR (400 MHz, d6-DMSO): 11.0 (s, 1H), 10.4 (br, 2H), 9.89 (s, 1H), 8.56 (d, 1H), 8.23 (d, 2H), 7.82-7.79 (m, 3H), 7.62 (br, 1H), 7.44 (d, 1H), 7.34 (br, 1H), 6.8 (br, 1H), 4.24 (s, 2H), 3.96-3.84 (m, 8H); MS (EI): 405.3 (MH+).

N-(4-phenylpyrimidin-2-yl)benzene-1,3-diamine: $^1$H-NMR (400 MHz, d6-DMSO): 9.37 (s, 1H), 8.51 (d, 1H), 8.19-8.16 (m, 2H), 7.57-7.53 (m, 3H), 7.37-7.36 (d, 1H), 7.10 (t, 1H), 7.00-6.91 (m, 2H), 6.22-6.20 (m, 1H), 5.00 (s, 2H). MS (EI): 263.3 (MH+).

N-[3-({4-[4-(acetylamino)-2-chlorophenyl]pyrimidin-2-yl}amino)phenyl]-2,6-dichlorobenzamide: $^1$H-NMR (400 MHz, d6-DMSO): 10.7 (s, 1H), 10.3 (s, 1H), 9.78 (s, 1H), 8.52 (d, 1H), 8.13-8.12 (m, 1H), 7.93 (s, 1H), 7.71 (d, 1H), 7.30-7.21 (m, 5H), 7.30-7.21 (m, 2H), 7.11 (d, 1H), 2.07 (s, 3H). MS (EI): 527.9 (MH+).

2,6-dichloro-N-{3-[(4-phenylpyrimidin-2-yl)amino]phenyl}benzamide: $^1$H-NMR (400 MHz, d6-DMSO): 10.7 (s, 1H), 9.76 (s, 1H), 8.56 (d, 1H), 8.39 (s, 1H), 8.26-8.23 (m, 2H), 7.61-7.59 (m, 2H), 7.55-7.48 (m, 5H), 7.44 (d, 1H), 7.31-7.24 (m, 2H); MS (EI): 437.0 (MH+).

4-(2,4-dichlorophenyl)-N-(4-morpholin-4-ylphenyl)pyrimidin-2-amine: $^1$H-NMR (400 MHz, d6-DMSO): 9.59 (s, 1H), 8.52 (d, 1H), 7.80 (d, 1H), 7.66 (d, 1H), 7.63-7.58 (m, 3H), 7.00 (d, 1H), 6.88 (d, 2H), 3.74-3.72 (m, 4H), 3.04-3.01 (m, 4H); MS (EI): 401.0 (MH+).

4-(2,4-dichlorophenyl)-N-{3-[(4-ethylpiperazin-1-yl)carbonyl]phenyl}pyrimidin-2-amine: $^1$H-NMR (400 MHz, d6-DMSO): 10.0 (s, 1H), 8.62 (d, 1H), 7.92 (s, 1H), 7.82 (d, 1H), 7.76 (dd, 1H), 7.70-7.68 (m, 1H), 7.62-7.59 (m, 1H), 7.34 (t, 1H), 7.13 (d, 1H), 6.96-6.94 (m, 1H), 3.59 (br s, 2H), 3.32 (br s, 2H), 2.37 (br s, 2H), 2.30 (q, 2H), 2.22 (br s, 2H), 0.99 (t, 3H); MS (EI): 456.0 (MH+).

2,6-dichloro-N-(3-{[4-(2,4-dichlorophenyl)pyrimidin-2-yl]amino}phenyl)benzamide: $^1$H-NMR (400 MHz, d6-DMSO): 10.7 (s, 1H), 9.89 (s, 1H), 8.59 (d, 1H), 8.14-8.13 (m, 1H), 7.80 (d, 1H), 7.77 (d, 1H), 7.59-7.48 (m, 5H), 7.32-7.23 (m, 2H), 7.14 (d, 1H); MS (EI): 504.9 (MH+).

N-(2-{2-[(4-morpholin-4-ylphenyl)amino]pyrimidin-4-yl}phenyl)acetamide: $^1$H-NMR (400 MHz, d6-DMSO): 11.3 (s, 1H), 9.61 (s, 1H), 8.53 (d, 1H), 8.19 (d, 1H), 7.79 (d, 1H), 7.50 (d, 2H), 7.48-7.44 (m, 1H), 7.22 (td, 1H), 7.14 (d, 1H), 6.94 (d, 2H), 3.75-3.73 (m, 4H), 3.06-3.03 (m, 4H), 1.69 (s, 3H). MS (EI): 390.1 (MH+).

4-[3-(methyloxy)phenyl]-N-(4-morpholin-4-ylphenyl)pyrimidin-2-amine: $^1$H-NMR (400 MHz, d6-DMSO): 9.45 (s, 1H), 8.49 (d, 1H), 7.73-7.66 (m, 4H), 7.45 (t, 1H), 7.34 (d, 1H), 7.13-7.10 (m, 1H), 6.92 (d, 2H), 3.86 (s, 3H), 3.75-3.35 (m, 4H), 2.51-2.50 (m, 4H). MS (EI): 363.1 (MH+).

4-(2,3-dihydro-1,4-benzodioxin-6-yl)-N-(4-morpholin-4-ylphenyl)pyrimidin-2-amine: $^1$H-NMR (400 MHz, d6-DMSO): 9.36 (s, 1H), 8.41 (d, 1H), 7.69-7.64 (m, 4H), 7.25 (d, 1H), 6.99 (d, 1H), 6.92 (d, 2H), 4.33-4.30 (m, 4H), 3.75-3.73 (m, 4H), 3.06-3.03 (m, 4H); MS (EI): 391.1 (MH+).

3-(methyloxy)-N-{4-[2-({4-[4-(piperazin-1-ylacetyl)piperazin-1-yl]phenyl}amino)-pyrimidin-4-yl]phenyl}propanamide: $^1$H-NMR (400 MHz, d6-DMSO): 10.2 (s, 1H), 9.43 (s, 1H), 8.79 (br, 1H), 8.45 (d, 1H), 8.12 (d, 2H), 7.77 (d, 2H), 7.69 (d, 2H), 7.29 (d, 1H), 6.98 (d, 2H), 3.64 (t, 2H), 3.59 (br s, 2H), 3.25 (s, 3H), 3.22 (br m, 8H), 3.13 (br m, 4H), 3.07 (br m, 4H), 2.60 (t, 2H). MS (EI): 559.3 (MH+).

$N^2,N^2$-dimethyl-N-[4-(2-{[4-(4-L-prolylpiperazin-1-yl)phenyl]amino}pyrimidin-4-yl)phenyl]glycinamide.1.3 AcOH: $^1$H-NMR (400 MHz, $d_6$-DMSO): 10.00 (s, 1H), 9.42 (s, 1H), 8.45 (d, 1H), 8.12 (d, 2H), 7.84 (d, 2H), 7.69 (d, 2H), 7.29 (d, 1H), 6.97 (d, 2H), 3.90 (m, 1H), 3.64 (m, 4H), 3.11 (s, 2H), 3.10-2.98 (m, 5H), 2.66 (m, 1H), 2.29 (s, 6H), 2.07-1.99 (m, 1H), 1.89 (s, 4H), 1.73-1.54 (m, 3H); MS (EI) $C_{29}H_{36}N_8O_2$: 529.2 (MH$^+$).

$N^2,N^2$-dimethyl-N-[4-(2-{[4-(4-D-prolylpiperazin-1-yl)phenyl]amino}pyrimidin-4-yl)phenyl]glycinamide 1.4 AcOH: $^1$H-NMR (400 MHz, $d_6$-DMSO): 10.00 (s, 1H), 9.42 (s, 1H), 8.45 (d, 1H), 8.12 (d, 2H), 7.84 (d, 2H), 7.69 (d, 2H), 7.29 (d, 1H), 6.97 (d, 2H), 3.97 (m, 1H), 3.64 (m, 4H), 3.12 (s, 2H), 3.11-3.0 (m, 5H), 2.70 (m, 1H), 2.29 (s, 6H), 2.07-1.99 (m, 1H), 1.90 (s, 4H), 1.75-1.55 (m, 3H); MS (EI) $C_{29}H_{36}N_5O_2$: 529.2 (MH$^+$).

2-(dimethylamino)-N-(4-(2-(4-(4-(2-(piperazin-1-yl)acetyl)piperazin-1-yl)phenylamino)pyrimidin-4-yl)phenyl)acetamide.3 AcOH: $^1$H-NMR (400 MHz, $d_6$-DMSO): 10.01 (s, 1H), 9.41 (s, 1H), 8.45 (d, 1H), 8.12 (d, 2H), 7.84 (d, 2H), 7.68 (d, 2H), 7.29 (d, 1H), 6.96 (d, 1H), 3.71 (m, 2H), 3.59 (m, 2H), 3.15 (s, 2H), 3.12 (s, 2H), 3.10 (m, 2H), 3.02 (m, 2H), 2.71 (m, 4H), 2.35 (m, 4H), 2.29 (s, 6H), 1.84 (s, 9H); MS (EI) $C_{30}H_{39}N_9O_2$: 558.5 (MH$^+$).

1,1-dimethylethyl[(4-{2-[(4-morpholin-4-ylphenyl)amino]pyrimidin-4-yl}-phenyl)methyl]carbamate: $^1$H NMR (400 MHz, CDCl3): 8.20-8.22 (b, 1H), 8.05 (d, 2H), 7.65 (d, 1H), 7.50 (d, 2H), 7.25 (s, 1H), 7.23 (d, 2H), 7.05 (d, 2H), 5.01 (d, 1H), 4.40-4.44 (b, 2H), 3.90 (t, 4H), 3.20 (t, 4H), 1.50 (s, 9H); MS (EI) for $C_{26}H_{31}N_5O_3$: 462 (MH$^+$).

4-(4-(aminomethyl)phenyl)-N-(4-morpholinophenyl)pyrimidin-2-amine: $^1$H NMR (400 MHz, CD3CN): 10.10-10.20 (b, 1H), 8.40 (d, 1H), 8.20 (d, 2H), 7.80 (d, 2H), 7.60 (d, 2H), 7.50 (d, 2H), 7.45 (d, 1H), 7.20-7.22 (b, 2H), 4.40-4.44 (b, 2H), 3.90 (t, 4H), 3.20 (t, 4H); MS (EI) for $C_{21}H_{23}N_5O$: 362 (MH$^+$).

methyl 4-{2-[(4-morpholin-4-ylphenyl)amino]pyrimidin-4-yl}benzoate: $^1$H NMR (400 MHz, CDCl$_3$): 8.45 (s, 1H), 8.20-8.30 (m, 4H), 7.65 (d, 1H), 7.25 (d, 2H), 7.15 (d, 2H), 6.85 (d, 1H), 4.01 (s, 3H), 3.90 (t, 4H), 3.20 (t, 4H); MS (EI) for $C_{22}H_{22}N_4O_3$: 391 (MH$^+$).

1-{4-[2-({4-[4-(2,2-dimethylpropanoyl)piperazin-1-yl]phenyl}amino)pyrimidin-4-yl]phenyl}-3-ethylurea: $^1$H NMR (400 MHz, d6-DMSO): 9.50-9.45 (b, 1H), 8.80 (s, 1H), 8.40 (s, 1H), 8.05 (d, 2H), 7.75-7.70 (m, 4H), 7.30 (d, 1H), 7.05 (d, 2H), 6.01 (d, 1H), 4.01 (q, 2H), 3.90 (m, 2H), 3.20 (m, 6H), 1.20 (s, 9H), 1.10 (t, 3H); MS (EI) for $C_{28}H_{35}N_7O_2$: 502 (MH$^+$).

1-{4-[2-({4-[4-(cyclobutylcarbonyl)piperazin-1-yl]phenyl}amino)pyrimidin-4-yl]phenyl}-3-ethylurea: $^1$H NMR (400 MHz, d6-DMSO): 9.45 (s, 1H), 8.80 (s, 1H), 8.40 (s, 1H), 8.05 (d, 2H), 7.75-7.70 (m, 4H), 7.30 (d, 1H), 7.05 (d, 2H), 6.01 (d, 1H), 3.80 (m, 4H), 3.50 (q, 2H), 3.40 (m, 4H), 3.30 (m, 1H), 3.20 (m, 6H), 1.10 (t, 3H); MS (EI) for $C_{28}H_{33}N_7O_2$: 500 (MH$^+$).

1-ethyl-3-{4-[2-({4-[4-(2-methylpropanoyl)piperazin-1-yl]phenyl}amino)pyrimidin-4-yl]phenyl}urea: $^1$H NMR (400 MHz, d$_6$-DMSO): 9.45 (s, 1H), 8.80 (s, 1H), 8.40 (s, 1H), 8.05 (d, 2H), 7.75-7.70 (m, 4H), 7.30 (d, 1H), 7.05 (d, 2H), 6.01 (d, 1H), 3.80 (m, 4H), 3.30 (q, 2H), 3.20 (m, 4H), 3.10 (m, 1H), 1.20 (m, 6H), 1.10 (t, 3H); MS (EI) for $C_{27}H_{33}N_7O_2$: 488 (MH$^+$).

N-ethyl-4-(4-({[4-4-{[(ethylamino)carbonyl]amino}phenyl)pyrimidin-2-yl]amino}-phenyl)piperazine-1-carboxamide: $^1$H NMR (400 MHz, d6-DMSO): 9.45 (s, 1H), 8.80 (s, 1H), 8.40 (m, 1H), 8.05 (d, 2H), 7.75-7.70 (m, 4H), 7.30 (d, 1H), 7.05 (d, 2H), 6.50 (s, 1H), 6.20 (d, 1H), 3.40-3.50 (m, 4H), 3.00-3.15 (m, 8H), 1.10-1.20 (m, 6H); MS (EI) for $C_{26}H_{32}N_8O_2$: 489 (MH$^+$).

1-ethyl-3-[4-(2-{[4-(4-L-prolylpiperazin-1-yl)phenyl]amino}pyrimidin-4-yl)phenyl]-urea: $^1$H NMR (400 MHz, d6-DMSO): 10.20-10.25 (b, 1H), 9.45 (s, 1H), 8.40 (m, 1H), 8.05 (d, 2H), 7.75-7.60 (m, 6H), 7.30 (d, 1H), 7.00-6.90 (m, 2H), 3.80-3.81 (m, 1H), 3.70-3.65 (m, 4H), 3.20-3.25 (m, 2H), 3.15-3.10 (m, 4H), 1.60-1.50 (m, 6H), 1.10-1.20 (m, 3H); MS (EI) for $C_{28}H_{34}NO_2$: 515 (MH$^+$).

1-[4-(2-{[4-(4-L-alanylpiperazin-1-yl)phenyl]amino}pyrimidin-4-yl)phenyl]-3-ethyl-urea: $^1$H NMR (400 MHz, d6-DMSO): 9.70-9.65 (b, 1H), 9.25 (s, 1H), 8.40 (m, 1H), 8.05 (d, 2H), 7.75-7.60 (m, 4H), 7.30 (d, 1H), 7.00-6.90 (m, 2H), 6.80-6.75 (m, 1H), 3.80-3.81 (m, 1H), 3.70-3.65 (m, 4H), 3.60-3.55 (b, 2H), 3.25-3.20 (m, 6H), 1.10-1.20 (m, 6H); MS (EI) for $C_{26}H_{32}N_8O_2$: 489 (MH$^+$).

1-ethyl-3-{4-[2-({4-[4-(piperazin-1-ylacetyl)piperazin-1-yl]phenyl}amino)pyrimidin-4-yl]phenyl}urea: $^1$H NMR (400 MHz, d4-MeOH): 8.40 (m, 1H), 8.05 (d, 2H), 7.75-7.60 (m, 4H), 7.30 (d, 1H), 7.00-6.90 (m, 2H), 3.80-3.81 (m, 4H), 3.30-3.10 (m, 16H), 2.80-2.90 (m, 4H), 1.20 (t, 3H); MS (EI) for $C_{29}H_{37}N_9O_2$: 544 (MH$^+$).

1-ethyl-3-[4-(2-{[4-(4-D-prolylpiperazin-1-yl)phenyl]amino}pyrimidin-4-yl)phenyl]-urea: $^1$H NMR (400 MHz, d6-DMSO): 10.20-10.25 (b, 1H), 9.40-9.35 (b, 1H), 9.20 (s, 1H), 8.40 (m, 1H), 8.05 (d, 2H), 7.75-7.60 (m, 4H), 7.30 (d, 1H), 7.00-6.90 (m, 2H), 6.80-6.75 (b, 1H), 3.80-3.81 (m, 1H), 3.70-3.65 (m, 4H), 3.20-3.25 (m, 2H), 3.15-3.10 (m, 4H), 1.60-1.50 (m, 6H), 1.10-1.20 (m, 3H); MS (EI) for $C_{28}H_{34}N_8O_2$: 515 (MH$^+$).

1-[4-(2-{[4-(4-D-alanylpiperazin-1-yl)phenyl]amino}pyrimidin-4-yl)phenyl]-3-ethyl-urea: $^1$H NMR (400 MHz, d6-DMSO): 11.00-10.90 (b, 1H), 9.25 (s, 1H), 8.40 (m, 1H), 8.05 (d, 2H), 7.75-7.60 (m, 4H), 7.30 (d, 1H), 7.00-6.90 (m, 2H), 6.80-6.75 (m, 1H), 3.80-3.81 (m, 1H), 3.70-3.65 (m, 4H), 3.60-3.55 (b, 2H), 3.25-3.20 (m, 6H), 1.10-1.20 (m, 6H); MS (EI) for $C_{26}H_{32}N_8O_2$: 489 (MH$^+$).

(R)—N-(4-(2-(4-(4-(2-ethoxyacetyl)piperazin-1-yl)phenylamino)pyrimidin-4-yl)-phenyl)pyrrolidine-2-carboxamide: $^1$H NMR (400 MHz, d6-DMSO): 10.20-10.25 (b, 1H), 9.40 (s, 1H), 8.50 (d, 1H), 8.05 (d, 2H), 7.75-7.60 (m, 4H), 7.30 (d, 1H), 7.00-6.90 (m, 2H), 4.20 (s, 2H), 3.80-3.81 (m, 2H), 3.70-3.65 (m, 1H), 3.20-3.25 (m, 2H), 3.25-2.85 (m, 6H), 2.20 (m, 1H), 1.80-1.60 (m, 6H), 1.20 (t, 3H); MS (EI) for $C_{29}H_{35}N_7O_3$: 530 (MH$^+$).

N-[4-(2-{[4-(4-formylpiperazin-1-yl)phenyl]amino}pyrimidin-4-yl)phenyl]-D-prolinamide: $^1$H NMR (400 MHz, CDCl3): 10.10-10.00 (b, 1H), 8.30 (d, 2H), 8.05 (s, 1H), 8.00 (d, 2H), 7.75-7.60 (m, 4H), 7.30 (d, 1H), 7.00-6.90 (m, 2H), 6.10-6.00 (b, 1H), 4.20 (m, 1H), 3.80-3.60 (m, 4H), 3.20-3.25 (m, 6H), 2.20 (m, 2H), 1.90-1.80 (m, 2H); MS (EI) for $C_{26}H_{29}N_7O_2$: 472 (MH$^+$).

N-(4-{2-[(4-{4-[4-(dimethylamino)butanoyl]piperazin-1-yl}phenyl)amino]pyrimidin-4-yl}phenyl)-D-prolinamide: $^1$H NMR (400 MHz, d6-DMSO): 10.20-10.25 (b, 1H), 9.40 (s, 1H), 8.50 (d, 1H), 8.05 (d, 2H), 7.75-7.60 (m, 4H), 7.30 (d, 1H), 7.00-6.90 (m, 2H), 4.20 (m, 1H), 3.80-3.60 (m, 4H), 3.20-3.25 (m, 6H), 2.90-2.85 (m, 4H), 2.40 (s, 3H), 2.30-2.22 (m, 2H), 2.20 (m, 3H), 2.05 (s, 3H), 1.90-1.80 (m, 2H); MS (EI) for $C_{31}H_{40}N_8O_2$: 557 (MH$^+$).

N-(4-(2-(3-aminophenylamino)pyrimidin-4-yl)phenyl)-2-phenoxyacetamide: $^1$H NMR (400 MHz, d6-DMSO): 10.41 (s, 1H), 12.4 (s, br, 1H), 8.56 (s, 1H), 8.19 (s, 1h), 7.97-7.82 (m, 3H), 7.61-7.26 (m, 5H), 7.07-7.02 (m, 3H), 6.98 (m, 1H), 4.79 (s, 2H). MS (EI): 412 (MH+).

N-(4-(2-(4-(4-acetylpiperazin-1-yl)phenylamino)pyrimidin-4-yl)phenyl)acetamide: $^1$H NMR (400 MHz, d4-MeOH): 10.22 (s, 1H), 9.41 (m, 1H), 8.12 (m, 2H), 7.75 (m, 2H), 7.68 (m, 2H), 7.27 (m, 1H), 3.72 (m, 4H), 6.94 (m, 2H), 3.58 (m, 4H), 3.09 (m, 2H), 3.02 (m, 2H), 2.09 (s, 3H), 2.03 (s, 3H). MS (EI): 431 (MH+).

N-(4-(2-(3-amino-2,4,5,6-tetrafluorophenylamino)pyrimidin-4-yl)phenyl)acetamide: $^1$H NMR (400 MHz, d4-MeOH): 8.26 (m, 1H), 8.07 (m, 2H), 7.82 (m, 2H), 7.41 (m, 1H), 2.18 (s, 3H). MS (EI): 392 (MH+).

N-(4-(2-(4-(piperazin-1-yl)phenylamino)pyrimidin-4-yl)phenyl)acetamide: MS (EI) for $C_{22}H_{24}N6O$: 389 (MH+).

1-amino-N-(4-(2-(4-morpholinophenylamino)pyrimidin-4-yl)phenyl)cyclopropane-carboxamide: $^1$H NMR (400 MHz, d6-DMSO): 10.27 (s 1H), 10.19 (s, 1H), 9.23 (m, 3H), 8.60 (m, 1H), 8.09 (m, 2H), 7.95 (m, 3H), 7.79 (m, 2H), 7.54 (m, 1H), 4.11 (m, 4H), 3.65 (m, 4H), 1.71 (m, 2H), 1.42 (m, 2H). MS (EI): 431 (MH+).

(S)—N-(4-(2-(4-morpholinophenylamino)pyrimidin-4-yl)phenyl)indoline-2-carboxamide: $^1$H NMR (400 MHz, d6-DMSO): 10.18 (s, 1H), 9.50 (m, 1H), 8.43 (m, 1H), 8.08 (m, 2H), 7.92 (m, 2H), 7.84 (m, 2H), 7.31 (m, 1H), 7.10-6.88 (m, 4H), 6.61 (m, 2H), 6.07 (m, 1H), 4.42 (m, 1H), 3.75 (m, 4H), 3.18-2.99 (m, 6H). MS (EI): 493 (MH+).

N-(4-(2-(4-morpholinophenylamino)pyrimidin-4-yl)phenyl)tetrahydrofuran-3-carboxamide: $^1$H NMR (400 MHz, d6-DMSO): 10.34 (s, 1H), 9.39 (s, 1H), 8.44 (d, 1H), 8.12 (d, 2H), 7.77 (d, 2H), 7.67 (d, 2H), 7.28 (d, 1H), 6.93 (d, 2H), 3.95 (t, 1H), 3.82-3.69 (m, 7H), 3.25-3.16 (m, 1H), 3.05 (t, 4H), 2.13-2.06 (m, 2H). MS (EI): 446 (MH+).

N-(4-(2-(4-morpholinophenylamino)pyrimidin-4-yl)phenyl)-2-(pyridin-3-yl)-acetamide: $^1$H NMR (400 MHz, d6-DMSO): 10.53 (s, 1H), 9.34 (s, 1H), 8.54 (s, 1H), 8.47 (d, 1H), 8.33 (d, 1H), 8.12 (d, 2H), 7.76 (d, 3H), 7.67 (d, 2H), 7.37 (m, 1H), 7.28 (d, 1H), 6.93 (d, 2H), 3.76-3.73 (m, 6H), 3.06-3.03 (m, 4H). MS (EI): 467 (MH+).

1-(4-(2-(4-(4-(3-(dimethylamino)-2,2-dimethylpropyl)piperazin-1-yl)phenyl-amino)pyrimidin-4-yl)phenyl)-3-ethylurea: $^1$H NMR (400 MHz, d6-DMSO): 9.33 (s, 1H), 9.00 (s, 1H), 8.40 (d, 1H), 8.04 (d, 2H), 7.66 (d, 2H), 7.55 (d, 2H), 7.23 (d, 1H), 6.93 (d, 2H), 6.39 (t, 1H), 3.17-3.08 (m, 10H), 2.85 (s, 6H), 2.74 (s, 4H), 1.08-1.04 (m, 9H). MS (EI): 531 (MH+).

(R)—N-(4-(2-(4-(4-(3-(dimethylamino)-2,2-dimethylpropyl)piperazin-1-yl)phenylamino)pyrimidin-4-yl)phenyl)pyrrolidine-2-carboxamide: ¹H NMR (400 MHz, d6-DMSO): 12.6.4 (s, 1H), 9.35 (s, 1H), 8.42 (d, 1H), 8.10 (d, 2H), 7.69-7.63 (m, 4H), 7.28 (d, 1H), 6.89 (d, 2H), 3.30-3.23 (m, 1H), 3.15 (d, 2H), 3.10-3.04 (m, 4H), 2.62-2.58 (m, 4H), 2.34-2.28 (m, 1H), 2.21 (s, 6H), 2.18 (s, 2H), 2.10 (s, 2H), 1.82-1.64 (m, 4H), 0.84 (s, 6H). MS (EI): 557 (MH+).

(R)-2-amino-N-(4-(2-(4-(4-(3-(dimethylamino)-2,2-dimethylpropyl)piperazin-1-yl)phenylamino)pyrimidin-4-yl)phenyl)propanamide: ¹H NMR (400 MHz, d6-DMSO): 9.35 (s, 1H), 8.42 (d, 1H), 8.10 (d, 2H), 7.80 (d, 2H), 7.63 (d, 2H), 7.27 (d, 1H), 6.89 (d, 2H), 3.49-3.43 (m, 1H), 3.05-3.01 (m, 4H), 2.62-2.58 (m, 4H), 2.19 (s, 6H), 2.15 (s, 2H), 2.07 (s, 2H), 1.21 (d, 3H), 0.82 (s, 6H). MS (EI): 531 (MH+).

N-(4-(2-(4-(4-(3-(dimethylamino)-2,2-dimethylpropyl)piperazin-1-yl)phenylamino)pyrimidin-4-yl)phenyl)-3-methoxypropanamide: ¹H NMR (400 MHz, d6-DMSO): 10.31 (s, 1H), 9.38 (s, 1H), 8.44 (d, 1H), 8.11 (d, 2H), 7.78 (d, 2H), 7.66 (d, 2H), 7.27 (d, 1H), 6.93 (d, 2H), 3.63 (t, 2H), 3.34 (s, 4H), 3.25 (s, 3H), 3.13 (s, 4H), 2.84 (s, 6H), 2.74 (s, 4H), 2.60 (t, 2H), 1.05 (s, 6H). MS (EI): 546 (MH+).

2-(dimethylamino)-N-(4-(2-(4-(4-(3-(dimethylamino)-2,2-dimethylpropyl)piperazin-1-yl)phenylamino)pyrimidin-4-yl)phenyl)acetamide: ¹H NMR (400 MHz, d6-DMSO): 9.98 (s, 1H), 9.33 (s, 1H), 8.41 (d, 1H), 8.08 (d, 2H), 7.81 (d, 2H), 7.62 (d, 2H), 7.24 (d, 1H) 6.88 (d, 2H), 3.09 (s, 2H), 3.05-3.02 (m, 4H), 2.60-2.45 (m, 4H), 2.27 (s, 6H), 2.20 (s, 6H), 2.15 (s, 2H), 2.09 (s, 2H), 0.82 (s, 6H). MS (EI): 545 (MH+).

N-(4-(2-(4-(4-(3-(dimethylamino)-2,2-dimethylpropyl)piperazin-1-yl)phenylamino)pyrimidin-4-yl)phenyl)butyramide: ¹H NMR (400 MHz, d6-DMSO): 10.18 (s, 1H), 9.36 (s, 1H), 8.41 (d, 1H), 8.08 (d, 2H), 7.75 (d, 2H), 7.64 (d, 2H), 7.26 (d, 1H), 6.92 (d, 2H), 3.12 (s, 4H), 3.07 (s, 4H), 2.84 (s, 6H), 2.73 (s, 4H), 2.31 (t, 2H), 1.66-1.58 (m, 2H), 1.03 (s, 6H), 0.91 (t, 3H). MS (EI): 530 (MH+).

(3S,7S)-7-(hydroxymethyl)-N-(4-(2-(4-morpholinophenylamino)pyrimidin-4-yl)phenyl)quinuclidine-3-carboxamide: ¹H NMR (400 MHz, d6-DMSO): 10.25 (s, 1H), 9.39 (s, 1H), 8.44 (d, 1H), 8.11 (d, 2H), 7.77 (d, 2H), 7.68 (d, 2H), 7.27 (d, 1H), 6.93 (d, 2H), 3.74 (t, 4H), 3.65-3.58 (m, 2H), 3.45-3.37 (m, 3H), 3.05 (t, 4H), 2.94-2.88 (m, 3H), 2.71-2.67 (m, 1H), 2.17 (s, 1H), 1.68-1.63 (m, 2H), 1.50-1.46 (m, 1H), 1.27-1.21 (m, 1H). MS (EI): 515 (MH+).

(R)—N-(4-(2-(3-ethoxy-4-morpholinophenylamino)pyrimidin-4-yl)phenyl)-pyrrolidine-2-carboxamide: ¹H NMR (400 MHz, d6-DMSO): 11.45 (s, 1H), 10.04 (s, 1H), 8.59 (d, 1H), 8.21 (d, 2H), 7.87 (d, 2H), 7.49 (d, 1H). 7.44-7.41 (m, 2H), 7.32 (s, 1H), 7.19 (s, 1H), 4.51-4.45 (m, 2H), 4.28-4.25 (m, 4H), 4.09-4.01 (m, 4H), 3.68-3.52 (m, 3H), 3.33-3.23 (m, 2H), 2.49-2.42 (m, 1H), 2.03-1.91 (m, 3H), 1.49 (t, 3H). MS (EI): 489 (MH+).

N-{4-[2-({4-morpholin-4-yl-3-[(phenylmethyl)oxy]phenyl}amino)pyrimidin-4-yl]-phenyl}-D-prolinamide: ¹H NMR (400 MHz, d6-DMSO): 11.57 (s, 1H), 10.17 (s, 1H), 8.59 (d, 1H), 8.23 (d, 2H), 8.09 (s, 1H), 7.90 (m, 3H), 7.59 (m, 2H), 7.48 (m, 5H), 5.34 (s, 2H), 4.51 (m, 4H), 4.06 (m, 5H), 3.29 (m, 3H), 1.98 (m, 3H). MS (EI) for $C_{32}H_{34}N_6O_3$: 551.7 (MH+).

4-methyl-N-(4-{2-[(4-morpholin-4-ylphenyl)amino]pyrimidin-4-yl}phenyl)piperazine-1-carboxamide: ¹H NMR (400 MHz, d6-DMSO): 9.35 (s, 1H), 8.88 (s, 1H), 8.41 (d, 1H), 8.15 (s, 1H), 8.06 (d, 1H), 7.66 (m, 3H), 7.25 (d, 1H), 6.93 (d, 2H), 3.74 (m, 4H), 3.53 (m, 8H), 3.04 (m, 4H), 3.32 (m, 3H). MS (EI) for $C_{26}H_{31}N_7O_2$: 474.6 (MH+).

1-[3-(dimethylamino)propyl]-3-(4-{2-[(4-morpholin-4-ylphenyl)amino]pyrimidin-4-yl}phenyl)urea: ¹H NMR (400 MHz, d6-DMSO): 9.34 (s, 1H), 9.22 (s, 1H), 8.40 (d, 1H), 8.05 (d, 2H), 7.67 (d, 2H), 7.57 (d, 2H), 7.24 (d, 1H), 6.93 (d, 2H), 6.66 (t, 1H), 3.74 (m, 4H), 3.17 (m, 2H), 3.05 (m, 4H), 2.90 (t, 2H), 2.62 (s, 6H), 1.78 (m, 2H). MS (EI) for $C_{26}H_{33}N_7O_2$: 476.6 (MH+).

1-[3-(methyloxy)propyl]-3-(4-{2-[(4-morpholin-4-ylphenyl)amino]pyrimidin-4-yl}phenyl)urea: ¹H NMR (400 MHz, d6-DMSO): 9.3 (s, 1H), 8.87 (s, 1H), 8.40 (d, 1H), 8.05 (d, 2H), 7.67 (d, 2H), 7.55 (d, 2H), 7.24 (d, 1H), 6.93 (d, 2H), 6.37 (t, 1H), 3.74 (m, 4H), 3.38 (d, 2H), 3.25 (s, 3H), 3.15 (m, 2H), 3.04 (m, 4H), 1.68 (m, 2H). MS (EI) for $C_{25}H_{30}N_6O_3$: 463.6 (MH+).

1-(2-morpholin-4-ylethyl)-3-(4-{2-[(4-morpholin-4-ylphenyl)amino]pyrimidin 4-yl}phenyl)urea: ¹H NMR (400 MHz, d6-DMSO): 9.34 (s, 1H), 9.00 (s, 1H), 8.40 (d, 1H), 8.17 (s, 1H), 8.05 (d, 2H), 7.68 (d, 2H), 7.55 (d, 2H), 7.24 (d, 1H), 6.93 (d, 2H), 6.25 (t, 1H), 3.74 (m, 4H), 3.60 (m, 4H), 3.22 (m, 2H), 3.04 (m, 4H), 2.40 (m, 5H). MS (EI) for $C_{27}H_{33}N_7O_3$: 504.5 (MH+).

1-[2-(dimethylamino)ethyl]-3-(4-{2-[(4-morpholin-4-ylphenyl)amino]pyrimidin-4-yl}phenyl)urea: ¹H NMR (400 MHz, d6-DMSO): 9.33 (s, 1H), 9.06 (s, 1H), 8.40 (d, 1H), 8.21 (s, 1H), 8.04 (d, 2H), 7.67 (d, 2H), 7.55 (d, 2H), 7.23 (d, 1H), 6.93 (d, 2H), 6.33 (t, 1H), 3.74 (d, 4H), 3.21 (m, 2H), 3.05 (m, 4H), 2.38 (t, 2H), 2.12 (s, 6H). MS (EI) for $C_{25}H_{31}N_7O_2$: 462.5 (MH+).

1-ethyl-N-(4-{2-[(4-morpholin-4-ylphenyl)amino]pyrimidin-4-yl}phenyl)-L-prolinamide: ¹H NMR (400 MHz, d6-DMSO): 9.53 (s, 1H), 9.40 (s, 1H), 8.45 (d, 1H), 8.14 (d, 2H), 7.85 (d, 2H), 7.67 (d, 2H), 7.29 (d, 1H), 6.93 (d, 1H), 3.75 (m, 4H), 3.21 (m, 1H), 3.09 (m, 4H), 2.65 (m, 1H), 2.54 (m, 2H), 2.35 (m, 1H), 2.14 (m, 1H), 1.79 (m, 3H), 1.08 (t, 3H). MS (EI) for $C_{27}H_{32}N_6O_2$: 473.6 (MH+).

1-(2-hydroxyethyl)-N-(4-{2-[(4-morpholin-4-ylphenyl)amino]pyrimidin-4-yl}-phenyl)-D-prolinamide: ¹H NMR (400 MHz, d6-DMSO): 10.31 (s, 1H), 9.40 (s, 1H), 8.44 (d, 1H), 8.13 (d, 2H), 7.81 (d, 2H), 7.67 (d, 2H), 7.30 (d, 1H), 6.93 (d, 1H), 5.05 (s, br, 1H), 3.75 (m, 4H), 3.05 (m, 4H), 2.75 (m, 2H), 2.63 (m, 1H), 2.40 (m, 2H), 2.18 (m, 2H), 1.80 (m, 3H). MS (EI) for $C_{27}H_{32}N_6O_3$: 489.5 (MH+).

N-(4-{2-[(4-{4-[3-(dimethylamino)-2,2-dimethylpropyl]piperazin-1-yl}phenyl)-amino]pyrimidin-4-yl}phenyl)tetrahydrofuran-3-carboxamide: ¹H NMR (400 MHz, d6-DMSO): 10.39 (s, 1H), 9.39 (s, 1H), 8.44 (d, 1H), 8.12 (d, 2H), 7.79 (d, 2H), 7.66 (d, 2H), 7.28 (d, 1H), 6.93 (d, 2H), 3.94 (t, 1H), 3.75 (m, 4H), 3.15 (m, 8H), 2.80 (m, 9H), 2.09 (m, 2H), 1.03 (s, 7H). MS (EI) for $C_{32}H_{43}N_7O_2$: 558.7 (MH+).

(2R)—N-(4-{2-[(4-{4-[3-(dimethylamino)-2,2-dimethylpropyl]piperazin-1-yl}-phenyl)amino]pyrimidin-4-yl}phenyl)tetrahydrofuran-2-carboxamide: ¹H NMR (400 MHz, d6-DMSO): 10.88 (s, 1H), 9.34 (s, 1H), 8.52 (s, 1H), 8.38 (s, 1H), 8.00 (s, 1H), 7.56 (m, 2H), 7.22 (d, 1H), 6.96 (d, 2H), 4.43 (m, 1H), 4.00 (m, 1H), 3.86 (m, 1H), 3.05 (m, 7H), 2.60 (m, 7H), 2.20 (m, 10H), 0.85 (s, 6H). $C_{32}H_{43}N_7O_2$. MS (EI) for $C_{32}H_{43}N_7O_2$: 558.7 (MH+).

N-(4-{2-[(4-{4-[3-(dimethylamino)-2,2-dimethylpropyl]piperazin-1-yl}phenyl)-amino]pyrimidin-4-yl}phenyl)cyclopropanecarboxamide: ¹H NMR (400 MHz, d6-DMSO): 10.47 (s, 1H), 9.36 (s, 1H), 8.42 (d, 1H), 8.10 (d, 2H), 7.75 (d, 2H), 7.64 (d, 2H), 7.26 (d, 1H), 6.90 (d, 2H), 3.05 (m, 4H), 2.61 (m, 4H), 2.21 (s, 6H), 2.17 (s, 2H), 2.10 (s, 2H), 1.90 (s, 1H), 1.82 (m, 1H), 0.84 (m, 9H). MS (EI) for $C_{31}H_{41}N_7O$: 528.6 (MH+).

(S)—N-(4-(2-(4-(4-(3-(dimethylamino)-2,2-dimethylpropyl)piperazin-1-yl)phenyl-amino)pyrimidin-4-yl)phenyl)tetrahydrofuran-2-carboxamide: ¹H NMR (400 MHz, d6-DMSO): 9.95 (s, 1H), 9.40 (s, 1H), 8.44 (d, 1H), 8.12 (d, 2H), 7.88 (d, 2H), 7.67 (d, 2H), 7.29 (d, 1H), 6.93 (d, 2H), 4.44 (t, 1H), 4.01 (m, 1H), 3.85 (m, 1H), 3.14 (m, 6H), 2.86 (s, 6H), 2.77 (m, 4H), 2.21 (m, 2H), 2.01 (m, 1H), 1.90 (m, 2H), 1.05 (s, 6H). MS (EI) for $C_{32}H_{43}N_7O_2$: 558.7 (MH+).

N-(4-(2-(4-(4-(piperidine-4-carbonyl)piperazin-1-yl)phenylamino)pyrimidin-4-yl)-phenyl)tetrahydrofuran-3-carboxamide: $^1$H NMR (400 MHz, d6-DMSO): 10.35 (s, 1H), 9.41 (s, 1H), 8.44 (s, 1H), 8.14 (d, 2H), 7.78 (d, 2H), 7.68 (d, 2H), 7.28 (d, 1H), 6.96 (d, 2H), 3.96 (m, 1H), 3.73 (m, 3H), 3.62 (m, 4H), 3.20 (m, 1H), 3.04 (m, 5H), 2.79 (m, 1H), 2.62 (t, 2H), 2.11 (m, 2H), 2.79 (m, 3H), 1.55 (m, 3H). MS (EI) for $C_{31}H_{37}N_7O_3$: 556.6 (MH+).

1-(1-methylethyl)-N-(4-{2-[(4-morpholin-4-ylphenyl)amino]pyrimidin-4-yl}phenyl)-D-prolinamide: $^1$H NMR (400 MHz, d6-DMSO): 9.98 (s, 1H), 9.40 (s, 1H), 8.44 (d, 1H), 8.13 (d, 2H), 7.84 (d, 2H), 7.67 (d, 2H), 7.29 (d, 1H), 6.93 (d, 2H), 3.74 (m, 4H), 3.14 (m, 1H), 3.05 (m, 4H), 2.81 (1H), 2.54 (m, 2H), 2.08 (m, 1H), 1.77 (m, 1H), 1.75 (m, 2H), 1.05 (m, 6H). MS (EI) for $C_{28}H_{34}N_6O_2$: 487.6 (MH+).

1-ethyl-N-(4-{2-[(4-morpholin-4-ylphenyl)amino]pyrimidin-4-yl}phenyl)-D-prolinamide: $^1$H NMR (400 MHz, d6-DMSO): 9.95 (s, 1H), 9.40 (s, 1H), 8.44 (d, 1H), 8.13 (d, 2H), 7.85 (d, 2H), 7.67 (d, 2H), 7.29 (d, 1H), 6.95 (d, 2H), 3.74 (m, 4H), 3.20 (m, 1H), 3.07 (m, 5H), 2.64 (m, 1H), 2.54 (m, 1H), 2.35 (m, 1H), 2.14 (m, 1H), 1.79 (m, 3H), 1.08 (t, 3H). MS (EI) for $C_{27}H_{32}N_6O_2$: 473.5 (MH+).

2-(2-fluorophenyl)-N-(4-{2-[(4-morpholin-4-ylphenyl)amino]pyrimidin-4-yl}phenyl)acetamide: $^1$H NMR (400 MHz, d6-DMSO): 10.50 (s, 1H), 9.32 (s, 1H), 8.44 (d, 1H), 8.12 (d, 2H), 7.76 (d, 2H), 7.67 (d, 1H), 7.41 (m, 1H), 7.34 (m, 1H), 7.28 (d, 1H), 7.18 (m, 2H), 6.93 (d, 2H), 3.79 (s, 2H), 3.74 (m, 4H), 3.05 (m, 4H). MS (EI) for $C_{25}H_{26}FN_5O_2$: 484.5 (MH+).

N-(4-{2-[(4-morpholin-4-ylphenyl)amino]pyrimidin-4-yl}phenyl)pyridine-4-carboxamide: $^1$H NMR (400 MHz, d6-DMSO): 10.76 (s, 1H), 9.42 (s, 1H), 8.82 (d, 2H), 8.47 (d, 1H), 8.20 (d, 2H), 7.96 (s, 2H), 7.89 (d, 2H), 7.68 (d, 2H), 7.32 (d, 1H), 6.95 (d, 2H), 3.75 (m, 4H), 3.07 (m, 4H). MS (EI) for $C_{26}H_{24}N_6O_2$: 453.5 (MH+).

(R)—N-(4-(5-methyl-2-(4-(4-((1-methyl-1H-imidazol-2-yl)methyl)piperazin-1-yl)-phenylamino)pyrimidin-4-yl)phenyl)pyrrolidine-2-carboxamide: $^1$H NMR (400 MHz, d6-DMSO): 10.19 (s, 1H), 9.25 (s, br, 1H), 8.31 (s, 1H), 7.81-7.58 (m, 6H), 7.09-6.76 (br m, 3H), 3.79 (m, 3H), 3.66 (s, 3H), 3.02-2.92 (m, 4H), 2.20 (m, 4H), 2.09 (m, 2H), 2.00 (m, 1H), 1.82 (m, 1H), 1.70 (m, 1H), 12.4 (s, 3H). MS (EI): 552 (MH+).

(R)-2-amino-N-(4-(5-methyl-2-(4-(4-((1-methyl-1H-imidazol-2-yl)methyl)piperazin-1-yl)phenylamino)pyrimidin-4-yl)phenyl)propanamide: $^1$H NMR (400 MHz, d6-DMSO): 10.20 (s, br, 1H), 9.24 (s, br, 1H), 8.31 (s, 1H), 7.80 (d, 2H), 7.66-7.69 (m, 4H), 7.09 (s, 1H), 6.85 (m, 2H), 6.76 (s, 1H), 3.80 (m, 3H), 3.66 (m, 3H), 3.00 (m, 4H), 2.95 (m, 4H), 2.22 (s, 3H), 1.24 (s, 3H). MS (EI): 526 (MH+).

(S)-2-amino-N-(4-(5-methyl-2-(4-(4-((1-methyl-1H-imidazol-2-yl)methyl)piperazin-1-yl)phenylamino)pyrimidin-4-yl)phenyl)propanamide: $^1$H NMR (400 MHz, d6-DMSO): 10.20 (s, br, 1H), 9.24 (s, br, 1H), 8.31 (s, 1H), 7.79 (d, 2H), 7.67-7.58 (m, 4H), 7.09 (s, 1H), 6.86 (m, 2H), 6.76 (s, 1H), 3.80 (m, 3H), 3.66 (m, 3H), 3.01 (m, 4H), 2.95 (m, 4H), 2.22 (s, 3H), 1.23 (s, 3H). MS (EI) for C29H35N9O: 526 (MH+).

N-[3-({2-[(4-morpholin-4-ylphenyl)amino]-7H-pyrrolo[2,3-d]pyrimidin-4-yl}-amino)phenyl]acetamide: $^1$H NMR (400 MHz, d6-DMSO): 11.14 (s, 1H), 9.87 (s, 1H), 9.15 (s, 1H), 8.47 (s, 1H), 8.04 (s, 1H), 7.80-7.73 (m, 1H), 7.70-7.63 (m, 2H), 7.25-7.18 (m, 2H), 6.89-6.81 (m, 3H), 6.67-6.64 (m, 1H), 3.77-3.71 (m, 4H), 3.04-2.98 (m, 4H), 2.06 (s, 3H). MS (EI) for C24H25N7O2: 444 (MH+).

N-(4-{2-[(2-methyl-4-morpholin-4-ylphenyl)amino]pyrimidin-4-yl}phenyl)-acetamide: $^1$H NMR (400 MHz, d6-DMSO): 10.36 (br s, 1H), 9.51 (br s, 1H), 8.34 (d, 1H), 8.08 (d, 2H), 7.74 (d, 2H), 7.39 (d, 2H), 7.05 (br d, 2H), 3.80 (s, 4H), 3.22 (s, 4H), 2.21 (s, 3H), 2.07 (s, 3H). MS (EI): (MH+).

N-(4-{2-[(4-pyrrolidin-1-ylphenyl)amino]pyrimidin-4-yl}phenyl)acetamide: $^1$H NMR (400 MHz, d6-DMSO): 10.33 (br s, 1H), 9.72 (br s, 1H), 8.44 (d, 1H), 8.13 (d, 2H), 7.77 (d, 2H), 7.69 (br s, 2H), 7.34 (d, 1H), 3.37 (m, 4H), 2.10 (s, 3H), 2.03 (s, 4H). MS (EI): 374 (MH+).

N-[4-(2-{[4-(diethylamino)phenyl]amino}pyrimidin-4-yl)phenyl]acetamide: $^1$H NMR (400 MHz, d6-DMSO): 10.34 (br s), 9.99 (br s, 1H), 8.56 (d, 1H), 8.12 (d, 2H), 8.06 (d, 2H), 7.79 (d, 2H), 7.72 (d, 2H), 7.44 (d, 1H), 3.49 (q, 4H), 2.10 (s, 3H), 1.05 (dt, 6H). MS (EI): 376 (MH+).

N-(4-{2-[(4-azepan-1-ylphenyl)amino]pyrimidin-4-yl}phenyl)acetamide: $^1$H NMR (400 MHz, d6-DMSO): 10.34 (br s), 9.99 (br s, 1H), 8.56 (d, 1H), 8.12 (d, 2H), 8.06 (d, 2H), 7.79 (d, 2H), 7.72 (d, 2H), 7.44 (d, 1H), 3.54 (m, 4H), 2.09 (s, 3H), 1.91 (m, 2H), 1.70 (m, 2H), 1.64 (m, 4H), 1.44 (m, 2H), 1.37 (m, 2H). MS (EI): 402 (MH+).

N-{4-[2-({4-methyl(2-phenylethyl)amino)phenyl}amino)pyrimidin-4-yl]phenyl}acetamide: $^1$H NMR (400 MHz, d6-DMSO): 10.34 (br s, 1H), 9.95 (br s, 1H), 8.54 (d, 1H), 8.15 (d, 2H), 7.98 (m, 1H), 7.79 (4, 2H), 7.43 (d, 1H), 7.31 (m, 3H), 7.23 (m, 4H), 3.71 (m, 2H), 3.13 (m, 2H), 2.10 (s, 1H), 1.99 (s, 3H). MS (EI): 438 (MH+).

N-[4-(2-{[4-(1,4-dioxa-8-azaspiro[4.5]dec-8-yl)phenyl]amino}pyrimidin-4-yl)phenyl]acetamide: $^1$H NMR (400 MHz, d6-DMSO): 10.34 (br s), 9.99 (br s, 1H), 8.56 (d, 1H), 8.12 (d, 2H), 8.06 (d, 2H), 7.79 (d, 2H), 7.72 (d, 2H), 7.44 (d, 1H), 3.90 (s, 4H), 2.70 (t, 4H), (2.10 (s, 3H), 1.76 (t, 4H). MS (EI): 446 (MH+).

N-[4-(2-{[4-(2-oxopiperidin-1-yl)phenyl]amino}pyrimidin-4-yl)phenyl]acetamide: $^1$H NMR (400 MHz, d6-DMSO): 10.32 (br s, 1H), 9.86 (br s 1H), 8.51 (d, 1H), 8.14 (d, 2H), 7.85 (t, 4H), 7.40 (d, 1H), 7.22 (d, 2H), 3.59 (m, 2H), 2.38 (t, 2H), 2.09 (s, 3H), 1.85 (m, 4H). MS (EI): 402 (MH+).

N-[4-(2-{[4-(2-methylpiperidin-1-yl)phenyl]amino}pyrimidin-4-yl)phenyl]-acetamide: $^1$H NMR (400 MHz, d6-DMSO): 10.21 (br s, 1H), 9.36 (br s, 1H), 8.43 (s, 1H), 8.27 (s, 1H), 8.10 (d, 2H), 7.74 (d, 2H), 7.65 (d, 2H), 7.26 (s, 1H), 6.92 (d, 2H), 2.09 (s, 3H), 3.41 (m, 3H), 1.60 (m, 6H), 0.88 (d, 3H). MS (EI): 402 (MH+).

N-(4-{2-[(4-morpholin-4-ylphenyl)amino]pyrimidin-4-yl}phenyl)-L-valinamide: $^1$H NMR (400 MHz, d6-DMSO): 11.51 (br s, 1H), 10.16 (br s, 1H), 8.57 (s, 1H), 8.48 (m, 2H), 8.20 (m, 2H), 7.93 (m, 3H), 7.78 (m, 1H), 7.50 (s, 1H), 5.45 (br s, 4H), 4.07 (s, 4H), 3.53 (s, 4H), 3.35 (m, 1H), 2.25 (m, 1H), 1.03 (m, 6H). MS (EI): 447 (MH+).

N-(4-{2-[(4-morpholin-4-ylphenyl)amino]pyrimidin-4-yl}phenyl)-D-valinamide: $^1$H NMR (400 MHz, d6-DMSO): 11.51 (brs, 1H), 10.16 (br s, 1H), 8.57 (s, 1H), 8.48 (m, 2H), 8.20 (m, 2H), 7.93 (m, 3H), 7.78 (m, 1H), 7.50 (s, 1H), 5.45 (br s, 4H), 4.07 (s, 4H), 3.53 (s, 4H), 3.35 (m, 1H), 2.25 (m, 1H), 1.03 (m, 6H). MS (EI): 447 (MH+).

2-methyl-N-(4-{2-[(4-morpholin-4-ylphenyl)amino]pyrimidin-4-yl}phenyl)-alaninamide: $^1$H NMR (400 MHz, d6-DMSO): 10.68 (br s, 1H), 10.02 (br s, 1H), 8.53 (m, 2H), 8.18 (d, 2H), 7.95 (d, 2H), 7.89 (d, 2H), 7.66 (m, 1H), 7.47 (d, 1H), 5.20 (br s, 4H), 4.01 (s, 4H), 3.44 (s, 4H), 1.66 (6H). MS (EI): 433 (MH+).

N-(4-{2-[(4-morpholin-4-ylphenyl)amino]pyrimidin-4-yl}phenyl)tryptophanamide: $^1$H NMR (400 MHz, d6-DMSO): 11.37 (s, 1H), 10.07 (s, 1H), 10.03 (s, 1H), 8.56 (d, 1H), 8.42 (d, 2H), 8.19 (d, 1H), 7.91 (d, 2H), (d, 2H), 7.73 (d, 1H), 7.66 (1H), 7.46 (d, 1H), 7.35 (d, 1H), 7.28 (d, 1H), 7.07 (t, 1H), 6.95 (t, 1H), 4.70 (br s, 4H), 4.34 (m, 1H), 4.03 (s, 4H), 3.49 (s, 4H), 3.36 (dq, 2H). MS (EI): 534 (MH+).

N-(4-{2-[(4-morpholin-4-ylphenyl)amino]pyrimidin-4-yl}phenyl)-L-prolinamide: $^1$H NMR (400 MHz, d6-DMSO): 11.43 (br s, 1H), 10.07 (br s, 2H), 8.73 (d, 1H), 8.57 (d, 1H), 8.21 (d, 2H), 7.91 (d, 2H), 7.98 (d, 2H), 7.71 (br s, 2H), 7.48 (d, 1H), 4.48 (m, 1H), 4.08 (s, 4H), 3.74 (m, 4H), 3.42 (m, 1H), 3.36 (m, 1H), 3.04 (m, 4H), 2.22 (m 1H), 1.90 (m, 2H), 1.82 (m, 2H). MS (EI): 445 (MH+).

N-(4-{2-[(4-morpholin-4-ylphenyl)amino]pyrimidin-4-yl}phenyl)-1,2,3,4-tetrahydro-isoquinoline-1-carboxamide: $^1$H NMR (400 MHz, d6-DMSO): 11.30 (br d, 1H), 10.04 (br s, 1H), 8.56 (d, 1H), 8.39 (s, 3H), 8.20 (d, 2H), 7.90 (m, 2H), 7.87 (m, 2H), 7.67 (m, 3H), 7.47 (d, 1H), 5.00 (br s, 3H), 4.65 (s, 1H), 4.20 (m, 2H), 4.03 (s, 4H), 3.97 (m, 1H), 3.94 (m, 2H), 3.80 (m, 1H), 3.49 (s, 4H). MS (EI): 507 (MH+).

O-(1,1-dimethylethyl)-N-(4-{2-[(4-morpholin-4-ylphenyl)amino]pyrimidin-4-yl}-phenyl)-L-serinamide: $^1$H NMR (400 MHz, d6-DMSO): 12.11 (br s, 1H), 10.65 (br s, 1H), 10.12 (s, 1H), 9.60 (s, 1H), 8.58 (d, 1H), 8.23 (d, 2H), 7.95 (d, 2H), 7.79 (s, 1H), 7.56 (d, 1H), 7.49 (d, 1H), 7.31 (s, 2H), 5.14 (br s, 4H), 4.06 (s, 4H), 3.79 (m, 1H), 3.54 (s, 4H), 3.45 (m, 1H), 3.15 (q, 1H), 1.21 (s, 9H). MS (EI): 491 (MH+).

3-amino-N-(4-{2-[(4-morpholin-4-ylphenyl)amino]pyrimidin-4-yl}phenyl)tetrahydro-furan-3-carboxamide: $^1$H NMR (400 MHz, d6-DMSO): 10.89 (br s, 1H), 9.92 (br s, 1H), 8.83 (s, 2H), 8.55 (d, 1H), 8.21 (d, 2H), 7.94 (d, 2H), 7.87 (d, 1H), 7.53 (s, 1H), 7.43 (d, 1H), 4.30 (br s, 4H), 4.21 (d, 1H), 4.07 (d, 1H), 4.05 (m, 1H), 4.02 (m, 1H), 3.97 (s, 4H), 3.42 (s, 4H), 2.79 (m, 1H), 2.28 (m, 1H). MS (EI): 461 (MH+).

bis(1,1-dimethylethyl)(2R)-2-{[(4-{2-[(4-morpholin-4-ylphenyl)amino]pyrimidin-4-yl}phenyl)amino]carbonyl}piperazine-1,4-dicarboxylate: $^1$H NMR (400 MHz, d6-DMSO): 10.41 (br s, 1H), 9.35 (s, 1H), 8.42 (d, 1H), 8.14 (d, 2H), 8.76 (d, 2H), 7.67 (d, 2H), 7.28 (d, 1H), 6.93 (d, 2H), 4.51 (m, 1H), 3.90 (m, 2H), 3.74 (m, 4H), 3.66 (t, 4H), 3.04 (t, 4H), 1.41 (s, 3H), 1.33 (s, 9H), 1.17 (s, 6H). MS (EI): 660 (MH+).

N-(4-{2-[(4-{4-[2-(2-fluorophenyl)acetyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.45 (d, 1H), 8.12 (d, 2H), 7.75 (d, 2H), 7.70 (d, 2H), 7.29 (m, 3H), 7.16 (m, 2H), 6.98 (d, 2H), 3.80 (s, 2H), 3.69 (m, 2H), 3.63 (m, 2H), 3.09 (m, 2H), 3.04 (m, 2H), 2.09 (s, 3H). MS (EI): 525.5 (MH+).

N-(4-{2-[(4-{4-[2-(2-methylphenyl)acetyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.45 (d, 1H), 8.12 (d, 2H), 7.75 (d, 2H), 7.69 (d, 2H), 7.28 (d, 1H), 7.12 (m, 4H), 6.97 (d, 2H), 3.74 (m, 2H), 3.65 (m, 4H), 3.05 (m, 4H), 2.20 (s, 3H), 2.09 (s, 3H). MS (EI): 521.6 (MH+).

N-(4-{2-[(4-{4-[2-(3-fluorophenyl)acetyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.45 (d, 1H), 8.12 (d, 2H), 7.75 (d, 2H), 7.69 (d, 2H), 7.35 (m, 1H), 7.28 (d, 1H), 7.08 (m, 3H), 6.96 (d, 2H), 3.81 (s, 2H), 3.64 (m, 4H), 3.02 (m, 4H), 2.09 (s, 3H). MS (EI): 525.4 (MH+).

N-{4-[2-({4-[4-(3-thienylcarbonyl)piperazin-1-yl]phenyl}amino)pyrimidin-4-yl]-phenyl}acetamide: $^1$H NMR (400 MHz, d6-DMSO): 10.21 (s, 1H), 9.40 (s, 1H), 8.45 (d, 1H), 8.12 (d, 2H), 7.83 (m, 1H), 7.75 (d, 2H), 7.70 (d, 2H), 7.64 (m, 1H), 7.25 (m, 2H), 6.98 (d, 2H), 3.68 (m, 4H), 3.11 (m, 4H), 2.09 (s, 3H). MS (EI): 499.4 (MH+).

N-(4-{2-[(4-{4-[(6-chloropyridin-3-yl)carbonyl]piperazin-1-yl}phenyl)amino]-pyrimidin-4-yl}phenyl)acetamide: $^1$H NMR (400 MHz, d6-DMSO): 10.21 (s, 1H), 9.41 (s, 1H), 8.53 (m, 1N), 8.45 (d, 1H), 8.12 (d, 2H), 7.98 (dd, 1H), 7.75 (d, 2H), 7.70 (d, 2H), 7.65 (d, 1H), 7.28 (d, 1H), 6.98 (d, 2H), 3.78 (m, 2H), 3.48 (m, 2H), 3.17 (m, 2H), 3.08 (m, 2H), 2.09 (s, 3H). MS (EI): 529.1 (MH+).

N-(4-{2-[(4-{4-[(3-methylfuran-2-yl)carbonyl]piperazin-1-yl}phenyl)amino]-pyrimidin-4-yl}phenyl)acetamide: $^1$H NMR (400 MHz, d6-DMSO): 10.21 (s, 1H), 9.41 (s, 1H), 8.45 (d, 1H), 8.12 (d, 2H), 7.75-7.68 (m, 5H), 7.28 (d, 1H), 6.98 (d, 2H), 6.52 (d, 1H), 3.73 (m, 4H), 3.11 (m, 4H), 2.17 (s, 3H), 2.09 (s, 3H). MS (EI): 497.6 (MH+).

N-(4-{2-[(4-{4-[(3-fluoro-2-methylphenyl)carbonyl]piperazin-1-yl}phenyl)amino]pyrimidin-4-yl}phenyl)acetamide: MS (EI) for $C_{30}H_{29}FN_6O_2$: 525.5 (MH+).

N-(4-{2-[(4-{4-[(imidazol-4-yl)carbonyl]piperazin-1-yl}phenyl)amino]pyrimidin-4-yl}phenyl)acetamide: MS (EI) for $C_{26}H_{26}N_8O_2$: 483.5 (MH+).

N-(4-{2-[(4-{4-[(2-methoxypyridin-3-yl)carbonyl]piperazin-1-yl}phenyl)amino]-pyrimidin-4-yl}phenyl)acetamide: $^1$H NMR (400 MHz, d6-DMSO): 10.21 (s, 1H), 9.41 (s, 1H), 8.44 (d, 1H), 8.26 (dd, 1H), 8.12 (d, 2H), 7.75-7.67 (m, 5H), 7.28 (d, 1H), 7.09 (dd, 1H), 6.97 (d, 2H), 3.90 (s, 3H), 3.77 (m, 2H), 3.29 (m, 2H), 3.14 (m, 2H), 3.04 (m, 2H), 2.09 (s, 3H). MS (EI): 524.6 (MH+).

N-(4-{2-[(4-{4-[(4-fluoro-3-methylphenyl)carbonyl]piperazin-1-yl}phenyl)amino]pyrimidin-4-yl}phenyl)acetamide: MS (EI) for $C_{30}H_{29}FN_6O_2$: 525.5 (MH+).

N-{4-[2-({4-[4-(naphthalen-2-ylsulfonyl)piperazin-1-yl]phenyl}amino)pyrimidin-4-yl]phenyl}acetamide: $^1$H NMR (400 MHz, d6-DMSO): 10.20 (s, 1H), 9.37 (s, 1H), 8.50 (d, 1H), 8.42 (d, 1H), 8.22 (dd, 2H), 8.09 (dd, 3H), 7.82-7.71 (m, 5H), 7.64 (d, 2H), 7.26 (d, 1H), 6.89 (d, 2H), 3.14 (m, 4H), 3.11 (m, 4H), 2.08 (s, 3H). MS (EI): 579.6 (MH+).

N-{4-[2-({4-[4-(quinolin-8-ylsulfonyl)piperazin-1-yl]phenyl}amino)pyrimidin-4-yl]phenyl}acetamide: $^1$H NMR (400 MHz, d6-DMSO): 10.20 (s, 1H), 9.37 (s, 1H), 9.10 (dd, 1H), 8.56 (dd, 1H), 8.42 (m, 1H), 8.34 (dd, 1H), 8.10 (d, 2H), 7.79 (m, 1H), 7.73 (m, 3H), 7.65 (d, 2H), 7.27 (d, 1H), 6.90 (d, 2H), 3.45 (m, 4H), 3.08 (m, 4H), 2.09 (s, 3H). MS (EI): 580.8 (MH+).

N-[4-(2-{[4-(4-{[4-(1,1-dimethylethyl)phenyl]sulfonyl}piperazin-1-yl)phenyl]amino}-pyrimidin-4-yl)phenyl]acetamide: $^1$H NMR (400 MHz, d6-DMSO): 10.20 (s, 1H), 9.38 (s, 1H), 8.43 (d, 1H), 8.10 (d, 2H), 7.74 (d, 2H), 7.70 (m, 4H), 7.66 (d, 2H), 7.27 (d, 1H), 6.91 (d, 2H), 3.16 (m, 4H), 3.01 (m, 4H), 2.08 (s, 3H), 1.32 (s, 9H). MS (EI): 585.5 (MH+).

N-[4-(2-{[4-(4-{[5-bromo-2-(methyloxy)phenyl]sulfonyl}piperazin-1-yl)phenyl]-amino}pyrimidin-4-yl)phenyl]acetamide: $^1$H NMR (400 MHz, d6-DMSO): 10.21 (s, 1H), 9.40 (s, 1H), 8.44 (d, 1H), 8.09 (dd, 2H), 7.84 (m, 2H), 7.74 (d, 2H), 7.68 (d, 2H), 7.28 (d, 1H), 6.94 (d, 2H), 3.92 (s, 3H), 3.27 (m, 4H), 3.11 (m, 4H), 2.09 (s, 3H). MS (EI) for C29H29BrN6O4S: 638.6 (MH+).

N-(4-{2-[(4-{4-[(phenylmethyl)sulfonyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.45 (d, 1H), 8.12 (d, 2H), 7.75 (d, 2H), 7.69 (d, 2H), 7.42 (m, 5H), 7.28 (d, 1H), 6.96 (d, 2H), 4.50 (s, 2H), 3.20 (m, 4H), 3.06 (m, 4H), 2.08 (s, 3H). MS (EI): 543.6 (MH+).

N-[4-(2-{[4-(4-([3-(trifluoromethyl)phenyl]sulfonyl)piperazin-1-yl)phenyl]amino}-pyrimidin-4-yl)phenyl]acetamide: $^1$H NMR (400 MHz, d6-DMSO): 10.21 (s, 1H), 9.39 (s, 1H), 8.44 (d, 1H), 8.18-8.08 (m, 4H), 8.02 (s, 1H), 7.97 (d, 1H), 7.74 (d, 2H), 7.67 (d, 2H), 7.27 (d, 1H), 6.92 (d, 2H), 3.15 (m, 4H), 3.10 (m, 4H), 2.09 (s, 3H). MS (EI): 597.7 (MH+).

N-(4-{2-[(4-{4-[(2-methylphenyl)sulfonyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.43 (d, 1H), 8.09 (dd, 2H), 7.85 (dd, 1H), 7.74 (d, 2H), 7.67-7.59 (m, 3H), 7.47 (m, 2H), 7.27 (d, 1H), 6.94 (d, 2H), 3.17 (m, 4H), 3.13 (m, 4H), 2.61 (s, 3H), 2.09 (s, 3H). MS (EI): 543.7 (MH+).

N-(4-{2-[(4-{4-[(3-fluorophenyl)sulfonyl]piperazin-1-yl}phenyl)amino]pyrimidin-4-yl}phenyl)acetamide: $^1$H NMR (400 MHz, d6-DMSO): 10.21 (s, 1H), 9.39 (s, 1H), 8.43 (d, 1H), 8.10 (dd, 2H), 7.73 (m, 3H), 7.67-7.62 (m, 5H), 7.27 (d, 1H), 6.92 (d, 2H), 3.14 (m, 4H), 3.08 (m, 4H), 2.09 (s, 3H). MS (EI): 547.7 (MH+).

N-(4-{2-[(4-{4-[(2,4-difluorophenyl)sulfonyl]piperazin-1-yl}phenyl)amino]-pyrimidin-4-yl}phenyl)acetamide: MS (EI) for $C_{25}H_{26}F_2N_6O_3S$: 565.6 (MH+).

N-{4-[2-({3-[4-({4-[(trifluoromethyl)oxy]phenyl})methyl]piperazin-1-yl]phenyl}-amino)pyrimidin-4-yl]phenyl}acetamide: $^1$H NMR (400 MHz, d6-DMSO): 10.21 (s, 1H), 9.47 (s, 1H), 8.49 (d, 1H), 8.14 (dd, 2H), 7.75 (d, 2H), 7.64 (s, 1H), 7.48 (dd, 2H), 7.33 (m, 3H), 7.22 (m, 1H), 7.13 (m, 1H), 6.56 (dd, 1H), 3.57 (s, 2H), 3.16 (m, 4H), 2.54 (m, 4H), 2.09 (s, 3H). MS (EI): 563.6 (MH+).

N-(4-{2-[(3-{4-[(1-methyl-1H-imidazol-2-yl)methyl]piperazin-1-yl}phenyl)amino]-pyrimidin-4-yl}phenyl)acetamide: $^1$H NMR (400 MHz, d6-DMSO): 10.22 (s, 1H), 9.45 (s, 1H), 8.49 (d, 1H), 8.13 (dd, 2H), 7.75 (d, 2H), 7.58 (s, 1H), 7.33 (d, 1H), 7.25 (dd, 1H), 7.15-7.09 (m, 2H), 6.77 (d, 1H), 6.56 (dd, 1H), 3.68 (s, 3H), 3.58 (s, 2H), 3.12 (m, 4H), 2.54 (m, 4H), 2.09 (s, 3H). MS (EI): 483.5 (MH+).

N-{4-[2-({3-[4-({2-[(trifluoromethyl)oxy]phenyl}methyl)piperazin-1-yl]phenyl}-amino)pyrimidin-4-yl]phenyl}acetamide: $^1$H NMR (400 MHz, d6-DMSO): 10.21 (s, 1H), 9.47 (s, 1H), 8.50 (d, 1H), 8.13 (dd, 2H), 7.75 (d, 2H), 7.64-7.62 (m, 2H), 7.44-7.36 (m, 4H), 7.23 (dd, 1H), 7.14 (m, 1H), 6.55 (dd, 1H), 3.62 (s, 2H), 3.16 (m, 4H), 2.57 (m, 4H), 2.09 (s, 3H). MS (EI): 563.6 (MH+).

N-(4-{2-[(3-{4-[(3-chlorophenyl)methyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.45 (d, 1H), 8.12 (d, 2H), 7.75 (d, 2H), 7.69 (d, 2H), 7.44-7.38 (m, 4H), 7.28 (d, 1H), 6.96 (d, 2H), 4.48 (s, 2H), 3.27 (m, 4H), 3.09 (m, 4H), 2.09 (s, 3H). MS (EI): 514.1 (MH+).

N-{4-[2-({3-[4-(2,3-dihydroxypropyl)piperazin-1-yl]phenyl}amino)pyrimidin-4-yl]phenyl}acetamide: $^1$H NMR (400 MHz, d6-DMSO): 10.23 (s, 1H), 9.46 (s, 1H), 8.49 (d, 1H), 8.14 (d, 2H), 7.75 (d, 2H), 7.63 (s, 1H), 7.33 (d, 1H), 7.22 (d, 1H), 7.13 (m, 1H), 6.56 (dd, 1H), 3.67 (s, 2H), 3.14 (m, 5H), 2.60 (m, 4H), 2.45 (m, 1H), 2.30 (m, 1H), 2.09 (s, 3H). MS (EI): 463.6 (MH+).

N-{4-[2-({3-[4-(1,3-benzodioxol-5-ylmethyl)piperazin-1-yl]phenyl}amino)pyrimidin-4-yl]phenyl}acetamide: $^1$H NMR (400 MHz, d6-DMSO): 10.21 (s, 1H), 9.46 (s, 1H), 8.49 (d, 1H), 8.12 (m, 2H), 7.75 (d, 2H), 7.62 (s, 1H), 7.33 (d, 1H), 7.23 (dd, 1H), 7.12 (t, 1H), 6.90-6.85 (m, 2H), 6.79 (m, 1H), 6.55 (dd, 1H), 5.99 (s, 2H), 3.44 (s, 2H), 3.15 (m, 4H), 2.52 (m, 4H), 2.09 (s, 3H). MS (EI): 523.5 (MH+).

N-{4-[2-({3-[4-(pyridin-2-ylmethyl)piperazin-1-yl]phenyl}amino)pyrimidin-4-yl]-phenyl}acetamide: $^1$H NMR (400 MHz, d6-DMSO): 10.21 (s, 1H), 9.47 (s, 1H), 8.52-8.49 (m, 2H), 8.13 (m, 2H), 7.81-7.72 (m, 3H), 7.63 (s, 1H), 7.50 (d, 1H), 7.33 (d, 1H), 7.30-7.21 (m, 2H), 7.13 (t, 1H), 6.57 (dd, 1H), 3.67 (s, 2H), 3.17 (m, 4H), 2.60 (m, 4H), 2.09 (s, 3H). MS (EI): 480.6 (MH+).

N-{4-[2-({3-[4-(pyridin-3-ylmethyl)piperazin-1-yl]phenyl}amino)pyrimidin-4-yl]phenyl}acetamide: $^1$H NMR (400 MHz, d6-DMSO): 10.22 (s, 1H), 9.47 (s, 1H), 8.54 (d, 1H), 8.49 (d, 2H), 8.12 (m, 2H), 7.78-7.73 (m, 3H), 7.63 (s, 1H), 7.40-7.37 (m, 1H), 7.33 (d, 1H), 7.23 (d, 1H), 7.13 (t, 1H), 6.55 (dd, 1H), 3.58 (s, 2H), 3.16 (m, 4H), 2.55 (m, 4H), 2.10 (s, 3H). MS (EI): 480.5 (MH+).

N-{4-[2-({3-[4-(pyridin-4-ylmethyl)piperazin-1-yl]phenyl}amino)pyrimidin-4-yl]-phenyl}acetamide: $^1$H NMR (400 MHz, d6-DMSO): 10.21 (s, 1H), 9.47 (s, 1H), 8.53 (dd, 2H), 8.49 (d, 1H), 8.14 (d, 2H), 7.75 (d, 2H), 7.64 (s, 1H), 7.38 (dd, 2H), 7.33 (d, 1H), 7.23 (d, 1H), 7.13 (t, 1H), 6.56 (dd, 1H), 3.59 (s, 2H), 3.18 (m, 4H), 2.56 (m, 4H), 2.09 (s, 3H). MS (EI): 480.7 (MH+).

N-{4-[2-({3-[4-(1H-pyrrol-2-ylmethyl)piperazin-1-yl]phenyl}amino)pyrimidin-4-yl]phenyl}acetamide: $^1$H NMR (400 MHz, d6-DMSO): 10.21 (s, 1H), 9.45 (s, 1H), 8.49 (d, 1H), 8.12 (m, 2H), 7.75 (d, 2H), 7.61 (s, 1H), 7.33 (d, 1H), 7.21 (d, 1H), 7.12 (t, 1H), 6.64 (m, 1H), 6.55 (dd, 1H), 5.92 (m, 2H), 3.46 (s, 2H), 3.14 (m, 4H), 2.51 (m, 4H), 2.09 (s, 3H). MS (EI): 468.6 (MH+).

4-[4-({4-[4-(acetylamino)phenyl]pyrimidin-2-yl}amino)phenyl]-N-(phenylmethyl)-piperazine-1-carboxamide: $^1$H NMR (400 MHz, d6-DMSO): 10.21 (s, 1H), 9.40 (s, 1H), 8.62 (s, 1H), 8.45 (d, 1H), 8.12 (d, 2H), 7.75 (d, 2H), 7.70 (d, 2H), 7.48 (dd, 2H), 7.28-7.21 (m, 3H), 7.00 (d, 2H), 6.94 (t, 1H), 4.41 (s, 2H), 3.60 (m, 4H), 310 (m, 4H), 2.09 (s, 3H). MS (EI): 522.4 (MH+).

N-[4-(2-{[3-(4-{[2-(methyloxy)phenyl]carbonyl}piperazin-1-yl)phenyl]amino}-pyrimidin-4-yl)phenyl]acetamide: $^1$H NMR (400 MHz, d6-DMSO): 10.22 (s, 1H), 9.50 (s, 1H), 8.50 (d, 1H), 8.13 (d, 2H), 7.74 (d, 2H), 7.64 (s, 1H), 7.41 (m, 1H), 7.34 (d, 1H), 7.29 (d, 1H), 7.23 (dd, 1H), 7.16 (t, 1H), 7.10 (d, 1H), 7.01 (t, 1H), 6.59 (dd, 1H), 3.79 (s, 3H), 3.21 (m, 4H), 3.07 (m, 4H), 2.09 (s, 3H). MS (EI): 523.5 (MH+).

N-{4-[2-({3-[4-(1H-pyrazol-4-ylcarbonyl)piperazin-1-yl]phenyl}amino)pyrimidin-4-yl]phenyl}acetamide: $^1$H NMR (400 MHz, d6-DMSO): 13.22 (s, 1H), 10.22 (s, 1H), 9.51 (s, 1H), 8.50 (d, 1H), 8.14 (m, 2H), 7.76 (d, 3H), 7.66 (s, 1H), 7.34 (d, 1H), 7.29 (d, 1H), 7.17 (t, 1H), 6.59 (dd, 1H), 3.78 (m, 4H), 3.20 (m, 4H), 2.09 (s, 3H). MS (EI): 483.5 (MH+).

N-{4-[2-({3-[4-(3-pyridin-3-ylpropanoyl)piperazin-1-yl]phenyl}amino)pyrimidin-4-yl]phenyl}acetamide: $^1$H NMR (400 MHz, d6-DMSO): 10.24 (s, 1H), 9.50 (s, 1H), 8.50 (d, 2H), 8.39 (dd, 1H), 8.14 (d, 2H), 7.76 (d, 2H), 7.69 (dd, 2H), 7.34-7.24 (m, 3H), 7.15 (t, 1H), 6.58 (dd, 1H), 3.61 (m, 4H), 3.10 (m, 4H), 2.86 (t, 2H), 2.74 (t, 2H), 2.09 (s, 3H). MS (EI): 522.7 (MH+).

N-(4-{2-[(3-{4-[3-(methyloxy)propanoyl]piperazin-1-yl}phenyl)amino]pyrimidin-4-yl}phenyl)acetamide: $^1$H NMR (400 MHz, d6-DMSO): 10.22 (s, 1H), 9.50 (s, 1H), 8.50 (d, 1H), 8.14 (d, 2H), 7.76 (d, 2H), 7.66 (s, 1H), 7.34 (d, 1H), 7.27 (d, 1H), 7.16 (t, 1H), 6.59 (dd, 1H), 3.63 (m, 4H), 3.58 (t, 2H), 3.23 (s, 3H), 3.12 (m, 4H), 2.63 (t, 2H), 2.09 (s, 3H). MS (EI): 475.6 (MH+).

N-[4-(2-{[3-(4-{2-[(4-fluorophenyl)oxy]acetyl}piperazin-1-yl)phenyl]amino}-pyrimidin-4-yl)phenyl]acetamide: $^1$H NMR (400 MHz, d6-DMSO): 10.23 (s, 1H), 9.51 (s, 1H), 8.50 (d, 1H), 8.14 (d, 2H), 7.76 (d, 2H), 7.66 (s, 1H), 7.34 (d, 1H), 7.29 (d, 1H), 7.19-7.10 (m, 3H), 6.96 (m, 2H), 6.60 (dd, 1H), 4.88 (s, 2H), 3.64 (m, 4H), 3.17 (m, 4H), 2.09 (s, 3H). MS (EI): 541.5 (MH+).

N-{4-[2-({3-[4-(cyclobutylcarbonyl)piperazin-1-yl]phenyl}amino)pyrimidin-4-yl]-phenyl}acetamide: $^1$H NMR (400 MHz, d6-DMSO): 10.24 (s, 1H), 9.50 (s, 1H), 8.50 (d, 1H), 8.14 (d, 2H), 7.76 (d, 2H), 7.69 (s, 1H), 7.34 (d, 1H), 7.24 (d, 1H), 7.15 (t, 1H), 6.58 (dd, 1H), 3.61 (m, 2H), 3.48 (m, 2H), 3.41 (t, 1H), 3.10 (m, 4H), 2.18 (m, 2H), 2.09 (s, 3H) 1.92 (m, 2H), 1.75 (m, 2H). MS (EI): 471.4 (MH+).

N-{4-[2-({3-[4-(pyridin-4-ylcarbonyl)piperazin-1-yl]phenyl}amino)pyrimidin-4-yl]phenyl}acetamide: $^1$H NMR (400 MHz, d6-DMSO): 10.22 (s, 1H), 9.51 (s, 1H), 8.69 (dd, 2H), 8.50 (d, 1H), 8.14 (d, 2H), 7.74 (d, 2H), 7.66 (s, 1H), 7.45 (dd, 2H), 7.34 (d, 1H), 7.28 (d, 1H), 7.16 (t, 1H), 6.60 (d, 1H), 3.81 (m, 2H), 3.43 (m, 2H), 3.27 (m, 2H), 3.14 (m, 2H), 2.10 (s, 3H). MS (EI): 494.6 (MH+).

N-{4-[2-({3-[4-(pyridin-2-ylcarbonyl)piperazin-1-yl]phenyl}amino)pyrimidin-4-yl]phenyl}acetamide: $^1$H NMR (400 MHz, d6-DMSO): 10.21 (s, 1H), 9.50 (s, 1H), 8.61 (d; 1H), 8.50 (d, 1H), 8.14 (d, 2H), 7.95 (t, 1H), 7.74 (d, 2H), 7.66 (d, 2H), 7.50 (t, 1H), 7.34 (d, 1H), 7.29 (d, 1H), 7.16 (t, 1H), 6.60 (d, 1H), 3.84 (m, 2H), 3.59 (m, 2H), 3.26 (m, 2H), 3.14 (m, 2H), 2.09 (s, 3H). MS (EI): 494.6 (MH+).

N-(4-{2-[(3-{4-[(2-methylphenyl)carbonyl]piperazin-1-yl}phenyl)amino]pyrimidin-4-yl}phenyl)acetamide: $^1$H NMR (400 MHz, d6-DMSO): 10.23 (s, 1H), 9.49 (s, 1H), 8.49 (d, 1H), 8.13 (d, 2H), 7.74 (d, 2H), 7.63 (s, 1H), 7.34-7.16 (m, 7H), 6.59 (d, 1H), 3.84 (m, 2H), 3.28 (m, 2H), 3.25 (m, 2H), 3.06 (m, 2H), 2.24 (s, 3H), 2.09 (s, 3H). MS (EI): 507.6 (MH+).

N-{4-[2-({3-[4-(2,2-dimethylpropanoyl)piperazin-1-yl]phenyl}amino)pyrimidin-4-yl]phenyl}acetamide: $^1$H NMR (400 MHz, d6-DMSO): 10.21 (s, 1H), 9.51 (s, 1H), 8.50 (dd, 1H), 8.14 (d, 2H), 7.76 (d, 2H), 7.68 (s, 1H), 7.34 (d, 1H), 7.26 (d, 1H), 7.16 (t, 1H), 6.59 (d, 1H), 3.72 (m, 4H), 3.13 (m, 4H), 2.09 (s, 3H), 1.23 (s, 9H). MS (EI): 473.5 (MH+).

N-{4-[2-({3-[4-(pyridin-3-ylcarbonyl)piperazin-1-yl]phenyl}amino)pyrimidin-4-yl]-phenyl}acetamide: $^1$H NMR (400 MHz, d6-DMSO): 10.23 (s, 1H), 9.51 (s, 1H), 8.67 (m, 2H), 8.50 (d, 1H), 8.13 (m, 2H), 7.90 (m, 1H), 7.75 (d, 2H), 7.66 (s, 1H), 7.50 (m, 1H), 7.34 (d, 1H), 7.29 (dd, 1H), 7.17 (t, 1H), 6.60 (dd, 1H), 3.82 (m, 2H), 3.50 (m, 2H), 3.29 (m, 2H), 3.16 (m, 2H), 2.09 (s, 3H). MS (EI): 494.7 (MH+).

N-{4-[2-({3-[4-(2-methylpropanoyl)piperazin-1-yl]phenyl}amino)pyrimidin-4-yl]-phenyl}acetamide: $^1$H NMR (400 MHz, d6-DMSO): 10.24 (s, 1H), 9.51 (s, 1H), 8.50 (d, 1H), 8.14 (dd, 2H), 7.76 (d, 2H), 7.69 (d, 2H), 7.34 (d, 1H), 7.26 (dd, 1H), 7.16 (t, 1H), 6.60 (dd, 1H), 3.66 (m, 4H), 3.11 (m, 4H), 2.90 (m, 1H), 2.09 (s, 3H), 1.03 (d, 6H). MS (EI): 459.6 (MH+).

N-[4-(2-{[3-(methyloxy)-4-morpholin-4-ylphenyl]amino}pyrimidin-4-yl)phenyl]-tetrahydrofuran-3-carboxamide: $^1$H NMR (400 MHz, d6-DMSO): 10.32 (s, 1H), 9.48 (s, 1H), 8.48 (d, 1H), 8.16 (d, 2H), 7.78 (d, 2H), 7.67 (s, 1H), 7.32 (d, 1H), 7.29 (dd, 1H), 6.87 (d, 1H), 3.95 (t, 2H), 3.81 (s, 3H), 3.78 (m, 2H), 3.71 (m, 4H), 3.29-3.17 (m, 1H), 2.91 (m, 4H), 2.13-2.07 (m, 2H). MS (EI): 476.5 (MH+).

(2R)—N-[4-(2-{[3-(methyloxy)-4-morpholin-4-ylphenyl]amino}pyrimidin-4-yl)-phenyl]tetrahydrofuran-2-carboxamide: $^1$H NMR (400 MHz, d6-DMSO): 9.94 (s, 1H), 9.48 (s, 1H), 8.48 (d, 1H), 8.16 (d, 2H), 7.89 (d, 2H), 7.66 (s, 1H), 7.33 (d, 1H), 7.30 (dd, 1H), 6.87 (d, 1H), 4.43 (dd, 1H), 4.01 (m, 1H), 3.86 (m, 1H), 3.81 (s, 3H), 3.72 (m, 4H), 2.91 (m, 4H), 2.22-2.19 (m, 1H), 2.03-1.98 (m, 1H), 1.89 (m, 2H). MS (EI): 476.4 (MH+).

(2S)—N-[4-(2-{[3-(methyloxy)-4-morpholin-4-ylphenyl]amino}pyrimidin-4-yl)-phenyl]tetrahydrofuran-2-carboxamide: $^1$H NMR (400 MHz, d6-DMSO): 9.94 (s, 1H), 9.48 (s, 1H), 8.48 (d, 1H), 8.16 (d, 2H), 7.89 (d, 2H), 7.66 (s, 1H), 7.33 (d, 1H), 7.30 (dd, 1H), 6.87 (d, 1H), 4.43 (dd, 1H), 4.01 (m, 1H), 3.86 (m, 1H), 3.81 (s, 3H), 3.72 (m, 4H), 2.91 (m, 4H), 2.24-2.19 (m, 1H), 2.03-1.98 (m, 1H), 1.89 (m, 2H). MS (EI): 476.5 (MH+).

N-(4-{2-[(4-{4-[(2-fluorophenyl)sulfonyl]piperazin-1-yl}phenyl)amino]pyrimidin-4-yl}phenyl)acetamide: $^1$H NMR (400 MHz, d6-DMSO): 10.21 (s, 1H), 9.40 (s, 1H), 8.44 (d, 1H), 8.11 (d, 2H), 7.85-7.77 (m, 2H), 7.74 (d, 2H), 7.68 (d, 2H), 7.56-7.46 (m, 2H), 7.28 (d, 1H), 6.93 (d, 2H), 3.18-3.16 (m, 8H), 2.09 (s, 3H). MS (EI): 547.7 (MH+).

N-(4-{2-[(3-{4-[(3,5-dichlorophenyl)carbonyl]piperazin-1-yl}phenyl)amino]-pyrimidin-4-yl}phenyl)acetamide: $^1$H NMR (400 MHz, d6-DMSO): 10.24 (s, 1H), 9.51 (s, 1H), 8.50 (d, 1H), 8.14 (d, 2H), 7.73 (m, 3H), 7.64 (s, 1H), 7.54 (d, 2H), 7.34 (d, 1H), 7.29 (d, 1H), 7.16 (t, 1H), 6.60 (dd, 1H), 3.79 (m, 2H), 3.46 (m, 2H), 3.26 (m, 2H), 3.15 (m, 2H), 2.09 (s, 3H). MS (EI): 562.5 (MH+).

ethyl 3-(4-(2-(4-morpholinophenylamino(pyrimidin-4-yl)phenylamino)-3-oxopropanoate: $^1$H NMR (400 MHz, d6-DMSO): 10.46 (s, 1H), 9.35 (s, 1H), 8.42 (d, 1H), 8.11 (d, 2H), 7.71 (d, 2H), 7.64 (d, 2H), 7.26 (d, 1H), 6.92 (d, 2H), 4.11 (q, 2H), 3.72 (m, 2H), 3.37 (m, 4H), 3.02 (m, 4H), 1.19 (t, 3H). MS (EI): 462 (MH+).

N-(4-(2-(4-(4-isobutyrylpiperazin-1-yl)phenylamino)pyrimidin-4-yl)phenyl)-tetrahydrofuran-3-carboxamide: $^1$H NMR (400 MHz, d6-DMSO): 10.30 (s, 1H), 9.43 (s, 1H), 8.45 (d, 1H), 8.13 (d, 2H), 7.77 (d, 2H), 7.68 (d, 2H), 7.29 (d, 1H), 6.97 (m, 2H), 3.96 (t, 1H), 3.76 (m, 2H), 3.63 (m, 4H), 3.19 (m, 2H), 3.06 (m, 4H), 2.93 (m, 1H), 2.10 (m, 2H), 1.02 (d, 6H). MS (EI): 515 (MH+).

N-(4-(2-(4-(4-(cyclobutanecarbonyl)piperazin-1-yl)phenylamino)pyrimidin-4-yl)phenyl)tetrahydrofuran-3-carboxamide: $^1$H NMR (400 MHz, d6-DMSO): 10.30 (s, 1H), 9.42 (s, 1H), 8.45 (d, 1H), 8.13 (d, 2H), 7.77 (d, 2H), 7.68 (d, 2H), 7.29 (d, 1H), 6.96 (d, 2H), 3.96 (t, 1H), 3.76 (m, 3H), 3.59 (m, 2H), 3.41 (m, 3H), 3.19 (m, 1H), 3.03 (m, 4H), 2.41 (m, 6H), 1.90 (m, 1H), 1.75 (m, 1H). MS (EI): 527 (MH+).

N-ethyl-4-(4-(4-(4-(tetrahydrofuran-3-carboxamido)phenyl)pyrimidin-2-yl-amino(phenyl)piperazine-1-carboxamide: $^1$H NMR (400 MHz, d6-DMSO): 10.30 (s, 1H), 9.40 (s, 1H), 8.44 (d, 1H), 8.13 (d, 2H), 7.77 (d, 2H), 7.67 (d, 2H), 7.28 (d, 1H), 6.96 (d, 2H), 6.59 (t, 1H), 3.96 (t, 1H), 3.75 (m, 3H), 3.42 (m, 4H), 3.19 (m, 1H), 3.05 (m, 6H), 2.10 (q, 2H), 1.02 (t, 3H). MS (EI): 516 (MH+).

N-(4-(2-(4-(4-((R)-2-aminopropanoyl)piperazin-1-yl)phenylamino)pyrimidin-4-yl)phenyl)tetrahydrofuran-3-carboxamide: $^1$H NMR (400 MHz, d6-DMSO): 10.31 (s, 1H), 9.42 (s, 1H), 8.45 (d, 1H), 8.13 (d, 2H), 7.77 (d, 2H), 7.69 (d, 2H), 7.29 (d, 1H), 6.97 (d, 2H), 3.96 (dd, 1H), 3.89 (m, 1H), 3.76 (m, 4H), 3.63 (m, 4H), 3.18 (m, 2H), 3.07 (m, 4H), 2.09 (m, 2H), 1.13 (d, 3H). MS (EI): 516 (MH+).

N-(4-(2-(4-(4-((S)-2-aminopropanoyl)piperazin-1-yl)phenylamino)pyrimidin-4-yl)phenyl)tetrahydrofuran-3-carboxamide: $^1$H NMR (400 MHz, d6-DMSO): 10.31 (s, 1H), 9.42 (s, 1H), 8.45 (d, 1H), 8.13 (d, 2H), 7.77 (d, 2H), 7.68 (d, 2H), 7.29 (d, 1H), 6.97 (d, 2H), 3.96 (t, 1H), 3.85 (q, 1H), 3.76 (m, 3H), 3.63 (m, 4H), 3.19 (m, 1H), 3.07 (m, 4H), 2.10 (m, 2H), 1.11 (d, 3H). MS (EI): 516 (MH+).

N-(4-(2-(4-(4-((R)-pyrrolidine-2-carbonyl)piperazin-1-yl)phenylamino)pyrimidin-4-yl)phenyl)tetrahydrofuran-3-carboxamide: $^1$H NMR (400 MHz, d6-DMSO): 10.31 (s, 1H), 9.42 (s, 1H), 8.45 (d, 1H), 8.13 (d, 2H), 7.77 (d, 2H), 7.69 (d, 2H), 7.29 (d, 1H), 6.97 (d, 2H), 3.97 (m, 2H), 3.76 (m, 3H), 3.64 (m, 4H), 3.19 (m, 1H), 3.06 (m, 6H), 2.73 (m, 1H), 2.09 (m, 2H), 1.67 (m, 4H). MS (EI): 542 (MH+).

N-(4-(2-(4-(4-((S)-pyrrolidine-2-carbonyl)piperazin-1-yl)phenylamino)pyrimidin-4-yl)phenyl)tetrahydrofuran-3- carboxamide: ¹H NMR (400 MHz, d6-DMSO): 10.31 (s, 1H), 9.42 (s, 1H), 8.45 (d, 1H), 8.13 (d, 2H), 7.77 (d, 2H), 7.69 (d, 2H), 7.29 (d, 1H), 6.97 (d, 2H), 3.96 (t, 1H), 3.86 (m, 1H), 3.76 (m, 3H), 3.64 (m, 4H), 3.18 (m, 1H), 3.05 (m, 6H), 2.64 (m, 1H), 2.10 (m, 1H), 2.00 (m, 1H), 1.62 (m, 4H). MS (EI): 542 (MH+).

N-{4-[2-(1H-benzimidazol-6-ylamino)-5-methylpyrimidin-4-yl]phenyl}acetamide: ¹H-NMR (400 MHz, $d_6$-DMSO): 10.25 (s, 1H), 8.97 (s, 1H), 8.78 (s, 1H), 8.21 (d, 2H), 7.86 (d, 2H), 7.80 (d, 2H), 6.96 (s, 1H), 6.78 (dd, 2H), 2.44 (s, 3H), 2.11 (s, 3H); MS (EI) $C_{20}H_{18}N_6O$: 359.3 $(M+H)^+$.

4-(4-furan-2-ylphenyl)-N-(4-morpholin-4-ylphenyl)pyrimidin-2-amine: ¹H-NMR (400 MHz, $d_6$-DMSO): 9.46 (s, 1H), 8.49 (d, 1H), 8.22 (d, 2H), 7.87 (d, 2H), 7.84 (dd, 1H), 7.68 (d, 2H), 7.37 (d, 1H), 7.12 (t, 1H), 6.94 (d, 2H), 6.66 (dd, 1H), 3.75 (t, 4H), 3.05 (t, 4H); MS (EI) $C_{24}H_{22}N_4O_2$: 399.3 $(M+H)^+$.

N-(4-morpholin-4-ylphenyl)-4-[4-(pyrimidin-2-ylamino)phenyl]pyrimidin-2-amine: ¹H-NMR (400 MHz, $d_6$-DMSO): 10.01 (s, 1H), 9.35 (s, 1H), 8.56 (d, 2H), 8.42 (d, 1H), 8.11 (dd, 2H), 7.95 (dd, 2H), 7.69 (d, 2H), 7.27 (d, 1H), 6.96-6.92 (m, 3H), 3.75 (t, 4H), 3.06 (t, 4H); MS (EI) $C_{24}H_{23}N_7O$: 426.3 $(M+H)^+$.

N-[4-(2-{[4-(4-ethylpiperazin-1-yl)phenyl]amino}-5-methylpyrimidin-4-yl)phenyl]-cyclopropanecarboxamide: ¹H-NMR (400 MHz, $d_6$-DMSO): 10.40 (s, 1H), 9.41 (bs, 1H), 9.30 (s, 1H), 8.30 (s, 1H), 7.23-7.70 (m, 2H), 7.65-7.62 (m, 3H), 6.91 (d, 2H), 3.70-3.50 (bs, 2H), 3.21-2.87 (m, 8H), 2.20 (s, 3H), 1.80 (p, 1H), 1.18 (bs, 3H), 0.81 (d, 4H); MS (EI) $C_{24}H_{23}N_7O$: 457.4 $(M+H)^+$.

N-[4-(2-{[4-(4-ethylpiperazin-1-yl)phenyl]amino}pyrimidin-4-yl)phenyl]-cyclopropanecarboxamide: ¹H-NMR (400 MHz, $d_6$-DMSO): 10.48 (s, 1H), 9.37 (s, 1H), 8.44 (d, 1H), 8.11 (d, 2H), 7.76 (d, 2H), 7.65 (d, 2H), 7.27 (d, 1H), 6.93 (d, 2H), 3.09 (bs, 4H), 2.60-2.35 (m, 6H), 1.83 (p, 1H), 1.06 (t, 3H), 0.84-0.82 (m, 4H); MS (EI) $C_{26}H_{30}N_6O$: 443.4 $(M+H)^+$.

N-(4-{2-[(3,5-dimorpholin-4-ylphenyl)amino]-5-methylpyrimidin-4-yl}phenyl)-$N^2,N^2$-dimethylglycinamide: ¹H-NMR (400 MHz, $d_6$-DMSO): 10.04 (s, 1H), 9.25 (s, 1H), 8.37 (s, 1H), 7.81 (d, 2H), 7.74 (d, 2H), 7.12 (s, 2H), 6.11 (s, 1H), 3.73 (t, 8H), 3.20 (bs, 2H), 3.06 (t, 8H), 2.34 (s, 6H), 2.28 (s, 3H); MS (EI) $C_{29}H_{37}N_7O_3$: 532.4 $(M+H)^+$.

$N^2,N^2$-dimethyl-N-(4-{5-methyl-2-[(4-morpholin-4-ylphenyl)amino]pyrimidin-4-yl}-phenyl)glycinamide: ¹H-NMR (400 MHz, $d_6$-DMSO): 10.43 (s, 1H), 9.28 (s, 1H), 8.33 (s, 1H), 7.77 (d, 2H), 7.69 (d, 2H), 7.63 (d, 2H), 6.88 (d, 2H), 3.73 (t, 4H), 3.35 (bs, 2H), 3.01 (t, 4H), 2.65 (s, 6H), 2.21 (s, 3H); MS (EI) $C_{25}H_{30}N_6O_2$: 447.4 $(M+H)^+$.

N-(4-{5-methyl-2-[(4-morpholin-4-ylphenyl)amino]pyrimidin-4-yl}phenyl)-D-prolinamide: ¹H-NMR (400 MHz, $d_6$-DMSO): 10.15 (s, 1H), 9.28 (s, 1H), 8.32 (s, 1H), 7.82-7.79 (m, 2H), 7.64 (t, 4H), 6.88 (d, 2H), 3.75-3.72 (t, 5H), 3.01 (t, 4H), 2.91 (t, 2H), 2.22 (s, 3H), 2.11-2.02 (m, 1H), 1.84-1.75 (m, 1H), 1.70-1.63 (m, 2H); MS (EI) $C_{26}H_{30}N_6O_2$: 459.4 $(M+H)^+$.

N-{4-[2-({4-[4-(2-methylpropanoyl)piperazin-1-yl]phenyl}amino)pyrimidin-4-yl]-phenyl}-D-prolinamide: ¹H-NMR (400 MHz, $d_6$-DMSO): 10.25 (s, 1H), 9.41 (s, 1H), 8.45 (d, 1H), 8.12 (d, 2H), 7.83 (d, 2H), 7.68 (d, 2H), 7.30 (d, 1H), 6.96 (d, 2H), 3.80-3.77 (m, 1H), 3.65-3.41 (m, 4H), 3.08-3.02 (m, 4H), 2.96-2.89 (m, 3H), 2.13-2.08 (m, 1H), 1.84-1.78 (m, 1H), 1.73-1.68 (m, 2H), 1.02 (d, 6H); MS (EI) $C_{29}H_{35}N_7O_2$: 514.4 $(M+H)^+$.

N-{4-[2-({4-[4-(2,2-dimethylpropanoyl)piperazin-1-yl]phenyl}amino)pyrimidin-4-yl]phenyl}-D-prolinamide: ¹H-NMR (400 MHz, $d_6$-DMSO): 10.85 (s, 1H), 9.41 (s, 1H), 8.47 (d, 1H), 8.18 (d, 2H), 7.78 (d, 2H), 7.68 (d, 2H), 7.31 (d, 1H), 6.96 (d, 2H), 4.40-4.34 (m, 1H), 3.70 (t, 4H), 3.32-3.25 (m, 2H), 3.05 (t, 4H), 2.44-2.38 (m, 1H), 2.05-1.94 (m, 3H), 1.23 (s, 9H); MS (EI) $C_{30}H_{37}N_7O_2$: 528.4 $(M+H)^+$.

N-{4-[2-({4-[4-(cyclobutylcarbonyl)piperazin-1-yl]phenyl}amino)pyrimidin-4-yl]-phenyl}-D-prolinamide: ¹H-NMR (400 MHz, $d_6$-DMSO): 10.19 (s, 1H), 9.41 (s, 1H), 8.44 (d, 1H), 8.12 (d, 2H), 7.84 (d, 2H), 7.67 (d, 2H), 7.30 (d, 1H), 6.95 (d, 2H), 3.74-3.70 (m, 1H), 3.60-3.46 (m, 4H), 3.04-3.00 (m, 4H), 2.91 (t, 2H), 2.22-2.02 (m, 6H), 1.95-1.87 (m, 1H), 1.82-1.73 (m, 2H), 1.70-1.64 (m, 2H); MS (EI) $C_{30}H_{35}N_7O_2$: 526.2 $(M+H)^+$.

N-ethyl-4-[4-({4-[4-(D-prolylamino)phenyl]pyrimidin-2-yl}amino)phenyl]-piperazine-1-carboxamide: ¹H-NMR (400 MHz, $d_6$-DMSO): 10.19 (s, 1H), 9.40 (s, 1H), 8.44 (d, 1H), 8.13 (d, 2H), 7.84 (d, 2H), 7.67 (d, 2H), 7.29 (d, 1H), 6.96 (d, 2H), 6.59 (t, 1H), 3.74-3.71 (m, 1H), 3.42 (t, 4H), 3.10-3.05 (m, 2H), 3.01 (t, 4H), 2.91 (t, 2H), 2.22 (s, 3H), 2.09-2.02 (m, 1H), 1.84-1.76 (m, 1H), 1.70-1.63 (m, 2H), 1.02 (t, 3H); MS (EI) $C_{28}H_{34}N_8O_2$: 515.5 $(M+H)^+$.

N-[4-(2-{[4-(4-D-prolylpiperazin-1-yl)phenyl]amino}pyrimidin-4-yl)phenyl]-D-prolinamide: ¹H-NMR (400 MHz, $d_6$-DMSO): 10.20 (s, 1H), 9.42 (s, 1H), 8.45 (d, 1H), 8.13 (d, 2H), 7.84 (d, 2H), 7.68 (d, 2H), 7.30 (d, 1H), 6.97 (d, 2H), 3.92-3.89 (m, 1H), 3.75-3.71 (m, 1H), 3.65-3.59 (m, 4H), 3.09-2.98 (m, 5H), 2.91 (t, 2H), 2.69-2.63 (m, 1H), 2.09-2.02 (m, 2H), 1.84-1.76 (m, 1H), 1.70-1.54 (m, 5H); MS (EI) $C_{30}H_{36}N_8O_2$: 541.4 $(M+H)^+$.

N-[4-(2-{[4-(4-L-prolylpiperazin-1-yl)phenyl]amino}pyrimidin-4-yl)phenyl]-D-prolinamide: ¹H-NMR (400 MHz, $d_6$-DMSO): 10.20 (s, 1H), 9.41 (s, 1H), 8.45 (d, 1H), 8.13 (d, 2H), 7.84 (d, 2H), 7.68 (d, 2H), 7.30 (d, 1H), 6.96 (d, 2H), 3.92-3.89 (m, 1H), 3.75-3.71 (m, 1H), 3.65-3.59 (m, 4H), 3.09-2.98 (m, 5H), 2.91 (t, 2H), 2.69-2.63 (m, 1H), 2.09-2.02 (m, 2H), 1.84-1.76 (m, 1H), 1.70-1.56 (m, 5H); MS (EI) $C_{30}H_{36}N_8O_2$: 541.4 $(M+H)^+$.

1-Methyl-N-(4-{2-[(4-morpholin-4-ylphenyl)amino]pyrimidin-4-yl}phenyl)-L-prolinamide: ¹H NMR (400 MHz, $d_6$-DMSO): 9.93 (s, 1H), 9.39 (s, 1H), 8.44 (d, 1H), 8.12 (d, 2H), 7.87 (d, 2H), 7.67 (d, 2H), 7.29 (d, 1H), 6.93 (d, 2H), 3.74 (m, 4H), 3.12 (m, 1H), 3.05 (m, 4H), 2.95 (m, 1H), 2.36 (m, 4H) 2.17 (m, 1H), 1.80 (m, 3H); MS (EI) for $C_{26}H_{30}N_6O_2$: 459 $(MH^+)$.

1-Methyl-N-(4-{2-[(4-morpholin-4-ylphenyl)amino]pyrimidin-4-yl}phenyl)piperidine-2-carboxamide: ¹H NMR (400 MHz, $d_6$-DMSO): 9.97 (s, 1H), 9.39 (s, 1H), 8.44 (d, 1H), 8.11 (d, 2H), 7.85 (d, 2H), 7.67 (d, 2H), 7.28 (d, 1H), 6.93 (d, 2H), 3.74 (m, 4H), 3.05 (m, 4H), 2.92 (m, 1H), 2.60 (dd, 1H), 2.16 (s, 3H) 2.03 (m, 1H), 1.76 (m, 2H), 1.60 (m, 3H), 1.25 (m, 1H); MS (EI) for $C_{27}H_{32}N_6O_2$: 473 $(MH^+)$.

N-{4-[2-({4-[4-(Piperidin-4-ylcarbonyl)piperazin-1-yl]phenyl}amino)pyrimidin-4-yl]phenyl}acetamide: ¹H NMR (400 MHz, $d_6$-DMSO): 10.25 (s, 1H), 9.41 (s, 1H), 8.44 (d, 1H), 8.36 (s, 1H), 8.11 (d, 2H), 7.74 (d, 2H), 7.69 (d, 2H), 7.28 (d, 1H), 6.97 (d, 2H), 3.64 (m, 4H), 3.17 (m, 2H), 3.06 (m, 4H), 2.93 (m, 1H), 2.81 (m, 2H), 2.09 (s, 3H) 1.60-1.75 (m, 4H); MS (EI) for $C_{25}H_{33}N_7O_2$: 500 $(MH^+)$.

N-(4-{2-[(4-morpholin-4-ylphenyl)amino]pyrimidin-4-yl}phenyl)-2-pyridin-4-ylacetamide: ¹H NMR (400 MHz, d6-DMSO): 10.53 (s, 1H), 9.38 (s, 1H), 8.53 (d, 2H), 8.44 (d, 1H), 8.12 (d, 2H), 7.95 (d, 1H), 7.76 (d, 2H), 7.67 (d, 2H), 7.35 (d, 4H), 6.92 (d, 2H), 3.75 (m, 6H), 3.04 (m, 4H). MS (EI): 467 (MH+).

2-(3-fluorophenyl)-N-(4-{2-[(4-morpholin-4-ylphenyl)amino]pyrimidin-4-yl}-phenyl)acetamide: ¹H NMR (400 MHz, d6-DMSO): 10.44 (s, 1H), 9.36 (s, 1H), 8.42 (m, 1H), 8.09 (d, 2H), 7.74 (d, 2H), 7.64 (d, 2H), 7.35 (m, 1H), 7.24 (m, 1H), 7.15 (d, 2H), 7.07 (m, 1H), 6.90 (d, 2H), 3.71 (m, 6H), 3.04 (m, 4H). MS (EI): 484 (MH+).

3-(4-chlorophenyl)-N-(4-{2-[(4-morpholin-4-ylphenyl)amino]pyrimidin-4-yl}-phenyl)propanamide: ¹H NMR (400 MHz, d6-DMSO): 10.19 (s, 1H), 9.38 (s, 1H), 8.43 (d, 1H), 8.10 (d, 2H), 7.73 (d, 2H), 7.68 (d, 2H), 7.35 (d, 2H), 7.26 (m, 3H), 6.93 (d, 2H), 3.74 (m, 4H), 3.04 (m, 4H), 2.92 (t, 2H), 2.67 (t, 2H). MS (EI): 515 (MH+).

2-(3-chlorophenyl)-N-(4-{2-[(4-morpholin-4-ylphenyl)amino]pyrimidin-4-yl}-phenyl)acetamide: ¹H NMR (400 MHz, d6-DMSO): 10.47 (s, 1H), 9.38 (s, 1H), 8.44 (d, 1H), 8.12 (d, 2H), 7.75 (d, 2H), 7.66 (d, 2H), 7.43 (s, 1H), 7.32 (m, 4H), 6.93 (d, 2H), 3.74 (m, 6H), 3.04 (m, 4H). MS (EI): 500 (MH+).

2-methyl-N-(4-{2-[(4-morpholin-4-ylphenyl)amino]pyrimidin-4-yl}phenyl)-3-phenyl-propanamide: ¹H NMR (400 MHz, d6-DMSO): 10.12 (s, 1H), 9.38 (s, 1H), 8.44 (d, 1H), 8.09 (d, 2H), 7.72 (d, 2H), 7.67 (d, 2H), 7.25 (m, 4H), 7.17 (m, 2H), 6.93 (d, 2H), 3.74 (m, 4H), 3.06 (m, 4H), 2.99 (m, 1H), 2.81 (m, 1H), 2.64 (m, 1H), 1.12 (d, 3H). MS (EI): 494 (MH+).

trans-N-(4-{2-[(4-morpholin-4-ylphenyl)amino]pyrimidin-4-yl}phenyl)-2-phenyl-cyclopropanecarboxamide: ¹H NMR (400 MHz, d6-DMSO): 10.53 (s, 1H), 9.38 (s, 1H), 8.44 (d, 1H), 8.11 (d, 2H), 7.77 (d, 2H), 7.67 (d, 2H), 7.28 (m, 3H), 7.21 (m, 3H), 6.93 (d, 2H), 3.74 (m, 4H), 3.04 (m, 4H), 2.39 (m, 1H), 2.11 (m, 1H), 1.53 (m, 1H), 1.42 (m, 1H). MS (EI): 492 (MH+).

2-(4-fluorophenyl)-N-(4-{2-[(4-morpholin-4-ylphenyl)amino]pyrimidin-4-yl}-phenyl)acetamide: ¹H NMR (400 MHz, d6-DMSO): 10.44 (s, 1H), 9.38 (s, 1H), 8.43 (d, 1H), 8.12 (d, 2H), 7.75 (d, 2H), 7.65 (d, 2H), 7.38 (m, 2H), 7.27 (d, 1H), 7.18 (dd, 2H), 6.93 (d, 2H), 3.71 (m, 4H), 3.69 (s, 2H), 3.04 (m, 4H). MS (EI): 484 (MH+).

3-(2-chlorophenyl)-N-(4-{2-[(4-morpholin-4-ylphenyl)amino]pyrimidin-4-yl}-phenyl)propanamide: ¹H NMR (400 MHz, d6-DMSO): 10.23 (s, 1H), 9.38 (s, 1H), 8.44 (d, 1H), 8.12 (d, 2H), 7.75 (d, 2H), 7.67 (d, 2H), 7.45 (dd, 1H), 7.40 (dd, 1H), 7.25 (m, 3H), 6.93 (d, 2H), 3.74 (m, 4H), 3.04 (m, 6H), 2.70 (t, 2H). MS (EI): 515 (MH+).

3-(3-chlorophenyl)-N-(4-{2-[(4-morpholin-4-ylphenyl)amino]pyrimidin-4-yl}-phenyl)propanamide: ¹H NMR (400 MHz, d6-DMSO): 10.19 (s, 1H), 9.38 (s, 1H), 8.44 (d, 1H), 8.12 (d, 2H), 7.75 (d, 2H), 7.67 (d, 2H), 7.27 (m, 5H), 6.93 (d, 2H), 3.74 (m, 4H), 3.04 (m, 4H), 2.94 (t, 2H), 2.69 (t, 2H). MS (EI): 515 (MH+).

3-(2-fluorophenyl)-N-(4-{2-[(4-morpholin-4-ylphenyl)amino]pyrimidin-4-yl}-phenyl)propanamide: ¹H NMR (400 MHz, d6-DMSO): 10.21 (s, 1H), 9.38 (s, 1H), 8.43 (d, 1H), 8.10 (d, 2H), 7.73 (d, 2H), 7.67 (d, 2H), 7.35 (t, 1H), 7.26 (d, 2H), 7.11 (m, 2H), 6.93 (d, 2H), 3.74 (m, 4H), 3.04 (m, 4H), 2.95 (t, 2H), 2.68 (t, 2H). MS (EI): 498 (MH+).

Nalpha,Nalpha-dimethyl-N-(4-{2-[(4-morpholin-4-ylphenyl)amino]-pyrimidin-4-yl}phenyl)-L-phenylalaninamide: ¹H NMR (400 MHz, d6-DMSO): 10.04 (s, 1H), 9.38 (s, 1H), 8.44 (d, 1H), 8.09 (d, 2H), 7.74 (d, 2H), 7.67 (d, 2H), 7.24 (m, 5H), 7.17 (m, 1H), 6.93 (d, 2H), 3.74 (m, 4H), 3.48 (dd, 1H), 3.06 (m, 5H), 2.86 (dd, 1H), 2.49 (s, 6H). MS (EI): 523 (MH+).

2-(2-chlorophenyl)-N-(4-{2-[(4-morpholin-4-ylphenyl)amino]pyrimidin-4-yl}-phenyl)acetamide: ¹H NMR (400 MHz, d6-DMSO): 10.54 (s, 1H), 9.38 (s, 1H), 8.44 (d, 1H), 8.12 (d, 2H), 7.76 (d, 2H), 7.67 (d, 2H), 7.46 (m, 2H), 7.33 (m, 2H), 7.29 (d, 2H), 6.93 (d, 2H), 3.89 (s, 2H), 3.74 (m, 4H), 3.04 (m, 4H). MS (EI): 500 (MH+).

N-(4-{(2-[(4-morpholin-4-ylphenyl)amino]pyrimidin-4-yl}phenyl)-2-pyridin-2-yl-acetamide: ¹H NMR (400 MHz, d6-DMSO): 10.51 (s, 1H), 9.35 (s, 1H), 8.49 (d, 1H), 8.41 (d, 1H), 8.10 (d, 2H), 7.77 (m, 3H), 7.64 (d, 2H), 7.39 (d, 1H), 7.26 (m, 2H), 6.92 (d, 2H), 3.87 (s, 2H), 3.71 (m, 4H), 3.02 (m, 4H). MS (EI): 467 (MH+).

2-(4-chlorophenyl)-N-(4-{2-[(4-morpholin-4-ylphenyl)amino]pyrimidin-4-yl}-phenyl)acetamide: ¹H NMR (400 MHz, d6-DMSO): 10.47 (s, 1H), 9.38 (s, 1H), 8.44 (d, 1H), 8.12 (d, 2H), 7.75 (d, 2H), 7.66 (d, 2H), 7.39 (m, 4H), 7.26 (m, 1H), 6.93 (d, 2H), 3.74 (m, 4H), 3.70 (s, 2H), 3.04 (m, 4H). MS (EI): 500 (MH+).

N-(4-{2-[(4-morpholin-4-ylphenyl)amino]pyrimidin-4-yl}phenyl)-2-{4-[(trifluoro-methyl)oxy]phenyl}acetamide: ¹H NMR (400 MHz, d6-DMSO): 10.50 (s, 1H), 9.38 (s, 1H), 8.43 (d, 1H), 8.12 (d, 2H), 7.75 (d, 2H), 7.66 (d, 2H), 7.47 (d, 2H), 7.35 (d, 2H), 7.27 (d, 1H), 6.93 (d, 2H), 3.74 (m, 6H), 3.04 (m, 4H). MS (EI): 550 (MH+).

2-[2-(methyloxy)phenyl]-N-(4-{2-[(4-morpholin-4-ylphenyl)amino]pyrimidin-4-yl}-phenyl)acetamide: ¹H NMR (400 MHz, d6-DMSO): 10.34 (s, 1H), 9.38 (s, 1H), 8.43 (d, 1H), 8.11 (d, 2H), 7.76 (d, 2H), 7.67 (d, 2H), 7.26 (m, 3H), 7.00 (d, 1H), 6.91 (m, 3H), 3.77 (s, 3H), 3.74 (m, 4H), 3.67 (s, 2H), 3.04 (m, 4H). MS (EI): 496 (MH+).

2-[3-(methyloxy)phenyl]-N-(4-{2-[(4-morpholin-4-ylphenyl)amino]pyrimidin-4-yl}phenyl)acetamide: ¹H NMR (400 MHz, d6-DMSO): 10.44 (s, 1H), 9.38 (s, 1H), 8.43 (d, 1H), 8.11 (d, 2H), 7.76 (d, 2H), 7.67 (d, 2H), 7.26 (m, 2H), 6.93 (m, 4H), 6.82 (dd, 1H), 3.74 (m, 7H), 3.55 (s, 2H), 3.04 (m, 4H). MS (EI): 496 (MH+).

2-[4-(methyloxy)phenyl]-N-(4-{2-[(4-morpholin-4-ylphenyl)amino]pyrimidin-4-yl}phenyl)acetamide: ¹H NMR (400 MHz, d6-DMSO): 10.38 (s, 1H), 9.38 (s, 1H), 8.43 (d, 1H), 8.11 (d, 2H), 7.75 (d, 2H), 7.67 (d, 2H), 7.26 (m, 3H), 6.93 (m, 4H), 3.74 (m, 7H), 3.60 (s, 2H), 3.04 (m, 4H). MS (EI): 496 (MH+).

N-[4-(2-{[4-(4-ethylpiperazin-1-yl)phenyl]amino}pyrimidin-4-yl)phenyl]-D-alaninamide: ¹H NMR (400 MHz, d6-DMSO): 9.35 (s, 1H), 8.43 (d, 1H), 8.13 (d, 2H), 7.82 (d, 2H), 7.63 (d, 2H), 7.28 (d, 1H), 6.92 (d, 2H), 3.48 (m, 1H), 2.35 (q, 2H), 1.86 (br s, 8H), 1.24 (d, 3H), 1.03 (t, 3H). MS (EI): 446 (MH+).

N-{4-[2-({4-[4-(N,N-dimethylglycyl)piperazin-1-yl]phenyl}amino)pyrimidin-4-yl]-phenyl}acetamide: ¹H NMR (400 MHz, d6-DMSO): 10.21 (s, 1H), 9.39 (s, 1H), 8.43 (d, 1H), 8.10 (d, 2H), 7.75 (d, 2H), 7.67 (d, 2H), 7.28 (d, 1H), 6.96 (d, 2H), 3.68 (m, 4H), 3.10 (s, 2H), 3.07 (m, 4H), 2.18 (s, 6H), 2.09 (s, 3H). MS (EI): 474 (MH+).

N-[4-(2-{[4-(4-ethylpiperazin-1-yl)phenyl]amino}pyrimidin-4-yl)phenyl]-3-(methyloxy)propanamide: ¹H NMR (400 MHz, d6-DMSO): 10.23 (s, 1H), 9.36 (s, 1H), 8.43 (d, 1H), 8.11 (d, 2H), 7.75 (d, 2H), 7.65 (d, 2H), 7.25 (d, 1H), 6.92 (d, 2H), 3.63 (t, 2H), 3.25 (s, 3H), 3.09 (m, 4H), 2.60 (t, 2H), 2.58 (m, 6H), 1.05 (t, 3H). MS (EI): 461 (MH+).

(2R)-2-amino-N-(4-{2-[(4-morpholin-4-ylphenyl)amino]pyrimidin-4-yl}phenyl)-2-phenylethanamide: ¹H NMR (400 MHz, d6-DMSO): 9.37 (s, 1H), 8.44 (d, 1H), 8.11 (d, 2H), 7.80 (d, 2H), 7.66 (d, 2H), 7.49 (d, 2H), 7.34 (t, 2H), 7.26 (m, 2H), 6.92 (d, 2H), 4.56 (s, 1H), 3.75 (m, 4H), 3.04 (m, 4H). MS (EI): 481 (MH+).

N'2',N'2'-dimethyl-N-(4-{2-[(4-morpholin-4-ylphenyl)amino]pyrimidin-4-yl}-phenyl)-D-alaninamide: ¹H NMR (400 MHz, d6-DMSO): 10.02 (s, 1H), 9.38 (s, 1H), 8.44 (d, 1H), 8.11 (d, 2H), 7.84 (d, 2H), 7.66 (d, 2H), 7.28 (d, 1H), 6.92 (d, 2H), 3.75 (m, 4H), 3.21 (q, 1H), 3.04 (m, 4H), 2.25 (s, 6H), 1.19 (d, 3H). MS (EI): 447 (MH+).

1-methyl-N-(4-{2-[(4-morpholin-4-ylphenyl)amino]pyrimidin-4-yl}phenyl)-D-prolinamide: ¹H NMR (400 MHz, d6-DMSO): 9.94 (s, 1H), 9.40 (s, 1H), 8.44 (d, 1H), 8.12 (d, 2H), 7.87 (d, 2H), 7.67 (d, 2H), 7.30 (d, 1H), 6.94 (d, 2H), 3.76 (m, 4H), 3.12 (m, 1H), 3.05 (m, 4H), 2.95 (m, 1H), 2.36 (s, 3H), 2.30 (m, 1H), 2.18 (m, 1H), 1.78 (m, 3H). MS (EI): 459 (MH+).

N'2',N'2'-dimethyl-N-(4-{2-[(4-morpholin-4-ylphenyl)amino]pyrimidin-4-yl}-phenyl)-L-alaninamide: ¹H NMR (400 MHz, d6-DMSO): 10.03 (s, 1H), 9.39 (s, 1H), 8.44 (d, 1H), 8.11 (d, 2H), 7.84 (d, 2H), 7.67 (d, 2H), 7.28 (d, 1H), 6.92 (d, 2H), 3.75 (m, 4H), 3.21 (q, 1H), 3.05 (m, 4H), 2.25 (s, 6H), 1.19 (d, 3H). MS (EI): 447 (MH+).

N-(4-{2-[(4-morpholin-4-ylphenyl)amino]pyrimidin-4-yl}phenyl)-1-phenyl-cyclopropanecarboxamide: ¹H NMR (400 MHz, d6-DMSO): 9.38 (s, 1H), 8.43 (d, 1H), 8.09 (d, 2H), 7.72 (d, 2H), 7.65 (d, 2H), 7.40 (m, 4H), 7.28 (m, 2H), 6.92 (d, 2H), 3.74 (m, 4H), 3.04 (m, 4H), 1.74 (dd, 2H), 1.15 (dd, 2H). MS (EI): 492 (MH+).

2-methyl-N-(4-{2-[(4-morpholin-4-ylphenyl)amino]pyrimidin-4-yl}phenyl)-butanamide: ¹H NMR (400 MHz, d6-DMSO): 10.12 (s, 1H), 9.38 (s, 1H), 8.44 (d, 1H), 8.11 (d, 2H), 7.78 (d, 2H), 7.67 (d, 2H), 7.27 (d, 1H), 6.93 (d, 2H), 3.75 (m, 4H), 3.04 (m, 4H), 2.46 (q, 1H), 1.65 (m, 1H), 1.41 (m, 1H), 1.10 (d, 3H), 0.87 (t, 3H). MS (EI): 432 (MH+).

(2S)-1-methyl-N-(4-{2-[(4-morpholin-4-ylphenyl)amino]pyrimidin-4-yl}phenyl)-azetidine-2-carboxamide: ¹H NMR (400 MHz, d6-DMSO): 9.88 (s, 1H), 9.39 (s, 1H), 8.44 (d, 1H), 8.13 (d, 2H), 7.89 (d, 2H), 7.67 (d, 2H), 7.29 (d, 1H), 6.93 (d, 2H), 3.74 (m, 4H), 3.56 (t, 1H), 3.36 (m, 1H), 3.04 (m, 4H), 2.93 (q, 1H), 2.33 (s, 3H), 2.30 (m, 1H), 2.12 (m, 1H). MS (EI): 445 (MH+).

2,4,6-trichloro-N-(3-{[4-(4-methyl-2-thienyl)pyrimidine-2-yl]amino}propyl)-benzamide: ¹H-NMR (400 MHz, d6-DMSO): 8.68 (br s, 1H), 8.24 (d, 1H), 7.72-7.70 (m, 3H), 7.29 (s, 1H), 7.17 (t, 1H), 6.98 (d, 1H), 3.37-3.35 (m, 2H), 3.28-3.27 (m, 2H), 2.22 (s, 3H), 1.77 (br t, 2H). MS (EI): 457.0 (MH+).

N-{4-[2-({4-[4-(2,2-dimethylpropanoyl)piperazin-1-yl]phenyl}amino)pyrimidin-4-yl]phenyl}cyclopropanecarboxamide: MS (EI) $C_{29}H_{34}N_6O_2$: 499 (MH+).

4-{(4-[(4-{[(cyclopropylcarbonyl)amino]phenyl}pyrimidin-2-yl)amino]phenyl}-N-ethylpiperazine-1-carboxamide: MS (EI) $C_{27}H_{31}N_7O_2$: 486 (MH+).

N-[3-({4-[3,4-bis(methyloxy)phenyl]pyrimidine-2-yl}amino)propyl]-2,6-dichloro-benzamide: ¹H-NMR (400 MHz, d6-DMSO): 8.67 (br s, 1N), 8.26 (d, 1H), 7.69-7.67 (m, 2H), 7.49-7.35 (m, 3H), 7.14-7.09 (m, 2H), 7.03 (d, 1H), 3.82 (s, 3H), 3.80 (s, 3H), 3.42 (m, 2H), 3.32 (m, 2H), 1.80 (m, 2H). MS (EI): 461.2 (MH+).

2,6-dichloro-N-[3-({4-[(4-morpholino-4-ylphenyl)amino]pyrimidin-2-yl}amino)-propyl]benzamide: ¹H-NMR (400 MHz, d6-DMSO): 8.85 (br s, 1H), 8.63 (t, 1H), 7.69 (d, 1H), 7.48 (d, 2H), 7.44 (d, 1H), 7.42 (s, 1H), 7.37-7.33 (m, 1H), 6.81 (d, 2H), 6.59 (br s, 1H), 5.83 (d, 1H), 3.67-3.65 (m, 4H), 3.23-3.20 (m, 4H), 2.97-2.94 (m, 4H), 1.70 (t, 2H). MS (EI): 501.2 (MH+).

2,6-dichloro-N-(3-{[4-(2,3-dihydro-1,4-benzodioxin-6-yl)-5-fluoropyrimidin-2-yl]amino}propyl)benzamide: ¹H-NMR (400 MHz, d6-DMSO): 8.62 (t, 1H), 8.29 (d, 1H), 7.49-7.42 (m, 4H), 7.37-7.33 (m, 1H), 7.15 (t, 1H), 6.94-6.92 (m, 1H), 4.27-4.21 (m, 4H), 3.33-3.22 (m, 4H), 1.74 (t, 2H); MS (EI): 477.1 (MH+).

2,6-dichloro-N-{3-[(4-{3-[(dimethylamino)methyl]phenyl}pyrimidin-2-yl)amino]propyl}benzamide: ¹H-NMR (400 MHz, d6-DMSO): 8.68 (t, 1H), 8.31 (d, 1H), 8.01-7.95 (m, 2H), 7.49-7.38 (m, 5H), 7.23 (br s, 1H), 7.10 (d, 1H), 3.43 (m, 2H), 3.33-3.29 (m, 4H), 2.14 (s, 6H), 1.82 (t, 2H); MS (EI): 460.2 (MH+).

2,6-dichloro-N-[3-({4-[3-(1-methylethyl)phenyl]pyrimidin-2-yl}amino)-propyl]-benzamide: ¹H-NMR (400 MHz, d6-DMSO): 8.66 (t, 1H), 8.31 (d, 1H), 7.95-7.88 (m, 2H), 7.55 (br s, 1H), 7.45-7.43 (m, 2H), 7.40-7.34 (m, 3H), 7.20 (br s, 1H), 3.30 (br s, 2H), 3.29-3.25 (m, 2H), 2.92 (septet, 1H), 1.78 (m, 2H), 1.18 (d, 6H); MS (EI): 443.0 (MH+).

2,6-dichloro-N-{3-[(4-{4-[(1-methylethyl)oxy]phenyl}pyrimidin-2-yl)amino]propyl}-benzamide: ¹H-NMR (400 MHz, d6-DMSO): 8.68 (t, 1H), 8.25 (d, 1H), 8.03 (d, 2H), 7.49-7.47 (m, 2H), 7.42-7.38 (m, 1H), 7.10 (t, 1H), 7.03 (d, 1H), 6.98 (d, 2H), 4.69 (septet, 1H), 3.42 (m, 2H), 3.30 (m, 2H), 1.80 (t, 2H), 1.27 (d, 6H); MS (EI): 459.0 (MH+).

N-[3-({4-[3-(acetylamino)phenyl]pyrimidin-2-yl}amino)propyl]-2,6-dichloro-benzamide: ¹H-NMR (400 MHz, d6-DMSO): 10.1 (s, 1H), 8.70 (t, 1N), 8.33-8.27 (m, 2H), 7.70 (m, 2H), 7.49-7.46 (m, 2H), 7.42-7.37 (m, 2H), 7.37 (br s, 1H), 7.01 (d, 1H), 3.43 (m, 4H), 2.02 (s, 3H), 1.97 (m, 2H). MS (EI): 458.2 (MH+).

2,6-dichloro-N-[3-({4-[(E)-2-phenylethenyl]pyrimidin-2-yl}amino)propyl]-benzamide: ¹H-NMR (400 MHz, d6-DMSO): 8.71 (t, 1H), 8.27 (d, 1H), 7.76 (d, 1H), 7.67-7.65 (m, 2H), 7.51-7.49 (m, 2H), 7.44-7.34 (m, 4H), 7.12-7.06 (m, 2H), 6.72 (d, 1H), 3.36 (m, 2H), 3.33 (m, 2H), 1.81 (t, 2H). MS (EI): 427.0 (MH+).

phenyl(4-{2-[(4-morpholin-4-ylphenyl)amino]pyrimidin-4-yl}phenyl)carbamate: ¹H-NMR (400 MHz, d6-DMSO): 8.59 (d, 1H), 7.90 (d, 2H), 7.69 (d, 1H), 7.44-7.40 (m, 2H), 7.28-7.20 (m, 5H), 6.97 (d, 2H), 6.62 (d, 2H), 5.90 (s, 2H), 3.74-3.72 (m, 4H), 3.13-3.11 (m, 4H). MS (EI): 468.1 (MH+).

phenylmethyl(4-{2-[(4-morpholin-4-ylphenyl)amino]pyrimidin-4-yl}phenyl)-carbamate: ¹H-NMR (400 MHz, d6-DMSO): 8.55 (d, 1H), 7.85 (d, 2H), 7.64 (d, 1H), 7.33-7.30 (m, 5H), 7.13 (d, 2H), 6.92 (d, 2H), 6.62 (d, 2H), 5.88 (s, 2H), 5.88 (s, 2H), 3.74-3.71 (m, 4H), 3.11-3.09 (m, 4H). MS (EI): 428.3 (MH+).

N-{4-[2-({4-[4-(2,2-dimethylpropanoyl)piperazin-1-yl]phenyl}amino)pyrimidin-4-yl]phenyl}-3-(methyloxy)propanamide: ¹H-NMR (400 MHz, d6-DMSO): 10.2 (s, 1H), 9.40 (s, 1H), 8.44 (d, 1H), 8.11 (d, 2H), 7.77 (d, 2H), 7.68 (d, 2H), 7.28 (d, 1H), 6.95 (d, 2H), 3.71-3.69 (m, 4H), 3.65 (t, 2H), 3.25 (s, 3H), 3.06-3.03 (m, 4H), 2.59 (t, 2H), 1.23 (s, 9H). MS (EI): 517.4 (MH+).

N-{4-[2-({4-[4-(cyclobutylcarbonyl)piperazin-1-yl]phenyl}amino)pyrimidin-4-yl]phenyl}-3-(methyloxy)propanamide: ¹H-NMR (400 MHz, d6-DMSO): 10.2 (s, 1H), 9.41 (s, 1H), 8.44 (d, 1H), 8.11 (d, 2H), 7.77 (d, 2H), 7.68 (d, 2H), 7.28 (d, 1H), 6.96 (d, 2H), 3.65-3.60 (m, 4H), 3.47-3.37 (m, 4H), 3.25 (s, 3H), 3.03-3.02 (m, 3H), 2.60 (t, 2H), 2.21-2.07 (m, 4H), 1.94-1.87 (m, 1H), 1.78-1.73 (m, 1H). MS (EI): 515.2 (MH+).

3-(methyloxy)-N-{4-[2-({4-[4-(2-methylpropanoyl)piperazin-1-yl]phenyl}amino)-pyrimidin-4-yl]phenyl}propanamide: ¹H-NMR (400 MHz, d6-DMSO): 10.2 (s, 1H), 9.41 (s, 1H), 8.44 (d, 1H), 8.12 (d, 2H), 7.76 (d, 2H), 7.68 (d, 2H), 7.28 (d, 1H), 6.96 (d, 2H), 3.65-3.62 (m, 6H), 3.25 (s, 3H), 3.08-3.02 (m, 4H), 2.92 (m, 1H), 2.59 (t, 2H), 1.02 (d, 6H). MS (EI): 503.4 (MH+).

N-ethyl-4-(4-{[4-{[3-(methyloxy)propanoyl]amino}phenyl)pyrimidin-2-yl]-amino}phenyl)piperazine-1-carboxamide: ¹H-NMR (400 MHz, d6-DMSO): 10.2 (s, 1H), 9.40 (s, 1H), 8.44 (d, 1H), 8.12 (d, 2H), 7.77 (d, 2H), 7.68 (d, 2H), 7.28 (d, 1H), 6.97 (d, 2H), 6.59 (t, 1H), 3.64 (t, 2H), 3.43 (m, 4H), 3.25 (s, 3H), 3.10-3.03 (m, 6H), 2.61 (t, 2H), 1.02 (t, 3H). MS (EI): 504.4 (MH+).

N-(4-(2-(4-(4-ethylpiperazin-1-yl)phenylamino)pyrimidin-4-yl)phenyl)-2-phenyl-acetamide: $^1$H-NMR (400 MHz, d6-DMSO): 10.45 (s, 1H), 9.36 (s, 1H), 8.43 (d, 1H), 8.12 (d, 2H), 7.76 (d, 2H), 7.64 (d, 2H), 7.38-7.33 (m, 3H), 7.27 (d, 1H), 6.92 (d, 2H), 3.69 (s, 2H), 3.10-3.04 (m, 4H), 2.35 (q, 3H), 1.89 (s, 2H), 1.03 (t, 2H); MS (EI): 493.1 (MH+).

1-(4-(2-(4-morpholinophenylamino)pyrimidin-4-yl)phenyl)pyrrolidin-2-one: $^1$H-NMR (400 MHz, d6-DMSO): 8.26 (d, 1H), 8.14 (d, 2H), 7.77 (d, 2H), 7.65 (d, 2H), 7.36 (d, 1H), 7.25 (d, 2H), 3.92-3.84 (m, 5H), 3.82-3.74 (m, 1H), 3.74-3.60 (m, 1H), 3.42-3.30 (m, 4H), 3.06-3.02 (m, 1H), 2.16-2.06 (m, 2H); MS (EI): 416.1 (MH+).

(R)-2-amino-N-(4-(2-(4-(4-(cyclobutanecarbonyl)piperazin-1-yl)phenylamino-pyrimidin-4-yl)phenyl)propanamide: $^1$H-NMR (400 MHz, d6-DMSO): 9.41 (s, 1H), 8.44 (d, 1H), 8.13 (d, 2H), 7.82 (d, 2H), 7.68 (d, 2H), 7.29 (d, 1H), 6.95 (d, 2H), 3.63-3.56 (m, 2H), 3.43-3.37 (m, 3H), 3.18 (d, 1H), 3.07-2.98 (m, 4H), 2.25-2.02 (m, 4H), 1.98-1.83 (m, 1H), 1.82-1.70 (m, 1H), 1.23 (d, 3H); MS (EI): 500.2 (MH+).

(R)-2-amino-N-(4-(2-(4-(4-pivaloylpiperazin-1-yl)phenylamino)pyrimidin-4-yl)phenyl)propanamide: $^1$H-NMR (400 MHz, d6-DMSO): 9.41 (s, 1H), 8.45 (d, 1H), 8.13 (d, 2H), 7.82 (d, 2H), 7.68 (d, 2H), 7.29 (d, 1H), 6.95 (d, 2H), 3.73-3.67 (m, 4H), 3.52-4.42 (m, 1H), 3.08-3.02 (m, 4H), 1.25 (s, 3H), 1.23 (d, 3H); MS (EI): 502.4 (MH+).

(S)-2-hydroxy-3-methyl-N-(4-(2-(4-morpholinophenylamino)pyrimidin-4-yl)-phenyl)butanamide: $^1$H-NMR (400 MHz, d6-DMSO): 9.90 (s, 1H), 9.39 (s, 1H), 8.45 (d, 1H), 8.12 (d, 2H), 7.90 (d, 2H), 7.68 (d, 2H), 7.29 (d, 2H), 6.94 (d, 2H), 5.76 (d, 1H), 3.86 (dd, 1H), 3.78-3.73 (m, 4H), 3.08-3.02 (m, 4H), 0.96 (d, 3H), 0.87 (d, 3H); MS (EI): 448.3 (MH+).

(R)-2-hydroxy-3-methyl-N-(4-(2-(4-morpholinophenylamino)pyrimidin-4-yl)-phenyl)butanamide: $^1$H-NMR (400 MHz, d6-DMSO): 9.90 (s, 1H), 9.39 (s, 1H), 8.45 (d, 1H), 8.12 (d, 2H), 7.90 (d, 2H), 7.68 (d, 2H), 7.29 (d, 2H), 6.94 (d, 2H), 5.76 (d, 1H), 3.86 (dd, 1H), 3.78-3.73 (m, 4H), 3.08-3.02 (m, 4H), 0.96 (d, 3H), 0.87 (d, 3H); MS (EI): 448.3 (MH+).

N-{4-[2-({4-[4-(cyclopropylcarbonyl)piperazin-1-yl]phenyl}amino)pyrimidin-4-yl]-phenyl}-D-alaninamide: $^1$H NMR (400 MHz, d6-DMSO): 11.17 (s, 1H), 10.04 (s, 1H), 8.58 (s, 1H), 8.40 (s, 2H), 8.11-8.09 (m, 2H), 7.96-7.82 (m, 3H), 7.76-7.65 (m, 2H), 7.45 (d, 1H), 4.05 (t, 4H), 3.75-3.70 (m, 1H), 3.50 (t, 4H), 2.10-2.00 (m, 1H), 1.45 (d, 3H), 0.82-0.72 (m, 4H). MS (EI): 486 (MH+).

(2S)-2-amino-N-(4-{2-[(4-morpholin-4-ylphenyl)amino]pyrimidin-4-yl}phenyl)-2-phenylethanamide: $^1$H NMR (400 MHz, d6-DMSO): 11.73 (s, 1H), 10.08 (s, 1H), 8.99 (s, br, 3H), 8.58 (s, 1H), 8.19 (d, 2H), 7.96-7.83 (m, 3H), 7.76-7.65 (m, 3H), 7.45-7.40 (m, 3H), 5.40 (s, br, 1H), 3.85 (s, br, 4H), 3.50 (s, br, 4H). MS (EI): 481 (MH+).

2-amino-2-(4-chlorophenyl)-N-(4-{2-[(4-morpholin-4-ylphenyl)amino]pyrimidin-4-yl}phenyl)acetamide: $^1$H NMR (400 MHz, d6-DMSO): 11.80 (s, 1H), 10.00 (s, 1H), 9.00 (s, 2H), 8.57 (d, 1H), 8.20 (d, 2H), 7.95-7.83 (m, 4H), 7.80-7.60 (m, 3H), 7.58 (d, 2H), 7.43 (d, 1H), 5.50 (s, 1H), 4.00 (t, 4H), 3.50 (t, 4H). MS (EI): 515 (MH+).

N-(4-{2-[(4-morpholin-4-ylphenyl)amino]pyrimidin-4-yl}phenyl)morpholine-3-carboxamide: $^1$H NMR (400 MHz, d6-DMSO): 11.60 (s, 1H), 10.20 (s, 1H), 10.00 (s, 1H), 9.40 (s, br, 1H), 8.58 (d, 1H), 8.20 (d, 2H), 7.95-7.88 (m, 3H), 7.60-7.20 (m, 4H), 4.42-4.30 (m, 1H), 4.05-3.90 (m, 2H), 3.85-3.70 (m, 4H), 3.60-3.45 (m, 4H), 3.25-3.10 (m, 3H). MS (EI): 461 (MH+).

1-ethyl-3-[4-(2-{[4-(4-ethylpiperazin-1-yl)-3-(methyloxy)phenyl]amino}pyrimidin-4-yl)phenyl]urea: $^1$H NMR (400 MHz, d6-DMSO): 9.40 (s, 1H), 8.90 (s, 1H), 8.42 (d, 1H), 8.20 (s, 1H), 8.05 (d, 2H), 7.56 (d, 2H), 7.28 (d, 2H), 6.83 (d, 1H), 6.36 (t, 1H), 3.80 (s, 3H), 3.12 (q, 2H), 2.98 (s, br, 4H), 2.58 (s, br, 4H), 2.42 (q, 2H), 1.08-1.00 (m, 6H). MS (EI): 476 (MH+).

N-[4-(2-{([4-(4-ethylpiperazin-1-yl)-3-(methyloxy)phenyl]amino}pyrimidin-4-yl)-phenyl]-D-prolinamide: $^1$H NMR (400 MHz, d6-DMSO): 11.23 (s, 1H), 11.05 (s, 1H), 10.18 (s, br, 1H), 10.00 (s, 1H), 8.75 (s, br, 1H), 8.57 (d, 1H), 8.21 (d, 2H), 7.85 (d, 2H), 7.63 (s, 1H), 7.44 (d, 1H), 7.33 (dd, 1H), 7.03 (d, 1H), 4.55-4.50 (m, 1H), 3.82 (s, 3H), 3.80-3.60 (m, 4H), 3.35-3.05 (m, 7H), 2.50-2.45 (m, 2H), 2.02-1.95 (m, 3H), 1.30 (t, 3H). MS (EI): 502 (MH+).

N-[4-(2-{[4-(4-ethylpiperazin-1-yl)-3-(methyloxy)phenyl]amino}pyrimidin-4-yl)-phenyl]acetamide: $^1$H NMR (400 MHz, d6-DMSO): 10.22 (s, 1H), 9.40 (s, 1H), 8.44 (s, 1H), 8.15 (d, 2H), 7.80-7.60 (m, 3H), 7.33 (d, 2H), 6.85 (d, 1H), 3.80 (s, 3H), 2.90 (s, br, 4H), 2.35 (q, 2H), 2.05 (s, 4H), 1.95 (s, 3H), 1.00 (s, 3H). MS (EI): 447 (MH+).

1-(2,6-dichlorophenyl)-3-(3-{[4-(4-methyl-2-thienyl)pyrimidin-2-yl]amino}propyl)-urea: $^1$H NMR (400 MHz, d$_6$-DMSO): 8.26 (d, 1H), 8.02 (br, 1H), 7.71 (s, 1H), 7.48 (d, 2H), 7.31 (s, 1H), 7.26 (t, 1H), 7.16 (t, 1H), 6.99 (d, 1H), 6.39 (t, 1H), 3.38 (t, 2H), 3.15 (t, 2H), 2.21 (s, 3H), 1.65 (m, 2H). MS (EI) for C$_{19}$H$_{19}$Cl$_2$N$_5$OS: 436 (MH+).

1-[2-fluoro-5-(trifluoromethyl)phenyl]-3-(3-{[4-(4-methyl-2-thienyl)pyrimidin-2-yl]amino}propyl)urea: $^1$H NMR (400 MHz, d$_6$-DMSO): 8.65 (d, 2H), 8.23 (s, 1H), 7.7 (s, 1H), 7.4 (t, 1H), 7.38-7.15 (m, 2H), 7.0 (s, 1H), 6.8 (t, 1H), 3.38 (t, 2H), 3.2 (t, 2H), 2.21 (s, 3H), 1.75 (m, 2H). MS (EI) for C$_{20}$H$_{19}$F$_4$N$_5$OS: 454 (MH$^+$).

2,6-dichloro-N-[3-({4-[4-(dimethylamino)phenyl]pyrimidin-2-yl}amino)propyl]-benzenesulfonamide: $^1$H NMR (400 MHz, d$_6$-DMSO): 8.16 (d, 1H), 8.12 (t, 1H), 7.94 (d, 2H), 7.58 (d, 2H), 7.48 (t, 1H), 6.97 (d, 1H), 6.92 (t, 6.76 (d, 2H) 3.28 (m, 2H), 3.02-2.96 (m, 8H), 1.68 (m, 2H). MS (EI) for C$_{21}$H$_{23}$Cl$_2$N$_5$O$_2$S: 480 (MH$^+$).

N-[3-({4-[4-(dimethylamino)phenyl]pyrimidin-2-yl}amino)propyl]-2,6-difluoro-benzenesulfonamide: $^1$H NMR (400 MHz, d$_6$-DMSO): 8.25 (T, 1H), 8.16 (d, 1H), 7.94 (d, 2H), 7.66 (m, 1H), 7.24 (t, 2H), 6.98 (d, 1H), 6.95 (t, 1H), 6.76 (d, 2H), 3.33 (t, 2H), 3.0 (t, 2H), 2.98 (s, 6H), 1.68 (m, 2H). MS (EI) for C$_{21}$H$_{23}$F$_2$N$_5$O$_2$S: 448 (MH$^+$).

N-[3-({4-[4-(dimethylamino)phenyl]pyrimidin-2-yl}amino)propyl]naphthalene-2-sulfonamide: $^1$H NMR (400 MHz, d$_6$-DMSO): 8.42 (br, 1H), 8.15-8.06 (m, 3H), 8.02 (d, 1H), 7.94 (d, 2H), 7.8 (dd, 1H), 7.74-7.62 (m, 3H), 6.96 (d, 1H), 6.92 (t, 1H), 6.74 (d, 2H), 3.3 (t, 2H), 2.98 (s, 6H), 2.83 (t, 2H), 1.63 (m, 2H). MS (EI) for C$_{25}$H$_{27}$N$_5$O$_2$S 462 (MH$^+$).

N-[3-({4-[4-(dimethylamino)phenyl]pyrimidin-2-yl}amino)propyl]-3,4-bis(methyloxy)benzenesulfonamide: $^1$H NMR (400 MHz, d$_6$-DMSO): 8.17 (d, 1H), 7.94 (d, 2H), 7.46 (t, 1H), 7.34 (dd, 1H), 7.27 (d, 1H), 7.06 (d, 1H), 6.97 (d, 1H), 6.93 (t, 1H), 6.76 (d, 2H), 3.8 (s, 6H), 3.3 (t, 2H), 2.98 (s, 6H), 2.8 (t, 2H), 1.65 (m, 2H). MS (EI) for C$_{23}$H$_{29}$N$_5$O$_4$S: 472 (MH$^+$).

3-chloro-N-[3-({4-[4-(dimethylamino)phenyl]pyrimidin-2-yl}amino)propyl]propane-1-sulfonamide: $^1$H NMR (400 MHz, d$_6$-DMSO): 8.2 (s, 1H), 7.98 (d, 2H), 7.2 (t, 1H), 7.0 (t, 2H), 6.8-6.7 (m, 2H), 3.7 (t, 2H), 3.1-2.9 (m, 10H), 2.05 (t, 2H), 1.7 (m, 2H), 1.2 (m, 2H). MS (EI) for C$_{18}$H$_{26}$ClN5O$_2$S: 412 (MH$^+$).

N-[3-({4-[4-(dimethylamino)phenyl]pyrimidin-2-yl}amino)propyl]propane-1-sulfonamide: $^1$H NMR (400 MHz, d$_6$-DMSO): 8.2 (d, 1H), 7.96 (d, 2H), 7.0-6.95 (m, 3H), 6.76 (d, 2H), 3.38 (t, 2H), 3.0-2.9 (m, 10H), 1.75 (t, 2H), 1.6 (q, 2H), 0.95 (t, 3H). MS (EI) for $C_{18}H_{27}N_5O_2S$: 378 (MH$^+$).

methyl (3-{[4-(2,4-dichlorophenyl)pyrimidin-2-yl]amino}propyl)carbamate: $^1$H NMR (400 MHz, $d_6$-DMSO): 8.4 (d, 1H), 7.75 (s, 1H), 7.63-7.55 (m, 2H), 7.35 (t, 1H), 7.12 (t, 1H), 6.8 (d, 1H), 3.5 (s, 3H), 3.28 (t, 2H), 3.03 (t, 2H), 1.65 (m, 2H). MS (EI) for $C_{15}H_{16}Cl_2N_4O_2$: 355 (MH$^+$).

1-methylethyl (3-{[4-(2,4-dichlorophenyl)pyrimidin-2-yl]amino}propyl)-arbamate: $^1$H NMR (400 MHz, $d_6$-DMSO): 8.38 (d, 1H), 7.75 (s, 1H), 7.63-7.55 (m, 2H), 7.35 (t, 1H), 7.0 (t, 1H), 6.8 (d, 1H), 4.72 (m, 1H), 3.28 (q, 2H), 3.0 (q, 2H), 1.65 (p, 2H), 1.12 (d, 6H). MS (EI) for $C_{17}H_2O\,Cl_2N_4O_2$: 383 (MH$^+$).

phenylmethyl(3-{[4-(2,4-dichlorophenyl)pyrimidin-2-yl]amino}propyl)carbamate: $^1$H NMR (400 MHz, $d_6$-DMSO): 8.46 (d, 1H), 8.2 (br, 1H), 7.8 (d, 1H), 7.66 (br, 1H), 7.6 (dd, 1H), 7.4-7.28 (m, 5H), 7.04 (br, 1H), 5.0 (s, 2H), 3.4 (t, 2H), 3.1 (t, 2H), 1.7 (m, 2H). MS (EI) for $C_{21}H_{20}Cl_2N_4O_2$: 431 (MH$^+$).

N-{4-[2-({[3-(3-chlorophenyl)isoxazol-5-yl]methyl}amino)pyrimidin-4-yl]-henyl}acetamide: $^1$H NMR (400 MHz, $d_6$-DMSO): 10.18 (s, 1H), 8.37 (d, 1H), 8.06 (d, 2H), 7.92 (t, 1H), 7.88-7.82 (m, 2H), 7.7 (d, 2H), 7.56-7.48 (m, 2H), 7.2 (d, 1H), 7.1 (d, 1H), 4.7 (s, 2H), 2.05 (s, 3H). MS (EI) for $C_{22}H_{18}ClN_5O_2$: 420 (MH$^+$).

ethyl 4-({4-[4-(acetylamino)phenyl]pyrimidin-2-yl}amino)piperidine-1-carboxylate: $^1$H MR (400 MHz, $d_6$-DMSO): 10.18 (s, 1H), 8.3 (d, 1H), 8.04 (d, 2H), 7.7 (d, 2H), 7.13 (d, 2H), 7.06 (d, 1H), 4.05 (q, 3H), 3.95 (br, 2H), 2.96 (br, 2H), 2.08 (s, 3H), 1.9 (br, 2H), 1.4 (q, 2H), 1.2 (t, 3H). MS (EI) for $C_{20}H_{25}N_5O_3$: 384 (MH$^+$).

1,1-dimethylethyl 4-({4-[4-(acetylamino)phenyl]pyrimidin-2-yl}amino)piperidine-1-carboxylate: $^1$H NMR (400 MHz, $d_6$-DMSO): 10.18 (s, 1H), 8.3 (d, 1H), 8.05 (d, 2H), 7.7 (d, 2H), 7.2 (br, 1H), 7.1 (d, 1H), 3.92 (br, 3H), 2.9 (br, 2H), 2.08 (s, 3H), 1.87 (br, 2H), 1.46-1.36 (m, 1H). MS (EI) for $C_{22}H_{29}N_5O_3$: 412 (MH$^+$).

N-{4-[2-(3,5-diamino-1H-1,2,4-triazol-1-yl)pyrimidin-4-yl]phenyl}acetamide: $^1$H NMR (400 MHz, $d_6$-DMSO): 10.28 (s, 1H), 8.7 (d, 1H), 8.16 (d, 2H), 7.78 (d, 2H), 7.7 (d, 1H), 7.58 (s, 2H), 2.03 (s, 3H). MS (EI) for $C_{14}H_{14}NO$: 311 (MH$^+$).

N-{4-[2-({5-[(4-ethylpiperazin-1-yl)carbonyl]pyridin-2-yl}amino)pyrimidin-4-yl]-phenyl}acetamide: $^1$H NMR (400 MHz, $d_6$-DMSO): 10.26 (s, 1H), 10.12 (s, 1H), 8.6 (d, 1H), 8.46 (d, 1H), 8.36 (d, 1H), 8.18 (d, 2H), 7.9 (dd, 1H), 7.77 (d, 2H), 7.54 (d, 1H), 2.46-2.32 (m, 6H), 2.1 (s, 3H), 1.0 (t, 3H). MS (EI) for $C_{24}H_{27}N_7O_2$: 446 (MH$^+$).

N-(4-{2-[(4-cyanophenyl)amino]pyrimidin-4-yl}phenyl)acetamide: $^1$H NMR (400 MHz, $d_6$-DMSO): 10.24 (d, 2H), 8.6 (d, 1H), 8.17 (d, 2H), 8.06 (d, 2H), 7.78 (d, 4H), 7.5 (d, 1H), 2.059s, 3H). MS (EI) for $C_{19}H_{15}N_5O$: 330 (MH$^+$).

N-(4-{2-[(4-morpholin-4-ylphenyl)amino]pyridin-4-yl}phenyl)acetamide: $^1$H NMR (400 MHz, $d_6$-DMSO): 10.14 (s, 1H), 8.82 (s, 1H), 8.12 (d, 1H), 7.729d, 2H), 7.62 (d, 2H), 7.53 (d, 2H), 6.97-6.92 (m, 2H), 6.9 (d, 2H), 3.74 (t, 4H), 3.02 (t, 4H), 2.07 (s, 3H). MS (EI) for $C_{23}H_{24}N_4O_2$: 389 (MH$^+$).

N-[4-(2-{[4-(4-ethylpiperazin-1-yl)phenyl]amino}-5-methylpyrimidin-4-yl)phenyl]-3-(methyloxy)propanamide: $^1$H NMR (400 MHz, $d_6$-DMSO): 10.18 (s, 1H), 9.25 (s, 1H), 8.3 (s, 1H), 7.75 (d, 2H); 7.63 (d, 2H), 7.61 (d, 2H), 6.86 (d, 2H), 3.64 (t, 2H), 3.25 (s, 3H), 3.03 (t, 4H), 2.6 (t, 2H), 2.38 (br, 2H), 2.2 (s, 3H), 1.03 (t, 3H). MS (EI) for $C_{72}H_{34}N_6O_2$: 475 (MH$^+$).

tert-butyl 1-(4-(4-(4-acetamidophenyl)pyrimidin-2-ylamino)phenyl)piperidin-4-ylcarbamate: $^1$H NMR (400 MHz, $d_6$-DMSO): 10.21 (s, 1H), 9.38 (s, br, 1H), 8.43 (s, 1H), 8.08 (m, 2H), 7.74 (m, 2H), 7.62 (m, 2H), 7.23 (m, 1H), 6.98 (m, 3H), 3.77 (m, 2H), 3.63 (m, 2H), 2.09 (s, 3H), 1.80 (m, 2H), 1.49 (m, 2H), 1.30 (s, 9H). MS (EI) for $C_{28}H_{34}N_6O_3$: 503 (MH$^+$).

4-(4-aminophenyl)-N-(4-(4-aminopiperidin-1-yl)phenyl)pyrimidin-2-amine: $^1$H NMR (400 MHz, $d_6$-DMSO): 9.19 (s, 1H), 8.3 (m, 1H), 7.87 (m, 2H), 7.63 (m, 2H), 7.14 (m, 1H), 6.92 (m, 2H), 6.62 (m, 2H), 5.74 (m, 2H), 3.57 (m, 2H), 2.67 (m, 2H), 1.81 (m, 2H), 1.38 (m, 2H). MS (EI) for $C_{21}H_{24}N_6$: 361 (MH$^+$).

N-(1-(4-(4-(4-acetamidophenyl)pyrimidin-2-ylamino)phenyl)piperidin-4-yl)-acetamide: $^1$H NMR (400 MHz, $d_6$-DMSO): 10.26 (s, 1H), 9.34 (s, 1H), 8.43 (d, 1H), 8.1 (d, 2H), 7.85 (d, 2H), 7.75 (d, 2H), 7.64 (d, 2H), 7.27 (d, 1H), 6.94 (d, 2H), 3.67 (m, 1H), 3.55 (m, 2H), 2.72 (t, 2H), 2.09 (s, 3H), 1.88-1.76 (m, 5H), 1.48 (m, 2H). MS (EI) for $C_{25}H_{28}N_6O_2$: 445 (MH$^+$).

N-(4-(2-(4-(4-(cyclopropanecarbonyl)piperazin-1-yl)phenylamino)pyrimidin-4-yl)-phenyl)cyclopropanecarboxamide: $^1$H NMR (400 MHz, $d_6$-DMSO): 10.51 (s, 1H), 9.41 (s, 1H), 8.44 (d, 1H), 8.13 (d, 2H), 7.87 (d, 2H), 7.69 (d, 2H), 7.28 (d, 1H), 6.97 (d, 2H), 3.82 (m, 2H), 3.61 (m, 2H), 3.25-2.99 (m, 4H), 2.04 (m, 1H), 1.83 (m, 1H), 0.89-0.68 (m, 8H). MS (EI) for $C_{28}H_{30}N_6O_2$: 483 (MH$^+$).

N-(4-(2-(4-(4-isobutyrylpiperazin-1-yl)phenylamino)pyrimidin-4-yl)phenyl)-tetrahydrofuran-2-carboxamide: $^1$H NMR (400 MHz, $d_6$-DMSO): 9.94 (s, 1H), 9.42 (s, 1H), 8.45 (d, 1H), 8.12 (d, 2H), 7.87 (d, 2H), 7.68 (d, 2H), 7.31 (d, 1H), 6.96 (d, 2H), 4.42 (m, 1H), 3.99 (m, 1H), 3.85 (m, 1H), 3.62 (m, 4H), 3.08 (m, 2H), 3.02 (m, 2H), 2.92 (m, 1H) 2.21 (m, 1H), 2.01 (m, 1H), 2.73 (m, 2H), 1.03 (d, 6H). MS (EI) for $C_{29}H_{34}N_6O_3$: 515 (MH$^+$).

N-(4-(2-(4-(4-(cyclobutanecarbonyl)piperazin-1-yl)phenylamino)pyrimidin-4-yl)phenyl)tetrahydrofuran-2-carboxamide: $^1$H NMR (400 MHz, $d_6$-DMSO): 9.94 (s, 1H), 9.41 (s, 1H), 8.44 (d, 1H), 8.13 (d, 2H), 7.87 (d, 2H), 7.68 (d, 2H), 7.30 (d, 2H), 6.95 (d, 2H), 4.43 (m, 1H), 3.99 (m, 1H), 3.84 (m, 1H), 3.59 (m, 2H), 3.43 (m, 2H), 3.01 (m, 4H), 2.28-1.69 (m, 10H). MS (EI) for $C_{30}H_{34}N_6O_3$: 527 (MH$^+$).

N-(4-(2-(4-(4-pivaloylpiperazin-1-yl)phenylamino)pyrimidin-4-yl)phenyl)-tetrahydrofuran-2-carboxamide: $^1$H NMR (400 MHz, $d_6$-DMSO): 9.95 (s, 1H), 9.42 (s, 1H), 8.45 (d, 1H), 8.12 (d, 2H), 7.88 (d, 2H), 7.69 (d, 2H), 7.30 (d, 1H), 6.95 (d, 2H), 4.43 (m, 1H), 4.0 (m, 1H), 3.84 (m, 1H), 3.7 (m, 4H), 3.04 (m, 4H), 2.22 (m, 1H), 2.02 (m, 1H), 1.86 (m, 2H), 1.23 (s, 9H). MS (EI) for $C_{30}H_{36}N_6O_3$: 529 (MH$^+$).

N-cyclopropyl-4-(2-(4-morpholinophenylamino)pyrimidin-4-yl)benzamide: $^1$H NMR (400 MHz, d6-DMSO): 9.51 (s, br, 1H), 8.58 (s, br, 1H), 8.52 (d, 1H), 8.21 (d, 2H), 7.96 (d, 2H), 7.67 (d, 2H), 7.39 (d, 1H), 6.93 (d, 2H), 3.76 (m, 4H), 3.05 (m, 4H), 2.89 (m, 1H), 0.71 (m, 2H), 0.60 (m, 2H). MS (EI): 416 (MH+).

N-(2-methoxyethyl)-4-(2-(4-morpholinophenylamino)pyrimidin-4-yl)benzamide: $^1$H NMR (400 MHz, d6-DMSO): 9.51 (s, br, 1H), 8.68 (s, br, 1H), 8.52 (d, 1H), 8.23 (d, 2H), 8.00 (d, 2H), 7.67 (d, 2H), 7.40 (d, 1H), 6.94 (d, 2H), 3.75 (m, 4H), 3.47 (m, 4H), 3.28 (s, 3H), 3.05 (m, 4H). MS (EI): 434 (MH+).

2,6-dichloro-n-{3-[(4-pyridin-3-ylpyrimidin-2-yl)amino]propyl}-benzamide: $^1$H-NMR (400 MHz, d6-DMSO): 9.25 (br s, 1H), 8.68-8.66 (m, 2H); 8.37 (m, 2H), 7.49-7.47 (m, 3H), 7.42-7.38 (m, 1H), 7.32 (m, 1H), 7.21-7.20 (m, 1H), 3.44 (m, 2H), 3.29 (m, 2H), 1.82 (m, 2H). MS (EI): 402.0 (MH+).

2,6-dichloro-n-(3-{[4-(4-methyl-3,4-dihydro-2h-1,4-benzoxazin-7-yl)pyrimidin-2-yl]amino}propyl)benzamide: $^1$H-NMR (400 MHz, d6-DMSO): 8.69 (t, 1H), 8.18 (d, 1H), 7.58 (dd, 1H), 7.51-7.40 (m, 4H), 7.02-6.97 (m, 2H), 6.73 (d, 1H), 4.25-4.23 (m, 2H), 3.41 (m, 2H), 3.32-3.29 (m, 4H), 2.91 (s, 3H), 1.81 (t, 2H). MS (EI): 472.3 (MH+).

2,6-dichloro-n-(3-{[4-(2,3-dihydro-1,4-benzodioxin-6-yl)-6-methyl-pyrimidin-2-yl]amino}propyl)benzamide: $^1$H-NMR (400 MHz, d6-DMSO): 8.68 (t, 1H), 7.62-7.59 (m, 2H), 7.51-7.49 (m, 2H), 7.44-7.40 (m, 1H), 7.02 (t, 1H), 6.97-6.92 (m, 2H), 4.30-4.28 (m, 4H), 3.44-3.43 (m, 2H), 3.32-3.29 (m, 2H), 2.27 (s, 3H), 1.80 (t, 2H); MS (EI): 473.3 (MH+).

N-(4-{2-[(3-{[2,6-dichlorophenyl)carbonyl]amino}propyl)-amino]pyrimidin-4-yl}phenyl)morpholine-4-carboxamide: $^1$H-NMR (400 MHz, d6-DMSO): 8.69 (m, 2H), 8.33 (d, 1H), 8.18 (m, 1H), 7.60 (m, 2H), 7.51-7.49 (m, 2H), 7.44-7.34 (m, 2H), 7.20 (m, 1H), 7.01 (d, 1H), 3.62-3.61 (m, 4H), 3.43 (m, 6H), 3.32 (m, 2H), 1.83 (m, 2H). MS (EI): 529.1 (MH+).

2,6-dichloro-n-(3-[(4-{4-[(cyclopropylcarbonyl)amino]-phenyl}pyrimidin-2-yl)amino]propyl)benzamide: $^1$H-NMR (400 MHz, d6-DMSO): 10.4 (s, 1H), 8.72 (t, 1H), 8.36-8.33 (m, 2H), 7.73 (m, 2H), 7.51-7.39 (m, 4H), 7.24 (m, 1H), 7.03 (d, 1H), 3.45 (m, 2H), 3.33 (m, 4H), 1.84-1.78 (m, 2H), 0.81-0.78 (m, 3H). MS (EI): 484.0 (MH+).

N-(4-{2-[(3-{[(2,6-dichlorophenyl)carbonyl]amino}propyl)-amino]pyrimidin-4-yl}phenyl)thiophene-2-carboxamide: $^1$H-NMR (400 MHz, d6-DMSO): 10.4 (s, 1H), 8.72 (t, 1H), 8.44 (t, 1H), 8.37 (d, 1H), 8.05 (s, 1H), 7.90-7.81 (m, 3H), 7.50-7.39 (m, 4H), 7.25-7.23 (m, 2H), 7.07 (d, 1H), 3.47 (m, 2H), 3.34 (m, 2H), 1.85 (m, 2H). MS (EI): 526.0 (MH+).

2,6-dichloro-n-(3-{[4-(4-{n-(2-morpholin-4-ylethyl)glycyl]-amino}phenyl)pyrimidin-2-yl]amino}propyl)benzamide: $^1$H-NMR (400 MHz, d6-DMSO): 10.0 (br s, 1H), 8.72 (t, 1H), 8.35-8.32 (m, 2H), 7.82-7.75 (m, 2H), 7.51-7.40 (m, 4H), 7.22 (s, 1H), 7.05 (d, 1H), 3.56 (m, 4H), 3.45 (m, 2H), 3.30 (m, 3H), 2.64 (m, 2H), 2.41-2.35 (m, 8H), 1.84 (br s, 2H). MS (EI): 586.1 (MH+).

1-(4-{2-[(4-morpholin-4-ylphenyl)amino]pyrimidin-4-yl}phenyl)-ethanone: $^1$H-NMR (400 MHz, d6-DMSO): 8.50 (d, 1H), 8.26-8.24 (m, 2H), 8.12-8.10 (m, 2H), 7.30 (s, 1H), 7.64-7.62 (m, 2H), 7.31 (d, 1H), 7.00-6.98 (m, 2H), 3.82-3.80 (m, 4H), 3.12-3.10 (m, 4H), 2.64 (s, 3H). MS (EI): 375.1 (MH+).

(1e)-1-(4-{2-[(4-morpholin-4-ylphenyl)amino]pyrimidin-4-yl}-phenyl)ethanone oxime: $^1$H-NMR (400 MHz, d6-DMSO): 11.4 (s, 1H), 9.82 (br s, 1H), 8.55 (d, 1H), 8.20 (d, 2H), 7.85-7.82 (m, 4H), 7.45 (d, 1H), 7.36 (br s, 1H), 4.69 (br, 1H), 3.91 (m, 4H), 3.34 (m, 4H), 2.21 (s, 3H). MS (EI): 388.1 (MH−).

N-{4-[2-({4-[4-(cyclopropylcarbonyl)piperazin-1-yl]phenyl}-amino)pyrimidin-4-yl]phenyl}-2-phenylacetamide: $^1$H-NMR (400 MHz, d6-DMSO): 10.4 (s, 1H), 9.43 (br s, 1H), 8.42 (d, 1H), 8.10 (d, 2H), 7.75 (d, 2H), 7.67 (d, 2H), 7.33-7.20 (m, 2H), 7.07 (s, 2H), 6.97-6.95 (m, 4H), 3.82 (m, 4H), 3.67 (s, 2H), 3.03 (m, 4H), 2.07 (m, 1H), 0.75-0.69 (m, 4H). MS (EI): 533.2 (MH+).

N-[3-({4-[4-(acetylamino)phenyl]pyrimidin-2-yl}amino)propyl]-2-bromobenzamide: $^1$H-NMR (400 MHz, d$_6$-DMSO): 10.14 ppm (s, 1H), 8.42 ppm (t, 1H), 8.29 ppm (d, 1H), 8.06 ppm (d, 1H), 7.70 ppm (d, 2H), 7.65 ppm (m, 1H), 7.39 ppm (m, 3H), 7.12 ppm (t, 1H), 7.07 ppm (d, 1H), 3.33 ppm (br. m, 2H), 3.31 ppm (m, 2H), 2.07 ppm (s, 3H), 1.81 ppm (m, 2H); MS (EI) $C_{22}H_{22}BrN_5O_2$: 468 (MH$^+$).

N-[3-({4-[4-(acetylamino)phenyl]pyrimidin-2-yl}amino)propyl]-2-fluorobenzamide: $^1$H-NMR (400 MHz, d$_6$-DMSO): 10.17 ppm (s, 1H), 8.37 ppm (t, 1H), 8.30 ppm (d, 1H), 8.06 ppm (d, 2H), 7.70 ppm (d, 2H), 7.61 ppm (m, 1H), 7.50 ppm (m, 1H), 7.26 ppm (m, 2H), 7.16 ppm (t, 1H), 7.08 ppm (d, 1H), 3.41 ppm (br. m, 2H), 3.33 ppm (m, 2H), 2.08 ppm (s, 3H), 1.81 ppm (br. m, 2H); MS (EI) $C_2H_{22}FN_5O_2$: 408 (MH$^+$).

N-[3-({4-[4-(acetylamino)phenyl]pyrimidin-2-yl}amino)propyl]-2-chlorobenzamide: $^1$H-NMR (400 MHz, d$_6$-DMSO): 10.14 ppm (s, 1H), 8.45 ppm (t, 1H), 8.28 ppm (d, 1H), 8.04 ppm (d, 2H), 7.68 ppm (d, 2H), 7.68 ppm (d, 2H), 7.47 ppm (m, 1H), 7.41 ppm (m, 2H), 7.35 ppm (m, 1H), 7.13 ppm (t, 1H). 7.06 ppm (d, 1H), 3.42 ppm (br. m, 2H), 3.29 ppm (m, 2H), 2.05 ppm (s, 3H), 1.78 ppm (br m, 2H); MS (EI) $C_{22}H_{22}BrN_5O_2$: 468 (MH$^+$).

N-[4-(2-{[3-(morpholin-4-ylsulfonyl)phenyl]amino}pyrimidin-4-yl)phenyl]-acetamide: $^1$H-NMR (400 MHz, d$_6$-DMSO): 10.23 ppm (s, 1H), 10.12 ppm (s, 1H), 8.74 ppm (s, 1H), 8.58 ppm (d, 1H), 8.21 ppm (d, 2H), 7.93 ppm (m, 1H), 7.76 ppm (d, 2H), 7.60 ppm (t, 1H), 7.47 ppm (d, 1H), 7.30 ppm (m, 1H), 3.64 ppm (m, 4H), 2.90 ppm (m, 4H), 2.10 ppm (s, 3H); MS (EI) $C_{22}H_2N_5O_4S$: 454 (MH$^+$).

N-{4-[2-({3-[(cyclohexylmethyl)amino]phenyl}amino)pyrimidin-4-yl]phenyl}-acetamide: $^1$H-NMR (400 MHz, d$_6$-DMSO): 10.43 ppm (s, 1H), 9.32 ppm (s, 1H), 8.46 ppm (d, 1H), 8.13 ppm (d, 2H), 7.77 ppm (d, 2H), 7.30 ppm (d, 2H), 7.17 ppm (s, 1H), 6.94 ppm (m, 2H), 6.22 ppm (m, 1H), 5.56 ppm (t, 1H), 2.87 ppm (t, 2H), 2.09 ppm (s, 3H), 1.85 ppm (br d, 2H), 1.69 ppm (br m, 2H), 1.64 ppm (br m, 1H), 1.19 ppm (m, 3H), 0.94 ppm (m, 2H); MS (EI) $C_{25}H_{29}N_5O$: 416 (MH$^+$).

N-(4-{2-[(3-{[(5-bromo-2-fluorophenyl)methyl]amino}phenyl)amino]pyrimidin-4-yl}phenyl)acetamide: $^1$H-NMR (400 MHz, d$_6$-DMSO): 10.21 ppm (s, 1H), 9.37 ppm (s, 1H), 8.45 ppm (d, 1H), 8.12 ppm (d, 2H), 7.74 ppm (d, 2H), 7.55 ppm (m, 1H), 7.47 ppm (m, 1H), 7.31 ppm (d, 1H), 7.20 ppm (m, 1H), 7.05 ppm (m, 1H), 7.00 ppm (t, 1H), 6.28 ppm (t, 1H), 6.22 ppm (m, 1H), 4.32 ppm (d, 2H), 2.09 ppm (s, 3H); MS (EI) $C_{25}H_{21}BrFN_5O$: 507 (MH$^+$).

N-(4-{2-[(3-{[(2,5-dimethylphenyl)methyl]amino}phenyl)amino]pyrimidin-4-yl}phenyl)acetamide: $^1$H-NMR (400 MHz, d$_6$-DMSO): 10.20 ppm (s, 1H), 9.33 ppm (s, 1H), 8.45 ppm (d, 1H), 8.13 ppm (d, 2H), 7.73 ppm (d, 2H), 7.30 ppm (d, 1H), 7.16 ppm (m, 2H), 7.06 ppm (d, 1H), 6.97 ppm (m, 3H), 6.23 ppm (m, 1H), 5.99 ppm (t, 1H), 4.17 ppm (d, 2H), 2.28 ppm (s, 3H), 2.21 ppm (s, 3H), 2.08 ppm (s, 3H); MS (EI) $C_{27}H_{27}N_5O$: 438 (MH$^+$).

N-(4-{2-[(3,4-dimorpholin-4-ylphenyl)amino]pyrimidin-4-yl}phenyl)acetamide: $^1$H-NMR (400 MHz, d$_6$-DMSO): 10.22 ppm (s, 1H), 9.43 ppm (s, 1H), 8.46 ppm (d, 1H), 8.14 ppm (d, 2H), 7.74 ppm (d, 2H), 7.65 ppm (s, 1H), 7.34 ppm (m, 2H), 7.29 ppm (d, 2H), 6.88 ppm (d, 1H), 3.75 ppm (m, 8H), 3.15 ppm (br s, 4H), 3.05 ppm (br s, 4H), 2.09 ppm (s, 3H); MS (EI) $C_{26}H_{30}N_6O_3$: 475 (MH$^+$).

N-{4-[2-({4-[4-(pyridin-3-ylcarbonyl)piperazin-1-yl]phenyl}amino)pyrimidin-4-yl]phenyl}cyclopropanecarboxamide: $^1$H-NMR (400 MHz, d$_6$-DMSO): 10.47 ppm (s, 1H), 9.41 ppm (s, 1H), 8.67 ppm (m, 2H), 8.44 ppm (d, 1H), 8.11 ppm (d, 2H), 7.89 ppm (m, 1H), 7.76 ppm (d, 2H), 7.69 ppm (d, 2H), 7.51 ppm (m, 1H), 7.28 ppm (d, 1H), 6.97 ppm (d, 2H), 3.80 ppm (s, 2H), 3.49 ppm (s, 2H), 3.13 ppm (br d, 4H), 1.83 ppm (m, 1H), 0.84 ppm (m, 4H); MS (EI) $C_{30}H_{29}N_7O_2$: 520 (MH$^+$).

N-{4-[2-({4-[4-(2-methylpropanoyl)piperazin-1-yl]phenyl}amino)pyrimidin-4-yl]-phenyl}butanamide: $^1$H-NMR (400 MHz, d$_6$-DMSO): 10.16 ppm (s, 1H), 9.41 ppm (s, 1H), 8.44 ppm (d, 1H), 8.11 ppm (d, 2H), 7.77 ppm (d, 2H), 7.68 ppm (d, 2H), 7.28 ppm (d, 1H), 6.96 ppm (d, 2H), 3.63 ppm (m, 4H), 3.05 ppm (m, 4H), 2.92 ppm (m, 1H), 2.33 ppm (t, 1H), 1.63 ppm (m, 2), 1.02 ppm (d, 6H), 0.93 ppm (t, 3H); MS (EI) $C_{28}H_{34}N_6O_2$: 487 (MH+).

N-{4-[2-({4-[4-(2,2-dimethylpropanoyl)piperazin-1-yl]phenyl}amino)pyrimidin-4-yl]phenyl}butanamide: $^1$H-NMR (400 MHz, d$_6$-DMSO): 10.15 ppm (s, 1H), 9.41 ppm (s, 1H), 8.44 ppm (d, 1H), 8.11 ppm (d, 2H), 7.77 ppm (d, 2H), 7.68 ppm (d, 2H), 7.28 ppm (d, 1H), 6.95 ppm (d, 2H), 3.70 ppm (m, 4H), 3.05 ppm (m, 4H), 2.33 ppm (t, 2H), 1.63 ppm (m, 2H), 1.23 ppm (s, 9H), 0.93 ppm (t, 3H); MS (EI) $C_{29}H_{36}N_6O_2$: 501 (MH+).

N-{4-[2-({4-[4-(cyclobutylcarbonyl)piperazin-1-yl]phenyl}amino)pyrimidin-4-yl]phenyl}butanamide: $^1$H-NMR (400 MHz, d$_6$-DMSO): 10.28 ppm (s, 1H), 9.41 ppm (s, 1H), 8.44 ppm (d, 1H), 8.11 ppm (d, 2H), 7.79 ppm (d, 2H), 7.68 ppm (d, 2H), 7.28 ppm (d, 1H), 6.95 ppm (d, 2H), 3.59 ppm (m, 2H), 3.46 ppm (m, 2H), 3.40 ppm (m, 1H), 3.02 ppm (m, 4H), 2.35 ppm (t, 2H), 2.14 ppm (m, 4H), 1.91 ppm (m, 1H), 1.75 ppm (m, 1H), 1.63 ppm (m 2H), 0.93 ppm (t, 3H); MS (EI) $C_{29}H_{34}N_6O_2$: 499 (MH+).

N-(4-{2-[(4-morpholin-4-ylphenyl)amino]pyrimidin-4-yl}phenyl)pyridine-2-carboxamide: $^1$H-NMR (400 MHz, d6-DMSO): 10.91 (s, 1H), 9.41 (s, 1H), 8.78 (d, 1H), 8.47 (d, 2H), 8.17 (m, 4H), 7.69 (m, 2H), 7.33 (d, 1H), 6.95 (d, 2H), 6.80 (d, 2H), 3.75 (m, 4H), 3.06 (m, 4H). MS (EI) for $C_{26}H_{24}N_6O_2$: 453.5 (MH+).

2-hydroxy-N-(4-{2-[(4-morpholin-4-ylphenyl)amino]pyrimidin-4-yl}phenyl)-benzamide: $^1$H-NMR (400 MHz, d6-DMSO): 10.39 (s, 1H), 9.51 (s, 1H), 8.47 (s, 1H), 8.16 (d, 2H), 7.91 (d, 2H), 7.17 (m, 3H), 7.53 (t, 1H), 7.34 (s, 2H) 7.20 (d, 1H), 7.07 (m, 3H), 3.91 (m, 4H), 3.12 (m, 4H). MS (EI) for $C_{27}H_{25}N_5O_3$: 468.5 (MH+).

3-(methyloxy)-N-(4-{2-[(4-morpholin-4-ylphenyl)amino]pyrimidin-4-yl}phenyl)-benzamide: $^1$H-NMR (400 MHz, d6-DMSO): 10.49 (s, 2H), 8.19 (m, 3H), 7.97 (m, 3H), 7.55 (m, 2H), 7.50 (m, 3H), 7.20 (dd, 3H), 3.86 (m, 8H), 3.77 (s, 3H). MS (EI) for $C_{28}H_{27}N_5O_3$: 482.6 (MH+).

4-(methyloxy)-N-(4-{2-[(4-morpholin-4-ylphenyl)amino]pyrimidin-4-yl}phenyl)-benzamide: $^1$H-NMR (400 MHz, d6-DMSO): 10.35 (s, 1H), 9.40 (s, 1H), 8.45 (s, 1H), 8.16 (d, 2H), 7.98 (m, 4H), 7.68 (d, 2H), 7.31 (d, 1H), 7.09 (d, 2H), 6.94 (d, 2H), 3.83 (s, 3H), 3.75 (m, 4H), 3.05 (m, 4H). MS (EI) for $C_{28}H_{27}N_5O_3$: 482.6 (MH+).

4-chloro-N-(4-{2-[(4-morpholin-4-ylphenyl)amino]pyrimidin-4-yl}phenyl)-benzamide: $^1$H-NMR (400 MHz, d6-DMSO): 10.58 (s, 1H), 9.41 (s, 1H), 8.46 (s, 1H), 8.17 (d, 2H), 8.01 (d, 2H), 7.95 (d, 2H), 7.66 (m, 4H), 7.32 (d, 1H), 6.94 (d, 2H), 3.75 (m, 4H), 3.05 (m, 4H). MS (EI) for $C_{27}H_{24}ClN_5O_2$: 487.0 (MH+).

(2R)—N-[4-(2-({[4-(4-ethylpiperazin-1-yl)phenyl]amino}pyrimidin-4-yl)phenyl]-tetrahydrofuran-2-carboxamide: $^1$H-NMR (400 MHz, d6-DMSO): 9.95 (s, 1H), 9.38 (s, 1H), 8.45 (s, 1H), 8.12 (d, 2H), 7.89 (d, 2H), 7.66 (d, 2H), 7.29 (s, 1H), 6.92 (d, 2H), 4.44 (t, 2H), 4.00 (m, 2H), 3.85 (m, 2H), 2.41 (m, 4H), 2.20 (m, 2H), 2.02 (m, 2H), 1.88 (m, 2H), 1.05 (m, 4H). MS (EI) for $C_{27}H_{32}N_6O_2$: 473.6 (MH+).

(2S)—N-[4-(2-{[4-(4-ethylpiperazin-1-yl)phenyl]amino}pyrimidin-4-yl)phenyl]-tetrahydrofuran-2-carboxamide: $^1$H-NMR (400 MHz, d6-DMSO): 9.94 (s, 1H, 9.38 (s, 1H), 8.44 (s, 1H), 8.12 (d, 2H), 7.87 (d, 2H), 7.65 (d, 2H), 7.29 (s, 1H), 6.99 (d, 2H), 4.43 (m, 2H), 3.99 (m, 2H), 3.86 (m, 2H), 2.43 (m, 2H), 2.22 (m, 2H), 2.02 (m, 2H), 1.88 (m, 3H), 1.05 (m, 5H). MS (EI) for $C_{27}H_{32}N_6O_2$: 473.6 (MH+).

1-(2-hydroxyethyl)-N-(4-{2-[(4-morpholin-4-ylphenyl)amino]pyrimidin-4-yl}-phenyl)-L-prolinamide: $^1$H-NMR (400 MHz, d6-DMSO): 10.31 (s, 1H), 9.39 (s, 1H), 8.44 (d, 1H), 8.14 (m, 2H), 7.81 (m, 2H), 7.67 (m, 2H), 7.29 (d, 1H), 6.95 (d, 2H), 5.05 (s, br, 1H), 3.74 (m, 4H), 3.59 (m, 3H), 3.49 (m, 1H), 3.23 (m, 2H), 3.05 (m, 4H), 2.77 (m, 1H), 2.63 (m, 1H), 2.41 (m, 1H), 2.16 (m, 1H), 1.80 (m, 3H). MS (EI) for $C_{27}H_{32}N_6O_3$: 489.6 (MH+).

N-(4-(2-[(4-morpholin-4-ylphenyl)amino]pyrimidin-4-yl)phenyl)thiophene-2-carboxamide: $^1$H-NMR (400 MHz, d6-DMSO): 10.47 (s, 1H), 9.45 (s, 1H), 8.47 (s, 1H), 8.17 (d, 2H), 8.08 (s, 1H), 7.92 (m, 3H), 7.70 (s, 2H), 7.32 (s, 1H), 7.26 (t, 1H), 6.99 (s, 2H), 3.76 (m, 4H), 3.09 (m, 4H). MS (EI) for $C_{25}H_{23}N_5O_2S$: 458.6 (MH+).

N-[4-(2-{[4-(4-ethylpiperazin-1-yl)phenyl]amino}pyrimidin-4-yl)phenyl]-tetrahydrofuran-3-carboxamide: $^1$H-NMR (400 MHz, d6-DMSO): 10.31 (s, 1H), 9.37 (s, 1H), 8.44 (s, 1H), 8.14 (m, 2H), 7.79 (d, 2H), 7.65 (d, 2H), 7.27 (d, 1H), 6.92 (d, 2H), 3.96 (t, 1H), 3.76 (m, 3H), 3.19 (m, 1H), 3.09 (m, 4H), 2.55 (m, 4H), 2.42 (m, 2H), 2.10 (m, 2H), 1.05 (t, 3H). MS (EI) for $C_{27}H_{32}N_6O_2$: 473.6 (MH+).

N-(4-{2-[4-(4-nicotynoylpiperazin-1-yl)phenylamino]pyrimidin-4-yl}phenyl)-2-phenylacetamide: $^1$H NMR (400 MHz, d6-DMSO): 8.8 (d, 2H), 8.40 (s, 1H), 8.05 (d, 2H), 7.80 (d, 1H), 7.60-7.2 (m, 10H), 7.1-6.90 (m, 5H), 3.80-3.60 (m, 4H), 3.7 (s, 2H) 3.20-3.25 (m, 4H); MS (EI) for $C_{34}H_{31}N_7O_2$: 570 (MH+).

3-({4-[4-(acetylamino)phenyl]pyrimidin-2-yl}amino)-N-(diphenylmethyl)benzamide: $^1$H-NMR (400 MHz, d6-DMSO): 10.22 (s, 1H), 9.78 (s, 1H), 9.24 (d, 1H), 8.52 (d, 1H), 8.39 (s br, 1H), 8.16 (d, 2H), 7.95 (d, 1H), 7.75 (d, 2H), 7.53 (d t, 1H), 7.39-7.43 (m, 3H), 7.38 (d, 3H), 7.32-7.36 (m, 4H), 7.24-7.28 (m, 2H), 6.43 (d, 1H), 2.10 (s, 3H). MS (EI) for $C_{32}H_{27}N_5O_2$: 514.3 (MH+).

N-[4-(2-{[4-(4-methylpiperazin-1-yl)phenyl]amino}pyrimidin-4-yl)phenyl]-acetamide: $^1$H-NMR (400 MHz, d6-DMSO): 10.24 (s, 1H), 9.35 (s, 1H), 8.44 (d, 1H), 8.11 (d, 2H), 7.74 (d, 2H), 7.65 (d, 2H), 7.26 (d, 1H), 6.93 (d, 2H), 3.07 (m, 4H), 2.45 (m, 4H), 2.22 (s, 3H), 2.09 (s, 3H). MS (EI) for $C_{23}H_{26}N_6O$: 403.4 (MH+).

N-{4-[2-({4-[4-(phenylcarbonyl)piperazin-1-yl]phenyl}amino)pyrimidin-4-yl]-phenyl}acetamide: $^1$H-NMR (400 MHz, d6-DMSO): 10.22 (s, 1H), 9.41 (s, 1H), 8.45 (d, 1H), 8.11 (d, 2H), 7.74 (d, 2H), 7.69 (d, 2H), 7.73-7.79 (m, 5H), 7.28 (d, 1H), 6.98 (d, 2H), 3.78 (m, 2H), 3.48 (m, 2H), 3.15 (m, 2H), 3.07 (m, 2H), 2.09 (s, 3H). MS (EI) for $C_{29}H_{28}N_6O_2$: 493.4 (MH+).

N-{4-[2-({4-[4-(2-cyclopentylacetyl)piperazin-1-yl]phenyl}amino)pyrimidin-4-yl]-phenyl}acetamide: $^1$H-NMR (400 MHz, d6-DMSO): 10.22 (s, 1H), 9.40 (s, 1H), 8.44 (d, 1H), 8.11 (d, 2H), 7.74 (d, 2H), 7.68 (d, 2H), 7.27 (s, 1H), 6.96 (d, 2H), 3.60 (m, 4H), 3.04 (m, 4H), 2.37 (d, 2H), 2.15 (m, 1H), 2.09 (s, 3H), 1.61-1.78 (m, 2H), 1.53-1.59 (m, 2H), 1.46-1.52 (m, 2H), 1.09-1.77 (m, 2H). MS (EI) for $C_{29}H_{34}N_6O_2$: 499.3 (MH+).

N-{4-[2-({4-[4-(cyclohexylcarbonyl)piperazin-1-yl]phenyl}amino)pyrimidin-4-yl]phenyl}acetamide: $^1$H-NMR (400 MHz, d6-DMSO): 10.22 (s, 1H), 9.40 (s, 1H), 8.44 (d, 1H), 8.11 (d, 2H), 7.74 (d, 2H), 7:68 (d, 2H), 7.27 (d, 1H), 6.96 (d, 2H), 3.61 (m, 4H), 3.04 (m, 4H), 2.09 (s, 3H), 1.62-1.70 (m, 6H), 1.26-1.38 (m, 5H). MS (EI) for $C_{29}H_{34}N_6O$: 499.2 (MH+).

N-(4-{2-[(4-{4-[(2-chlorophenyl)carbonyl]piperazin-1-yl}phenyl)amino]pyrimidin-4-yl}phenyl)acetamide: $^1$H-NMR (400 MHz, d6-DMSO): 10.21 (s, 1H), 9.41 (s, 1H), 8.44 (d, 1H), 8.10 (d, 2H), 7.74 (d, 2H), 7.69 (d. 2H), 7.56 (d, 1H), 7.41-7.49 (m, 3H), 7.27 (d, 1H), 6.96 (d, 2H), 3.81 (m, 2H), 3.28 (m, 2H), 3.16 (m, 2H), 3.05 (m, 2H), 2.09 (s, 3H). MS (EI) for $C_{29}H_{27}ClN_6O_2$: 527.8 (MH+).

N-(4-{2-[(4-{4-[(3-fluorophenyl)carbonyl]piperazin-1-yl}phenyl)amino]pyrimidin-4-yl}phenyl)acetamide: $^1$H-NMR (400 MHz, d6-DMSO): 10.21 (s, 1H), 9.41 (s, 1H), 8.44 (d, 1H), 8.11 (d, 2H), 7.74 (d, 2H), 7.69 (d, 2H), 7.53 (m, 1H), 7.27-7.35 (m, 4H), 6.97 (d, 2H), 3.77 (m, 2H), 3.46 (m, 2H), 3.16 (m, 2H), 3.07 (m, 2H), 2.09 (s, 3H). MS (EI) for $C_{29}H_{27}FN_6O_2$: 511.5 (MH+).

N-(4-{2-[(4-{4-[(3-fluoro-4-methylphenyl)carbonyl]piperazin-1-yl}phenyl)amino]-pyrimidin-4-yl}phenyl)acetamide: $^1$H-NMR (400 MHz, d6-DMSO): 10.21 (s, 1N), 9.41 (s, 1H), 8.44 (d, 1H), 8.11 (d, 2H), 7.74 (d, 2H), 7.69 (d, 2H), 7.38 (m, 1H), 7.28 (d, 1H), 7.25 (d, 1H), 7.18 (d, 1H), 6.56 (d, 2H), 3.75 (m, 2H), 3.49 (m, 2H), 3.14 (m, 2H), 3.07 (m, 2H), 2.28 (d, 3H), 2.09 (s, 3H). MS (EI) for $C_{30}H_{29}FN_6O_2$: 525.7 (MH+).

N-(4-{2-[(4-{4-[(3,4-dichlorophenyl)carbonyl]piperazin-1-yl}phenyl)amino]-pyrimidin-4-yl}phenyl)acetamide: $^1$H-NMR (400 MHz, d6-DMSO): 10.22 (s, 1H), 9.41 (s, 1H), 8.45 (s, 1H), 8.11 (d, 2H), 7.75 (m, 3H), 7.69 (d, 2H), 7.45 (dd, 1H), 7.28 (d, 1H), 6.97 (d, 2H), 3.77 (m, 2H), 3.47 (m, 2H), 3.16 (m, 2H), 3.07 (m, 2H), 2.09 (s, 3H). MS (EI) for $C_{29}H_{26}Cl_2N_6O_2$: 562.3 (MH+).

N-(4-{2-[(4-{4-[(3,5-dichlorophenyl)carbonyl]piperazin-1-yl}phenyl)amino]-pyrimidin-4-yl}phenyl)acetamide: $^1$H-NMR (400 MHz, d6-DMSO): 10.21 (s, 1H), 9.41 (s, 1H), 8.44 (d, 1H), 8.11 (d, 2H), 7.75 (d, 2H), 7.74 (d, 2H), 7.69 (d, 2H), 7.54 (d, 1H), 7.28 (d, 1H), 6.97 (d, 2H), 3.77 (m, 2H), 3.45 (m, 2H), 3.17 (m, 2H), 3.08 (m, 2H), 2.09 (s, 3H). MS (EI) for $C_{29}H_{26}Cl_2N_6O_2$: 562.6 (MH+).

N-[4-(2-{[4-(4-{[3-(methyloxy)phenyl]carbonyl}piperazin-1-yl)phenyl]amino}-pyrimidin-4-yl)phenyl]acetamide: $^1$H-NMR (400 MHz, d6-DMSO): 10.21 (s, 1H), 9.41 (s, 1H), 8.44 (d, 1H), 8.11 (d, 2H), 7.74 (d, 2H), 7.69 (d, 2H), 7.38 (t, 1H), 7.28 (d, 1H), 7.04 (dd, 1H), 6.95-6.99 (m, 4H), 3.79 (s, 3H), 3.77 (m, 2H), 3.47 (m, 2H), 3.15 (m, 2H), 3.06 (m, 2H), 2.09 (s, 3H). MS (EI) for $C_{30}H_{30}N_6O_3$: 523.5 (MH+).

N-(4-{2-[(4-{4-[(4-chlorophenyl)carbonyl]piperazin-1-yl}phenyl)amino]pyrimidin-4-yl}phenyl)acetamide: $^1$H-NMR (400 MHz, d6-DMSO): 10.22 (s, 1H), 9.41 (s, 1H), 8.44 (d, 1H), 8.11 (d, 2H), 7.74 (d, 2H), 7.69 (d, 2H), 7.53 (d, 2H), 7.49 (d, 2H), 7.27 (d, 1H), 6.97 (d, 2H), 3.77 (m, 2H), 3.47 (m, 2H), 3.15 (m, 2H), 3.06 (m, 2H), 2.09 (s, 3H). MS (EI) for $C_{29}H_{27}ClN_6O_2$: 527.8 (MH+).

N-(4-{2-[(4-{4-[(4-methylphenyl)carbonyl]piperazin-1-yl}phenyl)amino]pyrimidin-4-yl}phenyl)acetamide: $^1$H-NMR (400 MHz, d6-DMSO): 10.22 (s, 1H), 9.41 (s, 1H), 8.44) d, 1H), 8.11 (d, 2H), 7.74 (d, 2H), 7.69 (d, 2H), 7.34 (d, 2H), 7.27 (m, 1H), 6.97 (d, 2H), 3.75 (m, 2H), 3.51 (m, 2H), 3.10 (m, 4H), 2.36 (s, 2H), 2.09 (s, 3H). MS (EI) for $C_{30}H_{30}N_6O_2$: 507.3 (MH+).

N-(4-{2-[(4-{4-[(1-methyl-1H-pyrrol-2-yl)carbonyl]piperazin-1-yl}phenyl)amino]-pyrimidin-4-yl}phenyl)acetamide: $^1$H-NMR (400 MHz, d6-DMSO): 10.21 (s, 1H), 9.41 (s, 1H), 8.44 (d, 1H), 8.11 (d, 2H), 7.74 (d, 2H), 7.69 (d, 2H), 7.27 (d, 1H), 6.98 (d, 2H), 6.92 (t, 1H), 6.37 (dd, 1H), 6.05 (dd, 1H), 3.76 (m, 4H), 3.69 (s, 3H), 3.11 (m, 4H), 2.09 (s, 3H), MS (EI) for $C_{28}H_{29}N_7O_2$: 496.4 (MH+).

N-{4-[2-({4-[4-(furan-2-ylcarbonyl)piperazin-1-yl]phenyl}amino)pyrimidin-4-yl]-phenyl}acetamide: $^1$H-NMR (400 MHz, d6-DMSO): 10.22 (s, 1H), 9.41 (s, 1H), 8.44 (d, 1H), 8.11 (d, 2H), 7.87 (d, 1H), 7.74 (d, 2H), 7.69 (d, 2H), 7.28 (d, 1H), 7.04 (d, 1H), 6.98 (d, 2H), 6.66 (dd, 1H), 3.82 (m, 4H), 3.14 (m, 4H), 2.09 (s, 3H). MS (EI) for $C_{27}H_{26}N_6O_3$: 483.3 (MH+).

N-[4-(2-{[4-(4-{2-[(4-fluorophenyl)oxy]acetyl}piperazin-1-yl)phenyl]amino}-pyrimidin-4-yl)phenyl]acetamide: $^1$H-NMR (400 MHz, d6-DMSO): 10.22 (s, 1H), 9.41 (s, 1H), 8.44 (d, 1H), 8.11 (d, 2H), 7.74 (d, 2H), 7.27 (d, 1H), 7.12 (m, 2H), 6.94-6.99 (m, 4H), 4.87 (s, 2H), 3.61 (m, 4H), 3.13 (m, 2H), 3.06 (m, 2H), 2.09 (s, 3H). MS (EI) for $C_{30}H_{29}FN_6O_3$: 541.4 (MH+).

N-(4-{2-[(4-{4-[(3-methylphenyl)sulfonyl]piperazin-1-yl}phenyl)amino]pyrimidin-4-yl}phenyl)acetamide: MS (EI) for $C_{29}H_{30}N_6O_3S$: 543.5 (MH+).

N-{4-[2-({4-[4-(phenylsulfonyl)piperazin-1-yl]phenyl}amino)pyrimidin-4-yl]-phenyl}acetamide: $^1$H-NMR (400 MHz, d6-DMSO): 10.21 (s, 1H), 9.39 (s, 1H), 8.43 (d, 1H), 8.10 (d, 2H), 7.80 (m, 1H), 7.78 (d, 1H), 7.74-7.77 (m, 2H), 7.70-7.73 (m, 2H), 7.67-7.69 (m, 1H), 7.65 (d, 2H), 7.27 (d, 1H), 6.90 (d, 2H), 3.15 (m, 4H), 3.02 (m, 4H), 2.09 (s, 3H). MS (EI) for $C_{26}H_{26}N_6O_3S_2$: 529.4 (MH+).

N-{4-[2-({4-[4-(2-thienylsulfonyl)piperazin-1-yl]phenyl}amino)pyrimidin-4-yl]-phenyl}acetamide: $^1$H-NMR (400 MHz, d6-DMSO): 10.21 (s, 1H), 9.40 (s, 1H), 8.44 (d, 1H), 8.10 (m, 3H), 7.74 (d, 2H), 7.70 (dd, 1H), 7.66 (d, 2H), 7.33 (dd, 1H), 7.27 (d, 1H), 6.93 (d, 2H), 3.19 (m, 4H), 3.07 (m, 4H), 2.09 (s, 3H). MS (EI) for $C_{26}H_{26}N_6O_3S_2$: 535.6 (MH+).

N-(4-{(2-[(4-{4-[(4-fluorophenyl)sulfonyl]piperazin-1-yl}phenyl)amino]pyrimidin-4-yl}phenyl)acetamide: $^1$H-NMR (400 MHz, d6-DMSO): 10.21 (s, 1H), 9.40 (s, 1H), 8.44 (d, 1H), 8.10 (d, 2H), 7.87 (m, 2H), 7.74 (d, 2H), 7.66 (d, 2H), 7.53 (m, 2H), 7.27 (d, 1H), 6.91 (d, 2H), 3.15 (m, 4H), 3.04 (m, 4H), 2.09 (s, 3H). MS (EI) for $C_{28}H_{27}FN_6O_3S$: 547.4 (MH+).

N-[4-(2-{[4-(4-{[4-(methyloxy)phenyl]sulfonyl}piperazin-1-yl)phenyl]amino}-pyrimidin-4-yl)phenyl]acetamide: $^1$H-NMR (400 MHz, d6-DMSO): MS (EI) for $C_{29}H_{30}N_6O_4S$: 559.9 (MH+).

N-(4-{(2-[(4-{4-[(4-chlorophenyl)sulfonyl]piperazin-1-yl}phenyl)amino]pyrimidin-4-yl}phenyl)acetamide: $^1$H-NMR (400 MHz, d6-DMSO): 10.21 (s, 1H), 9.40 (s, 1H), 8.43 (d, 1H), 8.10 (d, 2H), 7.72-7.82 (d, 6H), 7.66 (d, 2H), 7.27 (d, 1H), 6.91 (d, 2H), 3.15 (m, 4H), 3.05 (m, 4H), 2.09 (s, 3H). MS (EI) for $C_{28}H_{27}ClN_6O_3S$: 563.9 (MH+).

N-(4-{2-[(4-{4-[(3-chlorophenyl)sulfonyl]piperazin-1-yl}phenyl)amino]pyrimidin-4-yl}phenyl)acetamide: $^1$H-NMR (400 MHz, d6-DMSO): 10.21 (s, 1H), 9.40 (s, 1H), 8.43 (d, 1H), 8.10 (d, 2H), 7.85 (m, 1H), 7.76-7.81 (m, 2H), 7.73 (d, 3H), 7.66 (d, 2H), 7.27 (d, 1H), 6.91 (d, 2H), 3.14 (m, 4H), 3.09 (m, 4H), 2.09 (s, 3H). MS (EI) for $C_{28}H_{27}ClN_6O_3S$: 5640 (MH+).

N-{4-[2-({4-[4-(biphenyl-4-ylsulfonyl)piperazin-1-yl]phenyl}amino)pyrimidin-4-yl]phenyl}acetamide: $^1$H-NMR (400 MHz, d6-DMSO): 10.21 (s, 1H), 9.39 (s, 1H), 8.43 (d, 1H), 8.08 (d, 2H), 7.96 (d, 2H), 7.86 (d, 2H), 7.77 (d, 2H), 7.73 (d, 2H), 7.66 (d, 2H), 7.51-7.55 (m, 2H), 7.46 (m, 1H), 7.26 (d, 1H), 6.91 (d, 2H), 3.18 (m, 4H), 3.08 (m, 4H), 2.09 (s, 3H). MS (EI) for $C_{34}H_{32}N_6O_3S$: 605.8 (MH+).

N-{4-[2-({4-[4-(naphthalen-1-ylsulfonyl)piperazin-1-yl]phenyl}amino)pyrimidin-4-yl]phenyl}acetamide: $^1$H-NMR (400 MHz, d6-DMSO): 10.21 (s, 1H), 9.38 (s, 1H), 8.72 (d, 1H), 8.42 (d, 1H), 8.33 (d, 1H), 8.20 (dd, 1H), 8.14 (d, 1H), 8.09 (d, 2H), 7.74-7.79 (m, 1H), 7.73 (d, 2H), 7.62-7.70 (m, 2H), 7.64 (d, 2H), 7.26 (d, 1H), 6.88 (d, 2H), 3.21 (m, 4H), 3.09 (m, 4H), 2.09 (s, 3H). MS (EI) for $C_{32}H_{30}N_6O_3S$: 579.6 (MH+).

N-(4-{2-[(3-{4-[(2-chlorophenyl)methyl]piperazin-1-yl}phenyl)amino]pyrimidin-4-yl}phenyl)acetamide: $^1$H-NMR (400 MHz, d6-DMSO): 10.21 (s, 1H), 9.46 (s, 1H), 8.49 (d, 1H), 8.14 (d, 2H), 7.74 (d, 2H), 7.64 (s br, 1H), 7.36 (dd, 1H), 7.33 (d, 1H), 7.20-7.27 (m, 2H), 7.13 (t, 1H), 6.92-7.00 (m, 2H), 6.55 (d, 1H), 3.54 (s, 2H), 3.16 (m, 4H), 2.57 (m, 4H), 2.09 (s, 3H). MS (EI) for $C_{29}H_{29}ClN_6O$: 513.8 (MH+).

N-[4-(2-{[3-(4-{[3-(methyloxy)phenyl]methyl}piperazin-1-yl)phenyl]amino}-pyrimidin-4-yl)phenyl]acetamide: $^1$H-NMR (400 MHz, d6-DMSO): 10.21 (s, 1H), 9.46 (s, 1H), 8.48 (d, 1H), 8.13 (d, 2H), 7.74 (d, 2H), 7.62 (s, 1H), 7.33 (d, 1H), 7.22-7.27 (m, 2H), 7.13 (t, 1H), 6.19 (m, 2H), 6.83 (d, 1H), 6.55 (d, 1H), 3.74 (s, 3H), 3.52 (s, 2H), 3.16 (m, 4H), 2.55 (m, 4H), 2.09 (s, 3H). MS (EI) for $C_{30}H_3N_8O_2$: 509.8 (MH+).

N-{4-[2-({(3-[4-(3-methylbutyl)piperazin-1-yl]phenyl}amino)pyrimidin-4-yl]-phenyl}acetamide: $^1$H-NMR (400 MHz, d6-DMSO): 10.22 (s, 1H), 9.47 (s, 1H), 8.49 (d, 1H), 8.14 (d, 2H), 7.75 (d, 2H), 7.68 (s, 1H), 7.33 (d, 1H), 7.19 (d, 1H), 7.13 (t, 1H), 6.55 (d, 1H), 3.15 (m, 4H), 2.54 (m, 4H), 2.34 (t, 2H), 2.09 (s, 3H), 1.57-1.62 (m, 1H), 1.34-1.40 (m, 2H), 0.90 (d, 6H). MS (EI) for $C_{27}H_{34}N_6O$: 459.7 (MH+).

N-{4-[2-({3-[4-(2,3-dihydro-1,4-benzodioxin-6-ylmethyl)piperazin-1-yl]phenyl}amino)pyrimidin-4-yl]phenyl}acetamide: $^1$H-NMR (400 MHz, d6-DMSO): MS (EI) for $C_{31}H_{32}N_6O_3$: 537.5 (MH+).

N-{4-[2-({3-[4-(cyclopropylmethyl)piperazin-1-yl]phenyl}amino)pyrimidin-4-yl]phenyl}acetamide: $^1$H-NMR (400 MHz, d6-DMSO): 10.22 (s, 1H), 9.47 (s, 1H), 8.49 (d, 1H), 8.14 (d, 2H), 7.75 (d, 2H), 7.69 (s, 1H), 7.33 (d, 1H), 7.19 (d, 1H), 7.13 (t, 1H), 6.56 (d, 1H), 3.17 (m, 4H), 2.60 (m, 4H), 2.24 (d, 2H), 2.09 (s, 3H), 0.88 (m, 1H), 0.47-0.51 (m, 2H), 0.11-0.13 (m, 2H). MS (EI) for $C_{28}H_{30}N_6O$: 443.8 (MH+).

N-(4-{2-[(3-{4-[3-(methylthio)propyl]piperazin-1-yl}phenyl)amino]pyrimidin-4-yl}phenyl)acetamide: $^1$H-NMR (400 MHz, d6-DMSO): 10.22 (s, 1H), 9.47 (s, 1H), 8.49 (d, 1H), 8.14 (d, 2H), 7.75 (d, 2H), 7.68 (s, 1H), 7.33 (d, 1H), 7.20 (d, 1H), 7.14 (t, 1H), 6.56 (d, 1H), 3.15 (m, 4H), 2.56 (m, 4H), 2.41 (t, 4H), 2.09 (s, 3H), 2.06 (s, 3H), 1.71-1.78 (m, 2H). MS (EI) for $C_{26}H_{32}N_6OS$: 477.5 (MH+).

N-(4-{2-[(3-{4-[(4-{[3-(dimethylamino)propyl]oxy}phenyl)methyl]piperazin-1-yl}-phenyl)amino]pyrimidin-4-yl}phenyl)acetamide: $^1$H-NMR (400 MHz, d6-DMSO): 10.22 (s, 1H), 9.46 (s, 1H), 8.48 (d, 1H), 8.13 (d, 2H), 7.74 (d, 2H), 7.62 (s, 1H), 7.33 (d, 1H), 7.23 (m 3H), 7.13 (t, 1H), 6.88 (d, 2H), 6.55 (d, 1H), 3.97 (t, 2H), 3.46 (s, 2H), 3.14 (m, 4H), 2.55 (m, 4H), 2.34 (t, 2H), 2.14 (s, 6H), 2.10 (s, 3H), 1.80-1.85 (m, 2H). MS (EI) for $C_{34}H_{41}N_7O_2$: 580.5 (MH+).

N-{4-[2-({3-[4-({3-[(trifluoromethyl)oxy]phenyl}methyl)piperazin-1-yl]phenyl}-amino)pyrimidin-4-yl]phenyl}acetamide: $^1$H-NMR (400 MHz, d6-DMSO): 10.21 (s, 1H), 9.47 (s, 1H), 8.49 (d, 1H), 8.13 (d, 2H), 7.74 (d, 2H), 7.63 (s, 1H), 7.47 (t, 1H), 7.41 (d, 1H), 7.33 (d, 2H), 7.22-7.28 (m, 2H), 7.13 (t, 1H), 6.56 (dd, 1H), 3.62 (s, 2H), 3.16 (m, 4H), 2.56 (m, 4H), 2.09 (s, 3H). MS (EI) for $C_{30}H_{29}F_3N_6O_2$: 563.7 (MH+).

4-[4-({4-[4-(acetylamino)phenyl]pyrimidin-2-yl}amino)phenyl]-N-phenylpiperazine-1-carboxamide: $^1$H-NMR (400 MHz, d6-DMSO): 10.21 (s, 1H), 9.40 (s, 1H), 8.63 (s, 1H), 8.44 (d, 1H), 8.11 (d, 2H), 7.75 (d, 2H), 7.70 (d, 2H), 7.48 (d, 2H), 7.21-7.28 (m, 3H), 7.00 (d, 2H), 6.94 (t, 1H), 3.61 (m, 4H), 3.11 (m, 4H), 2.09 (s, 3H). MS (EI) for $C_{29}H_{29}N_7O_2$: 508.6 (MH+).

N-[4-(2-{[3-(4-propanoylpiperazin-1-yl)phenyl]amino}pyrimidin-4-yl)phenyl]-acetamide: $^1$H-NMR (400 MHz, d6-DMSO): 10.24 (s, 1H), 9.51 (s, 1H), 8.50 (d, 1H), 8.14 (d, 2H), 7.76 (d, 2H), 7.68 (s, 1H), 7.34 (d, 1H), 7.26 (d, 1H), 7.16 (t, 1H), 6.59 (dd, 1H), 3.62 (m, 4H), 3.13 (m, 4H), 2.35-2.39 (m, 2H), 2.09 (s, 3H), 1.02 (t, 3H). MS (EI) for $C_{25}H_{28}N_8O_2$: 445.4 (MH+).

N-{4-[2-({3-[4-(phenylcarbonyl)piperazin-1-yl]phenyl}amino)pyrimidin-4-yl]-phenyl}acetamide: $^1$H-NMR (400 MHz, d6-DMSO): 10.21 (s, 1H), 9.48 (s, 1H), 8.47 (d, 1H), 8.11 (d, 2H), 7.72 (d, 2H), 7.63 (s, 1H), 7.41-7.47 (m, 5H), 7.31 (d, 1H), 7.26 (d, 1H), 7.14 (t, 1H), 6.56 (dd, 1H), 3.78 (m, 2H), 3.48 (m, 2H), 3.27 (m, 2H), 3.12 (m, 2H), 2.08 (s, 3H). MS (EI) for $C_{29}H_{28}N_6O_2$: 493.7 (MH+).

N-{4-[2-({3-[4-(2-phenylacetyl)piperazin-1-yl]phenyl}amino)pyrimidin-4-yl]-phenyl}acetamide: $^1$H-NMR (400 MHz, d6-DMSO): 10.25 (s, 1H), 9.50 (s, 1H), 8.49 (d, 1H), 8.13 (d, 2H), 7.76 (d, 2H), 7.63 (s, 1H), 7.33 (d, 1H), 7.30 (d, 2H), 7.26 (m, 3H), 7.22 (m, 1H), 7.15 (t, 1H), 6.56 (dd, 1H), 3.79 (s, 2H), 3.66 (m, 4H), 3.11 (m, 2H), 3.05 (m, 2H), 2.09 (s, 3H). MS (EI) for $C_{30}H_{30}N_6O_2$: 507.7 (MH+).

N-{4-[2-({3-[4-(cyclopentylcarbonyl)piperazin-1-yl]phenyl}amino)pyrimidin-4-yl]phenyl}acetamide: $^1$H-NMR (400 MHz, d6-DMSO): 10.24 (s, 1H), 9.52 (s, 1H), 8.49 (d, 1H), 8.14 (d, 2H), 7.76 (d, 2H), 7.71 (s, 1H), 7.34 (d, 1H), 7.24 (d, 1H), 7.16 (t, 1H), 6.59 (dd, 1H), 3.66 (m, 4H), 3.13 (m, 4H), 3.00-3.07 (m, 1H), 2.09 (s, 3H), 1.80 (m, 2H), 1.51-1.71 (m, 6H). MS (EI) for $C_{28}H_2N_6O_2$: 485.7 (MH+).

N-{4-[2-({3-[4-(2-pyridin-3-ylacetyl)piperazin-1-yl]phenyl}amino)pyrimidin-4-yl]-phenyl}acetamide: $^1$H-NMR (400 MHz, d6-DMSO): 10.24 (s, 1H), 9.51 (s, 1H), 8.50 (d, 1H), 8.43-8.46 (m, 2H), 8.14 (d, 2H), 7.76 (d, 2H), 7.63-7.67 (m, 2H), 7.32-7.35 (m, 2H), 7.26 (d, 1H), 7.16 (t, 1H), 6.59 (dd, 1H), 3.84 (s, 2H), 3.73 (m, 2H), 3.66 (m, 2H), 3.15 (m, 4H), 2.08 (s, 3H). MS (EI) for $C_{29}H_{29}N_7O_2$: 508.4 (MH+).

N-{4-[2-({3-[4-(2-cyclopentylacetyl)piperazin-1-yl]phenyl}amino)pyrimidin-4-yl]phenyl}acetamide: $^1$H-NMR (400 MHz, d6-DMSO): 10.24 (s, 1H), 9.51 (s, 1H), 8.50 (d, 1H), 8.14 (d, 2H), 7.76 (d, 2H), 7.70 (s, 1H), 7.34 (d, 1H), 7.25 (d, 1H), 7.16 (t, 1H), 6.59 (dd, 1H), 3.61 (m, 4H), 3.12 (m, 4H), 2.39 (d, 2H), 2.11-2.19 (m, 1H), 2.09 (s, 3H), 1.72-7.78 (m, 2H), 1.52-1.59 (m, 2H), 1.47-1.52 (m, 2H), 1.09-1.18 (m, 2H). MS (EI) for $C_{29}H_{34}N_8O_2$: 499.4 (MH+).

N-(4-{2-[(3-{4-[(2-chlorophenyl)carbonyl]piperazin-1-yl}phenyl)amino]pyrimidin-4-yl}phenyl)acetamide: $^1$H-NMR (400 MHz, d6-DMSO): 10.24 (s, 1H), 9.50 (s, 1H), 8.49 (d, 1H), 8.13 (d, 2H), 7.74 (d, 2H), 7.63 (s, 1H), 7.56 (d, 1H), 7.42-7.50 (m, 3H), 7.33 (d, 1H), 7.29 (d, 1H), 7.16 (t, 1H), 6.59 (dd, 1H), 3.79 (m, 2H), 3.50 (m, 2H), 3.24 (m, 2H), 3.15 (m, 2H), 2.09 (s, 3H). MS (EI) for $C_2H_{27}ClN_6O_2$: 527.9 (MH+).

N-(4-{2-[(3-{4-[(4-chlorophenyl)carbonyl]piperazin-1-yl}phenyl)amino]pyrimidin-4-yl}phenyl)acetamide: $^1$H-NMR (400 MHz, d6-DMSO): 10.23 (s, 1H), 9.51 (s, 1H), 8.49 (d, 1H), 8.14 (d, 2H), 7.74 (d, 2H), 7.66 (s, 1H), 7.53 (d, 2H), 7.49 (d, 2H), 7.34 (d, 1H), 7.27 (d, 1H), 7.17 (t, 1H), 6.59 (dd, 1H), 3.79 (m, 2H), 3.50 (m, 2H), 3.24 (m, 2H), 3.15 (m, 2H), 2.09 (s, 3H). MS (EI) for $C_{29}H_{27}Cl_2N_6O_2$: 528.1 (MH+).

N-(4-{2-[(3-{4-[(3,4-dichlorophenyl)carbonyl]piperazin-1-yl}phenyl)amino]-pyrimidin-4-yl}phenyl)acetamide: $^1$H-NMR (400 MHz, d6-DMSO): 10.23 (s, 1H), 9.51 (s, 1H), 8.49 (d, 1H), 8.13 (d, 2H), 7.74 (m, 4H), 7.60 (s, 1H), 7.46 (dd, 1H), 7.34 (d, 1H), 7.27 (d, 1H), 7.17 (t, 1H), 6.59 (dd, 1H), 3.79 (m, 2H), 3.50 (m, 2H), 3.24 (m, 2H), 3.15 (m, 2H), 2.09 (s, 3H). MS (EI) for $C_{29}H_{26}Cl_2N_6O_2$: 562.7 (MH+).

N-(4-{2-[(3-{4-[(1-methyl-1H-pyrrol-2-yl)carbonyl]piperazin-1-yl}phenyl)amino]-pyrimidin-4-yl}phenyl)acetamide: $^1$H-NMR (400 MHz, d6-DMSO): 10.23 (s, 1H), 9.51 (s, 1H), 8.50 (d, 1H), 8.14 (d, 2H), 7.75 (d, 2H), 7.67 (s, 1H), 7.34 (d, 1H), 7.28 (d, 1H), 7.17 (t, 1H), 6.92 (m, 1H), 6.59 (dd, 1H), 6.37 (dd, 1H), 6.05 (m, 1H), 3.80 (m, 4H), 3.69 (s, 3H), 3.19 (m, 4H), 2.09 (s, 3H). MS (EI) for $C_{28}H_{29}N_7O_2$: 450.7 (MH+).

$N^2,N^2$-dimethyl-N-[4-(2-{[3-(methyloxy)-4-morpholin-4-ylphenyl]amino}pyrimidin-4-yl)phenyl]glycinamide: $^1$H-NMR (400 MHz, d6-DMSO): 10.0 (s, 1H), 9.48 (s, 1H), 8.48 (d, 1H), 8.15 (d, 2H), 7.84 (d, 2H), 7.65 (s, 1H), 7.29-7.33 (m, 2H), 6.86 (d, 1H), 3.81 (s, 3H), 3.72 (m, 4H), 3.11 (s, 2H), 2.92 (m, 4H), 2.29 (s, 6H). MS (EI) for $C_{25}H_{30}N_6O_3$: 463.8 (MH+).

3-(methyloxy)-N-[4-(2-{[3-(methyloxy)-4-morpholin-4-ylphenyl]amino}pyrimidin-4-yl)phenyl]propanamide:
$^1$H-NMR (400 MHz, d6-DMSO): 10.21 (s, 1H), 9.46 (s, 1H), 8.45 (d, 1H), 8.13 (d, 2H), 7.74 (d, 2H), 7.64 (s, 1H), 7.26-7.30 (m, 2H), 6.84 (d, 1H), 3.79 (s, 3H), 3.70 (m, 4H), 3.61 (t, 2H), 3.23 (s, 3H), 2.89 (m, 4H), 2.57 (t, 2H). MS (EI) for $C_{25}H_{29}N_5O_4$: 464.8 (MH+).

N-(4-{2-[(4-{4-[(2-chlorophenyl)sulfonyl]piperazin-1-yl}phenyl)amino]pyrimidin-4-yl}phenyl)acetamide:
$^1$H-NMR (400 MHz, d6-DMSO): 10.19 (s, 1H), 9.38 (s, 1H), 8.42 (d, 1H), 8.08 (d, 2H), 8.00 (dd, 1H), 7.68-7.74 (m, 4H), 7.65 (d, 2H), 7.58 (m, 1H), 7.25 (d, 1H), 6.91 (d, 2H), 3.15 (m, 4H), 3.02 (m, 4H), 2.07 (s, 3H). MS (EI) for $C_{28}H_{27}ClN_6O_3S$: 563.9 (MH+).

N-{4-[2-({3-[4-(cyclopropylcarbonyl)piperazin-1-yl]phenyl}amino)pyrimidin-4-yl]phenyl}acetamide: $^1$H-NMR (400 MHz, d6-DMSO): 10.24 (s, 1H), 9.52 (s, 1H), 8.50 (d, 1H), 8.14 (d, 2H), 7.76 (d, 2H), 7.71 (s, 1H), 7.34 (d, 1H), 7.25 (d, 1H), 7.17 (t, 1H), 6.60 (dd, 1H), 3.56 (m, 2H), 3.65 (m, 2H), 3.20 (m, 2H), 3.13 (m, 2H), 2.09 (s, 3H), 2.04 (m, 1H), 0.77-0.49 (m, 4H). MS (EI) for $C_{26}H_{28}N_6O_2$: 457.5 (MH+).

N-{4-[2-({3-[4-(2-cyclopropylacetyl)piperazin-1-yl]phenyl}amino)pyrimidin-4-yl]phenyl}acetamide: $^1$H-NMR (400 MHz, d6-DMSO): 10.24 (s, 1H), 9.51 (s, 1H), 8.50 (d, 1H), 8.14 (d, 2H), 7.76 (d, 2H), 7.70 (s, 1H), 7.34 (d, 1H), 7.25 (d, 1H), 7.16 (t, 1H), 6.58 (dd, 1H), 3.62 (m, 4H), 3.13 (m, 4H), 2.32 (d, 2H), 2.09 (s, 3H), 0.99 (m, 1H), 0.45 (m, 2H), 0.14 (m, 2H). MS (EI) for $C_{27}H_{30}N_6O_2$: 477.5 (MH+).

N-[4-(2-{[3-(4-{[3-(methyloxy)phenyl]carbonyl}piperazin-1-yl)phenyl]amino}-pyrimidin-4-yl)phenyl]acetamide: $^1$H-NMR (400 MHz, d6-DMSO): 10.22 (s, 1H), 9.48 (s, 1H), 8.47 (d, 1H), 9.11 (d, 2H), 7.72 (d, 2H), 7.62 (s, 1H), 7.35 (t, 1H), 7.31 (d, 1H), 7.26 (d, 1H), 7.14 (t, 1H), 7.01 (m, 1H), 6.97 (m, 2H), 6.56 (dd, 1H), 3.76 (s, 3H), 3.73 (m, 2H), 3.47 (m, 2H), 3.14 (m, 4H), 2.07 (s, 3H). MS (EI) for $C_{30}H_{30}N_6O_3$: 523.7 (MH+).

N-{4-[2-({4-[4-(2,2-dimethylpropanoyl)piperazin-1-yl]phenyl}amino)pyrimidin-4-yl]phenyl}acetamide: $^1$H-NMR (400 MHz, d6-DMSO): 10.21 (s, 1H), 9.40 (s, 1H), 8.44 (d, 1H), 8.11 (d, 2H), 7.74 (d, 2H), 7.69 (d, 2H), 7.27 (d, 1H), 6.96 (d, 2H), 3.70 (m, 4H), 3.05 (m, 4H), 2.09 (s, 3H), 1.23 (s, 9H), MS (EI) for $C_{27}H_{32}N_6O_2$: 473.4 (MH+).

2,6-dichloro-N-(3-(4-(2,3-dihydrobenzo[b][1,4]dioxin-6-yl)pyrimidin-2-ylamino)propyl)benzamide: (400 MHz, CDCl3): 8.16 (br, 1H), 8.0-8.8 (m, 2H), 7.26 (m, 4H), 6.82 (d, 1H), 6.75 (br, 1H), 5.4 (t, 1H), 4.29 (m, 4H), 3.68 (m, 2H), 3.56 (m, 2H), 1.92 (m, 2H). MS (EI): 459 (MH+).

1-(4-(4-(4-acetamidophenyl)pyrimidin-2-ylamino)phenyl)piperidine-3-carboxylic acid: MS (EI) for $C_{24}H_{25}N_5O_3$: 432 (MH+).

tert-butyl methyl(2-(4-(2-(4-morpholinophenylamino)pyrimidin-4-ylphenylamino)-2-oxoethyl)carbamate: MS (EI) for $C_{28}H_{34}N_6O_4$: 519 (MH+).

tert-butyl 4-(2-(4-(4-ethylpiperazin-1-yl)phenylamino)pyrimidin-4-yl)phenyl-carbamate: MS (EI) for $C_{27}H_{34}N_6O_2$: 475 (MH+).

2-(dimethylamino-N-(4-(2-(4-(4-ethylpiperazin-1-yl)phenylamino)pyrimidin-4-yl)phenyl)acetamide: NMR (400 MHz, d6-DMSO): 10.0 (s, 1H), 9.37 (s, 1H), 8.41 (d, 1H), 8.11 (d, 1H), 7.85 (d, 2H), 7.63 (f, 2H), 7.46 (d, 1H), 7.25 (d, 1H), 6.83-6.92 (m, 2H), 3.11 (m, 4H), 2.51 (m, 4H), 2.37 (q, 2H), 2.36 (s, 6H), 2.26 (s, 2H), 1.05 (t, 3H). MS (EI): 460 (MH+).

4-(4-aminophenyl)-N-(4-(4-ethylpiperazin-1-yl)phenyl)pyrimidin-2-amine: MS (EI) for $C_{22}H_{26}N_6$: 375 (MH+).

(S)-tert-butyl 1-(4-(2-(4-morpholinophenylamino)pyrimidin-4-yl)phenylamino)-1-oxo-3-phenylpropan-2-ylcarbamate: MS (EI) for $C_{34}H_{38}N_6O_4$: 595 (MH+).

(R)-tert-butyl 1-(4-(2-(4-morpholinophenylamino)pyrimidin-4-yl)phenylamino)-1-oxo-3-phenylpropan-2-ylcarbamate: MS (EI) for $C_{34}H_{38}N_6O_4$: 595 (MH+).

(R)-2-amino-N-(4-(2-(4-morpholinophenylamino)pyrimidin-4-yl)phenyl)-3-phenylpropanamide: NMR (400 MHz, d6-DMSO): 11.40 (s, 1H), 10.20 (s, 1H), 8.43-8.62 (m, 3H), 8.17 (d, 2H), 7.91 (d, 2H), 7.89 (d, 2H), 7.84 (m, 2H), 7.20-7.38 (m, 4H), 4.10 (m, 4H), 3.63 (m, 2H), 3.40-3.57 (m, 6H), 3.20 (m, 1H), MS (EI): 495 (MH+).

(S)-2-amino-N-(4-(2-(4-morpholinophenylamino)pyrimidin-4-yl)phenyl)-3-phenylpropanamide: NMR (400 MHz, d6-DMSO): 11.40 (s, 1H), 10.20 (s, 1H), 8.43-8.62 (m, 3H), 8.17 (d, 2H), 7.91 (d, 2H), 7.89 (d, 2H), 7.84 (m, 2H), 7.20-7.38 (m, 4H), 4.10 (m, 4H), 3.63 (m, 2H), 3.40-3.57 (m, 6H), 3.20 (m, 1H), MS (EI): 495 (MH+).

(S)-2-amino-N-(4-(2-(4-(4-ethylpiperazin-1-yl)phenylamino)pyrimidin-4-yl)phenyl)-3-methylbutanamide: MS (EI) for $C_{27}H_{35}N_7O$: 474 (MH+).

(R)-2-amino-N-(4-(2-(4-(4-ethylpiperazin-1-yl)phenylamino)pyrimidin-4-yl)phenyl)-3-methylbutanamide: MS (EI) for $C_{27}H_{35}N_7O$: 474 (MH+).

1-ethyl-3-(4-(2-(3-methoxy-4-morpholinophenylamino)pyrimidin-4-yl)phenyl)urea: NMR (400 MHz, d6-DMSO): 9.41 (s, 1H), 8.75 (s, 1H), 8.42 (d, 1H), 8.10 (d, 2H), 7.64 (s, 1H), 7.54 (d, 2H), 7.26 (m, 2H), 6.85 (d, 1H), 6.21 (br, 1H), 3.79 (s, 3H), 3.70 (m, 4H), 3.11 (q, 2H), 2.89 (m, 4H), 1.06 (t, 3H). MS (EI): 449 (MH+).

(R)—N-(4-(2-(4-morpholinophenylamino)pyrimidin-4-yl)phenyl)piperidine-2-carboxamide: NMR (400 MHz, d6-DMSO): 11.36 (s, 1H), 10.0 (s, 1H), 9.4 (d, 1H), 8.84 (m, 1H), 8.57 (d, 1H), 8.2 (d, 2H), 7.82 (m, 4H), 7.6 (br, 1H), 7.4 (d, 1H), 4.0 (m, 4H), 3.82 (m, 1H), 3.42 (m, 4H), 3.23 (m, 1H), 2.94 (m, 1H), 2.3 (m, 1H), 1.82 (m, 1H), 1.54-1.92 (m, 4H). MS (EI): 458 (MH+).

N-[4-(2-{[4-(4-ethylpiperazin-1-yl)phenyl]amino}-5-methylpyrimidin-4-yl)phenyl]-acetamide: $^1$H NMR (400 MHz, d6-DMSO): 10.1 (s, 1H), 9.23 (s, 1H), 8.31 (s, 1H), 7.6-7.7 (m, 6H), 6.87 (d, 2H), 3.04 (m, 4H), 2.48 (m, 4H), 3.05 (m, 4H), 2.36 (q, 2H), 2.2 (s, 3H), 2.08 (s, 3H), 1.03 (s, 3H). MS (EI): 431 (MH+).

4-{4-[(4-{4-[(N,N-dimethylglycyl)amino]phenyl}pyrimidin-2-yl)amino]phenyl}-N-ethylpiperazine-1-carboxamide: $^1$H NMR (400 MHz, d6-DMSO): 10.0 (s, 1H), 9.4 (s, 1H), 8.43 (d, 1H), 8.12 (d, 2H), 7.82 (d, 2H), 7.68 (d, 2H), 7.27 (d, 1H), 6.97 (d, 2H), 3.42 (m, 4H), 3.12 (s, 2H), 3.06 (q, 2H), 3.02 (m, 4H), 2.3 (s, 6H), 1.11 (t, 3H). MS (EI): 503 (MH+).

N-{4-[2-({4-[4-(2,2-dimethylpropanoyl)piperazin-1-yl]phenyl}amino)pyrimidin-4-yl]phenyl}-$N^2$,$N^2$-dimethylglycinamide: $^1$H NMR (400 MHz, d6-DMSO): 10.0 (s, 1H), 9.4 (s, 1H), 8.44 (d, 1H), 8.11 (d, 2H), 7.83 (d, 2H), 7.69 (d, 2H), 7.29 (d, 1H), 6.96 (d, 2H), 3.7 (m, 4H), 3.16 (s, 2H), 3.05 (m, 4H), 2.31 (s, 6H), 1.2 (s, 9H). MS (EI): 516 (MH+).

N-{4-[2-({4-[4-(cyclobutylcarbonyl)piperazin-1-yl]phenyl}amino)pyrimidin-4-yl]phenyl}-$N^2$,$N^2$-dimethylglycinamide: $^1$H NMR (400 MHz, d6-DMSO): 10.0 (s, 1H), 9.4 (s, 1H), 8.45 (d, 1H), 8.12 (d, 2H), 7.84 (d, 2H), 7.67 (d, 2H), 7.30 (d, 1H), 6.95 (d, 2H), 3.56-3.62 (m, 4H), 3.1 (s, 2H), 2.99-3.05 (m, 4H), 2.31 (s, 6H), 1.8-2.25 (m, 7H). MS (EI): 514 (MH+).

$N^2$,$N^2$-dimethyl-N-{4-[2-({4-[4-(2-methylpropanoyl)piperazin-1-yl]phenyl}amino)-pyrimidin-4-yl]

phenyl}glycinamide: $^1$H NMR (400 MHz, d6-DMSO): 10.0 (s, 1H), 9.4 (s, 1H), 8.45 (d, 1H), 8.13 (d, 2H), 7.84 (d, 2H), 7.68 (d, 2H), 7.29 (d, 1H), 6.95 (d, 2H), 3.58-3.67 (m, 4H), 3.11 (s, 2H), 2.99-3.10 (m, 4H), 2.92 (m, 1H), 2.29 (s, 6H), 1.02 (d, 6H). MS (EI): 502 (MH+).

N-{4-[2-({4-[4-(cyclopropylcarbonyl)piperazin-1-yl]phenyl}amino)pyrimidin-4-yl]phenyl}-$N^2$,$N^2$-dimethylglycinamide: $^1$H NMR (400 MHz, d6-DMSO): 10.0 (s, 1H), 9.4 (s, 1H), 8.43 (d, 1H), 8.14 (d, 2H), 7.68 (d, 2H), 7.26 (d, 1H), 6.97 (d, 2H), 3.8 (m, 2H), 3.6 (m, 2H), 3.18 (m, 4H), 3.07 (m, 2H), 2.28 (s, 6H), 2.02 (m, 1H), 0.78 (m, 4H). MS (EI): 501 (MH+).

N-[4-(2-{[4-(4-D-alanylpiperazin-1-yl)phenyl]amino}pyrimidin-4-yl)phenyl]-$N^2$,$N^2$-dimethylglycinamide: $^1$H NMR (400 MHz, d6-DMSO): 10.0 (s, 1H), 9.4 (s, 1H), 8.55 (d, 1H), 8.23 (d, 2H), 7.84 (d, 2H), 7.71 (d, 2H), 7.28 (d, 1H), 6.97 (d, 2H), 3.8 (m, 2H), 3.84 (q, 1H), 3.62 (m, 4H), 3.12 (s, 2H), 3.05 (m, 4H), 2.31 (s, 6H), 1.12 (d, 3H). MS (EI): 504 (MH+).

N-[4-(2-{[4-(4-L-alanylpiperazin-1-yl)phenyl]amino}pyrimidin-4-yl)phenyl]-$N^2$,$N^2$-dimethylglycinamide: $^1$H NMR (400 MHz, d6-DMSO): 10.0 (s, 1H), 9.4 (s, 1H), 8.45 (d, 1H), 8.12 (d, 2H), 7.84 (d, 2H), 7.69 (d, 2H), 7.28 (d, 1H), 6.97 (d, 2H), 3.8 (m, 2H), 3.84 (q, 1H), 3.62 (m, 4H), 3.12 (s, 2H), 3.05 (m, 4H), 2.31 (s, 6H), 1.12 (d, 3H). MS (EI): 504 (MH+).

2,6-dichloro-N-(3-{[4-(4-fluorophenyl)pyrimidin-2-yl]amino}propyl)benzamide: $^1$H NMR (400 MHz, DMSO): 8.705 (t, 1H), 8.354 (d, 1H), 7.136 (br s, 2H), 7.515 (d, 2H), 7.5 (d, 2H), 7.425 (m, 1H), 7.34 (t, 2H), 7.26 (t, 1H), 7.14 (d, 1H), 3.456 (br s, 2H), 3.355 (m, 2H), 1.827 (t, 2H). MS (EI): 420.1 (MH$^+$).

N-(4-{2-[({1-[(2,6-dichlorophenyl)carbonyl]azetidin-3-yl}methyl)amino]pyrimidin-4-yl}phenyl)acetamide: $^1$H NMR (400 MHz, DMSO): 11.031 (s, 1H), 8.344 (d, 1H), 8.137 (d, 2H), 7.839 (d, 2H), 7.621 (d, 2H), 7.531 (m, 1H), 7.45 (t, 1H), 7.146 (d, 1H), 4.157 (m, 1H), 3.867 (t, 2H), 3.626-3.556 (m, 3H), 2.842 (br s, 1H), 1.725 (s, 3H). MS (EI) for $C_{23}H_{21}Cl_2N_5O_2$: 470.2 (MH$^+$).

N-(4-{2-[(3-morpholin-4-ylphenyl)amino]pyrimidin-4-yl}phenyl)acetamide: $^1$H NMR (400 MHz, DMSO): 10.22 (s, 1H), 9.511 (s, 1H), 8.504 (d, 1H), 8.154 (d, 2H), 7.76 (d, 3H), 7.343 (d, 1H), 7.215-7.153 (m, 2H), 6.584 (d, 1H), 3.775 (t, 4H), 3.14 (t, 4H), 2.094 (s, 3H). MS (EI) for $C_{22}H_{23}N_5O_2$: 390.1 (MH$^+$).

N-[3-({4-[4-(acetylamino)phenyl]pyrimidin-2-yl}amino)cyclohexyl]-2,6-dichloro-benzamide: $^1$H NMR (400 MHz, MeOD): 8.25 (d, 1H), 8.08 (d, 2H), 7.7 (d, 2H), 7.45-7.35 (m, 3H), 7.05 (d, 1H), 4.05 (m, 2H), 2.5 (m, 1H), 2.1 (m, 3H), 2.05 (s, 3H), 1.5 (m, 1H), 1.3 (m, 3H). MS (EI) for $C_{25}H_{25}Cl_2N_5O_2$: 498.3 (MH$^+$).

N-{4-[2-({[4-(4-methylpiperazin-1-yl)phenyl]methyl}amino)pyrimidin-4-yl]phenyl}-acetamide: $^1$H NMR (400 MHz, DMSO): 10.192 (s, 1H), 8.294 (d, 1H), 8.062 (d, 2H), 7.713 (d, 2H), 7.653 (t, 1H), 7.285 (br d, 2H), 7.09 (d, 1H), 6.953 (d, 2H), 4.485 (d, 2H), 3.3 (br s, 8H), 2.827 (s, 3H), 2.079 (s, 3H). MS (EI) for $C_{24}H_{28}N_6O$: 417.4 (MH$^+$).

N-[4-({4-[4-(acetylamino)phenyl]pyrimidin-2-yl}amino)phenyl]-2,6-dichloro-benzamide $^1$H NMR (400 MHz, DMSO): 10.66 (s, 1H), 10.324 (s, 1H), 9.638 (s, 1H), 8.501 (d, 1H), 8.144 (d, 2H), 7.782 (m, 4H), 7.65 (d, 2H), 7.597 (d, 2H), 7.498 (m, 1H), 7.349 (d, 1H), 2.11 (s, 3H). MS (EI) for $C_{25}H_{19}Cl_2N_5O_2$: 492 (MH$^+$).

N-{4-[2-(piperidin-4-ylamino)pyrimidin-4-yl]phenyl}acetamide: $^1$H NMR (400 MHz, DMSO): 10.184 (s, 1H), 8.288 (d, 1H), 8.044 (d, 2H), 7.71 (d, 2H), 7.049 (t, 2H), 3.8 (br s, 1H), 2.962 (d, 2H), 2.077 (s, 3H), 1.838 (br d, 2H), 1.372-1.334 (m, 2H). MS (EI) for $C_{17}H_{21}N_5O$: 312.3 (MH$^+$).

N-{4-[2-({1-[(2,6-dichlorophenyl)carbonyl]piperidin-4-yl}amino)pyrimidin-4-yl]-phenyl}acetamide: $^1$H NMR (400 MHz, DMSO): 10.171 (s, 1H), 8.312 (d, 1H), 8.067 (d, 2H), 7.71 9d, 2H), 7.584-7.546 (m, 2H), 7.461 (t, 1H), 7.246 (d, 1H), 7.093 (d, 1H), 4.468 (m, 1H), 4.1 (br s, 1H), 3.25-3.05 (m, 2H), 2.077 (s, 3H), 2.05 (m, 1H), 1.915 (br s, 1H), 1.58-1.532 (m, 2H). MS (EI) for $C_{24}H_{23}Cl_2N_5O_2$: 485.3 (MH$^+$).

N-{4-[2-({4-[(2-hydroxyethyl)oxy]phenyl}amino)pyrimidin-4-yl]phenyl}acetamide: $^1$H NMR (400 MHz, DMSO): 10.211 (s, 1H), 9.43 (s, 1H), 8.455 (d, 1H), 8.12 (d, 2H), 7.754-7.69 (m, 4H), 7.292 (d, 1H), 6.93 (m, 2H), 4.865 (t, 1H), 3.97 (t, 2H), 3.715 (q, 2H), 2.09 (s, 3H). MS (EI) for $C_{20}H_{20}N_4O_3$: 365.1 (MH$^+$).

1-(4-{2-[(4-morpholin-4-ylphenyl)amino]pyrimidin-4-yl}phenyl)-3-phenylurea: $^1$H NMR (400 MHz, DMSO): 9.371 (s, 1H), 8.986 (s, 1H), 8.7959s, 1H), 8.436 (d, 1H), 8.121 (d, 2H), 7.697 (d, 2H), 7.633 (d, 2H), 7.49 (d, 2H), 7.321-7.265 (m, 3H), 7.014-6.928 (t d, 3H), 3.758 (t, 4H), 3.063 (t, 4H). MS (EI) for $C_{27}H_{26}N_6O_2$: 467.3 (MH$^+$).

N-[5-({4-[4-(acetylamino)phenyl]pyrimidin-2-yl}amino)-2-(4-ethylpiperazin-1-yl)phenyl]-2,6-dichlorobenzamide: $^1$H NMR (400 MHz, DMSO): 10.224 (s, 1H), 9.623 (d, 2H), 8.6 (br s, 1H), 8.48 (d, 1H), 8.237 (d, 2H), 7.735 (d, 2H), 7.598 (d, 2H), 7.521 (m, 2H), 7.35 (d, 1H), 7.181 (d, 1H), 3.36 (br s, 4H), 2.877 (t, 4H), 2.344 (q, 2H), 2.071 (s, 3H), 1.005 (t, 3H). MS (EI) for $C_{31}H_{31}Cl_2N_7O_2$: 604.3 (MH$^+$).

1-[4-(2-{[4-(4-ethylpiperazin-1-yl)phenyl]amino}pyrimidin-4-yl)phenyl]-3-(phenylmethyl)urea: $^1$H NMR (400 MHz, MeOD): 8.082 (t, 3H), 7.53 (d, 2H), 7.422 (m, 3H), 7.236 (m, 4H), 7.159 (m, 1H), 7.037 (d, 2H), 4.32 (s, 2H), 3.971 (d, 2H), 3.608 (d, 2H), 3.195 (t, 2H), 3.126 (d, 2H), 3.045 (t, 2H), 1.3 (t, 3H). MS (EI) for $C_{30}H_{33}N_7O$: 508.4 (MH$^+$).

$N^2$,$N^2$-dimethyl-N-{4-[2-({4-[4-(pyridin-3-ylcarbonyl)piperazin-1-yl]phenyl}amino)pyrimidin-4-yl]phenyl}glycinamide: $^1$H NMR (400 MHz, DMSO): 9.994 (s, 1H), 9.418 (s, 1H), 8.667 (m, 2H), 8.454 (d, 1H), 8.127 (d, 2H), 7.907-7.827 (m d, 3H), 7.7 (d, 2H), 7.513 (m, 1H), 7.298 (d, 1H), 6.98 (d, 2H), 3.799 (br s, 2H), 3.489 (br s, 2H), 3.179 (br s, 2H), 3.113 (br s, 4H), 2.289 (s, 6H). MS (EI) for $C_{30}H_{32}N_8O_2$: 537.4 (MH$^+$).

N-(3-fluoro-4-{2-[(4-morpholin-4-ylphenyl)amino]pyrimidin-4-yl}phenyl)-cyclopropanecarboxamide: $^1$H NMR (400 MHz, DMSO): 10.671 (s, 1H), 9.452 (s, 1H), 8.47 (d, 1H), 8.045 (t, 1H), 7.758 (d, 1H), 7.656 (d, 2H), 7.46 (d, 1H), 7.12 (q, 1H), 6.932 (d, 2H), 3.749 (t, 4H), 3.052 (t, 4H), 1.813 (m, 1H), 0.847 (d, 4H). MS (EI) for $C_{24}H_{24}FN_5O_2$: 434.3 (MH$^+$).

N-(4-{2-[(4-{4-[(1-methyl-1H-imidazol-2-yl)methyl]piperazin-1-yl}phenyl)amino]-pyrimidin-4-yl}phenyl)cyclopropanecarboxamide: $^1$H NMR (400 MHz, DMSO): 7.851 (d, 1H), 7.67 (d, 2H), 7.452 (br d, 2H), 7.285 (d, 2H), 7.091 (d, 1H), 7.763 (d, 1H), 6.688 (d, 2H), 6.291 (br s, 1H), 3.668 (s, 3H), 3.561 (s, 2H), 2.946 (br s, 4H), 2.5 (br s, 4H), 1.413 (m, 1H), 0.541 (m, 2H), 0.3 (m, 2H). MS (EI) for $C_{29}H_{32}N_8O$: 509.4 (MH$^+$).

N-[4-(2-{[4-(4-L-alanylpiperazin-1-yl)phenyl]amino}pyrimidin-4-yl)phenyl]-acetamide: $^1$H NMR (400 MHz, DMSO): 10.212 (s, 1H), 9.407 (s, 1H), 8.449 (d, 1H), 8.121 (d, 2H), 7.732 (d, 2H), 7.698 (d, 2H), 7.282 (d, 1H), 6.978 (d, 2H), 3.804 (q, 1H), 3.621 (m, 4H), 3.037 (br m, 4H), 2.091 (s, 3H), 1.864 (br s, 2H), 1.10 (d, 3H). MS (EI) for $C_{25}H_{29}N_7O_2$: 460.4 (MH$^+$).

N-[4-(2-{[4-(4-L-prolylpiperazin-1-yl)phenyl]amino}pyrimidin-4-yl)phenyl]-acetamide: $^1$H NMR (400 MHz, DMSO): 10.234 (s, 1H), 9.409 (s, 1H), 8.449 (d, 1H), 8.121 (d, 2H), 7.757 (d, 2H), 7.699 (d, 2H), 7.282 (d, 1H), 6.979 (d, 2H), 3.849 (m, 1H), 3.619 (m, 4H), 2.992 (m, 6H), 2.625 (m, 1H), 2.092 (s, 3H), 1.986 (m, 1H), 1.685-1.536 (m, 3H). MS (EI) for $C_{27}H_{31}N_7O_2$: 486.2 (MH$^+$).

N-[4-(2-{[4-(4-D-alanylpiperazin-1-yl)phenyl]amino}pyrimidin-4-yl)phenyl-acetamide: $^1$H NMR (400 MHz, DMSO): 10.22 (s, 1H), 9.406 (s, 1H), 8.449 (d, 1H), 8.12 (d, 2H), 7.755 (d, 2H), 7.697 (d, 2H), 7.282 (d, 1H), 6.978 (d, 2H), 3.791 (q, 1H), 3.621 (br s, 4H), 3.081 (br d, 4H), 2.091 (s, 3H), 1.709 (br s, 2H), 1.096 (d, 3H). MS (EI) for $C_{25}H_{29}N_7O_2$: 460.4 (MH$^+$).

N-[4-(2-{[4-(4-D-prolylpiperazin-1-yl)phenyl]amino}pyrimidin-4-yl)phenyl]-acetamide: $^1$H NMR (400 MHz, DMSO): 10.211 (s, 1H), 9.407 (s, 1H), 8.449 (d, 1H), 8.121 (d, 2H), 7.754 (d, 2H), 7.698 (d, 2H), 7.282 (d, 1H), 6.979 (d, 2H), 3.872 (t, 1H), 3.621 (m, 4H), 3.082-2.979 (m, 6H), 2.656 (m, 1H), 2.091 (s, 3H), 2.013 (m, 2H), 1.676-1.522 (m, 3H). MS (EI) for $C_{27}H_{31}N_7O_2$: 486.4 (MH$^+$).

N-{4-[2-({4-[4-(2-piperazin-1-ylacetyl)piperazin-1-yl]phenyl}amino)pyrimidin-4-yl]phenyl}acetamide: $^1$H NMR (400 MHz, DMSO): 10.219 (s, 1H), 9.401 (s, 1H), 8.448 (d, 1H), 8.121 (d, 2H), 7.754 (d, 2H), 7.694 (d, 2H), 7.281 (d, 1H), 6.977 (d, 2H), 3.707 (t, 2H), 3.59 (t, 2H), 3.319 (s, 2H), 3.1 (t, 2H), 3.018 (t, 2H), 2.702 (s, 4H), 2.336 (br s, 4H), 2.090 (s, 3H). MS (EI) for $C_{25}H_{34}N_8O_2$: 515.2 (MH$^+$).

N-[4-(2-{[4-(4-L-alanylpiperazin-1-yl)phenyl]amino}pyrimidin-4-yl)phenyl]-tetrahydrofuran-2-carboxamide: $^1$H NMR (400 MHz, DMSO): 9.938 (s, 1H), 9.417 (s, 1H), 8.457 (d, 1H), 8.135 (d, 2H), 7.885 (d, 2H), 7.693 (d, 2H), 7.305 (d, 1H), 6.976 (d, 2H), 4.436 (q, 1H), 3.991 (q, 1H), 3.878-3.761 (q q, 4H), 3.622 (br s, 4H), 3.083 (br d, 4H), 2.222 (m, 1H), 2.019 (m, 1H), 1.913 (m, 2H), 1.843 (br s, 2H). MS (EI) for $C_{28}H_{33}N_7O_3$: 516.3 (MH$^+$).

N-[4-(2-{[4-(4-L-prolylpiperazin-1-yl)phenyl]amino}pyrimidin-4-yl)phenyl]-tetrahydrofuran-2-carboxamide: $^1$H NMR (400 MHz, DMSO): 9.945 (s, 1H), 9.419 (s, 1H), 8.458 (d, 1H), 8.135 (d, 2H), 7.887 (d, 2H), 7.696 (d, 2H), 7.306 (d, 1H), 6.978 (d, 2H), 4.452 (q, 1H), 4.011 (q, 1H), 3.861 (q, 2H), 3.633 (m, 4H), 3.084-2.968 (m, 6H), 2.62 (m, 1H), 2.191 (m, 1H), 2.002 (m, 2H), 1.897 (m, 2H), 1.691-1.544 (m, 3H). MS (EI) for $C_{30}H_{35}N_7O_3$: 542.3 (MH$^+$).

N-[4-(2-{[4-(4-D-alanylpiperazin-1-yl)phenyl]amino}pyrimidin-4-yl)phenyl]-tetrahydrofuran-2-carboxamide: $^1$H NMR (400 MHz, DMSO): 9.945 (s, 1H), 9.4189s, 1H), 8.457 (d, 1H), 8.135 (d, 2H), 7.887 (d, 2H), 7.694 (d, 2H), 7.305 (d, 1H), 6.976 (d, 2H), 4.452 (q, 1H), 4.028 (q, 1H), 3.878-3.768 (m, 2H), 3.633 (m, 4H), 3.083 (br d, 4H), 2.209 (m, 1H), 2.002 (m, 1H), 1.862 (m, 3H), 1.1 (d, 3H). MS (EI) for $C_{28}H_{33}N_7O_3$: 516.3 (MH$^+$).

N-[4-(2-{[4-(4-D-prolylpiperazin-1-yl)phenyl]amino}pyrimidin-4-yl)phenyl]-tetrahydrofuran-2-carboxamide: $^1$H NMR (400 MHz, DMSO). 9.954 (s, 1H), 9.421 (s, 1H), 8.458 (d, 1H), 8.136 (d, 2H), 7.889 (d, 2H), 7.697 (d, 2H), 7.306 (d, 1H), 6.978 (d, 2H), 4.454 (q, 1H), 4.028 (q, 1H), 3.889 (m, 2H), 3.645 (m, 4H), 3.083-2.985 (m, 6H), 2.669 (m, 1H), 2.209 (m, 1H), 2.002 (m, 2H), 1.879 (m, 2H), 1.681-1.548 (m, 3H), MS (EI) for $C_{30}H_{35}N_7O_3$: 542.3 (MH+).

(2,6-dichlorophenyl)(4-(4-(4-methylthiophen-2-yl)pyrimidin-2-ylamino)piperidin-1-yl)methanone: $^1$H-NMR (400 MHz, d6-DMSO): 8.28 (d, 1H), 7.72 (m, 1H), 7.57 (m, 2H), 7.47 (m, 1H), 7.32 (s, 1H), 7.27 (m, 1H), 7.01 (m, 1H), 4.45 (m, 1H), 4.03 (m, 1H), 3.28-3.05 (m, 3H), 2.45 (s, 3H), 2.03-1.80 (m, 2H), 1.59-1.48 (m, 2H); MS (EI): 447 (MH+).

(2,6-dichlorophenyl)(4-(4-(pyridin-3-yl)pyrimidin-2-ylamino)piperidin-1-yl)-methanone: $^1$H-NMR (400 MHz, d6-DMSO): 9.28 (br. s, 1H), 8.69 (m, 1H), 8.41 (m, 2H), 7.59-7.52 (m, 2H), 7.46 (m, 2H), 7.25 (d, 1H), 4.46 (m, 1H), 4.14 (m, 1H), 3.32-3.10 (m, 3H), 2.06-1.89 (m, 2H), 1.63-1.54 (m, 3H); MS (EI): 428 (MH+).

(2,6-dichlorophenyl)(4-(4-(5-methylthiophen-2-yl)pyrimidin-2-ylamino)piperidin-1-yl)methanone: $^1$H-NMR (400 MHz, d6-DMSO): 8.24 (d, 1H), 7.70 (m, 1H), 7.57 (m, 2H), 7.47 (m, 1H), 7.24 (m, 1H), 7.00 (m, 1H), 6.88 (m, 1H), 4.45 (m, 1H), 4.02 (m, 1H), 3.28-3.05 (m, 3H), 2.47 (s, 3H), 2.03-1.80 (m, 2H), 1.57-1.50 (m, 2H); MS (EI): 447 (MH+).

1-methyl-N-(4-{2-[(4-morpholin-4-ylphenyl)amino]pyrimidin-4-yl}phenyl)-1H-pyrrole-2-carboxamide: $^1$H NMR (400 MHz, d6-DMSO): 9.99 (s, 1H), 9.39 (s, 1H), 8.45 (d, 1H), 8.13 (d, 2H), 7.90 (d, 2H), 7.68 (d, 2H), 7.30 (d, 1H), 7.09-7.08 (m, 1H), 7.05 (t, 1H), 6.97 (d, 2H), 6.13-6.11 (m, 1H), 3.90 (s, 3H), 3.74 (t, 4H), 3.05 (t, 4H). MS (EI) for $C_{26}H_{26}N_6O_2$: 455 (MH+).

3-fluoro-N-(4-{2-[(4-morpholin-4-ylphenyl)amino]pyrimidin-4-yl}phenyl)pyridine-4-carboxamide: $^1$H NMR (400 MHz, d6-DMSO): 10.96 (s, 1H), 9.43 (s, 1H), 8.79 (s, 1H), 8.62 (d, 1H), 8.47 (d, 1H), 8.20 (d, 2H), 7.88 (d, 2H), 7.76-7.67 (m, 2H), 7.32 (d, 1H), 6.94 (d, 2H), 6.56 (s, 1H), 3.74 (t, 4H), 3.05 (t, 4H). MS (EI) for $C_{26}H_{23}FN_6O_2$: 471 (MH+).

6-methyl-N-(4-{2-[(4-morpholin-4-ylphenyl)amino]pyrimidin-4-yl}phenyl)pyridine-3-carboxamide: $^1$H NMR (400 MHz, d6-DMSO): 10.61 (s, 1H), 9.41 (s, 1H), 9.03 (d, 1H), 8.47 (d, 1H), 8.23 (dd, 1H), 8.19 (d, 2H), 7.95 (d, 2H), 7.68 (d, 2H), 7.45 (d, 1H), 7.31 (d, 1H), 6.94 (d, 2H), 3.74 (t, 4H), 3.05 (t, 4H), 2.57 (s, 3H). MS (EI) for $C_{27}H_{26}N_6O_2$: 467 (MH+).

N-(4-{2-[(4-morpholin-4-ylphenyl)amino]pyrimidin-4-yl}phenyl)pyridazine-4-carboxamide: $^1$H NMR (400 MHz, d6-DMSO): 10.98 (s, 1H), 9.67 (s, 1H), 9.52 (d, 1H), 9.42 (s, 1H), 8.47 (d, 1H), 8.21 (d, 2H), 8.16-8.14 (m, 1H), 7.96 (d, 2H), 7.68 (d, 2H), 7.33 (d, 2H), 7.33 (d, 1H), 6.95 (d, 2H), 3.74 (t, 4H), 3.05 (t, 4H). MS (EI) for $C_{25}H_{23}N_7O_2$: 454 (MH+).

2-cyclopropyl-N-(4-{2-[(4-morpholin-4-ylphenyl)amino]pyrimidin-4-yl}phenyl)acetamide: $^1$H NMR (400 MHz, d6-DMSO): 10.09 (s, 1H), 9.45 (s, 1H), 8.45 (d, 1H), 8.12 (d, 2H), 7.78 (d, 2H), 7.69 (d, 2H), 7.30 (d, 1H), 7.00 (s, 2H), 3.76 (s, 4H), 3.09 (s, 4H), 2.25 (d, 2H), 1.12-1.02 (m, 1H), 0.50-0.48 (m, 2H), 0.22-0.20 (m, 2H). MS (EI) for $C_{25}H_{27}N_5O_2$: 430 (MH+).

N-(4-{2-[(4-morpholin-4-ylphenyl)amino]pyrimidin-4-yl}phenyl)isoxazole-5-carboxamide: $^1$H NMR (400 MHz, d6-DMSO): 10.99 (s, 1H), 9.42 (s, 1H), 8.47 (d, 1H), 8.19 (d, 2H), 7.95 (d, 2H), 7.68 (d, 2H), 7.33-7.31 (m, 2H), 6.95 (d, 2H), 6.55 (s, 1H), 3.74 (t, 4H), 3.05 (t, 4H). MS (EI) for $C_{24}H_{22}N_6O_3$: 443 (MH+).

N-(4-{2-[(4-morpholin-4-ylphenyl)amino]pyrimidin-4-yl}phenyl)pyridine-3-carboxamide: $^1$H NMR (400 MHz, d6-DMSO): 10.69 (s, 1H), 9.41 (s, 1H), 9.14 (s, 1H), 8.79 (d, 1H), 8.47 (d, 1H), 8.34-8.31 (m, 1H), 8.20 (d, 2H), 7.97 (d, 2H), 7.70 (d, 2H), 7.67-7.58 (m, 1H), 7.33 (d, 1H), 6.95 (d, 2H), 3.78 (t, 4H), 3.05 (t, 4H). MS (EI) for $C_{26}H_{24}N_6O_2$: 453 (MH+).

4-methyl-N-(4-{2-[(4-morpholin-4-ylphenyl)amino]pyrimidin-4-yl}phenyl)-benzamide: $^1$H NMR (400 MHz, d6-DMSO): 10.42 (s, 1H), 9.53 (s, 1H), 8.47 (s, 1H), 8.17 (d, 2H), 7.98 (d, 2H), 7.91 (d, 2H), 7.72 (s, 2H), 7.37 (d, 3H), 7.05 (s, 2H), 3.78 (s, 4H), 3.14 (s, 4H), 2.40 (s, 3H). MS (EI) for $C_{28}H_{27}N_5O_2$: 466 (MH+).

N-[4-(2-{[4-(4-ethylpiperazin-1-yl)phenyl]amino}pyrimidin-4-yl)phenyl]-D-prolinamide: $^1$H NMR (400 MHz, d6-DMSO): 11.55 (s, 1H), 11.15 (s, 1H), 10.16 (s, 2H), 8.74 (s, 1H), 8.52 (s, 1H), 8.23 (d, 2H), 7.89 (d, 2H), 7.67 (d, 2H), 7.48 (s, 1H), 7.11 (d, 2H), 4.50 (s, br, 1H), 3.81 (d, 2H), 3.57 (d, 2H), 3.28-3.11 (m, 8H), 2.05-1.92 (m, 3H), 1.30 (t, 3H). MS (EI) for $C_{27}H_{33}N_7O$: 472 (MH+).

N-[4-(2-{[4-(4-ethylpiperazin-1-yl)phenyl]amino}pyrimidin-4-yl)phenyl]-butanamide: $^1$H NMR (400 MHz, d6-DMSO): 10.25 (s, 1H), 9.37 (s, 1H), 8.43 (s, 1H), 8.12 (d, 2H), 7.77 (d, 2H), 7.68 (d, 2H), 7.29 (s, 1H), 6.93 (d, 2H), 3.08 (s, 4H), 2.42-2.30 (m, 4H), 1.68-1.58 (m, 2H), 1.05 (t, 3H), 0.93 (t, 3H). MS (EI) for $C_{26}H_{32}N_6O$: 445 (MH+).

1-ethyl-3-[4-(2-{[4-(4-ethylpiperazin-1-yl)phenyl]amino}pyrimidin-4-yl)phenyl]urea: $^1$H NMR (400 MHz, d6-DMSO): 9.32 (s, 1H), 8.85 (s, 1H), 8.40 (d, 1H), 8.05 (d, 2H), 7.68 (d, 2H), 7.54 (d, 2H), 7.23 (d, 1H), 6.92 (d, 2H), 6.36 (t, 1H), 3.18-3.05 (m, 6H), 2.54 (t, 4H), 2.46-2.38 (m, 2H), 1.09-1.02 (m, 6H). MS (EI) for $C_{25}H_{31}N_7O$: 446 (MH+).

N-(4-{2-[(4-morpholin-4-ylphenyl)amino]pyrimidin-4-yl}phenyl)furan-3-carboxamide: $^1$H NMR (400 MHz, d6-DMSO): 10.17 (s, 1H), 9.46 (s, 1H), 8.47-8.43 (m, 2H), 8.18 (d, 2H), 7.91 (d, 2H), 7.83 (d, 1H), 7.70 (s, 2H), 7.32 (s, 1H), 7.03-6.95 (m, 3H), 3.76 (s, 4H), 3.09 (s, 4H). MS (EI) for $C_{25}H_{23}N_5O_3$: 442 (MH+).

N-(4-{2-[(4-morpholin-4-ylphenyl)amino]pyrimidin-4-yl}phenyl)-1,3-thiazole-4-carboxamide: $^1$H NMR (400 MHz, d6-DMSO): 10.61 (s, 1H), 9.40 (s, 1H), 9.30 (d, 1H), 8.56 (d, 1H), 8.46 (d, 1H), 8.16 (d, 2H), 8.06 (d, 2H), 7.69 (d, 2H), 7.32 (d, 1H), 6.96 (d, 2H), 6.56 (s, 1H), 3.74 (t, 4H), 3.05 (t, 4H). MS (EI) for $C_{24}H_{22}N_6O_2S$: 459 (MH+).

Based on the synthetic examples described hereinabove, the skilled artisan would be able to make the remainder of the compounds intended to be within the scope of the invention described in the appended claims.

Biological Assays

Assay Example 1

Measurement of JAK-2 Kinase Activity by ATP Hydrolysis

JAK-2 kinase activity was measured by monitoring peptide substrate dependent hydrolysis of ATP via quantitation of remaining ATP with luciferase based chemiluminescence. For compound evaluation, 0.5 μl of the compound dissolved in DMSO was added to 10 μl of JAK-2 dissolved in assay buffer (20 mM HEPES pH 7.5, 10 mM $MgCl_2$, 0.03% Triton and 1 mM DTT). After preincubation for 30 minutes at room temperature, the reaction was initiated by addition of 10 μl of ATP and the substrate peptide poly-Glu-Tyr in assay buffer. Final enzyme, ATP, and peptide concentrations were 3 nM, 1 μM, and 2 μM, respectively. After incubation for 60 minutes at room temperature, reaction progress was quantitated by addition of 10 μl Kinase-Glo (Promega) and measurement of chemiluminescence in a Victor reader (Perkin Elmer). A reaction in which compound was omitted was used to determine maximum reaction progress. Omission of compound and enzyme from the reaction was used to determine zero reaction progress.

Assay Example 2

Measurement of JAK-3 Kinase Activity by ATP Hydrolysis

JAK-3 was assayed similarly as JAK-2 (see Assay Example 1) except that the enzyme reaction was carried out for 180 minutes and enzyme, ATP, and peptide concentrations were 30 nM, 2 μM, and 4 μM, respectively.

Biological Activity

Compounds in Table 1 were determined to have inhibitory activity for JAK-2 of less than 10 μM. Other more preferred compounds of the invention have inhibitory activity for JAK-2 of less than 100 nm. One of ordinary skill in the art can use the disclosures herein as well as what is known in the art to test the inhibitory activity of a particular compound.

Pharmaceutical Composition Examples

The following are representative pharmaceutical formulations containing a compound of Formula I.

Tablet Formulation

The following ingredients are mixed intimately and pressed into single scored tablets.

| Ingredient | Quantity per tablet, mg |
|---|---|
| compound of this invention | 400 |
| Cornstarch | 50 |
| croscarmellose sodium | 25 |
| Lactose | 120 |
| magnesium stearate | 5 |

Capsule Formulation

The following ingredients are mixed intimately and loaded into a hard-shell gelatin capsule.

| Ingredient | Quantity per tablet, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| Flavoring | 0.035 mL |
| Colorings | 0.5 mg |
| distilled water | q.s. to 100 mL |

Injectable Formulation

The following ingredients are mixed to form an injectable formulation.

| Ingredient | Amount |
| --- | --- |
| compound of this invention | 1.2 g |
| sodium acetate buffer solution | 0.4 M 2.0 mL |
| HCl (1 N) or NaOH (1 M) | q.s. to suitable pH |
| water (distilled, sterile) | q.s. to 20 mL |

All of the above ingredients, except water, are combined and heated to 60°-70° with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol®H-15 (triglycerides of saturated vegetable fatty acid; Riches-Nelson, Inc., New York), and has the following composition:

| Ingredient | Quantity per tablet, mg |
| --- | --- |
| compound of this invention | 500 |
| Witepsol ® H-15 | balance |

The foregoing invention has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

What is claimed is:

1. A compound of Formula I:

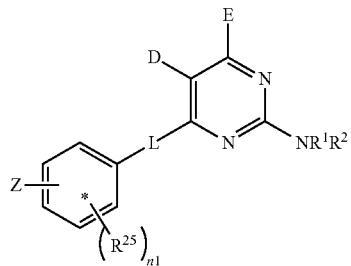

or a pharmaceutically acceptable salt thereof, wherein
D is hydrogen, halo, —CF$_3$, heterocycloalkyl or alkyl;
E is hydrogen, halo, —CF$_3$, heterocycloalkyl or alkyl; or
L is a bond;

Z is

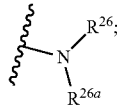

$R^{25}$ is selected from alkyl, alkenyl, lower alkyl, halo, haloalkyl, haloalkoxy, amino, alkylamino, dialkylamino, aminoalkyl, alkylaminoalkyl, —OR$^{12}$, cyano, —CH$_2$NHC(O)OR$^7$, —CH$_2$NHC(O)R$^7$, —SR$^7$, —S(O)$_2$R$^7$, —S(O)$_2$NR$^7$R$^8$, —C(O)OR$^8$, cycloalkyl, heterocycloalkyl, aryl and heteroaryl; wherein the cycloalkyl, heterocycloalkyl, aryl and heteroaryl are each optionally substituted with one, two or three groups independently selected from alkyl, alkenyl, halo, haloalkoxy, haloalkyl, amino, alkylamino, dialkylamino, aminoalkyl, alkylaminoalkyl, —OR$^8$, —NHS(O)$_2$R$^8$, cyano, —C(O)R$^8$, —CH$_2$NHC(O)OR$^7$, —CH$_2$NHC(O)R$^7$, —SR$^7$, —S(O)$_2$R$^7$, —S(O)$_2$NR$^7$R$^8$, —C(O)OR$^8$, —C(O)NR$^7$R$^8$, and —NR$^7$C(O)R$^8$;
n1 is 0, 1, 2, 3, or 4, and each n1 is independently selected when more than one n1 is present;
or Z and an $R^{25}$, together with the carbon atoms to which they are attached, join to form a 5 or 6 membered heterocycloalkyl, a 5 or 6 membered heteroaryl, or a 5 or 6 membered cycloalkyl ring, wherein the 5 or 6 membered heterocycloalkyl, 5 or 6 membered heteroaryl, and 5 or 6 membered cycloalkyl ring are fused to the phenyl moiety to which Z and $R^{25}$ are attached, and wherein the 5 or 6 membered heterocycloalkyl, 5 or 6 membered heteroaryl, or 5 or 6 membered cycloalkyl ring are each optionally substituted with 1, 2, or 3 groups independently selected from oxo, alkyl, alkoxy and halo;
n2 is 0, 1, 2, 3, or 4, and each n2 is independently selected when more than one n2 is present;
n5 is 0, 1, 2, 3 or 4;
$R^1$ is hydrogen;
$R^2$ is

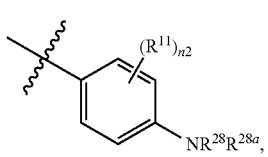

(a)

$R^7$, $R^{7'}$, $R^{12}$ and $R^{15}$ are each independently hydrogen, alkyl, alkoxy, or alkoxyalkyl;
$R^8$ is selected from hydrogen, hydroxy, alkyl, alkenyl, lower alkynyl, hydroxylamino, hydroxyalkyl, alkoxyalkyl, dihydroxyalkyl, alkylamino, dialkylamino, aminoalkyl, aminocarbonylalkyl, alkylaminocarbonylalkyl, dialkylaminocarbonylalkyl, alkylaminoalkyl, dialkylaminoalkyl, —(CH$_2$)$_r$—C(O)OR$^7$, —(CH$_2$)$_r$C(O)NR$^7$R$^{7'}$, aryl, heteroaryl, cycloalkyl, arylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, haloalkyl, haloalkoxy, lower alkoxy, amino, aryl, alkylamino, dialkylamino, heterocyclylalkoxy, oxo and haloalkyl;

each $R^{11}$, when $R^{11}$ is present, is independently selected from alkyl, alkenyl, lower alkynyl, —$CF_3$, alkoxy, halo, haloalkoxy, haloalkyl, aminoalkyl, aminoalkoxy, alkylaminoalkyl, alkylaminoalkoxy, dialkylaminoalkyl, dialkylaminoalkoxy, oxo, thioalkyl, alkylthioalkyl, —$(CH_2)_p$—$OR^{17}$, —CN, —O—$CH_2$—C(O)—$R^{17}$, —C(O)$R^{16}$, —$(CH_2)_p$—C(O)$OR^{17}$, —S(O)$_2R^{17}$, —S(O)$_2NR^{15}R^{17}$, aryl, heteroaryl, cycloalkyl, arylalkyl, arylalkoxy, heteroarylalkyl, cycloalkylalkyl, heterocycloalkyl, and heterocycloalkylalkyl; wherein the aryl, heteroaryl, cycloalkyl, arylalkyl, heteroarylalkyl, cycloalkylalkyl, heterocycloalkyl, and heterocycloalkylalkyl are each independently optionally substituted at any ring position with 1, 2, 3 or 4 $R^{21}$;

$R^{12a}$ is hydrogen or alkyl;

$R^{13}$ is selected from hydrogen, hydroxy, alkyl, alkenyl, lower alkynyl, hydroxylamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, —$(CH_2)_r$—C(O)$OR^7$, —$(CH_2)_r$—C(O)$NR^7R^{7'}$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with 1, 2, 3, 4 or 5 groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl are independently optionally substituted with 1, 2, 3, 4, or 5 groups selected from halo and hydroxy;

$R^{16}$ is selected from hydrogen, hydroxy, alkyl, alkenyl, lower alkynyl, hydroxyamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, dialkylaminoalkyl, —$(CH_2)_r$—C(O)$OR^7$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl is optionally substituted with 1, 2, 3, 4, or 5 groups selected from halo and hydroxy;

$R^{17}$ is selected from hydrogen, hydroxy, alkyl, alkenyl, lower alkynyl, hydroxyamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, dialkylaminoalkyl, —$(CH_2)_r$—C(O)$OR^7$, —$(CH_2)_r$—C(O)$NR^7R^{7'}$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl is optionally substituted with 1, 2, 3, 4, or 5 groups selected from halo and hydroxy;

each $R^{21}$, when $R^{21}$ is present, is independently selected from alkyl, alkenyl, lower alkynyl, cyano, halo, haloalkoxy, haloalkyl, hydroxyalkyl, amino, alkylamino, dialkylamino, dialkylaminoalkyl, dialkylaminoalkyloxy, haloalkyl, oxo, —$OR^{13}$, —NHS(O)$_2R^{17}$, —S(O)$_2R^{17}$, —C(O)$R^{17}$, —C(O)$OR^{17}$, —C(O)$NR^{15}R^{17}$, —NR aryl, arylalkyl, heteroarylalkyl, aryloxy, and heteroaryl; wherein each of the aryl, arylalkyl, heteroarylalkyl, aryloxy, and heteroaryl within $R^{21}$ are optionally substituted at any ring position with 1, 2, or 3 groups selected from alkyl, lower alkoxy halo, phenyl, heteroaryl and alkylheteroalkyl;

$R^{26}$ is hydrogen, —C(O)-phenyl or alkyl, wherein the —C(O)-phenyl is optionally substituted at any ring position with 1, 2 or 3 halo;

$R^{26a}$ is hydrogen, alkyl, heteroaryl, —C(O)$R^{32}$, —C(O)$NHR^{32a}$, —S(O)$_2R^9$, —$SR^9$, —C(O)$OR^{32}$, or —C(O)$NR^{32a}R^{32}$;

$R^{28}$ is selected from alkyl, alkenyl, hydroxy, alkoxy, and alkoxyalkyl;

$R^{28a}$ is selected from hydrogen, alkyl, alkenyl, alkoxyalkyl, alkoxycarbonylalkyl, hydroxyalkyl, aryl, arylalkyl, cycloalkyl, cycloalkylalkyl, dialkylaminoalkyl, arylcarbonylalkyl, aryloxyalkyl, alkyl-O—C(O)heterocycloalkyl, —$(CH_2)_{n4}$heterocycloalkyl, heterocycloalkylalkyl, heteroaryl, heteroarylalkyl, —$(CH_2)_{n4}$—C(O)$R^{29}$, —CH(phenyl)$_2$, —S(O)$_2R^{29}$, —C(O)$R^{29}$, —C(O)$OR^{29}$, and —C(O)$NR^{29a}R^{29}$, wherein the aryl, arylalkyl, cycloalkyl, cycloalkylalkyl, heteroaryl, heteroarylalkyl, heterocycloalkyl, and heterocycloalkylalkyl groups within $R^{27a}$ and $R^{28a}$ are each independently optionally substituted at any ring position with 1, 2, 3, 4, or 5 groups selected from halo, alkyl, alkoxy, alkylcarbonyl, phenyl, phenoxy, arylcarbonyl, —$CF_3$, oxo, —$OCF_3$, alkoxyphenyl, and heteroaryl optionally substituted with alkyl or halo;

or $R^{28}$ and $R^{28a}$ together with the nitrogen to which they are attached form heterocycloalkyl or heteroaryl, wherein the heterocycloalkyl and heteroaryl are each optionally substituted with 1, 2, 3, 4, or 5 $R^{31}$;

$R^{30}$ is selected from hydrogen, alkyl, hydroxyalkyl, alkoxyalkyl, alkoxyalkoxyalkyl, alkoxycarbonylalkyl, amino, alkylamino, dialkylamino, aminoalkyl, alkylaminoalkyl, dialkylaminoalkyl, aryl, arylalkyl, phenoxyalkyl, cycloalkyl, cycloalkylalkyl, heteroaryl, heteroarylalkyl, arylheteroarylalkyl, heterocycloalkyl, and heterocycloalkylalkyl; wherein the aryl, arylalkyl, phenoxyalkyl, cycloalkyl, arylheteroarylalkyl, cycloalkylalkyl, heteroaryl, heteroarylalkyl, heterocycloalkyl, and heterocycloalkylalkyl groups within $R^{30}$ are each independently optionally substituted at any ring position with 1, 2, 3, 4, or 5 groups selected from halo, alkyl, alkoxy, alkoxyalkyl, —C(O)OCH$_3$, —CF$_3$, —OCF$_3$, alkylcarbonyl, phenyl, phenoxy, alkylphenoxy, dialkylaminoalkoxy and heteroaryl;

$R^{31}$ is selected from alkyl, hydroxyalkyl, alkoxy, alkoxyalkyl, alkylthioalkyl, —C(O)R$^{30}$, —C(O)NR$^{30}$R$^{30a}$, —C(O)OR$^{30}$, —S(O)$_2$R$^{30}$, amino, dihydroxyalkyl, arylcarbonyl, alkylcarbonylamino, alkoxyphenyl, phenylalkoxyalkyl, arylheteroarylalkyl, alkylamino, —O-dialkylamino, dialkylamino, aminoalkyl, alkylaminoalkyl, dialkylaminoalkyl, dialkylaminoalkoxy, oxo, aryl, arylalkyl, cycloalkyl, cycloalkylalkyl, heteroaryl, heteroarylalkyl, heterocycloalkyl, spirocyclic cycloalkyl, spirocyclic heterocycloalkyl, and heterocycloalkylalkyl, wherein the aryl, arylalkyl, cycloalkyl, arylheteroarylalkyl, arylalkoxyalkyl, cycloalkylalkyl, heteroaryl, heteroarylalkyl, heterocycloalkyl, and heterocycloalkylalkyl groups within $R^{31}$ are each independently optionally substituted at any ring position with 1, 2, 3, 4, or 5 groups selected from halo, alkyl, —CF$_3$, —OCF$_3$, cyano, alkoxy, alkoxyalkyl, —C(O)OCH$_3$, alkylcarbonyl, phenyl optionally substituted at any ring position with halo, phenoxy, alkylphenoxy, arylalkoxyalkyl, dialkylaminoalkoxy and heteroaryl;

$R^{32a}$ is hydrogen, —OCF$_3$, —CF$_3$, or alkyl;

$R^{32}$ is selected from aryl, arylalkyl, arylalkoxy, arylcycloalkyl, alkoxycarbonylalkoxy, cycloalkyl, cycloalkylalkyl, cycloalkylhydroxyalkyl, heteroaryl, heteroarylalkyl, heterocycloalkyl, and heterocycloalkylalkyl, wherein the aryl, arylalkyl, cycloalkyl, arylcycloalkyl, cycloalkylalkyl, heteroaryl, heteroarylalkyl, heterocycloalkyl, and heterocycloalkylalkyl are each independently optionally substituted at any ring position with 1, 2, 3, 4, or 5 groups selected from hydroxy, oxo, alkyl, alkoxy, amino, hydroxyalkyl, alkylcarbonyl, alkoxycarbonyl, halo, —CF$_3$, —OCF$_3$, aminoalkyl, alkylaminoalkyl, aryl and dialkylaminoalkyl, and wherein the alkyl portion of the heteroarylalkyl can be substituted with amino;

or $R^{32}$ is alkyl optionally substituted with 1, 2, 3, 4, or 5 groups independently selected from hydroxy, alkoxycarbonyl, alkoxy, —CF$_3$, halo, aminocarbonyl, alkylaminocarbonyl, alkoxycarbonylalkylamino, dialkylaminocarbonyl, —NR$^{34}$R$^{34a}$ and phenyl optionally substituted with 1, 2, or 3 halo;

or $R^{32}$ is alkylamino or arylalkylamino;

$R^{34}$ is hydrogen or alkyl; and $R^{34a}$ is selected from hydrogen, alkyl, heteroaryl, aryl, aminoalkyl, aminocarbonylalkyl, heteroarylalkyl, arylalkoxy and arylalkyloxycarbonylalkyl; wherein the heteroaryl, aryl, heteroarylalkyl, arylalkoxy or arylalkyloxycarbonylalkyl are each independently optionally substituted at any ring position with 1, 2, 3, 4, or 5 groups selected from hydroxy, oxo, alkyl, amino, hydroxyalkyl, alkylcarbonyl, alkoxycarbonyl, halo, aminoalkyl, alkylaminoalkyl, and dialkylaminoalkyl.

2. The compound according to claim 1 having Formula II:

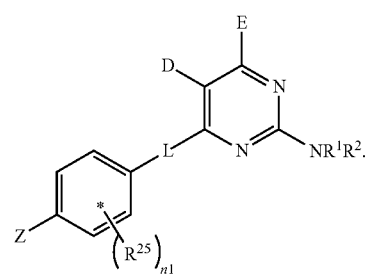

3. The compound according to claim 1 having Formula III:

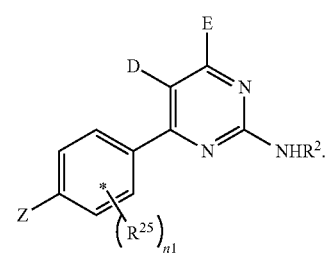

4. The compound according to claim 1,
wherein $R^{28a}$ is selected from lower alkyl, dialkylaminoalkyl, alkoxyalkyl, arylalkyl, heteroarylalkyl, and heterocycloalkylalkyl.

5. The compound according to claim 1,
wherein $R^{11}$ and n2 are as defined above for the compound of Formula I, and $R^{28}$ and $R^{28a}$, together with the nitrogen atom to which they are attached, join together to form a ring structure selected from thiazolidinyl, piperazinyl, piperidinyl, morpholinyl, thiomorpholinyl, pyrimidinyl, and pyridinyl, wherein the ring structure is optionally substituted with 1, 2, 3, 4 or 5 substituents selected from halo, lower alkyl or alkoxy.

6. The compound according to claim 1, wherein $R^{25}$ is hydrogen.

7. The compound according to claim 1, wherein $R^{25}$ is hydrogen and E and D are hydrogen.

8. The compound according to claim 1, wherein $R^{25}$ is on the 3 position.

9. The compound according to claim 1, wherein $R^{26a}$ is C(O)R$^{32}$.

10. The compound according to claim 1, wherein $R^{26a}$ is —C(O)R$^{32}$, and $R^{32}$ is selected from lower alkyl, cylcoalkyl, diaminoalkyl, aminoalkyl, arylalkyl, heterocycloalkyl, alkoxyalkyl, alkylamino, and hydroxyalkyl optionally substituted with amino.

11. The compound according to claim 1, wherein $R^{26a}$ is —C(O)R$^{32}$, and $R^{32}$ is cycloalkyl.

12. The compound according to claim 1, wherein $R^{26a}$ is —C(O)R$^{32}$, and $R^{32}$ is lower alkyl.

13. The compound according to claim 1, wherein $R^{26a}$ is —C(O)R$^{32}$, $R^{26}$ is hydrogen, wherein $R^{32}$ selected from aryl, arylalkyl, cycloalkyl, alkoxycarbonylalkyl, heteroaryl, heteroarylalkyl, heterocycloalkyl, and heterocycloalkylalkyl, wherein $R^{32}$ optionally substituted with 1, 2, 3, 4 or 5 groups selected from hydroxyl, oxo, alkyl, alkoxy, amino, hydroxyalkyl and halo.

14. The compound according to claim 1, wherein $R^{26a}$ is —C(O)$R^{32}$, $R^{26}$ is hydrogen, wherein $R^{32}$ is lower alkyl optionally substituted with 1, 2, 3, 4 or 5 groups selected from dialkylaminocarbonyl, hydroxy and —$NR^{34}R^{34a}$.

15. The compound according to claim 1, wherein is —C(O)$R^{32}$, $R^{26}$ is hydrogen, and $R^{32}$ selected from tetrahydrofuran, pyrrolidinyl or pryimidinyl, wherein $R^{32}$ optionally substituted with 1, 2, 3, 4 or 5 groups selected from hydroxyl, oxo, alkyl, alkoxy, amino, hydroxyalkyl and halo.

16. The compound according to claim 1, wherein $R^{32}$ is methyl.

17. The compound according to claim 1, wherein $R^{32}$ is alkyl substituted with —$NR^{34}R^{34a}$.

18. The compound according to claim 3, wherein $R^{32}$ is methyl.

19. The compound according to claim 2, wherein $R^{32}$ is methyl.

20. The compound according to claim 1, wherein $R^{32}$ is U or —CH$_2$—U, and wherein U is selected from pyrrolidinyl, thiazolidinyl, morpholinyl, azetidinyl, cyclobutyl, cyclopropyl, tetrahydrofuranyl, pyrazinyl, imidazolyl, piperazinyl, thienyl, thienylmethyl, furanyl, phenyl, prolinamidyl, pyridinyl, tetrahydronaphthalene, tetrazolyl, isoindolinyl, pyranyl, cyclopentyl, and octahydro-1H-indolyl.

21. The compound according to claim 1, wherein $R^{11}$, when present, is halo or lower alkyl.

22. The compound according to claim 1, wherein $R^{11}$, when present, is lower alkyl.

23. The compound according to claim 1, wherein n2 is 0.

24. The compound according to claim 1, wherein $R^2$ is

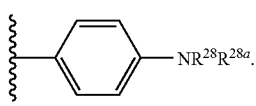

25. The compound according to claim 1, wherein $R^2$ is

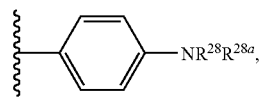

and wherein $R^{28}$ and $R^{28a}$, together with the nitrogen atom to which they are attached, form a heterocycloalkyl.

26. The compound according to claim 1 having Formula V:

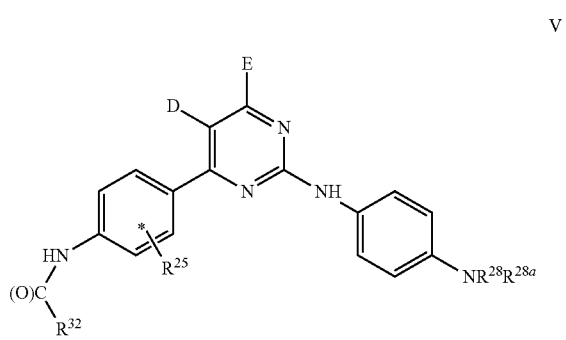

wherein $R^{28}$ and $R^{28a}$, together with the nitrogen atom to which they are attached, form a heterocycloalkyl, wherein the heterocycloalkyl is optionally substituted with one or two $R^{31}$.

27. The compound according to claim 26, wherein D, E and $R^{25}$ are each hydrogen.

28. The compound according to claim 26, wherein $R^{32}$ is heterocycloalkyl.

29. The compound according to claim 26, wherein $R^{32}$ is alkyl optionally substituted with alkoxy, hydroxy, amino, alkylamino, or dialkylamino.

30. A compound selected from

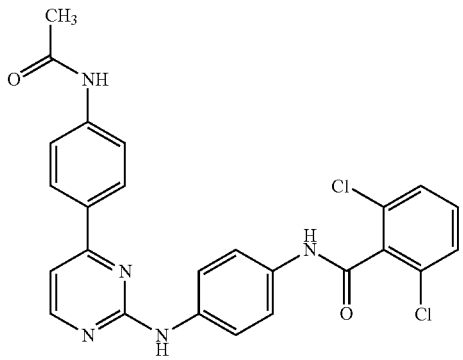

N-(4-{[4-[4-acetylamino)phenyl]pyrimidin-2-yl}amino)phenyl]-2,6-dichlorobenzamide

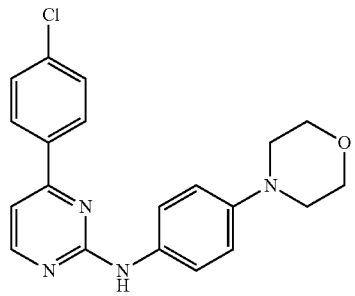

4-(4-chlorophenyl)-N-(4-morpholin-4-ylphenyl)pyrimidin-2-amine

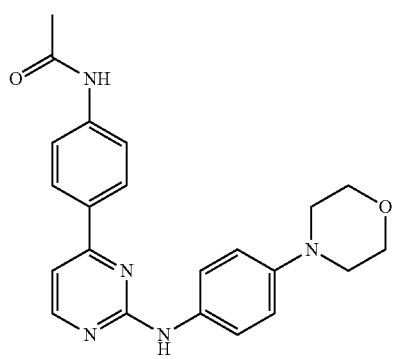

N-(4-{2-[(4-morpholin-4-ylphenyl)amino]pyrimidin-4-yl}phenyl)acetamide

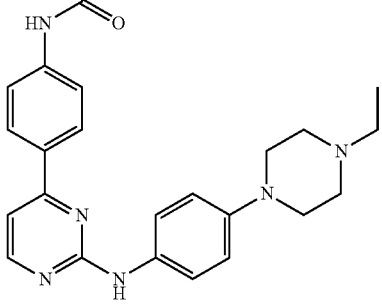

N-[4-(2-{[4-(4-ethylpiperazin-1-yl)phenyl]amino}pyrimidin-4-yl)phenyl]acetamide

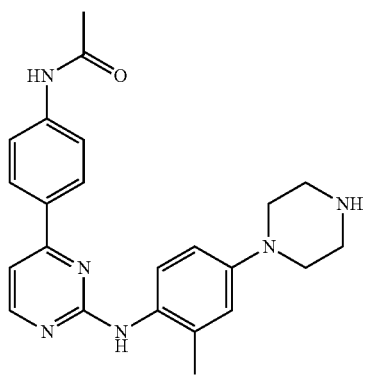

N-(4-{2-[(2-methyl-4-piperazin-1-ylphenyl)amino]pyrimidin-4-yl}phenyl)acetamide

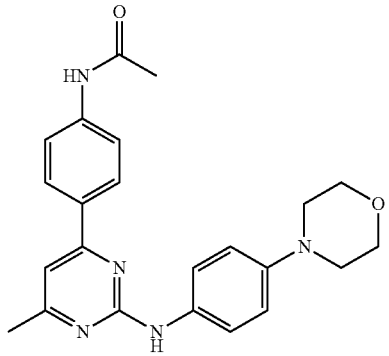

N-(4-{6-methyl-2-[(4-morpholin-4-ylphenyl)amino]pyrimidin-4-yl}phenyl)acetamide

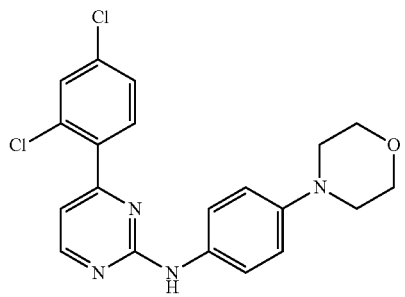

4-(2,4-dichlorophenyl)-N-(4-morpholin-4-ylphenyl)pyrimidin-2-amine

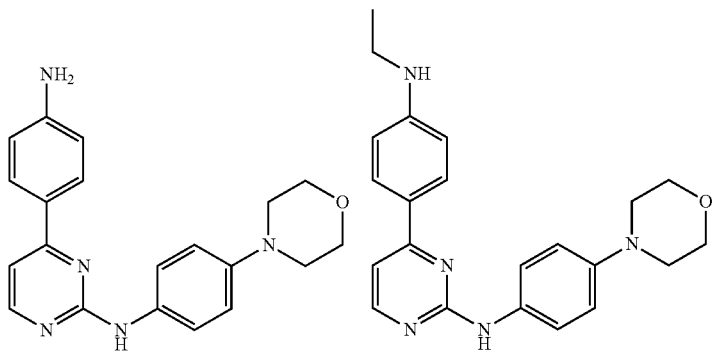

4-(4-aminophenyl)-N-(4-morpholin-4-ylphenyl)pyrimidin-2-amine

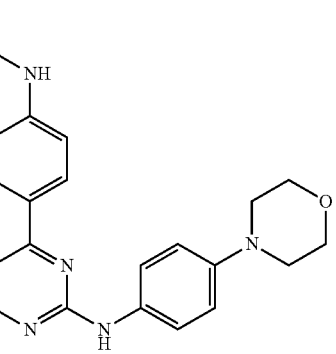

4-[4-ethylamino)-N-(4-morpholin-4-ylphenyl)pyrimidin-2-amine

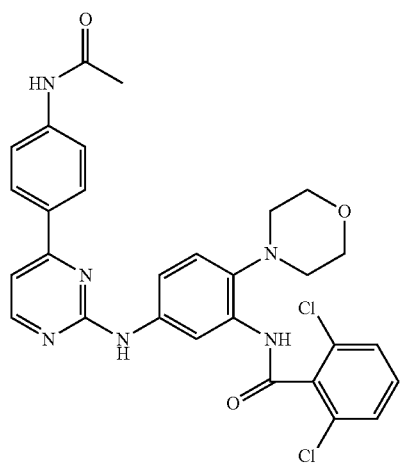

N-[5-({4-[4-(acetylamino)phenyl]pyrimidin-2-yl}amino)-2-morpholin-4-ylphenyl]-2,6-dichlorobenzamide

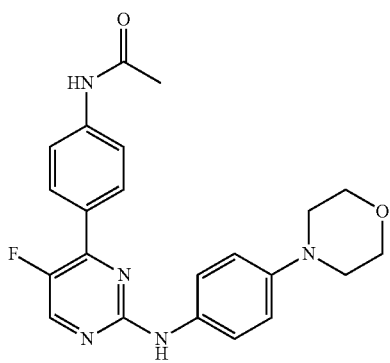

N-(4-{5-fluoro-2-[(4-morpholin-4-ylphenyl)amino]pyrimidin-4-yl}phenyl)acetamide

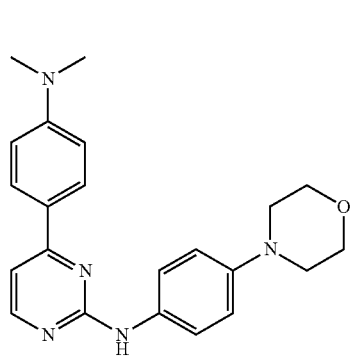

4-[4-(dimethylamino)phenyl]-N-(4-morpholin-4-ylphenyl)pyrimidin-2-amine

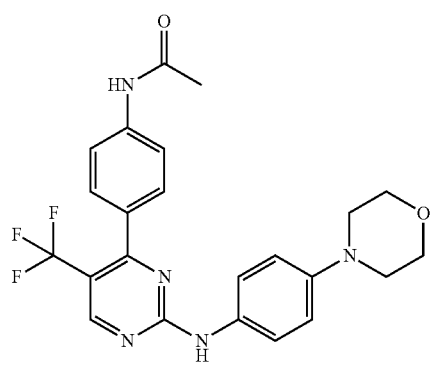

N-(4-{2-[(4-morpholin-4-ylphenyl)amino]-5-(trifluoromethyl)pyrimidin-4-yl}phenyl)acetamide

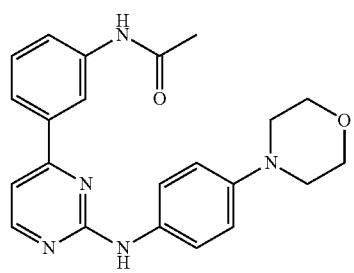

N-(3-{2-[(4-morpholin-4-ylphenyl)amino]pyrimidin-4-yl}phenyl)acetamide

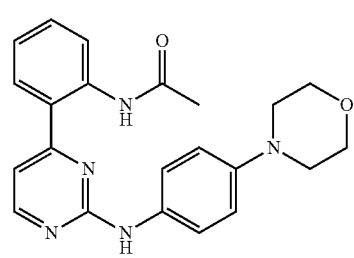

N-(2-{2-[(4-morpholin-4-ylphenyl)amino]pyrimidin-4-yl}phenyl)acetamide

-continued

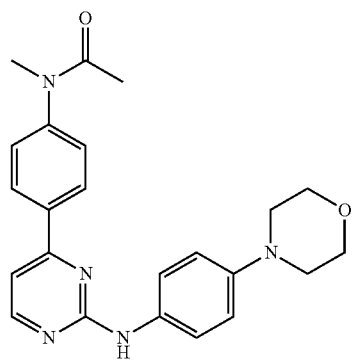

N-methyl-N-(4-{2-[(4-morpholin-4-ylphenyl)amino]pyrimidin-4-yl}phenyl)acetamide

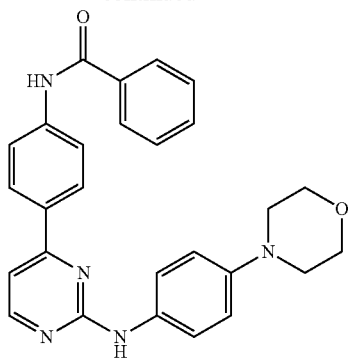

N-(4-{2-[(4-morpholin-4-ylphenyl)amino]pyrimidin-4-yl}phenyl)benzamide

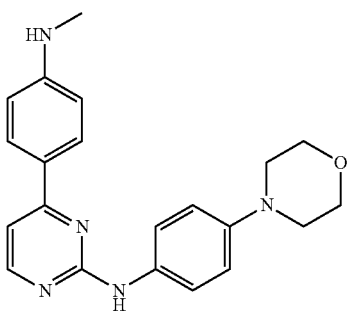

4-[4-(methylamino)phenyl]-N-(4-morpholin-4-ylphenyl)pyrimidin-2-amine

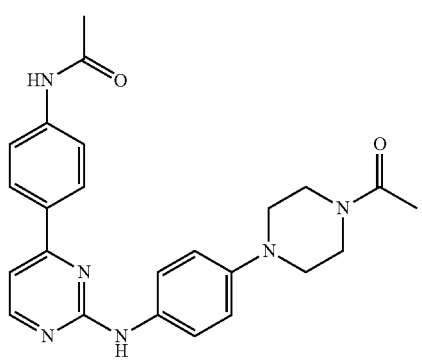

N-[4-(2-{[4-(4-acetylpiperazin-1-yl)phenyl]amino}pyrimidin-4-yl)phenyl]acetamide

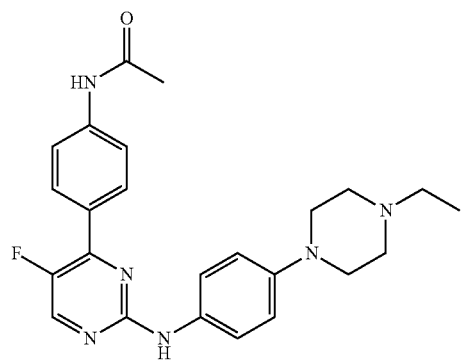

N-[4-(2-{[4-(4-ethylpiperazin-1-yl)phenyl]amino}-5-fluoropyrimidin-4-yl)phenyl]acetamide

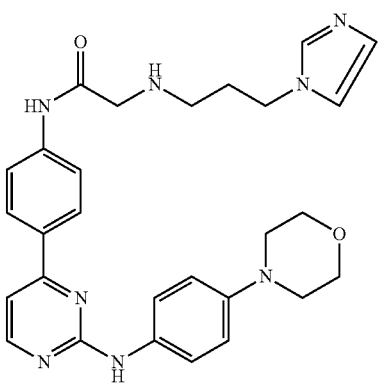

$N^2$-[3-(1H-imidazol-1-yl)propyl]-N-(4-{2-[(4-morpholin-4-ylphenyl)amino]pyrimidin-4-yl}phenyl)glycinamide -continued

| 701 | 702 |
|---|---|
| 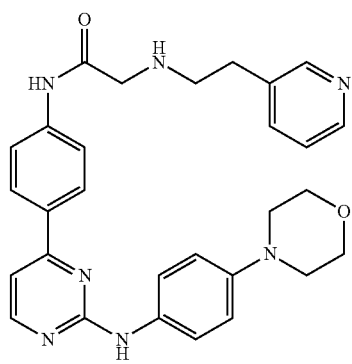 N-(4-{2-[(4-morpholin-4-ylphenyl)amino]pyrimidin-4-yl}phenyl)-N²-(2-pyridin-3-ylethyl)glycinamide | 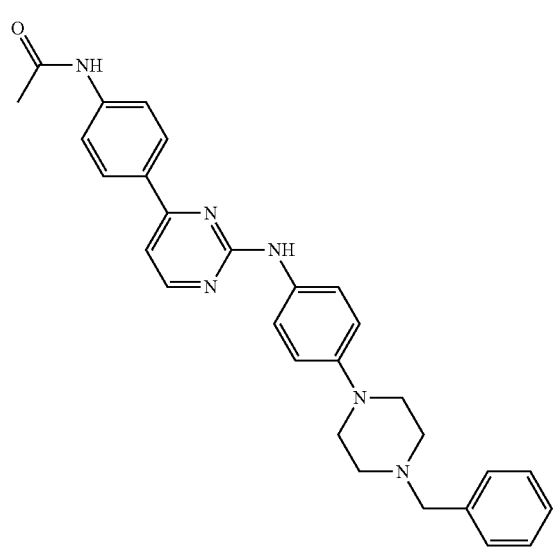 N-{4-[2-({4-[4-(phenylmethyl)piperazin-1-yl]phenyl}amino)pyrimidin-4-yl]phenyl}acetamide |

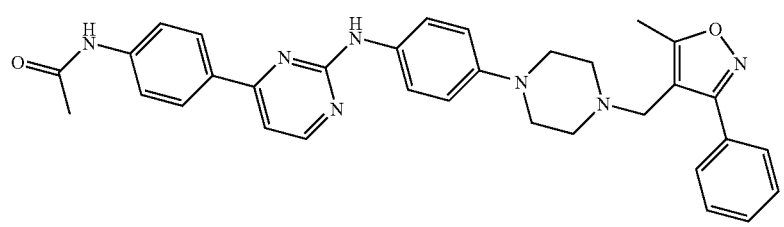

N-(4-{2-[(4-{4-[(5-methyl-3-phenylisoxazol-4-yl)methyl]piperazin-1-yl}phenyl)amino]pyrimidin-4-yl}phenyl)acetamide

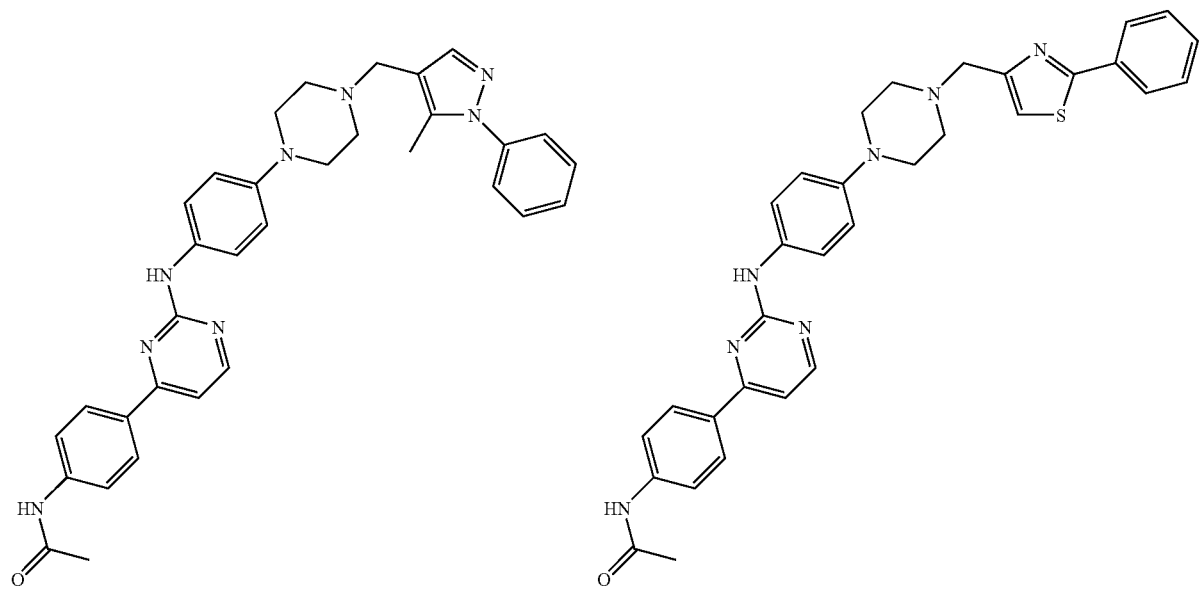

| N-(4-{2-[(4-{4-[(5-methyl-1-phenyl-1H-pyrazol-4-yl)methyl]piperazin-1-yl}phenyl)amino]pyrimidin-4-yl}phenyl)acetamide | N-(4-{2-[(4-{4-[(2-phenyl-1,3-thiazol-4-yl)methyl]piperazin-1-yl}phenyl)amino]pyrimidin-4-yl}phenyl)acetamide |

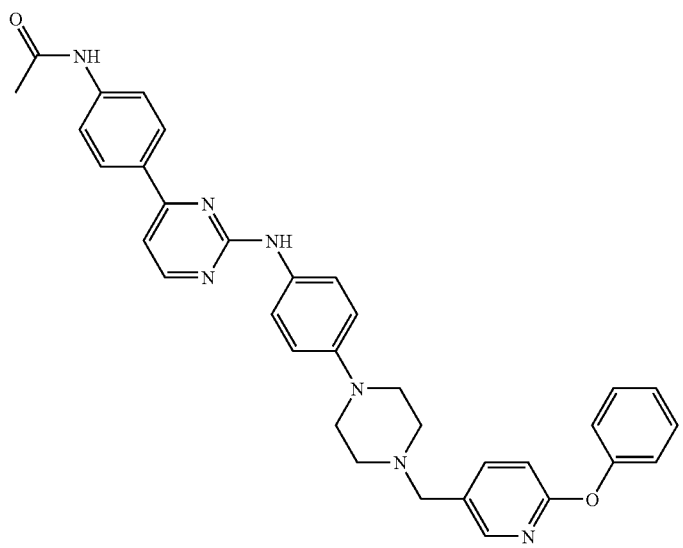
N-[4-(2-{[4-(4-{[6-(phenyloxy)pyridin-3-yl]methyl}piperazin-1-yl]phenyl]amino}pyrimidin-4-yl)phenyl]acetamide
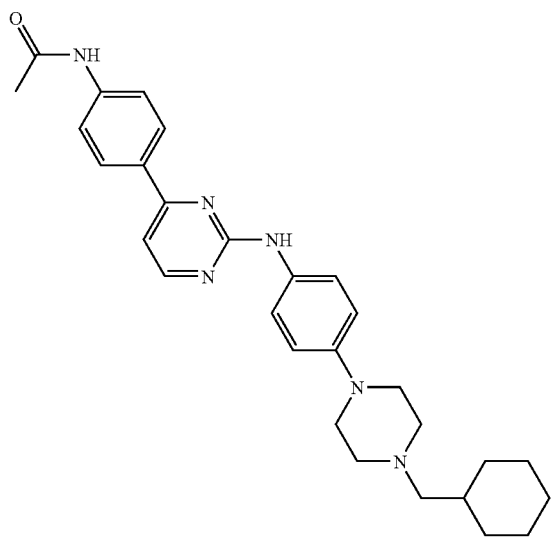
N-{4-[2-({4-[4-(cyclohexylmethyl)piperazin-1-yl]phenyl}amino)pyrimidin-4-yl]phenyl}acetamide
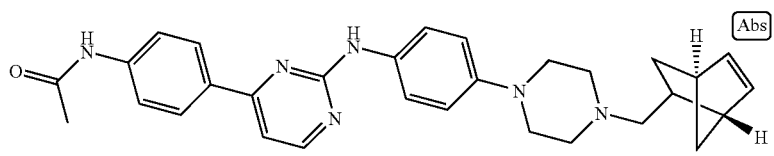
N-(4-{2-[(4-{4-[(1S,4S)-bicyclo[2.2.1]hept-2-en-2-ylmethyl]piperazin-1-yl}phenyl)amino]pyrimidin-4-yl}phenyl)acetamide -continued
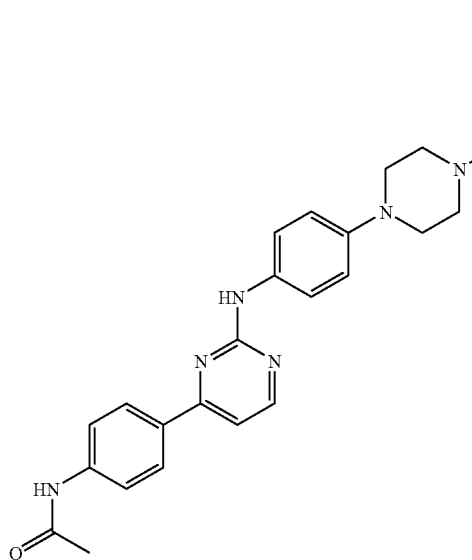
N-[4-(2-{[4-(4-pentylpiperazin-1-yl)phenyl]amino}pyrimidin-4-yl)phenyl]acetamide
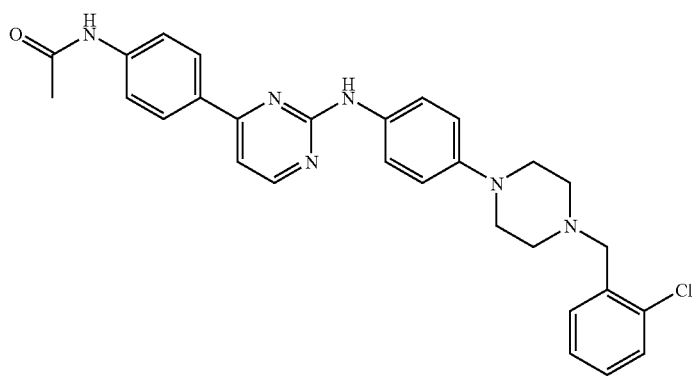
N-(4-{2-[(4-{4-[(2-chlorophenyl)methyl]piperazin-1-yl}phenyl)amino]pyrimidin-4-yl}phenyl)acetamide
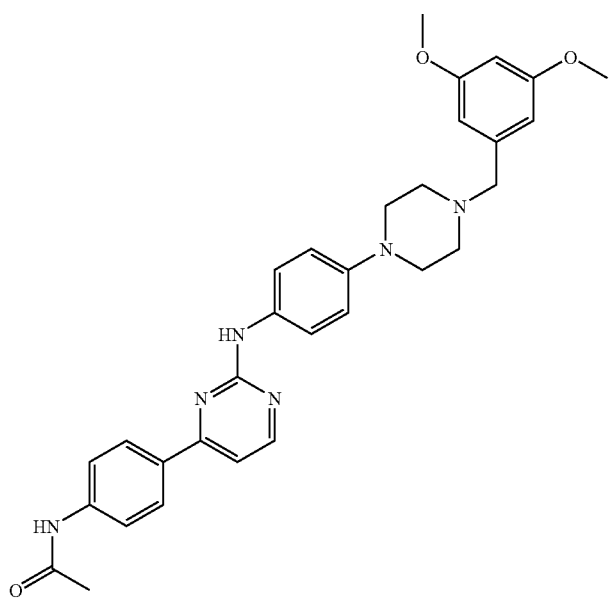
N-[4-(2-{[4-(4-{[3,5-bis(methyloxy)phenyl]methyl}piperazin-1-yl)phenyl]amino}pyrimidin-4-yl)phenyl]acetamide

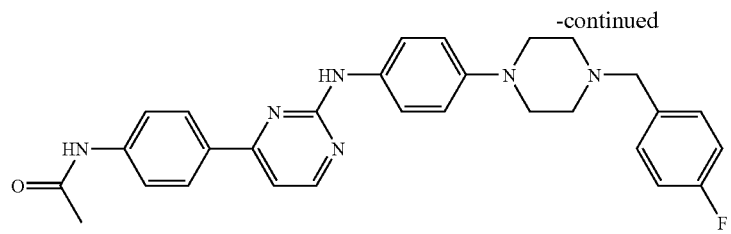

N-(4-{2-[(4-{4-[(4-fluorophenyl)methyl]piperazin-1-yl}phenyl)amino]pyrimidin-4-yl}phenyl)acetamide

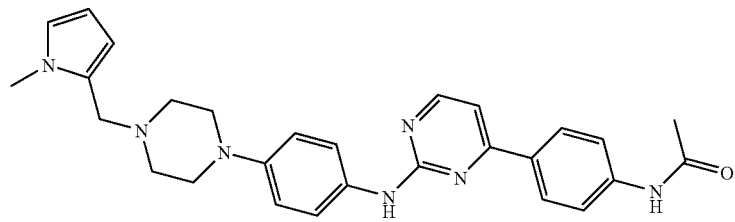

N-(4-{2-[(4-{4-[(1-methyl-1H-pyrrol-2-yl)methyl]piperazin-1-yl}phenyl)amino]pyrimidin-4-yl}phenyl)acetamide

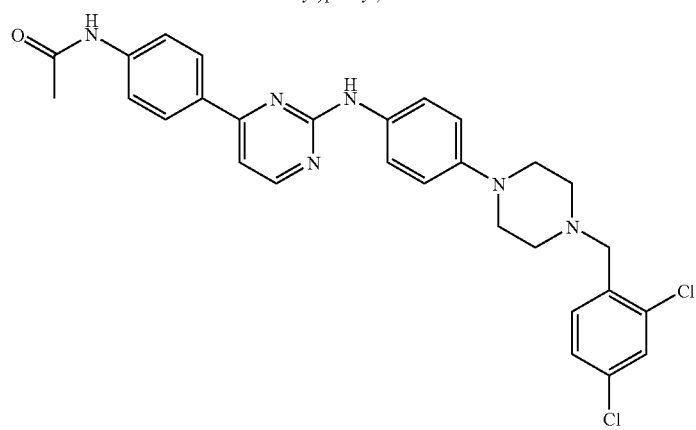

N-(4-{2-[(4-{4-[(2,4-dichlorophenyl)methyl]piperazin-1-yl}phenyl)amino]pyrimidin-4-yl}phenyl)acetamide

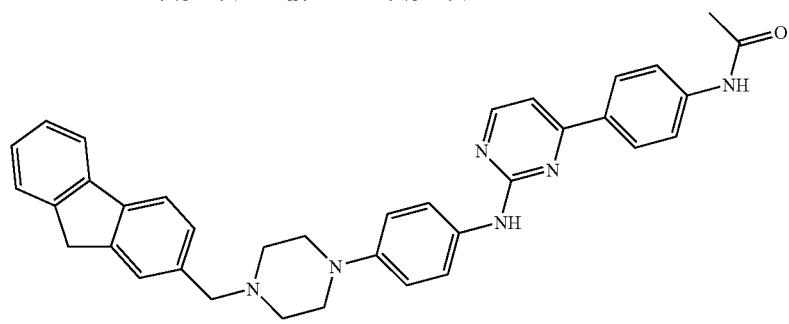

N-{4-[2-({4-[4-(9H-fluoren-2-ylmethyl)piperazin-1-yl]phenyl}amino)pyrimidin-4-yl]phenyl}acetamide

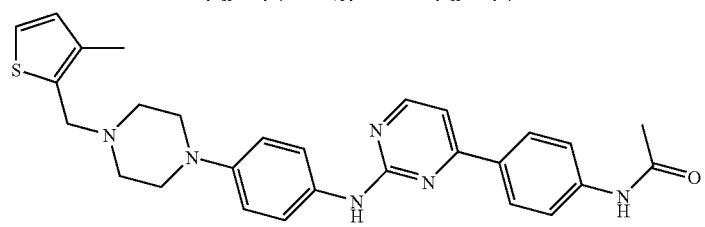

N-(4-{2-[(4-{4-[(3-methyl-2-thienyl)methyl]piperazin-1-yl}phenyl)amino]pyrimidin-4-yl}phenyl)acetamide -continued
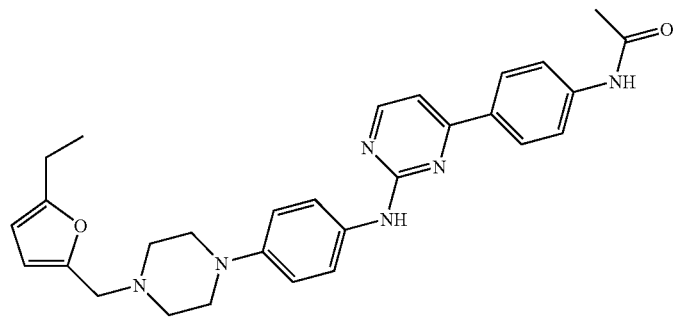
N-(4-{2-[(4-{4-[(5-ethylfuran-2-yl)methyl]piperazin-1-yl}phenyl)amino]pyrimidin-4-yl}phenyl)acetamide
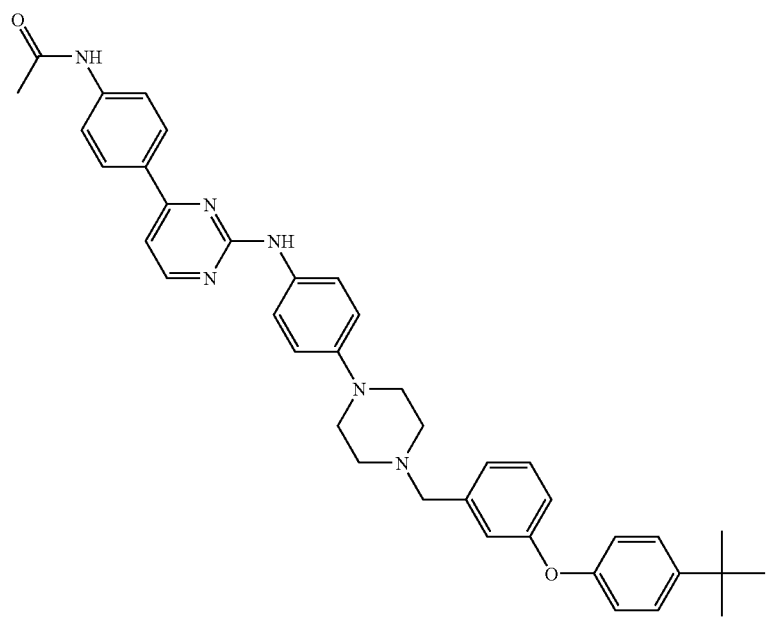
N-(4-{2-[(4-{4-[(3-{[4-(1,1-dimethylethyl)phenyl]oxy}phenyl)methyl]piperazin-1-yl}phenyl)amino]pyrimidin-4-yl}phenyl)acetamide
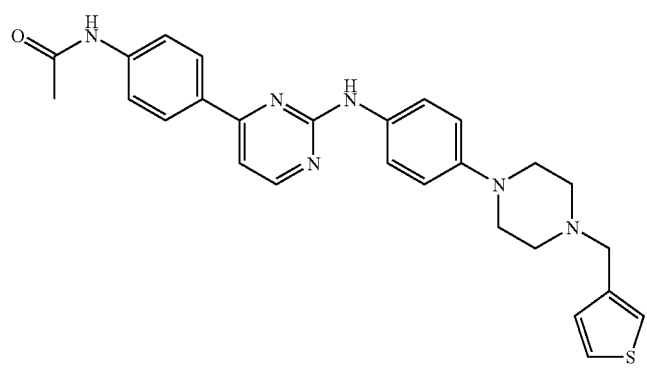
N-{4-[2-({4-[4-(3-thienylmethyl)piperazin-1-yl]phenyl}amino)pyrimidin-4-yl]phenyl}acetamide -continued
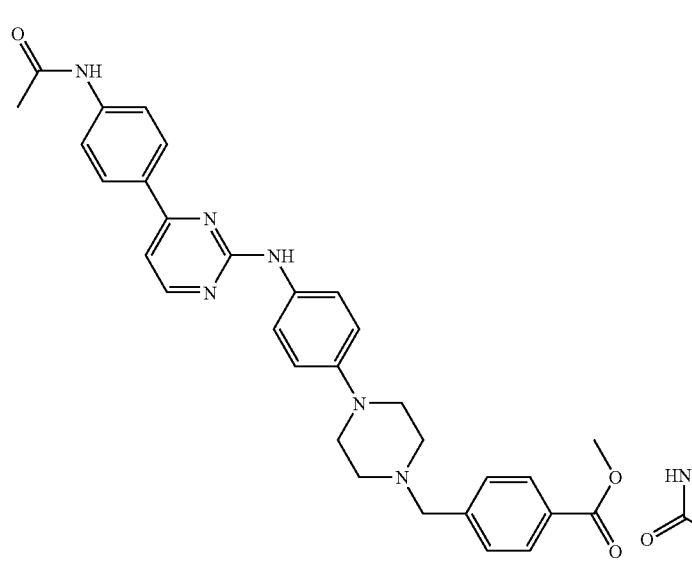
methyl 4-({4-[4-({4-[4-(acetylamino)phenyl]pyrimidin-2-yl}amino)phenyl]piperazin-1-yl}methyl)benzoate
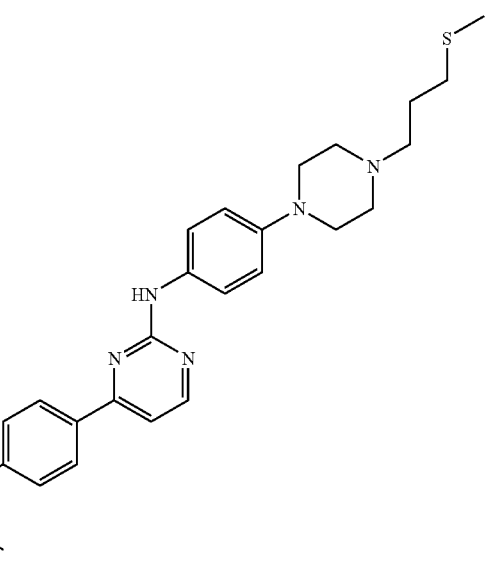
N-(4-{2-[(4-{4-[3-(methylthio)propyl]piperazin-1-yl}phenyl)amino]pyrimidin-4-yl}phenyl)acetamide
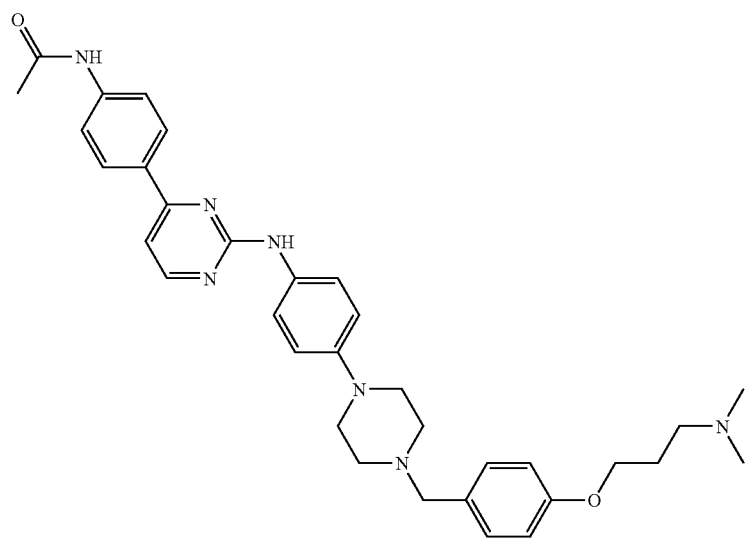
N-(4-{2-[(4-{4-[(4-{[3-(dimethylamino)propyl]oxy}phenyl)methyl]piperazin-1-yl}phenyl)amino]pyrimidin-4-yl}phenyl)acetamide

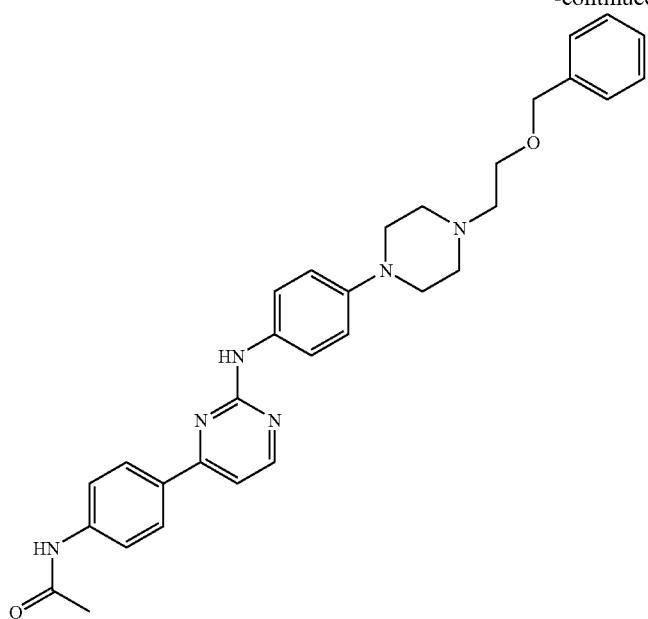
N-[4-(2-{[4-(4-{2-[(phenylmethyl)oxy]ethyl}piperazin-1-yl)phenyl]amino}pyrimidin-4-yl)phenyl]acetamide
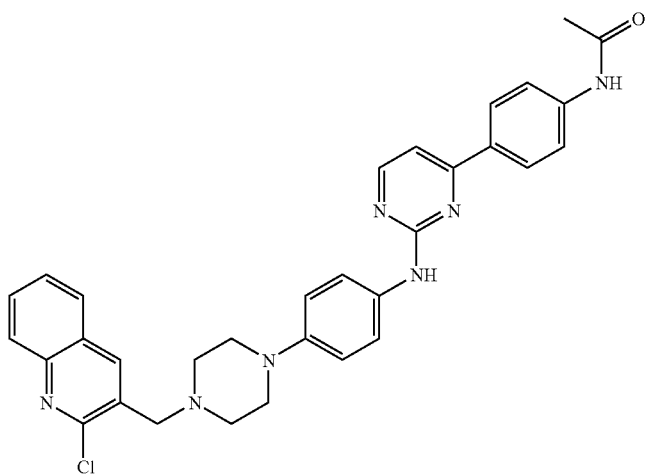
N-(4-{2-[(4-{4-[(2-chloroquinolin-3-yl)methyl]piperazin-1-yl}phenyl)amino]pyrimidin-4-yl}phenyl)acetamide
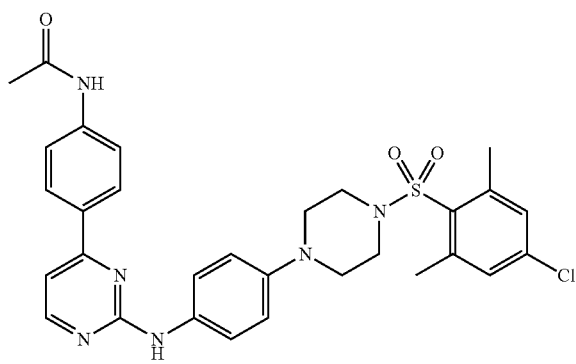
N-(4-{2-[(4-{4-[(4-chloro-2,6-dimethylphenyl)sulfonyl]piperazin-1-yl}phenyl)amino]pyrimidin-4-yl}phenyl)acetamide
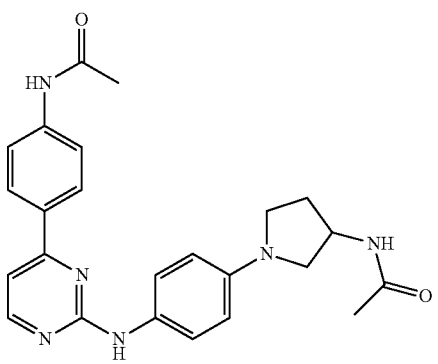
N-{1-[4-({4-[4-(acetylamino)phenyl]pyrimidin-2-yl}amino)phenyl]pyrrolidin-3-yl}acetamide -continued

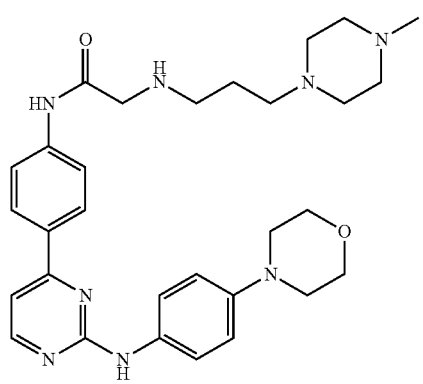

N²-[3-(4-methylpiperazin-1-yl)propyl]-N-(4-{2-[(4-morpholin-4-ylphenyl)amino]pyrimidin-4-yl}phenyl)glycinamide

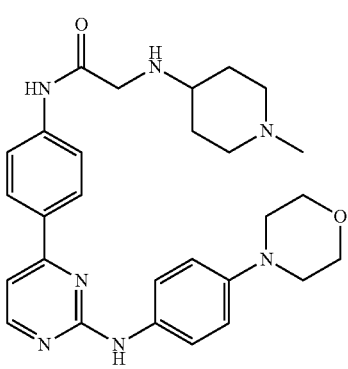

N²-(1-methylpiperadin-4-yl)-N-(4-{2-[(4-morpholin-4-ylphenyl)amino]pyrimidin-4-yl}phenyl)glycinamide

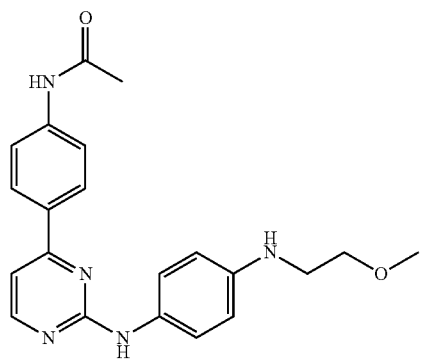

N-(4-{2-[(4-{[2-(methyloxy)ethyl]amino}phenyl)amino]pyrimidin-4-yl}phenyl)acetamide

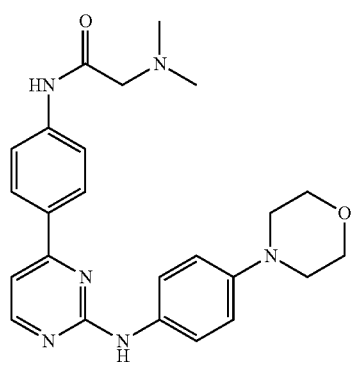

2-(dimethylamino)-N-4-(2-(4-morpholinophenylamino)pyrimidin-4-yl)phenyl)acetamide

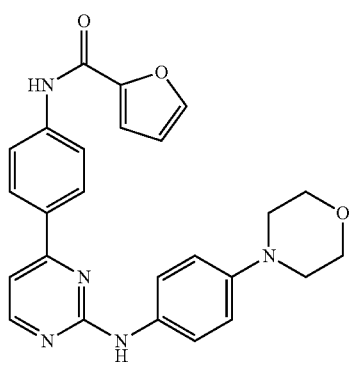

N-(4-{2-[(4-morpholin-4-ylphenyl)amino]pyrimidin-4-yl}phenyl)furan-2-carboxamide

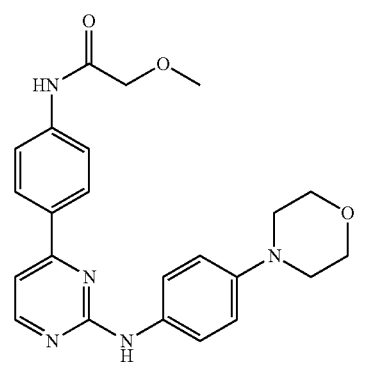

2-(methyloxy)-N-(4-{2-[(4-morpholin-4-ylphenyl)amino]pyrimidin-4-yl}phenyl)acetamide

717

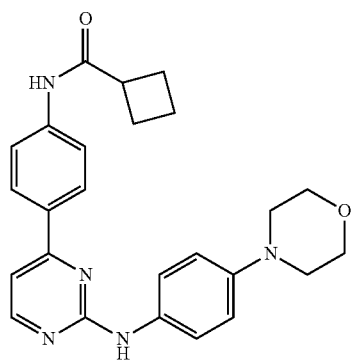

N-(4-{2-[(4-morpholin-4-
ylphenyl)amino]pyrimidin-4-
yl}phenyl)cyclobutanecarboxamide

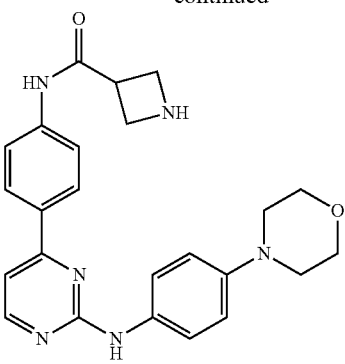

N-(4-{2-[(4-morpholin-4-
ylphenyl)amino]pyrimidin-4-yl}phenyl)azetidine-3-
carboxamide

718

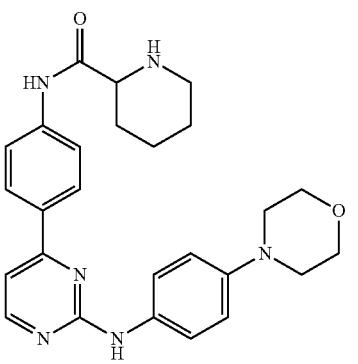

N-(4-{2-[(4-morpholin-4-
ylphenyl)amino]pyrimidin-4-yl}phenyl)piperidine-
2-carboxamide

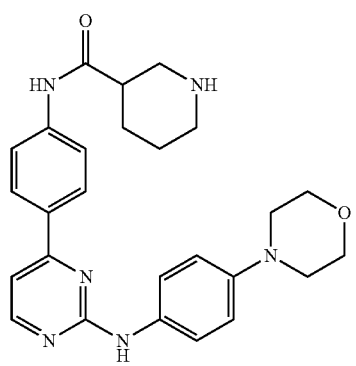

N-(4-{2-[(4-morpholin-4-
ylphenyl)amino]pyrimidin-4-yl}phenyl)piperidine-
3-carboxamide

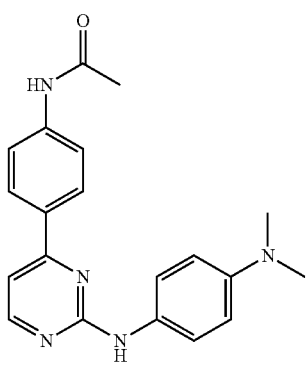

N-[4-(2-{[4-
(dimethylamino)phenyl]amino}pyrimidin-4-
yl)phenyl]acetamide

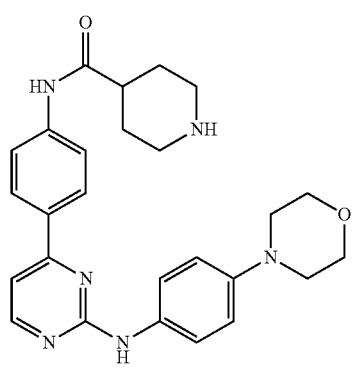

N-(4-{2-[(4-morpholin-4-
ylphenyl)amino]pyrimidin-4-yl}phenyl)piperidine-
4-carboxamide

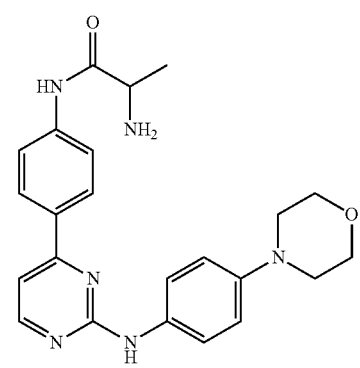

2-amino-N-(4-(2-(4-
morpholinophenylamino)pyrimidin-4-
yl)phenyl)propanamide

719

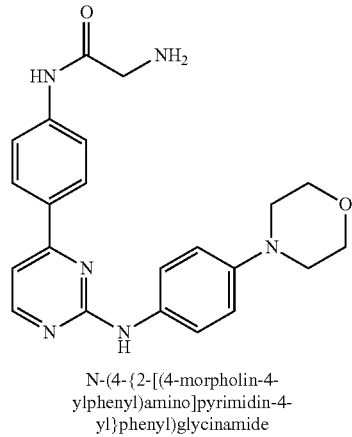

N-(4-{2-[(4-morpholin-4-
ylphenyl)amino]pyrimidin-4-
yl}phenyl)glycinamide

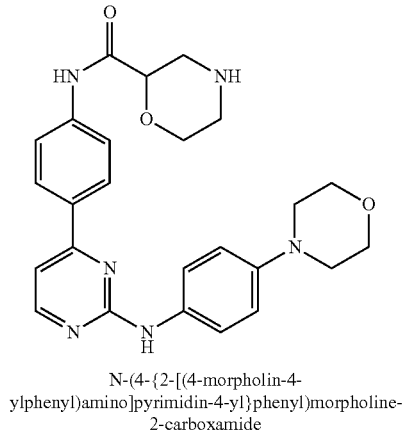

N-(4-{2-[(4-morpholin-4-
ylphenyl)amino]pyrimidin-4-yl}phenyl)morpholine-
2-carboxamide

720

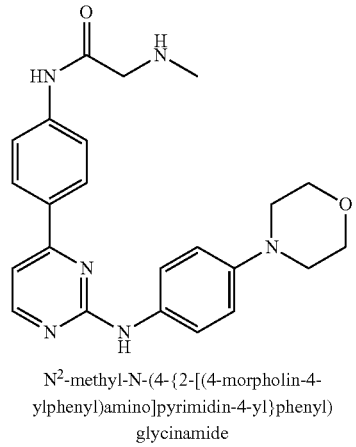

N²-methyl-N-(4-{2-[(4-morpholin-4-
ylphenyl)amino]pyrimidin-4-yl}phenyl)
glycinamide

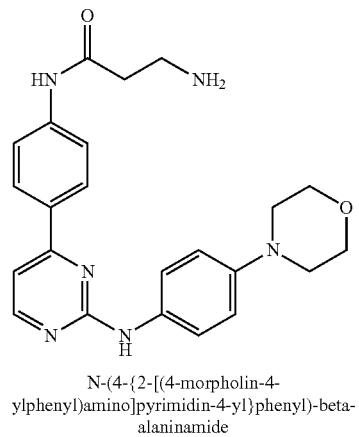

N-(4-{2-[(4-morpholin-4-
ylphenyl)amino]pyrimidin-4-yl}phenyl)-beta-
alaninamide

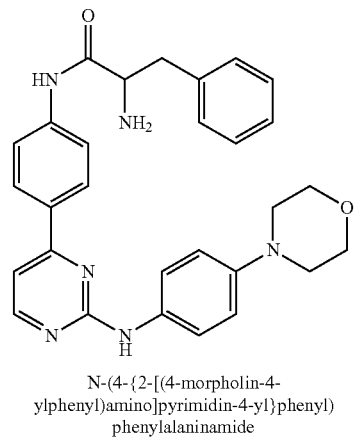

N-(4-{2-[(4-morpholin-4-
ylphenyl)amino]pyrimidin-4-yl}phenyl)
phenylalaninamide

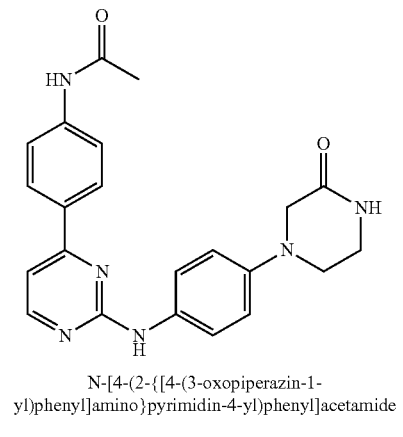

N-[4-(2-{[4-(3-oxopiperazin-1-
yl)phenyl]amino}pyrimidin-4-yl)phenyl]acetamide

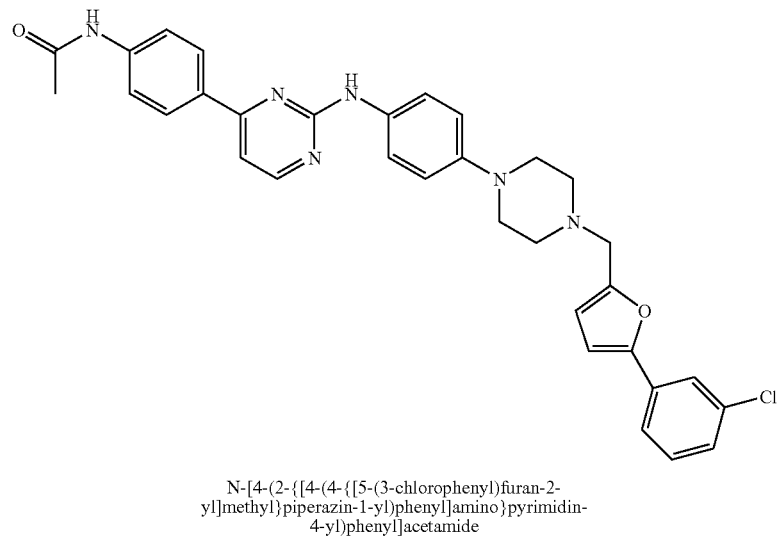

N-[4-(2-{[4-(4-{[5-(3-chlorophenyl)furan-2-
yl]methyl}piperazin-1-yl)phenyl]amino}pyrimidin-
4-yl)phenyl]acetamide -continued
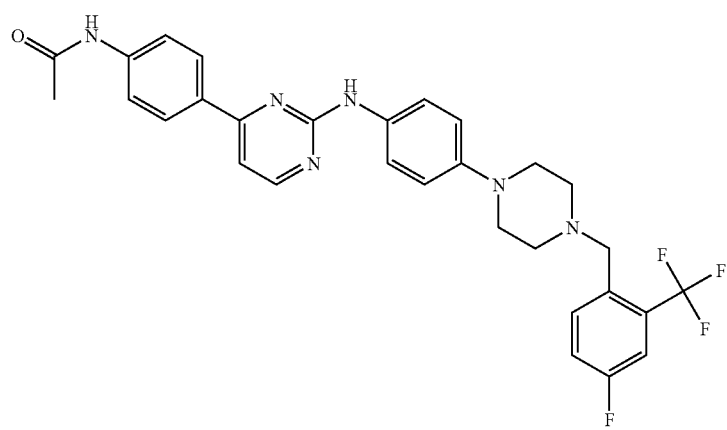
N-[4-(2-{[4-(4-{[4-fluoro-2-(trifluoromethyl)phenyl]methyl}piperazin-1-yl)phenyl]amino}pyrimidin-4-yl)phenyl]acetamide
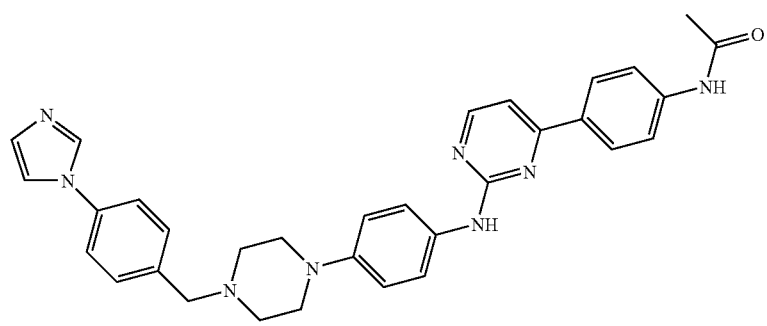
N-[4-(2-{[4-(4-{[4-(1H-imidazol-1-yl)phenyl]methyl}piperazin-1-yl)phenyl]amino}pyrimidin-4-yl)phenyl]acetamide
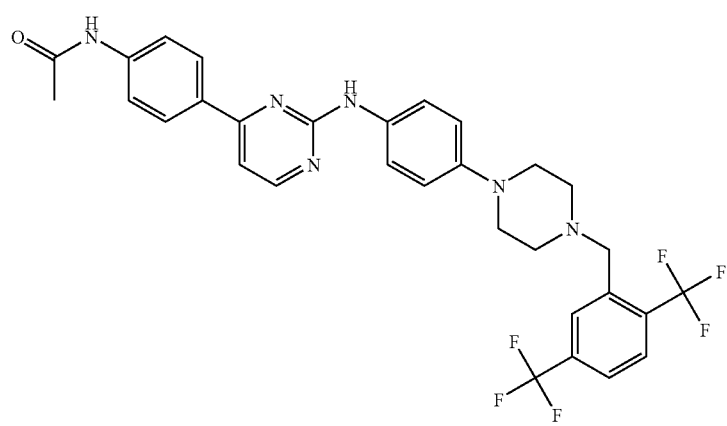
N-[4-(2-{[4-(4-{[2,5-bis(trifluoromethyl)phenyl]methyl}piperazin-1-yl)phenyl]amino}pyrimidin-4-yl)phenyl]acetamide 723
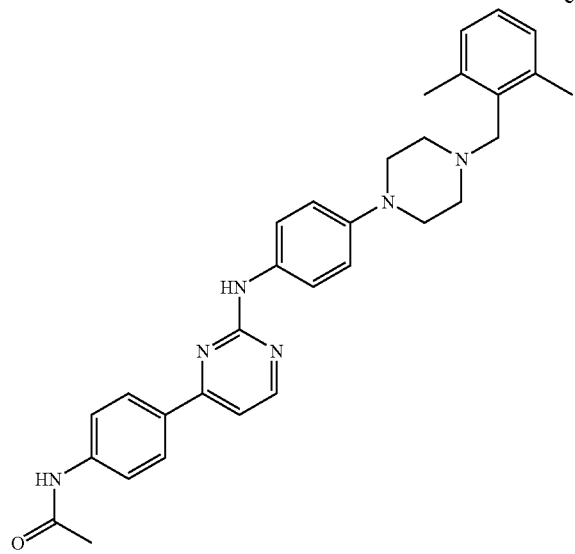
N-(4-{2-[(4-{4-[(2,6-dimethylphenyl)methyl]piperazin-1-yl}phenyl)amino]pyrimidin-4-yl}phenyl)acetamide
724
-continued
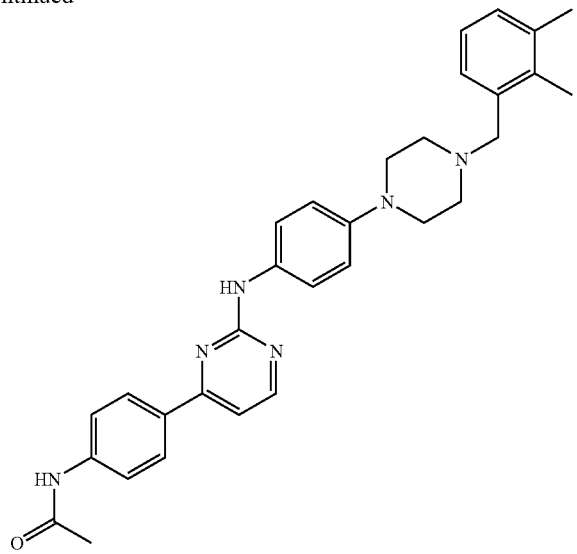
N-(4-{2-[(4-{4-[(2,3-dimethylphenyl)phenyl)]methyl]piperazin-1-yl}phenyl)amino]pyrimidin-4-yl}phenyl)acetamide
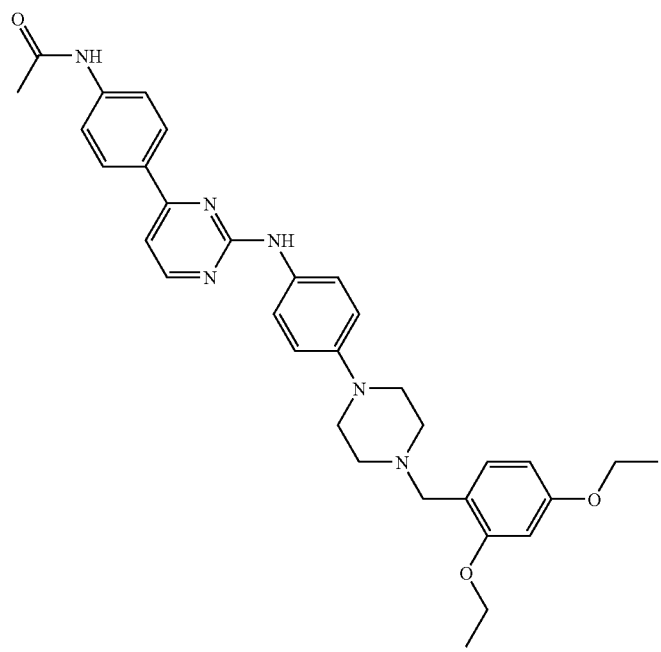
N-[4-(2-{[4-(4-{[2,4-bis(ethyloxy)phenyl]methyl}piperazin-1-yl)phenyl]amino}pyrimidin-4-yl)phenyl]acetamide

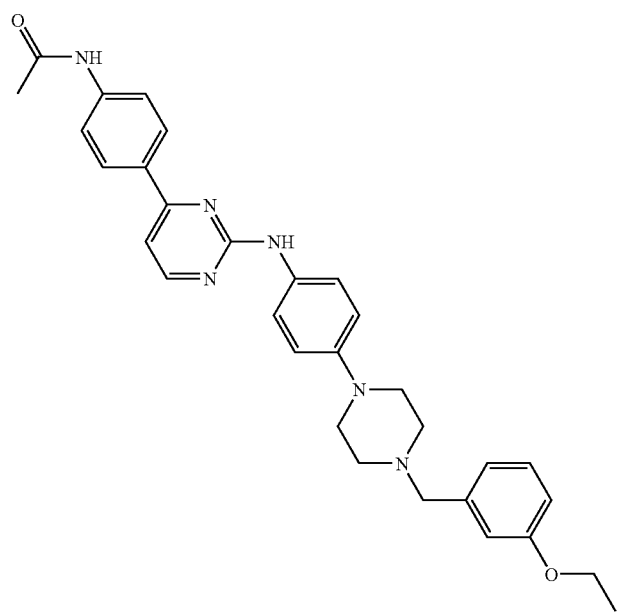
N-[4-(2-{[4-(4-{[3-(ethyloxy)phenyl]methyl}piperazin-1-yl)phenyl]amino}pyrimidin-4-yl)phenyl]acetamide
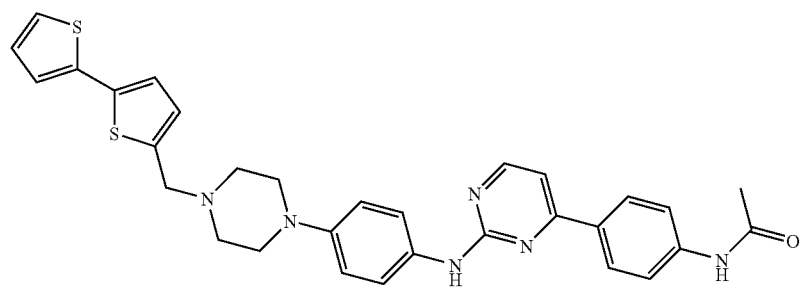
N-{4-[2-({4-[4-(2,2'-bithien-5-ylmethyl)piperazin-1-yl]phenyl}amino)pyrimidin-4-yl]phenyl}acetamide
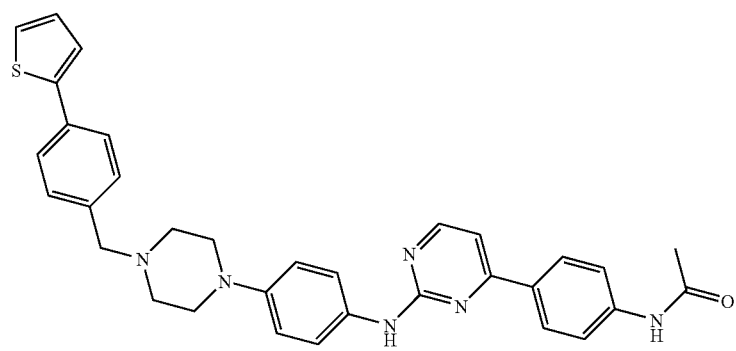
N-[4-(2-{[4-(4-{[4-(2-thienyl)phenyl]methyl}piperazin-1-yl)phenyl]amino}pyrimidin-4-yl)phenyl]acetamide -continued
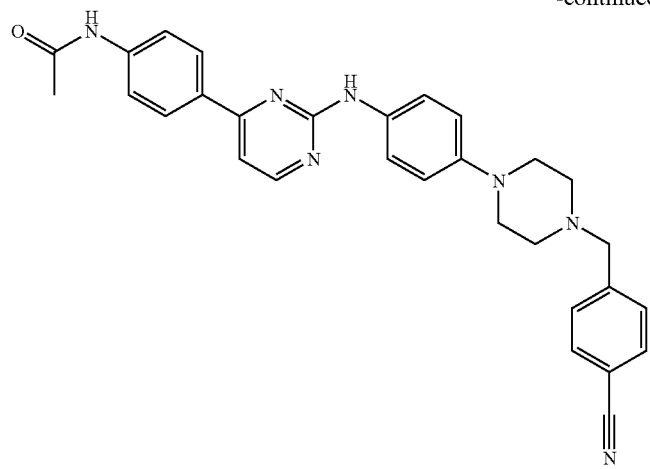
N-(4-{2-[(4-{4-[(4--cyanophenyl)methyl]piperazin-1-yl}phenyl)amino]pyrimidin-4-yl}phenyl)acetamide
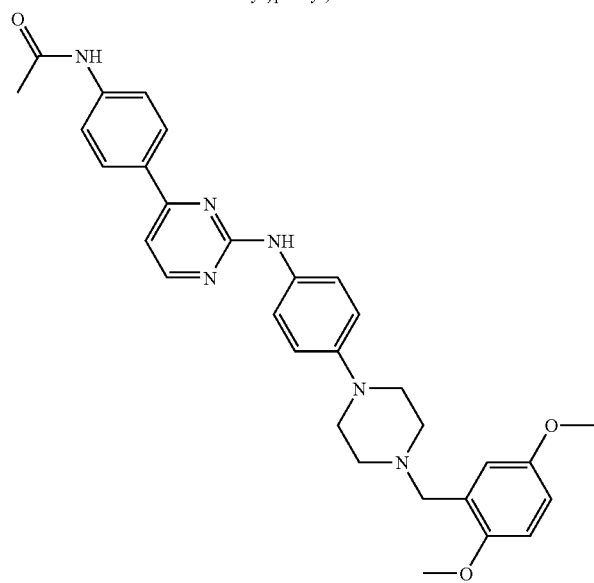
N-[4-(2-{[4-(4-{[2,5-bis(methyloxy)phenyl]methyl}piperazin-1-yl)phenyl]amino}pyrimidin-4-yl)phenyl]acetamide
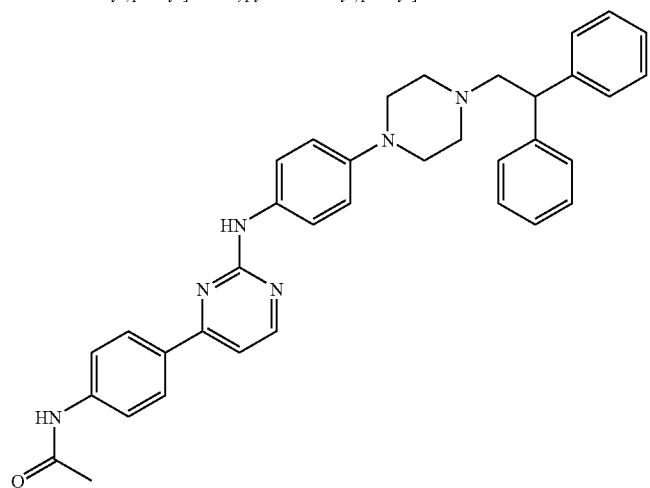
N-{4-[2-({4-[4-(2,2-diphenylethyl)piperazin-1-yl]phenyl}amino)pyrimidin-4-yl]phenyl}acetamide -continued
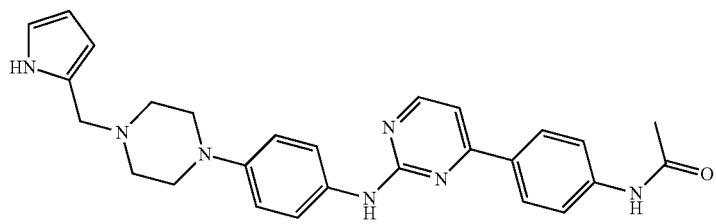
N-{4-[2-({4-[4-(1H-pyrrol-2-ylmethyl)piperazin-1-yl]phenyl}amino)pyrimidin-4-yl]phenyl}acetamide
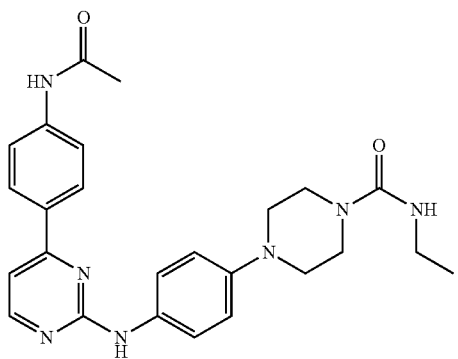
4-[4-({4-[4-(acetylamino)phenyl]pyrimidin-2-yl}amino)phenyl]-N-ethylpiperazine-1-carboxamide
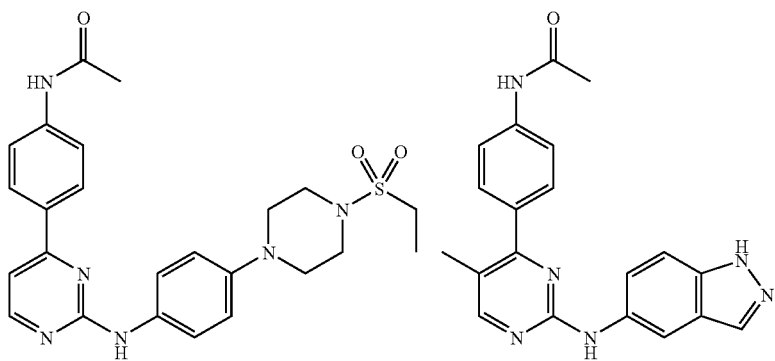
N-{4-[2-({4-[4-(ethylsulfonyl)piperazin-1-yl]phenyl}amino)pyrimidin-4-yl]phenyl}acetamide
N-{4-[2-(1H-indazol-5-ylamino)-5-methylpyrimidin-4-yl]phenyl}acetamide -continued

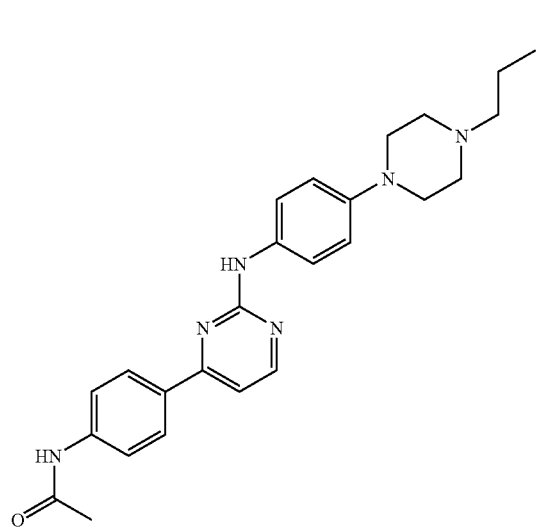

N-[4-(2-{[4-(4-propylpiperazin-1-yl)phenyl]amino}pyrimidin-4-yl)phenyl]acetamide

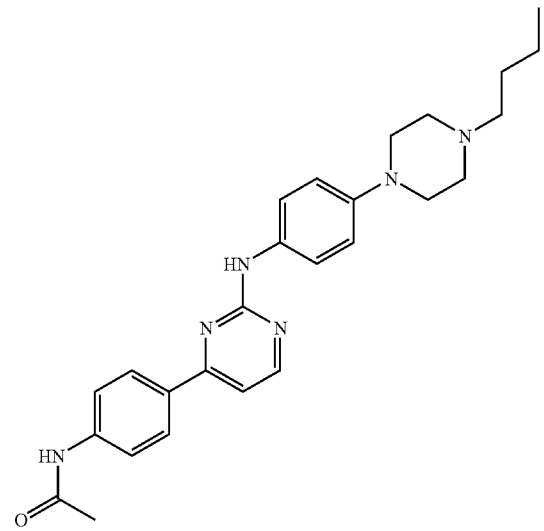

N-[4-(2-{[4-(4-butylpiperazin-1-yl)phenyl]amino}pyrimidin-4-yl)phenyl]acetamide

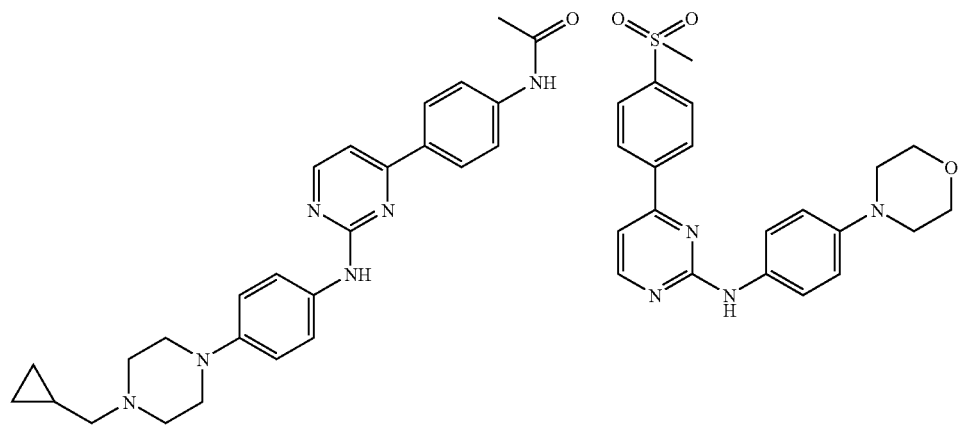

N-{4-[2-({4-[4-(cyclopropylmethyl)piperazin-1-yl]phenyl}amino)pyrimidin-4-yl]phenyl}acetamide 4-[4-(methylsulfonyl)phenyl]-N-(4-morpholin-4-ylphenyl)pyrimidin-2-amine

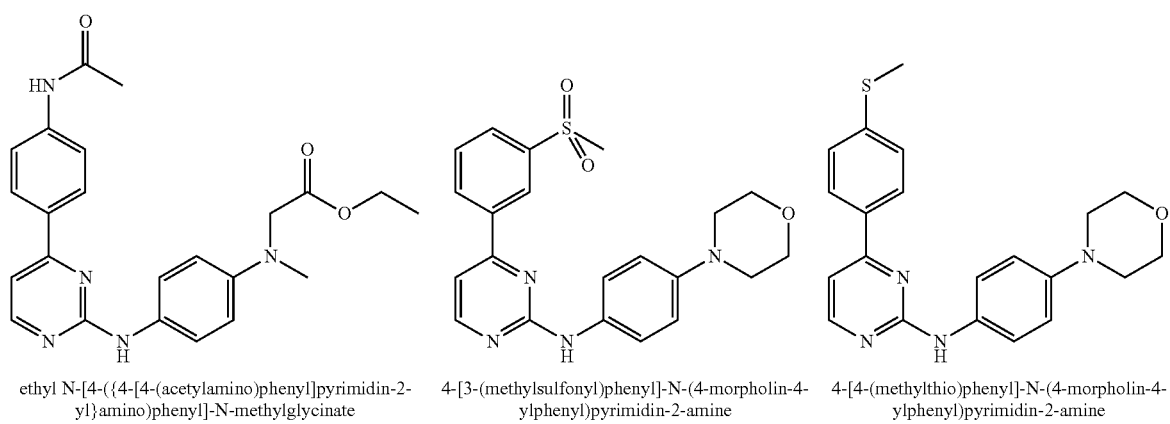

ethyl N-[4-({4-[4-(acetylamino)phenyl]pyrimidin-2-yl}amino)phenyl]-N-methylglycinate 4-[3-(methylsulfonyl)phenyl]-N-(4-morpholin-4-ylphenyl)pyrimidin-2-amine 4-[4-(methylthio)phenyl]-N-(4-morpholin-4-ylphenyl)pyrimidin-2-amine -continued

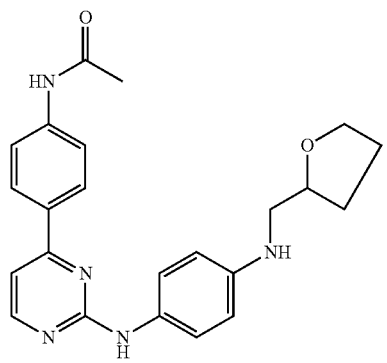

N-{4-[2-({4-[(tetrahydrofuran-2-ylmethyl)amino]phenyl}amino)pyrimidin-4-yl]phenyl}acetamide

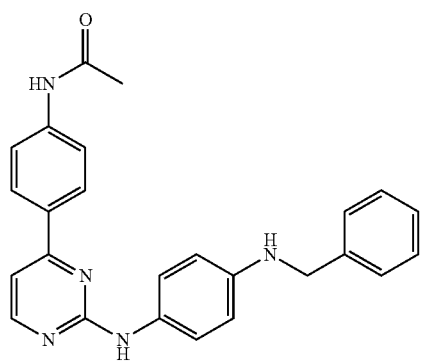

N-{4-[2-({4-[(phenylmethyl)amino]phenyl}amino)pyrimidin-4-yl]phenyl}acetamide

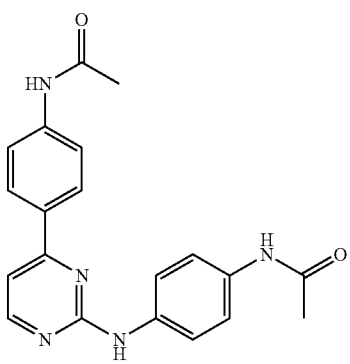

N-{4-[2-({4-(acetylamino)phenyl]amino}pyrimidin-4-yl)phenyl]acetamide

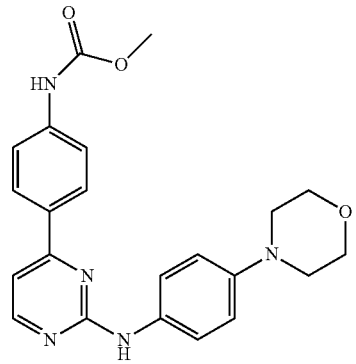

methyl(4-{2-[(4-morpholin-4-ylphenyl)amino]pyrimidin-4-yl}phenyl)carbamate

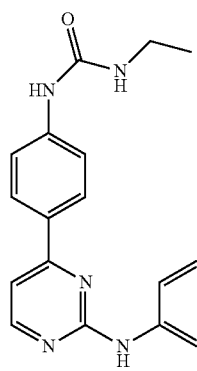

1-ethyl-3-(4-{2-[(4-morpholin-4-ylphenyl)amino]pyrimidin-4-yl}phenyl)urea

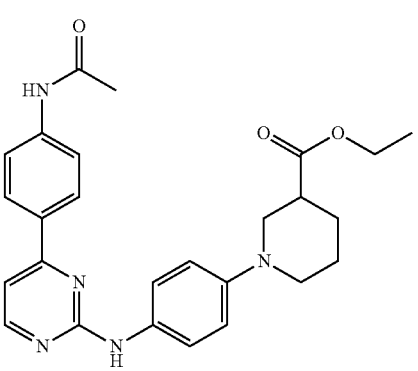

ethyl 1-[4-({4-[4-(acetylamino)phenyl]pyrimidin-2-yl}amino)phenyl]piperidine-3-carboxylate

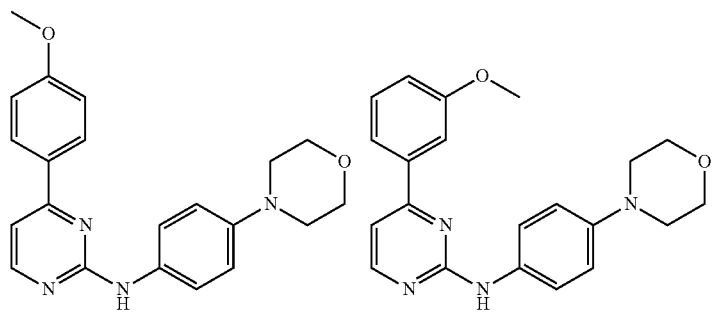

4-[4-(methyloxy)phenyl]-N-(4-morpholin-4-ylphenyl)pyrimidin-2-amine

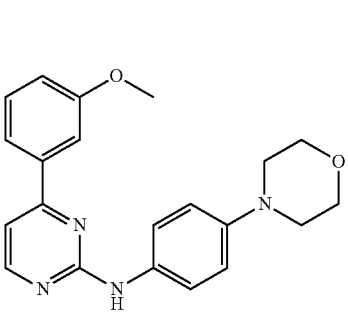

4-[3-(methyloxy)phenyl]-N-(4-morpholin-4-ylphenyl)pyrimidin-2-amine

-continued

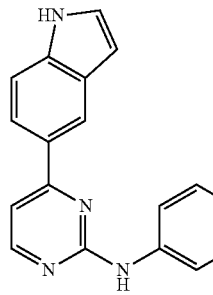

4-(1H-indol-5-yl)-N-(4-morpholin-4-ylphenyl)pyrimidin-2-amine

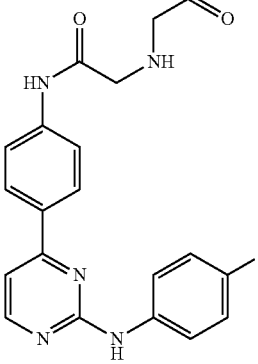

2-[(2-amino-2-oxoethyl)amino]-N-(4-{2-[(4-morpholin-4-ylphenyl)amino]pyrimidin-4-yl}phenyl)acetamide

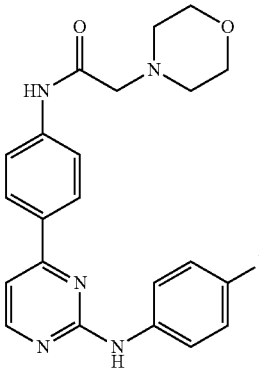

2-morpholin-4-yl-N-(4-{2-[(4-morpholin-4-ylphenyl)amino]pyrimidin-4-yl}phenyl)acetamide

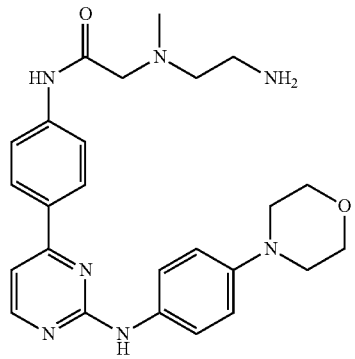

N²-(2-aminoethyl)-N²-methyl-N-(4-{2-[(4-morpholin-4-ylphenyl)amino]pyrimidin-4-yl}phenyl)glycinamide

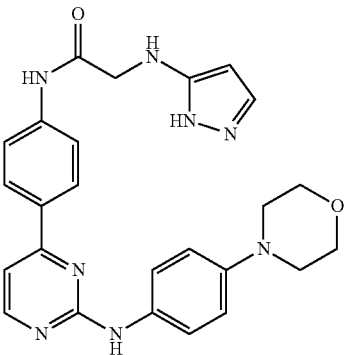

N-(4-{2-[(4-morpholin-4-ylphenyl)amino]pyrimidin-4-}phenyl)-N²-1H-pyrazol-5-ylglycinamide

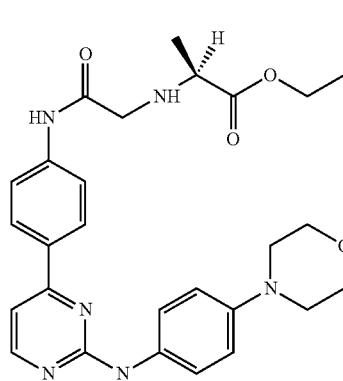

phenylmethyl N-{2-[(4-{2-[(4-morpholin-4-ylphenyl)amino]pyrimidin-4-l}phenyl)amino]-2-oxoethyl}-L-alaninate

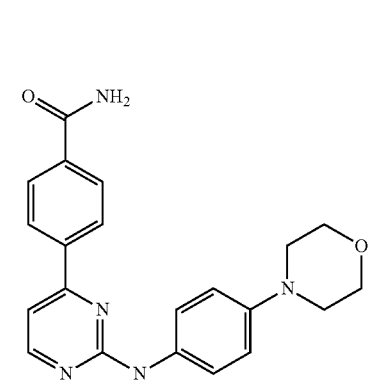

4-{2-[(4-morpholin-4-ylphenyl)amino]pyrimidin-4-yl}benzamide

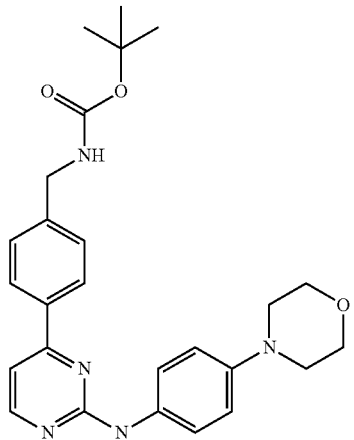

1,1-dimethylethyl[(4-{2-[(4-morpholin-4-ylphenyl)amino]pyrimidin-4-yl}phenyl)methyl]carbamate

737

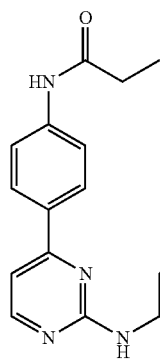

N-(4-{2-[(4-morpholin-4-ylphenyl)amino]pyrimidin-4-yl}phenyl)propanamide

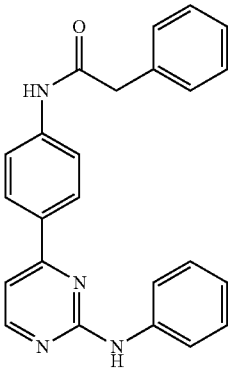

N-(4-{2-[(4-morpholin-4-ylphenyl)amino]pyrimidin-4-yl}phenyl)-2-phenylacetamide

-continued

738

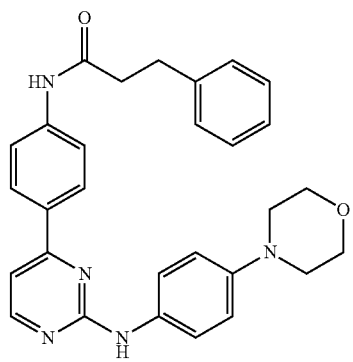

N-(4-{2-[(4-morpholin-4-ylphenyl)amino]pyrimidin-4-yl}phenyl)-3-phenylpropanamide

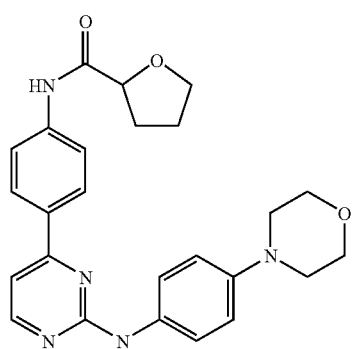

N-(4-{2-[(4-morpholin-4-ylphenyl)amino]pyrimidin-4-yl}phenyl)tetrahydrofuran-2-carboxamide

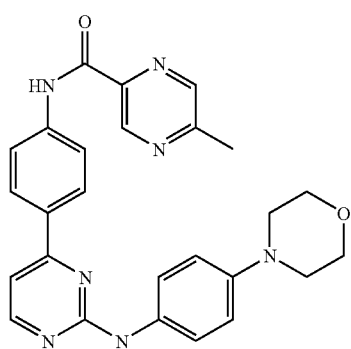

5-methyl-N-(4-{2-[(4-morpholin-4-ylphenyl)amino]pyrimidin-4-yl}phenyl)pyrazine-2-carboxamide

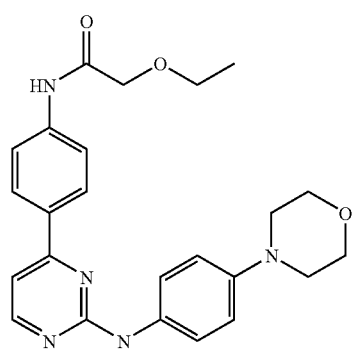

2-(ethyloxy)-N-(4-{2-[(4-morpholin-4-ylphenyl)amino]pyrimidin-4-yl}phenyl)acetamide

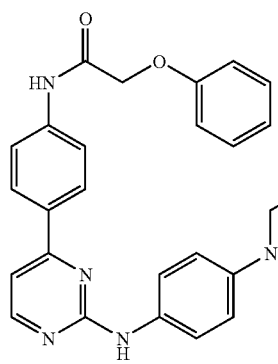

N-(4-{2-[(4-morpholin-4-ylphenyl)amino]pyrimidin-4-yl}phenyl)-2-(phenyloxy)acetamide

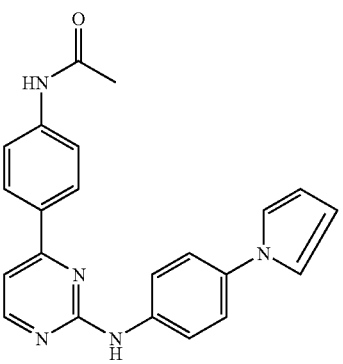

N-[4-(2-{[4-(1H-pyrrol-1-yl)phenyl]amino}pyrimidin-4-yl)phenyl]acetamide

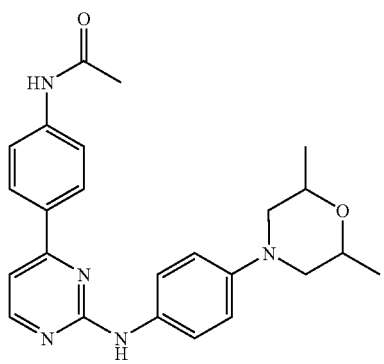

N-[4-(2-{(4-(2,6-dimethylmorpholin-4-yl)phenyl]amino}pyrimidin-4-yl)phenyl]acetamide -continued

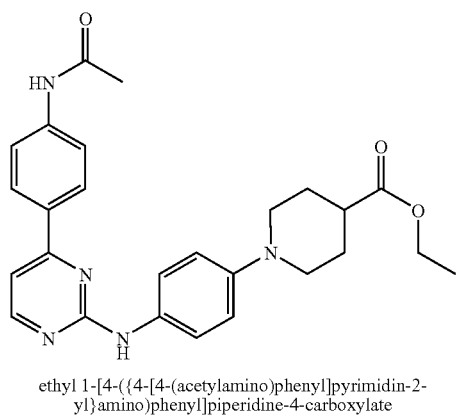

ethyl 1-[4-({4-[4-(acetylamino)phenyl]pyrimidin-2-yl}amino)phenyl]piperidine-4-carboxylate

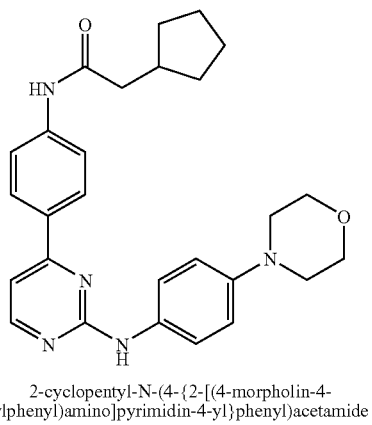

2-cyclopentyl-N-(4-{2-[(4-morpholin-4-ylphenyl)amino]pyrimidin-4-yl}phenyl)acetamide

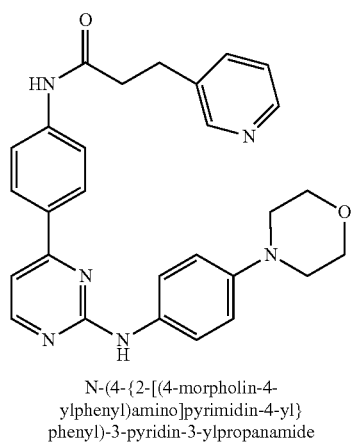

N-(4-{2-[(4-morpholin-4-ylphenyl)amino]pyrimidin-4-yl}phenyl)-3-pyridin-3-ylpropanamide

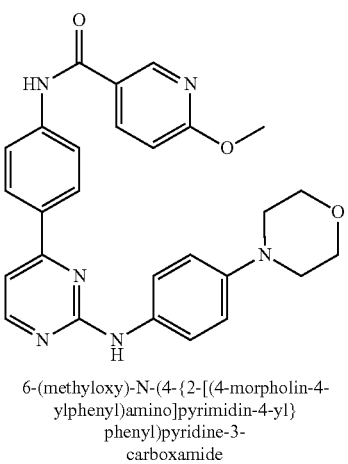

6-(methyloxy)-N-(4-{2-[(4-morpholin-4-ylphenyl)amino]pyrimidin-4-yl}phenyl)pyridine-3-carboxamide

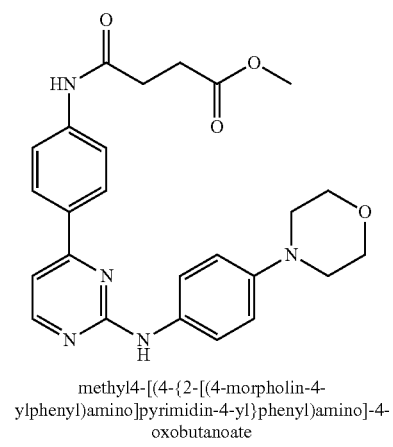

methyl 4-[(4-{2-[(4-morpholin-4-ylphenyl)amino]pyrimidin-4-yl}phenyl)amino]-4-oxobutanoate

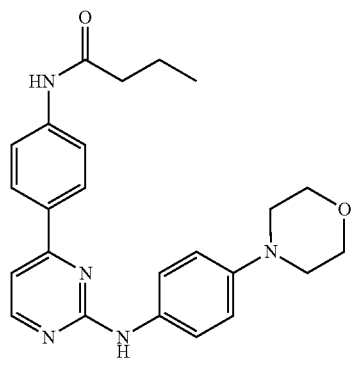

N-(4-{2-[(4-morpholin-4-ylphenyl)amino]pyrimidin-4-yl}phenyl)butanamide

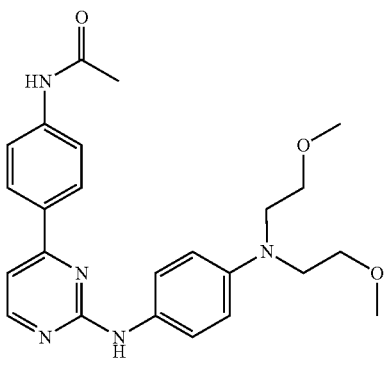

N-(4-{2-[(4-{bis[2-(methyloxy)ethyl]amino}phenyl)amino]pyrimidin-4-yl}phenyl)acetamide

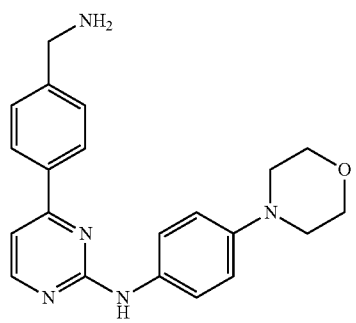

4-(4-(aminomethyl)phenyl)-N-(4-morpholinophenyl)pyrimidin-2-amine

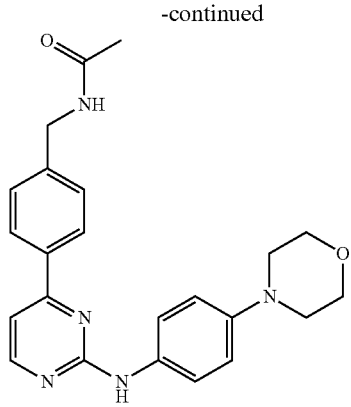

N-[(4-{2-[(4-morpholin-4-ylphenyl)amino]pyrimidin-4-yl}phenyl)methyl]acetamide

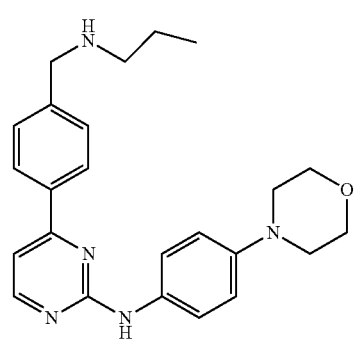

N-(4-morpholin-4-ylphenyl)-4-{4-[(propylamino)methyl]phenyl}pyrimidin-2-amine

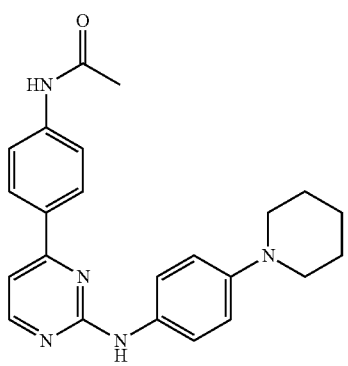

N-(4-{2-[(4-piperidin-1-ylphenyl)amino]pyrimidin-4-yl}phenyl)acetamide

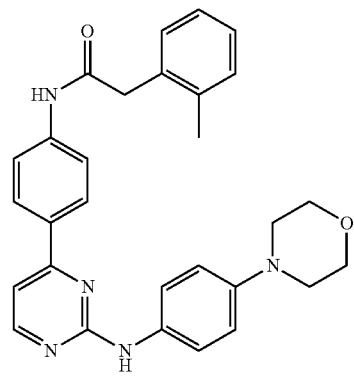

2-(2-methylphenyl)-N-(4-{2-[(4-morpholin-4-ylphenyl)amino]pyrimidin-4-yl}phenyl)acetamide

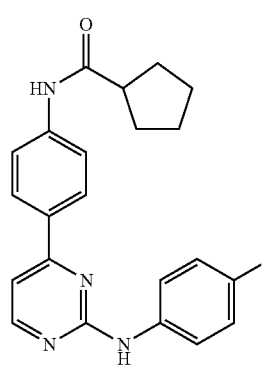

N-(4-{2-[(4-morpholin-4-ylphenyl)amino]pyrimidin-4-yl}phenyl)cyclopentanecarboxamide

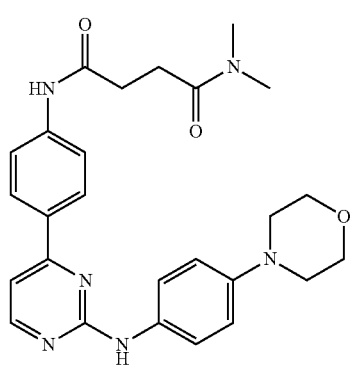

N,N-dimethyl-N'-(4-{2-[(4-morpholin-4-ylphenyl)amino]pyrimidin-4-yl}phenyl)butanediamide -continued

743

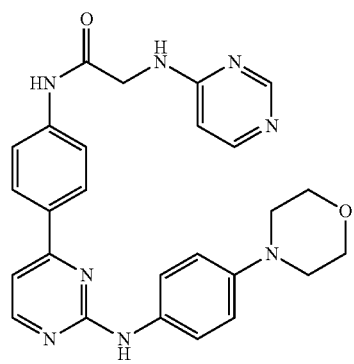

N-(4-{2-[(4-morpholin-4-ylphenyl)amino]pyrimidin-4-yl}phenyl)-N²-pyrimidin-4-ylglycinamide

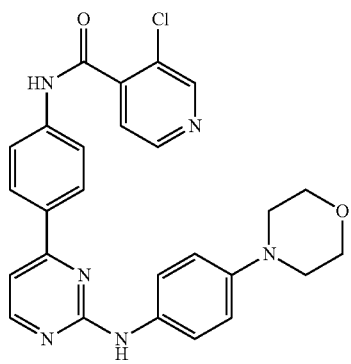

3-chloro-N-(4-{2-[(4-morpholin-4-ylphenyl)amino]pyrimidin-4-yl}phenyl)pyridine-4-carboxamide

744

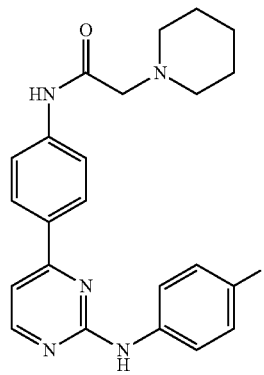

N-(4-{2-[(4-morpholin-4-ylphenyl)amino]pyrimidin-4-yl}phenyl)-2-piperidin-1-ylacetamide

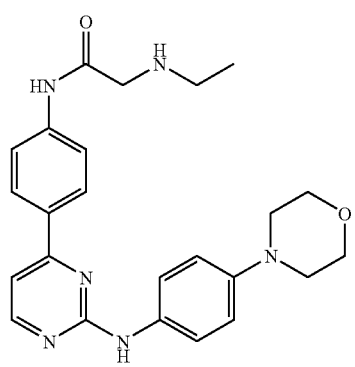

N²-ethyl-N-(4-{2-[(4-morpholilin-4-ylphenyl)amino]pyrimidin-4-yl}phenyl)glycinamide

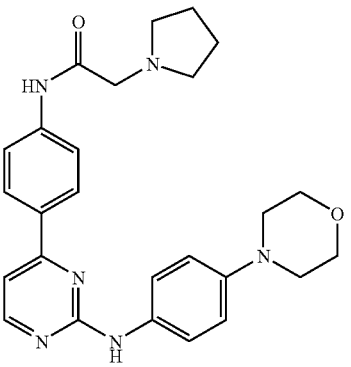

N-(4-{2-[(4-morpholin-4-ylphenyl)amino]pyrimidin-4-yl}phenyl)-2-pyrrolidin-1-ylacetamide

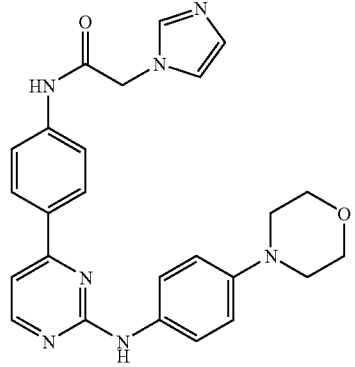

2-(1H-imidazol-1-yl)-N-(4-{2-[(4-morpholin-4-ylphenyl)amino]pyrimidin-4-yl}phenyl)acetamide

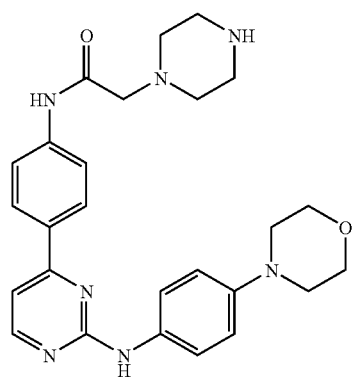

N-(4-{2-[(4-morpholin-4-ylphenyl)amino]pyrimidin-4-yl}phenyl)-2-piperazin-1-ylacetamide

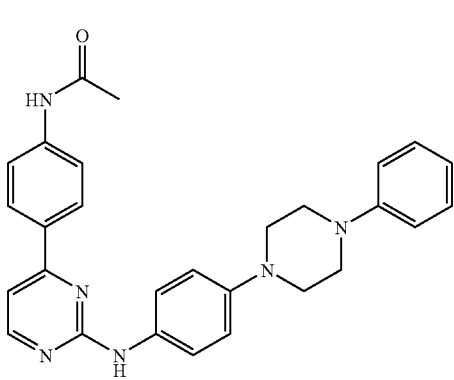

N-[4-(2-{[4-(4-phenylpiperazin-1-yl)phenyl]amino}pyrimidin-4-yl)phenyl]acetamide -continued

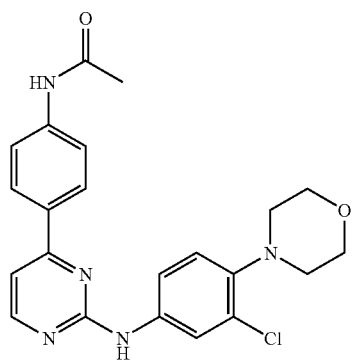

N-(4-{2-[(3-chloro-4-morpholin-4-ylphenyl)amino]pyrimidin-4-yl}phenyl)acetamide

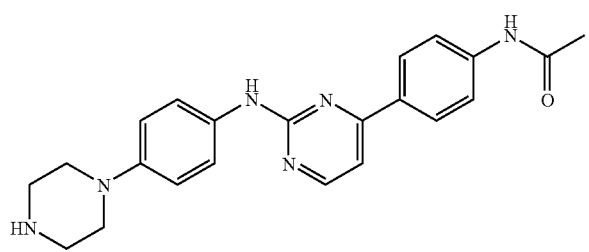

N-(4-{2-[(4-piperazin-1-ylphenyl)amino]pyrimidin-y-yl}phenyl)acetamide

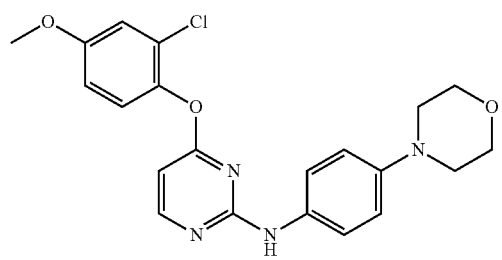

'4-{[2-chloro-4-(methyloxy)phenyl]oxy}-N-(4-morpholin-4-ylphenyl)pyrimidin-2-amine

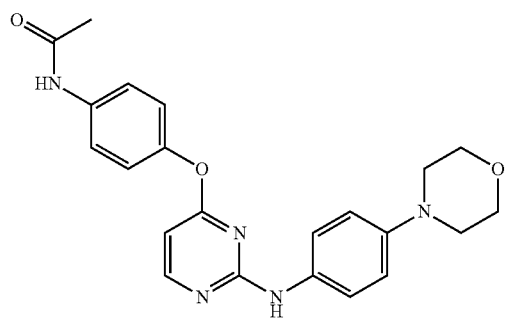

'N-[4-({2-[(4-morpholin-4-ylphenyl)amino]-pyrimidin-4-yl}oxy)phenyl]acetamide

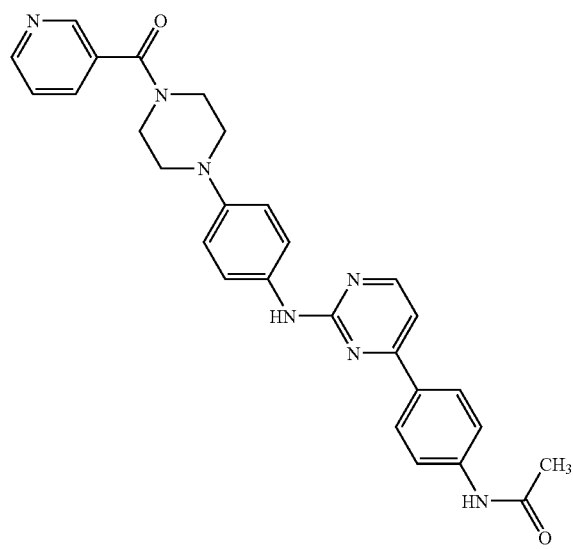

N-{4-[2-({4-[4-(pyridin-3-ylcarbonyl)piperazin-1-yl]phenyl}amino)pyrimidin-4-yl]phenyl}acetamide

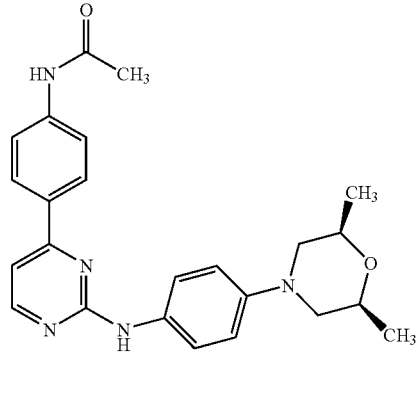

N-{4-[2-({4-[(2R,6S)-2,6-dimethylmorpholin-4-yl]phenyl}amino)pyrimidin-4-yl]phenyl}acetamide

747 748

-continued

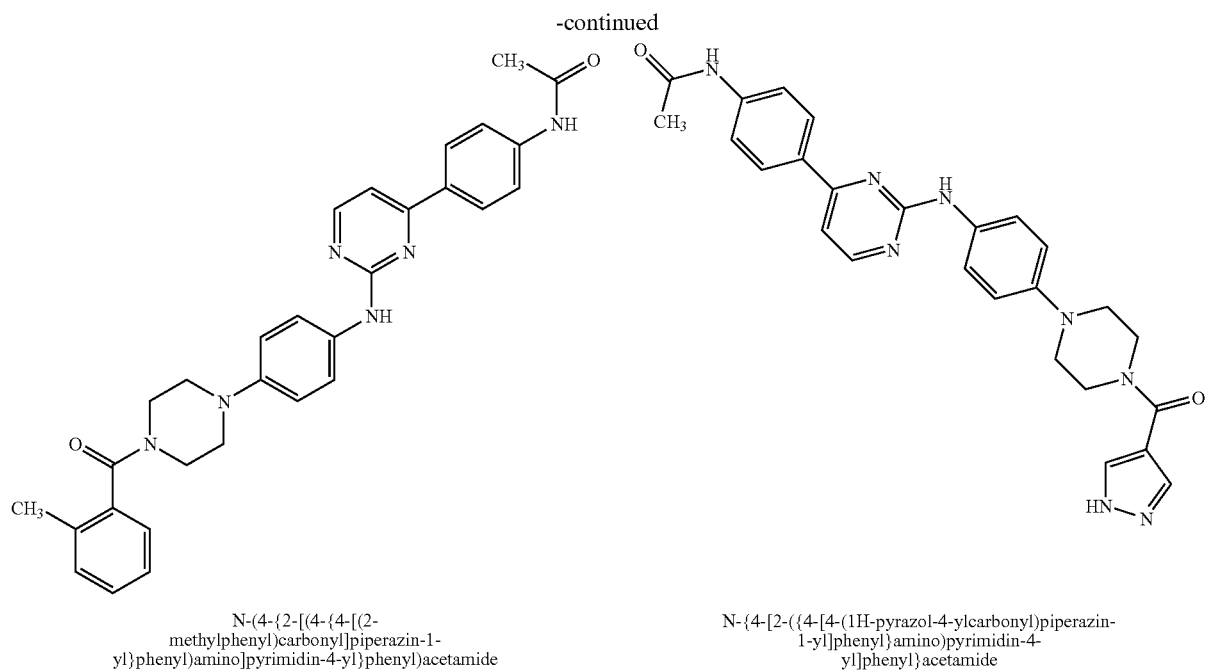

N-(4-{2-[(4-{4-[(2-methylphenyl)carbonyl]piperazin-1-yl}phenyl)amino]pyrimidin-4-yl}phenyl)acetamide N-{4-[2-({4-[4-(1H-pyrazol-4-ylcarbonyl)piperazin-1-yl]phenyl}amino)pyrimidin-4-yl]phenyl}acetamide

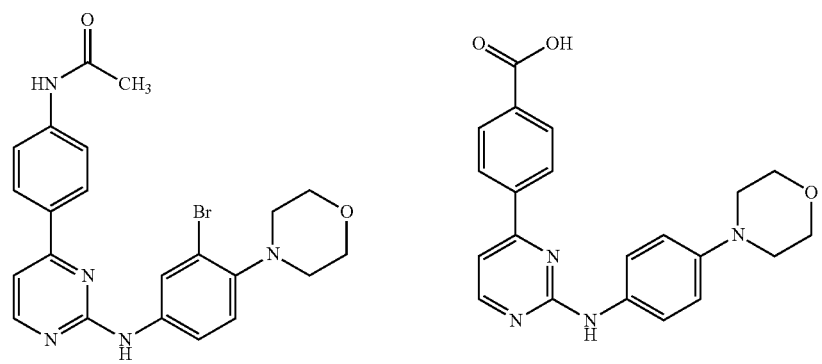

N-(4-{2-[(3-bromo-4-morpholin-4-ylphenyl)amino]pyrimidin-4-yl}phenyl)acetamide

4-{2-[(4-morpholin-4-ylphenyl)amino]pyrimidin-4-yl}benzoic acid

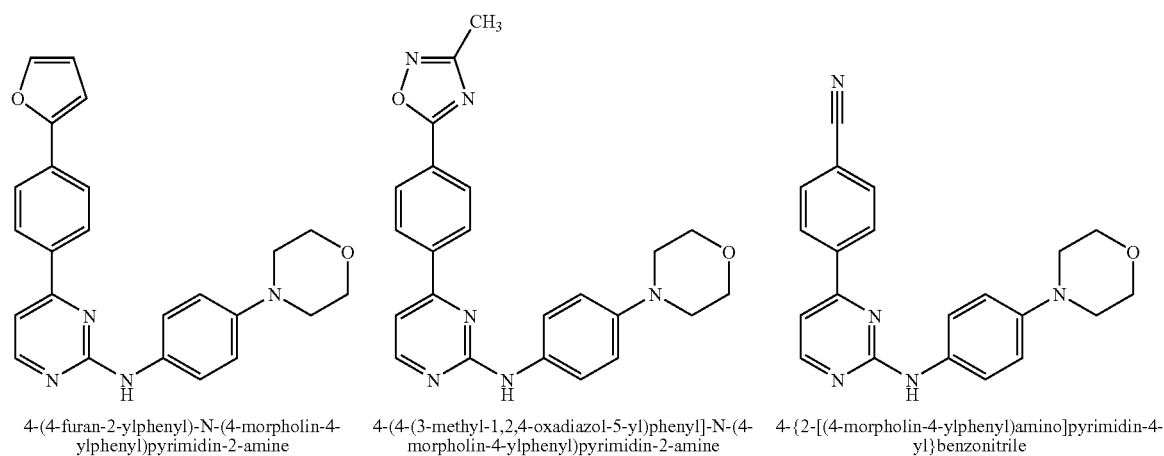

4-(4-furan-2-ylphenyl)-N-(4-morpholin-4-ylphenyl)pyrimidin-2-amine 4-(4-(3-methyl-1,2,4-oxadiazol-5-yl)phenyl]-N-(4-morpholin-4-ylphenyl)pyrimidin-2-amine 4-{2-[(4-morpholin-4-ylphenyl)amino]pyrimidin-4-yl}benzonitrile -continued

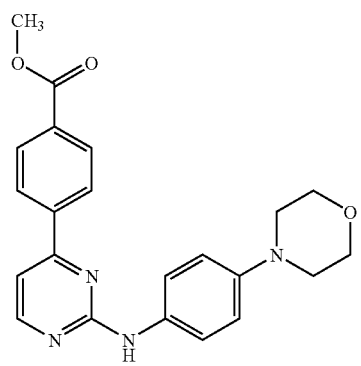

methyl 4-{2-[(4-morpholin-4-ylphenyl)amino]pyrimidin-4-yl}benzoate

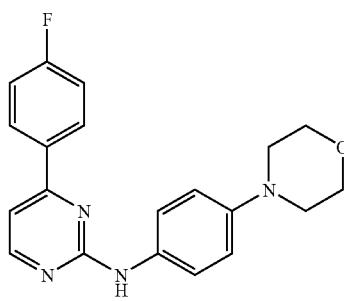

4-(4-fluorophenyl)-N-(4-morpholin-4-ylphenyl)pyrimidin-2-amine

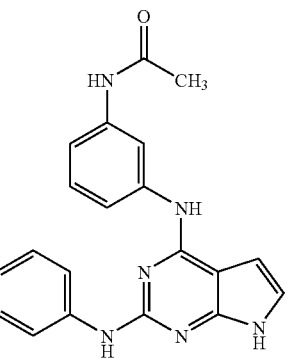

N-[3-({2-[(4-morpholin-4-ylphenyl)amino]-7H-pyrrolo[2,3-d]pyrimidin-4-yl}amino)phenyl]acetamide

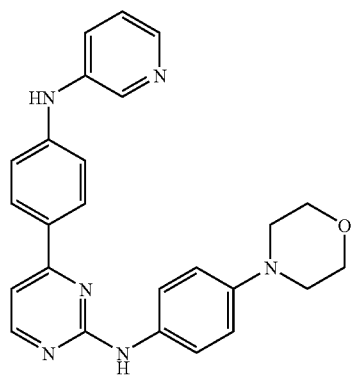

N-(4-morpholin-4-ylphenyl)-4-[4-(pyridin-3-ylamino)phenyl]pyrimidin-2-amine

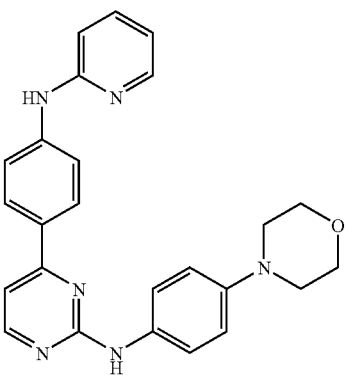

N-(4-morpholin-4-ylphenyl)-4-[4-(pyridin-2-ylamino)phenyl]pyrimidin-2-amine

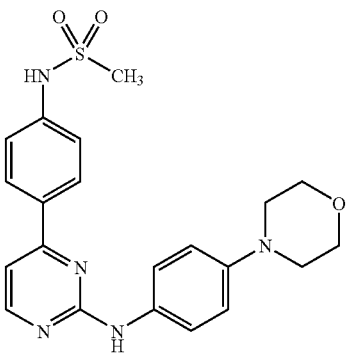

N-(4-{2-[(4-morpholin-4-ylphenyl)amino]pyrimidin-4-yl}phenyl)methanesulfonamide

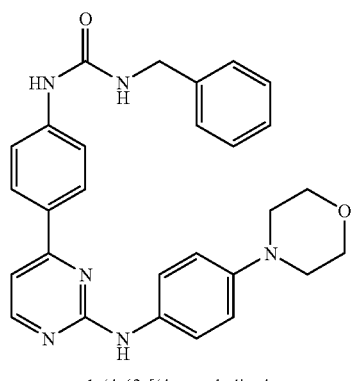

1-(4-{2-[(4-morpholin-4-ylphenyl)amino]pyrimidin-4-yl}phenyl)-3-(phenylmethyl)urea

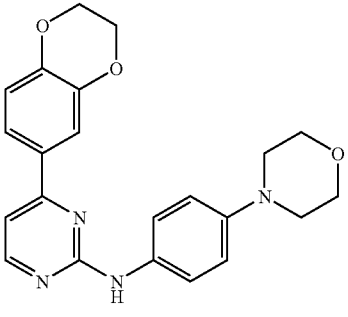

4-(2,3-dihydro-1,4-benzodioxin-6-yl)-N-(4-morpholin-4-ylphenyl)pyrimidin-2-amine

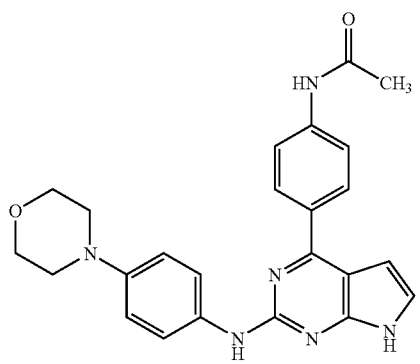

N-(4-{2-[(4-morpholin-4-ylphenyl)amino]-7H-pyrrolo[2,3-d]pyrimidin-4-yl}phenyl)acetamide -continued

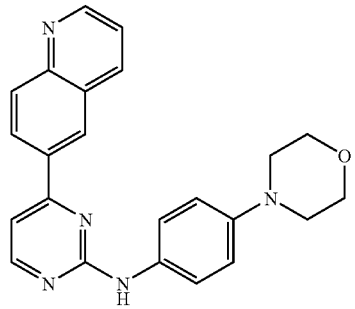
N-(4-morpholin-4-ylphenyl)-4-quinolin-6-ylpyrimidin-2-amine

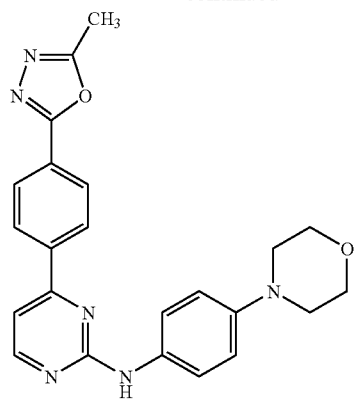
4-[4-(5-methyl-1,3,4-oxadiazol-2-yl)phenyl]-N-(4-morpholin-4-ylkphenyl)pyrimidin-2-amine

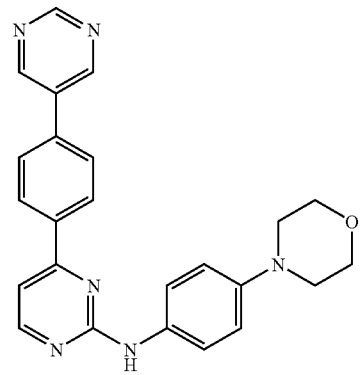
N-(4-morpholin-4-ylphenyl)-4-(4-pyrimidin-5-ylphenyl)pyrimidin-2-amine

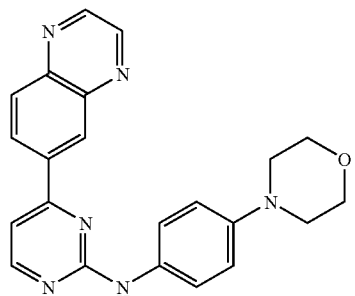
N-(4-morpholin-4-ylphenyl)-4-quinoxalin-6-ylpyrimidin-2-amine

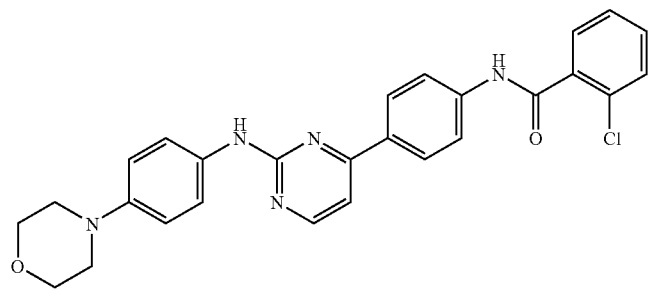
2-chloro-N-(4-{2-[(4-morpholin-4-ylphenyl)amino]pyrimidin-4-yl}phenyl)benzamide

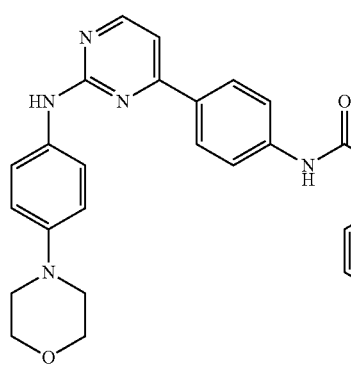
2-(2-fluorophenyl)-N-(4-{2-[(4-morpholin-4-ylphenyl)amino]pyrimidin-4-yl}phenyl)acetamide

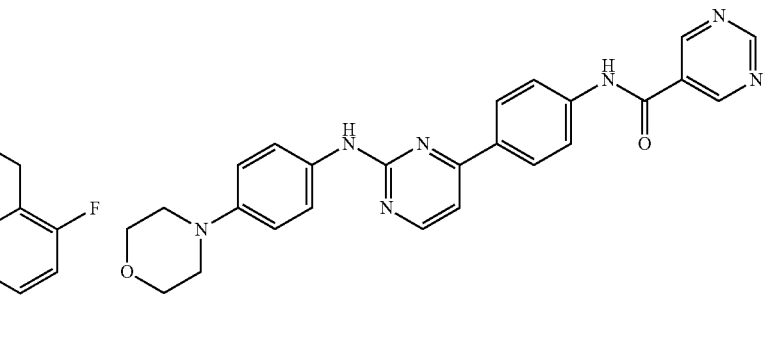
N-(4-{2-[(4-morpholin-4-ylphenyl)amino]pyrimidin-4-yl}phenyl)pyrimidine-5-carboxamide

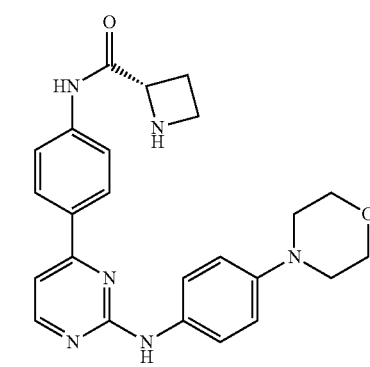
(2S)-N-(4-{2-[(4-morpholin-4-ylphenyl)amino]pyrimidin-4-yl}phenyl)azetidine-2-carboxamide

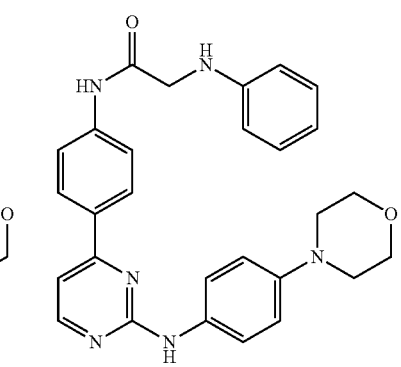
N-(4-{2-[(4-morpholin-4-ylphenyl)amino]pyrimidin-4-yl}phenyl)-$N^2$-phenylglycinamide -continued
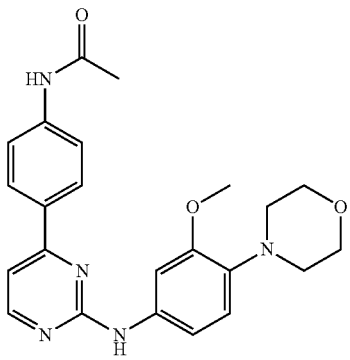
N-(4-(2-(3-methoxy-4-morpholino-
phenylamino)pyrimidin-4-yl)phenyl)acetamide
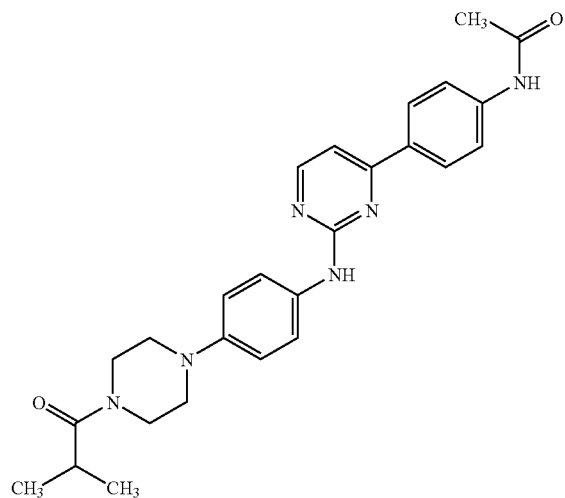
N-(4-(2-(4-(4-isobutyrylpiperazin-1-
yl)phenylamino)-pyrimidin-4-yl)phenyl)acetamide
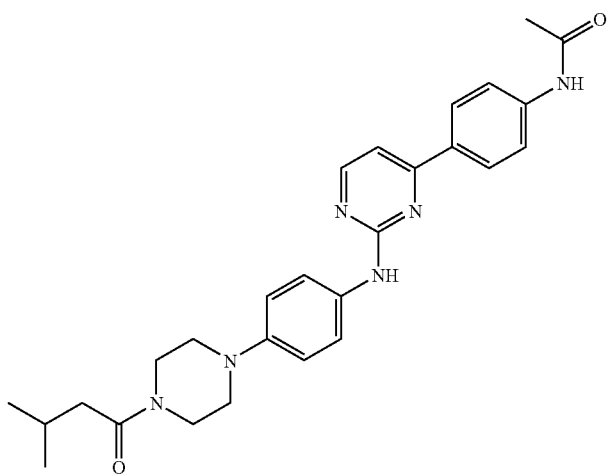
N-(4-(2-(4-(4-(3-methylbutanoyl)piperazin-1-
yl)phenylamino)-pyrimidin-4-yl)phenyl)acetamide
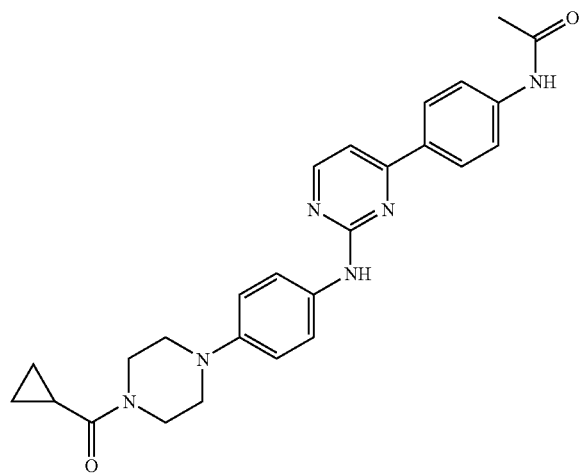
N-(4-(2-(4-(4-(cyclopropanecarbonyl)piperazin-1-
yl)phenylamino)-pyrimidin-4-yl)phenyl)acetamide -continued
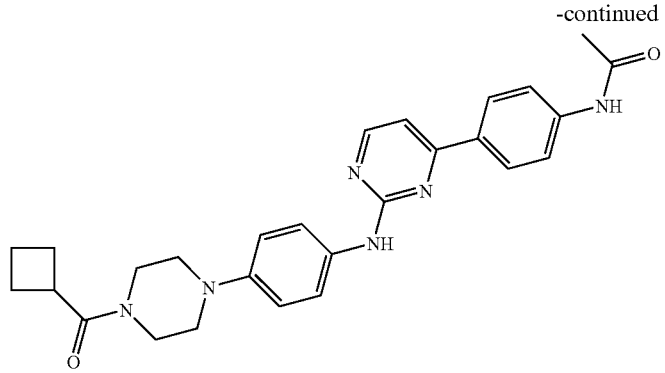
N-(4-(2-(4-(4-(cyclobutanecarbonyl)piperazin-1-yl)phenylamino)-pyrimidin-4-yl)phenyl)acetamide
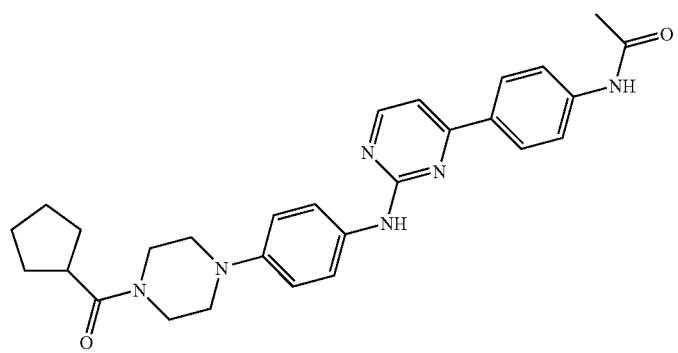
N-(4-(2-(4-(4-(cyclopentanecarbonyl)piperazin-1-yl)phenylamino)pyrimidin-4-yl)phenyl)acetamide
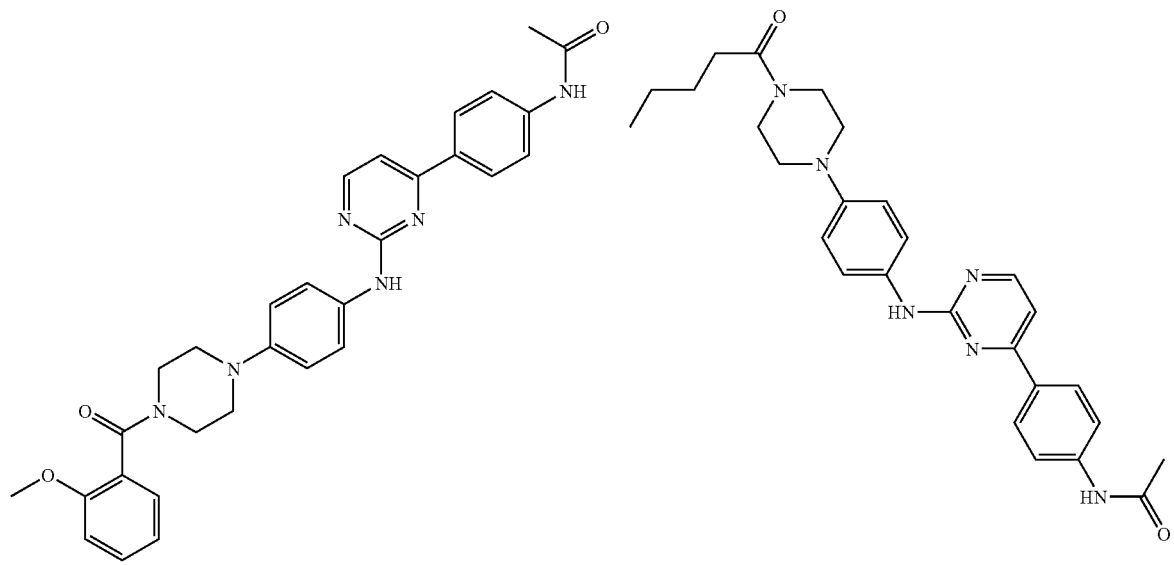
N-(4-(2-(4-(4-(2-methoxybenzoyl)piperazin-1-yl)phenylamino)pyrimidin-4-yl)phenyl)acetamide
N-(4-(2-(4-(4-pentanoylpiperazin-1-yl)phenylamino)pyrimidin-4-yl)phenyl)acetamide 757
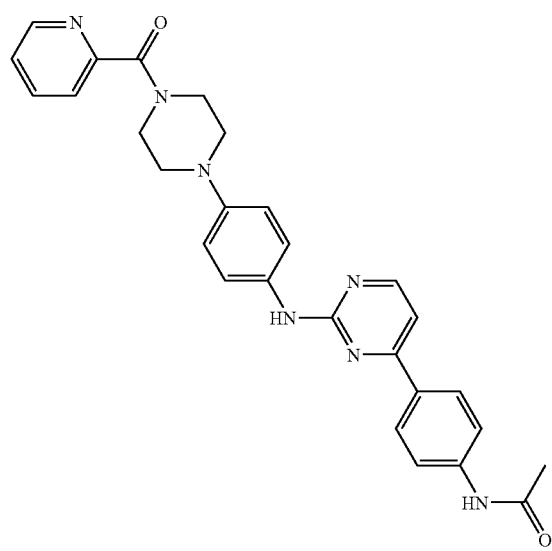
N-(4-(2-(4-(4-picolinoylpiperazin-1-yl)phenylamino)pyrimidin-4-yl)phenyl)acetamide
758
-continued
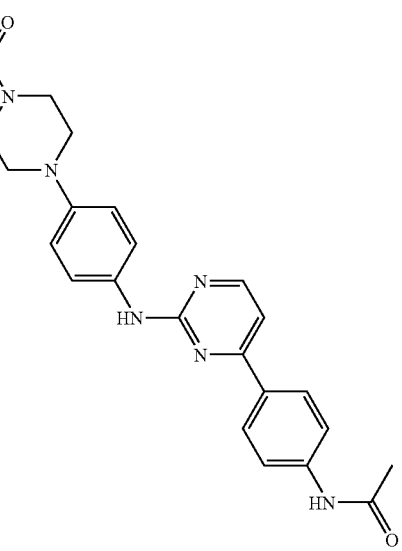
N-(4-(2-(4-(4-isonicotinoylpiperazin-1-yl)phenylamino)pyrimidin-4-yl)phenyl)acetamide
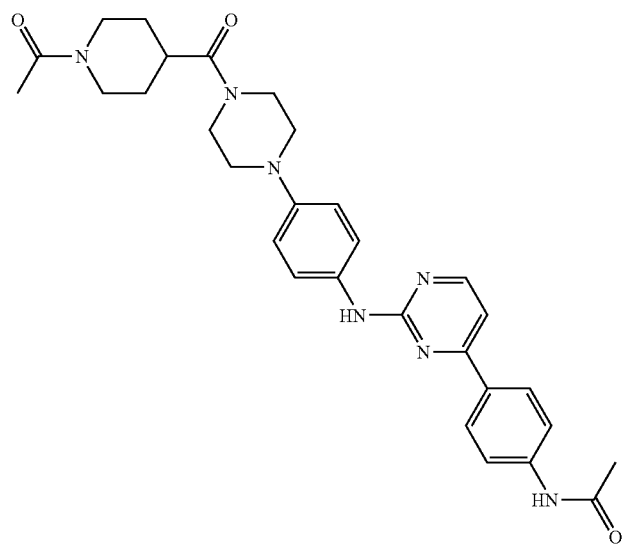
N-(4-(2-(4-(4-(1-acetylpiperidine-4-carbonyl)piperazin-1-yl)phenylamino)pyrimidin-4-yl)phenyl)acetamide
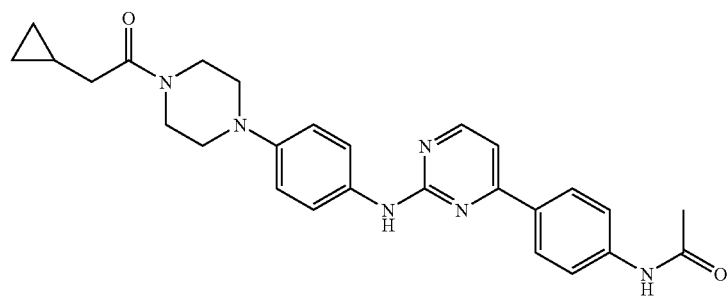
N-(4-(2-(4-(4-(2-cyclopropylacetyl)piperazin-1-yl)phenylamino)pyrimidin-4-yl)phenyl)acetamide -continued
759
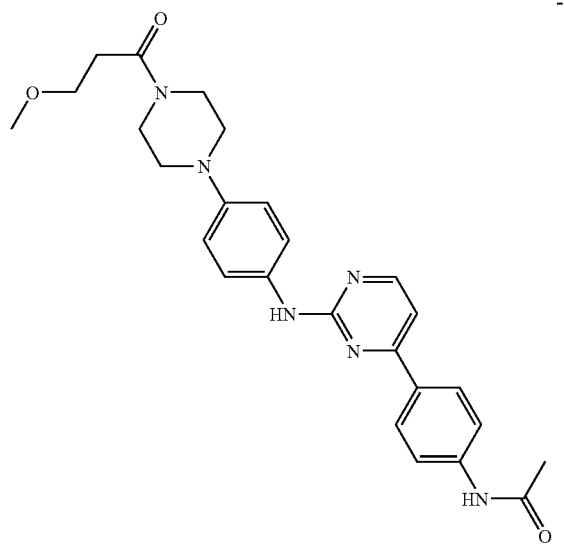
N-(4-(2-(4-(4-(3-methoxypropanoyl)piperazin-1-yl)phenylamino)pyrimidin-4-yl)phenyl)acetamide
760
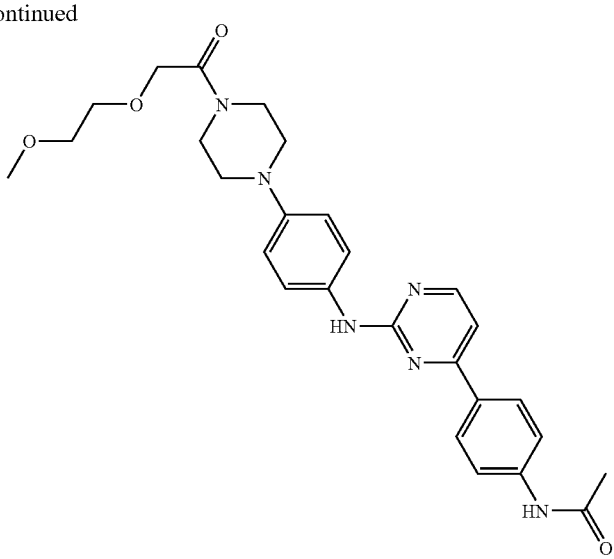
N-(4-(2-(4-(4-(2-(2-methoxyethoxy)acetyl)piperazin-1-yl)phenylamino)pyrimidin-4-yl)phenyl)acetamide
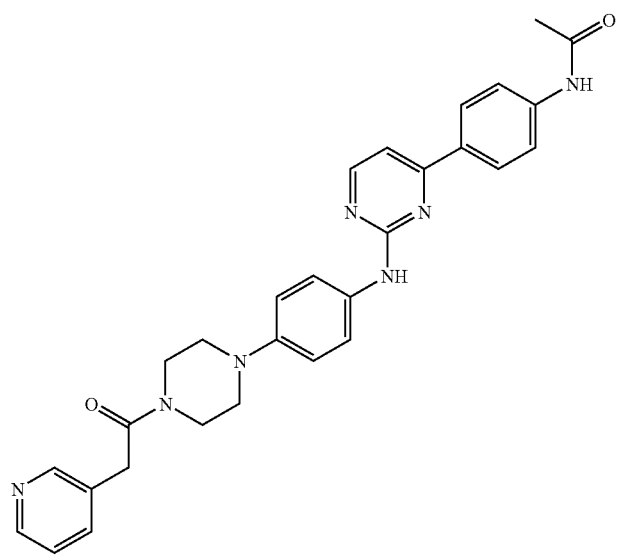
N-(4-(2-(4-(4-(2-(pyridin-3-yl)acetyl)piperazin-1-yl)phenylamino)pyrimidin-4-yl)phenyl)acetamide -continued
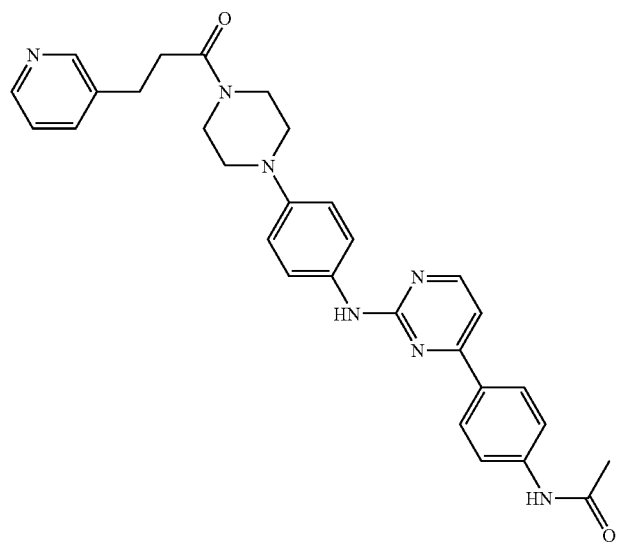
N-(4-(2-(4-(4-(3-(pyridin-3-yl)propanoyl)piperazin-1-yl)phenylamino)pyrimidin-4-yl)phenyl)acetamide
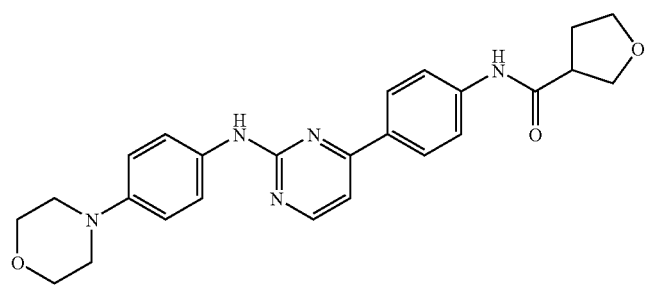
N-(4-(2-(4-morpholinophenylamino)pyrimidin-4-yl)phenyl)tetrahydrofuran-3-carboxamide
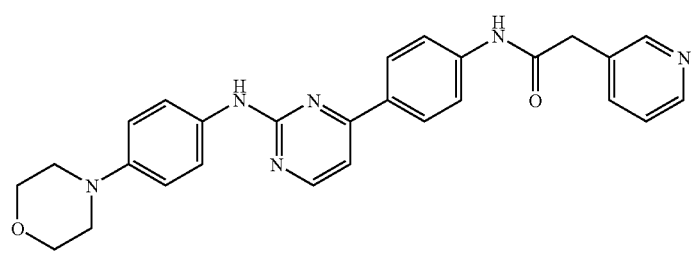
N-(4-(2-(4-morpholinophenylamino)pyrimidin-4-yl)phenyl)-2-(pyridin-3-yl)acetamide

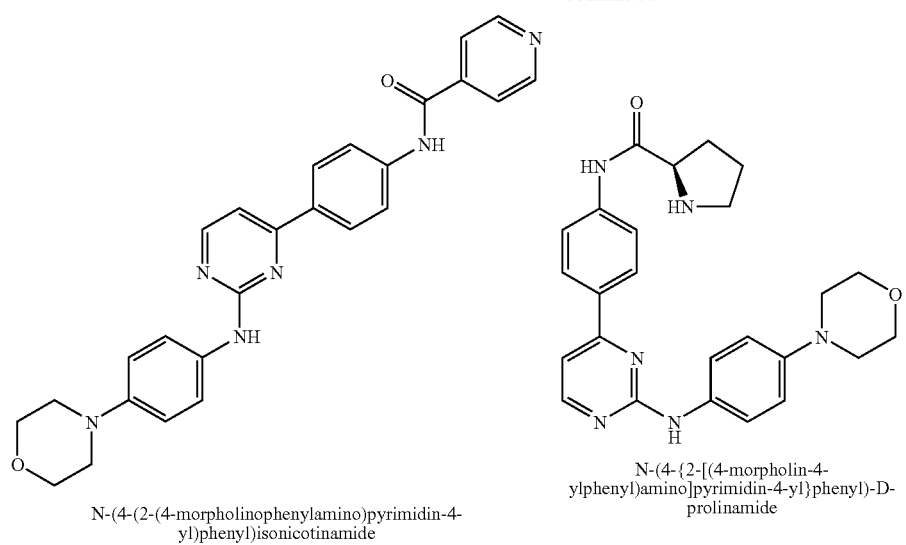

N-(4-(2-(4-morpholinophenylamino)pyrimidin-4-yl)phenyl)isonicotinamide

N-(4-{2-[(4-morpholin-4-ylphenyl)amino]pyrimidin-4-yl}phenyl)-D-prolinamide

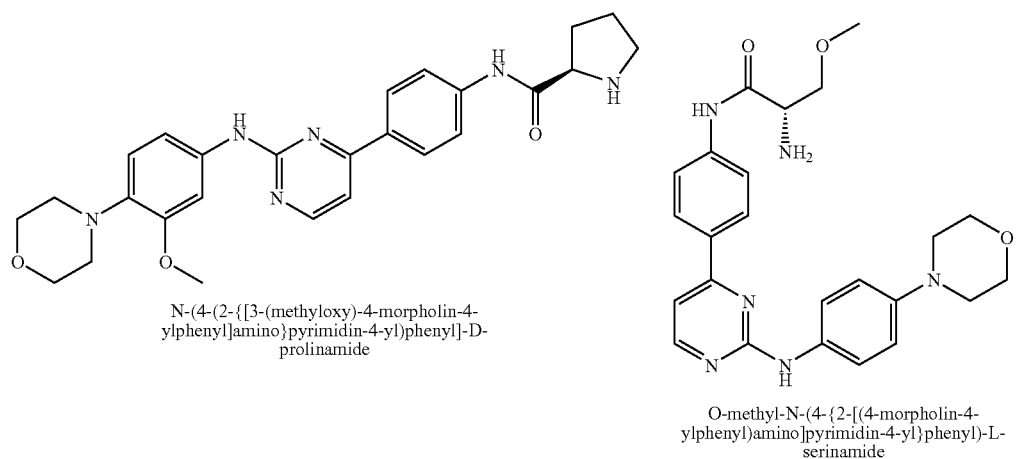

N-(4-(2-{[3-(methyloxy)-4-morpholin-4-ylphenyl]amino}pyrimidin-4-yl)phenyl]-D-prolinamide O-methyl-N-(4-{2-[(4-morpholin-4-ylphenyl)amino]pyrimidin-4-yl}phenyl)-L-serinamide

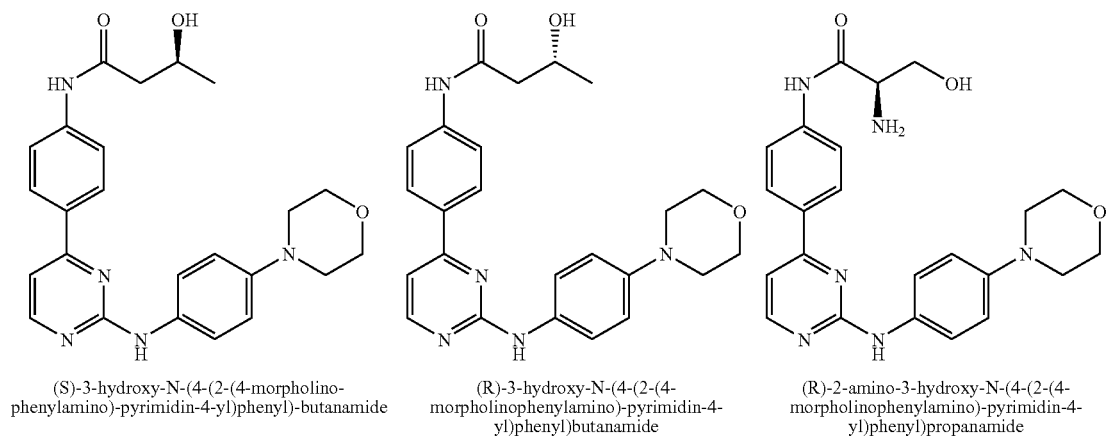

(S)-3-hydroxy-N-(4-(2-(4-morpholino-phenylamino)-pyrimidin-4-yl)phenyl)-butanamide (R)-3-hydroxy-N-(4-(2-(4-morpholinophenylamino)-pyrimidin-4-yl)phenyl)butanamide (R)-2-amino-3-hydroxy-N-(4-(2-(4-morpholinophenylamino)-pyrimidin-4-yl)phenyl)propanamide

765

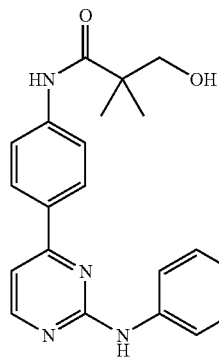

2-Hydroxy-2-methyl-N-(4-(2-(4-morpholinophenylamino)pyrimidin-4-yl)phenyl)propanamide

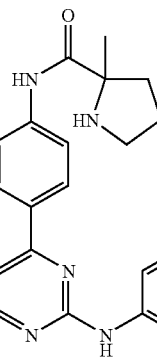

2-methyl-N-(4-(2-(4-morpholinophenylamino)pyrimidin-4-yl)phenyl)pyrrolidine-2-carboxamide

766

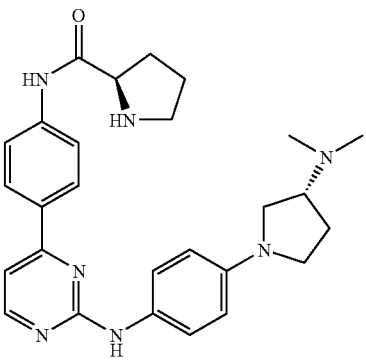

(R)-N-(4-(2-(4-((R)-3-(dimethylamino)pyrrolidin-1-yl)phenylamino)pyrimidin-4-yl)phenyl)pyrrolidine-2-carboxamide

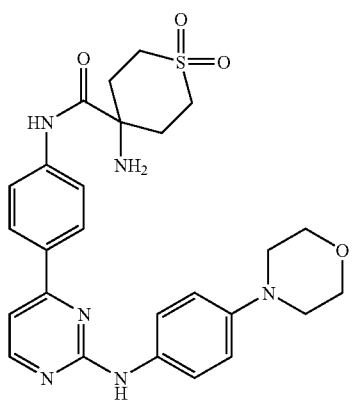

4-amino-1,1-dioxo-N-(4-(2-(4-morpholinophenylamino)pyrimidin-4-yl)phenyl)tetrahydro-2H-thiopyran-4-carboxamide

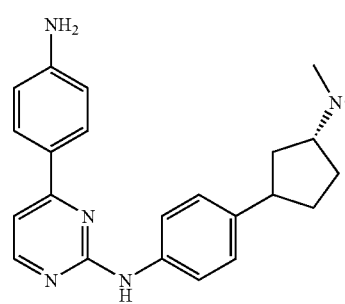

(R)-4-(4-aminophenyl)-N-(4-(3-(dimethylamino)-pyrrolidin-1-yl)phenyl)-pyrimidin-2-amine

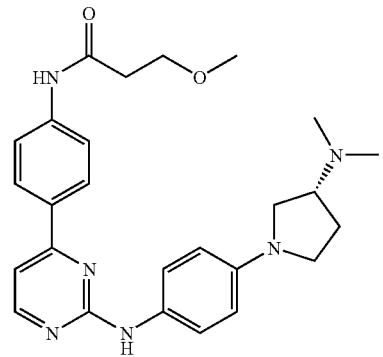

(R)-N-(4-(2-(4-(3-(dimethylamino)pyrrolidin-1-yl)phenylamino)-pyrimidin-4-yl)phenyl)-3-methoxy-propanamide

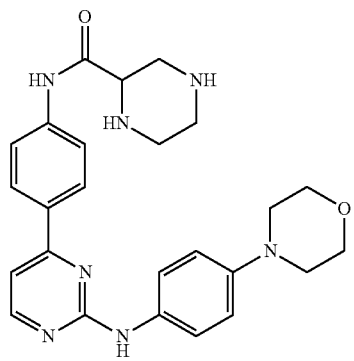

N-(4-(2-(4-morpholinophenylamino)pyrimidin-4-yl)phenyl)piperazine-2-carboxamide

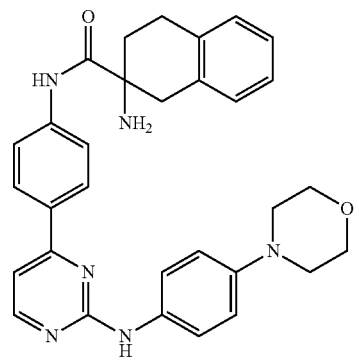

2-amino-N-(4-(2-(4-morpholinophenylamino)pyrimidin-4-yl)phenyl)-1,2,3,4-tetrahydronaphthalene-2-carboxamide

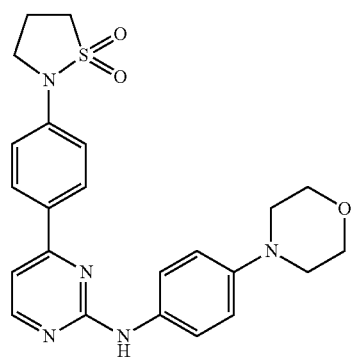

4-(4-(1,1-dioxo-isothiazolidin-2-yl)phenyl)-N-(4-morpholinophenyl)-pyrimidin-2-amine -continued

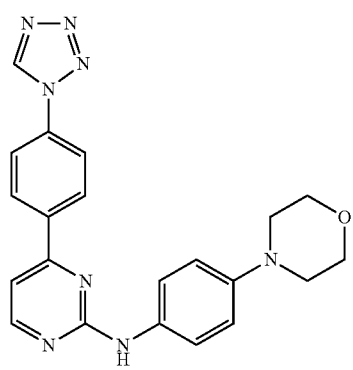

4-(4-(1H-tetrazol-1-yl)phenyl)-N-(4-morpholinophenyl)-pyrimidin-2-amine

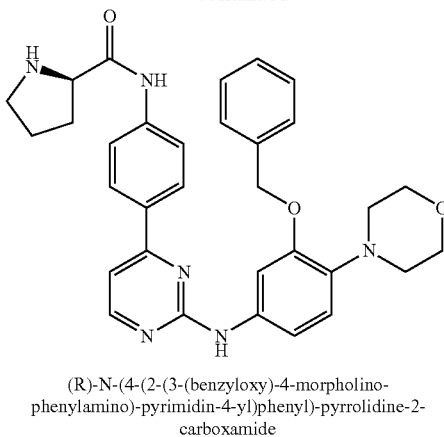

(R)-N-(4-(2-(3-(benzyloxy)-4-morpholino-phenylamino)-pyrimidin-4-yl)phenyl)-pyrrolidine-2-carboxamide

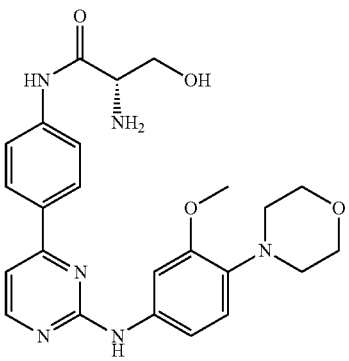

(S)-2-amino-3-hydroxy-N-(4-(2-(3-methoxy-4-morpholinophenylamino)pyrimidin-4-yl)phenyl)propanamide

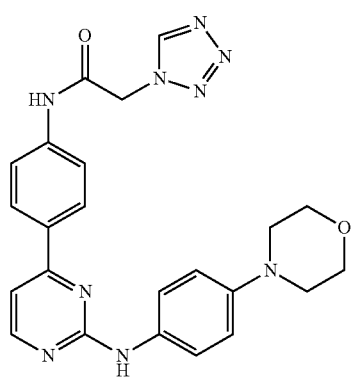

N-(4-(2-(4-morpholinophenylamino)pyrimidin-4-yl)phenyl)-2-(1H-tetrazol-1-yl)acetamide

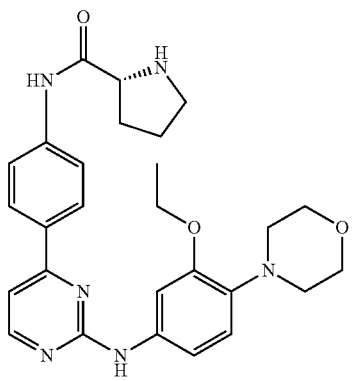

(R)-N-(4-(2-(3-ethoxy)-4-morpholinophenylamino)-pyrimidin-4-yl)phenyl)-pyrrolidine-2-carboxamide

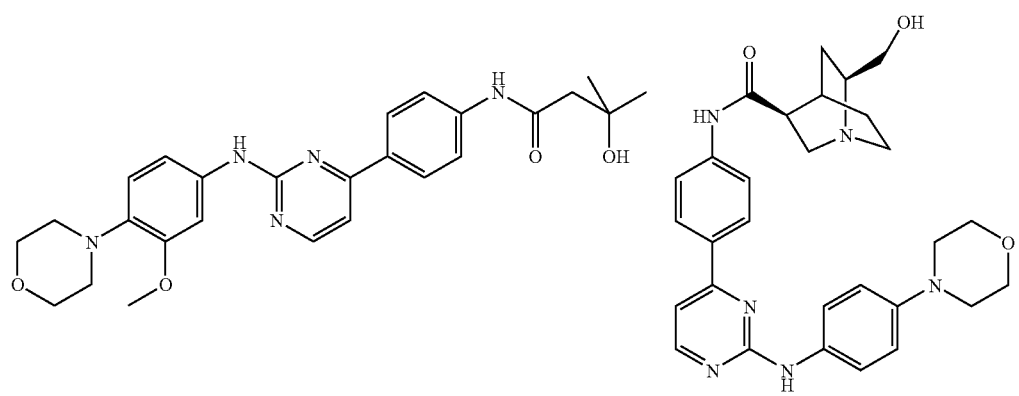

3-hydroxy-N-(4-(4-(2-(3-methoxy-4-morpholinophenylamino)pyrimidin-4-yl)phenyl)-3-methylbutanamide

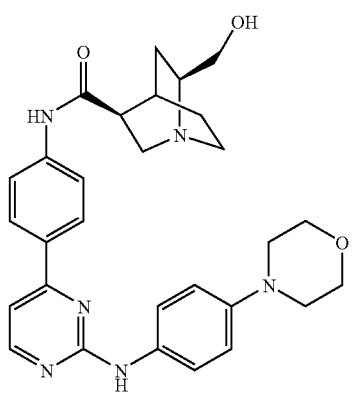

(3S,7S)-7-(hydroxymethyl)-N-(4-(2-(4-morpholinophenylamino)pyrimidin-4-yl)phenyl)quinuclidine-3-carboxamide -continued

769

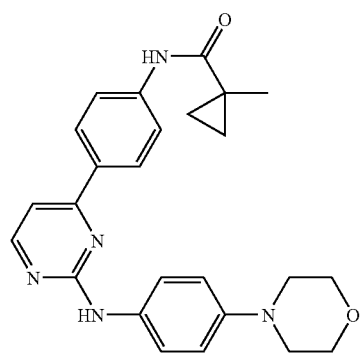

1-hydroxy-N-(4-(2-(4-morpholino-phenylamino)-
pyrimidin-4-yl)phenyl)cyclopropanecarboxamide

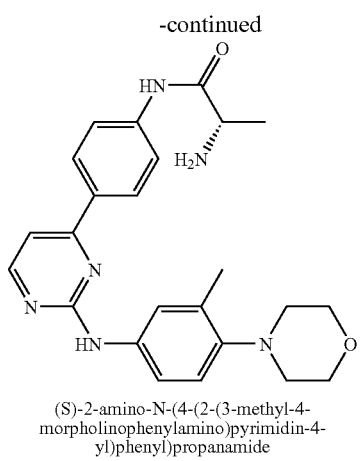

(S)-2-amino-N-(4-(2-(3-methyl-4-
morpholinophenylamino)pyrimidin-4-
yl)phenyl)propanamide

770

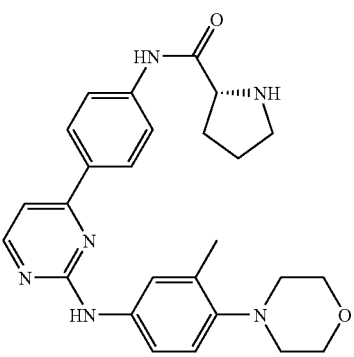

(R)-N-(4-(2-(3-methyl-4-
morpholinophenylamino)pyrimidin-4-
yl)phenyl)pyrrolidine-2-carboxamide

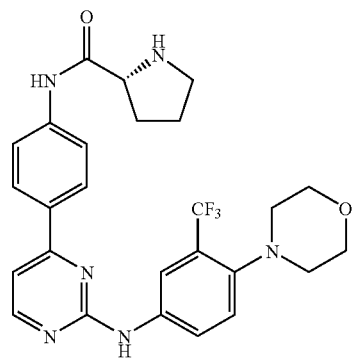

(R)-N-(4-(2-(4-morpholino-3-(trifluoromethyl)-
phenylamino)pyrimidin-4-yl)-phenyl)-pyrrolidine-2-
carboxamide

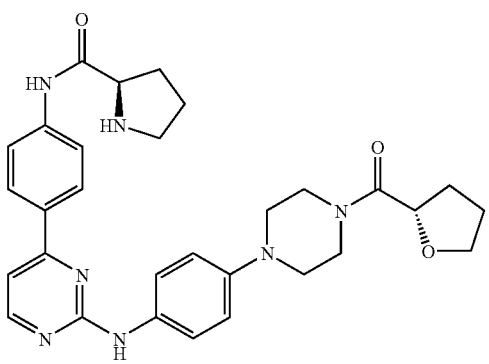

(R)-N-(4-(2-(4-(4-((S)-tetrahydrofuran-2-carbonyl)-
piperazin-1-yl)-phenylamino)pyrimidin-4-
yl)-phenyl)-pyrrolidine-2-carboxamide

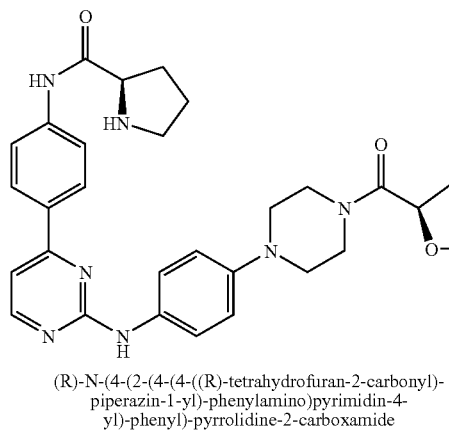

(R)-N-(4-(2-(4-(4-((R)-tetrahydrofuran-2-carbonyl)-
piperazin-1-yl)-phenylamino)pyrimidin-4-
yl)-phenyl)-pyrrolidine-2-carboxamide

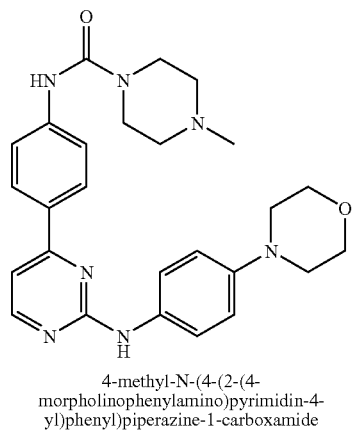

4-methyl-N-(4-(2-(4-
morpholinophenylamino)pyrimidin-4-
yl)phenyl)piperazine-1-carboxamide

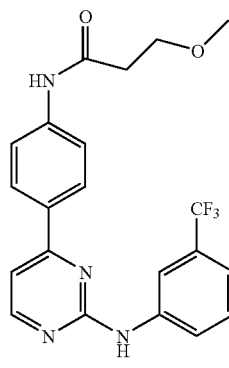

3-methyl-N-(4-(2-(4-morpholino-3-
(trifluoromethyl)phenylamino)pyrimidin-4-
yl)phenyl)propanamide

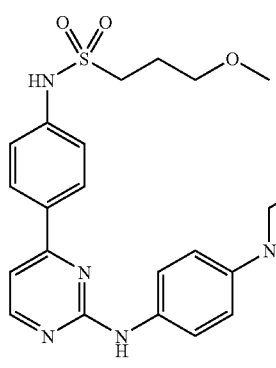

3-methyl-N-(4-(2-(4-morpholino-
phenylamino)pyrimidin-4-yl)phenyl)propane-1-
sulfonamide

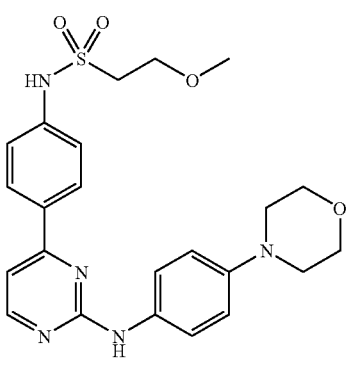

2-methoxy-N-(4-(2-(4-morpholino-
phenylamino)pyrimidin-4-yl)phenyl)-
ethanesulfonamide -continued

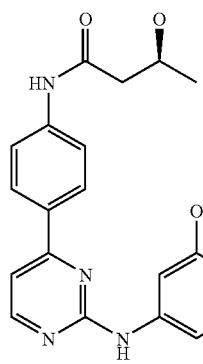

(S)-3-hydroxy-N-(4-(2-(3-methoxy-4-morpholinophenylamino)pyrimidin-4-yl)phenyl)butanamide

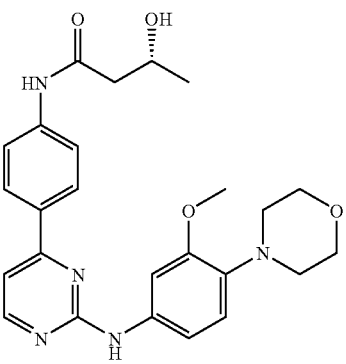

(R)-3-hydroxy-N-(4-(2-(3-methoxy-4-morpholinophenylamino)pyrimidin-4-yl)phenyl)butanamide

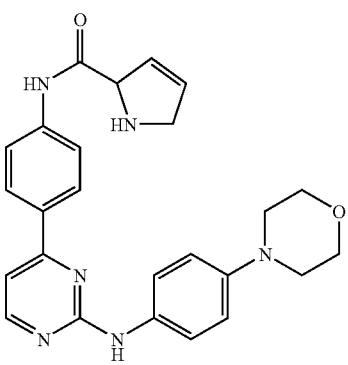

N-(4-(2-(4-morpholinophenylamino)pyrimidin-4-yl)phenyl)-2,5-dihydro-1H-pyrrole-2-carboxamide

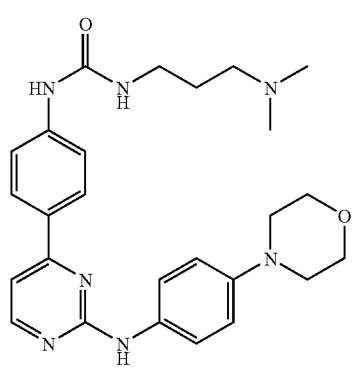

1-(3-(dimethylamino)propyl)-3-(4-(2-(4-morpholinophenylamino)pyrimidin-4-yl)phenyl)urea

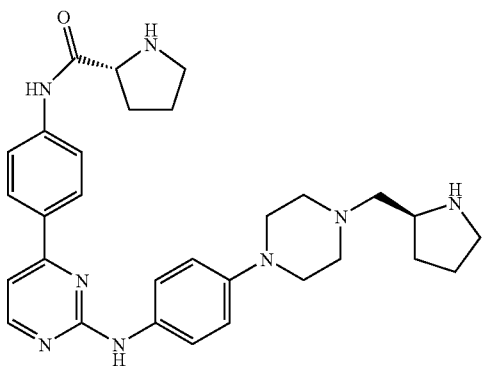

(R)-N-(4-(2-(4-(4-((S)-pyrrolidin-2-ylmethyl)piperazin-1-yl)phenylamino)pyrimidin-4-yl)phenyl)pyrrolidine-2-carboxamide

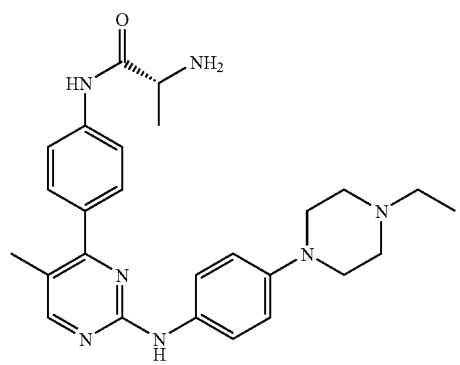

(R)-2-amino-N-(4-(2-(4-(4-ethylpiperazin-1-yl)phenylamino)-5-methylpyrimidin-4-yl)phenyl)propanamide

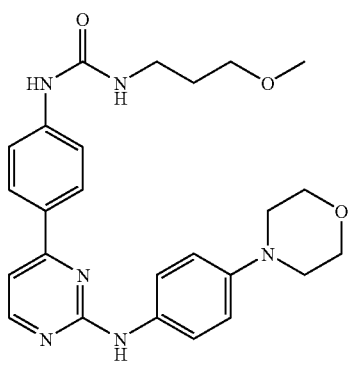

1-(3-methoxypropyl)-3-(4-(2-(4-morpholinophenylamino)pyrimidin-4-yl)phenyl)urea

773

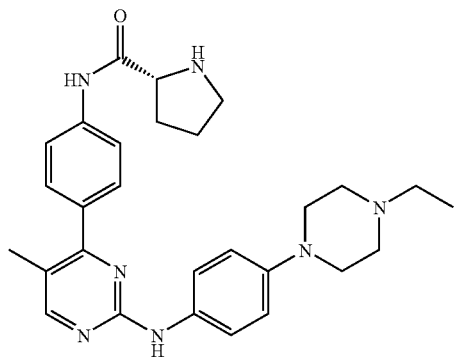

(R)-N-(4-(2-(4-(4-ethylpiperazin-1-yl)phenylamino)-
5-methylpyrimidin-4-yl)phenyl)pyrrolidine-2-
carboxamide

774

-continued

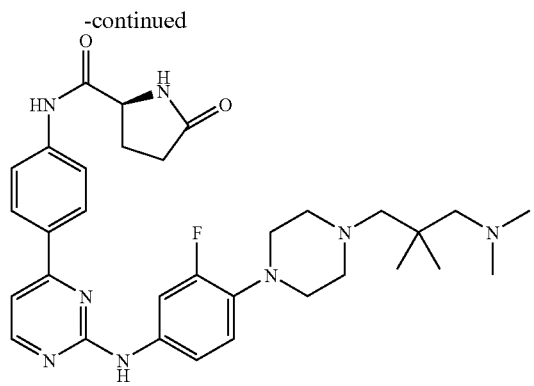

(S)-N-(4-(2-(4-(4-(3-(dimethylamino)-2,2-
dimethylpropyl)piperazin-1-yl)-3-
fluorophenylamino)pyrimidin-4-yl)phenyl)-5-
oxopyrrolidine-2-carboxamide

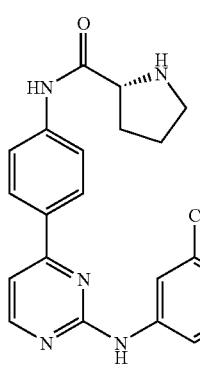

(R)-N-(4-(2-(3-chloro-4-
morpholinophenylamino)pyrimidin-4-
yl)phenyl)pyrrolidine-2-carboxamide

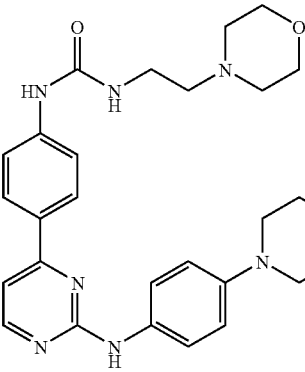

1-(2-morpholinoethyl)-3-(4-(2-(4-
morpholinophneylamino)pyrimidin-4-
yl)phenyl)urea

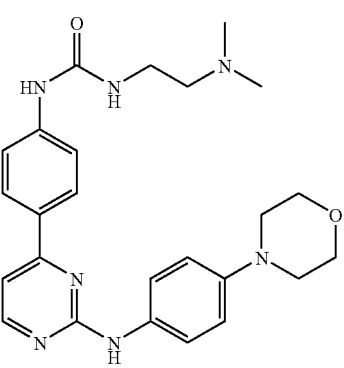

1-(2-dimethylamino)ethyl)-3-(4-(2-(4-
morpholinophenylamino)pyrimidin-4-
yl)phenyl)urea

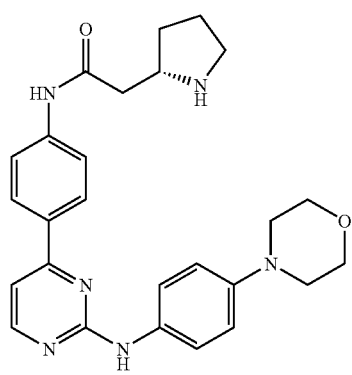

(S)-N-(4-(2-(4-morpholinophenylamino)pyrimidin-4-
yl)phenyl)-2-(pyrrolidine-2-yl)acetamide

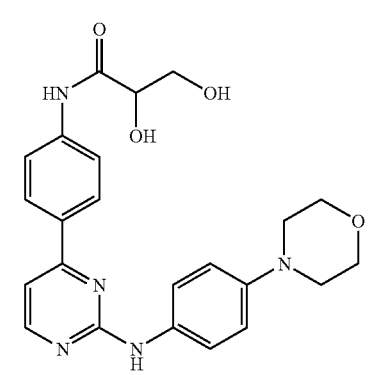

2,3-dihydroxy-N-)4-(2-(4-morpholino-
phenylamino)pyrimidin-4-yl)phenyl)-propanamide

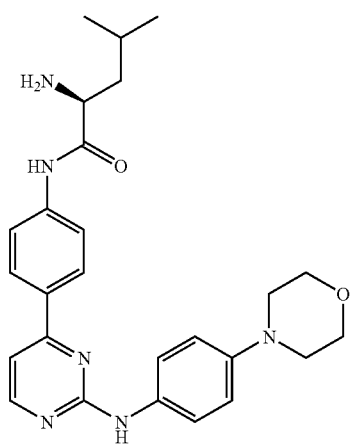

(S)-2-amino-4-methyl-N-(2-(4-
morpholinophenylamino)pyrimidin-4-
yl)phenyl)pentanamide -continued

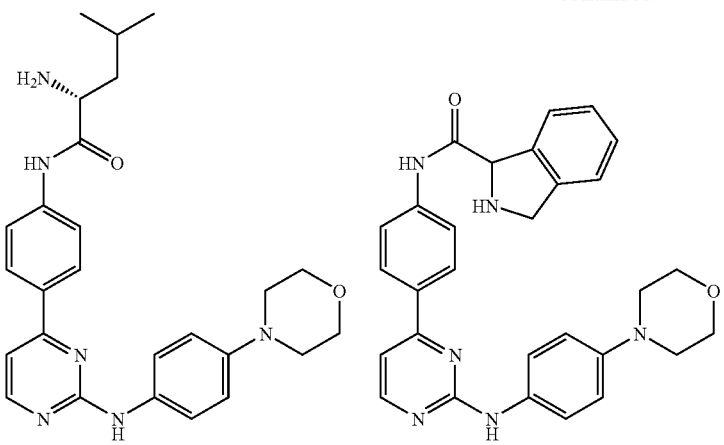

(R)-2-amino-4-methyl-N-(4-(2-(4-morpholinophenylamino)pyrimidin-4-yl)phenyl)pentanamide N-(4-(2-(4-morpholinophenylamino)pyrimidin-4-yl)phenyl)isoindoline-1-carboxamide

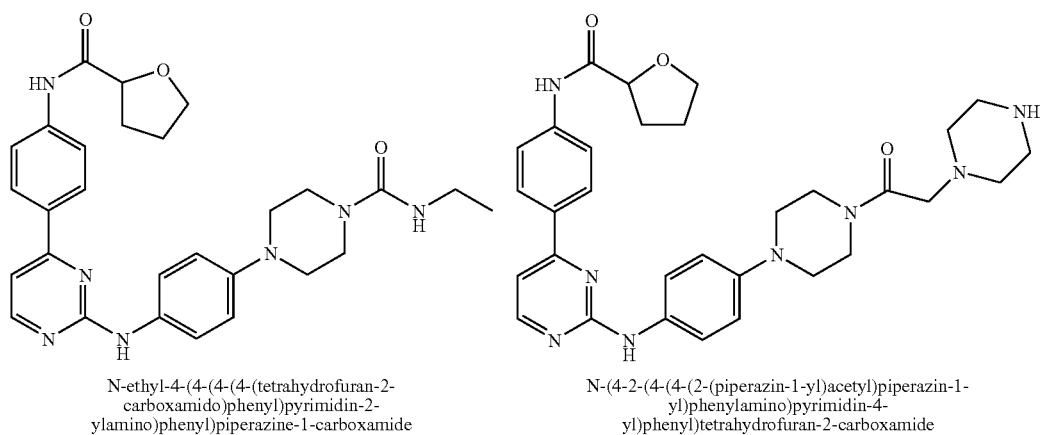

N-ethyl-4-(4-(4-(4-(tetrahydrofuran-2-carboxamido)phenyl)pyrimidin-2-ylamino)phenyl)piperazine-1-carboxamide N-(4-2-(4-(4-(2-(piperazin-1-yl)acetyl)piperazin-1-yl)phenylamino)pyrimidin-4-yl)phenyl)tetrahydrofuran-2-carboxamide

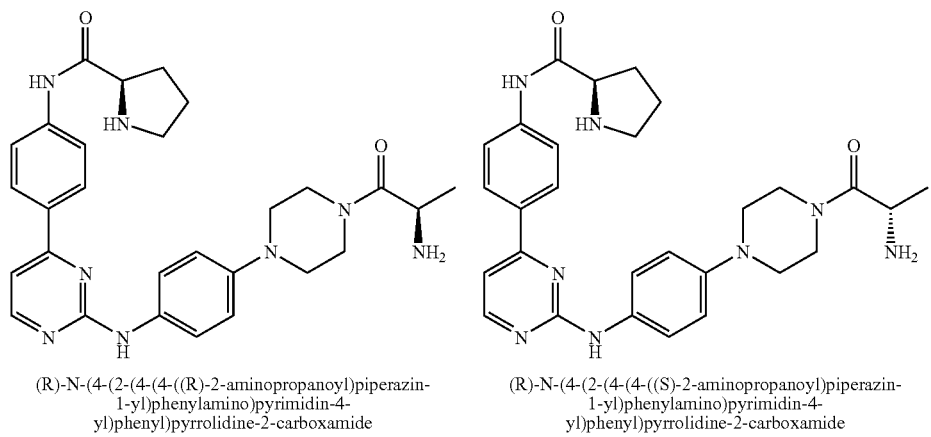

(R)-N-(4-(2-(4-(4-((R)-2-aminopropanoyl)piperazin-1-yl)phenylamino)pyrimidin-4-yl)phenyl)pyrrolidine-2-carboxamide (R)-N-(4-(2-(4-(4-((S)-2-aminopropanoyl)piperazin-1-yl)phenylamino)pyrimidin-4-yl)phenyl)pyrrolidine-2-carboxamide

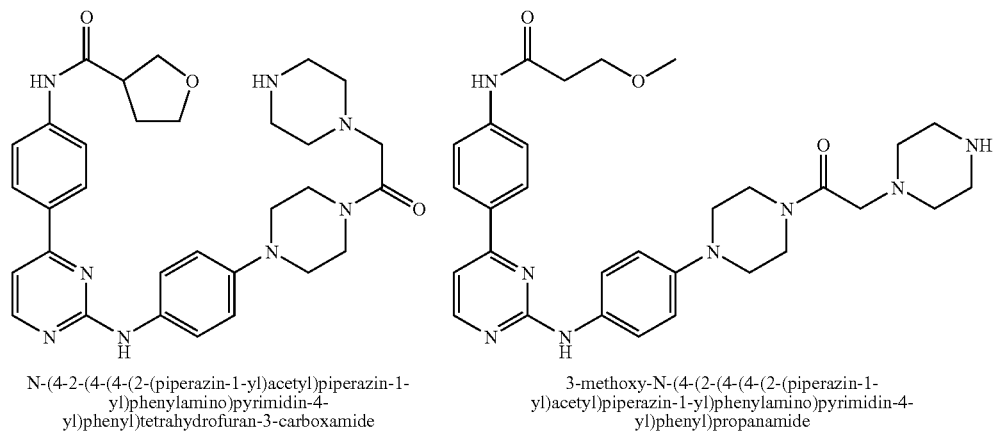

N-(4-2-(4-(4-(2-(piperazin-1-yl)acetyl)piperazin-1-yl)phenylamino)pyrimidin-4-yl)phenyl)tetrahydrofuran-3-carboxamide 3-methoxy-N-(4-(2-(4-(4-(2-(piperazin-1-yl)acetyl)piperazin-1-yl)phenylamino)pyrimidin-4-yl)phenyl)propanamide

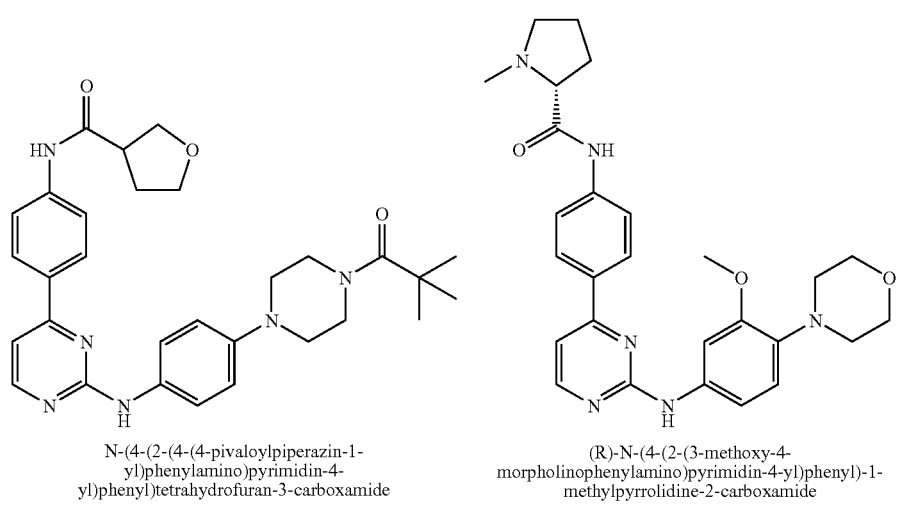

N-(4-(2-(4-(4-pivaloylpiperazin-1-yl)phenylamino)pyrimidin-4-yl)phenyl)tetrahydrofuran-3-carboxamide (R)-N-(4-(2-(3-methoxy-4-morpholinophenylamino)pyrimidin-4-yl)phenyl)-1-methylpyrrolidine-2-carboxamide

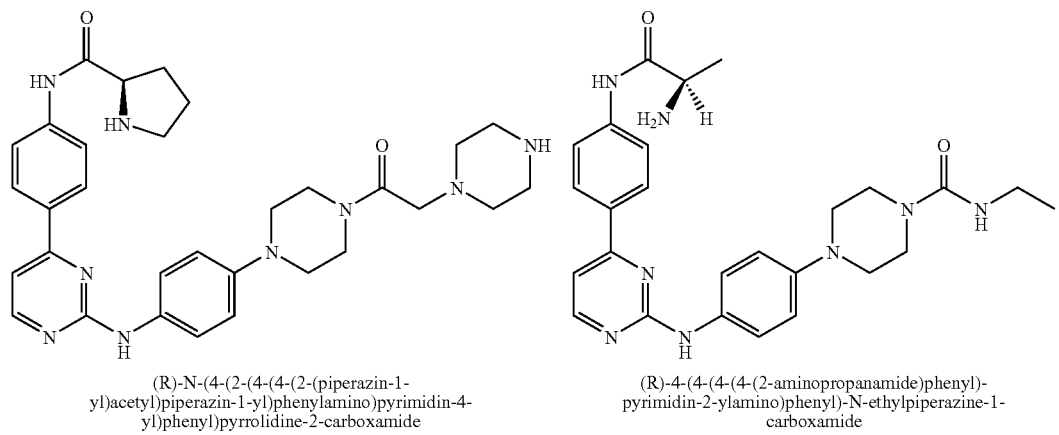

(R)-N-(4-(2-(4-(4-(2-(piperazin-1-yl)acetyl)piperazin-1-yl)phenylamino)pyrimidin-4-yl)phenyl)pyrrolidine-2-carboxamide (R)-4-(4-(4-(2-aminopropanamide)phenyl)-pyrimidin-2-ylamino)phenyl)-N-ethylpiperazine-1-carboxamide -continued

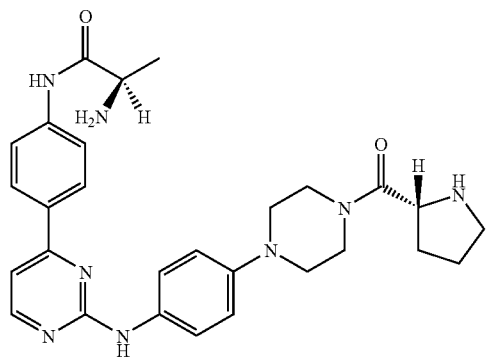

(R)-2-amino-N-(4-(2-(4-(4-((R)-pyrrolidine-2-
carbonyl)piperazin-1-yl)phenylamino)pyrimidin-4-
yl)phenyl)propanamide

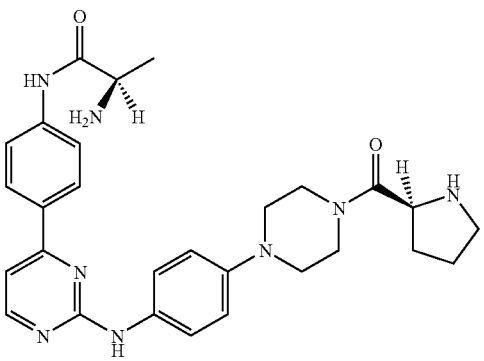

(R)-2-amino-N-(4-(2-(4-(4-((S)-pyrrolidine-2-
carbonyl)piperazin-1-yl)phenylamino)pyrimidin-4-
yl)phenyl)propanamide

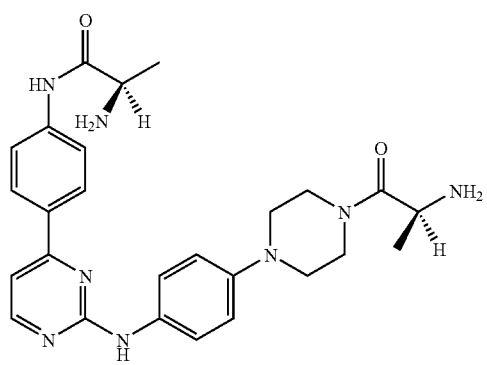

(R)-2-amino-N-(4-(2-(4-(4-((S)-2-
aminopropanoyl)piperazin-1-yl)phenylamino)pyrimidin-4-
yl)phenyl)propanamide

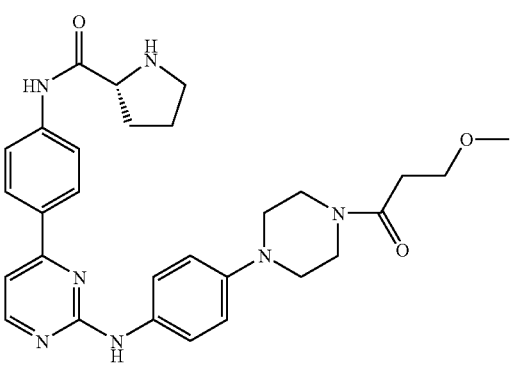

(R)-N-(4-(2-(4-(4-(3-methoxypropanoyl)piperazin-
1-yl)phenylamino)pyrimidin-4-
yl)phenyl)pyrrolidine-2-carboxamide

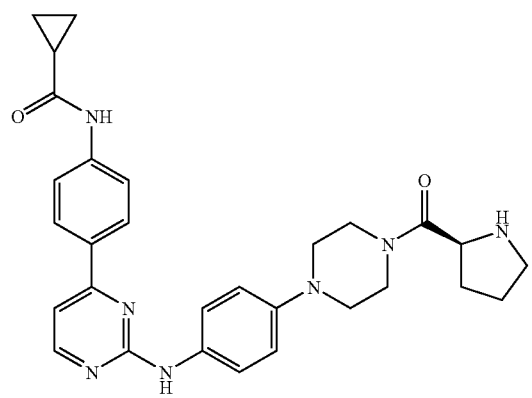

(S)-N-(4-(2-(4-(4-(pyrrolidine-2-carbonyl)piperazin-
1-yl)phenylamino)pyrimidin-4-
yl)phenyl)cyclopropanecarboxamide

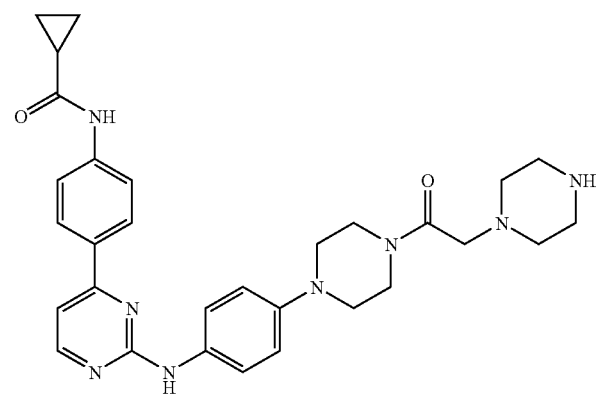

N-(4-(2-(4-(4-(2-piperazin-1-yl)acetyl)piperazin-1-
yl)phenylamino)pyrimidin-4-
yl)phenyl)cyclopropanecarboxamide

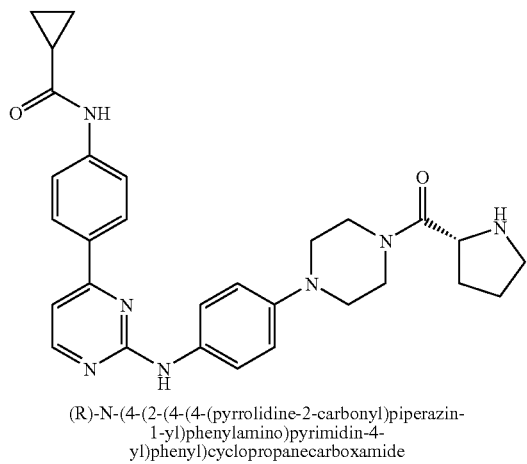

(R)-N-(4-(2-(4-(4-(pyrrolidine-2-carbonyl)piperazin-1-yl)phenylamino)pyrimidin-4-yl)phenyl)cyclopropanecarboxamide

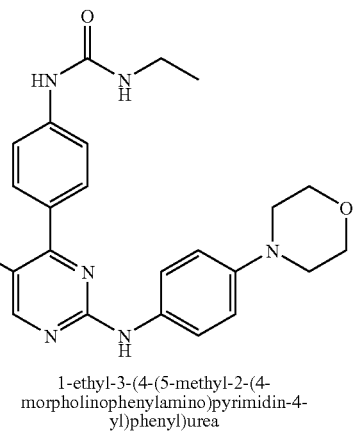

1-ethyl-3-(4-(5-methyl-2-(4-morpholinophenylamino)pyrimidin-4-yl)phenyl)urea

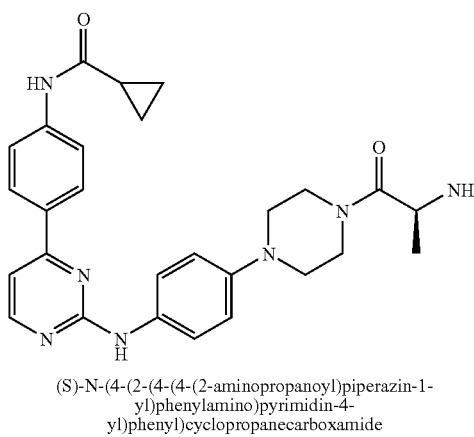

(S)-N-(4-(2-(4-(4-(2-aminopropanoyl)piperazin-1-yl)phenylamino)pyrimidin-4-yl)phenyl)cyclopropanecarboxamide

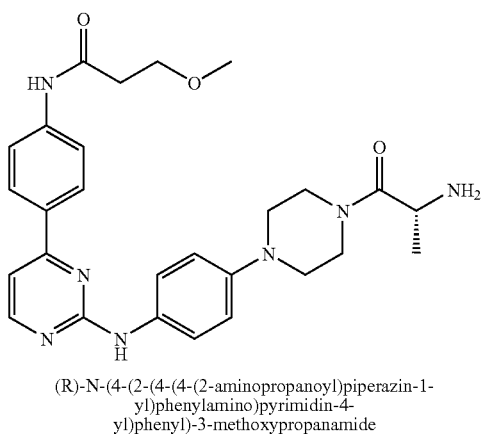

(R)-N-(4-(2-(4-(4-(2-aminopropanoyl)piperazin-1-yl)phenylamino)pyrimidin-4-yl)phenyl)-3-methoxypropanamide

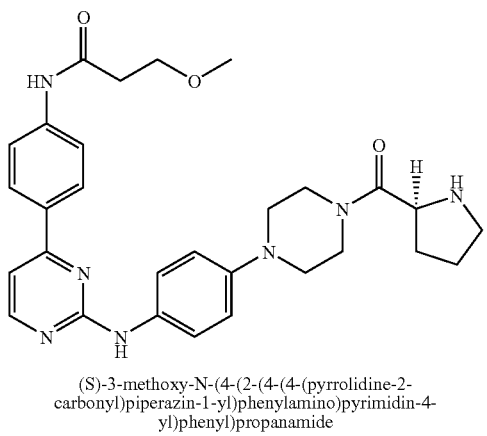

(S)-3-methoxy-N-(4-(2-(4-(4-(pyrrolidine-2-carbonyl)piperazin-1-yl)phenylamino)pyrimidin-4-yl)phenyl)propanamide

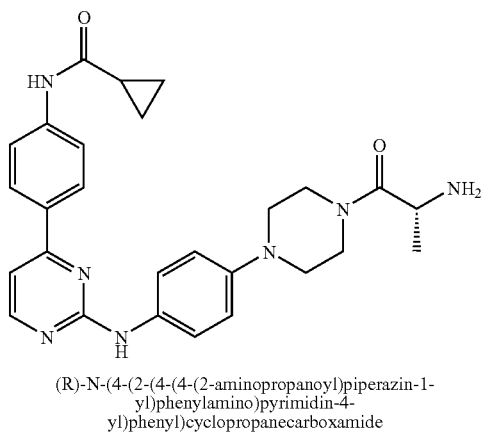

(R)-N-(4-(2-(4-(4-(2-aminopropanoyl)piperazin-1-yl)phenylamino)pyrimidin-4-yl)phenyl)cyclopropanecarboxamide -continued

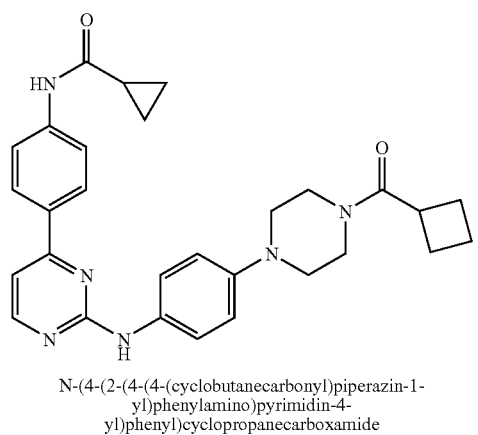

N-(4-(2-(4-(4-(cyclobutanecarbonyl)piperazin-1-yl)phenylamino)pyrimidin-4-yl)phenyl)cyclopropanecarboxamide

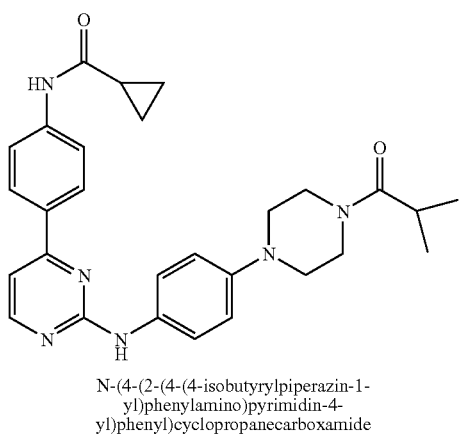

N-(4-(2-(4-(4-isobutyrylpiperazin-1-yl)phenylamino)pyrimidin-4-yl)phenyl)cyclopropanecarboxamide

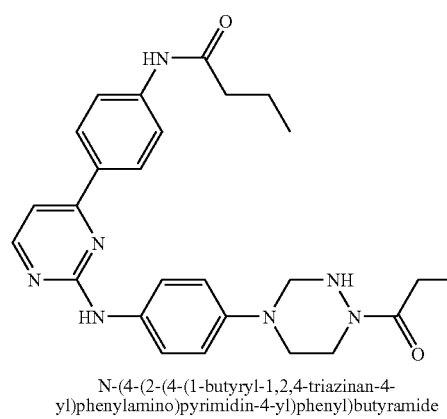

N-(4-(2-(4-(1-butyryl-1,2,4-triazinan-4-yl)phenylamino)pyrimidin-4-yl)phenyl)butyramide

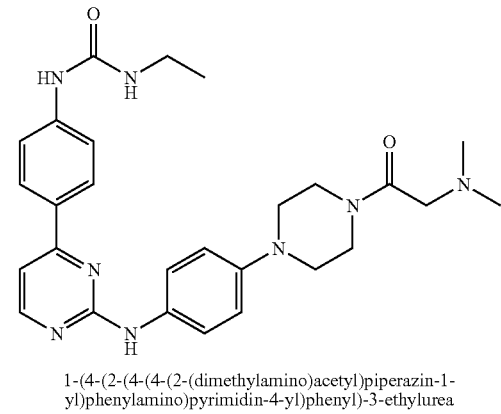

1-(4-(2-(4-(4-(2-(dimethylamino)acetyl)piperazin-1-yl)phenylamino)pyrimidin-4-yl)phenyl)-3-ethylurea

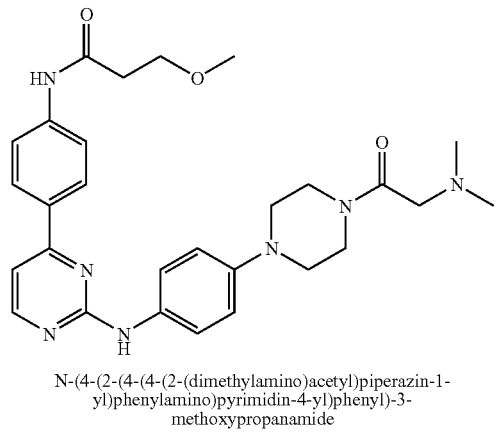

N-(4-(2-(4-(4-(2-(dimethylamino)acetyl)piperazin-1-yl)phenylamino)pyrimidin-4-yl)phenyl)-3-methoxypropanamide

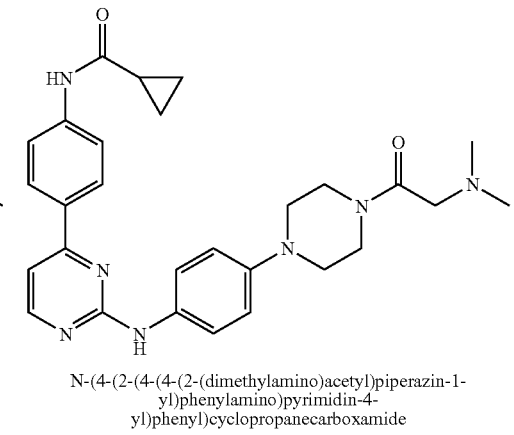

N-(4-(2-(4-(4-(2-(dimethylamino)acetyl)piperazin-1-yl)phenylamino)pyrimidin-4-yl)phenyl)cyclopropanecarboxamide

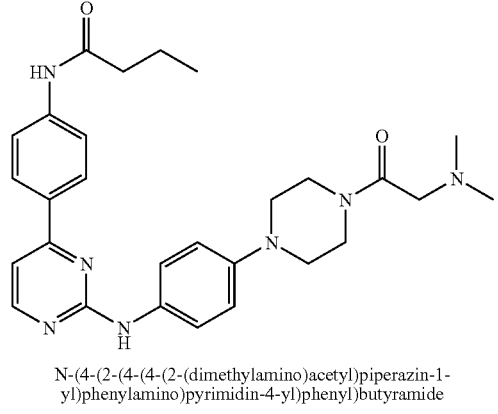

N-(4-(2-(4-(4-(2-(dimethylamino)acetyl)piperazin-1-yl)phenylamino)pyrimidin-4-yl)phenyl)butyramide

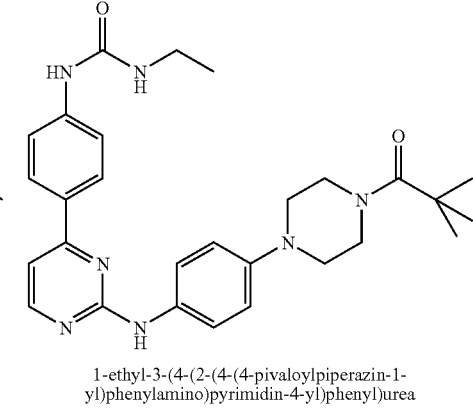

1-ethyl-3-(4-(2-(4-(4-pivaloylpiperazin-1-yl)phenylamino)pyrimidin-4-yl)phenyl)urea

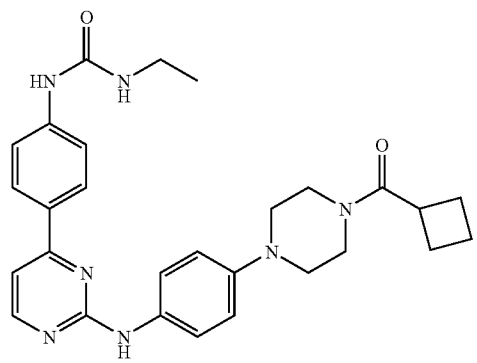

1-(4-(2-(4-(4-(cyclobutanecarbonyl)piperazin-1-yl)phenylamino)pyrimidin-4-yl)phenyl)-3-ethylurea

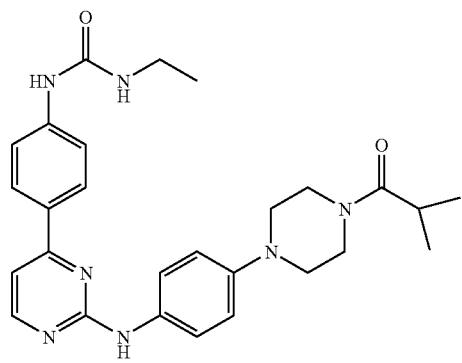

1-ethyl-3-(4-(2-(4-(4-isobutyrylpiperazin-1-yl)phenylamino)pyrimidin-4-yl)phenyl)urea

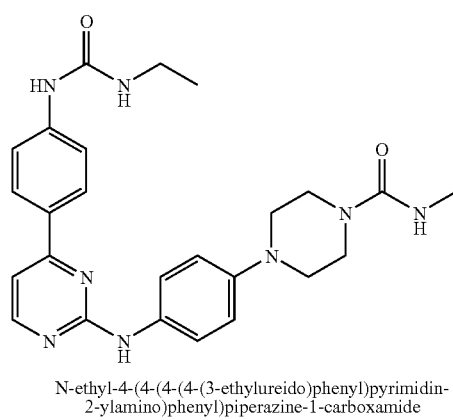

N-ethyl-4-(4-(4-(3-ethylureido)phenyl)pyrimidin-2-ylamino)phenyl)piperazine-1-carboxamide

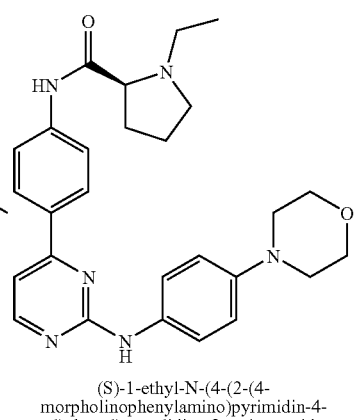

(S)-1-ethyl-N-(4-(2-(4-morpholinophenylamino)pyrimidin-4-yl)phenyl)pyrrolidine-2-carboxamide

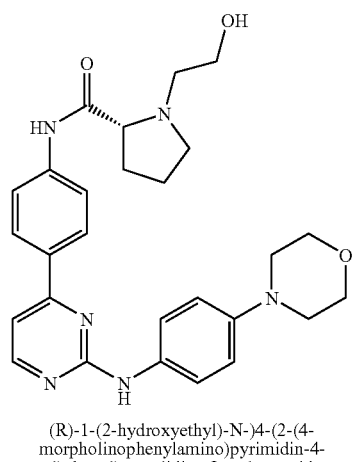

(R)-1-(2-hydroxyethyl)-N-)4-(2-(4-morpholinophenylamino)pyrimidin-4-yl)phenyl)pyrrolidine-2-carboxamide

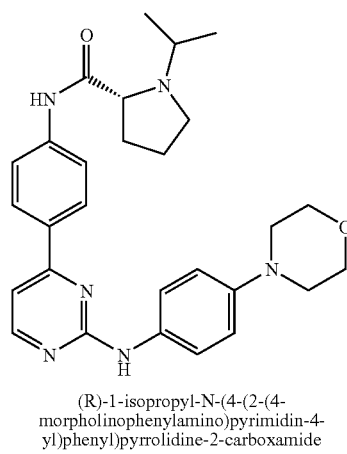

(R)-1-isopropyl-N-(4-(2-(4-morpholinophenylamino)pyrimidin-4-yl)phenyl)pyrrolidine-2-carboxamide

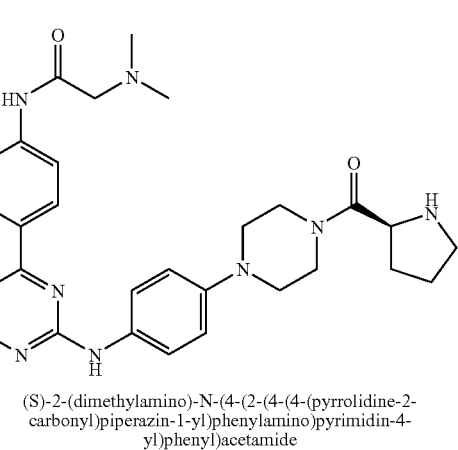

(S)-2-(dimethylamino)-N-(4-(2-(4-(4-(pyrrolidine-2-carbonyl)piperazin-1-yl)phenylamino)pyrimidin-4-yl)phenyl)acetamide -continued

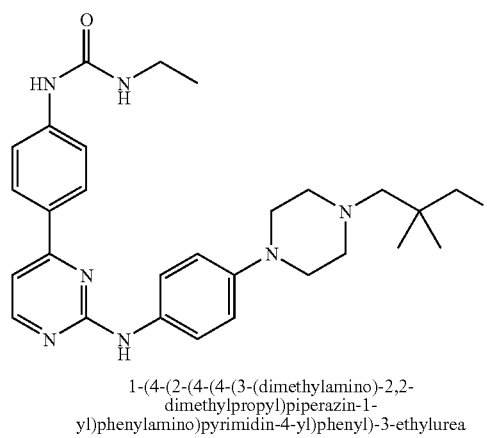

1-(4-(2-(4-(4-(3-(dimethylamino)-2,2-
dimethylpropyl)piperazin-1-
yl)phenylamino)pyrimidin-4-yl)phenyl)-3-ethylurea

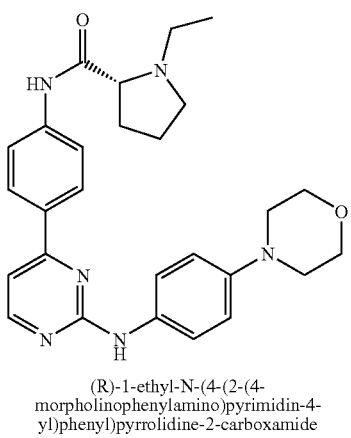

(R)-1-ethyl-N-(4-(2-(4-
morpholinophenylamino)pyrimidin-4-
yl)phenyl)pyrrolidine-2-carboxamide

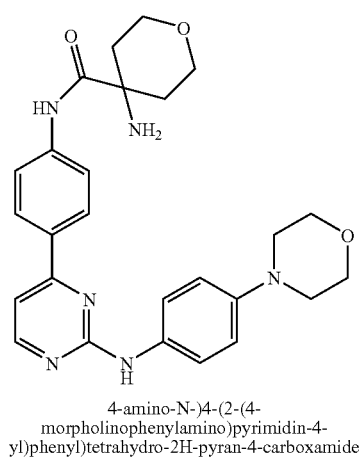

4-amino-N-)4-(2-(4-
morpholinophenylamino)pyrimidin-4-
yl)phenyl)tetrahydro-2H-pyran-4-carboxamide

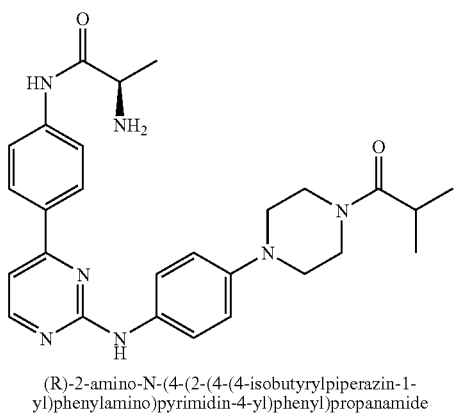

(R)-2-amino-N-(4-(2-(4-(4-isobutyrylpiperazin-1-
yl)phenylamino)pyrimidin-4-yl)phenyl)propanamide

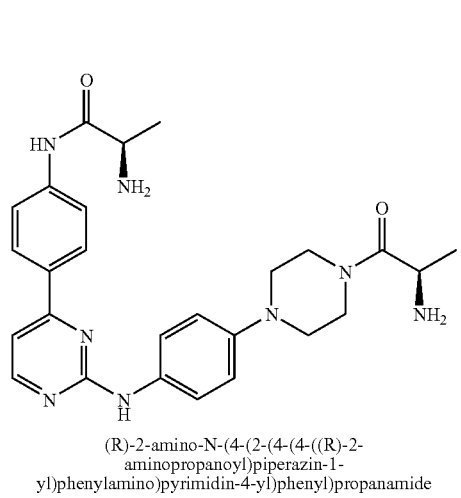

(R)-2-amino-N-(4-(2-(4-(4-((R)-2-
aminopropanoyl)piperazin-1-
yl)phenylamino)pyrimidin-4-yl)phenyl)propanamide

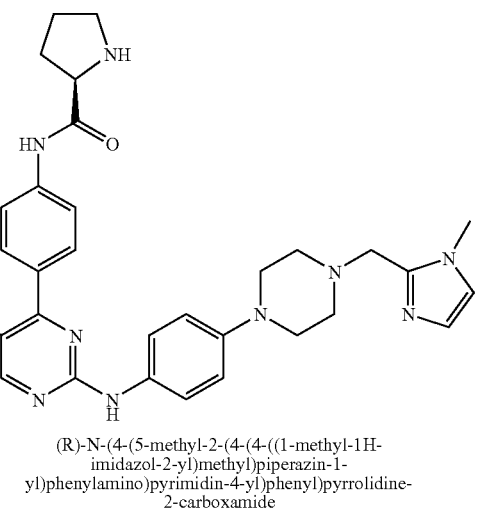

(R)-N-(4-(5-methyl-2-(4-(4-((1-methyl-1H-
imidazol-2-yl)methyl)piperazin-1-
yl)phenylamino)pyrimidin-4-yl)phenyl)pyrrolidine-
2-carboxamide

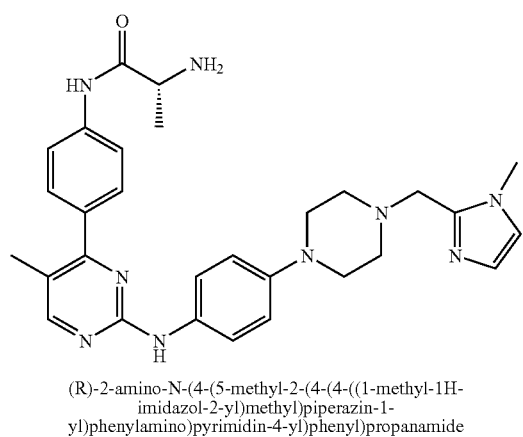

(R)-2-amino-N-(4-(5-methyl-2-(4-(4-((1-methyl-1H-imidazol-2-yl)methyl)piperazin-1-yl)phenylamino)pyrimidin-4-yl)phenyl)propanamide

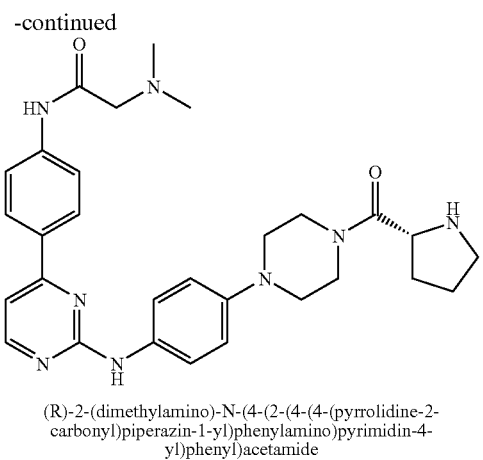

(R)-2-(dimethylamino)-N-(4-(2-(4-(4-(pyrrolidine-2-carbonyl)piperazin-1-yl)phenylamino)pyrimidin-4-yl)phenyl)acetamide

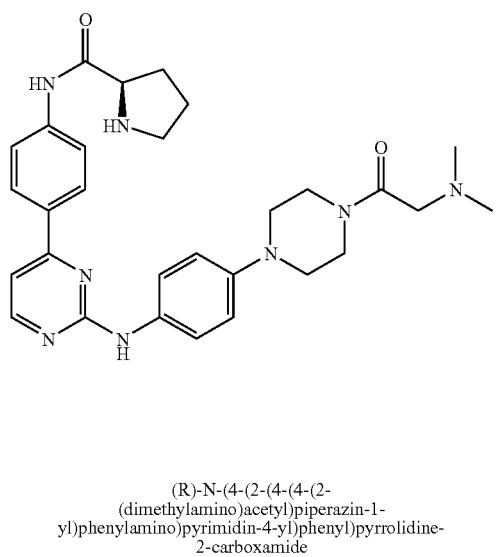

(R)-N-(4-(2-(4-(4-(2-(dimethylamino)acetyl)piperazin-1-yl)phenylamino)pyrimidin-4-yl)phenyl)pyrrolidine-2-carboxamide

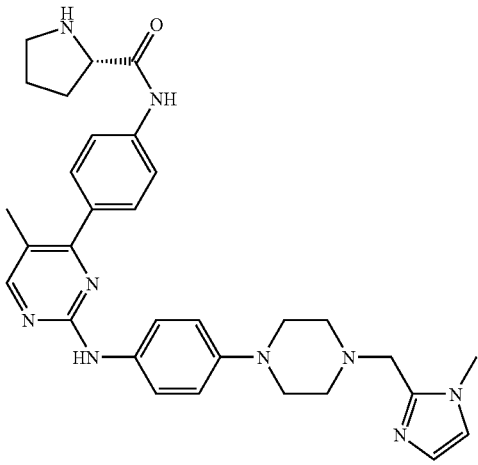

(S)-N-(4-(5-methyl-2-(4-(4-((1-methyl-1H-imidazol-2-yl)methyl)piperazin-1-yl)phenylamino)pyrimidin-4-yl)phenyl)pyrrolidine-2-carboxamide

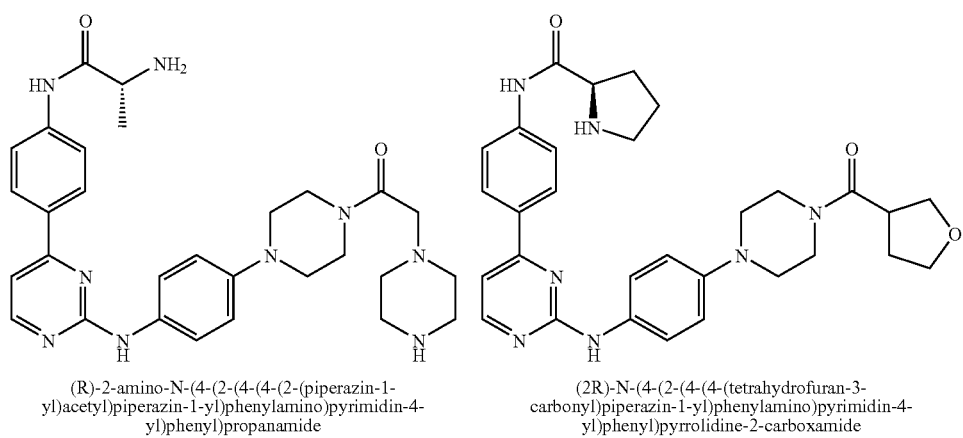

(R)-2-amino-N-(4-(2-(4-(4-(2-(piperazin-1-yl)acetyl)piperazin-1-yl)phenylamino)pyrimidin-4-yl)phenyl)propanamide (2R)-N-(4-(2-(4-(4-(tetrahydrofuran-3-carbonyl)piperazin-1-yl)phenylamino)pyrimidin-4-yl)phenyl)pyrrolidine-2-carboxamide -continued

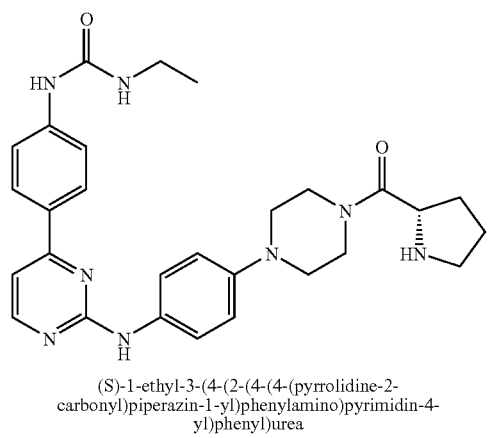

(S)-1-ethyl-3-(4-(2-(4-(4-(pyrrolidine-2-carbonyl)piperazin-1-yl)phenylamino)pyrimidin-4-yl)phenyl)urea

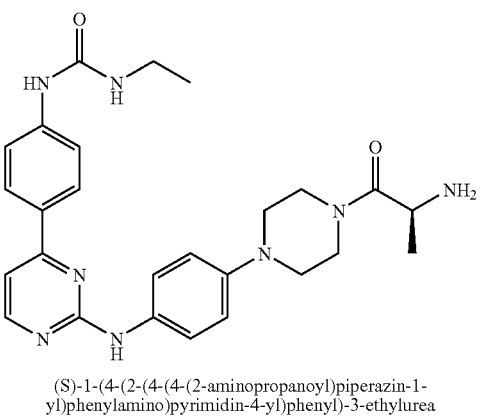

(S)-1-(4-(2-(4-(4-(2-aminopropanoyl)piperazin-1-yl)phenylamino)pyrimidin-4-yl)phenyl)-3-ethylurea

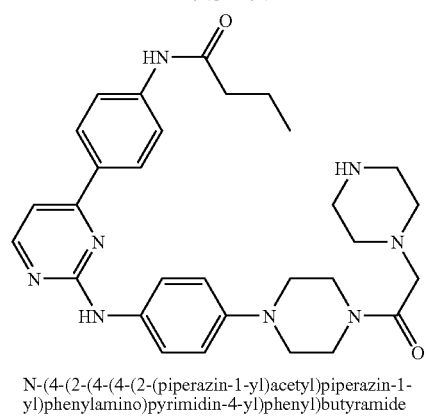

N-(4-(2-(4-(4-(2-(piperazin-1-yl)acetyl)piperazin-1-yl)phenylamino)pyrimidin-4-yl)phenyl)butyramide

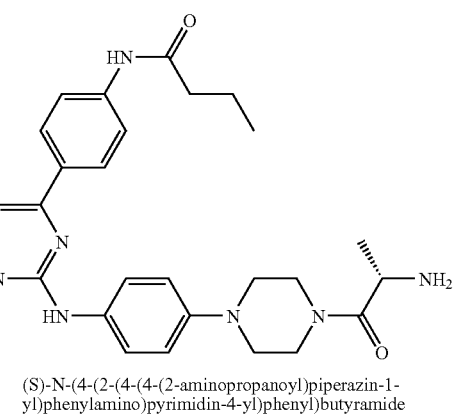

(S)-N-(4-(2-(4-(4-(2-aminopropanoyl)piperazin-1-yl)phenylamino)pyrimidin-4-yl)phenyl)butyramide

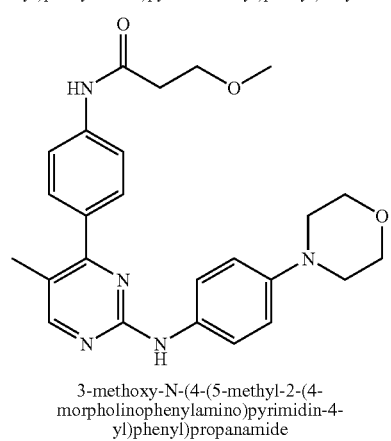

3-methoxy-N-(4-(5-methyl-2-(4-morpholinophenylamino)pyrimidin-4-yl)phenyl)propanamide

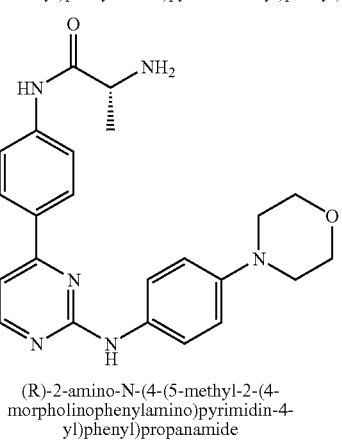

(R)-2-amino-N-(4-(5-methyl-2-(4-morpholinophenylamino)pyrimidin-4-yl)phenyl)propanamide

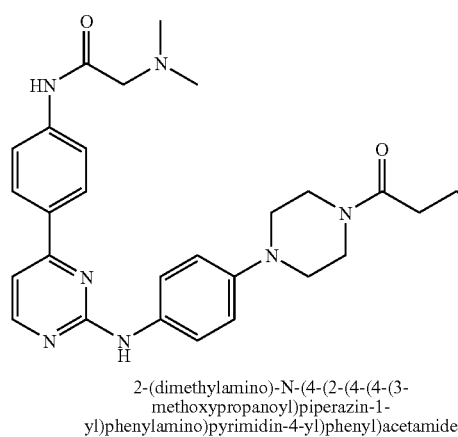

2-(dimethylamino)-N-(4-(2-(4-(4-(3-methoxypropanoyl)piperazin-1-yl)phenylamino)pyrimidin-4-yl)phenyl)acetamide

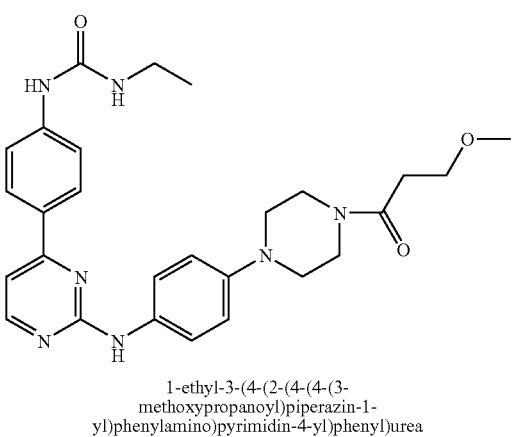

1-ethyl-3-(4-(2-(4-(4-(3-methoxypropanoyl)piperazin-1-yl)phenylamino)pyrimidin-4-yl)phenyl)urea -continued

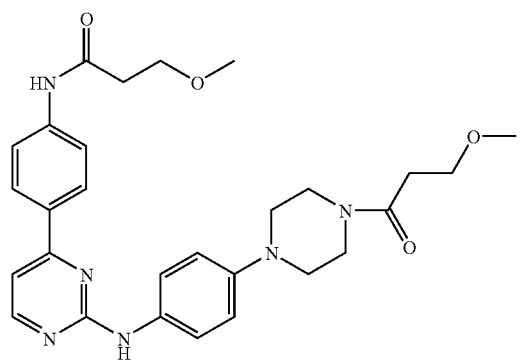

3-methoxy-N-(4-(2-(4-(4-(3-methoxypropanoyl)piperazin-1-yl)phenylamino)pyrimidin-4-yl)phenyl)propanamide

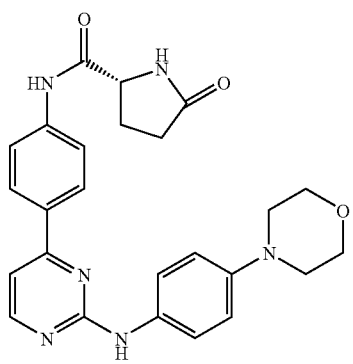

(R)-N-)4-(2-(4-morpholinophenylamino)pyrimidin-4-yl)phenyl)-5-oxopyrrolidine-2-carboxamide

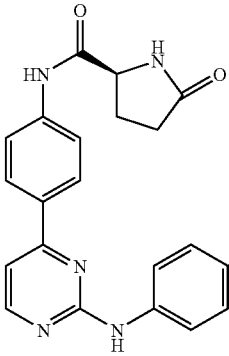

(S)-N-(4-(2-(4-morpholinophenylamino)pyrimidin-4-yl)phenyl)-5-oxopyrrolidine-2-carboxamide

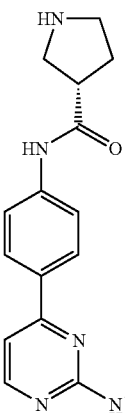

(S)-N-(4-(2-(4-morpholinophenylamino)pyrimidin-4-yl)phenyl)kpyrrolidine-3-carboxamide

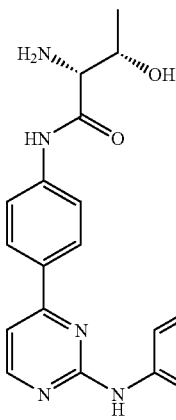

(2R,3S)-2-amino-3-hydroxy-N-(4-(4-(4-morpholinophenylamino)pyrimidin-4-yl)phenyl)butanamide

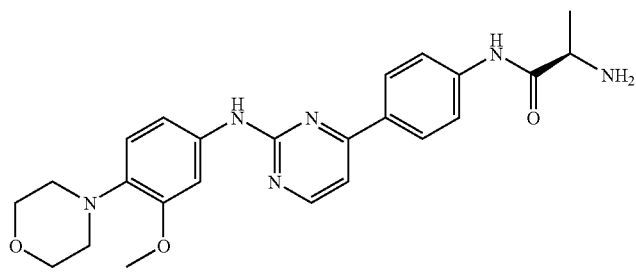

(R)-2-amino-N-(4-(2-(3-methoxy-4-morpholinophenylamino)pyrimidin-4-yl)phenyl)propanamide

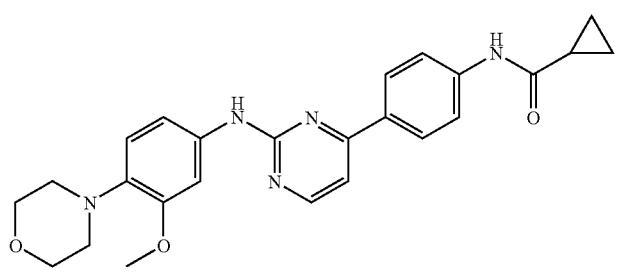

N-(4-(2-(3-methoxy-4-morpholinophenylamino)pyrimidin-4-yl)phenyl)cyclopropanecarboxamide -continued

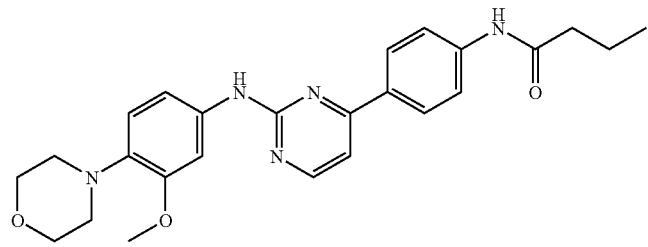

N-(4-(2-(3-methoxy-4-morpholinophenylamino)pyrimidin-4-yl)phenyl)butyramide

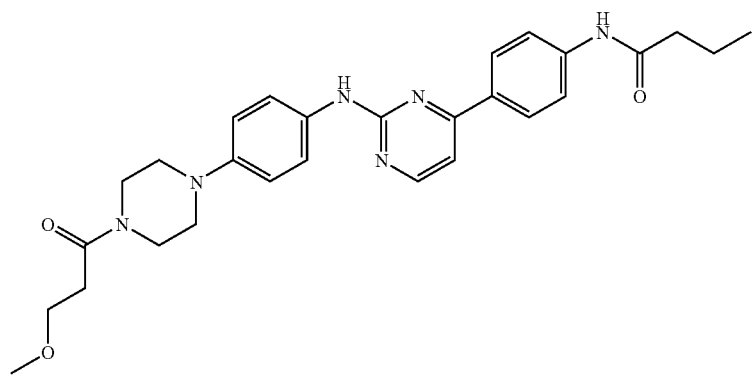

N-(4-(2-(4-(4-(3-methoxypropanoyl)piperazin-1-yl)phenylamino)pyrimidin-4-yl)phenyl)butyramide

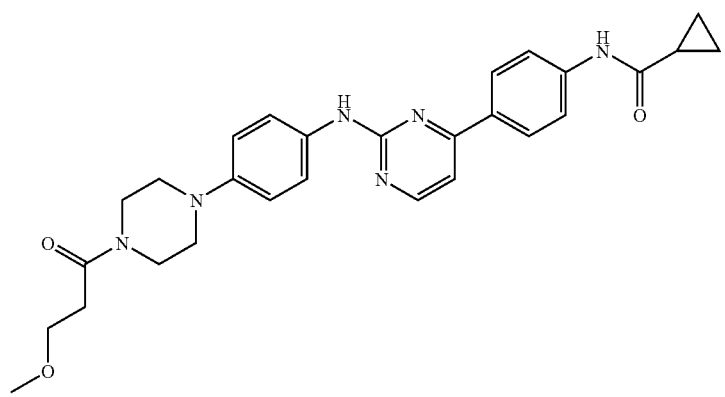

N-(4-(2-(4-(4-(3-methoxypropanoyl)piperazin-1-yl)phenylamino)pyrimidin-4-yl)phenyl)cyclopropanecarboxamide

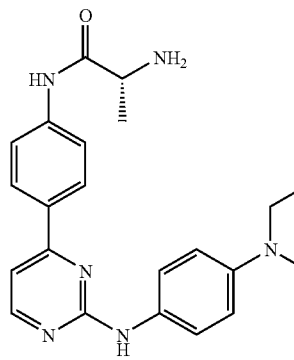

(R)-2-amino-N-(4-(2-(4-(4-(3-methoxypropanoyl)piperazin-1-yl)phenylamino)pyrimidin-4-yl)phenyl)propanamide

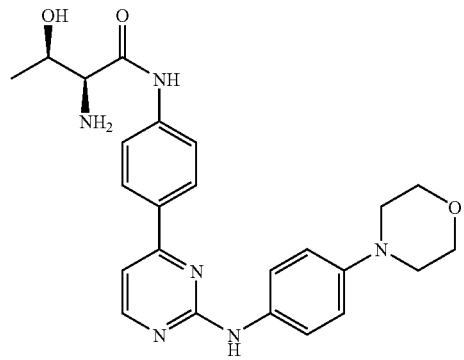

(2S,3R)-2-amino-3-hydroxy-N-(4-(2-(4-morpholinophenylamino)pyrimidin-4-yl)phenyl)butanamide -continued

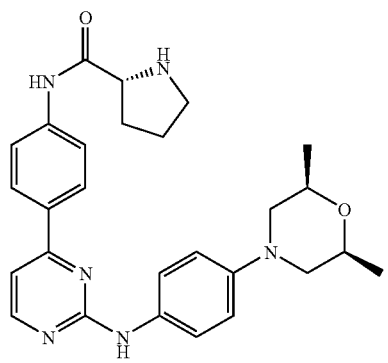

(R)-N-(4-(2-(4-((2S,6R)-2,6-dimethylmorpholino)phenylamino)pyrimidin-4-yl)phenyl)pyrrolidine-2-carboxamide

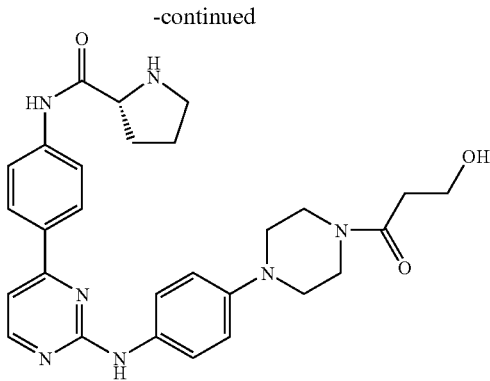

(R)-N-(4-(2-(4-(4-(3-hydroxypropanoyl)piperazin-1-yl)phenylamino)pyrimidin-4-yl)phenyl)pyrrolidine-2-carboxamide

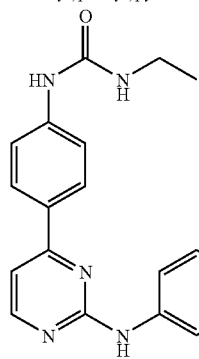

1-ethyl-3-(4-(2-(4-(4-(2-(piperazin-1-yl)acetyl)piperazin-1-yl)phenylamino)pyrimidin-4-yl)phenyl)urea

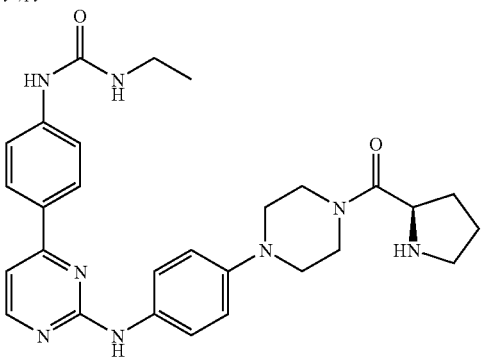

(R)-1-ethyl-3-(4-(2-(4-(4-(pyrrolidine-2-carbonyl)piperazin-1-yl)phenylamino)pyrimidin-4-yl)phenyl)urea

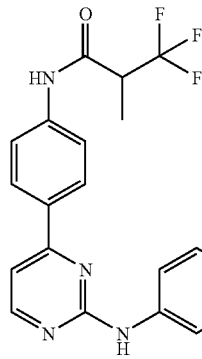

3,3,3-trifluoro-2-hydroxy-N-(4-(2-(4-morpholinophenylamino)pyrimidin-4-yl)phenyl)propanamide

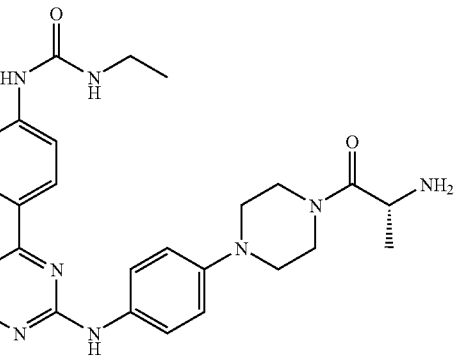

(R)-1-(4-(2-(4-(4-(2-aminopropanoyl)piperazin-1-yl)phenylamino)pyrimidin-4-yl)phenyl)-3-ethylurea

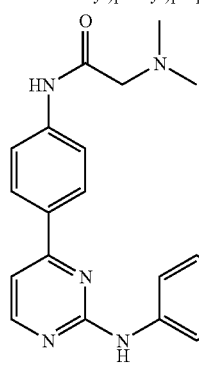

2-(dimethylamino)-N-(4-(2-(4-(4-(2-(dimethylamino)acetyl)piperazin-1-yl)phenylamino)pyrimidin-4-yl)phenyl)acetamide

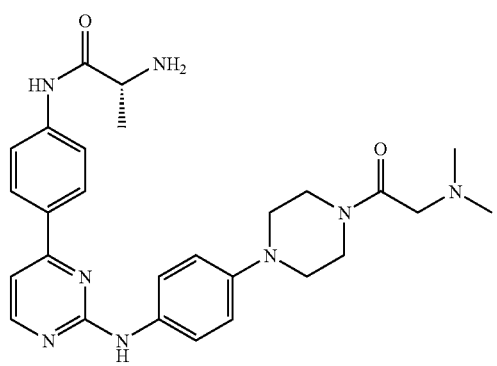

(R)-2-(amino-N-(4-(2-(4-(4-(2-(dimethylamino)acetyl)piperazin-1-yl)phenylamino)pyrimidin-4-yl)phenyl)propanamide

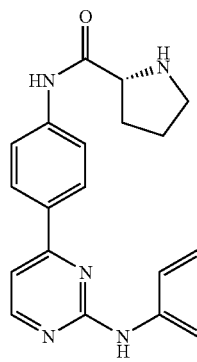

(R)-N-(4-(2-(4-(4-(3-(dimethylamino)-2,2-dimethylpropyl)piperazin-1-yl)phenylamino)pyrimidin-4-yl)phenyl)pyrrolidine-2-carboxamide

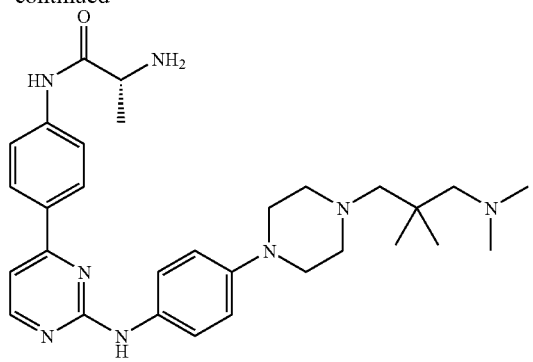

(R)-2-amino-N-(4-(2-(4-(4-(3-(dimethylamino)-2,2-dimethylpropyl)piperazin-1-yl)phenylamino)pyrimidin-4-yl)phenyl)propanamide

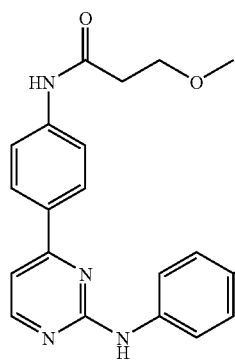

N-(4-(2-(4-(4-(3-(dimethylamino)-2,2-dimethylpropyl)piperazin-1-yl)phenylamino)pyrimidin-4-yl)phenyl)-3-methoxypropanamide

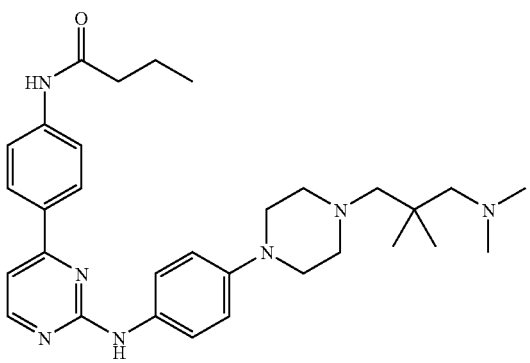

N-(4-(2-(4-(4-(3-(dimethylamino)-2,2-dimethylpropyl)piperazin-1-yl)phenylamino)pyrimidin-4-yl)phenyl)butyramide

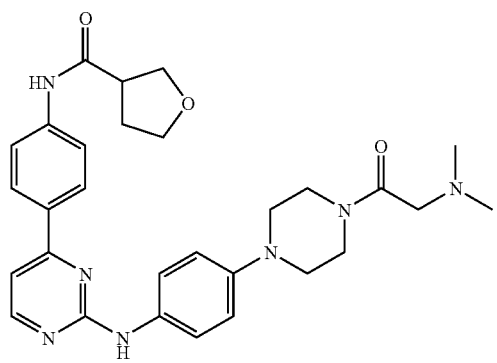

N-(4-(2-(4-(4-(2-(dimethylamino)acetyl)piperazin-1-yl)phenylamino)pyrimidin-4-yl)phenyl)tetrahydrofuran-3-carboxamide

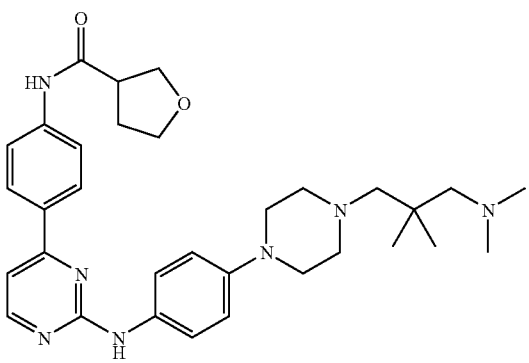

N-(4-(2-(4-(4-(3-(dimethylamino)-2,2-dimethylpropyl)piperazin-1-yl)phenylamino)pyrimidin-4-yl)phenyl)tetrahydrofuran-3-carboxamide

801

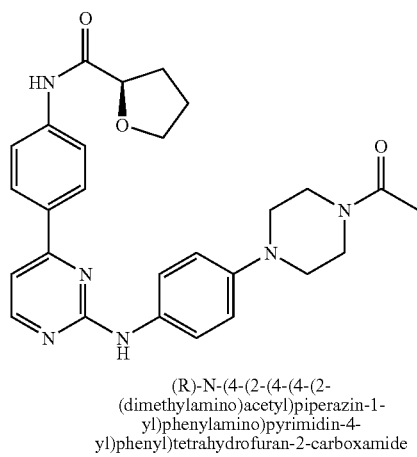

(R)-N-(4-(2-(4-(4-(2-
(dimethylamino)acetyl)piperazin-1-
yl)phenylamino)pyrimidin-4-
yl)phenyl)tetrahydrofuran-2-carboxamide

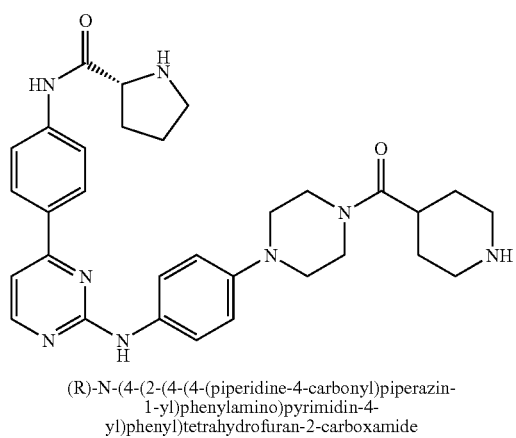

(R)-N-(4-(2-(4-(4-(piperidine-4-carbonyl)piperazin-
1-yl)phenylamino)pyrimidin-4-
yl)phenyl)tetrahydrofuran-2-carboxamide

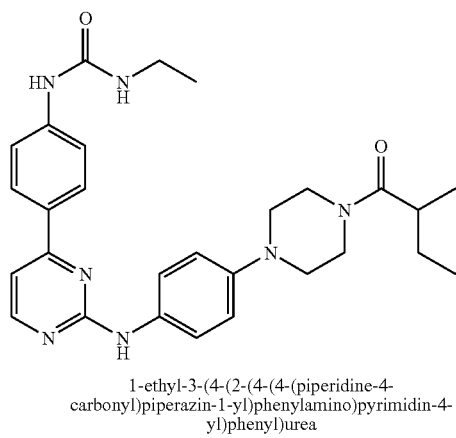

1-ethyl-3-(4-(2-(4-(4-(piperidine-4-
carbonyl)piperazin-1-yl)phenylamino)pyrimidin-4-
yl)phenyl)urea

802

-continued

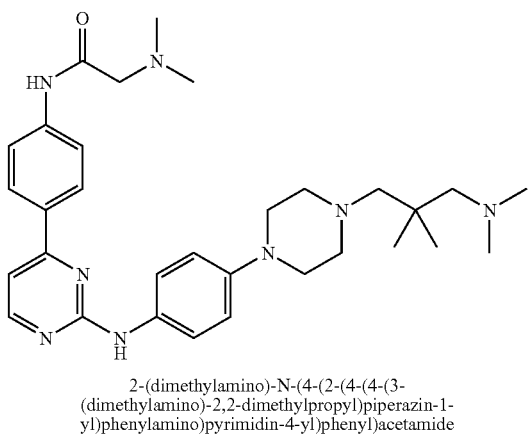

2-(dimethylamino)-N-(4-(2-(4-(4-(3-
(dimethylamino)-2,2-dimethylpropyl)piperazin-1-
yl)phenylamino)pyrimidin-4-yl)phenyl)acetamide

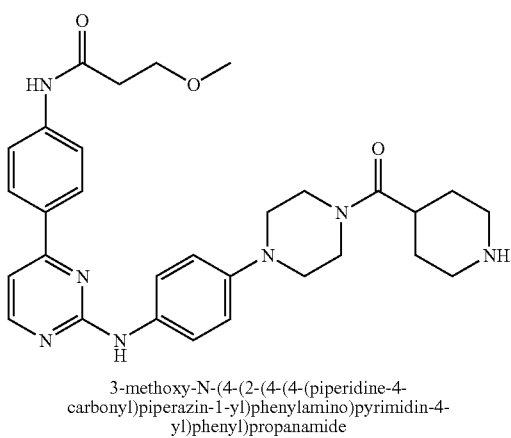

3-methoxy-N-(4-(2-(4-(4-(piperidine-4-
carbonyl)piperazin-1-yl)phenylamino)pyrimidin-4-
yl)phenyl)propanamide

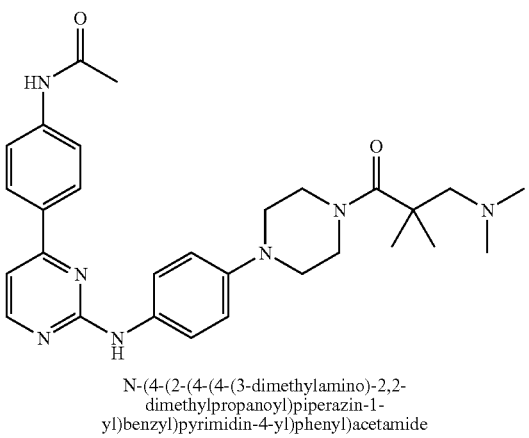

N-(4-(2-(4-(4-(3-dimethylamino)-2,2-
dimethylpropanoyl)piperazin-1-
yl)benzyl)pyrimidin-4-yl)phenyl)acetamide

803

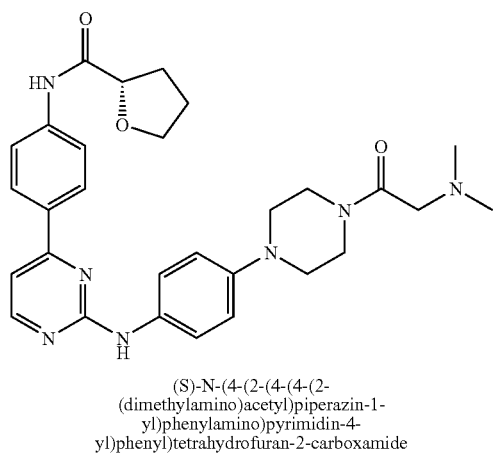

(S)-N-(4-(2-(4-(4-(2-(dimethylamino)acetyl)piperazin-1-yl)phenylamino)pyrimidin-4-yl)phenyl)tetrahydrofuran-2-carboxamide

804

-continued

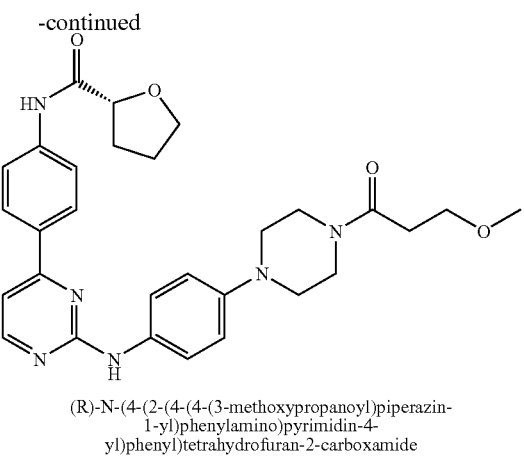

(R)-N-(4-(2-(4-(4-(3-methoxypropanoyl)piperazin-1-yl)phenylamino)pyrimidin-4-yl)phenyl)tetrahydrofuran-2-carboxamide

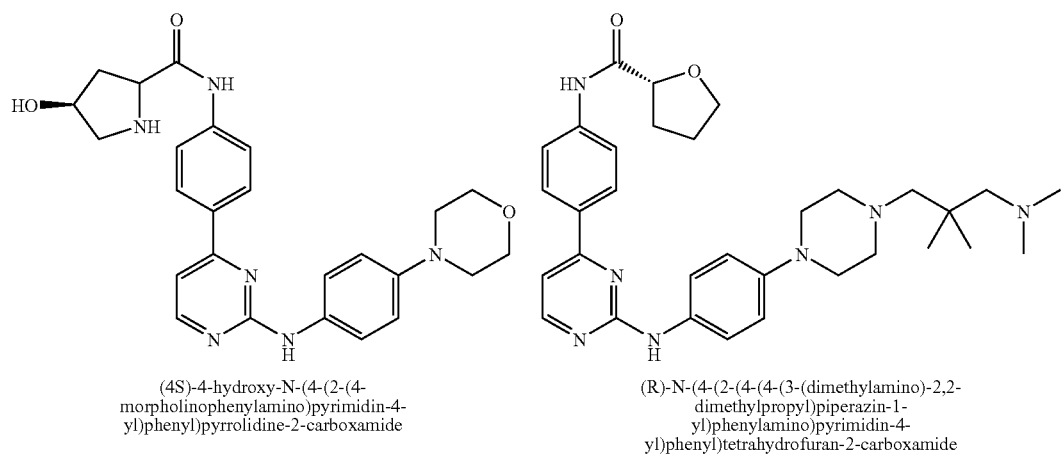

(4S)-4-hydroxy-N-(4-(2-(4-morpholinophenylamino)pyrimidin-4-yl)phenyl)pyrrolidine-2-carboxamide (R)-N-(4-(2-(4-(4-(3-(dimethylamino)-2,2-dimethylpropyl)piperazin-1-yl)phenylamino)pyrimidin-4-yl)phenyl)tetrahydrofuran-2-carboxamide

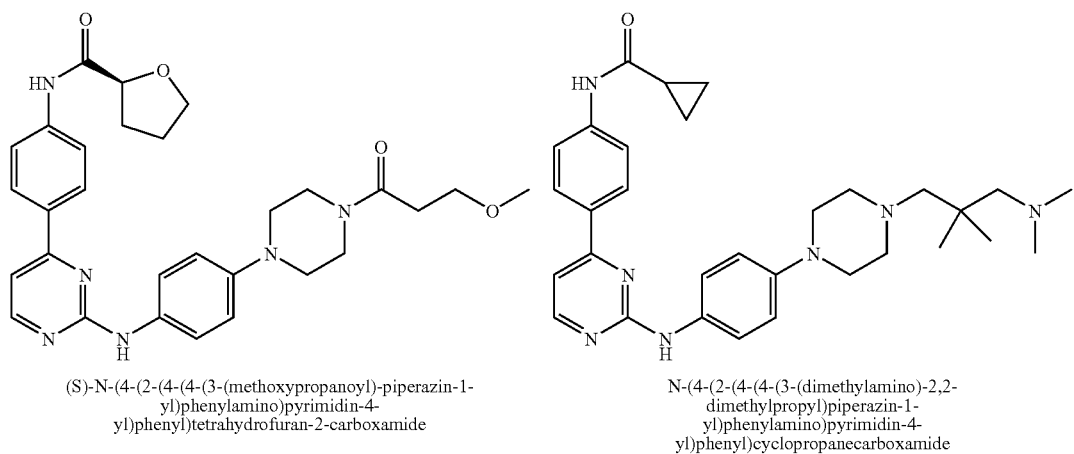

(S)-N-(4-(2-(4-(4-(3-(methoxypropanoyl)-piperazin-1-yl)phenylamino)pyrimidin-4-yl)phenyl)tetrahydrofuran-2-carboxamide N-(4-(2-(4-(4-(3-(dimethylamino)-2,2-dimethylpropyl)piperazin-1-yl)phenylamino)pyrimidin-4-yl)phenyl)cyclopropanecarboxamide

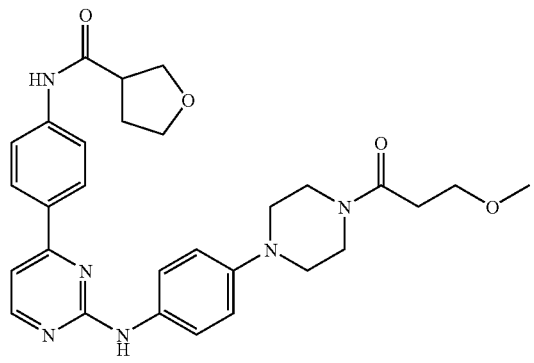

N-(4-(2-(4-(4-(3-(methoxypropanoyl)piperazin-1-yl)phenylamino)pyrimidin-4-yl)phenyl)tetrahydrofuran-3-carboxamide

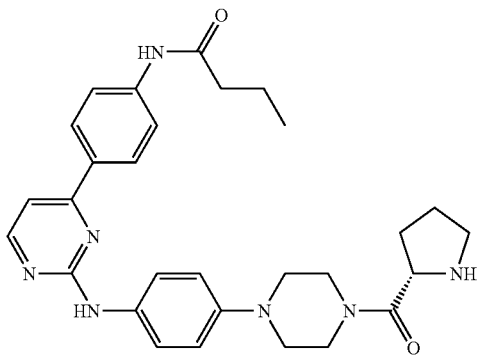

(S)-N-(4-(2-(4-(4-(pyrrolidine-2-carbonyl)piperazin-1-yl)phenylamino)pyrimidin-4-yl)phenyl)butyramide

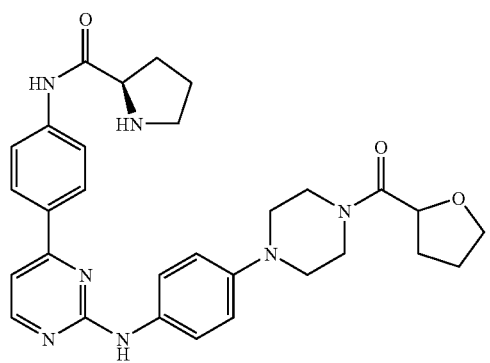

(2R)-N-(4-(2-(4-(4-(tetrahydrofuran-2-carbonyl)piperazin-1-yl)phenylamino)pyrimidin-4-yl)phenyl)pyrrolidine-2-carboxamide

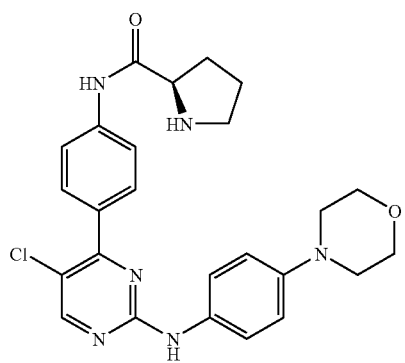

(R)-N-(4-(5-chloro-2-(4-morpholinophenylamino)pyrimidin-4-yl)phenyl)pyrrolidine-2-carboxamide

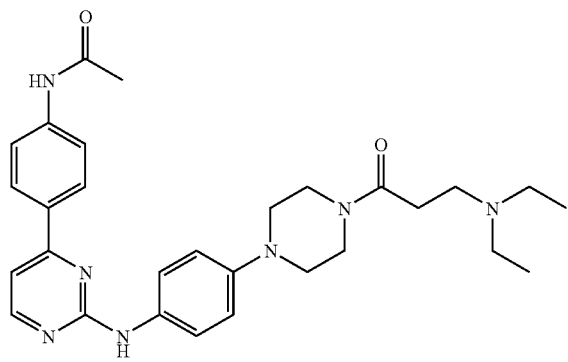

N-(4-(2-(4-(4-(3-(diethylamino)propanoyl)piperazin-1-yl)benzyl)pyrimidin-4-yl)phenyl)acetamide

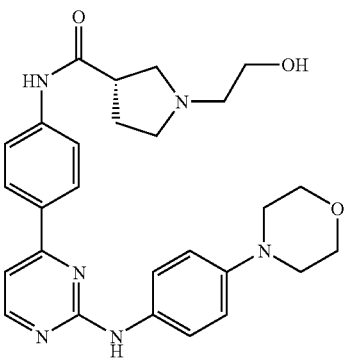

(S)-1-(2-hydroxyethyl)-N-(4-(2-(4-morpholinophenylamino)pyrimidin-4-yl)phenyl)pyrrolidine-3-carboxamide

807

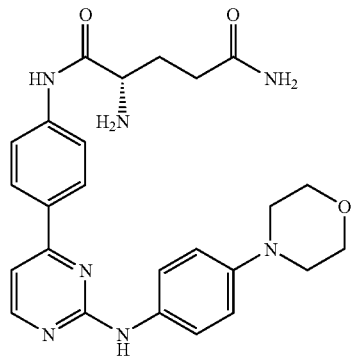

(S)-2-amino-N1-(4-(2-(4-morpholinophenylamino)pyrimidin-4-yl)phenyl)pentanediamide

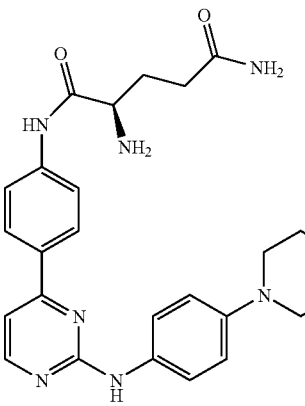

(R)-2-amino-N1-(4-(2-(4-morpholinophenylamino)pyrimidin-4-yl)phenyl)pentanediamide

808

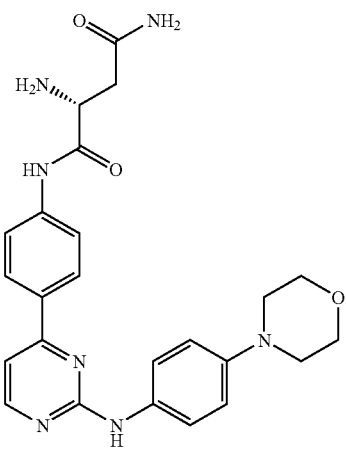

(R)-2-amino-N1-(4-(2-(4-morpholinophenylamino)pyrimidin-4-yl)phenyl)succinamide

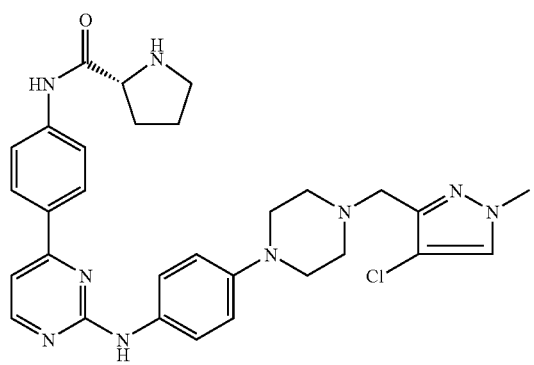

(R)-N-(4-(2-(4-(4-((4-chloro-1-methyl-1H-pyrazol-3-yl)methyl)piperazin-1-yl)phenylamino)pyrimidin-4-yl)phenyl)pyrrolidine-2-carboxamide

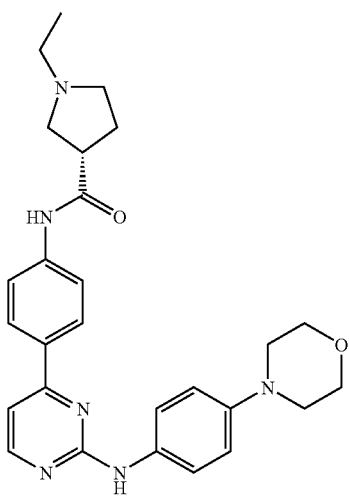

(S)-1-ethyl-N-(4-(2-(4-morpholinophenylamino)pyrimidin-4-yl)phenylpyrrolidine-3-carboxamide

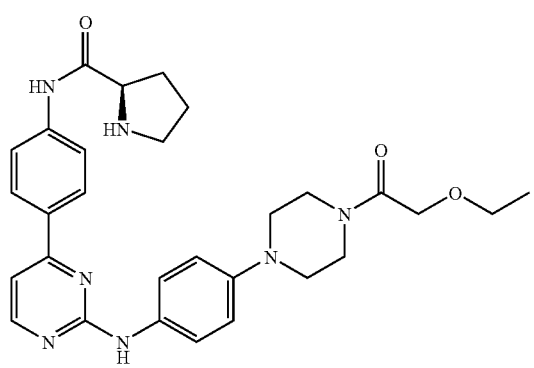

(R)-N-(4-(2-(4-(4-(2-ethoxyacetyl)piperazin-1-yl)phenylamino)pyrimidin-4-yl)phenyl)pyrrolidine-2-carboxamide

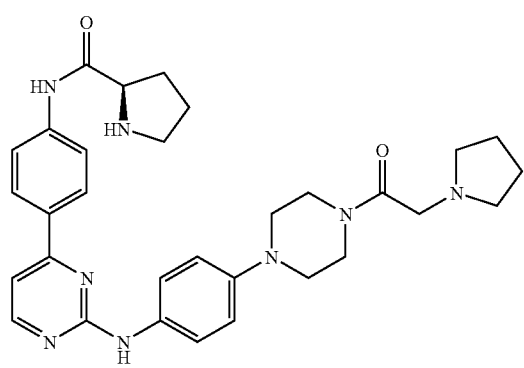

(R)-N-(4-(2-(4-(4-(2-pyrrolidin-1-yl)piperazin-1-yl)phenylamino)pyrimidin-4-yl)phenyl)pyrrolidine-2-carboxamide -continued

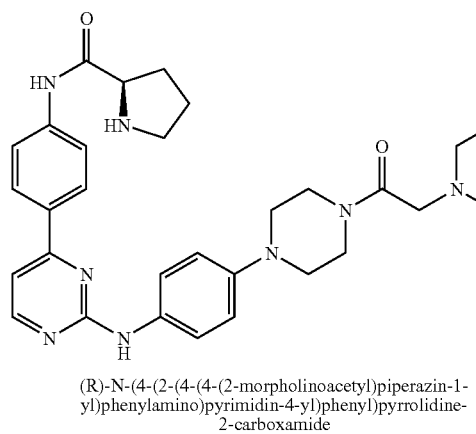

(R)-N-(4-(2-(4-(4-(2-morpholinoacetyl)piperazin-1-yl)phenylamino)pyrimidin-4-yl)phenyl)pyrrolidine-2-carboxamide

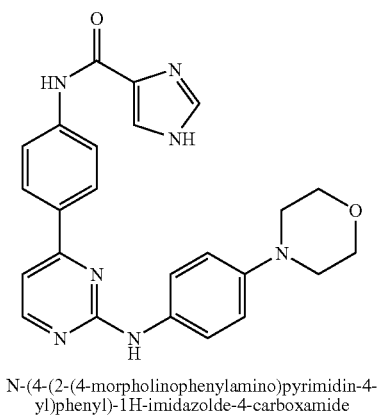

N-(4-(2-(4-morpholinophenylamino)pyrimidin-4-yl)phenyl)-1H-imidazolde-4-carboxamide

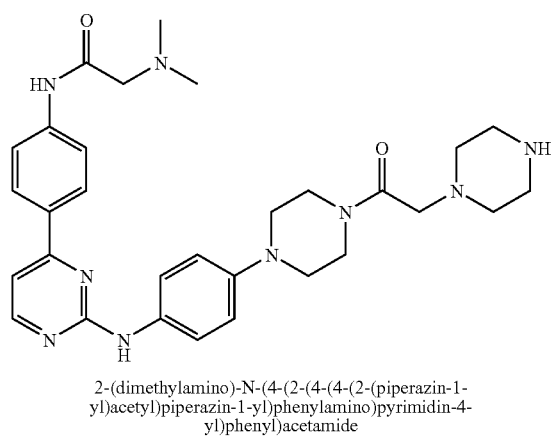

2-(dimethylamino)-N-(4-(2-(4-(4-(2-(piperazin-1-yl)acetyl)piperazin-1-yl)phenylamino)pyrimidin-4-yl)phenyl)acetamide

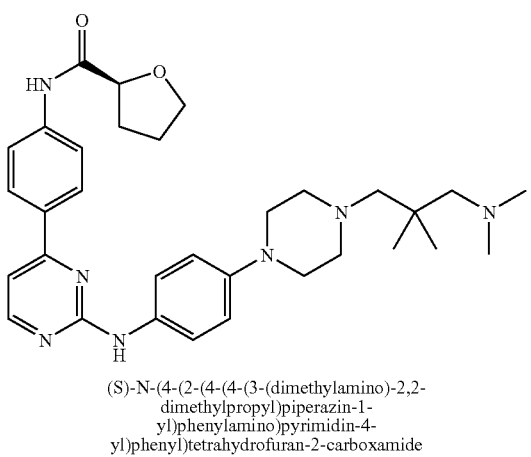

(S)-N-(4-(2-(4-(4-(3-(dimethylamino)-2,2-dimethylpropyl)piperazin-1-yl)phenylamino)pyrimidin-4-yl)phenyl)tetrahydrofuran-2-carboxamide

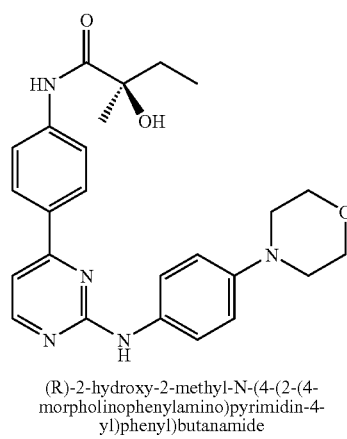

(R)-2-hydroxy-2-methyl-N-(4-(2-(4-morpholinophenylamino)pyrimidin-4-yl)phenyl)butanamide

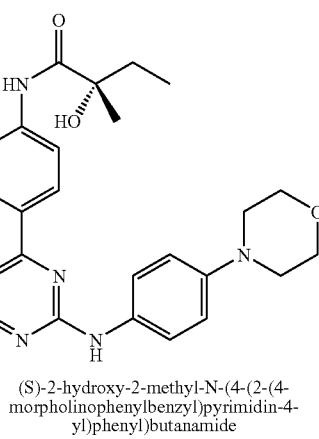

(S)-2-hydroxy-2-methyl-N-(4-(2-(4-morpholinophenylbenzyl)pyrimidin-4-yl)phenyl)butanamide

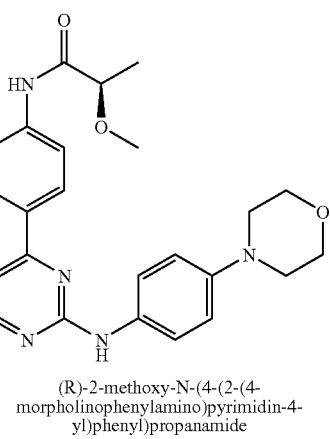

(R)-2-methoxy-N-(4-(2-(4-morpholinophenylamino)pyrimidin-4-yl)phenyl)propanamide

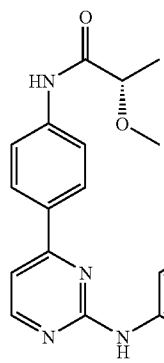

(S)-2-methoxy-N-(4-(2-(4-morpholinophenylamino)pyrimidin-4-yl)phenyl)propanamide

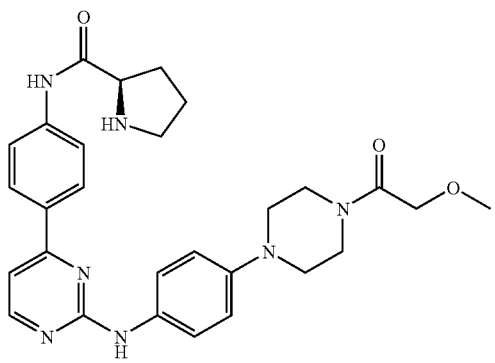

(R)-N-(4-(2-(4-(4-(2-methoxyacetyl)piperazin-1-yl)phenylamino)pyrimidin-4-yl)phenyl)pyrrolidine-2-carboxamide

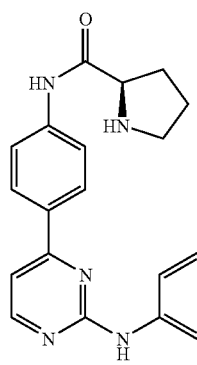

(R)-N-(4-(2-(4-(4-acetylpiperazin-1-yl)phenylamino)pyrimidin-4-yl)phenyl)pyrrolidine-2-carboxamide

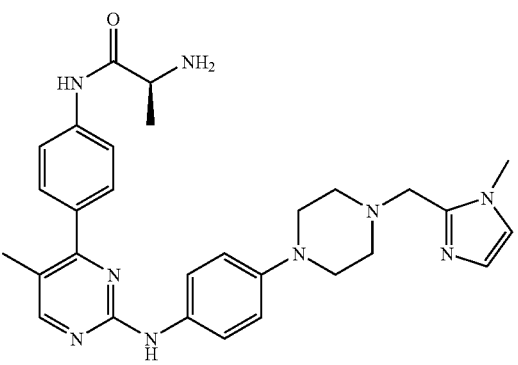

(S)-2-amino-N-(4-(5-methyl-2-(4-(4-((1-methyl-1H-imidazol-2-yl)methyl)piperazin-1-yl)phenylamino)pyrimidin-4-yl)phenyl)propanamide

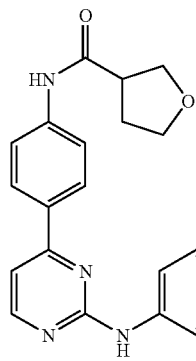

N-(4-(2-(4-(4-(piperidine-4-carbonyl)piperazin-1-yl)phenylamino)pyrimidin-4-yl)phenyl)tetrahydrofuran-3-carboxamide

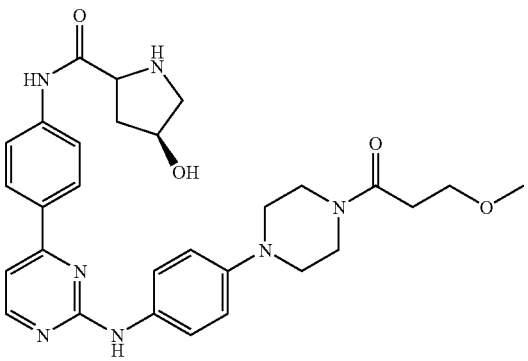

(2R,4S)-4-hydroxy-N-)4-(2-)4-(4-(3-methoxypropanoyl)piperazin-1-yl)phenylamino)pyrimidin-4-yl)phenyl)pyrrolidine-2-carboxamide

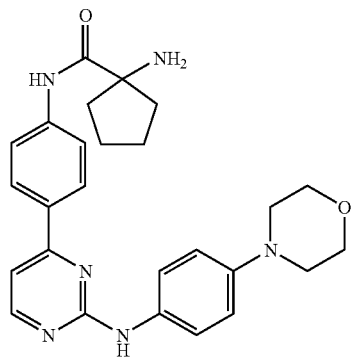

1-amino-N-(4-(2-(4-morpholinophenylamino)pyrimidin-4-yl)phenyl)cyclopentanecarboxamide

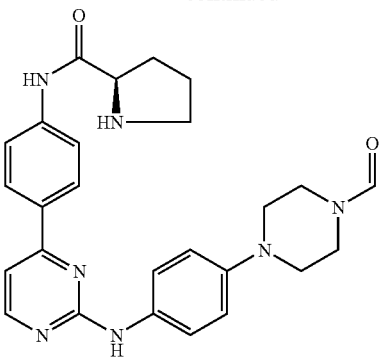

(R)-N-(4-(2-(4-(4-formylpiperazin-1-yl)phenylamino)pyrimidin-4-yl)phenyl)pyrrolidine-2-carboxamide

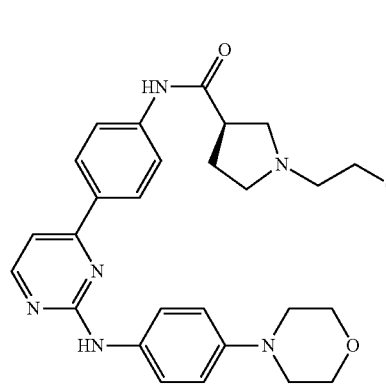

(R)-1-(2-hydroxyethyl)-N-(4-(2-(4-moprpholinophenylamino)pyrimidin-4-yl)phenyl)pyrrolidine-3-carboxamide

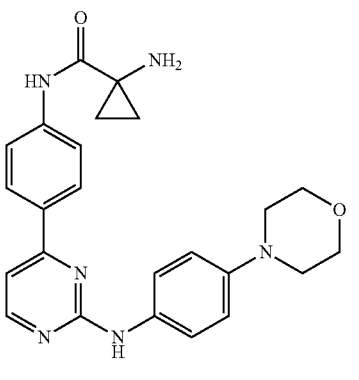

1-amino-N-(4-(2-(4-morpholinophenylamino)pyrimidin-4-yl)phenyl)cyclopropanecarboxamide

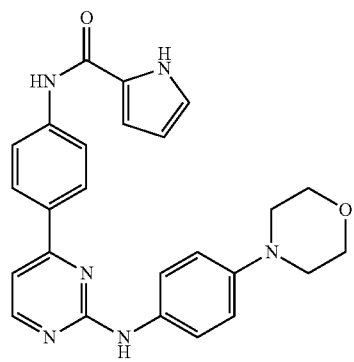

N-(4-(2-(4-morpholinophenylamino)pyrimidin-4-yl)phenyl)1H-pyrrole-2-carboxamide

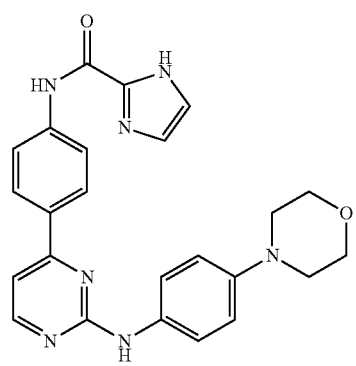

N-(4-(2-(4-morpholinophenylamino)pyrimidin-4-yl)phenyl)1H-imidazole-2-carboxamide

815  -continued  816

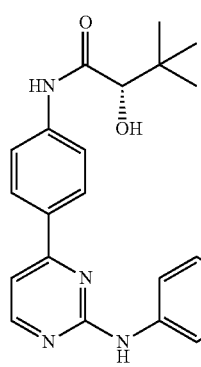

(S)-2-hydroxy-3,3-dimethyl-N-(4-(2-(4-morpholinophenylamino)pyrimidin-4-yl)phenyl)butanamide

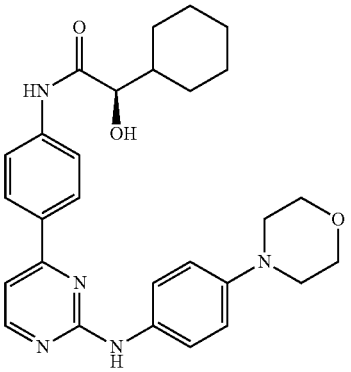

(R)-2-cyclohexyl-2-hydroxy-N-(4-(2-(4-morpholinophenylamino)pyrimidin-4-yl)phenyl)acetamide

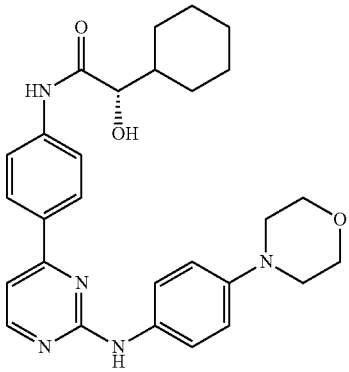

(S)-2-cyclohexyl-2-hydroxy-N-(4-(2-(4-morpholinophenylamino)pyrimidin-4-yl)phenyl)acetamide

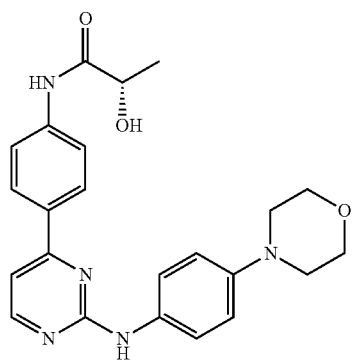

(S)-2-hydroxy-N-(4-(2-(4-morpholinophenylamino)pyrimidin-4-yl)phenyl)propanamide

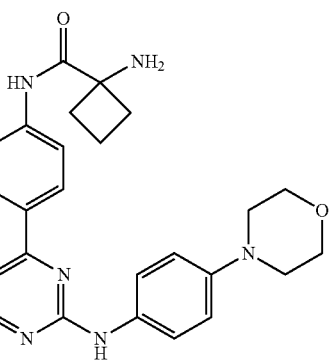

1-amino-N-(4-(2-(4-morpholinophenylamino)pyrimidin-4-yl)phenyl)cyclobutanecarboxamide

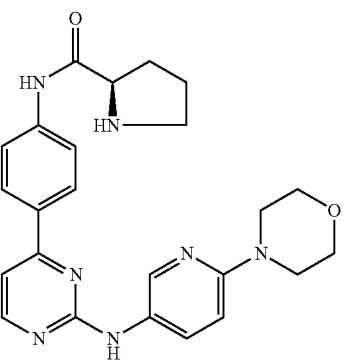

(R)-N-(4-(2-(6-morpholinopyridin-3-ylamino)pyrimidin-4-yl)phenyl)pyrrolidine-2-carboxamide

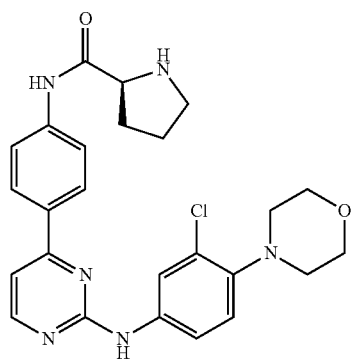

(S)-N-(4-(2-(3-chloro-4-morpholinophenylamino)pyrimidin-4-yl)phenyl)pyrrolidine-2-carboxamide

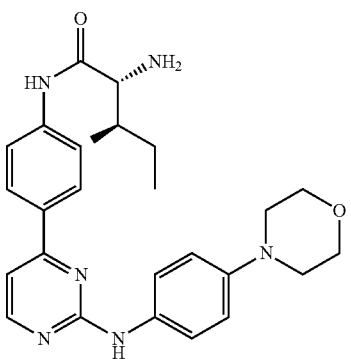

(2R,3R)-2-amino-3-methyl-N-(4-(2-(4-morpholinophenylamino)pyrimidin-4-yl)phenyl)pentanamide

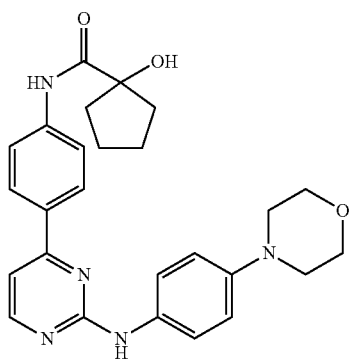

1-hydroxy-N-(4-(2-(4-morpholinophenylamino)pyrimidin-4-yl)phenyl)cyclopentanecarboxamide

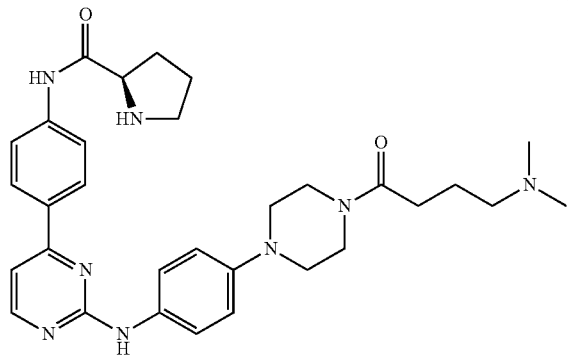

(R)-N-(4-(2-(4-(4-(4-dimethylamino)butanoyl)piperazin-1-yl)phenylamino)pyrimidin-4-yl)phenyl)pyrrolidine-2-carboxamide

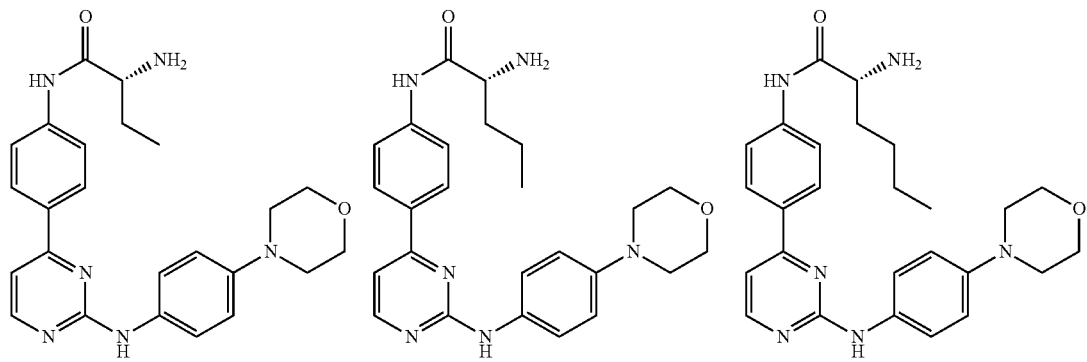

(R)-2-amino-N-(4-(2-(4-morpholinophenylamino)pyrimidin-4-yl)phenyl)butanamide (R)-2-amino-N-(4-(2-(4-morpholinophenylamino)pyrimidin-4-yl)phenyl)pentanamide (R)-2-amino-N-(4-(2-(4-morpholinophenylamino)pyrimidin-4-yl)phenyl)hexanamide

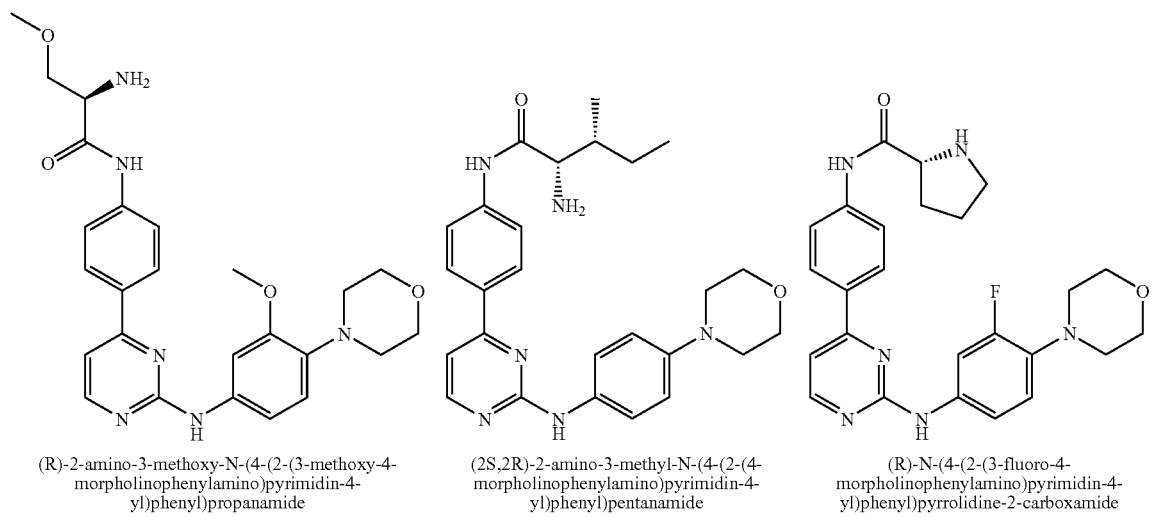

(R)-2-amino-3-methoxy-N-(4-(2-(3-methoxy-4-morpholinophenylamino)pyrimidin-4-yl)phenyl)propanamide (2S,2R)-2-amino-3-methyl-N-(4-(2-(4-morpholinophenylamino)pyrimidin-4-yl)phenyl)pentanamide (R)-N-(4-(2-(3-fluoro-4-morpholinophenylamino)pyrimidin-4-yl)phenyl)pyrrolidine-2-carboxamide -continued

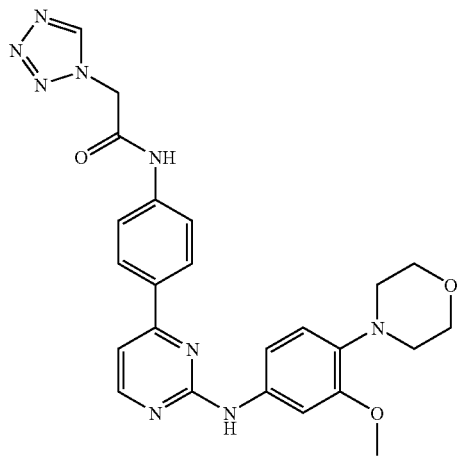

N-(4-(2-(3-methoxy-4-morpholinophenylamino)pyrimidin-4-yl)phenyl)-2-(1H)-tetrazol-1-yl)acetamide

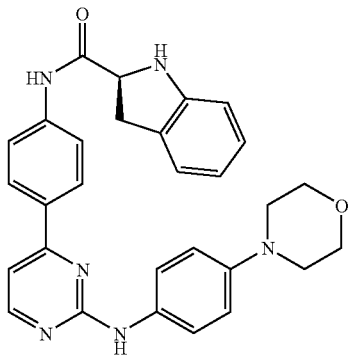

(S)-N-(4-(2-(4-morpholinophenylamino)pyrimidin-4-yl)phenyl)indoline-2-carboxamide

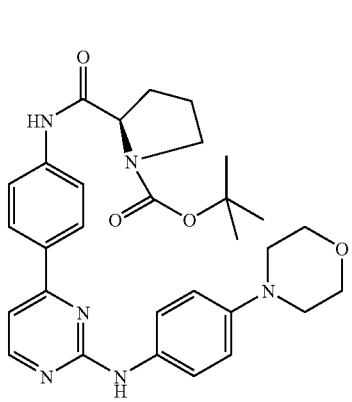

(R)-tert-butyl 2-((4-(2-(4-morpholinophenylamino)pyrimidin-4-yl)phenylcarbamoyl)pyrrolidine-1-carboxylate

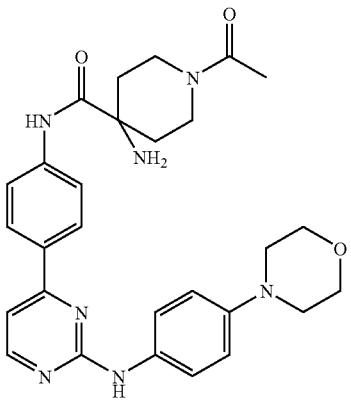

1-acetyl-4-amino-N-(4-(2-(4-morpholinophenylamino)pyrimidin-4-yl)phenyl)piperidine-4-carboxylate

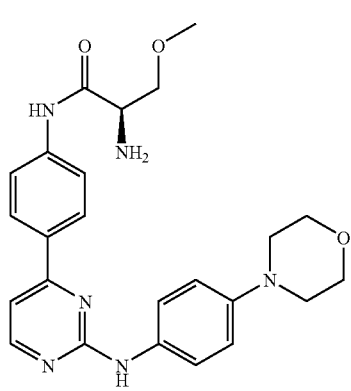

(R)-2-amino-3-methoxy-N-(4-(2-(4-morpholinophenylamino)pyrimidin-4-yl)phenyl)propanamide

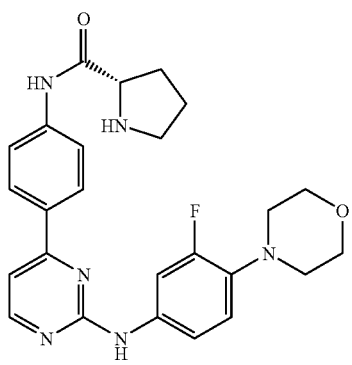

(S)-N-(4-(2-(3-fluoro-4-morpholinophenylamino)pyrimidin-4-yl)phenyl)pyrrolidin-2-carboxamide

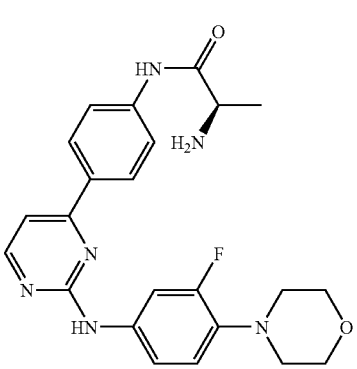

(R)-2-amino-N-(4-(2-(3-fluoro-4-morpholinophenylamino)pyrimidin-4-yl)phenyl)propanamide

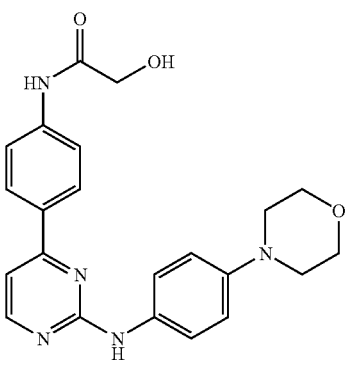

2-hydroxy-N-(4-(2-(4-morpholinophenylamino)pyrimidin-4-yl)phenyl)acetamide

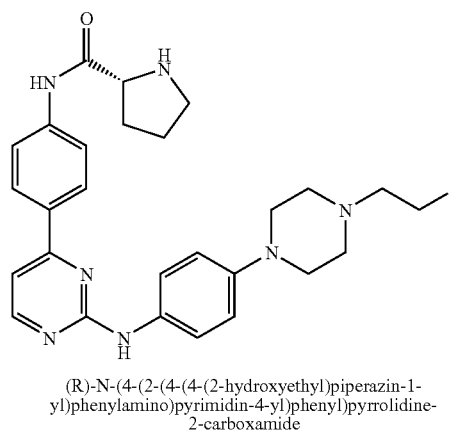

(R)-N-(4-(2-(4-(4-(2-hydroxyethyl)piperazin-1-yl)phenylamino)pyrimidin-4-yl)phenyl)pyrrolidine-2-carboxamide

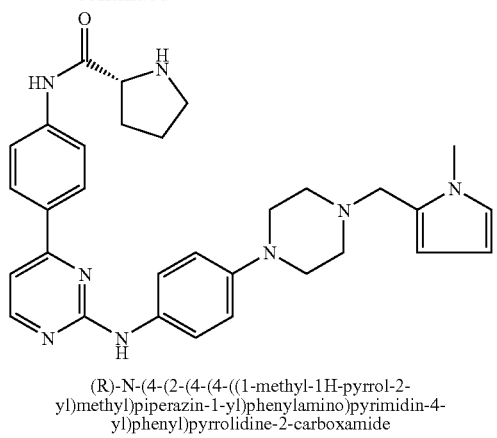

(R)-N-(4-(2-(4-(4-((1-methyl-1H-pyrrol-2-yl)methyl)piperazin-1-yl)phenylamino)pyrimidin-4-yl)phenyl)pyrrolidine-2-carboxamide

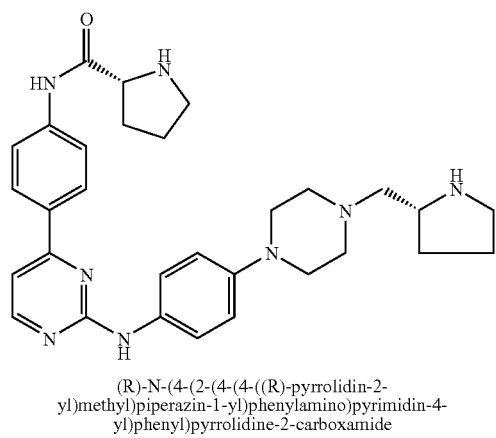

(R)-N-(4-(2-(4-(4-((R)-pyrrolidin-2-yl)methyl)piperazin-1-yl)phenylamino)pyrimidin-4-yl)phenyl)pyrrolidine-2-carboxamide

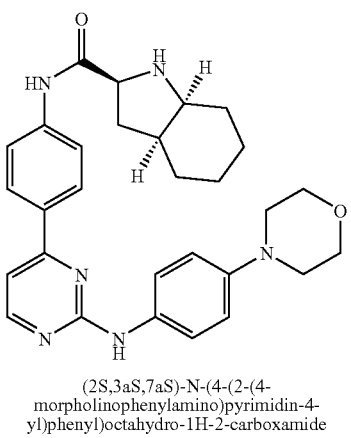

(2S,3aS,7aS)-N-(4-(2-(4-morpholinophenylamino)pyrimidin-4-yl)phenyl)octahydro-1H-2-carboxamide

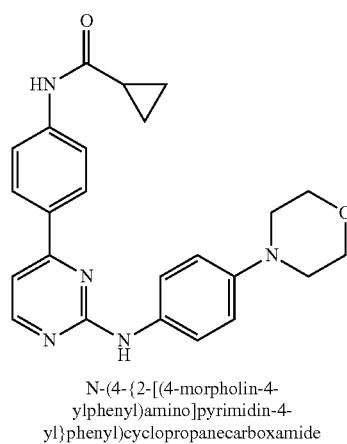

N-(4-{2-[(4-morpholin-4-ylphenyl)amino]pyrimidin-4-yl}phenyl)cyclopropanecarboxamide

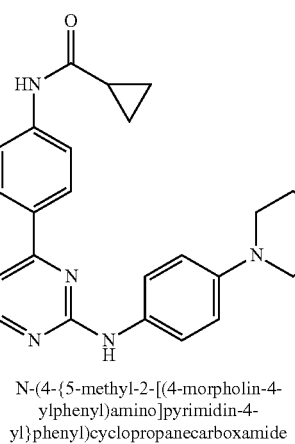

N-(4-{5-methyl-2-[(4-morpholin-4-ylphenyl)amino]pyrimidin-4-yl}phenyl)cyclopropanecarboxamide

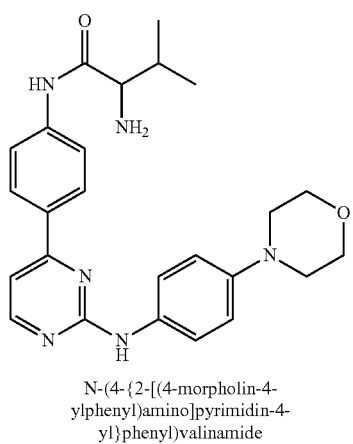

N-(4-{2-[(4-morpholin-4-ylphenyl)amino]pyrimidin-4-yl}phenyl)valinamide

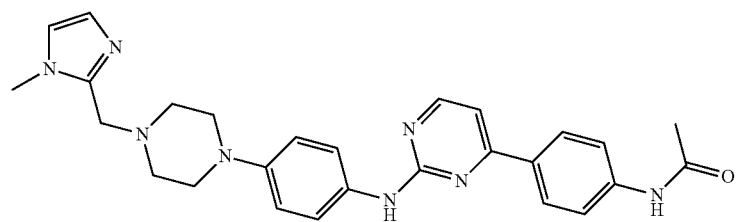

N-(4-{2-[(4-{4-[(1-methyl-1H-imidazol-2-yl)methyl]piperazin-1-yl}phenyl)amino]pyrimidin-4-yl}phenyl)acetamide -continued

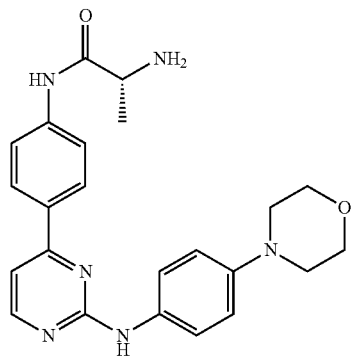

N-(4-{2-[(4-morpholin-4-
ylphenyl)amino]pyrimidin-4-yl}phenyl)-D-
alaninamide

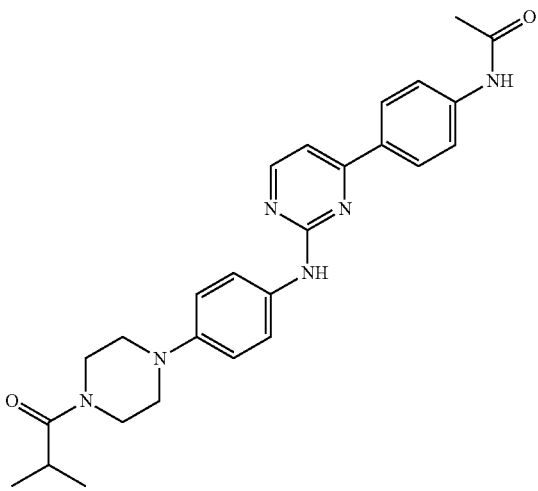

N-{4-[2-({4-[4-(2-methylpropanoyl)piperazin-1-
yl]phenyl}amino)pyrimidin-4-yl]phenyl}acetamide

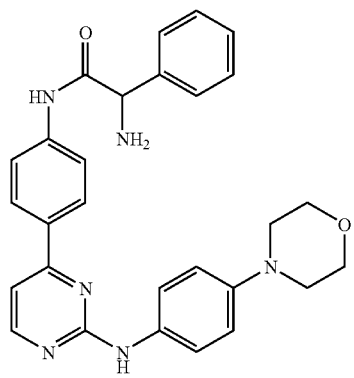

2-amino-N-(4-{2-[(4-morpholin-4-
ylphenyl)amino]pyrimidin-4-yl}phenyl)-2-
phenylacetamide

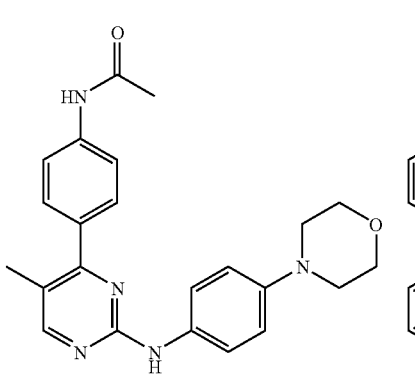

N-(4-{5-methyl-2-[(4-morpholin-4-
ylphenyl)amino]pyrimidin-4-yl}phenyl)acetamide

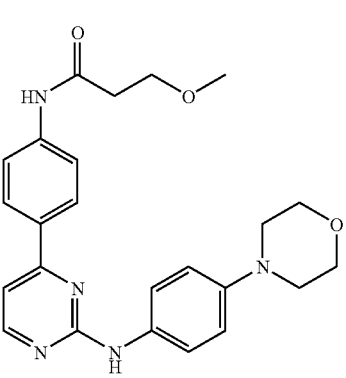

3-(methyloxy)-N-(4-{2-[(4-morpholin-4-
ylphenyl)amino]pyrimidin-4-
yl}phenyl)propanamide

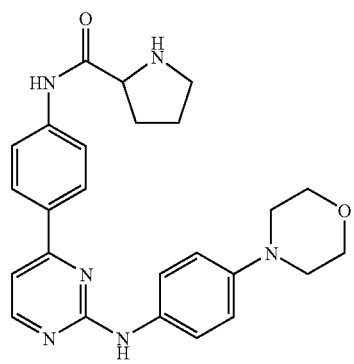

N-(4-{2-[(4-morpholin-4-
ylphenyl)amino]pyrimidin-4-yl}phenyl)prolinamide

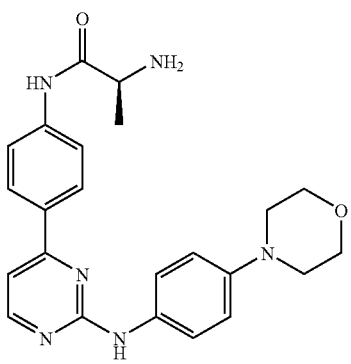

N-(4-{2-[(4-morpholin-4-
ylphenyl)amino]pyrimidin-4-yl}phenyl)-L-
alaninamide

825

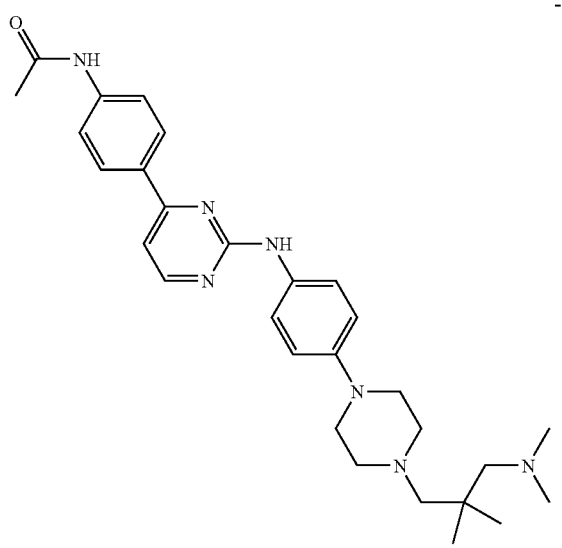

N-(4-{2-[(4-{4-[3-(dimethylamino)-2,2-dimethylpropyl]piperazin-1-yl}phenyl)amino]pyrimidin-4-yl}phenyl)acetamide

826

-continued

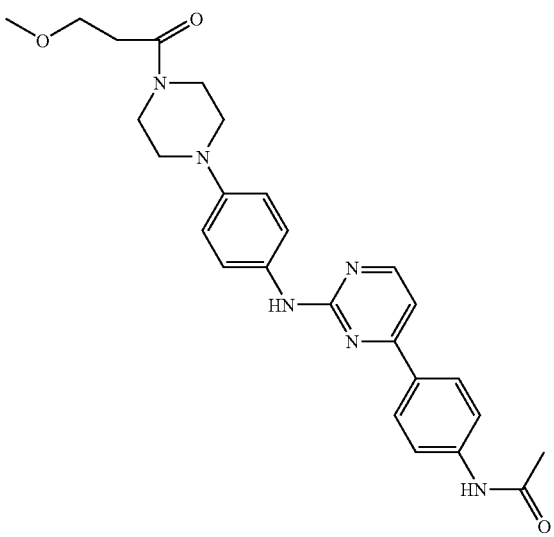

N-(4-{2-[(4-{4-[3-(methyloxy)propanoyl]piperazin-1-yl}phenyl)amino]pyrimidin-4-yl}phenyl)acetamide

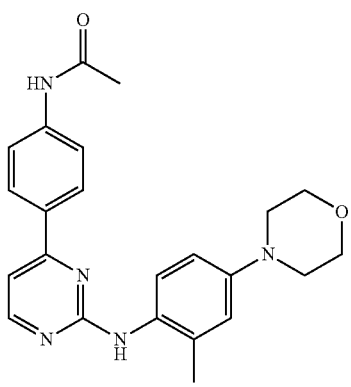

N-(4-{2-[2-methyl-4-morpholin-4-ylphenyl)amino]pyrimidin-4-yl}phenyl)acetamide

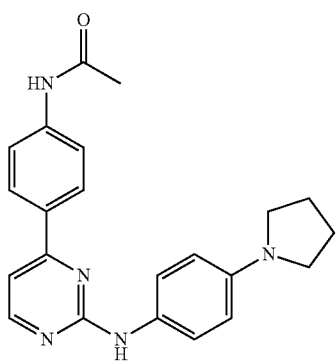

N-(4-{2-[(4-pyrrolidin-1-ylphenyl)amino]pyrimidin-4-yl}phenyl)acetamide

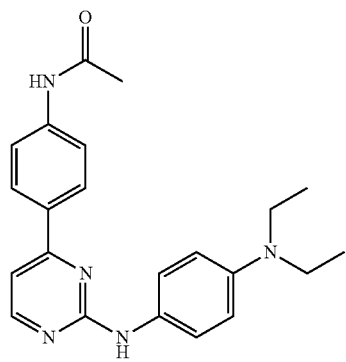

N-[4-(2-{[4-(diethylamino)phenyl]amino}pyrimidin-4-yl)phenyl]acetamide

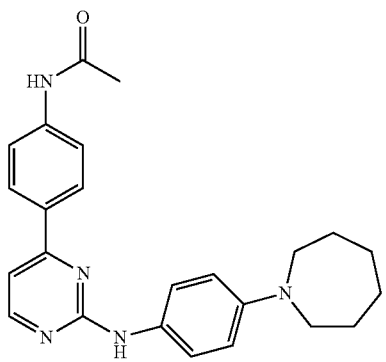

N-(4-{2-[(4-azepan-1-ylphenyl)amino]pyrimidin-4-yl}phenyl)acetamide

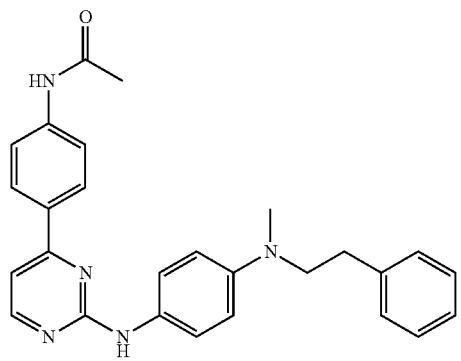

N-{4-[2-({4-[methyl(2-phenylethyl)amino]phenyl}
amino)pyrimidin-4-yl]phenyl}acetamide

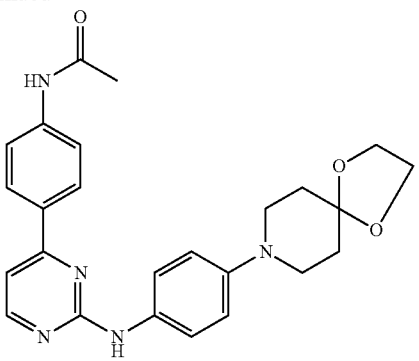

N-[4-{2-{[4-(1,4-dioxa-8-azaspiro[4.5]dec-8-
yl)phenyl]amino}pyrimidin-4-yl]phenyl]acetamide

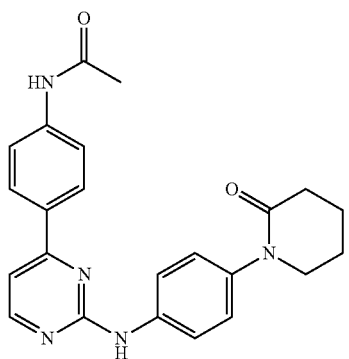

N-[4-(2-{[4-(2-oxopiperidin-1-yl)phenyl]amino}
pyrimidin-4-yl)phenyl]acetamide

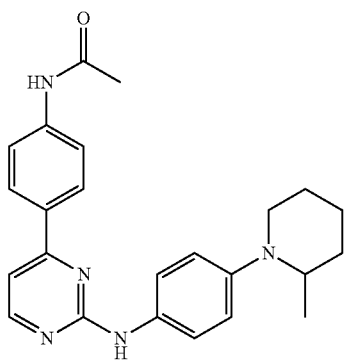

N-[4-(2-{[4-(2-methylpiperidin-1-yl)phenyl]amino}
pyrimidin-4-yl)phenyl]acetamide

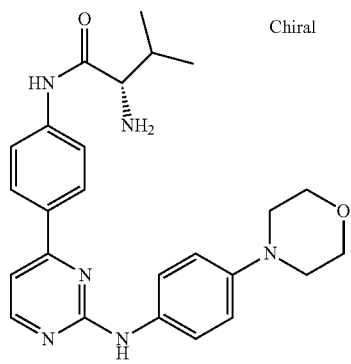

N-(4-{2-[(4-morpholin-4-ylphenyl)amino]
pyrimidin-4-yl}phenyl)-L-valinamide

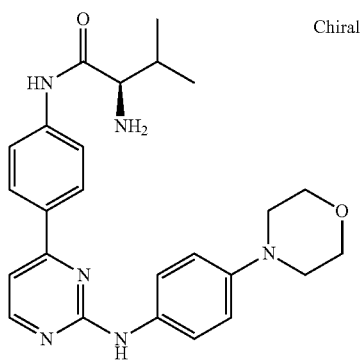

N-(4-{2-[(4-morpholin-4-ylphenyl)amino]pyrimidin-4-
yl}phenyl)-D-valinamide

829

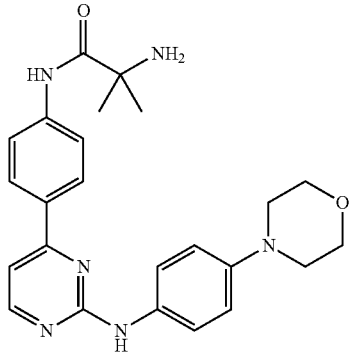

2-methyl-N-(4-{2-[(4-morpholin-4-ylphenyl)amino]
pyrimidin-4-yl}phenyl)alaninamide

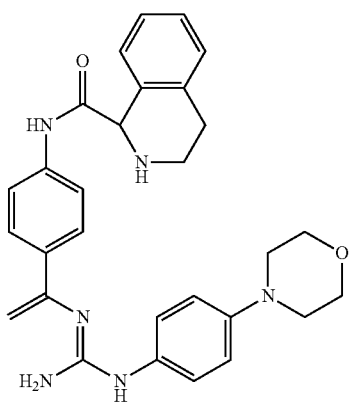

N-(4-{2-[(4-morpholin-4-ylphenyl)amino]pyrimidin-4-
yl}phenyl)-1,2,3,4-tetrahydroisoquinoline-1-carboxamide

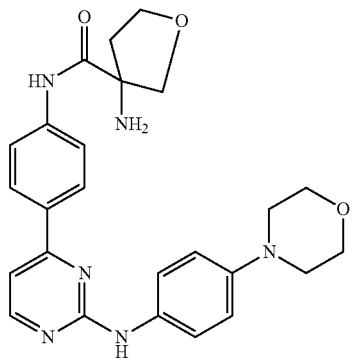

3-amino-N-(4-{2-[(4-morpholin-4-
ylphenyl)amino]pyrimidin-4-yl}phenyl)tetrahydrofuran-
3-carboxamide

830

-continued

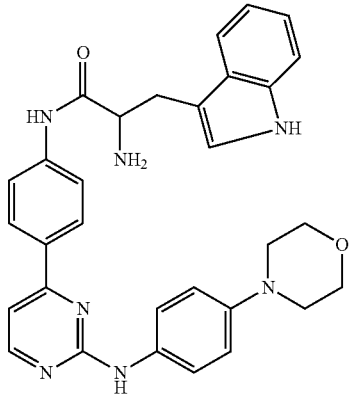

N-(4-{2-[(4-morpholin-4-ylphenyl)amino]pyrimidin-4-
yl}phenyl)tryptophanamide

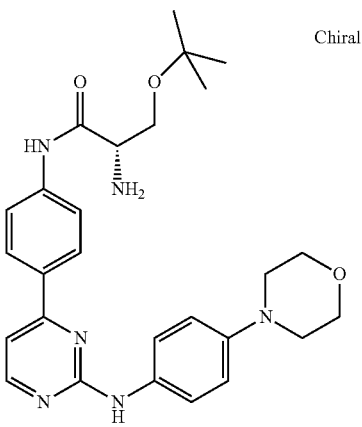

O-(1,1-dimethylethyl)-N-(4-{2-[(4-morpholin-4-
ylphenyl)amino]pyrimidin-4-yl}phenyl)-L-serinamide

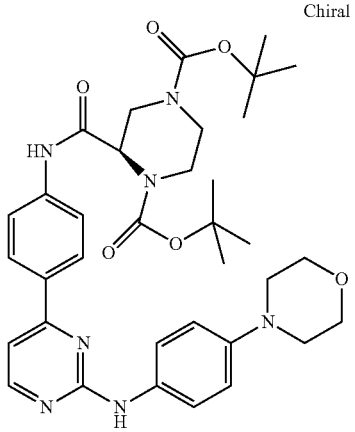

bis(1,1-dimethylethyl) (2R)-2-{[(4-{2-[4-morpholin-4-
ylphenyl)amino]pyrimidin-4-
yl}phenyl)amino]carbonyl}piperazine-1,4-dicarboxylate -continued
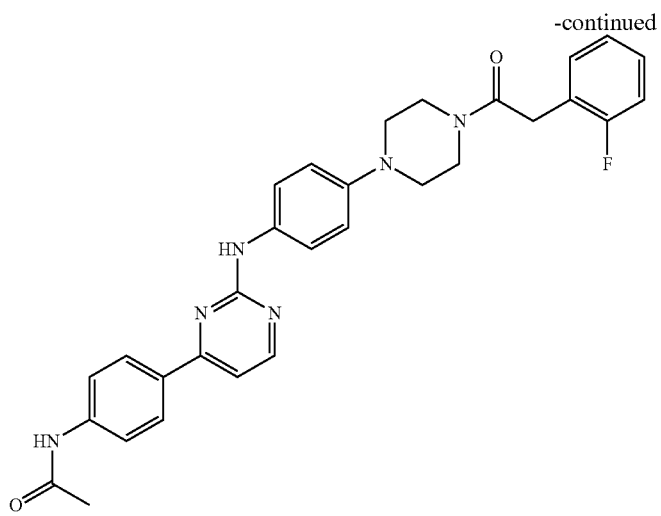
N-(4-{2-[(4-{4-[2-(2-fluorophenyl)acetyl]piperazin-1-yl}phenyl)amino]pyrimidin-4-yl}phenyl)acetamide
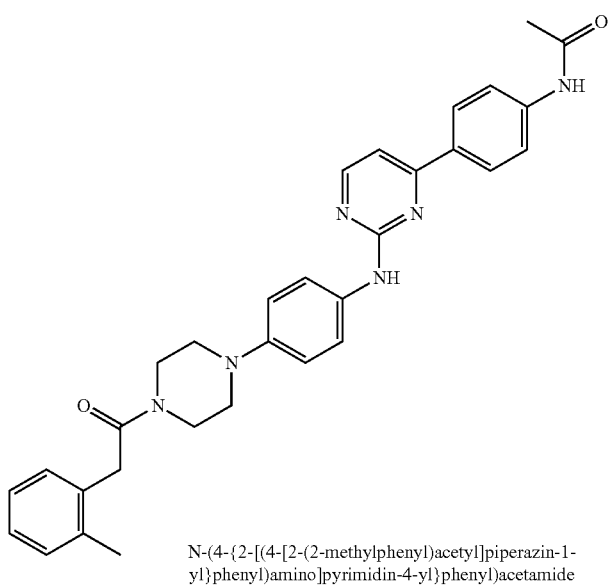
N-(4-{2-[(4-{4-[2-(2-methylphenyl)acetyl]piperazin-1-yl}phenyl)amino]pyrimidin-4-yl}phenyl)acetamide
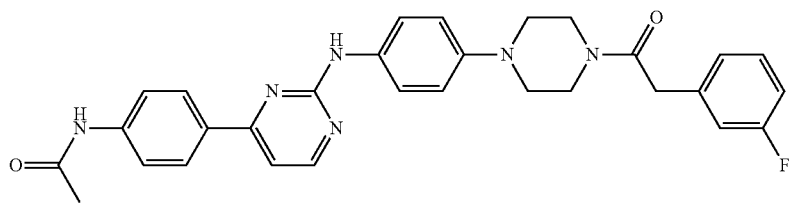
N-(4-{2-[(4-{4-[2-(3-fluorophenyl)acetyl]piperazin-1-yl}phenyl)amino]pyrimidin-4-yl}phenyl)acetamide

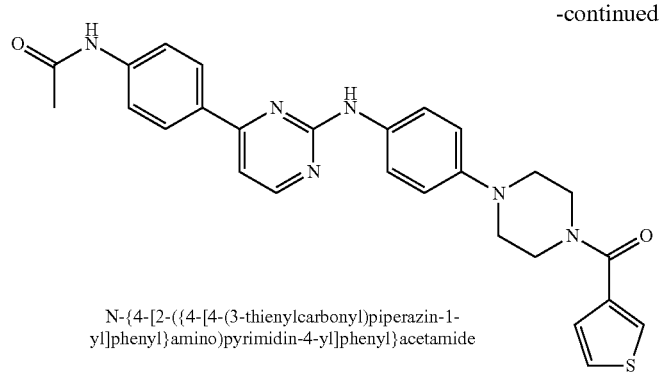
N-{4-[2-({4-[4-(3-thienylcarbonyl)piperazin-1-yl]phenyl}amino)pyrimidin-4-yl]phenyl}acetamide
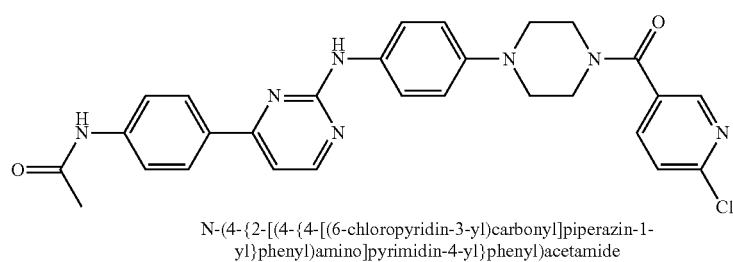
N-(4-{2-[(4-{4-[(6-chloropyridin-3-yl)carbonyl]piperazin-1-yl}phenyl)amino]pyrimidin-4-yl}phenyl)acetamide
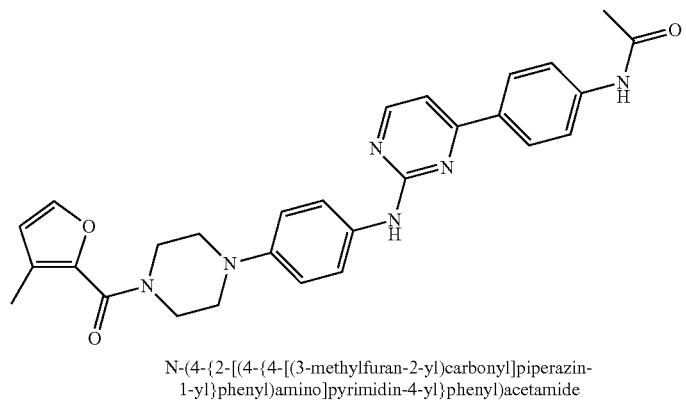
N-(4-{2-[(4-{4-[(3-methylfuran-2-yl)carbonyl]piperazin-1-yl}phenyl)amino]pyrimidin-4-yl}phenyl)acetamide
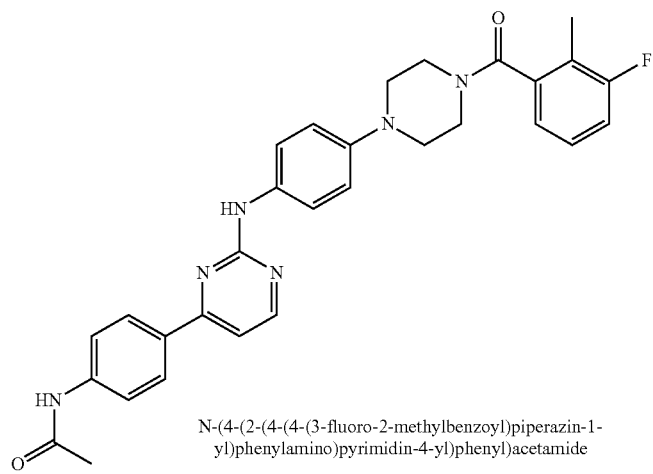
N-(4-(2-(4-(4-(3-fluoro-2-methylbenzoyl)piperazin-1-yl)phenylamino)pyrimidin-4-yl)phenyl)acetamide -continued
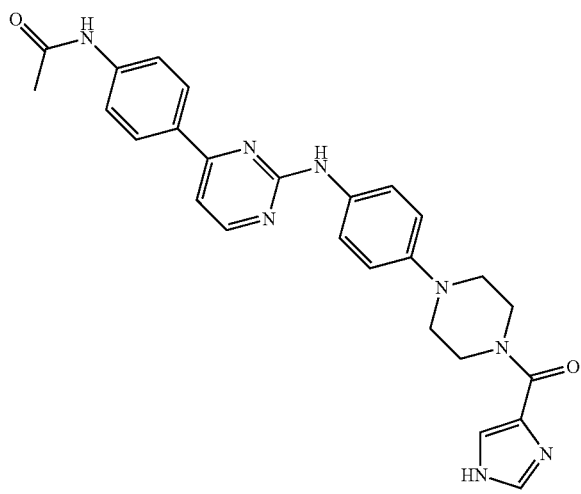
N-(4-(2-(4-(4-(1H-imidazole-4-carbonyl)piperazin-1-yl)phenylamino)pyrimidin-4-yl)phenyl)acetamide
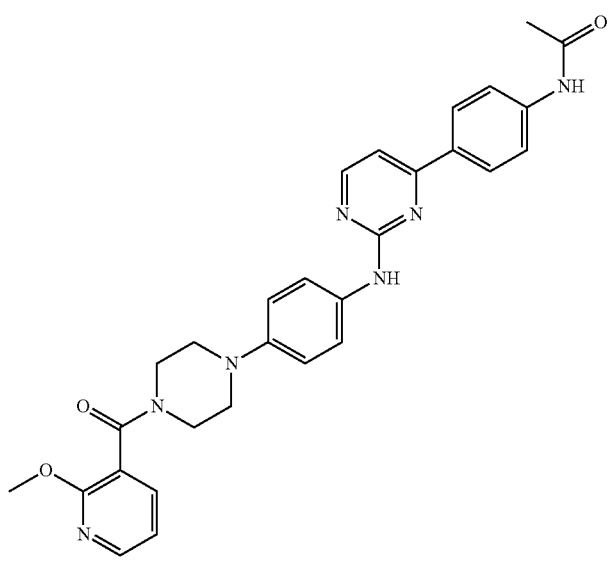
N-(4-(2-(4-(4-(2-methoxynicotinoyl)piperazin-1-yl)phenylamino)pyrimidin-4-yl)phenyl)acetamide
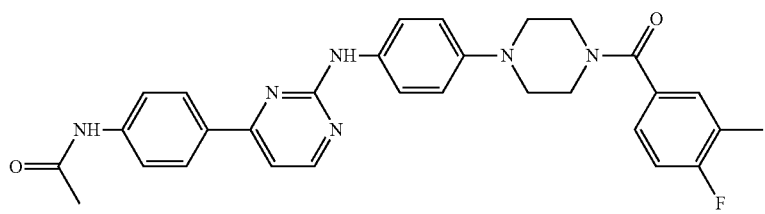
N-(4-(2-(4-(4-(4-fluoro-3-methylbenzoyl)piperazin-1-yl)phenylamino)pyrimidin-4-yl)phenyl)acetamide -continued
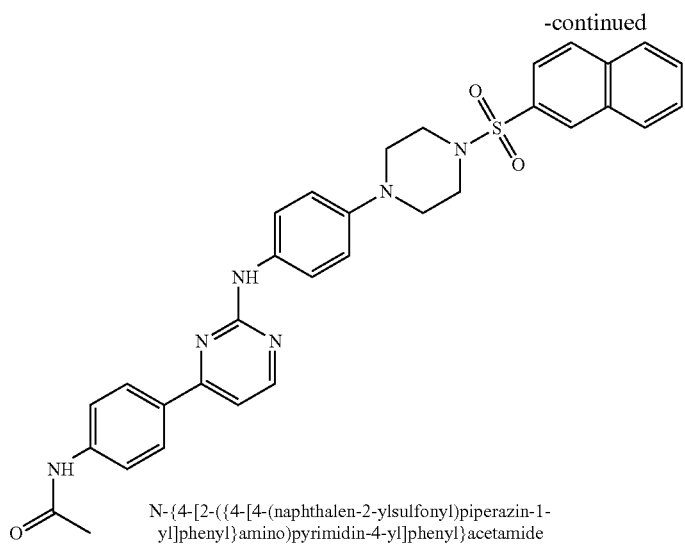
N-{4-[2-({4-[4-(naphthalen-2-ylsulfonyl)piperazin-1-yl]phenyl}amino)pyrimidin-4-yl]phenyl}acetamide
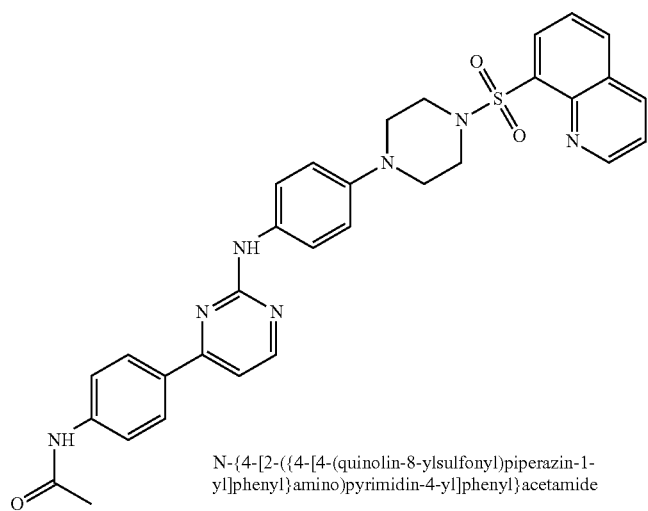
N-{4-[2-({4-[4-(quinolin-8-ylsulfonyl)piperazin-1-yl]phenyl}amino)pyrimidin-4-yl]phenyl}acetamide
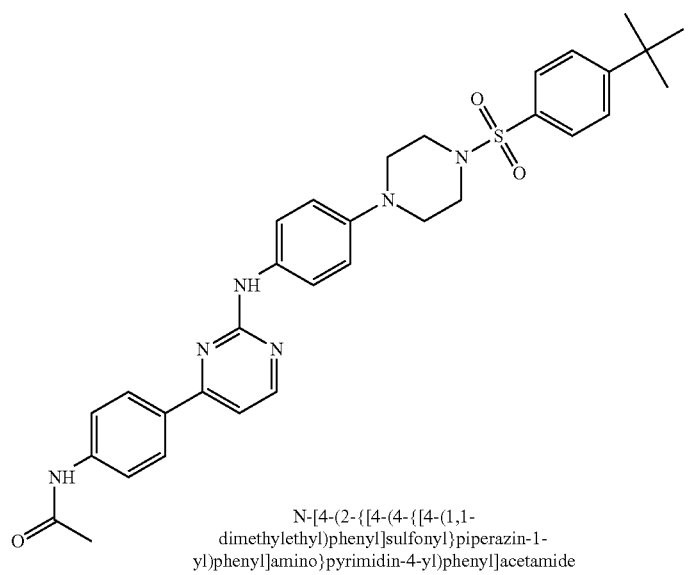
N-[4-(2-{[4-(4-{[4-(1,1-dimethylethyl)phenyl]sulfonyl}piperazin-1-yl)phenyl]amino}pyrimidin-4-yl)phenyl]acetamide

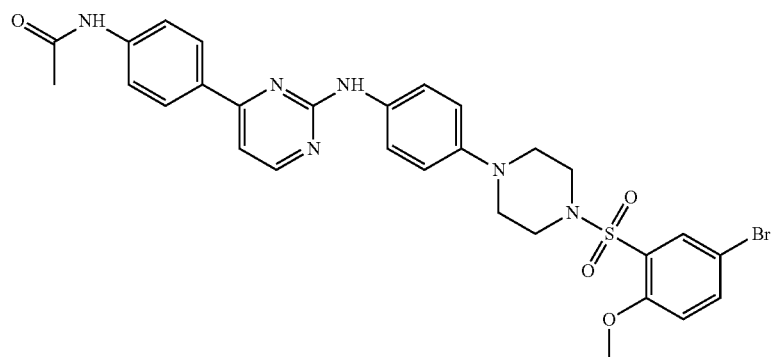
N-[4-(2-{[4-(4-{[5-bromo-2-
(methyloxy)phenyl]sulfonyl}piperazin-1-
yl)phenyl]amino}pyrimidin-4-yl)phenyl]acetamide
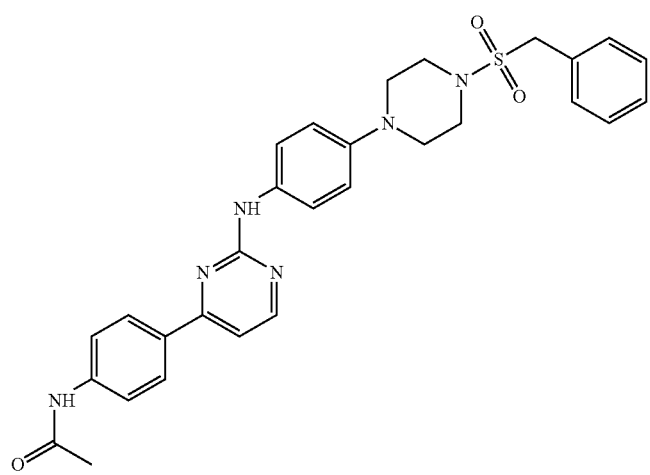
N-(4-{2-[(4-{4-[(phenylmethyl)sulfonyl]piperazin-1-
yl}phenyl)amino]pyrimidin-4-yl}phenyl)acetamide
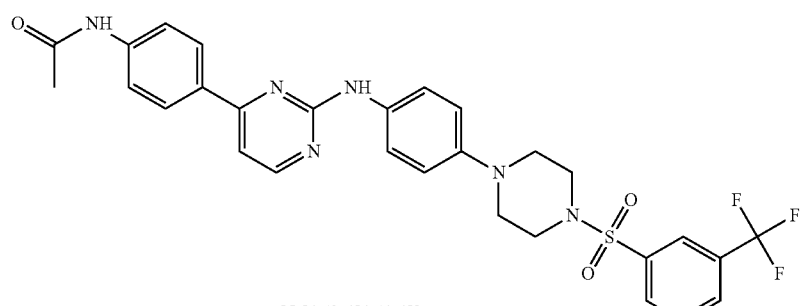
N-[4-(2-{[4-(4-{[3-
(trifluoromethyl)phenyl]sulfonyl}piperazin-1-
yl)phenyl]amino}pyrimidin-4-yl)phenyl]acetamide -continued
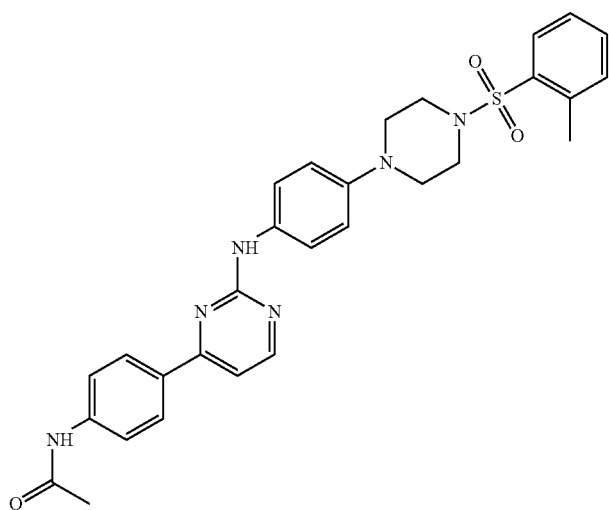
N-(4-{2-[(4-{4-[(2-methylphenyl)sulfonyl]piperazin-1-yl}phenyl)amino]pyrimidin-4-yl}phenyl)acetamide
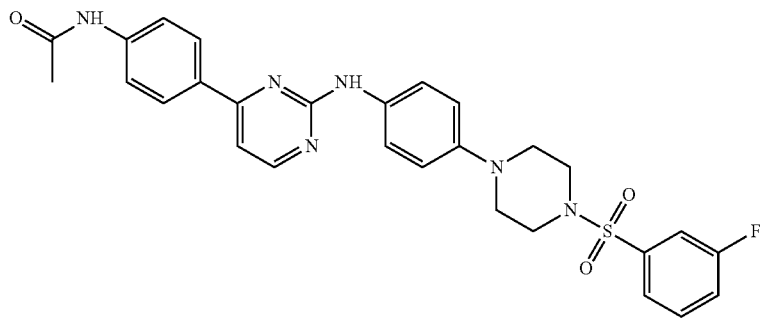
N-(4-{2-[(4-{4-[(3-fluorophenyl)sulfonyl]piperazin-1-yl}phenyl)amino]pyrimidin-4-yl}phenyl)acetamide
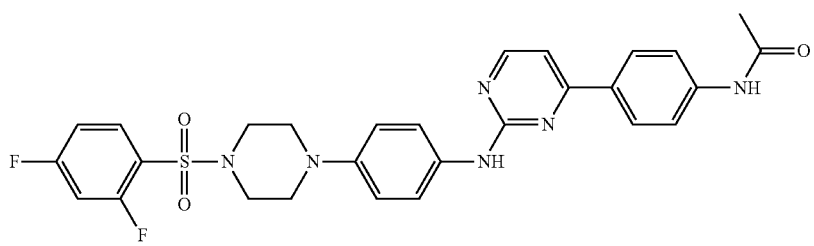
N-(4-{2-[(4-{4[(2,4-difluorophenyl)sulfonyl]piperazin-1-yl}phenyl)amino]pyrimidin-4-yl}phenyl)acetamide -continued

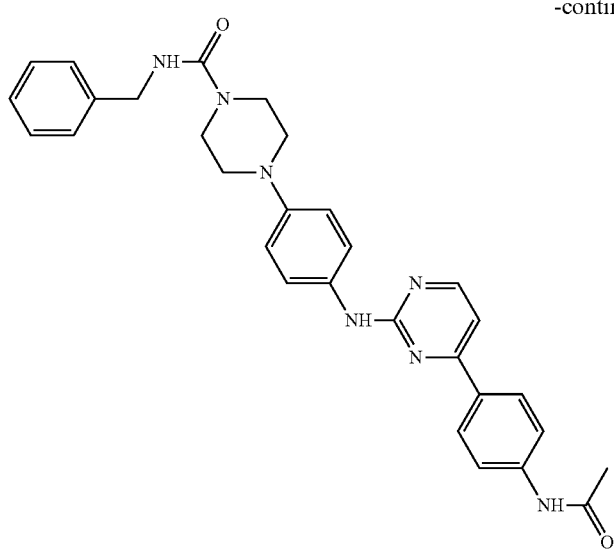

4-[4-({4-[4-(acetylamino)phenyl]pyrimidin-2-yl}amino)phenyl]-
N-(phenylmethyl)piperazine-1-carboxamide

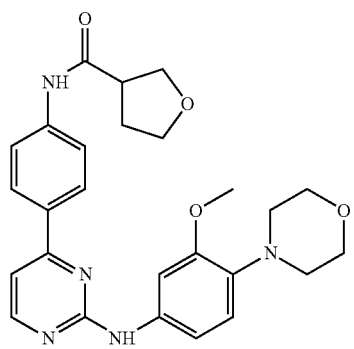

N-[4-(2-{[3-(methyloxy)-4-morpholin-4-
ylphenyl]amino}pyrimidin-4-
yl)phenyl]tetrahydrofuran-3-carboxamide

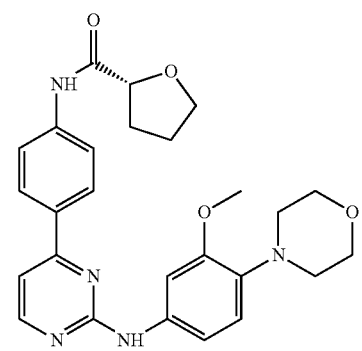

(2R)-N-[4-(2-{[3-(methyloxy)-4-morpholin-4-
ylphenyl]amino}pyrimidin-4-yl)phenyl]tetrahydrofuran-
2-carboxamide

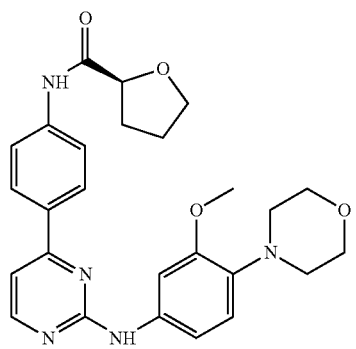

(2S)-N-[4-(2-{[3-(methyloxy)-4-morpholin-4-
ylphenyl]amino}pyrimidin-4-yl)phenyl]tetrahydrofuran-
2-carboxamide -continued

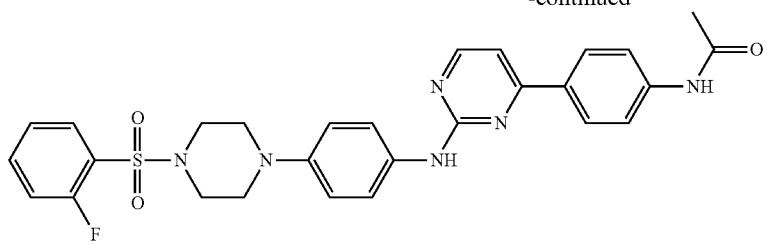

N-(4-{2-[(4-{4-[(2-fluorophenyl)sulfonyl]piperazin-1-yl}phenyl)amino]pyrimidin-4-yl}phenyl)acetamide

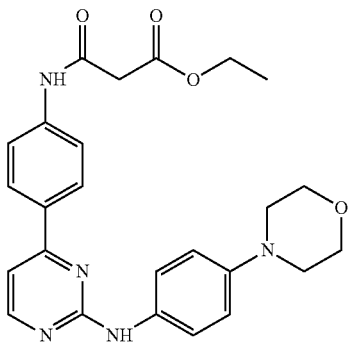

ethyl 3-[(4-{2-[(4-morpholin-4-ylphenyl)amino]pyrimidin-4-yl}phenyl)amino]-3-oxopropanoate

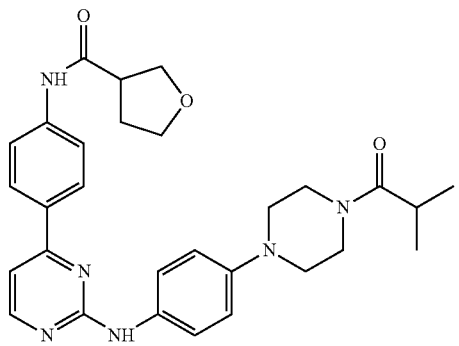

N-{4-[2-({4-[4-(2-methylpropanoyl)piperazin-1-yl]phenyl}amino)pyrimidin-4-yl]phenyl}tetrahydrofuran-3-carboxamide

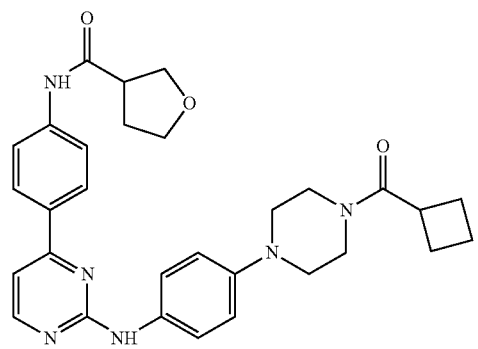

N-{4-[2-({4-[4-(cyclobutylcarbonyl)piperazin-1-yl]phenyl}amino)pyrimidin-4-yl]phenyl}tetrahydrofuran-3-carboxamide

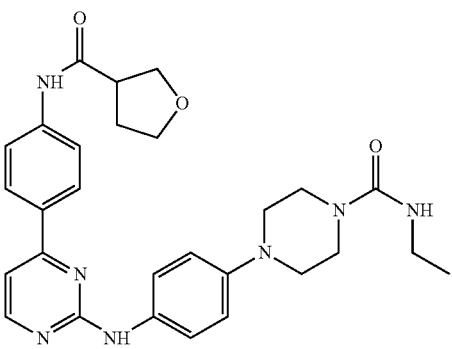

N-ethyl-4-{4-[(4-{4-[(tetrahydrofuran-3-ylcarbonyl)amino]phenyl}pyrimidin-2-yl)amino]phenyl}piperazine-1-carboxamide

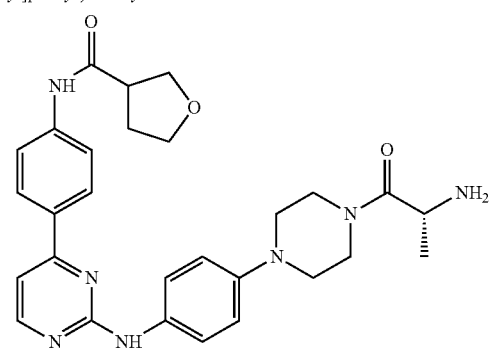

N-[4-(2-{[4-(4-D-alanylpiperazin-1-yl)phenyl]amino}pyrimidin-4-yl)phenyl]tetrahydrofuran-3-carboxamide

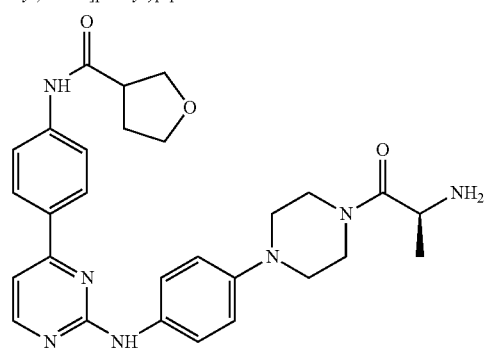

N-[4-(2-{[4-(4-L-alanylpiperazin-1-yl)phenyl]amino}pyrimidin-4-yl)phenyl]tetrahydrofuran-3-carboxamide

847

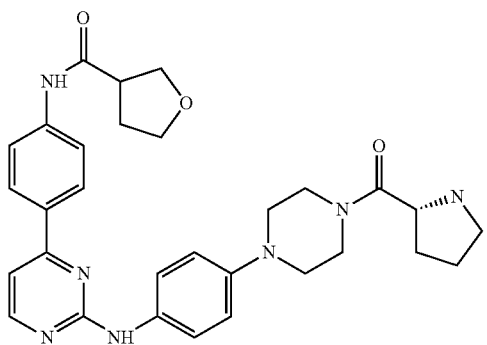

N-[4-(2-{[4-(4-D-prolylpiperazin-1-
yl)phenyl]amino}pyrimidin-4-yl)phenyl]tetrahydrofuran-
3-carboxamide

848

-continued

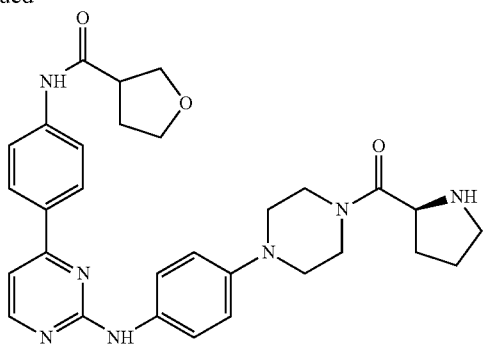

N-[4-(2-{[4-(4-L-prolylpiperazin-1-
yl)phenyl]amino}pyrimidin-4-yl)phenyl]tetrahydrofuran-
3-carboxamide

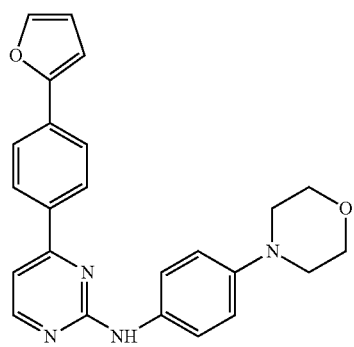

4-(4-furan-2-ylphenyl)-N-(4-morpholin-4-
ylphenyl)pyrimidin-2-amine

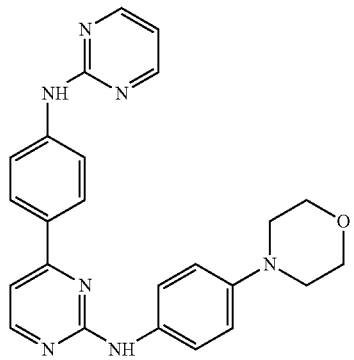

N-[4morpholin-4-ylphenyl)-4-[4-(pyrimidin-2-
ylamino)phenyl]pyrimidin-2-amine

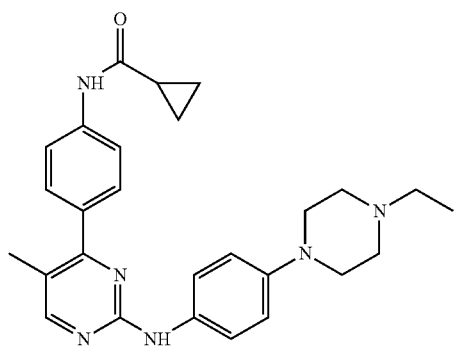

N-[4-(2-{[4-(4-ethylpiperazin-1-yl)phenyl]amino}-5-
methylpyrimidin-4-yl)phenyl]cyclopropanecarboxamide

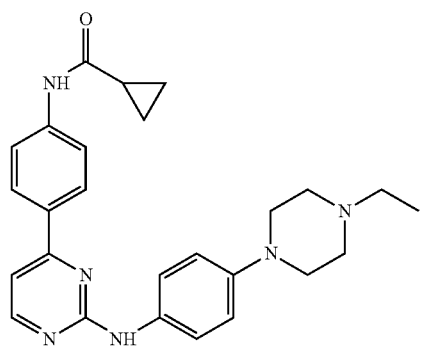

N-[4-(2-{[4-(4-ethylpiperazin-1-yl)phenyl]amino}pyrimidin-4-
yl)phenyl]cyclopropanecarboxamide

849

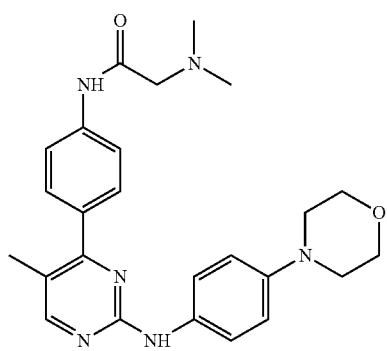

N~2~,N~2~-dimethyl-N-(4-{5-methyl-2-[(4-morpholin-4-ylphenyl)amino]pyrimidin-4-yl}phenyl)glycinamide

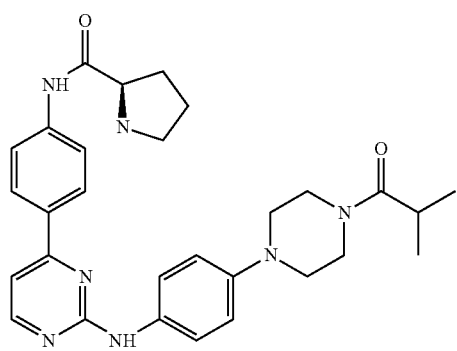

N-{4-[2-({4-(2-methylpropanoyl)piperazin-1-yl]phenyl}amino)pyrimidin-4-yl]phenyl}-D-prolinamide

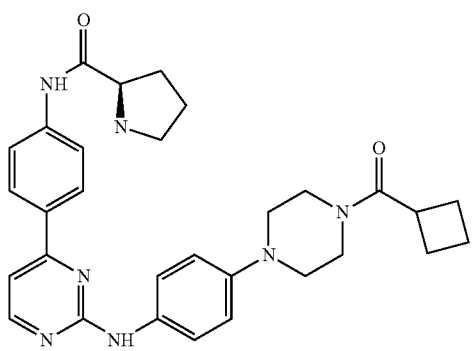

N-{4-[2-({4-[4-(cyclobutylcarbonyl)piperazin-1-yl]phenyl}amino)pyrimidin-4-yl]phenyl}-D-prolinamide

850

-continued

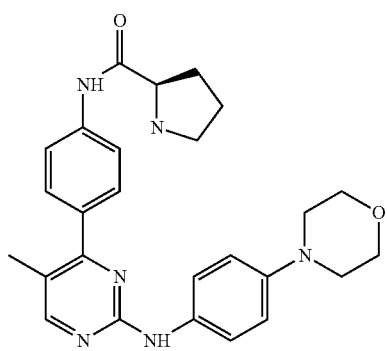

N-(4-{5-methyl-2-[(4-morpholin-4-ylphenyl)amino]pyrimidin-4-yl}phenyl)-D-prolinamide

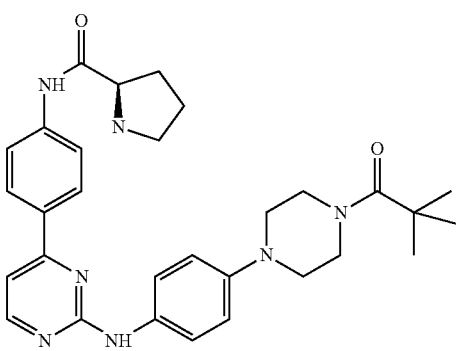

N-{4-[2-({4-(2,2-dimenthylpropanoyl)piperazin-1-yl]phenyl}amino)pyrimidin-4-yl]phenyl}-D-prolinamide

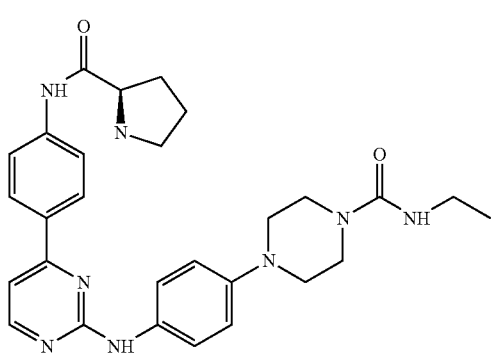

N-ethyl-4-[4-({4-[4-(D-prolylamino)phenyl]pyrimidin-2-yl}amino)phenyl]piperazine-1-carboxamide

851

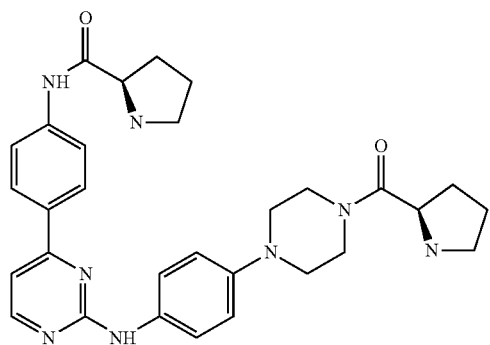

N-[4-(2-{[4-(4-D-prolypiperazin-1-
yl)phenyl]amino}pyrimidin-4-yl)phenyl]-D-prolinamide 852
-continued

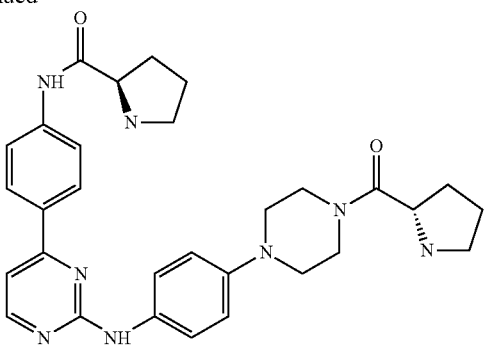

N-[4-(2-{[4-(4-L-prolylpiperazin-1-
yl)phenyl]amino}pyrimidin-4-yl)phenyl]-D-prolinamide

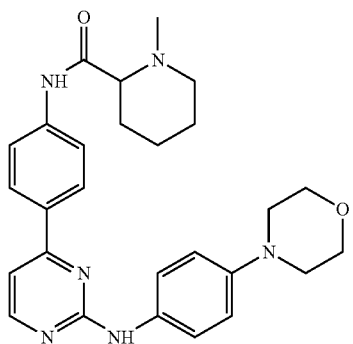

1-methyl-N-(4-{2-[(4-morpholin-4-ylphenyl)amino]pyrimidin-
4-yl}phenyl)piperidine-2-carboxamide

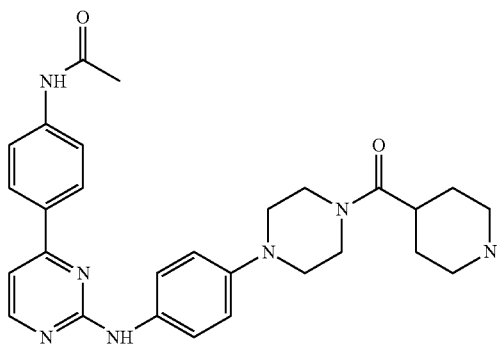

N-{4-[2-({4-[4-(piperidin-4-ylcarbonyl)piperazin-1-
yl]phenyl}amino)pyrimidin-4-yl]phenyl}acetamide

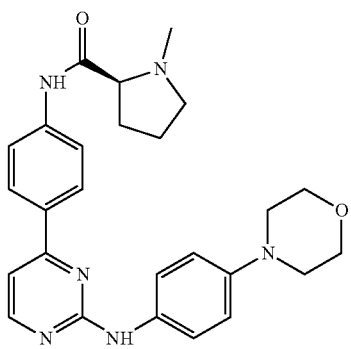

1-methyl-N-(4-{2-[(4-morpholin-4-ylphenyl)amino]pyrimidin-
4-yl}phenyl)piperidine-L-prolinamide

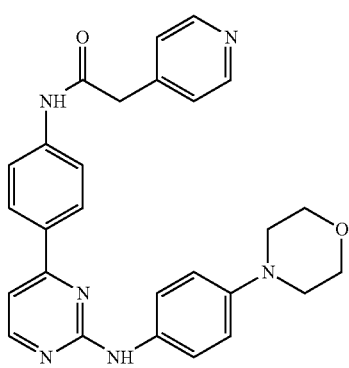

N-(4-{2-[(4-morpholin-4-ylphenyl)amino]pyrimidin-4-
yl}phenyl)-2-pyridin-4-ylacetamide -continued

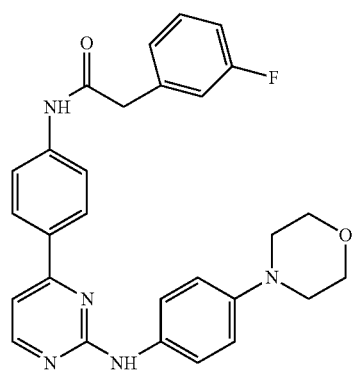

2-(3-fluorophenyl)-N-(4-{2-[(4-morpholin-4-ylphenyl)amino]pyrimidin-4-yl}phenyl)acetamide

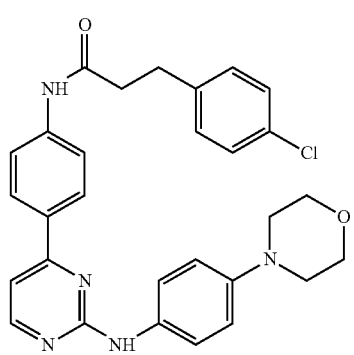

3-(4-chlorophenyl)-N-(4-{2-[(4-morpholin-4-ylphenyl)amino]pyrimidin-4-yl}phenyl)propanamide

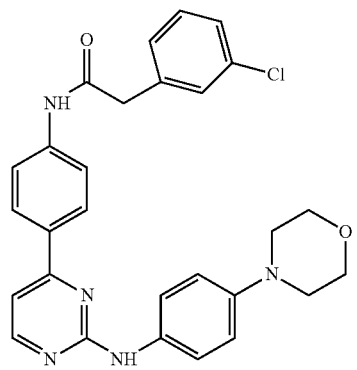

2-(3-chlorophenyl)-N-(4-{2-[(4-morpholin-4-ylphenyl)amino]pyrimidin-4-yl}phenyl)acetamide

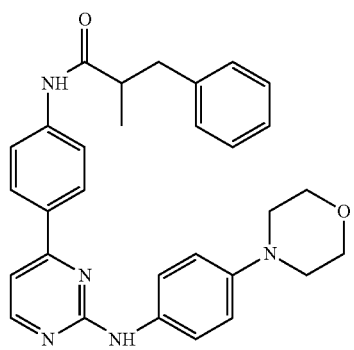

2-methyl-N-(4-{2-[(4-morpholin-4-ylphenyl)amino]pyrimidin-4-yl}phenyl)-3-phenylpropanamide

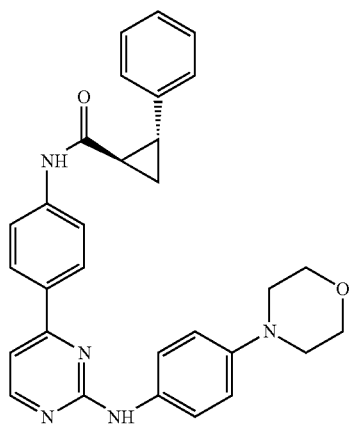

(1R,2R)-N-(4-{2-[(4-morpholin-4-ylphenyl)amino]pyrimidin-4-yl}phenyl)-2-phenylcyclopropanecarboxamide

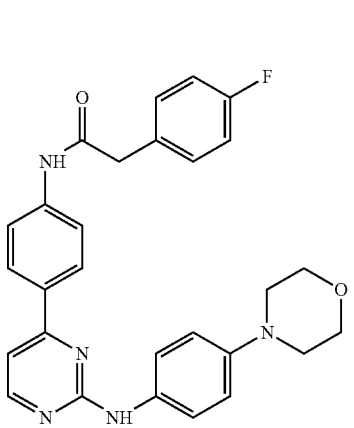

2-(4-fluorophenyl)-N-(4-{2-[(4-morpholin-4-ylphenyl)amino]pyrimidin-4-yl}phenyl)acetamide

855

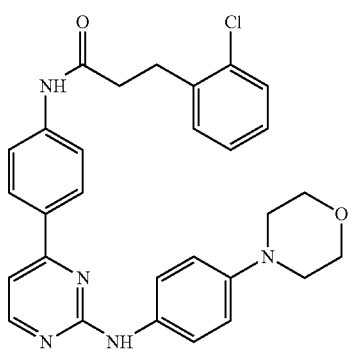

3-(2-chlorophenyl)-N-(4-{2-[(4-morpholin-4-ylphenyl)amino]pyrimidin-4-yl}phenyl)propanamide

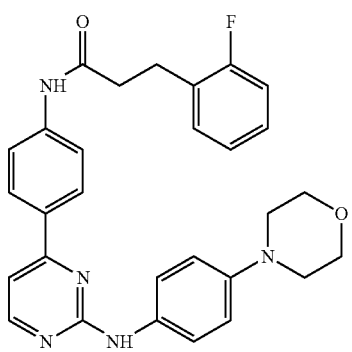

3-(2-fluorophenyl)-N-(4-{2-[(4-morpholin-4-ylphenyl)amino]pyrimidin-4-yl}phenyl)propanamide

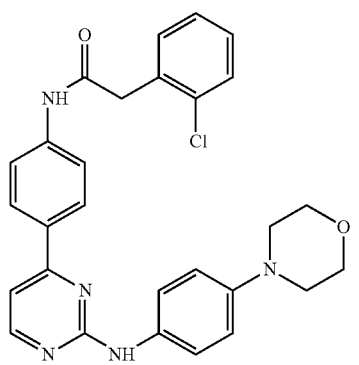

2-(2-chlorophenyl)-N-(4-{2-[(4-morpholin-4-ylphenyl)amino]pyrimidin-4-yl}phenyl)acetamide 856
-continued

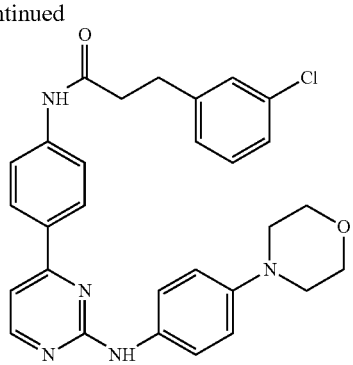

3-(3-chlorophenyl)-N-(4-{2-[(4-morpholin-4-ylphenyl)amino]pyrimidin-4-yl}phenyl)propanamide

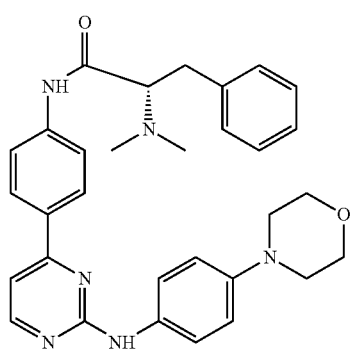

Nalpha,Nalpha-dimethyl-N-(4-{2-[(4-morpholin-4-ylphenyl)amino]pyrimidin-4-yl}phenyl)-L-phenylaminamide

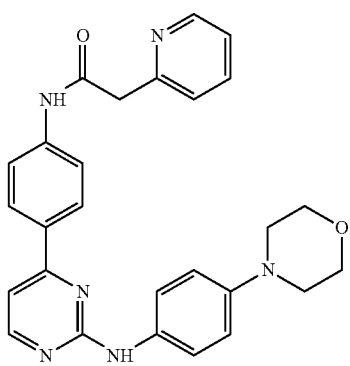

N-(4-{2-[(4-morpholin-4-ylphenyl)amino]pyrimidin-4-yl}phenyl)-2-pyridin-2-ylacetamide

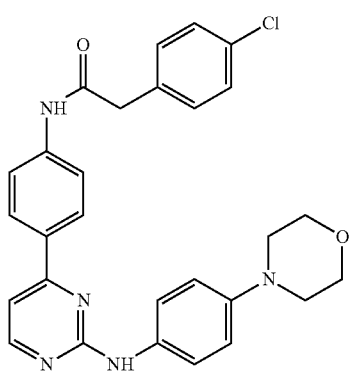

2-(4-chlorophenyl)-N-(4-{2-[(4-morpholin-4-ylphenyl)amino]pyrimidin-4-yl}phenyl)acetamide

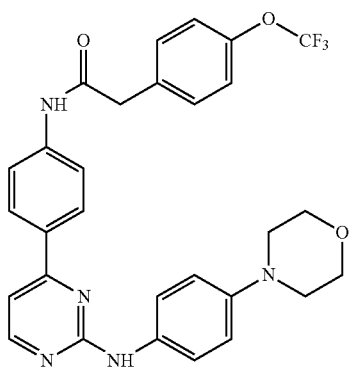

N-(4-{2-[(4-morpholin-4-ylphenyl)amino]pyrimidin-4-yl}phenyl)-2-{4-[(trifluoromethyl)oxy]phenyl}acetamide

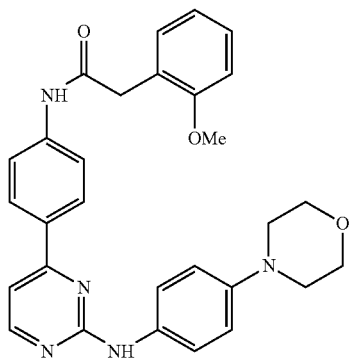

2-[2-(methyloxy)phenyl]-N-(4-{2-[(4-morpholin-4-ylphenyl)amino]pyrimidin-4-yl}phenyl)acetamide

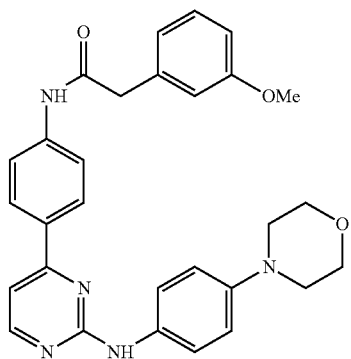

2-[3-(methyloxy)phenyl]-N-(4-{2-[(4-morpholin-4-ylphenyl)amino]pyrimidin-4-yl}phenyl)acetamide

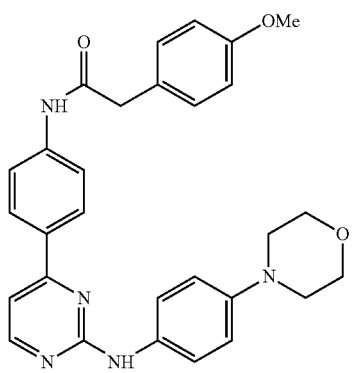

2-[4-(methyloxy)phenyl]-N-(4-{2-[(4-morpholin-4-ylphenyl)amino]pyrimidin-4-yl}phenyl)acetamide

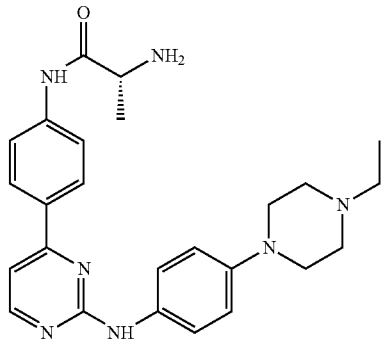

N-[4-(2-{[4-(4-ethylpiperazin-1-yl)phenyl]amino}pyrimidin-4-yl)phenyl]-D-alaninamide -continued

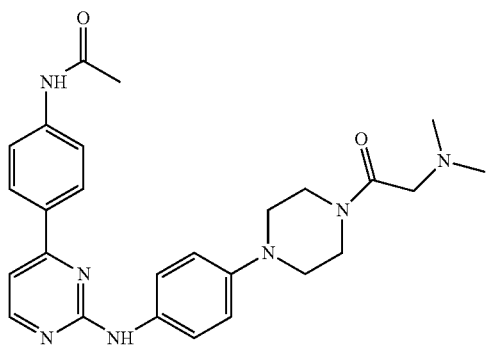

N-{4-[2-({4-[4-(N,N-dimethylglycyl)piperazin-1-yl]phenyl}amino)pyrimidin-4-yl]phenyl}acetamide

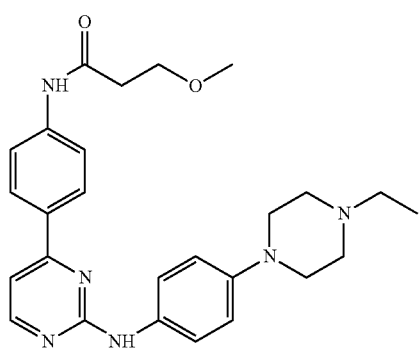

N-[4-(2-{[4-(4-ethylpiperazin-1-yl)phenyl]amino}pyrimidin-4-yl)phenyl]-3-(methyloxy)propanamide

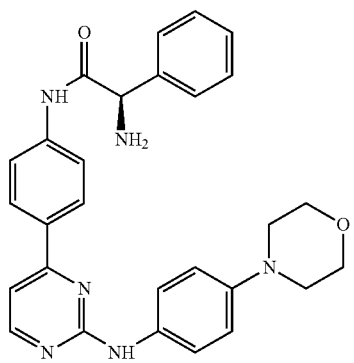

(2R)-2-amino-N-(4-{2-[(4-morpholin-4-ylphenyl)amino]pyrimidin-4-yl}phenyl)-2-phenylethanamide

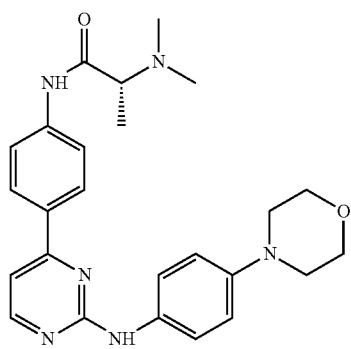

$N^2,N^2$-dimethyl-N-(4-{2-[(4-morpholin-4-ylphenyl)amino]pyrimidin-4-yl}phenyl)-D-alaninamide

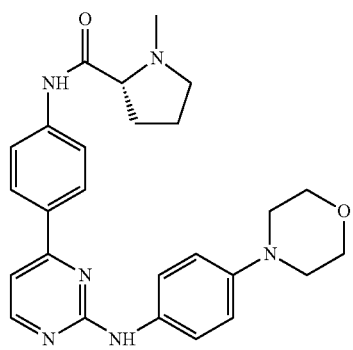

1-methyl-N-(4-{2-[(4-morpholin-4-ylphenyl)amino]pyrimidin-4-yl}phenyl)-D-prolinamide

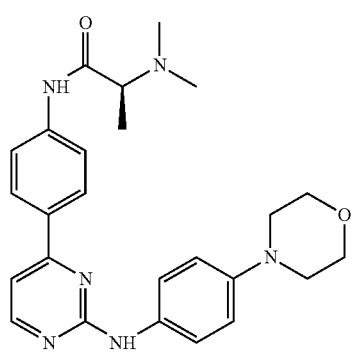

N~2~,N~2~-dimethyl-N-(4-{2-[(4-morpholin-4-ylphenyl)amino]pyrimidin-4-yl}-L-alaninamide

861

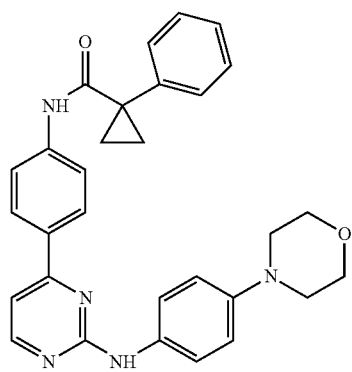

N-(4-{2-[(4-morpholin-4-ylphenyl)amino]pyrimidin-4-yl}phenyl)-1-phenylcyclopropanecarboxamide

862

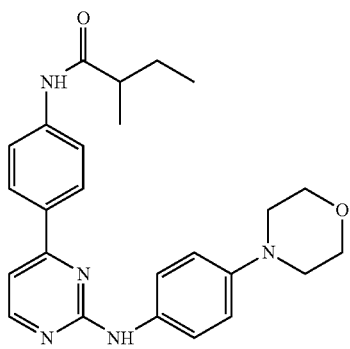

2-methyl-N-(4-{2-[(4-morpholin-4-ylphenyl)amino]pyrimidin-4-yl}phenyl)butanamide

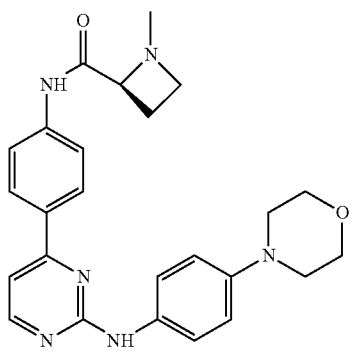

(2S)-1-methyl-N-(4-{2-[(4-morpholin-4-ylphenyl)amino]pyrimidin-4-yl}phenyl)azetidine-2-carboxamide

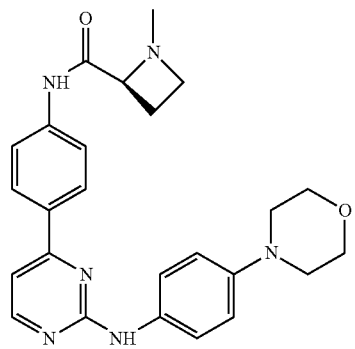

2,4,6-trichloro-N-(3-{[4-(4-methyl-2-thienyl)pyrimidin-2-yl]amino}propyl)benzamide

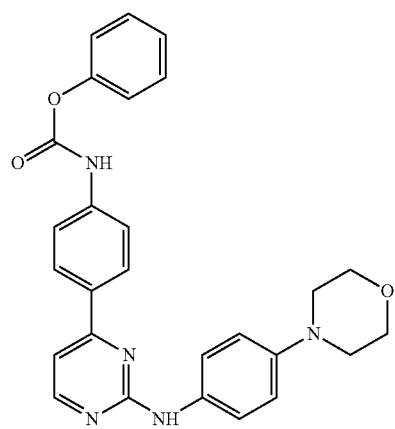

phenyl(4-{2-[(4-morpholin-4-ylphenyl)amino]pyrimidin-4-yl}phenyl)carbanate 863 864

-continued

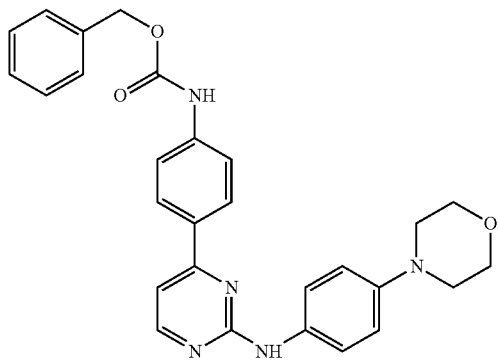

phenylmethyl(4-{2-[(4-morpholin-4-
ylphenyl)amino]pyrimidin-4-yl}phenyl)carbamte

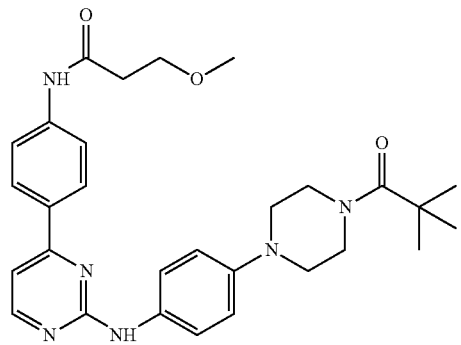

N-{4-[2-({4-[4-(2,2-dimethylpropanoyl)piperazin-1-
yl]phenyl}amino)pyrimidin-4-yl]phenyl}-3-
(methyloxy)propanamide

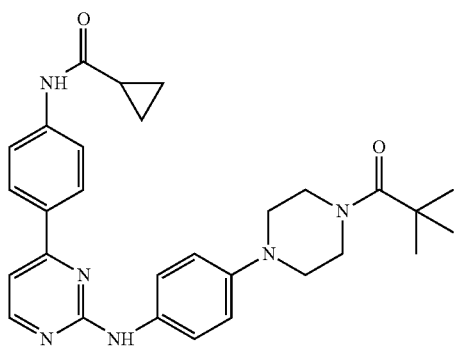

N-{4-[2-({4-[4-2,2-dimethylpropanoyl)piperazin-1-
yl]phenyl}amino)pyrimidin-4-
yl]phenyl}cyclopropanecarboxamide

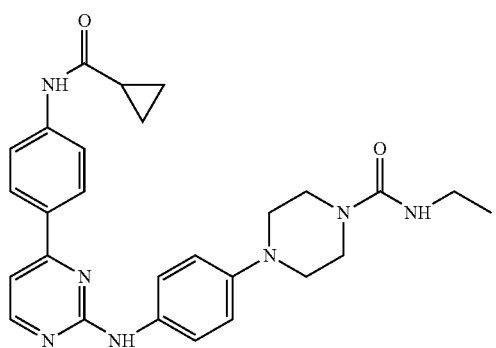

4-{4-[(4-{4-[(cyclopropylcarbonyl)amino]phenyl}pyrimidin-2-
yl)amino]phenyl}-N-ethylpiperazine-1-carboxamide

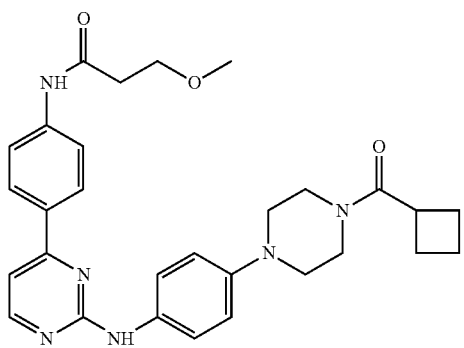

N-{4-[2-({4-[4-(cyclobutylcarbonyl)piperazin-1-
yl]phenyl}amino)pyrimidin-4-yl]phenyl}-3-
(methyloxy)propanamide

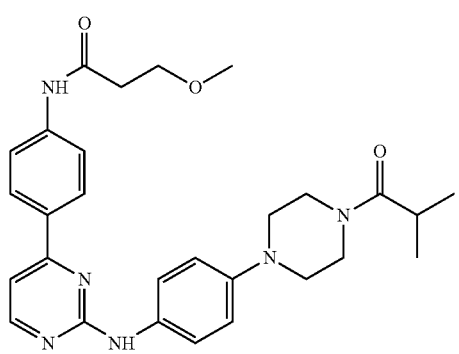

3-(methyloxy)-N-{4-[2-({4-[4-(2-methylpropanoyl)piperazin-
1-yl]phenyl}amino)pyrimidin-4-yl]phenyl}propanamide -continued

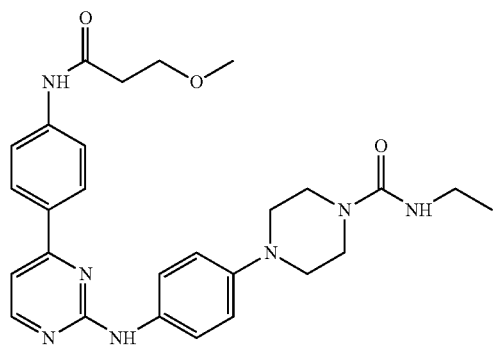

N-ethyl-4-(4-{[4-(4-{[3-(methyloxy)propanoyl]amino}phenyl)pyrimidin-2-yl]amino}phenyl)piperazine-1-carboxamide

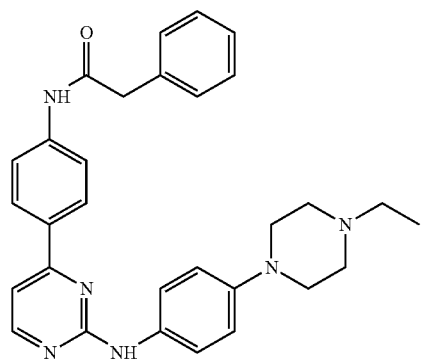

N-[4-(2-{[4-(4-ethylpiperazin-1-yl)phenyl]amino}pyrimidin-4-yl)phenyl]-2-phenylacetamide

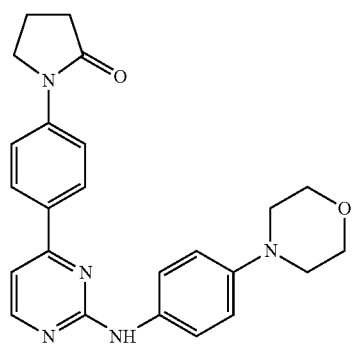

1-(4-{2-[(4-morpholin-4-ylphenyl)amino]pyrimidin-4-yl}phenyl)pyrrolidin-2-one

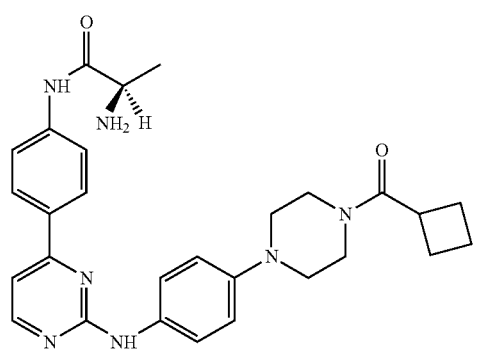

N-{4-[2-({4-[4-(cyclobutylcarbonyl)piperazin-1-yl]phenyl}amino)pyrimidin-4-yl]phenyl}-D-alaninamide

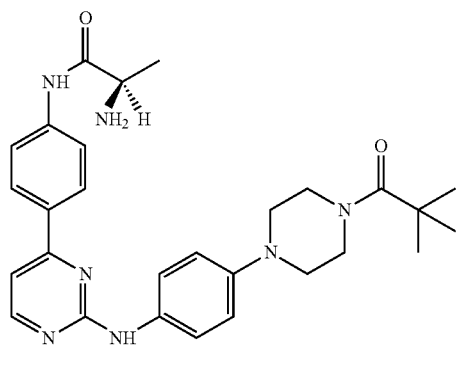

N-{4-[2-({4-[4-(2,2-dimethylpropanoyl)piperazin-1-yl]phenyl}amino)pyrimidin-4-yl]phenyl}-D-alaninamide

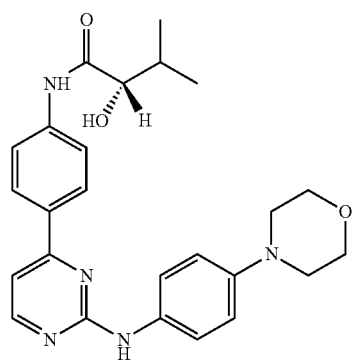

(2S)-2-hydroxy-3-methyl-N-(4-{2-[(4-morpholin-4-ylphenyl)amino]pyrimidin-4-yl}phenyl)butanamide -continued

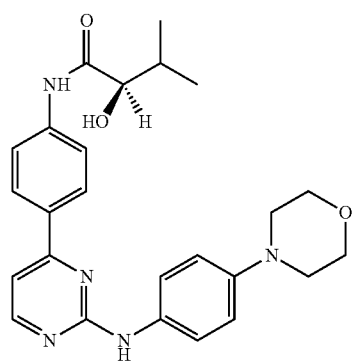

(2R)-2-hydroxy-3-methyl-N-(4-{2-[(4-morpholin-4-ylphenyl)amino]pyrimidin-4-yl}phenyl)butanamide

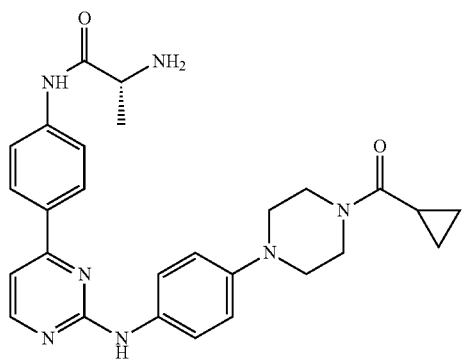

N-{4-[2-({4-[4-(cyclopropylcarbonyl)piperazin-1-yl]phenyl}amino)pyrimidin-4-yl]phenyl}-D-alaninamide

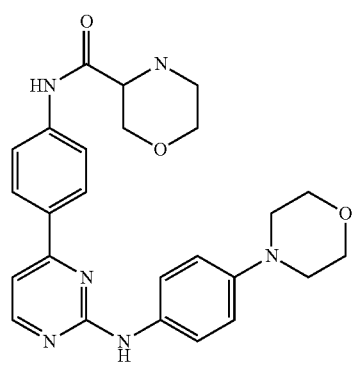

(2S)-2-amino-N-(4-{2-[(4-morpholin-4-ylphenyl)amino]pyrimidin-4-yl}phenyl)-2-phenylethanamide

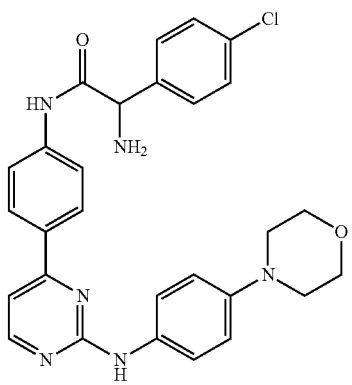

2-amino-2-(4-chlorphenyl)-N-(4-{2-[(4-morpholin-4-ylphenyl)amino]pyrimidin-4-yl}phenyl)acetamide

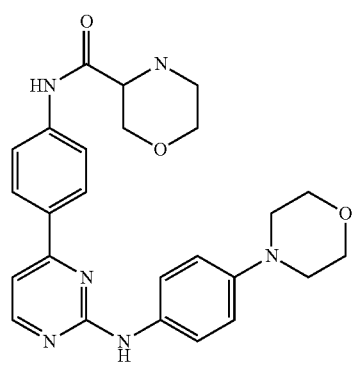

N-(4-{2-[(4-morpholin-4-ylphenyl)amino]pyrimidin-4-yl}phenyl)morpholine-3-carboxamide

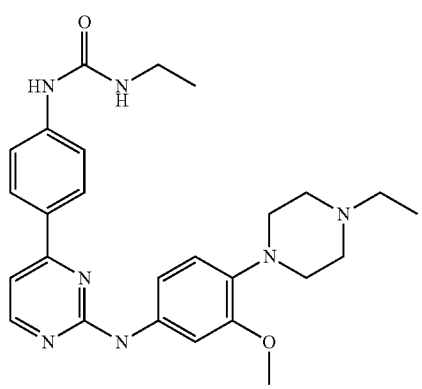

1-ethyl-3-[4-(2-{[4-(4-ethylpiperazin-1-yl)-3-(methyloxy)phenyl]amino}pyrimidin-4-yl)phenyl]urea -continued

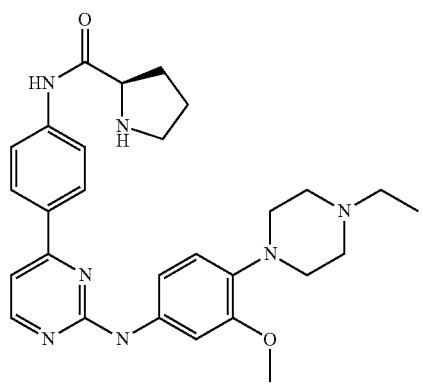

N-[4-(2-{[4-(4-ethylpiperazin-1-yl)-3-
(methyloxy)phenyl]amino}pyrimidin-4-yl)phenyl]-D-prolinamide

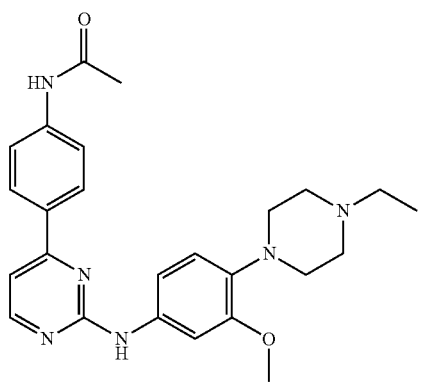

N-[4-(2-{[4-(4-ethylpiperazin-1-yl)-3-
(methyloxy)phenyl]amino}pyrimidin-4-yl)phenyl]acetamide

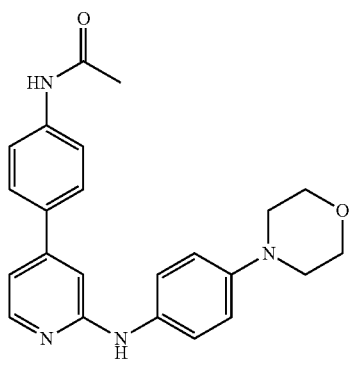

N-(4-{2-[(4-morpholin-4-ylphenyl)amino]pyridin-
4-yl}phenyl)acetamide

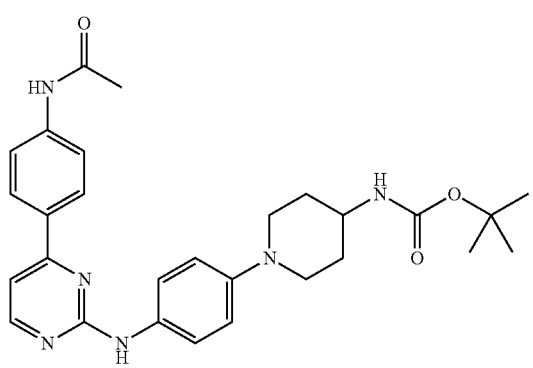

1,1-dimethylethyl{1-[4-({4-[4-(acetylamino)phenyl]pyrimidin-
2-yl}amino)phenyl]piperidin-4-yl}carbamate

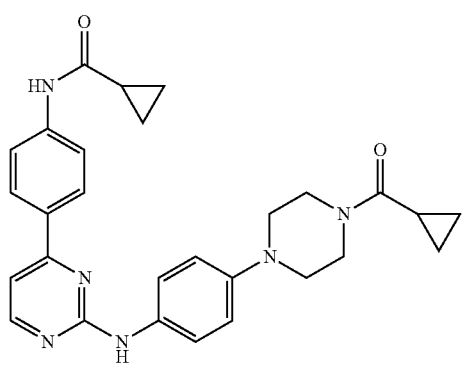

N-{4-[2-({4-[4-(cyclopropylcarbonyl)piperazin-1-
yl]phenyl}amino)pyrimidin-4-yl]phenyl}cyclopropanecarboxamide

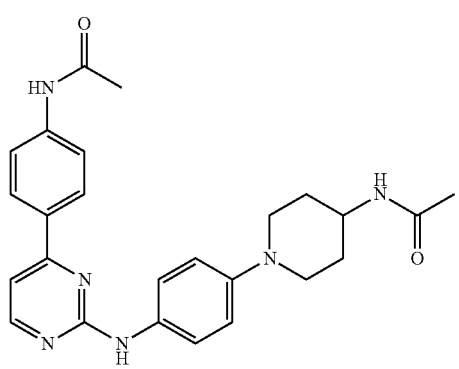

N-{1-[4-({4-[4-(acetylamino)phenyl]pyrimidin-2-
yl}amino)phenyl]piperidin-4-yl}acetamide -continued

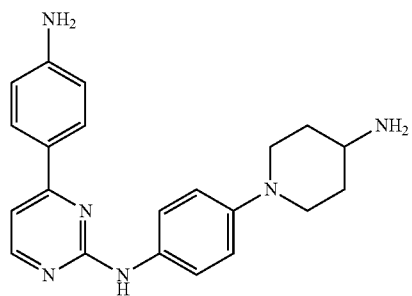

4-(4-aminophenyl)-N-[4-(4-aminopiperidin-1-yl)
phenyl]pyrimidin-2-amine

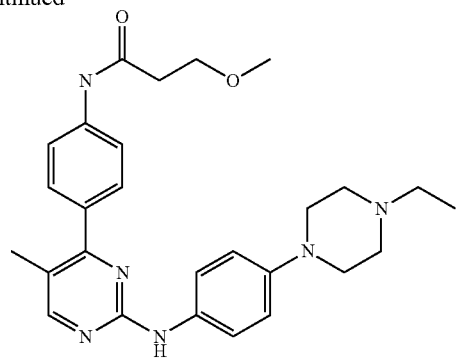

N-[4-(2-{[4-(4-ethylpiperazin-1-yl)phenyl]amino}-5-
methylpyrimidin-4-yl)phenyl]-3-(methyloxy)propanamide

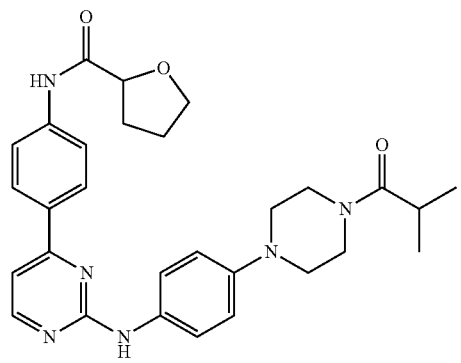

N-{4-[2-({4-[4-(2-methylpropanoyl)piperazin-1-
yl]phenyl}amino)pyrimidin-4-yl]phenyl}tetrahydrofuran-2-carboxamide

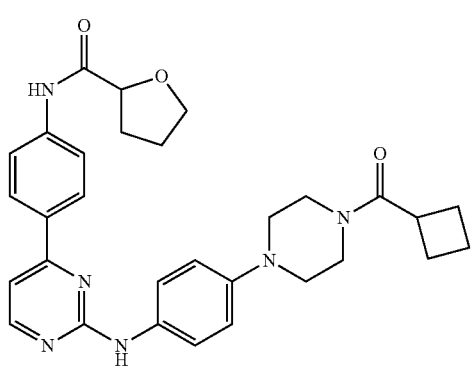

N-{4-[2-({4-[4-(cyclobutylcarbonyl)piperazin-1-
yl]phenyl}amino)pyrimidin-4-yl]phenyl}tetrahydrofuran-2-
carboxamide

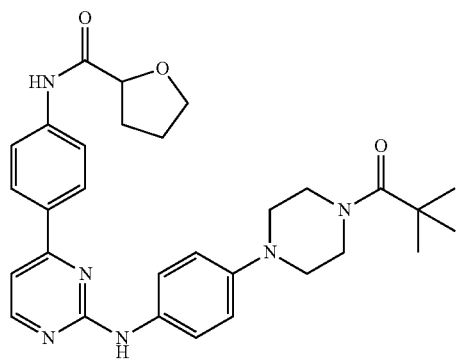

N-{4-[2-({4-[4-(2,2-dimethylpropanoyl)piperazin-1-
yl]phenyl}amino)pyrimidin-4-yl]phenyl}tetrahydrofuran-2-
carboxamide

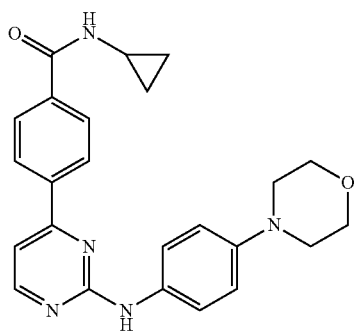

N-cyclopropyl-4-{2-[(4-morpholin-4-
ylphenyl)amino]pyrimidin-4-yl}benzamide

-continued

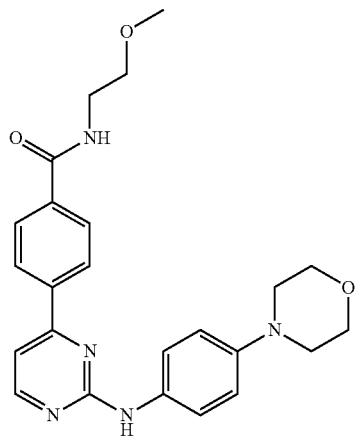

N-[2-(methyloxy)ethyl]-4-{2-[(4-morpholin-4-ylphenyl)amino]pyrimidin-4-yl}benzamide

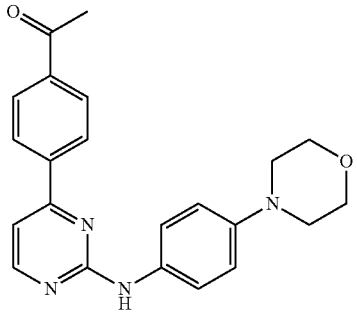

1-(4-{2-[(4-morpholin-4-ylphenyl)amino]pyrimidin-4-yl}phenyl)ethanone

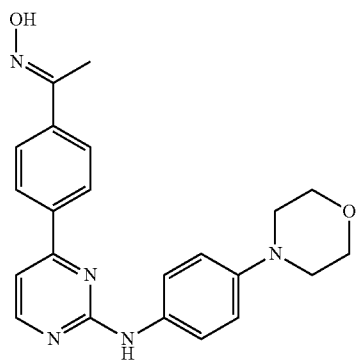

(1E)-1-(4-{2-[(4-morpholin-4-ylphenyl)amino]pyrimidin-4-yl}phenyl)ethanone oxime

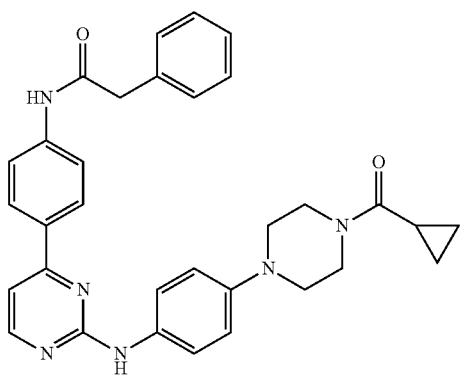

N-{4-[2-({4-[4-(cyclopropylcarbonyl)piperazin-1-yl]phenyl}amino)pyrimidin-4-yl]phenyl}-2-phenylacetamide

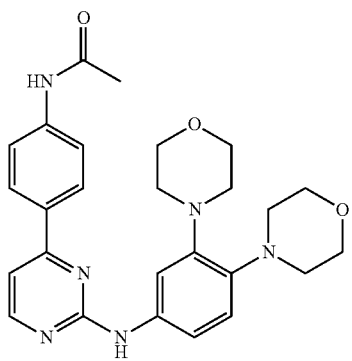

N-(4-{2-[(3,4-dimorpholin-4-ylphenyl)amino]pyrimidin-4-yl}phenyl)acetamide

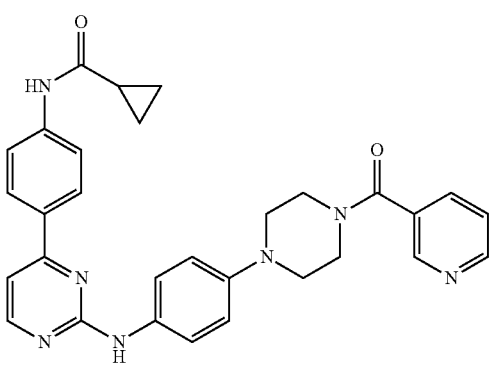

N-{4-[2-({4-[4-(pyridin-3-ylcarbonyl)piperazin-1-yl]phenyl}amino)pyrimidin-4-yl]phenyl}cyclopropanecarboxamide 875
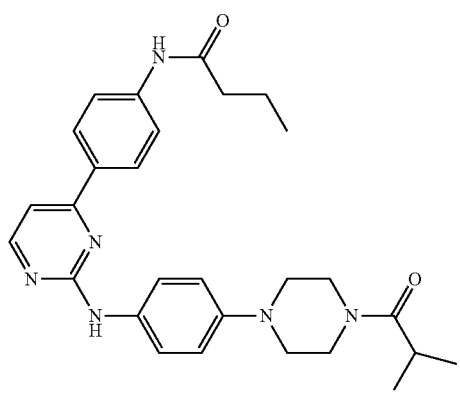
N-{4-[2-({4-[4-(2-methylpropanoyl)pipenrazin-1-yl]
phenyl}amino)pyrimidin-4-yl]phenyl}butanamide
876
-continued
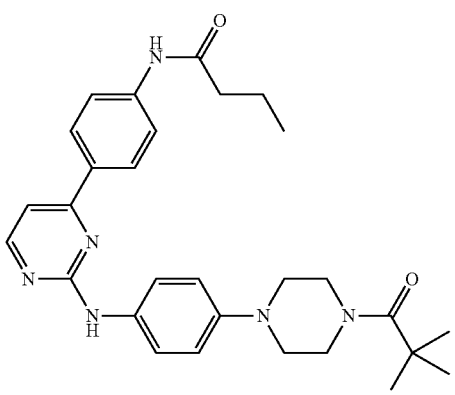
N-{4-[2-({4-[4-(2,2-dimethylpropanoyl)piperazin-1-
yl]phenyl}amino)pyrimidin-4-yl]phenyl}butanamide
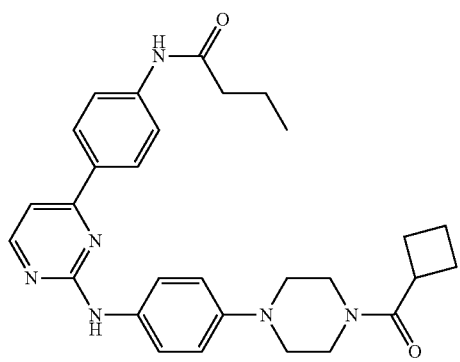
N-{4-[2-({4-[4-(cyclobutylcarbonyl)piperazin-1-
yl]phenyl}amino)pyrimidin-4-yl]phenyl}butanamide
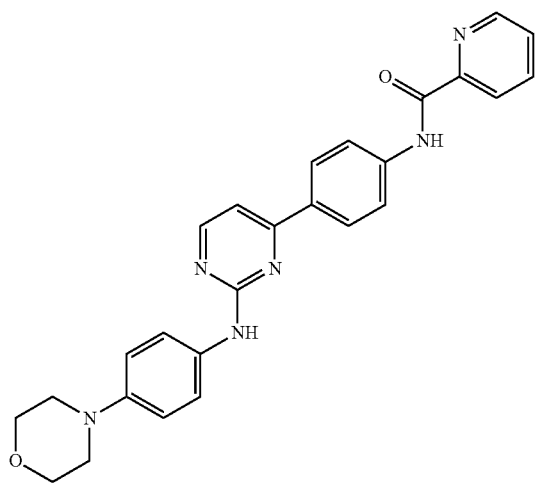
N-(4-{2-[(4-morpholin-4-ylphenyl)amino]pyrimidin-
4-yl}phenyl)pyridine-2-carboxamide -continued
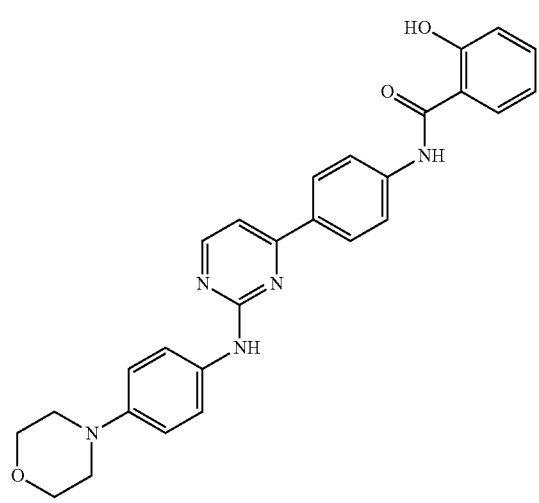
2-hydroxy-N-(4-{2-[(4-morpholin-4-ylphenyl)amino]pyrimidin-4-yl}phenyl)benzamide
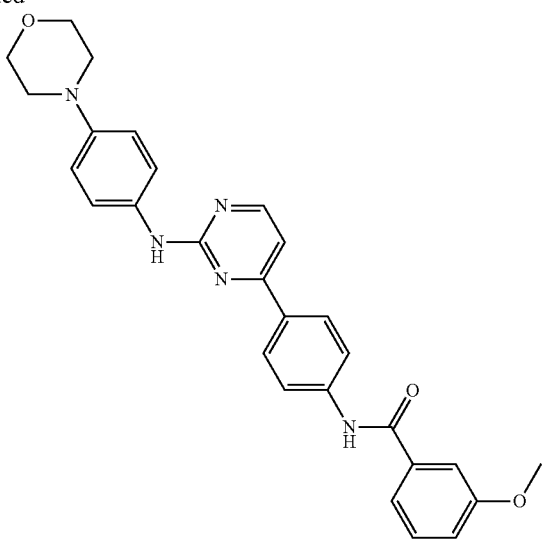
3-(methyloxy)-N-(4-{2-[(4-morpholin-4-ylphenyl)amino]pyrimidin-4-yl}phenyl)benzamide
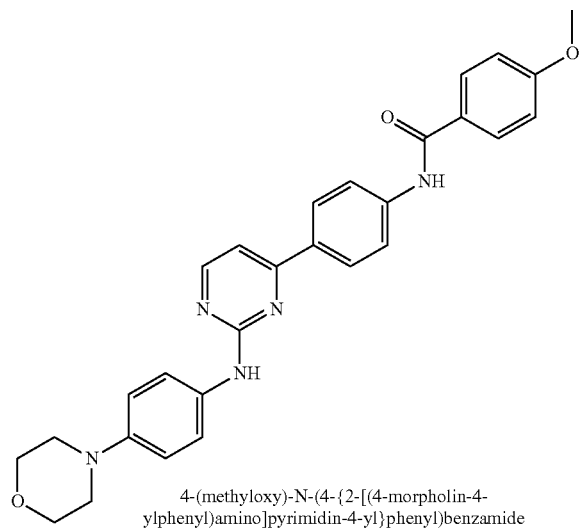
4-(methyloxy)-N-(4-{2-[(4-morpholin-4-ylphenyl)amino]pyrimidin-4-yl}phenyl)benzamide
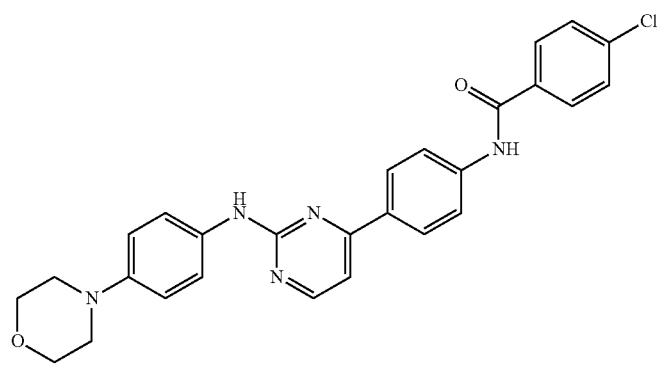
4-chloro-N-(4-{2-[(4-morpholin-4-ylphenyl)amino]pyrimidin-4-yl}phenyl)benzamide

| 879 | 880 |
|---|---|
| 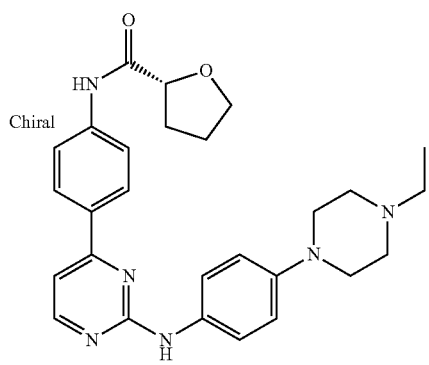 | 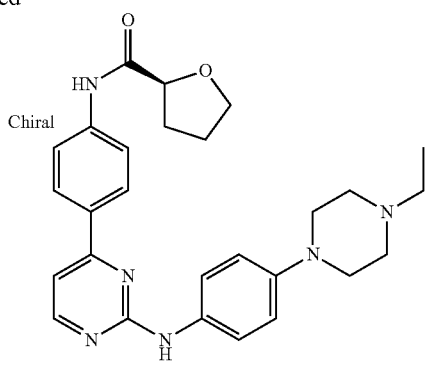 |
| (2R)-N-[4-(2-{[4-(4-ethylpiperazin-1-yl)phenyl]amino}pyrimidin-4-yl)phenyl]tetrahydrofuran-2-carboxamide | (2S)-N-[4-(2-{[4-(4-ethylpiperazin-1-yl)phenyl]amino}pyrimidin-4-yl)phenyl]tetrahydrofuran-2-carboxamide |
| 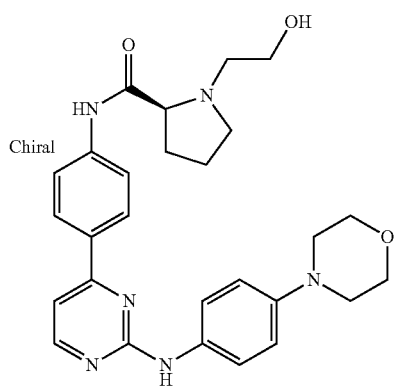 | 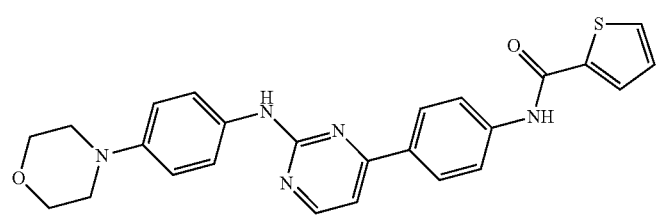 |
| 1-(2-hydroxyethyl)-N-(4-{2-[(4-morpholin-4-ylphenyl)amino]pyrimidin-4-yl}phenyl)-L-prolinamide | N-(4-{2-[(4-morpholin-4-ylphenyl)amino]pyrimidin-4-yl}phenyl)thiopene-2-carboxamide |
| 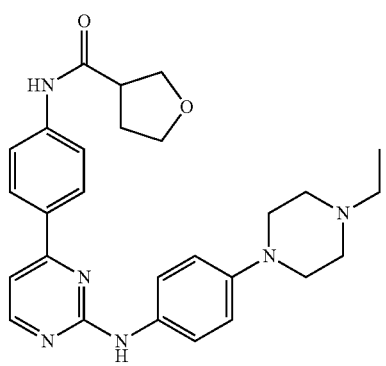 | 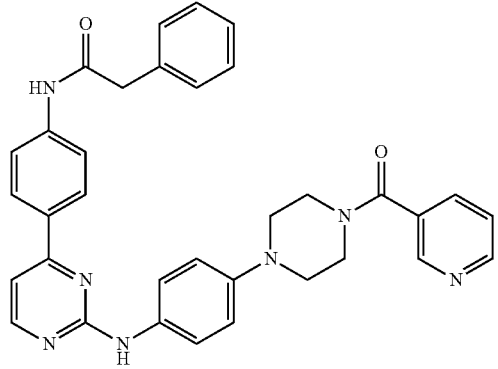 |
| N-[4-(2-{[4-(4-ethylpiperazin-1-yl)phenyl]amino}pyrimidin-4-yl)phenyl]tetrahydrofuran-3-carboxamide | 2-phenyl-N-{4-[2-({4-[4-(pyridin-3-ylcarbonyl)piperazin-1-yl]phenyl}amino)pyrimidin-4-yl]phenyl}acetamide |

881

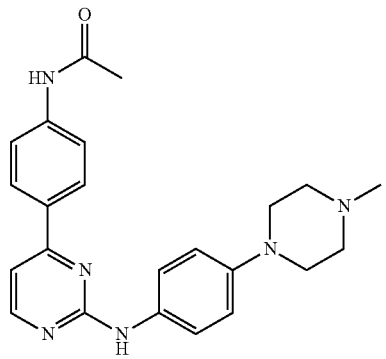

N-[4-(2-{[4-(4-methylpiperazin-1-yl)phenyl]amino}pyrimidin-4-yl)phenyl]acetamide

882

-continued

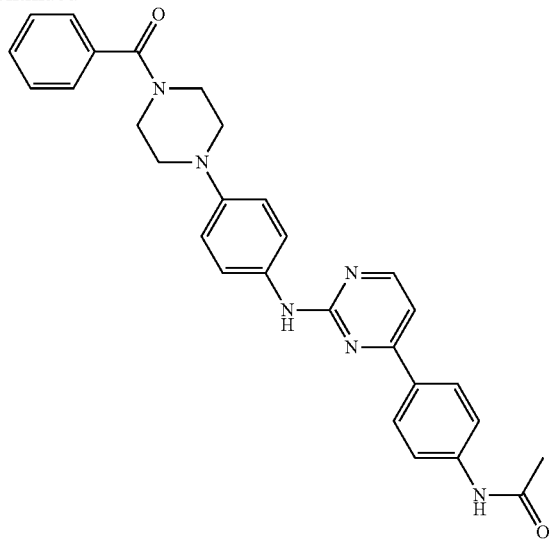

N-{4-[2-({4-[4-(phenylcarbonyl)piperazin-1-yl]phenyl}amino)pyrimidin-4-yl]phenyl}acetamide

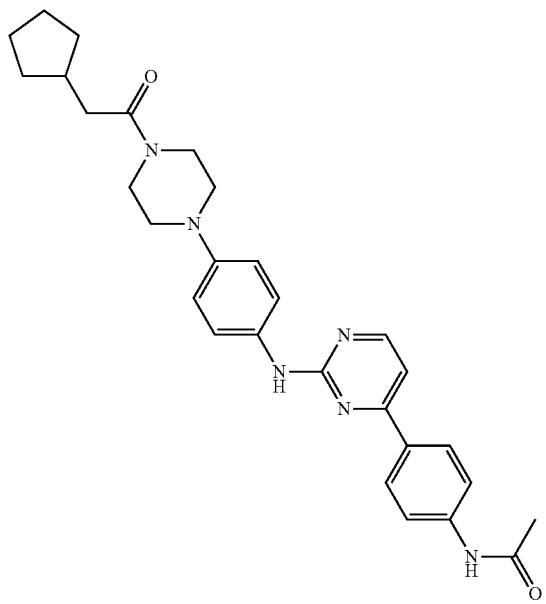

N-{4-[2-({4-[4-(2-cyclopentylacetyl)piperazin-1-yl]phenyl}amino)pyrimidin-4-yl]phenyl}acetamide

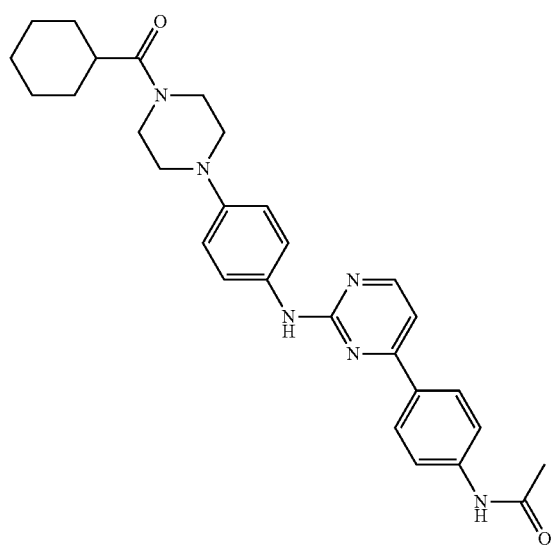

N-{4-[2-({4-[4-(cyclohexylcarbonyl)piperazin-1-yl]phenyl}amino)pyrimidin-4-yl]phenyl}acetamide

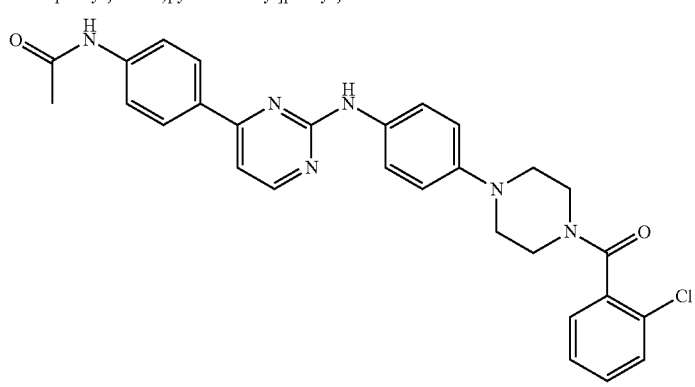

N-(4-{2-[(4-{4-[(2-chlorophenyl)carbonyl]piperazin-1-yl}phenyl)amino]pyrimidin-4-yl}phenyl)acetamide -continued
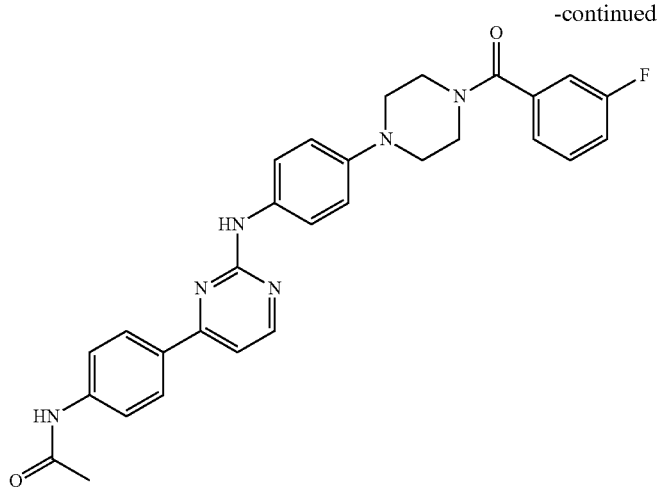
N-(4-{2-[(4-{4-[(3-fluorophenyl)carbonyl]piperazin-1-yl}
phenyl)amino]pyrimidin-4-yl}phenyl)acetamide
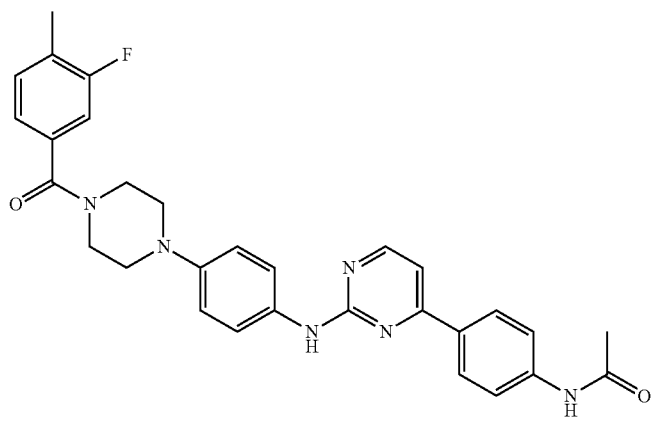
N-(4-{2-[(4-{4-[(3-fluoro-4-methylphenyl)carbonyl]piperazin-1-yl}
phenyl)amino]pyrimidin-4-yl}phenyl)acetamide
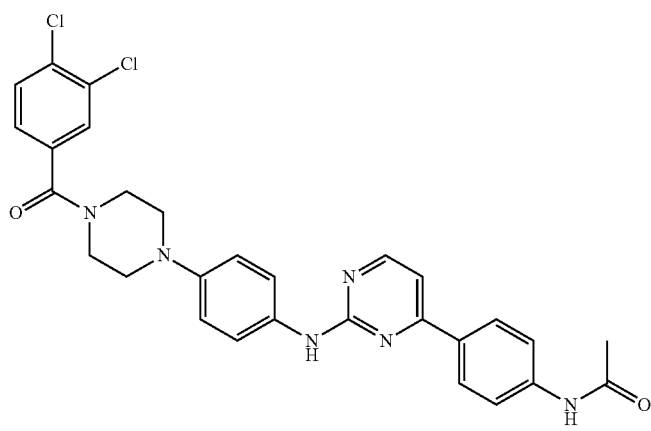
N-(4-{2-[(4-{4-[(3,4-dichlorophenyl)carbonyl]piperazin-1-yl}
phenyl)amino]pyrimidin-4-yl}phenyl)acetamide -continued
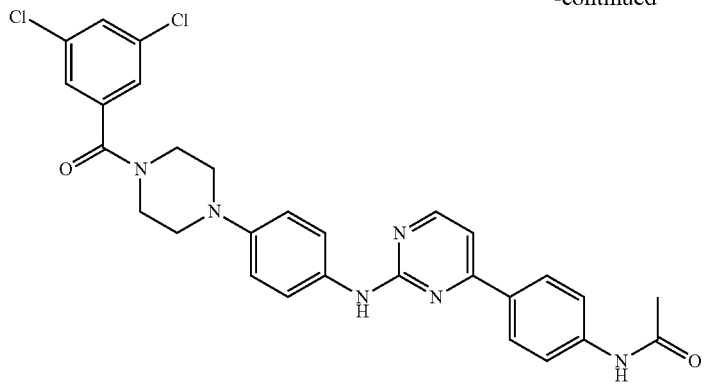
N-(4-{2-[(4-{4-[(3,5-dichlorophenyl)carbonyl]piperazin-1-yl}phenyl)amino]pyrimidin-4-yl}acetamide
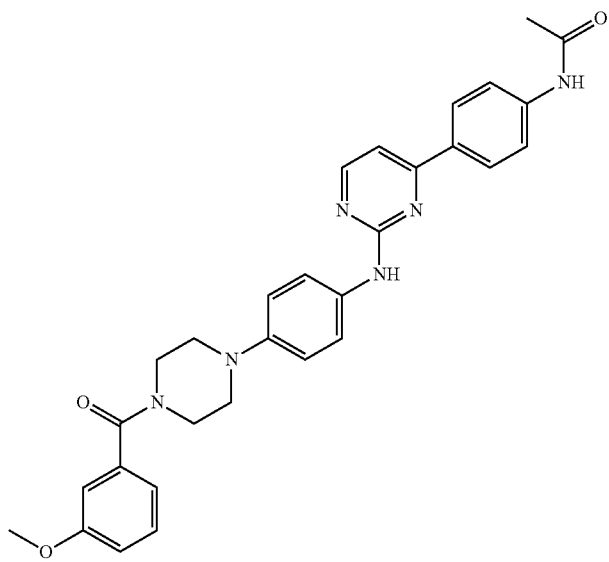
N-[4-(2-{[4-(4-{[3-(methyloxy)phenyl]carbonyl}piperazin-1-yl)phenyl]amino}pyrimidin-4-yl)phenyl]acetamide
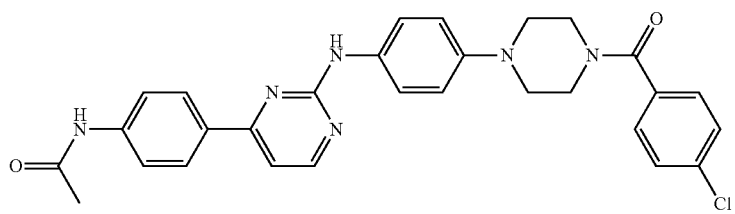
N-(4-{2-[(4-{4-[(4-chlorophenyl)carbonyl]piperazin-1-yl}phenyl)amino]pyrimidin-4-yl}phenyl)acetamide

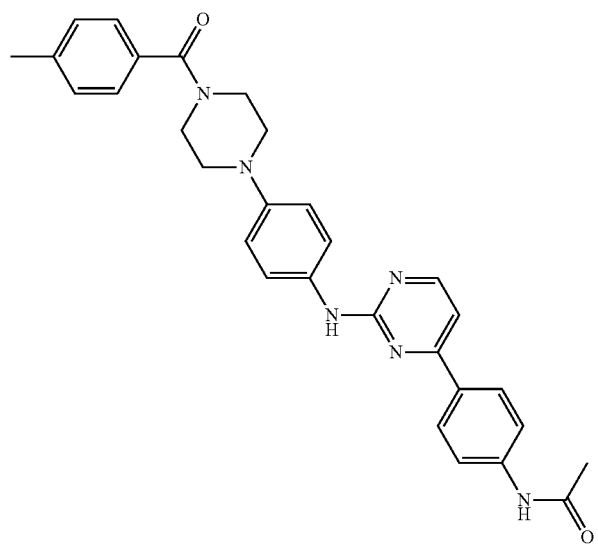
N-(4-{2-[(4-{4-[(4-methylphenyl)carbonyl]piperazin-1-yl}phenyl)amino]pyrimidin-4-yl}phenyl)acetamide
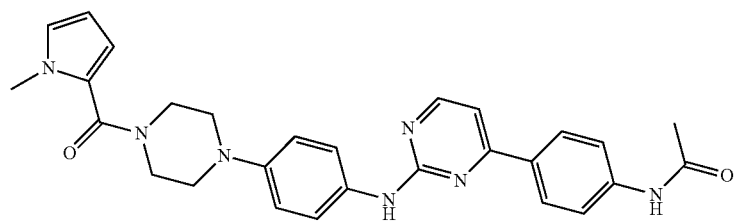
N-(4-{2-[(4-{4-[(1-methyl-1H-pyrrol-2-yl)carbonyl]piperazin-1-yl}phenyl)amino]pyrimidin-4-yl}phenyl)acetamide
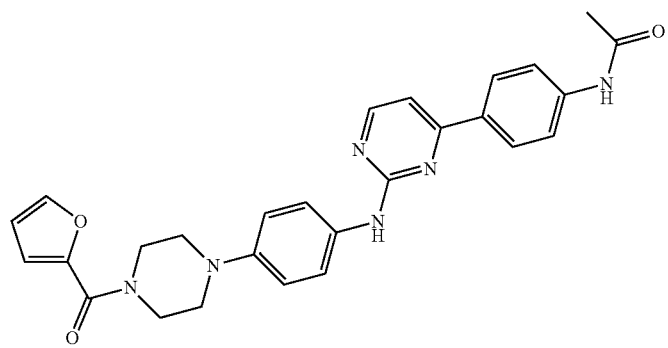
N-{4-[2-({4-[4-(furan-2-ylcarbonyl)piperazin-1-yl]phenyl}amino)pyrimidin-4-yl]phenyl}acetamide
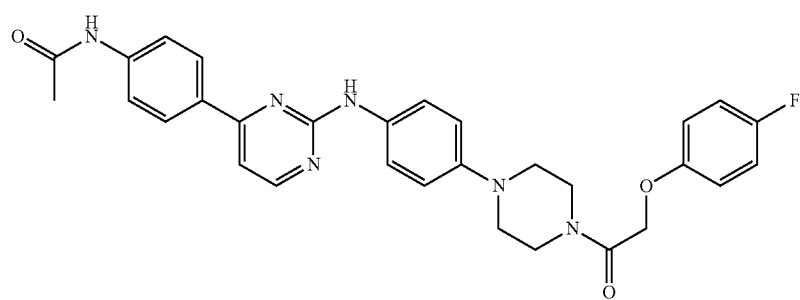
N-(4-{2-[(4-{4-[(3-methylphenyl)sulfonyl]piperazin-1-yl}phenyl)amino]pyrimidin-4-yl}phenyl)acetamide -continued
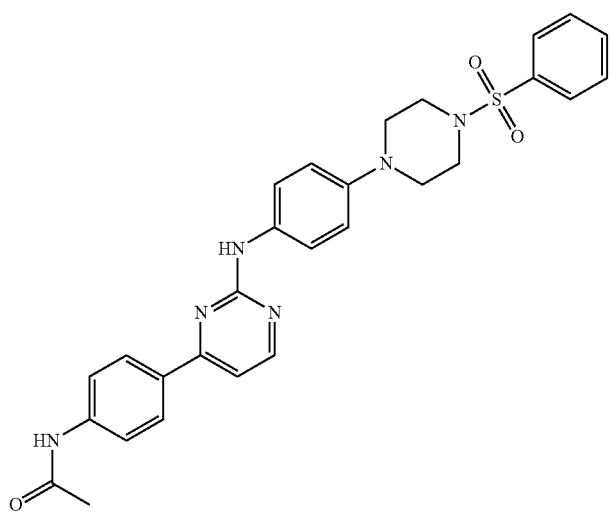
N-{4-[2-({4-[4-(phenylsulfonyl)piperazin-1-yl]phenyl}amino)pyrimidin-4-yl]phenyl}acetamide
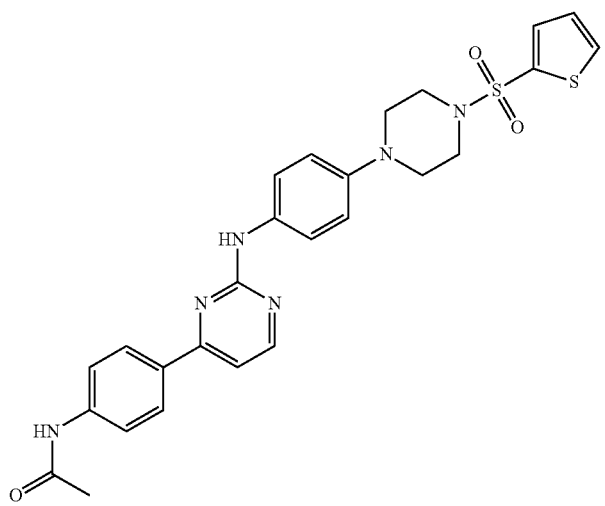
N-{4-[2-({4-[4-(2-thienylsulfonyl)piperazin-1-yl]phenyl}amino)pyrimidin-4-yl]phenyl}acetamide
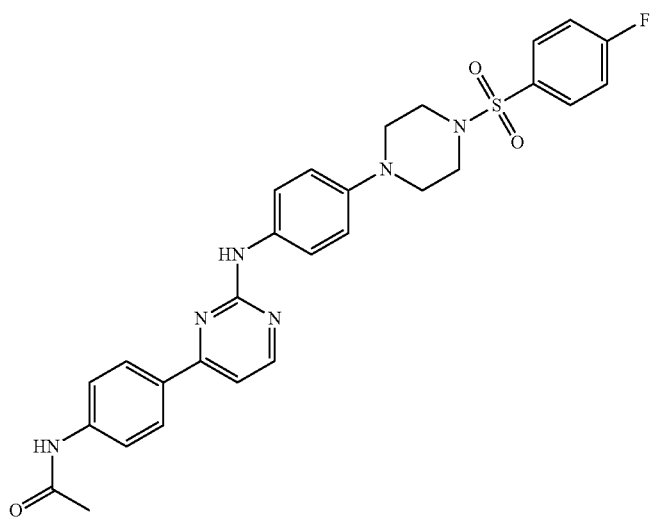
N-(4-{2-[(4-{4-[(4-fluorophenyl)sulfonyl]piperazin-1-yl}phenyl)amino]pyrimidin-4-yl}phenyl)acetamide -continued
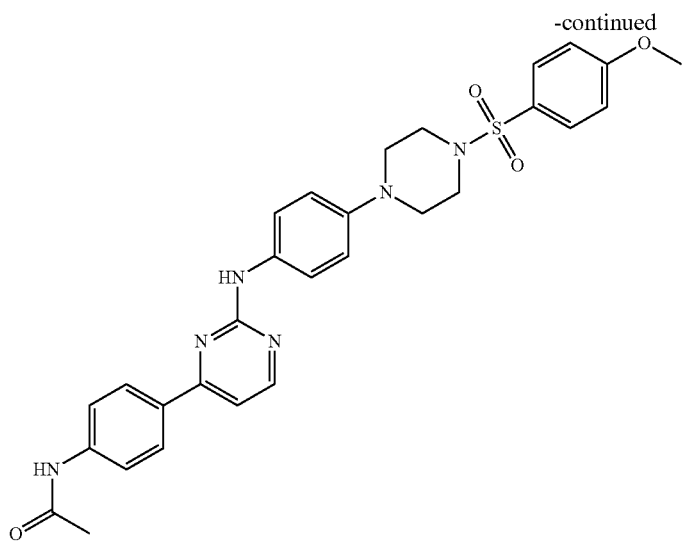
N-[4-(2-{[4-(4-{[4-(methyloxy)phenyl]sulfonyl}piperazin-1-yl)phenyl]amino}pyrimidin-4-yl)phenyl]acetamide
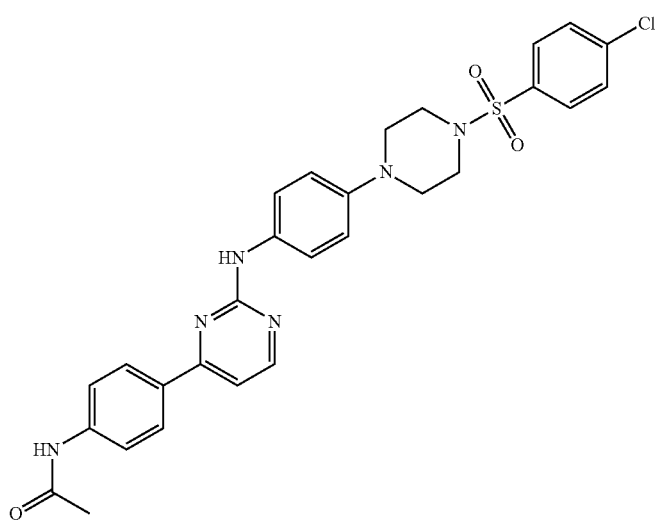
N-(4-{2-[(4-{4-[(4-chlorophenyl)sulfonyl]piperazin-1-yl}phenyl)amino]pyrimidin-4-yl}phenyl)acetamide
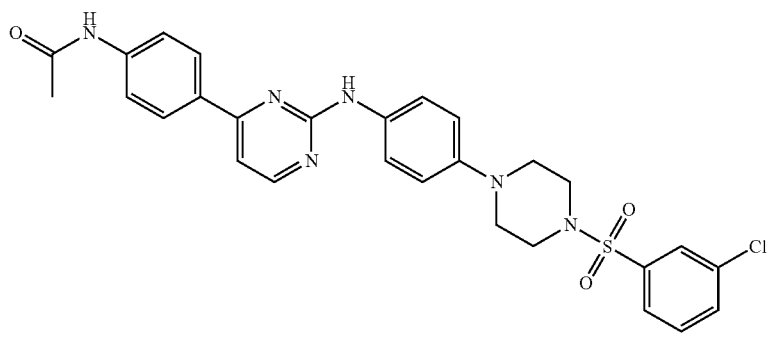
N-(4-{2-[(4-{4-[(3-chlorophenyl)sulfonyl]piperazin-1-yl}phenyl)amino]pyrimidin-4-yl}phenyl)acetamide -continued
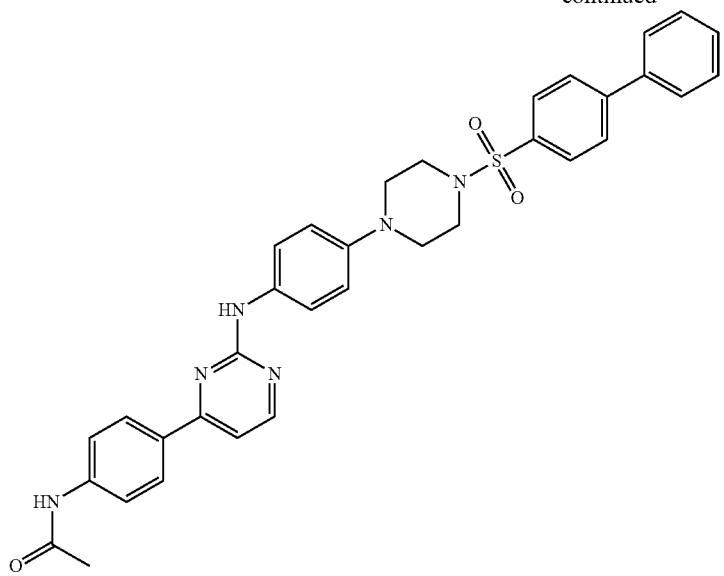
N-{4-[2-({4-[4-(biphenyl-4-ylsulfonyl)piperazin-1-yl]phenyl}amino)pyrimidin-4-yl]phenyl}acetamide
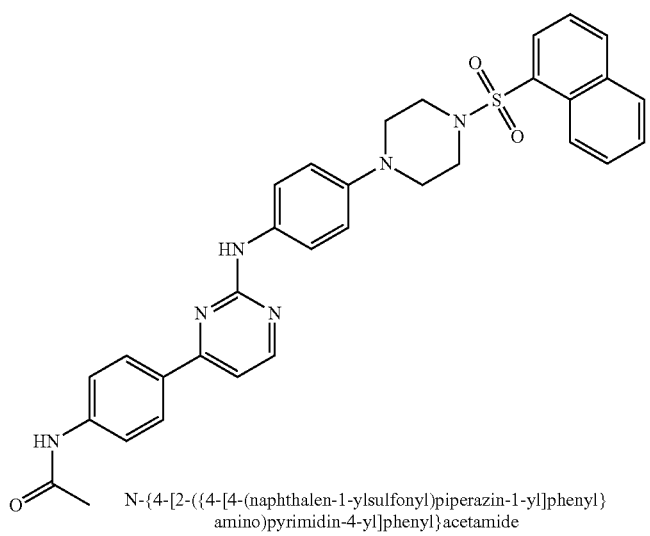
N-{4-[2-({4-[4-(naphthalen-1-ylsulfonyl)piperazin-1-yl]phenyl}amino)pyrimidin-4-yl]phenyl}acetamide -continued
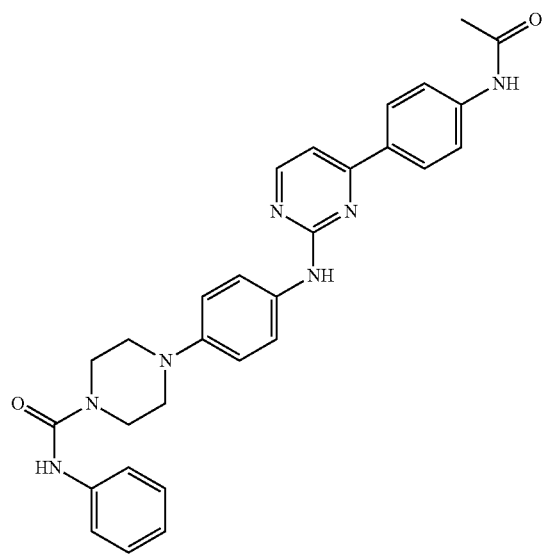
4-[4-({4-[4-(acetylamino)phenyl]pyrimidin-2-yl}amino)phenyl]-
N-phenylpiperazine-1-carboxamide
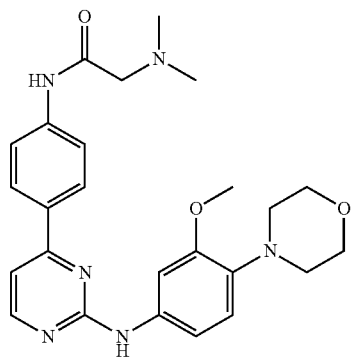
$N^2,N^2$-dimethyl-N-[4-(2-{[3-(methyloxy)-4-morpholin-4-ylphenyl]
amino}pyrimidin-4-yl)phenyl]glycinamide
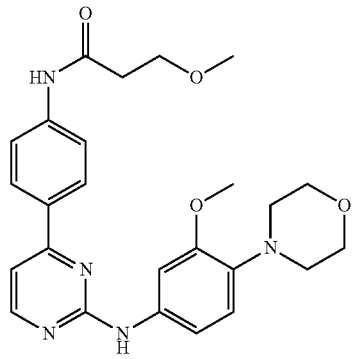
3-(methyloxy)-N-[4-(2-{[3-methyloxy)-4-morpholin-4-ylphenyl]
amino}pyrimidin-4-yl)phenyl]propanamide
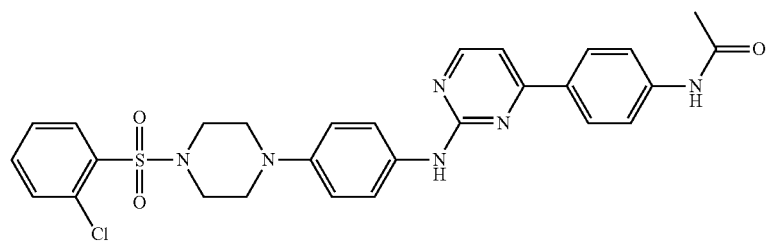
N-(4-{2-[(4-{4-[(2-chlorophenyl)sulfonyl]piperazin-1-yl}phenyl)
amino]pyrimidin-4-yl}phenyl)acetamide

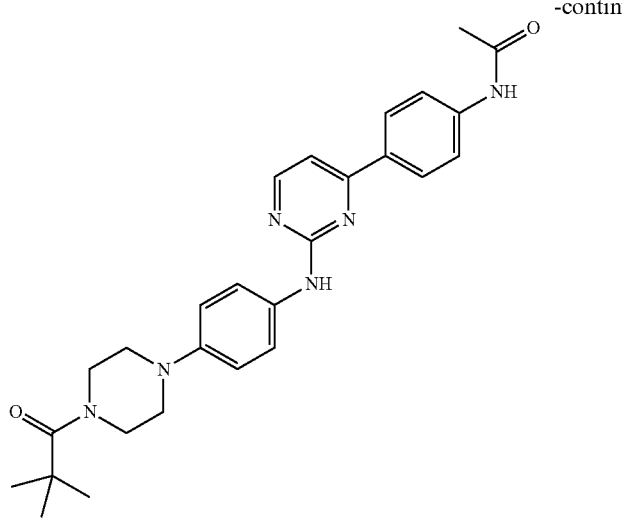
N-{4-[2-({4-[4-(2,2-dimethylpropanoyl)piperazin-1-yl]phenyl}amino)pyrimidin-4-yl]phenyl}acetamide
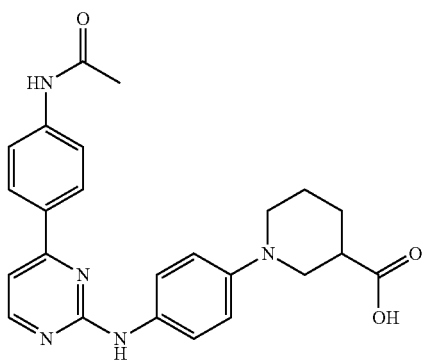
1-[4-({4-[4-(acetylamino)phenyl]pyrimidin-2-yl}amino)phenyl]piperidine-3-carboxylic acid
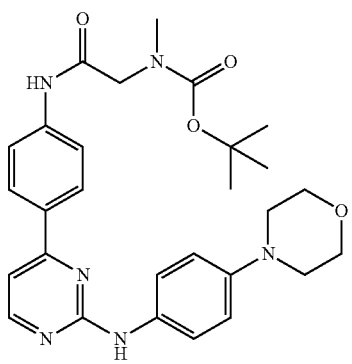
1,1-dimenthylethyl methyl{2-[(4-{2-[(4-morpholin-4-ylphenyl)amino]pyrimidin-4-yl}phenyl)amino]-2-oxoethyl}carbamate
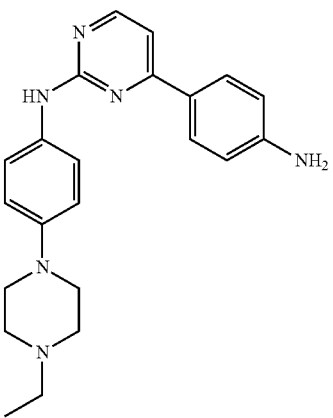
4-(4-aminophenyl)-N-[4-(4-ethylpiperazin-1-yl)phenyl]pyrimidin-2-amine

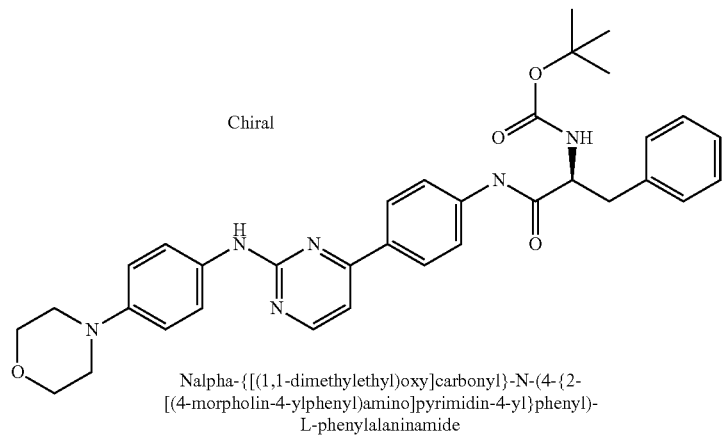

Nalpha-{[(1,1-dimethylethyl)oxy]carbonyl}-N-(4-{2-[(4-morpholin-4-ylphenyl)amino]pyrimidin-4-yl}phenyl)-L-phenylalaninamide

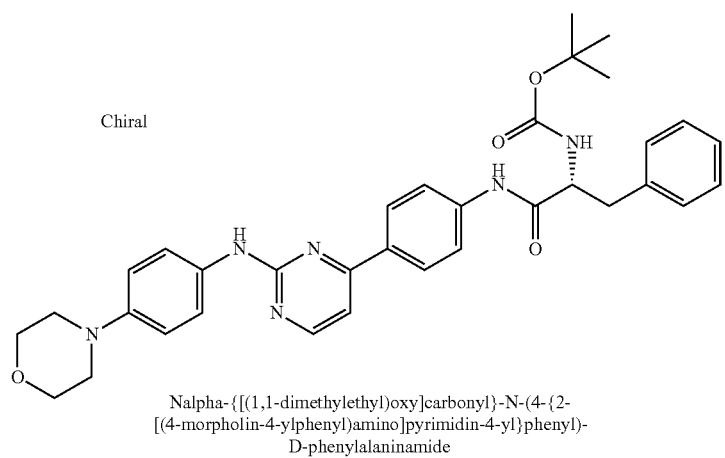

Nalpha-{[(1,1-dimethylethyl)oxy]carbonyl}-N-(4-{2-[(4-morpholin-4-ylphenyl)amino]pyrimidin-4-yl}phenyl)-D-phenylalaninamide

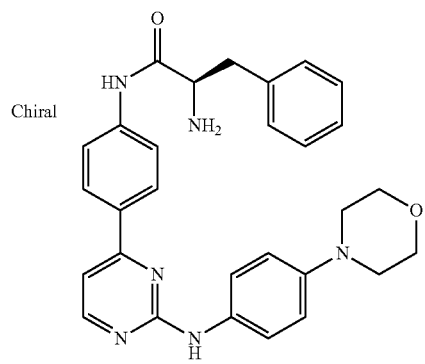

N-(4-{2-[(4-morpholin-4-ylphenyl)amino]pyrimidin-4-yl}phenyl)-D-phenylalaninamide

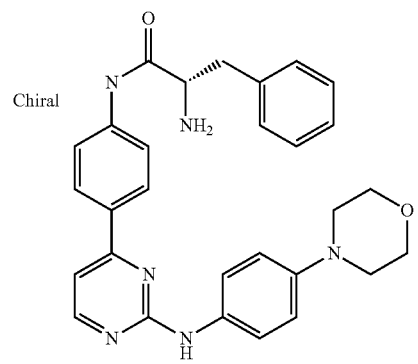

N-(4-{2-[(4-morpholin-4-ylphenyl)amino]pyrimidin-4-yl}phenyl)-L-phenylalaninamide

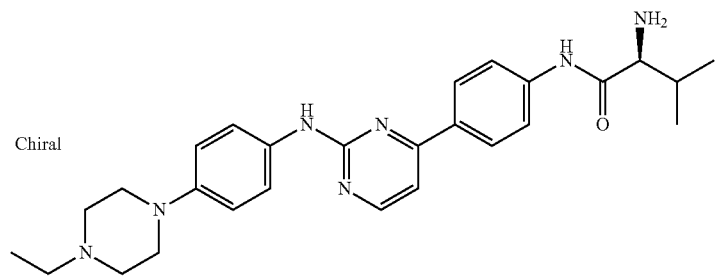

N-[4-(2-{[4-(4-ethylpiperazin-1-yl)phenyl]amino}pyrimidin-4-yl)phenyl]-L-valinamide

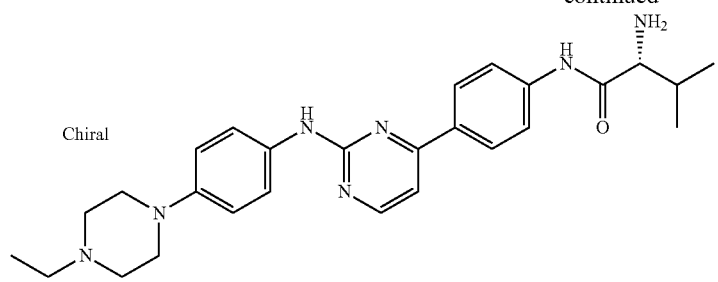

N-[4-(2-{[4-(4-ethylpiperazin-1-yl)phenyl]amino}pyrimidin-4-yl)
phenyl]-D-valinamide

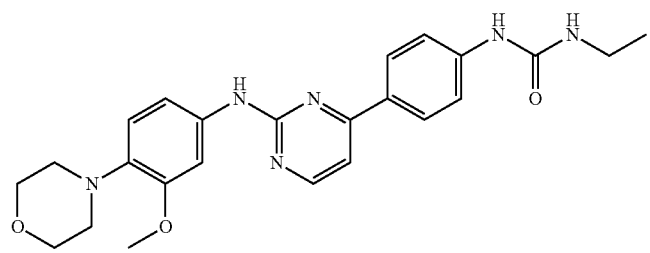

1-ethyl-3-[4-(2-{[3-(methyloxy)-4-morpholin-4-ylphenyl]amino}
pyrimidin-4-yl)phenyl]urea

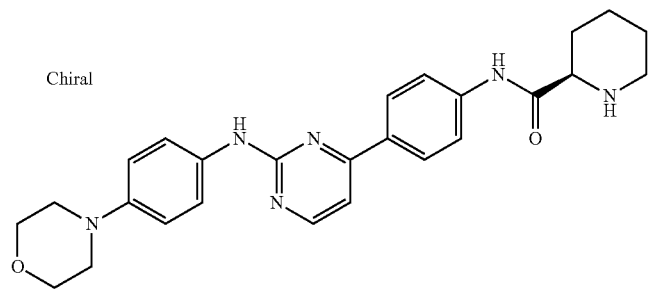

(2R)-N-(4-{2-[(4-morpholin-4-ylphenyl)amino]pyrimidin-4-yl}
phenyl)piperidine-2-carboxamide

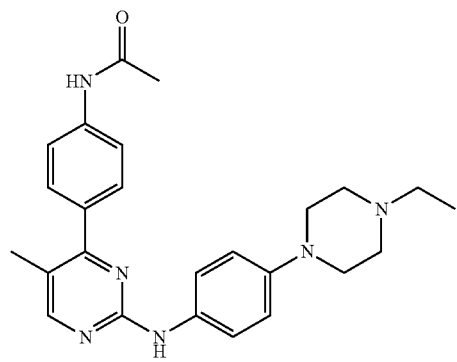

N-[4-(2-{[4-(4-ethylpiperazin-1-yl)phenyl]amino}-5-
methylpyrimidin-4-yl)phenyl]acetamide

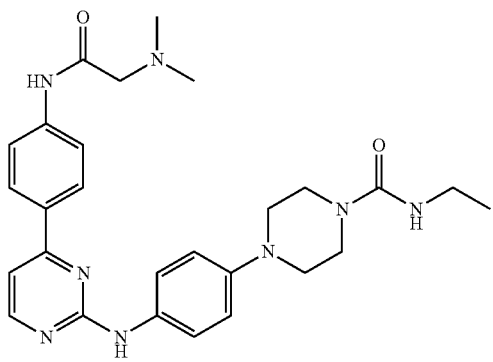

4-{4-[(4-{4-[(N,N-dimethylglycyl)amino]phenyl}pyrimidin-
2-yl)amino]phenyl}-N-ethylpiperazine-1-carboxamide

903

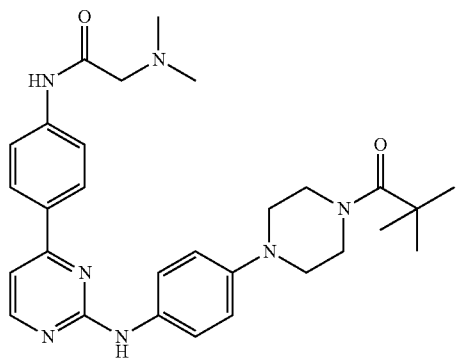

N-{4-[2-({4-[4-(2,2-dimethylpropanoyl)piperazin-1-yl]phenyl}
amino)pyrimidin-4-yl]phenyl}-N~2~,N~2~-dimethylglycinamide

904

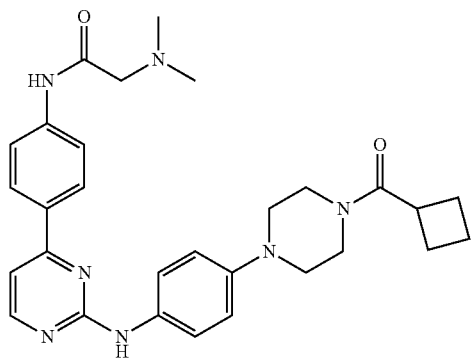

N-{4-[2-({4-[4-(cyclobutylcarbonyl)piperazin-1-yl]phenyl}amino)
pyrimidin-4-yl]phenyl}-N~2~,N~2~-dimethylglycinamide

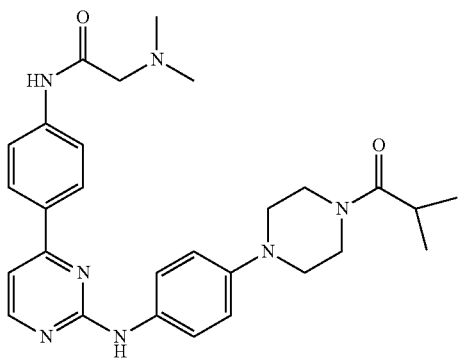

N$^2$,N$^2$-dimethyl-N-{4-[2-({4-[4-(2-methylpropanoyl)piperazin-1-yl]
phenyl}amino)pyrimidin-4-yl]phenyl}glycinamide

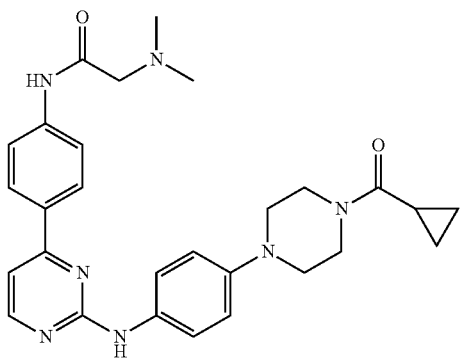

N-{4-[2-({4-[4-(cyclopropylcarbonyl)piperazin-1-yl]
phenyl}amino)pyrimidin-4-yl]phenyl}-N$^2$,N$^2$-dimethylglycinamide

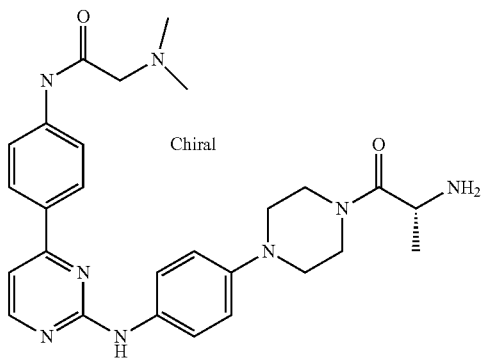

N-[4-(2-{[4-(4-D-alanylpiperazin-1-yl)phenyl]amino}pyrimidin-4-
yl)phenyl]-N~2~,N~2~-dimethylglycinamide

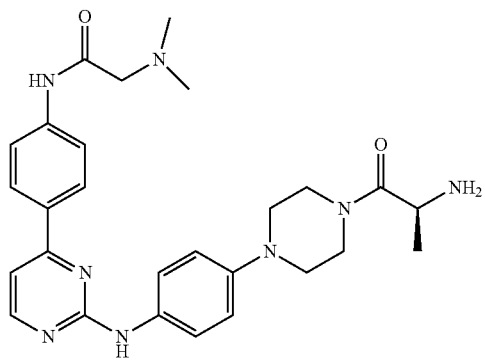

N-[4-(2-{[4-(4-L-alanylpiperazin-1-yl)phenyl]amino}pyrimidin-4-
yl)phenyl]-N$^2$,N$^2$-dimethylglycinamide

905

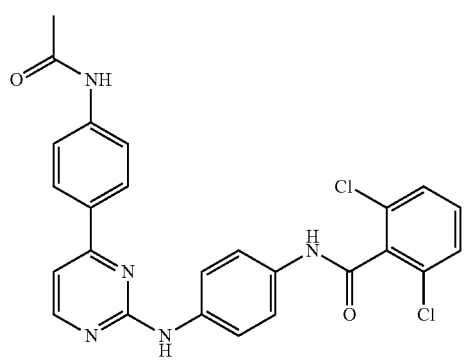

N-[4-({4-[4-(acetylamino)phenyl]pyrimidin-2-yl}amino)
phenyl]-2,6-dichlorobenzamide

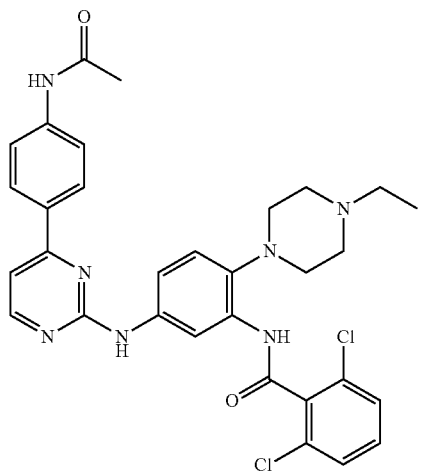

N-[5-({4-[4-(acetylamino)phenyl]pyrimidin-2-yl}amino)-2-(4-
ethylpiperazin-1-yl)phenyl]-2,6-dichlorobenzamide

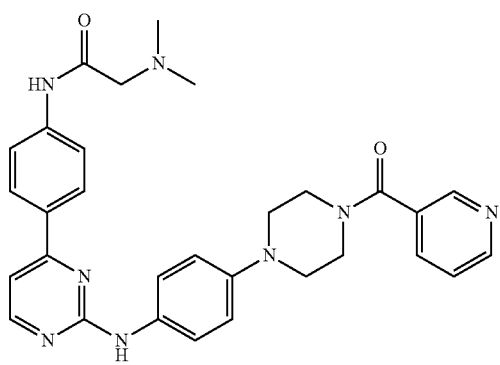

N²,N²-dimethyl-N-{4-[2-({4-[4-(pyridin-3-ylcarbonyl)
piperazin-1-yl]phenyl}amino)pyrimidin-4-yl]phenyl}glycinamide

906

-continued

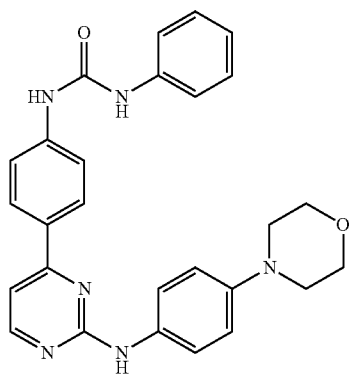

1-(4-{2-[(4-morpholin-4-ylphenyl)amino]pyrimidin-4-yl}
phenyl)-3-phenylurea

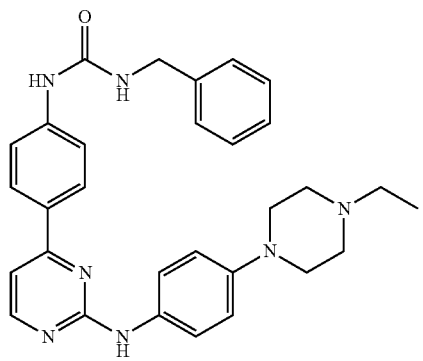

1-[4-(2-{[4-(4-ethylpiperazin-1-yl)phenyl]amino}pyrimidin-4-yl)
phenyl]-3-(phenylmethyl)urea

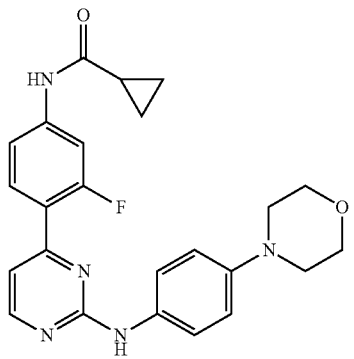

N-(3-fluoro-4-{2-[(4-morpholin-4-ylphenyl)amino]
pyrimidin-4-yl}phenyl)cyclopropanecarboxamide 907 908
-continued

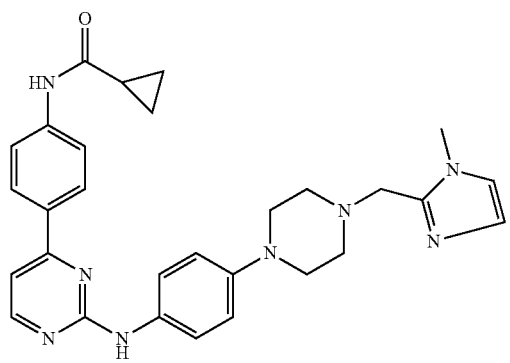

N-(4-{2-[(4-{4-[(1-methyl-1H-imidazol-2-yl)methyl]piperazin-1-yl}phenyl)amino]pyrimidin-4-yl}phenyl)cyclopropanecarboxamide

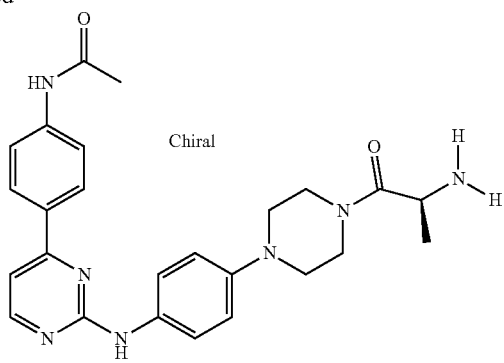

N-[4-(2-{[4-(4-L-alanylpiperazin-1-yl)phenyl]amino}pyrimidin-4-yl)phenyl]acetamide

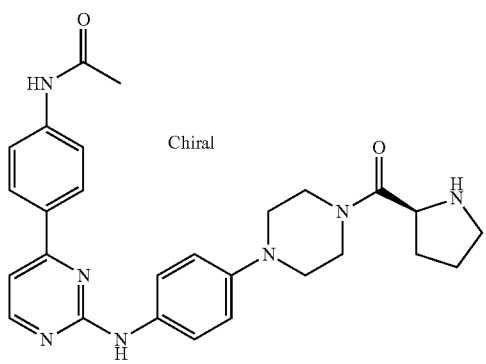

N-[4-(2-{[4-(4-L-prolylpiperazin-1-yl)phenyl]amino}pyrimidin-4-yl)phenyl]acetamide

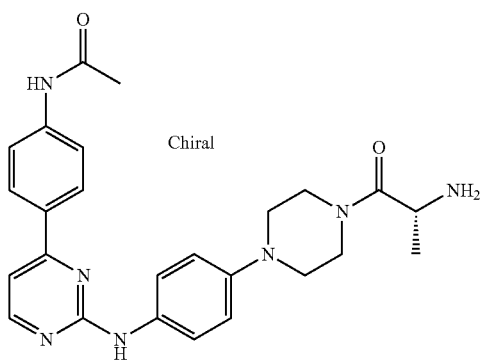

N-[4-(2-{[4-(4-D-alanylpiperazin-1-yl)phenyl]amino}pyrimidin-4-yl)phenyl]acetamide

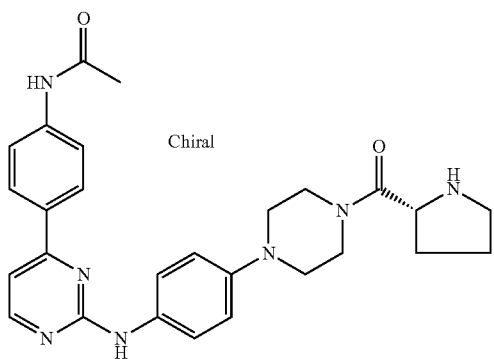

N-[4-(2-{[4-(4-D-prolylpiperazin-1-yl)phenyl]amino}pyrimidin-4-yl)phenyl]acetamide

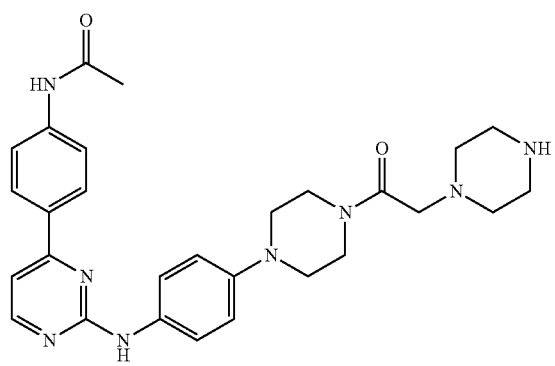

N-{4-[2-({4-[4-(2-piperazin-1-ylacetyl)piperazin-1-yl]phenyl}amino)pyrimidin-4-yl]phenyl}acetamide

909

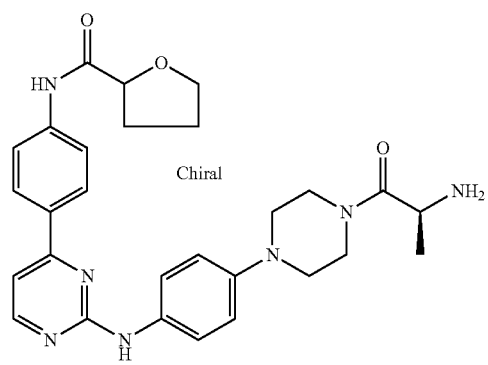

N-[4-(2-{[4-(4-L-alanylpiperazin-1-yl)phenyl]amino}pyrimidin-4-yl)
phenyl]tetrahydrofuran-2-carboxamide

910

-continued

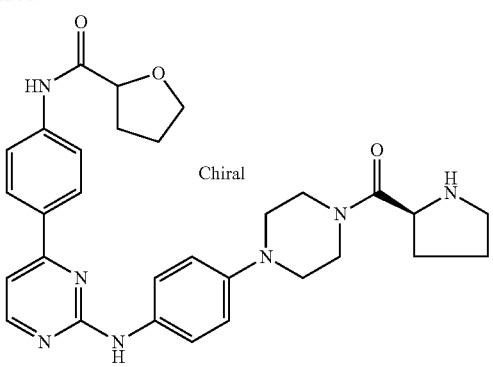

N-[4-(2-{[4-(4-L-prolylpiperazin-1-yl)phenyl]amino}pyrimidin-4-yl)
phenyl]tetrahydrofuran-2-carboxamide

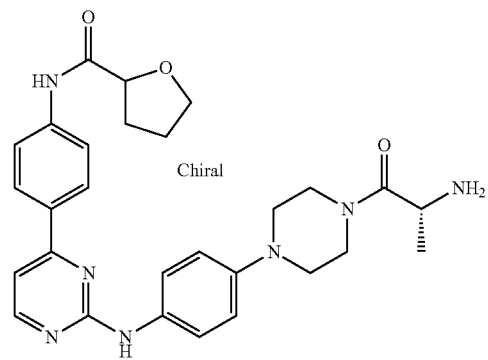

N-[4-(2-{[4-(4-D-alanylpiperazin-1-yl)phenyl]amino}pyrimidin-4-yl)
phenyl]tetrahydrofuran-2-carboxamide

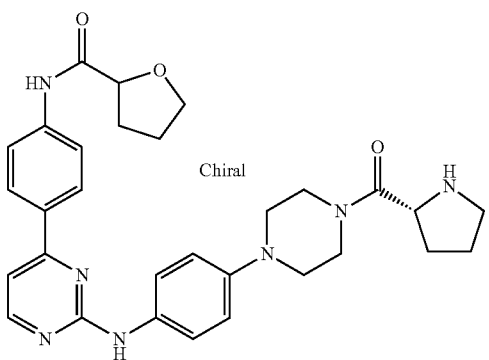

N-[4-(2-{[4-(4-D-prolylpiperazin-1-yl)phenyl]amino}pyrimidin-4-yl)
phenyl]tetrahydrofuran-2-carboxamide

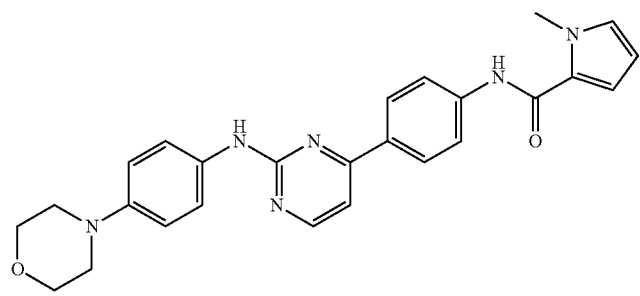

1-methyl-N-(4-{2-[(4-morpholin-4-ylphenyl)amino]
pyrimidin-4-yl}phenyl)-1H-pyrrole-2-carboxamide

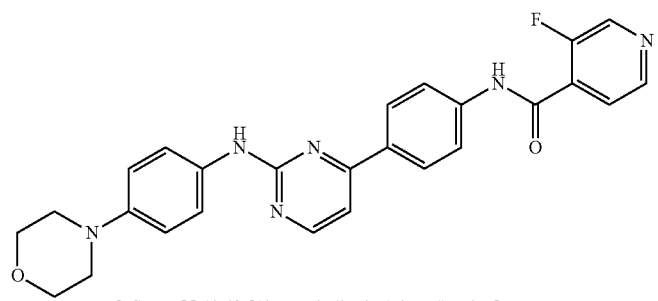

3-fluoro-N-(4-{2-[(4-morpholin-4-ylphenyl)amino]
pyrimidin-4-yl}phenyl)pyridine-4-carboxamide -continued

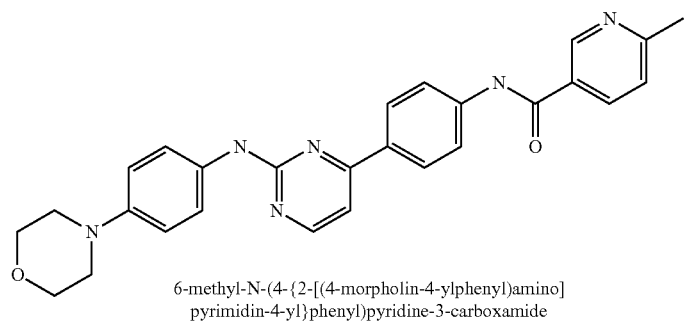

6-methyl-N-(4-{2-[(4-morpholin-4-ylphenyl)amino]
pyrimidin-4-yl}phenyl)pyridine-3-carboxamide

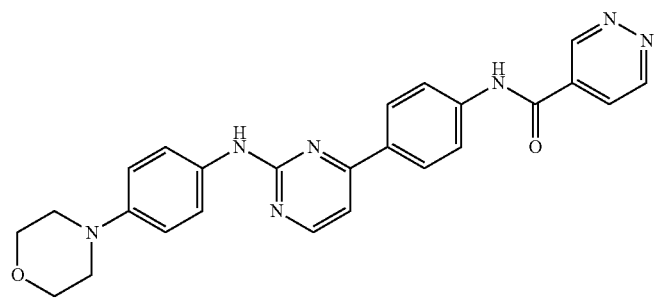

N-(4-{2-[(4-morpholin-4-ylphenyl)amino]pyrimidin-4-yl}
phenyl)pyridazine-4-carboxamide

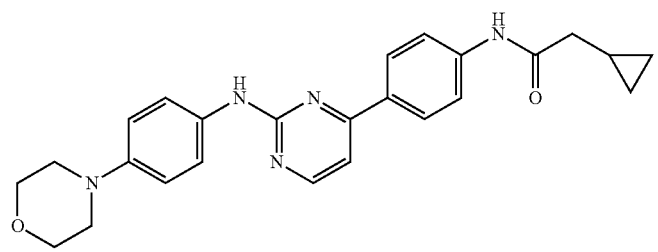

2-cyclopropyl-N-(4-{2-[(4-morpholin-4-ylphenyl)amino]
pyrimidin-4-yl}phenyl)acetamide

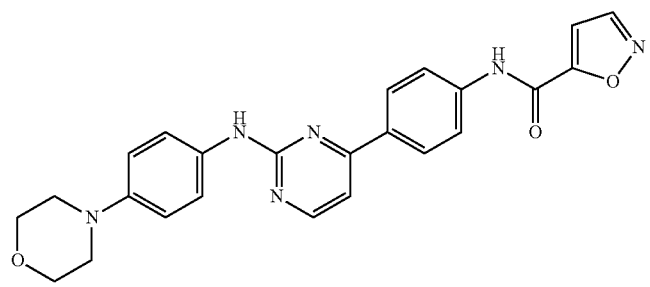

N-(4-{2-[(4-morpholin-4-ylphenyl)amino]pyrimidin-4-yl}
phenyl)isoxazole-5-carboxamide

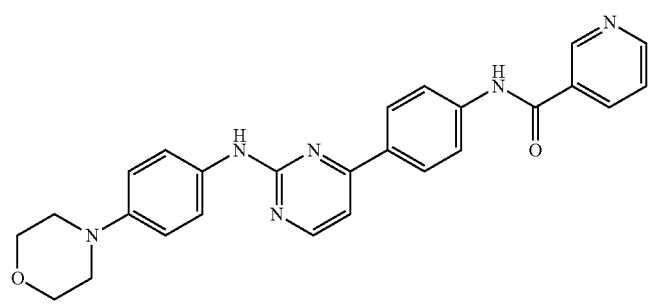

N-(4-{2-[(4-morpholin-4-ylphenyl)amino]pyrimidin-4-yl}
phenyl)pyridine-3-carboxmide -continued
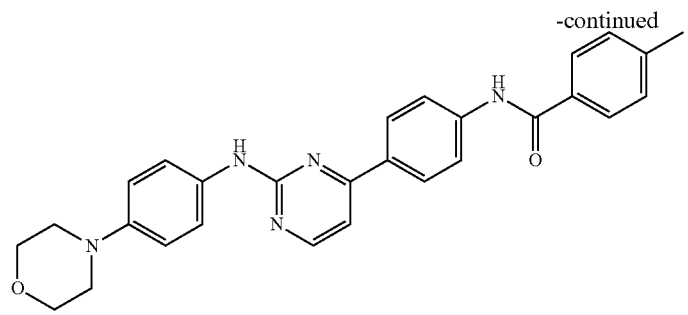
4-methyl-N-(4-{2-[(4-morpholin-4-ylphenyl)amino]pyrimidin-4-yl}phenyl)benzamide
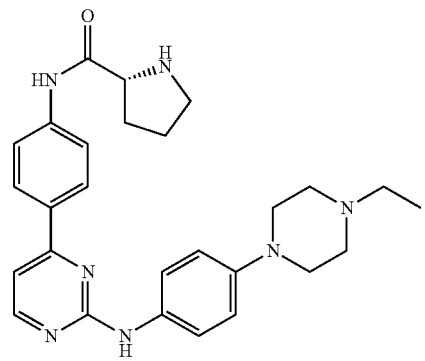
N-[4-(2-{[4-(4-ethylpiperazin-1-yl)phenyl]amino}pyrimidin-4-yl)phenyl]-D-prolinamide
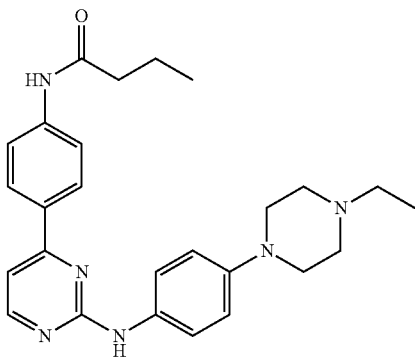
N-[4-(2-{[4-(4-ethylpiperazin-1-yl)phenyl]amino}pyrimidin-4-yl)phenyl]butanamide
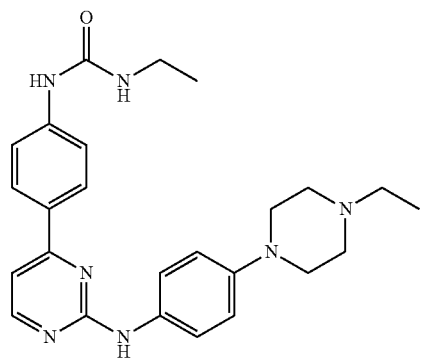
1-ethyl-3-[4-(2-{[4-(4-ethylpiperazin-1-yl)phenyl]amino}pyrimidin-4-yl)phenyl]urea
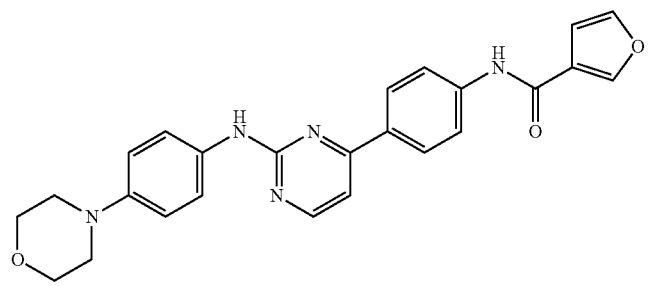
N-(4-{2-[(4-morpholin-4-ylphenyl)amino]pyrimidin-4-yl}phenyl)furan-3-carboxamide -continued

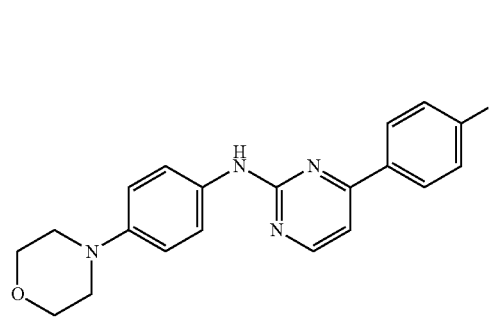

N-(4-{2-[(4-morpholin-4-ylphenyl)amino]pyrimidin-4-yl}phenyl)-1,3-thiazole-4-carboxamide

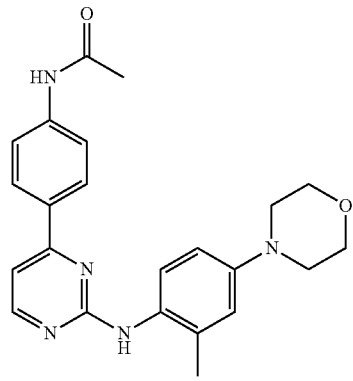

N-(4-{2-[(2-methyl-4-morpholin-4-ylphenyl)amino]pyrimidin-4-yl}phenyl)acetamide and

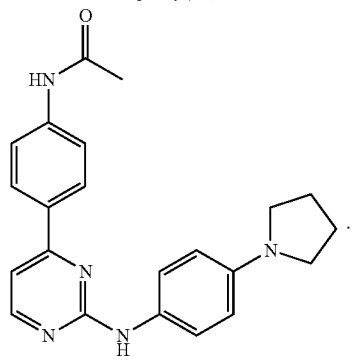

N-(4-{2-[(4-pyrrolidin-1-ylphenyl)amino]pyrimidin-4-yl}phenyl)acetamide

31. A compound according to claim 1 selected from
N-[4-(2-{[4-(4-ethylpiperazin-1-yl)phenyl]amino}pyrimidin-4-yl)phenyl]acetamide;
N-(4-{2-[(4-morpholin-4-ylphenyl)amino]pyrimidin-4-yl}phenyl)cyclopropanecarboxamide;
N-(4-{5-methyl-2-[(4-morpholin-4-ylphenyl)amino]pyrimidin-4-yl}phenyl)cyclopropanecarboxamide;
N-(4-{2-[(4-morpholin-4-ylphenyl)amino]pyrimidin-4-yl}phenyl)valinamide;
N-(4-{2-[(4-{4-[(1-methyl-1H-imidazol-2-yl)methyl]piperazin-1-yl}phenyl)amino]pyrimidin-4-yl}phenyl)acetamide;
2-(dimethylamino)-N-(4-(2-(4-morpholinophenylamino)pyrimidin-4-yl)phenyl)acetamide;
N-(4-{2-[(4-morpholin-4-ylphenyl)amino]pyrimidin-4-yl}phenyl)-D-alaninamide;
N-{4-[2-({4-[4-(2-methylpropanoyl)piperazin-1-yl]phenyl}amino)pyrimidin-4-yl]phenyl}acetamide;
2-amino-N-(4-{2-[(4-morpholin-4-ylphenyl)amino]pyrimidin-4-yl}phenyl)-2-phenylacetamide;
N-(4-{5-methyl-2-[(4-morpholin-4-ylphenyl)amino]pyrimidin-4-yl}phenyl)acetamide;
3-(methyloxy)-N-(4-{2-[(4-morpholin-4-ylphenyl)amino]pyrimidin-4-yl}phenyl)propanamide;
N-(4-{2-[(4-morpholin-4-ylphenyl)amino]pyrimidin-4-yl}phenyl)prolinamide;
N-(4-{2-[(4-morpholin-4-ylphenyl)amino]pyrimidin-4-yl}phenyl)-L-alaninamide;
N-(4-{2-[(4-{4-[3-(dimethylamino)-2,2-dimethylpropyl]piperazin-1-yl}phenyl)amino]pyrimidin-4-yl}phenyl)acetamide;
N-(4-{2-[(4-{4-[3-(methyloxy)propanoyl]piperazin-1-yl}phenyl)amino]pyrimidin-4-yl}phenyl)acetamide;
2-Hydroxy-2-methyl-N-(4-(2-(4-morpholinophenylamino)pyrimidin-4-yl)phenyl)propanamide:
N-(4-{2-[(4-morpholin-4-ylphenyl)amino]pyrimidin-4-yl}phenyl)-D-prolinamide;
N-[4-(2-{[3-(methyloxy)-4-morpholin-4-ylphenyl]amino}pyrimidin-4-yl)phenyl]-D-prolinamide;
N-(4-{2-[(4-morpholin-4-ylphenyl)amino]pyrimidin-4-yl}phenyl)tetrahydrofuran-3-carboxamide;
O-methyl-N-(4-{2-[(4-morpholin-4-ylphenyl)amino]pyrimidin-4-yl}phenyl)-L-serinamide;
1-ethyl-3-{4-[2-({4-[4-(2-methylpropanoyl)piperazin-1-yl]phenyl}amino)pyrimidin-4-yl]phenyl}urea;
N-ethyl-4-(4-{[4-(4-{[(ethylamino)carbonyl]amino}phenyl)pyrimidin-2-yl]amino}phenyl)piperazine-1-carboxamide;
$N^2,N^2$-dimethyl-N-(4-{2-[(4-{4-[3-(methyloxy)propanoyl]piperazin-1-yl}phenyl)amino]pyrimidin-4-yl}phenyl)glycinamide;
N-(4-(2-(3-methoxy-4-morpholino-phenylamino)pyrimidin-4-yl)phenyl)acetamide;
N-(4-{2-[(4-morpholin-4-ylphenyl)amino]pyrimidin-4-yl}phenyl)-D-serinamide;
3-hydroxy-N-(4-{2-[(4-morpholin-4-ylphenyl)amino]pyrimidin-4-yl}phenyl)butanamide;
3-hydroxy-N-(4-{2-[(4-morpholin-4-ylphenyl)amino]pyrimidin-4-yl}phenyl)butanamide;
N-{4-[2-({4-[4-(tetrahydrofuran-2-ylcarbonyl)piperazin-1-yl]phenyl}amino)pyrimidin-4-yl]phenyl}-D-prolinamide;

2-hydroxy-2-methyl-N-(4-{2-[(4-morpholin-4-ylphenyl) amino]pyrimidin-4-yl}phenyl)propanamide;

N-(4-{2-[(4-morpholin-4-ylphenyl)amino]pyrimidin-4-yl}phenyl)prolinamide;

N-(4-{2-[(4-morpholin-4-ylphenyl)amino]pyrimidin-4-yl}phenyl)-L-prolinamide;

N-(4-{2-[(4-morpholin-4-ylphenyl)amino]pyrimidin-4-yl}phenyl)-D-prolinamide;

O-methyl-N-(4-{2-[(4-morpholin-4-ylphenyl)amino]pyrimidin-4-yl}phenyl)-L-serinamide;

O-methyl-N-(4-{2-[(4-morpholin-4-ylphenyl)amino]pyrimidin-4-yl}phenyl)-D-serinamide;

O-methyl-N-(4-{2-[(4-morpholin-4-ylphenyl)amino]pyrimidin-4-yl}phenyl)-D-serinamide; and N-(4-{2-[(3-fluoro-4-morpholin-4-ylphenyl)amino]pyrimidin-4-yl}phenyl)-D-prolinamide.

32. A pharmaceutical composition comprising a compound according to claim 1, or a pharmaceutically acceptable salt thereof, and a pharmaceutically acceptable carrier, excipient, or diluent.

33. A method for treating a disease, disorder, or syndrome mediated, at least in part, by inhibiting JAK-2, wherein the disease, disorder, or syndrome is congestive heart failure, hypertension, or thrombocytosis, and which method comprises administering to an animal in need of said treatment a pharmaceutical composition comprising a therapeutically effective amount of a compound of formula I,

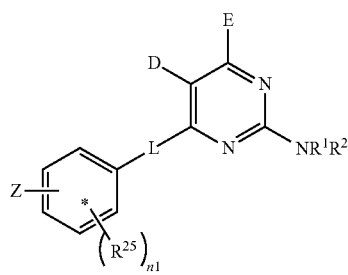

or a pharmaceutically acceptable salt thereof, wherein
D is hydrogen, halo, —$CF_3$, heterocycloalkyl or alkyl;
E is hydrogen, halo, —$CF_3$, heterocycloalkyl or alkyl; or
L is a bond;
Z is

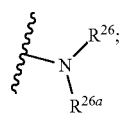

$R^{25}$ is selected from alkyl, alkenyl, lower alkyl, halo, haloalkyl, haloalkoxy, amino, alkylamino, dialkylamino, aminoalkyl, alkylaminoalkyl, —$OR^{12}$, cyano, —$CH_2NHC(O)OR^7$, —$CH_2NHC(O)R^7$, —$SR^7$, —$S(O)_2R^7$, —$S(O)_2NR^7R^8$, —$C(O)OR^8$, cycloalkyl, heterocycloalkyl, aryl and heteroaryl; wherein the cycloalkyl, heterocycloalkyl, aryl and heteroaryl are each optionally substituted with one, two or three groups independently selected from alkyl, alkenyl, halo, haloalkoxy, haloalkyl, amino, alkylamino, dialkylamino, aminoalkyl, alkylaminoalkyl, —$OR^8$, —NHS$(O)_2R^8$, cyano, —$C(O)R^8$, —$CH_2NHC(O)OR^7$, —$CH_2NHC(O)R^7$, —$SR^7$, —$S(O)_2R^7$, —$S(O)_2NR^7R^8$, —$C(O)OR^8$, —$C(O)NR^7R^8$, and —$NR^7C(O)R^8$;

n1 is 0, 1, 2, 3, or 4, and each n1 is independently selected when more than one n1 is present;

or Z and an $R^{25}$, together with the carbon atoms to which they are attached, join to form a 5 or 6 membered heterocycloalkyl, a 5 or 6 membered heteroaryl, or a 5 or 6 membered cycloalkyl ring, wherein the 5 or 6 membered heterocycloalkyl, 5 or 6 membered heteroaryl, and 5 or 6 membered cycloalkyl ring are fused to the phenyl moiety to which Z and $R^{25}$ are attached, and wherein the 5 or 6 membered heterocycloalkyl, 5 or 6 membered heteroaryl, or 5 or 6 membered cycloalkyl ring are each optionally substituted with 1, 2, or 3 groups independently selected from oxo, alkyl, alkoxy and halo.

n2 is 0, 1, 2, 3, or 4, and each n2 is independently selected when more than one n2 is present;

n5 is 0, 1, 2, 3 or 4;

$R^1$ is hydrogen; $R^2$ is (a)

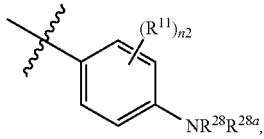

$R^7$, $R^{7'}$, $R^{12}$ and $R^{15}$ are each independently hydrogen, alkyl, alkoxy, or alkoxyalkyl;

$R^8$ is selected from hydrogen, hydroxy, alkyl, alkenyl, lower alkynyl, hydroxylamino, hydroxyalkyl, alkoxyalkyl, dihydroxyalkyl, alkylamino, dialkylamino, aminoalkyl, aminocarbonylalkyl, alkylaminocarbonylalkyl, dialkylaminocarbonylalkyl, alkylaminoalkyl, dialkylaminoalkyl, —$(CH_2)_r$—$C(O)OR^7$, —$(CH_2)_r$—$C(O)NR^7R^{7'}$, aryl, heteroaryl, cycloalkyl, arylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, haloalkyl, haloalkoxy, lower alkoxy, amino, aryl, alkylamino, dialkylamino, heterocyclylalkoxy, oxo and haloalkyl;

each $R^{11}$, when $R^{11}$ is present, is independently selected from alkyl, alkenyl, lower alkynyl, —$CF_3$, alkoxy, halo, haloalkoxy, haloalkyl, aminoalkyl, aminoalkoxy, alkylaminoalkyl, alkylaminoalkoxy, dialkylaminoalkyl, dialkylaminoalkoxy, oxo, thioalkyl, alkylthioalkyl, —$(CH_2)_p$—$OR^{17}$, —CN, —O—$CH_2$—$C(O)$—$R^{17}$, —$C(O)R^{16}$, —$(CH_2)_p$—$C(O)OR^{17}$, —$S(O)_2R^{17}$, —$S(O)_2NR^{15}R^{17}$, aryl, heteroaryl, cycloalkyl, arylalkyl, arylalkoxy, heteroarylalkyl, cycloalkylalkyl, heterocycloalkyl, and heterocycloalkylalkyl; wherein the aryl, heteroaryl, cycloalkyl, arylalkyl, heteroarylalkyl, cycloalkylalkyl, heterocycloalkyl, and heterocycloalkylalkyl are each independently optionally substituted at any ring position with 1, 2, 3 or 4 $R^{21}$;

$R^{12a}$ is hydrogen or alkyl;

$R^{13}$ is selected from hydrogen, hydroxy, alkyl, alkenyl, lower alkynyl, hydroxylamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, —(CH$_2$)$_r$—C(O)OR$^7$, —(CH$_2$)$_r$—C(O)NR$^7$R$^{7'}$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with 1, 2, 3, 4 or 5 groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl are independently optionally substituted with 1, 2, 3, 4, or 5 groups selected from halo and hydroxy;

R$^{16}$ is selected from hydrogen, hydroxy, alkyl, alkenyl, lower alkynyl, hydroxyamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, dialkylaminoalkyl, —(CH$_2$)$_r$—C(O)OR$^7$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl is optionally substituted with 1, 2, 3, 4, or 5 groups selected from halo and hydroxy;

R$^{17}$ is selected from hydrogen, hydroxy, alkyl, alkenyl, lower alkynyl, hydroxyamino, haloalkyl, alkyl substituted with halo and hydroxy, hydroxyalkyl, alkoxyalkyl, aminocarbonylalkyl, alkylaminocarbonylalkyl, dialkylaminocarbonylalkyl, dialkylaminoalkyl, —(CH$_2$)$_r$—C(O)OR$^7$, —(CH$_2$)$_r$—C(O)NR$^7$R$^{7'}$, aryl, heteroaryl, cycloalkyl, arylalkyl, diarylalkyl, aryloxyalkyl, heteroarylalkyl, cycloalkylalkyl, heterocycloalkyl, and heterocycloalkylalkyl; wherein the aryl, heteroaryl, cycloalkyl, arylalkyl, diarylalkyl, aryloxyalkyl, heteroarylalkyl, cycloalkylalkyl, heterocycloalkyl, and heterocycloalkylalkyl are each independently optionally substituted at the ring position with one, two, three, four or five groups independently selected from alkyl, alkenyl, lower alkynyl, halo, hydroxy, hydroxyalkyl, alkoxycarbonyl, alkylcarbonyl, haloalkyl, haloalkoxy, lower alkoxy, amino, aryl, alkylamino, dialkylamino, heterocyclylalkoxy, oxo and haloalkyl; and wherein the alkyl of cycloalkylalkyl, heterocycloalkylalkyl, arylalkyl, and heteroarylalkyl is optionally substituted with 1, 2, 3, 4, or 5 groups selected from halo and hydroxy;

each R$^{21}$, when R$^{21}$ is present, is independently selected from alkyl, alkenyl, lower alkynyl, cyano, halo, haloalkoxy, haloalkyl, hydroxyalkyl, amino, alkylamino, dialkylamino, dialkylaminoalkyl, dialkylaminoalkyloxy, haloalkyl, oxo, —OR$^{13}$, —NHS(O)$_2$R$^{17}$, —S(O)$_2$R$^{17}$, —C(O)R$^{17}$, —C(O)OR$^{17}$, —C(O)NR$^{15}$R$^{17}$, —NR$^{15}$C(O)R$^{17}$, aryl, arylalkyl, heteroarylalkyl, aryloxy, and heteroaryl; wherein each of the aryl, arylalkyl, heteroarylalkyl, aryloxy, and heteroaryl within R$^{21}$ are optionally substituted at any ring position with 1, 2, or 3 groups selected from alkyl, lower alkoxy halo, phenyl, heteroaryl and alkylheteroalkyl;

R$^{26}$ is hydrogen, —C(O)-phenyl or alkyl, wherein the —C(O)-phenyl is optionally substituted at any ring position with 1, 2 or 3 halo;

R$^{26a}$ is hydrogen, alkyl, heteroaryl, —C(O)R$^{32}$, —C(O)NHR$^{32a}$, —S(O)$_2$R$^9$, —SR$^9$, —C(O)OR$^{32}$, or —C(O)NR$^{32a}$R$^{32}$;

R$^{28}$ is selected from alkyl, alkenyl, hydroxy, alkoxy, and alkoxyalkyl;

R$^{28a}$ is selected from hydrogen, alkyl, alkenyl, alkoxyalkyl, alkoxycarbonylalkyl, hydroxyalkyl, aryl, arylalkyl, cycloalkyl, cycloalkylalkyl, dialkylaminoalkyl, arylcarbonylalkyl, aryloxyalkyl, alkyl-O—C(O)heterocyloalkyl, —(CH$_2$)$_{n4}$heterocycloalkyl, heterocycloalkylalkyl, heteroaryl, heteroarylalkyl, —(CH$_2$)$_{n4}$—C(O)R$^{29}$, —CH(phenyl)$_2$, —S(O)$_2$R$^{29}$, —C(O)R$^{29}$, —C(O)OR$^{29}$, and —C(O)NR$^{29a}$R$^{29}$, wherein the aryl, arylalkyl, cycloalkyl, cycloalkylalkyl, heteroaryl, heteroarylalkyl, heterocycloalkyl, and heterocycloalkylalkyl groups within R$^{27a}$ and R$^{28a}$ are each independently optionally substituted at any ring position with 1, 2, 3, 4, or 5 groups selected from halo, alkyl, alkoxy, alkylcarbonyl, phenyl, phenoxy, arylcarbonyl, —CF$_3$, oxo, —OCF$_3$, alkoxyphenyl, and heteroaryl optionally substituted with alkyl or halo;

or R$^{28}$ and R$^{28a}$ together with the nitrogen to which they are attached form heterocycloalkyl or heteroaryl, wherein the heterocycloalkyl and heteroaryl are each optionally substituted with 1, 2, 3, 4, or 5 R$^{31}$;

R$^{30}$ is selected from hydrogen, alkyl, hydroxyalkyl, alkoxyalkyl, alkoxyalkoxyalkyl, alkoxycarbonylalkyl, amino, alkylamino, dialkylamino, aminoalkyl, alkylaminoalkyl, dialkylaminoalkyl, aryl, arylalkyl, phenoxyalkyl, cycloalkyl, cycloalkylalkyl, heteroaryl, heteroarylalkyl, arylheteroarylalkyl, heterocycloalkyl, and heterocycloalkylalkyl; wherein the aryl, arylalkyl, phenoxyalkyl, cycloalkyl, arylheteroarylalkyl, cycloalkylalkyl, heteroaryl, heteroarylalkyl, heterocycloalkyl, and heterocycloalkylalkyl groups within R$^{30}$ are each independently optionally substituted at any ring position with 1, 2, 3, 4, or 5 groups selected from halo, alkyl, alkoxy, alkoxyalkyl, —C(O)OCH$_3$, —CF$_3$, —OCF$_3$, alkylcarbonyl, phenyl, phenoxy, alkylphenoxy, dialkylaminoalkoxy and heteroaryl;

R$^{31}$ is selected from alkyl, hydroxyalkyl, alkoxy, alkoxyalkyl, alkylthioalkyl, —C(O)R$^{30}$, —C(O)NR$^{30}$R$^{30a}$, —C(O)OR$^{30}$, —S(O)$_2$R$^{30}$, amino, dihydroxyalkyl, arylcarbonyl, alkylcarbonylamino, alkoxyphenyl, phenylalkoxyalkyl, arylheteroarylalkyl, alkylamino, —O-dialkylamino, dialkylamino, aminoalkyl, alkylaminoalkyl, dialkylaminoalkyl, dialkylaminoalkoxy, oxo, aryl, arylalkyl, cycloalkyl, cycloalkylalkyl, heteroaryl, heteroarylalkyl, heterocycloalkyl, spirocyclic cycloalkyl, spirocyclic heterocycloalkyl, and heterocycloalkylalkyl, wherein the aryl, arylalkyl, cycloalkyl, arylheteroarylalkyl, arylalkoxyalkyl, cycloalkylalkyl, heteroaryl, heteroarylalkyl, heterocycloalkyl, and heterocycloalkylalkyl groups within R$^{31}$ are each independently optionally substituted at any ring position with 1, 2, 3, 4, or 5 groups selected from halo, alkyl, —CF$_3$, —OCF$_3$, cyano, alkoxy, alkoxyalkyl, —C(O)OCH$_3$, alkylcarbonyl, phenyl optionally substituted at any ring position with halo, phenoxy, alkylphenoxy, arylalkoxyalkyl, dialkylaminoalkoxy and heteroaryl;

$R^{32a}$ is hydrogen, —$OCF_3$, —$CF_3$, or alkyl;

$R^{32}$ is selected from aryl, arylalkyl, arylalkoxy, arylcycloalkyl, alkoxycarbonylalkoxy, cycloalkyl, cycloalkylalkyl, cycloalkylhydroxyalkyl, heteroaryl, heteroarylalkyl, heterocycloalkyl, and heterocycloalkylalkyl, wherein the aryl, arylalkyl, cycloalkyl, arylcycloalkyl, cycloalkylalkyl, heteroaryl, heteroarylalkyl, heterocycloalkyl, and heterocycloalkylalkyl are each independently optionally substituted at any ring position with 1, 2, 3, 4, or 5 groups selected from hydroxy, oxo, alkyl, alkoxy, amino, hydroxyalkyl, alkylcarbonyl, alkoxycarbonyl, halo, —$CF_3$, —$OCF_3$, aminoalkyl, alkylaminoalkyl, aryl and dialkylaminoalkyl, and wherein the alkyl portion of the heteroarylalkyl can be substituted with amino;

or $R^{32}$ is alkyl optionally substituted with 1, 2, 3, 4, or 5 groups independently selected from hydroxy, alkoxycarbonyl, alkoxy, —$CF_3$, halo, aminocarbonyl, alkylaminocarbonyl, alkoxycarbonylalkylamino, dialkylaminocarbonyl, —$NR^{34}R^{34a}$ and phenyl optionally substituted with 1, 2, or 3 halo;

or $R^{32}$ is alkylamino or arylalkylamino;

$R^{34}$ is hydrogen or alkyl; and $R^{34a}$ is selected from hydrogen, alkyl, heteroaryl, aryl, aminoalkyl, aminocarbonylalkyl, heteroarylalkyl, arylalkoxy and arylalkyloxycarbonylalkyl; wherein the heteroaryl, aryl, heteroarylalkyl, arylalkoxy or arylalkyloxycarbonylalkyl are each independently optionally substituted at any ring position with 1, 2, 3, 4, or 5 groups selected from hydroxy, oxo, alkyl, amino, hydroxyalkyl, alkylcarbonyl, alkoxycarbonyl, halo, aminoalkyl, alkylaminoalkyl, and dialkylaminoalkyl.

\* \* \* \* \*